US012018275B2

(12) United States Patent
Zhang et al.

(10) Patent No.: US 12,018,275 B2
(45) Date of Patent: Jun. 25, 2024

(54) DELIVERY AND USE OF THE CRISPR-CAS SYSTEMS, VECTORS AND COMPOSITIONS FOR HEPATIC TARGETING AND THERAPY

(71) Applicants: The Broad Institute, Inc., Cambridge, MA (US); Massachusetts Institute of Technology, Cambridge, MA (US); President and Fellows of Harvard College, Cambridge, MA (US)

(72) Inventors: Feng Zhang, Cambridge, MA (US); Le Cong, Cambridge, MA (US); Fei Ran, Cambridge, MA (US)

(73) Assignees: THE BROAD INSTITUTE, INC., Cambridge, MA (US); MASSACHUSETTS INSTITUTE OF TECHNOLOGY, Cambridge, MA (US); PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 944 days.

(21) Appl. No.: 16/800,988

(22) Filed: Feb. 25, 2020

(65) Prior Publication Data

US 2020/0392541 A1 Dec. 17, 2020

Related U.S. Application Data

(60) Division of application No. 14/971,356, filed on Dec. 16, 2015, now Pat. No. 10,577,630, which is a continuation-in-part of application No. PCT/US2014/041804, filed on Jun. 10, 2014.

(60) Provisional application No. 61/836,123, filed on Jun. 17, 2013, provisional application No. 61/979,733, filed on Apr. 15, 2014, provisional application No. 61/915,325, filed on Dec. 12, 2013, provisional application No. 61/871,301, filed on Aug. 28, 2013, provisional application No. 61/862,355, filed on Aug. 5, 2013, provisional application No. 61/847,537, filed on Jul. 17, 2013.

(51) Int. Cl.

| | |
|---|---|
| ***A61K 48/00*** | (2006.01) |
| ***A01K 67/0275*** | (2024.01) |
| ***C12N 7/00*** | (2006.01) |
| ***C12N 9/22*** | (2006.01) |
| ***C12N 15/10*** | (2006.01) |
| ***C12N 15/63*** | (2006.01) |
| ***C12N 15/86*** | (2006.01) |
| ***C12N 15/90*** | (2006.01) |

(52) U.S. Cl.

CPC ........ *C12N 15/907* (2013.01); *A01K 67/0275* (2013.01); *A61K 48/0058* (2013.01); *A61K 48/0091* (2013.01); *C12N 7/00* (2013.01); *C12N 9/22* (2013.01); *C12N 15/1082* (2013.01); *C12N 15/63* (2013.01); *C12N 15/86* (2013.01); *A01K 2217/052* (2013.01); *A01K 2227/105* (2013.01); *A01K 2267/0312* (2013.01); *A01K 2267/0331* (2013.01); *A01K 2267/0362* (2013.01); *A61K 48/00* (2013.01); *C12N 2710/24144* (2013.01); *C12N 2740/15043* (2013.01); *C12N 2750/14132* (2013.01); *C12N 2750/14143* (2013.01); *C12N 2750/14152* (2013.01); *C12Y 301/00* (2013.01)

(58) Field of Classification Search

None

See application file for complete search history.

(56) References Cited

U.S. PATENT DOCUMENTS

| | | | |
|---|---|---|---|
| 5,622,856 | A | 4/1997 | Natsoulis |
| 6,251,677 | B1 | 6/2001 | Wilson et al. |
| 7,601,492 | B2 | 10/2009 | Fu et al. |
| 7,691,995 | B2 | 4/2010 | Zamore et al. |
| 8,697,359 | B1 | 4/2014 | Zhang |
| 8,771,945 | B1 | 7/2014 | Zhang |
| 8,865,406 | B2 | 10/2014 | Zhang et al. |
| 8,871,445 | B2 | 10/2014 | Cong et al. |
| 8,889,418 | B2 | 11/2014 | Zhang et al. |
| 8,895,308 | B1 | 11/2014 | Zhang et al. |
| 8,932,814 | B2 | 1/2015 | Cong et al. |

(Continued)

FOREIGN PATENT DOCUMENTS

| | | |
|---|---|---|
| BR | 112015013784 | 7/2017 |
| CN | 101228176 | 7/2008 |

(Continued)

OTHER PUBLICATIONS

Fin et al. Cell Reports 22:2227-2235, 2018 (Year: 2018).*

(Continued)

*Primary Examiner* — Marcia S Noble
(74) *Attorney, Agent, or Firm* — FOLEY & LARDNER LLP

(57) ABSTRACT

The invention provides for delivery, engineering and optimization of systems, methods, and compositions for manipulation of sequences and/or activities of target sequences. Provided are delivery systems and tissues of organ which are targeted as sites for delivery. Also provided are vectors and vector systems some of which encode one or more components of a CRISPR complex, as well as methods for the design and use of such vectors. Also provide dare methods of directing CRISPR complex formation in eukaryotic cells to ensure enhanced specificity for target recognition and avoidance of toxicity and to edit or modify a target site in a genomic locus of interest to alter or improve the status of a disease or a condition.

16 Claims, 147 Drawing Sheets

Specification includes a Sequence Listing.

(56) References Cited

U.S. PATENT DOCUMENTS

| | | | |
|---|---|---|---|
| 8,945,839 | B2 | 2/2015 | Zhang |
| 8,993,233 | B2 | 3/2015 | Zhang et al. |
| 9,512,446 | B1 | 12/2016 | Joung et al. |
| 9,549,901 | B2 | 1/2017 | Shi et al. |
| 9,597,357 | B2 | 3/2017 | Gregory et al. |
| 9,623,071 | B2 | 4/2017 | Guo et al. |
| 9,637,739 | B2 | 5/2017 | Siksnys et al. |
| 9,701,964 | B2 | 7/2017 | Clube et al. |
| 9,834,791 | B2 | 12/2017 | Zhang et al. |
| 9,873,894 | B2 | 1/2018 | Conway et al. |
| 10,190,137 | B2 | 1/2019 | Zhang et al. |
| 10,301,651 | B2 | 5/2019 | Doudna et al. |
| 10,494,621 | B2 | 12/2019 | Zhang et al. |
| 10,660,943 | B2 | 5/2020 | Bikard et al. |
| 10,669,557 | B2 | 6/2020 | Guschin et al. |
| 10,781,444 | B2 | 9/2020 | Zhang et al. |
| 10,851,357 | B2 | 12/2020 | Davidson et al. |
| 10,930,367 | B2 | 2/2021 | Zhang et al. |
| 2003/0186238 | A1 | 10/2003 | Allawi et al. |
| 2004/0111221 | A1 | 6/2004 | Beattie et al. |
| 2005/0196851 | A1 | 9/2005 | Uckun |
| 2005/0220796 | A1 | 10/2005 | Dynan et al. |
| 2006/0178297 | A1 | 8/2006 | Troy et al. |
| 2006/0234247 | A1 | 10/2006 | Puttaraju et al. |
| 2007/0016012 | A1 | 1/2007 | Hartlep et al. |
| 2007/0244031 | A1 | 10/2007 | Lu et al. |
| 2008/0293655 | A1 | 11/2008 | Aygun et al. |
| 2010/0055798 | A1 | 3/2010 | Battersby |
| 2010/0076057 | A1 | 3/2010 | Sontheimer et al. |
| 2010/0081707 | A1 | 4/2010 | Ali et al. |
| 2010/0093617 | A1 | 4/2010 | Barrangou et al. |
| 2010/0233084 | A1 | 9/2010 | Narasimhaswamy et al. |
| 2011/0016540 | A1 | 1/2011 | Weinstein et al. |
| 2011/0059502 | A1 | 3/2011 | Chalasani |
| 2011/0189776 | A1 | 8/2011 | Terns et al. |
| 2011/0223638 | A1 | 9/2011 | Wiedenheft et al. |
| 2011/0239315 | A1 | 9/2011 | Bonas et al. |
| 2012/0029891 | A1 | 2/2012 | Behlke et al. |
| 2013/0096182 | A1 | 4/2013 | Chatterjee et al. |
| 2013/0130248 | A1 | 5/2013 | Haurwitz et al. |
| 2013/0315831 | A1 | 11/2013 | Shi et al. |
| 2014/0068797 | A1 | 3/2014 | Doudna et al. |
| 2014/0294771 | A1 | 10/2014 | Schaffer et al. |
| 2014/0295557 | A1 | 10/2014 | Joung et al. |
| 2014/0315985 | A1 | 10/2014 | May et al. |
| 2014/0342456 | A1 | 11/2014 | Mali et al. |
| 2014/0356956 | A1 | 12/2014 | Church et al. |
| 2014/0357530 | A1 | 12/2014 | Zhang et al. |
| 2015/0045546 | A1 | 2/2015 | Siksnys et al. |
| 2015/0056705 | A1 † | 2/2015 | Conway |
| 2015/0071899 | A1 | 3/2015 | Liu et al. |
| 2015/0071903 | A1 | 3/2015 | Liu et al. |
| 2015/0071906 | A1 | 3/2015 | Liu et al. |
| 2015/0232881 | A1 | 8/2015 | Glucksmann et al. |
| 2015/0247150 | A1 | 9/2015 | Zhang et al. |
| 2015/0291965 | A1 | 10/2015 | Zhang et al. |
| 2015/0322457 | A1 | 11/2015 | Kim et al. |
| 2015/0353905 | A1 | 12/2015 | Weiss et al. |
| 2016/0017366 | A1 | 1/2016 | Chen et al. |
| 2016/0024510 | A1 | 1/2016 | Bikard et al. |
| 2016/0024524 | A1 | 1/2016 | Joung et al. |
| 2016/0130609 | A1 | 5/2016 | Doudna et al. |
| 2016/0237456 | A1 | 8/2016 | Church et al. |
| 2016/0251648 | A1 | 9/2016 | Wang et al. |
| 2016/0281072 | A1 | 9/2016 | Zhang |
| 2016/0298135 | A1 | 10/2016 | Chen et al. |
| 2016/0298137 | A1 | 10/2016 | Chen et al. |
| 2016/0324938 | A1 | 11/2016 | Bikard et al. |
| 2016/0340662 | A1 | 11/2016 | Zhang et al. |
| 2017/0175144 | A1 | 6/2017 | Zhang et al. |
| 2017/0191082 | A1 | 7/2017 | Chen et al. |
| 2017/0327806 | A1 | 11/2017 | Joung et al. |
| 2018/0127783 | A1 | 5/2018 | Zhang et al. |
| 2018/0230495 | A1 | 8/2018 | Doudna et al. |
| 2019/0010471 | A1 | 1/2019 | Zhang et al. |
| 2020/0282026 | A1 | 9/2020 | Bikard et al. |
| 2020/0282027 | A1 | 9/2020 | Bikard et al. |
| 2021/0060140 | A1 | 3/2021 | Bikard et al. |
| 2021/0060141 | A1 | 3/2021 | Bikard et al. |

FOREIGN PATENT DOCUMENTS

| | | | |
|---|---|---|---|
| CN | 103343120 | | 10/2013 |
| CN | 103388006 | | 11/2013 |
| CN | 103668472 | | 3/2014 |
| CN | 104520429 | A | 4/2015 |
| CN | 104854241 | A | 8/2015 |
| CN | 107532161 | A | 1/2018 |
| EP | 2 591 770 | A2 | 5/2013 |
| EP | 2 784 162 | | 1/2014 |
| EP | 2 764 103 | | 8/2014 |
| EP | 2 771 468 | | 9/2014 |
| EP | 2 828 386 | A1 | 1/2015 |
| FR | 2872170 | A1 | 12/2005 |
| IN | 49/2015 | | 12/2015 |
| JP | 2004-519245 | A | 7/2004 |
| JP | 2004-537285 | A | 12/2004 |
| JP | 2005-509409 | A | 4/2005 |
| JP | 2006-513694 | A | 4/2006 |
| JP | 2006-518996 | A | 8/2006 |
| JP | 2007-501626 | A | 2/2007 |
| JP | 2009-502170 | A | 1/2009 |
| JP | 2009-536827 | A | 10/2009 |
| JP | 2010-507680 | A | 3/2010 |
| JP | 2010-522547 | A | 7/2010 |
| JP | 2012-506254 | A | 3/2012 |
| JP | 2012-508235 | | 4/2012 |
| JP | 2012-510812 | A | 5/2012 |
| JP | 2012-511332 | A | 5/2012 |
| JP | 2012-523234 | A | 10/2012 |
| JP | 2012-529287 | A | 11/2012 |
| JP | 2013-500045 | A | 1/2013 |
| JP | 2013-513389 | A | 4/2013 |
| JP | 2013-518602 | A | 5/2013 |
| JP | 2013-544077 | A | 12/2013 |
| JP | 2014-526279 | A | 10/2014 |
| JP | 2015-523856 | A | 8/2015 |
| JP | 2016-500003 | A | 1/2016 |
| JP | 2016-500262 | | 1/2016 |
| JP | 2016-501531 | | 1/2016 |
| JP | 2016-501532 | A | 1/2016 |
| JP | 2016-025710 | A | 2/2016 |
| JP | 2016-502840 | A | 2/2016 |
| JP | 2016-504026 | A | 2/2016 |
| JP | 2016-505256 | A | 2/2016 |
| JP | 2016-093196 | | 5/2016 |
| JP | 2016-516169 | A | 6/2016 |
| JP | 2016-517954 | A | 6/2016 |
| JP | 2016-131404 | A | 7/2016 |
| JP | 2016-520317 | A | 7/2016 |
| JP | 2016-521554 | A | 7/2016 |
| JP | 2016-521975 | A | 7/2016 |
| JP | 2016-521995 | | 7/2016 |
| JP | 2016-523082 | A | 8/2016 |
| JP | 2016-524472 | | 8/2016 |
| JP | 2016-182140 | A | 10/2016 |
| JP | 2017-501151 | A | 1/2017 |
| JP | 2017-501699 | | 1/2017 |
| JP | 6395765 | | 9/2018 |
| RU | 2009136452 | A | 4/2011 |
| WO | WO-02/074968 | A1 | 9/2002 |
| WO | WO-02/080851 | A2 | 10/2002 |
| WO | WO-03/014318 | A2 | 2/2003 |
| WO | WO-03/104414 | A2 | 12/2003 |
| WO | WO-2004/029219 | A2 | 4/2004 |
| WO | WO-2004/046321 | A2 | 6/2004 |
| WO | WO-2004/062618 | A2 | 7/2004 |
| WO | WO-2005/014791 | | 2/2005 |
| WO | WO-2005/049642 | A2 | 6/2005 |
| WO | WO-2007/014275 | A2 | 2/2007 |
| WO | WO-2007/134161 | A2 | 11/2007 |
| WO | WO-2008/093152 | A1 | 8/2008 |
| WO | WO-2008/108989 | | 9/2008 |
| WO | WO-2008/116860 | A2 | 10/2008 |

(56) References Cited

FOREIGN PATENT DOCUMENTS

| | | | |
|---|---|---|---|
| WO | WO-2008/147438 | A2 | 12/2008 |
| WO | WO-2010/048228 | A2 | 4/2010 |
| WO | WO-2010/054108 | | 5/2010 |
| WO | WO-2010/065123 | A1 | 6/2010 |
| WO | WO-2010/068816 | A1 | 6/2010 |
| WO | WO-2010/075424 | A2 | 7/2010 |
| WO | WO-2010/079430 | A1 | 7/2010 |
| WO | WO-2010/118077 | A1 | 10/2010 |
| WO | WO-2010/143917 | | 12/2010 |
| WO | WO-2011/011767 | A1 | 1/2011 |
| WO | WO-2011/016840 | A2 | 2/2011 |
| WO | WO-2011/036510 | A1 | 3/2011 |
| WO | WO-2011/064736 | A1 | 6/2011 |
| WO | WO-2011/072246 | A2 | 6/2011 |
| WO | WO-2011/076873 | A1 | 6/2011 |
| WO | WO-2011/100058 | | 8/2011 |
| WO | WO-2011/146121 | A1 | 11/2011 |
| WO | WO-2012/012738 | A1 | 1/2012 |
| WO | WO-2012/031205 | | 3/2012 |
| WO | WO-2012/051343 | A1 | 4/2012 |
| WO | WO-2012/149470 | A1 | 11/2012 |
| WO | WO-2012/164565 | A1 | 12/2012 |
| WO | WO-2013/044008 | A2 | 3/2013 |
| WO | WO-2013/052681 | | 4/2013 |
| WO | WO-2013/5052681 | A1 | 4/2013 |
| WO | WO-2013/071440 | A1 | 5/2013 |
| WO | WO-2013/078400 | A1 | 5/2013 |
| WO | WO-2013/082519 | A2 | 6/2013 |
| WO | WO-2013/098244 | | 7/2013 |
| WO | WO-2013/130824 | A1 | 9/2013 |
| WO | WO-2013/141680 | A1 | 9/2013 |
| WO | WO-2013/142578 | A1 | 9/2013 |
| WO | WO-2013/155572 | | 10/2013 |
| WO | 2013176772 | A1 † | 11/2013 |
| WO | WO-2013/176772 | A1 | 11/2013 |
| WO | WO-2014/165349 | A1 | 3/2014 |
| WO | WO-2014/065596 | A1 | 5/2014 |
| WO | WO-2014/089290 | A1 | 6/2014 |
| WO | WO-2014/093479 | | 6/2014 |
| WO | WO-2014/093595 | | 6/2014 |
| WO | WO-2014/093622 | A2 | 6/2014 |
| WO | WO-2014/093635 | A1 | 6/2014 |
| WO | WO-2014/093655 | | 6/2014 |
| WO | WO-2014/093661 | | 6/2014 |
| WO | WO-2014/093694 | A1 | 6/2014 |
| WO | WO-2014/093701 | A1 | 6/2014 |
| WO | WO-2014/093709 | | 6/2014 |
| WO | WO-2014/093712 | A1 | 6/2014 |
| WO | WO-2014/093718 | | 6/2014 |
| WO | WO-2014/099744 | | 6/2014 |
| WO | WO-2014/099750 | A2 | 6/2014 |
| WO | 2014113493 | A1 † | 7/2014 |
| WO | WO-2015/031775 | | 8/2014 |
| WO | WO-2014/144761 | A2 | 9/2014 |
| WO | WO-2014/165825 | A2 | 10/2014 |
| WO | WO-2014/186585 | A2 | 11/2014 |
| WO | WO-2014/191518 | A1 | 12/2014 |
| WO | WO-2014/197568 | A2 | 12/2014 |
| WO | WO-2014/197748 | A2 | 12/2014 |
| WO | WO-2014/204724 | A1 | 12/2014 |
| WO | WO-2014/204725 | | 12/2014 |
| WO | WO-2014/204726 | A1 | 12/2014 |
| WO | WO-2014/204727 | A1 | 12/2014 |
| WO | WO-2014/204728 | | 12/2014 |
| WO | WO-2014/204729 | | 12/2014 |
| WO | WO-2015/006747 | A2 | 1/2015 |
| WO | WO-2015/035136 | A2 | 3/2015 |
| WO | WO-2015/048577 | | 4/2015 |
| WO | WO-2015/048690 | | 4/2015 |
| WO | WO-2015/065964 | A1 | 5/2015 |
| WO | WO-2015/070083 | A1 | 5/2015 |
| WO | WO-2015/071474 | A2 | 5/2015 |
| WO | WO-2015/089351 | A1 | 6/2015 |
| WO | WO-2015/089364 | | 6/2015 |
| WO | WO-2015/089419 | A2 | 6/2015 |
| WO | WO-2015/089427 | A1 | 6/2015 |
| WO | WO-2015/113063 | A1 | 7/2015 |
| WO | WO-2016/022866 | A1 | 2/2016 |
| WO | WO-2016/073955 | A2 | 5/2016 |
| WO | WO-2016/141224 | A1 | 9/2016 |

OTHER PUBLICATIONS

David et al. Pharmacological Research 62:100-114, 2010 (Year: 2010).*

Gjetting et al. (International Journal of Nanomedicine 5:371-383, 2010) (Year: 2010).*

Decision on Motions—PTAB, *The Regents of the University of California* v. *The Broad Institute, Inc*., filed Sep. 10, 2020, in Patent Interference No. 106,115 (DK), 113 pages.

Hirano et al., "Structure and Engineering of Francisella novicida Cas9," Cell, vol. 164, Feb. 25, 2016, pp. 950-961.

Ran, F.A., "CRISPR-Cas: Development and Applications for Mammalian Genome Editing", Ph.D. Dissertation, Harvard University, Apr. 2014.

Redeclaration—PTAB, *The Regents of the University of California* v. *The Broad Institute, Inc*., filed Aug. 26, 2019, in Patent Interference No. 106,115 (DK), 20 pages.

Redeclaration—PTAB, *The Regents of the University of California* v. *The Broad Institute, Inc*., filed Sep. 10, 2020, in Patent Interference No. 106,115 (DK), 3 pages.

Yamada et al., "Crystal Structure of the Minimal Cas9 from Campylobacter jejuni Reveals the Molecular Diversity in the CRISPR-Cas9 Systems," Molecular Cell, vol. 65, Mar. 16, 2017, pp. 1109-1121.

U.S. Appl. No. 14/054,414, filed Oct. 15, 2013.
U.S. Appl. No. 14/104,837, filed Dec. 12, 2013.
U.S. Appl. No. 14/104,900, filed Dec. 12, 2013.
U.S. Appl. No. 14/104,977, filed Dec. 12, 2013.
U.S. Appl. No. 14/104,990, filed Dec. 12, 2013.
U.S. Appl. No. 14/105,017, filed Dec. 12, 2013.
U.S. Appl. No. 14/105,031, filed Dec. 12, 2013.
U.S. Appl. No. 14/105,035, filed Dec. 12, 2013.
U.S. Appl. No. 14/183,429, filed Feb. 18, 2014.
U.S. Appl. No. 14/183,471, filed Feb. 18, 2014.
U.S. Appl. No. 14/183,486, filed Feb. 18, 2014.
U.S. Appl. No. 14/183,512, filed Feb. 18, 2014.
U.S. Appl. No. 14/222,930, filed Mar. 24, 2014.
U.S. Appl. No. 14/226,274, filed Mar. 26, 2014.
U.S. Appl. No. 14/256,912, filed Apr. 18, 2014.
U.S. Appl. No. 14/258,458, filed Apr. 22, 2014.
U.S. Appl. No. 14/25,9420, filed Apr. 23, 2014.
U.S. Appl. No. 14/290,575, filed May, 29, 2014.
U.S. Appl. No. 14/293,498, filed Jun. 2, 2014.
U.S. Appl. No. 14/293,674, filed Jun. 2, 2014.
U.S. Appl. No. 14/324,960, filed Jul. 7, 2014.
U.S. Appl. No. 14/463,253, filed Aug. 19, 2014.
U.S. Appl. No. 14/481,339, filed Sep. 9, 2014.
U.S. Appl. No. 14/497,627, filed Sep. 26, 2014.
U.S. Appl. No. 14/523,799, filed Oct. 24, 2014.
U.S. Appl. No. 14/681,382, filed Apr. 8, 2015.
U.S. Appl. No. 14/703,511, filed May 4, 2015.
U.S. Appl. No. 14/704,551, filed May 5, 2015.
U.S. Appl. No. 14/738,398, filed Jun. 12, 2015.
U.S. Appl. No. 14/738,483, filed Jun. 12, 2015.
U.S. Appl. No. 14/970,967, filed Dec. 16, 2015.
U.S. Appl. No. 14/971,169, filed Dec. 16, 2015.
U.S. Appl. No. 14/971,356, filed Dec. 16, 2015.
U.S. Appl. No. 14/972,523, filed Dec. 17, 2015.
U.S. Appl. No. 14/972,927, filed Dec. 17, 2015.
U.S. Appl. No. 14/973,062, filed Dec. 17, 2015.
U.S. Appl. No. 14/990,444, filed Jan. 7, 2016.
U.S. Appl. No. 14/991,083, filed Jan. 8, 2016.
U.S. Appl. No. 15/160,710, filed May 20, 2016.
U.S. Appl. No. 15/217,489, filed Jul. 22, 2016.
U.S. Appl. No. 15/229,702, filed Aug. 5, 2016.
U.S. Appl. No. 15/230,025, filed Aug. 5, 2016.

(56) References Cited

OTHER PUBLICATIONS

U.S. Appl. No. 15/230,161, filed Aug, 5, 2016.
U.S. Appl. No. 15/330,876, filed Nov. 7, 2016.
U.S. Appl. No. 15/349,603, filed Nov. 11, 2016.
U.S. Appl. No. 15/430,260, filed Dec. 10, 2017.
U.S. Appl. No. 15/834,736, filed Dec. 7, 2017.
U.S. Appl. No. 15/838,064, filed Dec. 11, 2017.
U.S. Appl. No. 15/887,377, filed Feb. 2, 2018.
U.S. Appl. No. 15/967,464, filed Apr. 30, 2018.
U.S. Appl. No. 15/967,495, filed Apr. 30, 2018.
U.S. Appl. No. 15/967,510, filed Apr. 30, 2018.
U.S. Appl. No. 16/012,692, filed Jun. 19, 2018.
U.S. Appl. No. 16/177,403, filed Oct. 31, 2018.
U.S. Appl. No. 16/178,551, filed Nov. 1, 2018.
U.S. Appl. No. 16/445,150, filed Jun. 18, 2019.
U.S. Appl. No. 16/445,156, filed Jun. 18, 2019.
U.S. Appl. No. 16/525,531, filed Jul. 29, 2019.
U.S. Appl. No. 16/532,442, filed Aug. 5, 2019.
U.S. Appl. No. 16/535,043, filed Aug. 7, 2019.
U.S. Appl. No. 16/844,548, filed Apr. 9, 2020.
U.S. Appl. No. 16/906,580, filed Jun. 19, 2020.
U.S. Appl. No. 16/938,110, filed Jul. 24, 2020.
U.S. Appl. No. 17/027,151, filed Sep. 21, 2020.
U.S. Appl. No. 17/034,754, filed Sep. 28, 2020.
U.S. Appl. No. 17/182,817, filed Feb. 23, 2021.
U.S. Appl. No. 17/201,347, filed Mar. 15, 2021.
U.S. Appl. No. 17/245,952, filed Apr. 30, 2021.
U.S. Appl. No. 17/321,872, filed May 17, 2021.
Jinek et al., "RNA-programmed genome editing in human cells", eLife, vol. 2, 2013, DOI: 10.7554/eLife.00471 (9 pages).
Stoddard, "Homing endonuclease structure and function," Quarterly Reviews of Biophysics, Cambridge University Press, 2005 (pp. 1-47).
Voytas, Daniel F., "Plant genome engineering with sequence-specific nucleases," Annual Review of Plant Biology May 1, 2013, vol. 64 (pp. 327-350).
Wiles et al., "CRISPR-Cas9-medicated genome editing and guide RNA Design," Mammalian Genome, May 20, 2015, vol. 26, No. 9 (10 pages).
Workman et al., "A natural single-guide RNA repurposes Cas9 to autoregulate CRISPR-Cas expression," Cell Press, vol. 184, Feb. 4, 2021 (pp. 675-688).
Declaration of Interference—*PTAB, The Broad Institute, Inc., Massachusetts Institute of Technology, and President and Fellows of Harvard College* v. *Toolgen, Inc.*, filed Dec. 14, 2020, in Patent Interference No. 106,126 (DK), 19 pages.
"Crispr Genome Engineering Resources" XP055167591, Oct. 5, 2013, https://web.archive.org/web/2013100500 [retrieved on Feb. 5, 2015].
"Fixes, extra genomes, and improvements to the CRISPR Design Tool" Google Groups, XP055167583, Oct. 21, 2013, URL:https://groups.google.com/forum/#!topic/crispr/g9Q8U1tNSis [retrieved on Feb. 5, 2015].
"The CRISPR Revolution," Catalyst Magazine, College of Chemistry, University of California, Berkeley, http://catalyst.berkeley.edu/slideshow/the-crispr-revolution/[Dec. 19, 2014 12:40:53] (Jul. 9, 2014).
A. Amsterdam et al., "Identification of 315 genes essential for early zebrafish development," proc Natl Acad Sci., vol. 101, Aug. 31, 2004, pp. 12792-12797, 6 pages.
A. Fire et al., "Potent and specific genetic interference by double-stranded RNA in Caenorhabditis elegans," Nature, vol. 391, Feb. 19, 1998, pp. 806-811, 6 pages.
A. Subramanian et al., "Gene set enrichment analysis: a knowledge-based approach for interpreting genome-wide expression profiles," Proc Natl Acad Sci., vol. 102, Oct. 25, 2005, pp. 15545-15550, 6 pages.
A.C. Spradling et al., "The Berkeley *Drosophila* Genome Project Gene Disruption Project: Single P-Element Insertions Mutating 25% of Vital *Drosophila* Genes," Genetics, vol. 153, Sep. 1999, pp. 135-177, 43 pages.
A.H. Tong et al., "Global mapping of the yeast genetic interaction network," Science, vol. 303, Feb. 6, 2004, pp. 808-813, 6 pages.
A.L. Lin and D.H Gutmann, "Advances in the treatment of neurofibromatosis-associated tumours," Nature, vol. 10, Nov. 2013, pp. 616-624, 9 pages.
A.P. Blanchard and L. Hood, "Sequence to array: probing the genome's secrets," Nat Biotechnol, vol. 14, Dec. 14, 1996, p. 1649.
Abudayyeh, et al., "C2c2 is a single-component programmable RNA-guided RNA-targeting CRISPR effector," Science, vol. 10, Jun. 2, 2016, pp. 1-16, 18 pages.
Addgene Materials, "CRISPR/cas Plasmids and Resources", downloaded from https://www.addgene.org/crispr/, May 6, 2015, 3 pages.
Addgene Materials, "Engineering with Addgene's Help", Addgene Newsletter, Mar. 2013, downloaded from https://archive.constantcontact.com/fs126/1103481513180/archive/1112756362265.html, Oct. 14, 2014, 4 pages.
Addgene Reagent distribution list for Zhang Lab with Plasmid Name, date unknown (prior to May 10, 2015), 2 pages.
Addgene, "gRNA_Cloning Vector", retrieved on Jan. 30, 2019, <https://www/addgenen.org/41824/> 2 pages.
Al-Attar, et al., "Clustered regularly interspaced short palindromic repeats (CRISPRs): the hallmark of an ingenious antiviral defense mechanism in prokaryotes" Biol Chem., vol. 392, No. 4, Apr. 2011, pp. 277-289, 13 pages.
Alberts, et al., "Intracellular Compartments and Protein Sorting," Garland Science, 4 ed., 2002, pp. 671-676, 8 pages.
Allen, et al., "Liposomal drug delivery systems: From concept to clinical applications" Advanced Drug Delivery Reviews, vol. 65, 2013, pp. 36-48, 13 pages.
Andreas, et al., "Enhanced efficiency through nuclear localization signal fusion on phage C31-integrase: activity comparison with Cre and FLPe recombinase in mammalian cells", Nucleic Acids Research, Apr. 15, 2002, vol. 30, No. 11, pp. 2299-2306, 8 pages.
*Arbitron, Inc.* v. *Kiefl*, No. 09-CV-04013 PAC, 2010 WL 3239414, at *1 (S.D.N.Y. Aug. 13, 2010), 7 pages.
Asuri, P., et al., "Directed Evolution of Adeno-Associated Virus for Enhanced Gene Delivery and Gene Targeting in Human Pluripotent Stem Cells," Molecular Therapy, vol. 30, 2012, No. pages 329-338, 10 pages.
Au, et al., "Characterization of a baculovirus nuclear localization signal domain in the late express factor 3 protein", Virology, vol. 385, 2009, pp. 209-217.
Ausubel, et al. "Compendium of Methods from Current Protocols in Molecular Biology", Short Protocols in Molecular Biology, 4 ed., 1999, 9-0, 9-4, 5 pages.
Autofluorescence MIT Flow Cytometry Core Facility (2018), 6 pages.
B. Langmead et al., "Ultrafast and memory-efficient alignment of short DNA sequences to the human genome," Genome biology, vol. 10, Mar. 4, 2009, 10 pages.
B.Langmead and S.L. Salzberg, "Fast gapped-read alignment with Bowtie 2," Nat Meth, vol. 9, 2012, pp. 357-359, 3 pages.
B.Scappini et al., "Changes associated with the development of resistance to imatinib (STI571) in two leukemia cell lines expressing p210 Bcr/Abl protein," Cancer, vol. 100, Apr. 1, 2004, pp. 1459-1471, 13 pages.
B.Sonnichsen et al., "Full-genome RNAi profiling of early embryogenesis in Caenorhabditis elegans," Nature, vol. 434, Mar. 24, 2005, pp. 462-469, 8 pages.
Bae, T. and Schneewind, O. "Allelic replacement in *Staphylococcus aureus* with inducible counter-selection," Plasmid, vol. 55, 2006, pp. 58-63, 6 pages.
Baena-Lopez, L., et al., "Accelerated homologous recombination and subsequent genome modification in *Drosophila*," Development, vol. 140, 2013, pp. 4818-4835, including Supplementary Material, 8 pages.
Baiker, et al. "The Immediate-Early 63 Protein of Varicella-Zoster Virus: Analysis of Functional Domains Required for Replication In

(56) References Cited

OTHER PUBLICATIONS

Vitro and for T-Cell and Skin Tropism in the SCIDhu Model In Vivo", Journal of Virology, 2004, vol. 78 pp. 1181-1194, 14 pages.
Baker, M., "Gene editing at CRISPR Speed," Nature Biotechnology, vol. 32, 2014, pp. 309-312, 4 pages.
Balboa, et al., "Conditionally Stabilized dCas9 Activator for Controlling Gene Expression in Human Cell Reprogramming and Differentiation. (plus Supplemental Information)", Stem Cell Reports, vol. 5, Sep. 8, 2015, pp. 448-459, 12 pages.
Banaszewska, A., et al., "Proprotein Convertase Subtilisin/Kexin Type 9: A New Target Molecule For Gene Therapy," Cellular & Molecular Biology Letters, vol. 17, 2012, pp. 228-239, 12 pages.
Barrangou and Van Der Oost (Eds.), "CRISPR-Cas Systems," Springer Heidelberg, 2013, pp. i-299.
Barrangou, R et al., "CRISPR provides acquired resistance against viruses in prokaryotes," Science, vol. 315, Mar. 23, 2007, pp. 1709-1712, 6 pages.
Barrangou, R., "RNA-mediated programmable DNA cleavage," Nature Biotechnology, vol. 30, 2012, pp. 836-388, 13 pages.
Bassett, et al. "Highly Efficient Targeted Mutagenesis of *Drosophila* with the CRISPR/Cas9 System" Cell Reports, vol. 4, Jul. 11, 2013, p. 220.
Bassett, et al., "A Genome-Wide CRISPR Library for High-Throughput Genetic Screening in *Drosophila* Cells," Journal of Genetics and Genomics, vol. 42, Apr. 18, 2015, pp. 301-309, 9 pages.
Bauer, et al., "An Erythroid Enhancer of BCL11A Subject to Genetic Variation Determines Fetal Hemoglobin Level," Science, vol. 342, Oct. 11, 2013, pp. 253-257, 4 pages.
Beerli, et al. "Positive and negative regulation of endogenous genes by designed transcription factors" PNAS, vol. 97, Feb. 15, 2000, pp. 1495-1500.
Beerli, et al., "Toward controlling gene expression at will: Specific regulation of the erbB-2/HER-2 promoter by using polydactyl zinc finger proteins constructed from modular building blocks", Proc. Natl. Acad. Sci., vol. 95, Oct. 7, 1998, pp. 14628-14633.
Beerli, R., et al., "Engineering polydactyl zinc-finger transcription factors," Nature Biotechnology, vol. 20, Feb. 2002, pp. 135-141.
Bennett, et al., "Stable transgene expression in rod photoreceptors after recombinant adeno-associated virus-mediated gene transfer to monkey retina", Proc. Natl. Acad. Sci., vol. 96, Aug. 1999, pp. 9920-9925.
Bergemann, et al., Excision of specific DNA-sequences from integrated retroviral vectors via site-specific recombination:, Nucleic Acids Res., vol. 23, Oct. 2, 1995, pp. 4451-4456.
Berns, K., et al., "A Large-Scale RNAi Screen in Human Cells Identifies New Components of the p53 Pathway," Nature, vol. 428, Mar. 25, 2004, pp. 431-437.
Bhaya, D., et al., "CRISPR-Cas Systems in Bacteria and Archaea: Versatile Small RNAs for Adaptive Defense and Regulation," Annual Review of Genetics, vol. 45, 2011, pp. 273-297.
Bikard, et al. "CRISPR Interference Can Prevent Natural Transformation and Virulence Acquisition During in Vivo Bacterial Infection," Cell Host & Microbe, vol. 12, 2012, pp. 177-186.
Bikard, et al., Supplementary Information for: "CRISPR Interference Can Prevent Natural Transformation and Virulence Acquisition During in Vivo Bacterial Infection," Cell Host & Microbe, vol. 12, 2012, pp. 177-186.
Birch, et al., "Plant Transformation: Problems and Strategies for Practical Application", Annu. Rev. Plant Physiol. Plant Mol. Biol., vol. 48, 1997, pp. 297-326.
Bloom, et al., "Inactivation of hepatitis B virus replication in cultured cells and in vivo with engineered transcription activator-like effector nucleases", Molecular Therapy, vol. 21, Oct. 2013, pp. 1889-1897.
Bobis-Wozowicz, S., et al., "Targeted genome editing in pluripotent stem cells using zinc-finger nucleases," Methods, vol. 53, 2012, pp. 339-346.
Boch, et al., "Breaking the Code of DNA Binding Specificity of TAL-Type III Effectors". Science, vol. 326, 2009, pp. 1509-1512.
Boch, et al., "Xanthomonas AvrBs3 Family-Type III Effectors: Discovery and Function", Annu. Rev. Phytopathol, vol. 48, 2010, pp. 419-436.
Boden, et al., "Efficient Gene Transfer of HIV-1-Specific Short Hairpin RNA into Human Lymphocytic Cells Using Recombinant Adeno-associated Virus Vectors", Molecular Therapy, vol. 9, 2004, pp. 396-402.
Bogdanove, et al., "TAL Effectors: Customizable Proteins for DNA Targeting", Science, vol. 333, 2011, pp. 1843-1846.
Bohm et al., "The computer program LUDI: A new method for the de novo design of enzyme inhibitors", Journal of Computer-Aided Molecular Design, vol. 6, 1992, pp. 61-78.
Botta, S. et al., "Transcriptional Repression with Zinc-Finger and Tale Protein Scaffold", Molecular Therapy, 2013, Supplement 1, p. S208, Abstract No. 539.
Bouard, et al., "Themed Section: Vector Design and Drug Delivery Review, Viral vectors: from virology to transgene expression", British Journal of Pharmacology, vol. 157, 2009, pp. 153-165.
Boutros, et al., "Genome-wide RNAi analysis of growth and viability in *Drosophila* cells," Science, American Association for the Advancement of Science, vol. 303, Feb. 6, 2004, pp. 832-835.
Branden, C., and Tooze, J., "Prediction, Engineering, and Design of Protein Structures: Introduction to Protein Structure," Garland Publishing, Inc., Chapter 16, 1991, p. 247.
Briner, et al., "Guide RNA Functional Modules Direct Cas9 Activity and Orthogonality", Molecular Cell, vol. 56, 2014, pp. 333-339.
Brouns, S., "A Swiss Army Knife of Immunity," Science, vol. 337, 2012, pp. 808-809.
Brouns, S., et al., "Small CRISPR RNAs Guide Antiviral Defense in Prokaryotes," Science, vol. 321, Aug. 15, 2008, pp. 960-964.
Brummelkamp TR et al., "A system for stable expression of short interfering RNAs in mammalian cells," Science, vol. 296, Apr. 19, 2002, pp. 550-553.
C. Cayrol et al., "The THAP-zinc finger protein THAP1 regulates endothelial cell proliferation through modulation of pRB/E2F cell-cycle target genes," Blood, vol. 109, 2007, pp. 584-594.
C. Trapnell et al., "Differential gene and transcript expression analysis of RNA-seq experiments with TopHat and Cufflinks," Nature protocols, vol. 7, 2012, p. 562.
C. Trapnell et al., "TopHat: discovering splice junctions with RNA-Seq.," Bioinformatics, vol. 25, 2009, pp. 1105-1111.
C.J, Echeverri et al., "Minimizing the risk of reporting false positives in large-scale RNAi screens," Nature methods, vol. 3, Oct. 2006, p. 777.
C.M Johannessen et al., "COT drives resistance to RAF inhibition through MAP kinase pathway reactivation," Nature, vol. 468, Dec. 16, 2010, p. 968.
C.M. Johnston et al., "Large-scale population study of human cell lines indicate that dosage compensation is virtually complete," PLoS Genet., vol. 4, Jan. 2008, pp. 88-98, 11 pages.
Campeau, et al., "A Versatile Viral System for Expression and Depletion of Proteins in Mammalian Cells", PLoS One, vol. 4, 2009, pp. 1-17.
Canver, et al., "BCL11A enhancer dissection by Cas9-mediated in situ saturating mutagenesis," Nature, vol. 527, 2015, pp. 192-197, including Supplementary Material.
Carr, et al., "Genome engineering", Nature Biotechnology, vol. 27, 2009, pp. 1151-1162.
Carroll, D., "A CRISPR Approach to Gene Targeting," Molecular Therapy, vol. 20, 2012, pp. 1658-1660.
Carroll., "Genome Engineering With Zing-Finger Nucleases", Genetics, vol. 188, 2011, pp. 773-782.
Carroll., "Progress and prospects: Zinc-finger nucleases as gene therapy agents", Gene Therapy, vol. 15, 2008, pp. 1463-1468.
Carte, J., et al., "Cas6 is an endoribonuclease that generates guide RNAs for invader defense in prokaryotes," Genes Dev., vol. 22, 2008, pp. 3489-3496.
Cermak, T., et al., "Efficient design and assembly of custom TALEN and other TAL Effector-Based Constructs For DNA Targeting", Nucleic Acids Research, vol. 39, 2011, pp. 1-11.

(56) References Cited

OTHER PUBLICATIONS

Chadderton, N., et al., "Improved Retinal Function in a Mouse Model of Dominant Retinitis Pigmentosa Following AAV-delivered Gene Therapy", Molecular Therapy, vol. 17, Apr. 2009, pp. 593-599.
Chan, et al. "Characterization of the Kinetochore Binding Domain of CENP-E Reveals Interactions with the Kinetochore Proteins CENP-F and hBuBR1", The Journal of Cell Biology, vol. 143, 1998, pp. 49-63.
Chan, Wai-Ting, et al., "Toxin-Antitoxin Genes of the Gram-Positive Pathogen *Streptococcus pneumoniae*: So Few and Yet So Many", Microbiology and Molecular Biology Reviews, vol. 76, 2012, pp. 773-791.
Chang, N., et al. "Genome editing with RNA-guided Cas9 nuclease in Zebrafish embryos", Cell Research, vol. 23, 2013, pp. 465-472.
Chen, B., et al., "Dynamic Imaging of Genomic Loci in Living Human Cells by an Optimized CRISPR/Cas System," Cell, vol. 155, 2013, pp. 1479-1491.
Chen, Fuqiang, et al., "High-frequency genome editing using ssDNA oligonucleotides with zinc-finger nucleases". Nature Methods, 2011, vol. 8, pp. 753-755, including Supplemental Online Methods.
Chen, Jieliang, et al., "An Efficient Antiviral Strategy for Targeting Hepatitis B Virus Genome Using Transcription Activator-Like Effector Nucelases", Molecular Therapy, vol. 22, 2014, pp. 303-311.
Chen, S., et al., "Genome-wide CRISPR Screen in a Mouse Model of Tumor Growth and Metastasis", Cell, vol. 160, 2015, pp. 1-15, http://dx.doi.org/10.1016/j.cell.2015.02.038.
Chevalier et al., "Homing endonuclease: structural and functional insight into the catalysts of intron/intein mobility," Oxford University Press., vol. 29, 2001, pp. 3757-3774.
Chinnasamy, D., et al., "Multicistronic lentiviral vectors containing the FMCV 2A Cleavage factor demonstrate robust expression of encoded genes at limiting MOI," Virology Journal, vol. 3, 2006, pp. 1-16.
Chiu, et al., "Engineered GFP as a vital reporter in plants", Current Biology, vol. 6, 1996, pp. 325-330.
Cho, A., et al., "Generation of Transgenic Mice," Current Protocols in Cell Biology, Chapter Unit 19.11, 2009, pp. 1-29.
Cho, Minseon, et al., "Quantitative selection and parallel characterization of aptamers," PNAS, vol. 110, Nov. 12, 2013, pp. 18460-18465.
Cho, Seung Woo, et al. "Analysis off-target effects of CRISPR/Cas-derived RNA-guided endonucleases and nickases" Genome Research, vol. 24, 2014, pp. 132-141.
Cho, Seung Woo, et al., "Targeted genome engineering in human cells with the Cas9 RNA-guided endonuclease," Nature Biotechnology, vol. 31 pp. 230-232, including Supplementary Information, 14 pages.
Chou, JY, and Mansfield, BC., "Recombinant AAV-directed gene therapy for type I glycogen storage diseases," Expert Opinion on Biological Therapy, vol. 11, Aug. 2011, pp. 1011-1024.
Choulika, et al., "Transfer of Single Gene-Containing Long Terminal Repeats into the Genome of Mammalian Cells by a Retroviral Vector Carrying the cre Gene and the IoxP site", Journal of Virology, vol. 70, 1996, pp. 1792-1798.
Christian, et al., "Supporting Information-Targeting DNA Double-Strand Breaks With TAL Effector Nucleases", Genetics, 2010, pp. 1-8, DOI: 10.1534/110.120717:1SI-8SI.
Christian, et al., "Targeting DNA Double-Strand Breaks With TAL Effector Nucleases", Genetics, vol. 186, 2010, pp. 757-761.
Chylinski, et al., "Classification and evolution of type II CRISPR-Cas systems", Nucleic Acids Research, vol. 42, 2014, pp. 6091-6105, doi:10.1093Inarlgku241.
Chylinski, K., et al., "The tracrRNA and Cas9 Families of Type II CRISPR-Cas Immunity Systems," RNA Biology, vol. 10, 2013, pp. 726-737.
Clark, K., et al., "A TALE of Two Nucleases: Gene Targeting for the Masses?" Zebrafish, vol. 8, No. 3, 2011, pp. 147-149.
Cockrell, "Berkeley's Wikipedian-in-residence is a first," NewsCenter, Feb. 25, 2014, downloaded from https://newscenter.berkeley.edu/2014/02/25/berkeleys-wikipedian-in-residence-is-a-first/, May 8, 2015, 3 pages.
Community Corner, "CRISPR technology for gene therapy," Nature Medicine, vol. 20, May 2014, pp. 476-477.
Cong, et al., Oct. 5, 2012 Manuscript including Supplementary Materials, "CRISPR-Assisted Mammalian Genome Engineering," published as "Multiplex Genome Engineering Using CRISPR-Cas Systems," Science, vol. 339, 2013, pp. 819-823.
Cong, L., et al., "Comprehensive interrogation of natural TALE DNA-binding modules and transcriptional repressor domains," Nature Communications, vol. 3, Jul. 24, 2012, pp. 968-973.
Cong, L., et al., "In Vivo Genome Engineering With AAV Vector Carrying CRISPR-Cas9 System," Molecular Therapy, vol. 22, May 2014, Supplement 1, p. S214.
Cong, L., et al., "Multiplex Genome Engineering Using CRISPR-Cas Systems," Science, vol. 339, 2013, pp. 819-823.
Cong, L., et al., Supplementary Material for: "Multiplex Genome Engineering Using CRISPR-Cas Systems," Science Express, Jul. 5, 2012, pp. 1-26.
Connor, S., "Scientific split—the human genome breakthrough dividing former colleagues," The Independent, http://www.independent.co.uk/news/science/scientific-split--the-human-genome-breakthrough-dividing-former-colleagues-9300456.html, dated Apr. 25, 2014, 5 pages.
Costantino, et al., "Enhanced levels of alpha Red-mediated recombinants in mismatch repair mutants", PNAS, vol. 100, 2003, pp. 15748-15753.
Cotropia, et al., "Copying in Patent Law," N.C.L. Rev., Stanford Public Law Working Paper No. 1270160, 2009, pp. 1-46.
Cummings et al., "Fourteen and counting: unraveling trinucleotide repeat diseases", Human Molecular Genetics, vol. 9, 2000, pp. 909-916.
D.J.Burgess et al., "Topoisomerase levels determine chemotherapy response in vitro and in vivo," Proceedings of the National Academy of Sciences, vol. 105, Jul. 1, 2008, pp. 9053-9058.
Daboussi, F., et al., "Chromosomal context and epigenetic mechanisms control the efficacy of genome editing by rare-cutting designer endonucleases," Nucleic Acids Research, vol. 40, 2012, pp. 6367-6379.
Dahlman, J., et al., "In vivo endothelial siRNA delivery using polymeric nanoparticles with low molecular weight," Nature Nanotechnology, vol. 9, 2014, pp. 648-655.
Dai, et al. "Genes:Structures and Regulation: The Transcription Factors GATA4 and dHAND Physically Interact to Synergistically Activate Cardiac Gene Expression through a p300-dependent Mechanism", J. Biol. Chem., vol. 277, 2002 pp. 24390-24398.
Daley, J., and Wilson, T., "Rejoining of DNA Double-Strand Breaks as a Function of Overhang Length," Molecular and Cellular Biology, vol. 25, 2005, pp. 896-906.
Damian, M., and Porteus, M., "A Crisper Look at Genome Editing: RNA-guided Genome Modification," Molecular Therapy, vol. 21, Apr. 2013, pp. 720-722abs.
Database GenBank, "*Staphylococcus aureus* subsp.aureus ORFX gene and pseudo SCCmec-SCC- SCCCRISPR element, strain M06/0171," Accession No. HE980450, http://www.ncbi.nlm.nih.gov/nuccore/HE980450, dated Aug. 18, 2016, 22 pages.
Database GenBank: "CRISPR-associated protein, Csn1 family, *Staphylococcus pseudintermedius* ED99," Accession No. ADX75954, http://www.uniprot.org/uniprot/G1UFN3.txt?version=3, dated Nov. 21, 2011, 1 page.
Database UniProt: "CRISPR-associated endonuclease Cas9: *Staphylococcus aureus*," UniProtKB, J7RUA5 (CAS9_STAAU), XP002738511M, https://www.uniprot.org/uniprot/J7RUA5#, dated Oct. 31, 2012, 7 pages.
Database UniProtKB/TrEMBL [online], Accession No. Q0P897, "The genome sequence of the food-borne pathogen Campylobacter jejuni reveals hypervariable sequences," Subname: Full=Putative CRISPR-associated protein, Oct. 3, 2012 uploaded, [retrieved on Nov. 22, 2017], URL, http://www.uniprot.org/uniprot/Q0P897.txt?version=28.

(56) References Cited

OTHER PUBLICATIONS

Database UniProtKB/TrEMBL, Accession No. D0W2Z9, http://www.uniprot.org/uniprot/D0W2Z9.txt?version=4, dated Oct. 3, 2012, 1 page.
Database UniProtKB/TrEMBL, Accession No. G1UFN3, http://www.uniprot.org/uniprot/G1UFN3.txt?version=3, dated Oct. 3, 2012, 1 page.
Database UniProtKB/TrEMBL, Accession No. J3TRJ9, http://www.uniprot.org/uniprot/J3TRJ9.txt?version=2, dated Oct. 31, 2012, 1 page.
Database UniProtKB/TrEMBL, Accession No. Q6NK13, http://www.uniprot.org/uniprot/Q6NKI3.txt?version=43, dated Jun. 13, 2012, 1 page.
Database UniProtKB/TrEMBL, Accession No. Q73QW6, http://www.uniprot.org/uniprot/Q73QW6.txt?version=4, dated Nov. 28, 2012, 2 pages.
Database WPI, Week 201437 Thomson Scientific, London, GB; An 2014-J79552, XP-002737563, 2 pages.
Datsenko, et al. "Molecular memory of prior infections activates the CRISPR/Cas adaptive bacterial immunity system", Nature Communications, vol. 3, 2012, pp. 1-7.
Dean., "Recent Advances in Drug Design Methods: Where Will They Lead?", BioEssays, vol. 16, Sep. 1994, pp. 683-687.
Declaration of Feng Zhang for US Appl. U.S. Appl. No. 14/054,414 dated Jan. 30, 2014 (10 pages).
Declaration of Technical Expert Paul Simons dated Dec. 22, 2015, 76 pages.
Deltcheva, E., et al., "CRISPR RNA maturation by trans-encoded small RNA and host Factor RNase III," Nature, vol. 471, 2011, pp. 602-609.
Deltcheva, et al., "Supplementary Information: CRISPR RNA Maturation By Trans-Encoded Small RNA and Host Factor RNase III" Nature, pp. 1-35.
Deveau, H. et al., "Phage response to CRISPR-encoded resistance in *Streptococcus thermophilus*," Journal of Bacteriology, vol. 190, Feb. 2008, pp. 1390-1400.
Deveau, H., et al., "CRISPR/Cas system and its role in phage-bacteria interactions," Annu. Rev. Microbiol., vol. 64, 2010, pp. 475-493.
Dicarlo, et al., "Genome engineering in *Saccharomyces cerevisiae* using CRISPTR-Cas systems", Nucleic Acids Research, vol. 41, 2013 pp. 4336-4343.
Dingwall, et al. "A Polypeptide Domain That Specifies Migration of Nucleoplasmin into The Nucleus", Cell, vol. 30, 1982, pp. 449-458, (Abstract only).
Dingwall, et al., "The Nucleoplasmin Nuclear Location Sequence is Larger and More Complex than That of SV-40 Large T Antigen", The Journal of Cell Biology, vol. 107, 1988, pp. 841-849.
Do, et al., "Identification of multiple nuclear localization signals in murine Elf3, an ETS transcription factor" FEBS Letters, vol. 580, 2006, pp. 1865-1871.
Doench, et al., "Rational design of highly active sgRNAs for CRISPR-Cas9-mediated gene inactivation," Nature Biotechnology, vol. 32, 2014, pp. 1262-1267, including Supplementary Material, 17 pages.
Dominguez, et al., "Beyond editing: repurposing CRISPR-Cas 9 for precision genome regulation and interrogation" Nat Rev Mol Cell Biol., vol. 17, 2016, 17 pp. 5-15.
Dong, et al., "The crystal structure of Cpf1 in complex with CRISPR RNA," Nature, vol. 532, 2016, pp. 523-525.
Drittanti, et al. "High throughput production, screening and anyalysis of adeno-associated viral vectors", Gene Therapy, vol. 7, 2000, pp. 924-929.
Dworetzky, S., et al., "The Effects of Variations in the No. and Sequence of Targeting Signals on Nuclear Uptake," The Journal of Cell Biology, vol. 107, 1988, pp. 1279-1287.
E.S. Lander, "Initial impact of the sequencing of the human genome," Nature, vol. 470, Feb. 10, 2011, p. 187-197.
Ebina, H., et al., "Harnessing the CRISPR/Cas9 system to disrupt latent HIV-1 provirus," Scientific Reports, vol. 3, 2013, pp. 1-7, art. 2510.
Edgar, R. and Qimron, U., "The *Escherichia coli* CRISPR system protects from λ lysogenization, lysogens, and prophage induction," Journal of Bacteriology, vol. 192, Dec. 2010, pp. 6291-6294.
Ellis, B., et al., "Zinc-finger nuclease-mediated gene correction using single AAV vector transduction and enhanced by Food and Drug Administration-Approved Drugs, " Gene Therapy, vol. 20, 2013, pp. 35-42.
Ellis, et al., "Macromolecular Crowding: Obvious But Underappreciated", TRENDS in Biochemical Sciences, vol. 26, 2001, pp. 597-604.
Ellis, Hilary, et al., "High efficiency mutagenesis, repair, and engineering of chromosomal DNA using single-stranded oligonucleotids" PNAS, vol. 98, 2001, pp. 6742-6746.
Enyeart, et al., "Biotechnological applications of mobile group II introns and their reverse transcriptases: gene targeting, RNA-seq, and non-coding RNA analysis", Mobile DNA, vol. 5, 2014, pp. 1-19 http://www.mobilednajournal.com/contents5/1/2.
Espinoza, et al., "Characterization of the structure, function, and mechanism of B2 RNA, an ncRNA repressor of RNA polymerase II transcription", RNA, vol. 13, 2007, pp. 583-596.
Esvelt et. al., "Orthogonal Cas9 proteins for RNA-guided gene regulation and editing", Nature Methods, vol. 10, No. 11, Nov. 2013 (available online Sep. 29, 2013), pp. 1116-1123.
Excerpt from Dr. Feng Zhang's Jan. 30, 2014 Declaration (Exhibit C1), 11 pages.
Federal Circuit decision in *Dow Chemical Co.* v. *Nova Chemicals Corp.*, Appeal Nos. 2014-1431, 2014-1462 (Fed. Cir. Aug. 28, 2015) (*Dow* v. *Nova*), 25 pages.
Feldgarden et al., "*Staphylococcus aureus* M0408 acrHk-supercont1.1, whole genome shotgun sequence", NCBI Reference Sequence: NK_KB821326.1, Direct Submission, Dec. 10, 2012, pp. 1-4.
Fieck, et al., "Modifications of the *E.coli* Lac repressor for expression in eukaryotic cells: effects of nuclear signal sequences on protein activity and nuclear accumulation", Nucleic Acids Research, vol. 20, 1992, pp. 1785-1791.
Fischer, S. et al., "An archaeal immune system can detect multiple Protospacer Adjacent Motifs (PAMs) to target invader DNA," J. Biol. Chem., vol. 287, Sep. 28, 2012, pp. 33351-33363.
Fischer-Fantuzzi, L., and Vesco, C., "Cell-dependent efficiency of reiterated nuclear signals in a mutant simian virus 40 oncoprotein targeted to the nucleus," Molecular and Cellular Biology, vol. 8, 1988, pp. 5495-5503.
Flannery, J. G., "Ribozyme-Mediated Gene Therapy for Autosomal Dominant Retinal Degeneration", Retinal Degenerative Diseases and Experimental Therapy, 1999, pp. 277-291.
Fleming, J., et al., "Adeno-Associated Virus and Lentivirus Vectors Mediate Efficient and Sustained Transduction of Cultured Mouse and Human Dorsal Root Ganglia Sensory Neurons," Human Gene Therapy, vol. 12, Jan. 1, 2001, pp. 77-86.
Foecking, et al. "Powerful and versatile enhance-promoter unit for mammalian expression vectors", Gene, vol. 45, 1986, pp. 101-105.
Fonfara et al., "Phylogeny of Cas9 determines functional exchangeability of dual-RNA and Cas9 among orthologous type II CRISPR-Cas systems", Nucleic Acids Research, 2014, vol. 42, No. 4, pp. 2577-2590.
Freitas, et al., "Mechanisms and Signals for the Nuclear Import of Proteins", Current Genomics, vol. 10, 2009, pp. 550-557.
Fu, et al., "High-frequency off-target mutagenesis induced by CRISPR-Cas nucleases in human cells", Nature Biotechnology, vol. 31, 2013, pp. 822-826.
Fu, et al., "Targeted genome editing in human cells using CRISPR/Cas nucleases and truncated guide RNAs", The Use of CRISPR/Cas9 ZFNs and Talens in Generating Site-Specific Genome Alterations; Elsivier Inc., 2014, pp. 21-45.
G. Giaever et al., "Functional profiling of the *Saccharomyces cerevisiae* genome," Nature, vol. 418, Jul. 25, 2002, pp. 387-391.
G. Guo et al., "Mismatch repair genes identified using genetic screens in Blm-deficient embryonic stem cells," Nature, vol. 429, Jun. 24, 2004, p. 891.

(56) References Cited

OTHER PUBLICATIONS

Gabriel, R., et al., "An unbiased genome-wide analysis of zinc-finger nuclease specificity," Nature Biotechnology, vol. 29, 2011, pp. 816-823.
Gaj, T., et al., "Targeted Gene knockout by direct delivery of zinc-finger nuclease proteins," Nature Methods, vol. 9, 2012, pp. 805-807, including supplemental pages.
Gaj, T., et al., "ZFN, TALEN, and CRISPR/Cas-Based Methods for Genome Engineering," Trends in Biotechnology, vol. 31, 2013, pp. 397-405.
Gama Sosa, M., et al., "Animal transgenesis: an overview," Brain Structure and Function, vol. 214,0 2010, pp. 91-109.
Gao, et al. "Engineered Cpf1 variants with altered PAM specificities", Nature Biotechnology, vol. 35, Jun. 8, 2017, pp. 1-4 (789-792), doi: 10.1038/nbt.3900, advanced online publication including Supplementary Information.
Gao, et al., "A Sustained, Cytoplasmic Transgene Expression System delivered by Cationic Liposomes", Biochemical and Biophysical Research Communications, vol. 200, May 16, 1994, pp. 1201-1206.
Garcia-Bustos, et al., "Nuclear protein localization", Biochimica et Biophysica Acta, vol. 1071, 1991, pp. 83-101.
Gardlik, R., et al., "Vectors and delivery systems in gene therapy," Medical Science Monitor, vol. 11, No. 4, pp. RA110-121, dated Apr. 1, 2005, 12 pages.
Garg, et al. "Engineering synthetic TAL effectors with orthogonal target sites", Nucleic Acids Research, 2012, vol. 40, pp. 7584-7595, doi: 10.1093/nar/gks404.
Garneau, et al., "The CRISPR-Cas bacterial immune systems cleaves bacteriophage and plasmid DNA", Nature, vol. 468, 2010, pp. 67-71.
Garriga-Canut, M., et al., "Synthetic zinc finger repressors reduce mutant huntingtin expression in the brain of R6/2 mice," Proceedings of the National Academy of Sciences, vol. 109, Oct. 10, 2012, pp. E3136-E3145.
Gasiunas, G, et al., "Cas9-crRNA ribonucleoprotein complex mediates specific DNA cleavage for adaptive immunity in bacteria," Proceedings of the National Academy of Sciences, vol. 109, 2012, pp. E2579-2586.
Geibler, et al., "Transcriptional Activators of Human Genes with Programmable DNA-Specificity", PLone, vol. 6, 2011, pp. 1-7 Doi: 10.1371/hournal.pone.0019509.
Geisinger, et al., "In vivo blunt-end cloning through CRISPR /CAS9-facilitated non-homologous end-joining", Nucleic Acid Research Advance Access, vol. 44, 2016, pp. 1-15.
GenBank: "CRISPR-associated protein Cas9/Csn1 [*Staphylococcus aureus* subsp. aureus]", GenBank: CCK74173.1, Year: 2012, http://www.ncbi.nlm.nih.gov/protein/403411236?sat=16&satkey=13804560, dated Dec. 14, 2016, 2 pages.
Gibson, D.G. et al., "Enzymatic assembly of DNA molecules up to several hundred kilobases," Nat methods, vol. 6, 2009, pp. 343-345.
Gilbert, L., et al., "CRISPR-Mediated Modular RNA-Guided Regulation of Transcription in Eukaryotes," Cell, vol. 154, 2013, pp. 442-451.
Goldfarb, et al. "Synthetic peptides as nuclear localization signals", Nature, vol. 322, 1986, pp. 641-644.
Gomaa, et al. "Programmable removal of bacterial strains by use of genome-targeting CRISPR-Cas systems", MBio., vol. 5, 2014, pp. 1-9.
Goncalves, M., et al., "Concerted nicking of donor and chromosomal acceptor DNA promotes homology-directed gene targeting in Human Cells," Nucleic Acids Research, vol. 40, 2012, pp. 3443-3455.
Gratz, et al., "Genome Engineering of *Drosophila* with the CRISPR RNA-Guided Cas9 Nuclease", Genetics, vol. 194, 2013, pp. 1029-1035.
Greenspan, et al., "Two Nuclear Location Signals in the Influenza Virus NS1 Nonstructural Protein", Journal of Virology, vol. 62, 1988, pp. 3020-3026.
Greenwald, D L, et al., "Engineered Zinc Finger Nuclease-Mediated Homologous Recombination of the Human Rhodopsin Gene", Investigative Ophthalmology & Visual Science, vol. 51, Dec. 2010, pp. 6374-6380.
Grens, "Enzyme Improves CRISPR A smaller Cas9 protein enables in vivo genome engineering via viral vectors", The Scientist, Apr. 1, 2015.
Grieger, J., and Samulski, R., "Packaging Capacity of Adeno-Associated Virus Serotypes: Impact of Larger Genomes on Infectivity and Postentry Steps," Journal of Virology, vol. 79, 2005, pp. 9933-9944.
Grissa, I., et al., "CRISPRFinder: a web tool to identify clustered regularly interspaced short palindromic repeats," Nucleic Acids Research, vol. 35, 2007, pp. W52-W57.
Grosse, et al. "Meganuclease-medicated Inhibition of HSV1 Infection in Cultured Cells", Molecular Therapy, vol. 19, No. 4, Apr. 1, 2011, pp. 694-702.
Guan, et al., "Heritable endogenous gene regulation in plants with designed polydactyl zinc finger transcription factors", PNAS, vol. 99, 2002, pp. 13296-13301.
Gudbergsdottir, S. et al., "Dynamic properties of the Sulfolobus CRISPR/Cas and CRISPR/Cmr systems when challenged with vector-borne viral and plasmid genes and protospacers," Mol. Microbiology, vol. 79, 2011, pp. 35-49.
Gustafsson, et al. "Codon Bias and heterologous protein expression", Trends in Biotechnology, Jul. 2004, vol. 22, pp. 346-353.
H. Davies et al., "Mutations of the BRAF gene in human cancer," Nature, vol. 417, Jun. 27, 2002, pp. 949-954.
H.W Cheung et al., "Systematic investigation of genetic vulnerabilities across cancer cell lines reveals lineage-specific dependencies in ovarian cancer," Proceedings of the National Academy of Sciences, vol. 108, Jul. 26, 2011, p. 12372-12377.
Habib, N., Assignment to Broad Institute, dated Jun. 9, 2014, 4 pages.
Haft, D., et al., "A Guild of 45 CRISPR-Associated (Cas) Protein Families and Multiple CRISPR/Cas Subtypes Exist in Prokaryotic Genomes," PLoS Computational Biology, vol. 1, 2005, pp. 0474-0483.
Haft, D.H., "Hmm Summary Page: TIGR04330", 2012, XP-002757584, http://jcvi.org/cgi-bin/tigrfams/HmmReportPage.cgi?acc=TIGR04330, 1 page.
Hale, et al. "Essential Features and Rational Design of CRISPR RNAs that Function With The Cas RAMP Module Complex to Cleave RNAs", Molecular Cell, vol. 45, 2012, pp. 292-302.
Hale, et al. "RNA-Guided RNA Cleavage by a CRISPR RNA-Cas Protein Complex", Cell, vol. 139, 2009, pp. 945-956.
Hale, et al., "Prokaryotic siliencing (psi) RNAs in Pyrococcus furiosus", RNA, vol. 14, 2008, pp. 2572-2579.
Hall, B., et al., "Overview: Generation of Gene Knockout Mice," Current Protocols in Cell Biology, unit 19.12, suppl. 44, Sep. 2009, pp. 1-17.
Handel, E., et al., "Versatile and Efficient Genome Editing in Human Cells by Combining Zinc-Finger Nucleases With Adeno-Associated Viral-Vectors," Human Gene Therapy, vol. 23, 2012, pp. 321-329.
Harrison, et al., "A Crispr view of development", Genes & Development, vol. 28, 2014, pp. 1859-1872.
Hatoum-Aslan, A., et al., "Mature clustered, regularly interspaced, short palindromic repeats RNA (crRNA) length is measured by a ruler mechanism anchored at the precursor processing site," Proc. Natl. Acad. Sci., vol. 108, Dec. 27, 2011, pp. 21218-21222.
Haurwitz, R.E., et al., "Sequence- and structure-specific RNA processing by a CRISPR endonuclease," Science, vol. 329, 2010, pp. 1355-1358.
Havarstein, L.S., et al., "An unmodified heptadecapeptide pheromone induces competence for genetic transformation in *Streptococcus pneumoniae*, " Proc. Natl. Acad. Sci., vol. 92, Nov. 1995, pp. 11140-11144.
Heintze, et al. "A CRISPR CASe for high-throughput silencing", Frontiers in Genetics, vol. 4, 2013, pp. 1-6 DOI:10.3389/gfene.2013.00193.

(56) References Cited

OTHER PUBLICATIONS

Hemann et al., "An epi-allelic series of p53 hypomorphs created by stable RNAi produces distinct tumor phenotypes in vivo," Nat Genetics, vol. 33, Mar. 2003, pp. 396-400.
Hibbitt, O., et al., "RNAi-mediated knockdown of HMG CoA reductase enhances gene expression from physiologically regulated low-density lipoprotein receptor therapeutic vectors in vivo," Gene Therapy, vol. 19, 2012, pp. 463-467.
Hicks, et al. "Protein Import Into the Nucleus: An Integrated View", Annu. Rev. Cell Dev. Biology, vol. 11, 1995, pp. 155-188.
Ho, et al., "Targeting non-coding RNAs with the CRISPR/Cas9 system in human cell lines," Nucleic Acids Research, vol. 43, 2015, pp. 1-11.
Hockemeyer, et al., "Highly efficient gene targeting of expressed and silent genes in human ESCs and iPSCs using zinc finger nucleases", Nat Biotechnology, vol. 27, 2009, pp. 851-857, doi:10.1038/nbt.1562.
Holkers, M., et al., "Adenoviral vector DNA for accurate genome editing with engineered nucleases," Nature Methods, vol. 11, 2014, pp. 1051-1057, (Only Abstract Available).
Holmes, "CRISPR Genome Engineering Resources" XP055167586, Oct. 2, 2013, https://groups.google/forum/#!top1c/crispr/5BpJj_Y3yIG [retrieved on Feb. 5, 2015].
Holmes, "Understanding Scores" XP055167918, Oct. 23, 2013, https://groups.google.com/forum/#!profo_nt50txrP9Yb6e_LXcco1b9hNf7gKeMLt6rgaVQ4fOsQ/crispr/fkhX7Fu3r-l/rziHxKT76pYJ [retrieved on Feb. 6, 2015].
Horinouchi, S. and Weisblum, B., "Nucleotide sequence and functional map of pC194, a plasmid that specifies inducible chloramphenicol resistance," J. Bacteriology, vol. 150, May 1982, pp. 815-825.
Horton, R.M., "In Vitro recombination and Mutagenesis of DNA: SOEing Together Tailor-Made Genes," Methods Mol. Biology, vol. 15, 1993, pp. 251-261.
Horvath, P. and Barrangou, R. "CRISPR/Cas, the immune system of bacteria and archaea," Science, vol. 327, Jan. 8, 2010, pp. 167-170.
Horvath, P., and Barrangou, R., "RNA-guided genome editing a la carte," Cell Research, vol. 23, 2013, pp. 733-734.
Hosaka, T. et al., "The novel mutation K87E in ribosomal protein S12 enhances protein synthesis activity during the late growth phase in *Escherichia coli*." Mol. Gen. Genomics, vol. 271, 2004, pp. 317-324.
Hoskins, J. et al., "Genome of the bacterium *Streptococcus pneumoniae* strain R6," Journal of Bacteriology, vol. 183, Oct. 2001, pp. 5709-5717.
Hou, Z., et al., "Efficient genome engineering in human pluripotent stem cells using Cas9 from Neisseria meningitides," Proceedings of the National Academy of Sciences, vol. 110, 2013, pp. 15644-15649.
Houdebine, L., "The methods to generate transgenic animals and to control transgene expression," Journal of Biotechnology, vol. 98, 2002, pp. 145-160.
Hsu et al., "Supplementary Information-DNA targeting specificity of RNA-guided Cas9 nucleases," Nature Biotechnology, 2013, doi:10.1038/nbt.2647.
Hsu, et al., "DNA targeting specificity of RNA-guided Cas9 nucleases," Nature Biotechnology, vol. 31, 2013, pp. 827-834.
Hsu, P., et al., "Development and Applications of CRISPR-Cas9 for Genome Engineering," Cell, vol. 157, 2014, pp. 1262-1278.
*Huang* v. *California Institute of Technology*, 2004 WL 2296330 (C.D. Cal. Feb. 18, 2004), 20 pages.
Hung, S., et al., "AAV-Mediated CRISPR/Cas Gene Editing of Retinal Cells in Vivo," Investigative Ophthalmology & Visual Science, vol. 57, 2016, pp. 3470-3476.
Husmann, L.K., et al., "Expression of the Arp protein, a member of the M protein family, is not sufficient to inhibit phagocytosis of *Streptococcus pyogenes*," Infection and immunity, vol. 63, Jan. 1995, pp. 345-348.
Hwang W., et al., "Efficient In Vivo Genome Editing Using RNA-Guided Nucleases," Nature Biotechnology, vol. 31, No. 3, Mar. 2013, pp. 227-229 (12 pages).
Hwang, W.Y., et al., "Efficient Genome Editing in Zebrafish Using a CRISPR-Cas System", Nature Biotechnology, vol. 31, No. 3, Jan. 29, 2013, pp. 227-229.
Imagawa, et al., "Two nuclear localization signals are required for nuclear translocation of nuclear factor 1-A", Febs Letters, vol. 484, 2000, pp. 118-124.
Incontro, S., et al., "Efficient, Complete Deletion of Synaptic Proteins using CRISPR," Neuron, vol. 83, 2014, pp. 1051-1057, 13 pages.
Ishino Y. et al., "Nucleotide sequence of the iap gene, responsible for alkaline phosphatase isozyme conversion in *Escherichia coli*, and identification of the gene product," J. Bacteriology, vol. 169, Dec. 1987, pp. 5429-5433, 5 pages.
Iwamoto et al., "A General Chemical Method to Regulate Protein Stability in the Mammalian Central Nervous System", Chemistry and Biology, Current Biology, vol. 17, Sep. 24, 2010, pp. 981-988, 8 pages.
J. Merkin et al., "Evolutionary dynamics of gene and isoform regulation in Mammalian tissues," Science, vol. 338, Dec. 21, 2012, pp. 1593-1599, 7 pages. Includes Supplementary Information, 34 pages.
J.E. Carette et al., "Haploid genetic screens in human cells identify host factors used by pathogens," Science, vol. 326, Nov. 27, 2009, pp. 1231-1235, 5 pages.
J.F. Rual et al., "Toward Improving Caenorhabditis elegans Phenome Mapping with an ORFeome-Based RNAi Library," Genome Research, vol. 14, 2004, pp. 2162-2168, 7 pages.
J.M. Engreitz et al., "The Xist IncRNA exploits three-dimensional genome architecture to spread across the X chromosome," Science, vol. 341, Aug. 16, 2013, pp. 1-8, 8 pages.
Jackson, A., et al., "Widespread siRNA "off-target" transcript silencing mediated by seed region sequence complementarity," RNA vol. 12, 2006, pp. 1179-1187, 10 pages.
Jansen R. et al., "Identification of genes that are associated with DNA repeats in prokaryotes," Molecular Microbiology, vol. 43, 2002, pp. 1565-1575, 11 pages.
Janssen, et al., "Mouse Models of K-ras-Initiated Carcinogenesis", Biochimicia et Biophysica Acta, vol. 1756 2005, pp. 145-154, 10 pages.
Jao, et al., "Efficient multiplex biallelic zebrafish genome editing using a CRISPR nuclease system", Proceeding of the National Academy of Sciences, PNAS 2013, pp. 1-6, includes supplementary information, pp. 1-10. www.pnas.org/cgi/doi/10.1073/pnas.1308335110.
Jiang, W., et al., "RNA-guided editing of bacterial genomes using CRISPR-Cas systems," Nature Biotechnology, vol. 31, Mar. 2013, pp. 233-239, 30 pages, including supplementary information.
Jinek, M., et al., "A Programmable Dual-RNA-Guided DNA Endonuclease in Adaptive Bacterial Immunity," Science, vol. 337, 2012, pp. 816-821, 6 pages, including supplementary information, 38 pages.
Jinek, M., et al., "RNA-programmed genome editing in human cells", eLIFE, vol. 2, No. e00471, 2013, 9 pages.
Jinek, M., et al., Figures and figure supplements for: "RNA-programmed genome editing in human cells," eLIFE, vol. 2, 2013, 5 pages.
JL. Mummery-Widmer et al., "Genome-wide analysis of Notch signalling in *Drosophila* by transgenic RNAi," Nature, vol. 458, Apr. 23, 2009, pp. 987-992, 6 pages. Includes Supplementary information, 2 pages.
Joseph, T., and Osman, R., "Thermodynamic basis of selectivity in guide-target-mismatched RNA interference," Proteins, vol. 80, 2012, pp. 1283-1298, 26 pages.
Joshi, et al., "Evolution of I-Scel homing endonucleases with increased DNA recognition site specificity", Journal of Molecular Biology, 2011, vol. 405, pp. 185-200, 16 pages. Includes supplementary information, 14 pages.
Joung, et al., "TALENS: a widely applicable technology for targeted genome editing", Nat Ref. Mol. Cell Biology, vol. 14, 2013, pp. 49-55, 7 pages. doi:10.1038/nrm3586.
K. Yoshimoto et al., "Complex DNA repair pathways as possible therapeutic targets to overcome temozolomide resistance in glioblastoma," Front Oncology, vol. 2, Dec. 2012, pp. 1-8, 8 pages.

(56) References Cited

OTHER PUBLICATIONS

K.T Flaherty et al., "Inhibition of mutated, activated BRAF in metastatic melanoma," The New England Journal of Medicine, vol. 363, Aug. 26, 2010, pp. 1-22, 22 pages.
Kalderon, et al., "A Short Amino Acid Sequence Able to Specify Nuclear Location", Cell, vol. 39, 1984, pp. 499-509, 11 pages.
Kanasty, R., et al., "Delivery materials for siRNA therapeutics," Nature Materials, vol. 12, 2013, pp. 967-977, 11 pages.
Karvelis, et al., "crRNA and tracrRNA guide Cas9-mediated DNA interference in *Streptococcus thermophiles*" RNA Biology, vol. 10, 2013, pp. 841-851, 11 pages.
Karvelis, et al., "Supplemental Material to: crRNA and tracrRNA guide Cas9-mediated DNA interference in *Streptococcus thermophiles*", Landes Bioscience, vol. 10, 2013, pp. 1-8, 9 pages. http://dx.doi.org/10.4161/rna.24203.
Kiani, et al., "CAS9 gRNA engineering for genome editing, activation and repression", Nature Methods, Advanced Online Publication, 2015, pp. 1-6. DOI: 10.1038/NMETH.3580.
Kim et al., "High Cleavage Efficiency of a 2A Peptide Derived from Porcine Teschovirus-1 in Human Cell Lines, Zebrafish and Mice," PLoS One, vol. 6, Apr. 2011, pp. 1-8, 8 pages.
Kim, E., et al., "Precision genome engineering with programmable DNA-nicking enzymes," Genome Research, vol. 22, 2012, pp. 1327-1333, 8 pages.
Kim, et al., "Crystal structure of Cas1 from Archaeoglobus fulgidus and characterization of its nucleolytic activity", Biochemical and Biophysical Research Communications, 2013, vol. 441, 2013, pp. 720-725, 6 pages.
Kim, S., et al., "CRISPER RNAs trigger innate immune responses in human cells," Genome Research, 2018, pp. 1-7, 8 pages.
Kinnevey, P., et al., "Emergence of Sequence Type 779 Methicillin-Resistant *Staphylococcus aureus* Harboring a Novel Pseudo Staphylococcal Cassette Chromosome mec (SCCmec)-SCC-SCC CRISPR Composite Element in Irish Hospitals," Antimicrobial Agents and Chemotherapy, vol. 57, 2013, pp. 524-531, 8 pages. Includes Supplementary information, 9 pages.
Kleinstiver et al., "High-fidelity CRISP-Cas9 nucleases with no detectable genome-wide off-target effects", Nature, vol. 529, Jan. 28, 2016, pp. 490-495, 6 pages. Includes Supplementary information, 12 pages.
Kleinstiver, et al. "Engineered CRISPR-Cas9 nucleases with altered PAM specificities," Nature, vol. 523, vol. 523, 2015, pp. 1-27, 27 pages.
Koike-Yusa, H., et al., "Genome-wide recessive genetic screening in mammalian cells with a lentiviral CRISPR-guide RNA library," Nat Biotechnology, vol. 32, Mar. 2014, pp. 267-273, 7 pages. Including Supplemental information, 3 pages. doi:10.1038/nbt.2800.
Kondo, et al., "Highly Improved Gene Targeting by Germline-Specific Cas9 Expression in *Drosphila*", Genetics, vol. 195, 2013, pp. 715-721, 7 pages. Including Supplemental information 14 pages.
Konermann, et al., "Genome-scale transcriptional activation by an engineered CRISPR-Cas9 complex", Nature, vol. 517, 2015, pp. 583-588, 6 pages. Including Supplemental information, 12 pages.
Koo et al., "Measuring and Reducing Off-Target Activities of Programmable Nucleases Including CRISPR-Cas9", Molecules and Cells, vol. 38, 2015, pp. 475-481, 7 pages.
Koornneef, A., et al., "Apoliprotein B Knockdown By AAV-Delivered shRNA Lowers Plasma Cholesterol In Mice," Molecular Therapy, vol. 19, 2011, pp. 731-740, 10 pages.
Kosugi, et al. "Six Classes of Nuclear Localization Signals Specific to Different Binding Grooves of Importin a . . . " The Journal of Biological Chemistry, 2009, vol. 284 pp. 478-485, 8 pages. Including Supplemental information, 21 pages.
Kowalski, Thomas J., PowerPoint Presentation, Presented and Discussed during Sep. 9, 2015 Interview (Exhibit B), 51 pages.
Krauer, et al. "Identification of the nuclear localization signals within the Epstein-Barr virus EBNA-6 protein", Journal of General Virology, vol. 85, 2005, pp. 165-172, 8 pages.
Kuhlman, et al. "A place for everything—Chromosomal intergration of large constructs", Bioengineered Bugs, vol. 1, 2010, pp. 296-299, 4 pages.
Kuhlman, et al., "Site-specific chromosomal integration of large synthetic constructs", Nucleic Acids Research, 2010, vol. 38, pp. 1-10, 10 pages. doi:10.1093/nar/gkp1193.
Kumar, M., et al., "Systematic Determination of the Packaging Limit of Lentiviral Vectors," Human Gene Therapy, vol. 12, Oct. 10, 2001, pp. 1893-1905, 21 pages.
Kuwayama, H., "Enhancement of Homologous Recombination Efficiency by Homologous Oligonucleotides," Cell 2012, pp. 233-244, 12 pages. IntechOpen, DOI: 10.5772/47779.
Laganiere et al., "An Engineered Zinc Finger Protein Activator of the Endogenous Glial Cell Line-Derived Neurotrophic Factor Gene Provides Functional Neuroprotection in a Rat Model of Parkinson's Disease", The Journal of Neuroscience, vol. 30, Dec. 8, 2010, pp. 16469-16474, 6 pages.
Lambowitz, et al., "Group II Introns: Mobile Ribozymes that Invade DNA", Cold Spring Harb Perspect Biology, 2011, pp. 1-20, 20 pages. 3:a003616.
Lanford, et al., "Induction of Nuclear Transport with a Synthetic Peptide Homologous to the SV40 T Antigen Transport Signal", Cell, vol. 46, Aug. 15, 1986, pp. 575-582, 8 pages.
Lange, et al. "Classical Nuclear Localization Signals: Definition, Function, and Interaction with Importin$2026" J. Biology, vol. 282, 2007, pp. 5101-5105, 5 pages. including Supplemental information, 5 pages.
Larson, et al., "CRISPR interference (CRISPRi) for sequence-specific control of gene expression", Nature Protocols, vol. 8, 2013, pp. 2180-2196, 17 pages.
Lebherz, C., et al., "Gene therapy with novel adeno-associated virus vectors substantially diminished atherosclerosis in a murine model of familial hypercholesterolemia," The Journal of Gene Medicine, vol. 6, 2004, pp. 663-672, 10 pages.
Lee, C., et al., "Correction of the F508 Mutation in the Cystic Fibrosis Transmembrane Conductance Regulator Gene by Zinc-Finger Nuclease Homology-Directed Repair," Bioresearch Open Access, vol. 1, No. 3, pp. 99-108, dated 2012, 12 pages.
Leenay, et al., "Identifying and Visualizing Functional PAM Diversity across CRISPR-Cas Systems", Molecular Cell, vol. 62, 2016, pp. 137-147, 11 pages.
Lemay, et al., "Folding of the Adenine Riboswitch", Chemistry & Biology, vol. 13, 2006, pp. 857-868, 12 pages.
Levitt, J., et al., "Intrinsic fluorescence and redox changes associated with apoptosis of primary human epithelial cells," Journal of Biomedical Optics, vol. 11, No. 6, pp. 064012-1 to 064012-10, dated Nov./Dec. 2006, 10 pages.
Lewin, et al., "Nuclear localization sequences target proteins to the nucleus" Cells, vol. 5, 2006, 224.
Lewis, et al., "The c-myc and PyMT oncogenes induce different tumor types in a somatic mouse model for pancreatic cancer" Genes & Development, 2003, vol. 17 pp. 3127-3138, 14 pages.
Li et al., "Coevolution of CRISPR-Cas system with bacteria and phages", Hereditas, vol. 33, 2011, pp. 213-218, 6 pages.
Li, et al., "In vivo genome editing restores hemostasis in a mouse model of hemophilia" Nature, 2011, vol. 475, pp. 217-221, 5 pages. doi: 10.1038/nature10177.
Li, et al., "Multiplex and homologous recombination-mediated genome editing in *Arabidopsis* and Nicotaina benthamiana using guide RNA and Cas9" Nature Biotechnology, 2013, vol. 31 pp. 688-691, 4 pages.
Li, P., et al., "Biallelic knockout of alpha-1,3 galactosyltransferase gene in porcine liver-derived cells using zing finger nucleases," Journal of Surgical Research, vol. 181, 2013, pp. E39-E45, 7 pages.
Li, Ting, et al. "Modularly assembled designer TAL effector nucleases for targeted gene knockout and gene replacement in eukaryotes" Nucleic Acids Research, vol. 39, 2011, pp. 6315-6325, 11 pages.
Liu, et al. "Epstein-Barr Virus DNase Contains Two Nuclear Localization Signals Which Are Different in Sensitivity to the Hydrophobic Regions" Virology, vol. 247, pp. 62-73, 10 pages.
Lombardo, A., et al., "Gene editing in human stem cells using zinc finger nucleases and integrase-defective lentiviral vector delivery," Nature Biotechnology, vol. 25, 2007, pp. 1298-1306, 9 pages.

(56) References Cited

OTHER PUBLICATIONS

Los, et al., "Halotag Technology: Cell Imaging and Protein Analysis" Cell Notes, vol. 14, 2006, pp. 10-14, 5 pages.
Luo, B., et al., "Highly parallel identification of essential genes in cancer cells," Proceeding of the National Academy of Sciences, vol. 105, 2006, pp. 20380-20385, 6 pages.
Luo, Ming, et al., "Multiple Nuclear Localization Sequences Allow Modulation of 5-Lipoxygenase Nuclear Import" Traffic, 2004, vol. 5, pp. 847-854, 8 pages.
Lyssenko, et al., "Cognate putative nuclear localization signal effects strong nuclear localization of a GFP reporter and facilitates gene expression studies in Caenorhabditis elegans" BioTechniques, 2007, vol. 43 pp. 596-600, 5 pages.
M. Booker et al., "False negative rates in *Drosophila* cell-based RNAi screens: a case study," BMC Genomics, vol. 12, 2011, pp. 1-11, 11 pages.
M. Costanzo et al., "The genetic landscape of a cell," Science, vol. 327, Jan. 22, 2010, pp. 425-431, 8 pages.
Ma, M., et al., "A Guide RNA Sequence Design Platform for the CRISPR/Cas9 System for Model Organism Genomes," Hindawi, vol. 2013, 2013, art. 270805, pp. 1-5, 5 pages.
Maczuga, P., et al., "Embedding siRNA sequences targeting Apolipoprotein B100 in shRNA and miRNA scaffolds results in differential processing and in vivo efficacy," Molecular Therapy, vol. 21, 2013, pp. 217-227, 11 pages.
Madisen et al., "A robust and high-throughput Cre reporting and characterization system for the whole mouse brain," Nat. Neuroscience, vol. 13, Jan. 2010, pp. 133-140, 8 pages.
Maeder, et al., "CRISPR RNA-guided activation of endogenous human genes" Nature Methods, vol. 10, 2013, pp. 977-979, 3 pages. doi.10.1038/nmeth.2556.
Maeder, M., and Gersbach, C., "Genome-editing Technologies for Gene and Cell Therapy," Molecular Therapy, vol. 24, 2016, pp. 430-446, 17 pages.
Maeder, M., et al., "Robust, synergistic regulation of human gene expression using TALE activators," Nature Methods, vol. 10, 2013, pp. 243-245, 3 pages. Including Supplemental information, 6 pages.
Mahfouz, et al., "Targeted transcriptional repression using a chimeric TALE-SRDX repressor protein" Plant Mol Biology, vol. 78, 2012, pp. 311-321, 11 pages.
Mahfouz, M., et al., "De novo-engineered transcription activator-like effector (TALE) hybrid nuclease with novel DNA binding specificity creates double-strand breaks," Proceedings of the National Academy of Science, vol. 108, 2011, pp. 2623-2628, 6 pages.
Makarova, et al., "An updated evolutionary classification of CRISPR-Cas systems" Nature Reviews-Microbiology, vol. 13 2015, pp. 722-736, 15 pages.
Makarova, K., et al., "Evolution and classification of the CRISPR-CAS Systems," Nature Reviews Microbiology, vol. 9, 2011, pp. 467-477, 11 pages. Including Supplemental information, 23 pages.
Makarova, K., et al., "Unification of Cas protein families and a simple scenario for the origin and evolution of CRISPR-Cas systems," Biology Direct, vol. 6, 2011, pp. 1-27, 27 pages.
Mali et al., "CAS9 transcriptional activators for target specificity screening and paired nickases for cooperative genome engineering", Nature Biotechnology, vol. 31, 2013, pp. 833-837, 5 pages.
Mali, et al. "RNA-Guided Human Genome engineering Via Cas9" Science, vol. 339, pp. 823-826, dated Feb. 15, 2013, 41 pages. (Includes Supplemental Information).
Mali, et al., Supplementary Information for "Use of adjacent sgRNA: Cas9 complexes for transcriptional activation and genome engineering," Nature Biotechnology, pp. 1-36, 36 pages. doi:10.1037/nbt.2675.
Mali, P., et al., "CAS9 transcriptional activators for target specificity screening and paired nickases for cooperative genome engineering," Nature Biotechnology, vol. 31, No. 9, pp. 833-838, dated Aug. 1, 2013, 44 pages. (Includes Supplemental Information).
Mali, P., et al., Supplementary Information for: "RNA-Guided Human Genome Engineering via Cas9," Science, vol. 339, pp. 823-826, 2013, 8 pages.
Malina, A., et al., "Repurposing CRISPR/Cas9 for in situ functional assays," Genes & Development, vol. 27, 2013, pp. 2602-2614, 13 pages.
Manjunath, N., et al., "Newer Gene Editing Technologies toward HIV Gene Therapy," Viruses, vol. 5, pp. 2748-2766, 2013, 19 pages.
*Manning* v. *Paradis*, 296 F.3d 1098 (Fed. Cir. 2012), 9 pages.
Marraffini, L., "CRISPR-Cas Immunity against Phages: Its Effects on the Evolution and Survival of Bacterial Pathogens," PLOS, Dec. 12, 2013, pp. 1-6, 6 pages.
Marraffini, L., Assignment to Rockefeller University, dated Dec. 12, 2013, 3 pages.
Marraffini, L., et al., "Self vs. non-self discrimination during CRISPR RNA-directed immunity," Nature, vol. 463, 2010, pp. 568-571, 13 pages.
Marraffini, L.A., et al., "Sortases and the art of anchoring proteins to the envelopes of gram-positive bacteria," Microbiol. Mol. Biology Review vol. 70, Mar. 2006, pp. 192-221, 3 pages.
Martin, M., "Cutadapt removes adapter sequences from high-throughput sequencing reads," EMBnet.journal, vol. 17, 2011, pp. 10-12, 3 pages.
Mastroianni, et al., "Group II Intron-Based Gene Targeting Reactions in Eukaryotes" Plos One, vol. 3, 2008, pp. 1-15, 15 pages. Doi:10.1371/journal.pone.0003121.
*Maxwell* v. *The Stanley Works*, 2006 WL 1967012, *5 (M.D. Tenn. Jul. 11, 2006), 7 pages.
Meshorer, et al., "Chromatin in pluripotent embryonic stem cells and differentiation" Nature Reviews Molecular Cell Biology, vol. 7, 2006, pp. 540-546, 7 pages.
Miller, et al., "A TALE nuclease architecture for efficient genome editing" Nature Biotechnology, vol. 29, 2011, pp. 143-150, 8 pages.
Mincer, J., and Simon, S., "Simulations of nuclear pore transport yield mechanistic insights and quantitative predictions," Proceedings of the National Academy of Science, vol. 108, pp. E351- E358, 8 pages.
Minton, "How can biochemical reactions within cells differ from those in test tubes?" Journal of Cell Science, 2006, vol. 119, pp. 2863-2869, 7 pages.
Moffat J et al., "A lentiviral RNAi library for human and mouse genes applied to an arrayed viral high-content screen," Cell, vol. 124, Mar. 24, 2006, pp. 1283-1298, 16 pages.
Mojica F. J. M et al., "Biological significance of a family of regularly spaced repeats in the genomes of Archaea, Bacteria and mitochondria," Molecular Microbiology, vol. 36, 2000, pp. 244-246, 3 pages.
Mojica, F. J., et al., "Short motif sequences determine the targets of the prokaryotic CRISPR defence system," Microbiology, vol. 155, 2009, pp. 733-740, 8 pages.
Mojica, F. J., et al., Supplementary Material for: "Short motif sequences determine the targets of the prokaryotic CRISPR defence system," Microbiology, vol. 155, 2009, 37 pages.
Morbitzer, et al., "Assembly of custom TALE-type DNA binding domains by modular cloning," Nucleic Acids Research, vol. 39, pp. 5790-5799, 10 pages.
Morbitzer, et al., "Regulation of selected genome loci using de novo-engineered transcription activator-like effector (TALE)-type transcription factors" PNAS, vol. 108, 2010, pp. 21617-21622, 6 pages.
Morgan, et al., "Inducible Expression and Cytogenetic Effects of the EcoRI Restriction Endonuclease in Chinese Hamster Ovary Cells" Molecular and Cellular Biology, vol. 8, 1988, pp. 4204-4211, 8 pages.
Morin, et al., "Nuclear Localization of the Adenovirus DNA-Binding Protein: Requirement for Two Signals and Complementation during Viral Infection" Molecular and Cellular Biology, vol. 9, 1989, pp. 4372-4380, 9 pages.
Morris et al., "Distributed automated docking of flexible ligands to proteins: Parallel applications of AutoDock 2.4*", Journal of Computer-Aided Molecular Design, 1996, vol. 10, pp. 293-304.
Moscou, et al., "A Simple Cipher Governs DNA Regognition by TAL Effectors" Science, vol. 326, 2009, p. 1501.
Motamedi, M.R., et al., "Double-strand-break repair recombination in *Escherichia coli*: physical evidence for a DNA replication mechanism in vivo," Genes Dev., vol. 13, 1999, pp. 2889-2903.

(56) References Cited

OTHER PUBLICATIONS

Mukhopadyay, R., "On the Same Wavelength," ASBMB Today, http://www.asbmb.org/asbmbtoday/201408/Features/Doudna/, dated Aug. 2014, 6 pages.
Mussolino, et al., "TALE nucleases: tailored genome engineering made easy" Current Opinion in Biotechnology, vol. 23, 2012, pp. 644-650, 7 pages.
Musunuru, "Abstract 18593: Use of a CRISPR/Cas System for Cardiovascular Disease Modeling and Therapeutic Applications", Circulation, vol. 128, 2013, 4 pages (Meeting info: American Heart Association, 2013 Scientific Sessions and Resuscitation Science Symposium, Dallas, TX, US, Nov. 16-20, 2013).
Muther, N., et al., "Viral Hybrid Vectors for Somatic Integration—Are They the Better Solution?" Viruses, vol. 1, 2009, pp. 1295-1324, 30 pages.
Nagarajan, et al., "A Hierarchy of Nuclear Localization Signals Governs the Import of the Regulatory Factor X Complex Subunits and MHC Class II Expression" The Journal of Immunology, vol. 173, 2004, pp. 410-419, 11 pages.
Nakai, et al., "PSORT: a program for detecting sorting signals in proteins and predicting their subcellular localization" Trends in Biochem Sciences, vol. 24, 1999, pp. 34-35, 2 pages.
Nakamura, et al., "Codon usage tabulated from international DNA sequence databases: status for the year 2000" Nucleic Acids Research, vol. 28, 2000, p. 292.
Nishimasu, et al., "Crystal Structure of Cas9 in Complex with Guide RNA and Target DNA", Cell, 2014, vol. 156, pp. 935-949, 15 pages.
Nishimasu, H., et al., "Crystal Structure of *Staphylococcus aureus* Cas9," Cell, vol. 162, Aug. 27, 2015, pp. 1113-1126, 15 pages.
Noguchi, et al., "PDX-1 Protein Containing Its Own Antennapedia-Like Protein Transduction Domain Can Transduce Pancreatic Duct and Islet Cells" Diabetes, 2003, vol. 52 pp. 1732-1737, 6 pages.
Nomura, S., et al., "Low-density lipoprotein receptor gene therapy using helper-dependent adenovirus produces long-term protection against atherosclerosis in a mouse model of familial hypercholesterolemia," Gene Therapy, vol. 11, 2004, pp. 1540-1548, 10 pages.
Notice of Opposition filed Aug. 11, 2017 by Schlich against EP Patent No. 2840140, 58 pages.
Notice of Opposition filed Aug. 14, 2017 by Grund against EP Patent No. 2840140, 64 pages.
Notice of Opposition filed Aug. 16, 2017 by Mathys & Squire LLP against EP Patent No. 2840140, 36 pages.
Notice of Opposition filed by Aug. 16, 2017 by Vossius against EP Patent No. 2840140, 67 pages.
O'Hare, et al., "Transformation of mouse fibroblasts to methotrexate resistance by a recombinant plasmid expressing a prokaryotic dihydrofolate reductase" Proc. Natl. Acad. Sci., vol. 78 2011, 1527-1531, 5 pages.
Opposition Against Appl. Ser. No. EP13818570.7 submitted by Schlich dated Oct. 26, 2015, 8 pages.
Opposition Against EP Appl. Ser. No. 2771468-B1 dated Oct. 26, 2015, 40 pages.
Ozawa, K., "Gene therapy using AAV," Virus, vol. 57, pp. 47-55, dated, 2007, 13 pages. (with English Abstract; No English Translation).
Paddison et al., "A resource for large-scale RNA-interference-based screens in mammals," Nature, vol. 428, Mar. 25, 2004, pp. 427-431, 5 pages.
Pandika, et al., www.ozy.com/rising-stars-and-provocateurs/jennifer-doudna-crispr-code-killer/4690; Jan. 7, 2014.
Panyam, J., and Labhasetwar, V., "Biodegradable nanoparticles for drug and gene delivery to cells and tissue," Advanced Drug Delivery Reviews, vol. 55, 2003, pp. 329-347, 19 pages.
Park, et al., "Regulation of Ribosomal S6 Kinase 2 by Mammalian Target of Rapamycin", The Journal of Biological Chemistry, vol. 277, 2002, pp. 31423-31429, 7 pages.
Pattanayak, et al., "High-throughput profiling of off-target DNA cleavage reveals RNA-programmed Cas9 nuclease specificity," Nature Biotechnology, vol. 31, 2013, pp. 839-843, 5 pages. Including Supplementary Materials, 2 pages.
Patterson, et al., "Codon optimization of bacterial luciferase (lux) for expression in mammalian cells" J. Ind. Microbio. Biotechnology, vol. 32, 2005, 115-123, 9 pages.
Perez-Pinera, et al., "Advances in Targeted Genome Editiong" Curr Opin Chem Biology, vol. 16, 2012, pp. 268-277, 10 pages. doi:10.1016/j.cbpa.2012.06.007, 17 pages.
Perez-Pinera, et al., "RNA-guided gene activation by CRISPR-Cas9-based transcription factors" Nature Methods, 2013, vol. 10, pp. 1-12.
Phillips, A., "The challenge of gene therapy and DNA delivery," The Journal of Pharmacy and Pharmacology, vol. 53, 2011, pp. 1169-1174, 6 pages.
Planey, et al. "Mechanisms of Signal Transduction: Inhibition of Glucocorticoid-induced Apoptosis in 697 Pre-B Lymphocytes by the Mineralocorticoid Receptor N-terminal Domain", Journal of Biological Chemistry, vol. 277, 2002, pp. 42188-42196, 9 pages.
Platt, R., et al., "CRISPR-Cas9 Knockin Mice for Genome Editing and Cancer Modeling," Cell, vol. 159, 2014, pp. 440-455, 16 pages.
Podbielski, A., et al., "R. Novel series of plasmid vectors for gene inactivation and expression analysis in group A streptococci (GAS)," Gene, vol. 177, 1996, pp. 137-147, 11 pages.
Porteus, et al., "Gene targeting using zinc finger nucleases" Nature Biotechnology, Aug. 2005, vol. 23 pp. 967-973, 7 pages.
Porteus, M., and Balitmore, D., "Chimeric Nucleases Stimulate Gene Targeting in Human Cells," Science, vol. 300, 2003, p. 763, 2 pages.
Posfai, et al., "Markerless gene replacement in *Escherichia coli* stimulated by a double-strand break in the chromosome" Nucleic Acids Resarch, vol. 27, 1999, pp. 4409-4415, 7 pages.
Pougach, et al., "Transcription, Processing and Function of CRISPR Cassettes in *Escherichia coli*" Mol. Microbiology, vol. 77, 2010, pp. 1367-1379, 14 pages.
Pougach, K.S., et al., "CRISPR Adaptive Immunity Systems of Prokaryotes," Molecular Biology, vol. 46, Apr. 2012, pp. 195-203, 1 page (English Abstract).
Pride, D., et al., "Analysis of Streptococcal CRISPRs from Human Saliva Reveals Substantial Sequence Diversity Within and Between Subjects Over Time," Genome Research, vol. 21, 2011, pp. 126-136, 11 pages.
Primo, et al., "Lentiviral vectors for cutaneous RNA managing" Experimental Dermatology, vol. 21, 2012. 162-170, 9 pages.
Qi, et al., "Repurposing CRISPR as an RNA-Guided Platform for Sequence-Specific Control of Gene Expression" Cell, vol. 152, 2013, pp. 1173-1183, 11 pages.
Qi, J., et al., "microRNAs regulate human embryonic stem cell division," Cell Cycle, vol. 8, 2009, pp. 3729-3741, 13 pages.
R. Rad et al., "PiggyBac transposon mutagenesis: a tool for cancer gene discovery in mice," Science, vol. 330, Nov. 19, 2010, p. 1104-1107, 4 pages.
R.D Kolodner and G.T. Marsischky, "Eukaryotic DNA mismatch repair," Current Opinion in Genetics and Development, vol. 9, 1999, p. 89-96, 8 pages.
R.Renella et al., "Codanin-1 mutations in congenital dyserthropoietic anemia type 1 affect HP1α localization in erythroblasts," Blood, vol. 117, Jun. 2011, pp. 6928-6938, 11 pages.
Radecke, S., et al., "Zinc-finger Nuclease-induced Gene Repair With Oligodeoxynucleotides: Wanted and Unwanted Target Locus Modifications," Molecular Therapy, vol. 18, Apr. 2010, pp. 743-753, 11 pages.
Radulovich, et al., "Modified gateway system for double shRNA expression and Cre/lox based gene expression" BMC Biotechnology, 2011, vol. 11, pp. 1-9, 10 pages.
Ran et al., "Double Nicking by RNA-guided CRISPR Cas9 for enhanced genome editing specificity", Cell, Sep. 12, 2013, vol. 154, pp. 1380-1389.
Ran, F., et al., "In vivo genome editing using *Staphylococcus aureus* Cas9," Nature, vol. 520, 2015, pp. 186-191,6 pages. Includes Supplemental information, 12 pages.
Ran, F., et al., "Genome engineering using the CRISPR-Cas9 system," Nature Protocols, vol. 8, 2013, pp. 2281-2308, 28 pages.
Rand, et al. "Argonaute2 Cleaves the Anti-Guide Strand of siRNA during RISC Activation" Cell, vol. 123, 2005, pp. 621-629, 9 pages.

(56) References Cited

OTHER PUBLICATIONS

Raymond, et al. "High-Efficiency FLP and φC31 Site-Specific Recombination in Mammalian Cells" PLoS ONE, vol. 2, Jan. 2007, pp. 1-4. Doi. 10.1371/journal.pone.0000162.
Rebar, et al., "Induction of angiogenesis in a mouse model using engineered transcription factors" Nature Medicine, vol. 8, 2002, pp. 1427-1432, 6 pages.
Redeclaration—37 C.F.R. 41.203(c); filed Mar. 17, 2016 in Patent Interference No. 106,048 (DK), 14 pages.
Reiss, et al., "RecA protein stimulates homologous recombination in plants" Proc. Natl. Acad. Sci. vol. 93, 1996, pp. 3094-3098, 5 pages.
Response to Third Party Observations in EP No. 13824232.6 filed Oct. 2, 2014, with Redlined and Clean Amended Claims, 14 pages.
Rho, M., et al., "Diverse CRISPRs Evolving in Human Microbiomes," PLOS Genetics, vol. 8, Jun. 2012 e1002441, 12 pages.
Rhun, A., and Charpentier, E., "Small RNAs in streptococci," RNA Biology, vol. 9, 2012, pp. 414-426, 13 pages.
Roberts, et al. "Nuclear location signal-mediated protein transport" Biochimica et Biophysica Act, vol. 1008, 1989, pp. 263-280, 18 pages.
Roberts, et al., "The Effect of Protein Content on Nuclear Location Signal Function" Cell, vol. 50, 1989, pp. 465-475, 11 pages.
Rockefeller University and Broad Institute of MIT and Harvard announce update to CRISPR-Cas9 portfolio filed by Broad, Press Release dated Jan. 15, 2018, retrieved from: https://www.broadinstitute.org/news/rockefeller-university-and-broad-institute-mit-and-harvard-announce-update-crispr-cas9, 3 pages.
Rodrigues, et al., "Red Fluorescent Protein (DsRed) as a Reporter in *Saccharomyces cerevisiae*" Journal of Bacteriology, vol. 183, 2001, pp. 3791-3794, 4 pages.
Rodriguez et al., "AAV-CRISPR: A New Therapeutic Approach to Nucleotide Repeat Diseases", Molecular Therapy, vol. 22, 2014, Supplement 1, Abstract 247, p. S94.
Rolling, "Recombinant AAV-mediated gene transfer to the retina: gene therapy perspectives", Gene Therapy, vol. 11, 2004, p. S26-S32, 5 pages.
*Rubin* v. *The General Hospital Corp*., 2011-1439 (Fed. Cir. Mar. 28, 2013), 8 pages.
S. Huang et al., "MED12 Controls the Response to Multiple Cancer Drugs through Regulation of TGF-ß; Receptor Signaling," Cell, vol. 151, 2012, pp. 937-950, 14 pages.
S. Konermann et al., "Optical control of mammalian endogenous transcription and epigenetic states," Nature, vol. 500, Aug. 22, 2013, pp. 472-476, 5 pages. Includes Supplemental Information, 13 pages.
S.H. Chen et al., "A Knockout Mouse Approach Reveals that TCTP Functions as an Essential Factor for Cell Proliferation and Survival in a Tissue- or Cell Type-specific Manner," Molecular Biology of the Cell, vol. 18, Jul. 2007, pp. 2525-2532, 8 pages.
S.R. Whittaker et al., "A Genome-Scale RNA Interference Screen Implicates NF1 Loss in Resistance to RAF Inhibition," Cancer Discovery, vol. 3, 2013, pp. 350-362, 14 pages.
S.S. Liu et al., "Identification and characterization of a novel gene, clorf109, encoding a CK2 substrate that is involved in cancer cell proliferation," Journal of Biomedical Science, vol. 19, 2012, 12 pages.
S.Xue and M. Barna, "Specialized ribosomes: a new frontier in gene regulation and organismal biology," Nat Rev Mol Cell Biology, vol. 13, Jun. 2012. pp. 355-369, 15 pages.
Sadowski, M., and Jones, D., "The sequence-structure relationship and protein function prediction," Current Opinion in Structural Biology, vol. 19, 2009, pp. 357-362, 6 pages.
Sambrook, et al., "Molecular Cloning, A Laboratory Manual on the Web", Cold Spring Harbor Laboratory Press, Chapter 16, 2001, downloaded from http://www.molecularcloning.com/members/chapter.jsp?chapter=127 on Feb. 19, 2002, 13 pages.
Sander, et al., "CRISPR-Cas systems for editing, regulating and targeting genomes," Nature Biotechnology, vol. 32, 2014, pp. 347-355, 9 pages.
Sanders, "Cheap and easy technique to snip DNA could revolutionize gene therapy", UC Berkeley Press Release, Jan. 7, 2013, available at http://newscenter.berkeley.edu/2013/01/07/cheap-and-easy-technique-to-snip-dna-could-revolutionize-gene-therapy/.
Sanders, et al., "Use of a macromolecular crowding agent to dissect interactions and define functions in transcriptional activation by a DNA-tracking protein: Bacteriophage T4 gene 45 protein and late transcription" PNAS, vol. 9 2014, pp. 7703-7707, 5 pages.
Sanjana, et al., "Improved vectors and genome-wide libraries for CRISPR screening," HHS Public Access Author Manuscript, vol. 11, 2014, pp. 2145-2148, 4 pages.
Sanjana, N., et al., "A Transcription Activator-Like Effector (TALE) Toolbox for Genome Engineering," Nature Protocols, vol. 7, 2012, pp. 171-192, 39 pages.
Sapranauskas, R., et al., "The *Streptococcus thermophilus* CRISPR-Cas system provides immunity in *Escherichia coli*," Nucleic Acids Research, vol. 3, 2011, pp. 9275-9282, 8 pages.
Sarra, G., et al., "Gene replacement therapy in the retinal degeneration slow (rds) mouse: the effect on retinal degeneration following partial transduction of the retina", Human Molecular Genetics, vol. 10, 2001, pp. 2353-2361, 9 pages.
Sato, et al. "Generation of Adeno-Associated Virus Vector Enabling Functional Expressionof Oxytocin Receptor and Fluorescence Marker Genes Using the Human eIF4G Internal Ribosome Entry Site Elemet" Biosci. Biotechno. Biochem, vol. 73, 2009, pp. 2145-2148, 4 pages.
Sauer, "Functional Expression of the cre-lox Site-Specific Recombination System in the Yeast *Saccharomyces cerevisiae*" Mol. Cell. Biology, vol. 7, 1987, pp. 2087-2096, 10 pages.
Sauer, et al. "Site-specific DNA recombination in mammalian cells by the Cre recombinase of bacteriophage P1" Proc. Natl. Acad. Sci. vol. 85, 1988, pp. 5166-5170, 5 pages.
Schiffer, et al. "Targeted DNA Mutagenesis for the Cure of Chronic Viral Infections" Journal of Virology, vol. 86, No. 17, Jun. 20, 2012, pp. 8920-8936.
Schiffer, et al., "Predictors of Hepatitis B Cure Using Gene Therapy to Deliver DNA Cleavage Enzymes: A Mathematical Modeling Approach" PLOS Computational Biology, vol. 9, 2013, pp. 1-16. www.ploscompbiol.org.
Scholze, et al., "TAL effector-DNA specificity", Virulence, vol. 1, No. 5, Sep. 1, 2010, pp. 428-432, 5 pages. DOI:10.4161/viru.1.5.12863.
Schramm et al., "Recruitment of RNA polymerase III to its target promoters" Genes & Development, vol. 16, 2002, 2593-2620, pp. 28 pages.
Schunder et al., "First indication for a functional CRISPR/Cas system in Francisella tularensis", International Journal of Medical Microbiology, vol. 303, 2013, pp. 51-60, 10 pages.
Sebastiani, et al., "BCL11A enhancer haplotypes and fetal hemoglobin in sickle cell anemia," Blood Cells, vol. 54, 2015, pp. 2240230, 7 pages.
Sebo, et al., "A simplified and efficient germline-specific CRISPR/Cas9 system for *Drosophila* genomic engineering" Fly, 2014, vol. 8, pp. 52-57, 8 pages.
Seffernick, J., et al., "Melamine Deaminase and Atrazine Chlorohydrolase: 98 Percent Identical but Functionally Different," Journal of Bacteriology, vol. 183, No. 8, Apr. 2001, pp. 2405-2410, 6 pages.
Semenova, E. et al., "Interference by clustered regularly interspaced short palindromic repeat (CRISPR) RNA is governed by a seed sequence," Proc. Natl. Acad. Sci., vol. 108, Jun. 21, 2011, pp. 10089-10103, 7 pages.
Senis, E., et al., "CRISPR/Cas9-mediated genome engineering: An adeno-associated viral (AAV) vector toolbox," Biotechnology Journal, vol. 9, 2014, pp. 1402-1412, 12 pages.
Senturk et al., "A rapid and tunable method to temporally control cas9 expression enables the identification of essential genes and the interrogation of functional gene interactions in vitro and in vivo," vol. 9, 2015, pp. 1-27, XP002756303, doi:10.1101/023366, Retrieved from the Internet: URL:http://biorxiv.org/content/early/2015/07/28/023366 [retrieved on Apr. 11, 2016).

(56) References Cited

OTHER PUBLICATIONS

Shalem, et al., "High-throughput functional genomics using CRISP-Cas9," Nature Reviews Genetics, vol. 16, No. 5, pp. 299-311, May 2015.
Shalem, O., et al., "Genome-Scale CRISPR-Cas9 Knockout Screening in Human Cells," Science, vol. 343, 2014, pp. 84-87, 5 pages.
Sharan, et al., "Recombineering: A Homologous Recombination-Based Method of Genetic Engineering" Nat. Protoc., 2009, vol. 4 pp. 206-223, 18 pages. doi:10.1038/nprot.2008.227.
Shen, B., et al., "Generation of gene-modified mice via Cas9/RNA-mediated gene targeting," Cell Research, vol. 23, 2013, pp. 720-723.
Shen, et al., "Efficient genome modification by CRISPR-Cas9 mickase with minimal off-target effects" 2014, Nature Methods, vol. 11, pp. 399-404, 6 pages.
Shengdar Tsai et al., "Dimeric CRISPR RNS-guided Fokl nucleases for highly specific genome editing", Nature Biotechnology, vol. 32, Jun. 2014, pp. 569-576, 18 pages.
Shieh, et al., "Nuclear Targeting of the Maize R. Protein Requires Two Nuclear Localization Sequences" Plant Physiol, 1993, vol. 101 pp. 353-361, 9 pages.
Siegl, et al., "I-Scel endonuclease: a new tool for DNA repair studies and genetic manipulations in streptomycetes" Appl Microbiol Bitotechnol, vol. 87, 2010, pp. 1525-1532, 8 pages.
Sims, D., et al., "High-throughput RNA interference screening using pooled shRNA libraries and next generation sequencing," Genome Biology, vol. 12, 2011, pp. 1-13.
Singer, et al., "Applications of Lentiviral Vectors for shRNA Delivery and Transgenesis" Curr Gene Ther., vol. 8, 2008 pp. 483-488, 6 pages.
Slaymaker et al., "Rationally engineered Cas9 nucleases with improved specificity", Science, American Association for the Advancement of Science, US, vol. 351, Jan. 1, 2016, pp. 84-88.
Sontheimer, "Project 7: Establishing RNA-Directed DNA Targeting in Eukaryotic Cells" Physical Sciences-Onc., Nov. 16, 2011-Dec. 31, 2012, 2 pages. htt://groups.molbiosci.northwestern.edu/sontheimer/Sontheimer_cv.php) Molecular Biosciences, 2 pages.
Spencer, J.M., et al., "Development of a Nuclease Screen to Improve Cas9 Targeting Specificity", Molecular Therapy, May 2015, vol. 23, Suppl. 1, S136(340).
Stewart SA et al., "Lentivirus-delivered stable gene silencing by RNAi in primary cells," RNA, vol. 9, 2003, pp. 493-501, 9 pages.
Stolfi, et al., "Tissue-specific genome editing in Ciona embryos by CRISPR/Cas9," Development, vol. 141, 2014, pp. 4115-4120, 6 pages. doi: 10.1242/dev.114488.
Stoller, J. and Aboussouan, L., "Alpha1-antitrypsin deficiency," The Lancet, Seminar, vol. 365, 2005, pp. 2225-2236, 12 pages.
Stratikopoulos, E., et al., "The hormonal action of IGF1 in postnatal mouse growth," Proceedings of the National Academy of Sciences, vol. 105, Dec. 9, 2008, pp. 19378-19383, 6 pages.
Straub, C., et al., "CRISPR/Cas9-Mediated Gene Knock-Down in Post-Mitotic Neurons," PLOS One, vol. 9, art. E105584, Aug. 20, 2014, pp. 1-5, 6 pages.
Sung, et al., "An rpsL Cassette, Janus, for Gene Replacement through Negative Selectionin Streptococcus pneumoniae" Applied and Environmental Microbiology, vol. 67, 2001, pp. 5190-5196, 7 pages.
Sung, M., et al., "The importance of valency in enhancing the import and cell routing potential of protein transduction domain-containing molecules," Biochimica et Biophysica Aeta, vol. 1758, pp. 355-363, dated 2006, 9 pages.
Sung, Young Hoon, et al., "Mouse genetics: Catalogue and scissors" BMB Reports, 2012, vol. 45 pp. 686-692, 7 pages.
Suzuki, K., et al., "In vivo genome editing via CRISPR/Cas9 mediated homology-independent targeted integration," Nature, vol. 540, art. 7631, 2015, pp. 1-44.
Swarthout, J., et al., "Zinc Finger Nucleases: A new era for transgenic animals," Annals of Neurosciences, vol. 18, 2011, pp. 25-28, 4 pages.
Swiech et al., "CRISPR-Mediated Genome Editing in the Mammalian Brain", Molecular Therapy, 747, vol. 22, 2014, p. S289.
Swiech, L., et al., "In vivo interrogation of gene function in the mammalian brain using CRISPR-Cas9," Nature Biotechnology, vol. 33, 2014, pp. 102-106, 5 pages. Including Supplemental information, 4 pages.
Symington et al., "Double-Strand Break End Resection and Repair Pathway Choice", Annual Review of Genetics, vol. 45, 2011, pp. 247-271, 25 pages.
T. Horii et al., "Generation of an ICF Syndrome Model by Efficient Genome Editing of Human Induced Pluripotent Stem Cells Using the CRISPR System," International Journal of Molecular Sciences, vol. 14, 2013, pp. 19774-19781, 9 pages.
T.J. Cradick et al., "CRISPR/Cas9 systems targeting ß-globin and CCR5 genes have substantial off-target activity," Nucleic Acids Research, vol. 41, 2013, 9584-9592, 9 pages.
T.Yan et al., "DNA mismatch repair (MMR) mediates 6-thioguanine genetoxicity by introducing single-strand breaks to signal a G2-M arrest in MMR-proficient RKO cells," Clinical Cancer Research, vol. 9, Jun. 2003, p. 2327-2334, 9 pages.
Takara Bio USA, Inc., "Lenti-X™ Tet-On@ 3G CRISPR/Cas9 System User Manual", 2016, pp. 1-35.
Tang, T., et al., "A mouse knockout library for secreted and transmembrane proteins," Nature Biotechnology, vol. 28, No. 7, Jul. 2010, pp. 749-755, pp. 7 pages. Including Supplemental information, 2 pages.
Terns, M., and Terns, R., "CRISPR-based adaptive immune systems," Current Opinion in Microbiology, vol. 14, 2011, pp. 321-327, 8 pages.
*The Broad Inst.* v. *The Regents of University of UCA*—Decision on Motions for Patent Interference No. 106,048 filed Feb. 15, 2017, 51 pages.
Third Party Observation for Application No. EP20130824232 dated Sep. 22, 2014, 19 pages.
Third Party Observation in Application No. PCT/US2013/074819 dated Apr. 10, 2015, 10 pages.
Third Party Observation Under Article 115 EPC in Application No. 13818570.7 dated Oct. 1, 2014.
Third Party Observations Concerning App. No. GB1420270.9, dated Jun. 30, 2015, 71 pages.
Third Party Observations Concerning Appl. No. EP2800811, dated Jul. 24, 2015, 108 pages.
Third Party Observations Concerning Appl. No. EP2800811, dated Sep. 4, 2015.
Third Party Observations Concerning Appl. No. GB1420270.9 dated Jun. 30, 2015.
Third Party Observations Concerning Appl. No. GB1420270.9, dated Jul. 13, 2015.
Third Party Observations in Accordance with Article 115 EPC, Appl. No. EP13824232.6, Pub. No. EP2764103A, Mar. 25, 2015.
Third Party Observations submitted by Broad Institute Inc. Concerning Appl. Ser. No. EP13793997.1 dated Jul. 24, 2015, 108 pages.
Third Party Observations submitted by Broad Institute Inc. Concerning Appl. Ser. No. EP13793997.1 dated Sep. 4, 2015, 25 pages.
Third Party Observations submitted by Regents of the University of California et al. Concerning App. No. GB1420270.9 dated Jul. 13, 2015, 18 pages.
Third Party-Observations, Appl. No. 1382432.6, Pub. No. EP2764103, dated Feb. 16, 2015, 12 pages.
Third-Party Observation for Application No. EP20130824232 dated Sep. 8, 2014, 47 pages.
Tinland, et al., "The T-DNA-linked VirD2 protein contains two distinct functional nuclear localization signals" Proc. Natl. Acad. Sci, vol. 89, 1992, pp. 7442-7446, 5 pages.
Tiscornia, et al. "Development of Lentiviral Vectors Expressing siRNA" Gene Transfer-Delivery and Expression of DNA and RNA—A Laboratory Manual, 2007, Chapter 3 pp. 23-34, 12 pages.
Tolia, et al., "Slicer and the Argonautes" Nature Chemical Biology, vol. 3, 2007, pp. 36-43, 8 pages.
Trafton, A., "CRISPR-carrying nanoparticles edit the genome," MIT News, dated Nov. 13, 2017, 3 pages.

(56) References Cited

OTHER PUBLICATIONS

Trevino, et al., "Genome Editing Using Cas9 Nickases" Methods in Enxymology, vol. 546 pp. 161-174, 14 pages.
Tulpan, D., et al., "Free energy estimation of short DNA duplex hybridizations," BMC Bioinformatics, vol. 11, 2012, pp. 105-127, 23 pages.
Type V CRISPR-associated protein Cpfi [*Acidaminococcus* sp. Bv3L6], 2017, NCBI Reference Sequence: WP_02173622.1, Non-redundant Protein Sequence, 2 pages.
*Ultra-Precision Mfg*. Ltd. v. *Ford Motor Co*., 2004 WL 3507671, *7, *11-12 (E.D. Mich. Mar. 30, 2004).
Urnov, et al., "Highly efficient endogenous human gene correction using designed zinc-finger nucleases" Nature, vol. 435, 2005, pp. 646-651, 6 pages.
Urnov, F., et al., "Genome editing with engineered zinc finger nucleases," Nature Reviews, Genetics, vol. 11, pp. 637-646, dated Sep. 2010, 11 pages.
Urrutia, et al., "KRAB-containing zing finger repressor proteins" Genome Biology, vol. 4, Sep. 23, 2003, pp. 231-231.8, 8 pages.
V.N. Ngo et al., "A loss-of-function RNA interference screen for molecular targets in cancer," Nature, vol. 441, May 4, 2006, pp. 106-110, 5 pages.
Van Den Ackerveken, et al., "Recognition of the Bacterial Avirulence Protein AvrBs3 Occurs inside the Host Plant Cell" Cell, vol. 87, Dec. 27, 1996, pp. 1307-1316, 10 pages.
Van Der Oost, "New tool for genome surgery", Science, vol. 339, Feb. 15, 2013, pp. 768-770, 3 pages.
Van Der Oost, J., et al., "CRISPR-based adaptive and heritable immunity in prokaryotes, " Trends. Biochem. Sci., vol. 34, 2009, pp. 401-407, 7 pages.
Van Nierop, G., et al., "Stimulation of homology-directed gene targeting at an endogenous human locus by a nicking endonuclease," Nucleic Acids Research, vol. 37, 2009, pp. 5725-5736, 12 pages.
Venken et al., "P[acman]: A BAC Transgenic Platform for Targeted Insertion of Large DNA Fragments in D. melanogaster", Science, vol. 314, Dec. 15, 2006, pp. 1747-1751, 5 pages.
Vestergaard et al.:., "CRISPR adaptive immune systems of Archaea", RNA Biology, vol. 11,2014, pp. 156-167, 12 pages.
Villion, et al., "The double-edged sword of CRISPR-Cas systems" Cell Research, 2013, vol. 23 pp. 15-17, 3 pages.
W.G. Kaelin., "Use and Abuse of RNAi to Study Mammalian Gene Function," Science, vol. 337, Jul. 27, 2012, p. 421-422, 2 pages.
Wang, et al. "Genetic Screens in Human Cells Using the CRISPR-Cas9 System", Science, 2014, 343:80-84.
Wang, H., et al., "One-Step Generation of Mice Carrying Mutations in Multiple Genes By CRISPR/Cas-Mediated Genome Engineering," Cell, vol. 153, 2013, pp. 910-918, 9 pages.
Wang, H.H et al., "Genome-scale promoter engineering by coselection MAGE," Nat methods, vol. 9, Jun. 2012, pp. 591-593, 3 pages.
Wayengera, M., "Identity of zinc finger nucleases with specificity to herpes simplex virus type II genomic DNA; novel HSV-2 vaccine/therapy precursors", Theoretical Biology and Medical Modelling, vol. 8, No. 1, Jun. 24, 2011, p. 23.
Wayengera, M., "Zinc finger arrays binding human papillomavirus types 16 and 18 genomic DNA: precursors of gene-therapeutics for in-situ reversal of associated cervical neoplasia", Theoretical Biology and Medical Modeling, vol. 9, No. 1, Jul. 28, 2012, p. 30.
Weber et al., "TALENs Targeting HBV: Designer Endonuclease Therapies for Viral Infections", Molecular Therapy, vol. 21, Oct. 2013, pp. 1819-1821, 3 pages.
Welch, et al., "Designing Genes For Successful Protein Expression" Methods in Enzymology, 2011, vol. 498, pp. 43-66, 24 pages. DOI: 10.1016/B978-0-12-385120-8.00003-6.
Wiedenheft, B. et al., "RNA-guided complex from a bacterial immune system enhances target recognition through seed sequence interactions," Proc. Natl. Acad. Sci., vol. 108, Jun. 21, 2011, 10092-10097, 7 pages.
Wiedenheft, B. et al., "RNA-guided genetic silencing systems in bacteria and archaea", Nature, vol. 482, Feb. 16, 2012, pp. 331-338.
Wienert, B., et al., "In vitro transcribed guide RNAs trigger an innate immune response via the RIG-I pathway," BioRxiv Preprint, 2018, 1-28, 28 pages.
Witkowski, A., et al., "Conversion of a Beta-Ketoacyl Synthase to a Malonyl Decarboxylase by Replacement of the Active-Site Cysteine with Glutamine," Biochemistry, vol. 38, 1999, pp. 11643-11650, 8 pages.
Wittmann et al., "Engineered riboswitches: Expanding researchers' toolbox with synthetic RNA regulators", FEBS Letters, vol. 586, 2012, pp. 2076-2083, 8 pages.
Wolff, et al., "Nuclear security breached" Nature Biotechnology, Dec. 2001, vol. 19, 1118-1120, 3 pages.
Wu, X., et al., "Genome-wide binding of the CRISPR endonuclease Cas9 in mammalian cells," Nature Biotechnology, 2014, 1-7, 7 pages. Including Supplemental information, 2 pages.
Wu, Y., et al., "Correction of a Genetic Disease in Mouse via Use of CRISPR-Cas9," Cell Stem Cell, vol. 13, 2013, pp. 659-662, 4 pages.
Wu, Z., et al., "Effect of Genome Size on AAV Vector Packaging," The American Society of Gene & Cell Therapy, vol. 18, 2010, pp. 80-86, 7 pages.
X.Liu et al., "STAGA recruits Mediator to the MYC oncoprotein to stimulate transcription and cell proliferation," Molecular and cellular biology, vol. 28, Jan. 2008, p. 108-121, 14 pages.
Xiao, et al., "Chromosomal deletions and inversions mediated by TALENs and CRIPPR/Cas in zebrafish" Nucleic Acids Research, vol. 41, 2013, pp. 1-11, Including Supplemental information, 31 pages. doi: 10.1093/nar/gkt464.
Xiao, et al., "Production of High-Titer Recombinant Adeno-Associated Virus Vectors in the Absence of Helper Adenovirus" Journal of Virology, Mar. 1998, vol. 72, No. 3, pp. 2224-2232, 9 pages.
Xiao, W., et al., "Gene Therapy Vectors Based on Adeno-Associated Virus Type 1", Journal of Virology, May 1999, vol. 73, No. 5, p. 3994-4003.
Xie, et al. "RNA-Guided Genome Editing in Plants Using a CRISPR-Cas System" Molecular Plant, vol. 6, Nov. 2013, 1975-1983, 9 pages.
Xu, Zhi-Li et al., "Regulated gene expression from adenovirus vectors: a systematic comparison of various inducible systems," Gene, vol. 309, 2003, pp. 145-151, 7 pages.
Yaghmai, et al., "Optimized Regulation of Gene Expression Using Artificial Transcription Factors", Molecular Therapy, Jun. 2002, vol. 5, No. 6, pp. 685-694.
Yamano, et al., "Crystal Structure of Cpf1 in Complex with Guide RNA and Target DNA" Cell, vol. 165, May 5, 2016, pp. 949-962, 14 pages.
Yanfang Fu et al., "Improving CRISPR-Cas nuclease specificity using truncated guide RNAs" (with Supplement Table), Nature Biotechnology, vol. 32, Mar. 2014, pp. 1-18.
Yang et al., "HIV-1 TAT-mediated protein transduction and subcellular localization using novel expression vectors," FEBS Letters, vol. 532, 2012, pp. 36-44, 9 pages.
Yang, H., et al., "One-Step Generation of Mice Carrying Reporter and Conditional Alleles by CRISPR/Cas-Mediated Genome Engineering," Cell, vol. 154, 2013, pp. 1370-1379, 10 pages. Including Supplemental information, 4 pages.
Yi, et al., "Current Advances in Retroviral Gene Therapy" Current Gene Therapy, vol. 11, 2011, pp. 218-228, 11 pages.
Yin, H., et al., "Structure-guided chemical modification of guide RNA enables potent non-viral in vivo genome editing," Nature Biotechnology, vol. 35, Dec. 2017, pp. 1-22.
Yu, et al., "An efficient recombination system for chromosome engineering in *Escherichia coli*" PNAS, 2000, vol. 97, pp. 5978-5983, 6 pages.
Yu, W., et al., "Nrl knockdown by AAV-delivered CRISPR/Cas9 prevents retinal degeneration in mice," Nature Communications, vol. 8, 2017, art. 14716, 15 pages.
Yu, Zhongshen, et al., "Highly Efficient Genome Modifications Mediated by CRISPR/Cas9 in Drosophila" Genetics, 2013, vol. 195 pp. 289-291, 3 pages.

(56) References Cited

OTHER PUBLICATIONS

Yusuke Miyazaki et al., Destabilizing Domains Derived from the Human Estrogen Receptor:, Journal of the American Chemical Society, vol. 134, Mar. 7, 2012, pp. 3942-3945, 4 pages.
Zahner, D. and Hakenbeck, R. "The Streptococcus pneumoniae beta-galactosidase is a surface protein," J. Bacteriology, vol. 182, Oct. 2000, pp. 5919-5921, 3 pages.
Zeng Y et al., "Both natural and designed micro RNAs can inhibit the expression of cognate mRNAs when expressed in human cells," Mol Cell., vol. 9, Jun. 2002, pp. 1327-1333, 7 pages.
Zetsche et al. "A split-Cas9 architecture for inducible genome editing and transcription modulation" Nature biotechnology, 2015, vol. 33, 139-142, 4 pages.
Zetsche et al., "Cpf1 is a single RNA-guided endonuclease of a class 2 CRISPR-Cas system", Cell, vol. 163, 2015, pp. 759-771, 13 pages.
Zhang, "Processing-Independent CRISPR RNAs Limit Natural Transformation in Neisseria meningitidis", Molecular Cell, vol. 50, May 23, 2013 pp. 488-503.
Zhang, et al. "Optogenetic interrogation of neural circuits: technology for probing mammalian brain structures" Nat Protoc., 2010, 5(3):439-456, doi:10.1038/nprot.2009.226.
Zhang, et al., "Optimized CRISPR Design", MIT, XP055167487, Oct. 23, 2013, URL:http//crispr.mit.edu/about[retrieved on Feb. 5, 2015].
Zhang, et al., "Efficient construction of sequence-specific TAL effectors for modulating mammalian transcription" nature biotechnology, vol. 29, 2011, 149-154, 6 pages.
Zhang, F., PowerPoint Presentation: "Development and Applications of CRISPR-Cas9 for Genome Editing," Broad Institute/MIT, dated Sep. 9, 2015, 50 pages.
Zhang, L., et al., "Efficient Expression of CFTR Function with Adeno-Associated Virus Vectors that Carry Shortened CFTR Genes," Proceedings of the National Academy of Science USA, vol. 95, 1998, p. 10158-10163, 6 pages.
Zhang, X. D., et al., "CSSMD: assessing collective activity for addressing off-target effects in genome-scale RNA interference screens," Bioinformatics, vol. 27, pp. 2775-2781, 2011, 7 p.
Zhou, et al., "High-throughput screening of a CRISPR/Cas9 library for functional genomics in human cells," Nature, vol. 509, pp. 487-491, 5 pages.
Zhu, et al. "Crystal structure of Cmr2 suggests a nucleotide cyclase-related enzyme in type III CRISPR-Cas sytems" FEBS Letters, 2012, 939-945, 6 pages. Doi:10.1016/j.febslet2012.02.036.
Zolkiewska, et al., "ADAM Proteases: Ligand Processing and Modulation of the Notch Pathway" Cell Mol Life Sci, 2008, vol. 65 pp. 2056-2068, 13 pages.
Zuris, et al., "Cationic lipid-mediated delivery proteins enables efficient protein-based genome editing In vitro and In vivo", Nature Biotechnology, vol. 33, No. 1, Jan. 2015, pp. 73-80.
Zuris, et al., "Efficient Delivery of Genome-Editing Proteins In Vitro and In Vivo" Nature Biotechnology, vol. 33, No. 1, Jan. 2015, pp. 1-26.
Zuris, et al., Supplementary Information—"Cationic lipid-mediated delivery proteins enables efficient protein-based genome editing in vitro and in vivo" Nature Biotechnology, vol. 33, No. 1, Jan. 2015, pp. 1-49. doi: 10.1038/nbt.3081.
Adhin et al., "Complete nucleotide sequence of the group I RN A bacteriophage fr," Biochimica et Biophysica Acta, Elsevier, vol. 1050, 1990 pp. 104-109.
Anders et al., "Structural basis of PAM-dependent target DNA recognition by the Cas9 endonuclease, " Nature, vol. 513, Sep. 25, 2014 pp. 569-573.
Anguela et al., "Robust ZFN-mediated geno1ne editing in adult hemophilic mice", Blood, vol. 122, No. 19, Nov. 7, 2013, (pp. 3283-3287).
Bikard et al., "Exploiting CRISPR-Cas nucleases to produce sequence-specific antimicrobials", Nature Biotechnology, vol. 32, No. 11, Nov. 2014 (pp. 1146-1151).
Chapdelaine et al., "Meganucleases can restore the reading frame of a mutated dystrophin", Gene Therapy, vol. 17, 2010 (pp. 846-858).
Database UniPro Accession No. J7RUA5, 2012, [online] downloaded from https://www.uniprot.org/uniprol/J7RUA5 on Mar. 23, 2021 (10 pages).
He et al., "Pollen fertility restoration by nuclear gene Fr in CMS common bean: an Fr linkage map and the mode of Fr action," Theor. Appl. Genet. vol. 90, 1995, pp. 1056-1062.
Hemphill et al., "Optical Control of CRISPR/Cas9 Gene Editing," Journal of the American Chemical Society, vol. 137, May 6, 2015 (9 pages).
Huang and Honkanen, "Molecular Cloning, Expression, and Characterization of a Novel Human Serine/Threonine Protein Phosphatase, PP7, That Is Homologous to 'Drosophila' Retinal Degeneration C Gene Product (rdgC)*," The Journal of Biological Chemistry, vol. 273, No. 3, Iss. 16, 1998, pp. 1462-1468.
Koonin et al., "Diversity, classification and evolution of CRISPR-Cas systems", Current Opinion in Microbiology vol. 37, 2017 (pp. 67-78).
Sorek et al., "CRISPR-Mediated Adaptive Immune Systems in Bacteria and Archea", Annual Review of Biochemistry, vol. 82, 2013, (pp. 237-266).
Cutrona et al., "Effects in live cells of a c-myc anti-gene PNA linked to a nuclear localization signal," Nature Biotechnology, Mar. 2000, vol. 18 (pp. 300-303).
Bachman et al., "Dnmt3a and Dnmt3b Are Transcriptional Repressors That Exhibit Unique Localization Properties to Heterochromatin," the Journal of Biological Chemistry, Aug. 24, 2001, vol. 276, No. 34, (pp. 32282-32287).
Brief of Amici Curiae Scientists in Support of Appellants and Reversal; Case: 22-1594; Document: 18; Nos. 22-1594, 22-1653; Filed: Oct. 7, 2022 (24 pages).
Corrected Opening Brief for Cross-Appellants; Appeal Nos. 2022-1594, 2022-1653; Document: 31; Filed: Feb. 15, 2023 (111 pages).
Johnson et al., "Achromatopsia caused by novel mutations in both CNGA3 and CNGB3," Journal of Medical Genetics, Online mutation report, Feb. 2004, vol. 41, No. 2 (5 pages).
Love et al., "Lipid-like materials for low-dose, in vivo gene silencing," Proceedings of the National Academy of Sciences, Feb. 2, 2010, vol. 107, No. 5 (pp. 1864-1869).
Mao et al., "Long-Term Rescue of Retinal Structure and Function by Rhodopsin RNA Replacement with a Single Adeno-Associated Viral Vector in P23H RHO Transgenic Mice," Human Gene Therapy, Apr. 2012, vol. 23 (pp. 356-366).
Motion of Regeneron Pharmaceuticals, Inc. for Leave to File a Brief as Amicus Curiae in Support of Appellants and Reversal; Case: 22-1594; Document: 22-1; Nos. 22-1594 and 22-1653; Filed: Oct. 7, 2022 (29 pages).
Opening Brief for Appellants The Regents of the University of California, University of Vienna, Emmanuelle Charpentier; Nos. 2022-1594 & 2022-1653; Case: 22-1594 Document: 17-1 Filed, Sep. 30, 2022 (81 pages).
Patent Interference No. 106, 115; Decision on Motions 37 C.F.R. Section 41.125(a); Filed: Sep. 10, 2020 (113 pages).
Patent Interference No. 106,115; Decision on Priority 37 C.F.R. Section 41.125(a), Filed: Feb. 28, 2022 (84 pages).
Patent Interference No. 106,126; Decision on Motions 37 C.F.R. Section 125(a); Filed: Sep. 28, 2022 (54 pages).
Patent Interference No. 106,133; Decision on Motions 37 C.F.R. Section 41.125(a) Filed: Dec. 14, 2022 (40 pages).
Semple et al., "Rational design of cationic lipids for siRNA delivery," Nature Biotechnology, Feb. 2010, vol. 28, No. 2 (pp. 172-178).
Gentarget Inc., "Crispr gRNA lentivector cloning kits," GenTarget Inc., Jan. 1, 2013 (pp. 1-2).
Hwang et al., "Efficient genome editing in zebrafish using a CRISPR-Cas system," Nature Biotechnology, Jan. 1, 2013, vol. 31, No. 3, Supplementary Materials (pp. 1-21).
Kocak D. D., "Synthetic Transcription Factors and their Effects on Endogenous DNA Methylation in Human Cells," Thesis Degree of Master of Science, Jan. 1, 2013, Department of Biomedical Engineering Duke University (35 pages).

(56) References Cited

OTHER PUBLICATIONS

Bhattacharya et al., "A simple genotyping method to detect small CRISPR-Cas9 induced indels by agarose gel electrophoresis," Scientific Reports, Mar. 14, 2019, vol. 9, No. 4437 (7 pages).
Cameron et al., "Mapping the genomic landscape of CRISPR-Cas9 cleavage," Nature Methods, Jun. 2017, vol. 14, No. 6 (pp. 600-606).
Guilinger et al., "Fusion of catalytically inactive Cas9 to Fokl nuclease improves the specificity of genome modification," Nature Biotechnology, vol. 32, No. 6, Jun. 2014 (pp. 577-582).
Raveux et al., "Optimization of the production of knock-in alleles by CRISPR/Cas9 microinjection into the mouse zygote," Scientific Reports, Feb. 17, 2017, vol. 7, No. 42661 (11 pages).
Shapiro et al., "Increasing CRISPR Efficiency and Measuring Its Specificity in HSPCs Using a Clinically Relevant System," Molecular Therapy: Methods & Clinical Development, Jun. 12, 2020, vol. 17 (pp. 1097-1107).
Slaymaker et al., "Rationally engineered Cas9 nucleases with improved specificity", Science, vol. 351, No. 6268, Jan. 1, 2016, pp. 84-88.
Taylor, G., "Introduction to phasing," Acta Crystallographica Section D Biological Crystallography, 2010, D66 (pp. 325-338).
Kugler et al., "Human synapsin 1 gene promoter confers highly neuron-specific long-term transgene expression from an adenoviral vector in the adult rat brain depending on the transduced area," Gene Therapy, 2003, vol. 10 (pp. 337-347).
Riley et al., "Improving the Performance of Cascade Correlation Neural Networks on Multimodal Functions," Proceedings of the World Congress on Engineering 2010 vol. III WCE 2010, Jun. 30-Jul. 2, 2010, London, U.K. (7 pages).
Satterwhite et al., "The BCL11 gene family: involvement of"BCL11A" in lymphoid malignancies," Blood, Neoplasia, vol. 98, No. 12, Dec. 1, 2001 (pp. 3413-3420).
Bauer et al., "Fine-Mapping and Genome Editing Reveal an Essential Erythroid Enhancer At The HbF-Associated BCL11A Locus," Blood, Nov. 15, 2013, vol. 122, No. 21 (3 pages).
Koller et al., "Inactivating the beta2-microglobulin locus in mouse embryonic stem cells by homologous recombination," Proceedings of the National Academy of Sciences, USA, Nov. 1989, vol. 86 (pp. 8932-8935).
Li et al., "Genetic correction using engineered nucleases for gene therapy applications," The Japanese Society of Developmental Biologists; Development, Growth & Differentiation, 2014, vol. 56 (pp. 63-77).
Reik et al., "Targeted Gene Modification in Hematopoietic Stem Cells: A Potential Treatment for Thalassemia and Sickle Cell Anemia," Blood, American Society of Hematology, Nov. 1, 2013, vol. 122, No. 21 (p. 434).
Xu et al., "Identification of BCL 11 A Structure Function Domains for Fetal Hemoglobin Silencing," Blood, Nov. 15, 2013, vol. 122, No. 21 (4 pages).
Singleton, "Exome sequencing: a transformative technology," The Lancet/neurology, Oct. 2011, vol. 10 (pp. 942-946).
Holmes et al., "In Vivo Delivery of Zinc Finger Nucleases Mediates Genome Editing to Correct Genetic Disease," Mol Ther. 19(Suppl. 1):S19-S20, (2011).†

* cited by examiner
† cited by third party

FIG 2E

```
Target locus  5'-..AGCTGGAGGAGGAAGGGCCTGAGTCCGAGCAGAAGAAGAAGGGCTCCCAC..-3'
                   ||||||||||||||||||||                    ||||||||||
              3'-..TCGACCTCCTCCTTCCCGGACTCAGGCTCGTCTTCTTCTTCCCGAGGGTG..-5'
                                       ||||||||||||||||||||
crRNA                              5'- GAGUCCGAGCAGAAGAAGAAGUUUUAGAGC..-3'
```

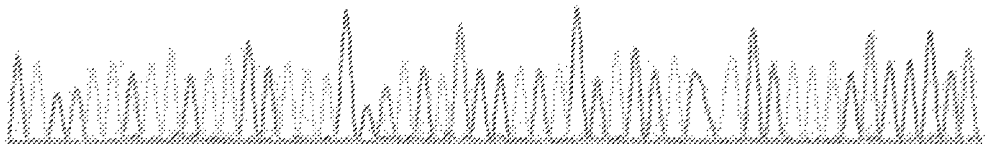

```
indel              AGCTGGAGGAGGAAGGGCCTGAGTCCGAGCAGAAGA-GAAGGGCTCCCAT
```

FIG 2F human *EMX1* protospacer target (mutation in 5 of 43 sequenced clones = 11.6%)

```
WT       5'-..CTGGAGGAGGAAGGGCCTGAGTCCGAGCAGAAG AAGAAGGGCTCCCATCACAT..-3'
Δ1            CTGGAGGAGGAAGGGCCTGAGTCCGAGCAGAAG--AGAAGGGCTCCCATCACAT
+1            CTGGAGGAGGAAGGGCCTGAGTCCGAGCAGAAGAAAGAAGGGCTCCCATCACAT
Δ3            CTGGAGGAGGAAGGGCCTGAGTCCGAGCAGAAG----AAGGGCTCCCATCACAT
m1, Δ6        CTGGAGGAGGAAGGGCCTGAGCCCGAGCAGAAG-------GGCTCCCATCACAT
```

| Cas9 | target species | gene | protospacer ID | protospacer sequence (5' to 3') | PAM | strand | cell line tested | % indel (pre-crRNA + tracrRNA) | % indel (chimeric RNA) |
|---|---|---|---|---|---|---|---|---|---|
| S. pyogenes SF370 type II CRISPR | Homo sapiens | EMX1 | 1 | GGAAGGGCCTGAGTCCGAGCAGAAGAAGAA | GGG | + | 293FT | 20 ± 1.8 | 6.7 ± 0.62 |
| | | EMX1 | 2 | CATTGGAGGTGACATCGATGTCCTCCCCAT | TGG | – | 293FT | 2.1 ± 0.31 | N.D. |
| | | EMX1 | 3 | GGACATCGATGTCACCTCCAATGACTAGGG | TGG | + | 293FT | 14 ± 1.1 | N.D. |
| | | EMX1 | 4 | CATCGATGTCCTCCCCATTGGCCTGCTTCG | TGG | – | 293FT | 11 ± 1.7 | N.D. |
| | | EMX1 | 5 | TTCGTGGCAATGCGCCACCGGTTGATGTGA | TGG | – | 293FT | 4.3 ± 0.46 | 2.1 ± 0.51 |
| | | EMX1 | 6 | TCGTGGCAATGCGCCACCGGTTGATGTGAT | GGG | – | 293FT | 4.0 ± 0.66 | 0.41 ± 0.25 |
| | | EMX1 | 7 | TCCAGCTTCTGCCGTTTGTACTTTGTCCTC | CGG | – | 293FT | 1.5 ± 0.12 | N.D. |
| | | EMX1 | 8 | GGAGGGAGGGGCACAGATGAGAAACTCAGG | AGG | – | 293FT | 7.8 ± 0.83 | 2.3 ± 1.2 |
| | Homo sapiens | PVALB | 9 | AGGGGCCGAGATTGGGTGTTCAGGGCAGAG | AGG | + | 293FT | 21 ± 2.6 | 6.5 ± 0.32 |
| | | PVALB | 10 | ATGCAGGAGGGTGGCGAGAGGGGCCGAGAT | TGG | + | 293FT | N.D. | N.D. |
| | | PVALB | 11 | GGTGGCGAGAGGGGCCGAGATTGGGTGTTC | AGG | + | 293FT | N.D. | N.D. |
| | Mus musculus | Th | 12 | CAAGCACTGAGTGCCATTAGCTAAATGCAT | AGG | – | Neuro2A | 27 ± 4.3 | 4.1 ± 2.2 |
| | | Th | 13 | AATGCATAGGGTACCACCCACAGGTGCCAG | GGG | – | Neuro2A | 4.8 ± 1.2 | N.D. |
| | | Th | 14 | ACACACATGGGAAAGCCTCTGGGCCAGGAA | AGG | + | Neuro2A | 11.3 ± 1.3 | N.D. |
| S. thermophilus LMD-9 CRISPR1 | Homo sapiens | EMX1 | 15 | GGAGGAGGTAGTATACAGAAACACAGAGAA | GTAGAAT | – | 293FT | 14 ± 0.88 | N.T. |
| | | EMX1 | 16 | AGAATGTAGAGGAGTCACAGAAACTCAGCA | CTAGAAA | – | 293FT | 7.8 ± 0.77 | N.T. |

FIG. 5

FIG. 9A
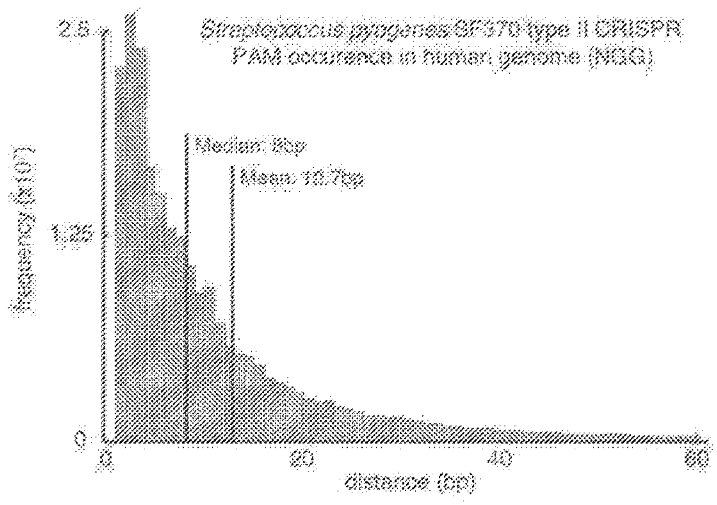
FIG. 9B
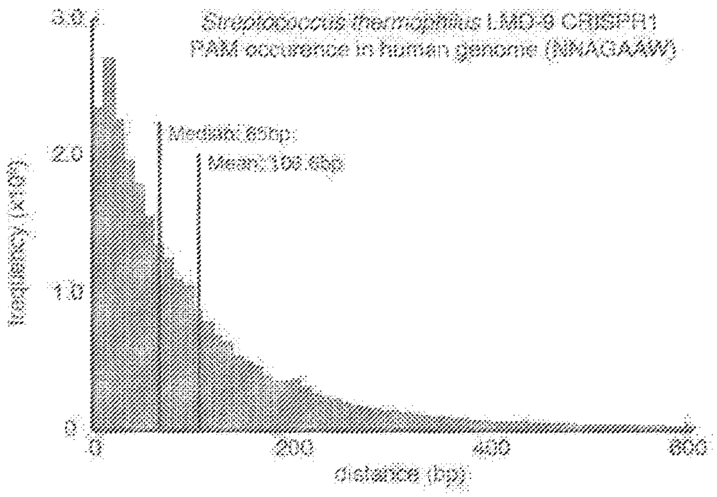
FIG 9C
| | NGG | | NNAGAAW | |
|---|---|---|---|---|
| Chr | median | mean | median | mean |
| 1 | 7 | 12.8 | 67 | 115.8 |
| 2 | 8 | 12.7 | 64 | 100.8 |
| 3 | 8 | 13.0 | 63 | 98.5 |
| 4 | 9 | 14.0 | 61 | 94.5 |
| 5 | 8 | 13.1 | 63 | 97.9 |
| 6 | 8 | 13.1 | 63 | 98.5 |
| 7 | 8 | 12.4 | 64 | 102.9 |
| 8 | 8 | 12.8 | 64 | 100.9 |
| 9 | 7 | 13.9 | 65 | 120.5 |
| 10 | 7 | 12.1 | 66 | 107.0 |
| 11 | 7 | 12.0 | 65 | 105.8 |
| 12 | 8 | 12.4 | 65 | 103.5 |
| 13 | 8 | 13.6 | 62 | 94.6 |
| 14 | 8 | 12.0 | 65 | 101.5 |
| 15 | 7 | 11.5 | 68 | 107.7 |
| 16 | 7 | 11.7 | 74 | 136.8 |
| 17 | 6 | 10.3 | 76 | 127.9 |
| 18 | 8 | 13.4 | 63 | 101.8 |
| 19 | 6 | 9.4 | 82 | 145.4 |
| 20 | 7 | 11.1 | 72 | 121.8 |
| 21 | 7 | 13.4 | 64 | 111.4 |
| 22 | 6 | 9.2 | 85 | 140.3 |
| X | 8 | 13.2 | 63 | 99.0 |
| Y | 8 | 29.2 | 62 | 223.7 |

| Primer name | Assay | Genomic Target | Primer sequence |
|---|---|---|---|
| Sp-EMX1-F | SURVEYOR assay, sequencing | *EMX1* | AAAACCACCCTTCTCTCTGGC |
| Sp-EMX1-R | SURVEYOR assay, sequencing | *EMX1* | GGAGATTGGAGACACGGAGAG |
| Sp-PVALB-F | SURVEYOR assay, sequencing | *PVALB* | CTGGAAAGCCAATGCCTGAC |
| Sp-PVALB-R | SURVEYOR assay, sequencing | *PVALB* | GGCAGCAAACTCCTTGTCCT |
| Sp-Th-F | SURVEYOR assay, sequencing | *Th* | GTGCTTTGCAGAGGCCTACC |
| Sp-Th-R | SURVEYOR assay, sequencing | *Th* | CCTGGAGCGCATGCAGTAGT |
| St-EMX1-F | SURVEYOR assay, sequencing | *EMX1* | ACCTTCTGTGTTTCCACCATTC |
| St-EMX1-R | SURVEYOR assay, sequencing | *EMX1* | TTGGGGAGTGCACAGACTTC |
| Sp-EMX1-RFLP-F | RFLP, sequencing | *EMX1* | GGCTCCCTGGGTTCAAAGTA |
| Sp-EMX1-RFLP-R | RFLP, sequencing | *EMX1* | AGAGGGGTCTGGATGTCGTAA |
| Pb_EMX1_sp1 | Northern Blot Probe | Not applicable | TAGCTCTAAAACTTCTTCTTCTGCTCGGAC |
| Pb_tracrRNA | Northern Blot Probe | Not applicable | CTAGCCTTATTTTAACTTGCTATGCTGTTT |

FIG. 15 hSpCas9

```
5'  CTGGAAGAGTCCTTCCTGGTGGAAGAGGATAAGAAGCACGAGCGGCACCCCATCTTCGGC  360
     L   E   E   S   F   L   V   E   E   D   K   K   H   E   R   H   P   I   F   G
    101 102 103 104 105 106 107 108 109 110 111 112 113 114 115 116 117 118 119 120

5'  AACATCGTGGACGAGGTGGCCTACCACGAGAAGTACCCCACCATCTACCACCTGAGAAAG  420
     N   I   V   D   E   V   A   Y   H   E   K   Y   P   T   I   Y   H   L   R   K
    121 122 123 124 125 126 127 128 129 130 131 132 133 134 135 136 137 138 139 140

5'  AAACTGGTGGACAGCACCGACAAGGCCGACCTGCGGCTGATCTATCTGGCCCTGGCCCAC  480
     K   L   V   D   S   T   D   K   A   D   L   R   L   I   Y   L   A   L   A   H
    141 142 143 144 145 146 147 148 149 150 151 152 153 154 155 156 157 158 159 160

5'  ATGATCAAGTTCCGGGGCCACTTCCTGATCGAGGGCGACCTGAACCCCGACAACAGCGAC  540
     M   I   K   F   R   G   H   F   L   I   E   G   D   L   N   P   D   N   S   D
    161 162 163 164 165 166 167 168 169 170 171 172 173 174 175 176 177 178 179 180

5'  GTGGACAAGCTGTTCATCCAGCTGGTGCAGACCTACAACCAGCTGTTCGAGGAAAACCCC  600
     V   D   K   L   F   I   Q   L   V   Q   T   Y   N   Q   L   F   E   E   N   P
    181 182 183 184 185 186 187 188 189 190 191 192 193 194 195 196 197 198 199 200

5'  ATCAACGCCAGCGGCGTGGACGCCAAGGCTATCCTGTTTGCCAGACTGAGCAAGAGCAGA  660
     I   N   A   S   G   V   D   A   K   A   I   L   S   A   R   L   S   K   S   R
    201 202 203 204 205 206 207 208 209 210 211 212 213 214 215 216 217 218 219 220
```

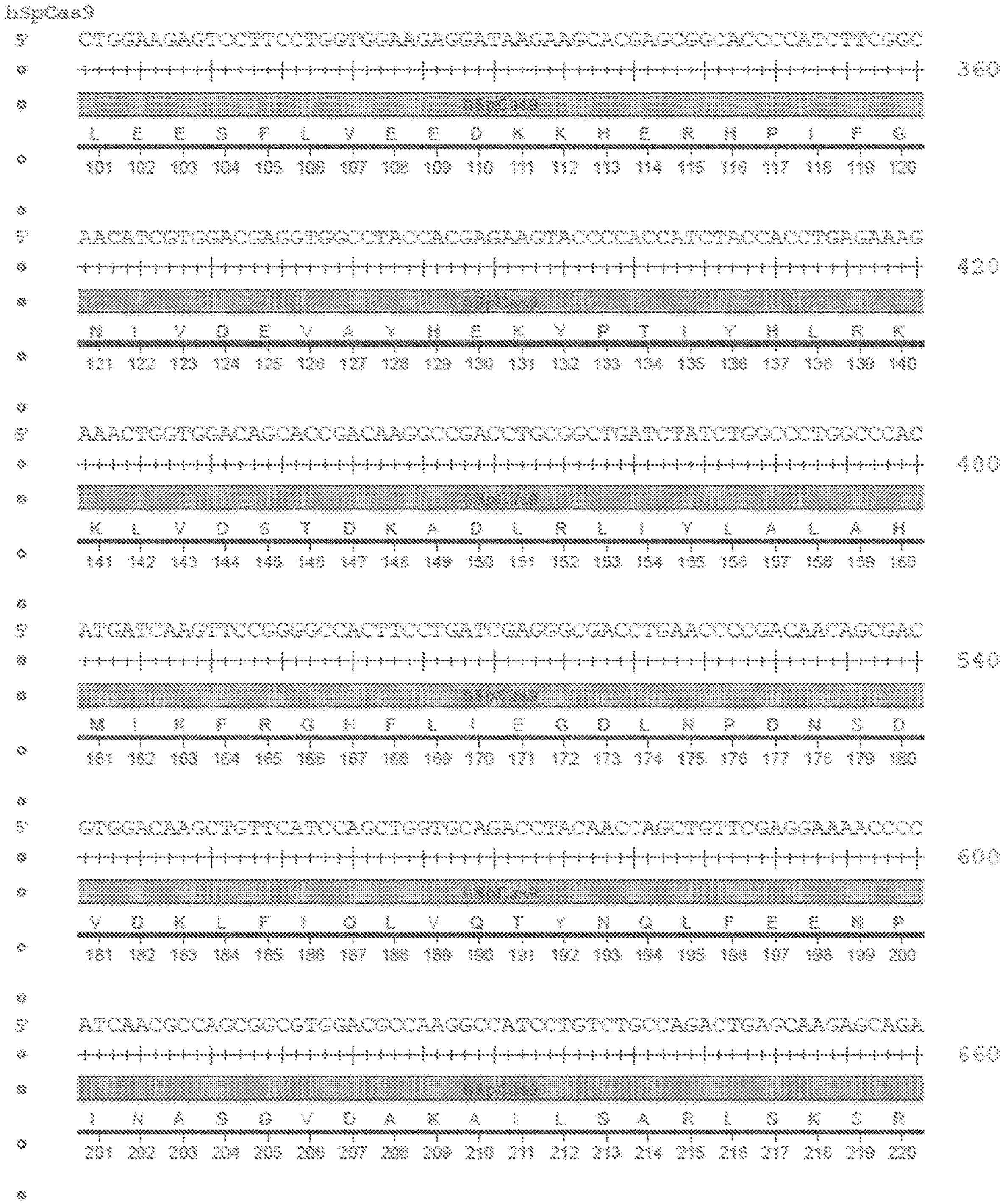

FIG. 24B hSpCas9

```
5' CAGCAGCTGCCTGAGAAGTACAAAGAGATTTTCTTCGACCAGAGCAAGAACGGCTACGCC
     Q  Q  L  P  E  K  Y  K  E  I  F  F  D  Q  S  K  N  G  Y  A
    341 342 343 344 345 346 347 348 349 350 351 352 353 354 355 356 357 358 359 360
```
1080

```
5' GGCTACATTGACGGCGGAGCCAGCCAGGAAGAGTTCTACAAGTTCATCAAGCCCATCCTG
     G  Y  I  D  G  G  A  S  Q  E  E  F  Y  K  F  I  K  P  I  L
    361 362 363 364 365 366 367 368 369 370 371 372 373 374 375 376 377 378 379 380
```
1140

```
5' GAAAAGATGGACGGCACCGAGGAACTGCTCGTGAAGCTGAACAGAGAGGACCTGCTGCGG
     E  K  M  D  G  T  E  E  L  L  V  K  L  N  R  E  D  L  L  R
    381 382 383 384 385 386 387 388 389 390 391 392 393 394 395 396 397 398 399 400
```
1200

```
5' AAGCAGCGGACCTTCGACAACGGCAGCATCCCCCACCAGATCCACTTGGGAGAGCTGCAC
     K  Q  R  T  F  D  N  G  S  I  P  H  Q  I  H  L  G  E  L  H
    401 402 403 404 405 406 407 408 409 410 411 412 413 414 415 416 417 418 419 420
```
1260

```
5' GCCATTCTGCGGCGGCAGGAAGATTTTTACCCATTCCTGAAGGACAACCGGGAAAAGATC
     A  I  L  R  R  Q  E  D  F  Y  P  F  L  K  D  N  R  E  K  I
    421 422 423 424 425 426 427 428 429 430 431 432 433 434 435 436 437 438 439 440
```
1320

```
5' GAGAAGATCCTGACCTTCCGCATCCCCTACTACGTGGGCCCTCTGGCCAGGGGAAACAGC
     E  K  I  L  T  F  R  I  P  Y  Y  V  G  P  L  A  R  G  N  S
    441 442 443 444 445 446 447 448 449 450 451 452 453 454 455 456 457 458 459 460
```
1380

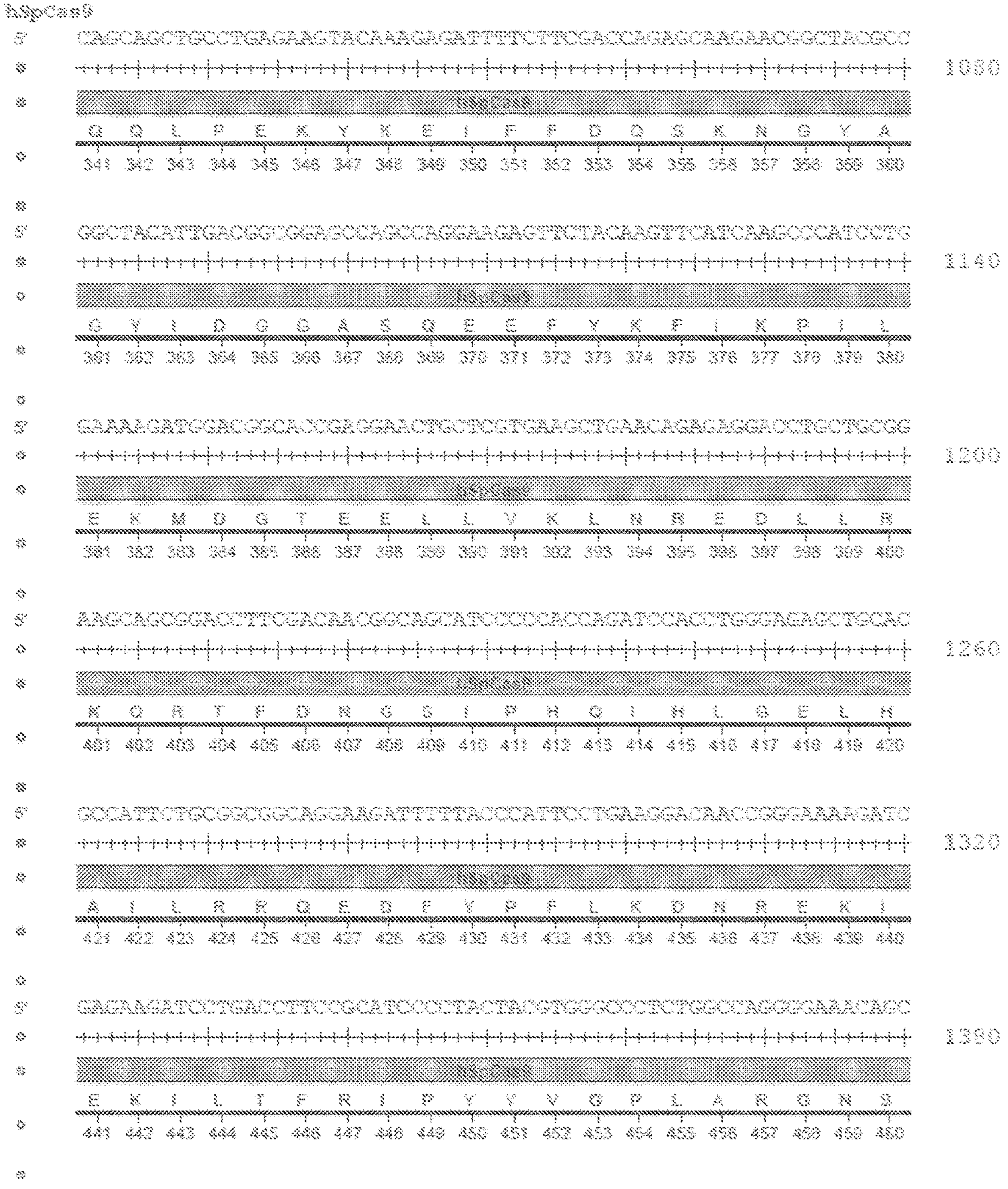

FIG. 24D hSpCas9

Figure 24E:
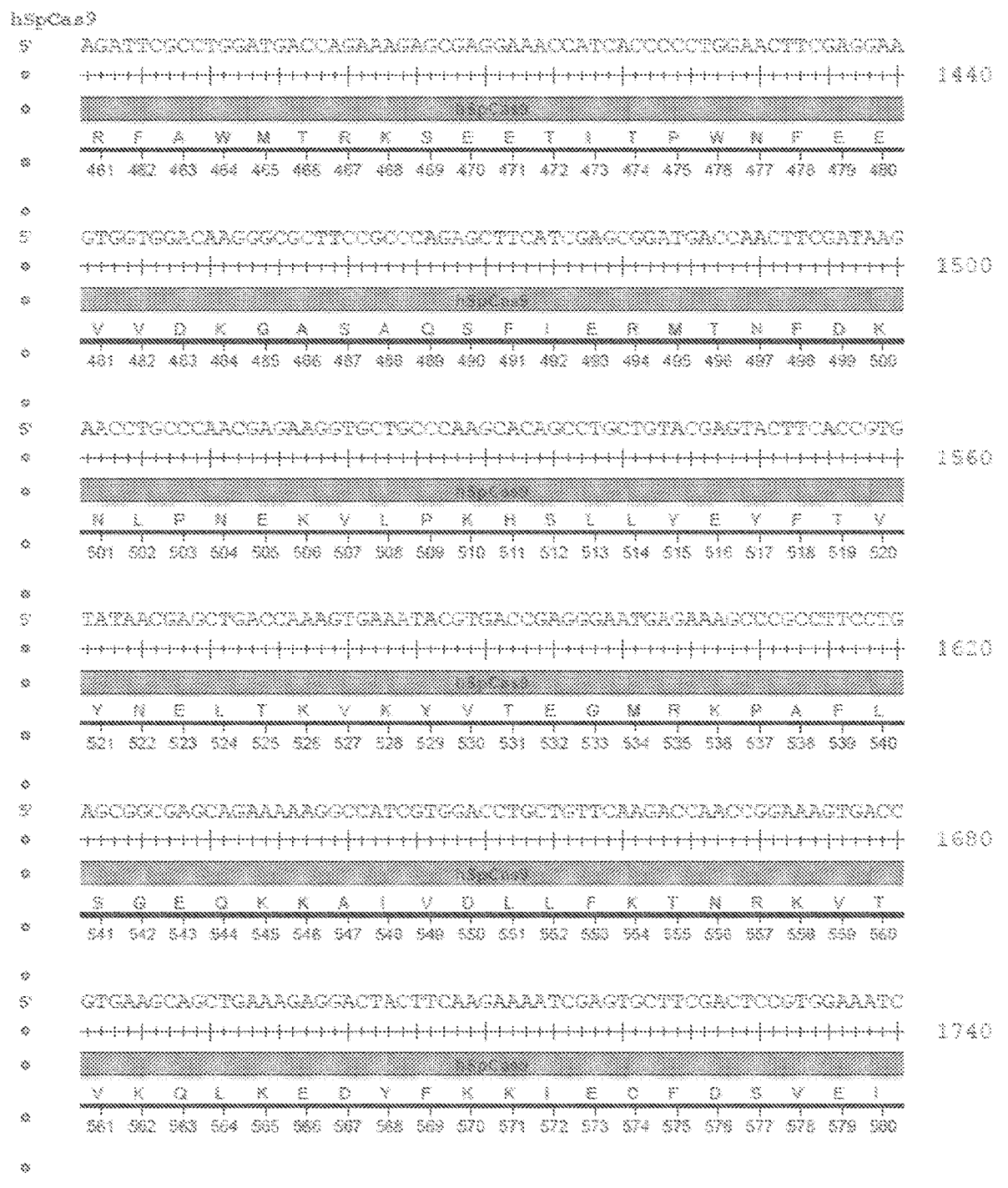

5' AGATTCGCCTGGATGACCAGAAAGAGCGAGGAAACCATCACCCCCTGGAACTTCGAGGAA 1440

R F A W M T R K S E E T I T P W N F E E 461 462 463 464 465 466 467 468 469 470 471 472 473 474 475 476 477 478 479 480

5' GTGGTGGACAAGGGCGCTTCCGCCCAGAGCTTCATCGAGCGGATGACCAACTTCGATAAG 1500

V V D K G A S A Q S F I E R M T N F D K 481 482 483 484 485 486 487 488 489 490 491 492 493 494 495 496 497 498 499 500

5' AACCTGCCCAACGAGAAGGTGCTGCCCAAGCACAGCCTGCTGTACGAGTACTTCACCGTG 1560

N L P N E K V L P K H S L L Y E Y F T V 501 502 503 504 505 506 507 508 509 510 511 512 513 514 515 516 517 518 519 520

5' TATAACGAGCTGACCAAAGTGAAATACGTGACCGAGGGAATGAGAAAGCCCGCCTTCCTG 1620

Y N E L T K V K Y V T E G M R K P A F L 521 522 523 524 525 526 527 528 529 530 531 532 533 534 535 536 537 538 539 540

5' AGCGGCGAGCAGAAAAAGGCCATCGTGGACCTGCTGTTCAAGACCAACCGGAAAGTGACC 1680

S G E Q K K A I V D L L F K T N R K V T 541 542 543 544 545 546 547 548 549 550 551 552 553 554 555 556 557 558 559 560

5' GTGAAGCAGCTGAAAGAGGACTACTTCAAGAAAATCGAGTGCTTCGACTCCGTGGAAATC 1740

V K Q L K E D Y F K K I E C F D S V E I 561 562 563 564 565 566 567 568 569 570 571 572 573 574 575 576 577 578 579 580

FIG. 24E hSpCas9

```
5' TCCGGCGTGAAGATCGGTTCAACGCCTCCCTGGGCACATACCACGATCTGCTGAAAATC
                                                              1800
    S  G  V  K  I  G  S  T  A  S  L  G  T  Y  H  D  L  L  K  I
   581 582 583 584 585 586 587 588 589 590 591 592 593 594 595 596 597 598 599 600

5' ATCAAGGACAAGGACTTCCTGGACAATGAGGAAAACGAGGACATTCTGGAAGATATCGTG
                                                              1860
    I  K  D  K  D  F  L  D  N  E  E  N  E  D  I  L  E  D  I  V
   601 602 603 604 605 606 607 608 609 610 611 612 613 614 615 616 617 618 619 620

5' CTGACCCTGACACTGTTTGAGGACAGAGAGATGATCGAGGAACGGCTGAAAACCTATGCC
                                                              1920
    L  T  L  T  L  F  E  D  R  E  M  I  E  E  R  L  K  T  Y  A
   621 622 623 624 625 626 627 628 629 630 631 632 633 634 635 636 637 638 639 640

5' CACCTGTTCGACGACAAAGTGATGAAGCAGCTGAAGCGGCGGAGATACACCGGCTGGGGC
                                                              1980
    H  L  F  D  D  K  V  M  K  Q  L  K  R  R  R  Y  T  G  W  G
   641 642 643 644 645 646 647 648 649 650 651 652 653 654 655 656 657 658 659 660

5' AGGCTGAGCCGGAAGCTGATCAACGGCATCCGGGACAAGCAGTCCGGCAAGACAATCCTG
                                                              2040
    R  L  S  R  K  L  I  N  G  I  R  D  K  Q  S  G  K  T  I  L
   661 662 663 664 665 666 667 668 669 670 671 672 673 674 675 676 677 678 679 680

5' GATTTCCTGAAGTCCGACGGCTTCGCCAACAGAAACTTCATGCAGCTGATCCACGACGAC
                                                              2100
    D  F  L  K  S  D  G  F  A  N  R  N  F  M  Q  L  I  H  D  D
   681 682 683 684 685 686 687 688 689 690 691 692 693 694 695 696 697 698 699 700
```

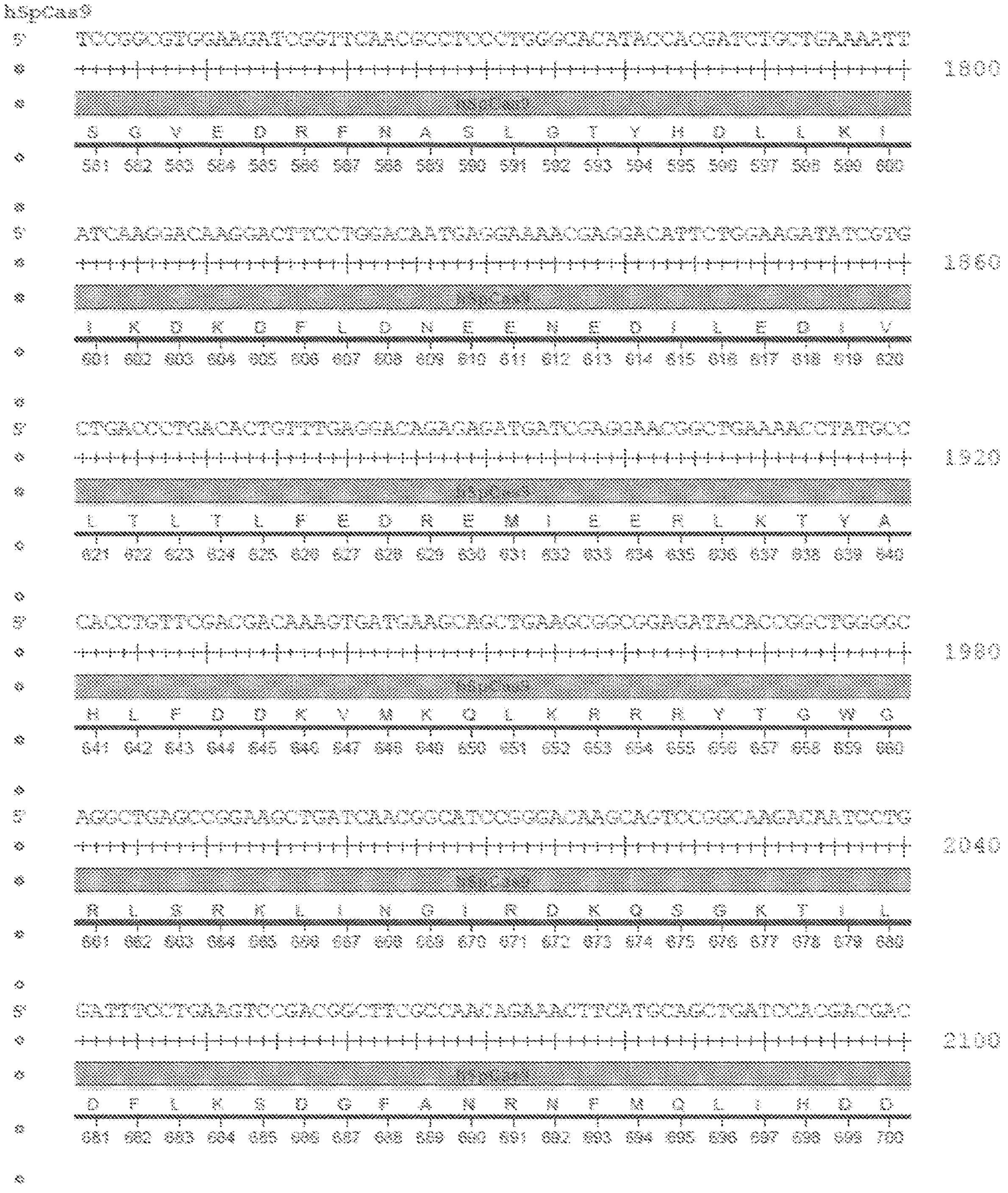

FIG. 24F

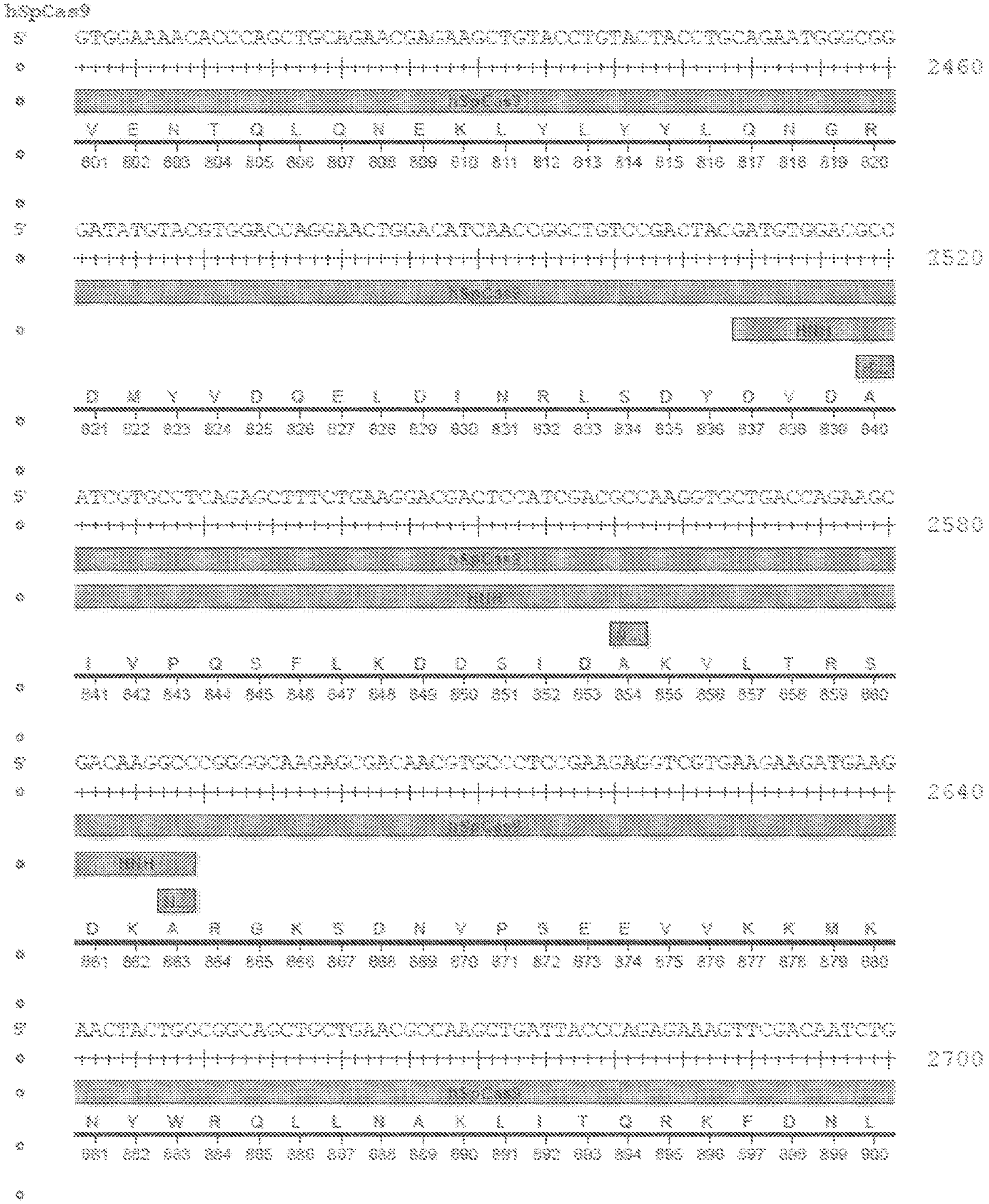

FIG. 24H hSpCas9

```
5' GTGGAAAACACCCAGCTGCAGAACGAGAAGCTGTACCTGTACTACCTGCAGAATGGCCGG
                                                              2460
   Y  E  N  T  Q  L  Q  N  E  K  L  Y  L  Y  Y  L  Q  N  G  R
   801 802 803 804 805 806 807 808 809 810 811 812 813 814 815 816 817 818 819 820

5' GATATGTACGTGGACCAGGAACTGGACATCAACCGGCTGTCCGACTACGATGTGGACGCC
                                                              2520
   D  M  Y  V  D  Q  E  L  D  I  N  R  L  S  D  Y  D  V  D  A
   821 822 823 824 825 826 827 828 829 830 831 832 833 834 835 836 837 838 839 840

5' ATCGTGCCTCAGAGCTTCCTGAAGGACGACTCCATCGACAACAAGGTGCTGACCAGAAGC
                                                              2580
   I  V  P  Q  S  F  L  K  D  D  S  I  D  N  K  V  L  T  R  S
   841 842 843 844 845 846 847 848 849 850 851 852 853 854 855 856 857 858 859 860

5' GACAAGGCCCGGGGCAAGAGCGACAACGTGCCCTCCGAAGAGGTCGTGAAGAAGATGAAG
                                                              2640
   D  K  A  R  G  K  S  D  N  V  P  S  E  E  V  V  K  K  M  K
   861 862 863 864 865 866 867 868 869 870 871 872 873 874 875 876 877 878 879 880

5' AACTACTGGCGGCAGCTGCTGAACGCCAAGCTGATTACCCAGAGAAAGTTCGACAATCTG
                                                              2700
   N  Y  W  R  Q  L  L  N  A  K  L  I  T  Q  R  K  F  D  N  L
   881 882 883 884 885 886 887 888 889 890 891 892 893 894 895 896 897 898 899 900
```

hSpCas9

```
5' GCCAGAAGAAGGACTGGGACCCTAAGAAGTACGGCGGCTTCGACAGCCCCACCGTGGCC 3420
    A  R  K  K  D  W  D  P  K  K  Y  G  G  F  D  S  P  T  V  A
   1121 1122 1123 1124 1125 1126 1127 1128 1129 1130 1131 1132 1133 1134 1135 1136 1137 1138 1139 1140

5' TATTCTGTGCTGGTGGTGGCCAAAGTGGAAAAGGGCAAGTCCAAGAAACTGAAGAGTGTG 3480
    Y  S  V  L  V  V  A  K  V  E  K  G  K  S  K  K  L  K  S  V
   1141 1142 1143 1144 1145 1146 1147 1148 1149 1150 1151 1152 1153 1154 1155 1156 1157 1158 1159 1160

5' AAAGAGCTGCTGGGGATCACCATCATGGAAAGAAGCAGCTTCGAGAAGAATCCCATCGAC 3540
    K  E  L  L  G  I  T  I  M  E  R  S  S  F  E  K  N  P  I  D
   1161 1162 1163 1164 1165 1166 1167 1168 1169 1170 1171 1172 1173 1174 1175 1176 1177 1178 1179 1180

5' TTCCTGGAAGCCAAGGGCTACAAAGAAGTGAAAAAGGACCTGATCATCAAGCTGCCTAAG 3600
    F  L  E  A  K  G  Y  K  E  V  K  K  D  L  I  I  K  L  P  K
   1181 1182 1183 1184 1185 1186 1187 1188 1189 1190 1191 1192 1193 1194 1195 1196 1197 1198 1199 1200

5' TACTCCCTGTTCGAGCTGGAAAACGGCCGGAAGAGAATGCTGGCCTCTGCCGGCGAACTG 3660
    Y  S  L  F  E  L  E  N  G  R  K  R  M  L  A  S  A  G  E  L
   1201 1202 1203 1204 1205 1206 1207 1208 1209 1210 1211 1212 1213 1214 1215 1216 1217 1218 1219 1220

5' CAGAAGGGAAACGAACTGGCCCTGCCCTCCAAATATGTGAACTTCCTGTACCTGGCCAGC 3720
    Q  K  G  N  E  L  A  L  P  S  K  Y  V  N  F  L  Y  L  A  S
   1221 1222 1223 1224 1225 1226 1227 1228 1229 1230 1231 1232 1233 1234 1235 1236 1237 1238 1239 1240
```

Conditional Cas9, Rosa26 targeting vector map

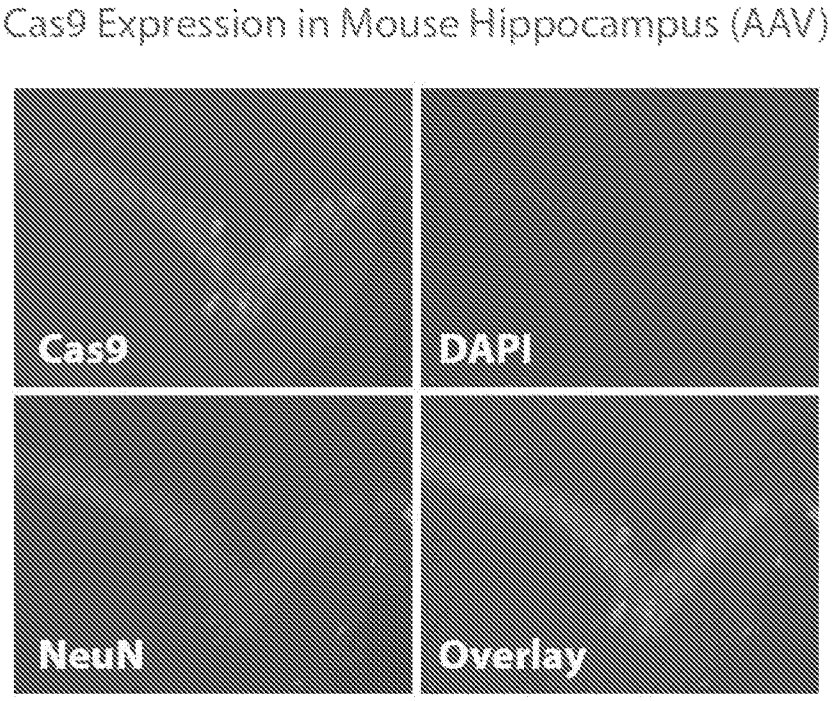
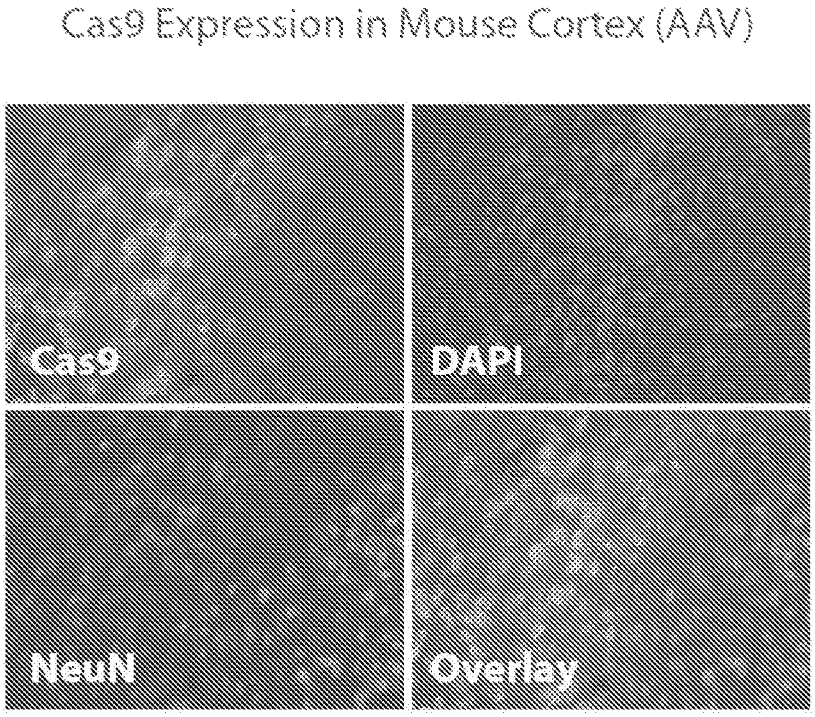
FIG. 27

GFP DNA
GFP RNA

Icam2
Sp1
Sp2
Untransfected

F7
Sp1
Sp2
Untransfected

HDR-Fwd
HDR-Rev
Genomic locus
HDR
HindIII
Plasmid repair template
1 kb
1 kb
PCR amplification
or
ssODN repair template
sense (s) 5' 3'
HindIII digest
antisense (a) 3' 5'
90 bp 90 bp Target
PAM
Genomic locus
Left arm (90 bp)
Insert (12 bp)
Right arm (90 bp)
(s)
ssODN repair template
HindIII
or
(a)

HEK
HUES9
Repair template:
ssODN (s)
ssODN (a)
Plasmid
Cas9:
WT D10A –
HDR (%):
30 2.4
27 1.0
4.3 0.18
2.2
6.0

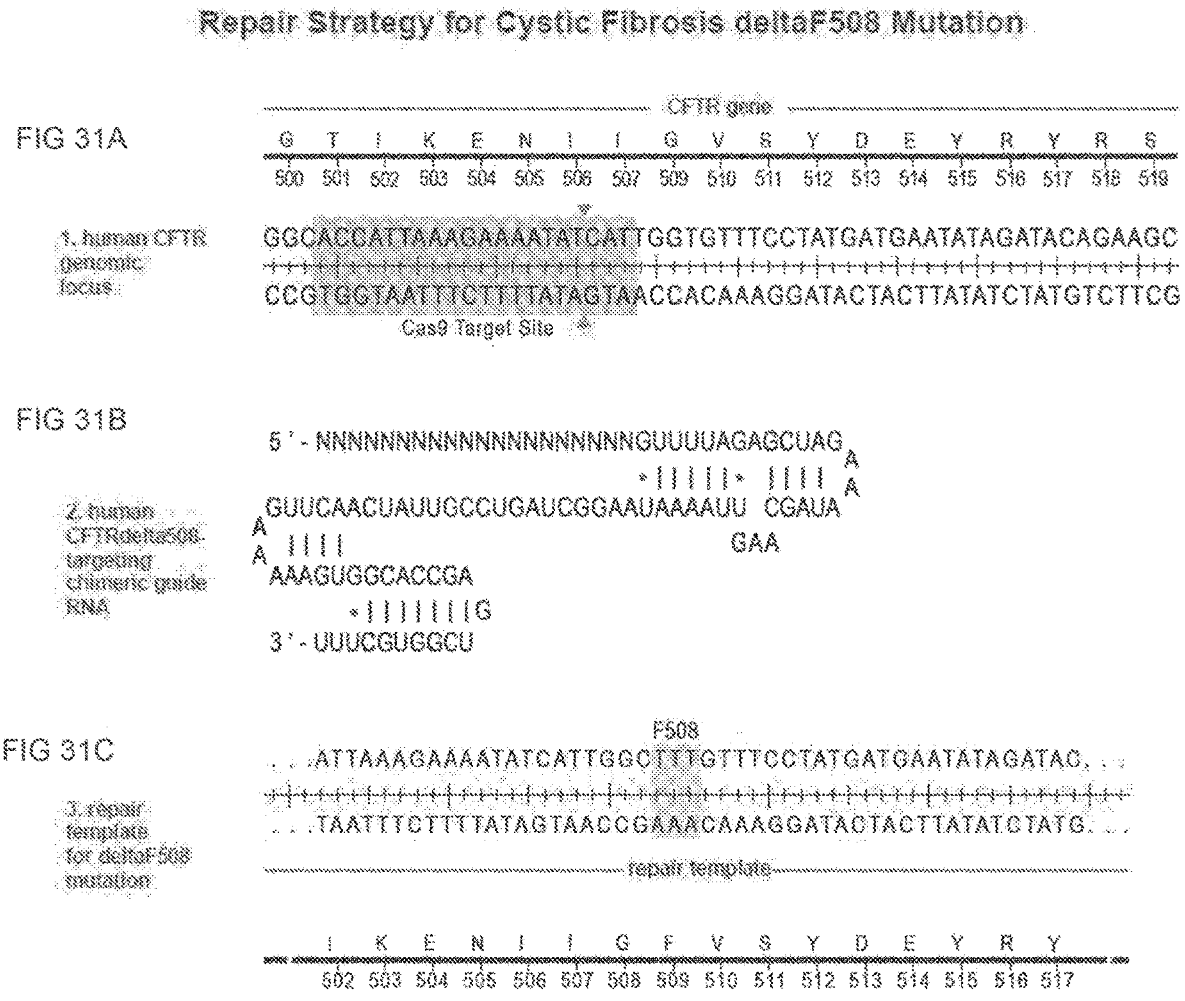
Repair Strategy for Cystic Fibrosis deltaF508 Mutation
FIG 31A
CFTR gene
G T I K E N I I G V S Y D E Y R Y R S
500 501 502 503 504 505 506 507 509 510 511 512 513 514 515 516 517 518 519
1. human CFTR genomic locus
GGCACCATTAAAGAAAATATCATTGGTGTTTCCTATGATGAATATAGATACAGAAGC
CCGTGGTAATTTCTTTTATAGTAACCACAAAGGATACTACTTATATCTATGTCTTCG
Cas9 Target Site
FIG 31B
2. human CFTRdelta508-targeting chimeric guide RNA
5'-NNNNNNNNNNNNNNNNNNNNGUUUUAGAGCUAG
GUUCAACUAUUGCCUGAUCGGAAUAAAAUU CGAUA
GAA
AAAGUGGCACCGA
3'-UUUCGUGGCU
FIG 31C
F508
...ATTAAAGAAAATATCATTGGCTTTGTTTCCTATGATGAATATAGATAC...
...TAATTTCTTTTATAGTAACCGAAACAAAGGATACTACTTATATCTATG...
3. repair template for deltaF508 mutation
repair template
I K E N I I G F V S Y D E Y R Y
502 503 504 505 506 507 508 509 510 511 512 513 514 515 516 517

| | pattern | overhang |
|---|---|---|
| 1 | CCnNNNNNNNNNNNNNNNNNnnnnnnnnnnnnNNNNNNNNNNNNNNNNNNnGG | 38 |
| 2 | CCnNNNNNNNNNNNNNNNNNnnnnnnnnNNNNNNNNNNNNNNNNNNnGG | 34 |
| 3 | CCnNNNNNNNNNNNNNNNNNnnnnNNNNNNNNNNNNNNNNNNnGG | 30 |
| 4 | CCnNNNNNNNNNNNNNNNNNNNNNNNNNNNNNNNnGG | 26 |
| 5 | CCnNNNNNNNNNNNNNNNNNNNNNNNNNNNNNnGG | 22 |
| 6 | CCnNNNNNNNNNNNNNNNNNNNNNNNNNnGG | 18 |
| 7 | CCnNNNNNNNNNNNNNNNNNNNNNnGG | 14 |
| 8 | CCnNNNNNNNNNNNNNNNNnGG | 10 |
| 9 | CCnNNNNNNNNNNNNnGG | 6 |
| 10 | CCnNNNNNNNNNNnGG | 4 |
| 11 | CCnNNNNNNNNNnGG | 3 |
| 12 | CCnNNNNNNNNnGG | 2 |
| 13 | CCnNNNNNNNnGG | 1 |
| 14 | CCnNNNNNNnGG | 0 |
| 15 | CCnNNNNNnGG | 1 |
| 16 | CCnNNNNnGG | 2 |
| 17 | CCnNNNnGG | 3 |
| 18 | CCnnGG | 4 |
| 19 | CCGG | 8 |
| 20 | GGCC | 10 |
| 21 | GGNNCC | 12 |
| 22 | GGNNNCC | 14 |
| 23 | GGNNNNCC | 16 |
| 24 | GGNNNNNNNNCC | 20 |

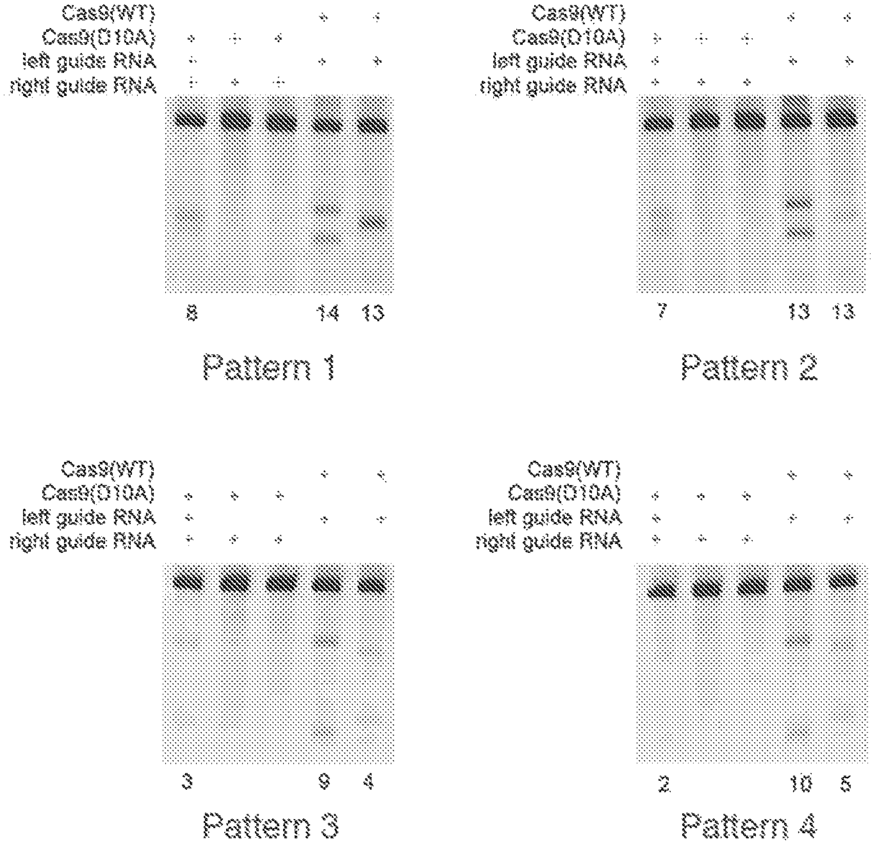

FIG. 51

Reverse PCR primers for generating U6-guide RNA expression Cassette (pair with U6 forward primer)

| | | |
|---|---|---|
| F20260 | AAAAAAAGCACCGACTCGGTGCCACTTTTTCAAGTTGATAACGGACTAGCCTTATTTTAACTTGCTATTTCTAGCTCTAAAACTCACATCAACCGGTGGCGCAGGTGTTTCGTCCTTTCCACAAG | Left guide RNA 1 |
| F20261 | AAAAAAAGCACCGACTCGGTGCCACTTTTTCAAGTTGATAACGGACTAGCCTTATTTTAACTTGCTATTTCTAGCTCTAAAACTCACATCAACCGGTGGCGCAGGTGTTTCGTCCTTTCCACAAG | Left guide RNA 2 |
| F20262 | AAAAAAAGCACCGACTCGGTGCCACTTTTTCAAGTTGATAACGGACTAGCCTTATTTTAACTTGCTATTTCTAGCTCTAAAACGAGGACAAAGTACAAACGGCGGTGTTTCGTCCTTTCCACAAG | Left guide RNA 3 |
| F20263 | AAAAAAAGCACCGACTCGGTGCCACTTTTTCAAGTTGATAACGGACTAGCCTTATTTTAACTTGCTATTTCTAGCTCTAAAACGAGGACAAAGTACAAACGGCGGTGTTTCGTCCTTTCCACAAG | Left guide RNA 4 |
| F20264 | AAAAAAAGCACCGACTCGGTGCCACTTTTTCAAGTTGATAACGGACTAGCCTTATTTTAACTTGCTATTTCTAGCTCTAAAACGTGGGCATTGCCACGAAGCGGTGTTTCGTCCTTTCCACAAG | Left guide RNA 5 |
| F20265 | AAAAAAAGCACCGACTCGGTGCCACTTTTTCAAGTTGATAACGGACTAGCCTTATTTTAACTTGCTATTTCTAGCTCTAAAACGGACGGCAGAGTGCTGCTTGGGTGTTTCGTCCTTTCCACAAG | Left guide RNA 6 |
| F20266 | AAAAAAAGCACCGACTCGGTGCCACTTTTTCAAGTTGATAACGGACTAGCCTTATTTTAACTTGCTATTTCTAGCTCTAAAACGAGTCCGAGCAGAAGAAGAAGGTGTTTCGTCCTTTCCACAAG | Left guide RNA 7 |
| F20267 | AAAAAAAGCACCGACTCGGTGCCACTTTTTCAAGTTGATAACGGACTAGCCTTATTTTAACTTGCTATTTCTAGCTCTAAAACGAGGACAAAGTACAAACGGCGGTGTTTCGTCCTTTCCACAAG | Left guide RNA 8 |
| F20268 | AAAAAAAGCACCGACTCGGTGCCACTTTTTCAAGTTGATAACGGACTAGCCTTATTTTAACTTGCTATTTCTAGCTCTAAAACAGCAGAAGAAGAAGGCTCCGGTGTTTCGTCCTTTCCACAAG | Left guide RNA 9 |
| F20269 | AAAAAAAGCACCGACTCGGTGCCACTTTTTCAAGTTGATAACGGACTAGCCTTATTTTAACTTGCTATTTCTAGCTCTAAAACTCACATCAACCGGTGGCGCAGGTGTTTCGTCCTTTCCACAAG | Left guide RNA 10 |
| F20270 | AAAAAAAGCACCGACTCGGTGCCACTTTTTCAAGTTGATAACGGACTAGCCTTATTTTAACTTGCTATTTCTAGCTCTAAAACCCCTGGCCCAGGTGAAGCTGGGTGTTTCGTCCTTTCCACAAG | Left guide RNA 11 |
| F20271 | AAAAAAAGCACCGACTCGGTGCCACTTTTTCAAGTTGATAACGGACTAGCCTTATTTTAACTTGCTATTTCTAGCTCTAAAACTCCCTCCCTGGCCCAGGTGAAGGTGTTTCGTCCTTTCCACAAG | Left guide RNA 12 |
| F20272 | AAAAAAAGCACCGACTCGGTGCCACTTTTTCAAGTTGATAACGGACTAGCCTTATTTTAACTTGCTATTTCTAGCTCTAAAACGAACCGGAGGACAAAGTACAGGTGTTTCGTCCTTTCCACAAG | Left guide RNA 13 |
| F20273 | AAAAAAAGCACCGACTCGGTGCCACTTTTTCAAGTTGATAACGGACTAGCCTTATTTTAACTTGCTATTTCTAGCTCTAAAACAGGTGAAGGTGTGGTTCCAGGGTGTTTCGTCCTTTCCACAAG | Left guide RNA 14 |
| F20274 | AAAAAAAGCACCGACTCGGTGCCACTTTTTCAAGTTGATAACGGACTAGCCTTATTTTAACTTGCTATTTCTAGCTCTAAAACGGTGAAGGTGTGGTTCCAGAGGTGTTTCGTCCTTTCCACAAG | Left guide RNA 15 |
| F20275 | AAAAAAAGCACCGACTCGGTGCCACTTTTTCAAGTTGATAACGGACTAGCCTTATTTTAACTTGCTATTTCTAGCTCTAAAACGAACCGGAGGACAAAGTACAGGTGTTTCGTCCTTTCCACAAG | Left guide RNA 16 |
| F20276 | AAAAAAAGCACCGACTCGGTGCCACTTTTTCAAGTTGATAACGGACTAGCCTTATTTTAACTTGCTATTTCTAGCTCTAAAACCCCTGGCCCAGGTGAAGGTGGGTGTTTCGTCCTTTCCACAAG | Left guide RNA 17 |
| F20277 | AAAAAAAGCACCGACTCGGTGCCACTTTTTCAAGTTGATAACGGACTAGCCTTATTTTAACTTGCTATTTCTAGCTCTAAAACAGGTGAAGGTGTGGTTCCAGGGTGTTTCGTCCTTTCCACAAG | Left guide RNA 18 |
| F20278 | AAAAAAAGCACCGACTCGGTGCCACTTTTTCAAGTTGATAACGGACTAGCCTTATTTTAACTTGCTATTTCTAGCTCTAAAACGAGGACAAAGTACAAACGGCGGTGTTTCGTCCTTTCCACAAG | Left guide RNA 19 |
| F20279 | AAAAAAAGCACCGACTCGGTGCCACTTTTTCAAGTTGATAACGGACTAGCCTTATTTTAACTTGCTATTTCTAGCTCTAAAACGGGAGGGCAGGGGCACAGATGGGTGTTTCGTCCTTTCCACAAG | Left guide RNA 20 |
| F20280 | AAAAAAAGCACCGACTCGGTGCCACTTTTTCAAGTTGATAACGGACTAGCCTTATTTTAACTTGCTATTTCTAGCTCTAAAACCACCTTCACCTGGGCCAGGCGGGTGTTTCGTCCTTTCCACAAG | Left guide RNA 21 |
| F20281 | AAAAAAAGCACCGACTCGGTGCCACTTTTTCAAGTTGATAACGGACTAGCCTTATTTTAACTTGCTATTTCTAGCTCTAAAACGACCCTAGTCATTGGAGGTGAGGTGTTTCGTCCTTTCCACAAG | Left guide RNA 22 |
| F20282 | AAAAAAAGCACCGACTCGGTGCCACTTTTTCAAGTTGATAACGGACTAGCCTTATTTTAACTTGCTATTTCTAGCTCTAAAACCAGAGCAGCCACTGGGGCCTGGGTGTTTCGTCCTTTCCACAAG | Left guide RNA 23 |
| F20283 | AAAAAAAGCACCGACTCGGTGCCACTTTTTCAAGTTGATAACGGACTAGCCTTATTTTAACTTGCTATTTCTAGCTCTAAAACCACCTTCACCTGGGCCAGGCGGGTGTTTCGTCCTTTCCACAAG | Left guide RNA 24 |
| F20284 | AAAAAAAGCACCGACTCGGTGCCACTTTTTCAAGTTGATAACGGACTAGCCTTATTTTAACTTGCTATTTCTAGCTCTAAAACCCCCATTGGCCTGCTTCGTGGGTGTTTCGTCCTTTCCACAAG | Right guide RNA 1 |
| F20285 | AAAAAAAGCACCGACTCGGTGCCACTTTTTCAAGTTGATAACGGACTAGCCTTATTTTAACTTGCTATTTCTAGCTCTAAAACATTGGCCTGCTTCGTGCAAGGTGTTTCGTCCTTTCCACAAG | Right guide RNA 2 |
| F20286 | AAAAAAAGCACCGACTCGGTGCCACTTTTTCAAGTTGATAACGGACTAGCCTTATTTTAACTTGCTATTTCTAGCTCTAAAACTCCTCCTCCAGGTTCTGCCGGGTGTTTCGTCCTTTCCACAAG | Right guide RNA 3 |
| F20287 | AAAAAAAGCACCGACTCGGTGCCACTTTTTCAAGTTGATAACGGACTAGCCTTATTTTAACTTGCTATTTCTAGCTCTAAAACCCTCCAGGTTCTGCCGTTTGGGTGTTTCGTCCTTTCCACAAG | Right guide RNA 4 |
| F20288 | AAAAAAAGCACCGACTCGGTGCCACTTTTTCAAGTTGATAACGGACTAGCCTTATTTTAACTTGCTATTTCTAGCTCTAAAACATTGGCCTGCTTCGTGCAAGGTGTTTCGTCCTTTCCACAAG | Right guide RNA 5 |
| F20289 | AAAAAAAGCACCGACTCGGTGCCACTTTTTCAAGTTGATAACGGACTAGCCTTATTTTAACTTGCTATTTCTAGCTCTAAAACGCAGCAAGGAGCACTCTGCCGGTGTTTCGTCCTTTCCACAAG | Right guide RNA 6 |
| F20290 | AAAAAAAGCACCGACTCGGTGCCACTTTTTCAAGTTGATAACGGACTAGCCTTATTTTAACTTGCTATTTCTAGCTCTAAAACTTCTTCTTCTGCTCGGACTCGGTGTTTCGTCCTTTCCACAAG | Right guide RNA 7 |
| F20291 | AAAAAAAGCACCGACTCGGTGCCACTTTTTCAAGTTGATAACGGACTAGCCTTATTTTAACTTGCTATTTCTAGCTCTAAAACACCGGAGGACAAAGTACAAAGGTGTTTCGTCCTTTCCACAAG | Right guide RNA 8 |
| F20292 | AAAAAAAGCACCGACTCGGTGCCACTTTTTCAAGTTGATAACGGACTAGCCTTATTTTAACTTGCTATTTCTAGCTCTAAAACTCTTCTTCTGCTCGGACTCAGGTGTTTCGTCCTTTCCACAAG | Right guide RNA 9 |
| F20293 | AAAAAAAGCACCGACTCGGTGCCACTTTTTCAAGTTGATAACGGACTAGCCTTATTTTAACTTGCTATTTCTAGCTCTAAAACGTTGATGTGATGGGAGCGCTGGGTGTTTCGTCCTTTCCACAAG | Right guide RNA 10 |
| F20294 | AAAAAAAGCACCGACTCGGTGCCACTTTTTCAAGTTGATAACGGACTAGCCTTATTTTAACTTGCTATTTCTAGCTCTAAAACGGGCCAGGGAGGGGAGGGCAGGTGTTTCGTCCTTTCCACAAG | Right guide RNA 11 |
| F20295 | AAAAAAAGCACCGACTCGGTGCCACTTTTTCAAGTTGATAACGGACTAGCCTTATTTTAACTTGCTATTTCTAGCTCTAAAACGGGAGGGCAGGGGCACAGATGGGTGTTTCGTCCTTTCCACAAG | Right guide RNA 12 |
| F20296 | AAAAAAAGCACCGACTCGGTGCCACTTTTTCAAGTTGATAACGGACTAGCCTTATTTTAACTTGCTATTTCTAGCTCTAAAACCCGGTTCTGGAAGCACAGCTGGTGTTTCGTCCTTTCCACAAG | Right guide RNA 13 |
| F20297 | AAAAAAAGCACCGACTCGGTGCCACTTTTTCAAGTTGATAACGGACTAGCCTTATTTTAACTTGCTATTTCTAGCTCTAAAACTCACCTGGGCCAGGGAGGGCAGGTGTTTCGTCCTTTCCACAAG | Right guide RNA 14 |
| F20298 | AAAAAAAGCACCGACTCGGTGCCACTTTTTCAAGTTGATAACGGACTAGCCTTATTTTAACTTGCTATTTCTAGCTCTAAAACTCACCTGGGCCAGGGAGGGGAGGTGTTTCGTCCTTTCCACAAG | Right guide RNA 15 |
| F20299 | AAAAAAAGCACCGACTCGGTGCCACTTTTTCAAGTTGATAACGGACTAGCCTTATTTTAACTTGCTATTTCTAGCTCTAAAACGTTCTGGAAGCACAGCTTCAGGTGTTTCGTCCTTTCCACAAG | Right guide RNA 16 |
| F20300 | AAAAAAAGCACCGACTCGGTGCCACTTTTTCAAGTTGATAACGGACTAGCCTTATTTTAACTTGCTATTTCTAGCTCTAAAACGGGAGGGGAGGGGCACAGATGGGTGTTTCGTCCTTTCCACAAG | Right guide RNA 17 |
| F20301 | AAAAAAAGCACCGACTCGGTGCCACTTTTTCAAGTTGATAACGGACTAGCCTTATTTTAACTTGCTATTTCTAGCTCTAAAACGCGGCGAGGGAGCGAGGGCAGGTGTTTCGTCCTTTCCACAAG | Right guide RNA 18 |
| F20302 | AAAAAAAGCACCGACTCGGTGCCACTTTTTCAAGTTGATAACGGACTAGCCTTATTTTAACTTGCTATTTCTAGCTCTAAAACGTTCTGGAAGCACAGCTTCAGGTGTTTCGTCCTTTCCACAAG | Right guide RNA 19 |
| F20303 | AAAAAAAGCACCGACTCGGTGCCACTTTTTCAAGTTGATAACGGACTAGCCTTATTTTAACTTGCTATTTCTAGCTCTAAAACAGGTGAAGGTGTGGTTCCAGGGTGTTTCGTCCTTTCCACAAG | Right guide RNA 20 |
| F20304 | AAAAAAAGCACCGACTCGGTGCCACTTTTTCAAGTTGATAACGGACTAGCCTTATTTTAACTTGCTATTTCTAGCTCTAAAACGAACCGGAGGACAAAGTACAGGTGTTTCGTCCTTTCCACAAG | Right guide RNA 21 |
| F20305 | AAAAAAAGCACCGACTCGGTGCCACTTTTTCAAGTTGATAACGGACTAGCCTTATTTTAACTTGCTATTTCTAGCTCTAAAACCAAACCCACCGAGGGCAGAGTGGGTGTTTCGTCCTTTCCACAAG | Right guide RNA 22 |
| F20306 | AAAAAAAGCACCGACTCGGTGCCACTTTTTCAAGTTGATAACGGACTAGCCTTATTTTAACTTGCTATTTCTAGCTCTAAAACGAGTTTCTCATCTGTGCCGCGGTGTTTCGTCCTTTCCACAAG | Right guide RNA 23 |
| F20307 | AAAAAAAGCACCGACTCGGTGCCACTTTTTCAAGTTGATAACGGACTAGCCTTATTTTAACTTGCTATTTCTAGCTCTAAAACGAGGACAAAGTACAAACGGCGGTGTTTCGTCCTTTCCACAAG | Right guide RNA 24 |

FIG. 52

| lane # | Cas9 to use | left gRNA | Right gRNA | Overhang (D10A) - number of bases protruding from 5' |
|---|---|---|---|---|
| 1 | D10A | left 23 | left 12 | -36 |
| 2 | D10A | right 4 | left 9 | -25 |
| 3 | D10A | left 23 | right 23 | -16 |
| 4 | D10A | right 7 | left 10 | -15 |
| 5 | D10A | right 16 | left 3 | -8 |
| 6 | D10A | right 22 | right 6 | 26 |
| 7 | D10A | left 12 | right 16 | 31 |
| 8 | D10A | left 12 | right 13 | 34 |
| 9 | D10A | left 10 | right 1 | 38 |
| 10 | D10A | right 23 | right 16 | 51 |
| 11 | D10A | right 23 | right 13 | 54 |
| 12 | D10A | left 3 | right 7 | 57 |
| 13 | D10A | left 12 | right 4 | 65 |
| 14 | D10A | left 12 | right 3 | 69 |
| 15 | D10A | left 3 | right 10 | 76 |
| 16 | D10A | right 23 | right 4 | 85 |
| 17 | D10A | left 12 | right 9 | 95 |
| 18 | D10A | left 12 | right 10 | 115 |
| 19 | D10A | right 23 | right 10 | 135 |
| 20 | D10A | left 12 | right 2 | 145 |
| 21 | D10A | left 12 | left 22 | 181 |
| 22 | D10A | right 23 | left 22 | 201 |
| 23 | D10A | left 12 | right 6 | 222 |
| 24 | D10A | right 23 | right 6 | 242 |

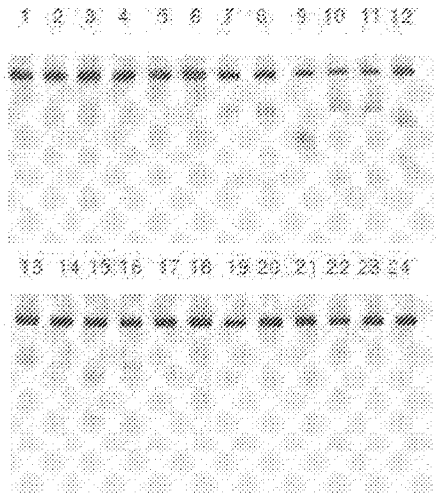

FIG. 54

```
                                    1              10              20              30
                                    |              |               |               |
                                    ╔══════════════════BMXF═══════════════════╗
hEMX1_TargetLocus_NGS(modi...       AAAACCACCCTTCTCTCTGGCCCACTGTGTCCT
Frame 1                              K  T  T  L  L  S  G  P  L  C  P
Complement                          TTTTGGTGGGAAGAGAGACCGGGTGACACAGGA

                                              160            170             180
                                               |              |               |
                                                            ╔═════left 25═══════════╗
hEMX1_TargetLocus_NGS(modi...       CAGCCTGAGTGTTGAGGCCCCAGTGGCTGCTCT
Frame 1                              S  A  *  V  L  R  P  Q  W  L  L
Complement                          GTCGGACTCACAACTCCGGGGTCACCGACGAGA

                                           310            320            330             340
                                            |              |              |               |
                                    ╔═▶right7═╗
                                    ╔═▶right9═══════╗╔══════right 10══════════╗
hEMX1_TargetLocus_NGS(modi...       GCAGAAGAAGAAGGGCTCCCATCACATCAACCG
Frame 1                              Q  K  K  K  G  S  H  H  I  N  R
Complement                          CGTCTTCTTCTTCCCGAGGGTAGTGTAGTTGGC
                                    ╚═left 7═══╝                    ╚═left 10═╝
                                    ╚══left 9════════╝

                                              470            480             490
                                               |              |               |
hEMX1_TargetLocus_NGS(modi...       TGGGCCCAAGCTGGACTCTGGCCACTCCCTGGC
Frame 1                              W  A  Q  A  G  L  W  F  L  P  G
Complement                          ACCCGGGTTCGACCTGAGACCGGTGAGGGACCG

                                              620            630             640
                                               |              |               |
hEMX1_TargetLocus_NGS(modi...       GCCTGCCTGCCTGGGCGGGCCCGCCCGCCACCG
Frame 1                              S  L  F  A  W  A  G  P  P  A  T
Complement                          CGGACGGACGGACCCGCCCGGGCGGGCGGTGGC
```

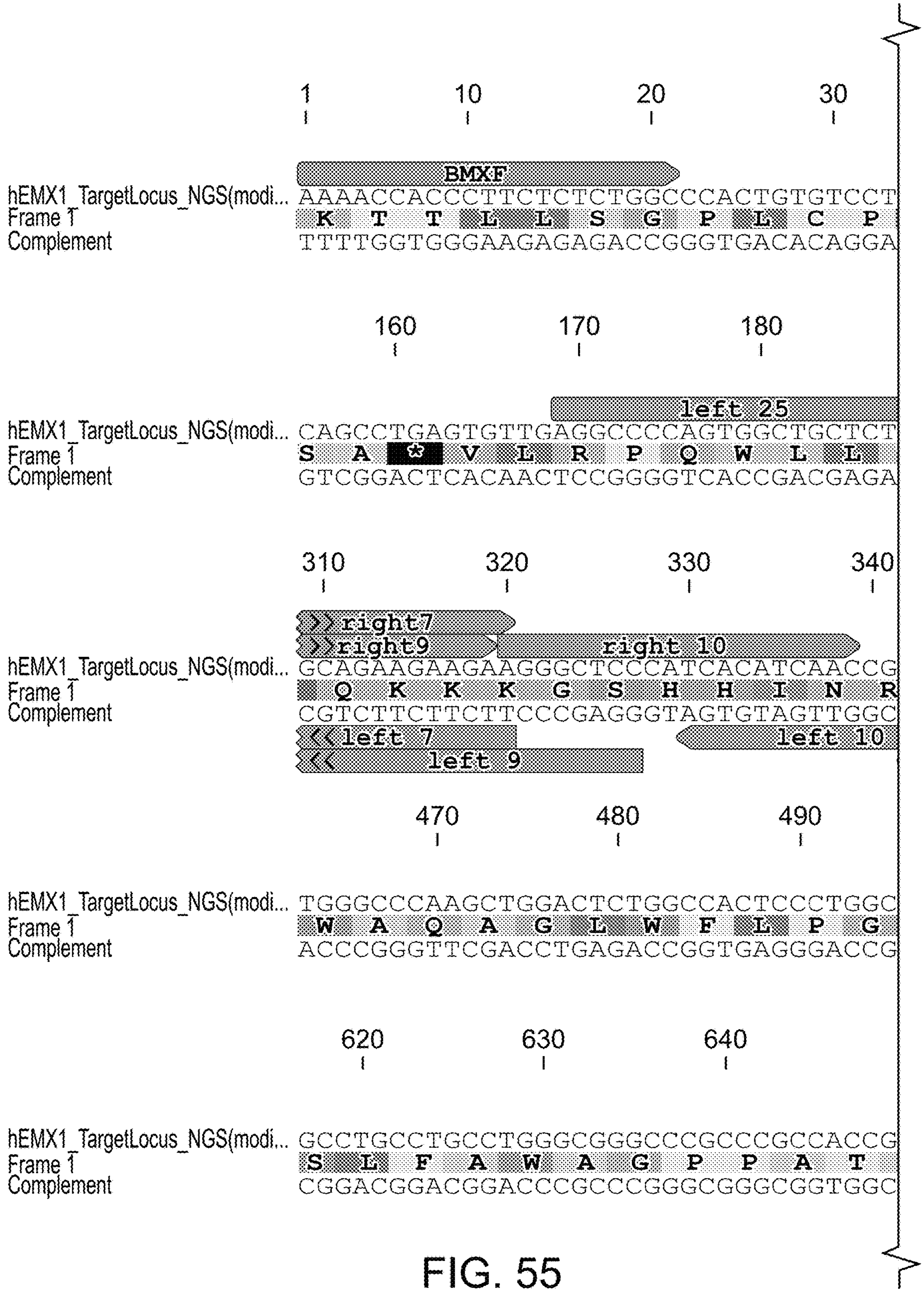

FIG. 55

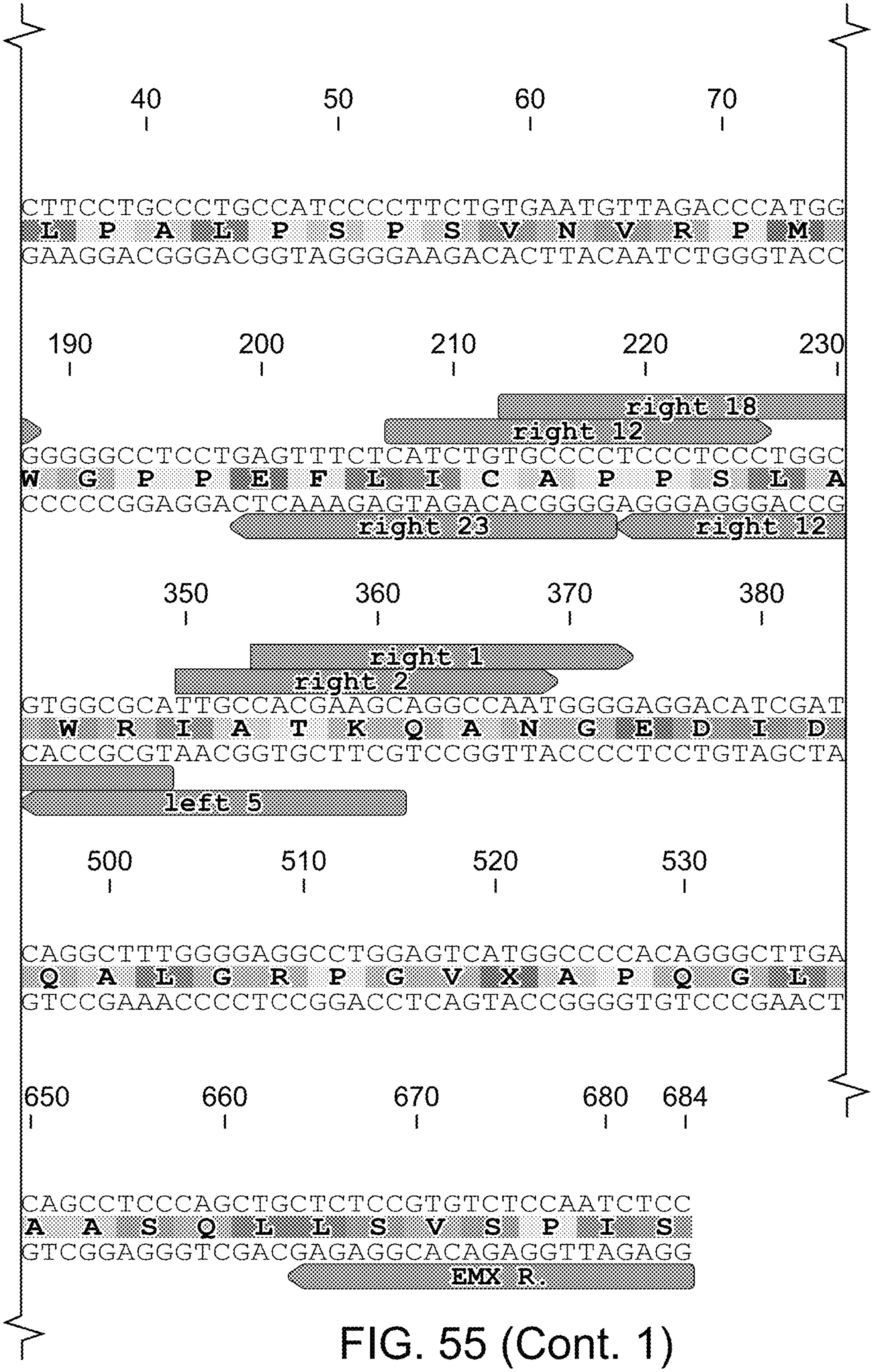
FIG. 55 (Cont. 1)

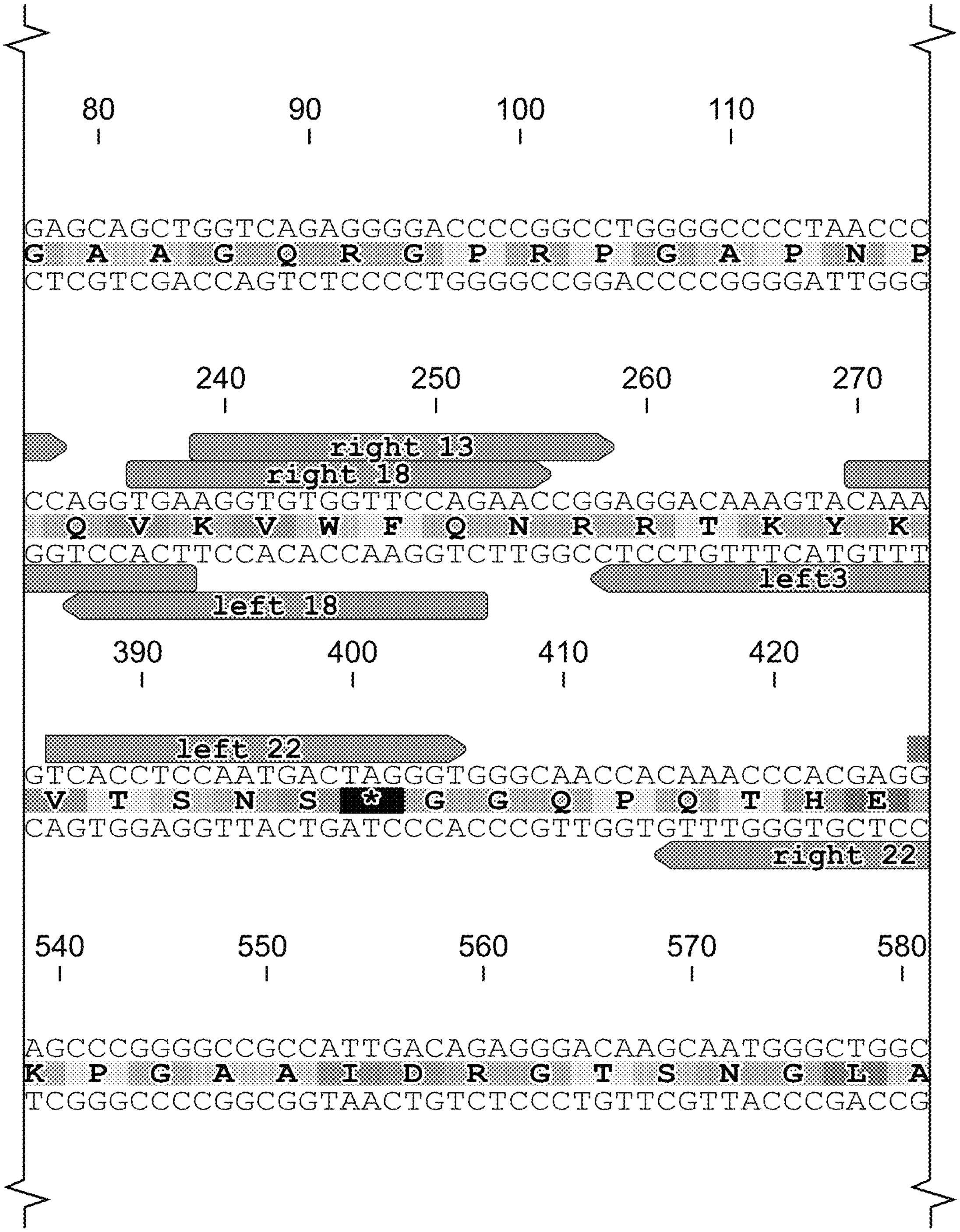
FIG. 55 (Cont. 2)

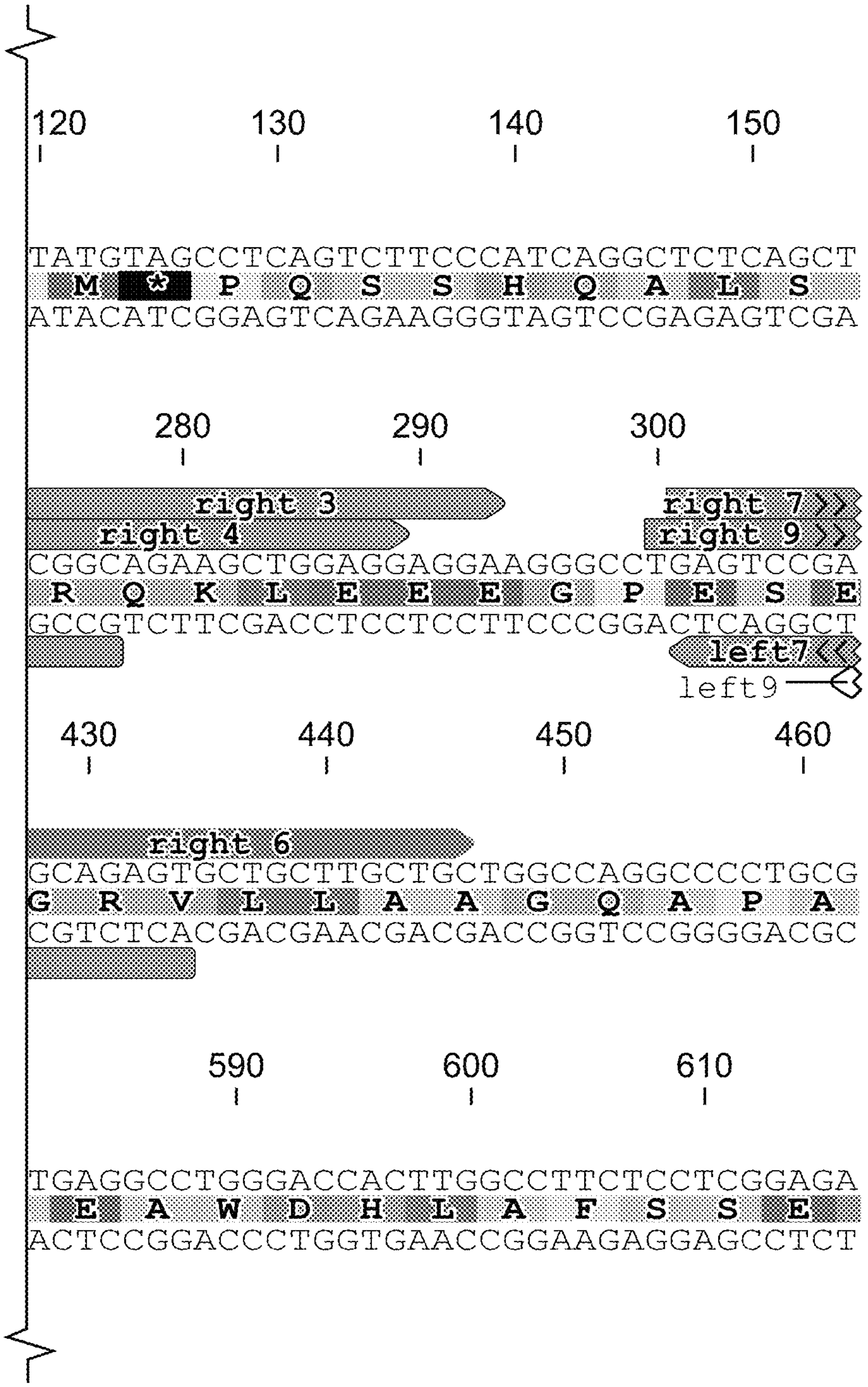
FIG. 55 (Cont. 3)

Human SERPINA1 Genome Surveyor Assay

Mouse Hmgcr Genome Surveyor Assay

| Genome Target Sapcers | Genome Cleavage Efficiency (%) |
|---|---|
| MmHmgcr-Spacer 1 | 15.4 |
| MmHmgcr-Spacer 2 | 18.3 |
| MmHmgcr-Spacer 3 | 6.1 |
| MmHmgcr-Spacer 4 | 6.5 |
| MmHmgcr-Spacer 5 | 11.8 |
| MmHmgcr-Spacer 6 | 5.8 |

pAAV-CMV-SaCas9-U6-sgRNA architecture (CMV: ubiquitous cytomegalovirus promoter)

pAAV-TBG-SaCas9-U6-sgRNA architecture (TBG: Thyroxine-binding globulin liver-specific promoter)

a

| | NNGRR | |
|---|---|---|
| Chr | median | mean |
| 1 | 4 | 7.5 |
| 2 | 4 | 7.8 |
| 3 | 4 | 7.9 |
| 4 | 4 | 8.3 |
| 5 | 4 | 8.0 |
| 6 | 4 | 7.8 |
| 7 | 4 | 7.7 |
| 8 | 4 | 7.8 |
| 9 | 4 | 7.7 |
| 10 | 4 | 7.5 |
| 11 | 4 | 7.5 |
| 12 | 4 | 7.7 |
| 13 | 4 | 8.2 |
| 14 | 4 | 7.7 |
| 15 | 4 | 7.5 |
| 16 | 4 | 7.0 |
| 17 | 4 | 6.8 |
| 18 | 4 | 7.8 |
| 19 | 3 | 6.5 |
| 20 | 4 | 7.1 |
| 21 | 4 | 8.0 |
| 22 | 3 | 6.7 |
| X | 4 | 8.0 |
| Y | 4 | 8.1 |

ApoB-T1 = Target 1; ApoB-T2 = Target 2, etc.

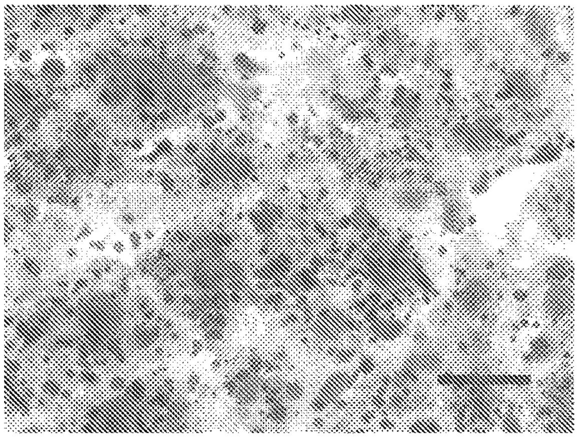
TBG-SaCas9-U6-sgRNA(Apob-T1)
4wk post injection
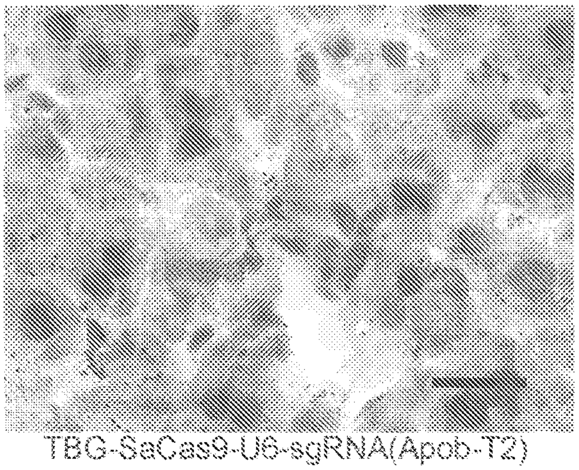
TBG-SaCas9-U6-sgRNA(Apob-T2)
4wk post injection
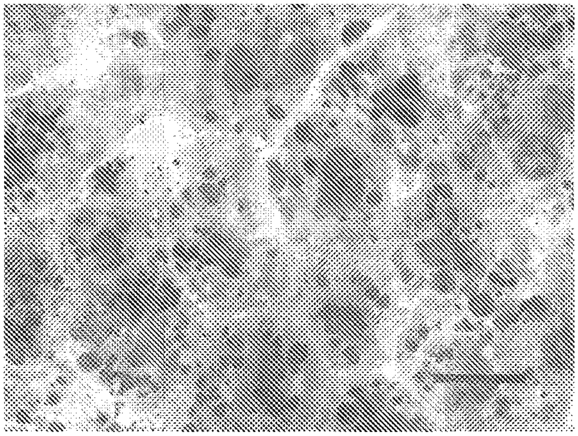
TBG-SaCas9-U6-sgRNA(Apob-T3)
4wk post injection
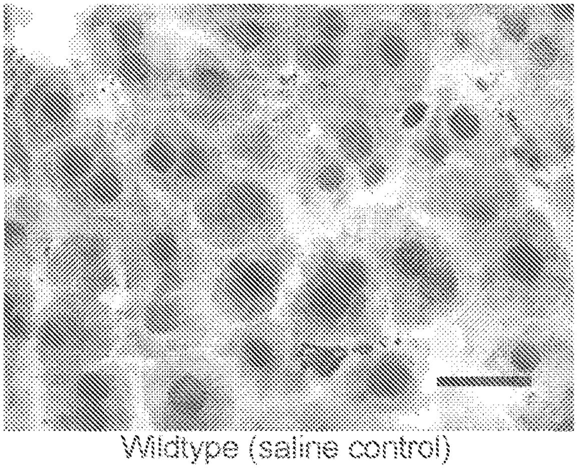
Wildtype (saline control)
4wk post injection
FIG. 79

FIG 85A
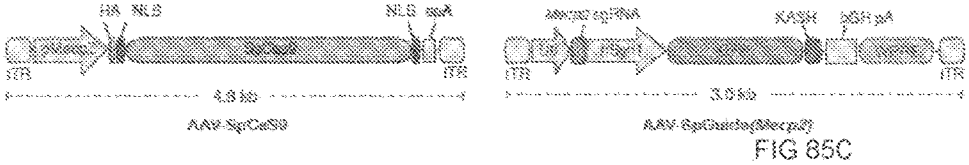
FIG 85B
FIG 85C
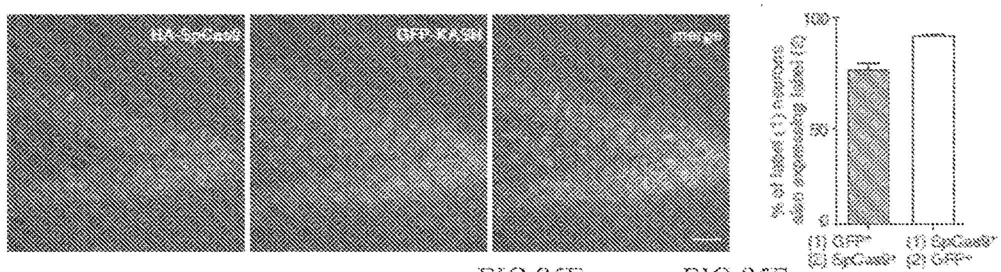
FIG 85D
FIG 85E
FIG 85F
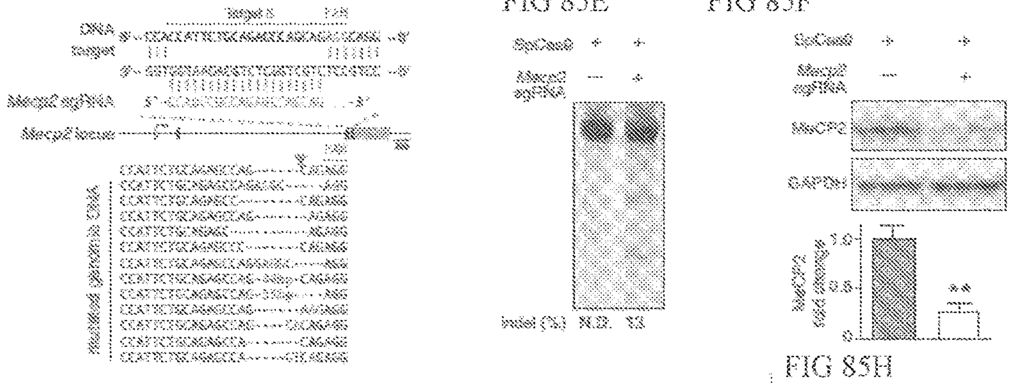
FIG 85G
FIG 85H
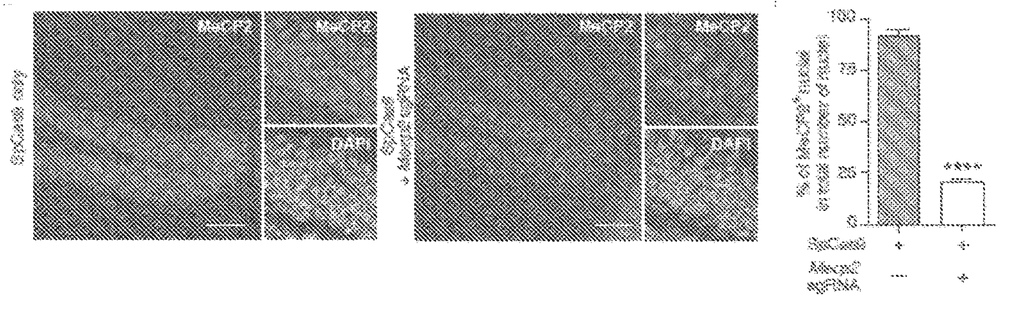

FIG 87A
FIG 87B
FIG 87C
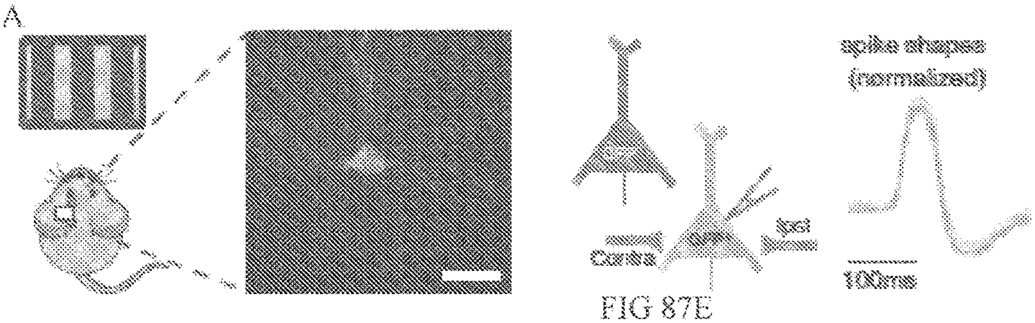
FIG 87D
FIG 87E
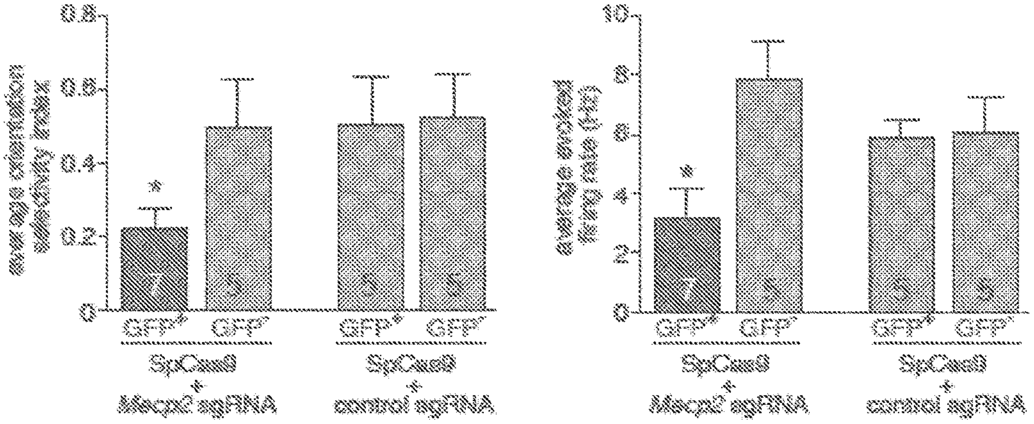

| | *Mecp2* target sequence | PAM |
|---|---|---|
| Target 1 | CTGGGAGAGGGAGCCCCTCC | AGG |
| Target 2 | AAAGGTGGGAGACACCTCCT | TGG |
| Target 3 | TCCAACCTTCAGGCAAGGTG | GGG |
| Target 4 | AGGAAGTCTGGCCGATCTGC | TGG |
| Target 5 | CCATTCTGCAGAGCCAGCAG | AGG |
| Target 6 | CTCTGAGGCCCTGGAGATCC | TGG |

| target | target sequence | PAM |
|---|---|---|
| *Dnmt3a* | TTGGCATGGGTCGCTGACGG | AGG |
| *Dnmt1* | CGGGCTGGAGCTGTTCGCGC | TGG |
| *Dnmt3b* | AGAGGGTGCCAGCGGGTATG | AGG |

FOG 94B

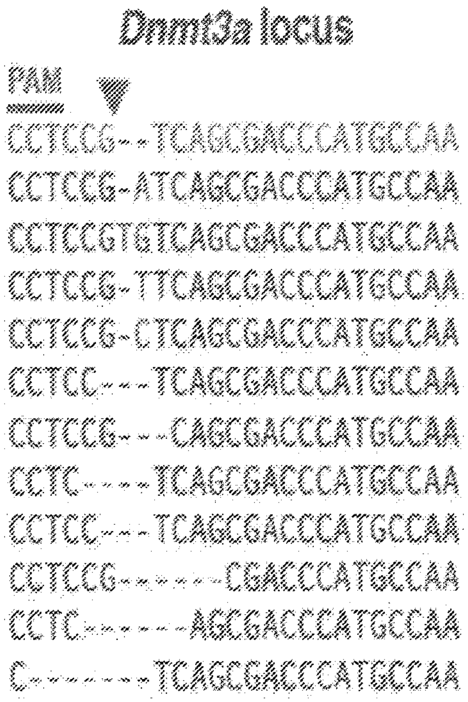

FIG 95A

Dnmt3a locus

PAM
CCTCCG--TCAGCGACCCATGCCAA
CCTCCG--ATCAGGACCCATGCCAA
CCTCCGTGTCAGCGACCCATGCCAA
CCTCCG--TTCAGCGACCCATGCCAA
CCTCCG-CTCAGCGACCCATGCCAA
CCTCC---TCAGCGACCCATGCCAA
CCTCCG--CAGCGACCCATGCCAA
CCTC-----CAGCGACCCATGCCAA
CCTCCC---TCAGCGACCCATGCCAA
CCTCCG-----CGAACCCATGCCAA
CCTCC------AGCGACCCATGCCAA
C-------TCAGCGACCCATGCCAA

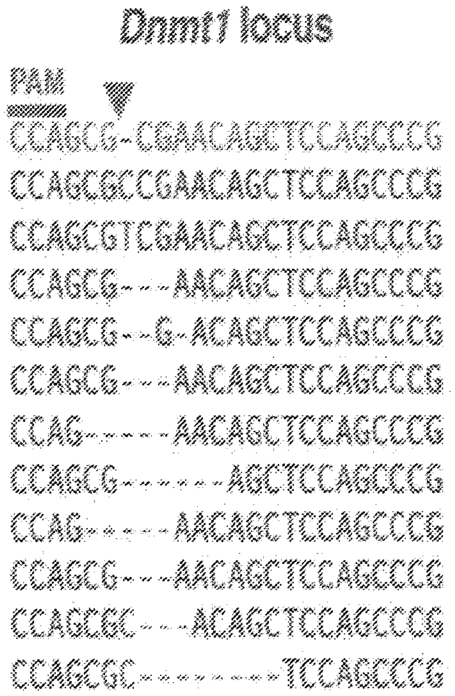

FIG 95B

Dnmt1 locus

PAM
CCAGCG--CGAACAGAGCTCCAGCCCG
CCAGCGCCGAACAGAGCTCCAGCCCG
CCAGCGTCGAACAGAGCTCCAGCCCG
CCAGCG----AACAGCTCCAGCCCG
CCAGCG--G-ACAGCTCCAGCCCG
CCAGCG----AACAGCTCCAGCCCG
CCAG------AACAGCTCCAGCCCG
CCAGCG----AGGCTCCAGCCCG
CCAGCG----AACAGCTCCAGCCCG
CCAGCGG---AACAGCTCCAGCCCG
CCAGCG----ACAGCTCCAGCCCG
CCAGCGG--------TCCAGCCCG

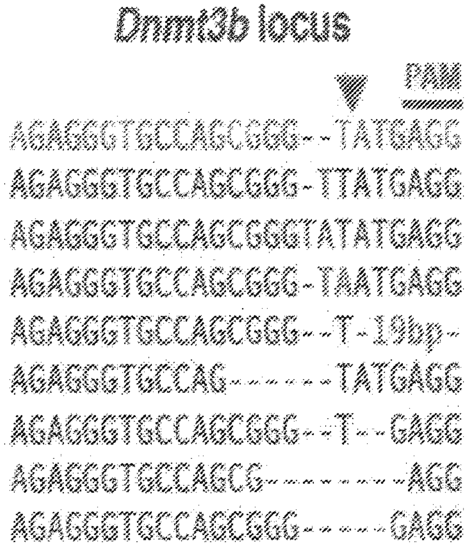

FIG 95C

Dnmt3b locus

PAM
AGAGGGTGCCAGCGGG--TATGAGG
AGAGGGTGCCAGCGGG--TTATGAGG
AGAGGGTGCCAGCGGGTATATGAGG
AGAGGGTGCCAGCGGG--TAATGAGG
AGAGGGTGCCAGCGGG--T--19bp-
AGAGGGTGCCAG------TATGAGG
AGAGGGTGCCAGCGGG--T--GAGG
AGAGGGTGCCAGCG-------AGG
AGAGGGTGCCAGCGGG-----GAGG

SEQUENCE LISTING

```
<160> NUMBER OF SEQ ID NOS: 926

<210> SEQ ID NO 1
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1

gcactgaggg cctatttccc atgattc                                    27


<210> SEQ ID NO 2
<211> LENGTH: 25
<212> TYPE: DNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"

<400> SEQUENCE: 2

cctccgtgtc agcgacccat gccaa                                          25


<210> SEQ ID NO 3
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 3

ccagcgtcga acagctccag cccg                                           24


<210> SEQ ID NO 4
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 4

agagggtgcc agcgggtata tgagg                                          25


<210> SEQ ID NO 5
<211> LENGTH: 20
<212> TYPE: DNA
<213> ORGANISM: Homo sapiens

<400> SEQUENCE: 5

gagtccgagc agaagaagaa                                                20


<210> SEQ ID NO 6
<211> LENGTH: 20
<212> TYPE: DNA
<213> ORGANISM: Homo sapiens

<400> SEQUENCE: 6

gagtcctagc aggagaagaa                                                20


<210> SEQ ID NO 7
<211> LENGTH: 20
<212> TYPE: DNA
<213> ORGANISM: Homo sapiens

<400> SEQUENCE: 7

gagtctaagc agaagaagaa                                                20


<210> SEQ ID NO 8
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, u, g, unknown or other
```

<220> FEATURE:
<221> NAME/KEY: modified_base
<222> LOCATION: (23)..(44)
<223> OTHER INFORMATION: a, c, u, g, unknown or other
<220> FEATURE:
<221> NAME/KEY: modified_base
<222> LOCATION: (47)..(60)
<223> OTHER INFORMATION: a, c, u, g, unknown or other

<400> SEQUENCE: 8
nnnnnnnnnn nnnnnnnnnn ccnnnnnnnn nnnnnnnnnn nnnnggnnnn nnnnnnnnnn 60

<210> SEQ ID NO 9
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (1)..(14)
<223> OTHER INFORMATION: a, c, u, g, unknown or other
<220> FEATURE:
<221> NAME/KEY: modified_base
<222> LOCATION: (17)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 9
nnnnnnnnnn nnnnccnnnn nnnnnnnnnn nnnnnnnngg nnnnnnnnnn nnnnnnnnnn 60

<210> SEQ ID NO 10
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(43)
<223> OTHER INFORMATION: a, c, u, g, unknown or other
<220> FEATURE:
<221> NAME/KEY: modified_base
<222> LOCATION: (46)..(60)
<223> OTHER INFORMATION: a, c, u, g, unknown or other

<400> SEQUENCE: 10
nnnnnnnnnn nnnnnnnnnn ccnnnnnnnn nnnnnnnnnn nnnggnnnnn nnnnnnnnnn 60

<210> SEQ ID NO 11
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (1)..(15)
<223> OTHER INFORMATION: a, c, u, g, unknown or other
<220> FEATURE:

<221> NAME/KEY: modified_base
<222> LOCATION: (18)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 11
nnnnnnnnnn nnnnnccnnn nnnnnnnnnn nnnnnnnngg nnnnnnnnnn nnnnnnnnnn 60

<210> SEQ ID NO 12
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(42)
<223> OTHER INFORMATION: a, c, u, g, unknown or other
<220> FEATURE:
<221> NAME/KEY: modified_base
<222> LOCATION: (45)..(60)
<223> OTHER INFORMATION: a, c, u, g, unknown or other

<400> SEQUENCE: 12
nnnnnnnnnn nnnnnnnnnn ccnnnnnnnn nnnnnnnnnn nnggnnnnnn nnnnnnnnnn 60

<210> SEQ ID NO 13
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (1)..(15)
<223> OTHER INFORMATION: a, c, u, g, unknown or other
<220> FEATURE:
<221> NAME/KEY: modified_base
<222> LOCATION: (18)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 13
nnnnnnnnnn nnnnnccnnn nnnnnnnnnn nnnnnnnngg nnnnnnnnnn nnnnnnnnnn 60

<210> SEQ ID NO 14
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base -continued
<222> LOCATION: (23)..(41)
<223> OTHER INFORMATION: a, c, u, g, unknown or other
<220> FEATURE:
<221> NAME/KEY: modified_base
<222> LOCATION: (44)..(60)
<223> OTHER INFORMATION: a, c, u, g, unknown or other

<400> SEQUENCE: 14
nnnnnnnnnn nnnnnnnnnn ccnnnnnnnn nnnnnnnnnn nggnnnnnnn nnnnnnnnnn 60

<210> SEQ ID NO 15
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: modified_base
<222> LOCATION: (1)..(17)
<223> OTHER INFORMATION: a, c, u, g, unknown or other
<220> FEATURE:
<221> NAME/KEY: modified_base
<222> LOCATION: (20)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 15
nnnnnnnnnn nnnnnnnccn nnnnnnnnnn nnnnnnnngg nnnnnnnnnn nnnnnnnnnn 60

<210> SEQ ID NO 16
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(40)
<223> OTHER INFORMATION: a, c, u, g, unknown or other
<220> FEATURE:
<221> NAME/KEY: modified_base
<222> LOCATION: (43)..(60)
<223> OTHER INFORMATION: a, c, u, g, unknown or other

<400> SEQUENCE: 16
nnnnnnnnnn nnnnnnnnnn ccnnnnnnnn nnnnnnnnnn ggnnnnnnnn nnnnnnnnnn 60

<210> SEQ ID NO 17
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: modified_base
<222> LOCATION: (1)..(18)
<223> OTHER INFORMATION: a, c, u, g, unknown or other
<220> FEATURE:
<221> NAME/KEY: modified_base
<222> LOCATION: (21)..(38)

-continued

<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 17
nnnnnnnnnn nnnnnnnncc nnnnnnnnnn nnnnnnnngg nnnnnnnnnn nnnnnnnnnn 60

<210> SEQ ID NO 18
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(39)
<223> OTHER INFORMATION: a, c, u, g, unknown or other
<220> FEATURE:
<221> NAME/KEY: modified_base
<222> LOCATION: (42)..(60)
<223> OTHER INFORMATION: a, c, u, g, unknown or other

<400> SEQUENCE: 18
nnnnnnnnnn nnnnnnnnnn ccnnnnnnnn nnnnnnnnng gnnnnnnnnn nnnnnnnnnn 60

<210> SEQ ID NO 19
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: modified_base
<222> LOCATION: (1)..(19)
<223> OTHER INFORMATION: a, c, u, g, unknown or other
<220> FEATURE:
<221> NAME/KEY: modified_base
<222> LOCATION: (22)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 19
nnnnnnnnnn nnnnnnnnnc cnnnnnnnnn nnnnnnnngg nnnnnnnnnn nnnnnnnnnn 60

<210> SEQ ID NO 20
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 20
nnnnnnnnnn nnnnnnnnnn ccnnnnnnnn nnnnnnnngg nnnnnnnnnn nnnnnnnnnn 60

<210> SEQ ID NO 21
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 21
nnnnnnnnnn nnnnnnnnnn ccnnnnnnnn nnnnnnnngg nnnnnnnnnn nnnnnnnnnn 60

<210> SEQ ID NO 22
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(37)
<223> OTHER INFORMATION: a, c, u, g, unknown or other
<220> FEATURE:
<221> NAME/KEY: modified_base
<222> LOCATION: (40)..(60)
<223> OTHER INFORMATION: a, c, u, g, unknown or other

<400> SEQUENCE: 22
nnnnnnnnnn nnnnnnnnnn ccnnnnnnnn nnnnnnnggn nnnnnnnnnn nnnnnnnnnn 60

<210> SEQ ID NO 23
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: modified_base
<222> LOCATION: (1)..(21)
<223> OTHER INFORMATION: a, c, u, g, unknown or other
<220> FEATURE:
<221> NAME/KEY: modified_base
<222> LOCATION: (24)..(38)
<223> OTHER INFORMATION: a, c, u, g, unknown or other
<220> FEATURE:

<221> NAME/KEY: modified_base
<222> LOCATION: (41)..(60)
<223> OTHER INFORMATION: a, c, u, g, unknown or other

<400> SEQUENCE: 23
nnnnnnnnnn nnnnnnnnnn nccnnnnnnn nnnnnnnngg nnnnnnnnnn nnnnnnnnnn 60

<210> SEQ ID NO 24
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(36)
<223> OTHER INFORMATION: a, c, u, g, unknown or other
<220> FEATURE:
<221> NAME/KEY: modified_base
<222> LOCATION: (39)..(60)
<223> OTHER INFORMATION: a, c, u, g, unknown or other

<400> SEQUENCE: 24
nnnnnnnnnn nnnnnnnnnn ccnnnnnnnn nnnnnnggnn nnnnnnnnnn nnnnnnnnnn 60

<210> SEQ ID NO 25
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (1)..(22)
<223> OTHER INFORMATION: a, c, u, g, unknown or other
<220> FEATURE:
<221> NAME/KEY: modified_base
<222> LOCATION: (25)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 25
nnnnnnnnnn nnnnnnnnnn nnccnnnnnn nnnnnnnngg nnnnnnnnnn nnnnnnnnnn 60

<210> SEQ ID NO 26
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(35)
<223> OTHER INFORMATION: a, c, u, g, unknown or other
<220> FEATURE:
<221> NAME/KEY: modified_base
<222> LOCATION: (38)..(60)
<223> OTHER INFORMATION: a, c, u, g, unknown or other

<400> SEQUENCE: 26
nnnnnnnnnn nnnnnnnnnn ccnnnnnnnn nnnnnggnnn nnnnnnnnnn nnnnnnnnnn 60

<210> SEQ ID NO 27
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (1)..(23)
<223> OTHER INFORMATION: a, c, u, g, unknown or other
<220> FEATURE:
<221> NAME/KEY: modified_base
<222> LOCATION: (26)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 27
nnnnnnnnnn nnnnnnnnnn nnnccnnnnn nnnnnnnngg nnnnnnnnnn nnnnnnnnnn 60

<210> SEQ ID NO 28
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(34)
<223> OTHER INFORMATION: a, c, u, g, unknown or other
<220> FEATURE:
<221> NAME/KEY: modified_base
<222> LOCATION: (37)..(60)
<223> OTHER INFORMATION: a, c, u, g, unknown or other

<400> SEQUENCE: 28
nnnnnnnnnn nnnnnnnnnn ccnnnnnnnn nnnnggnnnn nnnnnnnnnn nnnnnnnnnn 60

<210> SEQ ID NO 29
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (1)..(24)
<223> OTHER INFORMATION: a, c, u, g, unknown or other
<220> FEATURE:
<221> NAME/KEY: modified_base
<222> LOCATION: (27)..(38)
<223> OTHER INFORMATION: a, c, u, g, unknown or other
<220> FEATURE:
<221> NAME/KEY: modified_base
<222> LOCATION: (41)..(60)

<223> OTHER INFORMATION: a, c, u, g, unknown or other

<400> SEQUENCE: 29
nnnnnnnnnn nnnnnnnnnn nnnnccnnnn nnnnnnnngg nnnnnnnnnn nnnnnnnnnn 60

<210> SEQ ID NO 30
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(33)
<223> OTHER INFORMATION: a, c, u, g, unknown or other
<220> FEATURE:
<221> NAME/KEY: modified_base
<222> LOCATION: (36)..(60)
<223> OTHER INFORMATION: a, c, u, g, unknown or other

<400> SEQUENCE: 30
nnnnnnnnnn nnnnnnnnnn ccnnnnnnnn nnnggnnnnn nnnnnnnnnn nnnnnnnnnn 60

<210> SEQ ID NO 31
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (1)..(25)
<223> OTHER INFORMATION: a, c, u, g, unknown or other
<220> FEATURE:
<221> NAME/KEY: modified_base
<222> LOCATION: (28)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 31
nnnnnnnnnn nnnnnnnnnn nnnnnccnnn nnnnnnnngg nnnnnnnnnn nnnnnnnnnn 60

<210> SEQ ID NO 32
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(32)
<223> OTHER INFORMATION: a, c, u, g, unknown or other
<220> FEATURE:
<221> NAME/KEY: modified_base
<222> LOCATION: (35)..(60)
<223> OTHER INFORMATION: a, c, u, g, unknown or other

<400> SEQUENCE: 32
nnnnnnnnnn nnnnnnnnnn ccnnnnnnnn nnggnnnnnn nnnnnnnnnn nnnnnnnnnn 60

<210> SEQ ID NO 33
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (1)..(26)
<223> OTHER INFORMATION: a, c, u, g, unknown or other
<220> FEATURE:
<221> NAME/KEY: modified_base
<222> LOCATION: (29)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 33
nnnnnnnnnn nnnnnnnnnn nnnnnnccnn nnnnnnnngg nnnnnnnnnn nnnnnnnnnn 60

<210> SEQ ID NO 34
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(31)
<223> OTHER INFORMATION: a, c, u, g, unknown or other
<220> FEATURE:
<221> NAME/KEY: modified_base
<222> LOCATION: (34)..(60)
<223> OTHER INFORMATION: a, c, u, g, unknown or other

<400> SEQUENCE: 34
nnnnnnnnnn nnnnnnnnnn ccnnnnnnnn nggnnnnnnn nnnnnnnnnn nnnnnnnnnn 60

<210> SEQ ID NO 35
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (1)..(27)
<223> OTHER INFORMATION: a, c, u, g, unknown or other
<220> FEATURE:
<221> NAME/KEY: modified_base
<222> LOCATION: (30)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 35
nnnnnnnnnn nnnnnnnnnn nnnnnnnccn nnnnnnnngg nnnnnnnnnn nnnnnnnnnn 60

<210> SEQ ID NO 36
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(30)
<223> OTHER INFORMATION: a, c, u, g, unknown or other
<220> FEATURE:
<221> NAME/KEY: modified_base
<222> LOCATION: (33)..(60)
<223> OTHER INFORMATION: a, c, u, g, unknown or other

<400> SEQUENCE: 36
nnnnnnnnnn nnnnnnnnnn ccnnnnnnnn ggnnnnnnnn nnnnnnnnnn nnnnnnnnnn 60

<210> SEQ ID NO 37
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: modified_base
<222> LOCATION: (1)..(28)
<223> OTHER INFORMATION: a, c, u, g, unknown or other
<220> FEATURE:
<221> NAME/KEY: modified_base
<222> LOCATION: (31)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 37
nnnnnnnnnn nnnnnnnnnn nnnnnnnncc nnnnnnnngg nnnnnnnnnn nnnnnnnnnn 60

<210> SEQ ID NO 38
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(29)
<223> OTHER INFORMATION: a, c, u, g, unknown or other
<220> FEATURE:
<221> NAME/KEY: modified_base
<222> LOCATION: (32)..(60)
<223> OTHER INFORMATION: a, c, u, g, unknown or other

<400> SEQUENCE: 38
nnnnnnnnnn nnnnnnnnnn ccnnnnnnng gnnnnnnnnn nnnnnnnnnn nnnnnnnnnn 60

<210> SEQ ID NO 39
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: modified_base
<222> LOCATION: (1)..(29)
<223> OTHER INFORMATION: a, c, u, g, unknown or other
<220> FEATURE:
<221> NAME/KEY: modified_base
<222> LOCATION: (32)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 39
nnnnnnnnnn nnnnnnnnnn nnnnnnnnnc cnnnnnnngg nnnnnnnnnn nnnnnnnnnn 60

<210> SEQ ID NO 40
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(28)
<223> OTHER INFORMATION: a, c, u, g, unknown or other
<220> FEATURE:
<221> NAME/KEY: modified_base
<222> LOCATION: (31)..(60)
<223> OTHER INFORMATION: a, c, u, g, unknown or other

<400> SEQUENCE: 40
nnnnnnnnnn nnnnnnnnnn ccnnnnnngg nnnnnnnnnn nnnnnnnnnn nnnnnnnnnn 60

<210> SEQ ID NO 41
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: modified_base
<222> LOCATION: (1)..(30)
<223> OTHER INFORMATION: a, c, u, g, unknown or other
<220> FEATURE:
<221> NAME/KEY: modified_base
<222> LOCATION: (33)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 41
nnnnnnnnnn nnnnnnnnnn nnnnnnnnnn ccnnnnnngg nnnnnnnnnn nnnnnnnnnn 60

<210> SEQ ID NO 42
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(27)
<223> OTHER INFORMATION: a, c, u, g, unknown or other
<220> FEATURE:
<221> NAME/KEY: modified_base
<222> LOCATION: (30)..(60)
<223> OTHER INFORMATION: a, c, u, g, unknown or other

<400> SEQUENCE: 42
nnnnnnnnnn nnnnnnnnnn ccnnnnnggn nnnnnnnnnn nnnnnnnnnn nnnnnnnnnn 60

<210> SEQ ID NO 43
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (1)..(31)
<223> OTHER INFORMATION: a, c, u, g, unknown or other
<220> FEATURE:
<221> NAME/KEY: modified_base
<222> LOCATION: (34)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 43
nnnnnnnnnn nnnnnnnnnn nnnnnnnnnn nccnnnnngg nnnnnnnnnn nnnnnnnnnn 60

<210> SEQ ID NO 44
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(26)
<223> OTHER INFORMATION: a, c, u, g, unknown or other
<220> FEATURE:
<221> NAME/KEY: modified_base
<222> LOCATION: (29)..(60)
<223> OTHER INFORMATION: a, c, u, g, unknown or other

<400> SEQUENCE: 44
nnnnnnnnnn nnnnnnnnnn ccnnnnggnn nnnnnnnnnn nnnnnnnnnn nnnnnnnnnn 60

<210> SEQ ID NO 45
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: modified_base
<222> LOCATION: (1)..(32)
<223> OTHER INFORMATION: a, c, u, g, unknown or other
<220> FEATURE:
<221> NAME/KEY: modified_base
<222> LOCATION: (35)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 45
nnnnnnnnnn nnnnnnnnnn nnnnnnnnnn nnccnnnngg nnnnnnnnnn nnnnnnnnnn 60

<210> SEQ ID NO 46
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(25)
<223> OTHER INFORMATION: a, c, u, g, unknown or other
<220> FEATURE:
<221> NAME/KEY: modified_base
<222> LOCATION: (28)..(60)
<223> OTHER INFORMATION: a, c, u, g, unknown or other

<400> SEQUENCE: 46
nnnnnnnnnn nnnnnnnnnn ccnnnggnnn nnnnnnnnnn nnnnnnnnnn nnnnnnnnnn 60

<210> SEQ ID NO 47
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: modified_base
<222> LOCATION: (1)..(33)
<223> OTHER INFORMATION: a, c, u, g, unknown or other
<220> FEATURE:
<221> NAME/KEY: modified_base
<222> LOCATION: (36)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 47
nnnnnnnnnn nnnnnnnnnn nnnnnnnnnn nnnccnnngg nnnnnnnnnn nnnnnnnnnn 60

<210> SEQ ID NO 48
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(24)
<223> OTHER INFORMATION: a, c, u, g, unknown or other
<220> FEATURE:
<221> NAME/KEY: modified_base
<222> LOCATION: (27)..(60)
<223> OTHER INFORMATION: a, c, u, g, unknown or other

<400> SEQUENCE: 48
nnnnnnnnnn nnnnnnnnnn ccnnggnnnn nnnnnnnnnn nnnnnnnnnn nnnnnnnnnn 60

<210> SEQ ID NO 49
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (1)..(34)
<223> OTHER INFORMATION: a, c, u, g, unknown or other
<220> FEATURE:
<221> NAME/KEY: modified_base
<222> LOCATION: (37)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 49
nnnnnnnnnn nnnnnnnnnn nnnnnnnnnn nnnnccnngg nnnnnnnnnn nnnnnnnnnn 60

<210> SEQ ID NO 50
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(23)
<223> OTHER INFORMATION: a, c, u, g, unknown or other
<220> FEATURE:
<221> NAME/KEY: modified_base
<222> LOCATION: (26)..(60)
<223> OTHER INFORMATION: a, c, u, g, unknown or other

<400> SEQUENCE: 50
nnnnnnnnnn nnnnnnnnnn ccnggnnnnn nnnnnnnnnn nnnnnnnnnn nnnnnnnnnn 60

```
<210> SEQ ID NO 51
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(35)
<223> OTHER INFORMATION: a, c, u, g, unknown or other
<220> FEATURE:
<221> NAME/KEY: modified_base
<222> LOCATION: (38)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 51

nnnnnnnnnn nnnnnnnnnn nnnnnnnnnn nnnnnccngg nnnnnnnnnn nnnnnnnnnn     60


<210> SEQ ID NO 52
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(21)
<223> OTHER INFORMATION: a, c, u, g, unknown or other
<220> FEATURE:
<221> NAME/KEY: modified_base
<222> LOCATION: (26)..(60)
<223> OTHER INFORMATION: a, c, u, g, unknown or other

<400> SEQUENCE: 52

nnnnnnnnnn nnnnnnnnnn nccggnnnnn nnnnnnnnnn nnnnnnnnnn nnnnnnnnnn     60


<210> SEQ ID NO 53
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(35)
<223> OTHER INFORMATION: a, c, u, g, unknown or other
<220> FEATURE:
<221> NAME/KEY: modified_base
<222> LOCATION: (40)..(60)
<223> OTHER INFORMATION: a, c, u, g, unknown or other

<400> SEQUENCE: 53

nnnnnnnnnn nnnnnnnnnn nnnnnnnnnn nnnnnccggn nnnnnnnnnn nnnnnnnnnn     60


<210> SEQ ID NO 54
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
```

<221> NAME/KEY: modified_base
<222> LOCATION: (1)..(23)
<223> OTHER INFORMATION: a, c, u, g, unknown or other
<220> FEATURE:
<221> NAME/KEY: modified_base
<222> LOCATION: (26)..(60)
<223> OTHER INFORMATION: a, c, u, g, unknown or other

<400> SEQUENCE: 54
nnnnnnnnnn nnnnnnnnnn nnnggnnnnn nnnnnnnnnn nnnnnnnnnn nnnnnnnnnn 60

<210> SEQ ID NO 55
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (1)..(33)
<223> OTHER INFORMATION: a, c, u, g, unknown or other
<220> FEATURE:
<221> NAME/KEY: modified_base
<222> LOCATION: (38)..(60)
<223> OTHER INFORMATION: a, c, u, g, unknown or other

<400> SEQUENCE: 55
nnnnnnnnnn nnnnnnnnnn nnnnnnnnnn nnnggccnnn nnnnnnnnnn nnnnnnnnnn 60

<210> SEQ ID NO 56
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (1)..(22)
<223> OTHER INFORMATION: a, c, u, g, unknown or other
<220> FEATURE:
<221> NAME/KEY: modified_base
<222> LOCATION: (26)..(60)
<223> OTHER INFORMATION: a, c, u, g, unknown or other

<400> SEQUENCE: 56
nnnnnnnnnn nnnnnnnnnn nncggnnnnn nnnnnnnnnn nnnnnnnnnn nnnnnnnnnn 60

<210> SEQ ID NO 57
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (1)..(32)
<223> OTHER INFORMATION: a, c, u, g, unknown or other
<220> FEATURE:
<221> NAME/KEY: modified_base
<222> LOCATION: (35)..(35)
<223> OTHER INFORMATION: a, c, u, g, unknown or other
<220> FEATURE:
<221> NAME/KEY: modified_base
<222> LOCATION: (38)..(60)
<223> OTHER INFORMATION: a, c, u, g, unknown or other

<400> SEQUENCE: 57
nnnnnnnnnn nnnnnnnnnn nnnnnnnnnn nnggnccnnn nnnnnnnnnn nnnnnnnnnn 60

<210> SEQ ID NO 58
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (1)..(31)
<223> OTHER INFORMATION: a, c, u, g, unknown or other
<220> FEATURE:
<221> NAME/KEY: modified_base
<222> LOCATION: (34)..(35)
<223> OTHER INFORMATION: a, c, u, g, unknown or other
<220> FEATURE:
<221> NAME/KEY: modified_base
<222> LOCATION: (38)..(60)
<223> OTHER INFORMATION: a, c, u, g, unknown or other

<400> SEQUENCE: 58
nnnnnnnnnn nnnnnnnnnn nnnnnnnnnn nggnnccnnn nnnnnnnnnn nnnnnnnnnn 60

<210> SEQ ID NO 59
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (1)..(30)
<223> OTHER INFORMATION: a, c, u, g, unknown or other
<220> FEATURE:
<221> NAME/KEY: modified_base
<222> LOCATION: (33)..(35)
<223> OTHER INFORMATION: a, c, u, g, unknown or other
<220> FEATURE:
<221> NAME/KEY: modified_base
<222> LOCATION: (38)..(60)
<223> OTHER INFORMATION: a, c, u, g, unknown or other

<400> SEQUENCE: 59
nnnnnnnnnn nnnnnnnnnn nnnnnnnnnn ggnnnccnnn nnnnnnnnnn nnnnnnnnnn 60

<210> SEQ ID NO 60
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (1)..(29)
<223> OTHER INFORMATION: a, c, u, g, unknown or other
<220> FEATURE:
<221> NAME/KEY: modified_base
<222> LOCATION: (32)..(35)
<223> OTHER INFORMATION: a, c, u, g, unknown or other
<220> FEATURE:
<221> NAME/KEY: modified_base
<222> LOCATION: (38)..(60)
<223> OTHER INFORMATION: a, c, u, g, unknown or other

<400> SEQUENCE: 60
nnnnnnnnnn nnnnnnnnnn nnnnnnnnng gnnnnccnnn nnnnnnnnnn nnnnnnnnnn 60

<210> SEQ ID NO 61
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: modified_base
<222> LOCATION: (1)..(28)
<223> OTHER INFORMATION: a, c, u, g, unknown or other
<220> FEATURE:
<221> NAME/KEY: modified_base
<222> LOCATION: (31)..(35)
<223> OTHER INFORMATION: a, c, u, g, unknown or other
<220> FEATURE:
<221> NAME/KEY: modified_base
<222> LOCATION: (38)..(60)
<223> OTHER INFORMATION: a, c, u, g, unknown or other

<400> SEQUENCE: 61
nnnnnnnnnn nnnnnnnnnn nnnnnnnngg nnnnnccnnn nnnnnnnnnn nnnnnnnnnn 60

<210> SEQ ID NO 62
<211> LENGTH: 9
<212> TYPE: PRT
<213> ORGANISM: Unknown
<220> FEATURE:
<221> NAME/KEY: source
<223> OTHER INFORMATION: /note="Description of Unknown:
'LAGLIDADG' family motif peptide"

<400> SEQUENCE: 62

Leu Ala Gly Leu Ile Asp Ala Asp Gly
1 5

<210> SEQ ID NO 63
<211> LENGTH: 12
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 63
guuuuagagc ua 12

<210> SEQ ID NO 64
<211> LENGTH: 7
<212> TYPE: PRT
<213> ORGANISM: Simian virus 40

<400> SEQUENCE: 64

Pro Lys Lys Lys Arg Lys Val
1 5

<210> SEQ ID NO 65
<211> LENGTH: 16
<212> TYPE: PRT
<213> ORGANISM: Unknown
<220> FEATURE:
<221> NAME/KEY: source
<223> OTHER INFORMATION: /note="Description of Unknown:
Nucleoplasmin bipartite NLS sequence"

<400> SEQUENCE: 65

```
Lys Arg Pro Ala Ala Thr Lys Lys Ala Gly Gln Ala Lys Lys Lys Lys
1               5                   10                  15


<210> SEQ ID NO 66
<211> LENGTH: 9
<212> TYPE: PRT
<213> ORGANISM: Unknown
<220> FEATURE:
<221> NAME/KEY: source
<223> OTHER INFORMATION: /note="Description of Unknown:
      C-myc NLS sequence"

<400> SEQUENCE: 66

Pro Ala Ala Lys Arg Val Lys Leu Asp
1               5


<210> SEQ ID NO 67
<211> LENGTH: 11
<212> TYPE: PRT
<213> ORGANISM: Unknown
<220> FEATURE:
<221> NAME/KEY: source
<223> OTHER INFORMATION: /note="Description of Unknown:
      C-myc NLS sequence"

<400> SEQUENCE: 67

Arg Gln Arg Arg Asn Glu Leu Lys Arg Ser Pro
1               5                   10


<210> SEQ ID NO 68
<211> LENGTH: 38
<212> TYPE: PRT
<213> ORGANISM: Homo sapiens

<400> SEQUENCE: 68

Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
            20                  25                  30

Arg Asn Gln Gly Gly Tyr
        35


<210> SEQ ID NO 69
<211> LENGTH: 42
<212> TYPE: PRT
<213> ORGANISM: Unknown
<220> FEATURE:
<221> NAME/KEY: source
<223> OTHER INFORMATION: /note="Description of Unknown:
      IBB domain from importin-alpha sequence"

<400> SEQUENCE: 69

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20                  25                  30

Asp Glu Gln Ile Leu Lys Arg Arg Asn Val
        35                  40


<210> SEQ ID NO 70
<211> LENGTH: 8
<212> TYPE: PRT
<213> ORGANISM: Unknown
<220> FEATURE:
<221> NAME/KEY: source
```

<223> OTHER INFORMATION: /note="Description of Unknown:
      Myoma T protein sequence"

<400> SEQUENCE: 70

Val Ser Arg Lys Arg Pro Arg Pro
1               5

<210> SEQ ID NO 71
<211> LENGTH: 8
<212> TYPE: PRT
<213> ORGANISM: Unknown
<220> FEATURE:
<221> NAME/KEY: source
<223> OTHER INFORMATION: /note="Description of Unknown:
      Myoma T protein sequence"

<400> SEQUENCE: 71

Pro Pro Lys Lys Ala Arg Glu Asp
1               5

<210> SEQ ID NO 72
<211> LENGTH: 8
<212> TYPE: PRT
<213> ORGANISM: Homo sapiens

<400> SEQUENCE: 72

Pro Gln Pro Lys Lys Lys Pro Leu
1               5

<210> SEQ ID NO 73
<211> LENGTH: 12
<212> TYPE: PRT
<213> ORGANISM: Mus musculus

<400> SEQUENCE: 73

Ser Ala Leu Ile Lys Lys Lys Lys Lys Met Ala Pro
1               5                   10

<210> SEQ ID NO 74
<211> LENGTH: 5
<212> TYPE: PRT
<213> ORGANISM: Influenza virus

<400> SEQUENCE: 74

Asp Arg Leu Arg Arg
1               5

<210> SEQ ID NO 75
<211> LENGTH: 7
<212> TYPE: PRT
<213> ORGANISM: Influenza virus

<400> SEQUENCE: 75

Pro Lys Gln Lys Lys Arg Lys
1               5

<210> SEQ ID NO 76
<211> LENGTH: 10
<212> TYPE: PRT
<213> ORGANISM: Hepatitis delta virus

<400> SEQUENCE: 76

Arg Lys Leu Lys Lys Lys Ile Lys Lys Leu
1               5                   10

<210> SEQ ID NO 77
<211> LENGTH: 10
<212> TYPE: PRT
<213> ORGANISM: Mus musculus

<400> SEQUENCE: 77

Arg Glu Lys Lys Lys Phe Leu Lys Arg Arg
1 5 10

<210> SEQ ID NO 78
<211> LENGTH: 20
<212> TYPE: PRT
<213> ORGANISM: Homo sapiens

<400> SEQUENCE: 78

Lys Arg Lys Gly Asp Glu Val Asp Gly Val Asp Glu Val Ala Lys Lys
1 5 10 15

Lys Ser Lys Lys
20

<210> SEQ ID NO 79
<211> LENGTH: 17
<212> TYPE: PRT
<213> ORGANISM: Homo sapiens

<400> SEQUENCE: 79

Arg Lys Cys Leu Gln Ala Gly Met Asn Leu Glu Ala Arg Lys Thr Lys
1 5 10 15

Lys

<210> SEQ ID NO 80
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(22)
<223> OTHER INFORMATION: a, c, t, g, unknown or other

<400> SEQUENCE: 80
nnnnnnnnnn nnnnnnnnnn nnagaaw 27

<210> SEQ ID NO 81
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: modified_base
<222> LOCATION: (1)..(12)
<223> OTHER INFORMATION: a, c, t or g
<220> FEATURE:
<221> NAME/KEY: modified_base
<222> LOCATION: (13)..(14)
<223> OTHER INFORMATION: a, c, t, g, unknown or other

<400> SEQUENCE: 81
nnnnnnnnnn nnnnagaaw 19

<210> SEQ ID NO 82
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(22)
<223> OTHER INFORMATION: a, c, t, g, unknown or other

<400> SEQUENCE: 82
nnnnnnnnnn nnnnnnnnnn nnagaaw 27

<210> SEQ ID NO 83
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (1)..(11)
<223> OTHER INFORMATION: a, c, t or g
<220> FEATURE:
<221> NAME/KEY: modified_base
<222> LOCATION: (12)..(13)
<223> OTHER INFORMATION: a, c, t, g, unknown or other

<400> SEQUENCE: 83
nnnnnnnnnn nnnagaaw 18

<210> SEQ ID NO 84
<211> LENGTH: 137
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 84
nnnnnnnnnn nnnnnnnnnn gtttttgtac tctcaagatt tagaaataaa tcttgcagaa 60
gctacaaaga taaggcttca tgccgaaatc aacaccctgt cattttatgg cagggtgttt 120
tcgttattta atttttt 137

<210> SEQ ID NO 85
<211> LENGTH: 123
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 85
nnnnnnnnnn nnnnnnnnnn gtttttgtac tctcagaaat gcagaagcta caaagataag 60
gcttcatgcc gaaatcaaca ccctgtcatt ttatggcagg gtgttttcgt tatttaattt 120
ttt 123

<210> SEQ ID NO 86
<211> LENGTH: 110
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 86
nnnnnnnnnn nnnnnnnnnn gtttttgtac tctcagaaat gcagaagcta caaagataag 60
gcttcatgcc gaaatcaaca ccctgtcatt ttatggcagg gtgttttttt 110

<210> SEQ ID NO 87
<211> LENGTH: 102
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 87
nnnnnnnnnn nnnnnnnnnn gttttagagc tagaaatagc aagttaaaat aaggctagtc 60
cgttatcaac ttgaaaaagt ggcaccgagt cggtgctttt tt 102

<210> SEQ ID NO 88
<211> LENGTH: 88
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: modified_base
<222> LOCATION: (1)..(20)
<223> OTHER INFORMATION: a, c, t, g, unknown or other

<400> SEQUENCE: 88
nnnnnnnnnn nnnnnnnnnn gttttagagc tagaaatagc aagttaaaat aaggctagtc 60
cgttatcaac ttgaaaaagt gttttttt 88

<210> SEQ ID NO 89
<211> LENGTH: 76
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"
<220> FEATURE:
<221> NAME/KEY: modified_base
<222> LOCATION: (1)..(20)
<223> OTHER INFORMATION: a, c, t, g, unknown or other

<400> SEQUENCE: 89
nnnnnnnnnn nnnnnnnnnn gttttagagc tagaaatagc aagttaaaat aaggctagtc 60
cgttatcatt tttttt 76

<210> SEQ ID NO 90
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 90
gttttagagc ta 12

<210> SEQ ID NO 91
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 91
tagcaagtta aaataaggct agtccgtttt t 31

<210> SEQ ID NO 92
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (1)..(22)
<223> OTHER INFORMATION: a, c, t, g, unknown or other

<400> SEQUENCE: 92
nnnnnnnnnn nnnnnnnnnn nnagaaw 27

<210> SEQ ID NO 93
<211> LENGTH: 33
<212> TYPE: DNA
<213> ORGANISM: Homo sapiens

<400> SEQUENCE: 93
ggacatcgat gtcacctcca atgactaggg tgg 33

<210> SEQ ID NO 94
<211> LENGTH: 33
<212> TYPE: DNA
<213> ORGANISM: Homo sapiens

<400> SEQUENCE: 94
cattggaggt gacatcgatg tcctccccat tgg 33

<210> SEQ ID NO 95
<211> LENGTH: 33
<212> TYPE: DNA
<213> ORGANISM: Homo sapiens

<400> SEQUENCE: 95
ggaagggcct gagtccgagc agaagaagaa ggg 33

<210> SEQ ID NO 96
<211> LENGTH: 33
<212> TYPE: DNA
<213> ORGANISM: Homo sapiens

<400> SEQUENCE: 96
ggtggcgaga ggggccgaga ttgggtgttc agg 33

<210> SEQ ID NO 97
<211> LENGTH: 33
<212> TYPE: DNA
<213> ORGANISM: Homo sapiens

<400> SEQUENCE: 97
atgcaggagg gtggcgagag gggccgagat tgg 33

<210> SEQ ID NO 98
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 98
aaactctaga gagggcctat ttcccatgat tc 32

<210> SEQ ID NO 99
<211> LENGTH: 153
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 99
acctctagaa aaaaagcacc gactcggtgc cactttttca agttgataac ggactagcct 60
tattttaact tgctatgctg ttttgtttcc aaaacagcat agctctaaaa cccctagtca 120
ttggaggtga cggtgtttcg tcctttccac aag 153

<210> SEQ ID NO 100
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 100
taatacgact cactatagga agtgcgccac catggcccca aagaagaagc gg 52

<210> SEQ ID NO 101
<211> LENGTH: 60
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 101

ggttttttt tttttttttt tttttttttt ttttcttact ttttcttttt tgcctggccg    60

<210> SEQ ID NO 102
<211> LENGTH: 984
<212> TYPE: PRT
<213> ORGANISM: Campylobacter jejuni

<400> SEQUENCE: 102
```

| Met | Ala | Arg | Ile | Leu | Ala | Phe | Asp | Ile | Gly | Ile | Ser | Ser | Ile | Gly | Trp |
|---|---|---|---|---|---|---|---|---|---|---|---|---|---|---|---|
| 1 | | | | 5 | | | | | 10 | | | | | 15 | |

| Ala | Phe | Ser | Glu | Asn | Asp | Glu | Leu | Lys | Asp | Cys | Gly | Val | Arg | Ile | Phe |
|---|---|---|---|---|---|---|---|---|---|---|---|---|---|---|---|
| | | | 20 | | | | | 25 | | | | | 30 | | |

| Thr | Lys | Val | Glu | Asn | Pro | Lys | Thr | Gly | Glu | Ser | Leu | Ala | Leu | Pro | Arg |
|---|---|---|---|---|---|---|---|---|---|---|---|---|---|---|---|
| | | | 35 | | | | | 40 | | | | | 45 | | |

| Arg | Leu | Ala | Arg | Ser | Ala | Arg | Lys | Arg | Leu | Ala | Arg | Arg | Lys | Ala | Arg |
|---|---|---|---|---|---|---|---|---|---|---|---|---|---|---|---|
| | 50 | | | | | 55 | | | | | 60 | | | | |

| Leu | Asn | His | Leu | Lys | His | Leu | Ile | Ala | Asn | Glu | Phe | Lys | Leu | Asn | Tyr |
|---|---|---|---|---|---|---|---|---|---|---|---|---|---|---|---|
| 65 | | | | | 70 | | | | | 75 | | | | | 80 |

| Glu | Asp | Tyr | Gln | Ser | Phe | Asp | Glu | Ser | Leu | Ala | Lys | Ala | Tyr | Lys | Gly |
|---|---|---|---|---|---|---|---|---|---|---|---|---|---|---|---|
| | | | | 85 | | | | | 90 | | | | | 95 | |

| Ser | Leu | Ile | Ser | Pro | Tyr | Glu | Leu | Arg | Phe | Arg | Ala | Leu | Asn | Glu | Leu |
|---|---|---|---|---|---|---|---|---|---|---|---|---|---|---|---|
| | | | 100 | | | | | 105 | | | | | 110 | | |

| Leu | Ser | Lys | Gln | Asp | Phe | Ala | Arg | Val | Ile | Leu | His | Ile | Ala | Lys | Arg |
|---|---|---|---|---|---|---|---|---|---|---|---|---|---|---|---|
| | | 115 | | | | | 120 | | | | | 125 | | | |

| Arg | Gly | Tyr | Asp | Asp | Ile | Lys | Asn | Ser | Asp | Asp | Lys | Glu | Lys | Gly | Ala |
|---|---|---|---|---|---|---|---|---|---|---|---|---|---|---|---|
| 130 | | | | | 135 | | | | | 140 | | | | | |

| Ile | Leu | Lys | Ala | Ile | Lys | Gln | Asn | Glu | Glu | Lys | Leu | Ala | Asn | Tyr | Gln |
|---|---|---|---|---|---|---|---|---|---|---|---|---|---|---|---|
| 145 | | | | | 150 | | | | | 155 | | | | | 160 |

| Ser | Val | Gly | Glu | Tyr | Leu | Tyr | Lys | Glu | Tyr | Phe | Gln | Lys | Phe | Lys | Glu |
|---|---|---|---|---|---|---|---|---|---|---|---|---|---|---|---|
| | | | | 165 | | | | | 170 | | | | | 175 | |

| Asn | Ser | Lys | Glu | Phe | Thr | Asn | Val | Arg | Asn | Lys | Lys | Glu | Ser | Tyr | Glu |
|---|---|---|---|---|---|---|---|---|---|---|---|---|---|---|---|
| | | | 180 | | | | | 185 | | | | | 190 | | |

| Arg | Cys | Ile | Ala | Gln | Ser | Phe | Leu | Lys | Asp | Glu | Leu | Lys | Leu | Ile | Phe |
|---|---|---|---|---|---|---|---|---|---|---|---|---|---|---|---|
| | | 195 | | | | | 200 | | | | | 205 | | | |

| Lys | Lys | Gln | Arg | Glu | Phe | Gly | Phe | Ser | Phe | Ser | Lys | Lys | Phe | Glu | Glu |
|---|---|---|---|---|---|---|---|---|---|---|---|---|---|---|---|
| 210 | | | | | 215 | | | | | 220 | | | | | |

| Glu | Val | Leu | Ser | Val | Ala | Phe | Tyr | Lys | Arg | Ala | Leu | Lys | Asp | Phe | Ser |
|---|---|---|---|---|---|---|---|---|---|---|---|---|---|---|---|
| 225 | | | | | 230 | | | | | 235 | | | | | 240 |

| His | Leu | Val | Gly | Asn | Cys | Ser | Phe | Phe | Thr | Asp | Glu | Lys | Arg | Ala | Pro |
|---|---|---|---|---|---|---|---|---|---|---|---|---|---|---|---|
| | | | | 245 | | | | | 250 | | | | | 255 | |

| Lys | Asn | Ser | Pro | Leu | Ala | Phe | Met | Phe | Val | Ala | Leu | Thr | Arg | Ile | Ile |
|---|---|---|---|---|---|---|---|---|---|---|---|---|---|---|---|
| | | | 260 | | | | | 265 | | | | | 270 | | |

| Asn | Leu | Leu | Asn | Asn | Leu | Lys | Asn | Thr | Glu | Gly | Ile | Leu | Tyr | Thr | Lys |
|---|---|---|---|---|---|---|---|---|---|---|---|---|---|---|---|
| | | 275 | | | | | 280 | | | | | 285 | | | |

| Asp | Asp | Leu | Asn | Ala | Leu | Leu | Asn | Glu | Val | Leu | Lys | Asn | Gly | Thr | Leu |
|---|---|---|---|---|---|---|---|---|---|---|---|---|---|---|---|
| 290 | | | | | 295 | | | | | 300 | | | | | |

| Thr | Tyr | Lys | Gln | Thr | Lys | Lys | Leu | Leu | Gly | Leu | Ser | Asp | Asp | Tyr | Glu |
|---|---|---|---|---|---|---|---|---|---|---|---|---|---|---|---|
| 305 | | | | | 310 | | | | | 315 | | | | | 320 |

| Phe | Lys | Gly | Glu | Lys | Gly | Thr | Tyr | Phe | Ile | Glu | Phe | Lys | Lys | Tyr | Lys |
|---|---|---|---|---|---|---|---|---|---|---|---|---|---|---|---|

```
                325                 330                 335

Glu Phe Ile Lys Ala Leu Gly Glu His Asn Leu Ser Gln Asp Asp Leu
            340                 345                 350

Asn Glu Ile Ala Lys Asp Ile Thr Leu Ile Lys Asp Glu Ile Lys Leu
        355                 360                 365

Lys Lys Ala Leu Ala Lys Tyr Asp Leu Asn Gln Asn Gln Ile Asp Ser
    370                 375                 380

Leu Ser Lys Leu Glu Phe Lys Asp His Leu Asn Ile Ser Phe Lys Ala
385                 390                 395                 400

Leu Lys Leu Val Thr Pro Leu Met Leu Glu Gly Lys Lys Tyr Asp Glu
                405                 410                 415

Ala Cys Asn Glu Leu Asn Leu Lys Val Ala Ile Asn Glu Asp Lys Lys
            420                 425                 430

Asp Phe Leu Pro Ala Phe Asn Glu Thr Tyr Tyr Lys Asp Glu Val Thr
        435                 440                 445

Asn Pro Val Val Leu Arg Ala Ile Lys Glu Tyr Arg Lys Val Leu Asn
    450                 455                 460

Ala Leu Leu Lys Lys Tyr Gly Lys Val His Lys Ile Asn Ile Glu Leu
465                 470                 475                 480

Ala Arg Glu Val Gly Lys Asn His Ser Gln Arg Ala Lys Ile Glu Lys
                485                 490                 495

Glu Gln Asn Glu Asn Tyr Lys Ala Lys Lys Asp Ala Glu Leu Glu Cys
            500                 505                 510

Glu Lys Leu Gly Leu Lys Ile Asn Ser Lys Asn Ile Leu Lys Leu Arg
        515                 520                 525

Leu Phe Lys Glu Gln Lys Glu Phe Cys Ala Tyr Ser Gly Glu Lys Ile
    530                 535                 540

Lys Ile Ser Asp Leu Gln Asp Glu Lys Met Leu Glu Ile Asp His Ile
545                 550                 555                 560

Tyr Pro Tyr Ser Arg Ser Phe Asp Asp Ser Tyr Met Asn Lys Val Leu
                565                 570                 575

Val Phe Thr Lys Gln Asn Gln Glu Lys Leu Asn Gln Thr Pro Phe Glu
            580                 585                 590

Ala Phe Gly Asn Asp Ser Ala Lys Trp Gln Lys Ile Glu Val Leu Ala
        595                 600                 605

Lys Asn Leu Pro Thr Lys Lys Gln Lys Arg Ile Leu Asp Lys Asn Tyr
    610                 615                 620

Lys Asp Lys Glu Gln Lys Asn Phe Lys Asp Arg Asn Leu Asn Asp Thr
625                 630                 635                 640

Arg Tyr Ile Ala Arg Leu Val Leu Asn Tyr Thr Lys Asp Tyr Leu Asp
                645                 650                 655

Phe Leu Pro Leu Ser Asp Asp Glu Asn Thr Lys Leu Asn Asp Thr Gln
            660                 665                 670

Lys Gly Ser Lys Val His Val Glu Ala Lys Ser Gly Met Leu Thr Ser
        675                 680                 685

Ala Leu Arg His Thr Trp Gly Phe Ser Ala Lys Asp Arg Asn Asn His
    690                 695                 700

Leu His His Ala Ile Asp Ala Val Ile Ile Ala Tyr Ala Asn Asn Ser
705                 710                 715                 720

Ile Val Lys Ala Phe Ser Asp Phe Lys Lys Glu Gln Glu Ser Asn Ser
                725                 730                 735

Ala Glu Leu Tyr Ala Lys Lys Ile Ser Glu Leu Asp Tyr Lys Asn Lys
            740                 745                 750
```

```
Arg Lys Phe Phe Glu Pro Phe Ser Gly Phe Arg Gln Lys Val Leu Asp
        755                 760                 765

Lys Ile Asp Glu Ile Phe Val Ser Lys Pro Glu Arg Lys Lys Pro Ser
    770                 775                 780

Gly Ala Leu His Glu Glu Thr Phe Arg Lys Glu Glu Glu Phe Tyr Gln
785                 790                 795                 800

Ser Tyr Gly Gly Lys Glu Gly Val Leu Lys Ala Leu Glu Leu Gly Lys
                805                 810                 815

Ile Arg Lys Val Asn Gly Lys Ile Val Lys Asn Gly Asp Met Phe Arg
            820                 825                 830

Val Asp Ile Phe Lys His Lys Lys Thr Asn Lys Phe Tyr Ala Val Pro
        835                 840                 845

Ile Tyr Thr Met Asp Phe Ala Leu Lys Val Leu Pro Asn Lys Ala Val
    850                 855                 860

Ala Arg Ser Lys Lys Gly Glu Ile Lys Asp Trp Ile Leu Met Asp Glu
865                 870                 875                 880

Asn Tyr Glu Phe Cys Phe Ser Leu Tyr Lys Asp Ser Leu Ile Leu Ile
                885                 890                 895

Gln Thr Lys Asp Met Gln Glu Pro Glu Phe Val Tyr Tyr Asn Ala Phe
            900                 905                 910

Thr Ser Ser Thr Val Ser Leu Ile Val Ser Lys His Asp Asn Lys Phe
        915                 920                 925

Glu Thr Leu Ser Lys Asn Gln Lys Ile Leu Phe Lys Asn Ala Asn Glu
    930                 935                 940

Lys Glu Val Ile Ala Lys Ser Ile Gly Ile Gln Asn Leu Lys Val Phe
945                 950                 955                 960

Glu Lys Tyr Ile Val Ser Ala Leu Gly Glu Val Thr Lys Ala Glu Phe
                965                 970                 975

Arg Gln Arg Glu Asp Phe Lys Lys
            980
```

<210> SEQ ID NO 103
<211> LENGTH: 91
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 103

```
tataatctca taagaaattt aaaaagggac taaaataaag agtttgcggg actctgcggg     60

gttacaatcc cctaaaaccg cttttaaaat t                                    91
```

<210> SEQ ID NO 104
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 104

```
attttaccat aaagaaattt aaaaagggac taaaac                               36
```

<210> SEQ ID NO 105
<211> LENGTH: 95

<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (1)..(20)
<223> OTHER INFORMATION: a, c, u, g, unknown or other

<400> SEQUENCE: 105
nnnnnnnnnn nnnnnnnnnn guuuuagucc cgaaagggac uaaaauaaag aguuugcggg 60
acucugcggg guuacaaucc ccuaaaaccg cuuuu 95

<210> SEQ ID NO 106
<211> LENGTH: 1115
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 106

Met Ser Asp Leu Val Leu Gly Leu Asp Ile Gly Ile Gly Ser Val Gly
1 5 10 15

Val Gly Ile Leu Asn Lys Val Thr Gly Glu Ile Ile His Lys Asn Ser
20 25 30

Arg Ile Phe Pro Ala Ala Gln Ala Glu Asn Asn Leu Val Arg Arg Thr
35 40 45

Asn Arg Gln Gly Arg Arg Leu Ala Arg Arg Lys Lys His Arg Arg Val
50 55 60

Arg Leu Asn Arg Leu Phe Glu Glu Ser Gly Leu Ile Thr Asp Phe Thr
65 70 75 80

Lys Ile Ser Ile Asn Leu Asn Pro Tyr Gln Leu Arg Val Lys Gly Leu
85 90 95

Thr Asp Glu Leu Ser Asn Glu Glu Leu Phe Ile Ala Leu Lys Asn Met
100 105 110

Val Lys His Arg Gly Ile Ser Tyr Leu Asp Asp Ala Ser Asp Asp Gly
115 120 125

Asn Ser Ser Val Gly Asp Tyr Ala Gln Ile Val Lys Glu Asn Ser Lys
130 135 140

Gln Leu Glu Thr Lys Thr Pro Gly Gln Ile Gln Leu Glu Arg Tyr Gln
145 150 155 160

Thr Tyr Gly Gln Leu Arg Gly Asp Phe Thr Val Glu Lys Asp Gly Lys
165 170 175

Lys His Arg Leu Ile Asn Val Phe Pro Thr Ser Ala Tyr Arg Ser Glu
180 185 190

Ala Leu Arg Ile Leu Gln Thr Gln Gln Glu Phe Asn Pro Gln Ile Thr
195 200 205

Asp Glu Phe Ile Asn Arg Tyr Leu Glu Ile Leu Thr Gly Lys Arg Lys
210 215 220

Tyr Tyr His Gly Pro Gly Asn Glu Lys Ser Arg Thr Asp Tyr Gly Arg
225 230 235 240

Tyr Arg Thr Ser Gly Glu Thr Leu Asp Asn Ile Phe Gly Ile Leu Ile
245 250 255

Gly Lys Cys Thr Phe Tyr Pro Asp Glu Phe Arg Ala Ala Lys Ala Ser
260 265 270

-continued

```
Tyr Thr Ala Gln Glu Phe Asn Leu Leu Asn Asp Leu Asn Asn Leu Thr
        275                 280                 285

Val Pro Thr Glu Thr Lys Lys Leu Ser Lys Glu Gln Lys Asn Gln Ile
    290                 295                 300

Ile Asn Tyr Val Lys Asn Glu Lys Ala Met Gly Pro Ala Lys Leu Phe
305                 310                 315                 320

Lys Tyr Ile Ala Lys Leu Leu Ser Cys Asp Val Ala Asp Ile Lys Gly
                325                 330                 335

Tyr Arg Ile Asp Lys Ser Gly Lys Ala Glu Ile His Thr Phe Glu Ala
            340                 345                 350

Tyr Arg Lys Met Lys Thr Leu Glu Thr Leu Asp Ile Glu Gln Met Asp
        355                 360                 365

Arg Glu Thr Leu Asp Lys Leu Ala Tyr Val Leu Thr Leu Asn Thr Glu
    370                 375                 380

Arg Glu Gly Ile Gln Glu Ala Leu Glu His Glu Phe Ala Asp Gly Ser
385                 390                 395                 400

Phe Ser Gln Lys Gln Val Asp Glu Leu Val Gln Phe Arg Lys Ala Asn
                405                 410                 415

Ser Ser Ile Phe Gly Lys Gly Trp His Asn Phe Ser Val Lys Leu Met
            420                 425                 430

Met Glu Leu Ile Pro Glu Leu Tyr Glu Thr Ser Glu Glu Gln Met Thr
        435                 440                 445

Ile Leu Thr Arg Leu Gly Lys Gln Lys Thr Thr Ser Ser Ser Asn Lys
    450                 455                 460

Thr Lys Tyr Ile Asp Glu Lys Leu Leu Thr Glu Glu Ile Tyr Asn Pro
465                 470                 475                 480

Val Val Ala Lys Ser Val Arg Gln Ala Ile Lys Ile Val Asn Ala Ala
                485                 490                 495

Ile Lys Glu Tyr Gly Asp Phe Asp Asn Ile Val Ile Glu Met Ala Arg
            500                 505                 510

Glu Asn Gln Thr Thr Gln Lys Gly Gln Lys Asn Ser Arg Glu Arg Met
        515                 520                 525

Lys Arg Ile Glu Glu Gly Ile Lys Glu Leu Gly Ser Gln Ile Leu Lys
    530                 535                 540

Glu His Pro Val Glu Asn Thr Gln Leu Gln Asn Glu Lys Leu Tyr Leu
545                 550                 555                 560

Tyr Tyr Leu Gln Asn Gly Arg Asp Met Tyr Val Asp Gln Glu Leu Asp
                565                 570                 575

Ile Asn Arg Leu Ser Asp Tyr Asp Val Asp His Ile Val Pro Gln Ser
            580                 585                 590

Phe Leu Lys Asp Asp Ser Ile Asp Asn Lys Val Leu Thr Arg Ser Asp
        595                 600                 605

Lys Asn Arg Gly Lys Ser Asp Asn Val Pro Ser Glu Glu Val Val Lys
    610                 615                 620

Lys Met Lys Asn Tyr Trp Arg Gln Leu Leu Asn Ala Lys Leu Ile Thr
625                 630                 635                 640

Gln Arg Lys Phe Asp Asn Leu Thr Lys Ala Glu Arg Gly Gly Leu Ser
                645                 650                 655

Glu Leu Asp Lys Ala Gly Phe Ile Lys Arg Gln Leu Val Glu Thr Arg
            660                 665                 670

Gln Ile Thr Lys His Val Ala Gln Ile Leu Asp Ser Arg Met Asn Thr
        675                 680                 685
```

-continued

```
Lys Tyr Asp Glu Asn Asp Lys Leu Ile Arg Glu Val Lys Val Ile Thr
    690                 695                 700

Leu Lys Ser Lys Leu Val Ser Asp Phe Arg Lys Asp Phe Gln Phe Tyr
705                 710                 715                 720

Lys Val Arg Glu Ile Asn Asn Tyr His His Ala His Asp Ala Tyr Leu
                725                 730                 735

Asn Ala Val Val Gly Thr Ala Leu Ile Lys Lys Tyr Pro Lys Leu Glu
            740                 745                 750

Ser Glu Phe Val Tyr Gly Asp Tyr Lys Val Tyr Asp Val Arg Lys Met
        755                 760                 765

Ile Ala Lys Ser Glu Gln Glu Ile Gly Lys Ala Thr Ala Lys Tyr Phe
    770                 775                 780

Phe Tyr Ser Asn Ile Met Asn Phe Phe Lys Thr Glu Ile Thr Leu Ala
785                 790                 795                 800

Asn Gly Glu Ile Arg Lys Arg Pro Leu Ile Glu Thr Asn Gly Glu Thr
                805                 810                 815

Gly Glu Ile Val Trp Asp Lys Gly Arg Asp Phe Ala Thr Val Arg Lys
            820                 825                 830

Val Leu Ser Met Pro Gln Val Asn Ile Val Lys Lys Thr Glu Val Gln
        835                 840                 845

Thr Gly Gly Phe Ser Lys Glu Ser Ile Leu Pro Lys Arg Asn Ser Asp
    850                 855                 860

Lys Leu Ile Ala Arg Lys Lys Asp Trp Asp Pro Lys Lys Tyr Gly Gly
865                 870                 875                 880

Phe Asp Ser Pro Thr Val Ala Tyr Ser Val Leu Val Val Ala Lys Val
                885                 890                 895

Glu Lys Gly Lys Ser Lys Lys Leu Lys Ser Val Lys Glu Leu Leu Gly
            900                 905                 910

Ile Thr Ile Met Glu Arg Ser Ser Phe Glu Lys Asn Pro Ile Asp Phe
        915                 920                 925

Leu Glu Ala Lys Gly Tyr Lys Glu Val Lys Lys Asp Leu Ile Ile Lys
    930                 935                 940

Leu Pro Lys Tyr Ser Leu Phe Glu Leu Glu Asn Gly Arg Lys Arg Met
945                 950                 955                 960

Leu Ala Ser Ala Gly Glu Leu Gln Lys Gly Asn Glu Leu Ala Leu Pro
                965                 970                 975

Ser Lys Tyr Val Asn Phe Leu Tyr Leu Ala Ser His Tyr Glu Lys Leu
            980                 985                 990

Lys Gly Ser Pro Glu Asp Asn Glu  Gln Lys Gln Leu Phe  Val Glu Gln
        995                 1000                1005

His Lys  His Tyr Leu Asp Glu  Ile Ile Glu Gln Ile  Ser Glu Phe
    1010                1015                1020

Ser Lys  Arg Val Ile Leu Ala  Asp Ala Asn Leu Asp  Lys Val Leu
    1025                1030                1035

Ser Ala  Tyr Asn Lys His Arg  Asp Lys Pro Ile Arg  Glu Gln Ala
    1040                1045                1050

Glu Asn  Ile Ile His Leu Phe  Thr Leu Thr Asn Leu  Gly Ala Pro
    1055                1060                1065

Ala Ala  Phe Lys Tyr Phe Asp  Thr Thr Ile Asp Arg  Lys Arg Tyr
    1070                1075                1080

Thr Ser  Thr Lys Glu Val Leu  Asp Ala Thr Leu Ile  His Gln Ser
    1085                1090                1095

Ile Thr  Gly Leu Tyr Glu Thr  Arg Ile Asp Leu Ser  Gln Leu Gly
```

1100 1105 1110

Gly Asp
1115

<210> SEQ ID NO 107
<211> LENGTH: 1374
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 107

Met Asp Lys Lys Tyr Ser Ile Gly Leu Asp Ile Gly Thr Asn Ser Val
1 5 10 15

Gly Trp Ala Val Ile Thr Asp Glu Tyr Lys Val Pro Ser Lys Lys Phe
20 25 30

Lys Val Leu Gly Asn Thr Asp Arg His Ser Ile Lys Lys Asn Leu Ile
35 40 45

Gly Ala Leu Leu Phe Asp Ser Gly Glu Thr Ala Glu Ala Thr Arg Leu
50 55 60

Lys Arg Thr Ala Arg Arg Arg Tyr Thr Arg Arg Lys Asn Arg Ile Cys
65 70 75 80

Tyr Leu Gln Glu Ile Phe Ser Asn Glu Met Ala Lys Val Asp Asp Ser
85 90 95

Phe Phe His Arg Leu Glu Glu Ser Phe Leu Val Glu Glu Asp Lys Lys
100 105 110

His Glu Arg His Pro Ile Phe Gly Asn Ile Val Asp Glu Val Ala Tyr
115 120 125

His Glu Lys Tyr Pro Thr Ile Tyr His Leu Arg Lys Lys Leu Val Asp
130 135 140

Ser Thr Asp Lys Ala Asp Leu Arg Leu Ile Tyr Leu Ala Leu Ala His
145 150 155 160

Met Ile Lys Phe Arg Gly His Phe Leu Ile Glu Gly Asp Leu Asn Pro
165 170 175

Asp Asn Ser Asp Val Asp Lys Leu Phe Ile Gln Leu Val Gln Thr Tyr
180 185 190

Asn Gln Leu Phe Glu Glu Asn Pro Ile Asn Ala Ser Gly Val Asp Ala
195 200 205

Lys Ala Ile Leu Ser Ala Arg Leu Ser Lys Ser Arg Arg Leu Glu Asn
210 215 220

Leu Ile Ala Gln Leu Pro Gly Glu Lys Lys Asn Gly Leu Phe Gly Asn
225 230 235 240

Leu Ile Ala Leu Ser Leu Gly Leu Thr Pro Asn Phe Lys Ser Asn Phe
245 250 255

Asp Leu Ala Glu Asp Ala Lys Leu Gln Leu Ser Lys Asp Thr Tyr Asp
260 265 270

Asp Asp Leu Asp Asn Leu Leu Ala Gln Ile Gly Asp Gln Tyr Ala Asp
275 280 285

Leu Phe Leu Ala Ala Lys Asn Leu Ser Asp Ala Ile Leu Leu Ser Asp
290 295 300

Ile Leu Arg Val Asn Thr Glu Ile Thr Lys Ala Pro Leu Ser Ala Ser
305 310 315 320

Met Ile Lys Arg Tyr Asp Glu His His Gln Asp Leu Thr Leu Leu Lys
325 330 335

-continued

Ala Leu Val Arg Gln Gln Leu Pro Glu Lys Tyr Lys Glu Ile Phe Phe
340 345 350

Asp Gln Ser Lys Asn Gly Tyr Ala Gly Tyr Ile Asp Gly Gly Ala Ser
355 360 365

Gln Glu Glu Phe Tyr Lys Phe Ile Lys Pro Ile Leu Glu Lys Met Asp
370 375 380

Gly Thr Glu Glu Leu Leu Val Lys Leu Asn Arg Glu Asp Leu Leu Arg
385 390 395 400

Lys Gln Arg Thr Phe Asp Asn Gly Ser Ile Pro His Gln Ile His Leu
405 410 415

Gly Glu Leu His Ala Ile Leu Arg Arg Gln Glu Asp Phe Tyr Pro Phe
420 425 430

Leu Lys Asp Asn Arg Glu Lys Ile Glu Lys Ile Leu Thr Phe Arg Ile
435 440 445

Pro Tyr Tyr Val Gly Pro Leu Ala Arg Gly Asn Ser Arg Phe Ala Trp
450 455 460

Met Thr Arg Lys Ser Glu Glu Thr Ile Thr Pro Trp Asn Phe Glu Glu
465 470 475 480

Val Val Asp Lys Gly Ala Ser Ala Gln Ser Phe Ile Glu Arg Met Thr
485 490 495

Asn Phe Asp Lys Asn Leu Pro Asn Glu Lys Val Leu Pro Lys His Ser
500 505 510

Leu Leu Tyr Glu Tyr Phe Thr Val Tyr Asn Glu Leu Thr Lys Val Lys
515 520 525

Tyr Val Thr Glu Gly Met Arg Lys Pro Ala Phe Leu Ser Gly Glu Gln
530 535 540

Lys Lys Ala Ile Val Asp Leu Leu Phe Lys Thr Asn Arg Lys Val Thr
545 550 555 560

Val Lys Gln Leu Lys Glu Asp Tyr Phe Lys Lys Ile Glu Cys Phe Asp
565 570 575

Ser Val Glu Ile Ser Gly Val Glu Asp Arg Phe Asn Ala Ser Leu Gly
580 585 590

Thr Tyr His Asp Leu Leu Lys Ile Ile Lys Asp Lys Asp Phe Leu Asp
595 600 605

Asn Glu Glu Asn Glu Asp Ile Leu Glu Asp Ile Val Leu Thr Leu Thr
610 615 620

Leu Phe Glu Asp Arg Glu Met Ile Glu Glu Arg Leu Lys Thr Tyr Ala
625 630 635 640

His Leu Phe Asp Asp Lys Val Met Lys Gln Leu Lys Arg Arg Arg Tyr
645 650 655

Thr Gly Trp Gly Arg Leu Ser Arg Lys Leu Ile Asn Gly Ile Arg Asp
660 665 670

Lys Gln Ser Gly Lys Thr Ile Leu Asp Phe Leu Lys Ser Asp Gly Phe
675 680 685

Ala Asn Arg Asn Phe Met Gln Leu Ile His Asp Asp Ser Leu Thr Phe
690 695 700

Lys Glu Asp Ile Gln Lys Ala Gln Val Ser Gly Gln Gly Asp Ser Leu
705 710 715 720

His Glu His Ile Ala Asn Leu Ala Gly Ser Pro Ala Ile Lys Lys Gly
725 730 735

Ile Leu Gln Thr Val Lys Val Val Asp Glu Leu Val Lys Val Met Gly
740 745 750

-continued

```
Arg His Lys Pro Glu Asn Ile Val Ile Glu Met Ala Arg Glu Thr Asn
        755                 760                 765

Glu Asp Asp Glu Lys Lys Ala Ile Gln Lys Ile Gln Lys Ala Asn Lys
    770                 775                 780

Asp Glu Lys Asp Ala Ala Met Leu Lys Ala Ala Asn Gln Tyr Asn Gly
785                 790                 795                 800

Lys Ala Glu Leu Pro His Ser Val Phe His Gly His Lys Gln Leu Ala
                805                 810                 815

Thr Lys Ile Arg Leu Trp His Gln Gln Gly Glu Arg Cys Leu Tyr Thr
            820                 825                 830

Gly Lys Thr Ile Ser Ile His Asp Leu Ile Asn Asn Ser Asn Gln Phe
        835                 840                 845

Glu Val Asp His Ile Leu Pro Leu Ser Ile Thr Phe Asp Asp Ser Leu
    850                 855                 860

Ala Asn Lys Val Leu Val Tyr Ala Thr Ala Asn Gln Glu Lys Gly Gln
865                 870                 875                 880

Arg Thr Pro Tyr Gln Ala Leu Asp Ser Met Asp Asp Ala Trp Ser Phe
                885                 890                 895

Arg Glu Leu Lys Ala Phe Val Arg Glu Ser Lys Thr Leu Ser Asn Lys
            900                 905                 910

Lys Lys Glu Tyr Leu Leu Thr Glu Glu Asp Ile Ser Lys Phe Asp Val
        915                 920                 925

Arg Lys Lys Phe Ile Glu Arg Asn Leu Val Asp Thr Arg Tyr Ala Ser
    930                 935                 940

Arg Val Val Leu Asn Ala Leu Gln Glu His Phe Arg Ala His Lys Ile
945                 950                 955                 960

Asp Thr Lys Val Ser Val Val Arg Gly Gln Phe Thr Ser Gln Leu Arg
                965                 970                 975

Arg His Trp Gly Ile Glu Lys Thr Arg Asp Thr Tyr His His His Ala
            980                 985                 990

Val Asp Ala Leu Ile Ile Ala Ala  Ser Ser Gln Leu Asn  Leu Trp Lys
        995                 1000                1005

Lys Gln  Lys Asn Thr Leu Val  Ser Tyr Ser Glu Asp  Gln Leu Leu
    1010                1015                1020

Asp Ile  Glu Thr Gly Glu Leu  Ile Ser Asp Asp Glu  Tyr Lys Glu
    1025                1030                1035

Ser Val  Phe Lys Ala Pro Tyr  Gln His Phe Val Asp  Thr Leu Lys
    1040                1045                1050

Ser Lys  Glu Phe Glu Asp Ser  Ile Leu Phe Ser Tyr  Gln Val Asp
    1055                1060                1065

Ser Lys  Phe Asn Arg Lys Ile  Ser Asp Ala Thr Ile  Tyr Ala Thr
    1070                1075                1080

Arg Gln  Ala Lys Val Gly Lys  Asp Lys Ala Asp Glu  Thr Tyr Val
    1085                1090                1095

Leu Gly  Lys Ile Lys Asp Ile  Tyr Thr Gln Asp Gly  Tyr Asp Ala
    1100                1105                1110

Phe Met  Lys Ile Tyr Lys Lys  Asp Lys Ser Lys Phe  Leu Met Tyr
    1115                1120                1125

Arg His  Asp Pro Gln Thr Phe  Glu Lys Val Ile Glu  Pro Ile Leu
    1130                1135                1140

Glu Asn  Tyr Pro Asn Lys Gln  Ile Asn Glu Lys Gly  Lys Glu Val
    1145                1150                1155

Pro Cys  Asn Pro Phe Leu Lys  Tyr Lys Glu Glu His  Gly Tyr Ile
```

1160 1165 1170

Arg Lys Tyr Ser Lys Lys Gly Asn Gly Pro Glu Ile Lys Ser Leu
1175 1180 1185

Lys Tyr Tyr Asp Ser Lys Leu Gly Asn His Ile Asp Ile Thr Pro
1190 1195 1200

Lys Asp Ser Asn Asn Lys Val Val Leu Gln Ser Val Ser Pro Trp
1205 1210 1215

Arg Ala Asp Val Tyr Phe Asn Lys Thr Thr Gly Lys Tyr Glu Ile
1220 1225 1230

Leu Gly Leu Lys Tyr Ala Asp Leu Gln Phe Glu Lys Gly Thr Gly
1235 1240 1245

Thr Tyr Lys Ile Ser Gln Glu Lys Tyr Asn Asp Ile Lys Lys Lys
1250 1255 1260

Glu Gly Val Asp Ser Asp Ser Glu Phe Lys Phe Thr Leu Tyr Lys
1265 1270 1275

Asn Asp Leu Leu Leu Val Lys Asp Thr Glu Thr Lys Glu Gln Gln
1280 1285 1290

Leu Phe Arg Phe Leu Ser Arg Thr Met Pro Lys Gln Lys His Tyr
1295 1300 1305

Val Glu Leu Lys Pro Tyr Asp Lys Gln Lys Phe Glu Gly Gly Glu
1310 1315 1320

Ala Leu Ile Lys Val Leu Gly Asn Val Ala Asn Ser Gly Gln Cys
1325 1330 1335

Lys Lys Gly Leu Gly Lys Ser Asn Ile Ser Ile Tyr Lys Val Arg
1340 1345 1350

Thr Asp Val Leu Gly Asn Gln His Ile Ile Lys Asn Glu Gly Asp
1355 1360 1365

Lys Pro Lys Leu Asp Phe
1370

<210> SEQ ID NO 108
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 108

Gly Gly Gly Gly Ser Gly Gly Gly Gly Ser Gly Gly Gly Gly Ser
1 5 10 15

<210> SEQ ID NO 109
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 109

Glu Ala Ala Ala Lys Glu Ala Ala Ala Lys Glu Ala Ala Ala Lys
1 5 10 15

<210> SEQ ID NO 110
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 110

Gly Gly Gly Gly Gly Ser Gly Gly Gly Gly Gly Ser Gly Gly Gly Gly
1               5                   10                  15

Gly Ser

<210> SEQ ID NO 111
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 111
gccaaattgg acgaccctcg cgg 23

<210> SEQ ID NO 112
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 112
cgaggagacc cccgtttcgg tgg 23

<210> SEQ ID NO 113
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 113
cccgccgccg ccgtggctcg agg 23

<210> SEQ ID NO 114
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 114
tgagctctac gagatccaca agg 23

<210> SEQ ID NO 115
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 115
ctcaaaattc ataccggttg tgg 23

<210> SEQ ID NO 116
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 116
cgttaaacaa caaccggact tgg 23

<210> SEQ ID NO 117
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 117
ttcaccccgc ggcgctgaat ggg 23

<210> SEQ ID NO 118
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 118
accactacca gtccgtccac agg 23

<210> SEQ ID NO 119
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 119
agcctttctg aacacatgca cgg 23

<210> SEQ ID NO 120
<211> LENGTH: 39
<212> TYPE: DNA
<213> ORGANISM: Homo sapiens

<400> SEQUENCE: 120
cctgccatca atgtggccat gcatgtgttc agaaaggct 39

<210> SEQ ID NO 121
<211> LENGTH: 39
<212> TYPE: DNA
<213> ORGANISM: Homo sapiens

<400> SEQUENCE: 121
cctgccatca atgtggccgt gcatgtgttc agaaaggct 39

```
<210> SEQ ID NO 122
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 122

cactgcttaa gcctcgctcg agg                                             23


<210> SEQ ID NO 123
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 123

tcaccagcaa tattcgctcg agg                                             23


<210> SEQ ID NO 124
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 124

caccagcaat attccgctcg agg                                             23


<210> SEQ ID NO 125
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 125

tagcaacaga catacgctcg agg                                             23


<210> SEQ ID NO 126
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 126

gggcagtagt aatacgctcg agg                                             23


<210> SEQ ID NO 127
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 127
ccaattccca tacattattg tac 23

<210> SEQ ID NO 128
<211> LENGTH: 4677
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 128
tctttcttgc gctatgacac ttccagcaaa aggtagggcg ggctgcgaga cggcttcccg 60
gcgctgcatg caacaccgat gatgcttcga ccccccgaag ctccttcggg gctgcatggg 120
cgctccgatg ccgctccagg gcgagcgctg tttaaatagc caggcccccg attgcaaaga 180
cattatagcg agctaccaaa gccatattca aacacctaga tcactaccac ttctacacag 240
gccactcgag cttgtgatcg cactccgcta agggggcgcc tcttcctctt cgtttcagtc 300
acaacccgca aacatgtacc catacgatgt tccagattac gcttcgccga agaaaaagcg 360
caaggtcgaa gcgtccgaca agaagtacag catcggcctg gacatcggca ccaactctgt 420
gggctgggcc gtgatcaccg acgagtacaa ggtgcccagc aagaaattca aggtgctggg 480
caacaccgac cggcacagca tcaagaagaa cctgatcgga gccctgctgt tcgacagcgg 540
cgaaacagcc gaggccaccc ggctgaagag aaccgccaga agaagataca ccagacggaa 600
gaaccggatc tgctatctgc aagagatctt cagcaacgag atggccaagg tggacgacag 660
cttcttccac agactggaag agtccttcct ggtggaagag gataagaagc acgagcggca 720
ccccatcttc ggcaacatcg tggacgaggt ggcctaccac gagaagtacc ccaccatcta 780
ccacctgaga aagaaactgg tggacagcac cgacaaggcc gacctgcggc tgatctatct 840
ggccctggcc cacatgatca agttccgggg ccacttcctg atcgagggcg acctgaaccc 900
cgacaacagc gacgtggaca agctgttcat ccagctggtg cagacctaca accagctgtt 960
cgaggaaaac cccatcaacg ccagcggcgt ggacgccaag gccatcctgt ctgccagact 1020
gagcaagagc agacggctgg aaaatctgat cgcccagctg cccggcgaga agaagaatgg 1080
cctgttcggc aacctgattg ccctgagcct gggcctgacc cccaacttca agagcaactt 1140
cgacctggcc gaggatgcca aactgcagct gagcaaggac acctacgacg acgacctgga 1200
caacctgctg gcccagatcg gcgaccagta cgccgacctg tttctggccg ccaagaacct 1260
gtccgacgcc atcctgctga gcgacatcct gagagtgaac accgagatca ccaaggcccc 1320
cctgagcgcc tctatgatca agagatacga cgagcaccac caggacctga ccctgctgaa 1380
agctctcgtg cggcagcagc tgcctgagaa gtacaaagag attttcttcg accagagcaa 1440
gaacggctac gccggctaca ttgacggcgg agccagccag gaagagttct acaagttcat 1500
caagcccatc ctggaaaaga tggacggcac cgaggaactg ctcgtgaagc tgaacagaga 1560
ggacctgctg cggaagcagc ggaccttcga caacggcagc atcccccacc agatccacct 1620
gggagagctg cacgccattc tgcggcggca ggaagatttt tacccattcc tgaaggacaa 1680
ccgggaaaag atcgagaaga tcctgacctt ccgcatcccc tactacgtgg gccctctggc 1740
caggggaaac agcagattcg cctggatgac cagaaagagc gaggaaacca tcaccccctg 1800
gaacttcgag gaagtggtgg acaagggcgc ttccgcccag agcttcatcg agcggatgac 1860

-continued

```
caacttcgat aagaacctgc ccaacgagaa ggtgctgccc aagcacagcc tgctgtacga   1920
gtacttcacc gtgtataacg agctgaccaa agtgaaatac gtgaccgagg gaatgagaaa   1980
gcccgccttc ctgagcggcg agcagaaaaa ggccatcgtg gacctgctgt tcaagaccaa   2040
ccggaaagtg accgtgaagc agctgaaaga ggactacttc aagaaaatcg agtgcttcga   2100
ctccgtggaa atctccggcg tggaagatcg gttcaacgcc tccctgggca cataccacga   2160
tctgctgaaa attatcaagg acaaggactt cctggacaat gaggaaaacg aggacattct   2220
ggaagatatc gtgctgaccc tgacactgtt tgaggacaga gagatgatcg aggaacggct   2280
gaaaacctat gcccacctgt tcgacgacaa agtgatgaag cagctgaagc ggcggagata   2340
caccggctgg ggcaggctga gccggaagct gatcaacggc atccgggaca agcagtccgg   2400
caagacaatc ctggatttcc tgaagtccga cggcttcgcc aacagaaact tcatgcagct   2460
gatccacgac gacagcctga cctttaaaga ggacatccag aaagcccagg tgtccggcca   2520
gggcgatagc ctgcacgagc acattgccaa tctggccggc agccccgcca ttaagaaggg   2580
catcctgcag acagtgaagg tggtggacga gctcgtgaaa gtgatgggcc ggcacaagcc   2640
cgagaacatc gtgatcgaaa tggccagaga gaaccagacc acccagaagg gacagaagaa   2700
cagccgcgag agaatgaagc ggatcgaaga gggcatcaaa gagctgggca gccagatcct   2760
gaaagaacac cccgtggaaa acacccagct gcagaacgag aagctgtacc tgtactacct   2820
gcagaatggg cgggatatgt acgtggacca ggaactggac atcaaccggc tgtccgacta   2880
cgatgtggac catatcgtgc ctcagagctt tctgaaggac gactccatcg acaacaaggt   2940
gctgaccaga agcgacaaga accggggcaa gagcgacaac gtgccctccg aagaggtcgt   3000
gaagaagatg aagaactact ggcggcagct gctgaacgcc aagctgatta cccagagaaa   3060
gttcgacaat ctgaccaagg ccgagagagg cggcctgagc gaactggata aggccggctt   3120
catcaagaga cagctggtgg aaacccggca gatcacaaag cacgtggcac agatcctgga   3180
ctcccggatg aacactaagt acgacgagaa tgacaagctg atccgggaag tgaaagtgat   3240
caccctgaag tccaagctgg tgtccgattt ccggaaggat ttccagtttt acaaagtgcg   3300
cgagatcaac aactaccacc acgcccacga cgcctacctg aacgccgtcg tgggaaccgc   3360
cctgatcaaa aagtacccta agctggaaag cgagttcgtg tacggcgact acaaggtgta   3420
cgacgtgcgg aagatgatcg ccaagagcga gcaggaaatc ggcaaggcta ccgccaagta   3480
cttcttctac agcaacatca tgaacttttt caagaccgag attaccctgg ccaacggcga   3540
gatccggaag cggcctctga tcgagacaaa cggcgaaacc ggggagatcg tgtgggataa   3600
gggccgggat tttgccaccg tgcggaaagt gctgagcatg ccccaagtga atatcgtgaa   3660
aaagaccgag gtgcagacag gcggcttcag caaagagtct atcctgccca agaggaacag   3720
cgataagctg atcgccagaa agaaggactg ggaccctaag aagtacggcg gcttcgacag   3780
ccccaccgtg gcctattctg tgctggtggt ggccaaagtg gaaaagggca agtccaagaa   3840
actgaagagt gtgaaagagc tgctggggat caccatcatg gaaagaagca gcttcgagaa   3900
gaatcccatc gactttctgg aagccaaggg ctacaaagaa gtgaaaaagg acctgatcat   3960
caagctgcct aagtactccc tgttcgagct ggaaaacggc cggaagagaa tgctggcctc   4020
tgccggcgaa ctgcagaagg gaaacgaact ggccctgccc tccaaatatg tgaacttcct   4080
gtacctggcc agccactatg agaagctgaa gggctccccc gaggataatg agcagaaaca   4140
gctgtttgtg gaacagcaca agcactacct ggacgagatc atcgagcaga tcagcgagtt   4200
ctccaagaga gtgatcctgg ccgacgctaa tctggacaaa gtgctgtccg cctacaacaa   4260
```

```
gcaccgggat aagcccatca gagagcaggc cgagaatatc atccacctgt ttaccctgac   4320

caatctggga gcccctgccg ccttcaagta ctttgacacc accatcgacc ggaagaggta   4380

caccagcacc aaagaggtgc tggacgccac cctgatccac cagagcatca ccggcctgta   4440

cgagacacgg atcgacctgt ctcagctggg aggcgacagc cccaagaaga agagaaaggt   4500

ggaggccagc taaggatccg gcaagactgg ccccgcttgg caacgcaaca gtgagcccct   4560

ccctagtgtg tttggggatg tgactatgta ttcgtgtgtt ggccaacggg tcaacccgaa   4620

cagattgata cccgccttgg catttcctgt cagaatgtaa cgtcagttga tggtact      4677
```

<210> SEQ ID NO 129
<211> LENGTH: 3150
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 129

```
tctttcttgc gctatgacac ttccagcaaa aggtagggcg ggctgcgaga cggcttcccg     60

gcgctgcatg caacaccgat gatgcttcga ccccccgaag ctccttcggg gctgcatggg    120

cgctccgatg ccgctccagg gcgagcgctg tttaaatagc caggcccccg attgcaaaga    180

cattatagcg agctaccaaa gccatattca aacacctaga tcactaccac ttctacacag    240

gccactcgag cttgtgatcg cactccgcta agggggcgcc tcttcctctt cgtttcagtc    300

acaacccgca aacatgccta agaagaagag gaaggttaac acgattaaca tcgctaagaa    360

cgacttctct gacatcgaac tggctgctat cccgttcaac actctggctg accattacgg    420

tgagcgttta gctcgcgaac agttggccct tgagcatgag tcttacgaga tgggtgaagc    480

acgcttccgc aagatgtttg agcgtcaact taaagctggt gaggttgcgg ataacgctgc    540

cgccaagcct ctcatcacta ccctactccc taagatgatt gcacgcatca acgactggtt    600

tgaggaagtg aaagctaagc gcggcaagcg cccgacagcc ttccagttcc tgcaagaaat    660

caagccggaa gccgtagcgt acatcaccat taagaccact ctggcttgcc taaccagtgc    720

tgacaataca accgttcagg ctgtagcaag cgcaatcggt cgggccattg aggacgaggc    780

tcgcttcggt cgtatccgtg accttgaagc taagcacttc aagaaaaacg ttgaggaaca    840

actcaacaag cgcgtagggc acgtctacaa gaaagcattt atgcaagttg tcgaggctga    900

catgctctct aagggtctac tcggtggcga ggcgtggtct tcgtggcata aggaagactc    960

tattcatgta ggagtacgct gcatcgagat gctcattgag tcaaccggaa tggttagctt   1020

acaccgccaa aatgctggcg tagtaggtca agactctgag actatcgaac tcgcacctga   1080

atacgctgag gctatcgcaa cccgtgcagg tgcgctggct ggcatctctc cgatgttcca   1140

accttgcgta gttcctccta agccgtggac tggcattact ggtggtggct attgggctaa   1200

cggtcgtcgt cctctggcgc tggtgcgtac tcacagtaag aaagcactga tgcgctacga   1260

agacgtttac atgcctgagg tgtacaaagc gattaacatt gcgcaaaaca ccgcatggaa   1320

aatcaacaag aaagtcctag cggtcgccaa cgtaatcacc aagtggaagc attgtccggt   1380

cgaggacatc cctgcgattg agcgtgaaga actcccgatg aaaccggaag acatcgacat   1440

gaatcctgag gctctcaccg cgtggaaacg tgctgccgct gctgtgtacc gcaaggacaa   1500

ggctcgcaag tctcgccgta tcagccttga gttcatgctt gagcaagcca ataagtttgc   1560
```

-continued

```
taaccataag gccatctggt tcccttacaa catggactgg cgcggtcgtg tttacgctgt   1620

gtcaatgttc aacccgcaag gtaacgatat gaccaaagga ctgcttacgc tggcgaaagg   1680

taaaccaatc ggtaaggaag gttactactg gctgaaaatc cacggtgcaa actgtgcggg   1740

tgtcgacaag gttccgttcc ctgagcgcat caagttcatt gaggaaaacc acgagaacat   1800

catggcttgc gctaagtctc cactggagaa cacttggtgg gctgagcaag attctccgtt   1860

ctgcttcctt gcgttctgct ttgagtacgc tggggtacag caccacggcc tgagctataa   1920

ctgctccctt ccgctggcgt ttgacgggtc ttgctctggc atccagcact tctccgcgat   1980

gctccgagat gaggtaggtg gtcgcgcggt taacttgctt cctagtgaaa ccgttcagga   2040

catctacggg attgttgcta agaaagtcaa cgagattcta caagcagacg caatcaatgg   2100

gaccgataac gaagtagtta ccgtgaccga tgagaacact ggtgaaatct ctgagaaagt   2160

caagctgggc actaaggcac tggctggtca atggctggct tacggtgtta ctcgcagtgt   2220

gactaagcgt tcagtcatga cgctggctta cgggtccaaa gagttcggct tccgtcaaca   2280

agtgctggaa gataccattc agccagctat tgattccggc aagggtctga tgttcactca   2340

gccgaatcag gctgctggat acatggctaa gctgatttgg gaatctgtga gcgtgacggt   2400

ggtagctgcg gttgaagcaa tgaactggct taagtctgct gctaagctgc tggctgctga   2460

ggtcaaagat aagaagactg gagagattct tcgcaagcgt tgcgctgtgc attgggtaac   2520

tcctgatggt ttccctgtgt ggcaggaata caagaagcct attcagacgc gcttgaacct   2580

gatgttcctc ggtcagttcc gcttacagcc taccattaac accaacaaag atagcgagat   2640

tgatgcacac aaacaggagt ctggtatcgc tcctaacttt gtacacagcc aagacggtag   2700

ccaccttcgt aagactgtag tgtgggcaca cgagaagtac ggaatcgaat cttttgcact   2760

gattcacgac tccttcggta cgattccggc tgacgctgcg aacctgttca aagcagtgcg   2820

cgaaactatg gttgacacat atgagtcttg tgatgtactg gctgatttct acgaccagtt   2880

cgctgaccag ttgcacgagt ctcaattgga caaaatgcca gcacttccgg ctaaaggtaa   2940

cttgaacctc cgtgacatct tagagtcgga cttcgcgttc gcgtaaggat ccggcaagac   3000

tggccccgct tggcaacgca acagtgagcc cctccctagt gtgtttgggg atgtgactat   3060

gtattcgtgt gttggccaac gggtcaaccc gaacagattg atacccgcct tggcatttcc   3120

tgtcagaatg taacgtcagt tgatggtact                                    3150
```

<210> SEQ ID NO 130
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: modified_base
<222> LOCATION: (23)..(42)
<223> OTHER INFORMATION: a, c, t, g, unknown or other

<400> SEQUENCE: 130

```
gaaattaata cgactcacta tannnnnnnn nnnnnnnnnn nngttttaga gctagaaata     60

gcaagttaaa ataaggctag tccgttatca acttgaaaaa gtggcaccga gtcggtgctt    120

ttttt                                                                125
```

<210> SEQ ID NO 131
<211> LENGTH: 8452

<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 131
tgcggtattt cacaccgcat caggtggcac ttttcgggga aatgtgcgcg gaacccctat 60
ttgtttattt ttctaaatac attcaaatat gtatccgctc atgagattat caaaaaggat 120
cttcacctag atccttttaa attaaaaatg aagttttaaa tcaatctaaa gtatatatga 180
gtaaacttgg tctgacagtt accaatgctt aatcagtgag gcacctatct cagcgatctg 240
tctatttcgt tcatccatag ttgcctgact ccccgtcgtg tagataacta cgatacggga 300
gggcttacca tctggcccca gtgctgcaat gataccgcga gacccacgct caccggctcc 360
agatttatca gcaataaacc agccagccgg aagggccgag cgcagaagtg gtcctgcaac 420
tttatccgcc tccatccagt ctattaattg ttgccgggaa gctagagtaa gtagttcgcc 480
agttaatagt ttgcgcaacg ttgttgccat tgctacaggc atcgtggtgt cacgctcgtc 540
gtttggtatg gcttcattca gctccggttc ccaacgatca aggcgagtta catgatcccc 600
catgttgtgc aaaaaagcgg ttagctcctt cggtcctccg atcgttgtca gaagtaagtt 660
ggccgcagtg ttatcactca tggttatggc agcactgcat aattctctta ctgtcatgcc 720
atccgtaaga tgcttttctg tgactggtga gtactcaacc aagtcattct gagaatagtg 780
tatgcggcga ccgagttgct cttgcccggc gtcaatacgg gataataccg cgccacatag 840
cagaacttta aaagtgctca tcattggaaa acgttcttcg gggcgaaaac tctcaaggat 900
cttaccgctg ttgagatcca gttcgatgta acccactcgt gcacccaact gatcttcagc 960
atcttttact ttcaccagcg tttctgggtg agcaaaaaca ggaaggcaaa atgccgcaaa 1020
aaagggaata agggcgacac ggaaatgttg aatactcata ctcttccttt ttcaatatta 1080
ttgaagcatt tatcagggtt attgtctcat gaccaaaatc ccttaacgtg agttttcgtt 1140
ccactgagcg tcagaccccg tagaaaagat caaaggatct tcttgagatc cttttttct 1200 gcgcgtaatc tgctgcttgc aaacaaaaaa accaccgcta ccagcggtgg tttgtttgcc 1260
ggatcaagag ctaccaactc tttttccgaa ggtaactggc ttcagcagag cgcagatacc 1320
aaatactgtt cttctagtgt agccgtagtt aggccaccac ttcaagaact ctgtagcacc 1380
gcctacatac ctcgctctgc taatcctgtt accagtggct gttgccagtg gcgataagtc 1440
gtgtcttacc gggttggact caagacgata gttaccggat aaggcgcagc ggtcgggctg 1500
aacggggggt tcgtgcacac agcccagctt ggagcgaacg acctacaccg aactgagata 1560
cctacagcgt gagctatgag aaagcgccac gcttcccgaa gggagaaagg cggacaggta 1620
tccggtaagc ggcagggtcg gaacaggaga gcgcacgagg gagcttccag ggggaaacgc 1680
ctggtatctt tatagtcctg tcgggtttcg ccacctctga cttgagcgtc gatttttgtg 1740
atgctcgtca ggggggcgga gcctatggaa aaacgccagc aacgcggcct ttttacggtt 1800
cctggccttt tgctggcctt ttgctcacat gttctttcct gcgttatccc ctgattctgt 1860
ggataaccgt attaccgcct ttgagtgagc tgataccgct cgccgcagcc gaacgaccga 1920
gcgcagcgag tcagtgagcg aggaagcggt cgctgaggct tgacatgatt ggtgcgtatg 1980
tttgtatgaa gctacaggac tgatttggcg ggctatgagg gcgggggaag ctctggaagg 2040
gccgcgatgg ggcgcgcggc gtccagaagg cgccatacgg cccgctggcg gcacccatcc 2100
ggtataaaag cccgcgaccc cgaacggtga cctccacttt cagcgacaaa cgagcactta 2160
tacatacgcg actattctgc cgctatacat aaccactcag ctagcttaag atcccatcaa 2220
gcttgcatgc cgggcgcgcc agaaggagcg cagccaaacc aggatgatgt ttgatggggt 2280
atttgagcac ttgcaaccct tatccggaag ccccctggcc cacaaaggct aggcgccaat 2340
gcaagcagtt cgcatgcagc ccctggagcg gtgccctcct gataaaccgg ccagggggcc 2400
tatgttcttt actttttac aagagaagtc actcaacatc ttaaaatggc caggtgagtc 2460
gacgagcaag cccggcggat caggcagcgt gcttgcagat ttgacttgca acgcccgcat 2520
tgtgtcgacg aaggcttttg gctcctctgt cgctgtctca agcagcatct aaccctgcgt 2580
cgccgtttcc atttgcagga gattcgaggt accatgtacc catacgatgt tccagattac 2640
gcttcgccga agaaaaagcg caaggtcgaa gcgtccgaca agaagtacag catcggcctg 2700
gacatcggca ccaactctgt gggctgggcc gtgatcaccg acgagtacaa ggtgcccagc 2760
aagaaattca aggtgctggg caacaccgac cggcacagca tcaagaagaa cctgatcgga 2820
gccctgctgt tcgacagcgg cgaaacagcc gaggccaccc ggctgaagag aaccgccaga 2880
agaagataca ccagacggaa gaaccggatc tgctatctgc aagagatctt cagcaacgag 2940
atggccaagg tggacgacag cttcttccac agactggaag agtccttcct ggtggaagag 3000
gataagaagc acgagcggca ccccatcttc ggcaacatcg tggacgaggt ggcctaccac 3060
gagaagtacc ccaccatcta ccacctgaga aagaaactgg tggacagcac cgacaaggcc 3120
gacctgcggc tgatctatct ggccctggcc cacatgatca agttccgggg ccacttcctg 3180
atcgagggcg acctgaaccc cgacaacagc gacgtggaca agctgttcat ccagctggtg 3240
cagacctaca accagctgtt cgaggaaaac cccatcaacg ccagcggcgt ggacgccaag 3300
gccatcctgt ctgccagact gagcaagagc agacggctgg aaaatctgat cgcccagctg 3360
cccggcgaga agaagaatgg cctgttcggc aacctgattg ccctgagcct gggcctgacc 3420
cccaacttca agagcaactt cgacctggcc gaggatgcca aactgcagct gagcaaggac 3480
acctacgacg acgacctgga caacctgctg gcccagatcg gcgaccagta cgccgacctg 3540
tttctggccg ccaagaacct gtccgacgcc atcctgctga gcgacatcct gagagtgaac 3600
accgagatca ccaaggcccc cctgagcgcc tctatgatca agagatacga cgagcaccac 3660
caggacctga ccctgctgaa agctctcgtg cggcagcagc tgcctgagaa gtacaaagag 3720
attttcttcg accagagcaa gaacggctac gccggctaca ttgacggcgg agccagccag 3780
gaagagttct acaagttcat caagcccatc ctggaaaaga tggacggcac cgaggaactg 3840
ctcgtgaagc tgaacagaga ggacctgctg cggaagcagc ggaccttcga caacggcagc 3900
atcccccacc agatccacct gggagagctg cacgccattc tgcggcggca ggaagatttt 3960
tacccattcc tgaaggacaa ccgggaaaag atcgagaaga tcctgacctt ccgcatcccc 4020
tactacgtgg gccctctggc caggggaaac agcagattcg cctggatgac cagaaagagc 4080
gaggaaacca tcaccccctg gaacttcgag gaagtggtgg acaagggcgc ttccgcccag 4140
agcttcatcg agcggatgac caacttcgat aagaacctgc ccaacgagaa ggtgctgccc 4200
aagcacagcc tgctgtacga gtacttcacc gtgtataacg agctgaccaa agtgaaatac 4260
gtgaccgagg gaatgagaaa gcccgccttc ctgagcggcg agcagaaaaa ggccatcgtg 4320
gacctgctgt tcaagaccaa ccggaaagtg accgtgaagc agctgaaaga ggactacttc 4380
aagaaaatcg agtgcttcga ctccgtggaa atctccggcg tggaagatcg gttcaacgcc 4440
tccctgggca cataccacga tctgctgaaa attatcaagg acaaggactt cctggacaat 4500

-continued

```
gaggaaaacg aggacattct ggaagatatc gtgctgaccc tgacactgtt tgaggacaga   4560
gagatgatcg aggaacggct gaaaacctat gcccacctgt tcgacgacaa agtgatgaag   4620
cagctgaagc ggcggagata caccggctgg ggcaggctga gccggaagct gatcaacggc   4680
atccgggaca agcagtccgg caagacaatc ctggatttcc tgaagtccga cggcttcgcc   4740
aacagaaact tcatgcagct gatccacgac gacagcctga cctttaaaga ggacatccag   4800
aaagcccagg tgtccggcca gggcgatagc ctgcacgagc acattgccaa tctggccggc   4860
agccccgcca ttaagaaggg catcctgcag acagtgaagg tggtggacga gctcgtgaaa   4920
gtgatgggcc ggcacaagcc cgagaacatc gtgatcgaaa tggccagaga gaaccagacc   4980
acccagaagg gacagaagaa cagccgcgag agaatgaagc ggatcgaaga gggcatcaaa   5040
gagctgggca gccagatcct gaaagaacac cccgtggaaa acacccagct gcagaacgag   5100
aagctgtacc tgtactacct gcagaatggg cgggatatgt acgtggacca ggaactggac   5160
atcaaccggc tgtccgacta cgatgtggac catatcgtgc ctcagagctt tctgaaggac   5220
gactccatcg acaacaaggt gctgaccaga agcgacaaga accggggcaa gagcgacaac   5280
gtgccctccg aagaggtcgt gaagaagatg aagaactact ggcggcagct gctgaacgcc   5340
aagctgatta cccagagaaa gttcgacaat ctgaccaagg ccgagagagg cggcctgagc   5400
gaactggata aggccggctt catcaagaga cagctggtgg aaacccggca gatcacaaag   5460
cacgtggcac agatcctgga ctcccggatg aacactaagt acgacgagaa tgacaagctg   5520
atccgggaag tgaaagtgat caccctgaag tccaagctgg tgtccgattt ccggaaggat   5580
ttccagtttt acaaagtgcg cgagatcaac aactaccacc acgcccacga cgcctacctg   5640
aacgccgtcg tgggaaccgc cctgatcaaa aagtacccta agctggaaag cgagttcgtg   5700
tacggcgact acaaggtgta cgacgtgcgg aagatgatcg ccaagagcga gcaggaaatc   5760
ggcaaggcta ccgccaagta cttcttctac agcaacatca tgaacttttt caagaccgag   5820
attaccctgg ccaacggcga gatccggaag cggcctctga tcgagacaaa cggcgaaacc   5880
ggggagatcg tgtgggataa gggccgggat tttgccaccg tgcggaaagt gctgagcatg   5940
ccccaagtga atatcgtgaa aaagaccgag gtgcagacag gcggcttcag caaagagtct   6000
atcctgccca agaggaacag cgataagctg atcgccagaa agaaggactg ggaccctaag   6060
aagtacggcg gcttcgacag ccccaccgtg gcctattctg tgctggtggt ggccaaagtg   6120
gaaaagggca agtccaagaa actgaagagt gtgaaagagc tgctggggat caccatcatg   6180
gaaagaagca gcttcgagaa gaatcccatc gactttctgg aagccaaggg ctacaaagaa   6240
gtgaaaaagg acctgatcat caagctgcct aagtactccc tgttcgagct ggaaaacggc   6300
cggaagagaa tgctggcctc tgccggcgaa ctgcagaagg gaaacgaact ggccctgccc   6360
tccaaatatg tgaacttcct gtacctggcc agccactatg agaagctgaa gggctccccc   6420
gaggataatg agcagaaaca gctgtttgtg gaacagcaca agcactacct ggacgagatc   6480
atcgagcaga tcagcgagtt ctccaagaga gtgatcctgg ccgacgctaa tctggacaaa   6540
gtgctgtccg cctacaacaa gcaccgggat aagcccatca gagagcaggc cgagaatatc   6600
atccacctgt ttaccctgac caatctggga gcccctgccg ccttcaagta ctttgacacc   6660
accatcgacc ggaagaggta caccagcacc aaagaggtgc tggacgccac cctgatccac   6720
cagagcatca ccggcctgta cgagacacgg atcgacctgt ctcagctggg aggcgacagc   6780
cccaagaaga agagaaaggt ggaggccagc taacatatga ttcgaatgtc tttcttgcgc   6840
```

```
tatgacactt ccagcaaaag gtagggcggg ctgcgagacg gcttcccggc gctgcatgca   6900

acaccgatga tgcttcgacc ccccgaagct ccttcggggc tgcatgggcg ctccgatgcc   6960

gctccagggc gagcgctgtt taaatagcca ggcccccgat tgcaaagaca ttatagcgag   7020

ctaccaaagc catattcaaa cacctagatc actaccactt ctacacaggc cactcgagct   7080

tgtgatcgca ctccgctaag gggcgcctc ttcctcttcg tttcagtcac aacccgcaaa   7140

catgacacaa gaatccctgt tacttctcga ccgtattgat tcggatgatt cctacgcgag   7200

cctgcggaac gaccaggaat tctgggaggt gagtcgacga gcaagcccgg cggatcaggc   7260

agcgtgcttg cagatttgac ttgcaacgcc cgcattgtgt cgacgaaggc ttttggctcc   7320

tctgtcgctg tctcaagcag catctaaccc tgcgtcgccg tttccatttg cagccgctgg   7380

cccgccgagc cctggaggag ctcgggctgc cggtgccgcc ggtgctgcgg gtgcccggcg   7440

agagcaccaa ccccgtactg gtcggcgagc ccggcccggt gatcaagctg ttcggcgagc   7500

actggtgcgg tccggagagc ctcgcgtcgg agtcggaggc gtacgcggtc ctggcggacg   7560

ccccggtgcc ggtgccccgc ctcctcggcc gcggcgagct gcggcccggc accggagcct   7620

ggccgtggcc ctacctggtg atgagccgga tgaccggcac cacctggcgg tccgcgatgg   7680

acggcacgac cgaccggaac gcgctgctcg ccctggcccg cgaactcggc cgggtgctcg   7740

gccggctgca cagggtgccg ctgaccggga acaccgtgct caccccccat tccgaggtct   7800

tcccggaact gctgcgggaa cgccgcgcgg cgaccgtcga ggaccaccgc gggtggggct   7860

acctctcgcc ccggctgctg gaccgcctgg aggactggct gccggacgtg gacacgctgc   7920

tggccggccg cgaaccccgg ttcgtccacg gcgacctgca cgggaccaac atcttcgtgg   7980

acctggccgc gaccgaggtc accgggatcg tcgacttcac cgacgtctat gcgggagact   8040

cccgctacag cctggtgcaa ctgcatctca acgccttccg ggcgaccgc gagatcctgg   8100

ccgcgctgct cgacggggcg cagtggaagc ggaccgagga cttcgcccgc gaactgctcg   8160

ccttcacctt cctgcacgac ttcgaggtgt tcgaggagac cccgctggat ctctccggct   8220

tcaccgatcc ggaggaactg gcgcagttcc tctgggggcc gccggacacc gcccccggcg   8280

cctgataagg atccggcaag actggccccg cttggcaacg caacagtgag cccctcccta   8340

gtgtgtttgg ggatgtgact atgtattcgt gtgttggcca acgggtcaac ccgaacagat   8400

tgatacccgc cttggcattt cctgtcagaa tgtaacgtca gttgatggta ct           8452
```

```
<210> SEQ ID NO 132
<211> LENGTH: 27
<212> TYPE: DNA
<213> ORGANISM: Homo sapiens

<400> SEQUENCE: 132

ccgtgccggg cggggagacc gccatgg                                         27


<210> SEQ ID NO 133
<211> LENGTH: 22
<212> TYPE: DNA
<213> ORGANISM: Homo sapiens

<400> SEQUENCE: 133

ggcccggctg tggctgagga gc                                              22


<210> SEQ ID NO 134
<211> LENGTH: 20
<212> TYPE: DNA
<213> ORGANISM: Homo sapiens
```

<400> SEQUENCE: 134
cggtctcccg cccggcacgg 20

<210> SEQ ID NO 135
<211> LENGTH: 26
<212> TYPE: DNA
<213> ORGANISM: Homo sapiens

<400> SEQUENCE: 135
gctcctcagc cacagccggg ccgggt 26

<210> SEQ ID NO 136
<211> LENGTH: 12
<212> TYPE: DNA
<213> ORGANISM: Homo sapiens

<400> SEQUENCE: 136
cgaccctgga aa 12

<210> SEQ ID NO 137
<211> LENGTH: 14
<212> TYPE: DNA
<213> ORGANISM: Homo sapiens

<400> SEQUENCE: 137
ccccgccgcc accc 14

<210> SEQ ID NO 138
<211> LENGTH: 18
<212> TYPE: DNA
<213> ORGANISM: Homo sapiens

<400> SEQUENCE: 138
tttccagggt cgccatgg 18

<210> SEQ ID NO 139
<211> LENGTH: 10
<212> TYPE: DNA
<213> ORGANISM: Homo sapiens

<400> SEQUENCE: 139
ggcggcgggg 10

<210> SEQ ID NO 140
<211> LENGTH: 20
<212> TYPE: DNA
<213> ORGANISM: Homo sapiens

<400> SEQUENCE: 140
acccttgtta gccacctccc 20

<210> SEQ ID NO 141
<211> LENGTH: 20
<212> TYPE: DNA
<213> ORGANISM: Homo sapiens

<400> SEQUENCE: 141
gaacgcagtg ctcttcgaag 20

<210> SEQ ID NO 142
<211> LENGTH: 20
<212> TYPE: DNA

<213> ORGANISM: Homo sapiens

<400> SEQUENCE: 142
ctcacgccct gctccgtgta 20

<210> SEQ ID NO 143
<211> LENGTH: 20
<212> TYPE: DNA
<213> ORGANISM: Homo sapiens

<400> SEQUENCE: 143
ggcgacaact acttcctggt 20

<210> SEQ ID NO 144
<211> LENGTH: 20
<212> TYPE: DNA
<213> ORGANISM: Homo sapiens

<400> SEQUENCE: 144
ctcacgccct gctccgtgta 20

<210> SEQ ID NO 145
<211> LENGTH: 20
<212> TYPE: DNA
<213> ORGANISM: Homo sapiens

<400> SEQUENCE: 145
gggcgacaac tacttcctgg 20

<210> SEQ ID NO 146
<211> LENGTH: 20
<212> TYPE: DNA
<213> ORGANISM: Homo sapiens

<400> SEQUENCE: 146
cctcttcagg gccggggtgg 20

<210> SEQ ID NO 147
<211> LENGTH: 20
<212> TYPE: DNA
<213> ORGANISM: Homo sapiens

<400> SEQUENCE: 147
gaggacccag gtggaactgc 20

<210> SEQ ID NO 148
<211> LENGTH: 20
<212> TYPE: DNA
<213> ORGANISM: Homo sapiens

<400> SEQUENCE: 148
tcagctccag gcggtcctgg 20

<210> SEQ ID NO 149
<211> LENGTH: 20
<212> TYPE: DNA
<213> ORGANISM: Homo sapiens

<400> SEQUENCE: 149
agcagcagca gcagtggcag 20

<210> SEQ ID NO 150
<211> LENGTH: 20

<212> TYPE: DNA
<213> ORGANISM: Homo sapiens

<400> SEQUENCE: 150
tgggcaccgt cagctccagg 20

<210> SEQ ID NO 151
<211> LENGTH: 20
<212> TYPE: DNA
<213> ORGANISM: Homo sapiens

<400> SEQUENCE: 151
cagcagtggc agcggccacc 20

<210> SEQ ID NO 152
<211> LENGTH: 20
<212> TYPE: DNA
<213> ORGANISM: Homo sapiens

<400> SEQUENCE: 152
acctctcccc tggccctcat 20

<210> SEQ ID NO 153
<211> LENGTH: 20
<212> TYPE: DNA
<213> ORGANISM: Homo sapiens

<400> SEQUENCE: 153
ccaggaccgc ctggagctga 20

<210> SEQ ID NO 154
<211> LENGTH: 20
<212> TYPE: DNA
<213> ORGANISM: Homo sapiens

<400> SEQUENCE: 154
ccgtcagctc caggcggtcc 20

<210> SEQ ID NO 155
<211> LENGTH: 20
<212> TYPE: DNA
<213> ORGANISM: Homo sapiens

<400> SEQUENCE: 155
agcagcagca gcagtggcag 20

<210> SEQ ID NO 156
<211> LENGTH: 20
<212> TYPE: DNA
<213> ORGANISM: Homo sapiens

<400> SEQUENCE: 156
atgtgccaag caaagcctca 20

<210> SEQ ID NO 157
<211> LENGTH: 20
<212> TYPE: DNA
<213> ORGANISM: Homo sapiens

<400> SEQUENCE: 157
ttcggtcatg cccgtggatg 20

<210> SEQ ID NO 158

<211> LENGTH: 20
<212> TYPE: DNA
<213> ORGANISM: Homo sapiens

<400> SEQUENCE: 158
gtcgttgaaa ttcatcgtac 20

<210> SEQ ID NO 159
<211> LENGTH: 20
<212> TYPE: DNA
<213> ORGANISM: Homo sapiens

<400> SEQUENCE: 159
accacctgtg aagagtttcc 20

<210> SEQ ID NO 160
<211> LENGTH: 20
<212> TYPE: DNA
<213> ORGANISM: Homo sapiens

<400> SEQUENCE: 160
cgtcgttgaa attcatcgta 20

<210> SEQ ID NO 161
<211> LENGTH: 20
<212> TYPE: DNA
<213> ORGANISM: Homo sapiens

<400> SEQUENCE: 161
accacctgtg aagagtttcc 20

<210> SEQ ID NO 162
<211> LENGTH: 20
<212> TYPE: DNA
<213> ORGANISM: Mus musculus

<400> SEQUENCE: 162
gaacgcagtg cttttcgagg 20

<210> SEQ ID NO 163
<211> LENGTH: 20
<212> TYPE: DNA
<213> ORGANISM: Mus musculus

<400> SEQUENCE: 163
acccttgttg gccacctccc 20

<210> SEQ ID NO 164
<211> LENGTH: 20
<212> TYPE: DNA
<213> ORGANISM: Mus musculus

<400> SEQUENCE: 164
ggtgacaact actatctggt 20

<210> SEQ ID NO 165
<211> LENGTH: 20
<212> TYPE: DNA
<213> ORGANISM: Mus musculus

<400> SEQUENCE: 165
ctcacaccct gctccgtgta 20

<210> SEQ ID NO 166
<211> LENGTH: 20
<212> TYPE: DNA
<213> ORGANISM: Mus musculus

<400> SEQUENCE: 166
gggtgacaac tactatctgg 20

<210> SEQ ID NO 167
<211> LENGTH: 20
<212> TYPE: DNA
<213> ORGANISM: Mus musculus

<400> SEQUENCE: 167
ctcacaccct gctccgtgta 20

<210> SEQ ID NO 168
<211> LENGTH: 20
<212> TYPE: DNA
<213> ORGANISM: Mus musculus

<400> SEQUENCE: 168
cgagaacgca gtgcttttcg 20

<210> SEQ ID NO 169
<211> LENGTH: 20
<212> TYPE: DNA
<213> ORGANISM: Mus musculus

<400> SEQUENCE: 169
acccttgttg gccacctccc 20

<210> SEQ ID NO 170
<211> LENGTH: 20
<212> TYPE: DNA
<213> ORGANISM: Mus musculus

<400> SEQUENCE: 170
atgagccaag caaatcctca 20

<210> SEQ ID NO 171
<211> LENGTH: 20
<212> TYPE: DNA
<213> ORGANISM: Mus musculus

<400> SEQUENCE: 171
ttccgtcatg cccgtggaca 20

<210> SEQ ID NO 172
<211> LENGTH: 20
<212> TYPE: DNA
<213> ORGANISM: Mus musculus

<400> SEQUENCE: 172
cttcgttgaa aaccattgta 20

<210> SEQ ID NO 173
<211> LENGTH: 20
<212> TYPE: DNA
<213> ORGANISM: Mus musculus

<400> SEQUENCE: 173
ccacctctga agagtttcct 20

<210> SEQ ID NO 174
<211> LENGTH: 20
<212> TYPE: DNA
<213> ORGANISM: Mus musculus

<400> SEQUENCE: 174
cttcgttgaa aaccattgta 20

<210> SEQ ID NO 175
<211> LENGTH: 20
<212> TYPE: DNA
<213> ORGANISM: Mus musculus

<400> SEQUENCE: 175
accacctctg aagagtttcc 20

<210> SEQ ID NO 176
<211> LENGTH: 20
<212> TYPE: DNA
<213> ORGANISM: Mus musculus

<400> SEQUENCE: 176
cttccactca ctctgcgatt 20

<210> SEQ ID NO 177
<211> LENGTH: 20
<212> TYPE: DNA
<213> ORGANISM: Mus musculus

<400> SEQUENCE: 177
accatgtctc agtgtcaagc 20

<210> SEQ ID NO 178
<211> LENGTH: 20
<212> TYPE: DNA
<213> ORGANISM: Mus musculus

<400> SEQUENCE: 178
ggcggcaaca gcggcaacag 20

<210> SEQ ID NO 179
<211> LENGTH: 20
<212> TYPE: DNA
<213> ORGANISM: Mus musculus

<400> SEQUENCE: 179
actgctctgc gtggctgcgg 20

<210> SEQ ID NO 180
<211> LENGTH: 20
<212> TYPE: DNA
<213> ORGANISM: Mus musculus

<400> SEQUENCE: 180
ccgcagccac gcagagcagt 20

<210> SEQ ID NO 181
<211> LENGTH: 20
<212> TYPE: DNA
<213> ORGANISM: Mus musculus

<400> SEQUENCE: 181
gcacctctcc tcgccccgat 20

<210> SEQ ID NO 182
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 182
gagggcctat ttcccatgat tcc 23

<210> SEQ ID NO 183
<211> LENGTH: 126
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: modified_base
<222> LOCATION: (84)..(102)
<223> OTHER INFORMATION: a, c, t, g, unknown or other

<400> SEQUENCE: 183
aaaaaaagca ccgactcggt gccacttttt caagttgata acggactagc cttattttaa 60
cttgctattt ctagctctaa aacnnnnnnn nnnnnnnnnn nnccggtgtt tcgtcctttc 120
cacaag 126

<210> SEQ ID NO 184
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (6)..(24)
<223> OTHER INFORMATION: a, c, t, g, unknown or other

<400> SEQUENCE: 184
caccgnnnnn nnnnnnnnnn nnnn 24

<210> SEQ ID NO 185
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (5)..(23)
<223> OTHER INFORMATION: a, c, t, g, unknown or other

<400> SEQUENCE: 185
aaacnnnnnn nnnnnnnnnn nnnc 24

<210> SEQ ID NO 186
<211> LENGTH: 126
<212> TYPE: DNA
<213> ORGANISM: Artificial Sequence
<220> FEATURE:

<221> NAME/KEY: source
<223> OTHER INFORMATION: /note="Description of Artificial Sequence:
      Synthetic polynucleotide"

<400> SEQUENCE: 186
aaaaaaagca ccgactcggt gccacttttt caagttgata acggactagc cttattttaa     60
cttgctattt ctagctctaa aacccctagt cattggaggt gaccggtgtt tcgtcctttc    120
cacaag                                                               126

<210> SEQ ID NO 187
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 187
caccgtcacc tccaatgact aggg                                            24

<210> SEQ ID NO 188
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 188
aaacccctag tcattggagg tgac                                            24

<210> SEQ ID NO 189
<211> LENGTH: 192
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 189
cagaagaaga agggctccca tcacatcaac cggtggcgca ttgccacgaa gcaggccaat     60
ggggaggaca tcgatgtcac ctccaatgac aagcttgcta gcggtgggca accacaaacc    120
cacgagggca gagtgctgct tgctgctggc caggcccctg cgtgggccca agctggactc    180
tggccactcc ct                                                        192

<210> SEQ ID NO 190
<211> LENGTH: 192
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 190
agggagtggc cagagtccag cttgggccca cgcaggggcc tggccagcag caagcagcac     60
tctgccctcg tgggtttgtg gttgcccacc gctagcaagc ttgtcattgg aggtgacatc    120
gatgtcctcc ccattggcct gcttcgtggc aatgcgccac cggttgatgt gatgggagcc    180
cttcttcttc tg                                                        192

<210> SEQ ID NO 191
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 191
ccatcccctt ctgtgaatgt 20

<210> SEQ ID NO 192
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 192
ggagattgga gacacggaga 20

<210> SEQ ID NO 193
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 193
ggctccctgg gttcaaagta 20

<210> SEQ ID NO 194
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 194
agaggggtct ggatgtcgta a 21

<210> SEQ ID NO 195
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 195
cgccagggtt ttcccagtca cgac 24

<210> SEQ ID NO 196
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 196
gagggtctcg tccttgcggc cgcgctagcg agggcctatt tcccatgatt c 51

<210> SEQ ID NO 197
<211> LENGTH: 133
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"
<220> FEATURE:
<221> NAME/KEY: modified_base
<222> LOCATION: (95)..(114)
<223> OTHER INFORMATION: a, c, t, g, unknown or other

<400> SEQUENCE: 197
ctcggtctcg gtaaaaaagc accgactcgg tgccactttt tcaagttgat aacggactag 60
ccttatttta acttgctatt tctagctcta aaacnnnnnn nnnnnnnnnn nnnnggtgtt 120
tcgtcctttc cac 133

<210> SEQ ID NO 198
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 198
gagggtctct ttaccggtga gggcctattt cccatgattc c 41

<210> SEQ ID NO 199
<211> LENGTH: 133
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"
<220> FEATURE:
<221> NAME/KEY: modified_base
<222> LOCATION: (95)..(114)
<223> OTHER INFORMATION: a, c, t, g, unknown or other

<400> SEQUENCE: 199
ctcggtctcc tcaaaaaagc accgactcgg tgccactttt tcaagttgat aacggactag 60
ccttatttta acttgctatt tctagctcta aaacnnnnnn nnnnnnnnnn nnnnggtgtt 120
tcgtcctttc cac 133

<210> SEQ ID NO 200
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 200
gagggtctct ttgagctcga gggcctattt cccatgattc 40

-continued

<210> SEQ ID NO 201
<211> LENGTH: 133
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"
<220> FEATURE:
<221> NAME/KEY: modified_base
<222> LOCATION: (96)..(115)
<223> OTHER INFORMATION: a, c, t, g, unknown or other

<400> SEQUENCE: 201
ctcggtctcg cgtaaaaaag caccgactcg gtgccacttt ttcaagttga taacggacta 60
gccttatttt aacttgctat ttctagctct aaaacnnnnn nnnnnnnnnn nnnnnggtgt 120
ttcgtccttt cca 133

<210> SEQ ID NO 202
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 202
gagggtctct tacgcgtgtg tctagac 27

<210> SEQ ID NO 203
<211> LENGTH: 98
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 203
ctcggtctca aggacaggga agggagcagt ggttcacgcc tgtaatccca gcaatttggg 60
aggccaaggt gggtagatca cctgagatta ggagttgc 98

<210> SEQ ID NO 204
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 204
cctgtccttg cggccgcgct agcgagggcc 30

<210> SEQ ID NO 205
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 205
cacgcggccg caaggacagg gaagggagca g 31

<210> SEQ ID NO 206
<211> LENGTH: 327
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 206

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Ser
225                 230                 235                 240

Gly Leu Arg Ser Arg Glu Glu Glu Glu Glu Thr Asp Ser Arg Met Pro
                245                 250                 255

His Leu Asp Ser Pro Gly Ser Ser Gln Pro Arg Arg Ser Phe Leu Ser
            260                 265                 270

Arg Val Ile Arg Ala Ala Leu Pro Leu Gln Leu Leu Leu Leu Leu Leu
        275                 280                 285

Leu Leu Leu Ala Cys Leu Leu Pro Ala Ser Glu Asp Asp Tyr Ser Cys
    290                 295                 300

Thr Gln Ala Asn Asn Phe Ala Arg Ser Phe Tyr Pro Met Leu Arg Tyr
305                 310                 315                 320

Thr Asn Gly Pro Pro Pro Thr
                325
```

<210> SEQ ID NO 207
<211> LENGTH: 3243
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 207

accggtgcca ccatgtaccc atacgatgtt ccagattacg cttcgccgaa gaaaaagcgc     60

aaggtcgaag cgtccatgaa aaggaactac attctggggc tggacatcgg gattacaagc    120

gtggggtatg ggattattga ctatgaaaca agggacgtga tcgacgcagg cgtcagactg    180

ttcaaggagg ccaacgtgga aaacaatgag ggacggagaa gcaagagggg agccaggcgc    240

ctgaaacgac ggagaaggca cagaatccag agggtgaaga aactgctgtt cgattacaac    300

ctgctgaccg accattctga gctgagtgga attaatcctt atgaagccag ggtgaaaggc    360

ctgagtcaga agctgtcaga ggaagagttt tccgcagctc tgctgcacct ggctaagcgc    420

cgaggagtgc ataacgtcaa tgaggtggaa gaggacaccg gcaacgagct gtctacaaag    480

gaacagatct cacgcaatag caaagctctg gaagagaagt atgtcgcaga gctgcagctg    540

gaacggctga agaaagatgg cgaggtgaga gggtcaatta ataggttcaa gacaagcgac    600

tacgtcaaag aagccaagca gctgctgaaa gtgcagaagg cttaccacca gctggatcag    660

agcttcatcg atacttatat cgacctgctg gagactcgga gaacctacta tgagggacca    720

ggagaaggga gccccttcgg atggaaagac atcaaggaat ggtacgagat gctgatggga    780

cattgcacct attttccaga agagctgaga agcgtcaagt acgcttataa cgcagatctg    840

tacaacgccc tgaatgacct gaacaacctg gtcatcacca gggatgaaaa cgagaaactg    900

gaatactatg agaagttcca gatcatcgaa aacgtgttta agcagaagaa aaagcctaca    960

ctgaaacaga ttgctaagga gatcctggtc aacgaagagg acatcaaggg ctaccgggtg   1020

acaagcactg gaaaaccaga gttcaccaat ctgaaagtgt atcacgatat taaggacatc   1080

acagcacgga aagaaatcat tgagaacgcc gaactgctgg atcagattgc taagatcctg   1140

actatctacc agagctccga ggacatccag gaagagctga ctaacctgaa cagcgagctg   1200

acccaggaag agatcgaaca gattagtaat ctgaaggggt acaccggaac acacaacctg   1260

tccctgaaag ctatcaatct gattctggat gagctgtggc atacaaacga caatcagatt   1320

gcaatcttta accggctgaa gctggtccca aaaaaggtgg acctgagtca gcagaaagag   1380

atcccaacca cactggtgga cgatttcatt ctgtcacccg tggtcaagcg gagcttcatc   1440

cagagcatca aagtgatcaa cgccatcatc aagaagtacg gcctgcccaa tgatatcatt   1500

atcgagctgg ctagggagaa gaacagcaag gacgcacaga agatgatcaa tgagatgcag   1560

aaacgaaacc ggcagaccaa tgaacgcatt gaagagatta tccgaactac cgggaaagag   1620

aacgcaaagt acctgattga aaaaatcaag ctgcacgata tgcaggaggg aaagtgtctg   1680

tattctctgg aggccatccc cctggaggac ctgctgaaca atccattcaa ctacgaggtc   1740

gatcatatta tccccagaag cgtgtccttc gacaattcct ttaacaacaa ggtgctggtc   1800

aagcaggaag agaactctaa aaagggcaat aggactcctt tccagtacct gtctagttca   1860

gattccaaga tctcttacga aacctttaaa aagcacattc tgaatctggc caaaggaaag   1920

ggccgcatca gcaagaccaa aaaggagtac ctgctggaag agcgggacat caacagattc   1980

tccgtccaga aggattttat taaccggaat ctggtggaca caagatacgc tactcgcggc   2040

ctgatgaatc tgctgcgatc ctatttccgg gtgaacaatc tggatgtgaa agtcaagtcc   2100

atcaacggcg ggttcacatc ttttctgagg cgcaaatgga agtttaaaaa ggagcgcaac   2160
```

```
aaagggtaca agcaccatgc cgaagatgct ctgattatcg caaatgccga cttcatcttt   2220

aaggagtgga aaaagctgga caaagccaag aaagtgatgg agaaccagat gttcgaagag   2280

aagcaggccg aatctatgcc cgaaatcgag acagaacagg agtacaagga gattttcatc   2340

actcctcacc agatcaagca tatcaaggat ttcaaggact acaagtactc tcaccgggtg   2400

gataaaaagc ccaacagaga gctgatcaat gacaccctgt atagtacaag aaaagacgat   2460

aaggggaata ccctgattgt gaacaatctg aacggactgt acgacaaaga taatgacaag   2520

ctgaaaaagc tgatcaacaa aagtcccgag aagctgctga tgtaccacca tgatcctcag   2580

acatatcaga aactgaagct gattatggag cagtacggcg acgagaagaa cccactgtat   2640

aagtactatg aagagactgg gaactacctg accaagtata gcaaaaagga taatggcccc   2700

gtgatcaaga agatcaagta ctatgggaac aagctgaatg cccatctgga catcacagac   2760

gattacccta acagtcgcaa caaggtggtc aagctgtcac tgaagccata cagattcgat   2820

gtctatctgg acaacggcgt gtataaattt gtgactgtca agaatctgga tgtcatcaaa   2880

aaggagaact actatgaagt gaatagcaag tgctacgaag aggctaaaaa gctgaaaaag   2940

attagcaacc aggcagagtt catcgcctcc ttttacaaca acgacctgat taagatcaat   3000

ggcgaactgt atagggtcat cggggtgaac aatgatctgc tgaaccgcat tgaagtgaat   3060

atgattgaca tcacttaccg agagtatctg gaaaacatga atgataagcg ccccccctcga   3120

attatcaaaa caattgcctc taagactcag agtatcaaaa agtactcaac cgacattctg   3180

ggaaacctgt atgaggtgaa gagcaaaaag caccctcaga ttatcaaaaa gggctaagaa   3240

ttc                                                                3243
```

```
<210> SEQ ID NO 208
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 208

gcugcggauu gcggccgucu cucgauuugc uacucu                              36


<210> SEQ ID NO 209
<211> LENGTH: 123
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 209

uagcaaaucg agaggcgguc gcuuuucgca agcaaauuga ccccuugugc gggcucggca     60

ucccaagguc agcugccggu uauuaucgaa aaggcccacc gcaagcagcg cgugggccuu    120

uuu                                                                  123


<210> SEQ ID NO 210
<211> LENGTH: 122
<212> TYPE: RNA
<213> ORGANISM: Artificial Sequence
<220> FEATURE:
<221> NAME/KEY: source
<223> OTHER INFORMATION: /note="Description of Artificial Sequence:
```

Synthetic polynucleotide"

<400> SEQUENCE: 210
gcugcggauu gcgggaaauc gcuuuucgca agcaaauuga ccccuugugc gggcucggca 60
ucccaagguc agcugccggu uauuaucgaa aaggcccacc gcaagcagcg cgugggccuu 120
uu 122

<210> SEQ ID NO 211
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 211
acugggguuc aguucucaaa aacccugaua gacuuc 36

<210> SEQ ID NO 212
<211> LENGTH: 106
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 212
agucacuaac uuaauuaaau agaacugaac cucaguaagc auuggcucgu uuccaauguu 60
gauugcuccg ccggugcucc uuauuuuuaa gggcgccggc uuucuu 106

<210> SEQ ID NO 213
<211> LENGTH: 96
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 213
acugggguuc aggaaacuga accucaguaa gcauuggcuc guuuccaaug uugauugcuc 60
cgccggugcu ccuuauuuuu aagggcgccg gcuuuu 96

<210> SEQ ID NO 214
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 214
guuuuuguac ucucaagauu uaaguaaccg uaaaac 36

<210> SEQ ID NO 215
<211> LENGTH: 90
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 215
cuugcacggu uacuuaaauc uugcugagcc uacaaagaua aggcuuuaug ccgaauucaa 60
gcaccccaug uuuugacaug aggugcuuuu 90

<210> SEQ ID NO 216
<211> LENGTH: 81
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 216
guuuuuguac ucgaaagagc cuacaaagau aaggcuuuau gccgaauuca agcaccccau 60
guuuugacau gaggugcuuu u 81

<210> SEQ ID NO 217
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 217
guuguagcuc ccauucucau uucgcagugc uacaau 36

<210> SEQ ID NO 218
<211> LENGTH: 139
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 218
auugucgcac ugcgaaauga gaaccguugc uacaauaagg ccgucugaaa agaugugccg 60
caacgcucug ccccuuaaag cuucugcuuu aaggggcauc guuuauuucg guuaaaaaug 120
ccgucugaaa ccgguuuuu 139

<210> SEQ ID NO 219
<211> LENGTH: 162
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 219
guuguagcuc ccauucucga aagagaaccg uugcuacaau aaggccgucu gaaaagaugu 60
gccgcaacgc ucugccccuu aaagcuucug cuuuaagggg caucguuuau uucgguuaaa 120
aaugccgucu gaaaccgguu uuuagguuuc agacggcauu uu 162

<210> SEQ ID NO 220
<211> LENGTH: 36
<212> TYPE: RNA
<213> ORGANISM: Artificial Sequence
<220> FEATURE:

<221> NAME/KEY: source
<223> OTHER INFORMATION: /note="Description of Artificial Sequence: Synthetic oligonucleotide"

<400> SEQUENCE: 220
guuuuaguac ucuguaauuu uagguaugag guagac 36

<210> SEQ ID NO 221
<211> LENGTH: 85
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 221
auuguacuua uaccuaaaau uacagaaucu acuaaaacaa ggcaaaaugc cguguuuauc 60
ucgucaacuu guuggcgaga uuuuu 85

<210> SEQ ID NO 222
<211> LENGTH: 80
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 222
guuuuaguac ucuggaaaca gaaucuacua aaacaaggca aaaugccgug uuuaucucgu 60
caacuuguug gcgagauuuu 80

<210> SEQ ID NO 223
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 223
guuuuagucu cuuuuuaaau uucuuuauga uaaaau 36

<210> SEQ ID NO 224
<211> LENGTH: 124
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 224
aauucuugcu aaagaaauuu aaaaagagac uaaaauaagu gguuuuuggu cauccacgca 60
ggguuacaau cccuuuaaaa ccauuaaaau ucaaauaaac uagguuguau caacuuaguu 120
uuuu 124

<210> SEQ ID NO 225
<211> LENGTH: 114
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 225
guuuuagucu cugaaaagag acuaaaauaa gugguuuuug gucauccacg cagguuaca 60 aucccuuuaa aaccauuaaa auucaaauaa acuagguugu aucaacuuag uuuu 114

<210> SEQ ID NO 226
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 226
guuuuagagc uaugcuguuu ugaauggucc caaaac 36

<210> SEQ ID NO 227
<211> LENGTH: 87
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 227
guuggaacca uucaaaacag cauagcaagu uaaaauaagg cuaguccguu aucaacuuga 60
aaaaguggca ccgagucggu gcuuuuu 87

<210> SEQ ID NO 228
<211> LENGTH: 80
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 228
guuuuagagc uagaaauagc aaguuaaaau aaggcuaguc cguuaucaac uugaaaaagu 60
ggcaccgagu cggugcuuuu 80

<210> SEQ ID NO 229
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 229
guuuuuguac ucucaagauu uaaguaacug uacaac 36

<210> SEQ ID NO 230
<211> LENGTH: 89
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 230
cuuacacagu uacuuaaauc uugcagaagc uacaaagaua aggcuucaug ccgaaaucaa 60
cacccuguca uuuuauggca ggguguuuu 89

<210> SEQ ID NO 231
<211> LENGTH: 80
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 231
guuuuuguac ucgaaagaag cuacaaagau aaggcuucau gccgaaauca acacccuguc 60
auuuuauggc aggguguuuu 80

<210> SEQ ID NO 232
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 232
taatcactat ggatcttcta taccatt 27

<210> SEQ ID NO 233
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 233
tcttgtagga ggagagactt cagcatg 27

<210> SEQ ID NO 234
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 234
ggtgcaagcc gaacagatga tggacag 27

<210> SEQ ID NO 235
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 235
tatcctaaag ttcttattta aggtttg 27

<210> SEQ ID NO 236
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 236
ttaatttatg aaaatctcgt aggtgaa 27

<210> SEQ ID NO 237
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 237
atgccccatt cacatcagta cagtgac 27

<210> SEQ ID NO 238
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 238
gtgttgagta acatatacct gtttgta 27

<210> SEQ ID NO 239
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 239
taactaacca ggtaagttca tggagta 27

<210> SEQ ID NO 240
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 240
aatgatacaa acattaggat atgaata 27

<210> SEQ ID NO 241
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 241
atgtcaaatg atacaaacat taggata 27

<210> SEQ ID NO 242
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 242
ggtcactgta ctgatgtgaa tggggca 27

<210> SEQ ID NO 243
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 243
cggtcactgt actgatgtga atggggc 27

<210> SEQ ID NO 244
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 244
tgtcaaatga tacaaacatt aggatat 27

<210> SEQ ID NO 245
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 245
aacctcactt atcttcttgt aggagga 27

<210> SEQ ID NO 246
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 246
ccaggtaagt tcatggagta tcagaaa 27

<210> SEQ ID NO 247
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 247
taacatatac ctgtttgtag ttagaaa 27

<210> SEQ ID NO 248
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 248
tcacctccaa tgactagggt gggcaac 27

<210> SEQ ID NO 249
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 249
tgacggtgca agccgaacag atgatggaca g 31

<210> SEQ ID NO 250
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 250
acctggtggg cgacgtgctg gggagtc 27

<210> SEQ ID NO 251
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 251
atggagcagt ctcagtcttc gggcacc 27

<210> SEQ ID NO 252
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 252
gaatgaaaat gacggtgcaa gccgaacaga t 31

<210> SEQ ID NO 253
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 253
ttaatggtat agaagatcca tagtgat 27

<210> SEQ ID NO 254
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 254
tgtcacctcc aatgactagg gtgggca 27

<210> SEQ ID NO 255
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 255
ccatggagca gtctcagtct tcgggca 27

<210> SEQ ID NO 256
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 256
gcaccagcat cggcacagtg gtgggca 27

<210> SEQ ID NO 257
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 257
cgacggtcac tgtactgatg tgaatggggc a 31

<210> SEQ ID NO 258
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 258
ccgagcagaa gaagaagggc tcccatc 27

<210> SEQ ID NO 259
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 259
attttaatca ctatggatct tctataccat t 31

<210> SEQ ID NO 260
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 260
ccaaaactcg aattcaacct ggtcata 27

<210> SEQ ID NO 261
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 261
tgcagcacag tttcttcaag gagcata 27

<210> SEQ ID NO 262
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 262
gttcttaatt tatgaaaatc tcgtaggtga a 31

<210> SEQ ID NO 263
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 263
gagtccgagc agaagaagaa gggctcc 27

<210> SEQ ID NO 264
<211> LENGTH: 31
<212> TYPE: DNA

<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 264
tgacggtgca agccgaacag atgatggaca g 31

<210> SEQ ID NO 265
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 265
atcagaaaag aaagaacagc tggagtc 27

<210> SEQ ID NO 266
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 266
gcaacaacaa gatctgtggc tggaatt 27

<210> SEQ ID NO 267
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 267
tgttcccaca ataacttccc aggggtg 27

<210> SEQ ID NO 268
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 268
tgagtaacat atacctgttt gtagttagaa a 31

<210> SEQ ID NO 269
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 269
caaccacaaa cccacgaggg cagagtg 27

<210> SEQ ID NO 270
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 270
tagggttagg ggccccaggc cggggtc 27

<210> SEQ ID NO 271
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 271
cctctaacta accaggtaag ttcatggagt a 31

<210> SEQ ID NO 272
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 272
taagagagta ggctggtaga tggagtt 27

<210> SEQ ID NO 273
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 273
gagtaggctg gtagatggag ttgggtt 27

<210> SEQ ID NO 274
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 274
gttgaagatg aagcccagag cggagtg 27

<210> SEQ ID NO 275
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 275
tggatgccca ggatgggggt gagagta 27

<210> SEQ ID NO 276
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 276
aaagaaagag catgttaaaa taggata 27

<210> SEQ ID NO 277
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 277
tcagacatga gatcacagat gcgggtg 27

<210> SEQ ID NO 278
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 278
gatgcgggtg atgatgctct ttgggtc 27

<210> SEQ ID NO 279
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 279
tcatggctac cagttccacc cggggta 27

<210> SEQ ID NO 280
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 280
cccgggtgga actggtagcc atgaatg 27

<210> SEQ ID NO 281
<211> LENGTH: 27

<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 281
cttccgacga ggtggccatc aaggatt 27

<210> SEQ ID NO 282
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 282
caccatctct ccgtggtacc ccgggtg 27

<210> SEQ ID NO 283
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 283
atctcttaga taccagcatc cagggtg 27

<210> SEQ ID NO 284
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 284
tcaatctccc gatgggcacc ctggatg 27

<210> SEQ ID NO 285
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 285
gcccatcggg agattgaggg cagggtc 27

<210> SEQ ID NO 286
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 286
acttcaacag cgtgccggag gaggatg 27

<210> SEQ ID NO 287
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 287
ccgctgacca cacctgccag gtgggtg 27

<210> SEQ ID NO 288
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 288
tggcaggtgt ggtcagcggc cgggatg 27

<210> SEQ ID NO 289
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 289
atcagaaaag aaagaacagc tggagtc 27

<210> SEQ ID NO 290
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 290
gcaacaacaa gatctgtggc tggaatt 27

<210> SEQ ID NO 291
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 291
tgttcccaca ataacttccc aggggtg 27

<210> SEQ ID NO 292
<211> LENGTH: 26
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 292

gaggaccgcc ctgggcctgg gagaat                                          26


<210> SEQ ID NO 293
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 293

cacgagggga agagggggca agggat                                          26


<210> SEQ ID NO 294
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 294

cgcccatctt ctagaaagac tggagt                                          26


<210> SEQ ID NO 295
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 295

agtctttcta gaagatgggc gggagt                                          26


<210> SEQ ID NO 296
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 296

gtgtgggcgt tgtcctgcag ggaat                                           26


<210> SEQ ID NO 297
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 297

taggggcaaa taggaaaatg gaggat                                          26


<210> SEQ ID NO 298
```

<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 298
caaataggaa aatggaggat aggagt 26

<210> SEQ ID NO 299
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 299
aatggaggat aggagtcatc tggggt 26

<210> SEQ ID NO 300
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 300
tcctcatgga aatctccgag gcggat 26

<210> SEQ ID NO 301
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 301
aggagataaa gacatgtcac ccgagt 26

<210> SEQ ID NO 302
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 302
ctaagcagga gagtataaac tcgggt 26

<210> SEQ ID NO 303
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 303
ctgtagtagg atctaagcag gagagt 26

<210> SEQ ID NO 304
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 304
cactgtattt catactgtag taggat 26

<210> SEQ ID NO 305
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 305
ctgcagaagg agcgggagaa atggat 26

<210> SEQ ID NO 306
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 306
gagtgttgca ataccttttct gggagt 26

<210> SEQ ID NO 307
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 307
cctggacacc ccgttctcct gtggat 26

<210> SEQ ID NO 308
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 308
acagcatgtt tgctgcctcc agggat 26

<210> SEQ ID NO 309
<211> LENGTH: 26
<212> TYPE: DNA
<213> ORGANISM: Artificial Sequence
<220> FEATURE:

<221> NAME/KEY: source
<223> OTHER INFORMATION: /note="Description of Artificial Sequence:
      Synthetic oligonucleotide"

<400> SEQUENCE: 309
gtggtcccag ctcggggaca caggat 26

<210> SEQ ID NO 310
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 310
cggttaatgt ggctctggtt ctgggt 26

<210> SEQ ID NO 311
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 311
tgtccctagt ggccccactg tggggt 26

<210> SEQ ID NO 312
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 312
tccttcctag tctcctgata ttgggt 26

<210> SEQ ID NO 313
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 313
cctgaagtgg acataggggc ccgggt 26

<210> SEQ ID NO 314
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 314
gagagatggc tccaggaaat gggggt 26

<210> SEQ ID NO 315
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 315
ttgcttacga tggagccaga gaggat 26

<210> SEQ ID NO 316
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 316
gagccacatt aaccggccct gggaat 26

<210> SEQ ID NO 317
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 317
cacagtgggg ccactaggga caggat 26

<210> SEQ ID NO 318
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 318
gactaggaag gaggaggcct aaggat 26

<210> SEQ ID NO 319
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 319
gaatctgcct aacaggaggt gggggt 26

<210> SEQ ID NO 320
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 320
tgggggtgtg tcaccagata aggaat 26

<210> SEQ ID NO 321
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 321
ccctgccaag ctctccctcc caggat 26

<210> SEQ ID NO 322
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 322
ctgggaggga gagcttggca gggggt 26

<210> SEQ ID NO 323
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 323
cagggggtgg gagggaaggg ggggat 26

<210> SEQ ID NO 324
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 324
ggtggctaaa gccagggaga cggggt 26

<210> SEQ ID NO 325
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 325
tagggttagg ggccccaggc cggggt 26

<210> SEQ ID NO 326
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 326
atgggaagac tgaggctaca tagggt 26

<210> SEQ ID NO 327
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 327
catcaggctc tcagctcagc ctgagt 26

<210> SEQ ID NO 328
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 328
gtggctgctc tgggggcctc ctgagt 26

<210> SEQ ID NO 329
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 329
gaagctggag gaggaagggc ctgagt 26

<210> SEQ ID NO 330
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 330
tcgatgtcac ctccaatgac tagggt 26

<210> SEQ ID NO 331
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 331
gcaagcagca ctctgccctc gtgggt 26

<210> SEQ ID NO 332
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 332
caaccacaaa cccacgaggg cagagt 26

<210> SEQ ID NO 333
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 333
aagcctggcc agggagtggc cagagt 26

<210> SEQ ID NO 334
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 334
gcctccccaa agcctggcca gggagt 26

<210> SEQ ID NO 335
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 335
ggccaggctt tggggaggcc tggagt 26

<210> SEQ ID NO 336
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 336
caggctgagc tgagagcctg atggga 26

<210> SEQ ID NO 337
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 337
ctcaacactc aggctgagct gagagc 26

<210> SEQ ID NO 338
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 338
gcctcaacac tcaggctgag ctgaga 26

<210> SEQ ID NO 339
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 339
ctggggcctc aacactcagg ctgagc 26

<210> SEQ ID NO 340
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 340
gaggccccca gagcagccac tggggc 26

<210> SEQ ID NO 341
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 341
ggaggccccc agagcagcca ctgggg 26

<210> SEQ ID NO 342
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 342
tgagaaactc aggaggcccc cagagc 26

<210> SEQ ID NO 343
<211> LENGTH: 26
<212> TYPE: DNA

<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 343
ggggcacaga tgagaaactc aggagg 26

<210> SEQ ID NO 344
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 344
aggggcacag atgagaaact caggag 26

<210> SEQ ID NO 345
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 345
agggagggag gggcacagat gagaaa 26

<210> SEQ ID NO 346
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 346
ccagggaggg aggggcacag atgaga 26

<210> SEQ ID NO 347
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 347
ttcacctggg ccagggaggg aggggc 26

<210> SEQ ID NO 348
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 348
cttcacctgg gccagggagg gagggg 26

<210> SEQ ID NO 349
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 349
accttcacct gggccaggga gggagg 26

<210> SEQ ID NO 350
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 350
caccttcacc tgggccaggg agggag 26

<210> SEQ ID NO 351
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 351
accacacctt cacctgggcc agggag 26

<210> SEQ ID NO 352
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 352
acaccttcac ctgggccagg gaggga 26

<210> SEQ ID NO 353
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 353
ccacaccttc acctgggcca gggagg 26

<210> SEQ ID NO 354
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 354
aaccacacct tcacctgggc caggga 26

<210> SEQ ID NO 355
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 355
ttctggaacc acaccttcac ctgggc 26

<210> SEQ ID NO 356
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 356
tgtactttgt cctccggttc tggaac 26

<210> SEQ ID NO 357
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 357
ttgtactttg tcctccggtt ctggaa 26

<210> SEQ ID NO 358
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 358
gggagccctt cttcttctgc tcggac 26

<210> SEQ ID NO 359
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 359
gcgccaccgg ttgatgtgat gggagc 26

<210> SEQ ID NO 360
<211> LENGTH: 26

<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 360
tgcgccaccg gttgatgtga tgggag 26

<210> SEQ ID NO 361
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 361
atgcgccacc ggttgatgtg atggga 26

<210> SEQ ID NO 362
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 362
ctctcagctc agcctgagtg ttgagg 26

<210> SEQ ID NO 363
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 363
ttgaggcccc agtggctgct ctgggg 26

<210> SEQ ID NO 364
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 364
tgaggcccca gtggctgctc tggggg 26

<210> SEQ ID NO 365
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 365
gaggccccag tggctgctct gggggc 26

<210> SEQ ID NO 366
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 366
cccctccctc cctggcccag gtgaag 26

<210> SEQ ID NO 367
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 367
cccaggtgaa ggtgtggttc cagaac 26

<210> SEQ ID NO 368
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 368
gtgaaggtgt ggttccagaa ccggag 26

<210> SEQ ID NO 369
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 369
tgaaggtgtg gttccagaac cggagg 26

<210> SEQ ID NO 370
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 370
aaggtgtggt tccagaaccg gaggac 26

<210> SEQ ID NO 371
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 371
ggaggacaaa gtacaaacgg cagaag 26

<210> SEQ ID NO 372
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 372
caaagtacaa acggcagaag ctggag 26

<210> SEQ ID NO 373
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 373
aaagtacaaa cggcagaagc tggagg 26

<210> SEQ ID NO 374
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 374
agtacaaacg gcagaagctg gaggag 26

<210> SEQ ID NO 375
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 375
gtacaaacgg cagaagctgg aggagg 26

<210> SEQ ID NO 376
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 376
acaaacggca gaagctggag gaggaa 26

<210> SEQ ID NO 377

<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 377
caaacggcag aagctggagg aggaag 26

<210> SEQ ID NO 378
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 378
acggcagaag ctggaggagg aagggc 26

<210> SEQ ID NO 379
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 379
ggaggaggaa gggcctgagt ccgagc 26

<210> SEQ ID NO 380
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 380
aggaagggcc tgagtccgag cagaag 26

<210> SEQ ID NO 381
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 381
aagggcctga gtccgagcag aagaag 26

<210> SEQ ID NO 382
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 382
ggcctgagtc cgagcagaag aagaag 26

<210> SEQ ID NO 383
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 383
ctgagtccga gcagaagaag aagggc 26

<210> SEQ ID NO 384
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 384
tcaaccggtg gcgcattgcc acgaag 26

<210> SEQ ID NO 385
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 385
ggccactccc tggccaggct ttgggg 26

<210> SEQ ID NO 386
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 386
gccactccct ggccaggctt tgggga 26

<210> SEQ ID NO 387
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 387
ccactccctg gccaggcttt ggggag 26

<210> SEQ ID NO 388
<211> LENGTH: 26
<212> TYPE: DNA
<213> ORGANISM: Artificial Sequence
<220> FEATURE:

<221> NAME/KEY: source
<223> OTHER INFORMATION: /note="Description of Artificial Sequence:
      Synthetic oligonucleotide"

<400> SEQUENCE: 388
cactccctgg ccaggctttg gggagg 26

<210> SEQ ID NO 389
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 389
tggccaggct ttggggaggc ctggag 26

<210> SEQ ID NO 390
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 390
ggcctcccca aagcctggcc agggag 26

<210> SEQ ID NO 391
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 391
aggcctcccc aaagcctggc caggga 26

<210> SEQ ID NO 392
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 392
tgtcacctcc aatgactagg gtgggc 26

<210> SEQ ID NO 393
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 393
gtgggcaacc acaaacccac gagggc 26

<210> SEQ ID NO 394
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 394
tggttgccca ccctagtcat tggagg 26

<210> SEQ ID NO 395
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 395
gtggttgccc accctagtca ttggag 26

<210> SEQ ID NO 396
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 396
ggcctggagt catggcccca cagggc 26

<210> SEQ ID NO 397
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 397
gagtcatggc cccacagggc ttgaag 26

<210> SEQ ID NO 398
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 398
gccccgggct tcaagccctg tggggc 26

<210> SEQ ID NO 399
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 399
ggccccgggc ttcaagccct gtgggg 26

<210> SEQ ID NO 400
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 400
cattgccacg aagcaggcca atgggg 26

<210> SEQ ID NO 401
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 401
attgccacga agcaggccaa tgggga 26

<210> SEQ ID NO 402
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 402
ttgccacgaa gcaggccaat ggggag 26

<210> SEQ ID NO 403
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 403
tgccacgaag caggccaatg gggagg 26

<210> SEQ ID NO 404
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 404
ccacgaagca ggccaatggg gaggac 26

<210> SEQ ID NO 405
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 405
gggtgggcaa ccacaaaccc acgagg 26

<210> SEQ ID NO 406
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 406
gctgctggcc aggcccctgc gtgggc 26

<210> SEQ ID NO 407
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 407
gagtccagct tgggcccacg cagggg 26

<210> SEQ ID NO 408
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 408
tagggttagg ggccccaggc cgggg 25

<210> SEQ ID NO 409
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 409
cactgtgtcc tcttcctgcc 20

<210> SEQ ID NO 410
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 410
atgagaaact caggaggccc 20

<210> SEQ ID NO 411
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 411
tagggttagg gtccccaggt ttgaa 25

<210> SEQ ID NO 412
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 412
aggtttctgc ccatcctttc 20

<210> SEQ ID NO 413
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 413
gcccaggaaa tcctaaaggt 20

<210> SEQ ID NO 414
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 414
gagggttagg gcccccaggc aggga 25

<210> SEQ ID NO 415
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 415
cctaccagca ggaaaggaca 20

<210> SEQ ID NO 416
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 416
catcgtaacc gaaaggtcca 20

<210> SEQ ID NO 417
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 417
taaggttctg ggccccaggc aagaa 25

<210> SEQ ID NO 418
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 418
cagtgactca cagggtcagg 20

<210> SEQ ID NO 419
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 419
ggcgttccta tttcacaagc 20

<210> SEQ ID NO 420
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 420
aagagctagg ggccccaggc ctgag 25

<210> SEQ ID NO 421
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 421
aaaagggggt ggactagagc 20

<210> SEQ ID NO 422
<211> LENGTH: 20
<212> TYPE: DNA

<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 422
caccaggcct gagagagaag 20

<210> SEQ ID NO 423
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 423
tatgtttcgg ggccccaggc cggaa 25

<210> SEQ ID NO 424
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 424
caccttctgc attctgccta 20

<210> SEQ ID NO 425
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 425
tccagaccct caaagaccac 20

<210> SEQ ID NO 426
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 426
gaggggaagg ggccccaggc tggag 25

<210> SEQ ID NO 427
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 427
gcaaagacgg aaagagaagc 20

<210> SEQ ID NO 428
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 428
cagagccttc agaaattctc c 21

<210> SEQ ID NO 429
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 429
taggggcagg ggcaccaggc gggga 25

<210> SEQ ID NO 430
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 430
ccgtcttgct gtgtgaccta 20

<210> SEQ ID NO 431
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 431
atacggacgc tctgatcctg 20

<210> SEQ ID NO 432
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 432
ccgggtgagt ggccccaggc ctggg 25

<210> SEQ ID NO 433
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 433
cgacgtgaag gagaaattcg 20

<210> SEQ ID NO 434
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 434
gccagtcgga acactctga 19

<210> SEQ ID NO 435
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 435
gagggtgagt ggccccaggg cagaa 25

<210> SEQ ID NO 436
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 436
aacctggagt gggatgacag 20

<210> SEQ ID NO 437
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 437
ccacagggac tctgaggaga 20

<210> SEQ ID NO 438
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 438
caggtttagg ggctccagga ctggg 25

<210> SEQ ID NO 439
<211> LENGTH: 20

<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 439
tctgtcctct gggagctgac 20

<210> SEQ ID NO 440
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 440
gctttgcaga caccatctca 20

<210> SEQ ID NO 441
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 441
tgggtttagg ggccacaggt gggag 25

<210> SEQ ID NO 442
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 442
gggctctggc ttctgagag 19

<210> SEQ ID NO 443
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 443
ctgggtgctc tctacgtggt 20

<210> SEQ ID NO 444
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 444

-continued tggggtcagg ggacccaggg tgggg 25

<210> SEQ ID NO 445
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 445
ggggagtgtt ttccttccat 20

<210> SEQ ID NO 446
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 446
gccagggctc acagttattg 20

<210> SEQ ID NO 447
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 447
tagggttagg ggcctgcagc caggg 25

<210> SEQ ID NO 448
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 448
cagtcctatg ctcgggagag 20

<210> SEQ ID NO 449
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 449
gggaactgta gcctgtggag 20

<210> SEQ ID NO 450
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 450
tggggtgagg ggccccggcc aggag 25

<210> SEQ ID NO 451
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 451
cagaggcttc aggaggaagg 20

<210> SEQ ID NO 452
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 452
tggggatatg caacccttag 20

<210> SEQ ID NO 453
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 453
gaggattagg gtcaccaggc atgag 25

<210> SEQ ID NO 454
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 454
ctggcagggg aagtcaaata 20

<210> SEQ ID NO 455
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 455
attccgtctg tctggaatgc 20

<210> SEQ ID NO 456

<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 456
tggggccagg ggccgcaggc agggg 25

<210> SEQ ID NO 457
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 457
cccgttctct ctccttcctc 20

<210> SEQ ID NO 458
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 458
tgcaccaagt agcagaggtg 20

<210> SEQ ID NO 459
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 459
acgggttagg ggacacaggc ctgag 25

<210> SEQ ID NO 460
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 460
cctctctgag cccagtgttc 20

<210> SEQ ID NO 461
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 461
tcttgttctc cacccctcag 20

<210> SEQ ID NO 462
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 462
gaggggcagg gggcccaggc tgggg 25

<210> SEQ ID NO 463
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 463
gtctgctggg attctgggta 20

<210> SEQ ID NO 464
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 464
cagctttgtg gctctggaat 20

<210> SEQ ID NO 465
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 465
gagcgttggg ggccccagga cagga 25

<210> SEQ ID NO 466
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 466
ctcgtgagca acgggactat 20

<210> SEQ ID NO 467
<211> LENGTH: 20
<212> TYPE: DNA
<213> ORGANISM: Artificial Sequence
<220> FEATURE:

<221> NAME/KEY: source
<223> OTHER INFORMATION: /note="Description of Artificial Sequence: Synthetic oligonucleotide"

<400> SEQUENCE: 467
gtggaaacac ggtgctcttt 20

<210> SEQ ID NO 468
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 468
tagagttagg agacccagga atgag 25

<210> SEQ ID NO 469
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 469
caaccaagat caggcaacaa 20

<210> SEQ ID NO 470
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 470
aacttggtaa gtgcccagca 20

<210> SEQ ID NO 471
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 471
tggggagggg ggccccaggc agggg 25

<210> SEQ ID NO 472
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 472
ggcctctgaa ataacgttgg 20

<210> SEQ ID NO 473
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 473
ccctgctttc ttcactccag 20

<210> SEQ ID NO 474
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 474
aagggttagg ggcccaaagg tagag 25

<210> SEQ ID NO 475
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 475
ggaccctggg aacattttgt 20

<210> SEQ ID NO 476
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 476
aaagggcaga ggaaagaagg 20

<210> SEQ ID NO 477
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 477
gaggctgagt ggccccaggc ctgag 25

<210> SEQ ID NO 478
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 478
cccagtttga ggacagtggt 20

<210> SEQ ID NO 479
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 479
gggcttaggg actcaggaga 20

<210> SEQ ID NO 480
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 480
tcgggtgtgg ggctccaggc ccggg 25

<210> SEQ ID NO 481
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 481
caagagaggg aggatgcaag 20

<210> SEQ ID NO 482
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 482
gctgctgagg gatggagtt 19

<210> SEQ ID NO 483
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 483
gagggtgagt ggccccagga ctggg 25

<210> SEQ ID NO 484
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 484
cacagactca ggccatctca 20

<210> SEQ ID NO 485
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 485
gcagtgaaag aaggctagat cc 22

<210> SEQ ID NO 486
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 486
tagtgttagg agctccaggg aaggg 25

<210> SEQ ID NO 487
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 487
cctacagcca ttggacccta 20

<210> SEQ ID NO 488
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 488
cgaagggctc aaacatcttc 20

<210> SEQ ID NO 489
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 489
tagggtcagg ggctcaaggg atggg 25

<210> SEQ ID NO 490
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 490
gtcagtgctg acacctcacc 20

<210> SEQ ID NO 491
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 491
agtgcctcct cttcccactc 20

<210> SEQ ID NO 492
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 492
cagggatagc agccccaggc agggg 25

<210> SEQ ID NO 493
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 493
tgctagggtg gggaaattct 20

<210> SEQ ID NO 494
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 494
aaatccagca gagcagcaat 20

<210> SEQ ID NO 495
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 495
taggggtagg ggggccatgc agggg 25

<210> SEQ ID NO 496
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 496
acagaaggta agggggaagg 20

<210> SEQ ID NO 497
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 497
tctctctctg ctgcacctca 20

<210> SEQ ID NO 498
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 498
tgggggtagg ggtcccagga gagag 25

<210> SEQ ID NO 499
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 499
atacctgggg gaactgctct 20

<210> SEQ ID NO 500
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 500
gtaggccacc ttgacctctg 20

<210> SEQ ID NO 501
<211> LENGTH: 25
<212> TYPE: DNA

<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 501
caggcttggg ggccccaggt agggg 25

<210> SEQ ID NO 502
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 502
tctgagaaca ccaggaagca 20

<210> SEQ ID NO 503
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 503
tcttggcctc ctcacatagg 20

<210> SEQ ID NO 504
<211> LENGTH: 3174
<212> TYPE: DNA
<213> ORGANISM: Parvibaculum lavamentivorans

<400> SEQUENCE: 504
atgtacccat acgatgttcc agattacgct tcgccgaaga aaaagcgcaa ggtcgaagcg 60
tccatggaga ggattttcgg ctttgacatc ggcacaacaa gtatcggatt cagcgtgatt 120
gattacagta gcacccagtc cgcaggcaac atccagaggc tgggcgtgcg cattttccct 180
gaggcaaggg acccagatgg gacccccctg aaccagcagc ggagacagaa acgcatgatg 240
aggcgccagc tgcgacggag aaggattcgc cgaaaggcac tgaatgagac actgcacgaa 300
gccggctttc tgccagctta cggtctgca gattggcccg tggtcatggc cgacgagcct 360
tatgaactgc ggagaagggg actggaggaa ggcctgagtg cttacgagtt cggacgggca 420
atctatcatc tggcccagca ccggcatttt aaaggcagag aactggagga atccgataca 480
cccgaccctg atgtggacga tgagaaggaa gccgctaacg agagagcagc cactctgaag 540
gccctgaaaa atgaacagac cacactggga gcatggctgg cccgccgacc cccttctgac 600
cgcaagcgag gaatccacgc ccataggaac gtggtcgctg aggagttcga gcgcctgtgg 660
gaagtgcagt ccaagtttca ccccgctctg aaatctgagg aaatgcgggc aagaatcagt 720
gatacaattt tcgcccagag gcctgtgttt tggcgcaaga acactctggg agagtgcaga 780
ttcatgcctg gcgaaccact gtgtcccaag gggtcctggc tgtctcagca gcggagaatg 840
ctggagaaac tgaacaatct ggctatcgca ggcgggaatg ctaggccact ggatgcagag 900
gaacgcgacg ccattctgag taagctgcag cagcaggcca gcatgtcctg gccaggcgtg 960
cggtcagctc tgaaggcact gtacaaacag agaggcgagc ccggggctga aaagagcctg 1020

-continued

```
aaattcaacc tggagctggg aggcgaatcc aagctgctgg gaaatgccct ggaggctaaa   1080
ctggcagata tgtttggccc tgactggcca gctcaccccc gaaagcagga gatccggcac   1140
gcagtgcatg aacggctgtg ggctgcagat tacggcgaga cacccgacaa gaaaagagtc   1200
atcattctgt ccgagaagga tcgaaaagct catcgggaag ccgctgcaaa ctctttcgtg   1260
gcagactttg gaattactgg cgagcaggca gctcagctgc aggccctgaa gctgccaacc   1320
ggctgggaac cttatagcat cccagcactg aacctgttcc tggccgagct ggaaaagggg   1380
gagaggtttg gagccctggt gaatggacct gattgggaag gctggaggcg cacaaacttc   1440
ccccaccgca atcagcctac tggggagatc ctggacaagc tgccaagtcc cgcctcaaaa   1500
gaggaaaggg aacgcattag ccagctgcgc aacccaaccg tggtccgaac acagaatgag   1560
ctgagaaagg tggtcaacaa tctgatcggg ctgtatggaa aacccgatcg aatccggatt   1620
gaagtgggcc gggacgtcgg gaagtccaaa agagaaaggg aggaaatcca gtctggcatt   1680
cgacggaacg agaagcagag aaagaaagcc actgaagatc tgatcaaaaa cggaattgct   1740
aatcctagcc gggacgatgt ggagaagtgg atcctgtgga aagagggcca ggaaagatgc   1800
ccatacaccg gcgaccagat tggcttcaat gccctgttta gagaaggcag atatgaggtg   1860
gaacacatct ggcctcgctc tcgaagtttt gataacagcc caaggaataa gacactgtgt   1920
cgcaaagacg tgaacatcga gaagggaaat aggatgcctt tcgaggcatt tggccatgac   1980
gaagatcggt ggagcgccat ccagattaga ctgcagggca tggtgtcagc caaaggggga   2040
actgggatga gccccggaaa ggtcaaacgc ttcctggcta agaccatgcc tgaggatttt   2100
gcagcccggc agctgaacga cacaagatac gctgcaaagc agatcctggc ccagctgaaa   2160
aggctgtggc cagacatggg acctgaggct ccagtgaagg tcgaagcagt gactggacag   2220
gtcaccgccc agctgcgcaa actgtggact ctgaacaata ttctggctga cgatggggag   2280
aaaaccagag cagatcacag gcaccatgcc atcgacgctc tgacagtggc ctgcactcat   2340
cctggaatga ccaacaagct gagcaggtat tggcagctgc gcgacgatcc acgagcagag   2400
aagccagctc tgactccacc ctgggatacc atccgcgccg acgctgagaa agccgtgtct   2460
gaaattgtgg tcagtcaccg ggtgagaaag aaagtcagcg gcccactgca taaggagact   2520
acctacggcg atacagggac tgacattaag accaaatccg gcacatatag acagttcgtg   2580
accaggaaga aaatcgagtc actgagcaag ggggagctgg atgaaattcg cgacccccga   2640
atcaaagaaa ttgtggcagc tcacgtcgca ggacgaggag gcgaccccaa gaaggccttc   2700
cctccatacc cctgtgtgtc tcccggaggc cctgagatcc ggaaggtcag actgaccagt   2760
aaacagcagc tgaacctgat ggcccagaca gggaatggat acgctgacct gggctccaac   2820
caccatatcg caatctaccg gctgcccgat gggaaggccg acttcgagat tgtgtcactg   2880
tttgatgcta gcagaaggct ggcacagaga aatccaatcg tgcagaggac acgagcagac   2940
ggagccagct tcgtcatgtc cctggcagcc ggagaggcca tcatgattcc cgaaggctca   3000
aagaaaggga tctggattgt gcagggagtc tgggcaagcg gacaggtggt cctggagagg   3060
gacaccgatg ctgaccactc tacaactacc cgccctatgc caaaccccat cctgaaggac   3120
gatgccaaga aagtgagtat cgatcctatt ggccgagtcc ggccatcaaa tgac         3174
```

<210> SEQ ID NO 505
<211> LENGTH: 3315
<212> TYPE: DNA
<213> ORGANISM: Corynebacter diphtheria

<400> SEQUENCE: 505
atgtacccat acgatgttcc agattacgct tcgccgaaga aaaagcgcaa ggtcgaagcg 60
tccatgaagt accatgtcgg aatcgatgtc ggaacctttt ctgtggggct ggctgctatt 120
gaagtggatg acgctggaat gcctattaag accctgagtc tggtgtcaca cattcatgac 180
tcaggactgg atcctgacga gatcaagagc gctgtgacca ggctggcaag ctccggaatc 240
gcccggagaa caaggcgcct gtaccgacgg aagagaaggc gcctgcagca gctggataag 300
ttcatccaga ggcagggctg gccagtgatc gagctggaag attacagcga ccccctgtat 360
ccttggaagg tgcgcgccga actggccgct tcttatattg ctgacgagaa ggaacggggg 420
gagaaactga gtgtggctct gagacacatc gcaaggcatc gcggatggag gaaccettac 480
gccaaggtgt ctagtctgta tctgccagat ggcccctcag acgccttcaa ggctattagg 540
gaggaaatca aacgcgctag cggccagcct gtgccagaga ctgcaaccgt cgggcagatg 600
gtgaccctgt gcgaactggg cacactgaag ctgcgaggag agggaggagt gctgagtgca 660
cggctgcagc agtcagatta cgcccgcgag atccaggaaa tttgtcgaat gcaggagatc 720
ggccaggaac tgtatcgcaa gatcattgac gtggtgttcg cagccgagtc cccaaagggc 780
tctgcctcaa gccgggtggg gaaagatcct ctgcagccag gaaagaacag agcactgaaa 840
gccagcgacg cttttcagcg ataccggatt gctgcactga tcggcaatct gagagtcagg 900
gtggatgggg agaagaggat tctgagcgtg gaggagaaga acctggtgtt cgaccacctg 960
gtgaatctga ctccaaagaa agagcccgaa tgggtgacca tcgccgaaat tctgggcatc 1020
gatcgcgggc agctgatcgg aacagctact atgaccgacg atggagagcg agcaggagcc 1080
cgacccccta cacacgatac taacagaagt attgtgaaca gccggatcgc accactggtc 1140
gactggtgga aaacagctag cgcactggag cagcacgcca tggtgaaggc actgtccaac 1200
gccgaagtcg acgattttga ttctcccgag ggagcaaaag tgcaggcatt ctttgccgat 1260
ctggacgatg acgtccacgc caagctggac agcctgcatc tgcctgtggg acgagcagct 1320
tactccgagg acactctggt cagactgacc cgacggatgc tgagtgatgg ggtggacctg 1380
tataccgccc ggctgcagga gttcggaatt gaacctagct ggaccccacc cacaccaaga 1440
atcggagagc ctgtcggcaa tccagccgtc gaccgggtgc tgaaaacagt gagcagatgg 1500
ctggaatccg caacaaagac ttggggcgcc ccagagaggg tcatcattga gcacgtgcgc 1560
gaaggcttcg tcactgagaa acgcgctcga gaaatggatg gggacatgag aaggcgcgca 1620
gcccggaacg ccaagctgtt tcaggagatg caggaaaagc tgaatgtgca gggcaaaccc 1680
agtcgagccg atctgtggag ataccagtca gtgcagagac agaactgcca gtgtgcctat 1740
tgcgggtccc caattacctt ttctaatagt gaaatggacc acatcgtgcc cagagcaggg 1800
cagggatcca ccaacacaag ggagaatctg gtcgccgtgt gccatcgctg taaccagtct 1860
aagggcaata caccettcgc tatttgggca aaaaacactt ctatcgaagg ggtcagtgtg 1920
aaggaggccg tggaacggac cagacattgg gtcactgata ccggcatgag aagcactgac 1980
ttcaagaagt tcaccaaggc tgtggtcgag cggtttcaga gagcaacaat ggatgaggaa 2040
atcgacgcca gaagcatgga atccgtcgcc tggatggcta atgagctgag gagccgcgtg 2100
gctcagcact tcgcatccca tggaaccaca gtcagggtgt accgaggcag cctgacagca 2160
gaggctcgac gggcatctgg gatcagtgga aagctgaaat tctttgatgg cgtggggaag 2220
tccaggctgg atagaaggca ccatgctatt gacgctgcag tgatcgcatt cacctctgac 2280
tatgtggccg aaacactggc tgtccgctca aacctgaaac agagccaggc ccaccgacag 2340
gaggctcctc agtggagaga gttcaccggc aaggatgcag agcatcgagc agcttggaga 2400
gtgtggtgcc agaagatgga aaaactgagc gccctgctga ccgaggacct gcgagatgac 2460
cgggtggtcg tgatgtctaa cgtgcgactg cggctgggaa atggcagtgc ccacaaggaa 2520
accattggca aactgtcaaa ggtgaaactg tcctctcagc tgtcagtcag cgatatcgac 2580
aaagcaagtt cagaggccct gtggtgtgct ctgaccagag agcccggatt cgatcctaag 2640
gaaggcctgc ccgctaaccc tgagagacac atcagggtga atgggacaca tgtctacgcc 2700
ggggacaata ttggactgtt tccagtgtca gcaggaagca tcgcactgag gggaggatac 2760
gcagagctgg gcagctcctt ccaccatgct cgcgtgtata aaattacttc cggcaagaaa 2820
cccgcatttg ccatgctgag ggtgtacacc atcgatctgc tgccttatcg caaccaggac 2880
ctgtttagcg tggaactgaa gccacagaca atgtccatga ggcaggctga gaagaaactg 2940
cgcgacgctc tggcaactgg gaatgcagaa tatctgggat ggctggtcgt ggatgacgag 3000
ctggtcgtgg atacatctaa gattgccact gaccaggtca aagcagtgga ggccgaactg 3060
gggactatcc gccgatggcg ggtggatgga ttcttttccc cctctaaact gagactgagg 3120
cctctgcaga tgtccaagga ggggatcaag aaagagtccg ctcccgaact gtctaaaatc 3180
attgacagac caggatggct gcccgccgtg aacaagctgt tctctgatgg aaatgtcacc 3240
gtcgtgcgga gagactctct gggacgcgtg cgactggaga gtacagccca cctgcctgtc 3300
acttggaagg tgcag 3315

<210> SEQ ID NO 506
<211> LENGTH: 3453
<212> TYPE: DNA
<213> ORGANISM: Streptococcus pasteurianus

<400> SEQUENCE: 506
atgtacccat acgatgttcc agattacgct tcgccgaaga aaaagcgcaa ggtcgaagcg 60
tccatgacta acggcaagat tctggggctg gacattggca tcgcaagcgt gggggtgggg 120
attattgagg caaaaactgg aaaggtggtg catgccaatt cccggctgtt ctctgccgct 180
aacgctgaga acaatgcaga acggagaggg tttaggggat ctaggcgcct gaatcgacgg 240
aagaaacacc gcgtgaagcg agtccgggat ctgttcgaga aatacggaat cgtcaccgac 300
tttcgcaacc tgaatctgaa cccttatgag ctgcgagtga agggcctgac cgaacagctg 360
aaaaacgagg aactgttcgc agccctgaga acaatctcta agagaagggg gattagttac 420
ctggacgatg ccgaggacga tagtaccgga tcaacagact atgctaagag catcgatgag 480
aatcgccgac tgctgaaaaa caagacacca ggccagattc agctggagag gctggaaaag 540
tacggccagc tgcgcgggaa tttcaccgtc tatgacgaga acggggaagc ccatcgcctg 600
atcaatgtgt ttagtacatc agattacgag aaagaagcac ggaagatcct ggagacacag 660
gccgactaca acaagaaaat cacagctgag ttcattgacg attatgtgga aatcctgacc 720
cagaaacgaa agtactatca cggccccggg aacgaaaaga gccggactga ctacggacgg 780
ttccggaccg atgggaccac actggagaat attttcggaa tcctgattgg caagtgcaac 840
ttttaccctg atgaatatcg agcaagcaag gccagctaca ccgcacagga gtataatttc 900
ctgaacgacc tgaacaatct gaaggtgagc accgaaacag ggaagctgtc aacagagcag 960
aaagaaagcc tggtggagtt tgccaagaat actgctaccc tgggacccgc taaactgctg 1020
aaggagatcg caaaaattct ggactgtaag gtggatgaga tcaaaggata cagagaggac 1080

-continued

```
gataaaggca agccagatct gcataccttc gagccctata ggaaactgaa gtttaatctg   1140
gaaagcatca acattgacga tctgtcccgc gaagtgatcg acaagctggc tgatattctg   1200
actctgaaca ccgagagaga aggaatcgag gacgcaatta agaggaatct gccaaaccag   1260
ttcacagagg aacagatcag cgagatcatc aaggtgcgga agagccagtc cactgctttc   1320
aataagggct ggcactcttt tagtgcaaaa ctgatgaacg agctgatccc cgaactgtac   1380
gccacctccg acgagcagat gacaattctg actcggctgg aaaaattcaa ggtcaataag   1440
aaaagctcca aaaacacaaa gactatcgac gagaaggaag tcactgatga gatctacaat   1500
cctgtggtcg ccaagagcgt gagacagacc atcaaaatca ttaacgctgc agtcaagaaa   1560
tatggcgact tcgataagat cgtgattgaa atgccacggg ataaaaatgc tgacgatgag   1620
aagaagttca tcgacaagag aaataaggag aacaagaagg aaaaggacga tgccctgaaa   1680
agggccgctt acctgtataa ttctagtgac aagctgcccg atgaggtgtt ccacggcaac   1740
aagcagctgg aaaccaaaat ccgactgtgg tatcagcagg gggagcggtg cctgtatagt   1800
ggaaagccca tctcaattca ggagctggtg cataactcta acaatttcga aatcgatcac   1860
attctgcctc tgtcactgag ctttgacgat agtctggcca ataaggtgct ggtctacgct   1920
tggacaaacc aggagaaagg ccagaaaacc ccttatcagg tcatcgactc catggatgca   1980
gcctggtctt tcagggagat gaaggactac gtgctgaaac agaagggact gggcaagaaa   2040
aagcgcgact atctgctgac taccgagaac atcgataaga ttgaagtgaa gaagaagttc   2100
atcgagagga atctggtgga tactcgctac gcatctcgag tggtcctgaa ctctctgcag   2160
agtgccctga gagagctggg gaaagacact aaggtgtctg tggtcagggg acagttcacc   2220
agtcagctgc ggagaaaatg gaagatcgat aagagccgcg agacatacca ccatcacgca   2280
gtggacgccc tgatcattgc tgcatcaagc cagctgaaac tgtgggagaa gcaggacaat   2340
cccatgtttg tggattatgg caagaaccag gtggtcgaca aacagactgg ggagatcctg   2400
tccgtgtctg acgatgagta caaggaactg gtgttccagc cccttatca gggctttgtg    2460
aataccatct cctctaaagg gttcgaggac gaaattctgt ttagctacca ggtggattcc   2520
aaatataacc ggaaggtcag tgacgcaacc atctactcaa caagaaaagc caagattggc   2580
aaggataaga aagaggaaac ctacgtgctg ggaaaaaatca aggacatcta ctcccagaat  2640
ggcttcgata ccttcatcaa gaagtacaac aaagataaga ctcagttcct gatgtatcag   2700
aaggactctc tgacatggga gaacgtgatc gaagtcattc tgagggacta cccaacaact   2760
aagaaaagcg aggacggcaa aaatgatgtg aagtgcaacc cctttgagga atacaggcgc   2820
gagaatgggc tgatctgtaa gtattccaag aaagggaaag gaactcccat caagagcctg   2880
aagtactatg acaagaaact ggggaactgc atcgatatta ccccagagga atcacgcaat   2940
aaggtcatcc tgcagagcat taacccttgg cgagccgacg tgtacttcaa tccagagaca   3000
ctgaagtacg aactgatggg cctgaaatat tcagatctga gctttgaaaa gggcactggg   3060
aactaccata tcagccagga gaaatatgac gctatcaaag agaaggaagg aattggcaag   3120
aaatccgagt tcaagtttac actgtaccgc aacgacctga tcctgatcaa ggatatcgcc   3180
agtggcgagc aggaaatcta cagattcctg tcaagaacta tgcccaatgt gaaccactac   3240
gtcgagctga agccttacga caaggaaaag ttcgataacg tgcaggagct ggtcgaagca   3300
ctgggagagg cagataaagt gggacgatgt atcaaaggac tgaataagcc aaacatcagc   3360
atctacaagg tgagaaccga cgtcctggga aacaaatatt tcgtgaagaa aaagggcgac   3420
aaacccaagc tggattttaa gaacaacaag aag                                3453
```

<210> SEQ ID NO 507
<211> LENGTH: 3309
<212> TYPE: DNA
<213> ORGANISM: Neisseria cinerea

<400> SEQUENCE: 507
atgtacccat acgatgttcc agattacgct tcgccgaaga aaaagcgcaa ggtcgaagcg 60
tccatggctg ccttcaaacc taatcctatg aactacatcc tgggcctgga cattggaatc 120
gcttctgtcg ggtgggctat cgtggaaatc gacgaggaag agaaccctat cagactgatt 180
gatctgggag tcagagtgtt tgaaagggca gaggtgccaa agaccggcga ctccctggcc 240
gctgcacgga gactggctcg gtctgtcagg cgcctgacac gacggagagc acacaggctg 300
ctgcgagcta ggcgcctgct gaagagagag ggcgtgctgc aggccgctga cttcgatgaa 360
aacggcctga tcaagagcct gcccaatact ccttggcagc tgagagcagc cgctctggac 420
aggaagctga ccccactgga gtggtctgcc gtgctgctgc acctgatcaa gcatcgcggc 480
tacctgagtc agcgaaaaaa tgaaggggag acagcagata aggagctggg agcactgctg 540
aaaggagtgg ccgacaacac tcatgctctg cagaccggcg attttaggac acccgctgag 600
ctggcactga ataagttcga aaaagagagt ggacacattc gaaaccagcg gggcgactat 660
tcacatacct tcaaccgcaa ggatctgcag gccgagctga atctgctgtt tgaaaagcag 720
aaagagttcg ggaatcccca cgtgtccgac gggctgaaag aaggaatcga gacactgctg 780
atgactcaga ggcctgcact gtctggcgat gccgtgcaga agatgctggg gcattgcacc 840
tttgaaccaa cagagcccaa ggcagccaaa aacacctaca cagccgagag gttcgtgtgg 900
ctgacaaagc tgaacaatct gcgcatcctg gaacagggca gtgagcggcc cctgactgac 960
accgaaagag ccacactgat ggatgagcct tacaggaagt ctaaactgac ttatgcccag 1020
gctcgcaagc tgctggacct ggacgatact gccttcttta agggcctgag gtacgggaaa 1080
gataatgcag aagccagcac cctgatggag atgaaggcct atcacgctat ctcccgcgcc 1140
ctggaaaaag agggcctgaa ggacaagaaa tctcccctga acctgagtcc tgaactgcag 1200
gatgagattg ggaccgcttt tagcctgttc aagactgacg aggatatcac cggacgcctg 1260
aaagaccgag tgcagcccga aattctggag gcactgctga agcacatcag ttttgataaa 1320
ttcgtgcaga tttcactgaa ggccctgcga cggatcgtcc ctctgatgga gcagggcaat 1380
cggtacgacg aggcctgcac cgagatctac ggagatcatt atggcaagaa aaacacagaa 1440
gagaaaatct atctgccccc tattcctgcc gacgagatcc ggaatccagt ggtcctgaga 1500
gctctgtcac aggcaagaaa agtgatcaac ggagtggtca gaaggtacgg cagccctgct 1560
aggatccaca ttgaaaccgc acgcgaagtg ggaaagtcct ttaaagaccg caaggaaatc 1620
gagaagcgac aggaagagaa tagaaaagat agggaaaagt ctgctgcaaa attcagggag 1680
tactttccaa acttcgtggg cgaacccaag agtaaagaca tcctgaagct gcgcctgtac 1740
gagcagcagc acgggaagtg tctgtatagc ggaaaagaaa ttaacctggg ccggctgaat 1800
gaaaagggct atgtggagat cgatcatgca ctgccctttt ccagaacatg ggacgattct 1860
ttcaacaata aggtcctggc tctggggagc gagaaccaga acaagggaaa tcagactcct 1920
tacgaatatt tcaacgggaa ggacaatagc cgagaatggc aggagtttaa agcccgcgtg 1980
gagacaagcc ggttcccacg aagcaagaaa cagcggattc tgctgcagaa gtttgacgaa 2040
gatggattca aagagagaaa cctgaatgac acccggtaca tcaacagatt tctgtgccag 2100
ttcgtggctg atcacatgct gctgaccgga aagggcaaac gccgagtctt tgcaagcaac 2160
ggccagatca caaatctgct gaggggcttc tgggggctgc ggaaggtgag agccgagaat 2220
gaccgccacc atgcactgga tgccgtggtc gtggcttgtt ccactattgc aatgcagcag 2280
aagatcacca ggtttgtgcg ctataaagag atgaacgcct tcgacggaaa gacaattgat 2340
aaagaaactg gcgaggtgct gcaccagaag gcacattttc ctcagccatg ggagttcttc 2400
gcccaggaag tgatgatccg ggtctttggg aagcctgacg gaaaaccaga gttcgaagag 2460
gccgataccc cagaaaagct gcggacactg ctggctgaaa aactgagctc cagacccgag 2520
gcagtgcaca agtacgtcac ccccctgttc attagcaggg cccctaatcg caaaatgtcc 2580
gggcagggac atatggagac tgtgaaatca gctaagcggc tggacgaagg catcagcgtg 2640
ctgagagtcc cactgaccca gctgaagctg aaagatctgg agaagatggt gaaccgggaa 2700
agagagccca agctgtatga agctctgaaa gcaagactgg aggcccacaa ggacgatcca 2760
gctaaagcat ttgccgagcc cttctacaaa tatgacaagg ccggcaatcg gacacagcag 2820
gtgaaggctg tcagagtgga gcaggtccag aaaactgggg tctgggtgca caaccataat 2880
ggaattgccg acaacgctac aatcgtccgg gtggatgtgt tcgagaaagg cgggaagtac 2940
tatctggtgc ctatctactc ctggcaggtc gccaagggaa tcctgccaga tagagctgtc 3000
gtgcagggca aagacgaaga ggattggact gtgatggacg attctttcga gtttaagttc 3060
gtcctgtacg caaacgacct gatcaagctg acagccaaga aaaatgaatt tctggggtat 3120
ttcgtgtcac tgaacagggc aactggagcc atcgatattc gcacacatga cactgatagc 3180
accaagggaa aaaacggcat ctttcagtct gtgggcgtca agaccgccct gagtttccag 3240
aaatatcaga ttgacgaact ggggaaggag atccgaccct gtcggctgaa gaaacgacca 3300
cccgtgcgg 3309

<210> SEQ ID NO 508
<211> LENGTH: 3252
<212> TYPE: DNA
<213> ORGANISM: Staphylococcus aureus

<400> SEQUENCE: 508
atgaaaagga actacattct ggggctggac atcgggatta caagcgtggg gtatgggatt 60
attgactatg aaacaaggga cgtgatcgac gcaggcgtca gactgttcaa ggaggccaac 120
gtggaaaaca atgagggacg gagaagcaag aggggagcca ggcgcctgaa acgacggaga 180
aggcacagaa tccagagggt gaagaaactg ctgttcgatt acaacctgct gaccgaccat 240
tctgagctga gtggaattaa tccttatgaa gccagggtga aaggcctgag tcagaagctg 300
tcagaggaag agttttccgc agctctgctg cacctggcta agcgccgagg agtgcataac 360
gtcaatgagg tggaagagga caccggcaac gagctgtcta caaaggaaca gatctcacgc 420
aatagcaaag ctctggaaga gaagtatgtc gcagagctgc agctggaacg gctgaagaaa 480
gatggcgagg tgagagggtc aattaatagg ttcaagacaa gcgactacgt caaagaagcc 540
aagcagctgc tgaaagtgca gaaggcttac caccagctgg atcagagctt catcgatact 600
tatatcgacc tgctggagac tcggagaacc tactatgagg gaccaggaga agggagcccc 660
ttcggatgga aagacatcaa ggaatggtac gagatgctga tgggacattg cacctatttt 720
ccagaagagc tgagaagcgt caagtacgct tataacgcag atctgtacaa cgccctgaat 780
gacctgaaca acctggtcat caccagggat gaaaacgaga aactggaata ctatgagaag 840
ttccagatca tcgaaaacgt gtttaagcag aagaaaaagc ctacactgaa acagattgct 900

-continued

```
aaggagatcc tggtcaacga agaggacatc aagggctacc gggtgacaag cactggaaaa    960
ccagagttca ccaatctgaa agtgtatcac gatattaagg acatcacagc acggaaagaa   1020
atcattgaga acgccgaact gctggatcag attgctaaga tcctgactat ctaccagagc   1080
tccgaggaca tccaggaaga gctgactaac ctgaacagcg agctgaccca ggaagagatc   1140
gaacagatta gtaatctgaa ggggtacacc ggaacacaca acctgtccct gaaagctatc   1200
aatctgattc tggatgagct gtggcataca aacgacaatc agattgcaat ctttaaccgg   1260
ctgaagctgg tcccaaaaaa ggtggacctg agtcagcaga aagagatccc aaccacactg   1320
gtggacgatt tcattctgtc acccgtggtc aagcggagct tcatccagag catcaaagtg   1380
atcaacgcca tcatcaagaa gtacggcctg cccaatgata tcattatcga gctggctagg   1440
gagaagaaca gcaaggacgc acagaagatg atcaatgaga tgcagaaacg aaaccggcag   1500
accaatgaac gcattgaaga gattatccga actaccggga aagagaacgc aaagtacctg   1560
attgaaaaaa tcaagctgca cgatatgcag gagggaaagt gtctgtattc tctggaggcc   1620
atccccctgg aggacctgct gaacaatcca ttcaactacg aggtcgatca tattatcccc   1680
agaagcgtgt ccttcgacaa ttcctttaac aacaaggtgc tggtcaagca ggaagagaac   1740
tctaaaaagg gcaataggac tcctttccag tacctgtcta gttcagattc caagatctct   1800
tacgaaacct ttaaaaagca cattctgaat ctggccaaag gaaagggccg catcagcaag   1860
accaaaaagg agtacctgct ggaagagcgg gacatcaaca gattctccgt ccagaaggat   1920
tttattaacc ggaatctggt ggacacaaga tacgctactc gcggcctgat gaatctgctg   1980
cgatcctatt tccgggtgaa caatctggat gtgaaagtca agtccatcaa cggcgggttc   2040
acatcttttc tgaggcgcaa atggaagttt aaaaaggagc gcaacaaagg gtacaagcac   2100
catgccgaag atgctctgat tatcgcaaat gccgacttca tctttaagga gtggaaaaag   2160
ctggacaaag ccaagaaagt gatggagaac cagatgttcg aagagaagca ggccgaatct   2220
atgcccgaaa tcgagacaga acaggagtac aaggagattt tcatcactcc tcaccagatc   2280
aagcatatca aggatttcaa ggactacaag tactctcacc gggtggataa aaagcccaac   2340
agagagctga tcaatgacac cctgtatagt acaagaaaag acgataaggg gaataccctg   2400
attgtgaaca atctgaacgg actgtacgac aaagataatg acaagctgaa aaagctgatc   2460
aacaaaagtc ccgagaagct gctgatgtac caccatgatc ctcagacata tcagaaactg   2520
aagctgatta tggagcagta cggcgacgag aagaacccac tgtataagta ctatgaagag   2580
actgggaact acctgaccaa gtatagcaaa aaggataatg gccccgtgat caagaagatc   2640
aagtactatg ggaacaagct gaatgcccat ctggacatca cagacgatta ccctaacagt   2700
cgcaacaagg tggtcaagct gtcactgaag ccatacagat tcgatgtcta tctggacaac   2760
ggcgtgtata aatttgtgac tgtcaagaat ctggatgtca tcaaaaagga gaactactat   2820
gaagtgaata gcaagtgcta cgaagaggct aaaaagctga aaaagattag caaccaggca   2880
gagttcatcg cctcctttta caacaacgac ctgattaaga tcaatggcga actgtatagg   2940
gtcatcgggg tgaacaatga tctgctgaac cgcattgaag tgaatatgat tgacatcact   3000
taccgagagt atctggaaaa catgaatgat aagcgccccc ctcgaattat caaaacaatt   3060
gcctctaaga ctcagagtat caaaaagtac tcaaccgaca ttctgggaaa cctgtatgag   3120
gtgaagagca aaaagcaccc tcagattatc aaaaagggca gcggaggcaa gcgtcctgct   3180
gctactaaga aagctggtca agctaagaaa aagaaaggat cctacccata cgatgttcca   3240
```

-continued gattacgctt aa 3252

<210> SEQ ID NO 509
<211> LENGTH: 3072
<212> TYPE: DNA
<213> ORGANISM: Campylobacter lari

<400> SEQUENCE: 509
atgtacccat acgatgttcc agattacgct tcgccgaaga aaaagcgcaa ggtcgaagcg 60
tccatgagga ttctggggtt tgacattggc attaacagca tcgggtgggc ttttgtggag 120
aacgacgaac tgaaggactg cggagtgcgg atcttcacaa aggccgagaa cccaaaaaat 180
aaggaaagcc tggcactgcc ccggagaaat gcacgcagct ccaggcgccg actgaaacgg 240
agaaaggccc ggctgatcgc tattaagaga atcctggcca aagagctgaa gctgaactac 300
aaggactatg tcgcagctga tggagagctg ccaaaggcct acgaaggatc cctggcatct 360
gtgtacgagc tgcggtataa ggccctgaca cagaacctgg aaactaaaga tctggccaga 420
gtgatcctgc acattgctaa gcataggggg tacatgaaca agaacgagaa gaaatcaaac 480
gacgctaaga aaggaaagat cctgagcgct ctgaaaaaca atgcactgaa gctggagaac 540
taccagagcg tgggcgaata cttctacaag gagttctttc agaaatacaa gaaaaacaca 600
aagaacttca tcaagatccg caacactaag gataattaca acaattgcgt gctgtctagt 660
gacctggaaa aagagctgaa gctgatcctg gaaaaacaga aggagttcgg ctacaactac 720
tctgaagatt tcatcaacga gattctgaag gtcgccttct ttcagcggcc cctgaaggac 780
ttcagtcacc tggtgggggc ctgcactttc tttgaggaag agaaaagggc ctgtaagaac 840
agctactctg cctgggagtt tgtggctctg accaagatca ttaacgagat caagagcctg 900
gagaagatca gcggcgaaat tgtgccaacc cagacaatca acgaggtcct gaatctgatc 960
ctggacaagg ggtctatcac ctacaagaaa ttcagaagtt gtatcaatct gcatgagagt 1020
atcagcttca agagcctgaa gtatgataaa gaaaacgccg agaatgctaa actgatcgac 1080
ttccgcaagc tggtggagtt taagaaagcc ctgggagtcc acagcctgtc ccggcaggaa 1140
ctggatcaga tctccactca tatcaccctg attaaggaca acgtgaagct gaaaaccgtc 1200
ctggagaaat acaacctgag taatgaacag atcaacaatc tgctggaaat tgagttcaac 1260
gattatatca acctgagctt caaggccctg ggaatgattc tgccactgat gcgcgagggc 1320
aaacgatacg acgaggcctg cgagatcgcc aatctgaaac ctaagaccgt ggacgagaag 1380
aaagatttcc tgccagcatt ttgtgattcc attttcgccc acgagctgtc taaccccgtg 1440
gtcaataggg ctatcagcga ataccgcaag gtgctgaacg cactgctgaa gaaatatgga 1500
aaggtccaca aaattcatct ggagctggct cgcgacgtgg gcctgtccaa gaaagcacga 1560
gagaagatcg aaaaagagca gaaggaaaac caggccgtga atgcatgggc cctgaaggaa 1620
tgcgagaata ttggcctgaa ggccagcgca aagaacatcc tgaaactgaa gctgtggaaa 1680
gaacagaagg agatctgtat ctactccgga aataagatct ctattgagca cctgaaagat 1740
gaaaaggccc tggaggtgga ccatatctac ccctattcta ggagtttcga cgattctttt 1800
atcaacaaag tgctggtgtt caccaaggaa aatcaggaga aactgaacaa gacacctttc 1860
gaggcctttg gcaagaatat tgaaaaatgg agcaagatcc agaccctggc tcagaacctg 1920
ccatacaaga aaaagaataa gattctggac gagaacttca aagataagca gcaggaggac 1980
tttatctctc gaaatctgaa cgacacccgg tatatcgcta cactgattgc aaaatacaca 2040
aaggagtatc tgaacttcct gctgctgagc gaaaatgaga acgccaatct gaagagtggc 2100
gaaaaagggt caaagatcca cgtgcagact attagcggga tgctgacctc cgtcctgagg 2160
cacacatggg ggtttgacaa aaaggatcgc aacaatcatc tgcaccatgc actggatgcc 2220
atcattgtgg cctacagtac aaattcaatc attaaggctt tcagcgattt ccggaaaaac 2280
caggagctgc tgaaggccag attctacgct aaagaactga cttccgataa ctataaacat 2340
caggtcaagt tctttgagcc tttcaagagt tttagagaaa aaatcctgtc aaagatcgac 2400
gagattttcg tgtccaaacc acctcgaaag cgagctaggc gcgcactgca caaggatacc 2460
tttcattctg agaacaagat cattgacaag tgcagctaca actccaagga aggcctgcag 2520
attgccctga gctgtggaag agtgaggaaa atcggcacta agtatgtcga gaatgatacc 2580
atcgtgaggg tcgacatttt caaaaagcag aacaagtttt acgctatccc aatctacgca 2640
atggattttg ccctggggat cctgcccaat aagatcgtga ttactggaaa agataagaac 2700
aataacccca aacagtggca gaccattgac gaatcatacg agttctgctt tagcctgtat 2760
aagaatgacc tgatcctgct gcagaaaaag aacatgcagg aacctgagtt cgcctactat 2820
aacgattttt caatcagcac atcaagcatt tgtgtggaga aacacgacaa caagttcgaa 2880
aatctgacta gcaaccagaa gctgctgttt tccaatgcaa aagagggctc tgtgaaggtc 2940
gaaagtctgg ggatccagaa cctgaaagtg ttcgagaagt acatcattac ccccctggga 3000
gataaaatta aggctgactt tcagcctcga gaaaacatca gcctgaaaac cagtaaaaag 3060
tatggcctga gg 3072

<210> SEQ ID NO 510
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 510
ggagctggtc tgttggagaa 20

<210> SEQ ID NO 511
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 511
tcccaatcca taatcccacg tt 22

<210> SEQ ID NO 512
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 512
gcatactcgc atggctacct 20

<210> SEQ ID NO 513

<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 513
ctccctgcag cccctttta 20

<210> SEQ ID NO 514
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 514
tgtaatcagg agccgttggg 20

<210> SEQ ID NO 515
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 515
actgacgctt ctaagccacc 20

<210> SEQ ID NO 516
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 516
aagtggcaag caccgtgtta 20

<210> SEQ ID NO 517
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 517
agcgttcaaa caaggaccca 20

<210> SEQ ID NO 518
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 518
atgagccgtc taatgcgtgg 20

<210> SEQ ID NO 519
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 519
agtactcacc cacagacccg 20

<210> SEQ ID NO 520
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 520
caggcgtcca gtacccacac 20

<210> SEQ ID NO 521
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 521
atcaccccaa ccccaaagca 20

<210> SEQ ID NO 522
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 522
ccccttacct ctctagtctg tgc 23

<210> SEQ ID NO 523
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 523
ctcaggttct gggagagggt ag 22

<210> SEQ ID NO 524
<211> LENGTH: 20
<212> TYPE: DNA
<213> ORGANISM: Artificial Sequence
<220> FEATURE:

<221> NAME/KEY: source
<223> OTHER INFORMATION: /note="Description of Artificial Sequence: Synthetic primer"

<400> SEQUENCE: 524
cttgctctcc caaagtcgct 20

<210> SEQ ID NO 525
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 525
ccaatgctct gtctaggggt 20

<210> SEQ ID NO 526
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 526
cgcacgcgta attcgaacgc tgacgtcatc 30

<210> SEQ ID NO 527
<211> LENGTH: 130
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: modified_base
<222> LOCATION: (92)..(110)
<223> OTHER INFORMATION: a, c, t, g, unknown or other

<400> SEQUENCE: 527
cacacgcgta aaaaagcacc gactcggtgc cactttttca agttgataac ggactagcct 60
tattttaact tgctatttct agctctaaaa cnnnnnnnnn nnnnnnnnnn cggtgtttcg 120
tcctttccac 130

<210> SEQ ID NO 528
<211> LENGTH: 23
<212> TYPE: DNA
<213> ORGANISM: Escherichia coli

<400> SEQUENCE: 528
tgcgaatacg cccacgcgat ggg 23

<210> SEQ ID NO 529
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 529
gtgtctagac tgcagagggc cctg 24

<210> SEQ ID NO 530
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 530
gtgtcgtgcc tgagagcgca gtcgagaa 28

<210> SEQ ID NO 531
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 531
gagaagctta gctgaatggg gtccgcctc 29

<210> SEQ ID NO 532
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 532
ctcaccggtg cgcgcaaccg atgccgggac c 31

<210> SEQ ID NO 533
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 533
gagaagcttg gcgaaatgat ttgctgcaga tg 32

<210> SEQ ID NO 534
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 534
ctcaccggtg cgcgcgtcgc ctccccctcc gc 32

<210> SEQ ID NO 535
<211> LENGTH: 134
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic polynucleotide"

<400> SEQUENCE: 535

agcttcgcgc cgggaggagg ggggacgcag tgggcggagc ggagacagca ccttcggaga      60

taatcctttc tcctgccgca gagcagagga gcggcgggag aggaacactt ctcccaggct     120

ttagcagagc cgga                                                       134

<210> SEQ ID NO 536
<211> LENGTH: 134
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 536

ccggtccggc tctgctaaag cctgggagaa gtgttcctct cccgccgctc ctctgctctg      60

cggcaggaga aaggattatc tccgaaggtg ctgtctccgc tccgcccact gcgtcccccc     120

tcctcccggc gcga                                                       134

<210> SEQ ID NO 537
<211> LENGTH: 55
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 537

aattcaataa aagatcttta ttttcattag atctgtgtgt tggttttttg tgtgc           55

<210> SEQ ID NO 538
<211> LENGTH: 55
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 538

ggccgcacac aaaaaaccaa cacacagatc taatgaaaat aaagatcttt tattg           55

<210> SEQ ID NO 539
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 539

ggagctggag ctgttcacgt tgg                                              23

<210> SEQ ID NO 540
<211> LENGTH: 23
<212> TYPE: DNA
<213> ORGANISM: Artificial Sequence
<220> FEATURE:
<221> NAME/KEY: source
```

<223> OTHER INFORMATION: /note="Description of Artificial Sequence:
      Synthetic oligonucleotide"

<400> SEQUENCE: 540
cgggcagcag atgttcgcgt agg                                              23

<210> SEQ ID NO 541
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 541
agggcttgag atgttcgggc tgg                                              23

<210> SEQ ID NO 542
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 542
ccggctgggg ctgtcctcgc tag                                              23

<210> SEQ ID NO 543
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 543
cggggtgcag ctgctcacgc cag                                              23

<210> SEQ ID NO 544
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 544
ctggcgggag ctggtcgcgt gag                                              23

<210> SEQ ID NO 545
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 545
tgagcatggg ccgctggcgg tgg                                              23

<210> SEQ ID NO 546

<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 546
atggcatagg ccgctgacag agg 23

<210> SEQ ID NO 547
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 547
ttggcatggt gagctggcgg ggg 23

<210> SEQ ID NO 548
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 548
tgggcagggg tctctgaggg cag 23

<210> SEQ ID NO 549
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 549
ttggcatggg tctcttacca agg 23

<210> SEQ ID NO 550
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 550
acatggttcc agtgggtatg tag 23

<210> SEQ ID NO 551
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 551
ggaggtgggc agcgggtatg tag 23

<210> SEQ ID NO 552
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 552
agaaggtccc cgcgggcatg gag 23

<210> SEQ ID NO 553
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 553
ggagggaacc agccggtatg ggg 23

<210> SEQ ID NO 554
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 554
agagagtggc agtgggtaag cag 23

<210> SEQ ID NO 555
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 555
agaggtggcc agcgggcagg aag 23

<210> SEQ ID NO 556
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 556
tgagggggcc agctgggatg cag 23

<210> SEQ ID NO 557
<211> LENGTH: 20
<212> TYPE: DNA
<213> ORGANISM: Artificial Sequence
<220> FEATURE:

-continued

<221> NAME/KEY: source
<223> OTHER INFORMATION: /note="Description of Artificial Sequence:
Synthetic primer"

<400> SEQUENCE: 557
ggtctcatgt gtggcactca 20

<210> SEQ ID NO 558
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 558
atccctcctc agagggtcag c 21

<210> SEQ ID NO 559
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 559
ttcgggcata gcatggtctt cc 22

<210> SEQ ID NO 560
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 560
gttctgagcc gcacagtttg g 21

<210> SEQ ID NO 561
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 561
tgtccaacct tcaggcaagg 20

<210> SEQ ID NO 562
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 562
tacctcatgc acagctagca cc 22

<210> SEQ ID NO 563
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 563
gttctatttc agagggctga tccc 24

<210> SEQ ID NO 564
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 564
ggataagaag ggacaataca gg 22

<210> SEQ ID NO 565
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 565
gccggggtct cgttcagagc t 21

<210> SEQ ID NO 566
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 566
cctgtctctc tgtcctaggg ctcc 24

<210> SEQ ID NO 567
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 567
cccacaggaa acaatgaagg gagac 25

<210> SEQ ID NO 568
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 568
ccctgacacc agctgttcag cac 23

<210> SEQ ID NO 569
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 569
gagcaggcag agccgagcaa g 21

<210> SEQ ID NO 570
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 570
gggtcttgtt gtgagtaggg tgtg 24

<210> SEQ ID NO 571
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 571
cctggaatac tatttccacg ccg 23

<210> SEQ ID NO 572
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 572
gcagcacact ccaccctcac at 22

<210> SEQ ID NO 573
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 573
cggcgtcacg tgacctgagt aac 23

<210> SEQ ID NO 574
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 574
gtgtctgcct cgctctgctg c 21

<210> SEQ ID NO 575
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 575
ctatctgaaa tccaccacct tagacgc 27

<210> SEQ ID NO 576
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 576
gcctgagggg gccagaggt 19

<210> SEQ ID NO 577
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 577
gggactcccc gggtggtg 18

<210> SEQ ID NO 578
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 578
gaccctgtgt ttcaagtctc tctg 24

<210> SEQ ID NO 579
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 579
ggccatccag tacattcaat acg 23

<210> SEQ ID NO 580
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 580
gcagaagccg tgactcacag ca 22

<210> SEQ ID NO 581
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 581
cttgtgcttg tgattctgtc cttactgc 28

<210> SEQ ID NO 582
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 582
cgagaagtcg atgcagacac ttcaa 25

<210> SEQ ID NO 583
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 583
gctgaagact ggcgagcaca gct 23

<210> SEQ ID NO 584
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 584
gacctgaatg ttgtggctga gagtcc 26

<210> SEQ ID NO 585
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 585
ccctcacgtt cctgtccagc aa 22

<210> SEQ ID NO 586
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 586
ctaccgcctg cggacatggt 20

<210> SEQ ID NO 587
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 587
ccgtttgctg atgtagtagg ggtcc 25

<210> SEQ ID NO 588
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 588
catccttcgt gtctgaggac tggtc 25

<210> SEQ ID NO 589
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 589
ctctgggtga ccacacacga tgc 23

<210> SEQ ID NO 590
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 590
ggagagcgtc cgccaggag 19

<210> SEQ ID NO 591
<211> LENGTH: 22
<212> TYPE: DNA

<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 591
gaagctctct taactactgt tc 22

<210> SEQ ID NO 592
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 592
caggccctag cagcgagcag 20

<210> SEQ ID NO 593
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 593
ggaaggggct ttcctccgag c 21

<210> SEQ ID NO 594
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 594
gctccgaccc tgctctccca 20

<210> SEQ ID NO 595
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 595
cctgttcatc aggctcgtag ccc 23

<210> SEQ ID NO 596
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 596
cgattgctgg cttgccttga g 21

<210> SEQ ID NO 597
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 597
ggttcgcgtc cgcccgcgtg at 22

<210> SEQ ID NO 598
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 598
gagaggtggt cctgtcgcct atg 23

<210> SEQ ID NO 599
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 599
cccagcaggt cacagctgac atc 23

<210> SEQ ID NO 600
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 600
agcacagtat gtattctata aaataatacg ac 32

<210> SEQ ID NO 601
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 601
gtgggagggg acagagacca tg 22

<210> SEQ ID NO 602
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic primer"

<400> SEQUENCE: 602
ccttacctgt tcctcttcct tatccagc 28

<210> SEQ ID NO 603
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 603
atacccagtc cacatccctg cc 22

<210> SEQ ID NO 604
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 604
cctctgcatc tccctcagga agtatt 26

<210> SEQ ID NO 605
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 605
gcctcctgtc cccaggtccc 20

<210> SEQ ID NO 606
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 606
cactaggctt gggctgccct ct 22

<210> SEQ ID NO 607
<211> LENGTH: 102
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 607
gttttagagc tatgctgttt tgaatggtcc caaaacggaa gggcctgagt ccgagcagaa 60
gaagaagttt tagagctatg ctgttttgaa tggtcccaaa ac 102

<210> SEQ ID NO 608
<211> LENGTH: 100
<212> TYPE: DNA
<213> ORGANISM: Homo sapiens

<400> SEQUENCE: 608
cggaggacaa agtacaaacg gcagaagctg gaggaggaag ggcctgagtc cgagcagaag 60
aagaagggct cccatcacat caaccggtgg cgcattgcca 100

<210> SEQ ID NO 609
<211> LENGTH: 50
<212> TYPE: DNA
<213> ORGANISM: Homo sapiens

<400> SEQUENCE: 609
agctggagga ggaagggcct gagtccgagc agaagaagaa gggctcccac 50

<210> SEQ ID NO 610
<211> LENGTH: 30
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 610
gaguccgagc agaagaagaa guuuuagagc 30

<210> SEQ ID NO 611
<211> LENGTH: 49
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 611
agctggagga ggaagggcct gagtccgagc agaagagaag ggctcccat 49

<210> SEQ ID NO 612
<211> LENGTH: 53
<212> TYPE: DNA
<213> ORGANISM: Homo sapiens

<400> SEQUENCE: 612
ctggaggagg aagggcctga gtccgagcag aagaagaagg gctcccatca cat 53

<210> SEQ ID NO 613
<211> LENGTH: 52
<212> TYPE: DNA
<213> ORGANISM: Homo sapiens

<400> SEQUENCE: 613
ctggaggagg aagggcctga gtccgagcag aagagaaggg ctcccatcac at 52

<210> SEQ ID NO 614
<211> LENGTH: 54
<212> TYPE: DNA
<213> ORGANISM: Homo sapiens

<400> SEQUENCE: 614
ctggaggagg aagggcctga gtccgagcag aagaaagaag ggctcccatc acat 54

```
<210> SEQ ID NO 615
<211> LENGTH: 50
<212> TYPE: DNA
<213> ORGANISM: Homo sapiens

<400> SEQUENCE: 615

ctggaggagg aagggcctga gtccgagcag aagaagggct cccatcacat                50


<210> SEQ ID NO 616
<211> LENGTH: 47
<212> TYPE: DNA
<213> ORGANISM: Homo sapiens

<400> SEQUENCE: 616

ctggaggagg aagggcctga gcccgagcag aagggctccc atcacat                   47


<210> SEQ ID NO 617
<211> LENGTH: 48
<212> TYPE: DNA
<213> ORGANISM: Homo sapiens

<400> SEQUENCE: 617

ctggaggagg aagggcctga gtccgagcag aagaagaagg gctcccat                  48


<210> SEQ ID NO 618
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 618

gaguccgagc agaagaagau                                                 20


<210> SEQ ID NO 619
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 619

gaguccgagc agaagaagua                                                 20


<210> SEQ ID NO 620
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 620

gaguccgagc agaagaacaa                                                 20


<210> SEQ ID NO 621
<211> LENGTH: 20
<212> TYPE: RNA
<213> ORGANISM: Artificial Sequence
<220> FEATURE:
<221> NAME/KEY: source
```

<223> OTHER INFORMATION: /note="Description of Artificial Sequence:
Synthetic oligonucleotide"

<400> SEQUENCE: 621
gaguccgagc agaagaugaa 20

<210> SEQ ID NO 622
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 622
gaguccgagc agaaguagaa 20

<210> SEQ ID NO 623
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 623
gaguccgagc agaugaagaa 20

<210> SEQ ID NO 624
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 624
gaguccgagc acaagaagaa 20

<210> SEQ ID NO 625
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 625
gaguccgagg agaagaagaa 20

<210> SEQ ID NO 626
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 626
gaguccgugc agaagaagaa 20

<210> SEQ ID NO 627

<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 627
gagucggagc agaagaagaa 20

<210> SEQ ID NO 628
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 628
gagaccgagc agaagaagaa 20

<210> SEQ ID NO 629
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 629
aatgacaagc ttgctagcgg tggg 24

<210> SEQ ID NO 630
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 630
aaaacggaag ggcctgagtc cgagcagaag aagaagttt 39

<210> SEQ ID NO 631
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 631
aaacaggggc cgagattggg tgttcagggc agaggtttt 39

<210> SEQ ID NO 632
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 632
aaaacggaag ggcctgagtc cgagcagaag aagaagtt 38

<210> SEQ ID NO 633
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 633
aacggaggga ggggcacaga tgagaaactc agggttttag 40

<210> SEQ ID NO 634
<211> LENGTH: 38
<212> TYPE: DNA
<213> ORGANISM: Homo sapiens

<400> SEQUENCE: 634
agcccttctt cttctgctcg gactcaggcc cttcctcc 38

<210> SEQ ID NO 635
<211> LENGTH: 40
<212> TYPE: DNA
<213> ORGANISM: Homo sapiens

<400> SEQUENCE: 635
cagggaggga ggggcacaga tgagaaactc aggaggcccc 40

<210> SEQ ID NO 636
<211> LENGTH: 80
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 636
ggcaatgcgc caccggttga tgtgatggga gcccttctag gaggccccca gagcagccac 60
tggggcctca acactcaggc 80

<210> SEQ ID NO 637
<211> LENGTH: 33
<212> TYPE: DNA
<213> ORGANISM: Homo sapiens

<400> SEQUENCE: 637
catcgatgtc ctccccattg gcctgcttcg tgg 33

<210> SEQ ID NO 638
<211> LENGTH: 33
<212> TYPE: DNA
<213> ORGANISM: Homo sapiens

<400> SEQUENCE: 638
ttcgtggcaa tgcgccaccg gttgatgtga tgg 33

<210> SEQ ID NO 639
<211> LENGTH: 33
<212> TYPE: DNA
<213> ORGANISM: Homo sapiens

<400> SEQUENCE: 639
tcgtggcaat gcgccaccgg ttgatgtgat ggg 33

<210> SEQ ID NO 640
<211> LENGTH: 33
<212> TYPE: DNA
<213> ORGANISM: Homo sapiens

<400> SEQUENCE: 640
tccagcttct gccgtttgta ctttgtcctc cgg 33

<210> SEQ ID NO 641
<211> LENGTH: 33
<212> TYPE: DNA
<213> ORGANISM: Homo sapiens

<400> SEQUENCE: 641
ggagggaggg gcacagatga gaaactcagg agg 33

<210> SEQ ID NO 642
<211> LENGTH: 33
<212> TYPE: DNA
<213> ORGANISM: Homo sapiens

<400> SEQUENCE: 642
aggggccgag attgggtgtt cagggcagag agg 33

<210> SEQ ID NO 643
<211> LENGTH: 33
<212> TYPE: DNA
<213> ORGANISM: Mus musculus

<400> SEQUENCE: 643
caagcactga gtgccattag ctaaatgcat agg 33

<210> SEQ ID NO 644
<211> LENGTH: 33
<212> TYPE: DNA
<213> ORGANISM: Mus musculus

<400> SEQUENCE: 644
aatgcatagg gtaccaccca caggtgccag ggg 33

<210> SEQ ID NO 645
<211> LENGTH: 33
<212> TYPE: DNA
<213> ORGANISM: Mus musculus

<400> SEQUENCE: 645
acacacatgg gaaagcctct gggccaggaa agg 33

<210> SEQ ID NO 646
<211> LENGTH: 37
<212> TYPE: DNA
<213> ORGANISM: Homo sapiens

<400> SEQUENCE: 646
ggaggaggta gtatacagaa acacagagaa gtagaat 37

<210> SEQ ID NO 647
<211> LENGTH: 37
<212> TYPE: DNA
<213> ORGANISM: Homo sapiens

<400> SEQUENCE: 647
agaatgtaga ggagtcacag aaactcagca ctagaaa 37

<210> SEQ ID NO 648
<211> LENGTH: 98
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 648
ggacgaaaca ccggaaccat tcaaaacagc atagcaagtt aaaataaggc tagtccgtta 60
tcaacttgaa aaagtggcac cgagtcggtg ctttttt 98

<210> SEQ ID NO 649
<211> LENGTH: 186
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 649
ggacgaaaca ccggtagtat taagtattgt tttatggctg ataaatttct ttgaatttct 60
ccttgattat ttgttataaa agttataaaa taatcttgtt ggaaccattc aaaacagcat 120
agcaagttaa aataaggcta gtccgttatc aacttgaaaa agtggcaccg agtcggtgct 180
tttttt 186

<210> SEQ ID NO 650
<211> LENGTH: 95
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 650
gggttttaga gctatgctgt tttgaatggt cccaaaacgg gtcttcgaga agacgtttta 60
gagctatgct gttttgaatg gtcccaaaac ttttt 95

<210> SEQ ID NO 651
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (5)..(34)
<223> OTHER INFORMATION: a, c, t, g, unknown or other

<400> SEQUENCE: 651
aaacnnnnnn nnnnnnnnnn nnnnnnnnnn nnnngt 36

<210> SEQ ID NO 652
<211> LENGTH: 36
<212> TYPE: DNA

<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (7)..(36)
<223> OTHER INFORMATION: a, c, t, g, unknown or other

<400> SEQUENCE: 652
taaaacnnnn nnnnnnnnnn nnnnnnnnnn nnnnnn                       36

<210> SEQ ID NO 653
<211> LENGTH: 84
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 653
gtggaaagga cgaaacaccg ggtcttcgag aagacctgtt ttagagctag aaatagcaag    60
ttaaaataag gctagtccgt tttt                                           84

<210> SEQ ID NO 654
<211> LENGTH: 46
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(19)
<223> OTHER INFORMATION: a, c, u, g, unknown or other

<400> SEQUENCE: 654
nnnnnnnnnn nnnnnnnnng uuauuguacu cucaagauuu auuuuu             46

<210> SEQ ID NO 655
<211> LENGTH: 91
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 655
guuacuuaaa ucuugcagaa gcuacaaaga uaaggcuuca ugccgaaauc aacacccugu    60
cauuuuaugg caggguguuu ucguuauuua a                                  91

<210> SEQ ID NO 656
<211> LENGTH: 70
<212> TYPE: DNA
<213> ORGANISM: Homo sapiens

<400> SEQUENCE: 656
ttttctagtg ctgagtttct gtgactcctc tacattctac ttctctgtgt ttctgtatac    60
tacctcctcc                                                           70

<210> SEQ ID NO 657
<211> LENGTH: 122

<212> TYPE: DNA
<213> ORGANISM: Homo sapiens

<400> SEQUENCE: 657

```
ggaggaaggg cctgagtccg agcagaagaa gaagggctcc catcacatca accggtggcg    60
cattgccacg aagcaggcca atggggagga catcgatgtc acctccaatg actagggtgg   120
gc                                                                  122
```

<210> SEQ ID NO 658
<211> LENGTH: 48
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (3)..(32)
<223> OTHER INFORMATION: a, c, u, g, unknown or other

<400> SEQUENCE: 658

```
acnnnnnnnn nnnnnnnnnn nnnnnnnnnn nnguuuuaga gcuaugcu                 48
```

<210> SEQ ID NO 659
<211> LENGTH: 67
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 659

```
agcauagcaa guuaaaauaa ggctaguccg uuaucaacuu gaaaaagugg caccgagucg    60
gugcuuu                                                              67
```

<210> SEQ ID NO 660
<211> LENGTH: 62
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (1)..(20)
<223> OTHER INFORMATION: a, c, u, g, unknown or other

<400> SEQUENCE: 660

```
nnnnnnnnnn nnnnnnnnnn guuuuagagc uagaaauagc aaguuaaaau aaggcuaguc    60
cg                                                                   62
```

<210> SEQ ID NO 661
<211> LENGTH: 73
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 661

```
tgaatggtcc caaaacggaa gggcctgagt ccgagcagaa gaagaagttt tagagctatg    60
```

ctgttttgaa tgg 73

<210> SEQ ID NO 662
<211> LENGTH: 69
<212> TYPE: DNA
<213> ORGANISM: Homo sapiens

<400> SEQUENCE: 662
ctggtcttcc acctctctgc cctgaacacc caatctcggc ccctctcgcc accctcctgc 60
atttctgtt 69

<210> SEQ ID NO 663
<211> LENGTH: 138
<212> TYPE: DNA
<213> ORGANISM: Mus musculus

<400> SEQUENCE: 663
acccaagcac tgagtgccat tagctaaatg catagggtac cacccacagg tgccaggggc 60
ctttcccaaa gttcccagcc ccttctccaa cctttcctgg cccagaggct ttcccatgtg 120
tgtggctgga ccctttga 138

<210> SEQ ID NO 664
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 664
aaaaccaccc ttctctctgg c 21

<210> SEQ ID NO 665
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 665
ggagattgga gacacggaga g 21

<210> SEQ ID NO 666
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 666
ctggaaagcc aatgcctgac 20

<210> SEQ ID NO 667
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 667
ggcagcaaac tccttgtcct 20

<210> SEQ ID NO 668
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 668
gtgctttgca gaggcctacc 20

<210> SEQ ID NO 669
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 669
cctggagcgc atgcagtagt 20

<210> SEQ ID NO 670
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 670
accttctgtg tttccaccat tc 22

<210> SEQ ID NO 671
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 671
ttggggagtg cacagacttc 20

<210> SEQ ID NO 672
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 672
tagctctaaa acttcttctt ctgctcggac 30

<210> SEQ ID NO 673
<211> LENGTH: 30
<212> TYPE: DNA

<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 673
ctagccttat tttaacttgc tatgctgttt 30

<210> SEQ ID NO 674
<211> LENGTH: 99
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (1)..(20)
<223> OTHER INFORMATION: a, c, u, g, unknown or other

<400> SEQUENCE: 674
nnnnnnnnnn nnnnnnnnnn guuuuagagc uagaaauagc aaguuaaaau aaggcuaguc 60
cguuaucaac uugaaaaagu ggcaccgagu cggugcuuu 99

<210> SEQ ID NO 675
<211> LENGTH: 12
<212> TYPE: DNA
<213> ORGANISM: Homo sapiens

<400> SEQUENCE: 675
tagcgggtaa gc 12

<210> SEQ ID NO 676
<211> LENGTH: 12
<212> TYPE: DNA
<213> ORGANISM: Homo sapiens

<400> SEQUENCE: 676
tcggtgacat gt 12

<210> SEQ ID NO 677
<211> LENGTH: 12
<212> TYPE: DNA
<213> ORGANISM: Homo sapiens

<400> SEQUENCE: 677
actccccgta gg 12

<210> SEQ ID NO 678
<211> LENGTH: 12
<212> TYPE: DNA
<213> ORGANISM: Homo sapiens

<400> SEQUENCE: 678
actgcgtgtt aa 12

<210> SEQ ID NO 679
<211> LENGTH: 12
<212> TYPE: DNA
<213> ORGANISM: Homo sapiens

<400> SEQUENCE: 679
acgtcgcctg at 12

<210> SEQ ID NO 680
<211> LENGTH: 12
<212> TYPE: DNA
<213> ORGANISM: Homo sapiens

<400> SEQUENCE: 680
taggtcgacc ag 12

<210> SEQ ID NO 681
<211> LENGTH: 12
<212> TYPE: DNA
<213> ORGANISM: Homo sapiens

<400> SEQUENCE: 681
ggcgttaatg at 12

<210> SEQ ID NO 682
<211> LENGTH: 12
<212> TYPE: DNA
<213> ORGANISM: Homo sapiens

<400> SEQUENCE: 682
tgtcgcatgt ta 12

<210> SEQ ID NO 683
<211> LENGTH: 12
<212> TYPE: DNA
<213> ORGANISM: Homo sapiens

<400> SEQUENCE: 683
atggaaacgc at 12

<210> SEQ ID NO 684
<211> LENGTH: 12
<212> TYPE: DNA
<213> ORGANISM: Homo sapiens

<400> SEQUENCE: 684
gccgaattcc tc 12

<210> SEQ ID NO 685
<211> LENGTH: 12
<212> TYPE: DNA
<213> ORGANISM: Homo sapiens

<400> SEQUENCE: 685
gcatggtacg ga 12

<210> SEQ ID NO 686
<211> LENGTH: 12
<212> TYPE: DNA
<213> ORGANISM: Homo sapiens

<400> SEQUENCE: 686
cggtactctt ac 12

<210> SEQ ID NO 687
<211> LENGTH: 12
<212> TYPE: DNA
<213> ORGANISM: Homo sapiens

<400> SEQUENCE: 687
gcctgtgccg ta 12

<210> SEQ ID NO 688
<211> LENGTH: 12
<212> TYPE: DNA
<213> ORGANISM: Homo sapiens

<400> SEQUENCE: 688
tacggtaagt cg 12

<210> SEQ ID NO 689
<211> LENGTH: 12
<212> TYPE: DNA
<213> ORGANISM: Homo sapiens

<400> SEQUENCE: 689
cacgaaatta cc 12

<210> SEQ ID NO 690
<211> LENGTH: 12
<212> TYPE: DNA
<213> ORGANISM: Homo sapiens

<400> SEQUENCE: 690
aaccaagata cg 12

<210> SEQ ID NO 691
<211> LENGTH: 12
<212> TYPE: DNA
<213> ORGANISM: Homo sapiens

<400> SEQUENCE: 691
gagtcgatac gc 12

<210> SEQ ID NO 692
<211> LENGTH: 12
<212> TYPE: DNA
<213> ORGANISM: Homo sapiens

<400> SEQUENCE: 692
gtctcacgat cg 12

<210> SEQ ID NO 693
<211> LENGTH: 12
<212> TYPE: DNA
<213> ORGANISM: Homo sapiens

<400> SEQUENCE: 693
tcgtcgggtg ca 12

<210> SEQ ID NO 694
<211> LENGTH: 12
<212> TYPE: DNA
<213> ORGANISM: Homo sapiens

<400> SEQUENCE: 694
actccgtagt ga 12

<210> SEQ ID NO 695
<211> LENGTH: 12
<212> TYPE: DNA
<213> ORGANISM: Homo sapiens

<400> SEQUENCE: 695
caggacgtcc gt 12

<210> SEQ ID NO 696
<211> LENGTH: 12
<212> TYPE: DNA
<213> ORGANISM: Homo sapiens

<400> SEQUENCE: 696
tcgtatccct ac 12

<210> SEQ ID NO 697
<211> LENGTH: 12
<212> TYPE: DNA
<213> ORGANISM: Homo sapiens

<400> SEQUENCE: 697
tttcaaggcc gg 12

<210> SEQ ID NO 698
<211> LENGTH: 12
<212> TYPE: DNA
<213> ORGANISM: Homo sapiens

<400> SEQUENCE: 698
cgccggtgga at 12

<210> SEQ ID NO 699
<211> LENGTH: 12
<212> TYPE: DNA
<213> ORGANISM: Homo sapiens

<400> SEQUENCE: 699
gaacccgtcc ta 12

<210> SEQ ID NO 700
<211> LENGTH: 12
<212> TYPE: DNA
<213> ORGANISM: Homo sapiens

<400> SEQUENCE: 700
gattcatcag cg 12

<210> SEQ ID NO 701
<211> LENGTH: 12
<212> TYPE: DNA
<213> ORGANISM: Homo sapiens

<400> SEQUENCE: 701
acaccggtct tc 12

<210> SEQ ID NO 702
<211> LENGTH: 12
<212> TYPE: DNA
<213> ORGANISM: Homo sapiens

<400> SEQUENCE: 702
atcgtgccct aa 12

<210> SEQ ID NO 703
<211> LENGTH: 12
<212> TYPE: DNA
<213> ORGANISM: Homo sapiens

<400> SEQUENCE: 703
gcgtcaatgt tc 12

<210> SEQ ID NO 704
<211> LENGTH: 12
<212> TYPE: DNA
<213> ORGANISM: Homo sapiens

<400> SEQUENCE: 704
ctccgtatct cg 12

<210> SEQ ID NO 705
<211> LENGTH: 12
<212> TYPE: DNA
<213> ORGANISM: Homo sapiens

<400> SEQUENCE: 705
ccgattcctt cg 12

<210> SEQ ID NO 706
<211> LENGTH: 12
<212> TYPE: DNA
<213> ORGANISM: Homo sapiens

<400> SEQUENCE: 706
tgcgcctcca gt 12

<210> SEQ ID NO 707
<211> LENGTH: 12
<212> TYPE: DNA
<213> ORGANISM: Homo sapiens

<400> SEQUENCE: 707
taacgtcgga gc 12

<210> SEQ ID NO 708
<211> LENGTH: 12
<212> TYPE: DNA
<213> ORGANISM: Homo sapiens

<400> SEQUENCE: 708
aaggtcgccc at 12

<210> SEQ ID NO 709
<211> LENGTH: 12
<212> TYPE: DNA
<213> ORGANISM: Homo sapiens

<400> SEQUENCE: 709
gtcggggact at 12

<210> SEQ ID NO 710
<211> LENGTH: 12
<212> TYPE: DNA
<213> ORGANISM: Homo sapiens

<400> SEQUENCE: 710
ttcgagcgat tt 12

<210> SEQ ID NO 711
<211> LENGTH: 12
<212> TYPE: DNA
<213> ORGANISM: Homo sapiens

<400> SEQUENCE: 711
tgagtcgtcg ag 12

<210> SEQ ID NO 712
<211> LENGTH: 12
<212> TYPE: DNA
<213> ORGANISM: Homo sapiens

<400> SEQUENCE: 712
tttacgcaga gg 12

<210> SEQ ID NO 713
<211> LENGTH: 12
<212> TYPE: DNA
<213> ORGANISM: Homo sapiens

<400> SEQUENCE: 713
aggaagtatc gc 12

<210> SEQ ID NO 714
<211> LENGTH: 12
<212> TYPE: DNA
<213> ORGANISM: Homo sapiens

<400> SEQUENCE: 714
actcgatacc at 12

<210> SEQ ID NO 715
<211> LENGTH: 12
<212> TYPE: DNA
<213> ORGANISM: Homo sapiens

<400> SEQUENCE: 715
cgctacatag ca 12

<210> SEQ ID NO 716
<211> LENGTH: 12
<212> TYPE: DNA
<213> ORGANISM: Homo sapiens

<400> SEQUENCE: 716
ttcataaccg gc 12

<210> SEQ ID NO 717
<211> LENGTH: 12
<212> TYPE: DNA
<213> ORGANISM: Homo sapiens

<400> SEQUENCE: 717
ccaaacggtt aa 12

<210> SEQ ID NO 718
<211> LENGTH: 12
<212> TYPE: DNA
<213> ORGANISM: Homo sapiens

<400> SEQUENCE: 718
cgattccttc gt 12

<210> SEQ ID NO 719
<211> LENGTH: 12
<212> TYPE: DNA

<213> ORGANISM: Homo sapiens

<400> SEQUENCE: 719
cgtcatgaat aa 12

<210> SEQ ID NO 720
<211> LENGTH: 12
<212> TYPE: DNA
<213> ORGANISM: Homo sapiens

<400> SEQUENCE: 720
agtggcgatg ac 12

<210> SEQ ID NO 721
<211> LENGTH: 12
<212> TYPE: DNA
<213> ORGANISM: Homo sapiens

<400> SEQUENCE: 721
cccctacggc ac 12

<210> SEQ ID NO 722
<211> LENGTH: 12
<212> TYPE: DNA
<213> ORGANISM: Homo sapiens

<400> SEQUENCE: 722
gccaacccgc ac 12

<210> SEQ ID NO 723
<211> LENGTH: 12
<212> TYPE: DNA
<213> ORGANISM: Homo sapiens

<400> SEQUENCE: 723
tgggacaccg gt 12

<210> SEQ ID NO 724
<211> LENGTH: 12
<212> TYPE: DNA
<213> ORGANISM: Homo sapiens

<400> SEQUENCE: 724
ttgactgcgg cg 12

<210> SEQ ID NO 725
<211> LENGTH: 12
<212> TYPE: DNA
<213> ORGANISM: Homo sapiens

<400> SEQUENCE: 725
actatgcgta gg 12

<210> SEQ ID NO 726
<211> LENGTH: 12
<212> TYPE: DNA
<213> ORGANISM: Homo sapiens

<400> SEQUENCE: 726
tcacccaaag cg 12

<210> SEQ ID NO 727
<211> LENGTH: 12

<212> TYPE: DNA
<213> ORGANISM: Homo sapiens

<400> SEQUENCE: 727
gcaggacgtc cg 12

<210> SEQ ID NO 728
<211> LENGTH: 12
<212> TYPE: DNA
<213> ORGANISM: Homo sapiens

<400> SEQUENCE: 728
acaccgaaaa cg 12

<210> SEQ ID NO 729
<211> LENGTH: 12
<212> TYPE: DNA
<213> ORGANISM: Homo sapiens

<400> SEQUENCE: 729
cggtgtattg ag 12

<210> SEQ ID NO 730
<211> LENGTH: 12
<212> TYPE: DNA
<213> ORGANISM: Homo sapiens

<400> SEQUENCE: 730
cacgaggtat gc 12

<210> SEQ ID NO 731
<211> LENGTH: 12
<212> TYPE: DNA
<213> ORGANISM: Homo sapiens

<400> SEQUENCE: 731
taaagcgacc cg 12

<210> SEQ ID NO 732
<211> LENGTH: 12
<212> TYPE: DNA
<213> ORGANISM: Homo sapiens

<400> SEQUENCE: 732
cttagtcggc ca 12

<210> SEQ ID NO 733
<211> LENGTH: 12
<212> TYPE: DNA
<213> ORGANISM: Homo sapiens

<400> SEQUENCE: 733
cgaaaacgtg gc 12

<210> SEQ ID NO 734
<211> LENGTH: 12
<212> TYPE: DNA
<213> ORGANISM: Homo sapiens

<400> SEQUENCE: 734
cgtgccctga ac 12

<210> SEQ ID NO 735

-continued

```
<211> LENGTH: 12
<212> TYPE: DNA
<213> ORGANISM: Homo sapiens

<400> SEQUENCE: 735

tttaccatcg aa                                                              12

<210> SEQ ID NO 736
<211> LENGTH: 12
<212> TYPE: DNA
<213> ORGANISM: Homo sapiens

<400> SEQUENCE: 736

cgtagccatg tt                                                              12

<210> SEQ ID NO 737
<211> LENGTH: 12
<212> TYPE: DNA
<213> ORGANISM: Homo sapiens

<400> SEQUENCE: 737

cccaaacggt ta                                                              12

<210> SEQ ID NO 738
<211> LENGTH: 12
<212> TYPE: DNA
<213> ORGANISM: Homo sapiens

<400> SEQUENCE: 738

gcgttatcag aa                                                              12

<210> SEQ ID NO 739
<211> LENGTH: 12
<212> TYPE: DNA
<213> ORGANISM: Homo sapiens

<400> SEQUENCE: 739

tcgatggtaa ac                                                              12

<210> SEQ ID NO 740
<211> LENGTH: 12
<212> TYPE: DNA
<213> ORGANISM: Homo sapiens

<400> SEQUENCE: 740

cgactttttg ca                                                              12

<210> SEQ ID NO 741
<211> LENGTH: 12
<212> TYPE: DNA
<213> ORGANISM: Homo sapiens

<400> SEQUENCE: 741

tcgacgactc ac                                                              12

<210> SEQ ID NO 742
<211> LENGTH: 12
<212> TYPE: DNA
<213> ORGANISM: Homo sapiens

<400> SEQUENCE: 742

acgcgtcaga ta                                                              12
```

<210> SEQ ID NO 743
<211> LENGTH: 12
<212> TYPE: DNA
<213> ORGANISM: Homo sapiens

<400> SEQUENCE: 743
cgtacggcac ag 12

<210> SEQ ID NO 744
<211> LENGTH: 12
<212> TYPE: DNA
<213> ORGANISM: Homo sapiens

<400> SEQUENCE: 744
ctatgccgtg ca 12

<210> SEQ ID NO 745
<211> LENGTH: 12
<212> TYPE: DNA
<213> ORGANISM: Homo sapiens

<400> SEQUENCE: 745
cgcgtcagat at 12

<210> SEQ ID NO 746
<211> LENGTH: 12
<212> TYPE: DNA
<213> ORGANISM: Homo sapiens

<400> SEQUENCE: 746
aagatcggta gc 12

<210> SEQ ID NO 747
<211> LENGTH: 12
<212> TYPE: DNA
<213> ORGANISM: Homo sapiens

<400> SEQUENCE: 747
cttcgcaagg ag 12

<210> SEQ ID NO 748
<211> LENGTH: 12
<212> TYPE: DNA
<213> ORGANISM: Homo sapiens

<400> SEQUENCE: 748
gtcgtggact ac 12

<210> SEQ ID NO 749
<211> LENGTH: 12
<212> TYPE: DNA
<213> ORGANISM: Homo sapiens

<400> SEQUENCE: 749
ggtcgtcatc aa 12

<210> SEQ ID NO 750
<211> LENGTH: 12
<212> TYPE: DNA
<213> ORGANISM: Homo sapiens

<400> SEQUENCE: 750
gttaacagcg tg 12

<210> SEQ ID NO 751
<211> LENGTH: 12
<212> TYPE: DNA
<213> ORGANISM: Homo sapiens

<400> SEQUENCE: 751
tagctaaccg tt 12

<210> SEQ ID NO 752
<211> LENGTH: 12
<212> TYPE: DNA
<213> ORGANISM: Homo sapiens

<400> SEQUENCE: 752
agtaaaggcg ct 12

<210> SEQ ID NO 753
<211> LENGTH: 12
<212> TYPE: DNA
<213> ORGANISM: Homo sapiens

<400> SEQUENCE: 753
ggtaatttcg tg 12

<210> SEQ ID NO 754
<211> LENGTH: 15
<212> TYPE: DNA
<213> ORGANISM: Homo sapiens

<400> SEQUENCE: 754
cagaagaaga agggc 15

<210> SEQ ID NO 755
<211> LENGTH: 51
<212> TYPE: DNA
<213> ORGANISM: Homo sapiens

<400> SEQUENCE: 755
ccaatgggga ggacatcgat gtcacctcca atgactaggg tggtgggcaa c 51

<210> SEQ ID NO 756
<211> LENGTH: 15
<212> TYPE: DNA
<213> ORGANISM: Homo sapiens

<400> SEQUENCE: 756
ctctggccac tccct 15

<210> SEQ ID NO 757
<211> LENGTH: 52
<212> TYPE: DNA
<213> ORGANISM: Homo sapiens

<400> SEQUENCE: 757
acatcgatgt cacctccaat gacaagcttg ctagcggtgg gcaaccacaa ac 52

<210> SEQ ID NO 758
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<220> FEATURE:
<221> NAME/KEY: modified_base
<222> LOCATION: (6)..(25)
<223> OTHER INFORMATION: a, c, t, g, unknown or other

<400> SEQUENCE: 758
caccgnnnnn nnnnnnnnnn nnnnn 25

<210> SEQ ID NO 759
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (5)..(24)
<223> OTHER INFORMATION: a, c, t, g, unknown or other

<400> SEQUENCE: 759
aaacnnnnnn nnnnnnnnnn nnnnc 25

<210> SEQ ID NO 760
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 760
aacaccgggt cttcgagaag acctgtttta gagctagaaa tagcaagtta aaat 54

<210> SEQ ID NO 761
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 761
caaaacgggt cttcgagaag acgttttaga gctatgctgt tttgaatggt ccca 54

<210> SEQ ID NO 762
<211> LENGTH: 4104
<212> TYPE: DNA
<213> ORGANISM: Homo sapiens
<220> FEATURE:
<221> NAME/KEY: CDS
<222> LOCATION: (1)..(4104)

<400> SEQUENCE: 762

```
atg gac aag aag tac agc atc ggc ctg gac atc ggc acc aac tct gtg       48
Met Asp Lys Lys Tyr Ser Ile Gly Leu Asp Ile Gly Thr Asn Ser Val
1               5                   10                  15

ggc tgg gcc gtg atc acc gac gag tac aag gtg ccc agc aag aaa ttc       96
Gly Trp Ala Val Ile Thr Asp Glu Tyr Lys Val Pro Ser Lys Lys Phe
            20                  25                  30

aag gtg ctg ggc aac acc gac cgg cac agc atc aag aag aac ctg atc      144
Lys Val Leu Gly Asn Thr Asp Arg His Ser Ile Lys Lys Asn Leu Ile
        35                  40                  45

gga gcc ctg ctg ttc gac agc ggc gaa aca gcc gag gcc acc cgg ctg      192
```

-continued

```
Gly Ala Leu Leu Phe Asp Ser Gly Glu Thr Ala Glu Ala Thr Arg Leu
    50                  55                  60

aag aga acc gcc aga aga aga tac acc aga cgg aag aac cgg atc tgc      240
Lys Arg Thr Ala Arg Arg Arg Tyr Thr Arg Arg Lys Asn Arg Ile Cys
65                  70                  75                  80

tat ctg caa gag atc ttc agc aac gag atg gcc aag gtg gac gac agc      288
Tyr Leu Gln Glu Ile Phe Ser Asn Glu Met Ala Lys Val Asp Asp Ser
                85                  90                  95

ttc ttc cac aga ctg gaa gag tcc ttc ctg gtg gaa gag gat aag aag      336
Phe Phe His Arg Leu Glu Glu Ser Phe Leu Val Glu Glu Asp Lys Lys
            100                 105                 110

cac gag cgg cac ccc atc ttc ggc aac atc gtg gac gag gtg gcc tac      384
His Glu Arg His Pro Ile Phe Gly Asn Ile Val Asp Glu Val Ala Tyr
        115                 120                 125

cac gag aag tac ccc acc atc tac cac ctg aga aag aaa ctg gtg gac      432
His Glu Lys Tyr Pro Thr Ile Tyr His Leu Arg Lys Lys Leu Val Asp
    130                 135                 140

agc acc gac aag gcc gac ctg cgg ctg atc tat ctg gcc ctg gcc cac      480
Ser Thr Asp Lys Ala Asp Leu Arg Leu Ile Tyr Leu Ala Leu Ala His
145                 150                 155                 160

atg atc aag ttc cgg ggc cac ttc ctg atc gag ggc gac ctg aac ccc      528
Met Ile Lys Phe Arg Gly His Phe Leu Ile Glu Gly Asp Leu Asn Pro
                165                 170                 175

gac aac agc gac gtg gac aag ctg ttc atc cag ctg gtg cag acc tac      576
Asp Asn Ser Asp Val Asp Lys Leu Phe Ile Gln Leu Val Gln Thr Tyr
            180                 185                 190

aac cag ctg ttc gag gaa aac ccc atc aac gcc agc ggc gtg gac gcc      624
Asn Gln Leu Phe Glu Glu Asn Pro Ile Asn Ala Ser Gly Val Asp Ala
        195                 200                 205

aag gcc atc ctg tct gcc aga ctg agc aag agc aga cgg ctg gaa aat      672
Lys Ala Ile Leu Ser Ala Arg Leu Ser Lys Ser Arg Arg Leu Glu Asn
    210                 215                 220

ctg atc gcc cag ctg ccc ggc gag aag aag aat ggc ctg ttc ggc aac      720
Leu Ile Ala Gln Leu Pro Gly Glu Lys Lys Asn Gly Leu Phe Gly Asn
225                 230                 235                 240

ctg att gcc ctg agc ctg ggc ctg acc ccc aac ttc aag agc aac ttc      768
Leu Ile Ala Leu Ser Leu Gly Leu Thr Pro Asn Phe Lys Ser Asn Phe
                245                 250                 255

gac ctg gcc gag gat gcc aaa ctg cag ctg agc aag gac acc tac gac      816
Asp Leu Ala Glu Asp Ala Lys Leu Gln Leu Ser Lys Asp Thr Tyr Asp
            260                 265                 270

gac gac ctg gac aac ctg ctg gcc cag atc ggc gac cag tac gcc gac      864
Asp Asp Leu Asp Asn Leu Leu Ala Gln Ile Gly Asp Gln Tyr Ala Asp
        275                 280                 285

ctg ttt ctg gcc gcc aag aac ctg tcc gac gcc atc ctg ctg agc gac      912
Leu Phe Leu Ala Ala Lys Asn Leu Ser Asp Ala Ile Leu Leu Ser Asp
    290                 295                 300

atc ctg aga gtg aac acc gag atc acc aag gcc ccc ctg agc gcc tct      960
Ile Leu Arg Val Asn Thr Glu Ile Thr Lys Ala Pro Leu Ser Ala Ser
305                 310                 315                 320

atg atc aag aga tac gac gag cac cac cag gac ctg acc ctg ctg aaa     1008
Met Ile Lys Arg Tyr Asp Glu His His Gln Asp Leu Thr Leu Leu Lys
                325                 330                 335

gct ctc gtg cgg cag cag ctg cct gag aag tac aaa gag att ttc ttc     1056
Ala Leu Val Arg Gln Gln Leu Pro Glu Lys Tyr Lys Glu Ile Phe Phe
            340                 345                 350

gac cag agc aag aac ggc tac gcc ggc tac att gac ggc gga gcc agc     1104
Asp Gln Ser Lys Asn Gly Tyr Ala Gly Tyr Ile Asp Gly Gly Ala Ser
        355                 360                 365
```

-continued

```
cag gaa gag ttc tac aag ttc atc aag ccc atc ctg gaa aag atg gac      1152
Gln Glu Glu Phe Tyr Lys Phe Ile Lys Pro Ile Leu Glu Lys Met Asp
    370                 375                 380

ggc acc gag gaa ctg ctc gtg aag ctg aac aga gag gac ctg ctg cgg      1200
Gly Thr Glu Glu Leu Leu Val Lys Leu Asn Arg Glu Asp Leu Leu Arg
385                 390                 395                 400

aag cag cgg acc ttc gac aac ggc agc atc ccc cac cag atc cac ctg      1248
Lys Gln Arg Thr Phe Asp Asn Gly Ser Ile Pro His Gln Ile His Leu
                405                 410                 415

gga gag ctg cac gcc att ctg cgg cgg cag gaa gat ttt tac cca ttc      1296
Gly Glu Leu His Ala Ile Leu Arg Arg Gln Glu Asp Phe Tyr Pro Phe
            420                 425                 430

ctg aag gac aac cgg gaa aag atc gag aag atc ctg acc ttc cgc atc      1344
Leu Lys Asp Asn Arg Glu Lys Ile Glu Lys Ile Leu Thr Phe Arg Ile
        435                 440                 445

ccc tac tac gtg ggc cct ctg gcc agg gga aac agc aga ttc gcc tgg      1392
Pro Tyr Tyr Val Gly Pro Leu Ala Arg Gly Asn Ser Arg Phe Ala Trp
    450                 455                 460

atg acc aga aag agc gag gaa acc atc acc ccc tgg aac ttc gag gaa      1440
Met Thr Arg Lys Ser Glu Glu Thr Ile Thr Pro Trp Asn Phe Glu Glu
465                 470                 475                 480

gtg gtg gac aag ggc gct tcc gcc cag agc ttc atc gag cgg atg acc      1488
Val Val Asp Lys Gly Ala Ser Ala Gln Ser Phe Ile Glu Arg Met Thr
                485                 490                 495

aac ttc gat aag aac ctg ccc aac gag aag gtg ctg ccc aag cac agc      1536
Asn Phe Asp Lys Asn Leu Pro Asn Glu Lys Val Leu Pro Lys His Ser
            500                 505                 510

ctg ctg tac gag tac ttc acc gtg tat aac gag ctg acc aaa gtg aaa      1584
Leu Leu Tyr Glu Tyr Phe Thr Val Tyr Asn Glu Leu Thr Lys Val Lys
        515                 520                 525

tac gtg acc gag gga atg aga aag ccc gcc ttc ctg agc ggc gag cag      1632
Tyr Val Thr Glu Gly Met Arg Lys Pro Ala Phe Leu Ser Gly Glu Gln
    530                 535                 540

aaa aag gcc atc gtg gac ctg ctg ttc aag acc aac cgg aaa gtg acc      1680
Lys Lys Ala Ile Val Asp Leu Leu Phe Lys Thr Asn Arg Lys Val Thr
545                 550                 555                 560

gtg aag cag ctg aaa gag gac tac ttc aag aaa atc gag tgc ttc gac      1728
Val Lys Gln Leu Lys Glu Asp Tyr Phe Lys Lys Ile Glu Cys Phe Asp
                565                 570                 575

tcc gtg gaa atc tcc ggc gtg gaa gat cgg ttc aac gcc tcc ctg ggc      1776
Ser Val Glu Ile Ser Gly Val Glu Asp Arg Phe Asn Ala Ser Leu Gly
            580                 585                 590

aca tac cac gat ctg ctg aaa att atc aag gac aag gac ttc ctg gac      1824
Thr Tyr His Asp Leu Leu Lys Ile Ile Lys Asp Lys Asp Phe Leu Asp
        595                 600                 605

aat gag gaa aac gag gac att ctg gaa gat atc gtg ctg acc ctg aca      1872
Asn Glu Glu Asn Glu Asp Ile Leu Glu Asp Ile Val Leu Thr Leu Thr
    610                 615                 620

ctg ttt gag gac aga gag atg atc gag gaa cgg ctg aaa acc tat gcc      1920
Leu Phe Glu Asp Arg Glu Met Ile Glu Glu Arg Leu Lys Thr Tyr Ala
625                 630                 635                 640

cac ctg ttc gac gac aaa gtg atg aag cag ctg aag cgg cgg aga tac      1968
His Leu Phe Asp Asp Lys Val Met Lys Gln Leu Lys Arg Arg Arg Tyr
                645                 650                 655

acc ggc tgg ggc agg ctg agc cgg aag ctg atc aac ggc atc cgg gac      2016
Thr Gly Trp Gly Arg Leu Ser Arg Lys Leu Ile Asn Gly Ile Arg Asp
            660                 665                 670

aag cag tcc ggc aag aca atc ctg gat ttc ctg aag tcc gac ggc ttc      2064
Lys Gln Ser Gly Lys Thr Ile Leu Asp Phe Leu Lys Ser Asp Gly Phe
        675                 680                 685
```

-continued

```
gcc aac aga aac ttc atg cag ctg atc cac gac gac agc ctg acc ttt     2112
Ala Asn Arg Asn Phe Met Gln Leu Ile His Asp Asp Ser Leu Thr Phe
    690                 695                 700

aaa gag gac atc cag aaa gcc cag gtg tcc ggc cag ggc gat agc ctg     2160
Lys Glu Asp Ile Gln Lys Ala Gln Val Ser Gly Gln Gly Asp Ser Leu
705                 710                 715                 720

cac gag cac att gcc aat ctg gcc ggc agc ccc gcc att aag aag ggc     2208
His Glu His Ile Ala Asn Leu Ala Gly Ser Pro Ala Ile Lys Lys Gly
                725                 730                 735

atc ctg cag aca gtg aag gtg gtg gac gag ctc gtg aaa gtg atg ggc     2256
Ile Leu Gln Thr Val Lys Val Val Asp Glu Leu Val Lys Val Met Gly
            740                 745                 750

cgg cac aag ccc gag aac atc gtg atc gcc atg gcc aga gag aac cag     2304
Arg His Lys Pro Glu Asn Ile Val Ile Ala Met Ala Arg Glu Asn Gln
        755                 760                 765

acc acc cag aag gga cag aag aac agc cgc gag aga atg aag cgg atc     2352
Thr Thr Gln Lys Gly Gln Lys Asn Ser Arg Glu Arg Met Lys Arg Ile
    770                 775                 780

gaa gag ggc atc aaa gag ctg ggc agc cag atc ctg aaa gaa cac ccc     2400
Glu Glu Gly Ile Lys Glu Leu Gly Ser Gln Ile Leu Lys Glu His Pro
785                 790                 795                 800

gtg gaa aac acc cag ctg cag aac gag aag ctg tac ctg tac tac ctg     2448
Val Glu Asn Thr Gln Leu Gln Asn Glu Lys Leu Tyr Leu Tyr Tyr Leu
                805                 810                 815

cag aat ggg cgg gat atg tac gtg gac cag gaa ctg gac atc aac cgg     2496
Gln Asn Gly Arg Asp Met Tyr Val Asp Gln Glu Leu Asp Ile Asn Arg
            820                 825                 830

ctg tcc gac tac gat gtg gac gcc atc gtg cct cag agc ttt ctg aag     2544
Leu Ser Asp Tyr Asp Val Asp Ala Ile Val Pro Gln Ser Phe Leu Lys
        835                 840                 845

gac gac tcc atc gac gcc aag gtg ctg acc aga agc gac aag gcc cgg     2592
Asp Asp Ser Ile Asp Ala Lys Val Leu Thr Arg Ser Asp Lys Ala Arg
    850                 855                 860

ggc aag agc gac aac gtg ccc tcc gaa gag gtc gtg aag aag atg aag     2640
Gly Lys Ser Asp Asn Val Pro Ser Glu Glu Val Val Lys Lys Met Lys
865                 870                 875                 880

aac tac tgg cgg cag ctg ctg aac gcc aag ctg att acc cag aga aag     2688
Asn Tyr Trp Arg Gln Leu Leu Asn Ala Lys Leu Ile Thr Gln Arg Lys
                885                 890                 895

ttc gac aat ctg acc aag gcc gag aga ggc ggc ctg agc gaa ctg gat     2736
Phe Asp Asn Leu Thr Lys Ala Glu Arg Gly Gly Leu Ser Glu Leu Asp
            900                 905                 910

aag gcc ggc ttc atc aag aga cag ctg gtg gaa acc cgg cag atc aca     2784
Lys Ala Gly Phe Ile Lys Arg Gln Leu Val Glu Thr Arg Gln Ile Thr
        915                 920                 925

aag cac gtg gca cag atc ctg gac tcc cgg atg aac act aag tac gac     2832
Lys His Val Ala Gln Ile Leu Asp Ser Arg Met Asn Thr Lys Tyr Asp
    930                 935                 940

gag aat gac aag ctg atc cgg gaa gtg aaa gtg atc acc ctg aag tcc     2880
Glu Asn Asp Lys Leu Ile Arg Glu Val Lys Val Ile Thr Leu Lys Ser
945                 950                 955                 960

aag ctg gtg tcc gat ttc cgg aag gat ttc cag ttt tac aaa gtg cgc     2928
Lys Leu Val Ser Asp Phe Arg Lys Asp Phe Gln Phe Tyr Lys Val Arg
                965                 970                 975

gag atc aac aac tac cac cac gcc cac gcc gcc tac ctg aac gcc gtc     2976
Glu Ile Asn Asn Tyr His His Ala His Ala Ala Tyr Leu Asn Ala Val
            980                 985                 990

gtg gga acc gcc ctg atc aaa aag  tac cct aag ctg gaa  agc gag ttc   3024
Val Gly Thr Ala Leu Ile Lys Lys  Tyr Pro Lys Leu Glu  Ser Glu Phe
```

```
        995                 1000                1005

gtg tac  ggc gac tac aag gtg  tac gac gtg cgg aag  atg atc gcc      3069
Val Tyr  Gly Asp Tyr Lys Val  Tyr Asp Val Arg Lys  Met Ile Ala
    1010                 1015                1020

aag agc  gag cag gaa atc ggc  aag gct acc gcc aag  tac ttc ttc      3114
Lys Ser  Glu Gln Glu Ile Gly  Lys Ala Thr Ala Lys  Tyr Phe Phe
    1025                 1030                1035

tac agc  aac atc atg aac ttt  ttc aag acc gag att  acc ctg gcc      3159
Tyr Ser  Asn Ile Met Asn Phe  Phe Lys Thr Glu Ile  Thr Leu Ala
    1040                 1045                1050

aac ggc  gag atc cgg aag cgg  cct ctg atc gag aca  aac ggc gaa      3204
Asn Gly  Glu Ile Arg Lys Arg  Pro Leu Ile Glu Thr  Asn Gly Glu
    1055                 1060                1065

acc ggg  gag atc gtg tgg gat  aag ggc cgg gat ttt  gcc acc gtg      3249
Thr Gly  Glu Ile Val Trp Asp  Lys Gly Arg Asp Phe  Ala Thr Val
    1070                 1075                1080

cgg aaa  gtg ctg agc atg ccc  caa gtg aat atc gtg  aaa aag acc      3294
Arg Lys  Val Leu Ser Met Pro  Gln Val Asn Ile Val  Lys Lys Thr
    1085                 1090                1095

gag gtg  cag aca ggc ggc ttc  agc aaa gag tct atc  ctg ccc aag      3339
Glu Val  Gln Thr Gly Gly Phe  Ser Lys Glu Ser Ile  Leu Pro Lys
    1100                 1105                1110

agg aac  agc gat aag ctg atc  gcc aga aag aag gac  tgg gac cct      3384
Arg Asn  Ser Asp Lys Leu Ile  Ala Arg Lys Lys Asp  Trp Asp Pro
    1115                 1120                1125

aag aag  tac ggc ggc ttc gac  agc ccc acc gtg gcc  tat tct gtg      3429
Lys Lys  Tyr Gly Gly Phe Asp  Ser Pro Thr Val Ala  Tyr Ser Val
    1130                 1135                1140

ctg gtg  gtg gcc aaa gtg gaa  aag ggc aag tcc aag  aaa ctg aag      3474
Leu Val  Val Ala Lys Val Glu  Lys Gly Lys Ser Lys  Lys Leu Lys
    1145                 1150                1155

agt gtg  aaa gag ctg ctg ggg  atc acc atc atg gaa  aga agc agc      3519
Ser Val  Lys Glu Leu Leu Gly  Ile Thr Ile Met Glu  Arg Ser Ser
    1160                 1165                1170

ttc gag  aag aat ccc atc gac  ttt ctg gaa gcc aag  ggc tac aaa      3564
Phe Glu  Lys Asn Pro Ile Asp  Phe Leu Glu Ala Lys  Gly Tyr Lys
    1175                 1180                1185

gaa gtg  aaa aag gac ctg atc  atc aag ctg cct aag  tac tcc ctg      3609
Glu Val  Lys Lys Asp Leu Ile  Ile Lys Leu Pro Lys  Tyr Ser Leu
    1190                 1195                1200

ttc gag  ctg gaa aac ggc cgg  aag aga atg ctg gcc  tct gcc ggc      3654
Phe Glu  Leu Glu Asn Gly Arg  Lys Arg Met Leu Ala  Ser Ala Gly
    1205                 1210                1215

gaa ctg  cag aag gga aac gaa  ctg gcc ctg ccc tcc  aaa tat gtg      3699
Glu Leu  Gln Lys Gly Asn Glu  Leu Ala Leu Pro Ser  Lys Tyr Val
    1220                 1225                1230

aac ttc  ctg tac ctg gcc agc  cac tat gag aag ctg  aag ggc tcc      3744
Asn Phe  Leu Tyr Leu Ala Ser  His Tyr Glu Lys Leu  Lys Gly Ser
    1235                 1240                1245

ccc gag  gat aat gag cag aaa  cag ctg ttt gtg gaa  cag cac aag      3789
Pro Glu  Asp Asn Glu Gln Lys  Gln Leu Phe Val Glu  Gln His Lys
    1250                 1255                1260

cac tac  ctg gac gag atc atc  gag cag atc agc gag  ttc tcc aag      3834
His Tyr  Leu Asp Glu Ile Ile  Glu Gln Ile Ser Glu  Phe Ser Lys
    1265                 1270                1275

aga gtg  atc ctg gcc gac gct  aat ctg gac aaa gtg  ctg tcc gcc      3879
Arg Val  Ile Leu Ala Asp Ala  Asn Leu Asp Lys Val  Leu Ser Ala
    1280                 1285                1290

tac aac  aag cac cgg gat aag  ccc atc aga gag cag  gcc gag aat      3924
```

-continued

```
Tyr Asn  Lys His Arg Asp Lys  Pro Ile Arg Glu Gln  Ala Glu Asn
    1295                1300                1305

atc atc  cac ctg ttt acc ctg  acc aat ctg gga gcc  cct gcc gcc      3969
Ile Ile  His Leu Phe Thr Leu  Thr Asn Leu Gly Ala  Pro Ala Ala
    1310                1315                1320

ttc aag  tac ttt gac acc acc  atc gac cgg aag agg  tac acc agc      4014
Phe Lys  Tyr Phe Asp Thr Thr  Ile Asp Arg Lys Arg  Tyr Thr Ser
    1325                1330                1335

acc aaa  gag gtg ctg gac gcc  acc ctg atc cac cag  agc atc acc      4059
Thr Lys  Glu Val Leu Asp Ala  Thr Leu Ile His Gln  Ser Ile Thr
    1340                1345                1350

ggc ctg  tac gag aca cgg atc  gac ctg tct cag ctg  gga ggc gac      4104
Gly Leu  Tyr Glu Thr Arg Ile  Asp Leu Ser Gln Leu  Gly Gly Asp
    1355                1360                1365


<210> SEQ ID NO 763
<211> LENGTH: 1368
<212> TYPE: PRT
<213> ORGANISM: Homo sapiens

<400> SEQUENCE: 763

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
```

```
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700
```

-continued

Lys Glu Asp Ile Gln Lys Ala Gln Val Ser Gly Gln Gly Asp Ser Leu
705 710 715 720

His Glu His Ile Ala Asn Leu Ala Gly Ser Pro Ala Ile Lys Lys Gly
725 730 735

Ile Leu Gln Thr Val Lys Val Val Asp Glu Leu Val Lys Val Met Gly
740 745 750

Arg His Lys Pro Glu Asn Ile Val Ile Ala Met Ala Arg Glu Asn Gln
755 760 765

Thr Thr Gln Lys Gly Gln Lys Asn Ser Arg Glu Arg Met Lys Arg Ile
770 775 780

Glu Glu Gly Ile Lys Glu Leu Gly Ser Gln Ile Leu Lys Glu His Pro
785 790 795 800

Val Glu Asn Thr Gln Leu Gln Asn Glu Lys Leu Tyr Leu Tyr Tyr Leu
805 810 815

Gln Asn Gly Arg Asp Met Tyr Val Asp Gln Glu Leu Asp Ile Asn Arg
820 825 830

Leu Ser Asp Tyr Asp Val Asp Ala Ile Val Pro Gln Ser Phe Leu Lys
835 840 845

Asp Asp Ser Ile Asp Ala Lys Val Leu Thr Arg Ser Asp Lys Ala Arg
850 855 860

Gly Lys Ser Asp Asn Val Pro Ser Glu Glu Val Val Lys Lys Met Lys
865 870 875 880

Asn Tyr Trp Arg Gln Leu Leu Asn Ala Lys Leu Ile Thr Gln Arg Lys
885 890 895

Phe Asp Asn Leu Thr Lys Ala Glu Arg Gly Gly Leu Ser Glu Leu Asp
900 905 910

Lys Ala Gly Phe Ile Lys Arg Gln Leu Val Glu Thr Arg Gln Ile Thr
915 920 925

Lys His Val Ala Gln Ile Leu Asp Ser Arg Met Asn Thr Lys Tyr Asp
930 935 940

Glu Asn Asp Lys Leu Ile Arg Glu Val Lys Val Ile Thr Leu Lys Ser
945 950 955 960

Lys Leu Val Ser Asp Phe Arg Lys Asp Phe Gln Phe Tyr Lys Val Arg
965 970 975

Glu Ile Asn Asn Tyr His His Ala His Ala Ala Tyr Leu Asn Ala Val
980 985 990

Val Gly Thr Ala Leu Ile Lys Lys Tyr Pro Lys Leu Glu Ser Glu Phe
995 1000 1005

Val Tyr Gly Asp Tyr Lys Val Tyr Asp Val Arg Lys Met Ile Ala
1010 1015 1020

Lys Ser Glu Gln Glu Ile Gly Lys Ala Thr Ala Lys Tyr Phe Phe
1025 1030 1035

Tyr Ser Asn Ile Met Asn Phe Phe Lys Thr Glu Ile Thr Leu Ala
1040 1045 1050

Asn Gly Glu Ile Arg Lys Arg Pro Leu Ile Glu Thr Asn Gly Glu
1055 1060 1065

Thr Gly Glu Ile Val Trp Asp Lys Gly Arg Asp Phe Ala Thr Val
1070 1075 1080

Arg Lys Val Leu Ser Met Pro Gln Val Asn Ile Val Lys Lys Thr
1085 1090 1095

Glu Val Gln Thr Gly Gly Phe Ser Lys Glu Ser Ile Leu Pro Lys
1100 1105 1110

```
Arg Asn  Ser Asp Lys Leu Ile  Ala Arg Lys Lys Asp  Trp Asp Pro
    1115                 1120                 1125

Lys Lys  Tyr Gly Gly Phe Asp  Ser Pro Thr Val Ala  Tyr Ser Val
    1130                 1135                 1140

Leu Val  Val Ala Lys Val Glu  Lys Gly Lys Ser Lys  Lys Leu Lys
    1145                 1150                 1155

Ser Val  Lys Glu Leu Leu Gly  Ile Thr Ile Met Glu  Arg Ser Ser
    1160                 1165                 1170

Phe Glu  Lys Asn Pro Ile Asp  Phe Leu Glu Ala Lys  Gly Tyr Lys
    1175                 1180                 1185

Glu Val  Lys Lys Asp Leu Ile  Ile Lys Leu Pro Lys  Tyr Ser Leu
    1190                 1195                 1200

Phe Glu  Leu Glu Asn Gly Arg  Lys Arg Met Leu Ala  Ser Ala Gly
    1205                 1210                 1215

Glu Leu  Gln Lys Gly Asn Glu  Leu Ala Leu Pro Ser  Lys Tyr Val
    1220                 1225                 1230

Asn Phe  Leu Tyr Leu Ala Ser  His Tyr Glu Lys Leu  Lys Gly Ser
    1235                 1240                 1245

Pro Glu  Asp Asn Glu Gln Lys  Gln Leu Phe Val Glu  Gln His Lys
    1250                 1255                 1260

His Tyr  Leu Asp Glu Ile Ile  Glu Gln Ile Ser Glu  Phe Ser Lys
    1265                 1270                 1275

Arg Val  Ile Leu Ala Asp Ala  Asn Leu Asp Lys Val  Leu Ser Ala
    1280                 1285                 1290

Tyr Asn  Lys His Arg Asp Lys  Pro Ile Arg Glu Gln  Ala Glu Asn
    1295                 1300                 1305

Ile Ile  His Leu Phe Thr Leu  Thr Asn Leu Gly Ala  Pro Ala Ala
    1310                 1315                 1320

Phe Lys  Tyr Phe Asp Thr Thr  Ile Asp Arg Lys Arg  Tyr Thr Ser
    1325                 1330                 1335

Thr Lys  Glu Val Leu Asp Ala  Thr Leu Ile His Gln  Ser Ile Thr
    1340                 1345                 1350

Gly Leu  Tyr Glu Thr Arg Ile  Asp Leu Ser Gln Leu  Gly Gly Asp
    1355                 1360                 1365
```

<210> SEQ ID NO 764
<211> LENGTH: 57
<212> TYPE: DNA
<213> ORGANISM: Homo sapiens
<220> FEATURE:
<221> NAME/KEY: CDS
<222> LOCATION: (1)..(57)

<400> SEQUENCE: 764

```
ggc acc att aaa gaa aat atc att ggt gtt tcc tat gat gaa tat aga       48
Gly Thr Ile Lys Glu Asn Ile Ile Gly Val Ser Tyr Asp Glu Tyr Arg
1               5                   10                  15

tac aga agc                                                           57
Tyr Arg Ser
```

<210> SEQ ID NO 765
<211> LENGTH: 19
<212> TYPE: PRT
<213> ORGANISM: Homo sapiens

<400> SEQUENCE: 765

```
Gly Thr Ile Lys Glu Asn Ile Ile Gly Val Ser Tyr Asp Glu Tyr Arg
1               5                   10                  15
```

Tyr Arg Ser

<210> SEQ ID NO 766
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: CDS
<222> LOCATION: (1)..(48)

<400> SEQUENCE: 766 att aaa gaa aat atc att ggc ttt gtt tcc tat gat gaa tat aga tac 48
Ile Lys Glu Asn Ile Ile Gly Phe Val Ser Tyr Asp Glu Tyr Arg Tyr
1 5 10 15

<210> SEQ ID NO 767
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 767

Ile Lys Glu Asn Ile Ile Gly Phe Val Ser Tyr Asp Glu Tyr Arg Tyr
1 5 10 15

<210> SEQ ID NO 768
<211> LENGTH: 50
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (3)..(48)
<223> OTHER INFORMATION: a, c, t, g, unknown or other

<400> SEQUENCE: 768
ccnnnnnnnn nnnnnnnnnn nnnnnnnnnn nnnnnnnnnn nnnnnnnngg 50

<210> SEQ ID NO 769
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (3)..(44)
<223> OTHER INFORMATION: a, c, t, g, unknown or other

<400> SEQUENCE: 769
ccnnnnnnnn nnnnnnnnnn nnnnnnnnnn nnnnnnnnnn nnnngg 46

<210> SEQ ID NO 770
<211> LENGTH: 42
<212> TYPE: DNA
<213> ORGANISM: Artificial Sequence
<220> FEATURE:

<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (3)..(40)
<223> OTHER INFORMATION: a, c, t, g, unknown or other

<400> SEQUENCE: 770
ccnnnnnnnn nnnnnnnnnn nnnnnnnnnn nnnnnnnnnn gg 42

<210> SEQ ID NO 771
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (3)..(36)
<223> OTHER INFORMATION: a, c, t, g, unknown or other

<400> SEQUENCE: 771
ccnnnnnnnn nnnnnnnnnn nnnnnnnnnn nnnnnngg 38

<210> SEQ ID NO 772
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (3)..(32)
<223> OTHER INFORMATION: a, c, t, g, unknown or other

<400> SEQUENCE: 772
ccnnnnnnnn nnnnnnnnnn nnnnnnnnnn nngg 34

<210> SEQ ID NO 773
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (3)..(28)
<223> OTHER INFORMATION: a, c, t, g, unknown or other

<400> SEQUENCE: 773
ccnnnnnnnn nnnnnnnnnn nnnnnnnngg 30

<210> SEQ ID NO 774
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (3)..(24)
<223> OTHER INFORMATION: a, c, t, g, unknown or other

<400> SEQUENCE: 774
ccnnnnnnnn nnnnnnnnnn nnnngg 26

<210> SEQ ID NO 775
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (3)..(20)
<223> OTHER INFORMATION: a, c, t, g, unknown or other

<400> SEQUENCE: 775
ccnnnnnnnn nnnnnnnnnn gg 22

<210> SEQ ID NO 776
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (3)..(16)
<223> OTHER INFORMATION: a, c, t, g, unknown or other

<400> SEQUENCE: 776
ccnnnnnnnn nnnnnngg 18

<210> SEQ ID NO 777
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (3)..(14)
<223> OTHER INFORMATION: a, c, t, g, unknown or other

<400> SEQUENCE: 777
ccnnnnnnnn nnnngg 16

<210> SEQ ID NO 778
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (3)..(13)
<223> OTHER INFORMATION: a, c, t, g, unknown or other

<400> SEQUENCE: 778
ccnnnnnnnn nnngg 15

<210> SEQ ID NO 779

<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: modified_base
<222> LOCATION: (3)..(12)
<223> OTHER INFORMATION: a, c, t, g, unknown or other

<400> SEQUENCE: 779
ccnnnnnnnn nngg 14

<210> SEQ ID NO 780
<211> LENGTH: 13
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: modified_base
<222> LOCATION: (3)..(11)
<223> OTHER INFORMATION: a, c, t, g, unknown or other

<400> SEQUENCE: 780
ccnnnnnnnn ngg 13

<210> SEQ ID NO 781
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: modified_base
<222> LOCATION: (3)..(10)
<223> OTHER INFORMATION: a, c, t, g, unknown or other

<400> SEQUENCE: 781
ccnnnnnnnn gg 12

<210> SEQ ID NO 782
<211> LENGTH: 11
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: modified_base
<222> LOCATION: (3)..(9)
<223> OTHER INFORMATION: a, c, t, g, unknown or other

<400> SEQUENCE: 782
ccnnnnnnng g 11

<210> SEQ ID NO 783
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

```
<220> FEATURE:
<221> NAME/KEY: modified_base
<222> LOCATION: (3)..(8)
<223> OTHER INFORMATION: a, c, t, g, unknown or other

<400> SEQUENCE: 783

ccnnnnnngg                                                              10


<210> SEQ ID NO 784
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (3)..(10)
<223> OTHER INFORMATION: a, c, t, g, unknown or other

<400> SEQUENCE: 784

ggnnnnnnnn cc                                                           12


<210> SEQ ID NO 785
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 785

aaaaaaagca ccgactcggt gccacttttt caagttgata acggactagc cttattttaa      60

cttgctattt ctagctctaa aactcacatc aaccggtggc gcaggtgttt cgtcctttcc     120

acaag                                                                  125


<210> SEQ ID NO 786
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 786

aaaaaaagca ccgactcggt gccacttttt caagttgata acggactagc cttattttaa      60

cttgctattt ctagctctaa aactcacatc aaccggtggc gcaggtgttt cgtcctttcc     120

acaag                                                                  125


<210> SEQ ID NO 787
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 787

aaaaaaagca ccgactcggt gccacttttt caagttgata acggactagc cttattttaa      60

cttgctattt ctagctctaa aacgaggaca aagtacaaac ggcggtgttt cgtcctttcc     120
```

acaag 125

<210> SEQ ID NO 788
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 788
aaaaaaagca ccgactcggt gccacttttt caagttgata acggactagc cttattttaa 60
cttgctattt ctagctctaa aacgaggaca aagtacaaac ggcggtgttt cgtcctttcc 120
acaag 125

<210> SEQ ID NO 789
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 789
aaaaaaagca ccgactcggt gccacttttt caagttgata acggactagc cttattttaa 60
cttgctattt ctagctctaa aacgtggcgc attgccacga agcggtgttt cgtcctttcc 120
acaag 125

<210> SEQ ID NO 790
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 790
aaaaaaagca ccgactcggt gccacttttt caagttgata acggactagc cttattttaa 60
cttgctattt ctagctctaa aaccgagggc agagtgctgc ttgggtgttt cgtcctttcc 120
acaag 125

<210> SEQ ID NO 791
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 791
aaaaaaagca ccgactcggt gccacttttt caagttgata acggactagc cttattttaa 60
cttgctattt ctagctctaa aacgagtccg agcagaagaa gaaggtgttt cgtcctttcc 120
acaag 125

<210> SEQ ID NO 792
<211> LENGTH: 125
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic polynucleotide"

<400> SEQUENCE: 792

aaaaaaagca ccgactcggt gccacttttt caagttgata acggactagc cttattttaa     60

cttgctattt ctagctctaa aacgaggaca aagtacaaac ggcggtgttt cgtcctttcc    120

acaag                                                                125


<210> SEQ ID NO 793
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 793

aaaaaaagca ccgactcggt gccacttttt caagttgata acggactagc cttattttaa     60

cttgctattt ctagctctaa aacagcagaa gaagaagggc tccggtgttt cgtcctttcc    120

acaag                                                                125


<210> SEQ ID NO 794
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 794

aaaaaaagca ccgactcggt gccacttttt caagttgata acggactagc cttattttaa     60

cttgctattt ctagctctaa aactcacatc aaccggtggc gcaggtgttt cgtcctttcc    120

acaag                                                                125


<210> SEQ ID NO 795
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 795

aaaaaaagca ccgactcggt gccacttttt caagttgata acggactagc cttattttaa     60

cttgctattt ctagctctaa aacccctggc ccaggtgaag gtgggtgttt cgtcctttcc    120

acaag                                                                125


<210> SEQ ID NO 796
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 796
```

-continued

```
aaaaaaagca ccgactcggt gccacttttt caagttgata acggactagc cttattttaa     60

cttgctattt ctagctctaa aactccctcc ctggcccagg tgaggtgttt cgtcctttcc    120

acaag                                                                125


<210> SEQ ID NO 797
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 797

aaaaaaagca ccgactcggt gccacttttt caagttgata acggactagc cttattttaa     60

cttgctattt ctagctctaa aacgaaccgg aggacaaagt acaggtgttt cgtcctttcc    120

acaag                                                                125


<210> SEQ ID NO 798
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 798

aaaaaaagca ccgactcggt gccacttttt caagttgata acggactagc cttattttaa     60

cttgctattt ctagctctaa aacaggtgaa ggtgtggttc cagggtgttt cgtcctttcc    120

acaag                                                                125


<210> SEQ ID NO 799
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 799

aaaaaaagca ccgactcggt gccacttttt caagttgata acggactagc cttattttaa     60

cttgctattt ctagctctaa aacggtgaag gtgtggttcc agaggtgttt cgtcctttcc    120

acaag                                                                125


<210> SEQ ID NO 800
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 800

aaaaaaagca ccgactcggt gccacttttt caagttgata acggactagc cttattttaa     60

cttgctattt ctagctctaa aacgaaccgg aggacaaagt acaggtgttt cgtcctttcc    120

acaag                                                                125
```

<210> SEQ ID NO 801
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 801
aaaaaaagca ccgactcggt gccacttttt caagttgata acggactagc cttattttaa 60
cttgctattt ctagctctaa aacccctggc ccaggtgaag gtgggtgttt cgtcctttcc 120
acaag 125

<210> SEQ ID NO 802
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 802
aaaaaaagca ccgactcggt gccacttttt caagttgata acggactagc cttattttaa 60
cttgctattt ctagctctaa aacaggtgaa ggtgtggttc cagggtgttt cgtcctttcc 120
acaag 125

<210> SEQ ID NO 803
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 803
aaaaaaagca ccgactcggt gccacttttt caagttgata acggactagc cttattttaa 60
cttgctattt ctagctctaa aacgaggaca aagtacaaac ggcggtgttt cgtcctttcc 120
acaag 125

<210> SEQ ID NO 804
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 804
aaaaaaagca ccgactcggt gccacttttt caagttgata acggactagc cttattttaa 60
cttgctattt ctagctctaa aacgggaggg aggggcacag atgggtgttt cgtcctttcc 120
acaag 125

<210> SEQ ID NO 805
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic polynucleotide"

<400> SEQUENCE: 805
aaaaaaagca ccgactcggt gccacttttt caagttgata acggactagc cttattttaa 60
cttgctattt ctagctctaa aaccaccttc acctgggcca gggggtgttt cgtcctttcc 120
acaag 125

<210> SEQ ID NO 806
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 806
aaaaaaagca ccgactcggt gccacttttt caagttgata acggactagc cttattttaa 60
cttgctattt ctagctctaa aacaccctag tcattggagg tgaggtgttt cgtcctttcc 120
acaag 125

<210> SEQ ID NO 807
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 807
aaaaaaagca ccgactcggt gccacttttt caagttgata acggactagc cttattttaa 60
cttgctattt ctagctctaa aaccagagca gccactgggg cctggtgttt cgtcctttcc 120
acaag 125

<210> SEQ ID NO 808
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 808
aaaaaaagca ccgactcggt gccacttttt caagttgata acggactagc cttattttaa 60
cttgctattt ctagctctaa aaccaccttc acctgggcca gggggtgttt cgtcctttcc 120
acaag 125

<210> SEQ ID NO 809
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 809
aaaaaaagca ccgactcggt gccacttttt caagttgata acggactagc cttattttaa 60
cttgctattt ctagctctaa aacccccatt ggcctgcttc gtgggtgttt cgtcctttcc 120
acaag 125

<210> SEQ ID NO 810
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 810
aaaaaaagca ccgactcggt gccacttttt caagttgata acggactagc cttattttaa 60
cttgctattt ctagctctaa aacattggcc tgcttcgtgg caaggtgttt cgtcctttcc 120
acaag 125

<210> SEQ ID NO 811
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 811
aaaaaaagca ccgactcggt gccacttttt caagttgata acggactagc cttattttaa 60
cttgctattt ctagctctaa aactcctcct ccagcttctg ccgggtgttt cgtcctttcc 120
acaag 125

<210> SEQ ID NO 812
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 812
aaaaaaagca ccgactcggt gccacttttt caagttgata acggactagc cttattttaa 60
cttgctattt ctagctctaa aaccctccag cttctgccgt ttgggtgttt cgtcctttcc 120
acaag 125

<210> SEQ ID NO 813
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 813
aaaaaaagca ccgactcggt gccacttttt caagttgata acggactagc cttattttaa 60
cttgctattt ctagctctaa aacattggcc tgcttcgtgg caaggtgttt cgtcctttcc 120
acaag 125

<210> SEQ ID NO 814
<211> LENGTH: 125
<212> TYPE: DNA

<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 814
aaaaaaagca ccgactcggt gccacttttt caagttgata acggactagc cttattttaa 60
cttgctattt ctagctctaa aacgcagcaa gcagcactct gccggtgttt cgtcctttcc 120
acaag 125

<210> SEQ ID NO 815
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 815
aaaaaaagca ccgactcggt gccacttttt caagttgata acggactagc cttattttaa 60
cttgctattt ctagctctaa aacttcttct tctgctcgga ctcggtgttt cgtcctttcc 120
acaag 125

<210> SEQ ID NO 816
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 816
aaaaaaagca ccgactcggt gccacttttt caagttgata acggactagc cttattttaa 60
cttgctattt ctagctctaa aacaccggag gacaaagtac aaaggtgttt cgtcctttcc 120
acaag 125

<210> SEQ ID NO 817
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 817
aaaaaaagca ccgactcggt gccacttttt caagttgata acggactagc cttattttaa 60
cttgctattt ctagctctaa aactcttctt ctgctcggac tcaggtgttt cgtcctttcc 120
acaag 125

<210> SEQ ID NO 818
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 818
aaaaaaagca ccgactcggt gccacttttt caagttgata acggactagc cttattttaa 60
cttgctattt ctagctctaa aacgttgatg tgatgggagc cctggtgttt cgtcctttcc 120
acaag 125

<210> SEQ ID NO 819
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 819
aaaaaaagca ccgactcggt gccacttttt caagttgata acggactagc cttattttaa 60
cttgctattt ctagctctaa aacgggccag ggagggaggg gcaggtgttt cgtcctttcc 120
acaag 125

<210> SEQ ID NO 820
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 820
aaaaaaagca ccgactcggt gccacttttt caagttgata acggactagc cttattttaa 60
cttgctattt ctagctctaa aacgggaggg aggggcacag atgggtgttt cgtcctttcc 120
acaag 125

<210> SEQ ID NO 821
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 821
aaaaaaagca ccgactcggt gccacttttt caagttgata acggactagc cttattttaa 60
cttgctattt ctagctctaa aacccggttc tggaaccaca cctggtgttt cgtcctttcc 120
acaag 125

<210> SEQ ID NO 822
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 822
aaaaaaagca ccgactcggt gccacttttt caagttgata acggactagc cttattttaa 60
cttgctattt ctagctctaa aactcacctg ggccagggag ggaggtgttt cgtcctttcc 120
acaag 125

<210> SEQ ID NO 823
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 823
aaaaaaagca ccgactcggt gccacttttt caagttgata acggactagc cttattttaa 60
cttgctattt ctagctctaa aactcacctg ggccagggag ggaggtgttt cgtcctttcc 120
acaag 125

<210> SEQ ID NO 824
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 824
aaaaaaagca ccgactcggt gccacttttt caagttgata acggactagc cttattttaa 60
cttgctattt ctagctctaa aacgttctgg aaccacacct tcaggtgttt cgtcctttcc 120
acaag 125

<210> SEQ ID NO 825
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 825
aaaaaaagca ccgactcggt gccacttttt caagttgata acggactagc cttattttaa 60
cttgctattt ctagctctaa aacgggaggg aggggcacag atgggtgttt cgtcctttcc 120
acaag 125

<210> SEQ ID NO 826
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 826
aaaaaaagca ccgactcggt gccacttttt caagttgata acggactagc cttattttaa 60
cttgctattt ctagctctaa aacgggccag ggagggaggg gcaggtgttt cgtcctttcc 120
acaag 125

<210> SEQ ID NO 827
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 827
aaaaaaagca ccgactcggt gccacttttt caagttgata acggactagc cttattttaa 60
cttgctattt ctagctctaa aacgttctgg aaccacacct tcaggtgttt cgtcctttcc 120
acaag 125

<210> SEQ ID NO 828
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 828
aaaaaaagca ccgactcggt gccacttttt caagttgata acggactagc cttattttaa 60
cttgctattt ctagctctaa aacaggtgaa ggtgtggttc cagggtgttt cgtcctttcc 120
acaag 125

<210> SEQ ID NO 829
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 829
aaaaaaagca ccgactcggt gccacttttt caagttgata acggactagc cttattttaa 60
cttgctattt ctagctctaa aacgaaccgg aggacaaagt acaggtgttt cgtcctttcc 120
acaag 125

<210> SEQ ID NO 830
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 830
aaaaaaagca ccgactcggt gccacttttt caagttgata acggactagc cttattttaa 60
cttgctattt ctagctctaa aaccaaaccc acgagggcag agtggtgttt cgtcctttcc 120
acaag 125

<210> SEQ ID NO 831
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 831
aaaaaaagca ccgactcggt gccacttttt caagttgata acggactagc cttattttaa 60

```
cttgctattt ctagctctaa aacgagtttc tcatctgtgc cccggtgttt cgtcctttcc    120

acaag                                                                125


<210> SEQ ID NO 832
<211> LENGTH: 684
<212> TYPE: DNA
<213> ORGANISM: Homo sapiens
<220> FEATURE:
<221> NAME/KEY: CDS
<222> LOCATION: (1)..(123)
<220> FEATURE:
<221> NAME/KEY: CDS
<222> LOCATION: (127)..(159)
<220> FEATURE:
<221> NAME/KEY: CDS
<222> LOCATION: (163)..(399)
<220> FEATURE:
<221> NAME/KEY: CDS
<222> LOCATION: (403)..(684)

<400> SEQUENCE: 832

aaa acc acc ctt ctc tct ggc cca ctg tgt cct ctt cct gcc ctg cca       48
Lys Thr Thr Leu Leu Ser Gly Pro Leu Cys Pro Leu Pro Ala Leu Pro
1               5                   10                  15

tcc cct tct gtg aat gtt aga ccc atg gga gca gct ggt cag agg gga       96
Ser Pro Ser Val Asn Val Arg Pro Met Gly Ala Ala Gly Gln Arg Gly
            20                  25                  30

ccc cgg cct ggg gcc cct aac cct atg tag cct cag tct tcc cat cag      144
Pro Arg Pro Gly Ala Pro Asn Pro Met     Pro Gln Ser Ser His Gln
        35                  40                      45

gct ctc agc tca gcc tga gtg ttg agg ccc cag tgg ctg ctc tgg ggg      192
Ala Leu Ser Ser Ala     Val Leu Arg Pro Gln Trp Leu Leu Trp Gly
        50                  55                      60

cct cct gag ttt ctc atc tgt gcc cct ccc tcc ctg gcc cag gtg aag      240
Pro Pro Glu Phe Leu Ile Cys Ala Pro Pro Ser Leu Ala Gln Val Lys
        65                  70                  75

gtg tgg ttc cag aac cgg agg aca aag tac aaa cgg cag aag ctg gag      288
Val Trp Phe Gln Asn Arg Arg Thr Lys Tyr Lys Arg Gln Lys Leu Glu
    80                  85                  90

gag gaa ggg cct gag tcc gag cag aag aag aag ggc tcc cat cac atc      336
Glu Glu Gly Pro Glu Ser Glu Gln Lys Lys Lys Gly Ser His His Ile
95                  100                 105                 110

aac cgg tgg cgc att gcc acg aag cag gcc aat ggg gag gac atc gat      384
Asn Arg Trp Arg Ile Ala Thr Lys Gln Ala Asn Gly Glu Asp Ile Asp
                115                 120                 125

gtc acc tcc aat gac tag ggt ggg caa cca caa acc cac gag ggc aga      432
Val Thr Ser Asn Asp     Gly Gly Gln Pro Gln Thr His Glu Gly Arg
            130                 135                 140

gtg ctg ctt gct gct ggc cag gcc cct gcg tgg gcc caa gct gga ctc      480
Val Leu Leu Ala Ala Gly Gln Ala Pro Ala Trp Ala Gln Ala Gly Leu
            145                 150                 155

tgg cca ctc cct ggc cag gct ttg ggg agg cct gga gtc atg gcc cca      528
Trp Pro Leu Pro Gly Gln Ala Leu Gly Arg Pro Gly Val Met Ala Pro
        160                 165                 170

cag ggc ttg aag ccc ggg gcc gcc att gac aga ggg aca agc aat ggg      576
Gln Gly Leu Lys Pro Gly Ala Ala Ile Asp Arg Gly Thr Ser Asn Gly
    175                 180                 185

ctg gct gag gcc tgg gac cac ttg gcc ttc tcc tcg gag agc ctg cct      624
Leu Ala Glu Ala Trp Asp His Leu Ala Phe Ser Ser Glu Ser Leu Pro
190                 195                 200                 205

gcc tgg gcg ggc ccg ccc gcc acc gca gcc tcc cag ctg ctc tcc gtg      672
Ala Trp Ala Gly Pro Pro Ala Thr Ala Ala Ser Gln Leu Leu Ser Val
                210                 215                 220
```

```
tct cca atc tcc                                                   684
Ser Pro Ile Ser
            225


<210> SEQ ID NO 833
<211> LENGTH: 41
<212> TYPE: PRT
<213> ORGANISM: Homo sapiens

<400> SEQUENCE: 833

Lys Thr Thr Leu Leu Ser Gly Pro Leu Cys Pro Leu Pro Ala Leu Pro
1               5                   10                  15

Ser Pro Ser Val Asn Val Arg Pro Met Gly Ala Ala Gly Gln Arg Gly
            20                  25                  30

Pro Arg Pro Gly Ala Pro Asn Pro Met
        35                  40


<210> SEQ ID NO 834
<211> LENGTH: 11
<212> TYPE: PRT
<213> ORGANISM: Homo sapiens

<400> SEQUENCE: 834

Pro Gln Ser Ser His Gln Ala Leu Ser Ser Ala
1               5                   10


<210> SEQ ID NO 835
<211> LENGTH: 79
<212> TYPE: PRT
<213> ORGANISM: Homo sapiens

<400> SEQUENCE: 835

Val Leu Arg Pro Gln Trp Leu Leu Trp Gly Pro Pro Glu Phe Leu Ile
1               5                   10                  15

Cys Ala Pro Pro Ser Leu Ala Gln Val Lys Val Trp Phe Gln Asn Arg
            20                  25                  30

Arg Thr Lys Tyr Lys Arg Gln Lys Leu Glu Glu Glu Gly Pro Glu Ser
        35                  40                  45

Glu Gln Lys Lys Lys Gly Ser His His Ile Asn Arg Trp Arg Ile Ala
    50                  55                  60

Thr Lys Gln Ala Asn Gly Glu Asp Ile Asp Val Thr Ser Asn Asp
65                  70                  75


<210> SEQ ID NO 836
<211> LENGTH: 94
<212> TYPE: PRT
<213> ORGANISM: Homo sapiens

<400> SEQUENCE: 836

Gly Gly Gln Pro Gln Thr His Glu Gly Arg Val Leu Leu Ala Ala Gly
1               5                   10                  15

Gln Ala Pro Ala Trp Ala Gln Ala Gly Leu Trp Pro Leu Pro Gly Gln
            20                  25                  30

Ala Leu Gly Arg Pro Gly Val Met Ala Pro Gln Gly Leu Lys Pro Gly
        35                  40                  45

Ala Ala Ile Asp Arg Gly Thr Ser Asn Gly Leu Ala Glu Ala Trp Asp
    50                  55                  60

His Leu Ala Phe Ser Ser Glu Ser Leu Pro Ala Trp Ala Gly Pro Pro
65                  70                  75                  80
```

```
Ala Thr Ala Ala Ser Gln Leu Leu Ser Val Ser Pro Ile Ser
                85                  90


<210> SEQ ID NO 837
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(27)
<223> OTHER INFORMATION: a, c, t, g, unknown or other

<400> SEQUENCE: 837

gggactcaac caagtcattc nnnnnnn                                         27


<210> SEQ ID NO 838
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 838

gggacucaac caagucauuc                                                 20


<210> SEQ ID NO 839
<211> LENGTH: 157
<212> TYPE: RNA
<213> ORGANISM: Staphylococcus aureus
<220> FEATURE:
<221> NAME/KEY: modified_base
<222> LOCATION: (1)..(30)
<223> OTHER INFORMATION: a, c, u, g, unknown or other

<400> SEQUENCE: 839

nnnnnnnnnn nnnnnnnnnn nnnnnnnnnn guuuuaguac ucuguaauuu uagguaugag     60

guagacgaaa auuguacuua uaccuaaaau uacagaaucu acuaaaacaa ggcaaaaugc    120

cguguuuauc ucgucaacuu guuggcgaga uuuuuuu                             157


<210> SEQ ID NO 840
<211> LENGTH: 34
<212> TYPE: DNA
<213> ORGANISM: Mus sp.

<400> SEQUENCE: 840

cggccgctga ccacacctgc caggtgggtg ccgt                                 34


<210> SEQ ID NO 841
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 841

ccgcugacca caccugccag                                                 20


<210> SEQ ID NO 842
```

<211> LENGTH: 34
<212> TYPE: DNA
<213> ORGANISM: Mus sp.

<400> SEQUENCE: 842
ggccaccgca gccacgcaga gcagtgggtg ccca 34

<210> SEQ ID NO 843
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 843
caccgcagcc acgcagagca 20

<210> SEQ ID NO 844
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 844
ccggccgctg accacacctc aggtgggtgc c 31

<210> SEQ ID NO 845
<211> LENGTH: 32
<212> TYPE: DNA
<213> ORGANISM: Mus sp.

<400> SEQUENCE: 845
cggccgctga ccacacctgc caggtgggtg cc 32

<210> SEQ ID NO 846
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 846
cggccgctga ccacacctgc tcaggtgggt gcc 33

<210> SEQ ID NO 847
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 847
cggccgctga ccacacctgc aggtgggtgc c 31

<210> SEQ ID NO 848
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 848
cggccgctga ccacacatgc caggtgggtg cc 32

<210> SEQ ID NO 849
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 849
cggccgctga ccacacctca ggtgggtgcc 30

<210> SEQ ID NO 850
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 850
cggccgctga ccacacctgc ggtgggtgcc 30

<210> SEQ ID NO 851
<211> LENGTH: 48
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: modified_base
<222> LOCATION: (1)..(20)
<223> OTHER INFORMATION: a, c, u, g, unknown or other

<400> SEQUENCE: 851
nnnnnnnnnn nnnnnnnnnn gcugcggauu gcggccgucu cucgauuu 48

<210> SEQ ID NO 852
<211> LENGTH: 95
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 852
aaaucgagag gcggucgcuu uucgcaagca aauugacccc uugugcgggc ucggcauccc 60
aaggucagcu gccgguuauu aucgaaaagg cccac 95

<210> SEQ ID NO 853
<211> LENGTH: 13
<212> TYPE: RNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 853
gugggccuuu uuu 13

<210> SEQ ID NO 854
<211> LENGTH: 47
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (1)..(20)
<223> OTHER INFORMATION: a, c, u, g, unknown or other

<400> SEQUENCE: 854
nnnnnnnnnn nnnnnnnnnn guuuuuguac ucucaagauu uaaguaa 47

<210> SEQ ID NO 855
<211> LENGTH: 81
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 855
uuacuuaaau cuugcugagc cuacaaagau aaggcuuuau gccgaauuca agcaccccau 60
guuuugacau gaggugcuuu u 81

<210> SEQ ID NO 856
<211> LENGTH: 48
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (1)..(20)
<223> OTHER INFORMATION: a, c, u, g, unknown or other

<400> SEQUENCE: 856
nnnnnnnnnn nnnnnnnnnn guuuuaguac ucuguaauuu uagguaug 48

<210> SEQ ID NO 857
<211> LENGTH: 77
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 857
uauaccuaaa auuacagaau cuacuaaaac aaggcaaaau gccguguuua ucucgucaac 60
uuguuggcga gauuuuu 77

<210> SEQ ID NO 858
<211> LENGTH: 49
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: modified_base
<222> LOCATION: (1)..(20)
<223> OTHER INFORMATION: a, c, u, g, unknown or other

<400> SEQUENCE: 858
nnnnnnnnnn nnnnnnnnnn guuuuagagc uaugcuguuu ugaauggucc 49

<210> SEQ ID NO 859
<211> LENGTH: 82
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 859
aaccauucaa aacagcauag caaguuaaaa uaaggcuagu ccguuaucaa cuugaaaaag 60
uggcaccgag ucggugcuuu uu 82

<210> SEQ ID NO 860
<211> LENGTH: 55
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: modified_base
<222> LOCATION: (1)..(20)
<223> OTHER INFORMATION: a, c, u, g, unknown or other

<400> SEQUENCE: 860
nnnnnnnnnn nnnnnnnnnn acugggguuc aguucucaaa aacccugaua gacuu 55

<210> SEQ ID NO 861
<211> LENGTH: 103
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 861
agucacuaac uuaauuaaau agaacugaac cucaguaagc auuggcucgu uuccaauguu 60
gauugcuccg ccggugcucc uuauuuuuaa gggcgccggc uuu 103

<210> SEQ ID NO 862
<211> LENGTH: 50
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: modified_base
<222> LOCATION: (1)..(20)
<223> OTHER INFORMATION: a, c, u, g, unknown or other

<400> SEQUENCE: 862
nnnnnnnnnn nnnnnnnnnn guuguagcuc ccauucucau uucgcagugc 50

<210> SEQ ID NO 863
<211> LENGTH: 99
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 863
gcacugcgaa augagaaccg uugcuacaau aaggccgucu gaaaagaugu gccgcaacgc 60
ucugccccuu aaagcuucug cuuuaagggg caucguuuu 99

<210> SEQ ID NO 864
<211> LENGTH: 50
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (1)..(20)
<223> OTHER INFORMATION: a, c, u, g, unknown or other

<400> SEQUENCE: 864
nnnnnnnnnn nnnnnnnnnn guuuuagucu cuuuuuaaau uucuuuauga 50

<210> SEQ ID NO 865
<211> LENGTH: 116
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 865
ugcuaaagaa auuuaaaaag agacuaaaau aaguggoouuu uggucaucca cgcaggguua 60
caaucccuuu aaaaccauua aaauucaaau aaacuagguu guaucaacuu aguuuu 116

<210> SEQ ID NO 866
<211> LENGTH: 46
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (1)..(19)
<223> OTHER INFORMATION: a, c, u, g, unknown or other

<400> SEQUENCE: 866
nnnnnnnnnn nnnnnnnnng uuuuuguacu cucaagauuu aaguaa 46

<210> SEQ ID NO 867
<211> LENGTH: 90
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 867
uuacuuaaau cuugcagaag cuacaaagau aaggcuucau gccgaaauca acacccuguc 60
auuuuauggc agggguguuu cguuauuuaa 90

<210> SEQ ID NO 868
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (21)..(27)
<223> OTHER INFORMATION: a, c, t, g, unknown or other

<400> SEQUENCE: 868
gggactcaac caagtcattc nnnnnnngta gtaa 34

<210> SEQ ID NO 869
<211> LENGTH: 440
<212> TYPE: DNA
<213> ORGANISM: Mus sp.

<400> SEQUENCE: 869
tgggaagatg gaagcagcca ggtggaggtg tatctcttag ataccagcat ccagggtgcc 60
catcgggaga ttgagggcag ggtcaccatc accgacttca acagcgtgcc ggaggaggat 120
gggacacgct tccacagaca ggtgagtgtg actctcactt catctcagag gtgggtgaag 180
gtgggcagag gtaccacccc tggagcatta tgtcagtact gccatcattg gggtgctatg 240
tcagtctgtc cacaccctct cacgtgatcc ccgtgttgat tgatcaggcg agcaagtgtg 300
acagccacgg cacccacctg gcaggtgtgg tcagcggccg ggatgctggt gtggccaagg 360
gcaccagcct gcacagcctg cgtgtgctca actgtcaagg gaagggcaca gtcagcggca 420
ccctcatagg tgagtgactc 440

<210> SEQ ID NO 870
<211> LENGTH: 30
<212> TYPE: DNA
<213> ORGANISM: Mus sp.

<400> SEQUENCE: 870
ccaccattct gcagagccag cagaggcagg 30

<210> SEQ ID NO 871
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 871
ccauucugca gagccagcag 20

<210> SEQ ID NO 872
<211> LENGTH: 23
<212> TYPE: DNA
<213> ORGANISM: Artificial Sequence
<220> FEATURE:

<221> NAME/KEY: source
<223> OTHER INFORMATION: /note="Description of Artificial Sequence:
Synthetic oligonucleotide"

<400> SEQUENCE: 872
ccattctgca gagccagcag agg 23

<210> SEQ ID NO 873
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 873
ccattctgca gagccagagg cagg 24

<210> SEQ ID NO 874
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 874
ccattctgca gagcccagag g 21

<210> SEQ ID NO 875
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 875
ccattctgca gagccagaga gg 22

<210> SEQ ID NO 876
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 876
ccattctgca gagcagagg 19

<210> SEQ ID NO 877
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 877
ccattctgca gagccccaga gg 22

```
<210> SEQ ID NO 878
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 878

ccattctgca gagccaggag gcagg                                          25


<210> SEQ ID NO 879
<211> LENGTH: 67
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (18)..(61)
<223> OTHER INFORMATION: a, c, t, g, unknown or other

<400> SEQUENCE: 879

ccattctgca gagccagnnn nnnnnnnnnn nnnnnnnnnn nnnnnnnnnn nnnnnnnnnn    60

ncagagg                                                              67


<210> SEQ ID NO 880
<211> LENGTH: 55
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (18)..(52)
<223> OTHER INFORMATION: a, c, t, g, unknown or other

<400> SEQUENCE: 880

ccattctgca gagccagnnn nnnnnnnnnn nnnnnnnnnn nnnnnnnnnn nnagg         55


<210> SEQ ID NO 881
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 881

ccattctgca gagccagaag agg                                            23


<210> SEQ ID NO 882
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 882

ccattctgca gagccagcac agagg                                          25
```

<210> SEQ ID NO 883
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 883
ccattctgca gagccacaga gg 22

<210> SEQ ID NO 884
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 884
ccattctgca gagccagtca gagg 24

<210> SEQ ID NO 885
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 885
uuggcauggg ucgcugacgg 20

<210> SEQ ID NO 886
<211> LENGTH: 30
<212> TYPE: DNA
<213> ORGANISM: Mus sp.

<400> SEQUENCE: 886
ccagcctccg tcagcgaccc atgccaagac 30

<210> SEQ ID NO 887
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 887
cgggcuggag cuguucgcgc 20

<210> SEQ ID NO 888
<211> LENGTH: 30
<212> TYPE: DNA
<213> ORGANISM: Mus sp.

<400> SEQUENCE: 888
gatgccagcg cgaacagctc cagcccgagt 30

<210> SEQ ID NO 889
<211> LENGTH: 30

<212> TYPE: DNA
<213> ORGANISM: Mus sp.

<400> SEQUENCE: 889
agaagagggt gccagcgggt atgaggagtg 30

<210> SEQ ID NO 890
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 890
agagggugcc agcggguaug 20

<210> SEQ ID NO 891
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 891
ctgggagagg gagcccctcc agg 23

<210> SEQ ID NO 892
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 892
aaaggtggga gacacctcct tgg 23

<210> SEQ ID NO 893
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 893
tccaaccttc aggcaaggtg ggg 23

<210> SEQ ID NO 894
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 894
aggaagtctg gccgatctgc tgg 23

<210> SEQ ID NO 895

-continued

<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 895
ctctgaggcc ctggagatcc tgg 23

<210> SEQ ID NO 896
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 896
ttggcatggg tcgctgacgg agg 23

<210> SEQ ID NO 897
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 897
cgggctggag ctgttcgcgc tgg 23

<210> SEQ ID NO 898
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 898
agagggtgcc agcgggtatg agg 23

<210> SEQ ID NO 899
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 899
cctccgtcag cgacccatgc caa 23

<210> SEQ ID NO 900
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 900
cctccgatca gcgacccatg ccaa 24

<210> SEQ ID NO 901
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 901
cctccgttca gcgacccatg ccaa 24

<210> SEQ ID NO 902
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 902
cctccgctca gcgacccatg ccaa 24

<210> SEQ ID NO 903
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 903
cctcctcagc gacccatgcc aa 22

<210> SEQ ID NO 904
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 904
cctccgcagc gacccatgcc aa 22

<210> SEQ ID NO 905
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 905
cctctcagcg acccatgcca a 21

<210> SEQ ID NO 906
<211> LENGTH: 19
<212> TYPE: DNA
<213> ORGANISM: Artificial Sequence
<220> FEATURE:

<221> NAME/KEY: source
<223> OTHER INFORMATION: /note="Description of Artificial Sequence: Synthetic oligonucleotide"

<400> SEQUENCE: 906
cctccgcgac ccatgccaa 19

<210> SEQ ID NO 907
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 907
cctcagcgac ccatgccaa 19

<210> SEQ ID NO 908
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 908
ctcagcgacc catgccaa 18

<210> SEQ ID NO 909
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 909
ccagcgcgaa cagctccagc ccg 23

<210> SEQ ID NO 910
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 910
ccagcgccga acagctccag cccg 24

<210> SEQ ID NO 911
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 911
ccagcgaaca gctccagccc g 21

<210> SEQ ID NO 912
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 912
ccagcggaca gctccagccc g 21

<210> SEQ ID NO 913
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 913
ccagaacagc tccagcccg 19

<210> SEQ ID NO 914
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 914
ccagcgagct ccagcccg 18

<210> SEQ ID NO 915
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 915
ccagcgcaca gctccagccc g 21

<210> SEQ ID NO 916
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 916
ccagcgctcc agcccg 16

<210> SEQ ID NO 917
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 917
agagggtgcc agcgggttat gagg 24

<210> SEQ ID NO 918
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 918
agagggtgcc agcgggtaat gagg 24

<210> SEQ ID NO 919
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (18)..(36)
<223> OTHER INFORMATION: a, c, t, g, unknown or other

<400> SEQUENCE: 919
agagggtgcc agcgggtnnn nnnnnnnnnn nnnnnn 36

<210> SEQ ID NO 920
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 920
agagggtgcc agtatgagg 19

<210> SEQ ID NO 921
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 921
agagggtgcc agcgggtgag g 21

<210> SEQ ID NO 922
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 922
agagggtgcc agcgagg 17

-continued

```
<210> SEQ ID NO 923
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 923

agagggtgcc agcggggagg                                                20


<210> SEQ ID NO 924
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 924

aaaaaaaaaa aaaaaaaaaa aaaaaaaaaa aaaaaaaaaa aaaaaaaaaa aaaaaaaaaa     60

aaaaaaaaaa aaaaaaaaaa aaaaaaaaaa aaaaaaaaaa aaaaaaaaaa aaaaaaaaaa    120


<210> SEQ ID NO 925
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 925

His His His His His His
1               5


<210> SEQ ID NO 926
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: Ahx

<400> SEQUENCE: 926

Arg Xaa Arg Arg Arg Arg
1               5
```

DELIVERY AND USE OF THE CRISPR-CAS SYSTEMS, VECTORS AND COMPOSITIONS FOR HEPATIC TARGETING AND THERAPY

RELATED APPLICATIONS AND INCORPORATION BY REFERENCE

This application is a divisional of U.S. patent application Ser. No. 14/971,356, filed Dec. 16, 2015, which is a Continuation-in-Part of International Application Number PCT/US2014/041804 filed on Jun. 10, 2014, which published as PCT Publication Number WO2014/204726 on Dec. 24, 2014. Priority is claimed from U.S. provisional patent applications 61/836,123, filed Jun. 17, 2013, 61/847,537, filed Jul. 17, 2013, 61/862,355, filed Aug. 5, 2013, 61/871,301, filed Aug. 28, 2013, 61/915,325, filed Dec. 12, 2013, and 61/979,733, filed Apr. 15, 2014.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

STATEMENT AS TO FEDERALLY SPONSORED RESEARCH

This invention was made with government support under grant no. MH100706 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Feb. 25, 2020, is named 114203-5826_SL.txt and is 370,849 bytes in size.

FIELD OF THE INVENTION

The present invention generally relates to the delivery, engineering, optimization and therapeutic applications of systems, methods, and compositions used for the control of gene expression involving sequence targeting, such as genome perturbation or gene-editing, that relate to Clustered Regularly Interspaced Short Palindromic Repeats (CRISPR) and components thereof. In particular, the present invention relates to aspects related to delivery to the liver, for gene therapy of liver conditions, understanding liver or liver tissue gene function and the creation of liver models. Liver or liver tissue includes parenchymal cells commonly referred to as hepatocytes. Liver or Liver tissue can also be liver cells that are non-parenchymal cells, especially as such cells constitute 40% of the total number of liver cells even though only 6.5% of its volume; and, examples of such non-parenchymal cells liver cells or tissue include sinusoidal hepatic endothelial cells, Kupffer cells and hepatic stellate cells. Cells of the liver express one or more liver gene product(s). Advantageously the invention is practiced with respect to hepatocytes or liver or liver tissue comprising hepatocytes.

BACKGROUND OF THE INVENTION

Recent advances in genome sequencing techniques and analysis methods have significantly accelerated the ability to catalog and map genetic factors associated with a diverse range of biological functions and diseases. Precise genome targeting technologies are needed to enable systematic reverse engineering of causal genetic variations by allowing selective perturbation of individual genetic elements, as well as to advance synthetic biology, biotechnological, and medical applications. Although genome-editing techniques such as designer zinc fingers, transcription activator-like effectors (TALEs), or homing meganucleases are available for producing targeted genome perturbations, there remains a need for new genome engineering technologies that are affordable, easy to set up, scalable, and amenable to targeting multiple positions within the eukaryotic genome.

SUMMARY OF THE INVENTION

The CRISPR-Cas system does not require the generation of customized proteins to target specific sequences but rather a single Cas enzyme can be programmed by a short RNA molecule to recognize a specific DNA target. Adding the CRISPR-Cas system to the repertoire of genome sequencing techniques and analysis methods may significantly simplify the methodology and accelerate the ability to catalog and map genetic factors associated with a diverse range of biological functions and diseases. To utilize the CRISPR-Cas system effectively for genome editing without deleterious effects, it is critical to understand aspects of engineering, optimization and cell-type/tissue/organ specific delivery of these genome engineering tools, which are aspects of the claimed invention.

There exists a pressing need for alternative and robust systems and techniques for nucleic acid sequence targeting with a wide array of applications. Aspects of this invention address this need and provide related advantages. An exemplary CRISPR complex comprises a CRISPR enzyme complexed with a guide sequence hybridized or hybridizable to a target sequence within the target polynucleotide. The guide sequence is linked to a tracr mate sequence, which in turn hybridizes to a tracr sequence.

In one aspect, the invention provides methods for using one or more elements of a CRISPR-Cas system. The CRISPR complex of the invention provides an effective means for modifying a target polynucleotide. The CRISPR complex of the invention has a wide variety of utilities including modifying (e.g., deleting, inserting, translocating, inactivating, activating) a target polynucleotide in a multiplicity of cell types in various tissues and organs. As such the CRISPR complex of the invention has a broad spectrum of applications in, e.g., gene or genome editing, gene therapy, drug discovery, drug screening, disease diagnosis, and prognosis. In vivo, in vitro and ex vivo uses are envisaged.

Aspects of the invention relate to Cas9 enzymes having improved liver-targeting specificity in a CRISPR-Cas9 system having guide RNAs having optimal activity, smaller in length than wild-type Cas9 enzymes and nucleic acid molecules coding therefor, and chimeric Cas9 enzymes, as well as methods of improving the targeting specificity of a Cas9 enzyme or of designing a CRISPR-Cas9 system comprising designing or preparing guide RNAs having optimal activity and/or selecting or preparing a Cas9 enzyme having a smaller size or length than wild-type Cas9 whereby packaging a nucleic acid coding therefor into a delivery vector is more advanced as there is less coding therefor in the delivery vector than for wild-type Cas9, and/or generating chimeric Cas9 enzymes.

Also provided are uses of the present sequences, vectors, enzymes or systems, in medicine. Also provided are uses of the same in gene or genome editing. This is in relation to liver tissues or cells, whether in or ex vivo, In an additional aspect of the invention, a Cas9 enzyme may comprise one or more mutations and may be used as a generic DNA binding protein with or without fusion to a functional domain. The mutations may be artificially introduced mutations or gain- or loss-of-function mutations. The mutations may include but are not limited to mutations in one of the catalytic domains (D10 and H840) in the RuvC and HNH catalytic domains, respectively. Further mutations have been characterized and may be used in one or more compositions of the invention. In one aspect of the invention, the mutated Cas9 enzyme may be fused to a protein domain, e.g., such as a transcriptional activation domain. In one aspect, of the invention, the transcriptional activation domain may be VP64. In other aspects of the invention, the transcriptional repressor domain may be KRAB or SID4×. Other aspects of the invention relate to the mutated Cas 9 enzyme being fused to domains which include but are not limited to a transcriptional activator, repressor, a recombinase, a transposase, a histone remodeler, a demethylase, a DNA methyltransferase, a cryptochrome, a light inducible/controllable domain or a chemically inducible/controllable domain.

In a further embodiment, the invention provides for methods to generate mutant tracrRNA and direct repeat sequences or mutant chimeric guide sequences that allow for enhancing performance of these RNAs in cells. Aspects of the invention also provide for selection of said sequences.

Aspects of the invention also provide for methods of simplifying the cloning and delivery of components of the CRISPR complex. In the preferred embodiment of the invention, a suitable promoter, such as the U6 promoter, is amplified with a DNA oligo and added onto the guide RNA. The resulting PCR product can then be transfected into cells to drive expression of the guide RNA. Aspects of the invention also relate to the guide RNA being transcribed in vitro or ordered from a synthesis company and directly transfected.

In one aspect, the invention provides for methods to improve activity by using a more active polymerase. In a preferred embodiment, the expression of guide RNAs under the control of the T7 promoter is driven by the expression of the T7 polymerase in the cell. In an advantageous embodiment, the cell is a eukaryotic cell. In a preferred embodiment the eukaryotic cell is a human cell. In a more preferred embodiment the human cell is a patient specific cell.

In one aspect, the invention provides for methods of reducing the toxicity of Cas enzymes. In certain aspects, the Cas enzyme is any Cas9 as described herein, for instance any naturally-occurring bacterial Cas9 as well as any chimaeras, mutants, homologs or orthologs. In a preferred embodiment, the Cas9 is delivered into the cell in the form of mRNA. This allows for the transient expression of the enzyme thereby reducing toxicity. In another preferred embodiment, the invention also provides for methods of expressing Cas9 under the control of an inducible promoter, and the constructs used therein.

In another aspect, the invention provides for methods of improving the in vivo applications of the CRISPR-Cas system. In the preferred embodiment, the Cas enzyme is wildtype Cas9 or any of the modified versions described herein, including any naturally-occurring bacterial Cas9 as well as any chimaeras, mutants, homologs or orthologs. An advantageous aspect of the invention provides for the selection of Cas9 homologs that are easily packaged into viral vectors for delivery. Cas9 orthologs typically share the general organization of 3-4 RuvC domains and a HNH domain. The 5' most RuvC domain cleaves the non-complementary strand, and the HNH domain cleaves the complementary strand. All notations are in reference to the guide sequence.

The catalytic residue in the 5' RuvC domain is identified through homology comparison of the Cas9 of interest with other Cas9 orthologs (from *S. pyogenes* type II CRISPR locus, *S. thermophilus* CRISPR locus 1, *S. thermophilus* CRISPR locus 3, and *Franciscilla novicida* type II CRISPR locus), and the conserved Asp residue (D10) is mutated to alanine to convert Cas9 into a complementary-strand nicking enzyme. Similarly, the conserved His and Asn residues in the HNH domains are mutated to Alanine to convert Cas9 into a non-complementary-strand nicking enzyme. In some embodiments, both sets of mutations may be made, to convert Cas9 into a non-cutting enzyme.

In some embodiments, the CRISPR enzyme is a type I or III CRISPR enzyme, preferably a type II CRISPR enzyme. This type II CRISPR enzyme may be any Cas enzyme. A preferred Cas enzyme may be identified as Cas9 as this can refer to the general class of enzymes that share homology to the biggest nuclease with multiple nuclease domains from the type II CRISPR system. Most preferably, the Cas9 enzyme is from, or is derived from, spCas9 or saCas9. By derived, Applicants mean that the derived enzyme is largely based, in the sense of having a high degree of sequence homology with, a wildtype enzyme, but that it has been mutated (modified) in some way as described herein.

It will be appreciated that the terms Cas and CRISPR enzyme are generally used herein interchangeably, unless otherwise apparent. As mentioned above, many of the residue numberings used herein refer to the Cas9 enzyme from the type II CRISPR locus in *Streptococcus pyogenes*. However, it will be appreciated that this invention includes many more Cas9s from other species of microbes, such as SpCas9, SaCas9, St1Cas9 and so forth. Further examples are provided herein. The skilled person will be able to determine appropriate corresponding residues in Cas9 enzymes other than SpCas9 by comparison of the relevant amino acid sequences. Thus, where a specific amino acid replacement is referred to using the SpCas9 numbering, then, unless the context makes it apparent this is not intended to refer to other Cas9 enzymes, the disclosure is intended to encompass corresponding modifications in other Cas9 enzymes. SaCas9 is particularly preferred.

An example of a codon optimized sequence, in this instance optimized for humans (i.e. being optimized for expression in humans) is provided herein, e.g., see the SaCas9 human codon optimized sequence. Whilst this is preferred, it will be appreciated that other examples are possible, and codon optimization for a host species other than human, or for codon optimization for specific organs such as the brain, is known.

In further embodiments, the invention provides for methods of enhancing the function of Cas9 by generating chimeric Cas9 proteins. Chimeric Cas9 proteins chimeric Cas9s may be new Cas9 containing fragments from more than one naturally occurring Cas9. These methods may comprise fusing N-terminal fragments of one Cas9 homolog with C-terminal fragments of another Cas9 homolog. These methods also allow for the selection of new properties displayed by the chimeric Cas9 proteins.

It will be appreciated that in the present methods, where the organism is an animal or a plant, the modification may occur ex vivo or in vitro, for instance in a cell culture and in some instances not in vivo. In other embodiments, it may occur in vivo.

In one aspect, the invention provides a method of modifying an organism or a non-human organism by manipulation of a target sequence in a genomic locus of interest comprising: delivering a non-naturally occurring or engineered composition comprising:

A)—I. a CRISPR-Cas system chimeric RNA (chiRNA) polynucleotide sequence, wherein the polynucleotide sequence comprises:

(a) a guide sequence capable of hybridizing to a target sequence in a eukaryotic cell, (b) a tracr mate sequence, and (c) a tracr sequence, and II. a polynucleotide sequence encoding a CRISPR enzyme comprising at least one or more nuclear localization sequences, wherein (a), (b) and (c) are arranged in a 5' to 3' orientation, wherein when transcribed, the tracr mate sequence hybridizes to the tracr sequence and the guide sequence directs sequence-specific binding of a CRISPR complex to the target sequence, and wherein the CRISPR complex comprises the CRISPR enzyme complexed with (1) the guide sequence that is hybridized or hybridizable to the target sequence, and (2) the tracr mate sequence that is hybridized or hybridizable to the tracr sequence and the polynucleotide sequence encoding a CRISPR enzyme is DNA or RNA, or (B) I. polynucleotides comprising:

(a) a guide sequence capable of hybridizing to a target sequence in a eukaryotic cell, and (b) at least one or more tracr mate sequences, II. a polynucleotide sequence encoding a CRISPR enzyme, and III. a polynucleotide sequence comprising a tracr sequence, wherein when transcribed, the tracr mate sequence hybridizes to the tracr sequence and the guide sequence directs sequence-specific binding of a CRISPR complex to the target sequence, and wherein the CRISPR complex comprises the CRISPR enzyme complexed with (1) the guide sequence that is hybridized or hybridizable to the target sequence, and (2) the tracr mate sequence that is hybridized or hybridizable to the tracr sequence, and the polynucleotide sequence encoding a CRISPR enzyme is DNA or RNA.

In some embodiments, the second alternative above is preferred. The first alternative is particularly preferred, however, in most but not all aspects of the disclosure.

It will be appreciated that the present application is directed to the liver, whether that is the organ per se or a tissue within it or simply one or more liver cells, e.g., hepatocytes. Primary hepatocytes are preferred. The liver cells may be comprised within a vertebrate animal, either a patient (in the sense of an animal in need of CRISPR-directed gene therapy) or a model organism, or may be in cell culture, an organoid or other ex vivo tissue, such a "liver on a chip" for instance where hepatocytes are seeded and grown on a scaffold. Harvested hepatocytes from un-transplanted organs are also a useful target. With the development of 3-D printing techniques being applied to biology, printed tissues are within grasp and it is entirely feasible that liver cells or tissues printed in this way to create an organoid or onto a chip could also be targeted.

Thus, provided is a model organism comprising liver cells, such as hepatocytes, to which the present CRISPR-Cas system has been delivered. Similarly, also provided is an ex vivo collection of two or more liver cells, such as hepatocytes, to which the present CRISPR-Cas system has been delivered. Such collections may include liver organs, liver organoids, liver cells populating a scaffold (as.g., such as 'liver on a chip'). Methods of creating such models or collections are also provided.

In particular, such liver cells may express, or may comprise polynucleotides capable of expressing, a Cas enzyme. As discussed herein, this has the advantage of providing a ready model for interrogating gene function through gene perturbation, including knock down. This is particularly useful in studying conditions of the liver, such as amyloidosis and others those listed herein, as well as broader conditions such as obesity, where liver is only one of the affect components in the body.

Methods of interrogating liver gene function are also provided herein. These typically comprise delivering to liver cells, either in or ex vivo, the CRISPR-Cas system. However, if the cells already comprise Cas, whether expressed as a protein or encoded by polynucleotides already comprised within the cells, then only the CRISPR polynucleotide needs to be delivered. The method may include extraction from and, optionally, re-insertion back into the liver. By delivering, it is meant actually physical delivery of the polynucleotides to the nucleus of the cell, but also transfection. Therefore, delivery should also be read as including transfection unless otherwise apparent. Gene knockdown or perturbation Methods of gene therapy are also envisaged. For instance, correction of one or more deficient genotypes (for example single point mutations) is achievable through the use of the present CRISPR-Cas system in the liver cells discussed herein (including the models). Monogenic conditions associated with the liver are particularly preferred and are exemplified herein, see Example 38 where the CRISPR-Cas9 system target was ApoB, a lipid metabolism gene, was effective at inducing a phenotypic change in vivo. Compositions for use in gene therapy are also provided.

Although various Cas enzymes are envisaged, Cas9 is particularly preferred and we have shown particular efficacy in the liver for SaCa9. Tracr sequence from Sa is also preferred if the Cas enzyme is an Sa Cas enzyme. A suitable PAM in such circumstance is NNGRR. For *S. pyogenes* Cas9 or derived enzymes, a suitable PAM is 5'-NRG.

Although one guide may be used, so-called multiplexing with two, three, four or more guides, is particularly useful in interrogation of gene function and model creation (to provide multiple gene knock downs), but also in gene therapy where multiple defective genotypes are to be corrected (either multiple errors in a single gene or, more likely, multiple errors spread across several genes). Alternatively, multiplexing with two guides is useful in a dual nickase approach to reduce off-target effects or simply selection of multiple targets within one gene to ensure Cas recruitment. Triple and quadruple guides are preferred. Reference to gene herein is made interchangeably with genomic locus.

The intron approach described here is also useful in this regard, where the guide is positioned within the Cas intron.

Preferred means of delivery include the methods described by Kanasty below, such as LNP, especially where only the guide is to be delivered or it is to be delivered alone. However, viral vectors including lentiviral and AAV are generally preferred for the liver as they have been successful to date. Of these, AAV is preferred and especially serotype 8, with AAV2/8 shown to be effective.

Some preferred targets, to the extent that they are present in or conditions of the liver are metabolic disorders, such as any one of: Amyloid neuropathy (TTR, PALB); Amyloidosis (APOA1, APP, AAA, CVAP, AD1, GSN, FGA, LYZ, TTR, PALB); Cirrhosis (KRT18, KRT8, CIRH1A, NAIC, TEX292, KIAA1988); Cystic fibrosis (CFTR, ABCC7, CF, MRP7); Glycogen storage diseases (SLC2A2, GLUT2, G6PC, G6PT, G6PT1, GAA, LAMP2, LAMPB, AGL, GDE, GBE1, GYS2, PYGL, PFKM); Hepatic adenoma, 142330 (TCF1, HNF1A, MODY3), Hepatic failure, early onset, and neurologic disorder (SCOD1, SCO1), Hepatic lipase deficiency (LIPC), Hepatoblastoma, cancer and carcinomas (CTNNB1, PDGFRL, PDGRL, PRLTS, AXIN1, AXIN, CTNNB1, TP53, P53, LFS1, IGF2R, MPRI, MET, CASP8, MCH5; Medullary cystic kidney disease (UMOD, HNFJ, FJHN, MCKD2, ADMCKD2); Phenylketonuria (PAH, PKU1, QDPR, DHPR, PTS); Polycystic kidney and hepatic disease (FCYT, PKHD1, ARPKD, PKD1, PKD2, PKD4, PKDTS, PRKCSH, G19P1, PCLD, SEC63). Other preferred targets include any one or more of include one or more of: PCSK9; Hmgcr; SERPINA1; ApoB; and.or LDL.

It will be appreciated that methods of altering expression in the liver do not involve alteration of the germline, which may be excluded on moral grounds. In fact, although transfection of stem cells is envisage and certainly preferred in some embodiments, primary hepatocytes are particularly preferred, particularly where they may show or be stimulated to show some regeneration.

Type II CRISPRS are particularly preferred, especially for use in eukaryotes, as in the present case, where livers are only found in eukaryotes, particularly vertebrate animals, in any case.

Use of the CRISPR-Cas systems to invoke a phenotypic change is a particular advantage, especially in vivo. We have shown this in the present application.

Where therapeutic applications are envisaged, or for other genome engineering in the liver, then where a correction is required it will be appreciated that following nicking or cleavage of the genomic DNA target, then correction via the HDR pathway is preferred. For gene knockdown, NHEJ is advantageous, however, correction via the HDR pathway is preferred for therapy. In such circumstances, it is preferable to deliver a repair template. This is most preferably ssDNA although RNA via a retroviral vector to provide a corresponding DNA template is also possible. The skilled person can readily put the invention into practice from the herein teachings contributing to the knowledge in the art; and in this regard mention is made that the skilled person from the herein teachings contributing to the knowledge in the art can readily appreciate and implement considerations as to homologous arm length. Mention is made of patent applications and publications including herein inventor Zhang, including those cited herein. The repair template is preferably co-delivered with one or more elements of the CRISPR-Cas system.

Also provided is a method of altering expression of at least one liver gene product comprising introducing into a eukaryotic liver cell, for example a hepatocyte, containing and expressing a DNA molecule having a target sequence and encoding the gene product, an engineered, non-naturally occurring Clustered Regularly Interspaced Short Palindromic Repeats (CRISPR)-CRISPR associated (Cas) (CRISPR-Cas) system comprising one or more vectors comprising:

a) a first regulatory element operable in a eukaryotic cell operably linked to at least one nucleotide sequence encoding a CRISPR-Cas system guide RNA that hybridizes with the target sequence, and b) a second regulatory element operable in a eukaryotic cell operably linked to a nucleotide sequence encoding a Type-II Cas9 protein, wherein components (a) and (b) are located on same or different vectors of the system, whereby the guide RNA targets the target sequence and the Cas9 protein cleaves the DNA molecule, whereby expression of the at least one liver gene product is altered; and, wherein the Cas9 protein and the guide RNA do not naturally occur together.

Reference below to targets will be understood to be hepatic targets or genes otherwise expressed in the liver unless otherwise apparent.

Any or all of the polynucleotide sequence encoding a CRISPR enzyme, guide sequence, tracr mate sequence or tracr sequence, may be RNA. The polynucleotides comprising the sequence encoding a CRISPR enzyme, the guide sequence, tracr mate sequence or tracr sequence may be RNA and may be delivered via liposomes, nanoparticles, exosomes, microvesicles, or a gene-gun.

It will be appreciated that where reference is made to a polynucleotide, which is RNA and is said to 'comprise' a feature such a tracr mate sequence, the RNA sequence includes the feature. Where the polynucleotide is DNA and is said to comprise a feature such a tracr mate sequence, the DNA sequence is or can be transcribed into the RNA including the feature at issue. Where the feature is a protein, such as the CRISPR enzyme, the DNA or RNA sequence referred to is, or can be, translated (and in the case of DNA transcribed first).

Accordingly, in certain embodiments the invention provides a method of modifying the liver of an organism, e.g., mammal including human or a non-human mammal or organism by manipulation of a target sequence in a genomic locus of interest comprising delivering a non-naturally occurring or engineered composition comprising a viral or plasmid vector system comprising one or more viral or plasmid vectors operably encoding a composition for expression thereof, wherein the composition comprises: (A) a non-naturally occurring or engineered composition comprising a vector system comprising one or more vectors comprising I. a first regulatory element operably linked to a CRISPR-Cas system chimeric RNA (chiRNA) polynucleotide sequence, wherein the polynucleotide sequence comprises (a) a guide sequence capable of hybridizing to a target sequence in a eukaryotic cell, (b) a tracr mate sequence, and (c) a tracr sequence, and II. a second regulatory element operably linked to an enzyme-coding sequence encoding a CRISPR enzyme comprising at least one or more nuclear localization sequences (or optionally at least one or more nuclear localization sequences as some embodiments can involve no NLS), wherein (a), (b) and (c) are arranged in a 5' to 3' orientation, wherein components I and II are located on the same or different vectors of the system, wherein when transcribed, the tracr mate sequence hybridizes to the tracr sequence and the guide sequence directs sequence-specific binding of a CRISPR complex to the target sequence, and wherein the CRISPR complex comprises the CRISPR enzyme complexed with (1) the guide sequence that is hybridized or hybridizable to the target sequence, and (2) the tracr mate sequence that is hybridized or hybridizable to the tracr sequence, or (B) a non-naturally occurring or engineered composition comprising a vector system comprising one or more vectors comprising I. a first regulatory element operably linked to (a) a guide sequence capable of hybridizing to a target sequence in a eukaryotic cell, and (b) at least one or more tracr mate sequences, II. a second regulatory element operably linked to an enzyme-coding sequence encoding a CRISPR enzyme, and III. a third regulatory element operably linked to a tracr sequence, wherein components I, II and III are located on the same or different vectors of the system, wherein when transcribed, the tracr mate sequence hybridizes to the tracr sequence and the guide sequence directs sequence-specific binding of a CRISPR complex to the target sequence, and wherein the CRISPR complex comprises the CRISPR enzyme complexed with (1) the guide sequence that is hybridized or hybridizable to the target sequence, and (2) the tracr mate sequence that is hybridized or hybridizable to the tracr sequence. In some embodiments, components I, II and III are located on the same vector. In other embodiments, components I and II are located on the same vector, while component III is located on another vector. In other embodiments, components I and III are located on the same vector, while component II is located on another vector. In other embodiments, components II and III are located on the same vector, while component I is located on another vector. In other embodiments, each of components I, II and III is located on different vectors. The invention also provides a viral or plasmid vector system as described herein.

Preferably, the vector is a viral vector, such as a lenti- or baculo- or preferably adeno-viral/adeno-associated viral vectors, but other means of delivery are known (such as yeast systems, microvesicles, gene guns/means of attaching vectors to gold nanoparticles) and are provided. In some embodiments, one or more of the viral or plasmid vectors may be delivered via liposomes, nanoparticles, exosomes, microvesicles, or a gene-gun.

By manipulation of a target sequence, Applicants also mean the epigenetic manipulation of a target sequence. This may be of the chromatin state of a target sequence, such as by modification of the methylation state of the target sequence (i.e. addition or removal of methylation or methylation patterns or CpG islands), histone modification, increasing or reducing accessibility to the target sequence, or by promoting 3D folding.

It will be appreciated that where reference is made to a method of modifying an organism or mammal including human or a non-human mammal or organism by manipulation of a target sequence in a genomic locus of interest, this may apply to the organism (or mammal) as a whole or just a single cell or population of cells from that organism (if the organism is multicellular). In the case of humans, for instance, Applicants envisage, inter alia, a single cell or a population of cells and these may preferably be modified ex vivo and then re-introduced. In this case, a biopsy or other tissue or biological fluid sample may be necessary. Stem cells are also particularly preferred in this regard. But, of course, in vivo embodiments are also envisaged.

In certain embodiments the invention provides a method of treating or inhibiting a condition caused by a defect in a target sequence in a genomic locus of interest in a subject (e.g., mammal or human) or a non-human subject (e.g., mammal) in need thereof comprising modifying the subject or a non-human subject by manipulation of the target sequence and wherein the condition is susceptible to treatment or inhibition by manipulation of the target sequence comprising providing treatment comprising: delivering a non-naturally occurring or engineered composition comprising an AAV or lentivirus vector system comprising one or more AAV or lentivirus vectors operably encoding a composition for expression thereof, wherein the target sequence is manipulated by the composition when expressed, wherein the composition comprises: (A) a non-naturally occurring or engineered composition comprising a vector system comprising one or more vectors comprising I. a first regulatory element operably linked to a CRISPR-Cas system chimeric RNA (chiRNA) polynucleotide sequence, wherein the polynucleotide sequence comprises (a) a guide sequence capable of hybridizing to a target sequence in a eukaryotic cell, (b) a tracr mate sequence, and (c) a tracr sequence, and II. a second regulatory element operably linked to an enzyme-coding sequence encoding a CRISPR enzyme comprising at least one or more nuclear localization sequences (or optionally at least one or more nuclear localization sequences as some embodiments can involve no NLS) wherein (a), (b) and (c) are arranged in a 5' to 3' orientation, wherein components I and II are located on the same or different vectors of the system, wherein when transcribed, the tracr mate sequence hybridizes to the tracr sequence and the guide sequence directs sequence-specific binding of a CRISPR complex to the target sequence, and wherein the CRISPR complex comprises the CRISPR enzyme complexed with (1) the guide sequence that is hybridized or hybridizable to the target sequence, and (2) the tracr mate sequence that is hybridized or hybridizable to the tracr sequence, or (B) a non-naturally occurring or engineered composition comprising a vector system comprising one or more vectors comprising I. a first regulatory element operably linked to (a) a guide sequence capable of hybridizing to a target sequence in a eukaryotic cell, and (b) at least one or more tracr mate sequences, II. a second regulatory element operably linked to an enzyme-coding sequence encoding a CRISPR enzyme, and III. a third regulatory element operably linked to a tracr sequence, wherein components I, II and III are located on the same or different vectors of the system, wherein when transcribed, the tracr mate sequence hybridizes to the tracr sequence and the guide sequence directs sequence-specific binding of a CRISPR complex to the target sequence, and wherein the CRISPR complex comprises the CRISPR enzyme complexed with (1) the guide sequence that is hybridized or hybridizable to the target sequence, and (2) the tracr mate sequence that is hybridized or hybridizable to the tracr sequence. In some embodiments, components I, II and III are located on the same vector. In other embodiments, components I and II are located on the same vector, while component III is located on another vector. In other embodiments, components I and III are located on the same vector, while component II is located on another vector. In other embodiments, components II and III are located on the same vector, while component I is located on another vector. In other embodiments, each of components I, II and III is located on different vectors. The invention also provides a viral (e.g. AAV or lentivirus) vector system as described herein, and can be part of a vector system as described herein.

Some methods of the invention can include inducing expression. The organism or subject is a eukaryote (including mammal including human) or a non-human eukaryote or a non-human animal or a non-human mammal, provided it has a liver or hepatic function. In some embodiments, the organism or subject is a non-human animal, and may be an arthropod, for example, an insect, or may be a nematode. In some methods of the invention the organism or subject is a mammal or a non-human mammal. A non-human mammal may be for example a rodent (preferably a mouse or a rat), an ungulate, or a primate. In some methods of the invention the viral vector is an AAV or a lentivirus, and can be part of a vector system as described herein. In some methods of the invention the CRISPR enzyme is a Cas9. In some methods of the invention the expression of the guide sequence is under the control of the T7 promoter and is driven by the expression of T7 polymerase.

The invention in some embodiments comprehends a method of delivering a CRISPR enzyme comprising delivering to a cell mRNA encoding the CRISPR enzyme. In some of these methods the CRISPR enzyme is a Cas9.

The invention also provides methods of preparing the vector systems of the invention, in particular the viral vector systems as described herein. The invention in some embodiments comprehends a method of preparing the AAV of the invention comprising transfecting plasmid(s) containing or consisting essentially of nucleic acid molecule(s) coding for the AAV into AAV-infected cells, and supplying AAV rep and/or cap obligatory for replication and packaging of the AAV. In some embodiments the AAV rep and/or cap obligatory for replication and packaging of the AAV are supplied by transfecting the cells with helper plasmid(s) or helper virus(es). In some embodiments the helper virus is a poxvirus, adenovirus, herpesvirus or baculovirus. In some embodiments the poxvirus is a vaccinia virus. In some embodiments the cells are mammalian cells. And in some embodiments the cells are insect cells and the helper virus is baculovirus. In other embodiments, the virus is a lentivirus.

The invention further comprehends a composition of the invention or a CRISPR enzyme thereof (including or alternatively mRNA encoding the CRISPR enzyme) for use in medicine or in therapy. In some embodiments the invention comprehends a composition according to the invention or a CRISPR enzyme thereof (including or alternatively mRNA encoding the CRISPR enzyme) for use in a method according to the invention. In some embodiments the invention provides for the use of a composition of the invention or a CRISPR enzyme thereof (including or alternatively mRNA encoding the CRISPR enzyme) in ex vivo gene or genome editing. In certain embodiments the invention comprehends use of a composition of the invention or a CRISPR enzyme thereof (including or alternatively mRNA encoding the CRISPR enzyme) in the manufacture of a medicament for ex vivo gene or genome editing or for use in a method according of the invention. The invention comprehends in some embodiments a composition of the invention or a CRISPR enzyme thereof (including or alternatively mRNA encoding the CRISPR enzyme), wherein the target sequence is flanked at its 3' end by a PAM (protospacer adjacent motif) sequence comprising 5'-motif, especially where the Cas9 is (or is derived from) *S. pyogenes* or *S. aureus* Cas9. For example, a suitable PAM is 5'-NRG or 5'-NNGRR (where N is any Nucleotide) for SpCas9 or SaCas9 enzymes (or derived enzymes), respectively, as mentioned below.

It will be appreciated that SpCas9 or SaCas9 are those from or derived from *S. pyogenes* or *S. aureus* Cas9. It may of course, be mutated or otherwise changed from the wild type to suit the intended use, as described herein. The dual nickase D10A mutant or variant is preferred, especially in combination with two overlapping guides directed as opposing sites on differing strands of the same chromosome.

Aspects of the invention comprehend improving the specificity of a CRISPR enzyme, e.g. Cas9, mediated gene targeting and reducing the likelihood of off-target modification by the CRISPR enzyme, e.g. Cas9. The invention in some embodiments comprehends a method of modifying an organism or a non-human organism by minimizing off-target modifications by manipulation of a first and a second target sequence on opposite strands of a DNA duplex in a genomic locus of interest in a cell comprising delivering a non-naturally occurring or engineered composition comprising:

I. a first CRISPR-Cas system chimeric RNA (chiRNA) polynucleotide sequence, wherein the first polynucleotide sequence comprises:

(a) a first guide sequence capable of hybridizing to the first target sequence, (b) a first tracr mate sequence, and (c) a first tracr sequence, II. a second CRISPR-Cas system chiRNA polynucleotide sequence, wherein the second polynucleotide sequence comprises:

(a) a second guide sequence capable of hybridizing to the second target sequence, (b) a second tracr mate sequence, and (c) a second tracr sequence, and III. a polynucleotide sequence encoding a CRISPR enzyme comprising at least one or more nuclear localization sequences and comprising one or more mutations, wherein (a), (b) and (c) are arranged in a 5' to 3' orientation, wherein when transcribed, the first and the second tracr mate sequence hybridize to the first and second tracr sequence respectively and the first and the second guide sequence directs sequence-specific binding of a first and a second CRISPR complex to the first and second target sequences respectively, wherein the first CRISPR complex comprises the CRISPR enzyme complexed with (1) the first guide sequence that is hybridized or hybridizable to the first target sequence, and (2) the first tracr mate sequence that is hybridized or hybridizable to the first tracr sequence, wherein the second CRISPR complex comprises the CRISPR enzyme complexed with (1) the second guide sequence that is hybridized or hybridizable to the second target sequence, and (2) the second tracr mate sequence that is hybridized or hybridizable to the second tracr sequence, wherein the polynucleotide sequence encoding a CRISPR enzyme is DNA or RNA, and wherein the first guide sequence directs cleavage of one strand of the DNA duplex near the first target sequence and the second guide sequence directs cleavage of the other strand near the second target sequence inducing a double strand break, thereby modifying the organism or the non-human organism by minimizing off-target modifications.

In some methods of the invention any or all of the polynucleotide sequence encoding the CRISPR enzyme, the first and the second guide sequence, the first and the second tracr mate sequence or the first and the second tracr sequence, is/are RNA. In further embodiments of the invention the polynucleotides comprising the sequence encoding the CRISPR enzyme, the first and the second guide sequence, the first and the second tracr mate sequence or the first and the second tracr sequence, is/are RNA and are delivered via liposomes, nanoparticles, exosomes, microvesicles, or a gene-gun. In certain embodiments of the invention, the first and second tracr mate sequence share 100% identity and/or the first and second tracr sequence share 100% identity. In some embodiments, the polynucleotides may be comprised within a vector system comprising one or more vectors. In preferred embodiments of the invention the CRISPR enzyme is a Cas9 enzyme, e.g. SpCas9. In an aspect of the invention the CRISPR enzyme comprises one or more mutations in a catalytic domain, wherein the one or more mutations are selected from the group consisting of D10A, E762A, H840A, N854A, N863A and D986A. In a highly preferred embodiment the CRISPR enzyme has the D10A mutation. In preferred embodiments, the first CRISPR enzyme has one or more mutations such that the enzyme is a complementary strand nicking enzyme, and the second CRISPR enzyme has one or more mutations such that the enzyme is a non-complementary strand nicking enzyme. Alternatively the first enzyme may be a non-complementary strand nicking enzyme, and the second enzyme may be a complementary strand nicking enzyme.

In preferred methods of the invention the first guide sequence directing cleavage of one strand of the DNA duplex near the first target sequence and the second guide sequence directing cleavage of the other strand near the second target sequence results in a 5' overhang. In embodiments of the invention the 5' overhang is at most 200 base pairs, preferably at most 100 base pairs, or more preferably at most 50 base pairs. In embodiments of the invention the 5' overhang is at least 26 base pairs, preferably at least 30 base pairs or more preferably 34-50 base pairs. Most preferably, the overlap is between 5 and −1 base pairs.

The invention in some embodiments comprehends a method of modifying an organism or a non-human organism by minimizing off-target modifications by manipulation of a first and a second target sequence on opposite strands of a DNA duplex in a genomic locus of interest in a cell comprising delivering a non-naturally occurring or engineered composition comprising a vector system comprising one or more vectors comprising I. a first regulatory element operably linked to (a) a first guide sequence capable of hybridizing to the first target sequence, and (b) at least one or more tracr mate sequences, II. a second regulatory element operably linked to (a) a second guide sequence capable of hybridizing to the second target sequence, and (b) at least one or more tracr mate sequences, III. a third regulatory element operably linked to an enzyme-coding sequence encoding a CRISPR enzyme, and IV. a fourth regulatory element operably linked to a tracr sequence, wherein components I, II, III and IV are located on the same or different vectors of the system, when transcribed, the tracr mate sequence hybridizes to the tracr sequence and the first and the second guide sequence direct sequence-specific binding of a first and a second CRISPR complex to the first and second target sequences respectively, wherein the first CRISPR complex comprises the CRISPR enzyme complexed with (1) the first guide sequence that is hybridized or hybridizable to the first target sequence, and (2) the tracr mate sequence that is hybridized or hybridizable to the tracr sequence, wherein the second CRISPR complex comprises the CRISPR enzyme complexed with (1) the second guide sequence that is hybridized or hybridizable to the second target sequence, and (2) the tracr mate sequence that is hybridized or hybridizable to the tracr sequence, wherein the polynucleotide sequence encoding a CRISPR enzyme is DNA or RNA, and wherein the first guide sequence directs cleavage of one strand of the DNA duplex near the first target sequence and the second guide sequence directs cleavage of the other strand near the second target sequence inducing a double strand break, thereby modifying the organism or the non-human organism by minimizing off-target modifications.

The invention also provides a vector system as described herein. The system may comprise one, two, three or four different vectors. Components I, II, III and IV may thus be located on one, two, three or four different vectors, and all combinations for possible locations of the components are herein envisaged, for example: components I, II, III and IV can be located on the same vector; components I, II, III and IV can each be located on different vectors; components I, II, III and IV may be located on a total of two or three different vectors, with all combinations of locations envisaged, etc.

In some methods of the invention any or all of the polynucleotide sequence encoding the CRISPR enzyme, the first and the second guide sequence, the first and the second tracr mate sequence or the first and the second tracr sequence, is/are RNA. In further embodiments of the invention the first and second tracr mate sequence share 100% identity and/or the first and second tracr sequence share 100% identity. In preferred embodiments of the invention the CRISPR enzyme is a Cas9 enzyme, e.g. SpCas9. In an aspect of the invention the CRISPR enzyme comprises one or more mutations in a catalytic domain, wherein the one or more mutations are selected from the group consisting of D10A, E762A, H840A, N854A, N863A and D986A. In a highly preferred embodiment the CRISPR enzyme has the D10A mutation. In preferred embodiments, the first CRISPR enzyme has one or more mutations such that the enzyme is a complementary strand nicking enzyme, and the second CRISPR enzyme has one or more mutations such that the enzyme is a non-complementary strand nicking enzyme. Alternatively the first enzyme may be a non-complementary strand nicking enzyme, and the second enzyme may be a complementary strand nicking enzyme. In a further embodiment of the invention, one or more of the viral vectors are delivered via liposomes, nanoparticles, exosomes, microvesicles, or a gene-gun.

In preferred methods of the invention the first guide sequence directing cleavage of one strand of the DNA duplex near the first target sequence and the second guide sequence directing cleavage of other strand near the second target sequence results in a 5' overhang. In embodiments of the invention the 5' overhang is at most 200 base pairs, preferably at most 100 base pairs, or more preferably at most 50 base pairs. In embodiments of the invention the 5' overhang is at least 26 base pairs, preferably at least 30 base pairs or more preferably 34-50 base pairs.

The invention in some embodiments comprehends a method of modifying a genomic locus of interest by minimizing off-target modifications by introducing into a cell containing and expressing a double stranded DNA molecule encoding a gene product of interest an engineered, non-naturally occurring CRISPR-Cas system comprising a Cas protein having one or more mutations and two guide RNAs that target a first strand and a second strand of the DNA molecule respectively, whereby the guide RNAs target the DNA molecule encoding the gene product and the Cas protein nicks each of the first strand and the second strand of the DNA molecule encoding the gene product, whereby expression of the gene product is altered; and, wherein the Cas protein and the two guide RNAs do not naturally occur together.

In preferred methods of the invention the Cas protein nicking each of the first strand and the second strand of the DNA molecule encoding the gene product results in a 5' overhang. In embodiments of the invention the 5' overhang is at most 200 base pairs, preferably at most 100 base pairs, or more preferably at most 50 base pairs. In embodiments of the invention the 5' overhang is at least 26 base pairs, preferably at least 30 base pairs or more preferably 34-50 base pairs.

Embodiments of the invention also comprehend the guide RNAs comprising a guide sequence fused to a tracr mate sequence and a tracr sequence. In an aspect of the invention the Cas protein is codon optimized for expression in a eukaryotic cell, preferably a mammalian cell or a human cell. In further embodiments of the invention the Cas protein is a type II CRISPR-Cas protein, e.g. a Cas 9 protein. In a highly preferred embodiment the Cas protein is a Cas9 protein, e.g. SpCas9. In aspects of the invention the Cas protein has one or more mutations selected from the group consisting of D10A, E762A, H840A, N854A, N863A and D986A. In a highly preferred embodiment the Cas protein has the D10A mutation.

Aspects of the invention relate to the expression of the gene product being decreased or a template polynucleotide being further introduced into the DNA molecule encoding the gene product or an intervening sequence being excised precisely by allowing the two 5' overhangs to reanneal and ligate or the activity or function of the gene product being altered or the expression of the gene product being increased. In an embodiment of the invention, the gene product is a protein.

The invention also comprehends an engineered, non-naturally occurring CRISPR-Cas system comprising a Cas protein having one or more mutations and two guide RNAs that target a first strand and a second strand respectively of a double stranded DNA molecule encoding a gene product in a cell, whereby the guide RNAs target the DNA molecule encoding the gene product and the Cas protein nicks each of the first strand and the second strand of the DNA molecule encoding the gene product, whereby expression of the gene product is altered; and, wherein the Cas protein and the two guide RNAs do not naturally occur together.

In aspects of the invention the guide RNAs may comprise a guide sequence fused to a tracr mate sequence and a tracr sequence. In an embodiment of the invention the Cas protein is a type II CRISPR-Cas protein. In an aspect of the invention the Cas protein is codon optimized for expression in a eukaryotic cell, preferably a mammalian cell or a human cell. In further embodiments of the invention the Cas protein is a type II CRISPR-Cas protein, e.g. a Cas 9 protein. In a highly preferred embodiment the Cas protein is a Cas9 protein, e.g. SpCas9. In aspects of the invention the Cas protein has one or more mutations selected from the group consisting of D10A, E762A, H840A, N854A, N863A and D986A. In a highly preferred embodiment the Cas protein has the D10A mutation.

Aspects of the invention relate to the expression of the gene product being decreased or a template polynucleotide being further introduced into the DNA molecule encoding the gene product or an intervening sequence being excised precisely by allowing the two 5' overhangs to reanneal and ligate or the activity or function of the gene product being altered or the expression of the gene product being increased. In an embodiment of the invention, the gene product is a protein.

The invention also comprehends an engineered, non-naturally occurring vector system comprising one or more vectors comprising:

a) a first regulatory element operably linked to each of two CRISPR-Cas system guide RNAs that target a first strand and a second strand respectively of a double stranded DNA molecule encoding a gene product, b) a second regulatory element operably linked to a Cas protein, wherein components (a) and (b) are located on same or different vectors of the system, whereby the guide RNAs target the DNA molecule encoding the gene product and the Cas protein nicks each of the first strand and the second strand of the DNA molecule encoding the gene product, whereby expression of the gene product is altered; and, wherein the Cas protein and the two guide RNAs do not naturally occur together.

In aspects of the invention the guide RNAs may comprise a guide sequence fused to a tracr mate sequence and a tracr sequence. In an embodiment of the invention the Cas protein is a type II CRISPR-Cas protein. In an aspect of the invention the Cas protein is codon optimized for expression in a eukaryotic cell, preferably a mammalian cell or a human cell. In further embodiments of the invention the Cas protein is a type II CRISPR-Cas protein, e.g. a Cas 9 protein. In a highly preferred embodiment the Cas protein is a Cas9 protein, e.g. SpCas9. In aspects of the invention the Cas protein has one or more mutations selected from the group consisting of D10A, E762A, H840A, N854A, N863A and D986A. In a highly preferred embodiment the Cas protein has the D10A mutation.

Aspects of the invention relate to the expression of the gene product being decreased or a template polynucleotide being further introduced into the DNA molecule encoding the gene product or an intervening sequence being excised precisely by allowing the two 5' overhangs to reanneal and ligate or the activity or function of the gene product being altered or the expression of the gene product being increased. In an embodiment of the invention, the gene product is a protein. In preferred embodiments of the invention the vectors of the system are viral vectors. In a further embodiment, the vectors of the system are delivered via liposomes, nanoparticles, exosomes, microvesicles, or a gene-gun.

In one aspect, the invention provides a method of modifying a target polynucleotide in a liver cell. In some embodiments, the method comprises allowing a CRISPR complex to bind to the target polynucleotide to effect cleavage of said target polynucleotide thereby modifying the target polynucleotide, wherein the CRISPR complex comprises a CRISPR enzyme complexed with a guide sequence hybridized or hybridizable to a target sequence within said target polynucleotide, wherein said guide sequence is linked to a tracr mate sequence which in turn hybridizes to a tracr sequence. In some embodiments, said cleavage comprises cleaving one or two strands at the location of the target sequence by said CRISPR enzyme. In some embodiments, said cleavage results in decreased transcription of a target gene. In some embodiments, the method further comprises repairing said cleaved target polynucleotide by homologous recombination with an exogenous template polynucleotide, wherein said repair results in a mutation comprising an insertion, deletion, or substitution of one or more nucleotides of said target polynucleotide. In some embodiments, said mutation results in one or more amino acid changes in a protein expressed from a gene comprising the target sequence. In some embodiments, the method further comprises delivering one or more vectors to said eukaryotic cell, wherein the one or more vectors drive expression of one or more of: the CRISPR enzyme, the guide sequence linked to the tracr mate sequence, and the tracr sequence. In some embodiments, said vectors are delivered to the eukaryotic cell in a subject. In some embodiments, said modifying takes place in said eukaryotic cell in a cell culture. In some embodiments, the method further comprises isolating said eukaryotic cell from a subject prior to said modifying. In some embodiments, the method further comprises returning said eukaryotic cell and/or cells derived therefrom to said subject.

In one aspect, the invention provides a method of modifying expression of a polynucleotide in a liver cell. In some embodiments, the method comprises allowing a CRISPR complex to bind to the polynucleotide such that said binding results in increased or decreased expression of said polynucleotide; wherein the CRISPR complex comprises a CRISPR enzyme complexed with a guide sequence hybridized or hybridizable to a target sequence within said polynucleotide, wherein said guide sequence is linked to a tracr mate sequence which in turn hybridizes to a tracr sequence. In some embodiments, the method further comprises delivering one or more vectors to said eukaryotic cells, wherein the one or more vectors drive expression of one or more of: the CRISPR enzyme, the guide sequence linked to the tracr mate sequence, and the tracr sequence.

In one aspect, the invention provides a method of generating a model liver cell comprising a mutated disease gene. In some embodiments, a disease gene is any gene associated with an increase in the risk of having or developing a disease. In some embodiments, the method comprises (a) introducing one or more vectors into a eukaryotic cell, wherein the one or more vectors drive expression of one or more of: a CRISPR enzyme, a guide sequence linked to a tracr mate sequence, and a tracr sequence; and (b) allowing a CRISPR complex to bind to a target polynucleotide to effect cleavage of the target polynucleotide within said disease gene, wherein the CRISPR complex comprises the CRISPR enzyme complexed with (1) the guide sequence that is hybridized or hybridizable to the target sequence within the target polynucleotide, and (2) the tracr mate sequence that is hybridized or hybridizable to the tracr sequence, thereby generating a model eukaryotic cell comprising a mutated disease gene. In some embodiments, said cleavage comprises cleaving one or two strands at the location of the target sequence by said CRISPR enzyme. In some embodiments, said cleavage results in decreased transcription of a target gene. In some embodiments, the method further comprises repairing said cleaved target polynucleotide by homologous recombination with an exogenous template polynucleotide, wherein said repair results in a mutation comprising an insertion, deletion, or substitution of one or more nucleotides of said target polynucleotide. In some embodiments, said mutation results in one or more amino acid changes in a protein expression from a gene comprising the target sequence.

In one aspect the invention provides for a method of selecting one or more liver cell(s) by introducing one or more mutations in a gene in the one or more cell (s), the method comprising: introducing one or more vectors into the cell (s), wherein the one or more vectors drive expression of one or more of: a CRISPR enzyme, a guide sequence linked to a tracr mate sequence, a tracr sequence, and an editing template; wherein the editing template comprises the one or more mutations that abolish CRISPR enzyme cleavage; allowing homologous recombination of the editing template with the target polynucleotide in the cell(s) to be selected; allowing a CRISPR complex to bind to a target polynucleotide to effect cleavage of the target polynucleotide within said gene, wherein the CRISPR complex comprises the CRISPR enzyme complexed with (1) the guide sequence that is hybridized or hybridizable to the target sequence within the target polynucleotide, and (2) the tracr mate sequence that is hybridized or hybridizable to the tracr sequence, wherein binding of the CRISPR complex to the target polynucleotide induces cell death, thereby allowing one or more prokaryotic cell(s) in which one or more mutations have been introduced to be selected. In a preferred embodiment, the CRISPR enzyme is Cas9. Aspects of the invention allow for selection of specific cells without requiring a selection marker or a two-step process that may include a counter-selection system.

In one aspect, the invention provides for methods of modifying a target polynucleotide in a liver cell. In some embodiments, the method comprises allowing a CRISPR complex to bind to the target polynucleotide to effect cleavage of said target polynucleotide thereby modifying the target polynucleotide, wherein the CRISPR complex comprises a CRISPR enzyme complexed with a guide sequence hybridized or hybridizable to a target sequence within said target polynucleotide, wherein said guide sequence is linked to a tracr mate sequence which in turn hybridizes to a tracr sequence.

In other embodiments, this invention provides a method of modifying expression of a polynucleotide in a liver cell. The method comprises increasing or decreasing expression of a target polynucleotide by using a CRISPR complex that binds to the polynucleotide.

Where desired, to effect the modification of the expression in a cell, one or more vectors comprising a tracr sequence, a guide sequence linked to the tracr mate sequence, a sequence encoding a CRISPR enzyme is delivered to a cell. In some methods, the one or more vectors comprises a regulatory element operably linked to an enzyme-coding sequence encoding said CRISPR enzyme comprising a nuclear localization sequence; and a regulatory element operably linked to a tracr mate sequence and one or more insertion sites for inserting a guide sequence upstream of the tracr mate sequence. When expressed, the guide sequence directs sequence-specific binding of a CRISPR complex to a target sequence in a cell. Typically, the CRISPR complex comprises a CRISPR enzyme complexed with (1) the guide sequence that is hybridized or hybridizable to the target sequence, and (2) the tracr mate sequence that is hybridized or hybridizable to the tracr sequence.

In some methods, a target polynucleotide can be inactivated to effect the modification of the expression in a cell. For example, upon the binding of a CRISPR complex to a target sequence in a cell, the target polynucleotide is inactivated such that the sequence is not transcribed, the coded protein is not produced, or the sequence does not function as the wild-type sequence does. For example, a protein or microRNA coding sequence may be inactivated such that the protein is not produced.

In certain embodiments, the CRISPR enzyme comprises one or more mutations selected from the group consisting of D10A, E762A, H840A, N854A, N863A or D986A and/or the one or more mutations is in a RuvC1 or HNH domain of the CRISPR enzyme or is a mutation as otherwise as discussed herein. In some embodiments, the CRISPR enzyme has one or more mutations in a catalytic domain, wherein when transcribed, the tracr mate sequence hybridizes to the tracr sequence and the guide sequence directs sequence-specific binding of a CRISPR complex to the target sequence, and wherein the enzyme further comprises a functional domain. In some embodiments, the functional domain is a transcriptional activation domain, preferably VP64. In some embodiments, the functional domain is a transcription repression domain, preferably KRAB. In some embodiments, the transcription repression domain is SID, or concatemers of SID (eg SID4×). In some embodiments, the functional domain is an epigenetic modifying domain, such that an epigenetic modifying enzyme is provided. In some embodiments, the functional domain is an activation domain, which may be the P65 activation domain.

In some embodiments, the CRISPR enzyme is a type I or III CRISPR enzyme, but is preferably a type II CRISPR enzyme. This type II CRISPR enzyme may be any Cas enzyme. A Cas enzyme may be identified as Cas9 as this can refer to the general class of enzymes that share homology to the biggest nuclease with multiple nuclease domains from the type II CRISPR system. Most preferably, the Cas9 enzyme is from, or is derived from, spCas9 or saCas9. By derived, Applicants mean that the derived enzyme is largely based, in the sense of having a high degree of sequence homology with, a wildtype enzyme, but that it has been mutated (modified) in some way as described herein.

It will be appreciated that the terms Cas and CRISPR enzyme are generally used herein interchangeably, unless otherwise apparent. As mentioned above, many of the residue numberings used herein refer to the Cas9 enzyme from the type II CRISPR locus in *Streptococcus pyogenes*. However, it will be appreciated that this invention includes many more Cas9s from other species of microbes, such as SpCas9, SaCa9, St1Cas9 and so forth.

An example of a codon optimized sequence, in this instance optimized for humans (i.e. being optimized for expression in humans) is provided herein, see the SaCas9 human codon optimized sequence. Whilst this is preferred, it will be appreciated that other examples are possible and codon optimization for a host species is known.

Preferably, delivery is in the form of a vector which may be a viral vector, such as a *lenti*- or baculo- or preferably adeno-viral/adeno-associated viral vectors, but other means of delivery are known (such as yeast systems, microvesicles, gene guns/means of attaching vectors to gold nanoparticles) and are provided. A vector may mean not only a viral or yeast system (for instance, where the nucleic acids of interest may be operably linked to and under the control of (in terms of expression, such as to ultimately provide a processed RNA) a promoter), but also direct delivery of nucleic acids into a host cell. While in herein methods the vector may be a viral vector and this is advantageously an AAV, other viral vectors as herein discussed can be employed, such as lentivirus. For example, baculoviruses may be used for expression in insect cells. These insect cells may, in turn be useful for producing large quantities of further vectors, such as AAV or lentivirus vectors adapted for delivery of the present invention. Also envisaged is a method of delivering the present CRISPR enzyme comprising delivering to a cell mRNA encoding the CRISPR enzyme. It will be appreciated that in certain embodiments the CRISPR enzyme is truncated, and/or comprised of less than one thousand amino acids or less than four thousand amino acids, and/or is a nuclease or nickase, and/or is codon-optimized, and/or comprises one or more mutations, and/or comprises a chimeric CRISPR enzyme, and/or the other options as herein discussed. AAV and lentiviral vectors are preferred.

In certain embodiments, the target sequence is flanked or followed, at its 3' end, by a PAM suitable for the CRISPR enzyme, typically a Cas and in particular a Cas9.

For example, a suitable PAM is 5'-NRG or 5'-NNGRR for SpCas9 or SaCas9 enzymes (or derived enzymes), respectively.

It will be appreciated that SpCas9 or SaCas9 are those from or derived from *S. pyogenes* or *S. aureus* Cas9.

Some points in the present application are summarised below:

AAV2/8

Preferred delivery for the CRISPR-Cas system is through a viral vector. This vector may be a lentiviral vector or an AAV vector, as discussed at some length herein. Whet we have particularly showed is that AAV is a preferred example of a viral vector. Within that, we gone on to show that AAV8 and in particular AAV2/8 (AAV8 packaged with AAV2 packaging signal ITR) is useful in delivery to the liver, especially in vivo.

Phenotypic Changes Seen In Vivo

As discussed elsewhere, we have been able to show, in vivo, that phenotypic change can be detected. This is a significant step forward as a deficiency often leveled at RNAi is that no lasting effect is seen. With the present invention, phenotypic change can be seen in the liver for the first time. A preferred arrangement to achieve this is to use that in Example 36. Important elements of this are preferred alone or in combination, namely:

- Sa Cas9;
- Use of a chimeric guide RNA comprising the guide, tracr sequence and tracr mate;
- For the tracr sequence, Sa tracr is preferable to recruit the Sa Cas9;
- AAV8 or more preferably AAV2/8;
- For experimental purposes, Rosa26 is a useful negative control;
- Although use of the CMV promoter in an AAV vector is helpful, use of a liver-specific promoter such as TBG is particularly effective;
- The target or targets may be wide-ranging as CRISPR has been shown to have broad applicability across targets, once they guides are successfully delivered and the Css9 enzymes are suitably expressed. However, preferred targets in the liver (against which the guides may be designed) nevertheless include one or more of: PCSK9; Hmgcr; SERPINA1; ApoB; and.or LDL.

Accordingly, in some embodiments it is particularly preferred that the Cas enzyme is an Sa Cas9. Preferably, the CRISPRS-Cas polynucleotide sequence is chimeric and preferably includes an Sa tracr where the Cas9 is an Sa Cas9. A viral vector may be used which is preferably AAV2/8. Furthermore, a liver-specific promoter is ideal and a preferred example is TBG. All of these may be used in combination to provide a chimeric CRISPRS-Cas polynucleotide sequence including an Sa tracr, wherein the Cas9 is an SaCas9, and the vector is AAV2/8, with at least the Cas9 under the control of a liver-specific such as TBG. Any of the above targets may be sued with this system, in particular ApoB due to its importance in obesity.

Yin and Anderson's later Nature Biotech Paper (NBT 2884, referenced herein) provides further support for the in vivo phenotypic changes that we have already shown.

Additional data that we provide in Example 37, then adds further support by demonstrating efficient in vivo editing of somatic liver tissue via Cas9. Moreover, delivery via AAV2/8 and the use of an SaCas9 again show the usefulness of this particular approach in vivo. The preferred ApoB was again targeted.

Later examples 38 and 39 show excellent in vivo data for efficacy in inducing a phenotypic change in vivo: specifically ApoB, a lipid metabolism gene, whilst Example 40 shows the applicability of the technique to post-mitotic cells, of which liver is an important example. Example 41 shows that multiple epitope tags are preferable for detection purposes.

Although viral vectors are preferred, in some embodiments, the use of cell penetrating peptides is a viable alternative and so is also preferred.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2A-2F shows an exemplary CRISPR system, a possible mechanism of action, an example adaptation for expression in eukaryotic cells, and results of tests assessing nuclear localization and CRISPR activity. FIG. 2C discloses SEQ ID NOS 607 and 608, respectively, in order of appearance. FIG. 2E discloses SEQ ID NOS 609-611, respectively, in order of appearance. FIG. 2F discloses SEQ ID NOS 612-616, respectively, in order of appearance.

FIG. 3A discloses SEQ ID NOS 617, 610 and 618-628, respectively, in order of appearance. FIG. 3C discloses SEQ ID NO: 617.

FIG. 4E discloses SEQ ID NO: 629. FIG. 4F discloses SEQ ID NOS 630 and 631, respectively, in order of appearance. FIG. 4G discloses SEQ ID NOS 632-636, respectively, in order of appearance.

FIG. 5 provides a table of protospacer sequences (SEQ ID NOS 95, 94, 93, 637-642, 97, 96, and 643-647, respectively, in order of appearance) and summarizes modification efficiency results for protospacer targets designed based on exemplary *S. pyogenes* and *S. thermophilus* CRISPR systems with corresponding PAMs against loci in human and mouse genomes. Cells were transfected with Cas9 and either pre-crRNA/tracrRNA or chimeric RNA, and analyzed 72 hours after transfection. Percent indels are calculated based on Surveyor assay results from indicated cell lines (N=3 for all protospacer targets, errors are S.E.M., N.D. indicates not detectable using the Surveyor assay, and N.T. indicates not tested in this study).

FIG. 6A discloses SEQ ID NOS 648 and 649, respectively, in order of appearance.

FIG. 8A discloses SEQ ID NOS 650-652, respectively, in order of appearance. FIG. 8B discloses SEQ ID NOS 653, 184, and 185, respectively, in order of appearance.

FIG. 9A-9C shows histograms of distances between adjacent *S. pyogenes* SF370 locus 1 PAM (NGG) (FIG. 9A) and *S. thermophilus* LMD9 locus 2 PAM (NNAGAAW) (FIG. 9B) in the human genome; and distances for each PAM by chromosome (Chr) (FIG. 9C).

FIG. 10B discloses SEQ ID NOS 654 and 655, respectively, in order of appearance. FIG. 10C discloses SEQ ID NO: 656.

FIG. 11A discloses SEQ ID NO: 657. FIG. 11B discloses SEQ ID NOS 658-660, respectively, in order of appearance.

FIG. 12A discloses SEQ ID NO: 661.

FIG. 14 discloses SEQ ID NO: 656.

FIG. 15 provides a table of sequences (SEQ ID NOS 664-671, 193-194, and 672-673, respectively, in order of appearance) for primers and probes used for Surveyor, RFLP, genomic sequencing, and Northern blot assays.

FIG. 16A discloses SEQ ID NO: 674.

FIG. 18 discloses SEQ ID NOS 675-753, respectively, in order of appearance.

FIG. 21C discloses SEQ ID NOS 754-756, 754, 757, and 756, respectively, in order of appearance.

FIG. 22A discloses SEQ ID NOS 758-760, respectively, in order of appearance. FIG. 22B discloses SEQ ID NO: 761.

FIG. 24A-24M shows sequences where the mutation points are located within the SpCas9 gene. FIG. 24A-24M discloses the nucleotide sequence as SEQ ID NO: 762 and the amino acid sequence as SEQ ID NO: 763.

FIG. 27 shows delivery and in vivo mouse brain Cas9 expression data.

FIG. 30B discloses SEQ ID NOS 754-756, 754, 757, and 756, respectively, in order of appearance.

FIG. 31A-31C shows the repair strategy for Cystic Fibrosis delta F508 mutation. FIG. 31A discloses the nucleotide sequence as SEQ ID NO: 764 and the amino acid sequence as 765. FIG. 31B discloses SEQ ID NO: 674. FIG. 31C discloses the nucleotide sequence as SEQ ID NO: 766 and the amino acid sequence as SEQ ID NO: 767.

FIG. 51 shows (top) a list of spacing (as indicated by the pattern of arrangement for two PAM sequences) between pairs of guide RNAs (SEQ ID NOS 768-784, respectively, in order of appearance). Only guide RNA pairs satisfying patterns 1, 2, 3, 4 exhibited indels when used with SpCas9 (D10A) nickase. (bottom) Gel images showing that combination of SpCas9(D10A) with pairs of guide RNA satisfying patterns 1, 2, 3, 4 led to the formation of indels in the target site.

FIG. 52 shows a list of U6 reverse primer sequences (SEQ ID NOS 785-831 and 787, respectively, in order of appearance) used to generate U6-guide RNA expression cassettes. Each primer needs to be paired with the U6 forward primer “gcactgagggcctatttcccatgattc” (SEQ ID NO: 1) to generate amplicons containing U6 and the desired guide RNA.

FIG. 53 discloses the nucleotide sequence as SEQ ID NO: 832 and the amino acid sequences as SEQ ID NOS 833-836, respectively, in order of appearance.

FIG. 54 shows on (right) a gel image indicating the formation of indels at the target site when variable 5' overhangs are present after cleavage by the Cas9 nickase targeted by different pairs of guide RNAs. on (left) a table indicating the lane numbers of the gel on the right and various parameters including identifying the guide RNA pairs used and the length of the 5' overhang present following cleavage by the Cas9 nickase.

FIG. 55 shows a Genomic sequence map from the human Emx1 locus showing the locations of the different pairs of guide RNAs that result in the gel patterns of FIG. 54 (right) and which are further described in Example 35. FIG. 55 discloses the nucleotide sequence as SEQ ID NO: 832 and the amino acid sequences as SEQ ID NOS 833-836, respectively, in order of appearance.

FIG. 70B discloses SEQ ID NOS 837-838 and 837, respectively, in order of appearance.

FIG. 71A discloses SEQ ID NO: 839. FIG. 71F discloses SEQ ID NOS 408, 414, 426, and 429, respectively, in order of appearance.

FIG. 72B discloses SEQ ID NOS 840-843, respectively, in order of appearance. FIG. 72E discloses SEQ ID NOS 844-850, respectively, in order of appearance.

FIG. 73 discloses SEQ ID NOS 851-867, top to bottom, left to right, respectively, in order of appearance.

FIG. 74 discloses SEQ ID NO: 868.

FIG. 79 shows oil red staining to detect hepatic lipid accumulation phenotype in vivo following AAV-Cas9-sgRNA delivery. The scale bar in each square represents 20 micrometres.

FIG. 85A-85H (Example 40) shows CRISPR-Cas9 system delivery and targeting of Mecp2 locus in the mouse brain. (a) AAV-SpCas9 and AAV-SpGuide(Mecp2) expression vectors. The sgRNA vector contains encoding sequence of the GFP-KASH fusion protein for identification of transduced neurons. (b) Expression of HA-Cas9 and GFP-KASH in the dorsal dentate gyrus (DG) of mouse hippocampus. Scale bar, 100 μm. (c) Quantification of cells efficiently targeted by the dual-vector Cas9-CRISPR system. (d) Graphical representation of the mouse Mecp2 locus showing Cas9 target location; sgRNA indicated. PAM sequence. Representative mutation patterns detected by sequencing of Mecp2 locus were shown (e) SURVEYOR™ assay gel showing modification of the Mecp2 locus, 2 weeks after AAV delivery in the DG region. (f) Western blot analysis of MeCP2 protein expression in the targeted brain region and quantification of MeCP2 protein levels in dorsal DG (t-test, $^{}p<0.001$, n=4 from 3 animals, error bars: s.e.m.). (g) Images of the dorsal DG region, 2 weeks after CRISPR-Cas9 targeting of Mecp2 locus. Scale bar, 150 (h) Quantification of MeCP2 positive cells population within all detected cells (DAPI staining) in the targeted brain region in compare to control collateral site (t-test, $^{}p<0.0001$, n=290 and 249 cells from 2 animals, respectively; error bars: s.e.m). (ITR—inverted terminal repeat; HA—hemagglutinin tag; NLS—nuclear localization signal; spA—synthetic polyadenylation signal; U6—PolIII promoter; sgRNA—single guide RNA; hSyn—human synapsin 1 promoter; GFP—green fluorescent protein; KASH—Klarsicht, ANC1, Syne Homology nuclear transmembrane domain; bGH pA—bovine growth hormone polyadenylatio signal; WPRE—Woodchuck Hepatitis virus posttranscriptional regulatory element). FIG. 85**D discloses SEQ ID NOS 870-884, respectively, in order of appearance.

FIG. 87A-87E (Example 40) shows cell-autonomous defects in cellular response properties of neurons after CRISPR-mediated MeCP2 knockdown. (a) Cartoon showing in vivo experiment configuration from mouse visual cortex and visual stimulation parameter. $GFP^+$ neuron is shown. Scale bar, 20 (b) Cartoon showing recording configuration in layer 2/3 excitatory neurons that receive both contra- and ipsilateral eye specific input. (c) Normalized spike shape shows regular spiking excitatory neurons. (d,e) Average OSI (d) and evoked FR (e) were measured from $GFP^+$ cells expressing Mecp2 and control sgRNA, respectively (t-test, $^*p<0.05$; numbers in graph indicate numbers of recorded cells; n=2-3 animals; error bars: s.e.m).

FIG. 88**B discloses SEQ ID NOS 885-890, respectively, in order of appearance.

FIG. 90A discloses SEQ ID NOS 891-894, 872, and 895, respectively, in order of appearance.

FIG. 94A-94B (Example 40) shows multiplex genome targeting of DNMT family members in vitro. (a) Dnmt3a, Dnmt1 and Dnmt3b targeting sequences and corresponding protospacer adjacent motifs (PAM). (b) SURVEYOR™ nuclease assay analysis of Neuro-2a cells 48 hours after transfection with SpCas9 and DNMT 3×sgRNA vector targeting Dnmt3a, Dnmt1 and Dnmt3b loci. Efficient genome editing of all three targeted genes is shown. FIG. 94A discloses SEQ ID NOS 896-898, respectively, in order of appearance.

FIG. 95A-95C (Example 40) shows next generation sequencing of targeted Dnmt3a, Dnmt1 and Dnmt3b loci. Examples of sequencing results of mutated Dnmt3a (a) (SEQ ID NOS 899-900, 2, 901-905, 903, and 906-908, respectively, in order of appearance), Dnmt1 (b) (SEQ ID NOS 909-910, 3, 911-912, 911, 913-914, 913, 911, and 915-916, respectively, in order of appearance) and Dnmt3b (c) (SEQ ID NOS 898, 917, 4, and 918-923, respectively, in order of appearance) loci after in vivo delivery of SpCas9 and DNMT 3×sgRNA into the mouse dentate gyrus. Green: wild-type sequence, dashes: deleted bases, bases: insertion or mutations. Arrowheads indicate CRISPR-SpCas9 cutting site. The full sequences used in this figure are provide as SEQ ID NO: 2, SEQ ID NO: 3, and SEQ ID NO: 4 for the Dnmt3a, the Dnmt1 and the Dnmt3b loci, respectively. They are:

```
(Dnmt3a):
                                         SEQ ID NO: 2
CCT CCG TGT CAG CGA CCC ATG CCA A

(Dnmt1):
                                         SEQ ID NO: 3
CCA GCG TCG AAC AGC TCC AGC CCG

(Dnmt3b)
                                         SEQ ID NO: 4
AGA GGG TGC CAG CGG GTA TAT GAG G
```

Figure 96:
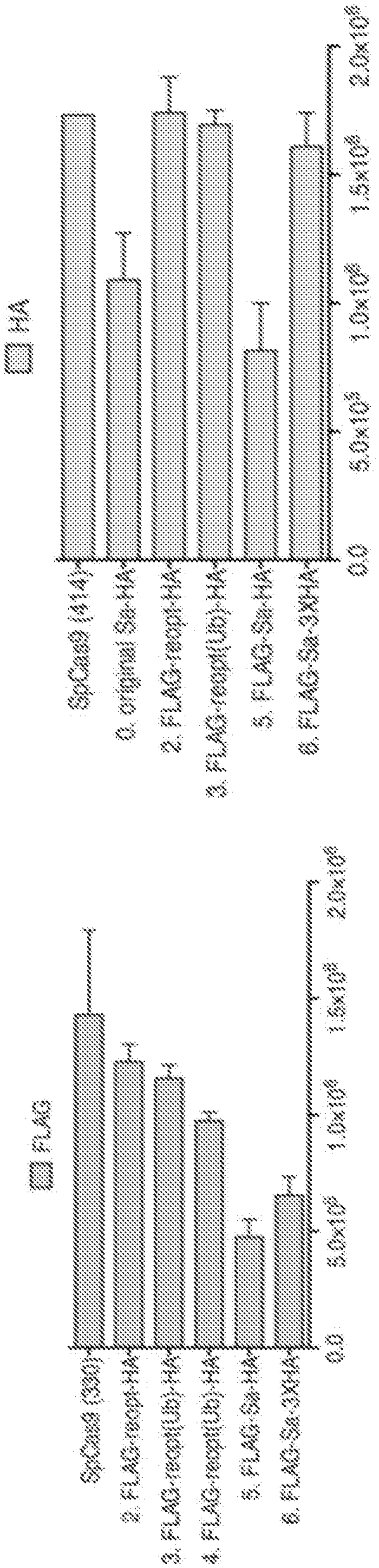

FIG. 96 shows SaCas9 protein sequences are codon optimized ("reopt") and have their ubiquitination signals removed ("reopt(Ub)") for enhanced expression. Protein blots against FLAG- and HA-tagged SaCas9 show approximately 2-fold increased expression of optimized SaCas9 (reopt, #2-4) relative to the original constructs (#0, 5, and 6), and similar level as SpCas9 (SpCas9 330, top bar left panel; SpCas9 414, top bar right panel). The addition of 3×HA tagging (right panel #6) improves detection signal over the 1×HA tag (right panel #5) by fold.

Figure 97:
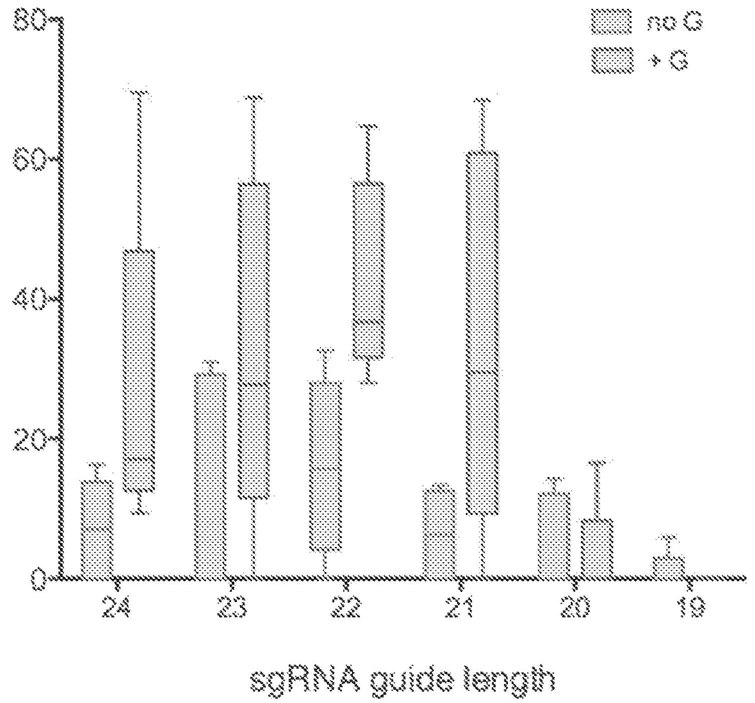

FIG. 97 shows indel efficiency using sgRNAs transcribed by U6 promoter as-is (left hand bar for each number of nts) or appending a "G" (right hand bar for each number of nts and with a thicker border) to 5'-most position of sgRNA for SaCas9. Total sgRNA spacer lengths (including G) are indicated on the x-axis. Graph represents with aggregated data from 5 sgRNAs.

Figure 98:
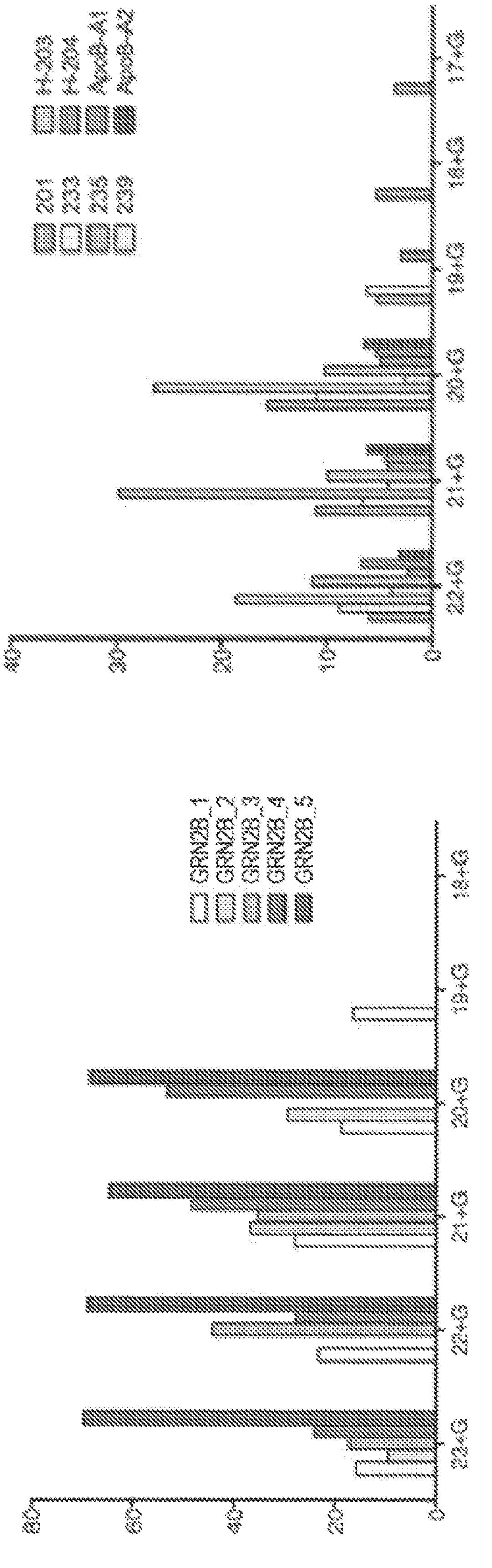

FIG. 98 shows optimization of sgRNA spacer length (x axis). Graphs show indel formation with different lengths of sgRNA spacer in HEK (left) and Hepa (right) cells.

The figures herein are for illustrative purposes only and are not necessarily drawn to scale.

DETAILED DESCRIPTION OF THE INVENTION

With respect to general information on CRISPR-Cas Systems: Reference is made to U.S. provisional patent applications 61/758,468; 61/802,174; 61/806,375; 61/814,263; 61/819,803 and 61/828,130, filed on Jan. 30, 2013; Mar. 15, 2013; Mar. 28, 2013; Apr. 20, 2013; May 6, 2013 and May 28, 2013 respectively. Reference is also made to U.S. provisional patent application 61/836,123, filed on Jun. 17, 2013. Reference is also made to U.S. provisional patent applications 61/736,527 and 61/748,427, filed on Dec. 12, 2012 and Jan. 2, 2013, respectively. Reference is also made to U.S. provisional patent application 61/791,409, filed on Mar. 15, 2013. Reference is also made to U.S. provisional patent application 61/799,800, filed Mar. 15, 2013. Reference is also made to U.S. provisional patent applications 61/835,931, 61/835,936, 61/836,127, 61/836,101, 61/836,080 and 61/835,973, each filed Jun. 17, 2013. Further reference is made to U.S. provisional patent applications 61/862,468 and 61/862,355 filed on Aug. 5, 2013; 61/871,301 filed on Aug. 28, 2013; 61/960,777 filed on Sep. 25, 2013 and 61/961,980 filed on Oct. 28, 2013. Further reference is made to U.S. provisional patent application 61/915,325, filed on Dec. 12, 2013. Each of these applications, and all documents cited therein or during their prosecution ("appln cited documents") and all documents cited or referenced in the appln cited documents, together with any instructions, descriptions, product specifications, and product sheets for any products mentioned therein or in any document therein and incorporated by reference herein, are hereby incorporated herein by reference, and may be employed in the practice of the invention. All documents (e.g., these applications and the appln cited documents) are incorporated herein by reference to the same extent as if each individual document was specifically and individually indicated to be incorporated by reference.

Also with respect to general information on CRISPR-Cas Systems, mention is made of:

*Multiplex genome engineering using CRISPR/Cas systems*. Cong, L., Ran, F. A., Cox, D., Lin, S., Barretto, R., Habib, N., Hsu, P. D., Wu, X., Jiang, W., Marraffini, L. A., & Zhang, F. *Science* February 15; 339(6121): 819-23 (2013);

*RNA-guided editing of bacterial genomes using CRISPR-Cas systems*. Jiang W., Bikard D., Cox D., Zhang F, Marraffini L A. Nat Biotechnol March; 31(3):233-9 (2013);

*One-Step Generation of Mice Carrying Mutations in Multiple Genes by CRISPR/Cas-Mediated Genome Engineering*. Wang H., Yang H., Shivalila C S., Dawlaty M M., Cheng A W., Zhang F., Jaenisch R. Cell May 9; 153(4):910-8 (2013);

*Optical control of mammalian endogenous transcription and epigenetic states. Konermann S, Brigham M D, Trevino A E, Hsu P D, Heidenreich M, Cong L, Platt R J, Scott D A, Church G M, Zhang F. Nature.* 2013 Aug. 22; 500(7463):472-6. doi: 10.1038/Nature12466. Epub 2013 Aug. 23;

*Double Nicking by RNA-Guided CRISPR Cas9 for Enhanced Genome Editing Specificity*. Ran, F A., Hsu, P D., Lin, C Y., Gootenberg, J S., Konermann, S., Trevino, A E., Scott, D A., Inoue, A., Matoba, S., Zhang, Y., & Zhang, F. Cell August 28. pii: S0092-8674(13)01015-5. (2013);

*DNA targeting specificity of RNA guided Cas9 nucleases*. Hsu, P., Scott, D., Weinstein, J., Ran, F A., Konermann, S., Agarwala, V., Li, Y., Fine, E., Wu, X., Shalem, O., Cradick, T J., Marraffini, L A., Bao, G., & Zhang, F. *Nat Biotechnol* doi:10.1038/nbt.2647 (2013);

*Genome engineering using the CRISPR-Cas9 system*. Ran, F A., Hsu, P D., Wright, J., Agarwala, V., Scott, D A., Zhang, F. Nature Protocols November; 8(11):2281-308. (2013);

*Genome-Scale CRISPR-Cas9 Knockout Screening in Human Cells*. Shalem, O., Sanjana, N E., Hartenian, E., Shi, X., Scott, D A., Mikkelson, T., Heckl, D., Ebert, B L., Root, D E., Doench, J G., Zhang, F. *Science December* 12. (2013). [Epub ahead of print];

*Crystal structure of cas9 in complex with guide RNA and target DNA*. Nishimasu, H., Ran, F A., Hsu, P D., Konermann, S., Shehata, S I., Dohmae, N., Ishitani, R., Zhang, F., Nureki, O. *Cell* February 27. (2014). 156 (5):935-49;

*Genome-wide binding of the CRISPR endonuclease Cas9 in mammalian cells*. Wu X., Scott D A., Kriz A J., Chiu A C., Hsu P D., Dadon D B., Cheng A W., Trevino A E., Konermann S., Chen S., Jaenisch R., Zhang F., Sharp P A. *Nat Biotechnol*. (2014) April 20. doi: 10.1038/nbt.2889, and

*Development and Applications of CRISPR-Cas9 for Genome Engineering*, Hsu et al, Cell 157, 1262-1278 (Jun. 5, 2014) (Hsu 2014), each of which is incorporated herein by reference, and discussed briefly below:

Cong et al. engineered type II CRISPR/Cas systems for use in eukaryotic cells based on both *Streptococcus thermophilus* Cas9 and also *Streptoccocus pyogenes* Cas9 and demonstrated that Cas9 nucleases can be directed by short RNAs to induce precise cleavage of DNA in human and mouse cells. Their study further showed that Cas9 as converted into a nicking enzyme can be used to facilitate homology-directed repair in eukaryotic cells with minimal mutagenic activity. Additionally, their study demonstrated that multiple guide sequences can be encoded into a single CRISPR array to enable simultaneous editing of several at endogenous genomic loci sites within the mammalian genome, demonstrating easy programmability and wide applicability of the RNA-guided nuclease technology. This ability to use RNA to program sequence specific DNA cleavage in cells defined a new class of genome engineering tools. These studies further showed that other CRISPR loci are likely to be transplantable into mammalian cells and can also mediate mammalian genome cleavage. Importantly, it can be envisaged that several aspects of the CRISPR/Cas system can be further improved to increase its efficiency and versatility.

Jiang et al. used the clustered, regularly interspaced, short palindromic repeats (CRISPR)-associated Cas9 endonuclease complexed with dual-RNAs to introduce precise mutations in the genomes of *Streptococcus pneumoniae* and *Escherichia coli*. The approach relied on dual-RNA:Cas9-directed cleavage at the targeted genomic site to kill unmutated cells and circumvents the need for selectable markers or counter-selection systems. The study reported reprogramming dual-RNA:Cas9 specificity by changing the sequence of short CRISPR RNA (crRNA) to make single- and multinucleotide changes carried on editing templates. The study showed that simultaneous use of two crRNAs enabled multiplex mutagenesis. Furthermore, when the approach was used in combination with recombineering, in *S. pneumoniae*, nearly 100% of cells that were recovered using the described approach contained the desired mutation, and in *E. coli*, 65% that were recovered contained the mutation.

Konermann et al. addressed the need in the art for versatile and robust technologies that enable optical and chemical modulation of DNA-binding domains based CRISPR Cas9 enzyme and also Transcriptional Activator Like Effectors As discussed in the present specification, the Cas9 nuclease from the microbial CRISPR-Cas system is targeted to specific genomic loci by a 20 nt guide sequence, which can tolerate certain mismatches to the DNA target and thereby promote undesired off-target mutagenesis. To address this, Ran et al. described an approach that combined a Cas9 nickase mutant with paired guide RNAs to introduce targeted double-strand breaks. Because individual nicks in the genome are repaired with high fidelity, simultaneous nicking via appropriately offset guide RNAs is required for double-stranded breaks and extends the number of specifically recognized bases for target cleavage. The authors demonstrated that using paired nicking can reduce off-target activity by 50- to 1,500-fold in cell lines and to facilitate gene knockout in mouse zygotes without sacrificing on-target cleavage efficiency. This versatile strategy enables a wide variety of genome editing applications that require high specificity.

Hsu et al. characterized SpCas9 targeting specificity in human cells to inform the selection of target sites and avoid off-target effects. The study evaluated >700 guide RNA variants and SpCas9-induced indel mutation levels at >100 predicted genomic off-target loci in 293T and 293FT cells. The authors that SpCas9 tolerates mismatches between guide RNA and target DNA at different positions in a sequence-dependent manner, sensitive to the number, position and distribution of mismatches. The authors further showed that SpCas9-mediated cleavage is unaffected by DNA methylation and that the dosage of SpCas9 and sgRNA can be titrated to minimize off-target modification. Additionally, to facilitate mammalian genome engineering applications, the authors reported providing a web-based software tool to guide the selection and validation of target sequences as well as off-target analyses.

Ran et al. described a set of tools for Cas9-mediated genome editing via non-homologous end joining (NHEJ) or homology-directed repair (HDR) in mammalian cells, as well as generation of modified cell lines for downstream functional studies. To minimize off-target cleavage, the authors further described a double-nicking strategy using the Cas9 nickase mutant with paired guide RNAs. The protocol provided by the authors experimentally derived guidelines for the selection of target sites, evaluation of cleavage efficiency and analysis of off-target activity. The studies showed that beginning with target design, gene modifications can be achieved within as little as 1-2 weeks, and modified clonal cell lines can be derived within 2-3 weeks.

Shalem et al. described a new way to interrogate gene function on a genome-wide scale. Their studies showed that delivery of a genome-scale CRISPR-Cas9 knockout (GeCKO) library targeted 18,080 genes with 64,751 unique guide sequences enabled both negative and positive selection screening in human cells. First, the authors showed use of the GeCKO library to identify genes essential for cell viability in cancer and pluripotent stem cells. Next, in a melanoma model, the authors screened for genes whose loss is involved in resistance to vemurafenib, a therapeutic that inhibits mutant protein kinase BRAF. Their studies showed that the highest-ranking candidates included previously validated genes NF1 and MED12 as well as novel hits NF2, CUL3, TADA2B, and TADA1. The authors observed a high level of consistency between independent guide RNAs targeting the same gene and a high rate of hit confirmation, and thus demonstrated the promise of genome-scale screening with Cas9.

Nishimasu et al. reported the crystal structure of *Streptococcus pyogenes* Cas9 in complex with sgRNA and its target DNA at 2.5 A° resolution. The structure revealed a bilobed architecture composed of target recognition and nuclease lobes, accommodating the sgRNA:DNA heteroduplex in a positively charged groove at their interface. Whereas the recognition lobe is essential for binding sgRNA and DNA, the nuclease lobe contains the HNH and RuvC nuclease domains, which are properly positioned for cleavage of the complementary and non-complementary strands of the target DNA, respectively. The nuclease lobe also contains a carboxyl-terminal domain responsible for the interaction with the protospacer adjacent motif (PAM). This high-resolution structure and accompanying functional analyses have revealed the molecular mechanism of RNA-guided DNA targeting by Cas9, thus paving the way for the rational design of new, versatile genome-editing technologies.

Wu et al. mapped genome-wide binding sites of a catalytically inactive Cas9 (dCas9) from *Streptococcus pyogenes* loaded with single guide RNAs (sgRNAs) in mouse embryonic stem cells (mESCs). The authors showed that each of the four sgRNAs tested targets dCas9 to between tens and thousands of genomic sites, frequently characterized by a 5-nucleotide seed region in the sgRNA and an NGG protospacer adjacent motif (PAM). Chromatin inaccessibility decreases dCas9 binding to other sites with matching seed sequences; thus 70% of off-target sites are associated with genes. The authors showed that targeted sequencing of 295 dCas9 binding sites in mESCs transfected with catalytically active Cas9 identified only one site mutated above background levels. The authors proposed a two-state model for Cas9 binding and cleavage, in which a seed match triggers binding but extensive pairing with target DNA is required for cleavage.

Hsu 2014 is a review article that discusses generally CRISPR-Cas9 history from yogurt to genome editing, including genetic screening of cells, that is in the information, data and findings of the applications in the lineage of this specification filed prior to Jun. 5, 2014. The general teachings of Hsu 2014 do not involve the specific models, animals of the instant specification.

The invention relates to the engineering and optimization of systems, methods and compositions used for the control of gene expression involving sequence targeting, such as genome perturbation or gene-editing, that relate to the CRISPR-Cas system and components thereof. In advantageous embodiments, the Cas enzyme is Cas9.

The CRISPRS-Cas polynucleotide sequence is generally referred to herein as the guide, or even as guide RNA (sgRNA), although it will be appreciated that this terminology was not as commonplace previously. Furthermore, reference is made herein to a CRISPR-Cas9 system, although it will be appreciated that the invention can be broadly practiced as to any CRISPR-Cas system. Advantageously the Cas has a nuclease function either to induce a DSB, a nick or a double nick. Cas9 is preferred and SaCas9 is particularly preferred.

Example 38 showed that both genotypic and, crucially, phenotypic changes are seen with CRISPR-Cas systems. Not only that, but the CRISPR-Cas9 system was effective at inducing a phenotypic change in vivo.

Specifically, the target was ApoB, a lipid metabolism gene. What is so encouraging is that ApoB can be said to be the “gold-standard” in liver delivery, and is widely used in mouse models of obesity.

Delivery was via intravenous injection. An AAV vector was used, as well as a Liver-specific promoter (TBG) for Cas9.

Delivery through expression from a viral vector as seen here is an improvement over Anderson/Yin’s (NBT 2884) use of hydrodynamic delivery as the delivery method, because hydrodynamic delivery requires several mls of fluid to be injected which is stressful on the murine body and can be fatal. Hydrodynamic delivery is best suited for delivery of plasmid (naked) DNA, whereas we have shown that packaging the guide and Cas9 sequences within a viral delivery vector is preferable in terms of greatly increased efficiency. Indeed, only relatively small volumes need to be introduced, and this can be done intravenously (i.v.), which is likely to be much more acceptable therapeutically.

What was particularly encouraging was that not only was a genotypic change seen in a “gold-standard” gene for liver such as ApoB, but phenotypic changes were also recorded. Previous work with PCSK9 had shown genotypic, but not phenotypic changes, so the phenotypic changes seen with ApoB validate the plausibility of CRISPR delivery to, and its ability to effect phenotypic change in, the Liver. This is in combination with the more therapeutically acceptable means of delivery (i.v. compared to hydrodynamic delivery). As such, viral delivery of CRISPR-Cas9 system (guide and Cas9) is preferred, especially intravenously).

Potential targets include: PCSK9, HMGCR, APOB, LDLR, ANGPTL3, F8, F9/FIX, AAT, FAH, HPD, TAT, ATP7B, UGT1A1, OTC, ARH.

Accordingly, provided are methods of inducing a phenotypic change in vivo comprising administering the CRISPR-Cas9 system to the target cells, for instance the liver. Suitable delivery routes are described herein but i.v. injection is preferred in some embodiments. Viral vectors are preferred, particularly AAV, in particular AAV serotype 2/8.

Also provided is a CRISPR-Cas9 system comprising one or more guides targeting lipid metabolism genes, for instance ApoB. Methods of treating obesity, comprising administering said CRISPR-Cas9 system, are also envisaged. A mouse model comprising one or more liver gene knock down(s), especially of lipid metabolism gene(s), for instance including ApoB, are preferred.

Liver specific promoters for the Cas9 will be apparent but may include those listed above. A preferred example is TBG.

As shown in Example 39, the guide may be 18-23 nucleotides in length. It may be 18-22, or 19-22, or 18-21, 20-22, but is preferably 22 and most preferably 21 nucleotides in length.

Also provided is proof of principle of successful packaging of a guide sequence into a SaCas9 intron. Accordingly, the CRISPR-Cas9 systems, wherein one or more guide sequences are packaged (positioned or inserted) into a Cas9 intron, are preferred.

The H1 promoter can be used and may be preferable in some circumstances.

Expanding on the work by Ran (Cell, 154, 21 Aug. 2013), the degree of overlap in the dual guide approach using a D10A Double-Nickase was investigated. Optimal results were shown between −5 and +1 bp (5' to 5'). Accordingly, it is prefer to use a dual guide approach to minimise off target effects. These preferably overlap, or come close to overlapping, at their 5' ends, on different stands of DNA at the genomic target. Preferably, the overlap is in the range of −5 to +1 bp. In these instances, it will be appreciated that the Cas9 is a double nickase, such as the preferred D10A variant.

Example 40 provides, inter alia: a first demonstration of successful AAV-mediated Cas9 delivery in vivo as well as efficient genome modification in post-mitotic neurons; for the development of a nuclear tagging technique which enables easy isolation of neuronal nuclei from Cas9 and sgRNA-expressing cells; a demonstration of applications toward RNAseq analysis of neuronal transcriptome; how electrophysiological studies and other techniques can be integrated with Cas9-mediated genome perturbation to determine phenotypic changes; how electrophysiological studies and other techniques can be integrated with Cas9-mediated genome perturbation to determine phenotypic changes; how electrophysiological studies and other techniques can be integrated with Cas9-mediated genome perturbation to determine phenotypic changes; and a demonstration of multiplex targeting and the ability to study gene function on rodent behavior using Cas9-mediated genome editing.

The present invention provides: understanding and testing of gene function, including the creation and testing of models; including as to gene therapy and hence gene therapy, gene therapy methods and uses for gene therapy are within the ambit of the skilled person from this disclosure.

An additional aspect, discussed further below, is in relation to a method for Nuclear Tagging.

It will be appreciated that reference to CRISPR-Cas9 systems herein is a short-hand for referring to the Cas9 enzymes provided herein in combination with the guides or guides used to target one or more genomic sequences. (And that the invention can also be broadly considered as to CRISPR-Cas systems.) Reference to guide(s) includes sgRNA, as well as the chimeric polynucleotide sequences described herein which comprises the guide sequences capable of hybridising to target sequences in the genome of the subject, a tracr mate sequence and a tracr sequence.

The data essentially shows phenotypic changes resulting from gene knock down using two separate CRISPR-Cas9 systems according to the invention (guide RNA in combination with a Cas9 enzyme), in this case to successfully perturb gene function. The chosen tissue was brain tissue, but the results provide proof of principle for a wide range of post-mitotic tissues. This is an important distinction, because previous work has focussed on dividing cells (i.e. pre-mitotic).

In other words, whereas SpCas9 has been broadly used to engineer dividing cells, we demonstrate that SpCas9 can also be used to engineer the genome of postmitotic neurons. This is done with high efficiency via NHEJ-mediated indel generation to create knock downs, but therapeutic uses involving correction via the HDR mechanism (upon provision of a repair template) are also envisaged. Both are dependent on successful delivery and functional expression of the Cas9 and RNA guide or guides, which is shown here.

The fact that genotypic changes induced by the CRISPR-Cas9 systems then results in a phenotypic change is also important for both of the above areas (gene function and gene therapy).

The first CRISPR-Cas9 system employed guide sequences directed at (targeting) Mecp2. A dual vector CRISPR-Cas9 system, with one vector comprising the guide and one comprising the Cas9, was successfully employed showing further proof of principle for such dual vector systems. The dual vector CRISPR-Cas9 system was successfully delivered, via stereotactical injection, to two separate locations in the brain, specifically the Hippocampal dentate gyrus and the visual cortex. In both cases, gene perturbation of the same gene, Mecp2, was seen indicating that the dual vector system was successfully delivered and acted as expected, with transcription and functional activity in the Cas9 enzyme (in this case an SpCas9), and successful recruitment of the Cas9 to the genomic target sequence by the guide sequences.

AAV-mediated in vivo delivery of SpCas9 and sgRNA provides a rapid and powerful technology for achieving precise genomic perturbations within intact neural circuits. As such, the vector used was an AAV vector, adding further evidence for their use in general and in dual vector CRISPR-Cas9 systems in particular, especially in post-mitotic cells and tissues, and in particular in the brain.

It will of course be appreciated that the choice of promoter is important in achieving expression from the CRISPR-Cas9 system, in particular the Cas9 or both guide(s) and Cas9. Suitable examples for cell and cell lifecycle stage specificity can be determined from the literature. Nevertheless, we provide some non-limiting examples: TBG, a liver-specific promoter and is used here to drive expression of SaCas9; the H1 promoter; a truncated H1 promoter; the U6 promoter. Also, as guides do not necessarily need a specific promoter, one or more guides could similarly packaged into a/the Cas9 intron.

The second CRISPR-Cas9 system used included a multiplex approach. One key advantage of the SpCas9 system is its ability to facilitate multiplex genome editing. This second system successfully targeted three or more genes from the same family (in this case, Dmnt1, 3a and 3b) by including suitable guides and resulted in stable knockouts of multiple genes. This has broad implications for probing the function of not only individual genes, but also whole gene families, in the tissues of living animals. This is particularly important for tissues such as the brain where this has not been possible before, or could only be achieved through long years of classical genetics. Applicants have shown that single or multiple gene perturbation (even complete knock down) can occur in post-mitotic cells in a normal animal. However, this could equally apply to a model organism (for instance one already carrying a gene mutation or perturbation or comprising altered expression of some kind) or a transgenic organism, lending a quick alternative to existing methods of producing model organisms and using model organisms to understand gene function. Further guides (and/or whole CRISPR-Cas9 systems) could be employed to make later rounds of gene perturbations and/or reinstatements (restoring gene function for instance by correction of the perturbed gene through provision, for instance, of a repair template, such as ssDNA suitable for HDR) within the same organism.

In fact, in general, SpCas9-mediated targeting of single or multiple genes can recapitulate morphological, electrophysiological, and behavioral phenotypes observed using classical, more time-consuming genetic mouse models.

Alternatively to knocking down whole gene families or related genes, the data here also provides proof of principle that simultaneous knock down or three or more unrelated genes is equally feasible. This is applicable across all tissues, but is particularly strongly presented in respect of post-mitotic tissues, especially the brain.

Another useful aspect of the work is that it showed that a combined, or integrated, approach could be taken to studying gene function, employing CRISPR to effect a genotypic change and then using classical tools such as electrophysiology (particularly relevant to brain and CNS tissue), biochemical, sequencing, electrophysiological, and/or behavioral readouts to establish what, if any, phenotypic changes result from the genotypic change induced by the CRISPR-Cas9 system. For example in the brain, this allows us to study the function of individual as wells as groups of genes in neural processes and their roles in brain disorders in vivo.

The successful perturbation of genes in this work is equally applicable to correction or reinstatement of gene function, i.e. the use of CRISPR-Cas9 systems in gene therapy. This is particularly in relation to targeting post-mitotic cells, especially the brain.

In general, the use of CRISPR-Cas9 systems show improvements over existing techniques such as Zn fingers, which take a long time to design and produce and cannot multiplex and shRNA, which has too many off-target effects whereas CRISPR off-target effects can be minimised by using double-nickase approaches.

Targeting of Tissues

The new work supports the use of CRISPR-Cas9 systems to target genes in post-mitotic cells through delivery of the CRISPR-Cas9 system to the appropriate location (i.e. to cells within the organs or tissues of interest). Preferred tissues are within the following organs:

- Kidney;
- Digestive System including the stomach, pancreas, duodenum, ileum and/or colon;
- Heart;
- Lung;
- Brain, in particular neurones, and/or CNS in general;
- Eye, including retinal tissue;
- Ear, including the inner ear;
- Skin;
- Muscle;
- Bone; and/or
- Liver in general, although this is excluded in some embodiments as it is also the subject of a separate application.

It will be appreciated that many of the above may comprise pre-mitotic cells, but that this aspect of the invention is directed to post-mitotic cells or tissues within those organs.

In particular, we prefer that the organ is the kidney or the brain. Within the brain, the data specifically shows delivery to the Hippocampal dentate gyrus and the visual cortex, which are preferred tissues, although other tissues including any one or more of the following: primary motor cortex, primary auditory cortex, primary somatosensory cortex, cerebellum, main olfactory bulb, prefrontal cortex, endopiriform nucleus, amygdala, substantia nigra, striatum, palladium, thalamus, hypothalamus, Parabranchial nucleus, superior olivary complex, cochlear nuclei, mammillary nuclei, are also preferred in some embodiments. Liver tissue are also preferred in some embodiments.

Cells from the brain, and neurones in particular, are especially preferred.

The choice of promoter to drive expression of the CRISPR-Cas9 system, especially the Cas9 is important, as mentioned above. To be considered when selecting a promoter are the cell cycle stage (early/late) and the cell type as promoters will be specific for one of more cell types and cell-cycle stages. Suitable promoters may include any one or more of the following, in some embodiments: Suitable promoters may include any one or more of the following, in some embodiments:

| Cell Type | Promoter |
|---|---|
| Excitatory neurons | CamkII |
| Fast spiking interneurons | Parvalbumin |
| All interneurons | vGAT |
| Dopaminoceptive neurons | DR1 |
| Dopaminoceptive neurons | DR2 |
| Astroglia | GFAP |
| Activated neurons | Arc |

The dual vector CRISPR-Cas9 system used in targeting the brain, in particular the Hippocampal dentate gyrus, packaged SpCas9 and sgRNA expression cassettes on two separate viral vectors. Cas9s, in particular SpCAs9s, are therefore preferably delivered by adenoviral vectors, especially AAV (i.e. as AAV-SpCas9). Guides are preferably delivered as sgRNA expression cassettes by adenoviral vectors, especially AAV (i.e. as AAV-SpGuide). A preferred route for this tissue (the Hippocampal dentate gyrus) and for the brain in general is stereotactical injection.

Understanding and Testing of Gene Function, and the Creation and Use of Models to so do Conditions include Huntington's, but essentially include any condition found in post-mitotic cells and especially those that may benefit from being studied in vivo or lack a useful model.

As mentioned above, CRISPR-Cas9 systems can be used to interrogate the function of one or more genes in post-mitotic cells. This may be achieved through delivery and expression of the CRISPR-Cas9 system to the post-mitotic cell, wherein the guide(s) of the CRISPR-Cas9 system are designed to recruit the Cas9 to the genomic target or targets of interest. Equally, where the Cas9 is already comprised within the post-mitotic cell, protein (transcribed) form, then delivery of the guides to the post-mitotic cell will suffice. Where the Cas9 is already comprised within the post-mitotic cell, in polynucleotide (untranscribed), then delivery of the guides to the post-mitotic cell as well as induction of transcription of the Cas9 polynucleotide will be necessary. Having the Cas9 under the control of an inducible or repressible promoter, such as the tet (tetracycline) on-off system may be advantageous here.

One aspect that is particularly promising is the integration of CRISPR techniques with phenotypic assays to determine the phenotypic changes, if any, resulting from gene perturbations, especially knock downs. For instance, Example 40 shows what can be achieved with targeted genomic perturbations coupled with quantitative readouts to provide insights into the biological function of specific genomic elements. In particular, Cas9-mediated in vivo genome editing in the brain can also be coupled with electrophysiological recording to study the effect of genomic perturbation on specific cell types or circuit components. In a broader sense, use of the CRISPR-Cas9 systems (to provide Cas9-mediated genomic perturbations) can be combined with biochemical, sequencing, electrophysiological, and behavioral analysis to study the function of the targeted genomic element.

Thus in one aspect, there is provided: a method of interrogating the function of one or more genes in a post-mitotic cell, comprising:

inducing a deficient genotype or gene knock down proliferative as described below; and determining changes in expression of the one or more genes in the proliferative condition thereby interrogating the function of the one or more genes.

Optionally, the method may also include:

transplanting the second population of cells into the subject thereby inducing the condition associated with the deficient genotype or gene knock down. This may be prior to the determining step.

The following applies broadly to appropriate aspects of the invention. The cell may be in a subject, such as a human, animal or model organism, so that gene function is interrogated in vivo. However, it is also envisaged that the cell may be ex vivo, for instance in a cell culture or in a model organ or organoid. In some embodiments, the method may include isolation a first population of cells from the subject, optionally culturing them and transducing them with one or more CRISPR-Cas9 systems. Further optional culturing may follow. Transplantation of the transduced cells back into the subject may then occur.

The cell may be from any of the tissues or organs described herein. The brain is one preferred example, providing for said method of interrogating the function of one or more genes, wherein the post-mitotic cell is a brain cell, for instance a neuron. Particularly in vivo, this allows for the interrogation of gene function on animal behaviour. The animal is preferably a mammal, for instance a rodent. Given the complexity of the nervous system, which consists of intricate networks of heterogeneous cell types, being able to efficiently edit the genome of neurons in vivo enables direct testing of gene function in relevant cell types embedded in native contexts. This is supported by our data where knockout mice showed impaired memory consolidation when tested under trained context conditions Our results demonstrate that CRIPSR-Cas9-mediated knockout of DNMT family members in dentate gyrus neurons is sufficient to probe the function of genes in behavioral tasks This shows the versatility of Cas9s in facilitating targeted gene knockout in the mammalian brain in vivo, for studying genes functions and, in particular, for dissection of neuronal circuits. Introducing stable knockouts of multiple genes in the brain of living animals will have potentially far-reaching applications, such as causal interrogation of multigenic mechanisms in physiological and neuropathological conditions.

The specifics of this work are that we chose the mouse Mecp2 promoter (235 bp, pMecp2)7 and a minimal polyadenylation signal (48 bp, spA) based on their ability to achieve sufficient levels of SpCas9 expression in cultured primary mouse cortical neurons. Mecp2 gene, plays a principal role in Rett syndrome, a type of autism spectrum disorder. To target Mecp2, we first designed several sgRNAs targeting exon 3 of the mouse Mecp2 gene and evaluated their efficacy using Neuro-2a cells. The most efficient sgRNA was identified using the SURVEYOR nuclease assay. The delivery was via stereotactical injection of a mixture (1:1 ratio) of high titer AAV-SpCas9 and AAV-SpGuide. We also successfully tested the possibility of multiplex genome editing in the brain we designed a multiplex sgRNA expression vector consisting of three sgRNAs in tandem, along with GFP-KASH for nuclei labelling.

Thus, also provided are methods of inducing conditions involving one or more gene knockdowns in a post-mitotic cell. Examples of such conditions are numerous, but may include Rett syndrome, as exemplified. Suitable promoters will be apparent, and the Mecp2 promoter is ideal for Rett syndrome. One way to select a promoter to drive expression of the CRISPR-Cas9 system, in particular the Cas9, is to select the promoter for the gene of interest.

Thus in one aspect, there is provided: A method of inducing a conditions involving one or more deficient genes (or genotypes) or gene knockdowns in a post-mitotic cell, comprising:

transducing a first population of cells with a non-naturally occurring or engineered composition comprising a vector system comprising one or more vectors comprising a first regulatory element operably linked to a CRISPR-Cas system chimeric RNA (chiRNA) polynucleotide sequence, wherein the polynucleotide sequence comprises one or more, preferably three or more, guide sequences capable of hybridizing to three or more target sequences in genome of the subject, a tracr mate sequence, and a tracr sequence, and a second regulatory element operably linked to an enzyme-coding sequence encoding a CRISPR enzyme comprising at list one or more nuclear localization sequences (NLSs), wherein (a), (b) and (c) are arranged in a 5' to 3' orientation, wherein components I and II are located on the same or different vectors of the system, wherein when transcribed, the tracr mate sequence hybridizes to the tracr sequence and the guide sequence direct sequence-specific binding of CRISPR complexes to the target sequence, wherein the CRISPR complex comprises the CRISPR enzyme complexed with (1) the guide sequence that is hybridized or hybridizable to the target sequence, and (2) the tracr mate sequence that is hybridized or hybridizable to the tracr sequence, wherein the CRISPR enzyme alters the genome of the first population of cells to obtain a second population of cells bearing the one or more deficient genes or knocked down genes.

Optionally, the method may also include:

isolating a first population of cells from the subject.

Optionally, the method may also include:

transplanting the second population of cells into the subject thereby inducing the proliferative condition.

This essentially involves inducing a non-functional (which include partially non-functional) genotype into the target cell, to thereby provide a model for study (including future restoration of the functional genotype).

CRISPR-Cas9 systems can also be used to facilitate the study of gene functions in cellular assays by enabling targeted knockout in post-mitotic neurons.

Methods for delivering nucleotides to neuronal cells are well known and reviewed in The Journal of Neuroscience, by Karra and Dahm (5 May 2010, 30(18): 6171-6177; doi: 10.1523/JNEUROSCI.0183-10.2010). Examples include electrical transfection methods (such as electroporation, nucleofection, and single-cell electroporation); chemical transfection methods (such as Ca2+ phosphate co/precipitation and lipofection); viral delivery (such as Adenoviral, Adeno-Associated Virus (AAV), Lentiviral and Herpes Simplex Virus); and physical transfection methods (such as microinjection and biolistics (DNA-coated gold particles). All of these can be used for delivery of the CRISPR-Cas9 system, but lipofection or viral methods are preferred, especially AAV or Lentiviral.

Models

Models are provided with single or multiple genes knocked down. An example would be a rodent model for Rett syndrome, a Mecp2 knock down. Others include Dmnt family knock downs, specifically Dmnt1, 3a and 3b knock downs. As such, models studying neurological conditions are provided. All that needs to be done is to identify the target genes of interest, design suitable guide(s) and include these in a suitable CRISPR-Cas9 system and deliver it to the post-mitotic cell(s) whether in vivo or ex vivo, as required. For instance, the models may have altered dendritic tree morphology and/or spine density are provided.

As mentioned above, models tissues are also provided, such as organoids or "Liver on a chip" or non-liver equivalents thereof such as ear, kidney and brain tissues, for instance on a chip or supported in a scaffold. Animal models and model tissues are preferred. These may be already transformed with Cas9 so that they comprise Cas9 in nucleotide or protein form, as mentioned above. These have the advantage that Cas9 does not need to be delivered alongside the guide(s) and this in turn may allow for a much greater degree of (guide) multiplexing to be accommodated within the delivery vectors. Again, use of inducible or repressible systems such as tet-on or tet-off, may be advantageous here.

Models obtainable using the CRISPR-Cas9 system are herein described and within the ambit of the skilled person from this disclosure and the knowledge in the art. Due to the versatility of the CRISPR-Cas9 system, the range of possible models, whether human, rodent, mammalian or otherwise is hugely diverse and this can be established by simple selection of appropriates guide(s). Methods of creating such models are also provided.

Gene Therapy

The data in Example 40 focuses on gene perturbation, primarily knock down. Gene knock down is likely to be only a small, if important, part of the total quorum of possible applications of CRISPR-Cas9 systems to gene therapy. As already shown in the Yin and Anderson paper (Nature Biotech 2884 published online 30 Mar. 2014), a functional phenotype can be restored following correction of a deficient mutation in hereditary tyrosinemia type I (HTI), an otherwise fatal condition caused by mutation of fumarylacetoacetate hydrolase (FAH) (G to A in the last nucleotide in exon 8) which causes skipping of exon 8 during splicing and results in the formation of a truncated, unstable FAH protein, leading to accumulation of toxic metabolites. Correction of the A mutation back to the wild-type G geneotype resulted in a restored phenotype.

As such, the approaches taken in the present work can plausibly be applied to gene therapy. In particular, the dual vector approach, the nuclear tagging approach, the specifics of the brain delivery (the form of injection, the promoters and/or viral vectors used), as well as the multiplexing (use of multiple guides for multiple targets either within the same or within different genes) could equally be applied to correctional gene therapy (i.e. where a deficient genotype is corrected) as to the exemplified gene knock down. The main difference between correctional gene therapy and gene knock down is that in order to correct a deficient genotype, such as a point mutation (for instance in Cystic Fibrosis, see ref Schwank et al, Cell Stem Cell 13, 653-658 5 Dec. 2013), it is advantageous to provide a repair template to stimulate the HDR mechanism and ideally provide a suitable Cas9 nickase as well.

Accordingly, the present vectors preferably target post-mitotic cells. Where the guide or guides target a deficient genotype, are preferably also provided with a repair template, for instance ssDNA corresponding to the corrected sequence (a genotype providing functional phenotype). Repair templates are described herein. The Cas9 may be provided in the same or a different vector from the guide or guides. The vectors are preferably viral vectors, more preferably adenoviral vectors and most preferably AAV vectors. Delivery to the cells is preferably by intravenous injection or by stereotactic injection, as appropriate. The selection of the promoter can also be important and preferred examples are provided herein.

Methods of treating genetic diseases or conditions caused by, or associated with, a deficient genotype in post-mitotic cells are provided, comprising delivery of the CRISPR-Cas9 system to the appropriate cell. A deficient genotype may be the non-wild type genotype. In particular, single point mutations and/or monogenic disorders are especially suited to treatment using CRISPR-Cas9 systems. Where multiple genes require editing or correcting, then a multiplex approach may be used to target them all simultaneously. Alternatively, two or more rounds of different CRISPR-Cas9 systems could be envisaged. Preferably, the wild-type genotype is corrected for. It does not necessarily have to be the most common genotype, provided that function is restored or improved in the phenotype.

An example of a restored phenotype is the restoration of hearing to restore VGLUT3 function and hence hearing in the inner ear of mice (Omar Akil, Rebecca P. Seal, Kevin Burke, Chuansong Wang, Aurash Alemi, Matthew During, Robert H. Edwards, Lawrence R. Lustig. Restoration of Hearing in the VGLUT3 Knockout Mouse Using Virally Mediated Gene Therapy. *Neuron,* 2012; 75 (2): 283 DOI: 10.1016/j.neuron.2012.05.019). This was using AAV-mediated delivery of VGLUT3 itself, but it is entirely plausible that CRISPR-Cas9 system could also be used, preferably also using AAV vectors, to target the cells of the inner ear and correct the non-functional VGLUT3 genotype, with similar phenotypic consequences, namely restoration of hearing. As such, delivery of the CRISPR-Cas9 system to the inner ear, preferably using AAV vectors, is preferred, thus treating hearing loss. Indeed, restoration of gene function in sensory organs such as the eye, including the retina, nose and ear (particularly the inner ear) is preferred.

A relatively recent overview, which includes a discussion of disorders in post-mitotic tissues (eye, ear and beyond) is Kaufmann et al (EMBO Mol Med (2013(5, p 1642-1661). This confirms the usefulness of AAV in the correction of monogenic disorders in post-mitotic tissues. It states that "in combination with other characteristics such as low inflammatory activity, they have shown to have an excellent safety profile and are therefore highly attractive tools for in vivo gene therapy. Indeed, Glybera® is a recombinant AAV for direct intramuscular injection . . . " The paper, with citations, reviews gene therapy in the retina, central nervous system, liver, skeletal and cardiac muscle as target tissues. And, with citations, indicates that "initial studies exploited the prototype AAV serotype 2 vector, the portfolio of AAV vectors has recently been expanded to include additional serotypes and even engineered capsids." Kaufmann and the documents cited in Kaufmann are hereby incorporated herein by reference.

RNAseq Analysis of the Transcriptome

The combination of SpCas9-mediated genome perturbation and population level RNAseq analysis provides a way to characterize transcriptional regulation and suggest genes that may be important to specific functions or disease processes in the cells under consideration. In particular, the cells are from the brain, in particular neurones. Fast-acting techniques such as a CRISPR-Cas9 system are advantageous in studying the transcriptome, which is, by its nature, transient. As such, the use of CRISPR-Cas9 systems according to the present invention in analysis of the transcriptome (RNAseq) are provided.

Nuclear Tagging Method

To facilitate immunofluorescence identification of SpCas9-expressing neurons, we tagged SpCas9 with a HA-epitope tag (derived from human influenza hemaglutinin, a general epitope tag widely used in expression vectors).

For the AAV-SpGuide vector, we packaged an U6-sgRNA expression cassette as well as the green fluorescent protein (GFP)-fused with the KASH nuclear trans-membrane domain driven by the human Synapsin I promoter. The GFP-KASH fusion protein directs GFP to the outer nuclear membrane and enables fluorescence-based identification and purification of intact neuronal nuclei transduced by AAV-SpGuide.

Accordingly, the vectors of the present invention are preferably adapted in a similar fashion. Thus, the vectors are provided wherein the Cas9 is tagged with an epitope tag, such as the HA-epitope tag. The Cas9 may be any of the Cas9s described herein, for instance Sp or SaCas9 and may be any variant (such as D10A double nickase etc), provide that it is or can be tagged appropriately.

The vectors of the present invention may also be adapted so that the guide RNA is packaged within an expression cassette, which comprises:

- a reporter protein; and
- optionally, a suitable promoter for the guide RNA, such as U6;
- wherein the reporter protein is fused with a nuclear trans-membrane domain operably linked to a suitable promoter therefor.

The reporter protein is preferably a fluorescent protein, for instance one of green, red or yellow fluorescent proteins (GFP, RFP, YFP) and so forth.

Examples of nuclear trans-membrane domains include KASH-like domains, Sun2 domains, LEM domains. In some preferred embodiments, the nuclear trans-membrane domain is the KASH nuclear trans-membrane. Preferably, the promoter for the trans-membrane domain is the human Synapsin I promoter; see also documents cited herein.

This tagging approach may be used within single or dual vector systems, but preferably within dual vector systems as space is limited in single vector systems and the need for separate tags lessened as well.

Furthermore, each aspect of this tagging technique can be used independently of the other, so that epitope tagging of the Cas9 can be used alone, or the reporter/fluorescent protein cassette approach can be used alone, or more preferably both can be used together.

Multiple or repeat epitope Tags are preferred for the Cas9. In particular, a triple epitope tag was shown in Example 41 to improve detection. The tag is preferably a repeat, more preferably a triple repeat. HA is a preferred Cas9 epitope tag. A triple HA epitope tag is, therefore, preferred in some embodiments.

Kanasty and Anderson (Nature Materials, Vol 12 Nov. 2013) is a useful review, initially submitted on 11 Mar. 2013 and published online on 23 Oct. 2013 of delivery of RNAi. Due to the similarities between RNAi and CRISPR guide sequences, the teaching of this and other art in respect of RNAi is informative for the mechanisms of delivering the guides in our CRISPR-Cas9 system. Some of the techniques described are also be suitable for delivery of the Cas9 as well. In some instance is may be useful to deliver the guides of our CRISPR-Cas9 system separately from the Cas9. This may be as part of a dual-vector delivery system, where the vectors are considered in the broadest light as simply any means of delivery, rather than specifically viral vectors. It is envisaged that the Cas9 may be delivered via a viral vector and that guides specific to genomic targets are delivered separately. As discussed herein, the guides could be delivered via the same vector types as the Cas9, for example a dual-vector system where the Cas9 is delivered in an AAV vector and the guide(s) are delivered in a separate AAV vector. This can be done substantially contemporaneously (i.e. co-delivery), but it could also be done at separate points in time, separated even by weeks or months. For example, if a first round of CRISPR-Cas9 systems have been delivered, but then it is subsequently required to provide further guides, then the original Cas9 which is hopefully still functional in the target cells may be re-used. If the Cas9 is under the control of an inducible promoter, then induction of transcription of new CAs9 in the target cells is preferred. Equally, if a CAs9-expressing model provided for herein is used, then only delivery of guide(s) is necessary. Accordingly, where delivery of guide(s) is required separately from Cas9, then it may be delivered in much the same way as RNAi. As such, the review by Kanasty is helpful in pointing out a number of known approaches that are suitable, with particular focus on the liver, although the means of delivery are generally appropriate for a broad range of cells. Examples include:

"Liposomal delivery system, as well as siRNA conjugated to lipophilic molecules, interact with serum lipoproteins and subsequently gain entry into hepatocytes that take up those lipoproteins;"

PEGylation;

Conjugates such as:

a. Dynamic Polyconjugates (DPCs, 10 nm nanoparticles), which have been shown to deliver RNAi to successfully suppress ApoB (thereby crossing over with our work on targeting ApoB via a CRISPR-Cas9 system); and
b. Triantennary GalNAc conjugates
c. are "both highly effective" especially GalNAc;

Other nanoparticles include:

d. Cyclodextrin Polymer nanoparticles (CDP), including additional formulation components such as adamantine-PEG (AD-PEG) and adamantine-PEG-transferrin (AD-PEG-Tf);
e. Lipid Nanoparticles (LNP), including cationic or ionisable lipids, shielding lipids, cholesterol and endogenous or exogenous targeting ligands. An example of an endogenous targeting ligand is Retinol Binding protein (RBP) useful for targeting hepatic and pancreatic stellate cells, which express the RBP receptor. An example of an exogenous targeting ligand is GalNac, which also targets the liver via the asialoglycoprotein receptor on hepatocytes. A combined approach is seen in Anlylams ALN-VSP;

"Fenestrations in the liver endothelium allow molecules 100-200 nm in diameter to diffuse out of the bloodstream and gain access to the hepatocytes and other liver cells";

Ligands such as GalNAc are suitable for delivery to non-parenchymal liver cells expressing the mannose receptor, and to hepatocytes where conjugation of suitable siRNA to a GalNAc ligand has been shown to successfully suppress PCSK9; and Oligonucleotide nanoparticles (ONPs) composed of composed of complimentary DNA fragments designed to hybridise into a pre-defined 3D structure. Using suitable 3' overhand sequences, 6 siRNA strands could be attached to each particle, even at a specified position. The hydrodynamic diameter was about 29 nm.

These approaches are preferred in some embodiments for delivery of at least the guides for a CRISPR-Cas9 system. Especially preferred are Dynamic Polyconjugates or the use of an endogenous targeting ligands such as Retinol Binding protein or exogenous targeting ligands such as GalNac.

An advantage of the present methods is that the CRISPR system avoids off-target binding and its resulting side effects. This is achieved using systems arranged to have a high degree of sequence specificity for the target DNA.

Cas9

Cas9 optimization may be used to enhance function or to develop new functions, one can generate chimeric Cas9 proteins. Examples that the Applicants have generated are provided in Example 6. Chimeric Cas9 proteins can be made by combining fragments from different Cas9 homologs. For example, two example chimeric Cas9 proteins from the Cas9s described herein. For example, Applicants fused the N-term of St1Cas9 (fragment from this protein is in bold) with C-term of SpCas9. The benefit of making chimeric Cas9s include any or all of: reduced toxicity; improved expression in eukaryotic cells; enhanced specificity; reduced molecular weight of protein, for example, making the protein smaller by combining the smallest domains from different Cas9 homologs; and/or altering the PAM sequence requirement.

The Cas9 may be used as a generic DNA binding protein. For example, and as shown in Example 7, Applicants used Cas9 as a generic DNA binding protein by mutating the two catalytic domains (D10 and H840) responsible for cleaving both strands of the DNA target. In order to upregulate gene transcription at a target locus Applicants fused a transcriptional activation domain (VP64) to Cas9. Other transcriptional activation domains are known. As shown in Example 17, transcriptional activation is possible. As also shown in Example 17, gene repression (in this case of the beta-catenin gene) is possible using a Cas9 repressor (DNA-binding domain) that binds to the target gene sequence, thus repressing its activity.

Cas9 and one or more guide RNA can be delivered using adeno associated virus (AAV), lentivirus, adenovirus or other plasmid or viral vector types, in particular, using formulations and doses from, for example, U.S. Pat. No. 8,454,972 (formulations, doses for adenovirus), U.S. Pat. No. 8,404,658 (formulations, doses for AAV) and U.S. Pat. No. 5,846,946 (formulations, doses for DNA plasmids) and from clinical trials and publications regarding the clinical trials involving lentivirus, AAV and adenovirus. For examples, for AAV, the route of administration, formulation and dose can be as in U.S. Pat. No. 8,454,972 and as in clinical trials involving AAV. For Adenovirus, the route of administration, formulation and dose can be as in U.S. Pat. No. 8,404,658 and as in clinical trials involving adenovirus. For plasmid delivery, the route of administration, formulation and dose can be as in U.S. Pat. No. 5,846,946 and as in clinical studies involving plasmids. Doses may be based on or extrapolated to an average 70 kg individual, and can be adjusted for patients, subjects, mammals of different weight and species. Frequency of administration is within the ambit of the medical or veterinary practitioner (e.g., physician, veterinarian), depending on usual factors including the age, sex, general health, other conditions of the patient or subject and the particular condition or symptoms being addressed.

The viral vectors can be injected into the tissue of interest. For cell-type specific genome modification, the expression of Cas9 can be driven by a cell-type specific promoter. For example, liver-specific expression might use the Albumin promoter and neuron-specific expression might use the Synapsin I promoter.

Transgenic Animals and Plants

Figure 25A:
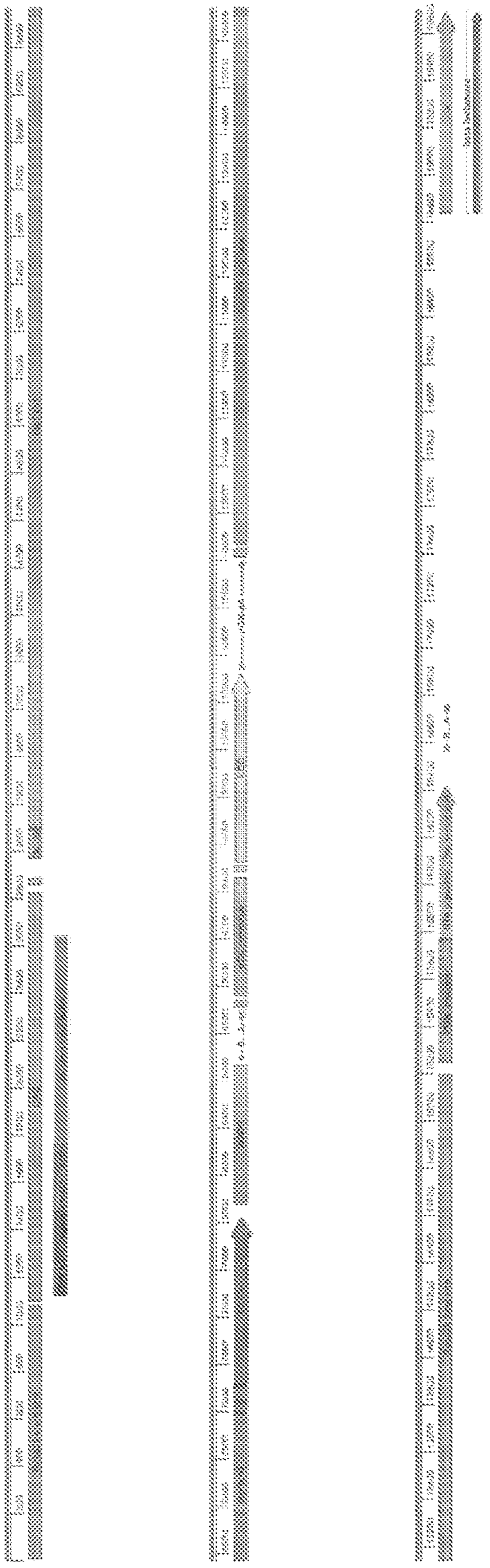
FIG. 25A shows the Conditional Cas9, Rosa26 targeting vector map.
Figure 25B:
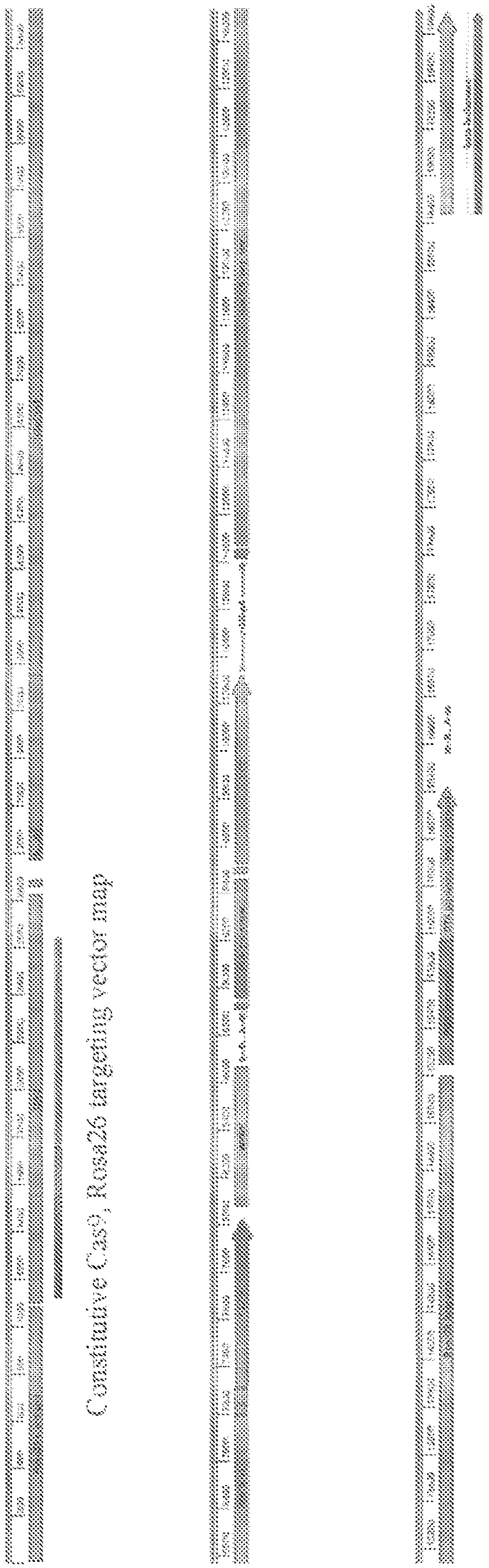
FIG. 25B shows the Constitutive Cas9, Rosa26 targeting vector map.
Figure 26:
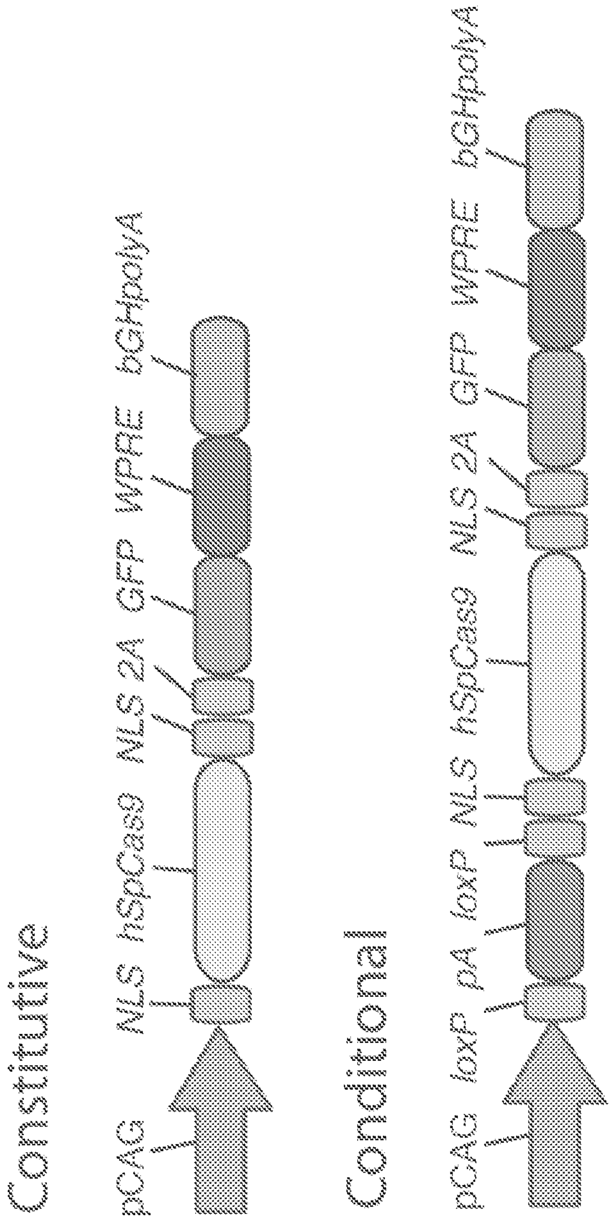
FIG. 26 shows a schematic of the important elements in the Constitutive and Conditional Cas9 constructs.

Transgenic animals (models) are also provided and the following applies equally to ex vivo model tissues and collections of tissues, such as organoids, liver on a chip and so forth. Preferred examples include animals comprising Cas9, in terms of polynucleotides encoding Cas9 or the protein itself. Mice, rats and rabbits are preferred. To generate transgenic mice with the constructs, as exemplified herein one may inject pure, linear DNA into the pronucleus of a zygote from a pseudo pregnant female, e.g. a CB56 female. Founders may then be identified, genotyped, and backcrossed to CB57 mice. The constructs may then be cloned and optionally verified, for instance by Sanger sequencing. Knock outs are envisaged where for instance one or more genes are knocked out in a model. However, are knockins are also envisaged (alone or in combination). An example knockin Cas9 mouse was generated and this is exemplified, but Cas9 knockins are preferred. To generate a Cas9 knock in mice one may target the same constitutive and conditional constructs to the Rosa26 locus, as described herein (FIGS. 25A-B and 26). Methods of US Patent Publication Nos. 20120017290 and 20110265198 assigned to Sangamo BioSciences, Inc. directed to targeting the Rosa locus may be modified to utilize the CRISPR Cas system of the present invention. In another embodiment, the methods of US Patent Publication No. 20130236946 assigned to Cellectis directed to targeting the Rosa locus may also be modified to utilize the CRISPR Cas system of the present invention.

Utility of the conditional Cas9 mouse: Applicants have shown in 293 cells that the Cas9 conditional expression construct can be activated by co-expression with Cre. Applicants also show that the correctly targeted R1 mESCs can have active Cas9 when Cre is expressed. Because Cas9 is followed by the P2A peptide cleavage sequence and then EGFP Applicants identify successful expression by observing EGFP. Applicants have shown Cas9 activation in mESCs. This same concept is what makes the conditional Cas9 mouse so useful. Applicants may cross their conditional Cas9 mouse with a mouse that ubiquitously expresses Cre (ACTB-Cre line) and may arrive at a mouse that expresses Cas9 in every cell. It should only take the delivery of chimeric RNA to induce genome editing in embryonic or adult mice. Interestingly, if the conditional Cas9 mouse is crossed with a mouse expressing Cre under a tissue specific promoter, there should only be Cas9 in the tissues that also express Cre. This approach may be used to edit the genome in only precise tissues by delivering chimeric RNA to the same tissue.

As mentioned above, transgenic animals are also provided. In this regard, transgenic animals, especially mammals such as livestock (cows, sheep, goats and pigs), but also poultry and edible insects, are preferred.

Adeno Associated Virus (AAV)

In terms of in vivo delivery, AAV is advantageous over other viral vectors for a couple of reasons:

Low toxicity (this may be due to the purification method not requiring ultra centrifugation of cell particles that can activate the immune response)

Low probability of causing insertional mutagenesis because it doesn't integrate into the host genome.

AAV has a packaging limit of 4.5 or 4.75 Kb. This means that Cas9 as well as a promoter and transcription terminator have to be all fit into the same viral vector. Constructs larger than 4.5 or 4.75 Kb will lead to significantly reduced virus production. SpCas9 is quite large, the gene itself is over 4.1 Kb, which makes it difficult for packing into AAV. Therefore embodiments of the invention include utilizing homologs of Cas9 that are shorter. For example:

| Cas9 | |
|---|---|
| Species | Size |
| *Corynebacter diphtheriae* | 3252 |
| *Eubacterium ventriosum* | 3321 |
| *Streptococcus pasteurianus* | 3390 |
| *Lactobacillus farciminis* | 3378 |
| *Sphaerochaeta globus* | 3537 |
| *Azospirillum* B510 | 3504 |
| *Gluconacetobacter diazotrophicus* | 3150 |
| *Neisseria cinerea* | 3246 |
| *Roseburia intestinalis* | 3420 |
| *Parvibaculum lavamentivorans* | 3111 |
| *Staphylococcus aureus* | 3159 |
| *Nitratifractor salsuginis* DSM 16511 | 3396 |
| *Campylobacter lari* CF89-12 | 3009 |
| *Streptococcus thermophilus* LMD-9 | 3396 |

These species are therefore, in general, preferred Cas9 species. Applicants have shown delivery and in vivo mouse brain Cas9 expression data.

Two ways to package Cas9 coding nucleic acid molecules, e.g., DNA, into viral vectors to mediate genome modification in vivo are preferred:

To achieve NHEJ-mediated gene knockout:

Single Virus Vector:

Vector containing two or more expression cassettes:

Promoter-Cas9 coding nucleic acid molecule-terminator

Promoter-gRNA1-terminator

Promoter-gRNA2-terminator

Promoter-gRNA(N)-terminator (up to size limit of vector)

Double Virus Vector:

Vector 1 containing one expression cassette for driving the expression of Cas9

Promoter-Cas9 coding nucleic acid molecule-terminator

Vector 2 containing one more expression cassettes for driving the expression of one or more guideRNAs Promoter-gRNA1-terminator Promoter-gRNA(N)-terminator (up to size limit of vector)

To mediate homology-directed repair. In addition to the single and double virus vector approaches described above, an additional vector is used to deliver a homology-direct repair template.

Promoter used to drive Cas9 coding nucleic acid molecule expression can include:

AAV ITR can serve as a promoter: this is advantageous for eliminating the need for an additional promoter element (which can take up space in the vector). The additional space freed up can be used to drive the expression of additional elements (gRNA, etc.). Also, ITR activity is relatively weaker, so can be used to reduce toxicity due to over expression of Cas9.

For ubiquitous expression, can use promoters: CMV, CAG, CBh, PGK, SV40, Ferritin heavy or light chains, etc.

For brain expression, can use promoters: SynapsinI for all neurons, CaMKIIalpha for excitatory neurons, GAD67 or GAD65 or VGAT for GABAergic neurons, etc.

For liver expression, can use Albumin promoter.

For lung expression, can use SP-B.

For endothelial cells, can use ICAM.

For hematopoietic cells can use IFNbeta or CD45.

For Osteoblasts can use OG-2.

Promoter used to drive guide RNA can include:

Pol III promoters such as U6 or H1

Use of Pol II promoter and intronic cassettes to express gRNA

As to AAV, the AAV can be AAV1, AAV2, AAV5 or any combination thereof. One can select the AAV of the AAV with regard to the cells to be targeted; e.g., one can select AAV serotypes 1, 2, 5 or a hybrid capsid AAV1, AAV2, AAV5 or any combination thereof for targeting brain or neuronal cells; and one can select AAV4 for targeting cardiac tissue. AAV8 is useful for delivery to the liver. The above promoters and vectors are preferred individually.

RNA delivery is also a useful method of in vivo delivery. FIG. 27 shows delivery and in vivo mouse brain Cas9 expression data. It is possible to deliver Cas9 and gRNA (and, for instance, HR repair template) into cells using liposomes or nanoparticles. Thus delivery of the CRISPR enzyme, such as a Cas9 and/or delivery of the RNAs of the invention may be in RNA form and via microvesicles, liposomes or nanoparticles. For example, Cas9 mRNA and gRNA can be packaged into liposomal particles for delivery in vivo. Liposomal transfection reagents such as lipofectamine from Life Technologies and other reagents on the market can effectively deliver RNA molecules into the liver.

Enhancing NHEJ or HR efficiency is also helpful for delivery. It is preferred that NHEJ efficiency is enhanced by co-expressing end-processing enzymes such as Trex2 (Dumitrache et al. Genetics. 2011 August; 188(4): 787-797). It is preferred that HR efficiency is increased by transiently inhibiting NHEJ machineries such as Ku70 and Ku86. HR efficiency can also be increased by co-expressing prokaryotic or eukaryotic homologous recombination enzymes such as RecBCD, RecA.

Various means of delivery are described herein, and further discussed in this section.

Viral delivery: The CRISPR enzyme, for instance a Cas9, and/or any of the present RNAs, for instance a guide RNA, can be delivered using adeno associated virus (AAV), lentivirus, adenovirus or other viral vector types, or combinations thereof. Cas9 and one or more guide RNAs can be packaged into one or more viral vectors. In some embodiments, the viral vector is delivered to the tissue of interest by, for example, an intramuscular injection, while other times the viral delivery is via intravenous, transdermal, intranasal, oral, mucosal, or other delivery methods. Such delivery may be either via a single dose, or multiple doses. One skilled in the art understands that the actual dosage to be delivered herein may vary greatly depending upon a variety of factors, such as the vector chose, the target cell, organism, or tissue, the general condition of the subject to be treated, the degree of transformation/modification sought, the administration route, the administration mode, the type of transformation/modification sought, etc.

Such a dosage may further contain, for example, a carrier (water, saline, ethanol, glycerol, lactose, sucrose, calcium phosphate, gelatin, dextran, agar, pectin, peanut oil, sesame oil, etc.), a diluent, a pharmaceutically-acceptable carrier (e.g., phosphate-buffered saline), a pharmaceutically-acceptable excipient, and/or other compounds known in the art. Such a dosage formulation is readily ascertainable by one skilled in the art. The dosage may further contain one or more pharmaceutically acceptable salts such as, for example, a mineral acid salt such as a hydrochloride, a hydrobromide, a phosphate, a sulfate, etc.; and the salts of organic acids such as acetates, propionates, malonates, benzoates, etc. Additionally, auxiliary substances, such as wetting or emulsifying agents, pH buffering substances, gels or gelling materials, flavorings, colorants, microspheres, polymers, suspension agents, etc. may also be present herein. In addition, one or more other conventional pharmaceutical ingredients, such as preservatives, humectants, suspending agents, surfactants, antioxidants, anticaking agents, fillers, chelating agents, coating agents, chemical stabilizers, etc. may also be present, especially if the dosage form is a reconstitutable form. Suitable exemplary ingredients include microcrystalline cellulose, carboxymethylcellulose sodium, polysorbate 80, phenylethyl alcohol, chlorobutanol, potassium sorbate, sorbic acid, sulfur dioxide, propyl gallate, the parabens, ethyl vanillin, glycerin, phenol, parachlorophenol, gelatin, albumin and a combination thereof. A thorough discussion of pharmaceutically acceptable excipients is available in REMINGTON'S PHARMACEUTICAL SCIENCES (Mack Pub. Co., N.J. 1991) which is incorporated by reference herein.

In an embodiment herein the delivery is via an adenovirus, which may be at a single booster dose containing at least $1\times10^5$ particles (also referred to as particle units, pu) of adenoviral vector. In an embodiment herein, the dose preferably is at least about $1\times10^6$ particles (for example, about $1\times10^6$-$1\times10^{12}$ particles), more preferably at least about $1\times10^{10}$ particles, more preferably at least about $1\times10^8$ particles (e.g., about $1\times10^8$-$1\times10^{11}$ particles or about $1\times10^8$-$1\times10^{12}$ particles), and most preferably at least about $1\times10^0$ particles (e.g., about $1\times10^9$-$1\times10^{10}$ particles or about $1\times10^9$-$1\times10^{12}$ particles), or even at least about $1\times10^{10}$ particles (e.g., about $1\times10^{10}$-$1\times10^{12}$ particles) of the adenoviral vector. Alternatively, the dose comprises no more than about $1\times10^{14}$ particles, preferably no more than about $1\times10^{13}$ particles, even more preferably no more than about $1\times10^{12}$ particles, even more preferably no more than about $1\times10^{11}$ particles, and most preferably no more than about $1\times10^{10}$ particles (e.g., no more than about $1\times10^9$ articles). Thus, the dose may contain a single dose of adenoviral vector with, for example, about $1\times10^6$ particle units (pu), about $2\times10^6$ pu, about $4\times10^6$ pu, about $1\times10^7$ pu, about $2\times10^7$ pu, about $4\times10^7$ pu, about $1\times10^8$ pu, about $2\times10^8$ pu, about $4\times10^8$ pu, about $1\times10^9$ pu, about $2\times10^9$ pu, about $4\times10^9$ pu, about $1\times10^{10}$ pu, about $2\times10^{10}$ pu, about $4\times10^{10}$ pu, about $1\times10^{11}$ pu, about $2\times10^{11}$ pu, about $4\times10^{11}$ pu, about $1\times10^{12}$ pu, about $2\times10^{12}$ pu, or about $4\times10^{12}$ pu of adenoviral vector. See, for example, the adenoviral vectors in U.S. Pat. No. 8,454,972 B2 to Nabel, et. al., granted on Jun. 4, 2013; incorporated by reference herein, and the dosages at col 29, lines 36-58 thereof. In an embodiment herein, the adenovirus is delivered via multiple doses.

In an embodiment herein, the delivery is via an AAV. A therapeutically effective dosage for in vivo delivery of the AAV to a human is believed to be in the range of from about 20 to about 50 ml of saline solution containing from about $1\times10^{10}$ to about $1\times10^{10}$ functional AAV/ml solution. The dosage may be adjusted to balance the therapeutic benefit against any side effects. In an embodiment herein, the AAV dose is generally in the range of concentrations of from about $1\times10^5$ to $1\times10^{50}$ genomes AAV, from about $1\times10^8$ to $1\times10^{20}$ genomes AAV, from about $1\times10^{10}$ to about $1\times10^{16}$ genomes, or about $1\times10^{11}$ to about $1\times10^{16}$ genomes AAV. A human dosage may be about $1\times10^{13}$ genomes AAV. Such concentrations may be delivered in from about 0.001 ml to about 100 ml, about 0.05 to about 50 ml, or about 10 to about 25 ml of a carrier solution. Other effective dosages can be readily established by one of ordinary skill in the art through routine trials establishing dose response curves. See, for example, U.S. Pat. No. 8,404,658 B2 to Hajjar, et al., granted on Mar. 26, 2013, at col. 27, lines 45-60.

In an embodiment herein the delivery is via a plasmid. In such plasmid compositions, the dosage should be a sufficient amount of plasmid to elicit a response. For instance, suitable quantities of plasmid DNA in plasmid compositions can be from about 0.1 to about 2 mg, or from about 1 μg to about 10 μg.

The doses herein are based on an average 70 kg individual. The frequency of administration is within the ambit of the medical or veterinary practitioner (e.g., physician, veterinarian), or scientist skilled in the art. Mice used in experiments are about 20 g. From that which is administered to a 20 g mouse, one can extrapolate to a 70 kg individual.

Lentivirus

Lentiviruses are complex retroviruses that have the ability to infect and express their genes in both mitotic and post-mitotic cells. The most commonly known lentivirus is the human immunodeficiency virus (HIV), which uses the envelope glycoproteins of other viruses to target a broad range of cell types.

Lentiviruses may be prepared as follows. After cloning pCasES10 (which contains a lentiviral transfer plasmid backbone), HEK293FT at low passage (p=5) were seeded in a T-75 flask to 50% confluence the day before transfection in DMEM with 10% fetal bovine serum and without antibiotics. After 20 hours, media was changed to OptiMEM (serum-free) media and transfection was done 4 hours later. Cells were transfected with 10 μg of lentiviral transfer plasmid (pCasES10) and the following packaging plasmids: 5 μg of pMD2. G (VSV-g pseudotype), and 7.5 ug of psPAX2 (gag/pol/rev/tat). Transfection was done in 4 mL OptiMEM with a cationic lipid delivery agent (50 uL Lipofectamine 2000 and 100 ul Plus reagent). After 6 hours, the media was changed to antibiotic-free DMEM with 10% fetal bovine serum.

Lentivirus may be purified as follows. Viral supernatants were harvested after 48 hours. Supernatants were first cleared of debris and filtered through a 0.45 um low protein binding (PVDF) filter. They were then spun in a ultracentrifuge for 2 hours at 24,000 rpm. Viral pellets were resuspended in 50 ul of DMEM overnight at 4 C. They were then aliquotted and immediately frozen at −80 C.

In another embodiment, minimal non-primate lentiviral vectors based on the equine infectious anemia virus (EIAV) are also contemplated, especially for ocular gene therapy (see, e.g., Balagaan, J Gene Med 2006; 8: 275-285, Published online 21 Nov. 2005 in Wiley InterScienc; available at the website: interscience.wiley.com. DOI: 10.1002/jgm.845). In another embodiment, RetinoStat®, an equine infectious anemia virus-based lentiviral gene therapy vector that expresses angiostatic proteins endostain and angiostatin that is delivered via a subretinal injection for the treatment of the web form of age-related macular degeneration is also contemplated (see, e.g., Binley et al., HUMAN GENE THERAPY 23:980-991 (September 2012)) may be modified for the CRISPR-Cas system of the present invention.

In another embodiment, self-inactivating lentiviral vectors with an siRNA targeting a common exon shared by HIV tat/rev, a nucleolar-localizing TAR decoy, and an anti-CCR5-specific hammerhead ribozyme (see, e.g., DiGiusto et al. (2010) Sci Transl Med 2:36ra43) may be used/and or adapted to the CRISPR-Cas system of the present invention. A minimum of $2.5\times10^6$ CD34+ cells per kilogram patient weight may be collected and prestimulated for 16 to 20 hours in X-VIVO 15 medium (Lonza) containing 2 micro mol/L-glutamine, stem cell factor (100 ng/ml), Flt-3 ligand (Flt-3L) (100 ng/ml), and thrombopoietin (10 ng/ml) (CellGenix) at a density of $2\times10^6$ cells/ml. Prestimulated cells may be transduced with lentiviral at a multiplicity of infection of 5 for 16 to 24 hours in 75-$cm^2$ tissue culture flasks coated with fibronectin (25 mg/$cm^2$) (RetroNectin, Takara Bio Inc.).

Lentiviral vectors have been disclosed as in the treatment for Parkinson's Disease, see, e.g., US Patent Publication No. 20120295960 and U.S. Pat. Nos. 7,303,910 and 7,351,585. Lentiviral vectors have also been disclosed for the treatment of ocular diseases, see e.g., US Patent Publication Nos. 20060281180, 20090007284, US20110117189; US20090017543; US20070054961, US20100317109. Lentiviral vectors have also been disclosed for delivery to the train, see, e.g., US Patent Publication Nos. US20110293571; US20110293571, US20040013648, US20070025970, US20090111106 and U.S. Pat. No. 7,259,015.

RNA Delivery

RNA delivery: The CRISPR enzyme, for instance a Cas9, and/or any of the present RNAs, for instance a guide RNA, can also be delivered in the form of RNA. Cas9 mRNA can be generated using in vitro transcription. For example, Cas9 mRNA can be synthesized using a PCR cassette containing the following elements: T7_promoter-kozak sequence (GCCACC)-Cas9-3' UTR from beta globin-polyA tail (a string of 120 or more adenines) (SEQ ID NO: 924). The cassette can be used for transcription by T7 polymerase. Guide RNAs can also be transcribed using in vitro transcription from a cassette containing T7_promoter-GG-guide RNA sequence.

To enhance expression and reduce toxicity, the CRISPR enzyme and/or guide RNA can be modified using pseudo-U or 5-Methyl-C.

mRNA delivery methods are especially promising for liver delivery currently. In particular, for AAV8 is particularly preferred for delivery to the liver.

Particle Delivery Systems and/or Formulations:

Several types of particle delivery systems and/or formulations are known to be useful in a diverse spectrum of biomedical applications. In general, a particle is defined as a small object that behaves as a whole unit with respect to its transport and properties. Particles are further classified according to diameter Coarse particles cover a range between 2,500 and 10,000 nanometers. Fine particles are sized between 100 and 2,500 nanometers. Ultrafine particles, or nanoparticles, are generally between 1 and 100 nanometers in size. The basis of the 100-nm limit is the fact that novel properties that differentiate particles from the bulk material typically develop at a critical length scale of under 100 nm.

As used herein, a particle delivery system/formulation is defined as any biological delivery system/formulation which includes a particle in accordance with the present invention. A particle in accordance with the present invention is any entity having a greatest dimension (e.g. diameter) of less than 100 microns (μm). In some embodiments, inventive particles have a greatest dimension of less than 10 In some embodiments, inventive particles have a greatest dimension of less than 2000 nanometers (nm). In some embodiments, inventive particles have a greatest dimension of less than 1000 nanometers (nm). In some embodiments, inventive particles have a greatest dimension of less than 900 nm, 800 nm, 700 nm, 600 nm, 500 nm, 400 nm, 300 nm, 200 nm, or 100 nm. Typically, inventive particles have a greatest dimension (e.g., diameter) of 500 nm or less. In some embodiments, inventive particles have a greatest dimension (e.g., diameter) of 250 nm or less. In some embodiments, inventive particles have a greatest dimension (e.g., diameter) of 200 nm or less. In some embodiments, inventive particles have a greatest dimension (e.g., diameter) of 150 nm or less. In some embodiments, inventive particles have a greatest dimension (e.g., diameter) of 100 nm or less. Smaller particles, e.g., having a greatest dimension of 50 nm or less are used in some embodiments of the invention. In some embodiments, inventive particles have a greatest dimension ranging between 25 nm and 200 nm.

Particle characterization (including e.g., characterizing morphology, dimension, etc.) is done using a variety of different techniques. Common techniques are electron microscopy (TEM, SEM), atomic force microscopy (AFM), dynamic light scattering (DLS), X-ray photoelectron spectroscopy (XPS), powder X-ray diffraction (XRD), Fourier transform infrared spectroscopy (FTIR), matrix-assisted laser desorption/ionization time-of-flight mass spectrometry (MALDI-TOF), ultraviolet-visible spectroscopy, dual polarisation interferometry and nuclear magnetic resonance (NMR). Characterization (dimension measurements) may be made as to native particles (i.e., preloading) or after loading of the cargo (herein cargo refers to e.g., one or more components of CRISPR-Cas system e.g., CRISPR enzyme or mRNA or guide RNA, or any combination thereof, and may include additional components, carriers and/or excipients) to provide particles of an optimal size for delivery for any in vitro, ex vivo and/or in vivo application of the present invention. In certain preferred embodiments, particle dimension (e.g., diameter) characterization is based on measurements using dynamic laser scattering (DLS).

Particles delivery systems within the scope of the present invention may be provided in any form, including but not limited to solid, semi-solid, emulsion, or colloidal particles. As such any of the delivery systems described herein, including but not limited to, e.g., lipid-based systems, liposomes, micelles, microvesicles, exosomes, or gene gun may be provided as particle delivery systems within the scope of the present invention.

Nanoparticles

In terms of this invention, it is preferred to have one or more components of CRISPR complex, e.g., CRISPR enzyme or mRNA or guide RNA delivered using nanoparticles or lipid envelopes. CRISPR enzyme mRNA and guide RNA may be delivered simultaneously using nanoparticles or lipid envelopes. Other delivery systems or vectors may be used in conjunction with the nanoparticle aspects of the invention.

In general, a "nanoparticle" refers to any particle having a diameter of less than 1000 nm. In certain preferred embodiments, nanoparticles of the invention have a greatest dimension (e.g., diameter) of 500 nm or less. In other preferred embodiments, nanoparticles of the invention have a greatest dimension ranging between 25 nm and 200 nm. In other preferred embodiments, nanoparticles of the invention have a greatest dimension of 100 nm or less. In other preferred embodiments, nanoparticles of the invention have a greatest dimension ranging between 35 nm and 60 nm.

Nanoparticles encompassed in the present invention may be provided in different forms, e.g., as solid nanoparticles (e.g., metal such as silver, gold, iron, titanium), non-metal, lipid-based solids, polymers), suspensions of nanoparticles, or combinations thereof. Metal, dielectric, and semiconductor nanoparticles may be prepared, as well as hybrid structures (e.g., core-shell nanoparticles). Nanoparticles made of semiconducting material may also be labeled quantum dots if they are small enough (typically sub 10 nm) that quantization of electronic energy levels occurs. Such nanoscale particles are used in biomedical applications as drug carriers or imaging agents and may be adapted for similar purposes in the present invention.

Semi-solid and soft nanoparticles have been manufactured, and are within the scope of the present invention. A prototype nanoparticle of semi-solid nature is the liposome. Various types of liposome nanoparticles are currently used clinically as delivery systems for anticancer drugs and vaccines. Nanoparticles with one half hydrophilic and the other half hydrophobic are termed Janus particles and are particularly effective for stabilizing emulsions. They can self-assemble at water/oil interfaces and act as solid surfactants.

For example, Su X, Fricke J, Kavanagh D G, Irvine D J ("In vitro and in vivo mRNA delivery using lipid-enveloped pH-responsive polymer nanoparticles" Mol Pharm. 2011 Jun. 6; 8(3):774-87. doi: 10.1021/mp100390w. Epub 2011 Apr. 1) describes biodegradable core-shell structured nanoparticles with a poly(β-amino ester) (PBAE) core enveloped by a phospholipid bilayer shell. These were developed for in vivo mRNA delivery. The pH-responsive PBAE component was chosen to promote endosome disruption, while the lipid surface layer was selected to minimize toxicity of the polycation core. Such are, therefore, preferred for delivering RNA of the present invention.

In one embodiment, nanoparticles based on self assembling bioadhesive polymers are contemplated, which may be applied to oral delivery of peptides, intravenous delivery of peptides and nasal delivery of peptides, all to the brain. Other embodiments, such as oral absorption and ocular deliver of hydrophobic drugs are also contemplated. The molecular envelope technology involves an engineered polymer envelope which is protected and delivered to the site of the disease (see, e.g., Mazza, M. et al. ACSNano, 2013. 7(2): 1016-1026; Siew, A., et al. Mol Pharm, 2012. 9(1):14-28; Lalatsa, A., et al. J Contr Rel, 2012. 161(2):523-36; Lalatsa, A., et al., Mol Pharm, 2012. 9(6):1665-80; Lalatsa, A., et al. Mol Pharm, 2012. 9(6):1764-74; Garrett, N. L., et al. J Biophotonics, 2012. 5(5-6):458-68; Garrett, N. L., et al. J Raman Spect, 2012. 43(5):681-688; Ahmad, S., et al. J Royal Soc Interface 2010. 7:S423-33; Uchegbu, I. F. Expert Opin Drug Deliv, 2006. 3(5):629-40; Qu, X., et al. Biomacromolecules, 2006. 7(12):3452-9 and Uchegbu, I. F., et al. Int J Pharm, 2001. 224:185-199). Doses of about 5 mg/kg are contemplated, with single or multiple doses, depending on the target tissue.

In one embodiment, nanoparticles that can deliver RNA to a cancer cell to stop tumor growth developed by Dan Anderson's lab at MIT may be used/and or adapted to the CRISPR Cas system of the present invention. In particular, the Anderson lab developed fully automated, combinatorial systems for the synthesis, purification, characterization, and formulation of new biomaterials and nanoformulations. See, e.g., Alabi et al., Proc Natl Acad Sci USA. 2013 Aug. 6; 110(32):12881-6; Zhang et al., Adv Mater. 2013 Sep. 6; 25(33):4641-5; Jiang et al., Nano Lett. 2013 Mar. 13; 13(3):1059-64; Karagiannis et al., ACS Nano. 2012 Oct. 23; 6(10):8484-7; Whitehead et al., ACS Nano. 2012 Aug. 28; 6(8):6922-9 and Lee et al., Nat Nanotechnol. 2012 Jun. 3; 7(6):389-93.

US patent application 20110293703 relates to lipidoid compounds are also particularly useful in the administration of polynucleotides, which may be applied to deliver the CRISPR Cas system of the present invention. In one aspect, the aminoalcohol lipidoid compounds are combined with an agent to be delivered to a cell or a subject to form microparticles, nanoparticles, liposomes, or micelles. The agent to be delivered by the particles, liposomes, or micelles may be in the form of a gas, liquid, or solid, and the agent may be a polynucleotide, protein, peptide, or small molecule. The minoalcohol lipidoid compounds may be combined with other aminoalcohol lipidoid compounds, polymers (synthetic or natural), surfactants, cholesterol, carbohydrates, proteins, lipids, etc. to form the particles. These particles may then optionally be combined with a pharmaceutical excipient to form a pharmaceutical composition.

US Patent Publication No. 0110293703 also provides methods of preparing the aminoalcohol lipidoid compounds. One or more equivalents of an amine are allowed to react with one or more equivalents of an epoxide-terminated compound under suitable conditions to form an aminoalcohol lipidoid compound of the present invention. In certain embodiments, all the amino groups of the amine are fully reacted with the epoxide-terminated compound to form tertiary amines. In other embodiments, all the amino groups of the amine are not fully reacted with the epoxide-terminated compound to form tertiary amines thereby resulting in primary or secondary amines in the aminoalcohol lipidoid compound. These primary or secondary amines are left as is or may be reacted with another electrophile such as a different epoxide-terminated compound. As will be appreciated by one skilled in the art, reacting an amine with less than excess of epoxide-terminated compound will result in a plurality of different aminoalcohol lipidoid compounds with various numbers of tails. Certain amines may be fully functionalized with two epoxide-derived compound tails while other molecules will not be completely functionalized with epoxide-derived compound tails. For example, a diamine or polyamine may include one, two, three, or four epoxide-derived compound tails off the various amino moieties of the molecule resulting in primary, secondary, and tertiary amines. In certain embodiments, all the amino groups are not fully functionalized. In certain embodiments, two of the same types of epoxide-terminated compounds are used. In other embodiments, two or more different epoxide-terminated compounds are used. The synthesis of the aminoalcohol lipidoid compounds is performed with or without solvent, and the synthesis may be performed at higher temperatures ranging from 30-100 C., preferably at approximately 50-90 C. The prepared aminoalcohol lipidoid compounds may be optionally purified. For example, the mixture of aminoalcohol lipidoid compounds may be purified to yield an aminoalcohol lipidoid compound with a particular number of epoxide-derived compound tails. Or the mixture may be purified to yield a particular stereo- or regioisomer. The aminoalcohol lipidoid compounds may also be alkylated using an alkyl halide (e.g., methyl iodide) or other alkylating agent, and/or they may be acylated.

US Patent Publication No. 0110293703 also provides libraries of aminoalcohol lipidoid compounds prepared by the inventive methods. These aminoalcohol lipidoid compounds may be prepared and/or screened using high-throughput techniques involving liquid handlers, robots, microtiter plates, computers, etc. In certain embodiments, the aminoalcohol lipidoid compounds are screened for their ability to transfect polynucleotides or other agents (e.g., proteins, peptides, small molecules) into the cell.

US Patent Publication No. 20130302401 relates to a class of poly(beta-amino alcohols) (PBAAs) has been prepared using combinatorial polymerization. The inventive PBAAs may be used in biotechnology and biomedical applications as coatings (such as coatings of films or multilayer films for medical devices or implants), additives, materials, excipients, non-biofouling agents, micropatterning agents, and cellular encapsulation agents. When used as surface coatings, these PBAAs elicited different levels of inflammation, both in vitro and in vivo, depending on their chemical structures. The large chemical diversity of this class of materials allowed us to identify polymer coatings that inhibit macrophage activation in vitro. Furthermore, these coatings reduce the recruitment of inflammatory cells, and reduce fibrosis, following the subcutaneous implantation of carboxylated polystyrene microparticles. These polymers may be used to form polyelectrolyte complex capsules for cell encapsulation. The invention may also have many other biological applications such as antimicrobial coatings, DNA or siRNA delivery, and stem cell tissue engineering. The teachings of US Patent Publication No. 20130302401 may be applied to the CRISPR Cas system of the present invention.

In another embodiment, lipid nanoparticles (LNPs) are contemplated. In particular, an antitransthyretin small interfering RNA encapsulated in lipid nanoparticles (see, e.g., Coelho et al., N Engl J Med 2013; 369:819-29) may be applied to the CRISPR Cas system of the present invention. Doses of about 0.01 to about 1 mg per kg of body weight administered intravenously are contemplated. Medications to reduce the risk of infusion-related reactions are contemplated, such as dexamethasone, acetaminophen, diphenhydramine or cetirizine, and ranitidine are contemplated. Multiple doses of about 0.3 mg per kilogram every 4 weeks for five doses are also contemplated.

LNPs have been shown to be highly effective in delivering siRNAs to the liver (see, e.g., Tabernero et al., Cancer Discovery, April 2013, Vol. 3, No. 4, pages 363-470) and are therefore contemplated for delivering CRISPR Cas to the liver. A dosage of about four doses of 6 mg/kg of the LNP (or RNA of the CRISPR-Cas) every two weeks may be contemplated. Tabernero et al. demonstrated that tumor regression was observed after the first 2 cycles of LNPs dosed at 0.7 mg/kg, and by the end of 6 cycles the patient had achieved a partial response with complete regression of the lymph node metastasis and substantial shrinkage of the liver tumors. A complete response was obtained after 40 doses in this patient, who has remained in remission and completed treatment after receiving doses over 26 months. Two patients with RCC and extrahepatic sites of disease including kidney, lung, and lymph nodes that were progressing following prior therapy with VEGF pathway inhibitors had stable disease at all sites for approximately 8 to 12 months, and a patient with PNET and liver metastases continued on the extension study for 18 months (36 doses) with stable disease.

However, the charge of the LNP must be taken into consideration. As cationic lipids combined with negatively charged lipids to induce nonbilayer structures that facilitate intracellular delivery. Because charged LNPs are rapidly cleared from circulation following intravenous injection, ionizable cationic lipids with pKa values below 7 were developed (see, e.g., Rosin et al, Molecular Therapy, vol. 19, no. 12, pages 1286-2200, December 2011). Negatively charged polymers such as siRNA oligonucleotides may be loaded into LNPs at low pH values (e.g., pH 4) where the ionizable lipids display a positive charge. However, at physiological pH values, the LNPs exhibit a low surface charge compatible with longer circulation times. Four species of ionizable cationic lipids have been focused upon, namely 1,2-dilineoyl-3-dimethylammonium-propane (DLinDAP), 1,2-dilinoleyloxy-3-N,N-dimethylaminopropane (DLinDMA), 1,2-dilinoleyloxy-keto-N,N-dimethyl-3-aminopropane (DLinKDMA), and 1,2-dilinoleyl-4-(2-dimethylaminoethyl)-[1,3]-dioxolane (DLinKC2-DMA). It has been shown that LNP siRNA systems containing these lipids exhibit remarkably different gene silencing properties in hepatocytes in vivo, with potencies varying according to the series DLinKC2-DMA>DLinKDMA>DLinDMA>>DLinDAP employing a Factor VII gene silencing model (see, e.g., Rosin et al, Molecular Therapy, vol. 19, no. 12, pages 1286-2200, December 2011). A dosage of 1 μg/ml levels may be contemplated, especially for a formulation containing DLinKC2-DMA. Preparation of LNPs and CRISPR Cas encapsulation may be used/and or adapted from Rosin et al, Molecular Therapy, vol. 19, no. 12, pages 1286-2200, December 2011). The cationic lipids 1,2-dilineoyl-3-dimethylammonium-propane (DLinDAP), 1,2-dilinoleyloxy-3-N,N-dimethylaminopropane (DLinDMA), 1,2-dilinoleyloxyketo-N,N-dimethyl-3-aminopropane (DLinK-DMA), 1,2-dilinoleyl-4-(2-dimethylaminoethyl)-[1,3]-dioxolane (DLinKC2-DMA), (3-o-[2"-(methoxypolyethyleneglycol 2000) succinoyl]-1,2-dimyristoyl-sn-glycol (PEG-S-DMG), and R-3-[(ω-methoxy-poly(ethylene glycol)2000) carbamoyl]-1,2-dimyristyloxlpropyl-3-amine (PEG-C-DOMG) may be provided by Tekmira Pharmaceuticals (Vancouver, Canada) or synthesized. Cholesterol may be purchased from Sigma (St Louis, MO). The specific CRISPR Cas RNA may be encapsulated in LNPs containing DLinDAP, DLinDMA, DLinK-DMA, and DLinKC2-DMA (cationic lipid:DSPC:CHOL: PEGS-DMG or PEG-C-DOMG at 40:10:40:10 molar ratios). When required, 0.2% SP-DiOC18 (Invitrogen, Burlington, Canada) may be incorporated to assess cellular uptake, intracellular delivery, and biodistribution. Encapsulation may be performed by dissolving lipid mixtures comprised of cationic lipid:DSPC:cholesterol:PEG-c-DOMG (40:10:40:10 molar ratio) in ethanol to a final lipid concentration of 10 mmol/1. This ethanol solution of lipid may be added drop-wise to 50 mmol/1 citrate, pH 4.0 to form multilamellar vesicles to produce a final concentration of 30% ethanol vol/vol. Large unilamellar vesicles may be formed following extrusion of multilamellar vesicles through two stacked 80 nm Nuclepore polycarbonate filters using the Extruder (Northern Lipids, Vancouver, Canada). Encapsulation may be achieved by adding RNA dissolved at 2 mg/ml in 50 mmol/1 citrate, pH 4.0 containing 30% ethanol vol/vol drop-wise to extruded preformed large unilamellar vesicles and incubation at 31° C. for 30 minutes with constant mixing to a final RNA/lipid weight ratio of 0.06/1 wt/wt. Removal of ethanol and neutralization of formulation buffer were performed by dialysis against phosphate-buffered saline (PBS), pH 7.4 for 16 hours using Spectra/Por 2 regenerated cellulose dialysis membranes. Nanoparticle size distribution may be determined by dynamic light scattering using a NICOMP 370 particle sizer, the vesicle/intensity modes, and Gaussian fitting (Nicomp Particle Sizing, Santa Barbara, CA). The particle size for all three LNP systems may be ~70 nm in diameter. siRNA encapsulation efficiency may be determined by removal of free siRNA using VivaPureD MiniH columns (Sartorius Stedim Biotech) from samples collected before and after dialysis. The encapsulated RNA may be extracted from the eluted nanoparticles and quantified at 260 nm. siRNA to lipid ratio was determined by measurement of cholesterol content in vesicles using the Cholesterol E enzymatic assay from Wako Chemicals USA (Richmond, VA). PEGylated liposomes (or LNPs) can also be used for delivery.

Preparation of large LNPs may be used/and or adapted from Rosin et al, Molecular Therapy, vol. 19, no. 12, pages 1286-2200, December 2011. A lipid premix solution (20.4 mg/ml total lipid concentration) may be prepared in ethanol containing DLinKC2-DMA, DSPC, and cholesterol at 50:10:38.5 molar ratios. Sodium acetate may be added to the lipid premix at a molar ratio of 0.75:1 (sodium acetate: DLinKC2-DMA). The lipids may be subsequently hydrated by combining the mixture with 1.85 volumes of citrate buffer (10 mmol/1, pH 3.0) with vigorous stirring, resulting in spontaneous liposome formation in aqueous buffer containing 35% ethanol. The liposome solution may be incubated at 37° C. to allow for time-dependent increase in particle size. Aliquots may be removed at various times during incubation to investigate changes in liposome size by dynamic light scattering (Zetasizer Nano ZS, Malvern Instruments, Worcestershire, UK). Once the desired particle size is achieved, an aqueous PEG lipid solution (stock=10 mg/ml PEG-DMG in 35% (vol/vol) ethanol) may be added to the liposome mixture to yield a final PEG molar concentration of 3.5% of total lipid. Upon addition of PEG-lipids, the liposomes should their size, effectively quenching further growth. RNA may then be added to the empty liposomes at an siRNA to total lipid ratio of approximately 1:10 (wt:wt), followed by incubation for 30 minutes at 37° C. to form loaded LNPs. The mixture may be subsequently dialyzed overnight in PBS and filtered with a 0.45-μm syringe filter.

Spherical Nucleic Acid (SNA™) constructs and other nanoparticles (particularly gold nanoparticles) are also contemplate as a means to delivery CRISPR/Cas system to intended targets. Significant data show that AuraSense Therapeutics' Spherical Nucleic Acid (SNA™) constructs, based upon nucleic acid-functionalized gold nanoparticles, are superior to alternative platforms based on multiple key success factors, such as:

High in vivo stability. Due to their dense loading, a majority of cargo (DNA or siRNA) remains bound to the constructs inside cells, conferring nucleic acid stability and resistance to enzymatic degradation.

Deliverability. For all cell types studied (e.g., neurons, tumor cell lines, etc.) the constructs demonstrate a transfection efficiency of 99% with no need for carriers or transfection agents.

Therapeutic targeting. The unique target binding affinity and specificity of the constructs allow exquisite specificity for matched target sequences (i.e., limited off-target effects).

Superior efficacy. The constructs significantly outperform leading conventional transfection reagents (Lipofectamine 2000 and Cytofectin).

Low toxicity. The constructs can enter a variety of cultured cells, primary cells, and tissues with no apparent toxicity.

No significant immune response. The constructs elicit minimal changes in global gene expression as measured by whole-genome microarray studies and cytokine-specific protein assays.

Chemical tailorability. Any number of single or combinatorial agents (e.g., proteins, peptides, small molecules) can be used to tailor the surface of the constructs.

This platform for nucleic acid-based therapeutics may be applicable to numerous disease states, including inflammation and infectious disease, cancer, skin disorders and cardiovascular disease.

Citable literature includes: Cutler et al., J. Am. Chem. Soc. 2011 133:9254-9257, Hao et al., Small. 2011 7:3158-3162, Zhang et al., ACS Nano. 2011 5:6962-6970, Cutler et al., J. Am. Chem. Soc. 2012 134:1376-1391, Young et al., Nano Lett. 2012 12:3867-71, Zheng et al., Proc. Natl. Acad. Sci. USA. 2012 109:11975-80, Mirkin, Nanomedicine 2012 7:635-638 Zhang et al., J. Am. Chem. Soc. 2012 134:16488-1691, Weintraub, Nature 2013 495:S14-S16, Choi et al., Proc. Natl. Acad. Sci. USA. 2013 110(19):7625-7630, Jensen et al., Sci. Transl. Med. 5, 209ra152 (2013) and Mirkin, et al., Small, doi.org/10.1002/smll.201302143.

Self-assembling nanoparticles with siRNA may be constructed with polyethyleneimine (PEI) that is PEGylated with an Arg-Gly-Asp (RGD) peptide ligand attached at the distal end of the polyethylene glycol (PEG), for example, as a means to target tumor neovasculature expressing integrins and used to deliver siRNA inhibiting vascular endothelial growth factor receptor-2 (VEGF R2) expression and thereby tumor angiogenesis (see, e.g., Schiffelers et al., Nucleic Acids Research, 2004, Vol. 32, No. 19). Nanoplexes may be prepared by mixing equal volumes of aqueous solutions of cationic polymer and nucleic acid to give a net molar excess of ionizable nitrogen (polymer) to phosphate (nucleic acid) over the range of 2 to 6. The electrostatic interactions between cationic polymers and nucleic acid resulted in the formation of polyplexes with average particle size distribution of about 100 nm, hence referred to here as nanoplexes. A dosage of about 100 to 200 mg of CRISPR Cas is envisioned for delivery in the self-assembling nanoparticles of Schiffelers et al.

The nanoplexes of Bartlett et al. (PNAS, Sep. 25, 2007, vol. 104, no. 39) may also be applied to the present invention. The nanoplexes of Bartlett et al. are prepared by mixing equal volumes of aqueous solutions of cationic polymer and nucleic acid to give a net molar excess of ionizable nitrogen (polymer) to phosphate (nucleic acid) over the range of 2 to 6. The electrostatic interactions between cationic polymers and nucleic acid resulted in the formation of polyplexes with average particle size distribution of about 100 nm, hence referred to here as nanoplexes. The DOTA-siRNA of Bartlett et al. was synthesized as follows: 1,4,7,10-tetraazacyclododecane-1,4,7,10-tetraacetic acid mono(N-hydroxysuccinimide ester) (DOTA-NHSester) was ordered from Macrocyclics (Dallas, TX). The amine modified RNA sense strand with a 100-fold molar excess of DOTA-NHS-ester in carbonate buffer (pH 9) was added to a microcentrifuge tube. The contents were reacted by stirring for 4 h at room temperature. The DOTA-RNAsense conjugate was ethanol-precipitated, resuspended in water, and annealed to the unmodified antisense strand to yield DOTA-siRNA. All liquids were pretreated with Chelex-100 (Bio-Rad, Hercules, CA) to remove trace metal contaminants. Tf-targeted and nontargeted siRNA nanoparticles may be formed by using cyclodextrin-containing polycations. Typically, nanoparticles were formed in water at a charge ratio of 3 (+/−) and an siRNA concentration of 0.5 g/liter. One percent of the adamantane-PEG molecules on the surface of the targeted nanoparticles were modified with Tf (adamantane-PEG-Tf). The nanoparticles were suspended in a 5% (wt/vol) glucose carrier solution for injection.

Davis et al. (Nature, Vol 464, 15 Apr. 2010) conducts a siRNA clinical trial that uses a targeted nanoparticle-delivery system (clinical trial registration number NCT00689065). Patients with solid cancers refractory to standard-of-care therapies are administered doses of targeted nanoparticles on days 1, 3, 8 and 10 of a 21-day cycle by a 30-min intravenous infusion. The nanoparticles consist of a synthetic delivery system containing: (1) a linear, cyclodextrin-based polymer (CDP), (2) a human transferrin protein (TF) targeting ligand displayed on the exterior of the nanoparticle to engage TF receptors (TFR) on the surface of the cancer cells, (3) a hydrophilic polymer (polyethylene glycol (PEG) used to promote nanoparticle stability in biological fluids), and (4) siRNA designed to reduce the expression of the RRM2 (sequence used in the clinic was previously denoted siR2B+5). The TFR has long been known to be upregulated in malignant cells, and RRM2 is an established anti-cancer target. These nanoparticles (clinical version denoted as CALAA-01) have been shown to be well tolerated in multi-dosing studies in non-human primates. Although a single patient with chronic myeloid leukaemia has been administered siRNA by liposomal delivery, Davis et al.'s clinical trial is the initial human trial to systemically deliver siRNA with a targeted delivery system and to treat patients with solid cancer. To ascertain whether the targeted delivery system can provide effective delivery of functional siRNA to human tumours, Davis et al. investigated biopsies from three patients from three different dosing cohorts; patients A, B and C, all of whom had metastatic melanoma and received CALAA-01 doses of 18, 24 and 30 mg $m^{-2}$ siRNA, respectively. Similar doses may also be contemplated for the CRISPR Cas system of the present invention. The delivery of the invention may be achieved with nanoparticles containing a linear, cyclodextrin-based polymer (CDP), a human transferrin protein (TF) targeting ligand displayed on the exterior of the nanoparticle to engage TF receptors (TFR) on the surface of the cancer cells and/or a hydrophilic polymer (for example, polyethylene glycol (PEG) used to promote nanoparticle stability in biological fluids).

Exosomes

Exosomes are endogenous nano-vesicles that transport RNAs and proteins which can deliver short interfering (si)RNA to the brain in mice. To reduce immunogenicity, Alvarez-Erviti et al. (2011, Nat Biotechnol 29: 341) used self-derived dendritic cells for exosome production. Targeting was achieved by engineering the dendritic cells to express Lamp2b, an exosomal membrane protein, fused to the neuron-specific RVG peptide. Purified exosomes were loaded with exogenous siRNA by electroporation. Intravenously injected RVG-targeted exosomes delivered GAPDH siRNA specifically to neurons, microglia, oligodendrocytes in the brain, resulting in a specific gene knockdown. Pre-exposure to RVG exosomes did not attenuate knockdown, and non-specific uptake in other tissues was not observed. The therapeutic potential of exosome-mediated siRNA delivery was demonstrated by the strong mRNA (60%) and protein (62%) knockdown of BACE1, a therapeutic target in Alzheimer's disease.

To obtain a pool of immunologically inert exosomes, Alvarez-Erviti et al. harvested bone marrow from inbred C57BL/6 mice with a homogenous major histocompatibility complex (MEW) haplotype. As immature dendritic cells produce large quantities of exosomes devoid of T-cell activators such as MHC-II and CD86, Alvarez-Erviti et al. selected for dendritic cells with granulocyte/macrophage-colony stimulating factor (GM-CSF) for 7 d. Exosomes were purified from the culture supernatant the following day using well-established ultracentrifugation protocols. The exosomes produced were physically homogenous, with a size distribution peaking at 80 nm in diameter as determined by nanoparticle tracking analysis (NTA) and electron microscopy. Alvarez-Erviti et al. obtained 6-12 μg of exosomes (measured based on protein concentration) per $10^6$ cells.

Next, Alvarez-Erviti et al. investigated the possibility of loading modified exosomes with exogenous cargoes using electroporation protocols adapted for nanoscale applications. As electroporation for membrane particles at the nanometer scale is not well-characterized, nonspecific Cy5-labeled siRNA was used for the empirical optimization of the electroporation protocol. The amount of encapsulated siRNA was assayed after ultracentrifugation and lysis of exosomes. Electroporation at 400 V and 125 μF resulted in the greatest retention of siRNA and was used for all subsequent experiments.

Alvarez-Erviti et al. administered 150 μg of each BACE1 siRNA encapsulated in 150 μg of RVG exosomes to normal C57BL/6 mice and compared the knockdown efficiency to four controls: untreated mice, mice injected with RVG exosomes only, mice injected with BACE1 siRNA complexed to an in vivo cationic liposome reagent and mice injected with BACE1 siRNA complexed to RVG-9R, the RVG pep tide conjugated to 9 D-arginines that electrostatically binds to the siRNA. Cortical tissue samples were analyzed 3 d after administration and a significant protein knockdown (45%, P<0.05, versus 62%, P<0.01) in both siRNA-RVG-9R-treated and siRNARVG exosome-treated mice was observed, resulting from a significant decrease in BACE1 mRNA levels (66% [+ or −] 15%, P<0.001 and 61% [+ or −] 13% respectively, P<0.01). Moreover, Applicants demonstrated a significant decrease (55%, P<0.05) in the total [beta]-amyloid 1-42 levels, a main component of the amyloid plaques in Alzheimer's pathology, in the RVG-exosome-treated animals. The decrease observed was greater than the β-amyloid 1-40 decrease demonstrated in normal mice after intraventricular injection of BACE1 inhibitors. Alvarez-Erviti et al. carried out 5'-rapid amplification of cDNA ends (RACE) on BACE1 cleavage product, which provided evidence of RNAi-mediated knockdown by the siRNA.

Finally, Alvarez-Erviti et al. investigated whether siRNA-RVG exosomes induced immune responses in vivo by assessing IL-6, IP-10, TNFα and IFN-α serum concentrations. Following siRNA-RVG exosome treatment, nonsignificant changes in all cytokines were registered similar to siRNA-transfection reagent treatment in contrast to siRNA-RVG-9R, which potently stimulated IL-6 secretion, confirming the immunologically inert profile of the exosome treatment. Given that exosomes encapsulate only 20% of siRNA, delivery with RVG-exosome appears to be more efficient than RVG-9R delivery as comparable mRNA knockdown and greater protein knockdown was achieved with fivefold less siRNA without the corresponding level of immune stimulation. This experiment demonstrated the therapeutic potential of RVG-exosome technology, which is potentially suited for long-term silencing of genes related to neurodegenerative diseases. The exosome delivery system of Alvarez-Erviti et al. may be applied to deliver the CRISPR-Cas system of the present invention to therapeutic targets, especially neurodegenerative diseases. A dosage of about 100 to 1000 mg of CRISPR Cas encapsulated in about 100 to 1000 mg of RVG exosomes may be contemplated for the present invention.

El-Andaloussi et al. (Nature Protocols 7, 2112-2126 (2012)) discloses how exosomes derived from cultured cells can be harnessed for delivery of siRNA in vitro and in vivo. This protocol first describes the generation of targeted exosomes through transfection of an expression vector, comprising an exosomal protein fused with a peptide ligand. Next, El-Andaloussi et al. explain how to purify and characterize exosomes from transfected cell supernatant. Next, El-Andaloussi et al. detail crucial steps for loading siRNA into exosomes. Finally, El-Andaloussi et al. outline how to use exosomes to efficiently deliver siRNA in vitro and in vivo in mouse brain. Examples of anticipated results in which exosome-mediated siRNA delivery is evaluated by functional assays and imaging are also provided. The entire protocol takes ~3 weeks. Delivery or administration according to the invention may be performed using exosomes produced from self-derived dendritic cells.

In another embodiment, the plasma exosomes of Wahlgren et al. (Nucleic Acids Research, 2012, Vol. 40, No. 17 e130) are contemplated. Exosomes are nano-sized vesicles (30-90 nm in size) produced by many cell types, including dendritic cells (DC), B cells, T cells, mast cells, epithelial cells and tumor cells. These vesicles are formed by inward budding of late endosomes and are then released to the extracellular environment upon fusion with the plasma membrane. Because exosomes naturally carry RNA between cells, this property might be useful in gene therapy.

Exosomes from plasma are prepared by centrifugation of buffy coat at 900 g for 20 min to isolate the plasma followed by harvesting cell supernatants, centrifuging at 300 g for 10 min to eliminate cells and at 16 500 g for 30 min followed by filtration through a 0.22 mm filter. Exosomes are pelleted by ultracentrifugation at 120 000 g for 70 min. Chemical transfection of siRNA into exosomes is carried out according to the manufacturer's instructions in RNAi Human/Mouse Starter Kit (Quiagen, Hilden, Germany). siRNA is added to 100 ml PBS at a final concentration of 2 mmol/ml. After adding HiPerFect transfection reagent, the mixture is incubated for 10 min at RT. In order to remove the excess of micelles, the exosomes are re-isolated using aldehyde/sulfate latex beads. The chemical transfection of CRISPR Cas into exosomes may be conducted similarly to siRNA. The exosomes may be co-cultured with monocytes and lymphocytes isolated from the peripheral blood of healthy donors. Therefore, it may be contemplated that exosomes containing CRISPR Cas may be introduced to monocytes and lymphocytes of and autologously reintroduced into a human. Accordingly, delivery or administration according to the invention may be performed using plasma exosomes.

Liposomes

Delivery or administration according to the invention can be performed with liposomes. Liposomes are spherical vesicle structures composed of a uni- or multilamellar lipid bilayer surrounding internal aqueous compartments and a relatively impermeable outer lipophilic phospholipid bilayer. Liposomes have gained considerable attention as drug delivery carriers because they are biocompatible, nontoxic, can deliver both hydrophilic and lipophilic drug molecules, protect their cargo from degradation by plasma enzymes, and transport their load across biological membranes and the blood brain barrier (BBB) (see, e.g., Spuch and Navarro, Journal of Drug Delivery, vol. 2011, Article ID 469679, 12 pages, 2011. doi:10.1155/2011/469679 for review).

Liposomes can be made from several different types of lipids; however, phospholipids are most commonly used to generate liposomes as drug carriers. Although liposome formation is spontaneous when a lipid film is mixed with an aqueous solution, it can also be expedited by applying force in the form of shaking by using a homogenizer, sonicator, or an extrusion apparatus (see, e.g., Spuch and Navarro, Journal of Drug Delivery, vol. 2011, Article ID 469679, 12 pages, 2011. doi:10.1155/2011/469679 for review).

Several other additives may be added to liposomes in order to modify their structure and properties. For instance, either cholesterol or sphingomyelin may be added to the liposomal mixture in order to help stabilize the liposomal structure and to prevent the leakage of the liposomal inner cargo. Further, liposomes are prepared from hydrogenated egg phosphatidylcholine or egg phosphatidylcholine, cholesterol, and dicetyl phosphate, and their mean vesicle sizes were adjusted to about 50 and 100 nm. (see, e.g., Spuch and Navarro, Journal of Drug Delivery, vol. 2011, Article ID 469679, 12 pages, 2011. doi:10.1155/2011/469679 for review).

Conventional liposome formulation is mainly comprised of natural phospholipids and lipids such as 1,2-distearoryl-sn-glycero-3-phosphatidyl choline (DSPC), sphingomyelin, egg phosphatidylcholines and monosialoganglioside. Since this formulation is made up of phospholipids only, liposomal formulations have encountered many challenges, one of the ones being the instability in plasma. Several attempts to overcome these challenges have been made, specifically in the manipulation of the lipid membrane. One of these attempts focused on the manipulation of cholesterol. Addition of cholesterol to conventional formulations reduces rapid release of the encapsulated bioactive compound into the plasma or 1,2-dioleoyl-sn-glycero-3-phosphoethanolamine (DOPE) increases the stability (see, e.g., Spuch and Navarro, Journal of Drug Delivery, vol. 2011, Article ID 469679, 12 pages, 2011. doi:10.1155/2011/469679 for review).

In a particularly advantageous embodiment, Trojan Horse liposomes (also known as Molecular Trojan Horses) are desirable and protocols may be found at cshprotocols.cshlp.org/content/2010/4/pdb.prot5407.long. These particles allow delivery of a transgene to the entire brain after an intravascular injection. Without being bound by limitation, it is believed that neutral lipid particles with specific antibodies conjugated to surface allow crossing of the blood brain barrier via endocytosis. Applicant postulates utilizing Trojan Horse Liposomes to deliver the CRISPR family of nucleases to the brain via an intravascular injection, which would allow whole brain transgenic animals without the need for embryonic manipulation. About 1-5 g of nucleic acid molecule, e.g., DNA, RNA, may be contemplated for in vivo administration in liposomes.

In another embodiment, the CRISPR Cas system may be administered in liposomes, such as a stable nucleic-acid-lipid particle (SNALP) (see, e.g., Morrissey et al., Nature Biotechnology, Vol. 23, No. 8, August 2005). Daily intravenous injections of about 1, 3 or 5 mg/kg/day of a specific CRISPR Cas targeted in a SNALP are contemplated. The daily treatment may be over about three days and then weekly for about five weeks. In another embodiment, a specific CRISPR Cas encapsulated SNALP) administered by intravenous injection to at doses of abpit 1 or 2.5 mg/kg are also contemplated (see, e.g., Zimmerman et al., Nature Letters, Vol. 441, 4 May 2006). The SNALP formulation may contain the lipids 3-N-[(wmethoxypoly(ethylene glycol) 2000) carbamoyl]-1,2-dimyristyloxy-propylamine (PEG-C-DMA), 1,2-dilinoleyloxy-N,N-dimethyl-3-aminopropane (DLinDMA), 1,2-distearoyl-sn-glycero-3-phosphocholine (DSPC) and cholesterol, in a 2:40:10:48 molar percent ratio (see, e.g., Zimmerman et al., Nature Letters, Vol. 441, 4 May 2006).

In another embodiment, stable nucleic-acid-lipid particles (SNALPs) have proven to be effective delivery molecules to highly vascularized HepG2-derived liver tumors but not in poorly vascularized HCT-116 derived liver tumors (see, e.g., Li, Gene Therapy (2012) 19, 775-780). The SNALP liposomes may be prepared by formulating D-Lin-DMA and PEG-C-DMA with distearoylphosphatidylcholine (DSPC), Cholesterol and siRNA using a 25:1 lipid/siRNA ratio and a 48/40/10/2 molar ratio of Cholesterol/D-Lin-DMA/DSPC/PEG-C-DMA. The resulted SNALP liposomes are about 80-100 nm in size.

In yet another embodiment, a SNALP may comprise synthetic cholesterol (Sigma-Aldrich, St Louis, MO, USA), dipalmitoylphosphatidylcholine (Avanti Polar Lipids, Alabaster, AL, USA), 3-N-[(w-methoxy poly(ethylene glycol) 2000)carbamoyl]-1,2-dimyrestyloxypropylamine, and cationic 1,2-dilinoleyloxy-3-N,Ndimethylaminopropane (see, e.g., Geisbert et al., Lancet 2010; 375: 1896-905). A dosage of about 2 mg/kg total CRISPR Cas per dose administered as, for example, a bolus intravenous infusion may be contemplated.

In yet another embodiment, a SNALP may comprise synthetic cholesterol (Sigma-Aldrich), 1,2-distearoyl-sn-glycero-3-phosphocholine (DSPC; Avanti Polar Lipids Inc.), PEG-cDMA, and 1,2-dilinoleyloxy-3-(N;N-dimethyl)aminopropane (DLinDMA) (see, e.g., Judge, J. Clin. Invest. 119:661-673 (2009)). Formulations used for in vivo studies may comprise a final lipid/RNA mass ratio of about 9:1.

The safety profile of RNAi nanomedicines has been reviewed by Barros and Gollob of Alnylam Pharmaceuticals (see, e.g., Advanced Drug Delivery Reviews 64 (2012) 1730-1737). The stable nucleic acid lipid particle (SNALP) is comprised of four different lipids—an ionizable lipid (DLinDMA) that is cationic at low pH, a neutral helper lipid, cholesterol, and a diffusible polyethylene glycol (PEG)-lipid. The particle is approximately 80 nm in diameter and is charge-neutral at physiologic pH. During formulation, the ionizable lipid serves to condense lipid with the anionic siRNA during particle formation. When positively charged under increasingly acidic endosomal conditions, the ionizable lipid also mediates the fusion of SNALP with the endosomal membrane enabling release of siRNA into the cytoplasm. The PEG-lipid stabilizes the particle and reduces aggregation during formulation, and subsequently provides a neutral hydrophilic exterior that improves pharmacokinetic properties.

To date, two clinical programs have been initiated using SNALPsiRNA formulations. Tekmira Pharmaceuticals recently completed a phase I single-dose study of SNALP-ApoB in adult volunteers with elevated LDL cholesterol. ApoB is predominantly expressed in the liver and jejunum and is essential for the assembly and secretion of VLDL and LDL. ApoB is also successfully targeted by our CrISPR-Cas systems, see examples 38-39. Seventeen subjects received a single dose of SNALP-ApoB (dose escalation across 7 dose levels). There was no evidence of liver toxicity (anticipated as the potential dose-limiting toxicity based on preclinical studies). One (of two) subjects at the highest dose experienced flu-like symptoms consistent with immune system stimulation, and the decision was made to conclude the trial.

Alnylam Pharmaceuticals has similarly advanced ALN-TTR01, which employs the SNALP technology described above and targets hepatocyte production of both mutant and wild-type TTR to treat TTR amyloidosis (ATTR). Three ATTR syndromes have been described: familial amyloidotic polyneuropathy (FAP) and familial amyloidotic cardiomyopathy (FAC) both caused by autosomal dominant mutations in TTR; and senile systemic amyloidosis (SSA) cause by wildtype TTR. A placebo-controlled, single dose-escalation phase I trial of ALN-TTR01 was recently completed in patients with ATTR. ALN-TTR01 was administered as a 15-minute IV infusion to 31 patients (23 with study drug and 8 with placebo) within a dose range of 0.01 to 1.0 mg/kg (based on siRNA). Treatment was well tolerated with no significant increases in liver function tests. Infusion-related reactions were noted in 3 of 23 patients at ≥0.4 mg/kg; all responded to slowing of the infusion rate and all continued on study. Minimal and transient elevations of serum cytokines IL-6, IP-10 and IL-1ra were noted in two patients at the highest dose of 1 mg/kg (as anticipated from preclinical and NHP studies). Lowering of serum TTR, the expected pharmacodynamics effect of ALN-TTR01, was observed at 1 mg/kg.

In yet another embodiment, a SNALP may be made by solubilizing a cationic lipid, DSPC, cholesterol and PEG-lipid were solubilized in ethanol at a molar ratio of 40:10:40:10, respectively (see, Semple et al., Nature Biotechnology, Volume 28 Number 2 Feb. 2010, pp. 172-177). The lipid mixture was added to an aqueous buffer (50 mM citrate, pH 4) with mixing to a final ethanol and lipid concentration of 30% (vol/vol) and 6.1 mg/ml, respectively, and allowed to equilibrate at 22° C. for 2 min before extrusion. The hydrated lipids were extruded through two stacked 80 nm pore-sized filters (Nuclepore) at 22° C. using a Lipex Extruder (Northern Lipids) until a vesicle diameter of 70-90 nm, as determined by dynamic light scattering analysis, was obtained. This generally required 1-3 passes. The siRNA (solubilized in a 50 mM citrate, pH 4 aqueous solution containing 30% ethanol) was added to the pre-equilibrated (35° C.) vesicles at a rate of ~5 ml/min with mixing. After a final target siRNA/lipid ratio of 0.06 (wt/wt) was reached, the mixture was incubated for a further 30 min at 35° C. to allow vesicle reorganization and encapsulation of the siRNA. The ethanol was then removed and the external buffer replaced with PBS (155 mM NaCl, 3 mM Na2HPO4, 1 mM KH2PO4, pH 7.5) by either dialysis or tangential flow diafiltration. siRNA were encapsulated in SNALP using a controlled step-wise dilution method process. The lipid constituents of KC2-SNALP were DLin-KC2-DMA (cationic lipid), dipalmitoylphosphatidylcholine (DPPC; Avanti Polar Lipids), synthetic cholesterol (Sigma) and PEG-C-DMA used at a molar ratio of 57.1:7.1:34.3:1.4. Upon formation of the loaded particles, SNALP were dialyzed against PBS and filter sterilized through a 0.2 μm filter before use. Mean particle sizes were 75-85 nm and 90-95% of the siRNA was encapsulated within the lipid particles. The final siRNA/lipid ratio in formulations used for in vivo testing was ~0.15 (wt/wt). LNP-siRNA systems containing Factor VII siRNA were diluted to the appropriate concentrations in sterile PBS immediately before use and the formulations were administered intravenously through the lateral tail vein in a total volume of 10 ml/kg. This method may be extrapolated to the CRISPR Cas system of the present invention.

Other Lipids

Other cationic lipids, such as amino lipid 2,2-dilinoleyl-4-dimethylaminoethyl-[1,3]-dioxolane (DLin-KC2-DMA) may be utilized to encapsulate CRISPR Cas similar to SiRNA (see, e.g., Jayaraman, Angew. Chem. Int. Ed. 2012, 51, 8529-8533). A preformed vesicle with the following lipid composition may be contemplated: amino lipid, distearoylphosphatidylcholine (DSPC), cholesterol and (R)-2, 3-bis(octadecyloxy) propyl-1-(methoxy poly(ethylene glycol)2000)propylcarbamate (PEG-lipid) in the molar ratio 40/10/40/10, respectively, and a FVII siRNA/total lipid ratio of approximately 0.05 (w/w). To ensure a narrow particle size distribution in the range of 70-90 nm and a low polydispersity index of 0.11_0.04 (n=56), the particles may be extruded up to three times through 80 nm membranes prior to adding the CRISPR Cas RNA. Particles containing the highly potent amino lipid 16 may be used, in which the molar ratio of the four lipid components 16, DSPC, cholesterol and PEG-lipid (50/10/38.5/1.5) which may be further optimized to enhance in vivo activity.

Michael S D Kormann et al. ("Expression of therapeutic proteins after delivery of chemically modified mRNA in mice: Nature Biotechnology, Volume: 29, Pages: 154-157 (2011) Published online 9 Jan. 2011) describes the use of lipid envelopes to deliver RNA. Use of lipid envelopes is also preferred in the present invention.

In another embodiment, lipids may be formulated with the CRISPR Cas system of the present invention to form lipid nanoparticles (LNPs). Lipids include, but are not limited to, DLin-KC2-DMA4, C12-200 and colipids disteroylphosphatidyl choline, cholesterol, and PEG-DMG may be formulated with CRISPR Cas instead of siRNA (see, e.g., Novobrantseva, Molecular Therapy—Nucleic Acids (2012) 1, e4; doi:10.1038/mtna.2011.3) using a spontaneous vesicle formation procedure. The component molar ratio may be about 50/10/38.5/1.5 (DLin-KC2-DMA or C12-200/disteroylphosphatidyl choline/cholesterol/PEG-DMG). The final lipid:siRNA weight ratio may be ~12:1 and 9:1 in the case of DLin-KC2-DMA and C12-200 lipid nanoparticles (LNPs), respectively. The formulations may have mean particle diameters of ~80 nm with >90% entrapment efficiency. A 3 mg/kg dose may be contemplated.

Tekmira has a portfolio of approximately 95 patent families, in the U.S. and abroad, that are directed to various aspects of LNPs and LNP formulations (see, e.g., U.S. Pat. Nos. 7,982,027; 7,799,565; 8,058,069; 8,283,333; 7,901,708; 7,745,651; 7,803,397; 8,101,741; 8,188,263; 7,915,399; 8,236,943 and 7,838,658 and European Pat. Nos 0.1766035; 1519714; 1781593 and 1664316), all of which may be used/and or adapted to the present invention.

The CRISPR Cas system may be delivered encapsulated in PLGA Microspheres such as that further described in US published applications 20130252281 and 20130245107 and 20130244279 (assigned to Moderna Therapeutics) which relate to aspects of formulation of compositions comprising modified nucleic acid molecules which may encode a protein, a protein precursor, or a partially or fully processed form of the protein or a protein precursor. The formulation may have a molar ratio 50:10:38.5:1.5-3.0 (cationic lipid: fusogenic lipid:cholesterol:PEG lipid). The PEG lipid may be selected from, but is not limited to PEG-c-DOMG, PEG-DMG. The fusogenic lipid may be DSPC. See also, Schrum et al., Delivery and Formulation of Engineered Nucleic Acids, US published application 20120251618.

Nanomerics' technology addresses bioavailability challenges for a broad range of therapeutics, including low molecular weight hydrophobic drugs, peptides, and nucleic acid based therapeutics (plasmid, siRNA, miRNA). Specific administration routes for which the technology has demonstrated clear advantages include the oral route, transport across the blood-brain-barrier, delivery to solid tumours, as well as to the eye. See, e.g., Mazza et al., 2013, ACS Nano. 2013 Feb. 26; 7(2):1016-26; Uchegbu and Siew, 2013, J Pharm Sci. 102(2):305-10 and Lalatsa et al., 2012, J Control Release. 2012 Jul. 20; 161(2):523-36.

US Patent Publication No. 20050019923 describes cationic dendrimers for delivering bioactive molecules, such as polynucleotide molecules, peptides and polypeptides and/or pharmaceutical agents, to a mammalian body. The dendrimers are suitable for targeting the delivery of the bioactive molecules to, for example, the liver, spleen, lung, kidney or heart. Dendrimers are synthetic 3-dimensional macromolecules that are prepared in a step-wise fashion from simple branched monomer units, the nature and functionality of which can be easily controlled and varied. Dendrimers are synthesised from the repeated addition of building blocks to a multifunctional core (divergent approach to synthesis), or towards a multifunctional core (convergent approach to synthesis) and each addition of a 3-dimensional shell of building blocks leads to the formation of a higher generation of the dendrimers. Polypropylenimine dendrimers start from a diaminobutane core to which is added twice the number of amino groups by a double Michael addition of acrylonitrile to the primary amines followed by the hydrogenation of the nitriles. This results in a doubling of the amino groups. Polypropylenimine dendrimers contain 100% protonable nitrogens and up to 64 terminal amino groups (generation 5, DAB 64). Protonable groups are usually amine groups which are able to accept protons at neutral pH. The use of dendrimers as gene delivery agents has largely focused on the use of the polyamidoamine. and phosphorous containing compounds with a mixture of amine/amide or N—P($O_2$)S as the conjugating units respectively with no work being reported on the use of the lower generation polypropylenimine dendrimers for gene delivery. Polypropylenimine dendrimers have also been studied as pH sensitive controlled release systems for drug delivery and for their encapsulation of guest molecules when chemically modified by peripheral amino acid groups. The cytotoxicity and interaction of polypropylenimine dendrimers with DNA as well as the transfection efficacy of DAB 64 has also been studied.

US Patent Publication No. 20050019923 is based upon the observation that, contrary to earlier reports, cationic dendrimers, such as polypropylenimine dendrimers, display suitable properties, such as specific targeting and low toxicity, for use in the targeted delivery of bioactive molecules, such as genetic material. In addition, derivatives of the cationic dendrimer also display suitable properties for the targeted delivery of bioactive molecules. See also, Bioactive Polymers, US published application 20080267903, which discloses "Various polymers, including cationic polyamine polymers and dendrimeric polymers, are shown to possess anti-proliferative activity, and may therefore be useful for treatment of disorders characterised by undesirable cellular proliferation such as neoplasms and tumours, inflammatory disorders (including autoimmune disorders), psoriasis and atherosclerosis. The polymers may be used alone as active agents, or as delivery vehicles for other therapeutic agents, such as drug molecules or nucleic acids for gene therapy. In such cases, the polymers' own intrinsic anti-tumour activity may complement the activity of the agent to be delivered."

Supercharged Proteins

Supercharged proteins are a class of engineered or naturally occurring proteins with unusually high positive or negative net theoretical charge. Both supernegatively and superpositively charged proteins exhibit a remarkable ability to withstand thermally or chemically induced aggregation. Superpositively charged proteins are also able to penetrate mammalian cells. Associating cargo with these proteins, such as plasmid DNA, siRNA, or other proteins, can enable the functional delivery of these macromolecules into mammalian cells both in vitro and in vivo. David Liu's lab reported the creation and characterization of supercharged proteins in 2007 (Lawrence et al., 2007, Journal of the American Chemical Society 129, 10110-10112).

The nonviral delivery of siRNA and plasmid DNA into mammalian cells are valuable both for research and therapeutic applications (Akinc et al., 2010, Nat. Biotech. 26, 561-569). Purified +36 GFP protein (or other superpositively charged protein) is mixed with siRNAs in the appropriate serum-free media and allowed to complex prior addition to cells. Inclusion of serum at this stage inhibits formation of the supercharged protein-siRNA complexes and reduces the effectiveness of the treatment. The following protocol has been found to be effective for a variety of cell lines (McNaughton et al., 2009, Proc. Natl. Acad. Sci. USA 106, 6111-6116). However, pilot experiments varying the dose of protein and siRNA should be performed to optimize the procedure for specific cell lines.

(1) One day before treatment, plate $1\times10^5$ cells per well in a 48-well plate.

(2) On the day of treatment, dilute purified +36 GFP protein in serumfree media to a final concentration 200 nM. Add siRNA to a final concentration of 50 nM. Vortex to mix and incubate at room temperature for 10 min.

(3) During incubation, aspirate media from cells and wash once with PBS.

(4) Following incubation of +36 GFP and siRNA, add the protein-siRNA complexes to cells.

(5) Incubate cells with complexes at 37 C for 4 h.

(6) Following incubation, aspirate the media and wash three times with 20 U/mL heparin PBS. Incubate cells with serum-containing media for a further 48 h or longer depending upon the assay for knockdown.

(7) Analyze cells by immunoblot, qPCR, phenotypic assay, or other appropriate method.

It has been found that +36 GFP is an effective plasmid delivery reagent in a range of cells. As plasmid DNA is a larger cargo than siRNA, proportionately more +36 GFP protein is required to effectively complex plasmids. For effective plasmid delivery Applicants have developed a variant of +36 GFP bearing a C-terminal HA2 peptide tag, a known endosome-disrupting peptide derived from the influenza virus hemagglutinin protein. The following protocol has been effective in a variety of cells, but as above it is advised that plasmid DNA and supercharged protein doses be optimized for specific cell lines and delivery applications.

(1) One day before treatment, plate $1\times10^5$ per well in a 48-well plate.

(2) On the day of treatment, dilute purified þ36 GFP protein in serumfree media to a final concentration 2 mM. Add 1 mg of plasmid DNA. Vortex to mix and incubate at room temperature for 10 min.

(3) During incubation, aspirate media from cells and wash once with PBS.

(4) Following incubation of þ36 GFP and plasmid DNA, gently add the protein-DNA complexes to cells.

(5) Incubate cells with complexes at 37 C for 4 h.

(6) Following incubation, aspirate the media and wash with PBS. Incubate cells in serum-containing media and incubate for a further 24-48 h.

(7) Analyze plasmid delivery (e.g., by plasmid-driven gene expression) as appropriate.

See also, e.g., McNaughton et al., Proc. Natl. Acad. Sci. USA 106, 6111-6116 (2009); Cronican et al., ACS Chemical Biology 5, 747-752 (2010); Cronican et al., Chemistry & Biology 18, 833-838 (2011); Thompson et al., Methods in Enzymology 503, 293-319 (2012); Thompson, D. B., et al., Chemistry & Biology 19 (7), 831-843 (2012). The methods of the super charged proteins may be used and/or adapted for delivery of the CRISPR Cas system of the present invention.

Cell Penetrating Peptides

In yet another embodiment, cell penetrating peptides (CPPs) are contemplated for the delivery of the CRISPR Cas system. CPPs are short peptides that facilitate cellular uptake of various molecular cargo (from nanosize particles to small chemical molecules and large fragments of DNA). The term "cargo" as used herein includes but is not limited to the group consisting of therapeutic agents, diagnostic probes, peptides, nucleic acids, antisense oligonucleotides, plasmids, proteins, nanoparticles, liposomes, chromophores, small molecules and radioactive materials. In aspects of the invention, the cargo may also comprise any component of the CRISPR Cas system or the entire functional CRISPR Cas system. Aspects of the present invention further provide methods for delivering a desired cargo into a subject comprising: (a) preparing a complex comprising the cell penetrating peptide of the present invention and a desired cargo, and (b) orally, intraarticularly, intraperitoneally, intrathecally, intrarterially, intranasally, intraparenchymally, subcutaneously, intramuscularly, intravenously, dermally, intrarectally, or topically administering the complex to a subject. The cargo is associated with the peptides either through chemical linkage via covalent bonds or through non-covalent interactions.

The function of the CPPs are to deliver the cargo into cells, a process that commonly occurs through endocytosis with the cargo delivered to the endosomes of living mammalian cells. Cell-penetrating peptides are of different sizes, amino acid sequences, and charges but all CPPs have one distinct characteristic, which is the ability to translocate the plasma membrane and facilitate the delivery of various molecular cargoes to the cytoplasm or an organelle. CPP translocation may be classified into three main entry mechanisms: direct penetration in the membrane, endocytosis-mediated entry, and translocation through the formation of a transitory structure. CPPs have found numerous applications in medicine as drug delivery agents in the treatment of different diseases including cancer and virus inhibitors, as well as contrast agents for cell labeling. Examples of the latter include acting as a carrier for GFP, MRI contrast agents, or quantum dots. CPPs hold great potential as in vitro and in vivo delivery vectors for use in research and medicine. CPPs typically have an amino acid composition that either contains a high relative abundance of positively charged amino acids such as lysine or arginine or has sequences that contain an alternating pattern of polar/charged amino acids and non-polar, hydrophobic amino acids. These two types of structures are referred to as polycationic or amphipathic, respectively. A third class of CPPs are the hydrophobic peptides, containing only apolar residues, with low net charge or have hydrophobic amino acid groups that are crucial for cellular uptake. One of the initial CPPs discovered was the trans-activating transcriptional activator (Tat) from Human Immunodeficiency Virus 1 (HIV-1) which was found to be efficiently taken up from the surrounding media by numerous cell types in culture. Since then, the number of known CPPs has expanded considerably and small molecule synthetic analogues with more effective protein transduction properties have been generated. CPPs include but are not limited to Penetratin, Tat (48-60), Transportan, and (R-AhX-R4) (Ahx=aminohexanoyl) (SEQ ID NO: 926).

As described in U.S. Pat. No. 8,372,951, there is provided a CPP derived from eosinophil cationic protein (ECP) which exhibits highly cell-penetrating efficiency and low toxicity. Aspects of delivering the CPP with its cargo into a vertebrate subject are also provided. Further aspects of CPPs and their delivery are described in U.S. Pat. Nos. 8,575,305; 8; 614,194 and 8,044,019.

That CPPs can be employed to deliver the CRISPR-Cas system is also provided in the manuscript "Gene disruption by cell-penetrating peptide-mediated delivery of Cas9 protein and guide RNA", by Suresh Ramakrishna, Abu-Bonsrah Kwaku Dad, Jagadish Beloor, et al. Genome Res. 2014 Apr. 2. [Epub ahead of print], incorporated by reference in its entirety, wherein it is demonstrated that treatment with CPP-conjugated recombinant Cas9 protein and CPP-complexed guide RNAs lead to endogenous gene disruptions in human cell lines. In the paper the Cas9 protein was conjugated to CPP via a thioether bond, whereas the guide RNA was complexed with CPP, forming condensed, positively charged nanoparticles. It was shown that simultaneous and sequential treatment of human cells, including embryonic stem cells, dermal fibroblasts, HEK293T cells, HeLa cells, and embryonic carcinoma cells, with the modified Cas9 and guide RNA led to efficient gene disruptions with reduced off-target mutations relative to plasmid transfections.

Implantable Devices

In another embodiment, implantable devices are also contemplated for delivery of the CRISPR Cas system. For example, US Patent Publication 20110195123 discloses an implantable medical device which elutes a drug locally and in prolonged period is provided, including several types of such a device, the treatment modes of implementation and methods of implantation. The device comprising of polymeric substrate, such as a matrix for example, that is used as the device body, and drugs, and in some cases additional scaffolding materials, such as metals or additional polymers, and materials to enhance visibility and imaging. The selection of drug is based on the advantageous of releasing drug locally and in prolonged period, where drug is released directly to the extracellular matrix (ECM) of the diseased area such as tumor, inflammation, degeneration or for symptomatic objectives, or to injured smooth muscle cells, or for prevention. One kind of drug is the gene silencing drugs based on RNA interference (RNAi), including but not limited to si RNA, shRNA, or antisense RNA/DNA, ribozyme and nucleoside analogs. Therefore, this system may be used/and or adapted to the CRISPR Cas system of the present invention. The modes of implantation in some embodiments are existing implantation procedures that are developed and used today for other treatments, including brachytherapy and needle biopsy. In such cases the dimensions of the new implant described in this invention are similar to the original implant. Typically a few devices are implanted during the same treatment procedure.

As described in US Patent Publication 20110195123, there is provided a drug delivery implantable or insertable system, including systems applicable to a cavity such as the abdominal cavity and/or any other type of administration in which the drug delivery system is not anchored or attached, comprising a biostable and/or degradable and/or bioabsorbable polymeric substrate, which may for example optionally be a matrix. It should be noted that the term "insertion" also includes implantation. The drug delivery system is preferably implemented as a "Loder" as described in US Patent Publication 20110195123.

The polymer or plurality of polymers are biocompatible, incorporating an agent and/or plurality of agents, enabling the release of agent at a controlled rate, wherein the total volume of the polymeric substrate, such as a matrix for example, in some embodiments is optionally and preferably no greater than a maximum volume that permits a therapeutic level of the agent to be reached. As a non-limiting example, such a volume is preferably within the range of 0.1 $m^3$ to 1000 $mm^3$, as required by the volume for the agent load. The Loder may optionally be larger, for example when incorporated with a device whose size is determined by functionality, for example and without limitation, a knee joint, an intra-uterine or cervical ring and the like.

The drug delivery system (for delivering the composition) is designed in some embodiments to preferably employ degradable polymers, wherein the main release mechanism is bulk erosion; or in some embodiments, non degradable, or slowly degraded polymers are used, wherein the main release mechanism is diffusion rather than bulk erosion, so that the outer part functions as membrane, and its internal part functions as a drug reservoir, which practically is not affected by the surroundings for an extended period (for example from about a week to about a few months). Combinations of different polymers with different release mechanisms may also optionally be used. The concentration gradient at the surface is preferably maintained effectively constant during a significant period of the total drug releasing period, and therefore the diffusion rate is effectively constant (termed "zero mode" diffusion). By the term "constant" it is meant a diffusion rate that is preferably maintained above the lower threshold of therapeutic effectiveness, but which may still optionally feature an initial burst and/or fluctuate, for example increasing and decreasing to a certain degree. The diffusion rate is preferably so maintained for a prolonged period, and it can be considered constant to a certain level to optimize the therapeutically effective period, for example the effective silencing period.

The drug delivery system optionally and preferably is designed to shield the nucleotide based therapeutic agent from degradation, whether chemical in nature or due to attack from enzymes and other factors in the body of the subject.

The drug delivery system as described in US Patent Publication 20110195123 is optionally associated with sensing and/or activation appliances that are operated at and/or after implantation of the device, by non and/or minimally invasive methods of activation and/or acceleration/deceleration, for example optionally including but not limited to thermal heating and cooling, laser beams, and ultrasonic, including focused ultrasound and/or RF (radiofrequency) methods or devices.

According to some embodiments of US Patent Publication 20110195123, the site for local delivery may optionally include target sites characterized by high abnormal proliferation of cells, and suppressed apoptosis, including tumors, active and or chronic inflammation and infection including autoimmune diseases states, degenerating tissue including muscle and nervous tissue, chronic pain, degenerative sites, and location of bone fractures and other wound locations for enhancement of regeneration of tissue, and injured cardiac, smooth and striated muscle. The site for local delivery also may optionally include sites enabling performing preventive activities including pregnancy, prevention of infection and aging.

The site for implantation of the composition, or target site, preferably features a radius, area and/or volume that is sufficiently small for targeted local delivery. For example, the target site optionally has a diameter in a range of from about 0.1 mm to about 5 cm.

The location of the target site is preferably selected for maximum therapeutic efficacy. For example, the composition of the drug delivery system (optionally with a device for implantation as described above) is optionally and preferably implanted within or in the proximity of a tumor environment, or the blood supply associated thereof.

For example the composition (optionally with the device) is optionally implanted within or in the proximity to pancreas, prostate, breast, liver, via the nipple, within the vascular system and so forth.

The target location is optionally selected from the group consisting of (as non-limiting examples only, as optionally any site within the body may be suitable for implanting a Loder): 1. brain at degenerative sites like in Parkinson or Alzheimer disease at the basal ganglia, white and gray matter; 2. spine as in the case of amyotrophic lateral sclerosis (ALS); 3. uterine cervix to prevent HPV infection; 4. active and chronic inflammatory joints; 5. dermis as in the case of psoriasis; 6. sympathetic and sensoric nervous sites for analgesic effect; 7. Intra osseous implantation; 8. acute and chronic infection sites; 9. Intra vaginal; 10. Inner ear—auditory system, labyrinth of the inner ear, vestibular system; 11. Intra tracheal; 12. Intra-cardiac; coronary, epicardiac; 13. urinary bladder; 14. biliary system; 15. parenchymal tissue including and not limited to the kidney, liver, spleen; 16. lymph nodes; 17. salivary glands; 18. dental gums; 19. Intra-articular (into joints); 20. Intra-ocular; 21. Brain tissue; 22. Brain ventricles; 23. Cavities, including abdominal cavity (for example but without limitation, for ovary cancer); 24. Intra esophageal and 25. Intra rectal.

Optionally insertion of the system (for example a device containing the composition) is associated with injection of material to the ECM at the target site and the vicinity of that site to affect local pH and/or temperature and/or other biological factors affecting the diffusion of the drug and/or drug kinetics in the ECM, of the target site and the vicinity of such a site.

Optionally, according to some embodiments, the release of said agent could be associated with sensing and/or activation appliances that are operated prior and/or at and/or after insertion, by non and/or minimally invasive and/or else methods of activation and/or acceleration/deceleration, including laser beam, radiation, thermal heating and cooling, and ultrasonic, including focused ultrasound and/or RF (radiofrequency) methods or devices, and chemical activators.

According to other embodiments of US Patent Publication 20110195123, the drug preferably comprises a gene silencing biological RNAi drug, for example for localized cancer cases in breast, pancreas, brain, kidney, bladder, lung, and prostate as described below. Moreover, many drugs other than siRNA are applicable to be encapsulated in Loder, and can be used in association with this invention, as long as such drugs can be encapsulated with the Loder substrate, such as a matrix for example. Such drugs include approved drugs that are delivered today by methods other than of this invention, including Amphotericin B for fungal infection; antibiotics such as in osteomyelitis; pain killers such as narcotics; anti degenerative such as in Alzheimer or Parkinson diseases in a Loder implanted in the vicinity of the spine in the case of back pain. Such a system may be used and/or adapted to deliver the CRISPR Cas system of the present invention.

For example, for specific applications such as prevention of growth or regrowth of smooth muscle cells (that are injured during a stenting procedure and as a result tend to proliferate), the drug may optionally be siRNA that silence smooth muscle cells, including H19 silencing, or a drug selected from the group consisting of taxol, rapamycin and rapamycin-analogs. In such cases the Loder is preferably either a Drug Eluting Stent (DES), with prolonged release at constant rate, or a dedicated device that is implanted separately, in association to the stent. All of this may be used/and or adapted to the CRISPR Cas system of the present invention.

As another example of a specific application, neuro and muscular degenerative diseases develop due to abnormal gene expression. Local delivery of silencing RNAs may have therapeutic properties for interfering with such abnormal gene expression. Local delivery of anti apoptotic, anti inflammatory and anti degenerative drugs including small drugs and macromolecules may also optionally be therapeutic. In such cases the Loder is applied for prolonged release at constant rate and/or through a dedicated device that is implanted separately. All of this may be used and/or adapted to the CRISPR Cas system of the present invention.

As yet another example of a specific application, psychiatric and cognitive disorders are treated with gene modifiers. Gene knockdown with silencing RNA is a treatment option. Loders locally delivering nucleotide based agents to central nervous system sites are therapeutic options for psychiatric and cognitive disorders including but not limited to psychosis, bi-polar diseases, neurotic disorders and behavioral maladies. The Loders could also deliver locally drugs including small drugs and macromolecules upon implantation at specific brain sites. All of this may be used and/or adapted to the CRISPR Cas system of the present invention.

As another example of a specific application, silencing of innate and/or adaptive immune mediators at local sites enables the prevention of organ transplant rejection. Local delivery of silencing RNAs and immunomodulating reagents with the Loder implanted into the transplanted organ and/or the implanted site renders local immune suppression by repelling immune cells such as CD8 activated against the transplanted organ. All of this may be used/and or adapted to the CRISPR Cas system of the present invention.

As another example of a specific application, vascular growth factors including VEGFs and angiogenin and others are essential for neovascularization. Local delivery of the factors, peptides, peptidomimetics, or suppressing their repressors is an important therapeutic modality; silencing the repressors and local delivery of the factors, peptides, macromolecules and small drugs stimulating angiogenesis with the Loder is therapeutic for peripheral, systemic and cardiac vascular disease.

The method of insertion, such as implantation, may optionally already be used for other types of tissue implantation and/or for insertions and/or for sampling tissues, optionally without modifications, or alternatively optionally only with non-major modifications in such methods. Such methods optionally include but are not limited to brachytherapy methods, biopsy, endoscopy with and/or without ultrasound, such as ERCP, stereotactic methods into the brain tissue, Laparoscopy, including implantation with a laparoscope into joints, abdominal organs, the bladder wall and body cavities.

CRISPR Enzyme mRNA and Guide RNA

CRISPR enzyme mRNA and guide RNA might also be delivered separately. CRISPR enzyme mRNA can be delivered prior to the guide RNA to give time for CRISPR enzyme to be expressed. CRISPR enzyme mRNA might be administered 1-12 hours (preferably around 2-6 hours) prior to the administration of guide RNA.

Alternatively, CRISPR enzyme mRNA and guide RNA can be administered together. Advantageously, a second booster dose of guide RNA can be administered 1-12 hours (preferably around 2-6 hours) after the initial administration of CRISPR enzyme mRNA+guide RNA.

Additional administrations of CRISPR enzyme mRNA and/or guide RNA might be useful to achieve the most efficient levels of genome modification.

For minimization of toxicity and off-target effect, it will be important to control the concentration of CRISPR enzyme mRNA and guide RNA delivered. Optimal concentrations of CRISPR enzyme mRNA and guide RNA can be determined by testing different concentrations in a cellular or animal model and using deep sequencing the analyze the extent of modification at potential off-target genomic loci. For example, for the guide sequence targeting 5'-GAGTCCGAGCAGAAGAAGAA-3' (SEQ ID NO: 5) in the EMX1 gene of the human genome, deep sequencing can be used to assess the level of modification at the following two off-target loci, 1: 5'-GAGTCCTAGCAGGAGAAGAA-3' (SEQ ID NO: 6) and 2: 5'-GAGTCTAAGCAGAAGAAGAA-3' (SEQ ID NO: 7). The concentration that gives the highest level of on-target modification while minimizing the level of off-target modification should be chosen for in vivo delivery.

Alternatively, to minimize the level of toxicity and off-target effect, CRISPR enzyme nickase mRNA (for example *S. pyogenes* Cas9 with the D10A mutation) can be delivered with a pair of guide RNAs targeting a site of interest. The two guide RNAs need to be spaced as follows. Guide sequences in single underline and double underline respectively (these examples are based on the PAM requirement for *Streptococcus pyogenes* Cas9).

| Over-hang length (bp) | Guide RNA design (guide sequence and PAM color coded) |
|---|---|
| 14 | 5'-NNNNNNNNNNNNNNNNNNNNCCNNNNNNNNNNNNNNNNNNNNNNGGNNNNNNNNNNNNNN-3' (SEQ ID NO: 8)<br>3'-NNNNNNNNNNNNNNNNNNNNGGNNNNNNNNNNNNNNNNNNNNNNCCNNNNNNNNNNNNNN-5' (SEQ ID NO: 9) |
| 13 | 5'-NNNNNNNNNNNNNNNNNNNNCCNNNNNNNNNNNNNNNNNNNNNGGNNNNNNNNNNNNNNN-3' (SEQ ID NO: 10)<br>3'-NNNNNNNNNNNNNNNNNNNNGGNNNNNNNNNNNNNNNNNNNNNCCNNNNNNNNNNNNNNN-5' (SEQ ID NO: 11) |
| 12 | 5'-NNNNNNNNNNNNNNNNNNNNCCNNNNNNNNNNNNNNNNNNNNGGNNNNNNNNNNNNNNNN-3' (SEQ ID NO: 12)<br>3'-NNNNNNNNNNNNNNNNNNNNGGNNNNNNNNNNNNNNNNNNNNCCNNNNNNNNNNNNNNNN-5' (SEQ ID NO: 13) |
| 11 | 5'-NNNNNNNNNNNNNNNNNNNNCCNNNNNNNNNNNNNNNNNNNGGNNNNNNNNNNNNNNNNN-3' (SEQ ID NO: 14)<br>3'-NNNNNNNNNNNNNNNNNNNNGGNNNNNNNNNNNNNNNNNNNCCNNNNNNNNNNNNNNNNN-5' (SEQ ID NO: 15) |
| 10 | 5'-NNNNNNNNNNNNNNNNNNNNCCNNNNNNNNNNNNNNNNNNGGNNNNNNNNNNNNNNNNNN-3' (SEQ ID NO: 16)<br>3'-NNNNNNNNNNNNNNNNNNNNGGNNNNNNNNNNNNNNNNNNCCNNNNNNNNNNNNNNNNNN-5' (SEQ ID NO: 17) |
| 9 | 5'-NNNNNNNNNNNNNNNNNNNNCCNNNNNNNNNNNNNNNNNGGNNNNNNNNNNNNNNNNNNN-3' (SEQ ID NO: 18)<br>3'-NNNNNNNNNNNNNNNNNNNNGGNNNNNNNNNNNNNNNNNCCNNNNNNNNNNNNNNNNNNN-5' (SEQ ID NO: 19) |
| 8 | 5'-NNNNNNNNNNNNNNNNNNNNCCNNNNNNNNNNNNNNNNGGNNNNNNNNNNNNNNNNNNNN-3' (SEQ ID NO: 20)<br>3'-NNNNNNNNNNNNNNNNNNNNGGNNNNNNNNNNNNNNNNCCNNNNNNNNNNNNNNNNNNNN-5' (SEQ ID NO: 21) |
| 7 | 5'-NNNNNNNNNNNNNNNNNNNNCCNNNNNNNNNNNNNNNGGNNNNNNNNNNNNNNNNNNNNN-3' (SEQ ID NO: 22)<br>3'-NNNNNNNNNNNNNNNNNNNNGGNNNNNNNNNNNNNNNCCNNNNNNNNNNNNNNNNNNNNN-5' (SEQ ID NO: 23) |
| 6 | 5'-NNNNNNNNNNNNNNNNNNNNCCNNNNNNNNNNNNNNGGNNNNNNNNNNNNNNNNNNNNNN-3' (SEQ ID NO: 24)<br>3'-NNNNNNNNNNNNNNNNNNNNGGNNNNNNNNNNNNNNCCNNNNNNNNNNNNNNNNNNNNNN-5' (SEQ ID NO: 25) |
| 5 | 5'-NNNNNNNNNNNNNNNNNNNNCCNNNNNNNNNNNNNGGNNNNNNNNNNNNNNNNNNNNNNN-3' (SEQ ID NO: 26)<br>3'-NNNNNNNNNNNNNNNNNNNNGGNNNNNNNNNNNNNCCNNNNNNNNNNNNNNNNNNNNNNN-5' (SEQ ID NO: 27) |
| 4 | 5'-NNNNNNNNNNNNNNNNNNNNCCNNNNNNNNNNNNGGNNNNNNNNNNNNNNNNNNNNNNNN-3' (SEQ ID NO: 28)<br>3'-NNNNNNNNNNNNNNNNNNNNGGNNNNNNNNNNNNCCNNNNNNNNNNNNNNNNNNNNNNNN-5' (SEQ ID NO: 29) |
| 3 | 5'-NNNNNNNNNNNNNNNNNNNNCCNNNNNNNNNNNGGNNNNNNNNNNNNNNNNNNNNNNNNN-3' (SEQ ID NO: 30)<br>3'-NNNNNNNNNNNNNNNNNNNNGGNNNNNNNNNNNCCNNNNNNNNNNNNNNNNNNNNNNNNN-5' (SEQ ID NO: 31) |
| 2 | 5'-NNNNNNNNNNNNNNNNNNNNCCNNNNNNNNNNGGNNNNNNNNNNNNNNNNNNNNNNNNNN-3' (SEQ ID NO: 32)<br>3'-NNNNNNNNNNNNNNNNNNNNGGNNNNNNNNNNCCNNNNNNNNNNNNNNNNNNNNNNNNNN-5' (SEQ ID NO: 33) |
| 1 | 5'-NNNNNNNNNNNNNNNNNNNNCCNNNNNNNNNGGNNNNNNNNNNNNNNNNNNNNNNNNNNN-3' (SEQ ID NO: 34)<br>3'-NNNNNNNNNNNNNNNNNNNNGGNNNNNNNNNCCNNNNNNNNNNNNNNNNNNNNNNNNNNN-5' (SEQ ID NO: 35) |
| blunt | 5'-NNNNNNNNNNNNNNNNNNNNCCNNNNNNNNGGNNNNNNNNNNNNNNNNNNNNNNNNNNNN-3' (SEQ ID NO: 36)<br>3'-NNNNNNNNNNNNNNNNNNNNGGNNNNNNNNCCNNNNNNNNNNNNNNNNNNNNNNNNNNNN-5' (SEQ ID NO: 37) |
| 1 | 5'-NNNNNNNNNNNNNNNNNNNNCCNNNNNNNGGNNNNNNNNNNNNNNNNNNNNNNNNNNNNN-3' (SEQ ID NO: 38)<br>3'-NNNNNNNNNNNNNNNNNNNNGGNNNNNNNCCNNNNNNNNNNNNNNNNNNNNNNNNNNNNN-5' (SEQ ID NO: 39) |

-continued

| Overhang length (bp) | Guide RNA design (guide sequence and PAM color coded) |
|---|---|
| 2 | 5'-NNNNNNNNNNNNNNNNNNNNCCNNNNNNGGNNNNNNNNNNNNNNNNNNNNNNNNNNNNNN-3' (SEQ ID NO: 40)<br>3'-NNNNNNNNNNNNNNNNNNNNGGNNNNNNCCNNNNNNNNNNNNNNNNNNNNNNNNNNNNNN-5' (SEQ ID NO: 41) |
| 3 | 5'-NNNNNNNNNNNNNNNNNNNNCCNNNNNGGNNNNNNNNNNNNNNNNNNNNNNNNNNNNNNN-3' (SEQ ID NO: 42)<br>3'-NNNNNNNNNNNNNNNNNNNNGGNNNNNCCNNNNNNNNNNNNNNNNNNNNNNNNNNNNNNN-5' (SEQ ID NO: 43) |
| 4 | 5'-NNNNNNNNNNNNNNNNNNNNCCNNNNGGNNNNNNNNNNNNNNNNNNNNNNNNNNNNNNNN-3' (SEQ ID NO: 44)<br>3'-NNNNNNNNNNNNNNNNNNNNGGNNNNCCNNNNNNNNNNNNNNNNNNNNNNNNNNNNNNNN-5' (SEQ ID NO: 45) |
| 5 | 5'-NNNNNNNNNNNNNNNNNNNNCCNNNGGNNNNNNNNNNNNNNNNNNNNNNNNNNNNNNNNN-3' (SEQ ID NO: 46)<br>3'-NNNNNNNNNNNNNNNNNNNNGGNNNCCNNNNNNNNNNNNNNNNNNNNNNNNNNNNNNNNN-5' (SEQ ID NO: 47) |
| 6 | 5'-NNNNNNNNNNNNNNNNNNNNCCNNGGNNNNNNNNNNNNNNNNNNNNNNNNNNNNNNNNNN-3' (SEQ ID NO: 48)<br>3'-NNNNNNNNNNNNNNNNNNNNGGNNCCNNNNNNNNNNNNNNNNNNNNNNNNNNNNNNNNNN-5' (SEQ ID NO: 49) |
| 7 | 5'-NNNNNNNNNNNNNNNNNNNNCCNGGNNNNNNNNNNNNNNNNNNNNNNNNNNNNNNNNNNN-3' (SEQ ID NO: 50)<br>3'-NNNNNNNNNNNNNNNNNNNNGGNCCNNNNNNNNNNNNNNNNNNNNNNNNNNNNNNNNNNN-5' (SEQ ID NO: 51) |
| 8 | 5'-NNNNNNNNNNNNNNNNNNNNNCCGGNNNNNNNNNNNNNNNNNNNNNNNNNNNNNNNNNNN-3' (SEQ ID NO: 52)<br>3'-NNNNNNNNNNNNNNNNNNNNNGGCCNNNNNNNNNNNNNNNNNNNNNNNNNNNNNNNNNNN-5' (SEQ ID NO: 53) |
| 12 | 5'-NNNNNNNNNNNNNNNNNNNNNNNGGNNNNNNNNNNNNNNNNNNNNNNNNNNNNNNNNNNN-3' (SEQ ID NO: 54)<br>3'-NNNNNNNNNNNNNNNNNNNNNNNCCGGNNNNNNNNNNNNNNNNNNNNNNNNNNNNNNNNN-5' (SEQ ID NO: 55) |
| 13 | 5'-NNNNNNNNNNNNNNNNNNNNNNCGGNNNNNNNNNNNNNNNNNNNNNNNNNNNNNNNNNNN-3' (SEQ ID NO: 56)<br>3'-NNNNNNNNNNNNNNNNNNNNNNNCCNGGNNNNNNNNNNNNNNNNNNNNNNNNNNNNNNNN-5' (SEQ ID NO: 57) |
| 14 | 5'-NNNNNNNNNNNNNNNNNNNNNNCGGNNNNNNNNNNNNNNNNNNNNNNNNNNNNNNNNNNN-3' (SEQ ID NO: 56)<br>3'-NNNNNNNNNNNNNNNNNNNNNNNCCNNGGNNNNNNNNNNNNNNNNNNNNNNNNNNNNNNN-5' (SEQ ID NO: 58) |
| 15 | 5'-NNNNNNNNNNNNNNNNNNNNNNCGGNNNNNNNNNNNNNNNNNNNNNNNNNNNNNNNNNNN-3' (SEQ ID NO: 56)<br>3'-NNNNNNNNNNNNNNNNNNNNNNNCCNNNGGNNNNNNNNNNNNNNNNNNNNNNNNNNNNNN-5' (SEQ ID NO: 59) |
| 16 | 5'-NNNNNNNNNNNNNNNNNNNNNNCGGNNNNNNNNNNNNNNNNNNNNNNNNNNNNNNNNNNN-3' (SEQ ID NO: 56)<br>3'-NNNNNNNNNNNNNNNNNNNNNNNCCNNNNGGNNNNNNNNNNNNNNNNNNNNNNNNNNNNN-5' (SEQ ID NO: 60) |
| 17 | 5'-NNNNNNNNNNNNNNNNNNNNNNCGGNNNNNNNNNNNNNNNNNNNNNNNNNNNNNNNNNNN-3' (SEQ ID NO: 56)<br>3'-NNNNNNNNNNNNNNNNNNNNNNNCCNNNNNGGNNNNNNNNNNNNNNNNNNNNNNNNNNNN-5' (SEQ ID NO: 61) |

Further interrogation of the system have given Applicants evidence of the 5' overhang (see, e.g., Ran et al., Cell. 2013 Sep. 12; 154(6):1380-9 and U.S. Provisional Patent Application Ser. No. 61/871,301 filed Aug. 28, 2013). Applicants have further identified parameters that relate to efficient cleavage by the Cas9 nickase mutant when combined with two guide RNAs and these parameters include but are not limited to the length of the 5' overhang. In embodiments of the invention the 5' overhang is at most 200 base pairs, preferably at most 100 base pairs, or more preferably at most 50 base pairs. In embodiments of the invention the 5' overhang is at least 26 base pairs, preferably at least 30 base pairs or more preferably 34-50 base pairs or 1-34 base pairs. In other preferred methods of the invention the first guide sequence directing cleavage of one strand of the DNA duplex near the first target sequence and the second guide sequence directing cleavage of other strand near the second target sequence results in a blunt cut or a 3' overhang. In embodiments of the invention the 3' overhang is at most 150, 100 or 25 base pairs or at least 15, 10 or 1 base pairs. In preferred embodiments the 3' overhang is 1-100 basepairs.

Aspects of the invention relate to the expression of the gene product being decreased or a template polynucleotide being further introduced into the DNA molecule encoding the gene product or an intervening sequence being excised precisely by allowing the two 5' overhangs to reanneal and ligate or the activity or function of the gene product being altered or the expression of the gene product being increased. In an embodiment of the invention, the gene product is a protein.

Only sgRNA pairs creating 5' overhangs with less than 8 bp overlap between the guide sequences (offset greater than −8 bp) were able to mediate detectable indel formation. Importantly, each guide used in these assays is able to efficiently induce indels when paired with wildtype Cas9, indicating that the relative positions of the guide pairs are the most important parameters in predicting double nicking activity.

Since Cas9n and Cas9H840A nick opposite strands of DNA, substitution of Cas9n with Cas9H840A with a given sgRNA pair should result in the inversion of the overhang type. For example, a pair of sgRNAs that will generate a 5' overhang with Cas9n should in principle generate the corresponding 3' overhang instead. Therefore, sgRNA pairs that lead to the generation of a 3' overhang with Cas9n might be used with Cas9H840A to generate a 5' overhang. Unexpectedly, Applicants tested Cas9H840A with a set of sgRNA pairs designed to generate both 5' and 3' overhangs (offset range from −278 to +58 bp), but were unable to observe indel formation. Further work may be needed to identify the necessary design rules for sgRNA pairing to allow double nicking by Cas9H840A.

Liver, Proprotein Convertase Subtilisin Kexin 9 (PCSK9)

The data shows phenotypic conversion.

Proprotein convertase subtilisin kexin 9 (PCSK9) is a member of the subtilisin serine protease family. PCSK9 is primarily expressed by the liver and is critical for the down regulation of hepatocyte LDL receptor expression. LDL-C levels in plasma are highly elevated in humans with gain of function mutations in PCSK9, classifying them as having severe hypercholesterolemia. Therefore, PCSK9 is an attractive target for CRISPR. PCS9K-targeted CRISPR may be formulated in a lipid particle and for example administered at about 15, 45, 90, 150, 250 and 400 μg/kg intravenously (see, e.g., available at worldwideweb.alnylam.com/capella/wp-content/uploads/2013/08/ALN-PCS02-001-Protocol-Lancet.pdf).

Bailey et al. (J Mol Med (Berl). 1999 January; 77(1):244-9) discloses insulin delivery by ex-vivo somatic cell gene therapy involves the removal of non-B-cell somatic cells (e.g. fibroblasts) from a diabetic patient, and genetically altering them in vitro to produce and secrete insulin. The cells can be grown in culture and returned to the donor as a source of insulin replacement. Cells modified in this way could be evaluated before implantation, and reserve stocks could be cryopreserved. By using the patient's own cells, the procedure should obviate the need for immunosuppression and overcome the problem of tissue supply, while avoiding a recurrence of cell destruction. Ex-vivo somatic cell gene therapy requires an accessible and robust cell type that is amenable to multiple transfections and subject to controlled proliferation. Special problems associated with the use of non-B-cell somatic cells include the processing of proinsulin to insulin, and the conferment of sensitivity to glucose-stimulated proinsulin biosynthesis and regulated insulin release. Preliminary studies using fibroblasts, pituitary cells, kidney (COS) cells and ovarian (CHO) cells suggest that these challenges could be met, and that ex-vivo somatic cell gene therapy offers a feasible approach to insulin replacement therapy. The system of Bailey et al. may be used/and or adapted to the CRISPR Cas system of the present invention for delivery to the liver.

The methods of Sato et al. (Nature Biotechnology Volume 26 Number 4 Apr. 2008, Pages 431-442) may be applied to the CRISPR Cas system of the present invention for delivery to the liver. Sato et al. found that treatments with the siRNA-bearing vitamin A-coupled liposomes almost completely resolved liver fibrosis and prolonged survival in rats with otherwise lethal dimethylnitrosamine-induced liver cirrhosis in a dose- and duration-dependent manner. Cationic liposomes (Lipotrust) containing O,O'-ditetradecanoyl-N-(a-trimethylammonioacetyl) diethanolamine chloride (DC-6-14) as a cationic lipid, cholesterol and dioleoylphosphatidylethanolamine at a molar ratio of 4:3:3 (which has shown high transfection efficiency under serum containing conditions for in vitro and in vivo gene delivery) were purchased from Hokkaido System Science. The liposomes were manufactured using a freeze-dried empty liposomes method and prepared at a concentration of 1 mM (DC-16-4) by addition of double-distilled water (DDW) to the lyophilized lipid mixture under vortexing before use. To prepare VA-coupled liposomes, 200 nmol of vitamin A (retinol, Sigma) dissolved in DMSO was mixed with the liposome suspensions (100 nmol as DC-16-4) by vortexing in a 1.5 ml tube at 25 1C. To prepare VA-coupled liposomes carrying siRNAgp46 (VA-lip-siRNAgp46), a solution of siRNAgp46 (580 pmol/ml in DDW) was added to the retinol-coupled liposome solution with stirring at 25 C. The ratio of siRNA to DC-16-4 was 1:11.5 (mol/mol) and the siRNA to liposome ratio (wt/wt) was 1:1. Any free vitamin A or siRNA that was not taken up by liposomes were separated from liposomal preparations using a micropartition system (VIVASPIN 2 concentrator 30,000 MWCO PES, VIVASCIENCE). The liposomal suspension was added to the filters and centrifuged at 1,500 g for 5 min 3 times at 25 1C. Fractions were collected and the material trapped in the filter was reconstituted with PBS to achieve the desired dose for in vitro or in vivo use. Three injections of 0.75 mg/kg siRNA were given every other day to rats. The system of Sato et al. may be used/and or adapted to the CRISPR Cas system of the present invention for delivery to the liver by delivering about 0.5 to 1 mg/kg of CRISPR Cas RNA in the liposomes as described by Sato et al. to humans.

The methods of Rozema et al. (PNAS, Aug. 7, 2007, vol. 104, no. 32) for a vehicle for the delivery of siRNA to hepatocytes both in vitro and in vivo, which Rozema et al. have named siRNA Dynamic PolyConjugates may also be applied to the present invention. Key features of the Dynamic Poly-Conjugate technology include a membrane-active polymer, the ability to reversibly mask the activity of this polymer until it reaches the acidic environment of endosomes, and the ability to target this modified polymer and its siRNA cargo specifically to hepatocytes in vivo after simple, low-pressure i.v. injection. SATA-modified siRNAs are synthesized by reaction of 5' amine modified siRNA with 1 weight equivalents (wt eq) of Nsuccinimidyl-S-acetylthioacetate (SATA) reagent (Pierce) and 0.36 wt eq of $NaHCO_3$ in water at 4° C. for 16 h. The modified siRNAs are then precipitated by the addition of 9 vol of ethanol and incubation at 80° C. for 2 h. The precipitate is resuspended in 1× siRNA buffer (Dharmacon) and quantified by measuring absorbance at the 260-nm wavelength. PBAVE (30 mg/ml in 5 mMTAPS, pH 9) is modified by addition of 1.5 wt % SMPT (Pierce). After a 1-h incubation, 0.8 mg of SMPT-PBAVE was added to 400 μl of isotonic glucose solution containing 5 mM TAPS (pH 9). To this solution was added 50 μg of SATA-modified siRNA. For the dose-response experiments where [PBAVE] was constant, different amounts of siRNA are added. The mixture is then incubated for 16 h. To the solution is then added 5.6 mg of Hepes free base followed by a mixture of 3.7 mg of CDM-NAG and 1.9 mg of CDM-PEG. The solution is then incubated for at least 1 h at room temperature before injection. CDM-PEG and CDM-NAG are synthesized from the acid chloride generated by using oxalyl chloride. To the acid chloride is added 1.1 molar equivalents polyethylene glycol monomethyl ether (molecular weight average of 450) to generate CDM-PEG or (aminoethoxy)ethoxy-2-(acetylamino)-2-deoxy-β-D-glucopyranoside to generate CDM-NAG. The final product is purified by using reverse-phase HPLC with a 0.1% TFA water/acetonitrile gradient. About 25 to 50 μg of siRNA was delivered to mice. The system of Rozema et al. may be applied to the CRISPR Cas system of the present invention for delivery to the liver, for example by envisioning a dosage of about 50 to about 200 mg of CRISPR Cas for delivery to a human.

Targeted Deletion, Therapeutic Applications

Targeted deletion of genes is preferred. Examples are exemplified in Example 18. Preferred are, therefore, genes involved in cholesterol biosynthesis, fatty acid biosynthesis, and other metabolic disorders, genes encoding mis-folded proteins involved in amyloid and other diseases, oncogenes leading to cellular transformation, latent viral genes, and genes leading to dominant-negative disorders, amongst other disorders. As exemplified here, Applicants prefer gene delivery of a CRISPR-Cas system to the liver, brain, ocular, epithelial, hematopoetic, or another tissue of a subject or a patient in need thereof, suffering from metabolic disorders, amyloidosis and protein-aggregation related diseases, cellular transformation arising from genetic mutations and translocations, dominant negative effects of gene mutations, latent viral infections, and other related symptoms, using either viral or nanoparticle delivery system.

Therapeutic applications of the CRISPR-Cas system include Glaucoma, Amyloidosis, and Huntington's disease. These are exemplified in Example 20 and the features described therein are preferred alone or in combination.

Another example of a polyglutamine expansion disease that may be treated by the present invention includes spinocerebellar ataxia type 1 (SCA1). Upon intracerebellar injection, recombinant adenoassociated virus (AAV) vectors expressing short hairpin RNAs profoundly improve motor coordination, restored cerebellar morphology and resolved characteristic ataxin-1 inclusions in Purkinje cells of SCA1 mice (see, e.g., Xia et al., Nature Medicine, Vol. 10, No. 8, August 2004). In particular, AAV1 and AAV5 vectors are preferred and AAV titers of about $1\times10^{12}$ vector genomes/ml are desirable.

As an example, chronic infection by HIV-1 may be treated or prevented. In order to accomplish this, one may generate CRISPR-Cas guide RNAs that target the vast majority of the HIV-1 genome while taking into account HIV-1 strain variants for maximal coverage and effectiveness. One may accomplish delivery of the CRISPR-Cas system by conventional adenoviral or lentiviral-mediated infection of the host immune system. Depending on approach, host immune cells could be a) isolated, transduced with CRISPR-Cas, selected, and re-introduced in to the host or b) transduced in vivo by systemic delivery of the CRISPR-Cas system. The first approach allows for generation of a resistant immune population whereas the second is more likely to target latent viral reservoirs within the host. This is discussed in more detail in the Examples section.

In another example, US Patent Publication No. 20130171732 assigned to Sangamo BioSciences, Inc. relates to insertion of an anti-HIV transgene into the genome, methods of which may be applied to the CRISPR Cas system of the present invention. In another embodiment, the CXCR4 gene may be targeted and the TALE system of US Patent Publication No. 20100291048 assigned to Sangamo BioSciences, Inc. may be modified to the CRISPR Cas system of the present invention. The method of US Patent Publication Nos. 20130137104 and 20130122591 assigned to Sangamo BioSciences, Inc. and US Patent Publication No. 20100146651 assigned to Cellectis may be more generally applicable for transgene expression as it involves modifying a hypoxanthine-guanine phosphoribosyltransferase (HPRT) locus for increasing the frequency of gene modification.

It is also envisaged that the present invention generates a gene knockout cell library. Each cell may have a single gene knocked out. This is exemplified in Example 23.

One may make a library of ES cells where each cell has a single gene knocked out, and the entire library of ES cells will have every single gene knocked out. This library is useful for the screening of gene function in cellular processes as well as diseases. To make this cell library, one may integrate Cas9 driven by an inducible promoter (e.g. doxycycline inducible promoter) into the ES cell. In addition, one may integrate a single guide RNA targeting a specific gene in the ES cell. To make the ES cell library, one may simply mix ES cells with a library of genes encoding guide RNAs targeting each gene in the human genome. One may first introduce a single BxB1 attB site into the AAVS1 locus of the human ES cell. Then one may use the BxB1 integrase to facilitate the integration of individual guide RNA genes into the BxB1 attB site in AAVS1 locus. To facilitate integration, each guide RNA gene may be contained on a plasmid that carries of a single attP site. This way BxB1 will recombine the attB site in the genome with the attP site on the guide RNA containing plasmid. To generate the cell library, one may take the library of cells that have single guide RNAs integrated and induce Cas9 expression. After induction, Cas9 mediates double strand break at sites specified by the guide RNA.

Chronic administration of protein therapeutics may elicit unacceptable immune responses to the specific protein. The immunogenicity of protein drugs can be ascribed to a few immunodominant helper T lymphocyte (HTL) epitopes. Reducing the MHC binding affinity of these HTL epitopes contained within these proteins can generate drugs with lower immunogenicity (Tangri S, et al. ("Rationally engineered therapeutic proteins with reduced immunogenicity" J Immunol. 2005 Mar. 15; 174(6):3187-96.) In the present invention, the immunogenicity of the CRISPR enzyme in particular may be reduced following the approach first set out in Tangri et al with respect to erythropoietin and subsequently developed. Accordingly, directed evolution or rational design may be used to reduce the immunogenicity of the CRISPR enzyme (for instance a Cas9) in the host species (human or other species).

In Example 28, Applicants used 3 guideRNAs of interest and able to visualize efficient DNA cleavage in vivo occurring only in a small subset of cells. Essentially, what Applicants have shown here is targeted in vivo cleavage. In particular, this provides proof of concept that specific targeting in higher organisms such as mammals can also be achieved. It also highlights multiplex aspect in that multiple guide sequences (i.e. separate targets) can be used simultaneously (in the sense of co-delivery). In other words, Applicants used a multiple approach, with several different sequences targeted at the same time, but independently.

A suitable example of a protocol for producing AAV, a preferred vector of the invention is provided in Example 34.

Trinucleotide repeat disorders are preferred conditions to be treated. These are also exemplified herein.

For example, US Patent Publication No. 20110016540, describes use of zinc finger nucleases to genetically modify cells, animals and proteins associated with trinucleotide repeat expansion disorders. Trinucleotide repeat expansion disorders are complex, progressive disorders that involve developmental neurobiology and often affect cognition as well as sensory-motor functions.

Trinucleotide repeat expansion proteins are a diverse set of proteins associated with susceptibility for developing a trinucleotide repeat expansion disorder, the presence of a trinucleotide repeat expansion disorder, the severity of a trinucleotide repeat expansion disorder or any combination thereof. Trinucleotide repeat expansion disorders are divided into two categories determined by the type of repeat. The most common repeat is the triplet CAG, which, when present in the coding region of a gene, codes for the amino acid glutamine (Q). Therefore, these disorders are referred to as the polyglutamine (polyQ) disorders and comprise the following diseases: Huntington Disease (HD); Spinobulbar Muscular Atrophy (SBMA); Spinocerebellar Ataxias (SCA types 1, 2, 3, 6, 7, and 17); and Dentatorubro-Pallidoluysian Atrophy (DRPLA). The remaining trinucleotide repeat expansion disorders either do not involve the CAG triplet or the CAG triplet is not in the coding region of the gene and are, therefore, referred to as the non-polyglutamine disorders. The non-polyglutamine disorders comprise Fragile X Syndrome (FRAXA); Fragile XE Mental Retardation (FRAXE); Friedreich Ataxia (FRDA); Myotonic Dystrophy (DM); and Spinocerebellar Ataxias (SCA types 8, and 12).

The proteins associated with trinucleotide repeat expansion disorders are typically selected based on an experimental association of the protein associated with a trinucleotide repeat expansion disorder to a trinucleotide repeat expansion disorder. For example, the production rate or circulating concentration of a protein associated with a trinucleotide repeat expansion disorder may be elevated or depressed in a population having a trinucleotide repeat expansion disorder relative to a population lacking the trinucleotide repeat expansion disorder. Differences in protein levels may be assessed using proteomic techniques including but not limited to Western blot, immunohistochemical staining, enzyme linked immunosorbent assay (ELISA), and mass spectrometry. Alternatively, the proteins associated with trinucleotide repeat expansion disorders may be identified by obtaining gene expression profiles of the genes encoding the proteins using genomic techniques including but not limited to DNA microarray analysis, serial analysis of gene expression (SAGE), and quantitative real-time polymerase chain reaction (Q-PCR).

Non-limiting examples of proteins associated with trinucleotide repeat expansion disorders include AR (androgen receptor), FMR1 (fragile X mental retardation 1), HTT (huntingtin), DMPK (dystrophia myotonica-protein kinase), FXN (frataxin), ATXN2 (ataxin 2), ATN1 (atrophin 1), FEN1 (flap structure-specific endonuclease 1), TNRC6A (trinucleotide repeat containing 6A), PABPN1 (poly(A) binding protein, nuclear 1), JPH3 (junctophilin 3), MED15 (mediator complex subunit 15), ATXN1 (ataxin 1), ATXN3 (ataxin 3), TBP (TATA box binding protein), CACNA1A (calcium channel, voltage-dependent, P/Q type, alpha 1A subunit), ATXN8OS (ATXN8 opposite strand (non-protein coding)), PPP2R2B (protein phosphatase 2, regulatory subunit B, beta), ATXN7 (ataxin 7), TNRC6B (trinucleotide repeat containing 6B), TNRC6C (trinucleotide repeat containing 6C), CELF3 (CUGBP, Elav-like family member 3), MAB21L1 (mab-21-like 1 (*C. elegans*)), MSH2 (mutS homolog 2, colon cancer, nonpolyposis type 1 (*E. coli*)), TMEM185A (transmembrane protein 185A), SIX5 (SIX homeobox 5), CNPY3 (canopy 3 homolog (zebrafish)), FRAXE (fragile site, folic acid type, rare, fra(X)(q28) E), GNB2 (guanine nucleotide binding protein (G protein), beta polypeptide 2), RPL14 (ribosomal protein L14), ATXN8 (ataxin 8), INSR (insulin receptor), TTR (transthyretin), EP400 (E1A binding protein p400), GIGYF2 (GRB10 interacting GYF protein 2), OGG1 (8-oxoguanine DNA glycosylase), STC1 (stanniocalcin 1), CNDP1 (carnosine dipeptidase 1 (metallopeptidase M20 family)), C10orf2 (chromosome 10 open reading frame 2), MAML3 mastermind-like 3 (*Drosophila*), DKC1 (dyskeratosis congenita 1, dyskerin), PAXIP1 (PAX interacting (with transcription-activation domain) protein 1), CASK (calcium/calmodulin-dependent serine protein kinase (MAGUK family)), MAPT (microtubule-associated protein tau), SP1 (Sp1 transcription factor), POLG (polymerase (DNA directed), gamma), AFF2 (AF4/FMR2 family, member 2), THBS1 (thrombospondin 1), TP53 (tumor protein p53), ESR1 (estrogen receptor 1), CGGBP1 (CGG triplet repeat binding protein 1), ABT1 (activator of basal transcription 1), KLK3 (kallikrein-related peptidase 3), PRNP (prion protein), JUN (jun oncogene), KCNN3 (potassium intermediate/small conductance calcium-activated channel, subfamily N, member 3), BAX (BCL2-associated X protein), FRAXA (fragile site, folic acid type, rare, fra(X)(q27.3) A (macroorchidism, mental retardation)), KBTBD10 (kelch repeat and BTB (POZ) domain containing 10), MBNL1 (muscle blind-like (*Drosophila*)), RAD51 (RAD51 homolog (RecA homolog, *E. coli*) (*S. cerevisiae*)), NCOA3 (nuclear receptor coactivator 3), ERDA1 (expanded repeat domain, CAG/CTG 1), TSC1 (tuberous sclerosis 1), COMP (cartilage oligomeric matrix protein), GCLC (glutamate-cysteine ligase, catalytic subunit), RRAD (Ras-related associated with diabetes), MSH3 (mutS homolog 3 (*E. coli*)), DRD2 (dopamine receptor D2), CD44 (CD44 molecule (Indian blood group)), CTCF (CCCTC-binding factor (zinc finger protein)), CCND1 (cyclin D1), CLSPN (claspin homolog (*Xenopus laevis*)), MEF2A (myocyte enhancer factor 2A), PTPRU (protein tyrosine phosphatase, receptor type, U), GAPDH (glyceraldehyde-3-phosphate dehydrogenase), TRIM22 (tripartite motif-containing 22), WT1 (Wilms tumor 1), AHR (aryl hydrocarbon receptor), GPX1 (glutathione peroxidase 1), TPMT (thiopurine S-methyltransferase), NDP (Norrie disease (pseudoglioma)), ARX (aristaless related homeobox), MUS81 (MUS81 endonuclease homolog (*S. cerevisiae*)), TYR (tyrosinase (oculocutaneous albinism IA)), EGR1 (early growth response 1), UNG (uracil-DNA glycosylase), NUMBL (numb homolog (*Drosophila*)-like), FABP2 (fatty acid binding protein 2, intestinal), EN2 (engrailed homeobox 2), CRYGC (crystallin, gamma C), SRP14 (signal recognition particle 14 kDa (homologous Alu RNA binding protein)), CRYGB (crystallin, gamma B), PDCD1 (programmed cell death 1), HOXA1 (homeobox A1), ATXN2L (ataxin 2-like), PMS2 (PMS2 postmeiotic segregation increased 2 (*S. cerevisiae*)), GLA (galactosidase, alpha), CBL (Cas-Br-M (murine) ecotropic retroviral transforming sequence), FTH1 (ferritin, heavy polypeptide 1), IL12RB2 (interleukin 12 receptor, beta 2), OTX2 (orthodenticle homeobox 2), HOXA5 (homeobox A5), POLG2 (polymerase (DNA directed), gamma 2, accessory subunit), DLX2 (distal-less homeobox 2), SIRPA (signal-regulatory protein alpha), OTX1 (orthodenticle homeobox 1), AHRR (aryl-hydrocarbon receptor repressor), MANF (mesencephalic astrocyte-derived neurotrophic factor), TMEM158 (transmembrane protein 158 (gene/pseudogene)), and ENSG00000078687.

Preferred proteins associated with trinucleotide repeat expansion disorders include HTT (Huntingtin), AR (androgen receptor), FXN (frataxin), Atxn3 (ataxin), Atxn1 (ataxin), Atxn2 (ataxin), Atxn7 (ataxin), Atxn10 (ataxin), DMPK (dystrophia myotonica-protein kinase), Atn1 (atrophin 1), CBP (creb binding protein), VLDLR (very low density lipoprotein receptor), and any combination thereof.

According to another aspect, a method of gene therapy for the treatment of a subject having a mutation in the CFTR gene is provided and comprises administering a therapeutically effective amount of a CRISPR-Cas gene therapy particle, optionally via a biocompatible pharmaceutical carrier, to the cells of a subject. Preferably, the target DNA comprises the mutation deltaF508. In general, it is of preferred that the mutation is repaired to the wildtype. In this case, the mutation is a deletion of the three nucleotides that comprise the codon for phenylalanine (F) at position 508. Accordingly, repair in this instance requires reintroduction of the missing codon into the mutant.

To implement this Gene Repair Strategy, it is preferred that an adenovirus/AAV vector system is introduced into the host cell, cells or patient. Preferably, the system comprises a Cas9 (or Cas9 nickase) and the guide RNA along with a adenovirus/AAV vector system comprising the homology repair template containing the F508 residue. This may be introduced into the subject via one of the methods of delivery discussed earlier. The CRISPR-Cas system may be guided by the CFTRdelta 508 chimeric guide RNA. It targets a specific site of the CFTR genomic locus to be nicked or cleaved. After cleavage, the repair template is inserted into the cleavage site via homologous recombination correcting the deletion that results in cystic fibrosis or causes cystic fibrosis related symptoms. This strategy to direct delivery and provide systemic introduction of CRISPR systems with appropriate guide RNAs can be employed to target genetic mutations to edit or otherwise manipulate genes that cause metabolic, liver, kidney and protein diseases and disorders such as those in Table B.

Genome Editing

The CRISPR/Cas9 systems of the present invention can be used to correct genetic mutations that were previously attempted with limited success using TALEN and ZFN. For example, WO2013163628 A2, Genetic Correction of Mutated Genes, published application of Duke University describes efforts to correct, for example, a frameshift mutation which causes a premature stop codon and a truncated gene product that can be corrected via nuclease mediated non-homologous end joining such as those responsible for Duchenne Muscular Dystrophy, ("DMD") a recessive, fatal, X-linked disorder that results in muscle degeneration due to mutations in the dystrophin gene. The majority of dystrophin mutations that cause DMD are deletions of exons that disrupt the reading frame and cause premature translation termination in the dystrophin gene. Dystrophin is a cytoplasmic protein that provides structural stability to the dystroglycan complex of the cell membrane that is responsible for regulating muscle cell integrity and function. The dystrophin gene or "DMD gene" as used interchangeably herein is 2.2 megabases at locus Xp21. The primary transcription measures about 2,400 kb with the mature mRNA being about 14 kb. 79 exons code for the protein which is over 3500 amino acids. Exon 51 is frequently adjacent to frame-disrupting deletions in DMD patients and has been targeted in clinical trials for oligonucleotide-based exon skipping. A clinical trial for the exon 51 skipping compound eteplirsen recently reported a significant functional benefit across 48 weeks, with an average of 47% dystrophin positive fibers compared to baseline. Mutations in exon 51 are ideally suited for permanent correction by NHEJ-based genome editing.

The methods of US Patent Publication No. 20130145487 assigned to Cellectis, which relates to meganuclease variants to cleave a target sequence from the human dystrophin gene (DMD), may also be modified to for the CRISPR Cas system of the present invention.

Blood

The present invention also contemplates delivering the CRISPR-Cas system to the blood.

The plasma exosomes of Wahlgren et al. (Nucleic Acids Research, 2012, Vol. 40, No. 17 e130) were previously described and may be utilized to deliver the CRISPR Cas system to the blood.

The CRISPR Cas system of the present invention is also contemplated to treat hemoglobinopathies, such as thalassemias and sickle cell disease. See, e.g., International Patent Publication No. WO 2013/126794 for potential targets that may be targeted by the CRISPR Cas system of the present invention.

US Patent Publication Nos. 20110225664, 20110091441, 20100229252, 20090271881 and 20090222937 assigned to Cellectis, relates to CREI variants, wherein at least one of the two I-CreI monomers has at least two substitutions, one in each of the two functional subdomains of the LAGLIDADG core domain (SEQ ID NO: 62) situated respectively from positions 26 to 40 and 44 to 77 of I-CreI, said variant being able to cleave a DNA target sequence from the human interleukin-2 receptor gamma chain (IL2RG) gene also named common cytokine receptor gamma chain gene or gamma C gene. The target sequences identified in US Patent Publication Nos. 20110225664, 20110091441, 20100229252, 20090271881 and 20090222937 may be utilized for the CRISPR Cas system of the present invention.

Severe Combined Immune Deficiency (SCID) results from a defect in lymphocytes T maturation, always associated with a functional defect in lymphocytes B (Cavazzana-Calvo et al., Annu. Rev. Med., 2005, 56, 585-602; Fischer et al., Immunol. Rev., 2005, 203, 98-109). Overall incidence is estimated to 1 in 75 000 births. Patients with untreated SCID are subject to multiple opportunist micro-organism infections, and do generally not live beyond one year. SCID can be treated by allogenic hematopoietic stem cell transfer, from a familial donor. Histocompatibility with the donor can vary widely. In the case of Adenosine Deaminase (ADA) deficiency, one of the SCID forms, patients can be treated by injection of recombinant Adenosine Deaminase enzyme.

Since the ADA gene has been shown to be mutated in SCID patients (Giblett et al., Lancet, 1972, 2, 1067-1069), several other genes involved in SCID have been identified (Cavazzana-Calvo et al., Annu. Rev. Med., 2005, 56, 585-602; Fischer et al., Immunol. Rev., 2005, 203, 98-109). There are four major causes for SCID: (i) the most frequent form of SCID, SCID-X1 (X-linked SCID or X-SCID), is caused by mutation in the IL2RG gene, resulting in the absence of mature T lymphocytes and NK cells. IL2RG encodes the gamma C protein (Noguchi, et al., Cell, 1993, 73, 147-157), a common component of at least five interleukin receptor complexes. These receptors activate several targets through the JAK3 kinase (Macchi et al., Nature, 1995, 377, 65-68), which inactivation results in the same syndrome as gamma C inactivation; (ii) mutation in the ADA gene results in a defect in purine metabolism that is lethal for lymphocyte precursors, which in turn results in the quasi absence of B, T and NK cells; (iii) V(D)J recombination is an essential step in the maturation of immunoglobulins and T lymphocytes receptors (TCRs). Mutations in Recombination Activating Gene 1 and 2 (RAG1 and RAG2) and Artemis, three genes involved in this process, result in the absence of mature T and B lymphocytes; and (iv) Mutations in other genes such as CD45, involved in T cell specific signaling have also been reported, although they represent a minority of cases (Cavazzana-Calvo et al., Annu. Rev. Med., 2005, 56, 585-602; Fischer et al., Immunol. Rev., 2005, 203, 98-109).

Since when their genetic bases have been identified, the different SCID forms have become a paradigm for gene therapy approaches (Fischer et al., Immunol. Rev., 2005, 203, 98-109) for two major reasons. First, as in all blood diseases, an ex vivo treatment can be envisioned. Hematopoietic Stem Cells (HSCs) can be recovered from bone marrow, and keep their pluripotent properties for a few cell divisions. Therefore, they can be treated in vitro, and then reinjected into the patient, where they repopulate the bone marrow. Second, since the maturation of lymphocytes is impaired in SCID patients, corrected cells have a selective advantage. Therefore, a small number of corrected cells can restore a functional immune system. This hypothesis was validated several times by (i) the partial restoration of immune functions associated with the reversion of mutations in SCID patients (Hirschhorn et al., Nat. Genet., 1996, 13, 290-295; Stephan et al., N. Engl. J. Med., 1996, 335, 1563-1567; Bousso et al., Proc. Natl., Acad. Sci. USA, 2000, 97, 274-278; Wada et al., Proc. Natl. Acad. Sci. USA, 2001, 98, 8697-8702; Nishikomori et al., Blood, 2004, 103, 4565-4572), (ii) the correction of SCID-X1 deficiencies in vitro in hematopoietic cells (Candotti et al., Blood, 1996, 87, 3097-3102; Cavazzana-Calvo et al., Blood, 1996, Blood, 88, 3901-3909; Taylor et al., Blood, 1996, 87, 3103-3107; Hacein-Bey et al., Blood, 1998, 92, 4090-4097), (iii) the correction of SCID-X1 (Soudais et al., Blood, 2000, 95, 3071-3077; Tsai et al., Blood, 2002, 100, 72-79), JAK-3 (Bunting et al., Nat. Med., 1998, 4, 58-64; Bunting et al., Hum. Gene Ther., 2000, 11, 2353-2364) and RAG2 (Yates et al., Blood, 2002, 100, 3942-3949) deficiencies in vivo in animal models and (iv) by the result of gene therapy clinical trials (Cavazzana-Calvo et al., Science, 2000, 288, 669-672; Aiuti et al., Nat. Med., 2002; 8, 423-425; Gaspar et al., Lancet, 2004, 364, 2181-2187).

US Patent Publication No. 20110182867 assigned to the Children's Medical Center Corporation and the President and Fellows of Harvard College relates to methods and uses of modulating fetal hemoglobin expression (HbF) in a hematopoietic progenitor cells via inhibitors of BCL11A expression or activity, such as RNAi and antibodies. The targets disclosed in US Patent Publication No. 20110182867, such as BCL11A, may be targeted by the CRISPR Cas system of the present invention for modulating fetal hemoglobin expression. See also Bauer et al. (Science 11 Oct. 2013: Vol. 342 no. 6155 pp. 253-257) and Xu et al. (Science 18 Nov. 2011: Vol. 334 no. 6058 pp. 993-996) for additional BCL11A targets.

Suitable cells can be identified by analyzing (e.g., qualitatively or quantitatively) the presence of one or more tissue specific genes. For example, gene expression can be detected by detecting the protein product of one or more tissue-specific genes. Protein detection techniques involve staining proteins (e.g., using cell extracts or whole cells) using antibodies against the appropriate antigen. In this case, the appropriate antigen is the protein product of the tissue-specific gene expression. Although, in principle, a first antibody (i.e., the antibody that binds the antigen) can be labeled, it is more common (and improves the visualization) to use a second antibody directed against the first (e.g., an anti-IgG). This second antibody is conjugated either with fluorochromes, or appropriate enzymes for colorimetric reactions, or gold beads (for electron microscopy), or with the biotin-avidin system, so that the location of the primary antibody, and thus the antigen, can be recognized.

In some embodiments the RNA molecules of the invention are delivered in liposome or lipofectin formulations and the like and can be prepared by methods well known to those skilled in the art. Such methods are described, for example, in U.S. Pat. Nos. 5,593,972, 5,589,466, and 5,580,859, which are herein incorporated by reference.

Delivery systems aimed specifically at the enhanced and improved delivery of siRNA into mammalian cells have been developed, (see, for example, Shen et al FEBS Let. 2003, 539:111-114; Xia et al., Nat. Biotech. 2002, 20:1006-1010; Reich et al., Mol. Vision. 2003, 9: 210-216; Sorensen et al., J. Mol. Biol. 2003, 327: 761-766; Lewis et al., Nat. Gen. 2002, 32: 107-108 and Simeoni et al., NAR 2003, 31, 11: 2717-2724) and may be applied to the present invention. siRNA has recently been successfully used for inhibition of gene expression in primates (see for example. Tolentino et al., Retina 24(4):660 which may also be applied to the present invention.

Kidneys

The present invention also contemplates delivering the CRISPR-Cas system to the kidney. Delivery strategies to induce cellular uptake of the therapeutic nucleic acid include physical force or vector systems such as viral-, lipid- or complex-based delivery, or nanocarriers. From the initial applications with less possible clinical relevance, when nucleic acids were addressed to renal cells with hydrodynamic high pressure injection systemically, a wide range of gene therapeutic viral and non-viral carriers have been applied already to target posttranscriptional events in different animal kidney disease models in vivo (Csaba Rèvèsz and Pèter Hamar (2011). Delivery Methods to Target RNAs in the Kidney, Gene Therapy Applications, Prof. Chunsheng Kang (Ed.), ISBN: 978-953-307-541-9, InTech, Available at the website: intecho[1]pen.com/books/gene-therapy-applications/delivery-methods-to-target-rnas-in-the-kidney). Delivery methods to the kidney are summarized as follows:

| Delivery method | Carrier | Target RNA | Disease | Model | Functional assays | Author |
|---|---|---|---|---|---|---|
| Hydro-dynamic/ Lipid | TransIT In Vivo Gene Delivery System, DOTAP | p85α | Acute renal injury | Ischemia-reperfusion | Uptake, biodistribution | Larson et al., Surgery, (August 2007), Vol. 142, No. 2, pp. (262-269) |
| Hydro-dynamic/ Lipid | Lipofectamine 2000 | Fas | Acute renal injury | Ischemia-reperfusion | Blood urea nitrogen, Fas Immunohistochemistry, apoptosis, histological scoring | Hamar et al., Proc Natl Acad Sci, (October 2004), Vol. 101, No. 41, pp. (14883-14888) |
| Hydro-dynamic | n.a. | Apoptosis cascade elements | Acute renal injury | Ischemia-reperfusion | n.a. | Zheng et al., Am J Pathol, (October 2008), Vol. 173, No. 4, pp. (973-980) |
| Hydro-dynamic | n.a. | Nuclear factor kappa-b (NFkB) | Acute renal injury | Ischemia-reperfusion | n.a. | Feng et al., Transplantation, (May 2009), Vol. 87, No. 9, pp. (1283-1289) |
| Hydro-dynamic/ Viral | Lipofectamine 2000 | Apoptosis antagonizing transcription factor (AATF) | Acute renal injury | Ischemia-reperfusion | Apoptosis, oxidative stress, caspase activation, membrane lipid peroxidation | Xie & Guo, Am Soc Nephrol, (December 2006), Vol. 17, No. 12, pp. (3336-3346) |

-continued

| Delivery method | Carrier | Target RNA | Disease | Model | Functional assays | Author |
|---|---|---|---|---|---|---|
| Hydro-dynamic | pBAsi mU6 Neo/ TransIT-EE Hydrodynamic Delivery System | Gremlin | Diabetic nephropathy | Streptozotozin-induced diabetes | Proteinuria, serum creatinine, glomerula and tubular diameter, collagen type IV/BMP7 expression | Q. Zhang et al., PloS ONE, (July 2010), Vol. 5, No. 7, e11709, pp. (1-13) |
| Viral/ Lipid | pSUPER vector/Lipofectamine | TGF-β type II receptor | Interstitial renal fibrosis | Unilateral urethral obstruction | α-SMA expression, collagen content, | Kushibikia et al., J Controlled Release, (July 2005), Vol. 105, No. 3, pp. (318-331) |
| Viral | Adeno-associated virus-2 | Mineral corticoid receptor | Hyper-tension caused renal damage | Cold-induced hypertension | blood pressure, serum albumin, serum urea nitrogen, serum creatinine, kidney weight, urinary sodium | Wang et al., Gene Therapy, (July 2006), Vol. 13, No. 14, pp. (1097-1103) |
| Hydro-dynamic/ Viral | pU6 vector | Luciferase | n.a. | n.a. | uptake | Kobayashi et al., Journal of Pharmacology and Experimental Therapeutics, (February 2004), Vol. 308, No. 2, pp. (688-693) |
| Lipid | Lipoproteins, albumin | apoB1, apoM | n.a. | n.a. | Uptake, binding affinity to lipoproteins and albumin | Wolfrum et al., Nature Biotechnology, (September 2007), Vol. 25, No. 10, pp. (1149-1157) |
| Lipid | Lipofectamine2000 | p53 | Acute renal injury | Ischemic and cisplatin-induced acute injury | Histological scoring, apoptosis | Molitoris et al., J Am Soc Nephrol, (August 2009), Vol. 20, No. 8, pp. (1754-1764) |
| Lipid | DOTAP/DOPE, DOTAP/DO PE/DOPE-PEG2000 | COX-2 | Breast adeno-carcinoma | MDA-MB-231 breast cancer xenograft-bearing mouse | Cell viability, uptake | Mikhaylova et al., Cancer Gene Therapy, (March 2011), Vol. 16, No. 3, pp. (217-226) |
| Lipid | Cholesterol | 12/15-lipoxygenase | Diabetic nephro-pathy | Streptozotocin-induced diabetes | Albuminuria, urinary creatinine, histology, type I and IV collagen, TGF-β, fibronectin, plasminogen activator inhibitor 1 | Yuan et al., Am J Physiol Renal Physiol, (June 2008), Vol. 295, pp. (F605-F617) |
| Lipid | Lipofectamine 2000 | Mitochondrial membrane 44 (TIM44) | Diabetic nephro-pathy | Streptozotocin-induced diabetes | Cell proliferation and apoptosis, histology, ROS, mitochondrial import of Mn-SOD and glutathione peroxidase, cellular membrane polarization | Y. Zhang et al., J Am Soc Nephrol, (April 2006), Vol. 17, No. 4, pp. (1090-1101) |
| Hydro-dynamic/ Lipid | Proteolipo-some | RLIP76 | Renal carcinoma | Caki-2 kidney cancer xenograft-bearing mouse | uptake | Singhal et al., Cancer Res, (May 2009), Vol. 69, No. 10, pp. (4244-4251) |
| Polymer | PEGylated PEI | Luciferase pGL3 | n.a. | n.a. | Uptake, biodistribution, erythrocyte aggregation | Malek et al., Toxicology and Applied Pharmacology, (April 2009), Vol. 236, No. 1, pp. (97-108) |
| Polymer | PEGylated poly-L-lysine | MAPK1 | Lupus glomerulo-nephritis | Glomerulo-nephritis | Proteinuria, glomerulosclerosis, TGF-β, fibronectin, plasminogen activator inhibitor 1 | Shimizu et al., J Am Soc Nephrology, (April 2010), Vol. 21, No. 4, pp. (622-633) |
| Polymer/ Nano particle | Hyaluronic acid/ Quantum dot/ PEI | VEGF | Kidney cancer/ melanoma | B16F1 melanoma tumor-bearing mouse | Biodistribution, citotoxicity, tumor volume, endocytosis | Jiang et al., Molecular Pharmaceutics, (May-June 2009), Vol. 6, No. 3, pp. (727-737) |
| Polymer/ Nano particle | PEGylated polycapro-lactone nanofiber | GAPDH | n.a. | n.a. | cell viability, uptake | Cao et al, J Controlled Release, (June 2010), Vol. 144, No. 2, pp. (203-212) |

-continued

| Delivery method | Carrier | Target RNA | Disease | Model | Functional assays | Author |
|---|---|---|---|---|---|---|
| Aptamer | Spiegelmer mNOX-E36 | CC chemokine ligand 2 | Glomerulo sclerosis | Uninephrecto-mized mouse | urinary albumin, urinary creatinine, histopathology, glomerular filtration rate, macrophage count, serum Cc12, Mac-2+, Ki-67+ | Ninichuk et al Am J Pathol, (March 2008), Vol. 172, No. 3, pp. (628-637) |
| Aptamer | Aptamer NOX-F37 | vasopressin (AVP) | Congestive heart failure | n.a. | Binding affinity to D-AVP, Inhibition of AVP Signaling, Urine osmolality and sodium concentration, | Purschke et al., Proc Natl Acad Sci, (March 2006), Vol. 103, No. 13, pp. (5173-5178) |

Similar methods may be employed for delivery to the liver.

Although relevant to the lungs, CFTR is an excellent example of a serious monogenic condition that is now being successfully targeted by CRISPR. For an example of CFTRdelta508 chimeric guide RNA, see Example 22 which demonstrates gene transfer or gene delivery of a CRISPR-Cas system in airways of subject or a patient in need thereof, suffering from cystic fibrosis or from cystic fibrosis (CF) related symptoms, using adeno-associated virus (AAV) particles. In particular, they exemplify a repair strategy for Cystic Fibrosis delta F508 mutation. This type of strategy should apply across all organisms. With particular reference to CF, suitable patients may include: Human, non-primate human, canine, feline, bovine, equine and other domestic animals. In this instance, Applicants utilized a CRISPR-Cas system comprising a Cas9 enzyme to target deltaF508 or other CFTR-inducing mutations.

The treated subjects in this instance receive pharmaceutically effective amount of aerosolized AAV vector system per lung endobronchially delivered while spontaneously breathing. As such, aerosolized delivery is preferred for AAV delivery in general. An adenovirus or an AAV particle may be used for delivery. Suitable gene constructs, each operably linked to one or more regulatory sequences, may be cloned into the delivery vector. In this instance, the following constructs are provided as examples: Cbh or EF1a promoter for Cas9, U6 or H1 promoter for chimeric guide RNA: A preferred arrangement is to use a CFTRdelta508 targeting chimeric guide, a repair template for deltaF508 mutation and a codon optimized Cas9 enzyme (preferred Cas9s are those with nuclease or nickase activity) with optionally one or more nuclear localization signal or sequence(s) (NLS(s)), e.g., two (2) NLSs. Constructs without NLS are also envisaged.

In order to identify the Cas9 target site, Applicants analyzed the human CFTR genomic locus and identified the Cas9 target site. Preferably, in general and in this CF case, the PAM may contain a NGG or a NNAGAAW motif.

Accordingly, in the case of CF, the present method comprises manipulation of a target sequence in a genomic locus of interest comprising delivering a non-naturally occurring or engineered composition comprising a viral vector system comprising one or more viral vectors operably encoding a composition for expression thereof, wherein the composition comprises:

a non-naturally occurring or engineered composition comprising a vector system comprising one or more vectors comprising I. a first regulatory element operably linked to a CRISPR-Cas system chimeric RNA (chiRNA) polynucleotide sequence, wherein the polynucleotide sequence comprises (a) a guide sequence capable of hybridizing to the CF target sequence in a suitable mammalian cell, (b) a tracr mate sequence, and (c) a tracr sequence, and II. a second regulatory element operably linked to an enzyme-coding sequence encoding a CRISPR enzyme comprising at least one or more nuclear localization sequences, wherein (a), (b) and (c) are arranged in a 5' to 3' orientation, wherein components I and II are located on the same or different vectors of the system, wherein when transcribed, the tracr mate sequence hybridizes to the tracr sequence and the guide sequence directs sequence-specific binding of a CRISPR complex to the target sequence, and wherein the CRISPR complex comprises the CRISPR enzyme complexed with (1) the guide sequence that is hybridized or hybridizable to the target sequence, and (2) the tracr mate sequence that is hybridized or hybridizable to the tracr sequence. In respect of CF, preferred target DNA sequences comprise the CFTRdelta508 mutation. A preferred PAM is described above. A preferred CRISPR enzyme is any Cas (described herein, but particularly that described in Example 22).

Alternatives to CF include any genetic disorder and examples of these are well known. Another preferred method or use of the invention is for correcting defects in the EMP2A and EMP2B genes that have been identified to be associated with Lafora disease.

In some embodiments, a "guide sequence" may be distinct from "guide RNA". A guide sequence may refer to an approx. 20 bp sequence, within the guide RNA, that specifies the target site.

In some embodiments, the Cas9 is (or is derived from) SpCas9. In such embodiments, preferred mutations are at any or all or positions 10, 762, 840, 854, 863 and/or 986 of SpCas9 or corresponding positions in other Cas9s (which may be ascertained for instance by standard sequence comparison tools. In particular, any or all of the following mutations are preferred in SpCas9: D10A, E762A, H840A, N854A, N863A and/or D986A; as well as conservative substitution for any of the replacement amino acids is also envisaged. The same (or conservative substitutions of these mutations) at corresponding positions in other Cas9s are also preferred. Particularly preferred are D10 and H840 in SpCas9. However, in other Cas9s, residues corresponding to SpCas9 D10 and H840 are also preferred. These are advantageous as they provide nickase activity. Such mutations may be applied to all aspects of the present invention, not only treatment of CF.

Schwank et al. (Cell Stem Cell, 13:653-58, 2013) used CRISPR/Cas9 to correct a defect associated with cystic fibrosis in human stem cells. The team's target was the gene for an ion channel, cystic fibrosis transmembrane conductor receptor (CFTR). A deletion in CFTR causes the protein to misfold in cystic fibrosis patients. Using cultured intestinal stem cells developed from cell samples from two children with cystic fibrosis, Schwank et al. were able to correct the defect using CRISPR along with a donor plasmid containing the reparative sequence to be inserted. The researchers then grew the cells into intestinal "organoids," or miniature guts, and showed that they functioned normally. In this case, about half of clonal organoids underwent the proper genetic correction.

Hepatitis Viruses

The present invention may also be applied to treat hepatitis B virus (HBV). However, the CRISPR Cas system must be adapted to avoid the shortcomings of RNAi, such as the risk of oversatring endogenous small RNA pathways, by for example, optimizing dose and sequence (see, e.g., Grimm et al., Nature vol. 441, 26 May 2006). For example, low doses, such as about 1-10×$10^{14}$ particles per humane are contemplated.

In another embodiment, the CRISPR Cas system directed against HBV may be administered in liposomes, such as a stable nucleic-acid-lipid particle (SNALP) (see, e.g., Morrissey et al., Nature Biotechnology, Vol. 23, No. 8, August 2005). Daily intravenous injections of about 1, 3 or 5 mg/kg/day of CRISPR Cas targeted to HBV RNA in a SNALP are contemplated. The daily treatment may be over about three days and then weekly for about five weeks.

In another embodiment, the system of Chen et al. (Gene Therapy (2007) 14, 11-19) may be used/and or adapted for the CRISPR Cas system of the present invention. Chen et al. use a double-stranded adenoassociated virus 8-pseudotyped vector (dsAAV2/8) to deliver shRNA. A single administration of dsAAV2/8 vector (1×$10^{12}$ vector genomes per mouse), carrying HBV-specific shRNA, effectively suppressed the steady level of HBV protein, mRNA and replicative DNA in liver of HBV transgenic mice, leading to up to 2-3 $\log_{10}$ decrease in HBV load in the circulation. Significant HBV suppression sustained for at least 120 days after vector administration. The therapeutic effect of shRNA was target sequence dependent and did not involve activation of interferon. For the present invention, a CRISPR Cas system directed to HBV may be cloned into an AAV vector, such as a dsAAV2/8 vector and administered to a human, for example, at a dosage of about 1×$10^{15}$ vector genomes to about 1×$10^{16}$ vector genomes per human.

In another embodiment, the method of Wooddell et al. (Molecular Therapy vol. 21 no. 5, 973-985 May 2013) may be used/and or adapted to the CRISPR Cas system of the present invention. Woodell et al. show that simple coinjection of a hepatocyte-targeted, N-acetylgalactosamine-conjugated melittin-like peptide (NAG-MLP) with a liver-tropic cholesterol-conjugated siRNA (chol-siRNA) targeting coagulation factor VII (F7) results in efficient F7 knockdown in mice and nonhuman primates without changes in clinical chemistry or induction of cytokines. Using transient and transgenic mouse models of HBV infection, Wooddell et al. show that a single coinjection of NAG-MLP with potent chol-siRNAs targeting conserved HBV sequences resulted in multilog repression of viral RNA, proteins, and viral DNA with long duration of effect. Intravenous coinjections, for example, of about 6 mg/kg of NAG-MLP and 6 mg/kg of HBV specific CRISPR Cas may be envisioned for the present invention. In the alternative, about 3 mg/kg of NAG-MLP and 3 mg/kg of HBV specific CRISPR Cas may be delivered on day one, followed by administration of about 2-3 mg/kg of NAG-MLP and 2-3 mg/kg of HBV specific CRISPR Cas two weeks later.

The present invention may also be applied to treat hepatitis C virus (HCV). The methods of Roelvinki et al. (Molecular Therapy vol. 20 no. 9, 1737-1749 September 2012) may be applied to the CRISPR Cas system. For example, an AAV vector such as AAV8 may be a contemplated vector and for example a dosage of about 1.25×$10^{11}$ to 1.25×$10^{13}$ vector genomes per kilogram body weight (vg/kg) may be contemplated.

In yet another embodiment, CRISPR-Cas9-mediated genome editing can be used to correct a disease mutation and/or phenotype. That CRISPR-Cas9-mediated genome editing can be used to correct a disease mutation and/or phenotype in the liver and or hepatocytes is illustrated in the manuscript entitled "Genome editing with Cas9 in adult mice corrects a disease mutation and phenotype" by Hao Yin et al. published at Nature Biotechnology published online 30 Mar. 2014; corrected online 31 Mar. 2014, available at the website nature.com/doifinder/10.1038/nbt.2884, incorporated herein by reference in its entirety. The paper relates to CRISPR-Cas9-mediated correction of a Fah mutation in hepatocytes in a mouse model of the human disease hereditary tyrosinemia. It was shown that delivery of components of the CRISPR-Cas9 system by hydrodynamic injection resulted in initial expression of the wild-type Fah protein in ~1/250 liver cells. It was further shown that expansion of Fah-positive hepatocytes rescued the body weight loss phenotype.

It will be readily apparent that a host of other diseases can be treated in a similar fashion. Some examples of genetic diseases caused by mutations are provided herein, but many more are known. The above strategy can be applied to these diseases.

Nucleic Acids, Amino Acids and Proteins

The invention uses nucleic acids to bind target DNA sequences. This is advantageous as nucleic acids are much easier and cheaper to produce than proteins, and the specificity can be varied according to the length of the stretch where homology is sought. Complex 3-D positioning of multiple fingers, for example is not required.

The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. The term also encompasses nucleic-acid-like structures with synthetic backbones, see, e.g., WO 97/03211; WO 96/39154. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

As used herein the term "wild type" is a term of the art understood by skilled persons and means the typical form of an organism, strain, gene or characteristic as it occurs in nature as distinguished from mutant or variant forms.

As used herein the term "variant" should be taken to mean the exhibition of qualities that have a pattern that deviates from what occurs in nature.

The terms "non-naturally occurring" or "engineered" are used interchangeably and indicate the involvement of the hand of man. The terms, when referring to nucleic acid molecules or polypeptides mean that the nucleic acid molecule or the polypeptide is at least substantially free from at least one other component with which they are naturally associated in nature and as found in nature.

"Complementarity" refers to the ability of a nucleic acid to form hydrogen bond(s) with another nucleic acid sequence by either traditional Watson-Crick base pairing or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry And Molecular Biology-Hybridization With Nucleic Acid Probes Part I, Second Chapter "Overview of principles of hybridization and the strategy of nucleic acid probe assay", Elsevier, N.Y. Where reference is made to a polynucleotide sequence, then complementary or partially complementary sequences are also envisaged. These are preferably capable of hybridising to the reference sequence under highly stringent conditions. Generally, in order to maximize the hybridization rate, relatively low-stringency hybridization conditions are selected: about 20 to 25° C. lower than the thermal melting point ($T_m$). The $T_m$ is the temperature at which 50% of specific target sequence hybridizes to a perfectly complementary probe in solution at a defined ionic strength and pH. Generally, in order to require at least about 85% nucleotide complementarity of hybridized or hybridizable sequences, highly stringent washing conditions are selected to be about 5 to 15° C. lower than the $T_m$. In order to require at least about 70% nucleotide complementarity of hybridized or hybridizable sequences, moderately-stringent washing conditions are selected to be about 15 to 30° C. lower than the $T_m$. Highly permissive (very low stringency) washing conditions may be as low as 50° C. below the $T_m$, allowing a high level of mis-matching between hybridized or hybridizable sequences. Those skilled in the art will recognize that other physical and chemical parameters in the hybridization and wash stages can also be altered to affect the outcome of a detectable hybridization signal from a specific level of homology between target and probe sequences. Preferred highly stringent conditions comprise incubation in 50% formamide, 5×SSC, and 1% SDS at 42° C., or incubation in 5×SSC and 1% SDS at 65° C., with wash in 0.2×SSC and 0.1% SDS at 65° C.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence.

As used herein, the term "genomic locus" or "locus" (plural loci) is the specific location of a gene or DNA sequence on a chromosome. A "gene" refers to stretches of DNA or RNA that encode a polypeptide or an RNA chain that has functional role to play in an organism and hence is the molecular unit of heredity in living organisms. For the purpose of this invention it may be considered that genes include regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

As used herein, "expression of a genomic locus" or "gene expression" is the process by which information from a gene is used in the synthesis of a functional gene product. The products of gene expression are often proteins, but in non-protein coding genes such as rRNA genes or tRNA genes, the product is functional RNA. The process of gene expression is used by all known life—eukaryotes (including multicellular organisms), prokaryotes (bacteria and archaea) and viruses to generate functional products to survive. As used herein "expression" of a gene or nucleic acid encompasses not only cellular gene expression, but also the transcription and translation of nucleic acid(s) in cloning systems and in any other context. As used herein, "expression" also refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

The terms "polypeptide", "peptide" and "protein" are used interchangeably herein to refer to polymers of amino acids of any length. The polymer may be linear or branched, it may comprise modified amino acids, and it may be interrupted by non amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" includes natural and/or unnatural or synthetic amino acids, including glycine and both the D or L optical isomers, and amino acid analogs and peptidomimetics.

As used herein, the term "domain" or "protein domain" refers to a part of a protein sequence that may exist and function independently of the rest of the protein chain.

As described in aspects of the invention, sequence identity is related to sequence homology. Homology comparisons may be conducted by eye, or more usually, with the aid of readily available sequence comparison programs. These commercially available computer programs may calculate percent (%) homology between two or more sequences and may also calculate the sequence identity shared by two or more amino acid or nucleic acid sequences. In some preferred embodiments, the capping region of the dTALEs described herein have sequences that are at least 95% identical or share identity to the capping region amino acid sequences provided herein.

Sequence homologies may be generated by any of a number of computer programs known in the art, for example BLAST or FASTA, etc. A suitable computer program for carrying out such an alignment is the GCG Wisconsin Bestfit package (University of Wisconsin, U.S.A; Devereux et al., 1984, Nucleic Acids Research 12:387). Examples of other software than may perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However it is preferred to use the GCG Bestfit program.

Percentage (%) sequence homology may be calculated over contiguous sequences, i.e., one sequence is aligned with the other sequence and each amino acid or nucleotide in one sequence is directly compared with the corresponding amino acid or nucleotide in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion may cause the following amino acid residues to be put out of alignment, thus potentially resulting in a large reduction in % homology when a global alignment is performed. Consequently, most sequence comparison methods are designed to produce optimal alignments that take into consideration possible insertions and deletions without unduly penalizing the overall homology or identity score. This is achieved by inserting "gaps" in the sequence alignment to try to maximize local homology or identity.

However, these more complex methods assign "gap penalties" to each gap that occurs in the alignment so that, for the same number of identical amino acids, a sequence alignment with as few gaps as possible—reflecting higher relatedness between the two compared sequences—may achieve a higher score than one with many gaps. "Affinity gap costs" are typically used that charge a relatively high cost for the existence of a gap and a smaller penalty for each subsequent residue in the gap. This is the most commonly used gap scoring system. High gap penalties may, of course, produce optimized alignments with fewer gaps. Most alignment programs allow the gap penalties to be modified. However, it is preferred to use the default values when using such software for sequence comparisons. For example, when using the GCG Wisconsin Bestfit package the default gap penalty for amino acid sequences is −12 for a gap and −4 for each extension.

Calculation of maximum % homology therefore first requires the production of an optimal alignment, taking into consideration gap penalties. A suitable computer program for carrying out such an alignment is the GCG Wisconsin Bestfit package (Devereux et al., 1984 *Nuc. Acids Research* 12 p 387). Examples of other software than may perform sequence comparisons include, but are not limited to, the BLAST package (see Ausubel et al., 1999 *Short Protocols in Molecular Biology,* 4$^{th}$ Ed. —Chapter 18), FASTA (Altschul et al., 1990 *J. Mol. Biol.* 403-410) and the GENEWORKS suite of comparison tools. Both BLAST and FASTA are available for offline and online searching (see Ausubel et al., 1999, *Short Protocols in Molecular Biology*, pages 7-58 to 7-60). However, for some applications, it is preferred to use the GCG Bestfit program. A new tool, called BLAST 2 Sequences is also available for comparing protein and nucleotide sequences (see *FEMS Microbiol Lett.* 1999 174 (2): 247-50; *FEMS Microbiol Lett.* 1999 177(1): 187-8 and the website of the National Center for Biotechnology information at the website of the National Institutes for Health).

Although the final % homology may be measured in terms of identity, the alignment process itself is typically not based on an all-or-nothing pair comparison. Instead, a scaled similarity score matrix is generally used that assigns scores to each pair-wise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table, if supplied (see user manual for further details). For some applications, it is preferred to use the public default values for the GCG package, or in the case of other software, the default matrix, such as BLOSUM62.

Alternatively, percentage homologies may be calculated using the multiple alignment feature in DNASIS™ (Hitachi Software), based on an algorithm, analogous to CLUSTAL (Higgins D G & Sharp P M (1988), *Gene* 73(1), 237-244). Once the software has produced an optimal alignment, it is possible to calculate % homology, preferably % sequence identity. The software typically does this as part of the sequence comparison and generates a numerical result.

The sequences may also have deletions, insertions or substitutions of amino acid residues which produce a silent change and result in a functionally equivalent substance. Deliberate amino acid substitutions may be made on the basis of similarity in amino acid properties (such as polarity, charge, solubility, hydrophobicity, hydrophilicity, and/or the amphipathic nature of the residues) and it is therefore useful to group amino acids together in functional groups. Amino acids may be grouped together based on the properties of their side chains alone. However, it is more useful to include mutation data as well. The sets of amino acids thus derived are likely to be conserved for structural reasons. These sets may be described in the form of a Venn diagram (Livingstone C. D. and Barton G. J. (1993) "Protein sequence alignments: a strategy for the hierarchical analysis of residue conservation" *Comput. Appl. Biosci.* 9: 745-756) (Taylor W. R. (1986) "The classification of amino acid conservation" *J. Theor. Biol.* 119; 205-218). Conservative substitutions may be made, for example according to the table below which describes a generally accepted Venn diagram grouping of amino acids.

| Set | | Sub-set | |
|---|---|---|---|
| Hydro-phobic | F W Y H K M I L V A G C | Aromatic | F W Y H |
| | | Aliphatic | I L V |
| Polar | W Y H K R E D C S T N Q | Charged | H K R E D |
| | | Positively charged | H K R |
| | | Negatively charged | E D |
| Small | V C A G S P T N D | Tiny | A G S |

Embodiments of the invention include sequences (both polynucleotide or polypeptide) which may comprise homologous substitution (substitution and replacement are both used herein to mean the interchange of an existing amino acid residue or nucleotide, with an alternative residue or nucleotide) that may occur i.e., like-for-like substitution in the case of amino acids such as basic for basic, acidic for acidic, polar for polar, etc. Non-homologous substitution may also occur i.e., from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, which involves the presence of one or more amino acid residues in peptoid form, may be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., *PNAS* (1992) 89(20), 9367-9371 and Horwell D C, *Trends Biotechnol.* (1995) 13(4), 132-134.

The practice of the present invention employs, unless otherwise indicated, conventional techniques of immunology, biochemistry, chemistry, molecular biology, microbiology, cell biology, genomics and recombinant DNA, which are within the skill of the art. See Sambrook, Fritsch and Maniatis, MOLECULAR CLONING: A LABORATORY MANUAL, 2nd edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

Vectors

In one aspect, the invention provides for vectors that are used in the engineering and optimization of CRISPR-Cas systems.

A used herein, a "vector" is a tool that allows or facilitates the transfer of an entity from one environment to another. It is a replicon, such as a plasmid, phage, or cosmid, into which another DNA segment may be inserted so as to bring about the replication of the inserted segment. Generally, a vector is capable of replication when associated with the proper control elements. In general, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses (AAVs)). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell). With regards to recombination and cloning methods, mention is made of U.S. patent application Ser. No. 10/815,730, published Sep. 2, 2004 as US 2004-0171156 A1, the contents of which are herein incorporated by reference in their entirety.

Aspects of the invention relate to vectors for chimeric RNA and Cas9. Bicistronic expression vectors for chimeric RNA and Cas9 are preferred. In general and particularly in this embodiment Cas9 is preferably driven by the CBh promoter. The chimeric RNA may preferably be driven by a U6 promoter. Ideally the two are combined. The chimeric guide RNA typically consists of a 20 bp guide sequence (Ns) and this may be joined to the tracr sequence (running from the first "U" of the lower strand to the end of the transcript). The tracr sequence may be truncated at various positions as indicated. The guide and tracr sequences are separated by the tracr-mate sequence, which may be GUUUUAGAGCUA (SEQ ID NO: 63). This may be followed by the loop sequence GAAA as shown. Both of these are preferred examples. Applicants have demonstrated Cas9-mediated indels at the human EMX1 and PVALB loci by SURVEYOR assays. ChiRNAs are indicated by their "+n" designation, and crRNA refers to a hybrid RNA where guide and tracr sequences are expressed as separate transcripts. Throughout this application, chimeric RNA may also be called single guide, or synthetic guide RNA (sgRNA). The loop is preferably GAAA, but it is not limited to this sequence or indeed to being only 4 bp in length. Indeed, preferred loop forming sequences for use in hairpin structures are four nucleotides in length, and most preferably have the sequence GAAA. However, longer or shorter loop sequences may be used, as may alternative sequences. The sequences preferably include a nucleotide triplet (for example, AAA), and an additional nucleotide (for example C or G). Examples of loop forming sequences include CAAA and AAAG.

The term "regulatory element" is intended to include promoters, enhancers, internal ribosomal entry sites (IRES), and other expression control elements (e.g. transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g. liver, pancreas), or particular cell types (e.g. lymphocytes). Regulatory elements may also direct expression in a temporal-dependent manner, such as in a cell-cycle dependent or developmental stage-dependent manner, which may or may not also be tissue or cell-type specific. In some embodiments, a vector comprises one or more pol III promoter (e.g. 1, 2, 3, 4, 5, or more pol III promoters), one or more pol II promoters (e.g. 1, 2, 3, 4, 5, or more pol II promoters), one or more pol I promoters (e.g. 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981). It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein (e.g., clustered regularly interspersed short palindromic repeats (CRISPR) transcripts, proteins, enzymes, mutant forms thereof, fusion proteins thereof, etc.). With regards to regulatory sequences, mention is made of U.S. patent application Ser. No. 10/491,026, the contents of which are incorporated by reference herein in their entirety. With regards to promoters, mention is made of PCT publication WO 2011/028929 and U.S. application Ser. No. 12/511,940, the contents of which are incorporated by reference herein in their entirety.

Vectors can be designed for expression of CRISPR transcripts (e.g. nucleic acid transcripts, proteins, or enzymes) in prokaryotic or eukaryotic cells. For example, CRISPR transcripts can be expressed in bacterial cells such as *Escherichia coli*, insect cells (using baculovirus expression vectors), yeast cells, or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

Vectors may be introduced and propagated in a prokaryote or prokaryotic cell. In some embodiments, a prokaryote is used to amplify copies of a vector to be introduced into a eukaryotic cell or as an intermediate vector in the production of a vector to be introduced into a eukaryotic cell (e.g. amplifying a plasmid as part of a viral vector packaging system). In some embodiments, a prokaryote is used to amplify copies of a vector and express one or more nucleic acids, such as to provide a source of one or more proteins for delivery to a host cell or host organism. Expression of proteins in prokaryotes is most often carried out in *Escherichia coli* with vectors containing constitutive or inducible promoters directing the expression of either fusion or non-fusion proteins. Fusion vectors add a number of amino acids to a protein encoded therein, such as to the amino terminus of the recombinant protein. Such fusion vectors may serve one or more purposes, such as: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Example fusion expression vectors include pGEX (Pharmacia Biotech Inc; Smith and Johnson, 1988. *Gene* 67: 31-40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

Examples of suitable inducible non-fusion *E. coli* expression vectors include pTrc (Amrann et al., (1988) Gene 69:301-315) and pET 11d (Studier et al., GENE EXPRESSION TECHNOLOGY: METHODS IN ENZYMOLOGY 185, Academic Press, San Diego, Calif. (1990) 60-89).

In some embodiments, a vector is a yeast expression vector. Examples of vectors for expression in yeast *Saccharomyces cerivisae* include pYepSec1 (Baldari, et al., 1987. EMBO J. 6: 229-234), pMFa (Kuijan and Herskowitz, 1982. Cell 30: 933-943), pJRY88 (Schultz et al., 1987. Gene 54: 113-123), pYES2 (Invitrogen Corporation, San Diego, Calif.), and picZ (InVitrogen Corp, San Diego, Calif.).

In some embodiments, a vector drives protein expression in insect cells using baculovirus expression vectors. Baculovirus vectors available for expression of proteins in cultured insect cells (e.g., SF9 cells) include the pAc series (Smith, et al., 1983. Mol. Cell. Biol. 3: 2156-2165) and the pVL series (Lucklow and Summers, 1989. Virology 170: 31-39).

In some embodiments, a vector is capable of driving expression of one or more sequences in mammalian cells using a mammalian expression vector. Examples of mammalian expression vectors include pCDM8 (Seed, 1987. Nature 329: 840) and pMT2PC (Kaufman, et al., 1987. EMBO J. 6: 187-195). When used in mammalian cells, the expression vector's control functions are typically provided by one or more regulatory elements. For example, commonly used promoters are derived from polyoma, adenovirus 2, cytomegalovirus, simian virus 40, and others disclosed herein and known in the art. For other suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In some embodiments, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. *Genes Dev.* 1: 268-277), lymphoid-specific promoters (Calame and Eaton, 1988. *Adv. Immunol.* 43: 235-275), in particular promoters of T cell receptors (Winoto and Baltimore, 1989. *EMBO J.* 8: 729-733) and immunoglobulins (Baneiji, et al., 1983. *Cell* 33: 729-740; Queen and Baltimore, 1983. *Cell* 33: 741-748), neuron-specific promoters (e.g., the neurofilament promoter; Byrne and Ruddle, 1989. *Proc. Natl. Acad. Sci. USA* 86: 5473-5477), pancreas-specific promoters (Edlund, et al., 1985. *Science* 230: 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, 1990. *Science* 249: 374-379) and the α-fetoprotein promoter (Campes and Tilghman, 1989. *Genes Dev.* 3: 537-546). With regards to these prokaryotic and eukaryotic vectors, mention is made of U.S. Pat. No. 6,750,059, the contents of which are incorporated by reference herein in their entirety. Other embodiments of the invention may relate to the use of viral vectors, with regards to which mention is made of U.S. patent application Ser. No. 13/092,085, the contents of which are incorporated by reference herein in their entirety. Tissue-specific regulatory elements are known in the art and in this regard, mention is made of U.S. Pat. No. 7,776,321, the contents of which are incorporated by reference herein in their entirety.

Regulatory Elements

In some embodiments, a regulatory element is operably linked to one or more elements of a CRISPR system so as to drive expression of the one or more elements of the CRISPR system. In general, CRISPRs (Clustered Regularly Interspaced Short Palindromic Repeats), also known as SPIDRs (SPacer Interspersed Direct Repeats), constitute a family of DNA loci that are usually specific to a particular bacterial species. The CRISPR locus comprises a distinct class of interspersed short sequence repeats (SSRs) that were recognized in *E. coli* (Ishino et al., J. Bacteriol., 169:5429-5433 [1987]; and Nakata et al., J. Bacteriol., 171:3553-3556 [1989]), and associated genes. Similar interspersed SSRs have been identified in *Haloferax mediterranei, Streptococcus pyogenes, Anabaena*, and *Mycobacterium tuberculosis* (See, Groenen et al., Mol. Microbiol., 10:1057-1065 [1993]; Hoe et al., Emerg. Infect. Dis., 5:254-263 [1999]; Masepohl et al., Biochim. Biophys. Acta 1307:26-30 [1996]; and Mojica et al., Mol. Microbiol., 17:85-93 [1995]). The CRISPR loci typically differ from other SSRs by the structure of the repeats, which have been termed short regularly spaced repeats (SRSRs) (Janssen et al., OMICS J. Integ. Biol., 6:23-33 [2002]; and Mojica et al., Mol. Microbiol., 36:244-246 [2000]). In general, the repeats are short elements that occur in clusters that are regularly spaced by unique intervening sequences with a substantially constant length (Mojica et al., [2000], supra). Although the repeat sequences are highly conserved between strains, the number of interspersed repeats and the sequences of the spacer regions typically differ from strain to strain (van Embden et al., J. Bacteriol., 182:2393-2401 [2000]). CRISPR loci have been identified in more than 40 prokaryotes (See e.g., Jansen et al., Mol. Microbiol., 43:1565-1575 [2002]; and Mojica et al., [2005]) including, but not limited to *Aeropyrum, Pyrobaculum, Sulfolobus, Archaeoglobus, Halocarcula, Methanobacterium, Methanococcus, Methanosarcina, Methanopyrus, Pyrococcus, Picrophilus, Thermoplasma, Corynebacterium, Mycobacterium, Streptomyces, Aquifex, Porphyromonas, Chlorobium, Thermus, Bacillus, Listeria, Staphylococcus, Clostridium, Thermoanaerobacter, Mycoplasma, Fusobacterium, Azarcus, Chromobacterium, Neisseria, Nitrosomonas, Desulfovibrio, Geobacter, Myxococcus, Campylobacter, Wolinella, Acinetobacter, Erwinia, Escherichia, Legionella, Methylococcus, Pasteurella, Photobacterium, Salmonella, Xanthomonas, Yersinia, Treponema*, and *Thermotoga*.

In general, "CRISPR system" refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or other sequences and transcripts from a CRISPR locus. In embodiments of the invention the terms guide sequence and guide RNA are used interchangeably. In some embodiments, one or more elements of a CRISPR system is derived from a type I, type II, or type III CRISPR system. In some embodiments, one or more elements of a CRISPR system is derived from a particular organism comprising an endogenous CRISPR system, such as *Streptococcus pyogenes*. In general, a CRISPR system is characterized by elements that promote the formation of a CRISPR complex at the site of a target sequence (also referred to as a protospacer in the context of an endogenous CRISPR system). In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise any polynucleotide, such as DNA or RNA polynucleotides. In some embodiments, a target sequence is located in the nucleus or cytoplasm of a cell.

In some embodiments, direct repeats may be identified in silico by searching for repetitive motifs that fulfill any or all of the following criteria:

1. found in a 2 Kb window of genomic sequence flanking the type II CRISPR locus;
2. span from 20 to 50 bp; and
3. interspaced by 20 to 50 bp.

In some embodiments, 2 of these criteria may be used, for instance 1 and 2, 2 and 3, or 1 and 3. In some embodiments, all 3 criteria may be used.

In some embodiments, candidate tracrRNA may be subsequently predicted by sequences that fulfill any or all of the following criteria:

1. sequence homology to direct repeats (motif search in Geneious with up to 18-bp mismatches);
2. presence of a predicted Rho-independent transcriptional terminator in direction of transcription; and
3. stable hairpin secondary structure between tracrRNA and direct repeat.

In some embodiments, 2 of these criteria may be used, for instance 1 and 2, 2 and 3, or 1 and 3. In some embodiments, all 3 criteria may be used.

In some embodiments, chimeric synthetic guide RNAs (sgRNAs) designs may incorporate at least 12 bp of duplex structure between the direct repeat and tracrRNA.

In preferred embodiments of the invention, the CRISPR system is a type II CRISPR system and the Cas enzyme is Cas9, which catalyzes DNA cleavage. Enzymatic action by Cas9 derived from *Streptococcus pyogenes* or any closely related Cas9 generates double stranded breaks at target site sequences which hybridize to 20 nucleotides of the guide sequence and that have a protospacer-adjacent motif (PAM) sequence (examples include NGG/NRG or a PAM that can be determined as described herein) following the 20 nucleotides of the target sequence. CRISPR activity through Cas9 for site-specific DNA recognition and cleavage is defined by the guide sequence, the tracr sequence that hybridizes in part to the guide sequence and the PAM sequence. More aspects of the CRISPR system are described in Karginov and Hannon, The CRISPR system: small RNA-guided defence in bacteria and archaea, Mole Cell 2010, January 15; 37(1): 7.

Figure 1:
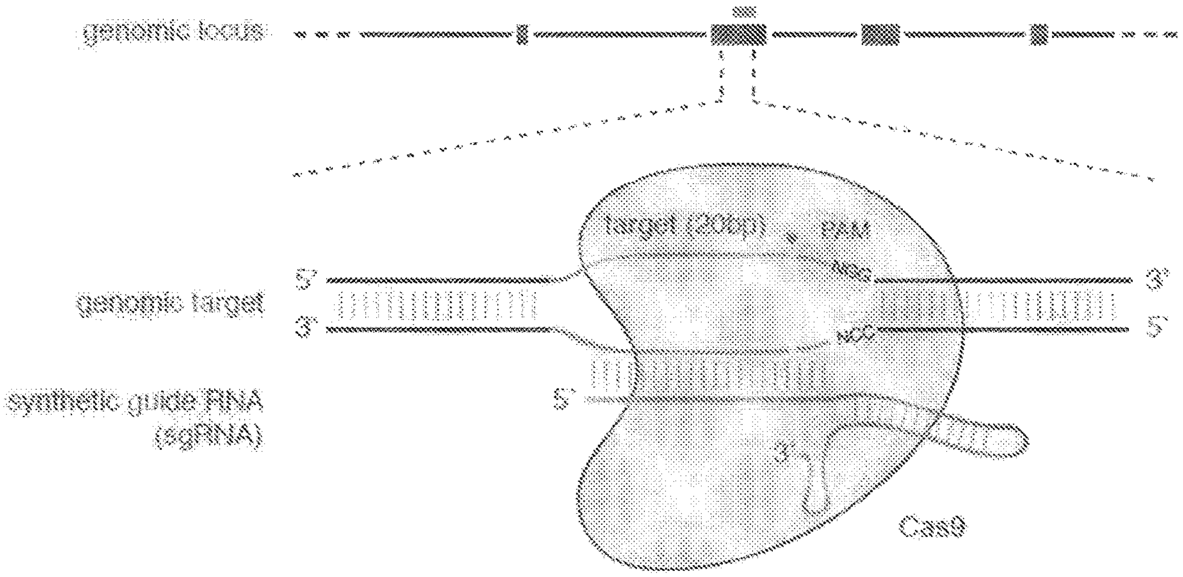
FIG. 1 shows a schematic model of the CRISPR system. The Cas9 nuclease from *Streptococcus pyogenes* is targeted to genomic DNA by a synthetic guide RNA (sgRNA) consisting of a 20-nt guide sequence and a scaffold. The guide sequence base-pairs with the DNA target, directly upstream of a requisite 5'-NGG protospacer adjacent motif (PAM), and Cas9 mediates a double-stranded break (DSB) ~3 bp upstream of the PAM.
Figure 2A:
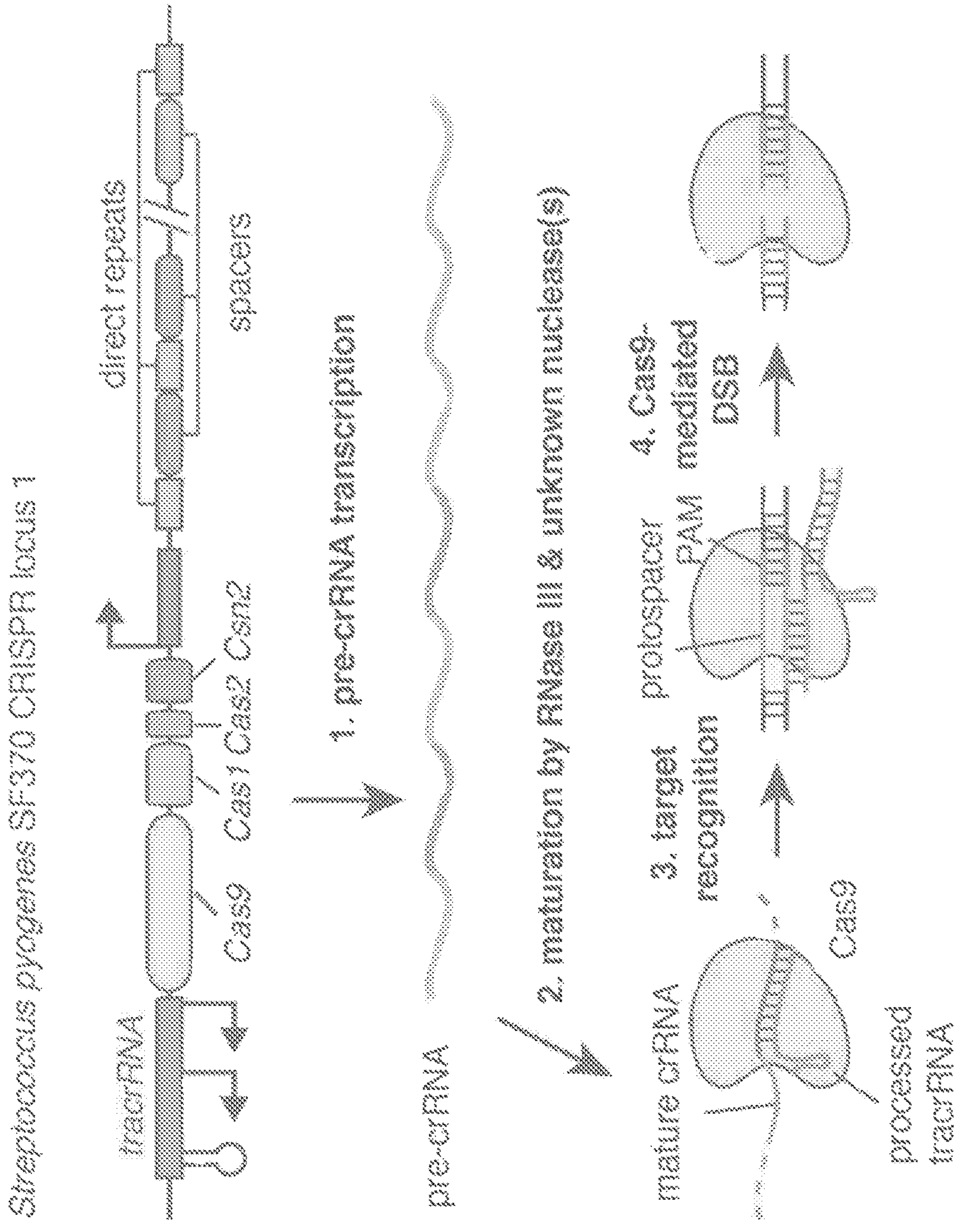
Figure 2B:
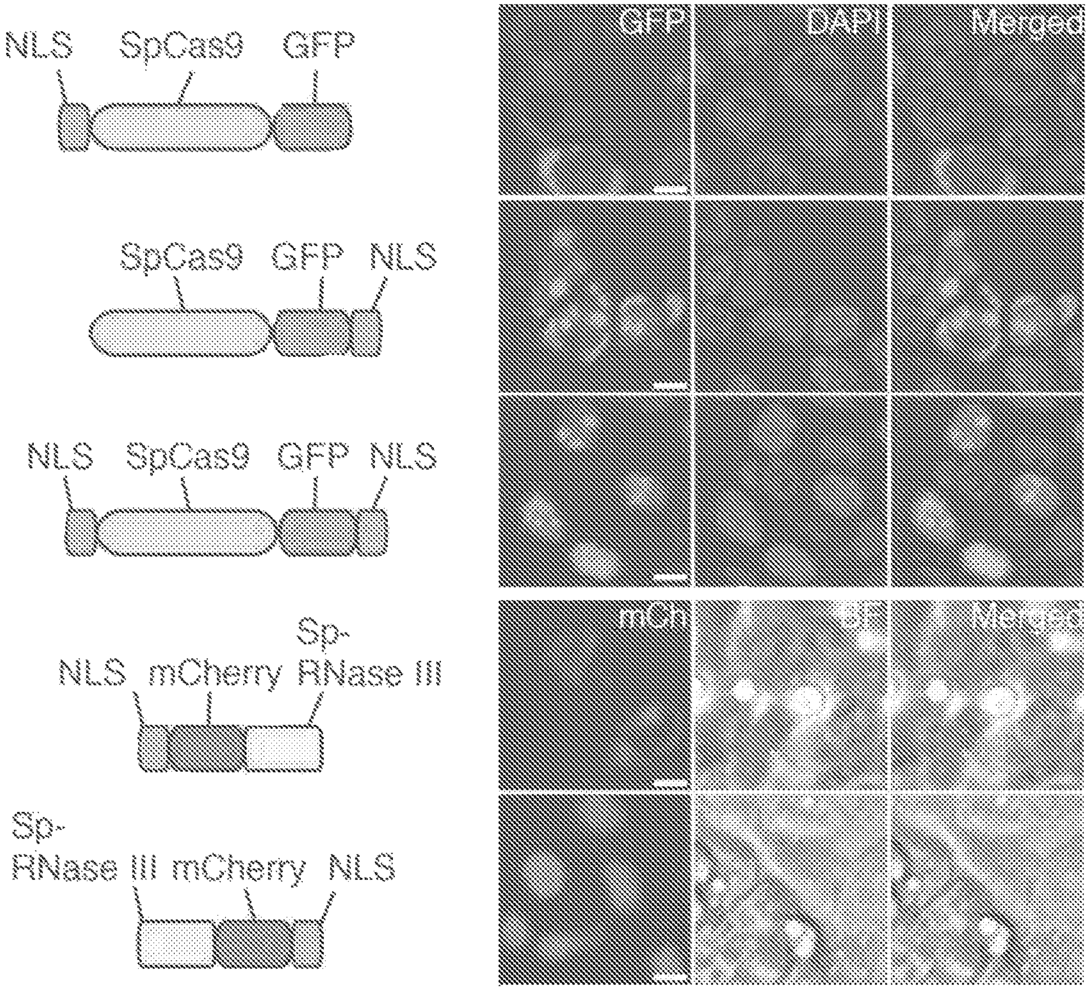
Figure 2C:
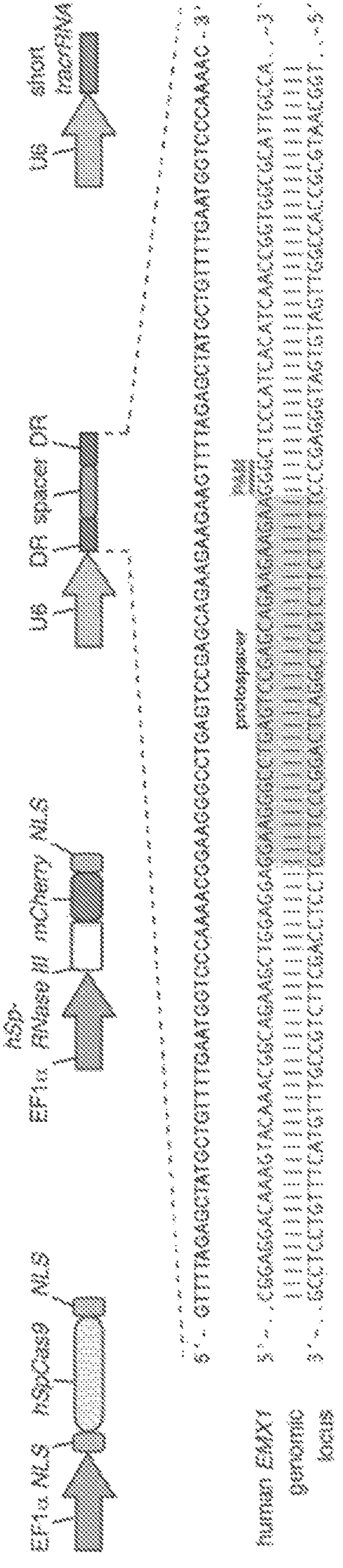

The type II CRISPR locus from *Streptococcus pyogenes* SF370, which contains a cluster of four genes Cas9, Cas1, Cas2, and Csn1, as well as two non-coding RNA elements, tracrRNA and a characteristic array of repetitive sequences (direct repeats) interspaced by short stretches of non-repetitive sequences (spacers, about 30 bp each). In this system, targeted DNA double-strand break (DSB) is generated in four sequential steps (FIG. 2A). First, two non-coding RNAs, the pre-crRNA array and tracrRNA, are transcribed from the CRISPR locus. Second, tracrRNA hybridizes to the direct repeats of pre-crRNA, which is then processed into mature crRNAs containing individual spacer sequences. Third, the mature crRNA:tracrRNA complex directs Cas9 to the DNA target consisting of the protospacer and the corresponding PAM via heteroduplex formation between the spacer region of the crRNA and the protospacer DNA. Finally, Cas9 mediates cleavage of target DNA upstream of PAM to create a DSB within the protospacer (FIG. 2A). FIG. 2B demonstrates the nuclear localization of the codon optimized Cas9. To promote precise transcriptional initiation, the RNA polymerase III-based U6 promoter was selected to drive the expression of tracrRNA (FIG. 2C). Similarly, a U6 promoter-based construct was developed to express a pre-crRNA array consisting of a single spacer flanked by two direct repeats (DRs, also encompassed by the term "tracr-mate sequences"; FIG. 2C). The initial spacer was designed to target a 33-base-pair (bp) target site (30-bp protospacer plus a 3-bp CRISPR motif (PAM) sequence satisfying the NGG recognition motif of Cas9) in the human EMX1 locus (FIG. 2C), a key gene in the development of the cerebral cortex.

Typically, in the context of an endogenous CRISPR system, formation of a CRISPR complex (comprising a guide sequence hybridized or hybridizable to a target sequence and complexed with one or more Cas proteins) results in cleavage of one or both strands in or near (e.g. within 1, 2, 3, 4, 5, 6, 7, 8, 9, 10, 20, 50, or more base pairs from) the target sequence. Without wishing to be bound by theory, the tracr sequence, which may comprise or consist of all or a portion of a wild-type tracr sequence (e.g. about or more than about 20, 26, 32, 45, 48, 54, 63, 67, 85, or more nucleotides of a wild-type tracr sequence), may also form part of a CRISPR complex, such as by hybridization along at least a portion of the tracr sequence to all or a portion of a tracr mate sequence that is operably linked to the guide sequence. In some embodiments, one or more vectors driving expression of one or more elements of a CRISPR system are introduced into a host cell such that expression of the elements of the CRISPR system direct formation of a CRISPR complex at one or more target sites. For example, a Cas enzyme, a guide sequence linked to a tracr-mate sequence, and a tracr sequence could each be operably linked to separate regulatory elements on separate vectors. Alternatively, two or more of the elements expressed from the same or different regulatory elements, may be combined in a single vector, with one or more additional vectors providing any components of the CRISPR system not included in the first vector. CRISPR system elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. In some embodiments, a single promoter drives expression of a transcript encoding a CRISPR enzyme and one or more of the guide sequence, tracr mate sequence (optionally operably linked to the guide sequence), and a tracr sequence embedded within one or more intron sequences (e.g. each in a different intron, two or more in at least one intron, or all in a single intron). In some embodiments, the CRISPR enzyme, guide sequence, tracr mate sequence, and tracr sequence are operably linked to and expressed from the same promoter.

In some embodiments, a vector comprises one or more insertion sites, such as a restriction endonuclease recognition sequence (also referred to as a "cloning site"). In some embodiments, one or more insertion sites (e.g. about or more than about 1, 2, 3, 4, 5, 6, 7, 8, 9, 10, or more insertion sites) are located upstream and/or downstream of one or more sequence elements of one or more vectors. In some embodiments, a vector comprises an insertion site upstream of a tracr mate sequence, and optionally downstream of a regulatory element operably linked to the tracr mate sequence, such that following insertion of a guide sequence into the insertion site and upon expression the guide sequence directs sequence-specific binding of a CRISPR complex to a target sequence in a eukaryotic cell. In some embodiments, a vector comprises two or more insertion sites, each insertion site being located between two tracr mate sequences so as to allow insertion of a guide sequence at each site. In such an arrangement, the two or more guide sequences may comprise two or more copies of a single guide sequence, two or more different guide sequences, or combinations of these. When multiple different guide sequences are used, a single expression construct may be used to target CRISPR activity to multiple different, corresponding target sequences within a cell. For example, a single vector may comprise about or more than about 1, 2, 3, 4, 5, 6, 7, 8, 9, 10, 15, 20, or more guide sequences. In some embodiments, about or more than about 1, 2, 3, 4, 5, 6, 7, 8, 9, 10, or more such guide-sequence-containing vectors may be provided, and optionally delivered to a cell.

In some embodiments, a vector comprises a regulatory element operably linked to an enzyme-coding sequence encoding a CRISPR enzyme, such as a Cas protein. Non-limiting examples of Cas proteins include Cas1, Cas1B, Cas2, Cas3, Cas4, Cas5, Cash, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, or modified versions thereof. In some embodiments, the unmodified CRISPR enzyme has DNA cleavage activity, such as Cas9. In some embodiments, the CRISPR enzyme directs cleavage of one or both strands at the location of a target sequence, such as within the target sequence and/or within the complement of the target sequence. In some embodiments, the CRISPR enzyme directs cleavage of one or both strands within about 1, 2, 3, 4, 5, 6, 7, 8, 9, 10, 15, 20, 25, 50, 100, 200, 500, or more base pairs from the first or last nucleotide of a target sequence. In some embodiments, a vector encodes a CRISPR enzyme that is mutated to with respect to a corresponding wild-type enzyme such that the mutated CRISPR enzyme lacks the ability to cleave one or both strands of a target polynucleotide containing a target sequence. For example, an aspartate-to-alanine substitution (D10A) in the RuvC I catalytic domain of Cas9 from *S. pyogenes* converts Cas9 from a nuclease that cleaves both strands to a nickase (cleaves a single strand). Other examples of mutations that render Cas9 a nickase include, without limitation, H840A, N854A, and N863A. As a further example, two or more catalytic domains of Cas9 (RuvC I, RuvC II, and RuvC III or the HNH domain) may be mutated to produce a mutated Cas9 substantially lacking all DNA cleavage activity. In some embodiments, a D10A mutation is combined with one or more of H840A, N854A, or N863A mutations to produce a Cas9 enzyme substantially lacking all DNA cleavage activity. In some embodiments, a CRISPR enzyme is considered to substantially lack all DNA cleavage activity when the DNA cleavage activity of the mutated enzyme is less than about 25%, 10%, 5%, 1%, 0.1%, 0.01%, or lower with respect to its non-mutated form. Where the enzyme is not SpCas9, mutations may be made at any or all residues corresponding to positions 10, 762, 840, 854, 863 and/or 986 of SpCas9 (which may be ascertained for instance by standard sequence comparison tools. In particular, any or all of the following mutations are preferred in SpCas9: D10A, E762A, H840A, N854A, N863A and/or D986A; as well as conservative substitution for any of the replacement amino acids is also envisaged. The same (or conservative substitutions of these mutations) at corresponding positions in other Cas9s are also preferred. Particularly preferred are D10 and H840 in SpCas9. However, in other Cas9s, residues corresponding to SpCas9 D10 and H840 are also preferred.

An aspartate-to-alanine substitution (D10A) in the RuvC I catalytic domain of SpCas9 was engineered to convert the nuclease into a nickase (SpCas9n) (see e.g. Sapranauskas et al., 2011, Nucleic Acids Research, 39: 9275; Gasiunas et al., 2012, Proc. Natl. Acad. Sci. USA, 109:E2579), such that nicked genomic DNA undergoes the high-fidelity homology-directed repair (HDR). Surveyor assay confirmed that SpCas9n does not generate indels at the EMX1 protospacer target. Co-expression of EMX1-targeting chimeric crRNA (having the tracrRNA component as well) with SpCas9 produced indels in the target site, whereas co-expression with SpCas9n did not (n=3). Moreover, sequencing of 327 amplicons did not detect any indels induced by SpCas9n. The same locus was selected to test CRISPR-mediated HR by co-transfecting HEK 293FT cells with the chimeric RNA targeting EMX1, hSpCas9 or hSpCas9n, as well as a HR template to introduce a pair of restriction sites (HindIII and NheI) near the protospacer.

Preferred orthologs are described herein. A Cas enzyme may be identified Cas9 as this can refer to the general class of enzymes that share homology to the biggest nuclease with multiple nuclease domains from the type II CRISPR system. Most preferably, the Cas9 enzyme is from, or is derived from, spCas9 or saCas9. By derived, Applicants mean that the derived enzyme is largely based, in the sense of having a high degree of sequence homology with, a wildtype enzyme, but that it has been mutated (modified) in some way as described herein.

It will be appreciated that the terms Cas and CRISPR enzyme are generally used herein interchangeably, unless otherwise apparent. As mentioned above, many of the residue numberings used herein refer to the Cas9 enzyme from the type II CRISPR locus in *Streptococcus pyogenes*. However, it will be appreciated that this invention includes many more Cas9s from other species of microbes, such as SpCas9, SaCa9, St1Cas9 and so forth.

Codon Optimization

An example of a codon optimized sequence, in this instance optimized for humans (i.e. being optimized for expression in humans) is provided herein, see the SaCas9 human codon optimized sequence. Whilst this is preferred, it will be appreciated that other examples are possible and codon optimization for a host species is known.

In some embodiments, an enzyme coding sequence encoding a CRISPR enzyme is codon optimized for expression in particular cells, such as eukaryotic cells. The eukaryotic cells may be those of or derived from a particular organism, such as a mammal, including but not limited to human, mouse, rat, rabbit, dog, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded.

In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at worldwideweb.kazusa.orjp/codon/ (visited Jul. 9, 2002), and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, PA), are also available. In some embodiments, one or more codons (e.g. 1, 2, 3, 4, 5, 10, 15, 20, 25, 50, or more, or all codons) in a sequence encoding a CRISPR enzyme correspond to the most frequently used codon for a particular amino acid.

Nuclear Localization Sequences (NLSs)

In some embodiments, a vector encodes a CRISPR enzyme comprising one or more nuclear localization sequences (NLSs), such as about or more than about 1, 2, 3, 4, 5, 6, 7, 8, 9, 10, or more NLSs. In some embodiments, the CRISPR enzyme comprises about or more than about 1, 2, 3, 4, 5, 6, 7, 8, 9, 10, or more NLSs at or near the amino-terminus, about or more than about 1, 2, 3, 4, 5, 6, 7, 8, 9, 10, or more NLSs at or near the carboxy-terminus, or a combination of these (e.g. one or more NLS at the amino-terminus and one or more NLS at the carboxy terminus). When more than one NLS is present, each may be selected independently of the others, such that a single NLS may be present in more than one copy and/or in combination with one or more other NLSs present in one or more copies. In a preferred embodiment of the invention, the CRISPR enzyme comprises at most 6 NLSs. In some embodiments, an NLS is considered near the N- or C-terminus when the nearest amino acid of the NLS is within about 1, 2, 3, 4, 5, 10, 15, 20, 25, 30, 40, 50, or more amino acids along the polypeptide chain from the N- or C-terminus. Non-limiting examples of NLSs include an NLS sequence derived from: the NLS of the SV40 virus large T-antigen, having the amino acid sequence PKKKRKV (SEQ ID NO: 64); the NLS from nucleoplasmin (e.g. the nucleoplasmin bipartite NLS with the sequence KRPAATKKAGQAKKKK (SEQ ID NO: 65)); the c-myc NLS having the amino acid sequence PAAKRVKLD (SEQ ID NO: 66) or RQRRNELKRSP (SEQ ID NO: 67); the hRNPA1 M9 NLS having the sequence NQSSNFGPMKGGNFGGRSSGPYGGGGQYFAK-PRNQGGY (SEQ ID NO: 68); the sequence RMRIZFKNKGKDTAELRRRRVEVSVELRKAKKD-EQILKRRNV (SEQ ID NO: 69) of the IBB domain from importin-alpha; the sequences VSRKRPRP (SEQ ID NO: 70) and PPKKARED (SEQ ID NO: 71) of the myoma T protein; the sequence PQPKKKPL (SEQ ID NO: 72) of human p53; the sequence SALIKKKKKMAP (SEQ ID NO: 73) of mouse c-abl IV; the sequences DRLRR (SEQ ID NO: 74) and PKQKKRK (SEQ ID NO: 75) of the influenza virus NS1; the sequence RKLKKKIKKL (SEQ ID NO: 76) of the Hepatitis virus delta antigen; the sequence REKKKFLKRR (SEQ ID NO: 77) of the mouse Mx1 protein; the sequence KRKGDEVDGVDEVAKKKSKK (SEQ ID NO: 78) of the human poly(ADP-ribose) polymerase; and the sequence RKCLQAGMNLEARKTKK (SEQ ID NO: 79) of the steroid hormone receptors (human) glucocorticoid.

In general, the one or more NLSs are of sufficient strength to drive accumulation of the CRISPR enzyme in a detectable amount in the nucleus of a eukaryotic cell. In general, strength of nuclear localization activity may derive from the number of NLSs in the CRISPR enzyme, the particular NLS(s) used, or a combination of these factors. Detection of accumulation in the nucleus may be performed by any suitable technique. For example, a detectable marker may be fused to the CRISPR enzyme, such that location within a cell may be visualized, such as in combination with a means for detecting the location of the nucleus (e.g. a stain specific for the nucleus such as DAPI). Cell nuclei may also be isolated from cells, the contents of which may then be analyzed by any suitable process for detecting protein, such as immunohistochemistry, Western blot, or enzyme activity assay. Accumulation in the nucleus may also be determined indirectly, such as by an assay for the effect of CRISPR complex formation (e.g. assay for DNA cleavage or mutation at the target sequence, or assay for altered gene expression activity affected by CRISPR complex formation and/or CRISPR enzyme activity), as compared to a control no exposed to the CRISPR enzyme or complex, or exposed to a CRISPR enzyme lacking the one or more NLSs.

Guide Sequence

Particularly preferred guides are in the range of 20-22 nts, as discussed herein; see Example 41.

In general, a guide sequence is any polynucleotide sequence having sufficient complementarity with a target polynucleotide sequence to hybridize with the target sequence and direct sequence-specific binding of a CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies; available at worldwideweb.novocraft.com), ELAND (Illumina, San Diego, CA), SOAP (available at soap.genomics.org.cn), and Maq (available at maq.sourceforge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art.

A guide sequence may be selected to target any target sequence. In some embodiments, the target sequence is a sequence within a genome of a cell. Exemplary target sequences include those that are unique in the target genome. For example, for the *S. pyogenes* Cas9, a unique target sequence in a genome may include a Cas9 target site of the form MMMMMMMMNNNNNNNNNNNNXGG where NNNNNNNNNNNNXGG (N is A, G, T, or C; and X can be anything) has a single occurrence in the genome. A unique target sequence in a genome may include an *S. pyogenes* Cas9 target site of the form MMMMMMMMMNNNNNNNNNNNXGG where NNNNNNNNNNNXGG (N is A, G, T, or C; and X can be anything) has a single occurrence in the genome. For the *S. thermophilus* CRISPR1 Cas9, a unique target sequence in a genome may include a Cas9 target site of the form MMMMMMMMNNNNNNNNNNNNXXAGAAW (SEQ ID NO: 80) where NNNNNNNNNNNNXXAGAAW (SEQ ID NO: 81) (N is A, G, T, or C; X can be anything; and W is A or T) has a single occurrence in the genome. A unique target sequence in a genome may include an *S. thermophilus* CRISPR1 Cas9 target site of the form MMMMMMMMMNNNNNNNNNNNXXAGAAW (SEQ ID NO: 82) where NNNNNNNNNNNXXAGAAW (SEQ ID NO: 83) (N is A, G, T, or C; X can be anything; and W is A or T) has a single occurrence in the genome. For the *S. pyogenes* Cas9, a unique target sequence in a genome may include a Cas9 target site of the form MMMMMMMMNNNNNNNNNNNNXGGXG where NNNNNNNNNNNNNXGGXG (N is A, G, T, or C; and X can be anything) has a single occurrence in the genome. A unique target sequence in a genome may include an *S. pyogenes* Cas9 target site of the form MMMMMMMMMNNNNNNNNNNNXGGXG where NNNNNNNNNNNNXGGXG (N is A, G, T, or C; and X can be anything) has a single occurrence in the genome. In each of these sequences "M" may be A, G, T, or C, and need not be considered in identifying a sequence as unique.

In some embodiments, a guide sequence is selected to reduce the degree secondary structure within the guide sequence. In some embodiments, about or less than about 75%, 50%, 40%, 30%, 25%, 20%, 15%, 10%, 5%, 1%, or fewer of the nucleotides of the guide sequence participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g. A. R. Gruber et al., 2008, *Cell* 106(1): 23-24; and PA Carr and GM Church, 2009, *Nature Biotechnology* 27(12): 1151-62).

Tracr Mate Sequence

In general, a tracr mate sequence includes any sequence that has sufficient complementarity with a tracr sequence to promote one or more of: (1) excision of a guide sequence flanked by tracr mate sequences in a cell containing the corresponding tracr sequence; and (2) formation of a CRISPR complex at a target sequence, wherein the CRISPR complex comprises the tracr mate sequence hybridized or hybridizable to the tracr sequence. In general, degree of complementarity is with reference to the optimal alignment of the tracr mate sequence and tracr sequence, along the length of the shorter of the two sequences. Optimal alignment may be determined by any suitable alignment algorithm, and may further account for secondary structures, such as self-complementarity within either the tracr sequence or tracr mate sequence. In some embodiments, the degree of complementarity between the tracr sequence and tracr mate sequence along the length of the shorter of the two when optimally aligned is about or more than about 25%, 30%, 40%, 50%, 60%, 70%, 80%, 90%, 95%, 97.5%, 99%, or higher. In some embodiments, the tracr sequence is about or more than about 5, 6, 7, 8, 9, 10, 11, 12, 13, 14, 15, 16, 17, 18, 19, 20, 25, 30, 40, 50, or more nucleotides in length. In some embodiments, the tracr sequence and tracr mate sequence are contained within a single transcript, such that hybridization between the two produces a transcript having a secondary structure, such as a hairpin. In an embodiment of the invention, the transcript or transcribed polynucleotide sequence has at least two or more hairpins. In preferred embodiments, the transcript has two, three, four or five hairpins. In a further embodiment of the invention, the transcript has at most five hairpins. In a hairpin structure the portion of the sequence 5' of the final "N" and upstream of the loop corresponds to the tracr mate sequence, and the portion of the sequence 3' of the loop corresponds to the tracr sequence Further non-limiting examples of single polynucleotides comprising a guide sequence, a tracr mate sequence, and a tracr sequence are as follows (listed 5' to 3'), where "N" represents a base of a guide sequence, the first block of lower case letters represent the tracr mate sequence, and the second block of lower case letters represent the tracr sequence, and the final poly-T sequence represents the transcription terminator: (1) NNNNNNNNNNNNNNNNNNNNgtttttgtactctcaagatttaGAAAtaaatcttgcagaagctacaaagataa ggcttcatgccgaaatcaacaccctgtcattttatggcagggtgttttcgttatttaaTTTTTT (SEQ ID NO: 84); (2) NNNNNNNNNNNNNNNNNNNNgtttttgtactctcaGAAAtgcagaagctacaaagataaggcttcatgccg aaatcaacaccctgtcattttatggcagggtgttttcgttatttaaTTTTTT (SEQ ID NO: 85); (3) NNNNNNNNNNNNNNNNNNNNgtttttgtactctcaGAAAtgcagaagctacaaagataaggcttcatgccg aaatcaacaccctgtcattttatggcagggtgtTTTTTT (SEQ ID NO: 86); (4) NNNNNNNNNNNNNNNNNNNNgttttagagctaGAAAtagcaagttaaaataaggctagtccgttatcaactt gaaaaagtggcaccgagtcggtgcTTTTTT (SEQ ID NO: 87); (5) NNNNNNNNNNNNNNNNNNNNgttttagagctaGAAATAGcaagttaaaataaggctagtccgttatcaac ttgaaaaagtgTTTTTTT (SEQ ID NO: 88); and (6) NNNNNNNNNNNNNNNNNNNNgttttagagctagAAATAGcaagttaaaataaggctagtccgttatcaTT TTTTTT (SEQ ID NO: 89). In some embodiments, sequences (1) to (3) are used in combination with Cas9 from *S. thermophilus* CRISPR1. In some embodiments, sequences (4) to (6) are used in combination with Cas9 from *S. pyogenes*. In some embodiments, the tracr sequence is a separate transcript from a transcript comprising the tracr mate sequence.

Recombination Template

In some embodiments, a recombination template is also provided. A recombination template may be a component of another vector as described herein, contained in a separate vector, or provided as a separate polynucleotide. In some embodiments, a recombination template is designed to serve as a template in homologous recombination, such as within or near a target sequence nicked or cleaved by a CRISPR enzyme as a part of a CRISPR complex. A template polynucleotide may be of any suitable length, such as about or more than about 10, 15, 20, 25, 50, 75, 100, 150, 200, 500, 1000, or more nucleotides in length. In some embodiments, the template polynucleotide is complementary to a portion of a polynucleotide comprising the target sequence. When optimally aligned, a template polynucleotide might overlap with one or more nucleotides of a target sequences (e.g.

about or more than about 1, 5, 10, 15, 20, or more nucleotides). In some embodiments, when a template sequence and a polynucleotide comprising a target sequence are optimally aligned, the nearest nucleotide of the template polynucleotide is within about 1, 5, 10, 15, 20, 25, 50, 75, 100, 200, 300, 400, 500, 1000, 5000, 10000, or more nucleotides from the target sequence. Additional discussion about the HDR pathway is herein provided; for instance, as to 'CRISPR Complexes.'

Fusion Protein

In some embodiments, the CRISPR enzyme is part of a fusion protein comprising one or more heterologous protein domains (e.g. about or more than about 1, 2, 3, 4, 5, 6, 7, 8, 9, 10, or more domains in addition to the CRISPR enzyme). A CRISPR enzyme fusion protein may comprise any additional protein sequence, and optionally a linker sequence between any two domains. Examples of protein domains that may be fused to a CRISPR enzyme include, without limitation, epitope tags, reporter gene sequences, and protein domains having one or more of the following activities: methylase activity, demethylase activity, transcription activation activity, transcription repression activity, transcription release factor activity, histone modification activity, RNA cleavage activity and nucleic acid binding activity. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-S-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP). A CRISPR enzyme may be fused to a gene sequence encoding a protein or a fragment of a protein that bind DNA molecules or bind other cellular molecules, including but not limited to maltose binding protein (MBP), S-tag, Lex A DNA binding domain (DBD) fusions, GAL4 DNA binding domain fusions, and herpes simplex virus (HSV) BP16 protein fusions. Additional domains that may form part of a fusion protein comprising a CRISPR enzyme are described in US20110059502, incorporated herein by reference. In some embodiments, a tagged CRISPR enzyme is used to identify the location of a target sequence.

Inducible System

In some embodiments, a CRISPR enzyme may form a component of an inducible system. The inducible nature of the system would allow for spatiotemporal control of gene editing or gene expression using a form of energy. The form of energy may include but is not limited to electromagnetic radiation, sound energy, chemical energy and thermal energy. Examples of inducible system include tetracycline inducible promoters (Tet-On or Tet-Off), small molecule two-hybrid transcription activations systems (FKBP, ABA, etc), or light inducible systems (Phytochrome, LOV domains, or cryptochrome). In one embodiment, the CRISPR enzyme may be a part of a Light Inducible Transcriptional Effector (LITE) to direct changes in transcriptional activity in a sequence-specific manner. The components of a light may include a CRISPR enzyme, a light-responsive cytochrome heterodimer (e.g. from *Arabidopsis thaliana*), and a transcriptional activation/repression domain. Further examples of inducible DNA binding proteins and methods for their use are provided in U.S. 61/736,465 and U.S. 61/721,283, which is hereby incorporated by reference in its entirety.

Delivery

In some aspects, the invention provides methods comprising delivering one or more polynucleotides, such as or one or more vectors as described herein, one or more transcripts thereof, and/or one or proteins transcribed therefrom, to a host cell. In some aspects, the invention further provides cells produced by such methods, and animals comprising or produced from such cells. In some embodiments, a CRISPR enzyme in combination with (and optionally complexed with) a guide sequence is delivered to a cell. Conventional viral and non-viral based gene transfer methods can be used to introduce nucleic acids in mammalian cells or target tissues. Such methods can be used to administer nucleic acids encoding components of a CRISPR system to cells in culture, or in a host organism. Non-viral vector delivery systems include DNA plasmids, RNA (e.g. a transcript of a vector described herein), naked nucleic acid, and nucleic acid complexed with a delivery vehicle, such as a liposome. Viral vector delivery systems include DNA and RNA viruses, which have either episomal or integrated genomes after delivery to the cell. For a review of gene therapy procedures, see Anderson, Science 256:808-813 (1992); Nabel & Felgner, TIBTECH 11:211-217 (1993); Mitani & Caskey, TIBTECH 11:162-166 (1993); Dillon, TIBTECH 11:167-175 (1993); Miller, Nature 357:455-460 (1992); Van Brunt, Biotechnology 6(10):1149-1154 (1988); Vigne, Restorative Neurology and Neuroscience 8:35-36 (1995); Kremer & Perricaudet, British Medical Bulletin 51(1):31-44 (1995); Haddada et al., in Current Topics in Microbiology and Immunology Doerfler and Bohm (eds) (1995); and Yu et al., Gene Therapy 1:13-26 (1994).

Methods of non-viral delivery of nucleic acids include lipofection, microinjection, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424; WO 91/16024. Delivery can be to cells (e.g. in vitro or ex vivo administration) or target tissues (e.g. in vivo administration).

The preparation of lipid:nucleic acid complexes, including targeted liposomes such as immunolipid complexes, is well known to one of skill in the art (see, e.g., Crystal, Science 270:404-410 (1995); Blaese et al., Cancer Gene Ther. 2:291-297 (1995); Behr et al., Bioconjugate Chem. 5:382-389 (1994); Remy et al., Bioconjugate Chem. 5:647-654 (1994); Gao et al., Gene Therapy 2:710-722 (1995); Ahmad et al., Cancer Res. 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

The use of RNA or DNA viral based systems for the delivery of nucleic acids take advantage of highly evolved processes for targeting a virus to specific cells in the body and trafficking the viral payload to the nucleus. Viral vectors can be administered directly to patients (in vivo) or they can be used to treat cells in vitro, and the modified cells may optionally be administered to patients (ex vivo). Conventional viral based systems could include retroviral, lentivirus, adenoviral, adeno-associated and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system would therefore depend on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immuno deficiency virus (SIV), human immuno deficiency virus (HIV), and combinations thereof (see, e.g., Buchscher et al., J. Virol. 66:2731-2739 (1992); Johann et al., J. Virol. 66:1635-1640 (1992); Sommnerfelt et al., Virol. 176:58-59 (1990); Wilson et al., J. Virol. 63:2374-2378 (1989); Miller et al., J. Virol. 65:2220-2224 (1991); PCT/US94/05700).

In another embodiment, Cocal vesiculovirus envelope pseudotyped retroviral vector particles are contemplated (see, e.g., US Patent Publication No. 20120164118 assigned to the Fred Hutchinson Cancer Research Center). Cocal virus is in the Vesiculovirus genus, and is a causative agent of vesicular stomatitis in mammals. Cocal virus was originally isolated from mites in Trinidad (Jonkers et al., Am. J. Vet. Res. 25:236-242 (1964)), and infections have been identified in Trinidad, Brazil, and Argentina from insects, cattle, and horses. Many of the vesiculoviruses that infect mammals have been isolated from naturally infected arthropods, suggesting that they are vector-borne. Antibodies to vesiculoviruses are common among people living in rural areas where the viruses are endemic and laboratory-acquired; infections in humans usually result in influenza-like symptoms. The Cocal virus envelope glycoprotein shares 71.5% identity at the amino acid level with VSV-G Indiana, and phylogenetic comparison of the envelope gene of vesiculoviruses shows that Cocal virus is serologically distinct from, but most closely related to, VSV-G Indiana strains among the vesiculoviruses. Jonkers et al., Am. J. Vet. Res. 25:236-242 (1964) and Travassos da Rosa et al., Am. J. Tropical Med. & Hygiene 33:999-1006 (1984). The Cocal vesiculovirus envelope pseudotyped retroviral vector particles may include for example, lentiviral, alpharetroviral, betaretroviral, gammaretroviral, deltaretroviral, and epsilonretroviral vector particles that may comprise retroviral Gag, Pol, and/or one or more accessory protein(s) and a Cocal vesiculovirus envelope protein. Within certain aspects of these embodiments, the Gag, Pol, and accessory proteins are lentiviral and/or gammaretroviral.

In applications where transient expression is preferred, adenoviral based systems may be used. Adenoviral based vectors are capable of very high transduction efficiency in many cell types and do not require cell division. With such vectors, high titer and levels of expression have been obtained. This vector can be produced in large quantities in a relatively simple system.

Adeno-associated virus ("AAV") vectors may also be used to transduce cells with target nucleic acids, e.g., in the in vitro production of nucleic acids and peptides, and for in vivo and ex vivo gene therapy procedures (see, e.g., West et al., Virology 160:38-47 (1987); U.S. Pat. No. 4,797,368; WO 93/24641; Kotin, Human Gene Therapy 5:793-801 (1994); Muzyczka, J. Clin. Invest. 94:1351 (1994). Construction of recombinant AAV vectors are described in a number of publications, including U.S. Pat. No. 5,173,414; Tratschin et al., Mol. Cell. Biol. 5:3251-3260 (1985); Tratschin, et al., Mol. Cell. Biol. 4:2072-2081 (1984); Hermonat & Muzyczka, PNAS 81:6466-6470 (1984); and Samulski et al., J. Virol. 63:03822-3828 (1989).

Packaging cells are typically used to form virus particles that are capable of infecting a host cell. Such cells include 293 cells, which package adenovirus, and ψ2 cells or PA317 cells, which package retrovirus. Viral vectors used in gene therapy are usually generated by producer a cell line that packages a nucleic acid vector into a viral particle. The vectors typically contain the minimal viral sequences required for packaging and subsequent integration into a host, other viral sequences being replaced by an expression cassette for the polynucleotide(s) to be expressed. The missing viral functions are typically supplied in trans by the packaging cell line. For example, AAV vectors used in gene therapy typically only possess ITR sequences from the AAV genome which are required for packaging and integration into the host genome. Viral DNA is packaged in a cell line, which contains a helper plasmid encoding the other AAV genes, namely rep and cap, but lacking ITR sequences. The cell line may also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

Accordingly, AAV is considered an ideal candidate for use as a transducing vector. Such AAV transducing vectors can comprise sufficient cis-acting functions to replicate in the presence of adenovirus or herpesvirus or poxvirus (e.g., vaccinia virus) helper functions provided in trans. Recombinant AAV (rAAV) can be used to carry exogenous genes into cells of a variety of lineages. In these vectors, the AAV cap and/or rep genes are deleted from the viral genome and replaced with a DNA segment of choice. Current AAV vectors may accommodate up to 4300 bases of inserted DNA.

There are a number of ways to produce rAAV, and the invention provides rAAV and methods for preparing rAAV. For example, plasmid(s) containing or consisting essentially of the desired construct are transfected into AAV-infected cells. In addition, a second or additional helper plasmid is cotransfected into these cells to provide the AAV rep and/or cap genes which are obligatory for replication and packaging of the recombinant viral construct. Under these conditions, the rep and/or cap proteins of AAV act in trans to stimulate replication and packaging of the rAAV construct. Two to Three days after transfection, rAAV is harvested. Traditionally rAAV is harvested from the cells along with adenovirus. The contaminating adenovirus is then inactivated by heat treatment. In the instant invention, rAAV is advantageously harvested not from the cells themselves, but from cell supernatant. Accordingly, in an initial aspect the invention provides for preparing rAAV, and in addition to the foregoing, rAAV can be prepared by a method that comprises or consists essentially of: infecting susceptible cells with a rAAV containing exogenous DNA including DNA for expression, and helper virus (e.g., adenovirus, herpesvirus, poxvirus such as vaccinia virus) wherein the rAAV lacks functioning cap and/or rep (and the helper virus (e.g., adenovirus, herpesvirus, poxvirus such as vaccinia virus) provides the cap and/or rev function that the rAAV lacks); or infecting susceptible cells with a rAAV containing exogenous DNA including DNA for expression, wherein the recombinant lacks functioning cap and/or rep, and transfecting said cells with a plasmid supplying cap and/or rep function that the rAAV lacks; or infecting susceptible cells with a rAAV containing exogenous DNA including DNA for expression, wherein the recombinant lacks functioning cap and/or rep, wherein said cells supply cap and/or rep function that the recombinant lacks; or transfecting the susceptible cells with an AAV lacking functioning cap and/or rep and plasmids for inserting exogenous DNA into the recombinant so that the exogenous DNA is expressed by the recombinant and for supplying rep and/or cap functions whereby transfection results in an rAAV containing the exogenous DNA including DNA for expression that lacks functioning cap and/or rep.

The rAAV can be from an AAV as herein described, and advantageously can be an rAAV1, rAAV2, AAV5 or rAAV having hybrid capsid which may comprise AAV1, AAV2, AAV5 or any combination thereof. One can select the AAV of the rAAV with regard to the cells to be targeted by the rAAV; e.g., one can select AAV serotypes 1, 2, 5 or a hybrid capsid AAV1, AAV2, AAV5 or any combination thereof for targeting brain or neuronal cells; and one can select AAV4 for targeting cardiac tissue.

In addition to 293 cells, other cells that can be used in the practice of the invention and the relative infectivity of certain AAV serotypes in vitro as to these cells (see Grimm, D. et al, J. Virol. 82: 5887-5911 (2008)) are as follows:

| Cell Line | AAV-1 | AAV-2 | AAV-3 | AAV-4 | AAV-5 | AAV-6 | AAV-8 | AAV-9 |
|---|---|---|---|---|---|---|---|---|
| Huh-7 | 13 | 100 | 2.5 | 0.0 | 0.1 | 10 | 0.7 | 0.0 |
| HEK293 | 25 | 100 | 2.5 | 0.1 | 0.1 | 5 | 0.7 | 0.1 |
| HeLa | 3 | 100 | 2.0 | 0.1 | 6.7 | 1 | 0.2 | 0.1 |
| HepG2 | 3 | 100 | 16.7 | 0.3 | 1.7 | 5 | 0.3 | ND |
| Hep1A | 20 | 100 | 0.2 | 1.0 | 0.1 | 1 | 0.2 | 0.0 |
| 911 | 17 | 100 | 11 | 0.2 | 0.1 | 17 | 0.1 | ND |
| CHO | 100 | 100 | 14 | 1.4 | 333 | 50 | 10 | 1.0 |
| COS | 33 | 100 | 33 | 3.3 | 5.0 | 14 | 2.0 | 0.5 |
| MeWo | 10 | 100 | 20 | 0.3 | 6.7 | 10 | 1.0 | 0.2 |
| NIH3T3 | 10 | 100 | 2.9 | 2.9 | 0.3 | 10 | 0.3 | ND |
| A549 | 14 | 100 | 20 | ND | 0.5 | 10 | 0.5 | 0.1 |
| HT1180 | 20 | 100 | 10 | 0.1 | 0.3 | 33 | 0.5 | 0.1 |
| Monocytes | 1111 | 100 | ND | ND | 125 | 1429 | ND | ND |
| Immature DC | 2500 | 100 | ND | ND | 222 | 2857 | ND | ND |
| Mature DC | 2222 | 100 | ND | ND | 333 | 3333 | ND | ND |

The invention provides rAAV that contains or consists essentially of an exogenous nucleic acid molecule encoding a CRISPR (Clustered Regularly Interspaced Short Palindromic Repeats) system, e.g., a plurality of cassettes comprising or consisting a first cassette comprising or consisting essentially of a promoter, a nucleic acid molecule encoding a CRISPR-associated (Cas) protein (putative nuclease or helicase proteins), e.g., Cas9 and a terminator, and a two, or more, advantageously up to the packaging size limit of the vector, e.g., in total (including the first cassette) five, cassettes comprising or consisting essentially of a promoter, nucleic acid molecule encoding guide RNA (gRNA) and a terminator (e.g., each cassette schematically represented as Promoter-gRNA1-terminator, Promoter-gRNA2-terminator . . . Promoter-gRNA(N)-terminator (where N is a number that can be inserted that is at an upper limit of the packaging size limit of the vector), or two or more individual rAAVs, each containing one or more than one cassette of a CRISPR system, e.g., a first rAAV containing the first cassette comprising or consisting essentially of a promoter, a nucleic acid molecule encoding Cas, e.g., Cas9 and a terminator, and a second rAAV containing a plurality, four, cassettes comprising or consisting essentially of a promoter, nucleic acid molecule encoding guide RNA (gRNA) and a terminator (e.g., each cassette schematically represented as Promoter-gRNA1-terminator, Promoter-gRNA2-terminator Promoter-gRNA(N)-terminator (where N is a number that can be inserted that is at an upper limit of the packaging size limit of the vector). As rAAV is a DNA virus, the nucleic acid molecules in the herein discussion concerning AAV or rAAV are advantageously DNA. The promoter is in some embodiments advantageously human Synapsin I promoter (hSyn).

Additional methods for the delivery of nucleic acids to cells are known to those skilled in the art. See, for example, US20030087817, incorporated herein by reference. See also the Kanasty reference, also incorporated by reference and discussed herein.

In some embodiments, a host cell is transiently or non-transiently transfected with one or more vectors described herein. In some embodiments, a cell is transfected as it naturally occurs in a subject. In some embodiments, a cell that is transfected is taken from a subject. In some embodiments, the cell is derived from cells taken from a subject, such as a cell line. A wide variety of cell lines for tissue culture are known in the art. Examples of cell lines include, but are not limited to, C8161, CCRF-CEM, MOLT, mIMCD-3, NHDF, HeLa-S3, Huh1, Huh4, Huh7, HUVEC, HASMC, HEKn, HEKa, MiaPaCell, Panc1, PC-3, TF1, CTLL-2, C1R, Rat6, CV1, RPTE, A10, T24, J82, A375, ARH-77, Calu1, SW480, SW620, SKOV3, SK-UT, CaCo2, P388D1, SEM-K2, WEHI-231, HB56, TIB55, Jurkat, J45.01, LRMB, Bcl-1, BC-3, IC21, DLD2, Raw264.7, NRK, NRK-52E, MRC5, MEF, Hep G2, HeLa B, HeLa T4, COS, COS-1, COS-6, COS-M6A, BS-C-1 monkey kidney epithelial, BALB/3T3 mouse embryo fibroblast, 3T3 Swiss, 3T3-L1, 132-d5 human fetal fibroblasts; 10.1 mouse fibroblasts, 293-T, 3T3, 721, 9L, A2780, A2780ADR, A2780cis, A172, A20, A253, A431, A-549, ALC, B16, B35, BCP-1 cells, BEAS-2B, bEnd.3, BHK-21, BR 293, BxPC3, C3H-10T1/2, C6/36, Cal-27, CHO, CHO-7, CHO-IR, CHO-K1, CHO-K2, CHO-T, CHO Dhfr −/−, COR-L23, COR-L23/CPR, COR-L23/5010, COR-L23/R23, COS-7, COV-434, CML T1, CMT, CT26, D17, DH82, DU145, DuCaP, EL4, EM2, EM3, EMT6/AR1, EMT6/AR10.0, FM3, H1299, H69, HB54, HB55, HCA2, HEK-293, HeLa, Hepa1c1c7, HL-60, HMEC, HT-29, Jurkat, JY cells, K562 cells, Ku812, KCL22, KG1, KYO1, LNCap, Ma-Mel 1-48, MC-38, MCF-7, MCF-10A, MDA-MB-231, MDA-MB-468, MDA-MB-435, MDCK II, MDCK II, MOR/0.2R, MONO-MAC 6, MTD-1A, MyEnd, NCI-H69/CPR, NCI-H69/LX10, NCI-H69/LX20, NCI-H69/LX4, NIH-3T3, NALM-1, NW-145, OPCN/OPCT cell lines, Peer, PNT-1A/PNT 2, RenCa, RIN-5F, RMA/RMAS, Saos-2 cells, Sf-9, SkBr3, T2, T-47D, T84, THP1 cell line, U373, U87, U937, VCaP, Vero cells, WM39, WT-49, X63, YAC-1, YAR, and transgenic varieties thereof. Cell lines are available from a variety of sources known to those with skill in the art (see, e.g., the American Type Culture Collection (ATCC) (Manassas, Va.)). In some embodiments, a cell transfected with one or more vectors described herein is used to establish a new cell line comprising one or more vector-derived sequences. In some embodiments, a cell transiently transfected with the components of a CRISPR system as described herein (such as by transient transfection of one or more vectors, or transfection with RNA), and modified through the activity of a CRISPR complex, is used to establish a new cell line comprising cells containing the modification but lacking any other exogenous sequence. In some embodiments, cells transiently or non-transiently transfected with one or more vectors described herein, or cell lines derived from such cells are used in assessing one or more test compounds.

In some embodiments, one or more vectors described herein are used to produce a non-human transgenic animal or transgenic plant. In some embodiments, the transgenic animal is a mammal, such as a mouse, rat, or rabbit. Methods for producing transgenic animals and plants are known in the art, and generally begin with a method of cell transfection, such as described herein.

In another embodiment, a fluid delivery device with an array of needles (see, e.g., US Patent Publication No. 20110230839 assigned to the Fred Hutchinson Cancer Research Center) may be contemplated for delivery of CRISPR Cas to solid tissue. A device of US Patent Publication No. 20110230839 for delivery of a fluid to a solid tissue may comprise a plurality of needles arranged in an array; a plurality of reservoirs, each in fluid communication with a respective one of the plurality of needles; and a plurality of actuators operatively coupled to respective ones of the plurality of reservoirs and configured to control a fluid pressure within the reservoir. In certain embodiments each of the plurality of actuators may comprise one of a plurality of plungers, a first end of each of the plurality of plungers being received in a respective one of the plurality of reservoirs, and in certain further embodiments the plungers of the plurality of plungers are operatively coupled together at respective second ends so as to be simultaneously depressable. Certain still further embodiments may comprise a plunger driver configured to depress all of the plurality of plungers at a selectively variable rate. In other embodiments each of the plurality of actuators may comprise one of a plurality of fluid transmission lines having first and second ends, a first end of each of the plurality of fluid transmission lines being coupled to a respective one of the plurality of reservoirs. In other embodiments the device may comprise a fluid pressure source, and each of the plurality of actuators comprises a fluid coupling between the fluid pressure source and a respective one of the plurality of reservoirs. In further embodiments the fluid pressure source may comprise at least one of a compressor, a vacuum accumulator, a peristaltic pump, a master cylinder, a microfluidic pump, and a valve. In another embodiment, each of the plurality of needles may comprise a plurality of ports distributed along its length.

Modifying a Target

In one aspect, the invention provides for methods of modifying a target polynucleotide in a eukaryotic cell, which may be in vivo, ex vivo or in vitro. In some embodiments, the method comprises sampling or biopsying a cell or population of cells from a human or non-human animal, and modifying the cell or cells. Culturing may occur at any stage ex vivo. The cell or cells may even be re-introduced into the non-human animal. For re-introduced cells it is particularly preferred that the cells are stem cells, although primary hepatocytes are also preferred.

In some embodiments, the method comprises allowing a CRISPR complex to bind to the target polynucleotide to effect cleavage of said target polynucleotide thereby modifying the target polynucleotide, wherein the CRISPR complex comprises a CRISPR enzyme complexed with a guide sequence hybridized or hybridizable to a target sequence within said target polynucleotide, wherein said guide sequence is linked to a tracr mate sequence which in turn hybridizes to a tracr sequence.

In one aspect, the invention provides a method of modifying expression of a polynucleotide in a eukaryotic cell. In some embodiments, the method comprises allowing a CRISPR complex to bind to the polynucleotide such that said binding results in increased or decreased expression of said polynucleotide; wherein the CRISPR complex comprises a CRISPR enzyme complexed with a guide sequence hybridized or hybridizable to a target sequence within said polynucleotide, wherein said guide sequence is linked to a tracr mate sequence which in turn hybridizes to a tracr sequence. Similar considerations and conditions apply as above for methods of modifying a target polynucleotide. In fact, these sampling, culturing and re-introduction options apply across the aspects of the present invention.

Indeed, in any aspect of the invention, the CRISPR complex may comprise a CRISPR enzyme complexed with a guide sequence hybridized or hybridizable to a target sequence, wherein said guide sequence may be linked to a tracr mate sequence which in turn may hybridize to a tracr sequence. Similar considerations and conditions apply as above for methods of modifying a target polynucleotide.

Kits

In one aspect, the invention provides kits containing any one or more of the elements disclosed in the above methods and compositions. Elements may be provided individually or in combinations, and may be provided in any suitable container, such as a vial, a bottle, or a tube. In some embodiments, the kit includes instructions in one or more languages, for example in more than one language.

In some embodiments, a kit comprises one or more reagents for use in a process utilizing one or more of the elements described herein. Reagents may be provided in any suitable container. For example, a kit may provide one or more reaction or storage buffers. Reagents may be provided in a form that is usable in a particular assay, or in a form that requires addition of one or more other components before use (e.g. in concentrate or lyophilized form). A buffer can be any buffer, including but not limited to a sodium carbonate buffer, a sodium bicarbonate buffer, a borate buffer, a Tris buffer, a MOPS buffer, a HEPES buffer, and combinations thereof. In some embodiments, the buffer is alkaline. In some embodiments, the buffer has a pH from about 7 to about 10. In some embodiments, the kit comprises one or more oligonucleotides corresponding to a guide sequence for insertion into a vector so as to operably link the guide sequence and a regulatory element. In some embodiments, the kit comprises a homologous recombination template polynucleotide. In some embodiments, the kit comprises one or more of the vectors and/or one or more of the polynucleotides described herein. The kit may advantageously allows to provide all elements of the systems of the invention.

CRISPR Complex

In one aspect, the invention provides methods for using one or more elements of a CRISPR system. The CRISPR complex of the invention provides an effective means for modifying a target polynucleotide. The CRISPR complex of the invention has a wide variety of utility including modifying (e.g., deleting, inserting, translocating, inactivating, activating) a target polynucleotide in a multiplicity of cell types. As such the CRISPR complex of the invention has a broad spectrum of applications in, e.g., gene therapy, drug screening, disease diagnosis, and prognosis. An exemplary CRISPR complex comprises a CRISPR enzyme complexed with a guide sequence hybridized or hybridizable to a target sequence within the target polynucleotide. The guide sequence is linked to a tracr mate sequence, which in turn hybridizes to a tracr sequence.

In one embodiment, this invention provides a method of cleaving a target polynucleotide. The method comprises modifying a target polynucleotide using a CRISPR complex that binds to the target polynucleotide and effect cleavage of said target polynucleotide. Typically, the CRISPR complex of the invention, when introduced into a cell, creates a break (e.g., a single or a double strand break) in the genome sequence. For example, the method can be used to cleave a disease gene in a cell.

Figure 29:
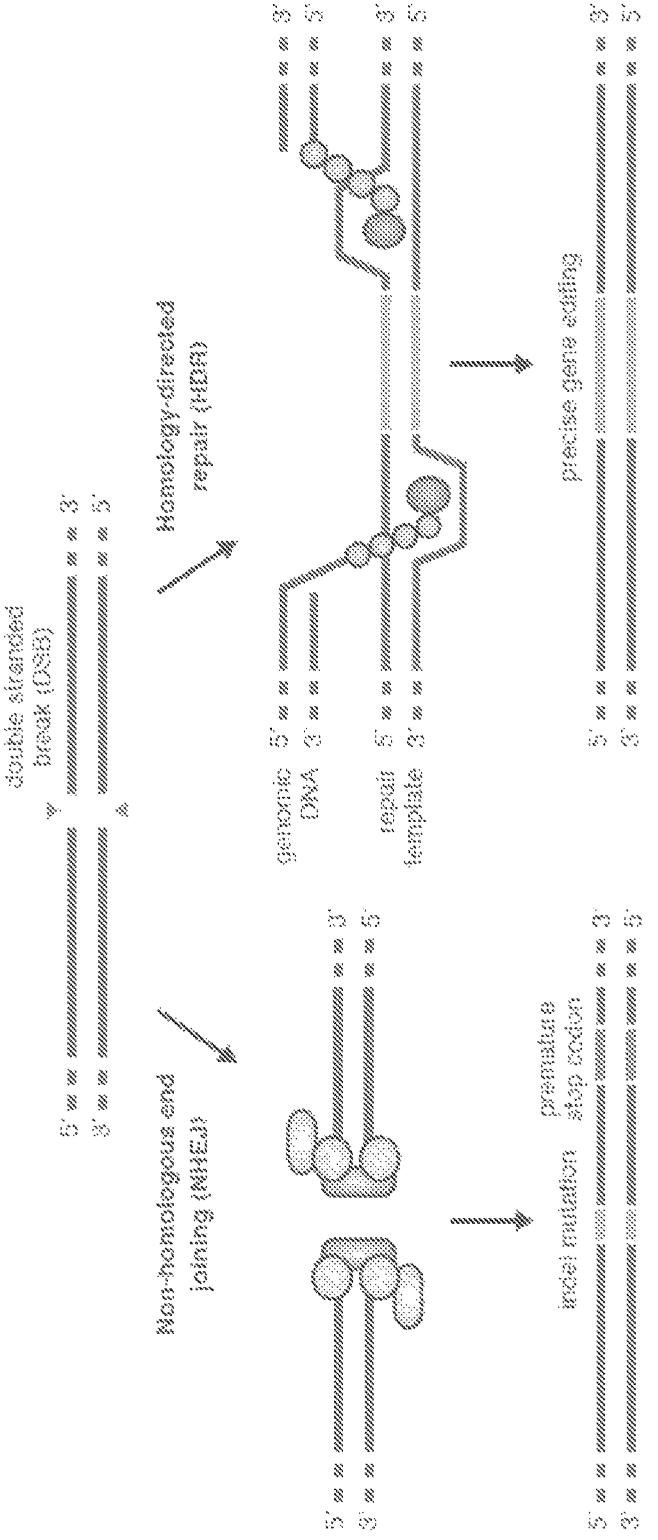
FIG. 29 shows how DNA double-strand break (DSB) repair promotes gene editing. In the error-prone non-homologous end joining (NHEJ) pathway, the ends of a DSB are processed by endogenous DNA repair machineries and rejoined together, which can result in random insertion/deletion (indel) mutations at the site of junction. Indel mutations occurring within the coding region of a gene can result in frame-shift and a premature stop codon, leading to gene knockout. Alternatively, a repair template in the form of a plasmid or single-stranded oligodeoxynucleotides (ssODN) can be supplied to leverage the homology-directed repair (HDR) pathway, which allows high fidelity and precise editing.

The break created by the CRISPR complex can be repaired by a repair processes such as the error prone non-homologous end joining (NHEJ) pathway or the high fidelity homology-directed repair (HDR) (FIG. 29). During these repair process, an exogenous polynucleotide template can be introduced into the genome sequence. In some methods, the HDR process is used modify genome sequence. For example, an exogenous polynucleotide template comprising a sequence to be integrated flanked by an upstream sequence and a downstream sequence is introduced into a cell. The upstream and downstream sequences share sequence similarity with either side of the site of integration in the chromosome.

Where desired, a donor polynucleotide can be DNA, e.g., a DNA plasmid, a bacterial artificial chromosome (BAC), a yeast artificial chromosome (YAC), a viral vector, a linear piece of DNA, a PCR fragment, a naked nucleic acid, or a nucleic acid complexed with a delivery vehicle such as a liposome or poloxamer.

The exogenous polynucleotide template comprises a sequence to be integrated (e.g., a mutated gene). The sequence for integration may be a sequence endogenous or exogenous to the cell. Examples of a sequence to be integrated include polynucleotides encoding a protein or a non-coding RNA (e.g., a microRNA). Thus, the sequence for integration may be operably linked to an appropriate control sequence or sequences. Alternatively, the sequence to be integrated may provide a regulatory function.

The upstream and downstream sequences in the exogenous polynucleotide template are selected to promote recombination between the chromosomal sequence of interest and the donor polynucleotide. The upstream sequence is a nucleic acid sequence that shares sequence similarity with the genome sequence upstream of the targeted site for integration. Similarly, the downstream sequence is a nucleic acid sequence that shares sequence similarity with the chromosomal sequence downstream of the targeted site of integration. The upstream and downstream sequences in the exogenous polynucleotide template can have 75%, 80%, 85%, 90%, 95%, or 100% sequence identity with the targeted genome sequence. Preferably, the upstream and downstream sequences in the exogenous polynucleotide template have about 95%, 96%, 97%, 98%, 99%, or 100% sequence identity with the targeted genome sequence. In some methods, the upstream and downstream sequences in the exogenous polynucleotide template have about 99% or 100% sequence identity with the targeted genome sequence.

An upstream or downstream sequence may comprise from about 20 bp to about 2500 bp, for example, about 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, or 2500 bp. In some methods, the exemplary upstream or downstream sequence have about 200 bp to about 2000 bp, about 600 bp to about 1000 bp, or more particularly about 700 bp to about 1000 bp.

In some methods, the exogenous polynucleotide template may further comprise a marker. Such a marker may make it easy to screen for targeted integrations. Examples of suitable markers include restriction sites, fluorescent proteins, or selectable markers. The exogenous polynucleotide template of the invention can be constructed using recombinant techniques (see, for example, Sambrook et al., 2001 and Ausubel et al., 1996).

In an exemplary method for modifying a target polynucleotide by integrating an exogenous polynucleotide template, a double stranded break is introduced into the genome sequence by the CRISPR complex, the break is repaired via homologous recombination by an exogenous polynucleotide template such that the template is integrated into the genome. The presence of a double-stranded break facilitates integration of the template.

In other embodiments, this invention provides a method of modifying expression of a polynucleotide in a eukaryotic cell. The method comprises increasing or decreasing expression of a target polynucleotide by using a CRISPR complex that binds to the polynucleotide.

In some methods, a target polynucleotide can be inactivated to effect the modification of the expression in a cell. For example, upon the binding of a CRISPR complex to a target sequence in a cell, the target polynucleotide is inactivated such that the sequence is not transcribed, the coded protein is not produced, or the sequence does not function as the wild-type sequence does. For example, a protein or microRNA coding sequence may be inactivated such that the protein is not produced.

In some methods, a control sequence can be inactivated such that it no longer functions as a control sequence. As used herein, "control sequence" refers to any nucleic acid sequence that effects the transcription, translation, or accessibility of a nucleic acid sequence. Examples of a control sequence include, a promoter, a transcription terminator, and an enhancer are control sequences.

The inactivated target sequence may include a deletion mutation (i.e., deletion of one or more nucleotides), an insertion mutation (i.e., insertion of one or more nucleotides), or a nonsense mutation (i.e., substitution of a single nucleotide for another nucleotide such that a stop codon is introduced). In some methods, the inactivation of a target sequence results in "knock-out" of the target sequence.

Disease Models

A method of the invention may be used to create an animal or cell that may be used as a disease model. As used herein, "disease" refers to a disease, disorder, or indication in a subject. For example, a method of the invention may be used to create an animal or cell that comprises a modification in one or more nucleic acid sequences associated with a disease, or a plant, animal or cell in which the expression of one or more nucleic acid sequences associated with a disease are altered. Such a nucleic acid sequence may encode a disease associated protein sequence or may be a disease associated control sequence. Accordingly, it is understood that in embodiments of the invention, a plant, subject, patient, organism or cell can be a non-human subject, patient, organism or cell. Thus, the invention provides an animal or cell, produced by the present methods, or a progeny thereof. The progeny may be a clone of the produced animal, or may result from sexual reproduction by crossing with other individuals of the same species to introgress further desirable traits into their offspring. The cell may be in vivo or ex vivo in the cases of multicellular organisms, particularly animals. In the instance where the cell is in cultured, a cell line may be established if appropriate culturing conditions are met and preferably if the cell is suitably adapted for this purpose (for instance a stem cell). Hence, cell lines are also envisaged.

In some methods, the disease model can be used to study the effects of mutations on the animal or cell and development and/or progression of the disease using measures commonly used in the study of the disease. Alternatively, such a disease model is useful for studying the effect of a pharmaceutically active compound on the disease.

In some methods, the disease model can be used to assess the efficacy of a potential gene therapy strategy. That is, a disease-associated gene or polynucleotide can be modified such that the disease development and/or progression is inhibited or reduced. In particular, the method comprises modifying a disease-associated gene or polynucleotide such that an altered protein is produced and, as a result, the animal or cell has an altered response. Accordingly, in some methods, a genetically modified animal may be compared with an animal predisposed to development of the disease such that the effect of the gene therapy event may be assessed.

In another embodiment, this invention provides a method of developing a biologically active agent that modulates a cell signaling event associated with a disease gene. The method comprises contacting a test compound with a cell comprising one or more vectors that drive expression of one or more of a CRISPR enzyme, a guide sequence linked to a tracr mate sequence, and a tracr sequence; and detecting a change in a readout that is indicative of a reduction or an augmentation of a cell signaling event associated with, e.g., a mutation in a disease gene contained in the cell.

A cell model, including an organoid or cell collection as described herein, or animal model can be constructed in combination with the method of the invention for screening a cellular function change. Such a model may be used to study the effects of a genome sequence modified by the CRISPR complex of the invention on a cellular function of interest. For example, a cellular function model may be used to study the effect of a modified genome sequence on intracellular signaling or extracellular signaling. Alternatively, a cellular function model may be used to study the effects of a modified genome sequence on sensory perception. In some such models, one or more genome sequences associated with a signaling biochemical pathway in the model are modified.

Several disease models have been specifically investigated. These include de novo autism risk genes CHD8, KATNAL2, and SCN2A; and the syndromic autism (Angelman Syndrome) gene UBE3A. These genes and resulting autism models are of course preferred, but serve to show the broad applicability of the invention across genes and corresponding models.

An altered expression of one or more genome sequences associated with a signaling biochemical pathway can be determined by assaying for a difference in the mRNA levels of the corresponding genes between the test model cell and a control cell, when they are contacted with a candidate agent. Alternatively, the differential expression of the sequences associated with a signaling biochemical pathway is determined by detecting a difference in the level of the encoded polypeptide or gene product.

To assay for an agent-induced alteration in the level of mRNA transcripts or corresponding polynucleotides, nucleic acid contained in a sample is first extracted according to standard methods in the art. For instance, mRNA can be isolated using various lytic enzymes or chemical solutions according to the procedures set forth in Sambrook et al. (1989), or extracted by nucleic-acid-binding resins following the accompanying instructions provided by the manufacturers. The mRNA contained in the extracted nucleic acid sample is then detected by amplification procedures or conventional hybridization assays (e.g. Northern blot analysis) according to methods widely known in the art or based on the methods exemplified herein.

For purpose of this invention, amplification means any method employing a primer and a polymerase capable of replicating a target sequence with reasonable fidelity. Amplification may be carried out by natural or recombinant DNA polymerases such as TaqGold™, T7 DNA polymerase, Klenow fragment of *E. coli* DNA polymerase, and reverse transcriptase. A preferred amplification method is PCR. In particular, the isolated RNA can be subjected to a reverse transcription assay that is coupled with a quantitative polymerase chain reaction (RT-PCR) in order to quantify the expression level of a sequence associated with a signaling biochemical pathway.

Detection of the gene expression level can be conducted in real time in an amplification assay. In one aspect, the amplified products can be directly visualized with fluorescent DNA-binding agents including but not limited to DNA intercalators and DNA groove binders. Because the amount of the intercalators incorporated into the double-stranded DNA molecules is typically proportional to the amount of the amplified DNA products, one can conveniently determine the amount of the amplified products by quantifying the fluorescence of the intercalated dye using conventional optical systems in the art. DNA-binding dye suitable for this application include SYBR green, SYBR blue, DAPI, propidium iodine, Hoeste, SYBR gold, ethidium bromide, acridines, proflavine, acridine orange, acriflavine, fluorcoumanin, ellipticine, daunomycin, chloroquine, distamycin D, chromomycin, homidium, mithramycin, ruthenium polypyridyls, anthramycin, and the like.

In another aspect, other fluorescent labels such as sequence specific probes can be employed in the amplification reaction to facilitate the detection and quantification of the amplified products. Probe-based quantitative amplification relies on the sequence-specific detection of a desired amplified product. It utilizes fluorescent, target-specific probes (e.g., TaqMan® probes) resulting in increased specificity and sensitivity. Methods for performing probe-based quantitative amplification are well established in the art and are taught in U.S. Pat. No. 5,210,015.

In yet another aspect, conventional hybridization assays using hybridization probes that share sequence homology with sequences associated with a signaling biochemical pathway can be performed. Typically, probes are allowed to form stable complexes with the sequences associated with a signaling biochemical pathway contained within the biological sample derived from the test subject in a hybridization reaction. It will be appreciated by one of skill in the art that where antisense is used as the probe nucleic acid, the target polynucleotides provided in the sample are chosen to be complementary to sequences of the antisense nucleic acids. Conversely, where the nucleotide probe is a sense nucleic acid, the target polynucleotide is selected to be complementary to sequences of the sense nucleic acid.

Hybridization can be performed under conditions of various stringency. Suitable hybridization conditions for the practice of the present invention are such that the recognition interaction between the probe and sequences associated with a signaling biochemical pathway is both sufficiently specific and sufficiently stable. Conditions that increase the stringency of a hybridization reaction are widely known and published in the art. See, for example, (Sambrook, et al., (1989); Nonradioactive In Situ Hybridization Application Manual, Boehringer Mannheim, second edition). The hybridization assay can be formed using probes immobilized on any solid support, including but are not limited to nitrocellulose, glass, silicon, and a variety of gene arrays. A preferred hybridization assay is conducted on high-density gene chips as described in U.S. Pat. No. 5,445,934.

For a convenient detection of the probe-target complexes formed during the hybridization assay, the nucleotide probes are conjugated to a detectable label. Detectable labels suitable for use in the present invention include any composition detectable by photochemical, biochemical, spectroscopic, immunochemical, electrical, optical or chemical means. A wide variety of appropriate detectable labels are known in the art, which include fluorescent or chemiluminescent labels, radioactive isotope labels, enzymatic or other ligands. In preferred embodiments, one will likely desire to employ a fluorescent label or an enzyme tag, such as digoxigenin, β-galactosidase, urease, alkaline phosphatase or peroxidase, avidin/biotin complex.

The detection methods used to detect or quantify the hybridization intensity will typically depend upon the label selected above. For example, radiolabels may be detected using photographic film or a phosphoimager. Fluorescent markers may be detected and quantified using a photodetector to detect emitted light. Enzymatic labels are typically detected by providing the enzyme with a substrate and measuring the reaction product produced by the action of the enzyme on the substrate; and finally colorimetric labels are detected by simply visualizing the colored label.

An agent-induced change in expression of sequences associated with a signaling biochemical pathway can also be determined by examining the corresponding gene products. Determining the protein level typically involves a) contacting the protein contained in a biological sample with an agent that specifically bind to a protein associated with a signaling biochemical pathway; and (b) identifying any agent:protein complex so formed. In one aspect of this embodiment, the agent that specifically binds a protein associated with a signaling biochemical pathway is an antibody, preferably a monoclonal antibody.

The reaction is performed by contacting the agent with a sample of the proteins associated with a signaling biochemical pathway derived from the test samples under conditions that will allow a complex to form between the agent and the proteins associated with a signaling biochemical pathway. The formation of the complex can be detected directly or indirectly according to standard procedures in the art. In the direct detection method, the agents are supplied with a detectable label and unreacted agents may be removed from the complex; the amount of remaining label thereby indicating the amount of complex formed. For such method, it is preferable to select labels that remain attached to the agents even during stringent washing conditions. It is preferable that the label does not interfere with the binding reaction. In the alternative, an indirect detection procedure may use an agent that contains a label introduced either chemically or enzymatically. A desirable label generally does not interfere with binding or the stability of the resulting agent:polypeptide complex. However, the label is typically designed to be accessible to an antibody for an effective binding and hence generating a detectable signal.

A wide variety of labels suitable for detecting protein levels are known in the art. Non-limiting examples include radioisotopes, enzymes, colloidal metals, fluorescent compounds, bioluminescent compounds, and chemiluminescent compounds.

The amount of agent:polypeptide complexes formed during the binding reaction can be quantified by standard quantitative assays. As illustrated above, the formation of agent:polypeptide complex can be measured directly by the amount of label remained at the site of binding. In an alternative, the protein associated with a signaling biochemical pathway is tested for its ability to compete with a labeled analog for binding sites on the specific agent. In this competitive assay, the amount of label captured is inversely proportional to the amount of protein sequences associated with a signaling biochemical pathway present in a test sample.

A number of techniques for protein analysis based on the general principles outlined above are available in the art. They include but are not limited to radioimmunoassays, ELISA (enzyme linked immunoradiometric assays), "sandwich" immunoassays, immunoradiometric assays, in situ immunoassays (using e.g., colloidal gold, enzyme or radioisotope labels), western blot analysis, immunoprecipitation assays, immunofluorescent assays, and SDS-PAGE.

Antibodies that specifically recognize or bind to proteins associated with a signaling biochemical pathway are preferable for conducting the aforementioned protein analyses. Where desired, antibodies that recognize a specific type of post-translational modifications (e.g., signaling biochemical pathway inducible modifications) can be used. Post-translational modifications include but are not limited to glycosylation, lipidation, acetylation, and phosphorylation. These antibodies may be purchased from commercial vendors. For example, anti-phosphotyrosine antibodies that specifically recognize tyrosine-phosphorylated proteins are available from a number of vendors including Invitrogen and Perkin Elmer. Anti-phosphotyrosine antibodies are particularly useful in detecting proteins that are differentially phosphorylated on their tyrosine residues in response to an ER stress. Such proteins include but are not limited to eukaryotic translation initiation factor 2 alpha (eIF-2α). Alternatively, these antibodies can be generated using conventional polyclonal or monoclonal antibody technologies by immunizing a host animal or an antibody-producing cell with a target protein that exhibits the desired post-translational modification.

In practicing the subject method, it may be desirable to discern the expression pattern of an protein associated with a signaling biochemical pathway in different bodily tissue, in different cell types, and/or in different subcellular structures. These studies can be performed with the use of tissue-specific, cell-specific or subcellular structure specific antibodies capable of binding to protein markers that are preferentially expressed in certain tissues, cell types, or subcellular structures.

An altered expression of a gene associated with a signaling biochemical pathway can also be determined by examining a change in activity of the gene product relative to a control cell. The assay for an agent-induced change in the activity of a protein associated with a signaling biochemical pathway will dependent on the biological activity and/or the signal transduction pathway that is under investigation. For example, where the protein is a kinase, a change in its ability to phosphorylate the downstream substrate(s) can be determined by a variety of assays known in the art. Representative assays include but are not limited to immunoblotting and immunoprecipitation with antibodies such as anti-phosphotyrosine antibodies that recognize phosphorylated proteins. In addition, kinase activity can be detected by high throughput chemiluminescent assays such as AlphaScreen™ (available from Perkin Elmer) and eTag™ assay (Chan-Hui, et al. (2003) Clinical Immunology 111: 162-174).

Where the protein associated with a signaling biochemical pathway is part of a signaling cascade leading to a fluctuation of intracellular pH condition, pH sensitive molecules such as fluorescent pH dyes can be used as the reporter molecules. In another example where the protein associated with a signaling biochemical pathway is an ion channel, fluctuations in membrane potential and/or intracellular ion concentration can be monitored. A number of commercial kits and high-throughput devices are particularly suited for a rapid and robust screening for modulators of ion channels. Representative instruments include FLIPR™ (Molecular Devices, Inc.) and VIPR (Aurora Biosciences). These instruments are capable of detecting reactions in over 1000 sample wells of a microplate simultaneously, and providing real-time measurement and functional data within a second or even a minisecond.

In practicing any of the methods disclosed herein, a suitable vector can be introduced to a cell or an embryo via one or more methods known in the art, including without limitation, microinjection, electroporation, sonoporation, biolistics, calcium phosphate-mediated transfection, cationic transfection, liposome transfection, dendrimer transfection, heat shock transfection, nucleofection transfection, magnetofection, lipofection, impalefection, optical transfection, proprietary agent-enhanced uptake of nucleic acids, and delivery via liposomes, immunoliposomes, virosomes, or artificial virions. In some methods, the vector is introduced into an embryo by microinjection. The vector or vectors may be microinjected into the nucleus or the cytoplasm of the embryo. In some methods, the vector or vectors may be introduced into a cell by nucleofection.

The target polynucleotide of a CRISPR complex can be any polynucleotide endogenous or exogenous to the eukaryotic cell. For example, the target polynucleotide can be a polynucleotide residing in the nucleus of the eukaryotic cell. The target polynucleotide can be a sequence coding a gene product (e.g., a protein) or a non-coding sequence (e.g., a regulatory polynucleotide or a junk DNA).

Examples of target polynucleotides include a sequence associated with a signaling biochemical pathway, e.g., a signaling biochemical pathway-associated gene or polynucleotide. Examples of target polynucleotides include a disease associated gene or polynucleotide. A "disease-associated" gene or polynucleotide refers to any gene or polynucleotide which is yielding transcription or translation products at an abnormal level or in an abnormal form in cells derived from a disease-affected tissues compared with tissues or cells of a non disease control. It may be a gene that becomes expressed at an abnormally high level; it may be a gene that becomes expressed at an abnormally low level, where the altered expression correlates with the occurrence and/or progression of the disease. A disease-associated gene also refers to a gene possessing mutation(s) or genetic variation that is directly responsible or is in linkage disequilibrium with a gene(s) that is responsible for the etiology of a disease. The transcribed or translated products may be known or unknown, and may be at a normal or abnormal level.

The target polynucleotide of a CRISPR complex can be any polynucleotide endogenous or exogenous to the eukaryotic cell. For example, the target polynucleotide can be a polynucleotide residing in the nucleus of the eukaryotic cell. The target polynucleotide can be a sequence coding a gene product (e.g., a protein) or a non-coding sequence (e.g., a regulatory polynucleotide or a junk DNA). Without wishing to be bound by theory, it is believed that the target sequence should be associated with a PAM (protospacer adjacent motif); that is, a short sequence recognized by the CRISPR complex. The precise sequence and length requirements for the PAM differ depending on the CRISPR enzyme used, but PAMs are typically 2-5 base pair sequences adjacent the protospacer (that is, the target sequence) Examples of PAM sequences are given in the examples section below, and the skilled person will be able to identify further PAM sequences for use with a given CRISPR enzyme.

The target polynucleotide of a CRISPR complex may include a number of disease-associated genes and polynucleotides as well as signaling biochemical pathway-associated genes and polynucleotides as listed in U.S. provisional patent applications 61/736,527 and 61/748,427 having Broad reference BI-2011/008/WSGR Docket No. 44063-701.101 and BI-2011/008/WSGR Docket No. 44063-701.102 respectively, both entitled SYSTEMS METHODS AND COMPOSITIONS FOR SEQUENCE MANIPULATION filed on Dec. 12, 2012 and Jan. 2, 2013, respectively, the contents of all of which are herein incorporated by reference in their entirety.

Examples of target polynucleotides include a sequence associated with a signaling biochemical pathway, e.g., a signaling biochemical pathway-associated gene or polynucleotide. Examples of target polynucleotides include a disease associated gene or polynucleotide. A "disease-associated" gene or polynucleotide refers to any gene or polynucleotide which is yielding transcription or translation products at an abnormal level or in an abnormal form in cells derived from a disease-affected tissues compared with tissues or cells of a non disease control. It may be a gene that becomes expressed at an abnormally high level; it may be a gene that becomes expressed at an abnormally low level, where the altered expression correlates with the occurrence and/or progression of the disease. A disease-associated gene also refers to a gene possessing mutation(s) or genetic variation that is directly responsible or is in linkage disequilibrium with a gene(s) that is responsible for the etiology of a disease. The transcribed or translated products may be known or unknown, and may be at a normal or abnormal level.

Examples of disease-associated genes and polynucleotides are listed in Tables A and B. Disease specific information is available from McKusick-Nathans Institute of Genetic Medicine, Johns Hopkins University (Baltimore, Md.) and National Center for Biotechnology Information, National Library of Medicine (Bethesda, Md.), available on the World Wide Web. Examples of signaling biochemical pathway-associated genes and polynucleotides are listed in Table C.

Mutations in these genes and pathways can result in production of improper proteins or proteins in improper amounts which affect function. Further examples of genes, diseases and proteins are hereby incorporated by reference from U.S. Provisional application 61/736,527 filed Dec. 12, 2012. Such genes, proteins and pathways may be the target polynucleotide of a CRISPR complex.

TABLE A

| DISEASE/ DISORDERS | GENE(S) |
|---|---|
| Neoplasia | PTEN; ATM; ATR; EGFR; ERBB2; ERBB3; ERBB4; Notch1; Notch2; Notch3; Notch4; AKT; AKT2; AKT3; HIF; HIF1a; HIF3a; Met; HRG; Bcl2; PPAR alpha; PPAR gamma; WT1 (Wilms Tumor); FGF Receptor Family members (5 members: 1, 2, 3, 4, 5); CDKN2a; APC; RB (retinoblastoma); MEN1; VHL; BRCA1; BRCA2; AR (Androgen Receptor); TSG101; IGF; IGF Receptor; Igf1 (4 variants); Igf2 (3 variants); Igf 1 Receptor; Igf 2 Receptor; Bax; Bcl2; caspases family (9 members: 1, 2, 3, 4, 6, 7, 8, 9, 12); Kras; Apc |
| Age-related Macular Degeneration | Aber; Ccl2; Cc2; cp (ceruloplasmin); Timp3; cathepsinD; Vldlr; Ccr2 |
| Schizo-phrenia | Neuregulin1 (Nrg1); Erb4 (receptor for Neuregulin); Complexin1 (Cplx1); Tph1 Tryptophan hydroxylase; Tph2 Tryptophan hydroxylase 2; Neurexin 1; GSK3; GSK3a; GSK3b |
| Disorders | 5-HTT (Slc6a4); COMT; DRD (Drd1a); SLC6A3; DAOA; DTNBP1; Dao (Dao1) |

TABLE A-continued

| DISEASE/ DISORDERS | GENE(S) |
|---|---|
| Trinucleotide Repeat Disorders | HTT (Huntington's Dx); SBMA/SMAX1/AR (Kennedy's Dx); FXN/X25 (Friedrich's Ataxia); ATX3 (Machado-Joseph's Dx); ATXN1 and ATXN2 (spinocerebellar ataxias); DMPK (myotonic dystrophy); Atrophin-1 and Atn1 (DRPLA Dx); CBP (Creb-BP-global instability); VLDLR (Alzheimer's); Atxn7; Atxn10 |
| Fragile X Syndrome | FMR2; FXR1; FXR2; mGLUR5 |
| Secretase Related Disorders | APH-1 (alpha and beta); Presenilin (Psen1); nicastrin (Ncstn); PEN-2 |
| Others | Nos1; Parp1; Nat1; Nat2 |
| Prion-related disorders | Prp |
| ALS | SOD1; ALS2; STEX; FUS; TARDBP; VEGF (VEGF-a; VEGF-b; VEGF-c) |
| Drug addiction | Prkce (alcohol); Drd2; Drd4; ABAT (alcohol); GRIA2; Grm5; Grin1; Htr1b; Grin2a; Drd3; Pdyn; Gria1 (alcohol) |
| Autism | Mecp2; BZRAP1; MDGA2; Sema5A; Neurexin 1; Fragile X (FMR2 (AFF2); FXR1; FXR2; Mglur5) |
| Alzheimer's Disease | E1; CHIP; UCH; UBB; Tau; LRP; PICALM; Clusterin; PS1; SORL1; CR1; Vldlr; Uba1; Uba3; CHIP28 (Aqp1, Aquaporin 1); Uchl1; Uchl3; APP |
| Inflammation | IL-10; IL-1 (IL-1a; IL-1b); IL-13; IL-17 (IL-17a (CTLA8); IL-17b; IL-17c; IL-17d; IL-17f); II-23; Cx3cr1; ptpn22; TNFa; NOD2/CARD15 for IBD; IL-6; IL-12 (IL-12a; IL-12b); CTLA4; Cx3cl1 |
| Parkinson's Disease | x-Synuclein; DJ-1; LRRK2; Parkin; PINK1 |

TABLE B

| | |
|---|---|
| Blood and coagulation diseases and disorders | Anemia (CDAN1, CDA1, RPS19, DBA, PKLR, PK1, NT5C3, UMPH1, PSN1, RHAG, RH50A, NRAMP2, SPTB, ALAS2, ANH1, ASB, ABCB7, ABC7, ASAT); Bare lymphocyte syndrome (TAPBP, TPSN, TAP2, ABCB3, PSF2, RING11, MHC2TA, C2TA, RFX5, RFXAP, RFX5), Bleeding disorders (TBXA2R, P2RX1, P2X1); Factor H and factor H-like 1 (HF1, CFH, HUS); Factor V and factor VIII (MCFD2); Factor VII deficiency (F7); Factor X deficiency (F10); Factor XI deficiency (F11); Factor XII deficiency (F12, HAF); Factor XIIIA deficiency (F13A1, F13A); Factor XIIIB deficiency (F13B); Fanconi anemia (FANCA, FACA, FA1, FA, FAA, FAAP95, FAAP90, FLJ34064, FANCB, FANCC, FACC, BRCA2, FANCD1, FANCD2, FANCD, FACD, FAD, FANCE, FACE, FANCF, XRCC9, FANCG, BRIP1, BACH1, FANCJ, PHF9, FANCL, FANCM, KIAA1596); Hemophagocytic lymphohistiocytosis disorders (PRF1, HPLH2, UNC13D, MUNC13-4, HPLH3, HLH3, FHL3); Hemophilia A (F8, F8C, HEMA); Hemophilia B (F9, HEMB), Hemorrhagic disorders (PI, ATT, F5); Leukocyde deficiencies and disorders (ITGB2, CD18, LCAMB, LAD, EIF2B1, EIF2BA, EIF2B2, EIF2B3, EIF2B5, LVWM, CACH, CLE, EIF2B4); Sickle cell anemia (HBB); Thalassemia (HBA2, HBB, HBD, LCRB, HBA1). |
| Cell dysregulation and oncology diseases and disorders | B-cell non-Hodgkin lymphoma (BCL7A, BCL7); Leukemia (TAL1, TCL5, SCL, TAL2, FLT3, NBS1, NBS, ZNFN1A1, IK1, LYF1, HOXD4, HOX4B, BCR, CML, PHL, ALL, ARNT, KRAS2, RASK2, GMPS, AF10, ARHGEF12, LARG, KIAA0382, CALM, CLTH, CEBPA, CEBP, CHIC2, BTL, FLT3, KIT, PBT, LPP, NPM1, NUP214, D9546E, CAN, CAIN, RUNX1, CBFA2, AML1, WHSC1L1, NSD3, FLT3, AF1Q, NPM1, NUMA1, ZNF145, PLZF, PML, MYL, STAT5B, AF10, CALM, CLTH, ARL11, ARLTS1, P2RX7, P2X7, BCR, CML, PHL, ALL, GRAF, NF1, VRNF, WSS, NFNS, PTPN11, PTP2C, SHP2, NS1, BCL2, CCND1, PRAD1, BCL1, TCRA, GATA1, GF1, ERYF1, NFE1, ABL1, NQO1, DIA4, NMOR1, NUP214, D9S46E, CAN, CAIN). |
| Inflammation and immune related diseases and disorders | AIDS (KIR3DL1, NKAT3, NKB1, AMB11, KIR3DS1, IFNG, CXCL12, SDF1); Autoimmune lymphoproliferative syndrome (TNFRSF6, APT1, FAS, CD95, ALPS1A); Combined immunodeficiency, (IL2RG, SCIDX1, SCIDX, IMD4); HIV-1 (CCL5, SCYA5, D17S136E, TCP228), HIV susceptibility or infection (IL10, CSIF, CMKBR2, CCR2, CMKBR5, CCCKR5 (CCR5)); Immunodeficiencies (CD3E, CD3G, AICDA, AID, HIGM2, TNFRSF5, CD40, UNG, DGU, HIGM4, TNFSF5, CD40LG, HIGM1, IGM, FOXP3, IPEX, AIID, XPID, PIDX, TNFRSF14B, TACI); Inflammation (IL-10, IL-1 (IL-1a, IL-1b), IL-13, IL-17 (IL-17a (CTLA8), IL-17b, IL-17c, IL-17d, IL-17f), II-23, Cx3cr1, |

TABLE B-continued

| | |
|---|---|
| | ptpn22, TNFa, NOD2/CARD15 for IBD, IL-6, IL-12 (IL-12a, IL-12b), CTLA4, Cx3cl1); Severe combined immunodeficiencies (SCIDs)(JAK3, JAKL, DCLRE1C, ARTEMIS, SCIDA, RAG1, RAG2, ADA, PTPRC, CD45, LCA, IL7R, CD3D, T3D, IL2RG, SCIDX1, SCIDX, IMD4). |
| Metabolic, liver, kidney and protein diseases and disorders | Amyloid neuropathy (TTR, PALB); Amyloidosis (APOA1, APP, AAA, CVAP, AD1, GSN, FGA, LYZ, TTR, PALB); Cirrhosis (KRT18, KRT8, CIRH1A, NAIC, TEX292, KIAA1988); Cystic fibrosis (CFTR, ABCC7, CF, MRP7); Glycogen storage diseases (SLC2A2, GLUT2, G6PC, G6PT, G6PT1, GAA, LAMP2, LAMPB, AGL, GDE, GBE1, GYS2, PYGL, PFKM); Hepatic adenoma, 142330 (TCF1, HNF1A, MODY3), Hepatic failure, early onset, and neurologic disorder (SCOD1, SCO1), Hepatic lipase deficiency (LIPC), Hepatoblastoma, cancer and carcinomas (CTNNB1, PDGFRL, PDGRL, PRLTS, AXIN1, AXIN, CTNNB1, TP53, P53, LFS1, IGF2R, MPRI, MET, CASP8, MCH5; Medullary cystic kidney disease (UMOD, HNFJ, FJHN, MCKD2, ADMCKD2); Phenylketonuria (PAH, PKU1, QDPR, DHPR, PTS); Polycystic kidney and hepatic disease (FCYT, PKHD1, ARPKD, PKD1, PKD2, PKD4, PKDTS, PRKCSH, G19P1, PCLD, SEC63). |

TABLE C

| CELLULAR FUNCTION | GENES |
|---|---|
| PI3K/AKT Signaling | PRKCE; ITGAM; ITGA5; IRAK1; PRKAA2; EIF2AK2; PTEN; EIF4E; PRKCZ; GRK6; MAPK1; TSC1; PLK1; AKT2; IKBKB; PIK3CA; CDK8; CDKN1B; NFKB2; BCL2; PIK3CB; PPP2R1A; MAPK8; BCL2L1; MAPK3; TSC2; ITGA1; KRAS; EIF4EBP1; RELA; PRKCD; NOS3; PRKAA1; MAPK9; CDK2; PPP2CA; PIM1; ITGB7; YWHAZ; ILK; TP53; RAF1; IKBKG; RELB; DYRK1A; CDKN1A; ITGB1; MAP2K2; JAK1; AKT1; JAK2; PIK3R1; CHUK; PDPK1; PPP2R5C; CTNNB1; MAP2K1; NFKB1; PAK3; ITGB3; CCND1; GSK3A; FRAP1; SFN; ITGA2; TTK; CSNK1A1; BRAF; GSK3B; AKT3; FOXO1; SGK; HSP90AA1; RPS6KB1 |
| ERK/MAPK Signaling | PRKCE; ITGAM; ITGA5; HSPB1; IRAK1; PRKAA2; EIF2AK2; RAC1; RAP1A; TLN1; EIF4E; ELK1; GRK6; MAPK1; RAC2; PLK1; AKT2; PIK3CA; CDK8; CREB1; PRKCI; PTK2; FOS; RPS6KA4; PIK3CB; PPP2R1A; PIK3C3; MAPK8; MAPK3; ITGA1; ETS1; KRAS; MYCN; EIF4EBP1; PPARG; PRKCD; PRKAA1; MAPK9; SRC; CDK2; PPP2CA; PIM1; PIK3C2A; ITGB7; YWHAZ; PPP1CC; KSR1; PXN; RAF1; FYN; DYRK1A; ITGB1; MAP2K2; PAK4; PIK3R1; STAT3; PPP2R5C; MAP2K1; PAK3; ITGB3; ESR1; ITGA2; MYC; TTK; CSNK1A1; CRKL; BRAF; ATF4; PRKCA; SRF; STAT1; SGK |
| Glucocorticoid Receptor Signaling | RAC1; TAF4B; EP300; SMAD2; TRAF6; PCAF; ELK1; MAPK1; SMAD3; AKT2; IKBKB; NCOR2; UBE2I; PIK3CA; CREB1; FOS; HSPA5; NFKB2; BCL2; MAP3K14; STAT5B; PIK3CB; PIK3C3; MAPK8; BCL2L1; MAPK3; T5C22D3; MAPK10; NRIP1; KRAS; MAPK13; RELA; STAT5A; MAPK9; NOS2A; PBX1; NR3C1; PIK3C2A; CDKN1C; TRAF2; SERPINE1; NCOA3; MAPK14; TNF; RAF1; IKBKG; MAP3K7; CREBBP; CDKN1A; MAP2K2; JAK1; IL8; NCOA2; AKT1; JAK2; PIK3R1; CHUK; STAT3; MAP2K1; NFKB1; TGFBR1; ESR1; SMAD4; CEBPB; JUN; AR; AKT3; CCL2; MMP1; STAT1; IL6; HSP90AA1 |
| Axonal Guidance Signaling | PRKCE; ITGAM; ROCK1; ITGA5; CXCR4; ADAM12; IGF1; RAC1; RAP1A; EIF4E; PRKCZ; NRP1; NTRK2; ARHGEF7; SMO; ROCK2; MAPK1; PGF; RAC2; PTPN11; GNAS; AKT2; PIK3CA; ERBB2; PRKCI; PTK2; CFL1; GNAQ; PIK3CB; CXCL12; PIK3C3; WNT11; PRKD1; GNB2L1; ABL1; MAPK3; ITGA1; KRAS; RHOA; PRKCD; PIK3C2A; ITGB7; GLI2; PXN; VASP; RAF1; FYN; ITGB1; MAP2K2; PAK4; ADAM17; AKT1; PIK3R1; GLI1; WNT5A; ADAM10; MAP2K1; PAK3; ITGB3; CDC42; VEGFA; ITGA2; EPHA8; CRKL; RND1; GSK3B; AKT3; PRKCA |
| Ephrin Receptor Signaling | PRKCE; ITGAM; ROCK1; ITGA5; CXCR4; IRAK1; PRKAA2; EIF2AK2; RAC1; RAP1A; GRK6; ROCK2; MAPK1; PGF; RAC2; PTPN11; GNAS; PLK1; AKT2; DOK1; CDK8; CREB1; PTK2; CFL1; GNAQ; MAP3K14; CXCL12; MAPK8; GNB2L1; ABL1; MAPK3; ITGA1; KRAS; RHOA; PRKCD; PRKAA1; MAPK9; SRC; CDK2; PIM1; ITGB7; PXN; RAF1; FYN; DYRK1A; ITGB1; |

TABLE C-continued

| CELLULAR FUNCTION | GENES |
|---|---|
| | MAP2K2; PAK4; AKT1; JAK2; STAT3; ADAM10; MAP2K1; PAK3; ITGB3; CDC42; VEGFA; ITGA2; EPHA8; TTK; CSNK1A1; CRKL; BRAF; PTPN13; ATF4; AKT3; SGK |
| Actin Cytoskeleton Signaling | ACTN4; PRKCE; ITGAM; ROCK1; ITGA5; IRAK1; PRKAA2; EIF2AK2; RAC1; INS; ARHGEF7; GRK6; ROCK2; MAPK1; RAC2; PLK1; AKT2; PIK3CA; CDK8; PTK2; CFL1; PIK3CB; MYH9; DIAPH1; PIK3C3; MAPK8; F2R; MAPK3; SLC9A1; ITGA1; KRAS; RHOA; PRKCD; PRKAA1; MAPK9; CDK2; PIM1; PIK3C2A; ITGB7; PPP1CC; PXN; VIL2; RAF1; GSN; DYRK1A; ITGB1; MAP2K2; PAK4; PIP5K1A; PIK3R1; MAP2K1; PAK3; ITGB3; CDC42; APC; ITGA2; TTK; CSNK1A1; CRKL; BRAF; VAV3; SGK |
| Huntington's Disease Signaling | PRKCE; IGF1; EP300; RCOR1; PRKCZ; HDAC4; TGM2; MAPK1; CAPNS1; AKT2; EGFR; NCOR2; SP1; CAPN2; PIK3CA; HDAC5; CREB1; PRKCI; HSPA5; REST; GNAQ; PIK3CB; PIK3C3; MAPK8; IGF1R; PRKD1; GNB2L1; BCL2L1; CAPN1; MAPK3; CASP8; HDAC2; HDAC7A; PRKCD; HDAC11; MAPK9; HDAC9; PIK3C2A; HDAC3; TP53; CASP9; CREBBP; AKT1; PIK3R1; PDPK1; CASP1; APAF1; FRAP1; CASP2; JUN; BAX; ATF4; AKT3; PRKCA; CLTC; SGK; HDAC6; CASP3 |
| Apoptosis Signaling | PRKCE; ROCK1; BID; IRAK1; PRKAA2; EIF2AK2; BAK1; BIRC4; GRK6; MAPK1; CAPNS1; PLK1; AKT2; IKBKB; CAPN2; CDK8; FAS; NFKB2; BCL2; MAP3K14; MAPK8; BCL2L1; CAPN1; MAPK3; CASP8; KRAS; RELA; PRKCD; PRKAA1; MAPK9; CDK2; PIM1; TP53; TNF; RAF1; IKBKG; RELB; CASP9; DYRK1A; MAP2K2; CHUK; APAF1; MAP2K1; NFKB1; PAK3; LMNA; CASP2; BIRC2; TTK; CSNK1A1; BRAF; BAX; PRKCA; SGK; CASP3; BIRC3; PARP1 |
| B Cell Receptor Signaling | RAC1; PTEN; LYN; ELK1; MAPK1; RAC2; PTPN11; AKT2; IKBKB; PIK3CA; CREB1; SYK; NFKB2; CAMK2A; MAP3K14; PIK3CB; PIK3C3; MAPK8; BCL2L1; ABL1; MAPK3; ETS1; KRAS; MAPK13; RELA; PTPN6; MAPK9; EGR1; PIK3C2A; BTK; MAPK14; RAF1; IKBKG; RELB; MAP3K7; MAP2K2; AKT1; PIK3R1; CHUK; MAP2K1; NFKB1; CDC42; GSK3A; FRAP1; BCL6; BCL10; JUN; GSK3B; ATF4; AKT3; VAV3; RPS6KB1 |
| Leukocyte Extravasation Signaling | ACTN4; CD44; PRKCE; ITGAM; ROCK1; CXCR4; CYBA; RAC1; RAP1A; PRKCZ; ROCK2; RAC2; PTPN11; MNIP14; PIK3CA; PRKCI; PTK2; PIK3CB; CXCL12; PIK3C3; MAPK8; PRKD1; ABL1; MAPK10; CYBB; MAPK13; RHOA; PRKCD; MAPK9; SRC; PIK3C2A; BTK; MAPK14; NOX1; PXN; VIL2; VASP; ITGB1; MAP2K2; CTNND1; PIK3R1; CTNNB1; CLDN1; CDC42; F11R; ITK; CRKL; VAV3; CTTN; PRKCA; MMP1; MMP9 |
| Integrin Signaling | ACTN4; ITGAM; ROCK1; ITGA5; RAC1; PTEN; RAP1A; TLN1; ARHGEF7; MAPK1; RAC2; CAPNS1; AKT2; CAPN2; PIK3CA; PTK2; PIK3CB; PIK3C3; MAPK8; CAV1; CAPN1; ABL1; MAPK3; ITGA1; KRAS; RHOA; SRC; PIK3C2A; ITGB7; PPP1CC; ILK; PXN; VASP; RAF1; FYN; ITGB1; MAP2K2; PAK4; AKT1; PIK3R1; TNK2; MAP2K1; PAK3; ITGB3; CDC42; RND3; ITGA2; CRKL; BRAF; GSK3B; AKT3 |
| Acute Phase Response Signaling | IRAK1; SOD2; MYD88; TRAF6; ELK1; MAPK1; PTPN11; AKT2; IKBKB; PIK3CA; FOS; NFKB2; MAP3K14; PIK3CB; MAPK8; RIPK1; MAPK3; IL6ST; KRAS; MAPK13; IL6R; RELA; SOCS1; MAPK9; FTL; NR3C1; TRAF2; SERPINE1; MAPK14; TNF; RAF1; PDK1; IKBKG; RELB; MAP3K7; MAP2K2; AKT1; JAK2; PIK3R1; CHUK; STAT3; MAP2K1; NFKB1; FRAP1; CEBPB; JUN; AKT3; IL1R1; IL6 |
| PTEN Signaling | ITGAM; ITGA5; RAC1; PTEN; PRKCZ; BCL2L11; MAPK1; RAC2; AKT2; EGFR; IKBKB; CBL; PIK3CA; CDKN1B; PTK2; NFKB2; BCL2; PIK3CB; BCL2L1; MAPK3; ITGA1; KRAS; ITGB7; ILK; PDGFRB; INSR; RAF1; IKBKG; CASP9; CDKN1A; ITGB1; MAP2K2; AKT1; PIK3R1; CHUK; PDGFRA; PDPK1; MAP2K1; NFKB1; ITGB3; CDC42; CCND1; GSK3A; ITGA2; GSK3B; AKT3; FOXO1; CASP3; RPS6KB1 |
| p53 Signaling | PTEN; EP300; BBC3; PCAF; FASN; BRCA1; GADD45A; BIRC5; AKT2; PIK3CA; CHEK1; TP53INP1; BCL2; PIK3CB; PIK3C3; MAPK8; THBS1; ATR; BCL2L1; E2F1; PMAIP1; CHEK2; TNFRSF10B; TP73; RB1; HDAC9; CDK2; PIK3C2A; MAPK14; TP53; LRDD; CDKN1A; |

TABLE C-continued

| CELLULAR FUNCTION | GENES |
|---|---|
| | HIPK2; AKT1; PIK3R1; RRM2B; APAF1; CTNNB1; SIRT1; CCND1; PRKDC; ATM; SFN; CDKN2A; JUN; SNAI2; GSK3B; BAX; AKT3 |
| Aryl Hydrocarbon Receptor Signaling | HSPB1; EP300; FASN; TGM2; RXRA; MAPK1; NQO1; NCOR2; SP1; ARNT; CDKN1B; FOS; CHEK1; SMARCA4; NFKB2; MAPK8; ALDH1A1; ATR; E2F1; MAPK3; NRIP1; CHEK2; RELA; TP73; GSTP1; RB1; SRC; CDK2; AHR; NFE2L2; NCOA3; TP53; TNF; CDKN1A; NCOA2; APAF1; NFKB1; CCND1; ATM; ESR1; CDKN2A; MYC; JUN; ESR2; BAX; IL6; CYP1B1; HSP90AA1 |
| Xenobiotic Metabolism Signaling | PRKCE; EP300; PRKCZ; RXRA; MAPK1; NQO1; NCOR2; PIK3CA; ARNT; PRKCI; NFKB2; CAMK2A; PIK3CB; PPP2R1A; PIK3C3; MAPK8; PRKD1; ALDH1A1; MAPK3; NRIP1; KRAS; MAPK13; PRKCD; GSTP1; MAPK9; NOS2A; ABCB1; AHR; PPP2CA; FTL; NFE2L2; PIK3C2A; PPARGC1A; MAPK14; TNF; RAF1; CREBBP; MAP2K2; PIK3R1; PPP2R5C; MAP2K1; NFKB1; KEAP1; PRKCA; EIF2AK3; IL6; CYP1B1; HSP90AA1 |
| SAPK/JNK Signaling | PRKCE; IRAK1; PRKAA2; EIF2AK2; RAC1; ELK1; GRK6; MAPK1; GADD45A; RAC2; PLK1; AKT2; PIK3CA; FADD; CDK8; PIK3CB; PIK3C3; MAPK8; RIPK1; GNB2L1; IRS1; MAPK3; MAPK10; DAXX; KRAS; PRKCD; PRKAA1; MAPK9; CDK2; PIM1; PIK3C2A; TRAF2; TP53; LCK; MAP3K7; DYRK1A; MAP2K2; PIK3R1; MAP2K1; PAK3; CDC42; JUN; TTK; CSNK1A1; CRKL; BRAF; SGK |
| PPAr/RXR Signaling | PRKAA2; EP300; INS; SMAD2; TRAF6; PPARA; FASN; RXRA; MAPK1; SMAD3; GNAS; IKBKB; NCOR2; ABCA1; GNAQ; NFKB2; MAP3K14; STAT5B; MAPK8; IRS1; MAPK3; KRAS; RELA; PRKAA1; PPARGC1A; NCOA3; MAPK14; INSR; RAF1; IKBKG; RELB; MAP3K7; CREBBP; MAP2K2; JAK2; CHUK; MAP2K1; NFKB1; TGFBR1; SMAD4; JUN; IL1R1; PRKCA; IL6; HSP90AA1; ADIPOQ |
| NF-KB Signaling | IRAK1; EIF2AK2; EP300; INS; MYD88; PRKCZ; TRAF6; TBK1; AKT2; EGFR; IKBKB; PIK3CA; BTRC; NFKB2; MAP3K14; PIK3CB; PIK3C3; MAPK8; RIPK1; HDAC2; KRAS; RELA; PIK3C2A; TRAF2; TLR4; PDGFRB; TNF; INSR; LCK; IKBKG; RELB; MAP3K7; CREBBP; AKT1; PIK3R1; CHUK; PDGFRA; NFKB1; TLR2; BCL10; GSK3B; AKT3; TNFAIP3; IL1R1 |
| Neuregulin Signaling | ERBB4; PRKCE; ITGAM; ITGA5; PTEN; PRKCZ; ELK1; MAPK1; PTPN11; AKT2; EGFR; ERBB2; PRKCI; CDKN1B; STAT5B; PRKD1; MAPK3; ITGA1; KRAS; PRKCD; STAT5A; SRC; ITGB7; RAF1; ITGB1; MAP2K2; ADAM17; AKT1; PIK3R1; PDPK1; MAP2K1; ITGB3; EREG; FRAP1; PSEN1; ITGA2; MYC; NRG1; CRKL; AKT3; PRKCA; HSP90AA1; RPS6KB1 |
| Wnt & Beta catenin Signaling | CD44; EP300; LRP6; DVL3; CSNK1E; GJA1; SMO; AKT2; PIN1; CDH1; BTRC; GNAQ; MARK2; PPP2R1A; WNT11; SRC; DKK1; PPP2CA; SOX6; SFRP2; ILK; LEF1; SOX9; TP53; MAP3K7; CREBBP; TCF7L2; AKT1; PPP2R5C; WNT5A; LRP5; CTNNB1; TGFBR1; CCND1; GSK3A; DVL1; APC; CDKN2A; MYC; CSNK1A1; GSK3B; AKT3; SOX2 |
| Insulin Receptor Signaling | PTEN; INS; EIF4E; PTPN1; PRKCZ; MAPK1; TSC1; PTPN11; AKT2; CBL; PIK3CA; PRKCI; PIK3CB; PIK3C3; MAPK8; IRS1; MAPK3; TSC2; KRAS; EIF4EBP1; SLC2A4; PIK3C2A; PPP1CC; INSR; RAF1; FYN; MAP2K2; JAK1; AKT1; JAK2; PIK3R1; PDPK1; MAP2K1; GSK3A; FRAP1; CRKL; GSK3B; AKT3; FOXO1; SGK; RPS6KB1 |
| IL-6 Signaling | HSPB1; TRAF6; MAPKAPK2; ELK1; MAPK1; PTPN11; IKBKB; FOS; NFKB2; MAP3K14; MAPK8; MAPK3; MAPK10; IL6ST; KRAS; MAPK13; IL6R; RELA; SOCS1; MAPK9; ABCB1; TRAF2; MAPK14; TNF; RAF1; IKBKG; RELB; MAP3K7; MAP2K2; IL8; JAK2; CHUK; STAT3; MAP2K1; NFKB1; CEBPB; JUN; IL1R1; SRF; IL6 |
| Hepatic Cholestasis | PRKCE; IRAK1; INS; MYD88; PRKCZ; TRAF6; PPARA; RXRA; IKBKB; PRKCI; NFKB2; MAP3K14; MAPK8; PRKD1; MAPK10; RELA; PRKCD; MAPK9; ABCB1; TRAF2; TLR4; TNF; INSR; IKBKG; RELB; MAP3K7; IL8; CHUK; NR1H2; TJP2; NFKB1; ESR1; SREBF1; FGFR4; JUN; IL1R1; PRKCA; IL6 |

TABLE C-continued

| CELLULAR FUNCTION | GENES |
|---|---|
| IGF-1 Signaling | IGF1; PRKCZ; ELK1; MAPK1; PTPN11; NEDD4; AKT2; PIK3CA; PRKCI; PTK2; FOS; PIK3CB; PIK3C3; MAPK8; IGF1R; IRS1; MAPK3; IGFBP7; KRAS; PIK3C2A; YWHAZ; PXN; RAF1; CASP9; MAP2K2; AKT1; PIK3R1; PDPK1; MAP2K1; IGFBP2; SFN; JUN; CYR61; AKT3; FOXO1; SRF; CTGF; RPS6KB1 |
| NRF2-mediated Oxidative Stress Response | PRKCE; EP300; SOD2; PRKCZ; MAPK1; SQSTM1; NQO1; PIK3CA; PRKCI; FOS; PIK3CB; PIK3C3; MAPK8; PRKD1; MAPK3; KRAS; PRKCD; GSTP1; MAPK9; FTL; NFE2L2; PIK3C2A; MAPK14; RAF1; MAP3K7; CREBBP; MAP2K2; AKT1; PIK3R1; MAP2K1; PPIB; JUN; KEAP1; GSK3B; ATF4; PRKCA; EIF2AK3; HSP90AA1 |
| Hepatic Fibrosis/Hepatic Stellate Cell Activation | EDN1; IGF1; KDR; FLT1; SMAD2; FGFR1; MET; PGF; SMAD3; EGFR; FAS; CSF1; NFKB2; BCL2; MYH9; IGF1R; IL6R; RELA; TLR4; PDGFRB; TNF; RELB; IL8; PDGFRA; NFKB1; TGFBR1; SMAD4; VEGFA; BAX; IL1R1; CCL2; HGF; MMP1; STAT1; IL6; CTGF; MIMP9 |
| PPAR Signaling | EP300; INS; TRAF6; PPARA; RXRA; MAPK1; IKBKB; NCOR2; FOS; NFKB2; MAP3K14; STAT5B; MAPK3; NRIP1; KRAS; PPARG; RELA; STAT5A; TRAF2; PPARGC1A; PDGFRB; TNF; INSR; RAF1; IKBKG; RELB; MAP3K7; CREBBP; MAP2K2; CHUK; PDGFRA; MAP2K1; NFKB1; JUN; IL1R1; HSP90AA1 |
| Fc Epsilon RI Signaling | PRKCE; RAC1; PRKCZ; LYN; MAPK1; RAC2; PTPN11; AKT2; PIK3CA; SYK; PRKCI; PIK3CB; PIK3C3; MAPK8; PRKD1; MAPK3; MAPK10; KRAS; MAPK13; PRKCD; MAPK9; PIK3C2A; BTK; MAPK14; TNF; RAF1; FYN; MAP2K2; AKT1; PIK3R1; PDPK1; MAP2K1; AKT3; VAV3; PRKCA |
| G-Protein Coupled Receptor Signaling | PRKCE; RAP1A; RGS16; MAPK1; GNAS; AKT2; IKBKB; PIK3CA; CREB1; GNAQ; NFKB2; CAMK2A; PIK3CB; PIK3C3; MAPK3; KRAS; RELA; SRC; PIK3C2A; RAF1; IKBKG; RELB; FYN; MAP2K2; AKT1; PIK3R1; CHUK; PDPK1; STAT3; MAP2K1; NFKB1; BRAF; ATF4; AKT3; PRKCA |
| Inositol Phosphate Metabolism | PRKCE; IRAK1; PRKAA2; EIF2AK2; PTEN; GRK6; MAPK1; PLK1; AKT2; PIK3CA; CDK8; PIK3CB; PIK3C3; MAPK8; MAPK3; PRKCD; PRKAA1; MAPK9; CDK2; PIM1; PIK3C2A; DYRK1A; MAP2K2; PIP5K1A; PIK3R1; MAP2K1; PAK3; ATM; TTK; CSNK1A1; BRAF; SGK |
| PDGF Signaling | EIF2AK2; ELK1; ABL2; MAPK1; PIK3CA; FOS; PIK3CB; PIK3C3; MAPK8; CAV1; ABL1; MAPK3; KRAS; SRC; PIK3C2A; PDGFRB; RAF1; MAP2K2; JAK1; JAK2; PIK3R1; PDGFRA; STAT3; SPHK1; MAP2K1; MYC; JUN; CRKL; PRKCA; SRF; STAT1; SPHK2 |
| VEGF Signaling | ACTN4; ROCK1; KDR; FLT1; ROCK2; MAPK1; PGF; AKT2; PIK3CA; ARNT; PTK2; BCL2; PIK3CB; PIK3C3; BCL2L1; MAPK3; KRAS; HIF1A; NOS3; PIK3C2A; PXN; RAF1; MAP2K2; ELAVL1; AKT1; PIK3R1; MAP2K1; SFN; VEGFA; AKT3; FOXO1; PRKCA |
| Natural Killer Cell Signaling | PRKCE; RAC1; PRKCZ; MAPK1; RAC2; PTPN11; KIR2DL3; AKT2; PIK3CA; SYK; PRKCI; PIK3CB; PIK3C3; PRKD1; MAPK3; KRAS; PRKCD; PTPN6; PIK3C2A; LCK; RAF1; FYN; MAP2K2; PAK4; AKT1; PIK3R1; MAP2K1; PAK3; AKT3; VAV3; PRKCA |
| Cell Cycle: G1/S Checkpoint Regulation | HDAC4; SMAD3; SUV39H1; HDAC5; CDKN1B; BTRC; ATR; ABL1; E2F1; HDAC2; HDAC7A; RB1; HDAC11; HDAC9; CDK2; E2F2; HDAC3; TP53; CDKN1A; CCND1; E2F4; ATM; RBL2; SMAD4; CDKN2A; MYC; NRG1; GSK3B; RBL1; HDAC6 |
| T Cell Receptor Signaling | RAC1; ELK1; MAPK1; IKBKB; CBL; PIK3CA; FOS; NFKB2; PIK3CB; PIK3C3; MAPK8; MAPK3; KRAS; RELA; PIK3C2A; BTK; LCK; RAF1; IKBKG; RELB; FYN; MAP2K2; PIK3R1; CHUK; MAP2K1; NFKB1; ITK; BCL10; JUN; VAV3 |
| Death Receptor Signaling | CRADD; HSPB1; BID; BIRC4; TBK1; IKBKB; FADD; FAS; NFKB2; BCL2; MAP3K14; MAPK8; RIPK1; CASP8; DAXX; TNFRSF10B; RELA; TRAF2; TNF; IKBKG; RELB; CASP9; CHUK; APAF1; NFKB1; CASP2; BIRC2; CASP3; BIRC3 |
| FGF Signaling | RAC1; FGFR1; MET; MAPKAPK2; MAPK1; PTPN11; AKT2; PIK3CA; CREB1; PIK3CB; PIK3C3; MAPK8; MAPK3; MAPK13; PTPN6; PIK3C2A; MAPK14; RAF1; AKT1; PIK3R1; STAT3; MAP2K1; FGFR4; CRKL; ATF4; AKT3; PRKCA; HGF |

TABLE C-continued

| CELLULAR FUNCTION | GENES |
|---|---|
| GM-CSF Signaling | LYN; ELK1; MAPK1; PTPN11; AKT2; PIK3CA; CAMK2A; STAT5B; PIK3CB; PIK3C3; GNB2L1; BCL2L1; MAPK3; ETS1; KRAS; RUNX1; PIM1; PIK3C2A; RAF1; MAP2K2; AKT1; JAK2; PIK3R1; STAT3; MAP2K1; CCND1; AKT3; STAT1 |
| Amyotrophic Lateral Sclerosis Signaling | BID; IGF1; RAC1; BIRC4; PGF; CAPNS1; CAPN2; PIK3CA; BCL2; PIK3CB; PIK3C3; BCL2L1; CAPN1; PIK3C2A; TP53; CASP9; PIK3R1; RAB5A; CASP1; APAF1; VEGFA; BIRC2; BAX; AKT3; CASP3; BIRC3 |
| JAK/Stat Signaling | PTPN1; MAPK1; PTPN11; AKT2; PIK3CA; STAT5B; PIK3CB; PIK3C3; MAPK3; KRAS; SOCS1; STAT5A; PTPN6; PIK3C2A; RAF1; CDKN1A; MAP2K2; JAK1; AKT1; JAK2; PIK3R1; STAT3; MAP2K1; FRAP1; AKT3; STAT1 |
| Nicotinate and Nicotinamide Metabolism | PRKCE; IRAK1; PRKAA2; EIF2AK2; GRK6; MAPK1; PLK1; AKT2; CDK8; MAPK8; MAPK3; PRKCD; PRKAA1; PBEF1; MAPK9; CDK2; PIM1; DYRK1A; MAP2K2; MAP2K1; PAK3; NT5E; TTK; CSNK1A1; BRAF; SGK |
| Chemokine Signaling | CXCR4; ROCK2; MAPK1; PTK2; FOS; CFL1; GNAQ; CAMK2A; CXCL12; MAPK8; MAPK3; KRAS; MAPK13; RHOA; CCR3; SRC; PPP1CC; MAPK14; NOX1; RAF1; MAP2K2; MAP2K1; JUN; CCL2; PRKCA |
| IL-2 Signaling | ELK1; MAPK1; PTPN11; AKT2; PIK3CA; SYK; FOS; STAT5B; PIK3CB; PIK3C3; MAPK8; MAPK3; KRAS; SOCS1; STAT5A; PIK3C2A; LCK; RAF1; MAP2K2; JAK1; AKT1; PIK3R1; MAP2K1; JUN; AKT3 |
| Synaptic Long Term Depression | PRKCE; IGF1; PRKCZ; PRDX6; LYN; MAPK1; GNAS; PRKCI; GNAQ; PPP2R1A; IGF1R; PRKD1; MAPK3; KRAS; GRN; PRKCD; NOS3; NOS2A; PPP2CA; YWHAZ; RAF1; MAP2K2; PPP2R5C; MAP2K1; PRKCA |
| Estrogen Receptor Signaling | TAF4B; EP300; CARM1; PCAF; MAPK1; NCOR2; SMARCA4; MAPK3; NRIP1; KRAS; SRC; NR3C1; HDAC3; PPARGC1A; RBM9; NCOA3; RAF1; CREBBP; MAP2K2; NCOA2; MAP2K1; PRKDC; ESR1; ESR2 |
| Protein Ubiquitination Pathway | TRAF6; SMURF1; BIRC4; BRCA1; UCHL1; NEDD4; CBL; UBE2I; BTRC; HSPA5; USP7; USP10; FBW7; USP9X; STUB1; USP22; B2M; BIRC2; PARK2; USP8; USP1; VHL; HSP90AA1; BIRC3 |
| IL-10 Signaling | TRAF6; CCR1; ELK1; IKBKB; SP1; FOS; NFKB2; MAP3K14; MAPK8; MAPK13; RELA; MAPK14; TNF; IKBKG; RELB; MAP3K7; JAK1; CHUK; STAT3; NFKB1; JUN; IL1R1; IL6 |
| VDR/RXR Activation | PRKCE; EP300; PRKCZ; RXRA; GADD45A; HES1; NCOR2; SP1; PRKCI; CDKN1B; PRKD1; PRKCD; RUNX2; KLF4; YY1; NCOA3; CDKN1A; NCOA2; SPP1; LRP5; CEBPB; FOXO1; PRKCA |
| TGF-beta Signaling | EP300; SMAD2; SMURF1; MAPK1; SMAD3; SMAD1; FOS; MAPK8; MAPK3; KRAS; MAPK9; RUNX2; SERPINE1; RAF1; MAP3K7; CREBBP; MAP2K2; MAP2K1; TGFBR1; SMAD4; JUN; SMAD5 |
| Toll-like Receptor Signaling | IRAK1; EIF2AK2; MYD88; TRAF6; PPARA; ELK1; IKBKB; FOS; NFKB2; MAP3K14; MAPK8; MAPK13; RELA; TLR4; MAPK14; IKBKG; RELB; MAP3K7; CHUK; NFKB1; TLR2; JUN |
| p38 MAPK Signaling | HSPB1; IRAK1; TRAF6; MAPKAPK2; ELK1; FADD; FAS; CREB1; DDIT3; RPS6KA4; DAXX; MAPK13; TRAF2; MAPK14; TNF; MAP3K7; TGFBR1; MYC; ATF4; IL1R1; SRF; STAT1 |
| Neurotrophin/TRK Signaling | NTRK2; MAPK1; PTPN11; PIK3CA; CREB1; FOS; PIK3CB; PIK3C3; MAPK8; MAPK3; KRAS; PIK3C2A; RAF1; MAP2K2; AKT1; PIK3R1; PDPK1; MAP2K1; CDC42; JUN; ATF4 |
| FXR/RXR Activation | INS; PPARA; FASN; RXRA; AKT2; SDC1; MAPK8; APOB; MAPK10; PPARG; MTTP; MAPK9; PPARGC1A; TNF; CREBBP; AKT1; SREBF1; FGFR4; AKT3; FOXO1 |
| Synaptic Long Term Potentiation | PRKCE; RAP1A; EP300; PRKCZ; MAPK1; CREB1; PRKCI; GNAQ; CAMK2A; PRKD1; MAPK3; KRAS; PRKCD; PPP1CC; RAF1; CREBBP; MAP2K2; MAP2K1; ATF4; PRKCA |
| Calcium Signaling | RAP1A; EP300; HDAC4; MAPK1; HDAC5; CREB1; CAMK2A; MYH9; MAPK3; HDAC2; HDAC7A; HDAC11; HDAC9; HDAC3; CREBBP; CALR; CAMKK2; ATF4; HDAC6 |
| EGF Signaling | ELK1; MAPK1; EGFR; PIK3CA; FOS; PIK3CB; PIK3C3; MAPK8; MAPK3; PIK3C2A; RAF1; JAK1; PIK3R1; STAT3; MAP2K1; JUN; PRKCA; SRF; STAT1 |

TABLE C-continued

| CELLULAR FUNCTION | GENES |
|---|---|
| Hypoxia Signaling in the Cardiovascular System | EDN1; PTEN; EP300; NQO1; UBE2I; CREB1; ARNT; HIF1A; SLC2A4; NOS3; TP53; LDHA; AKT1; ATM; VEGFA; JUN; ATF4; VHL; HSP90AA1 |
| LPS/IL-1 Mediated Inhibition of RXR Function | IRAK1; MYD88; TRAF6; PPARA; RXRA; ABCA1; MAPK8; ALDH1A1; GSTP1; MAPK9; ABCB1; TRAF2; TLR4; TNF; MAP3K7; NR1H2; SREBF1; JUN; IL1R1 |
| LXR/RXR Activation | FASN; RXRA; NCOR2; ABCA1; NFKB2; IRF3; RELA; NOS2A; TLR4; TNF; RELB; LDLR; NR1H2; NFKB1; SREBF1; IL1R1; CCL2; IL6; MMP9 |
| Amyloid Processing | PRKCE; CSNK1E; MAPK1; CAPNS1; AKT2; CAPN2; CAPN1; MAPK3; MAPK13; MAPT; MAPK14; AKT1; PSEN1; CSNK1A1; GSK3B; AKT3; APP |
| IL-4 Signaling | AKT2; PIK3CA; PIK3CB; PIK3C3; IRS1; KRAS; SOCS1; PTPN6; NR3C1; PIK3C2A; JAK1; AKT1; JAK2; PIK3R1; FRAP1; AKT3; RPS6KB 1 |
| Cell Cycle: G2/M DNA Damage Checkpoint Regulation | EP300; PCAF; BRCA1; GADD45A; PLK1; BTRC; CHEK1; ATR; CHEK2; YWHAZ; TP53; CDKN1A; PRKDC; ATM; SFN; CDKN2A |
| Nitric Oxide Signaling in the Cardiovascular System | KDR; FLT1; PGF; AKT2; PIK3CA; PIK3CB; PIK3C3; CAV1; PRKCD; NOS3; PIK3C2A; AKT1; PIK3R1; VEGFA; AKT3; HSP90AA1 |
| Purine Metabolism | NME2; SMARCA4; MYH9; RRM2; ADAR; EIF2AK4; PKM2; ENTPD1; RAD51; RRM2B; TJP2; RAD51C; NT5E; POLD1; NME1 |
| cAMP-mediated Signaling | RAP1A; MAPK1; GNAS; CREB1; CAMK2A; MAPK3; SRC; RAF1; MAP2K2; STAT3; MAP2K1; BRAF; ATF4 |
| Mitochondrial Dysfunction | SOD2; MAPK8; CASP8; MAPK10; MAPK9; CASP9; PARK7; PSEN1; PARK2; APP; CASP3 |
| Notch Signaling | HES1; JAG1; NUMB; NOTCH4; ADAM17; NOTCH2; PSEN1; NOTCH3; NOTCH1; DLL4 |
| Endoplasmic Reticulum Stress Pathway | HSPA5; MAPK8; XBP1; TRAF2; ATF6; CASP9; ATF4; EIF2AK3; CASP3 |
| Pyrimidine Metabolism | NME2; AICDA; RRM2; EIF2AK4; ENTPD1; RRM2B; NT5E; POLD1; NME1 |
| Parkinson's Signaling | UCHL1; MAPK8; MAPK13; MAPK14; CASP9; PARK7; PARK2; CASP3 |
| Cardiac & Beta Adrenergic Signaling | GNAS; GNAQ; PPP2R1A; GNB2L1; PPP2CA; PPP1CC; PPP2R5C |
| Glycolysis/ Gluconeogenesis | HK2; GCK; GPI; ALDH1A1; PKM2; LDHA; HK1 |
| Interferon Signaling | IRF1; SOCS1; JAK1; JAK2; IFITM1; STAT1; IFIT3 |
| Sonic Hedgehog Signaling | ARRB2; SMO; GLI2; DYRK1A; GLI1; GSK3B; DYRK1B |
| Glycerophospholipid Metabolism | PLD1; GRN; GPAM; YWHAZ; SPHK1; SPHK2 |
| Phospholipid Degradation | PRDX6; PLD1; GRN; YWHAZ; SPHK1; SPHK2 |
| Tryptophan Metabolism | SIAH2; PRMT5; NEDD4; ALDH1A1; CYP1B1; SIAH1 |
| Lysine Degradation | SUV39H1; EHMT2; NSD1; SETD7; PPP2R5C |
| Nucleotide Excision Repair Pathway | ERCC5; ERCC4; XPA; XPC; ERCC1 |
| Starch and Sucrose Metabolism | UCHL1; HK2; GCK; GPI; HK1 |
| Aminosugars Metabolism | NQO1; HK2; GCK; HK1 |
| Arachidonic Acid Metabolism | PRDX6; GRN; YWHAZ; CYP1B1 |
| Circadian Rhythm Signaling | CSNK1E; CREB1; ATF4; NR1D1 |
| Coagulation System | BDKRB1; F2R; SERPINE1; F3 |
| Dopamine Receptor Signaling | PPP2R1A; PPP2CA; PPP1CC; PPP2R5C |
| Glutathione Metabolism | IDH2; GSTP1; ANPEP; IDH1 |
| Glycerolipid Metabolism | ALDH1A1; GPAM; SPHK1; SPHK2 |
| Linoleic Acid Metabolism | PRDX6; GRN; YWHAZ; CYP1B1 |
| Methionine Metabolism | DNMT1; DNMT3B; AHCY; DNMT3A |
| Pyruvate Metabolism | GLO1; ALDH1A1; PKM2; LDHA |
| Arginine and Proline Metabolism | ALDH1A1; NOS3; NOS2A |
| Eicosanoid Signaling | PRDX6; GRN; YWHAZ |
| Fructose and Mannose Metabolism | HK2; GCK; HK1 |

TABLE C-continued

| CELLULAR FUNCTION | GENES |
|---|---|
| Galactose Metabolism | HK2; GCK; HK1 |
| Stilbene, Coumarine and Lignin Biosynthesis | PRDX6; PRDX1; TYR |
| Antigen Presentation Pathway | CALR; B2M |
| Biosynthesis of Steroids | NQO1; DHCR7 |
| Butanoate Metabolism | ALDH1A1; NLGN1 |
| Citrate Cycle | IDH2; IDH1 |
| Fatty Acid Metabolism | ALDH1A1; CYP1B1 |
| Glycerophospholipid Metabolism | PRDX6; CHKA |
| Histidine Metabolism | PRMT5; ALDH1A1 |
| Inositol Metabolism | ERO1L; APEX1 |
| Metabolism of Xenobiotics by Cytochrome p450 | GSTP1; CYP1B1 |
| Methane Metabolism | PRDX6; PRDX1 |
| Phenylalanine Metabolism | PRDX6; PRDX1 |
| Propanoate Metabolism | ALDH1A1; LDHA |
| Selenoamino Acid Metabolism | PRMT5; AHCY |
| Sphingolipid Metabolism | SPHK1; SPHK2 |
| Aminophosphonate Metabolism | PRMT5 |
| Androgen and Estrogen Metabolism | PRMT5 |
| Ascorbate and Aldarate Metabolism | ALDH1A1 |
| Bile Acid Biosynthesis | ALDH1A1 |
| Cysteine Metabolism | LDHA |
| Fatty Acid Biosynthesis | FASN |
| Glutamate Receptor Signaling | GNB2L1 |
| NRF2-mediated Oxidative Stress Ressonse | PRDX1 |
| Pentose Phos I hate Pathway | GPI |
| Pentose and Glucuronate Interconversions | UCHL1 |
| Retinol Metabolism | ALDH1A1 |
| Riboflavin Metabolism | TYR |
| Tyrosine Metabolism | PRMT5, TYR |
| Ubiquinone Biosynthesis | PRMT5 |
| Valine, Leucine and Isoleucine Degradation | ALDH1A1 |
| Glycine, Serine and Threonine Metabolism | CHKA |
| Lysine Degradation | ALDH1A1 |
| Pain/Taste | TRPM5; TRPA1 |
| Pain | TRPM7; TRPC5; TRPC6; TRPC1; Cnr1; cnr2; Grk2; Trpa1; Pomc; Cgrp; Crf; Pka; Era; Nr2b; TRPM5; Prkaca; Prkacb; Prkar1a; Prkar2a |
| Mitochondrial Function | AIF; CytC; SMAC (Diablo); Aifm-1; Aifm-2 |
| Developmental Neurology | BMP-4; Chordin (Chrd); Noggin (Nog); WNT (Wnt2; Wnt2b; Wnt3a; Wnt4; Wnt5a; Wnt6; Wnt7b; Wnt8b; Wnt9a; Wnt9b; Wnt10a; Wnt10b; Wnt16); beta-catenin; Dkk-1; Frizzled related proteins; Otx-2; Gbx2; FGF-8; Reelin; Dab1; unc-86 (Pou4f1 or Brn3a); Numb; Reln |

The metabolism-related targets described above, especially those highlighted, are particularly preferred where they are expressed in the liver.

Embodiments of the invention also relate to methods and compositions related to knocking out genes, amplifying genes and repairing particular mutations associated with DNA repeat instability and neurological disorders (Robert D. Wells, Tetsuo Ashizawa, Genetic Instabilities and Neurological Diseases, Second Edition, Academic Press, Oct. 13, 2011—Medical). Specific aspects of tandem repeat sequences have been found to be responsible for more than twenty human diseases (New insights into repeat instability: role of RNA•DNA hybrids. McIvor E I, Polak U, Napierala M. RNA Biol. 2010 September-October; 7(5):551-8). The CRISPR-Cas system may be harnessed to correct these defects of genomic instability.

A further aspect of the invention relates to utilizing the CRISPR-Cas system for correcting defects in the EMP2A and EMP2B genes that have been identified to be associated with Lafora disease. Lafora disease is an autosomal recessive condition which is characterized by progressive myoclonus epilepsy which may start as epileptic seizures in adolescence. A few cases of the disease may be caused by mutations in genes yet to be identified. The disease causes seizures, muscle spasms, difficulty walking, dementia, and eventually death. There is currently no therapy that has proven effective against disease progression. Other genetic abnormalities associated with epilepsy may also be targeted by the CRISPR-Cas system and the underlying genetics is further described in Genetics of Epilepsy and Genetic Epilepsies, edited by Giuliano Avanzini, Jeffrey L. Noebels, Mariani Foundation Paediatric Neurology: 20; 2009).

The methods of US Patent Publication No. 20110158957 assigned to Sangamo BioSciences, Inc. involved in inactivating T cell receptor (TCR) genes may also be modified to the CRISPR Cas system of the present invention. In another example, the methods of US Patent Publication No. 20100311124 assigned to Sangamo BioSciences, Inc. and US Patent Publication No. 20110225664 assigned to Cellectis, which are both involved in inactivating glutamine synthetase gene expression genes may also be modified to the CRISPR Cas system of the present invention.

Several further aspects of the invention relate to correcting defects associated with a wide range of genetic diseases which are further described on the website of the National Institutes of Health under the topic subsection Genetic Disorders (website at health.nih.gov/topic/GeneticDisorders). The genetic brain diseases may include but are not limited to Adrenoleukodystrophy, Agenesis of the Corpus Callosum, Aicardi Syndrome, Alpers' Disease, Alzheimer's Disease, Barth Syndrome, Batten Disease, CADASIL, Cerebellar Degeneration, Fabry's Disease, Gerstmann-Straussler-Scheinker Disease, Huntington's Disease and other Triplet Repeat Disorders, Leigh's Disease, Lesch-Nyhan Syndrome, Menkes Disease, Mitochondrial Myopathies and NINDS Colpocephaly. These diseases are further described on the website of the National Institutes of Health under the subsection Genetic Brain Disorders.

In some embodiments, the condition may be neoplasia. In some embodiments, where the condition is neoplasia, the genes to be targeted are any of those listed in Table A (in this case PTEN and so forth). In some embodiments, the condition may be Age-related Macular Degeneration. In some embodiments, the condition may be a Schizophrenic Disorder. In some embodiments, the condition may be a Trinucleotide Repeat Disorder. In some embodiments, the condition may be Fragile X Syndrome. In some embodiments, the condition may be a Secretase Related Disorder. In some embodiments, the condition may be a Prion-related disorder. In some embodiments, the condition may be ALS. In some embodiments, the condition may be a drug addiction. In some embodiments, the condition may be Autism. In some embodiments, the condition may be Alzheimer's Disease. In some embodiments, the condition may be inflammation. In some embodiments, the condition may be Parkinson's Disease.

For example, US Patent Publication No. 20110023145, describes use of zinc finger nucleases to genetically modify cells, animals and proteins associated with autism spectrum disorders (ASD). Autism spectrum disorders (ASDs) are a group of disorders characterized by qualitative impairment in social interaction and communication, and restricted repetitive and stereotyped patterns of behavior, interests, and activities. The three disorders, autism, Asperger syndrome (AS) and pervasive developmental disorder-not otherwise specified (PDD-NOS) are a continuum of the same disorder with varying degrees of severity, associated intellectual functioning and medical conditions. ASDs are predominantly genetically determined disorders with a heritability of around 90%.

US Patent Publication No. 20110023145 comprises editing of any chromosomal sequences that encode proteins associated with ASD which may be applied to the CRISPR Cas system of the present invention. The proteins associated with ASD are typically selected based on an experimental association of the protein associated with ASD to an incidence or indication of an ASD. For example, the production rate or circulating concentration of a protein associated with ASD may be elevated or depressed in a population having an ASD relative to a population lacking the ASD. Differences in protein levels may be assessed using proteomic techniques including but not limited to Western blot, immunohistochemical staining, enzyme linked immunosorbent assay (ELISA), and mass spectrometry. Alternatively, the proteins associated with ASD may be identified by obtaining gene expression profiles of the genes encoding the proteins using genomic techniques including but not limited to DNA microarray analysis, serial analysis of gene expression (SAGE), and quantitative real-time polymerase chain reaction (Q-PCR).

Non limiting examples of disease states or disorders that may be associated with proteins associated with ASD include autism, Asperger syndrome (AS), pervasive developmental disorder-not otherwise specified (PDD-NOS), Rett's syndrome, tuberous sclerosis, phenylketonuria, Smith-Lemli-Opitz syndrome and fragile X syndrome. By way of non-limiting example, proteins associated with ASD include but are not limited to the following proteins: ATP10C aminophospholipid-MET MET receptor transporting ATPase tyrosine kinase (ATP10C) BZRAP1 MGLUR5 (GRM5) Metabotropic glutamate receptor 5 (MGLUR5) CDH10 Cadherin-10 MGLUR6 (GRM6) Metabotropic glutamate receptor 6 (MGLUR6) CDH9 Cadherin-9 NLGN1 Neuroligin-1 CNTN4 Contactin-4 NLGN2 Neuroligin-2 CNTNAP2 Contactin-associated SEMA5A Neuroligin-3 protein-like 2 (CNTNAP2) DHCR7 7-dehydrocholesterol NLGN4X Neuroligin-4 X-reductase (DHCR7) linked DOC2A Double C2-like domain-NLGN4Y Neuroligin-4 Y-containing protein alpha linked DPP6 Dipeptidyl NLGN5 Neuroligin-5 aminopeptidase-like protein 6 EN2 engrailed 2 (EN2) NRCAM Neuronal cell adhesion molecule (NRCAM) MDGA2 fragile X mental retardation NRXN1 Neurexin-1 1 (MDGA2) FMR2 (AFF2) AF4/FMR2 family member 2 OR4M2 Olfactory receptor (AFF2) 4M2 FOXP2 Forkhead box protein P2 OR4N4 Olfactory receptor (FOXP2) 4N4 FXR1 Fragile X mental OXTR oxytocin receptor retardation, autosomal (OXTR) homolog 1 (FXR1) FXR2 Fragile X mental PAH phenylalanine retardation, autosomal hydroxylase (PAH) homolog 2 (FXR2) GABRA1 Gamma-aminobutyric acid PTEN Phosphatase and receptor subunit alpha-1 tensin homologue (GABRA1) (PTEN) GABRA5 GABAA (.gamma.-aminobutyric PTPRZ1 Receptor-type acid) receptor alpha 5 tyrosine-protein subunit (GABRA5) phosphatase zeta (PTPRZ1) GABRB1 Gamma-aminobutyric acid RELN Reelin receptor subunit beta-1 (GABRB1) GABRB3 GABAA (.gamma.-aminobutyric RPL10 60S ribosomal acid) receptor .beta.3 subunit protein L10 (GABRB3) GABRG1 Gamma-aminobutyric acid SEMA5A Semaphorin-5A receptor subunit gamma-1 (SEMA5A) (GABRG1) HIRIP3 HIRA-interacting protein 3 SEZ6L2 seizure related 6 homolog (mouse)-like 2 HOXA1 Homeobox protein Hox-A1 SHANK3 SH3 and multiple (HOXA1) ankyrin repeat domains 3 (SHANK3) IL6 Interleukin-6 SHBZRAP1 SH3 and multiple ankyrin repeat domains 3 (SHBZRAP1) LAMB1 Laminin subunit beta-1 SLC6A4 Serotonin (LAMB1) transporter (SERT) MAPK3 Mitogen-activated protein TAS2R1 Taste receptor kinase 3 type 2 member 1 TAS2R1 MAZ Myc-associated zinc finger TSC1 Tuberous sclerosis protein protein 1 MDGA2 MAM domain containing TSC2 Tuberous sclerosis glycosylphosphatidylinositol protein 2 anchor 2 (MDGA2) MECP2 Methyl CpG binding UBE3A Ubiquitin protein protein 2 (MECP2) ligase E3A (UBE3A) MECP2 methyl CpG binding WNT2 Wingless-type protein 2 (MECP2) MMTV integration site family, member 2 (WNT2)

The identity of the protein associated with ASD whose chromosomal sequence is edited can and will vary. In preferred embodiments, the proteins associated with ASD whose chromosomal sequence is edited may be the benzodiazapine receptor (peripheral) associated protein 1 (BZRAP1) encoded by the BZRAP1 gene, the AF4/FMR2 family member 2 protein (AFF2) encoded by the AFF2 gene (also termed MFR2), the fragile X mental retardation autosomal homolog 1 protein (FXR1) encoded by the FXR1 gene, the fragile X mental retardation autosomal homolog 2 protein (FXR2) encoded by the FXR2 gene, the MAM domain containing glycosylphosphatidylinositol anchor 2 protein (MDGA2) encoded by the MDGA2 gene, the methyl CpG binding protein 2 (MECP2) encoded by the MECP2 gene, the metabotropic glutamate receptor 5 (MGLUR5) encoded by the MGLUR5-1 gene (also termed GRM5), the neurexin 1 protein encoded by the NRXN1 gene, or the semaphorin-5A protein (SEMA5A) encoded by the SEMA5A gene. In an exemplary embodiment, the genetically modified animal is a rat, and the edited chromosomal sequence encoding the protein associated with ASD is as listed below: BZRAP1 benzodiazapine receptor XM_002727789, (peripheral) associated XM_213427, protein 1 (BZRAP1) XM_002724533, XM_001081125 AFF2 (FMR2) AF4/FMR2 family member 2 XM_219832, (AFF2) XM_001054673 FXR1 Fragile X mental NM_001012179 retardation, autosomal homolog 1 (FXR1) FXR2 Fragile X mental NM_001100647 retardation, autosomal homolog 2 (FXR2) MDGA2 MAM domain containing NM_199269 glycosylphosphatidylinositol anchor 2 (MDGA2) MECP2 Methyl CpG binding NM_022673 protein 2 (MECP2) MGLUR5 Metabotropic glutamate NM_017012 (GRM5) receptor 5 (MGLUR5) NRXN1 Neurexin-1 NM_021767 SEMA5A Semaphorin-5A (SEMA5A) NM_001107659

Exemplary animals or cells may comprise one, two, three, four, five, six, seven, eight, or nine or more inactivated chromosomal sequences encoding a protein associated with ASD, and zero, one, two, three, four, five, six, seven, eight, nine or more chromosomally integrated sequences encoding proteins associated with ASD. The edited or integrated chromosomal sequence may be modified to encode an altered protein associated with ASD. Non-limiting examples of mutations in proteins associated with ASD include the L18Q mutation in neurexin 1 where the leucine at position 18 is replaced with a glutamine, the R451C mutation in neuroligin 3 where the arginine at position 451 is replaced with a cysteine, the R87 W mutation in neuroligin 4 where the arginine at position 87 is replaced with a tryptophan, and the I425V mutation in serotonin transporter where the isoleucine at position 425 is replaced with a valine. A number of other mutations and chromosomal rearrangements in ASD-related chromosomal sequences have been associated with ASD and are known in the art. See, for example, Freitag et al. (2010) Eur. Child. Adolesc. Psychiatry 19:169-178, and Bucan et al. (2009) PLoS Genetics 5: e1000536, the disclosure of which is incorporated by reference herein in its entirety.

Examples of proteins associated with Parkinson's disease include but are not limited to α-synuclein, DJ-1, LRRK2, PINK1, Parkin, UCHL1, Synphilin-1, and NURR1.

Examples of addiction-related proteins may include ABAT for example.

Examples of inflammation-related proteins may include the monocyte chemoattractant protein-1 (MCP1) encoded by the Ccr2 gene, the C-C chemokine receptor type 5 (CCR5) encoded by the Ccr5 gene, the IgG receptor IIB (FCGR2b, also termed CD32) encoded by the Fcgr2b gene, or the Fc epsilon R1 g (FCER1 g) protein encoded by the Fcer1 g gene, for example.

Examples of cardiovascular diseases associated proteins may include IL1B (interleukin 1, beta), XDH (xanthine dehydrogenase), TP53 (tumor protein p53), PTGIS (prostaglandin 12 (prostacyclin) synthase), MB (myoglobin), IL4 (interleukin 4), ANGPT1 (angiopoietin 1), ABCG8 (ATP-binding cassette, sub-family G (WHITE), member 8), or CTSK (cathepsin K), for example.

For example, US Patent Publication No. 20110023153, describes use of zinc finger nucleases to genetically modify cells, animals and proteins associated with Alzheimer's Disease. Once modified cells and animals may be further tested using known methods to study the effects of the targeted mutations on the development and/or progression of AD using measures commonly used in the study of AD—such as, without limitation, learning and memory, anxiety, depression, addiction, and sensory motor functions as well as assays that measure behavioral, functional, pathological, metabolic and biochemical function.

The present disclosure comprises editing of any chromosomal sequences that encode proteins associated with AD. The AD-related proteins are typically selected based on an experimental association of the AD-related protein to an AD disorder. For example, the production rate or circulating concentration of an AD-related protein may be elevated or depressed in a population having an AD disorder relative to a population lacking the AD disorder. Differences in protein levels may be assessed using proteomic techniques including but not limited to Western blot, immunohistochemical staining, enzyme linked immunosorbent assay (ELISA), and mass spectrometry. Alternatively, the AD-related proteins may be identified by obtaining gene expression profiles of the genes encoding the proteins using genomic techniques including but not limited to DNA microarray analysis, serial analysis of gene expression (SAGE), and quantitative real-time polymerase chain reaction (Q-PCR).

Examples of Alzheimer's disease associated proteins may include the very low density lipoprotein receptor protein (VLDLR) encoded by the VLDLR gene, the ubiquitin-like modifier activating enzyme 1 (UBA1) encoded by the UBA1 gene, or the NEDD8-activating enzyme E1 catalytic subunit protein (UBE1C) encoded by the UBA3 gene, for example.

By way of non-limiting example, proteins associated with AD include but are not limited to the proteins listed as follows: Chromosomal Sequence Encoded Protein ALAS2 Delta-aminolevulinate synthase 2 (ALAS2) ABCA1 ATP-binding cassette transporter (ABCA1) ACE Angiotensin I-converting enzyme (ACE) APOE Apolipoprotein E precursor (APOE) APP amyloid precursor protein (APP) AQP1 aquaporin 1 protein (AQP1) BIN1 Myc box-dependent-interacting protein 1 or bridging integrator 1 protein (BIN1) BDNF brain-derived neurotrophic factor (BDNF) BTNL8 Butyrophilin-like protein 8 (BTNL8) C1ORF49 chromosome 1 open reading frame 49 CDH4 Cadherin-4 CHRNB2 Neuronal acetylcholine receptor subunit beta-2 CKLFSF2 CKLF-like MARVEL transmembrane domain-containing protein 2 (CKLFSF2) CLEC4E C-type lectin domain family 4, member e (CLEC4E) CLU clusterin protein (also known as apoplipoprotein J) CR1 Erythrocyte complement receptor 1 (CR1, also known as CD35, C3b/C4b receptor and immune adherence receptor) CR1L Erythrocyte complement receptor 1 (CR1L) CSF3R granulocyte colony-stimulating factor 3 receptor (CSF3R) CST3 Cystatin C or cystatin 3 CYP2C Cytochrome P450 2C DAPK1 Death-associated protein kinase 1 (DAPK1) ESR1 Estrogen receptor 1 FCAR Fc fragment of IgA receptor (FCAR, also known as CD89) FCGR3B Fc fragment of IgG, low affinity Mb, receptor (FCGR3B or CD16b) FFA2 Free fatty acid receptor 2 (FFA2) FGA Fibrinogen (Factor I) GAB2 GRB2-associated-binding protein 2 (GAB2) GAB2 GRB2-associated-binding protein 2 (GAB2) GALP Galanin-like peptide GAPDHS Glyceraldehyde-3-phosphate dehydrogenase, spermatogenic (GAPDHS) GMPB GMBP HP Haptoglobin (HP) HTR7 5-hydroxytryptamine (serotonin) receptor 7 (adenylate cyclase-coupled) IDE Insulin degrading enzyme IF127 IF127 IFI6 Interferon, alpha-inducible protein 6 (IFI6) IFIT2 Interferon-induced protein with tetratricopeptide repeats 2 (IFIT2) IL1RN interleukin-1 receptor antagonist (IL-1RA) IL8RA Interleukin 8 receptor, alpha (IL8RA or CD181) IL8RB Interleukin 8 receptor, beta (IL8RB) JAG1 Jagged 1 (JAG1) KCNJ15 Potassium inwardly-rectifying channel, subfamily J, member 15 (KCNJ15) LRP6 Low-density lipoprotein receptor-related protein 6 (LRP6) MAPT microtubule-associated protein tau (MAPT) MARK4 MAP/microtubule affinity-regulating kinase 4 (MARK4) MPHOSPH1 M-phase phosphoprotein 1 MTHFR 5,10-methylenetetrahydrofolate reductase MX2 Interferon-induced GTP-binding protein Mx2 NBN Nibrin, also known as NBN NCSTN Nicastrin NIACR2 Niacin receptor 2 (NIACR2, also known as GPR109B) NMNAT3 nicotinamide nucleotide adenylyltransferase 3 NTM Neurotrimin (or HNT) ORM1 Orosmucoid 1 (ORM1) or Alpha-1-acid glycoprotein 1 P2RY13 P2Y purinoceptor 13 (P2RY13) PBEF1 Nicotinamide phosphoribosyltransferase (NAmPRTase or Nampt) also known as pre-B-cell colony-enhancing factor 1 (PBEF1) or visfatin PCK1 Phosphoenolpyruvate carboxykinase PICALM phosphatidylinositol binding clathrin assembly protein (PICALM) PLAU Urokinase-type plasminogen activator (PLAU) PLXNC1 Plexin C1 (PLXNC1) PRNP Prion protein PSEN1 presenilin 1 protein (PSEN1) PSEN2 presenilin 2 protein (PSEN2) PTPRA protein tyrosine phosphatase receptor type A protein (PTPRA) RALGPS2 Ral GEF with PH domain and SH3 binding motif 2 (RALGPS2) RGSL2 regulator of G-protein signaling like 2 (RGSL2) SELENBP1 Selenium binding protein 1 (SELNBP1) SLC25A37 Mitoferrin-1 SORL1 sortilin-related receptor L(DLR class) A repeats-containing protein (SORL1) TF Transferrin TFAM Mitochondrial transcription factor A TNF Tumor necrosis factor TNFRSF10C Tumor necrosis factor receptor superfamily member 10C (TNFRSF10C) TNFSF10 Tumor necrosis factor receptor superfamily, (TRAIL) member 10a (TNFSF10) UBA1 ubiquitin-like modifier activating enzyme 1 (UBA1) UBA3 NEDD8-activating enzyme E1 catalytic subunit protein (UBE1C) UBB ubiquitin B protein (UBB) UBQLN1 Ubiquilin-1 UCHL1 ubiquitin carboxyl-terminal esterase L1 protein (UCHL1) UCHL3 ubiquitin carboxyl-terminal hydrolase isozyme L3 protein (UCHL3) VLDLR very low density lipoprotein receptor protein (VLDLR)

In exemplary embodiments, the proteins associated with AD whose chromosomal sequence is edited may be the very low density lipoprotein receptor protein (VLDLR) encoded by the VLDLR gene, the ubiquitin-like modifier activating enzyme 1 (UBA1) encoded by the UBA1 gene, the NEDD8-activating enzyme E1 catalytic subunit protein (UBE1C) encoded by the UBA3 gene, the aquaporin 1 protein (AQP1) encoded by the AQP1 gene, the ubiquitin carboxyl-terminal esterase L1 protein (UCHL1) encoded by the UCHL1 gene, the ubiquitin carboxyl-terminal hydrolase isozyme L3 protein (UCHL3) encoded by the UCHL3 gene, the ubiquitin B protein (UBB) encoded by the UBB gene, the microtubule-associated protein tau (MAPT) encoded by the MAPT gene, the protein tyrosine phosphatase receptor type A protein (PTPRA) encoded by the PTPRA gene, the phosphatidylinositol binding clathrin assembly protein (PICALM) encoded by the PICALM gene, the clusterin protein (also known as apoplipoprotein J) encoded by the CLU gene, the presenilin 1 protein encoded by the PSEN1 gene, the presenilin 2 protein encoded by the PSEN2 gene, the sortilin-related receptor L(DLR class) A repeats-containing protein (SORL1) protein encoded by the SORL1 gene, the amyloid precursor protein (APP) encoded by the APP gene, the Apolipoprotein E precursor (APOE) encoded by the APOE gene, or the brain-derived neurotrophic factor (BDNF) encoded by the BDNF gene. In an exemplary embodiment, the genetically modified animal is a rat, and the edited chromosomal sequence encoding the protein associated with AD is as follows: APP amyloid precursor protein (APP) NM_019288 AQP1 aquaporin 1 protein (AQP1) NM_012778 BDNF Brain-derived neurotrophic factor NM_012513 CLU clusterin protein (also known as NM_053021 apoplipoprotein J) MAPT microtubule-associated protein NM_017212 tau (MAPT) PICALM phosphatidylinositol binding NM_053554 clathrin assembly protein (PICALM) PSEN1 presenilin 1 protein (PSEN1) NM_019163 PSEN2 presenilin 2 protein (PSEN2) NM_031087 PTPRA protein tyrosine phosphatase NM_012763 receptor type A protein (PTPRA) SORL1 sortilin-related receptor L(DLR NM_053519, class) A repeats-containing XM_001065506, protein (SORL1) XM_217115 UBA1 ubiquitin-like modifier activating NM_001014080 enzyme 1 (UBA1) UBA3 NEDD8-activating enzyme E1 NM_057205 catalytic subunit protein (UBE1C) UBB ubiquitin B protein (UBB) NM_138895 UCHL1 ubiquitin carboxyl-terminal NM_017237 esterase L1 protein (UCHL1) UCHL3 ubiquitin carboxyl-terminal NM_001110165 hydrolase isozyme L3 protein (UCHL3) VLDLR very low density lipoprotein NM_013155 receptor protein (VLDLR)

The animal or cell may comprise 1, 2, 3, 4, 5, 6, 7, 8, 9, 10, 11, 12, 13, 14, 15 or more disrupted chromosomal sequences encoding a protein associated with AD and zero, 1, 2, 3, 4, 5, 6, 7, 8, 9, 10, 11, 12, 13, 14, 15 or more chromosomally integrated sequences encoding a protein associated with AD.

The edited or integrated chromosomal sequence may be modified to encode an altered protein associated with AD. A number of mutations in AD-related chromosomal sequences have been associated with AD. For instance, the V7171 (i.e. valine at position 717 is changed to isoleucine) missense mutation in APP causes familial AD. Multiple mutations in the presenilin-1 protein, such as H163R (i.e. histidine at position 163 is changed to arginine), A246E (i.e. alanine at position 246 is changed to glutamate), L286V (i.e. leucine at position 286 is changed to valine) and C410Y (i.e. cysteine at position 410 is changed to tyrosine) cause familial Alzheimer's type 3. Mutations in the presenilin-2 protein, such as N141 I (i.e. asparagine at position 141 is changed to isoleucine), M239V (i.e. methionine at position 239 is changed to valine), and D439A (i.e. aspartate at position 439 is changed to alanine) cause familial Alzheimer's type 4. Other associations of genetic variants in AD-associated genes and disease are known in the art. See, for example, Waring et al. (2008) Arch. Neurol. 65:329-334, the disclosure of which is incorporated by reference herein in its entirety.

Examples of proteins associated Autism Spectrum Disorder may include the benzodiazapine receptor (peripheral) associated protein 1 (BZRAP1) encoded by the BZRAP1 gene, the AF4/FMR2 family member 2 protein (AFF2) encoded by the AFF2 gene (also termed MFR2), the fragile X mental retardation autosomal homolog 1 protein (FXR1) encoded by the FXR1 gene, or the fragile X mental retardation autosomal homolog 2 protein (FXR2) encoded by the FXR2 gene, for example.

Examples of proteins associated Macular Degeneration may include the ATP-binding cassette, sub-family A (ABC1) member 4 protein (ABCA4) encoded by the ABCR gene, the apolipoprotein E protein (APOE) encoded by the APOE gene, or the chemokine (C-C motif) Ligand 2 protein (CCL2) encoded by the CCL2 gene, for example.

Examples of proteins associated Schizophrenia may include NRG1, ErbB4, CPLX1, TPH1, TPH2, NRXN1, GSK3A, BDNF, DISC1, GSK3B, and combinations thereof.

Examples of proteins involved in tumor suppression may include ATM (ataxia telangiectasia mutated), ATR (ataxia telangiectasia and Rad3 related), EGFR (epidermal growth factor receptor), ERBB2 (v-erb-b2 erythroblastic leukemia viral oncogene homolog 2), ERBB3 (v-erb-b2 erythroblastic leukemia viral oncogene homolog 3), ERBB4 (v-erb-b2 erythroblastic leukemia viral oncogene homolog 4), Notch 1, Notch2, Notch 3, or Notch 4, for example.

Examples of proteins associated with a secretase disorder may include PSENEN (presenilin enhancer 2 homolog (*C. elegans*)), CTSB (cathepsin B), PSEN1 (presenilin 1), APP (amyloid beta (A4) precursor protein), APH1B (anterior pharynx defective 1 homolog B (*C. elegans*)), PSEN2 (presenilin 2 (Alzheimer disease 4)), or BACE1 (beta-site APP-cleaving enzyme 1), for example.

For example, US Patent Publication No. 20110023146, describes use of zinc finger nucleases to genetically modify cells, animals and proteins associated with secretase-associated disorders. Secretases are essential for processing pre-proteins into their biologically active forms. Defects in various components of the secretase pathways contribute to many disorders, particularly those with hallmark amyloidogenesis or amyloid plaques, such as Alzheimer's disease (AD).

A secretase disorder and the proteins associated with these disorders are a diverse set of proteins that effect susceptibility for numerous disorders, the presence of the disorder, the severity of the disorder, or any combination thereof. The present disclosure comprises editing of any chromosomal sequences that encode proteins associated with a secretase disorder. The proteins associated with a secretase disorder are typically selected based on an experimental association of the secretase-related proteins with the development of a secretase disorder. For example, the production rate or circulating concentration of a protein associated with a secretase disorder may be elevated or depressed in a population with a secretase disorder relative to a population without a secretase disorder. Differences in protein levels may be assessed using proteomic techniques including but not limited to Western blot, immunohistochemical staining, enzyme linked immunosorbent assay (ELISA), and mass spectrometry. Alternatively, the protein associated with a secretase disorder may be identified by obtaining gene expression profiles of the genes encoding the proteins using genomic techniques including but not limited to DNA microarray analysis, serial analysis of gene expression (SAGE), and quantitative real-time polymerase chain reaction (Q-PCR).

By way of non-limiting example, proteins associated with a secretase disorder include PSENEN (presenilin enhancer 2 homolog (*C. elegans*)), CTSB (cathepsin B), PSEN1 (presenilin 1), APP (amyloid beta (A4) precursor protein), APH1B (anterior pharynx defective 1 homolog B (*C. elegans*)), PSEN2 (presenilin 2 (Alzheimer disease 4)), BACE1 (beta-site APP-cleaving enzyme 1), ITM2B (integral membrane protein 2B), CTSD (cathepsin D), NOTCH1 (Notch homolog 1, translocation-associated (*Drosophila*)), TNF (tumor necrosis factor (TNF superfamily, member 2)), INS (insulin), DYT10 (dystonia 10), ADAM17 (ADAM metallopeptidase domain 17), APOE (apolipoprotein E), ACE (angiotensin I converting enzyme (peptidyl-dipeptidase A) 1), STN (statin), TP53 (tumor protein p53), IL6 (interleukin 6 (interferon, beta 2)), NGFR (nerve growth factor receptor (TNFR superfamily, member 16)), IL1B (interleukin 1, beta), ACHE (acetylcholinesterase (Yt blood group)), CTNNB1 (catenin (cadherin-associated protein), beta 1, 88 kDa), IGF1 (insulin-like growth factor 1 (somatomedin C)), IFNG (interferon, gamma), NRG1 (neuregulin 1), CASP3 (caspase 3, apoptosis-related cysteine peptidase), MAPK1 (mitogen-activated protein kinase 1), CDH1 (cadherin 1, type 1, E-cadherin (epithelial)), APBB1 (amyloid beta (A4) precursor protein-binding, family B, member 1 (Fe65)), HMGCR (3-hydroxy-3-methylglutaryl-Coenzyme A reductase), CREB1 (cAMP responsive element binding protein 1), PTGS2 (prostaglandin-endoperoxide synthase 2 (prostaglandin G/H synthase and cyclooxygenase)), HES1 (hairy and enhancer of split 1, (*Drosophila*)), CAT (catalase), TGFB1 (transforming growth factor, beta 1), ENO2 (enolase 2 (gamma, neuronal)), ERBB4 (v-erb-a erythroblastic leukemia viral oncogene homolog 4 (avian)), TRAPPC10 (trafficking protein particle complex 10), MAOB (monoamine oxidase B), NGF (nerve growth factor (beta polypeptide)), MMP12 (matrix metallopeptidase 12 (macrophage elastase)), JAG1 (jagged 1 (Alagille syndrome)), CD40LG (CD40 ligand), PPARG (peroxisome proliferator-activated receptor gamma), FGF2 (fibroblast growth factor 2 (basic)), IL3 (interleukin 3 (colony-stimulating factor, multiple)), LRP1 (low density lipoprotein receptor-related protein 1), NOTCH4 (Notch homolog 4 (*Drosophila*)), MAPK8 (mitogen-activated protein kinase 8), PREP (prolyl endopeptidase), NOTCH3 (Notch homolog 3 (*Drosophila*)), PRNP (prion protein), CTSG (cathepsin G), EGF (epidermal growth factor (beta-urogastrone)), REN (renin), CD44 (CD44 molecule (Indian blood group)), SELP (selectin P (granule membrane protein 140 kDa, antigen CD62)), GHR (growth hormone receptor), ADCYAP1 (adenylate cyclase activating polypeptide 1 (pituitary)), INSR (insulin receptor), GFAP (glial fibrillary acidic protein), MMP3 (matrix metallopeptidase 3 (stromelysin 1, progelatinase)), MAPK10 (mitogen-activated protein kinase 10), SP1 (Sp1 transcription factor), MYC (v-myc myelocytomatosis viral oncogene homolog (avian)), CTSE (cathepsin E), PPARA (peroxisome proliferator-activated receptor alpha), JUN (jun oncogene), TIMP1 (TIMP metallopeptidase inhibitor 1), IL5 (interleukin 5 (colony-stimulating factor, eosinophil)), IL1A (interleukin 1, alpha), MMP9 (matrix metallopeptidase 9 (gelatinase B, 92 kDa gelatinase, 92 kDa type IV collagenase)), HTR4 (5-hydroxytryptamine (serotonin) receptor 4), HSPG2 (heparan sulfate proteoglycan 2), KRAS (v-Ki-ras2 Kirsten rat sarcoma viral oncogene homolog), CYCS (cytochrome c, somatic), SMG1 (SMG1 homolog, phosphatidylinositol 3-kinase-related kinase (*C. elegans*)), IL1R1 (interleukin 1 receptor, type I), PROK1 (prokineticin 1), MAPK3 (mitogen-activated protein kinase 3), NTRK1 (neurotrophic tyrosine kinase, receptor, type 1), IL13 (interleukin 13), MME (membrane metallo-endopeptidase), TKT (transketolase), CXCR2 (chemokine (C-X-C motif) receptor 2), IGF1R (insulin-like growth factor 1 receptor), RARA (retinoic acid receptor, alpha), CREBBP (CREB binding protein), PTGS1 (prostaglandin-endoperoxide synthase 1 (prostaglandin G/H synthase and cyclooxygenase)), GALT (galactose-1-phosphate uridylyltransferase), CHRM1 (cholinergic receptor, muscarinic 1), ATXN1 (ataxin 1), PAWR (PRKC, apoptosis, WT1, regulator), NOTCH2 (Notch homolog 2 (*Drosophila*)), M6PR (mannose-6-phosphate receptor (cation dependent)), CYP46A1 (cytochrome P450, family 46, subfamily A, polypeptide 1), CSNK1 D (casein kinase 1, delta), MAPK14 (mitogen-activated protein kinase 14), PRG2 (proteoglycan 2, bone marrow (natural killer cell activator, eosinophil granule major basic protein)), PRKCA (protein kinase C, alpha), L1 CAM (L1 cell adhesion molecule), CD40 (CD40 molecule, TNF receptor superfamily member 5), NR1I2 (nuclear receptor subfamily 1, group I, member 2), JAG2 (jagged 2), CTNND1 (catenin (cadherin-associated protein), delta 1), CDH2 (cadherin 2, type 1, N-cadherin (neuronal)), CMA1 (chymase 1, mast cell), SORT1 (sortilin 1), DLK1 (delta-like 1 homolog (*Drosophila*)), THEM4 (thioesterase superfamily member 4), JUP (junction plakoglobin), CD46 (CD46 molecule, complement regulatory protein), CCL11 (chemokine (C-C motif) ligand 11), CAV3 (caveolin 3), RNASE3 (ribonuclease, RNase A family, 3 (eosinophil cationic protein)), HSPA8 (heat shock 70 kDa protein 8), CASP9 (caspase 9, apoptosis-related cysteine peptidase), CYP3A4 (cytochrome P450, family 3, subfamily A, polypeptide 4), CCR3 (chemokine (C-C motif) receptor 3), TFAP2A (transcription factor AP-2 alpha (activating enhancer binding protein 2 alpha)), SCP2 (sterol carrier protein 2), CDK4 (cyclin-dependent kinase 4), HIF1A (hypoxia inducible factor 1, alpha subunit (basic helix-loop-helix transcription factor)), TCF7L2 (transcription factor 7-like 2 (T-cell specific, HMG-box)), IL1R2 (interleukin 1 receptor, type II), B3GALTL (beta 1,3-galactosyltransferase-like), MDM2 (Mdm2 p53 binding protein homolog (mouse)), RELA (v-rel reticuloendotheliosis viral oncogene homolog A (avian)), CASP7 (caspase 7, apoptosis-related cysteine peptidase), IDE (insulin-degrading enzyme), FABP4 (fatty acid binding protein 4, adipocyte), CASK (calcium/calmodulin-dependent serine protein kinase (MAGUK family)), ADCYAP1R1 (adenylate cyclase activating polypeptide 1 (pituitary) receptor type I), ATF4 (activating transcription factor 4 (tax-responsive enhancer element B67)), PDGFA (platelet-derived growth factor alpha polypeptide), C21 or f33 (chromosome 21 open reading frame 33), SCG5 (secretogranin V (7B2 protein)), RNF123 (ring finger protein 123), NFKB1 (nuclear factor of kappa light polypeptide gene enhancer in B-cells 1), ERBB2 (v-erb-b2 erythroblastic leukemia viral oncogene homolog 2, neuro/glioblastoma derived oncogene homolog (avian)), CAV1 (caveolin 1, caveolae protein, 22 kDa), MMP7 (matrix metallopeptidase 7 (matrilysin, uterine)), TGFA (transforming growth factor, alpha), RXRA (retinoid X receptor, alpha), STX1A (syntaxin 1A (brain)), PSMC4 (proteasome (prosome, macropain) 26S subunit, ATPase, 4), P2RY2 (purinergic receptor P2Y, G-protein coupled, 2), TNFRSF21 (tumor necrosis factor receptor superfamily, member 21), DLG1 (discs, large homolog 1 (*Drosophila*)), NUMBL (numb homolog (*Drosophila*)-like), SPN (sialophorin), PLSCR1 (phospholipid scramblase 1), UBQLN2 (ubiquilin 2), UBQLN1 (ubiquilin 1), PCSK7 (proprotein convertase subtilisin/kexin type 7), SPON1 (spondin 1, extracellular matrix protein), SILV (silver homolog (mouse)), QPCT (glutaminyl-peptide cyclotransferase), HESS (hairy and enhancer of split 5 (*Drosophila*)), GCC1 (GRIP and coiled-coil domain containing 1), and any combination thereof.

The genetically modified animal or cell may comprise 1, 2, 3, 4, 5, 6, 7, 8, 9, 10 or more disrupted chromosomal sequences encoding a protein associated with a secretase disorder and zero, 1, 2, 3, 4, 5, 6, 7, 8, 9, 10 or more chromosomally integrated sequences encoding a disrupted protein associated with a secretase disorder.

Examples of proteins associated with Amyotrophic Lateral Sclerosis may include SOD1 (superoxide dismutase 1), ALS2 (amyotrophic lateral sclerosis 2), FUS (fused in sarcoma), TARDBP (TAR DNA binding protein), VAGFA (vascular endothelial growth factor A), VAGFB (vascular endothelial growth factor B), and VAGFC (vascular endothelial growth factor C), and any combination thereof.

For example, US Patent Publication No. 20110023144, describes use of zinc finger nucleases to genetically modify cells, animals and proteins associated with amyotrophyic lateral sclerosis (ALS) disease. ALS is characterized by the gradual steady degeneration of certain nerve cells in the brain cortex, brain stem, and spinal cord involved in voluntary movement.

Motor neuron disorders and the proteins associated with these disorders are a diverse set of proteins that effect susceptibility for developing a motor neuron disorder, the presence of the motor neuron disorder, the severity of the motor neuron disorder or any combination thereof. The present disclosure comprises editing of any chromosomal sequences that encode proteins associated with ALS disease, a specific motor neuron disorder. The proteins associated with ALS are typically selected based on an experimental association of ALS-related proteins to ALS. For example, the production rate or circulating concentration of a protein associated with ALS may be elevated or depressed in a population with ALS relative to a population without ALS. Differences in protein levels may be assessed using proteomic techniques including but not limited to Western blot, immunohistochemical staining, enzyme linked immunosorbent assay (ELISA), and mass spectrometry. Alternatively, the proteins associated with ALS may be identified by obtaining gene expression profiles of the genes encoding the proteins using genomic techniques including but not limited to DNA microarray analysis, serial analysis of gene expression (SAGE), and quantitative real-time polymerase chain reaction (Q-PCR).

By way of non-limiting example, proteins associated with ALS include but are not limited to the following proteins: SOD1 superoxide dismutase 1, ALS3 amyotrophic lateral soluble sclerosis 3 SETX senataxin ALS5 amyotrophic lateral sclerosis 5 FUS fused in sarcoma ALS7 amyotrophic lateral sclerosis 7 ALS2 amyotrophic lateral DPP6 Dipeptidyl-peptidase 6 sclerosis 2 NEFH neurofilament, heavy PTGS1 prostaglandin-polypeptide endoperoxide synthase 1 SLC1A2 solute carrier family 1 TNFRSF10B tumor necrosis factor (glial high affinity receptor superfamily, glutamate transporter), member 10b member 2 PRPH peripherin HSP90AA1 heat shock protein 90 kDa alpha (cytosolic), class A member 1 GRIA2 glutamate receptor, IFNG interferon, gamma ionotropic, AMPA 2 S100B S100 calcium binding FGF2 fibroblast growth factor 2 protein B AOX1 aldehyde oxidase 1 CS citrate synthase TARDBP TAR DNA binding protein TXN thioredoxin RAPH1 Ras association MAP3K5 mitogen-activated protein (RaIGDS/AF-6) and kinase 5 pleckstrin homology domains 1 NBEAL1 neuro-beachin-like 1 GPX1 glutathione peroxidase 1 ICA1L islet cell autoantigen RAC1 ras-related C3 botulinum 1.69 kDa-like toxin substrate 1 MAPT microtubule-associated ITPR2 inositol 1,4,5-protein tau triphosphate receptor, type 2 ALS2CR4 amyotrophic lateral GLS glutaminase sclerosis 2 (juvenile) chromosome region, candidate 4 ALS2CR8 amyotrophic lateral CNTFR ciliary neurotrophic factor sclerosis 2 (juvenile) receptor chromosome region, candidate 8 ALS2CR11 amyotrophic lateral FOLH1 folate hydrolase 1 sclerosis 2 (juvenile) chromosome region, candidate 11 FAM117B family with sequence P4HB prolyl 4-hydroxylase, similarity 117, member B beta polypeptide CNTF ciliary neurotrophic factor SQSTM1 sequestosome 1 STRADB STE20-related kinase NAIP NLR family, apoptosis adaptor beta inhibitory protein YWHAQ tyrosine 3-SLC33A1 solute carrier family 33 monooxygenase/tryptoph (acetyl-CoA transporter), an 5-monooxygenase member 1 activation protein, theta polypeptide TRAK2 trafficking protein, FIG. 4 FIG. 4 homolog, SAC1 kinesin binding 2 lipid phosphatase domain containing NIF3L1 NIF3 NGG1 interacting INA internexin neuronal factor 3-like 1 intermediate filament protein, alpha PARD3B par-3 partitioning COX8A cytochrome c oxidase defective 3 homolog B subunit VIIIA CDK15 cyclin-dependent kinase HECW1 HECT, C2 and WW 15 domain containing E3 ubiquitin protein ligase 1 NOS1 nitric oxide synthase 1 MET met proto-oncogene SOD2 superoxide dismutase 2, HSPB1 heat shock 27 kDa mitochondrial protein 1 NEFL neurofilament, light CTSB cathepsin B polypeptide ANG angiogenin, HSPA8 heat shock 70 kDa ribonuclease, RNase A protein 8 family, 5 VAPB VAMP (vesicle-ESR1 estrogen receptor 1 associated membrane protein)-associated protein B and C SNCA synuclein, alpha HGF hepatocyte growth factor CAT catalase ACTB actin, beta NEFM neurofilament, medium TH tyrosine hydroxylase polypeptide BCL2 B-cell CLL/lymphoma 2 FAS Fas (TNF receptor superfamily, member 6) CASP3 caspase 3, apoptosis-CLU clusterin related cysteine peptidase SMN1 survival of motor neuron G6PD glucose-6-phosphate 1, telomeric dehydrogenase BAX BCL2-associated X HSF1 heat shock transcription protein factor 1 RNF19A ring finger protein 19A JUN jun oncogene ALS2CR12 amyotrophic lateral HSPA5 heat shock 70 kDa sclerosis 2 (juvenile) protein 5 chromosome region, candidate 12 MAPK14 mitogen-activated protein IL10 interleukin 10 kinase 14 APEX1 APEX nuclease TXNRD1 thioredoxin reductase 1 (multifunctional DNA repair enzyme) 1 NOS2 nitric oxide synthase 2, TIMP1 TIMP metallopeptidase inducible inhibitor 1 CASP9 caspase 9, apoptosis-XIAP X-linked inhibitor of related cysteine apoptosis peptidase GLG1 golgi glycoprotein 1 EPO erythropoietin VEGFA vascular endothelial ELN elastin growth factor A GDNF glial cell derived NFE2L2 nuclear factor (erythroid-neurotrophic factor derived 2)-like 2 SLC6A3 solute carrier family 6 HSPA4 heat shock 70 kDa (neurotransmitter protein 4 transporter, dopamine), member 3 APOE apolipoprotein E PSMB8 proteasome (prosome, macropain) subunit, beta type, 8 DCTN1 dynactin 1 TIMP3 TIMP metallopeptidase inhibitor 3 KIFAP3 kinesin-associated SLC1A1 solute carrier family 1 protein 3 (neuronal/epithelial high affinity glutamate transporter, system Xag), member 1 SMN2 survival of motor neuron CCNC cyclin C 2, centromeric MPP4 membrane protein, STUB1 STIP1 homology and U-palmitoylated 4 box containing protein 1 ALS2 amyloid beta (A4) PRDX6 peroxiredoxin 6 precursor protein SYP synaptophysin CABIN1 calcineurin binding protein 1 CASP1 caspase 1, apoptosis-GART phosphoribosylglycinami related cysteine de formyltransferase, peptidase phosphoribosylglycinami de synthetase, phosphoribosylaminoimi dazole synthetase CDK5 cyclin-dependent kinase 5 ATXN3 ataxin 3 RTN4 reticulon 4 C1QB complement component 1, q subcomponent, B chain VEGFC nerve growth factor HTT huntingtin receptor PARK7 Parkinson disease 7 XDH xanthine dehydrogenase GFAP glial fibrillary acidic MAP2 microtubule-associated protein protein 2 CYCS cytochrome c, somatic FCGR3B Fc fragment of IgG, low affinity IIIb, CCS copper chaperone for UBL5 ubiquitin-like 5 superoxide dismutase MMP9 matrix metallopeptidase SLC18A3 solute carrier family 18 9 ((vesicular acetylcholine), member 3 TRPM7 transient receptor HSPB2 heat shock 27 kDa potential cation channel, protein 2 subfamily M, member 7 AKT1 v-akt murine thymoma DERL1 Der1-like domain family, viral oncogene homolog 1 member 1 CCL2 chemokine (C-C motif) NGRN neugrin, neurite ligand 2 outgrowth associated GSR glutathione reductase TPPP3 tubulin polymerization-promoting protein family member 3 APAF1 apoptotic peptidase BTBD10 BTB (POZ) domain activating factor 1 containing 10 GLUD1 glutamate CXCR4 chemokine (C-X-C motif) dehydrogenase 1 receptor 4 SLC1A3 solute carrier family 1 FLT1 fms-related tyrosine (glial high affinity glutamate transporter), member 3 kinase 1 PON1 paraoxonase 1 AR androgen receptor LIF leukemia inhibitory factor ERBB3 v-erb-b2 erythroblastic leukemia viral oncogene homolog 3 LGALS1 lectin, galactoside-CD44 CD44 molecule binding, soluble, 1 TP53 tumor protein p53 TLR3 toll-like receptor 3 GRIA1 glutamate receptor, GAPDH glyceraldehyde-3-ionotropic, AMPA 1 phosphate dehydrogenase GRIK1 glutamate receptor, DES desmin ionotropic, kainate 1 CHAT choline acetyltransferase FLT4 fms-related tyrosine kinase 4 CHMP2B chromatin modifying BAG1 BCL2-associated protein 2B athanogene MT3 metallothionein 3 CHRNA4 cholinergic receptor, nicotinic, alpha 4 GSS glutathione synthetase BAK1 BCL2-antagonist/killer 1 KDR kinase insert domain GSTP1 glutathione S-transferase receptor (a type III pi 1 receptor tyrosine kinase) OGG1 8-oxoguanine DNA IL6 interleukin 6 (interferon, glycosylase beta 2).

The animal or cell may comprise 1, 2, 3, 4, 5, 6, 7, 8, 9, 10 or more disrupted chromosomal sequences encoding a protein associated with ALS and zero, 1, 2, 3, 4, 5, 6, 7, 8, 9, 10 or more chromosomally integrated sequences encoding the disrupted protein associated with ALS. Preferred proteins associated with ALS include SOD1 (superoxide dismutase 1), ALS2 (amyotrophic lateral sclerosis 2), FUS (fused in sarcoma), TARDBP (TAR DNA binding protein), VAGFA (vascular endothelial growth factor A), VAGFB (vascular endothelial growth factor B), and VAGFC (vascular endothelial growth factor C), and any combination thereof.

Examples of proteins associated with prion diseases may include SOD1 (superoxide dismutase 1), ALS2 (amyotrophic lateral sclerosis 2), FUS (fused in sarcoma), TARDBP (TAR DNA binding protein), VAGFA (vascular endothelial growth factor A), VAGFB (vascular endothelial growth factor B), and VAGFC (vascular endothelial growth factor C), and any combination thereof.

Examples of proteins related to neurodegenerative conditions in prion disorders may include A2M (Alpha-2-Macroglobulin), AATF (Apoptosis antagonizing transcription factor), ACPP (Acid phosphatase prostate), ACTA2

(Actin alpha 2 smooth muscle aorta), ADAM22 (ADAM metallopeptidase domain), ADORA3 (Adenosine A3 receptor), or ADRA1D (Alpha-1D adrenergic receptor for Alpha-1D adrenoreceptor), for example.

Examples of proteins associated with Immunodeficiency may include A2M [alpha-2-macroglobulin]; AANAT [arylalkylamine N-acetyltransferase]; ABCA1 [ATP-binding cassette, sub-family A (ABC1), member 1]; ABCA2 [ATP-binding cassette, sub-family A (ABC1), member 2]; or ABCA3 [ATP-binding cassette, sub-family A (ABC1), member 3]; for example.

Examples of proteins associated with Trinucleotide Repeat Disorders include AR (androgen receptor), FMR1 (fragile X mental retardation 1), HTT (huntingtin), or DMPK (dystrophia myotonica-protein kinase), FXN (frataxin), ATXN2 (ataxin 2), for example.

Examples of proteins associated with Neurotransmission Disorders include SST (somatostatin), NOS1 (nitric oxide synthase 1 (neuronal)), ADRA2A (adrenergic, alpha-2A-, receptor), ADRA2C (adrenergic, alpha-2C-, receptor), TACR1 (tachykinin receptor 1), or HTR2c (5-hydroxytryptamine (serotonin) receptor 2C), for example.

Examples of neurodevelopmental-associated sequences include A2BP1 [ataxin 2-binding protein 1], AADAT [aminoadipate aminotransferase], AANAT [arylalkylamine N-acetyltransferase], ABAT [4-aminobutyrate aminotransferase], ABCA1 [ATP-binding cassette, sub-family A (ABC1), member 1], or ABCA13 [ATP-binding cassette, sub-family A (ABC1), member 13], for example.

Further examples of preferred conditions treatable with the present system include may be selected from: Aicardi-Goutières Syndrome; Alexander Disease; Allan-Herndon-Dudley Syndrome; POLG-Related Disorders; Alpha-Mannosidosis (Type II and III); Alström Syndrome; Angelman; Syndrome; Ataxia-Telangiectasia; Neuronal Ceroid-Lipofuscinoses; Beta-Thalassemia; Bilateral Optic Atrophy and (Infantile) Optic Atrophy Type 1; Retinoblastoma (bilateral); Canavan Disease; Cerebrooculofacioskeletal Syndrome 1 [COFS1]; Cerebrotendinous Xanthomatosis; Cornelia de Lange Syndrome; MAPT-Related Disorders; Genetic Prion Diseases; Dravet Syndrome; Early-Onset Familial Alzheimer Disease; Friedreich Ataxia [FRDA]; Fryns Syndrome; Fucosidosis; Fukuyama Congenital Muscular Dystrophy; Galactosialidosis; Gaucher Disease; Organic Acidemias; Hemophagocytic Lymphohistiocytosis; Hutchinson-Gilford Progeria Syndrome; Mucolipidosis II; Infantile Free Sialic Acid Storage Disease; PLA2 G6-Associated Neurodegeneration; Jervell and Lange-Nielsen Syndrome; Junctional Epidermolysis Bullosa; Huntington Disease; Krabbe Disease (Infantile); Mitochondrial DNA-Associated Leigh Syndrome and NARP; Lesch-Nyhan Syndrome; LIS1-Associated Lissencephaly; Lowe Syndrome; Maple Syrup Urine Disease; MECP2 Duplication Syndrome; ATP7A-Related Copper Transport Disorders; LAMA2-Related Muscular Dystrophy; Arylsulfatase A Deficiency; Mucopolysaccharidosis Types I, II or III; Peroxisome Biogenesis Disorders, Zellweger Syndrome Spectrum; Neurodegeneration with Brain Iron Accumulation Disorders; Acid Sphingomyelinase Deficiency; Niemann-Pick Disease Type C; Glycine Encephalopathy; ARX-Related Disorders; Urea Cycle Disorders; COL1A1/2-Related Osteogenesis Imperfecta; Mitochondrial DNA Deletion Syndromes; PLP1-Related Disorders; Perry Syndrome; Phelan-McDermid Syndrome; Glycogen Storage Disease Type II (Pompe Disease) (Infantile); MAPT-Related Disorders; MECP2-Related Disorders; Rhizomelic Chondrodysplasia Punctata Type 1; Roberts Syndrome; Sandhoff Disease; Schindler Disease—Type 1; Adenosine Deaminase Deficiency; Smith-Lemli-Opitz Syndrome; Spinal Muscular Atrophy; Infantile-Onset Spinocerebellar Ataxia; Hexosaminidase A Deficiency; Thanatophoric Dysplasia Type 1; Collagen Type VI-Related Disorders; Usher Syndrome Type I; Congenital Muscular Dystrophy; Wolf-Hirschhorn Syndrome; Lysosomal Acid Lipase Deficiency; and Xeroderma Pigmentosum.

As will be apparent, it is envisaged that the present system can be used to target any polynucleotide sequence of interest. Some examples of conditions or diseases that might be usefully treated using the present system are included in the Tables above and examples of genes currently associated with those conditions are also provided there. However, the genes exemplified are not exhaustive.

For example, "wild type StCas9" refers to wild type Cas9 from *S. thermophilus*, the protein sequence of which is given in the SwissProt database under accession number G3ECR1. Similarly, *S. pyogenes* Cas9 is included in SwissProt under accession number Q99ZW2.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1: CRISPR Complex Activity in the Nucleus of a Eukaryotic Cell

An example type II CRISPR system is the type II CRISPR locus from *Streptococcus pyogenes* SF370, which contains a cluster of four genes Cas9, Cas1, Cas2, and Csn1, as well as two non-coding RNA elements, tracrRNA and a characteristic array of repetitive sequences (direct repeats) interspaced by short stretches of non-repetitive sequences (spacers, about 30 bp each). In this system, targeted DNA double-strand break (DSB) is generated in four sequential steps (FIG. 2A). First, two non-coding RNAs, the pre-crRNA array and tracrRNA, are transcribed from the CRISPR locus. Second, tracrRNA hybridizes to the direct repeats of pre-crRNA, which is then processed into mature crRNAs containing individual spacer sequences. Third, the mature crRNA:tracrRNA complex directs Cas9 to the DNA target consisting of the protospacer and the corresponding PAM via heteroduplex formation between the spacer region of the crRNA and the protospacer DNA. Finally, Cas9 mediates cleavage of target DNA upstream of PAM to create a DSB within the protospacer (FIG. 2A). This example describes an example process for adapting this RNA-programmable nuclease system to direct CRISPR complex activity in the nuclei of eukaryotic cells.

Cell Culture and Transfection

Human embryonic kidney (HEK) cell line HEK 293FT (Life Technologies) was maintained in Dulbecco's modified Eagle's Medium (DMEM) supplemented with 10% fetal bovine serum (HyClone), 2 mM GlutaMAX (Life Technologies), 100 U/mL penicillin, and 100 μg/mL streptomycin at 37° C. with 5% $CO_2$ incubation. Mouse neuro2A (N2A) cell line (ATCC) was maintained with DMEM supplemented with 5% fetal bovine serum (HyClone), 2 mM GlutaMAX (Life Technologies), 100 U/mL penicillin, and 100 μg/mL streptomycin at 37° C. with 5% $CO_2$.

HEK 293FT or N2A cells were seeded into 24-well plates (Corning) one day prior to transfection at a density of 200,000 cells per well. Cells were transfected using Lipofectamine 2000 (Life Technologies) following the manufacturer's recommended protocol. For each well of a 24-well plate a total of 800 ng of plasmids were used.

Surveyor Assay and Sequencing Analysis for Genome Modification

HEK 293FT or N2A cells were transfected with plasmid DNA as described above. After transfection, the cells were incubated at 37° C. for 72 hours before genomic DNA extraction. Genomic DNA was extracted using the QuickExtract DNA extraction kit (Epicentre) following the manufacturer's protocol. Briefly, cells were resuspended in QuickExtract solution and incubated at 65° C. for 15 minutes and 98° C. for 10 minutes. Extracted genomic DNA was immediately processed or stored at −20° C.

Figure 7:
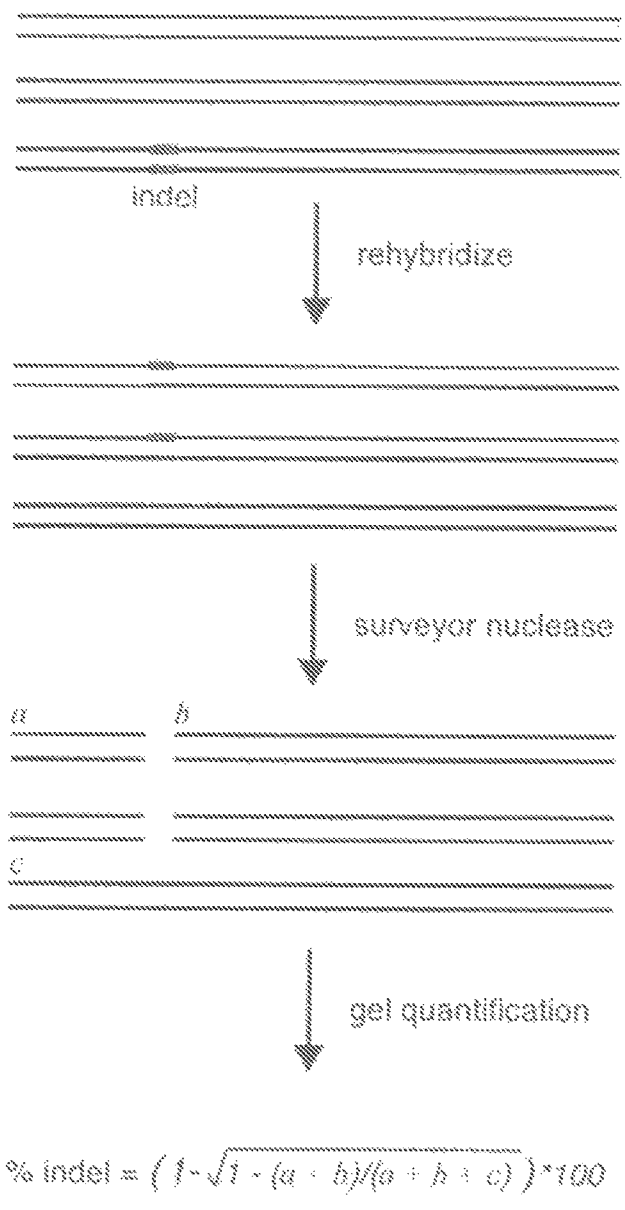
FIG. 7 shows a schematic of a surveyor nuclease assay for detection of double strand break-induced micro-insertions and -deletions.

The genomic region surrounding a CRISPR target site for each gene was PCR amplified, and products were purified using QiaQuick Spin Column (Qiagen) following manufacturer's protocol. A total of 400 ng of the purified PCR products were mixed with 2 μl 10× Taq polymerase PCR buffer (Enzymatics) and ultrapure water to a final volume of 20 μl, and subjected to a re-annealing process to enable heteroduplex formation: 95° C. for 10 min, 95° C. to 85° C. ramping at −2° C./s, 85° C. to 25° C. at −0.25° C./s, and 25° C. hold for 1 minute. After re-annealing, products were treated with Surveyor nuclease and Surveyor enhancer S (Transgenomics) following the manufacturer's recommended protocol, and analyzed on 4-20% Novex TBE poly-acrylamide gels (Life Technologies). Gels were stained with SYBR Gold DNA stain (Life Technologies) for 30 minutes and imaged with a Gel Doc gel imaging system (Bio-rad). Quantification was based on relative band intensities, as a measure of the fraction of cleaved DNA. FIG. 7 provides a schematic illustration of this Surveyor assay.

Restriction Fragment Length Polymorphism Assay for Detection of Homologous Recombination.

HEK 293FT and N2A cells were transfected with plasmid DNA, and incubated at 37° C. for 72 hours before genomic DNA extraction as described above. The target genomic region was PCR amplified using primers outside the homology arms of the homologous recombination (HR) template. PCR products were separated on a 1% agarose gel and extracted with MinElute GelExtraction Kit (Qiagen). Purified products were digested with HindIII (Fermentas) and analyzed on a 6% Novex TBE poly-acrylamide gel (Life Technologies).

RNA Secondary Structure Prediction and Analysis

RNA secondary structure prediction was performed using the online webserver RNAfold developed at Institute for Theoretical Chemistry at the University of Vienna, using the centroid structure prediction algorithm (see e.g. A. R. Gruber et al., 2008, Cell 106(1): 23-24; and PA Carr and GM Church, 2009, Nature Biotechnology 27(12): 1151-62).

RNA Purification

HEK 293FT cells were maintained and transfected as stated above. Cells were harvested by trypsinization followed by washing in phosphate buffered saline (PBS). Total cell RNA was extracted with TRI reagent (Sigma) following manufacturer's protocol. Extracted total RNA was quantified using Naonodrop (Thermo Scientific) and normalized to same concentration.

Northern Blot Analysis of crRNA and tracrRNA Expression in Mammalian Cells

RNAs were mixed with equal volumes of 2× loading buffer (Ambion), heated to 95° C. for 5 min, chilled on ice for 1 min, and then loaded onto 8% denaturing polyacrylamide gels (SequaGel, National Diagnostics) after pre-running the gel for at least 30 minutes. The samples were electrophoresed for 1.5 hours at 40 W limit. Afterwards, the RNA was transferred to Hybond N+ membrane (GE Healthcare) at 300 mA in a semi-dry transfer apparatus (Bio-rad) at room temperature for 1.5 hours. The RNA was crosslinked to the membrane using autocrosslink button on Stratagene UV Crosslinker the Stratalinker (Stratagene). The membrane was pre-hybridized in ULTRAhyb-Oligo Hybridization Buffer (Ambion) for 30 min with rotation at 42° C., and probes were then added and hybridized overnight. Probes were ordered from IDT and labeled with [gamma-$^{32}$P] ATP (Perkin Elmer) with T4 polynucleotide kinase (New England Biolabs). The membrane was washed once with pre-warmed (42° C.) 2×SSC, 0.5% SDS for 1 min followed by two 30 minute washes at 42° C. The membrane was exposed to a phosphor screen for one hour or overnight at room temperature and then scanned with a phosphorimager (Typhoon).

Bacterial CRISPR System Construction and Evaluation

Figure 6A:
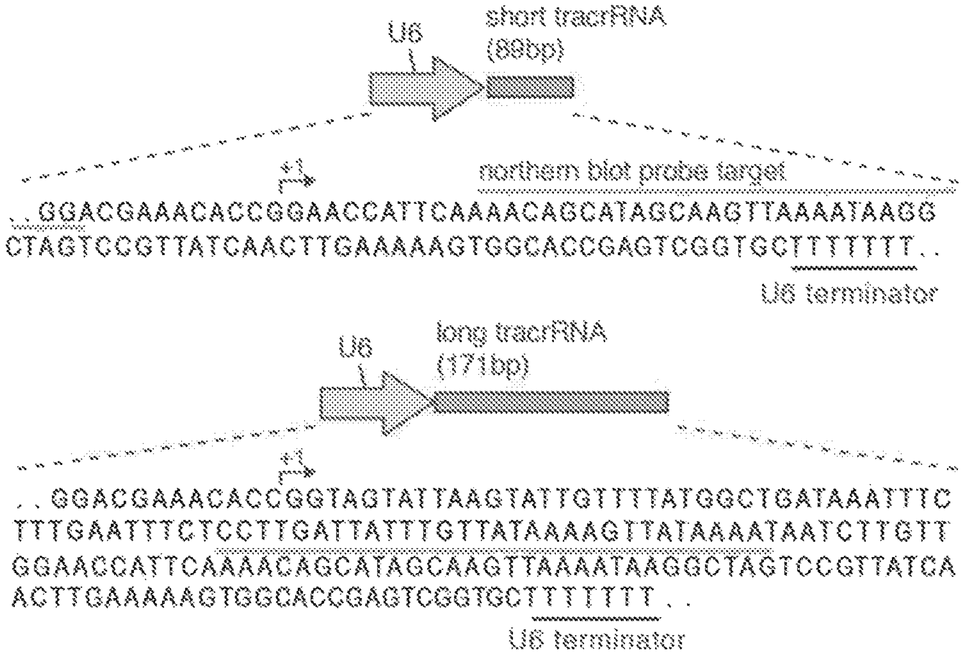
FIG. 6A-6C shows a comparison of different tracrRNA transcripts for Cas9-mediated gene targeting.
Figure 6B:
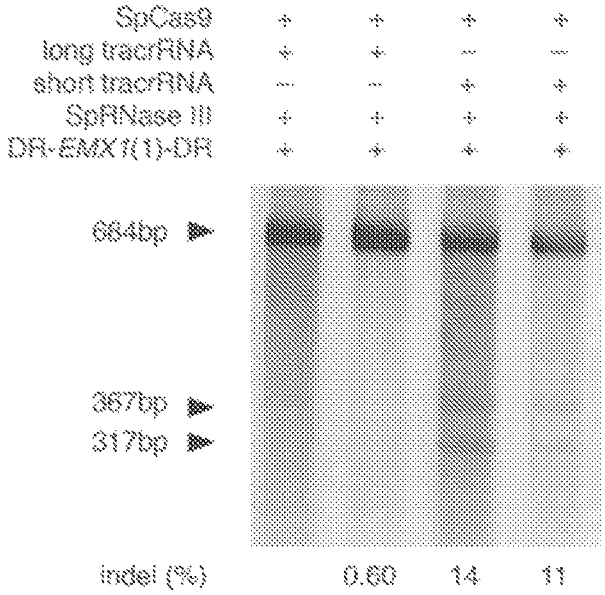
Figure 6C:
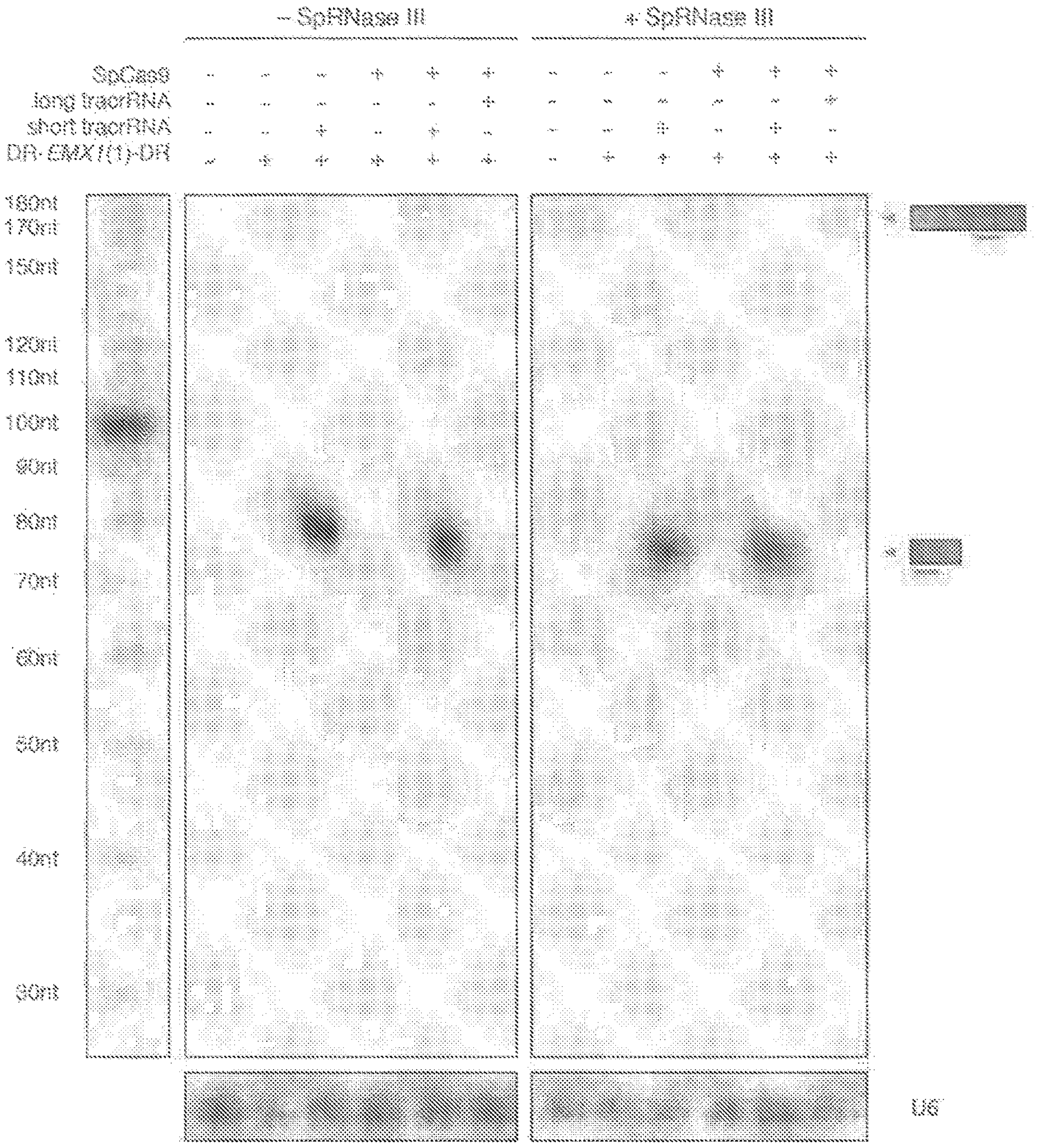

CRISPR locus elements, including tracrRNA, Cas9, and leader were PCR amplified from *Streptococcus pyogenes* SF370 genomic DNA with flanking homology arms for Gibson Assembly. Two BsaI type IIS sites were introduced in between two direct repeats to facilitate easy insertion of spacers (FIG. 8). PCR products were cloned into EcoRV-digested pACYC184 downstream of the tet promoter using Gibson Assembly Master Mix (NEB). Other endogenous CRISPR system elements were omitted, with the exception of the last 50 bp of Csn2. Oligos (Integrated DNA Technology) encoding spacers with complimentary overhangs were cloned into the BsaI-digested vector pDC000 (NEB) and then ligated with T7 ligase (Enzymatics) to generate pCRISPR plasmids. Challenge plasmids containing spacers with PAM expression in mammalian cells (expression constructs illustrated in FIG. 6A, with functionality as determined by results of the Surveyor assay shown in FIG. 6B). Transcription start sites are marked as +1, and transcription terminator and the sequence probed by northern blot are also indicated. Expression of processed tracrRNA was also confirmed by Northern blot. FIG. 6C shows results of a Northern blot analysis of total RNA extracted from 293FT cells transfected with U6 expression constructs carrying long or short tracrRNA, as well as SpCas9 and DR-EMX1(1)-DR. Left and right panels are from 293FT cells transfected without or with SpRNase III, respectively. U6 indicate loading control blotted with a probe targeting human U6 snRNA. Transfection of the short tracrRNA expression construct led to abundant levels of the processed form of tracrRNA (~75 bp). Very low amounts of long tracrRNA are detected on the Northern blot.

To promote precise transcriptional initiation, the RNA polymerase III-based U6 promoter was selected to drive the expression of tracrRNA (FIG. 2C). Similarly, a U6 promoter-based construct was developed to express a pre-crRNA array consisting of a single spacer flanked by two direct repeats (DRs, also encompassed by the term "tracr-mate sequences"; FIG. 2C). The initial spacer was designed to target a 33-base-pair (bp) target site (30-bp protospacer plus a 3-bp CRISPR motif (PAM) sequence satisfying the NGG recognition motif of Cas9) in the human EMX1 locus (FIG. 2C), a key gene in the development of the cerebral cortex.

Figure 2D:
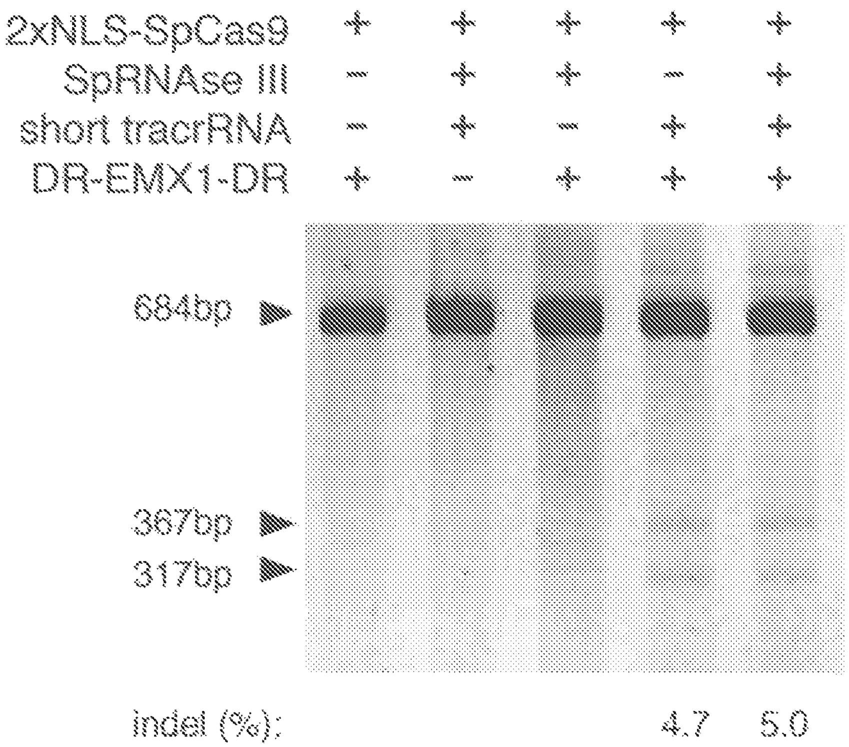

To test whether heterologous expression of the CRISPR system (SpCas9, SpRNase III, tracrRNA, and pre-crRNA) in mammalian cells can achieve targeted cleavage of mammalian chromosomes, HEK 293FT cells were transfected with combinations of CRISPR components. Since DSBs in mammalian nuclei are partially repaired by the non-homologous end joining (NHEJ) pathway, which leads to the formation of indels, the Surveyor assay was used to detect potential cleavage activity at the target EMX1 locus (FIG. 7) (see e.g. Guschin et al., 2010, Methods Mol Biol 649: 247). Co-transfection of all four CRISPR components was able to induce up to 5.0% cleavage in the protospacer (see FIG. 2D). Co-transfection of all CRISPR components minus SpRNase III also induced up to 4.7% indel in the protospacer, suggesting that there may be endogenous mammalian RNases that are capable of assisting with crRNA maturation, such as for example the related Dicer and Drosha enzymes. Removing any of the remaining three components abolished the genome cleavage activity of the CRISPR system (FIG. 2D). Sanger sequencing of amplicons containing the target locus verified the cleavage activity: in 43 sequenced clones, 5 mutated alleles (11.6%) were found. Similar experiments using a variety of guide sequences produced indel percentages as high as 29% (see FIGS. 3-6, 10, and 11). These results define a three-component system for efficient CRISPR-mediated genome modification in mammalian cells. To optimize the cleavage efficiency, Applicants also tested whether different isoforms of tracrRNA affected the cleavage efficiency and found that, in this example system, only the short (89-bp) transcript form was able to mediate cleavage of the human EMX1 genomic locus (FIG. 6B).

Figure 12A:
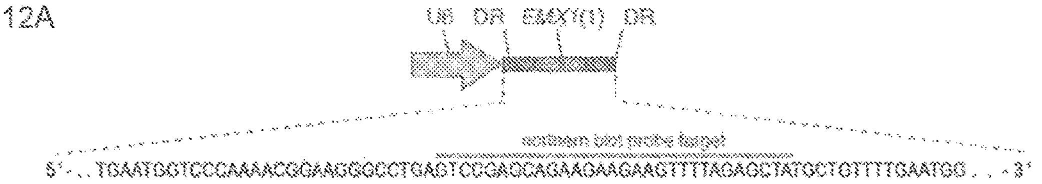
FIG. 12A-12B shows the results of a Northern blot analysis of crRNA processing in mammalian cells.
Figure 12B:
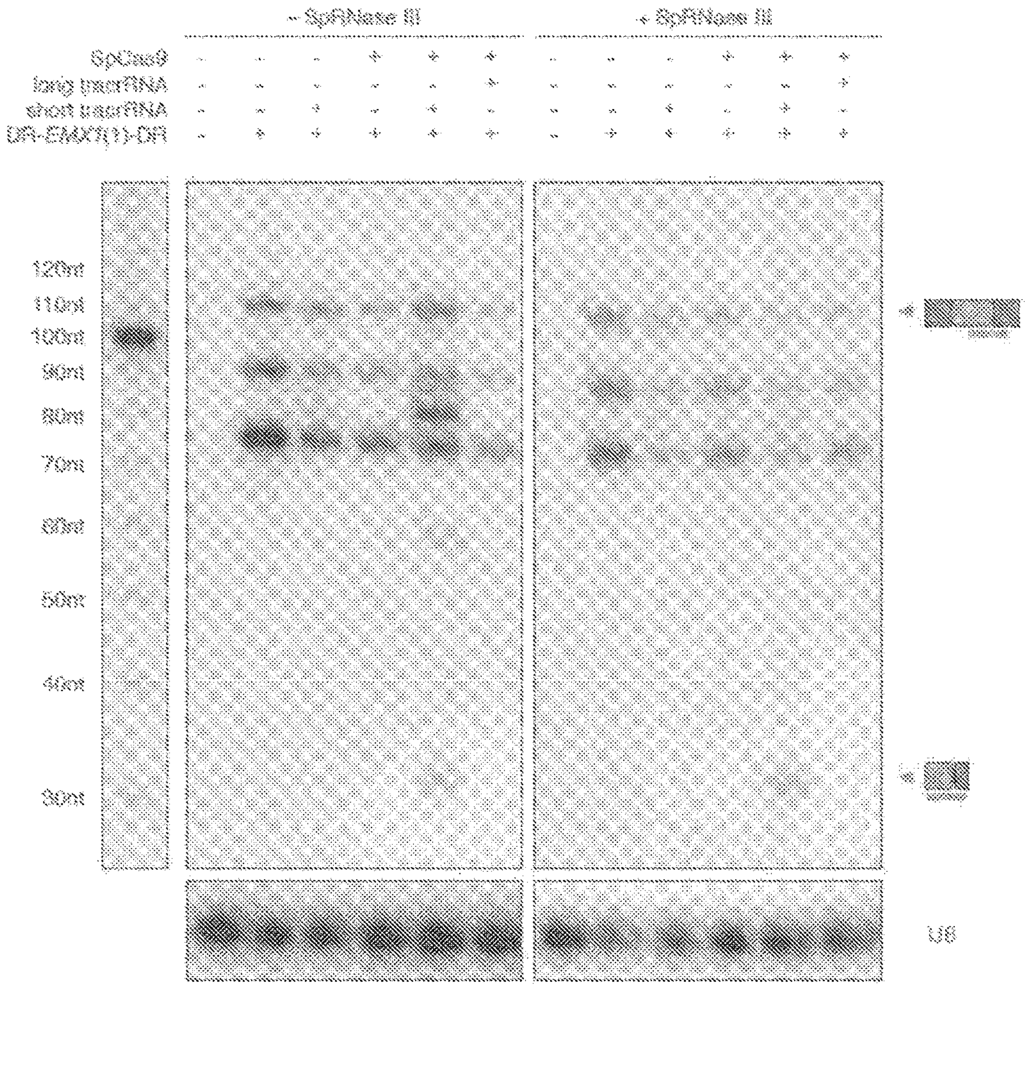

FIG. 12 provides an additional Northern blot analysis of crRNA processing in mammalian cells. FIG. 12A illustrates a schematic showing the expression vector for a single spacer flanked by two direct repeats (DR-EMX1(1)-DR). The 30 bp spacer targeting the human EMX1 locus protospacer 1 (see FIG. 6) and the direct repeat sequences are shown in the sequence beneath FIG. 12A. The line indicates the region whose reverse-complement sequence was used to generate Northern blot probes for EMX1(1) crRNA detection. FIG. 12B shows a Northern blot analysis of total RNA extracted from 293FT cells transfected with U6 expression constructs carrying DR-EMX1(1)-DR. Left and right panels are from 293FT cells transfected without or with SpRNase III respectively. DR-EMX1(1)-DR was processed into mature crRNAs only in the presence of SpCas9 and short tracrRNA and was not dependent on the presence of SpRNase III. The mature crRNA detected from transfected 293FT total RNA is ~33 bp and is shorter than the 39-42 bp mature crRNA from *S. pyogenes*. These results demonstrate that a CRISPR system can be transplanted into eukaryotic cells and reprogrammed to facilitate cleavage of endogenous mammalian target polynucleotides.

FIG. 2 illustrates the bacterial CRISPR system described in this example. FIG. 2A illustrates a schematic showing the CRISPR locus 1 from *Streptococcus pyogenes* SF370 and a proposed mechanism of CRISPR-mediated DNA cleavage by this system. Mature crRNA processed from the direct repeat-spacer array directs Cas9 to genomic targets consisting of complimentary protospacers and a protospacer-adjacent motif (PAM). Upon target-spacer base pairing, Cas9 mediates a double-strand break in the target DNA. FIG. 2B illustrates engineering of *S. pyogenes* Cas9 (SpCas9) and RNase III (SpRNase III) with nuclear localization signals (NLSs) to enable import into the mammalian nucleus. FIG. 2C illustrates mammalian expression of SpCas9 and SpRNase III driven by the constitutive EF1a promoter and tracrRNA and pre-crRNA array (DR-Spacer-DR) driven by the RNA Pol3 promoter U6 to promote precise transcription initiation and termination. A protospacer from the human EMX1 locus with a satisfactory PAM sequence is used as the spacer in the pre-crRNA array. FIG. 2D illustrates surveyor nuclease assay for SpCas9-mediated minor insertions and deletions. SpCas9 was expressed with and without SpRNase III, tracrRNA, and a pre-crRNA array carrying the EMX1-target spacer. FIG. 2E illustrates a schematic representation of base pairing between target locus and EMX1-targeting crRNA, as well as an example chromatogram showing a micro deletion adjacent to the SpCas9 cleavage site. FIG. 2F illustrates mutated alleles identified from sequencing analysis of 43 clonal amplicons showing a variety of micro insertions and deletions. Dashes indicate deleted bases, and non-aligned or mismatched bases indicate insertions or mutations. Scale bar=10 μm.

Figure 8A:
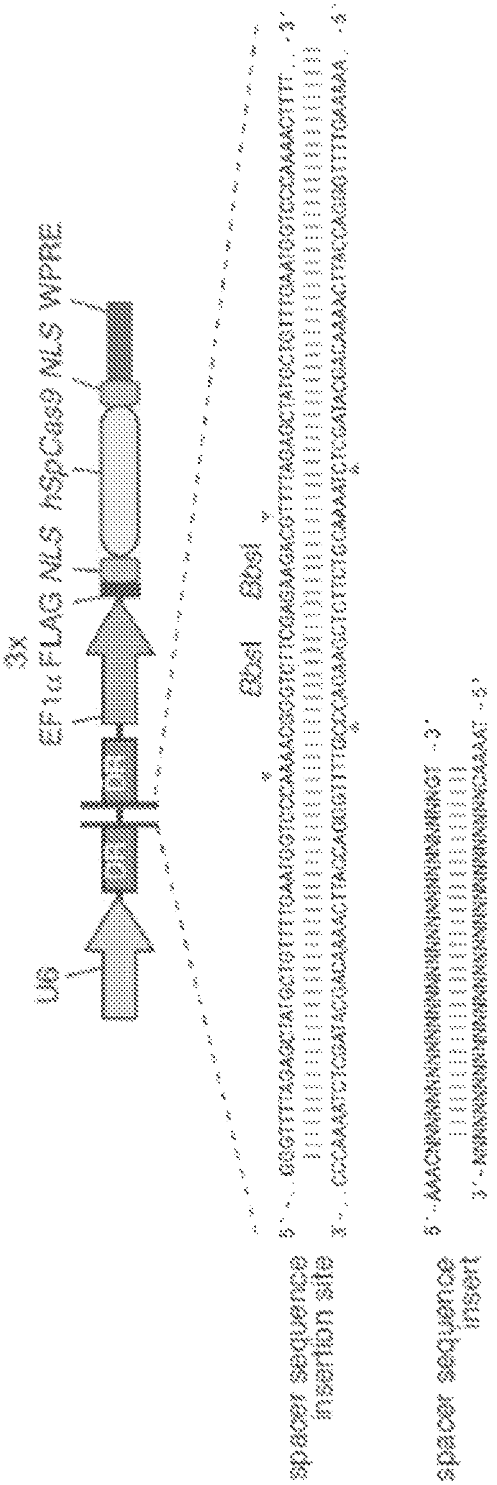
FIG. 8A-8B shows exemplary bicistronic expression vectors for expression of CRISPR system elements in eukaryotic cells.
Figure 8B:
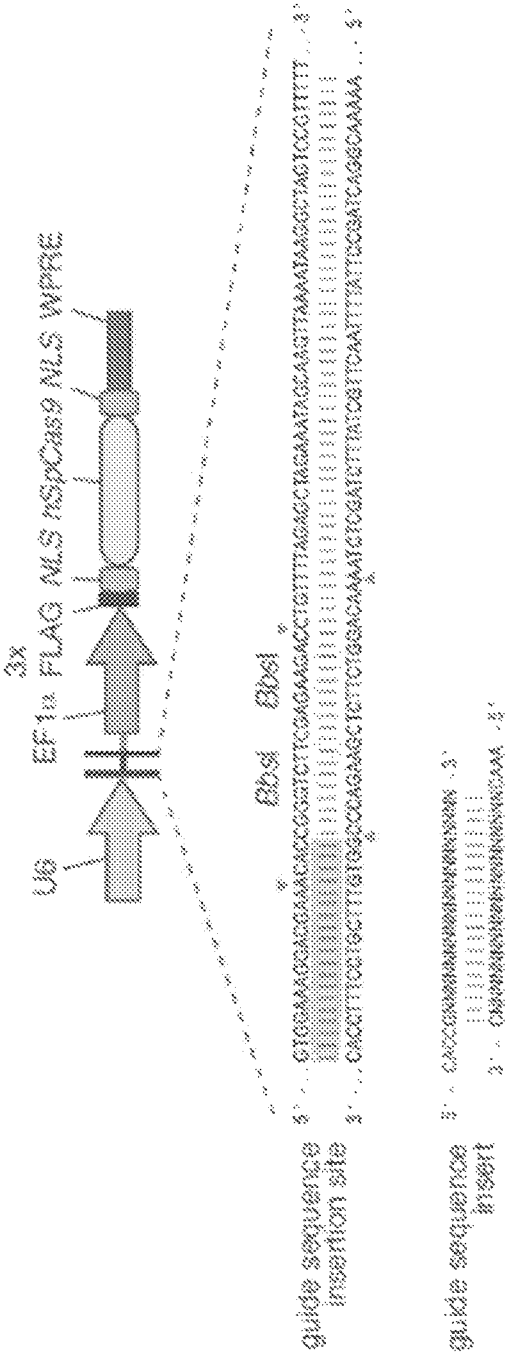

To further simplify the three-component system, a chimeric crRNA-tracrRNA hybrid design was adapted, where a mature crRNA (comprising a guide sequence) may be fused to a partial tracrRNA via a stem-loop to mimic the natural crRNA:tracrRNA duplex. To increase co-delivery efficiency, a bicistronic expression vector was created to drive co-expression of a chimeric RNA and SpCas9 in transfected cells. In parallel, the bicistronic vectors were used to express a pre-crRNA (DR-guide sequence-DR) with SpCas9, to induce processing into crRNA with a separately expressed tracrRNA (compare FIG. 11B top and bottom). FIG. 8 provides schematic illustrations of bicistronic expression vectors for pre-crRNA array (FIG. 8A) or chimeric crRNA (represented by the short line downstream of the guide sequence insertion site and upstream of the EF1α promoter in FIG. 8B) with hSpCas9, showing location of various elements and the point of guide sequence insertion. The expanded sequence around the location of the guide sequence insertion site in FIG. 8B also shows a partial DR sequence (GTTTTAGAGCTA SEQ ID NO: 90) and a partial tracrRNA sequence (TAGCAAGTTAAAATAAGGCTAGTCCGTTTTT SEQ ID NO: 91). Guide sequences can be inserted between BbsI sites using annealed oligonucleotides. Sequence design for the oligonucleotides are shown below the schematic illustrations in FIG. 8, with appropriate ligation adapters indicated. WPRE represents the Woodchuck hepatitis virus post-transcriptional regulatory element. The efficiency of chimeric RNA-mediated cleavage was tested by targeting the same EMX1 locus described above. Using both Surveyor assay and Sanger sequencing of amplicons, Applicants confirmed that the chimeric RNA design facilitates cleavage of human EMX1 locus with approximately a 4.7% modification rate (FIG. 3).

Figure 13A:
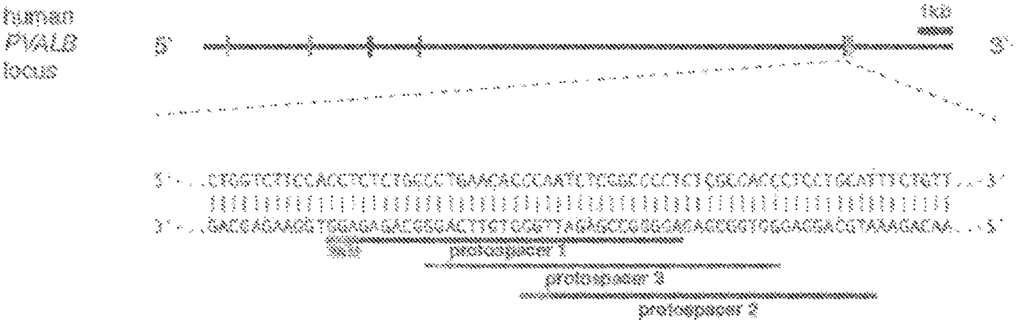
FIG. 13A-13B shows an exemplary selection of protospacers in the human PVALB (SEQ ID NO: 662) and mouse Th loci (SEQ ID NO: 663).
Figure 13B:
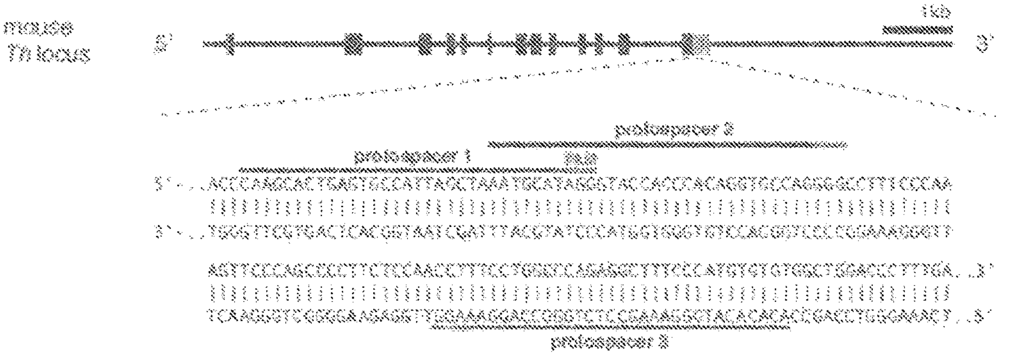

Generalizability of CRISPR-mediated cleavage in eukaryotic cells was tested by targeting additional genomic loci in both human and mouse cells by designing chimeric RNA targeting multiple sites in the human EMX1 and PVALB, as well as the mouse Th loci. FIG. 13 illustrates the selection of some additional targeted protospacers in human PVALB (FIG. 13A) and mouse Th (FIG. 13B) loci. Schematics of the gene loci and the location of three protospacers within the last exon of each are provided. The underlined sequences include 30 bp of protospacer sequence and 3 bp at the 3' end corresponding to the PAM sequences. Protospacers on the sense and anti-sense strands are indicated above and below the DNA sequences, respectively. A modification rate of 6.3% and 0.75% was achieved for the human PVALB and mouse Th loci respectively, demonstrating the broad applicability of the CRISPR system in modifying different loci across multiple organisms (FIG. 5). While cleavage was only detected with one out of three spacers for each locus using the chimeric constructs, all target sequences were cleaved with efficiency of indel production reaching 27% when using the co-expressed pre-crRNA arrangement (FIGS. 6 and 13).

Figures 11A, 11B, 11C:
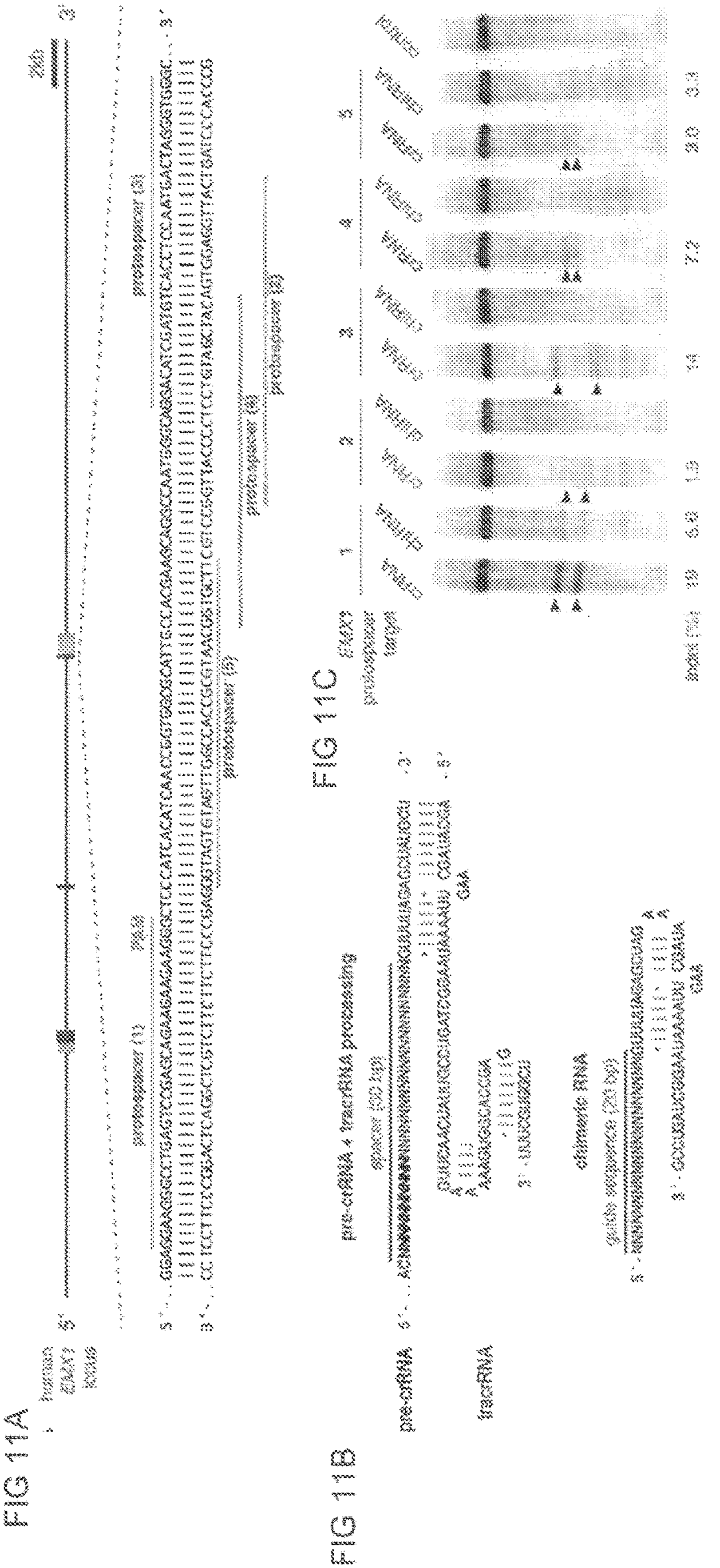
FIG. 11A-11C shows exemplary manipulations of a CRISPR system for targeting of genomic loci in mammalian cells.

FIG. 11 provides a further illustration that SpCas9 can be reprogrammed to target multiple genomic loci in mammalian cells. FIG. 11A provides a schematic of the human EMX1 locus showing the location of five protospacers, indicated by the underlined sequences. FIG. 11B provides a schematic of the pre-crRNA/trcrRNA complex showing hybridization between the direct repeat region of the pre-crRNA and tracrRNA (top), and a schematic of a chimeric RNA design comprising a 20 bp guide sequence, and tracr mate and tracr sequences consisting of partial direct repeat and tracrRNA sequences hybridized in a hairpin structure (bottom). Results of a Surveyor assay comparing the efficacy of Cas9-mediated cleavage at five protospacers in the human EMX1 locus is illustrated in FIG. 11C. Each protospacer is targeted using either processed pre-crRNA/tracrRNA complex (crRNA) or chimeric RNA (chiRNA).

Since the secondary structure of RNA can be crucial for intermolecular interactions, a structure prediction algorithm based on minimum free energy and Boltzmann-weighted structure ensemble was used to compare the putative secondary structure of all guide sequences used in the genome targeting experiment (see e.g. Gruber et al., 2008, Nucleic Acids Research, 36: W70). Analysis revealed that in most cases, the effective guide sequences in the chimeric crRNA context were substantially free of secondary structure motifs, whereas the ineffective guide sequences were more likely to form internal secondary structures that could prevent base pairing with the target protospacer DNA. It is thus possible that variability in the spacer secondary structure might impact the efficiency of CRISPR-mediated interference when using a chimeric crRNA.

Figure 22A:
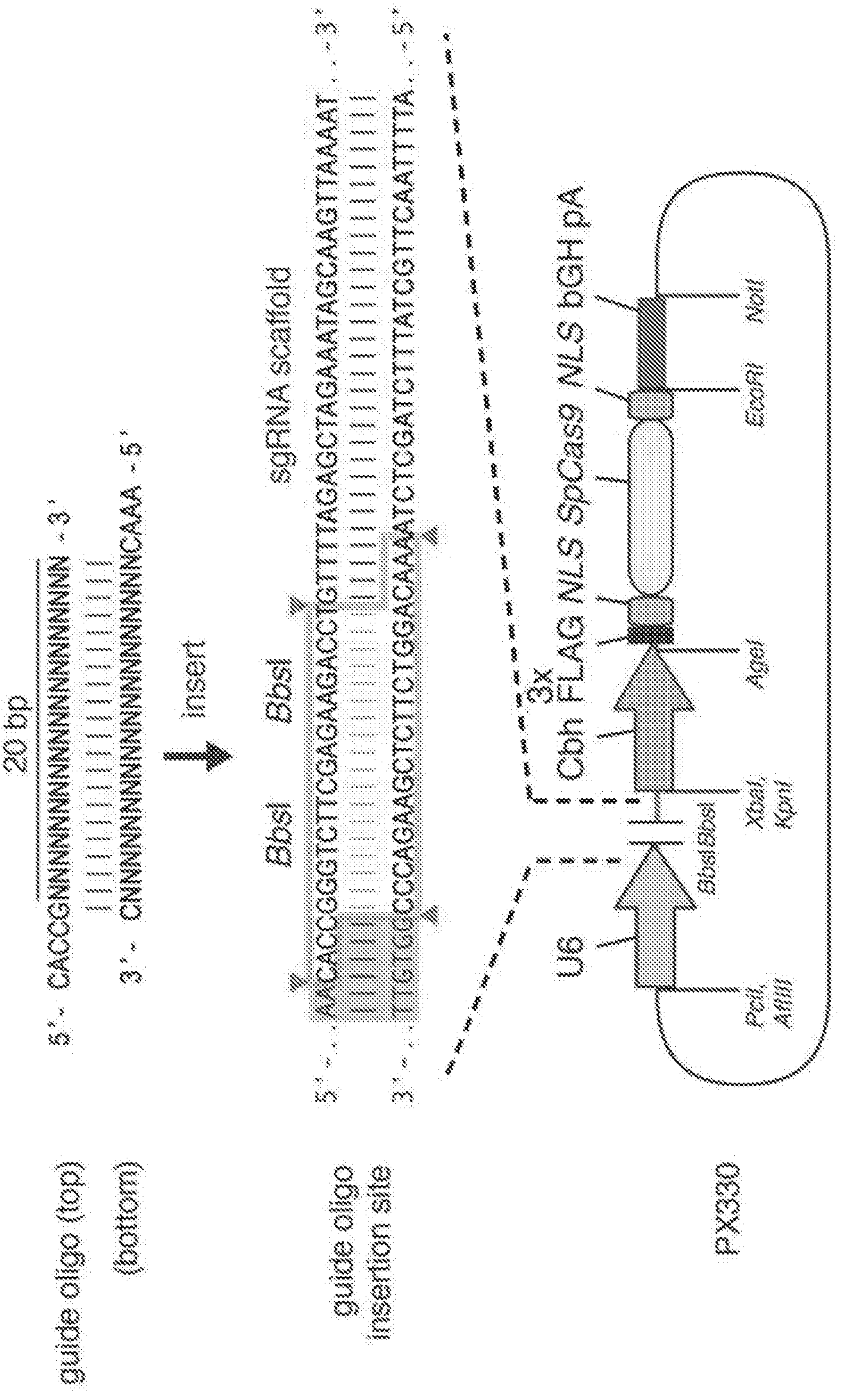
FIG. 22A-22B shows single vector designs for SpCas9.
Figure 22B:
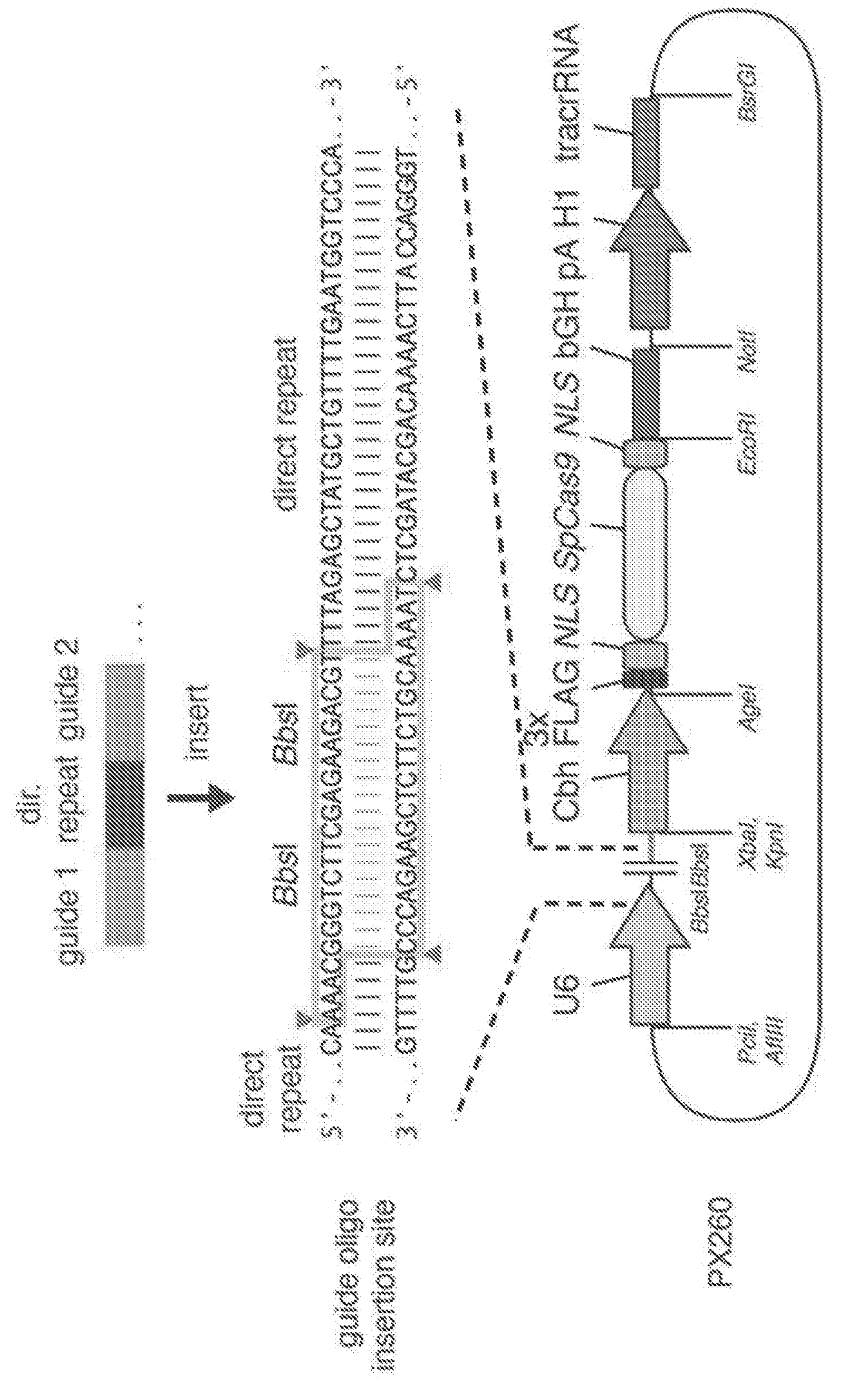

Further vector designs for SpCas9 are shown in FIG. 22, which illustrates single expression vectors incorporating a U6 promoter linked to an insertion site for a guide oligo, and a Cbh promoter linked to SpCas9 coding sequence. The vector shown in FIG. **22*b*** includes a tracrRNA coding sequence linked to an H1 promoter.

Figure 3A:
FIG. 3A-3D shows results of an evaluation of SpCas9 specificity for an example target.
Figure 3B:
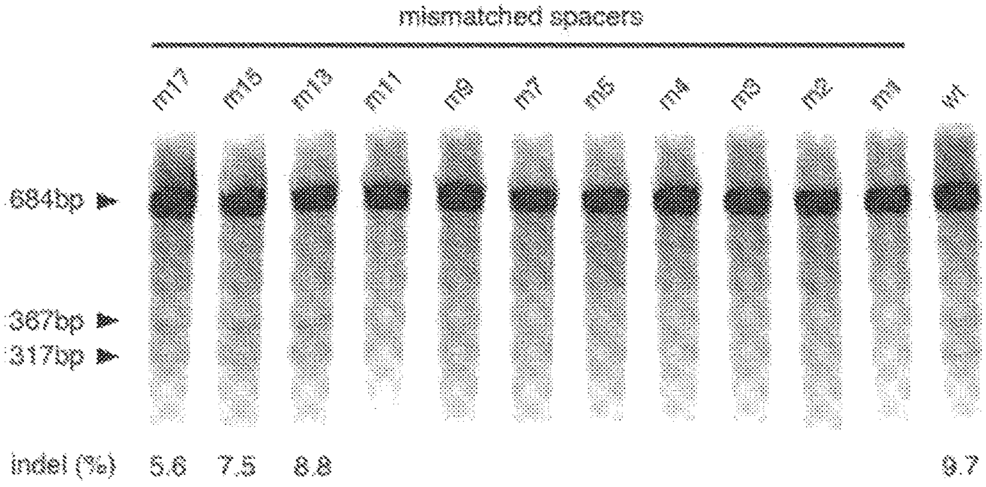
Figure 3C:
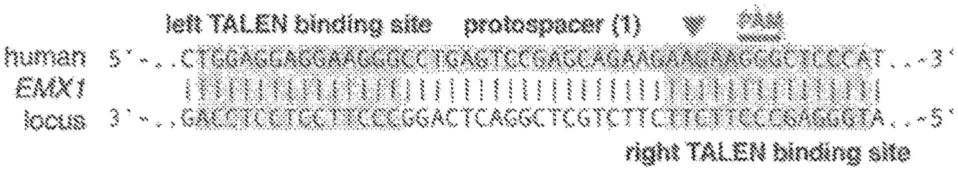

In the bacterial assay, all spacers facilitated efficient CRISPR interference (FIG. 3C). These results suggest that there may be additional factors affecting the efficiency of CRISPR activity in mammalian cells.

Figure 3D:
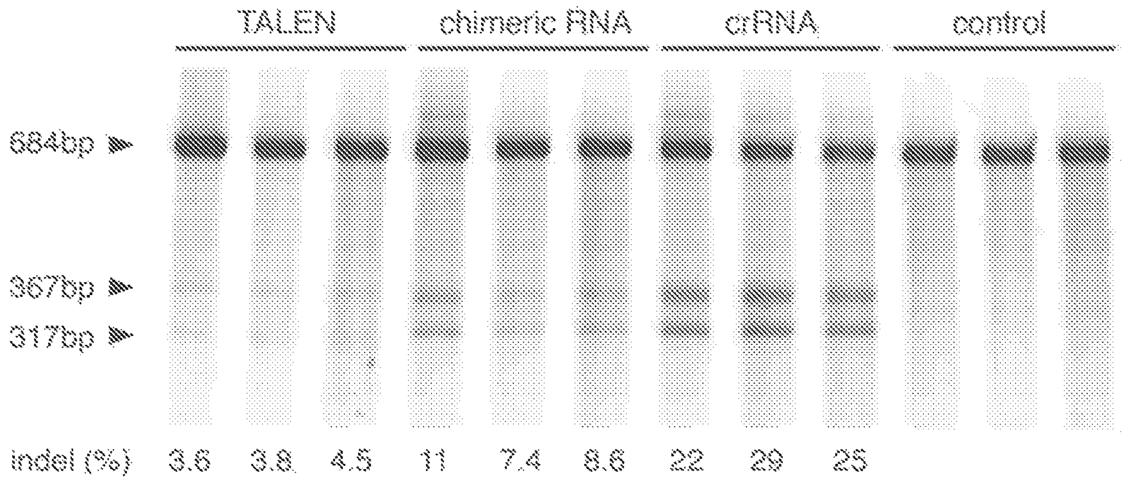

To investigate the specificity of CRISPR-mediated cleavage, the effect of single-nucleotide mutations in the guide sequence on protospacer cleavage in the mammalian genome was analyzed using a series of EMX1-targeting chimeric crRNAs with single point mutations (FIG. 3A). FIG. 3B illustrates results of a Surveyor nuclease assay comparing the cleavage efficiency of Cas9 when paired with different mutant chimeric RNAs. Single-base mismatch up to 12-bp 5' of the PAM substantially abrogated genomic cleavage by SpCas9, whereas spacers with mutations at farther upstream positions retained activity against the original protospacer target (FIG. 3B). In addition to the PAM, SpCas9 has single-base specificity within the last 12-bp of the spacer. Furthermore, CRISPR is able to mediate genomic cleavage as efficiently as a pair of TALE nucleases (TALEN) targeting the same EMX1 protospacer. FIG. 3C provides a schematic showing the design of TALENs targeting EMX1, and FIG. 3D shows a Surveyor gel comparing the efficiency of TALEN and Cas9 (n=3).

Figure 4A:
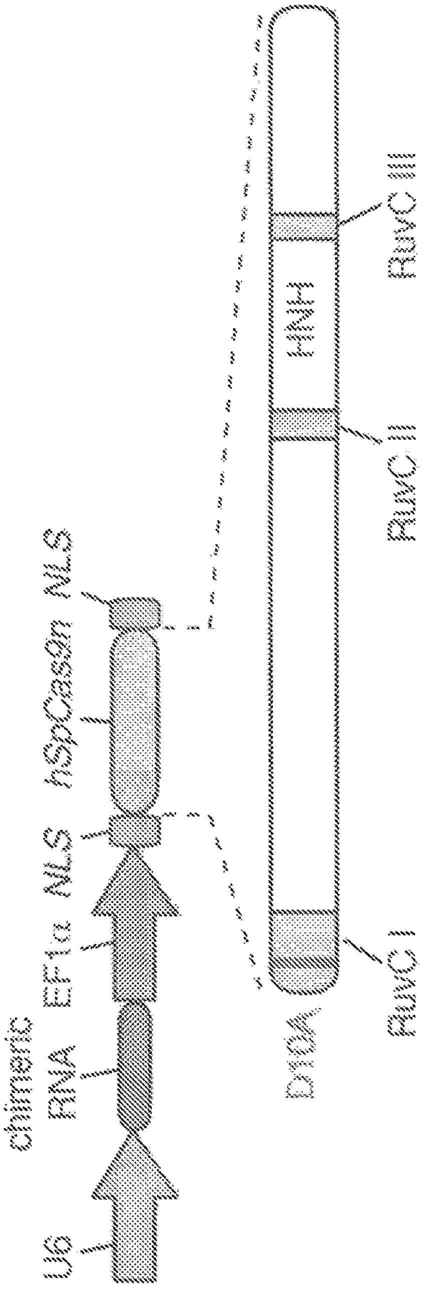
FIG. 4A-4G show an exemplary vector system and results for its use in directing homologous recombination in eukaryotic cells.
Figure 4B:
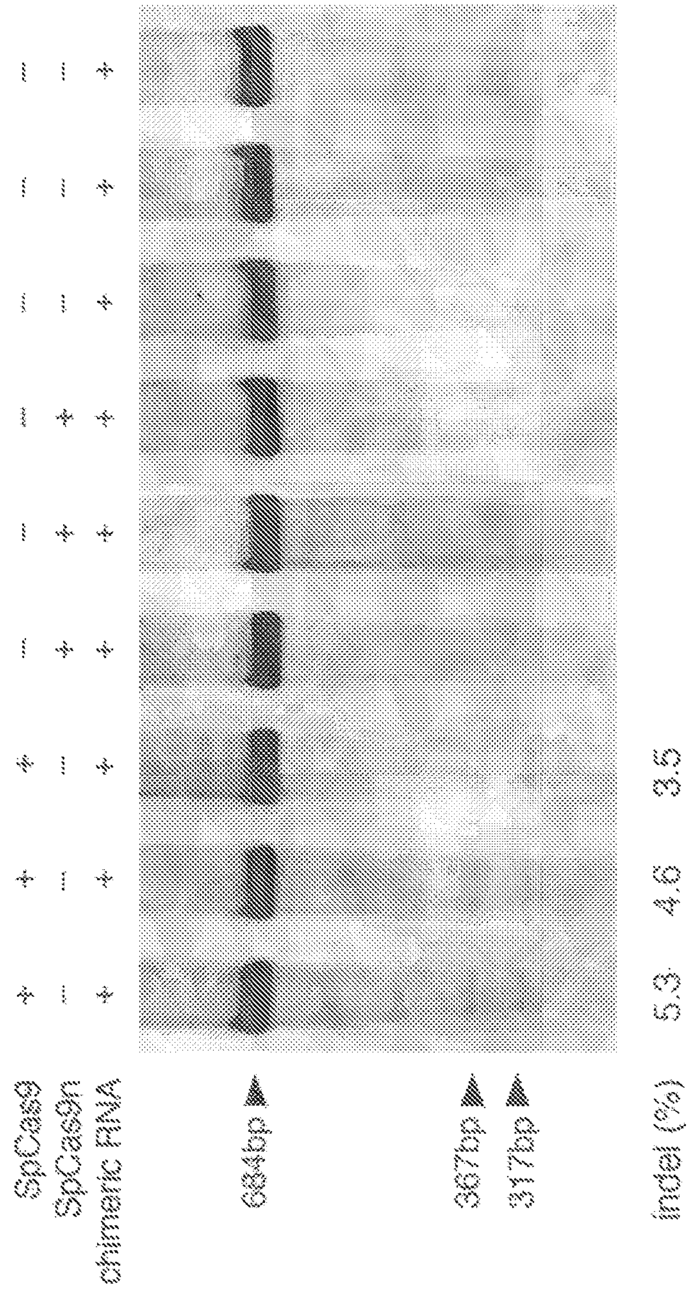
Figure 4C:
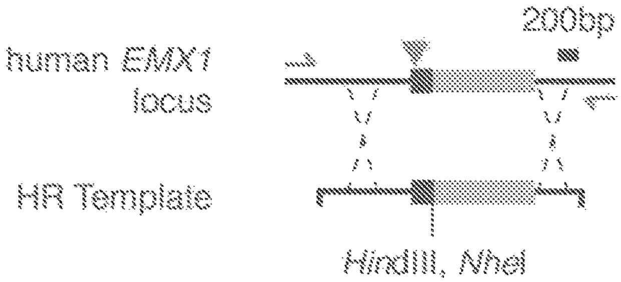
Figure 4D:
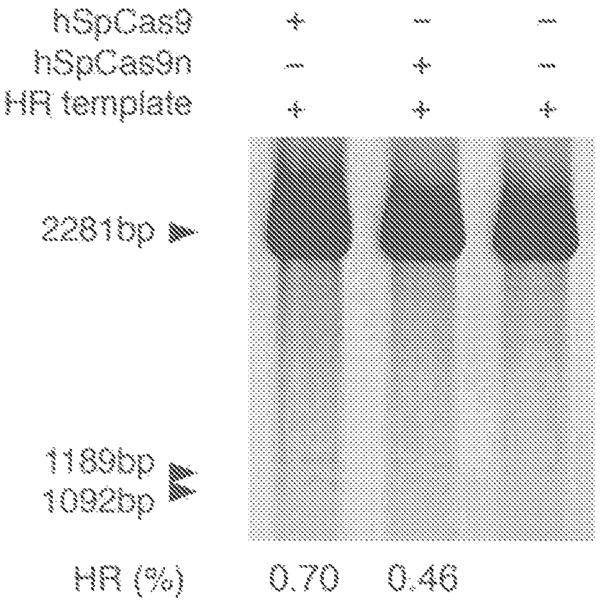
Figure 4E:
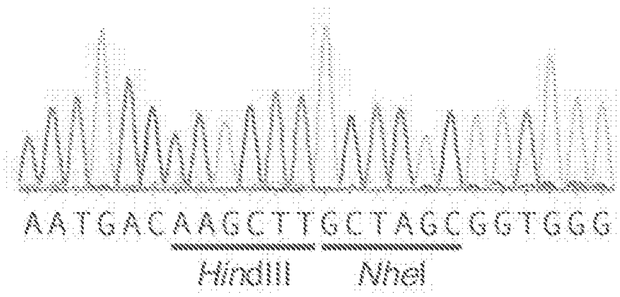

Having established a set of components for achieving CRISPR-mediated gene editing in mammalian cells through the error-prone NHEJ mechanism, the ability of CRISPR to stimulate homologous recombination (HR), a high fidelity gene repair pathway for making precise edits in the genome, was tested. The wild type SpCas9 is able to mediate site-specific DSBs, which can be repaired through both NHEJ and HR. In addition, an aspartate-to-alanine substitution (D10A) in the RuvC I catalytic domain of SpCas9 was engineered to convert the nuclease into a nickase (SpCas9n; illustrated in FIG. 4A) (see e.g. Sapranausaks et al., 2011, Nucleic Acids Resch, 39: 9275; Gasiunas et al., 2012, Proc. Natl. Acad. Sci. USA, 109:E2579), such that nicked genomic DNA undergoes the high-fidelity homology-directed repair (HDR). Surveyor assay confirmed that SpCas9n does not generate indels at the EMX1 protospacer target. As illustrated in FIG. 4B, co-expression of EMX1-targeting chimeric crRNA with SpCas9 produced indels in the target site, whereas co-expression with SpCas9n did not (n=3). Moreover, sequencing of 327 amplicons did not detect any indels induced by SpCas9n. The same locus was selected to test CRISPR-mediated HR by co-transfecting HEK 293FT cells with the chimeric RNA targeting EMX1, hSpCas9 or hSpCas9n, as well as a HR template to introduce a pair of restriction sites (HindIII and NheI) near the protospacer. FIG. 4C provides a schematic illustration of the HR strategy, with relative locations of recombination points and primer annealing sequences (arrows). SpCas9 and SpCas9n indeed catalyzed integration of the HR template into the EMX1 locus. PCR amplification of the target region followed by restriction digest with HindIII revealed cleavage products corresponding to expected fragment sizes (arrows in restriction fragment length polymorphism gel analysis shown in FIG. 4D), with SpCas9 and SpCas9n mediating similar levels of HR efficiencies. Applicants further verified HR using Sanger sequencing of genomic amplicons (FIG. 4E). These results demonstrate the utility of CRISPR for facilitating targeted gene insertion in the mammalian genome. Given the 14-bp (12-bp from the spacer and 2-bp from the PAM) target specificity of the wild type SpCas9, the availability of a nickase can significantly reduce the likelihood of off-target modifications, since single strand breaks are not substrates for the error-prone NHEJ pathway.

Figure 4F:
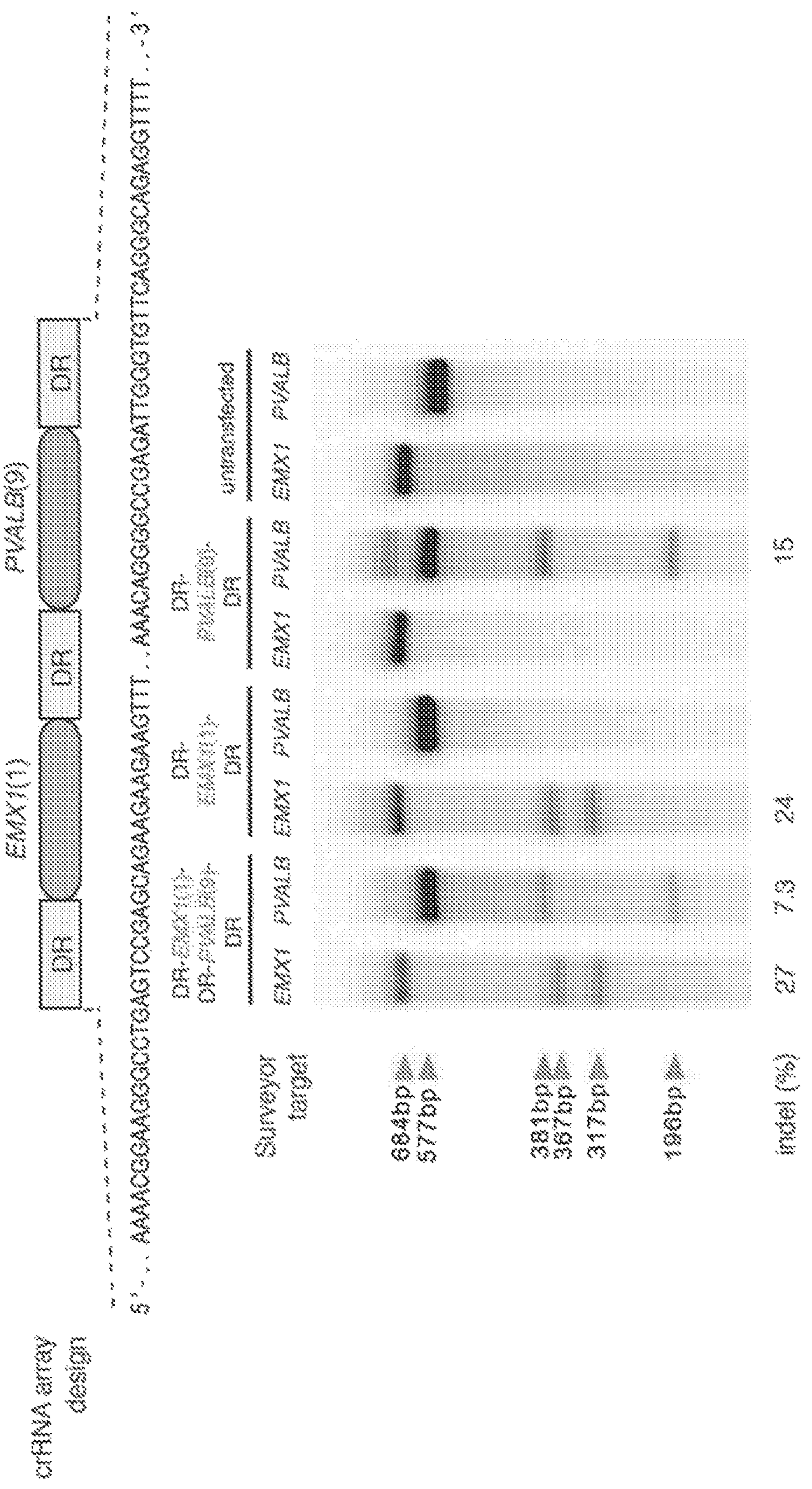
Figure 4G:
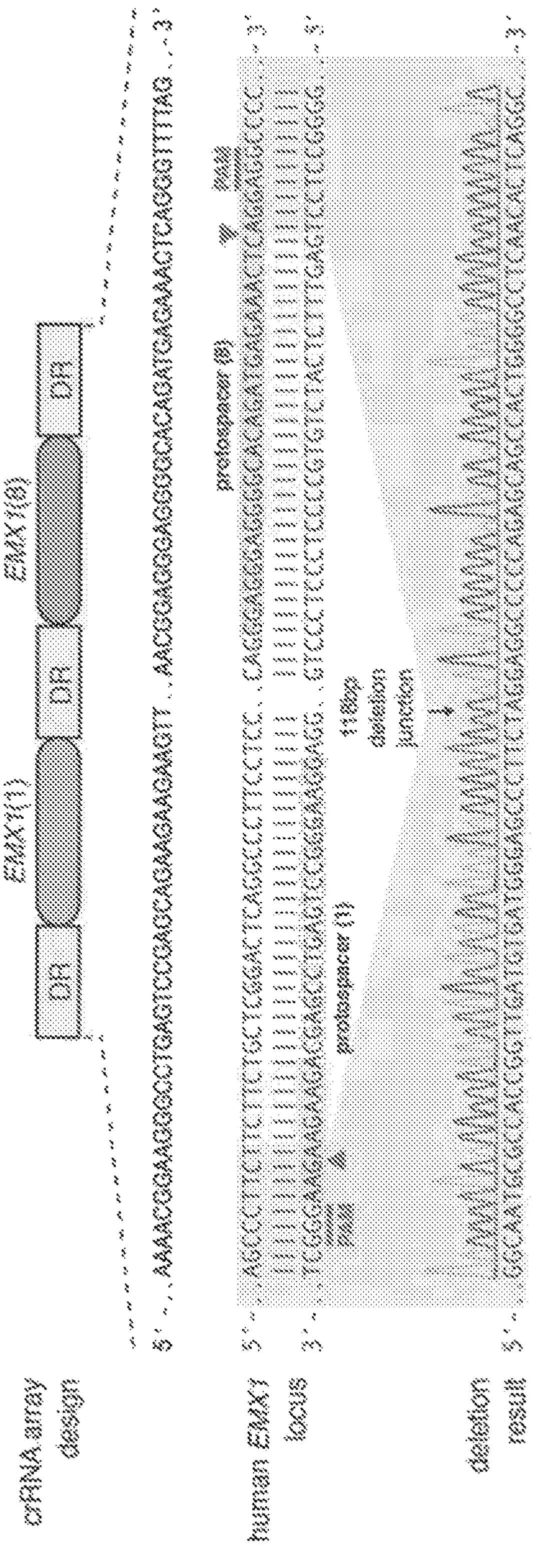

Expression constructs mimicking the natural architecture of CRISPR loci with arrayed spacers (FIG. 2A) were constructed to test the possibility of multiplexed sequence targeting. Using a single CRISPR array encoding a pair of EMX1- and PVALB-targeting spacers, efficient cleavage at both loci was detected (FIG. 4F, showing both a schematic design of the crRNA array and a Surveyor blot showing efficient mediation of cleavage). Targeted deletion of larger genomic regions through concurrent DSBs using spacers against two targets within EMX1 spaced by 119 bp was also tested, and a 1.6% deletion efficacy (3 out of 182 amplicons; FIG. 4G) was detected. This demonstrates that the CRISPR system can mediate multiplexed editing within a single genome.

Example 2: CRISPR System Modifications and Alternatives

Figure 10A:
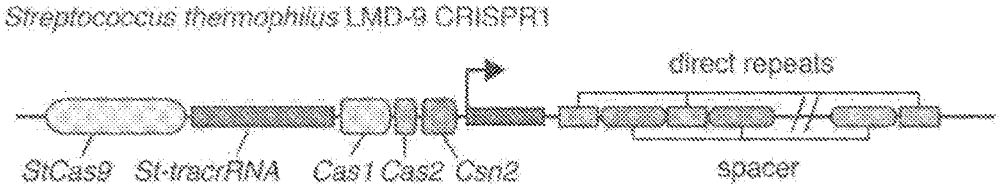
FIG. 10A-10D shows an exemplary CRISPR system, an example adaptation for expression in eukaryotic cells, and results of tests assessing CRISPR activity.
Figure 10B:
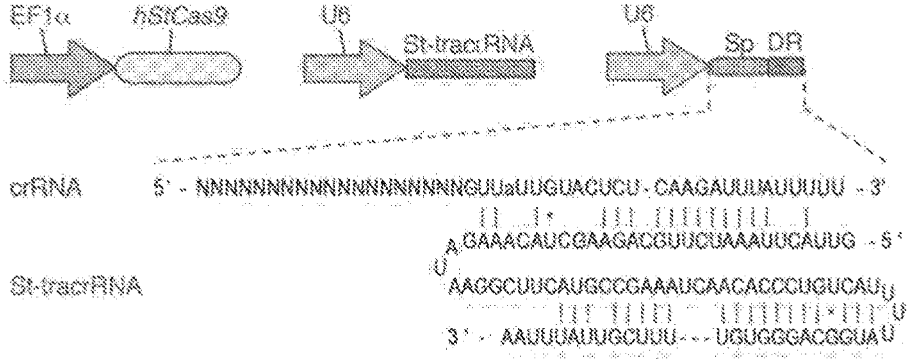
Figure 10C:
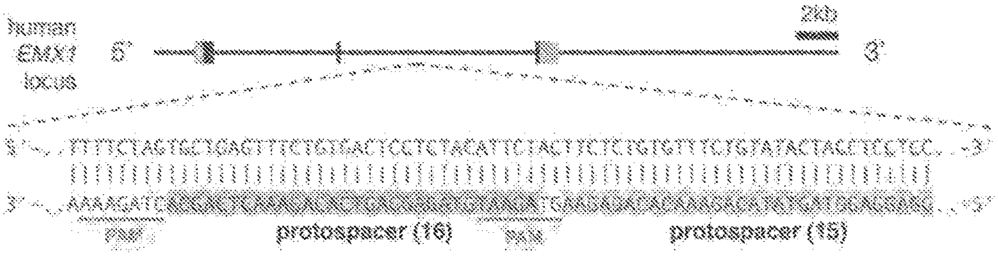
Figure 10D:
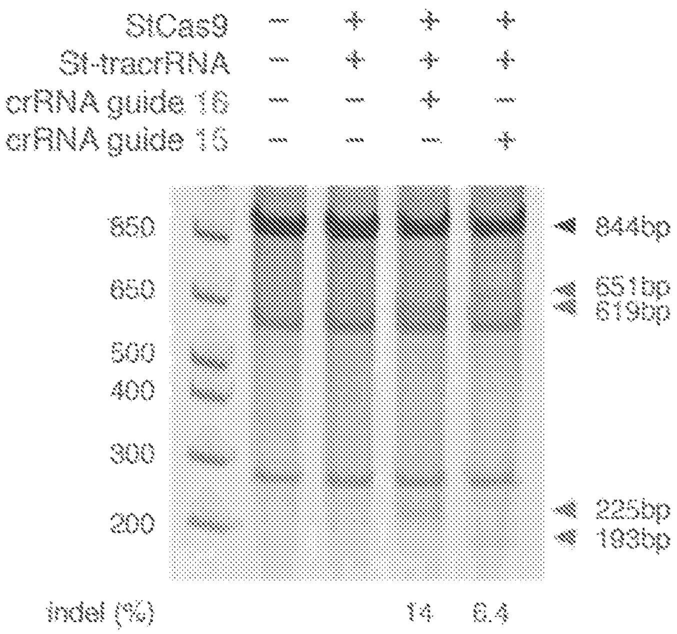
Figure 14:
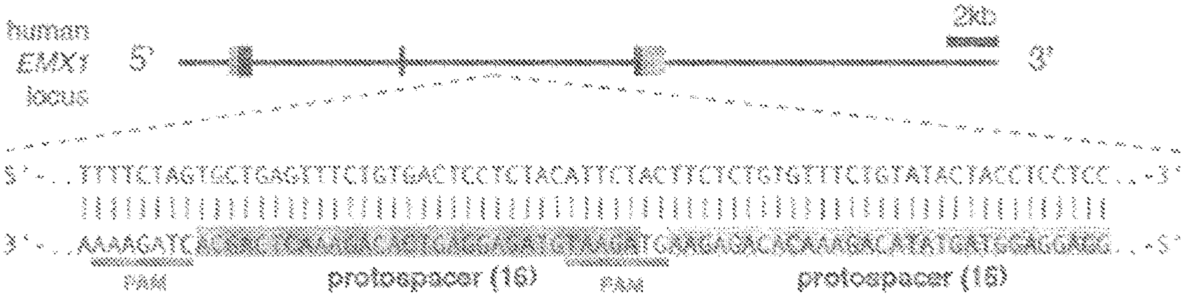
FIG. 14 shows example protospacer and corresponding PAM sequence targets of the *S. thermophilus* CRISPR system in the human EMX1 locus.

The ability to use RNA to program sequence-specific DNA cleavage defines a new class of genome engineering tools for a variety of research and industrial applications. Several aspects of the CRISPR system can be further improved to increase the efficiency and versatility of CRISPR targeting. Optimal Cas9 activity may depend on the availability of free $Mg^{2+}$ at levels higher than that present in the mammalian nucleus (see e.g. Jinek et al., 2012, Science, 337:816), and the preference for an NGG motif immediately downstream of the protospacer restricts the ability to target on average every 12-bp in the human genome (FIG. 9, evaluating both plus and minus strands of human chromosomal sequences). Some of these constraints can be overcome by exploring the diversity of CRISPR loci across the microbial metagenome (see e.g. Makarova et al., 2011, Nat Rev Microbiol, 9:467). Other CRISPR loci may be transplanted into the mammalian cellular milieu by a process similar to that described in Example 1. For example, FIG. 10 illustrates adaptation of the Type II CRISPR system from CRISPR 1 of *Streptococcus thermophilus* LMD-9 for heterologous expression in mammalian cells to achieve CRISPR-mediated genome editing. FIG. 10A provides a Schematic illustration of CRISPR 1 from *S. thermophilus* LMD-9. FIG. 10B illustrates the design of an expression system for the *S. thermophilus* CRISPR system. Human codon-optimized hStCas9 is expressed using a constitutive EF1a promoter. Mature versions of tracrRNA and crRNA are expressed using the U6 promoter to promote precise transcription initiation. Sequences from the mature crRNA and tracrRNA are illustrated. A single base indicated by the lower case "a" in the crRNA sequence is used to remove the polyU sequence, which serves as a RNA polIII transcriptional terminator. FIG. 10C provides a schematic showing guide sequences targeting the human EMX1 locus. FIG. 10D shows the results of hStCas9-mediated cleavage in the target locus using the Surveyor assay. RNA guide spacers 1 and 2 induced 14% and 6.4%, respectively. Statistical analysis of cleavage activity across biological replica at these two protospacer sites is also provided in FIG. 5. FIG. 14 provides a schematic of additional protospacer and corresponding PAM sequence targets of the *S. thermophilus* CRISPR system in the human EMX1 locus. Two protospacer sequences are highlighted and their corresponding PAM sequences satisfying NNAGAAW motif are indicated by underlining 3' with respect to the corresponding highlighted sequence. Both protospacers target the anti-sense strand.

Example 3: Sample Target Sequence Selection Algorithm

A software program is designed to identify candidate CRISPR target sequences on both strands of an input DNA sequence based on desired guide sequence length and a CRISPR motif sequence (PAM) for a specified CRISPR enzyme. For example, target sites for Cas9 from *S. pyogenes*, with PAM sequences NGG, may be identified by searching for 5'-$N_x$-NGG-3' both on the input sequence and on the reverse-complement of the input. Likewise, target sites for Cas9 of *S. thermophilus* CRISPR1, with PAM sequence NNAGAAW, may be identified by searching for 5'-$N_x$-NNAGAAW-3' (SEQ ID NO: 92) both on the input sequence and on the reverse-complement of the input. Likewise, target sites for Cas9 of *S. thermophilus* CRISPR3, with PAM sequence NGGNG, may be identified by searching for 5'-$N_x$-NGGNG-3' both on the input sequence and on the reverse-complement of the input. The value "x" in $N_x$ may be fixed by the program or specified by the user, such as 20.

Figure 18:
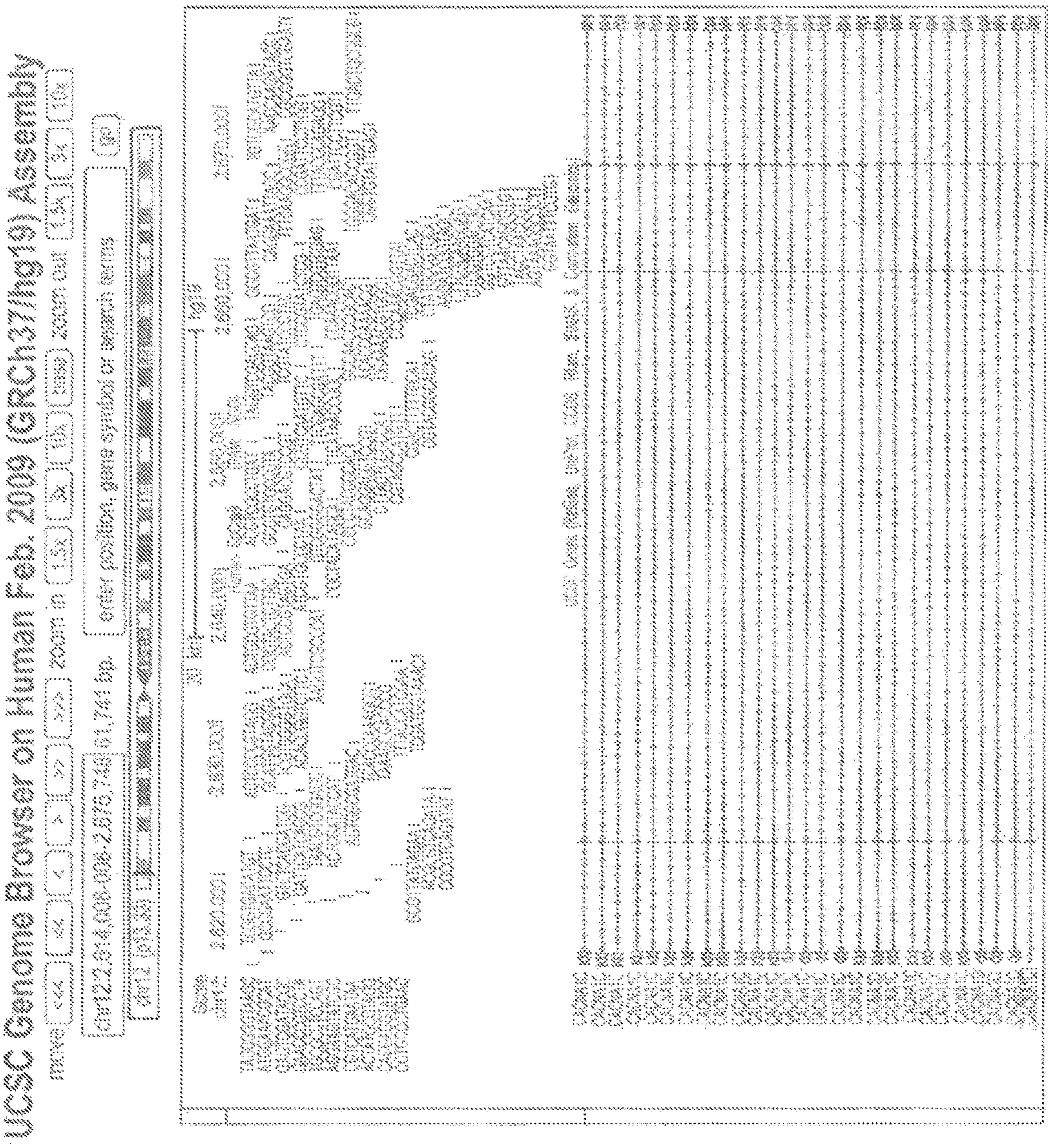
FIG. 18 shows an exemplary visualization of some *S. pyogenes* Cas9 target sites in the human genome using the UCSC genome browser.
Figure 19A:
FIG. 19A-19D shows a circular depiction of the phylogenetic analysis revealing five families of Cas9s, including three groups of large Cas9s (~1400 amino acids) and two of small Cas9s (~1100 amino acids).
Figure 19B:
Figure 19C:
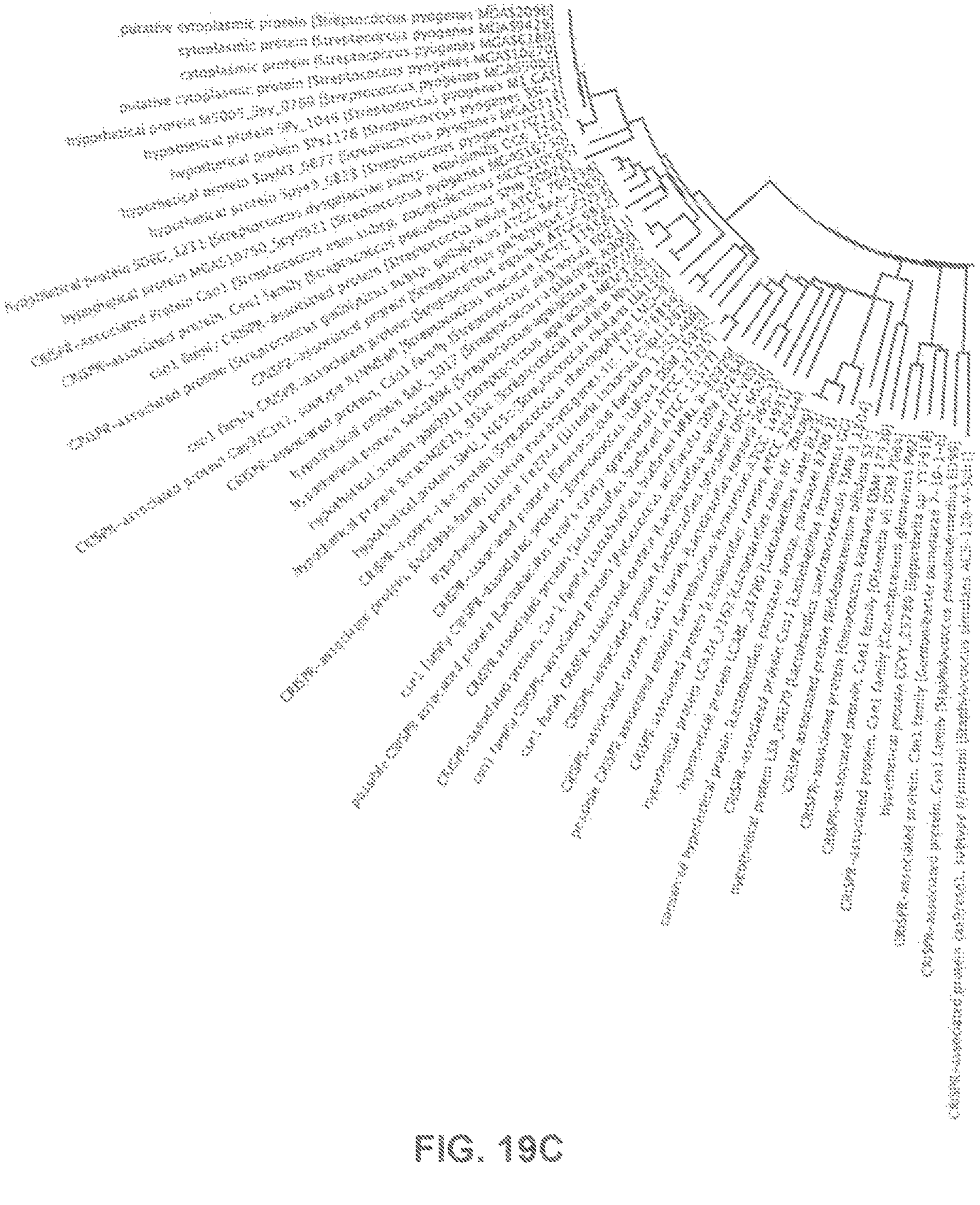
Figure 19D:
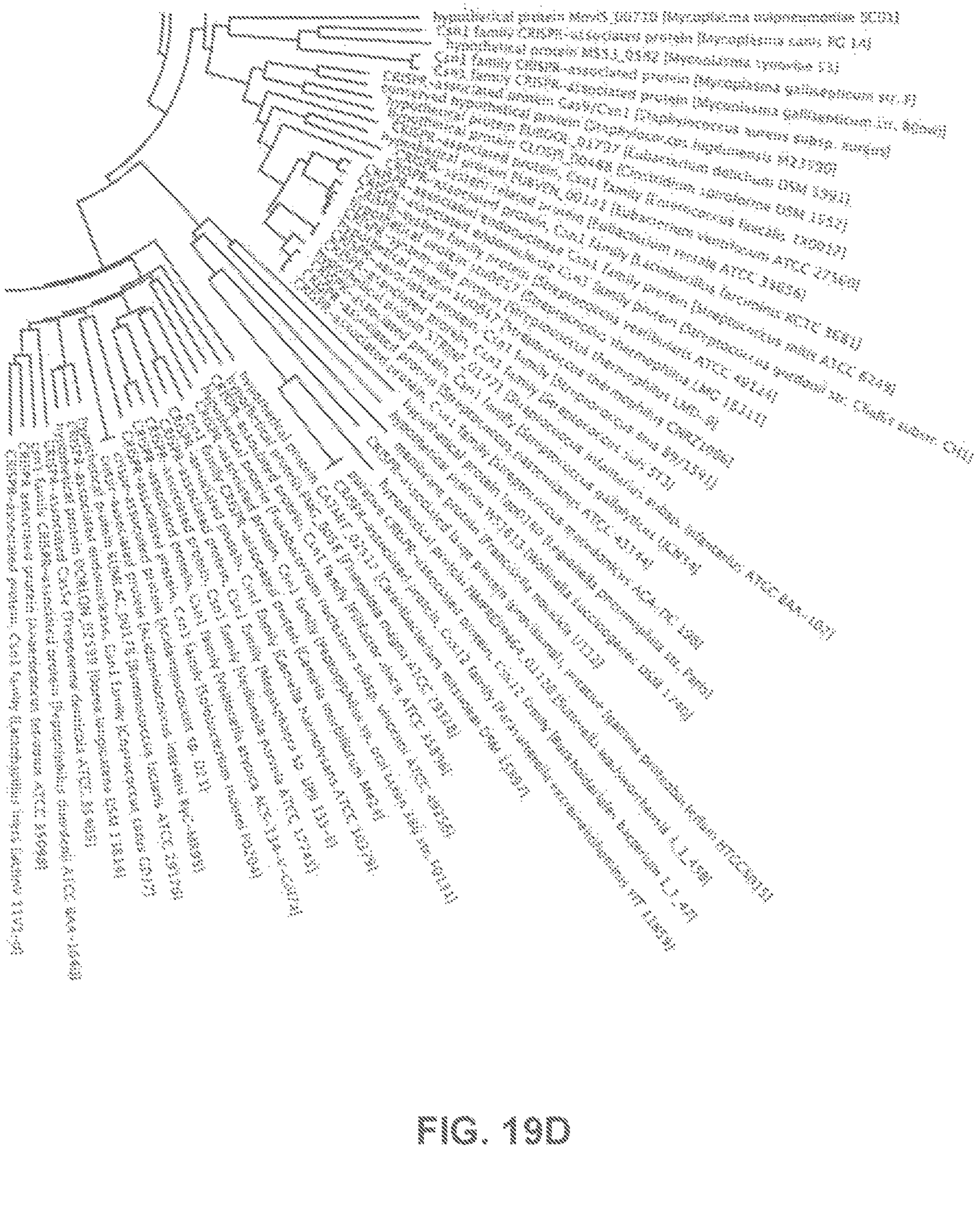
Figure 20A:
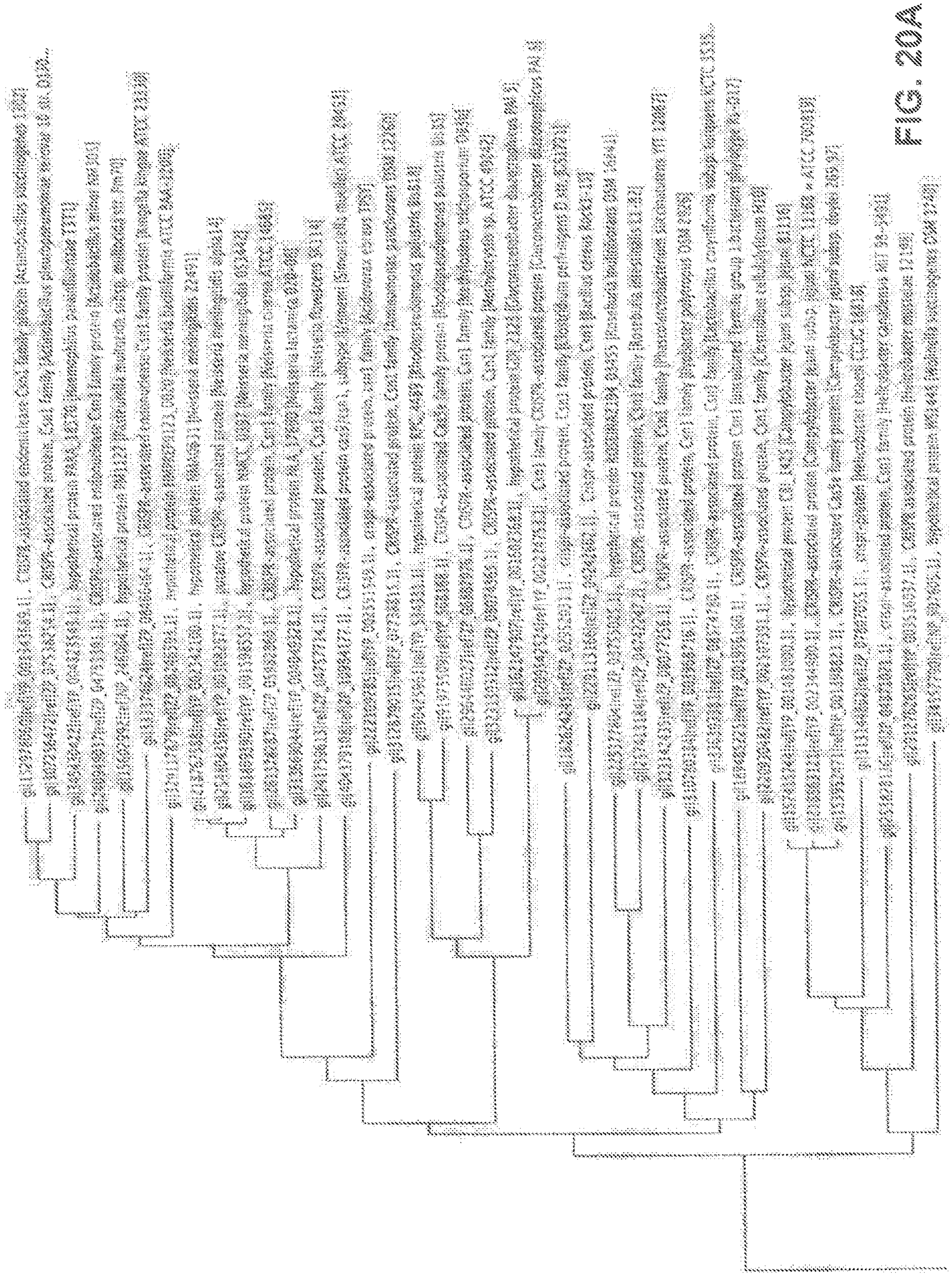
FIG. 20A-20F shows the linear depiction of the phylogenetic analysis revealing five families of Cas9s, including three groups of large Cas9s (~1400 amino acids) and two of small Cas9s (~1100 amino acids).
Figure 20B:
Figure 20C:
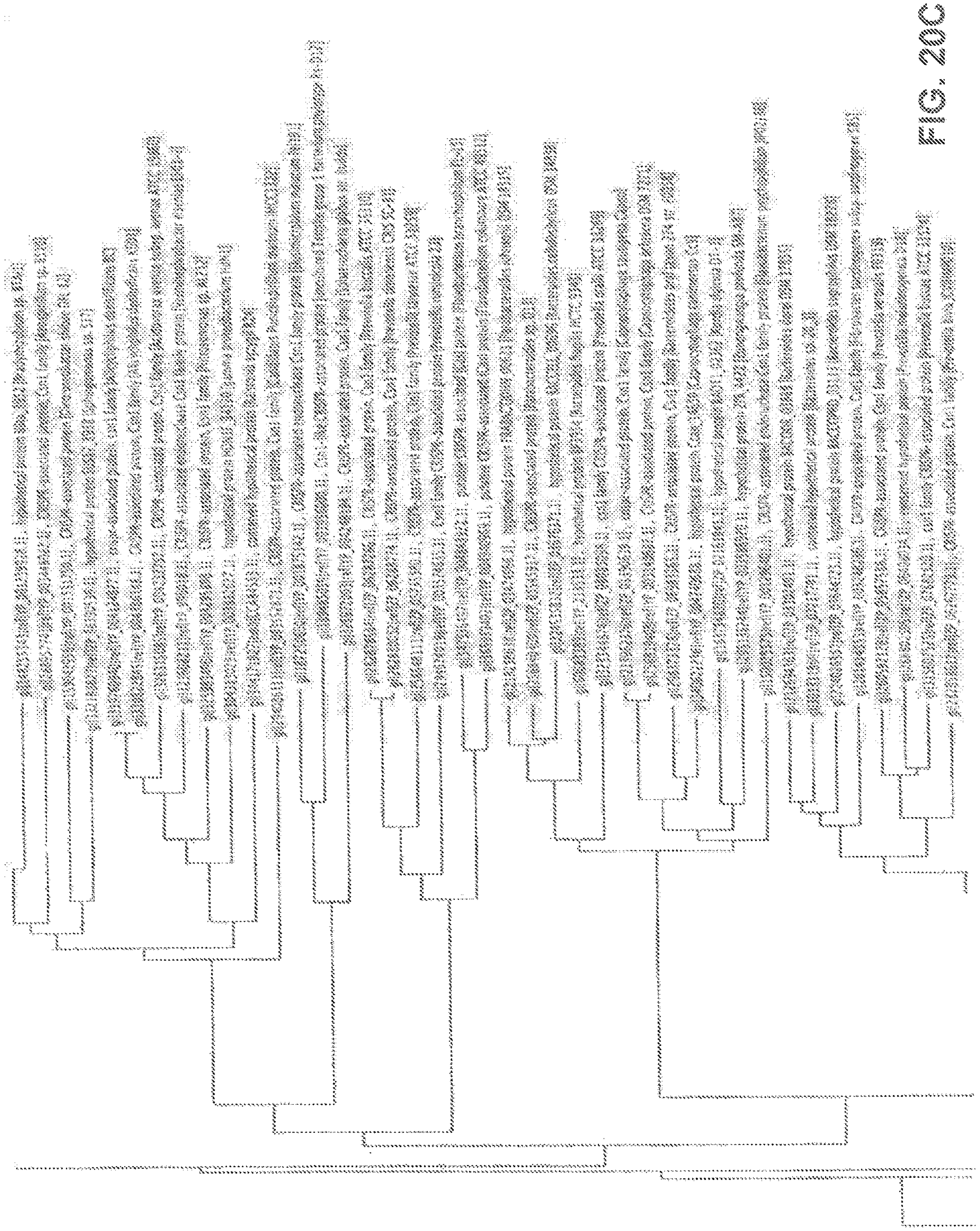
Figure 20D:
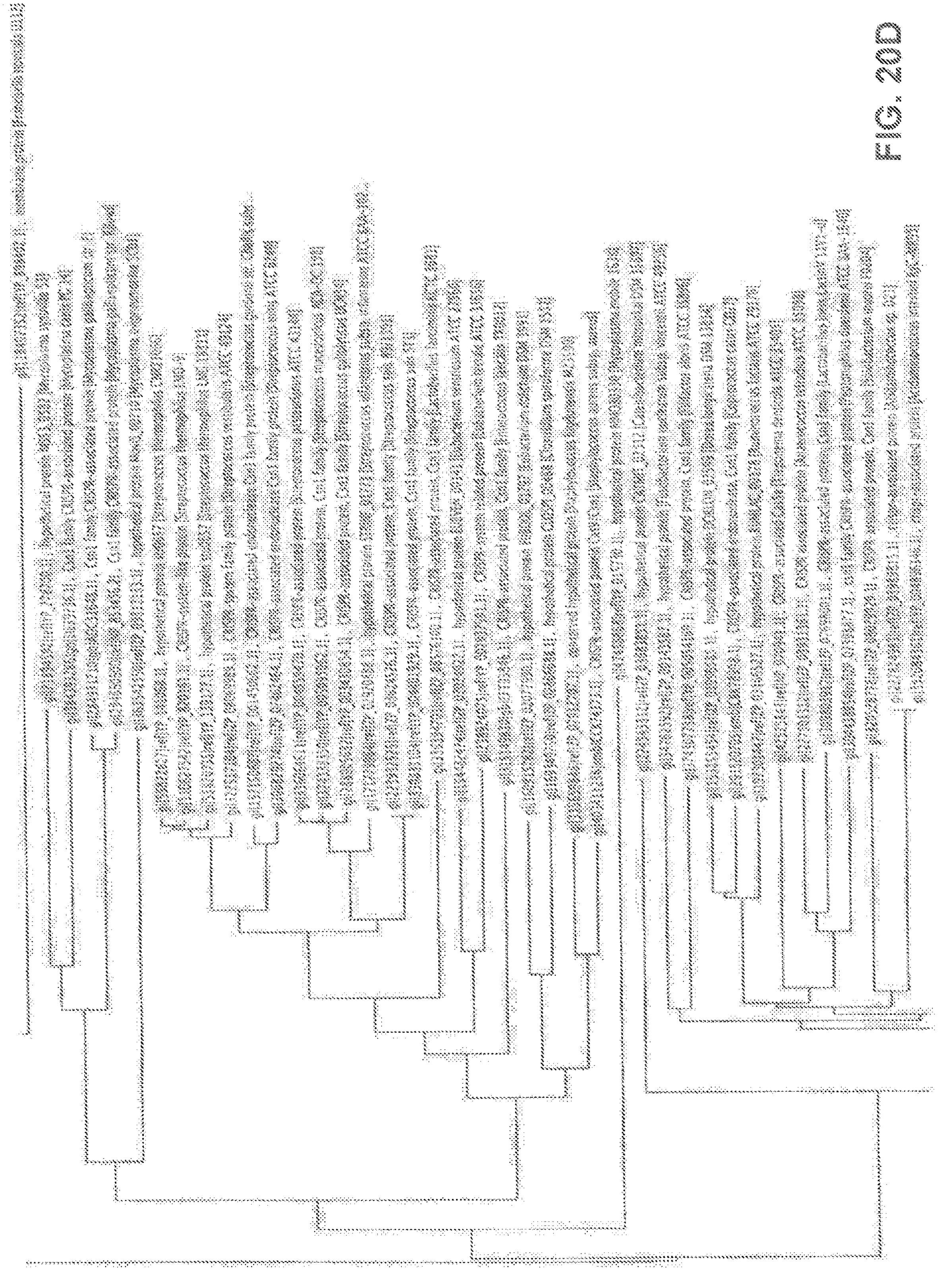
Figure 20E:
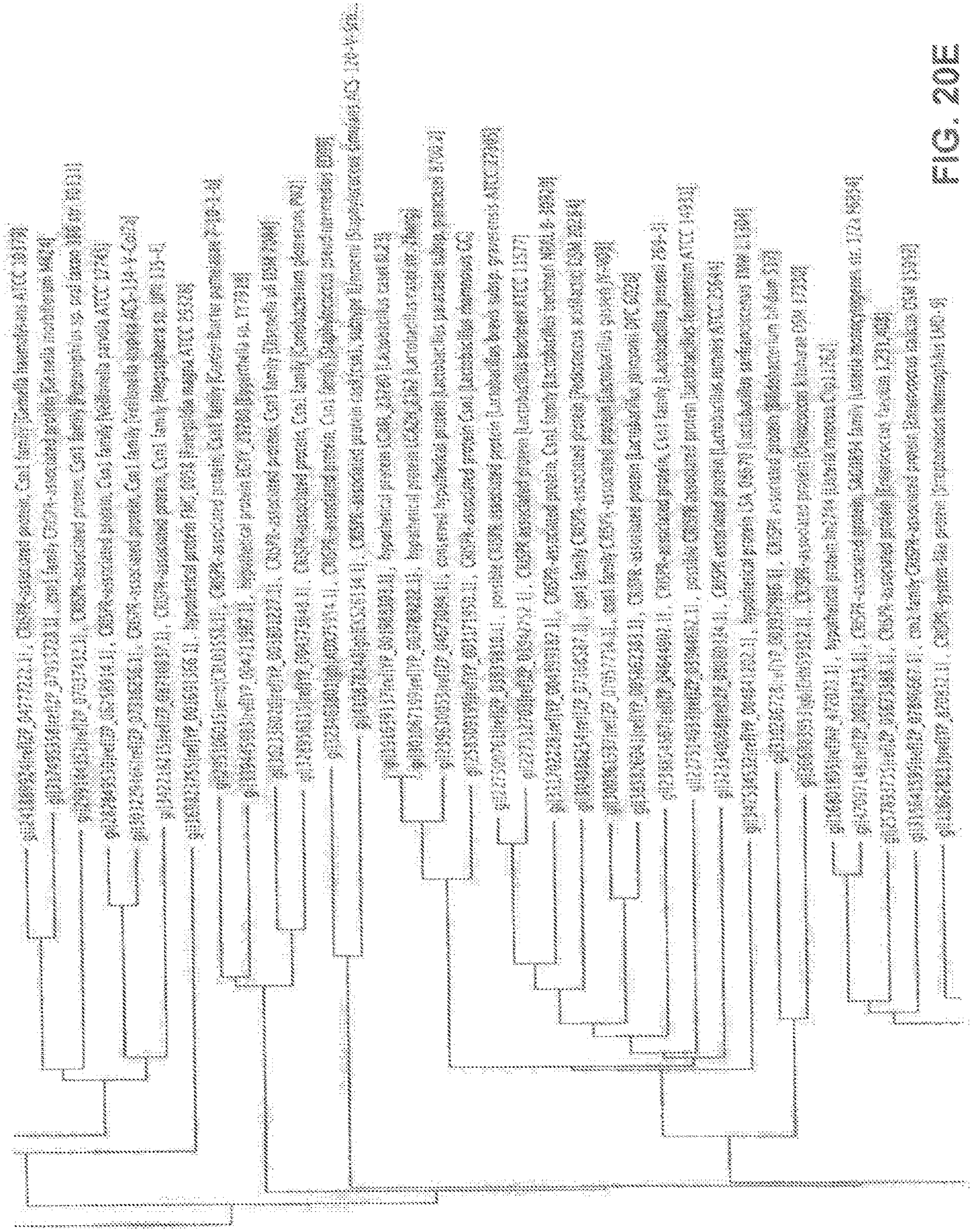
Figure 20F:
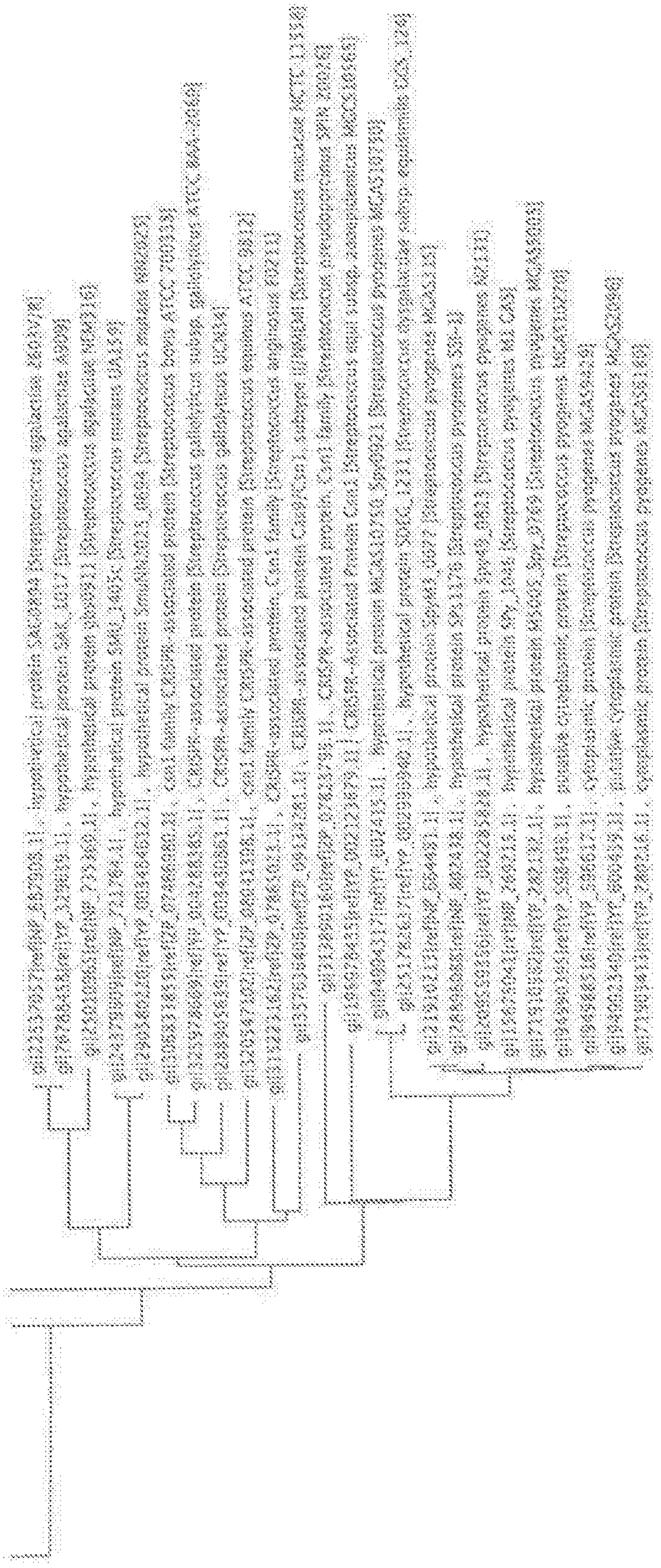
Figure 21A:
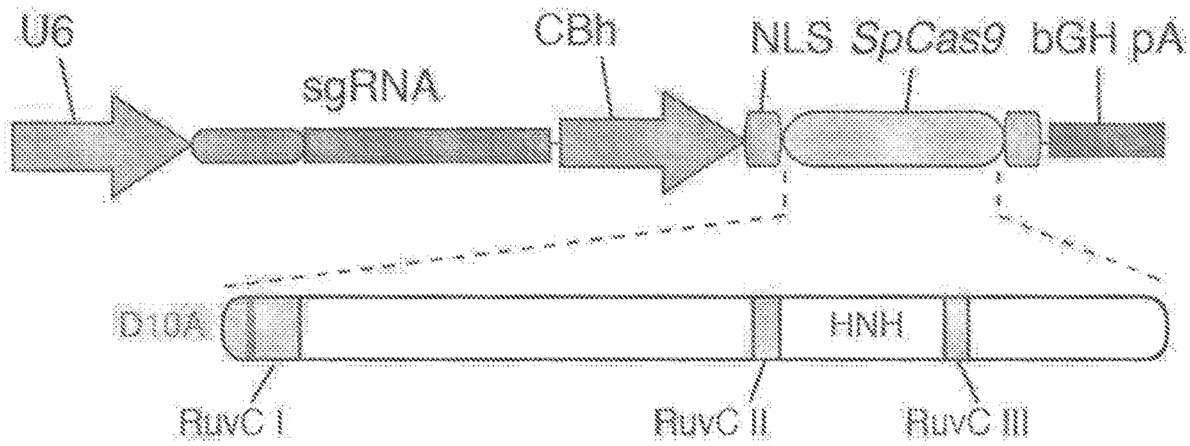
FIG. 21A-21D shows genome editing via homologous recombination. (a) Schematic of SpCas9 nickase, with D10A mutation in the RuvC I catalytic domain. (b) Schematic representing homologous recombination (HR) at the human EMX1 locus using either sense or antisense single stranded oligonucleotides as repair templates. The arrow above indicates sgRNA cleavage site; PCR primers for genotyping (Tables J and K) are indicated as arrows in right panel. (c) Sequence of region modified by HR. d, SURVEYOR assay for wildtype (wt) and nickase (D10A) SpCas9-mediated indels at the EMX1 target 1 locus (n=3). Arrows indicate positions of expected fragment sizes.
Figure 21B:
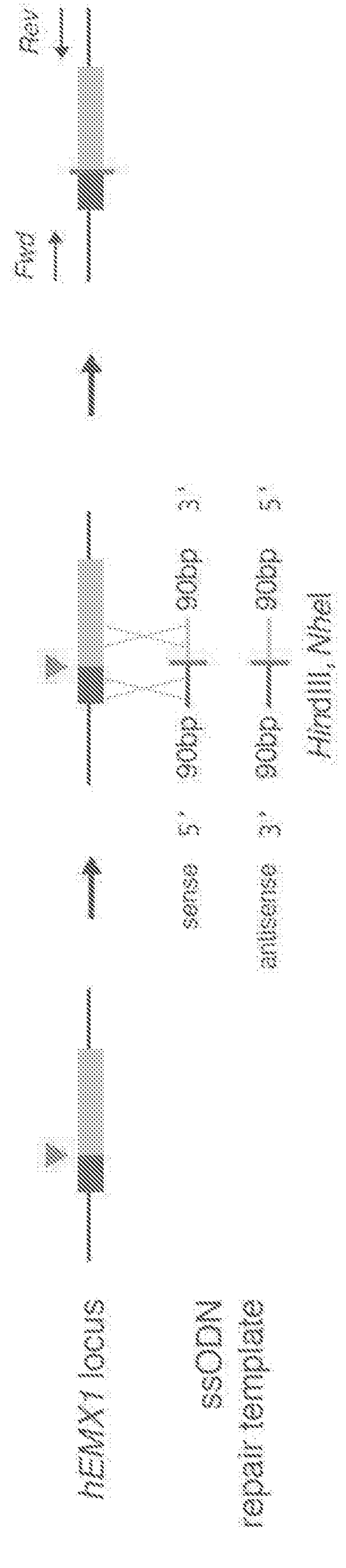
Figure 21C:
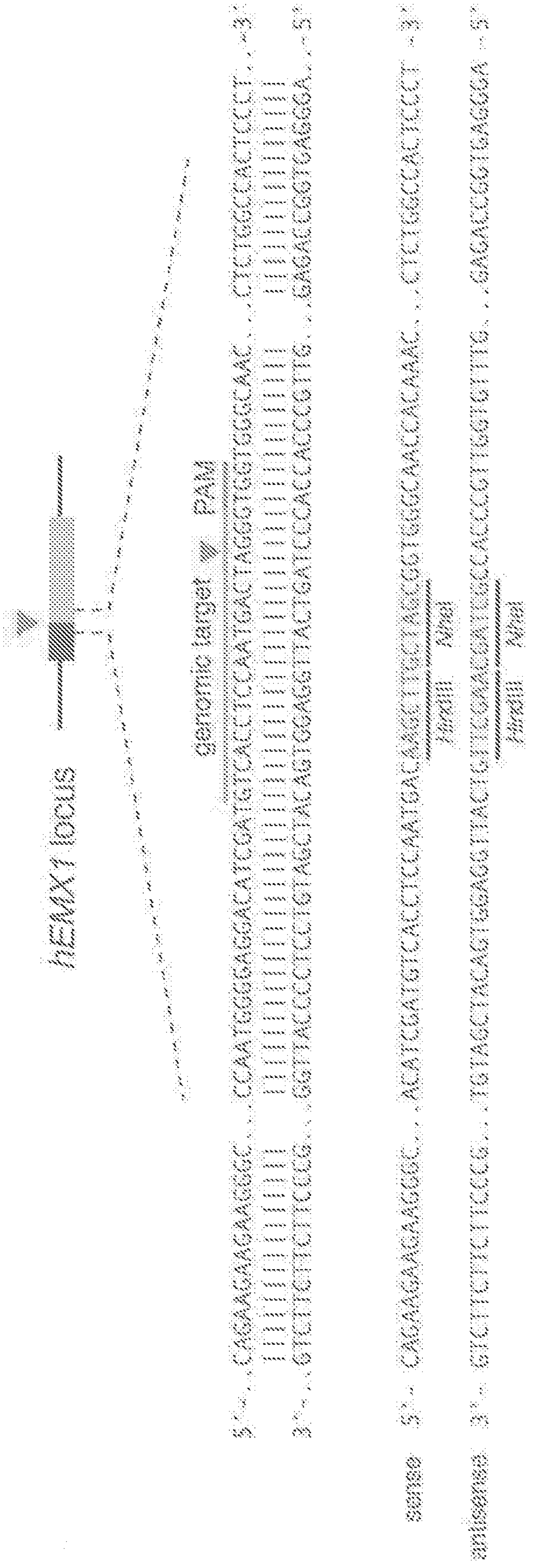
Figure 21D:
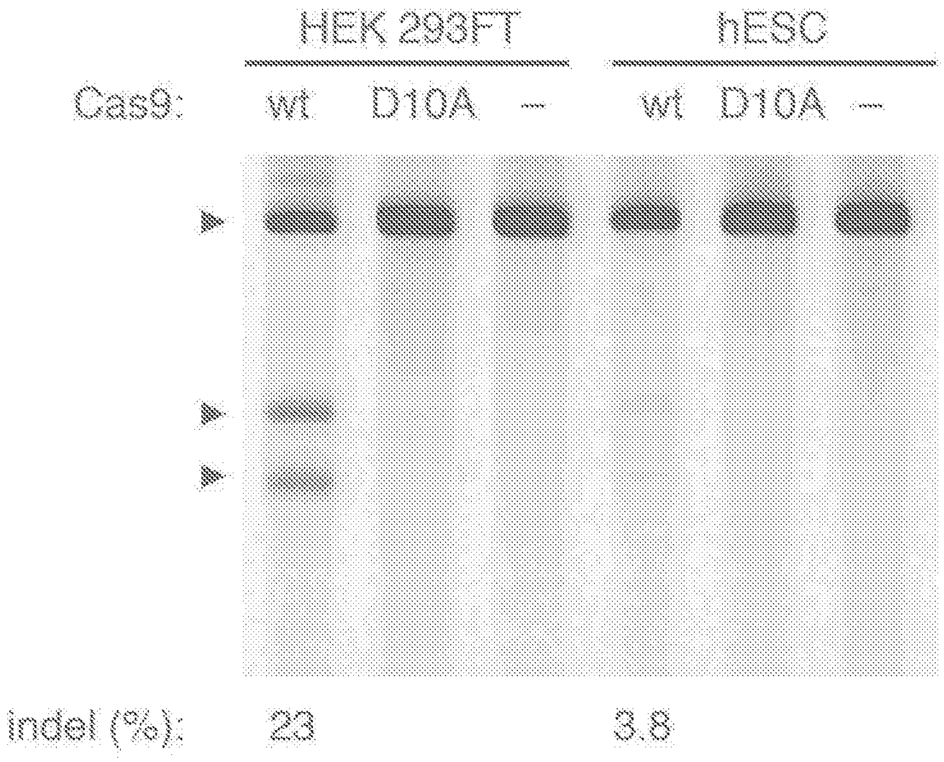

Since multiple occurrences in the genome of the DNA target site may lead to nonspecific genome editing, after identifying all potential sites, the program filters out sequences based on the number of times they appear in the relevant reference genome. For those CRISPR enzymes for which sequence specificity is determined by a 'seed' sequence, such as the 11-12 bp 5' from the PAM sequence, including the PAM sequence itself, the filtering step may be based on the seed sequence. Thus, to avoid editing at additional genomic loci, results are filtered based on the number of occurrences of the seed:PAM sequence in the relevant genome. The user may be allowed to choose the length of the seed sequence. The user may also be allowed to specify the number of occurrences of the seed:PAM sequence in a genome for purposes of passing the filter. The default is to screen for unique sequences. Filtration level is altered by changing both the length of the seed sequence and the number of occurrences of the sequence in the genome. The program may in addition or alternatively provide the sequence of a guide sequence complementary to the reported target sequence(s) by providing the reverse complement of the identified target sequence(s). An example visualization of some target sites in the human genome is provided in FIG. 18.

Further details of methods and algorithms to optimize sequence selection can be found in U.S. application Ser. No. 61/064,798 (Broad Reference BI-2012/084); incorporated herein by reference.

Example 4: Evaluation of Multiple Chimeric crRNA-tracrRNA Hybrids

Figure 16A:
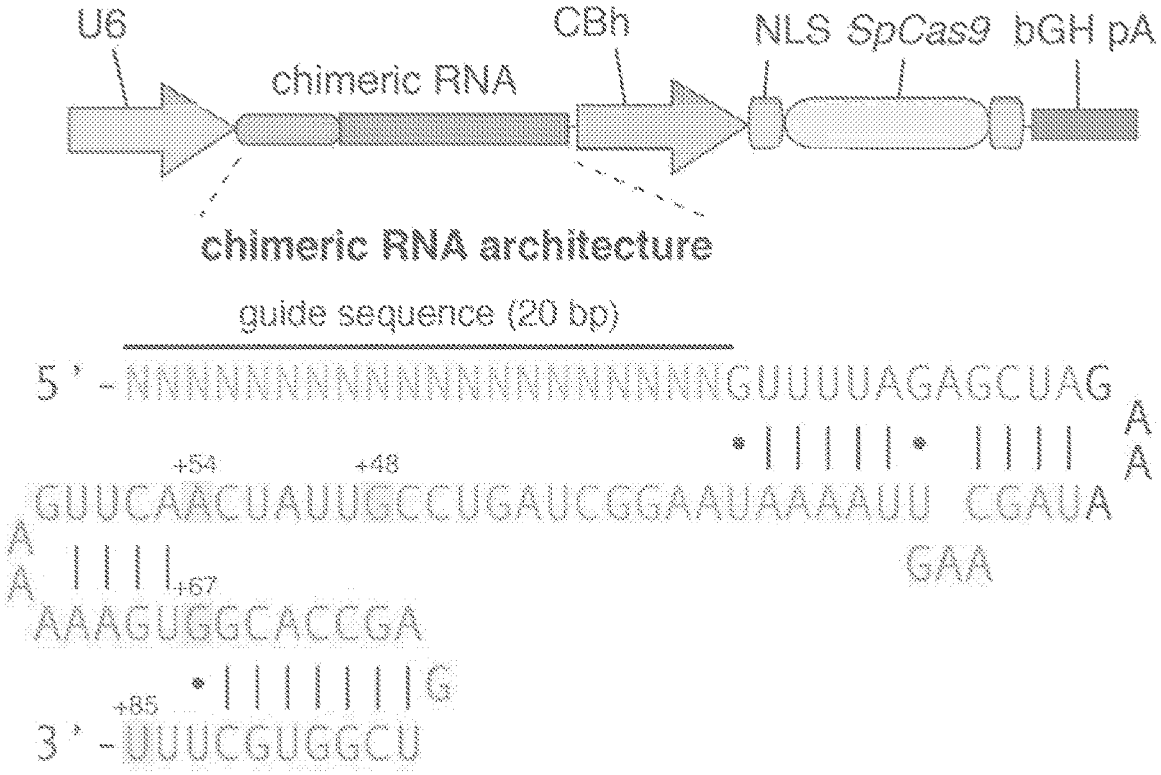
FIG. 16A-16C shows exemplary manipulation of a CRISPR system with chimeric RNAs and results of SURVEYOR assays for system activity in eukaryotic cells.
Figure 16B:
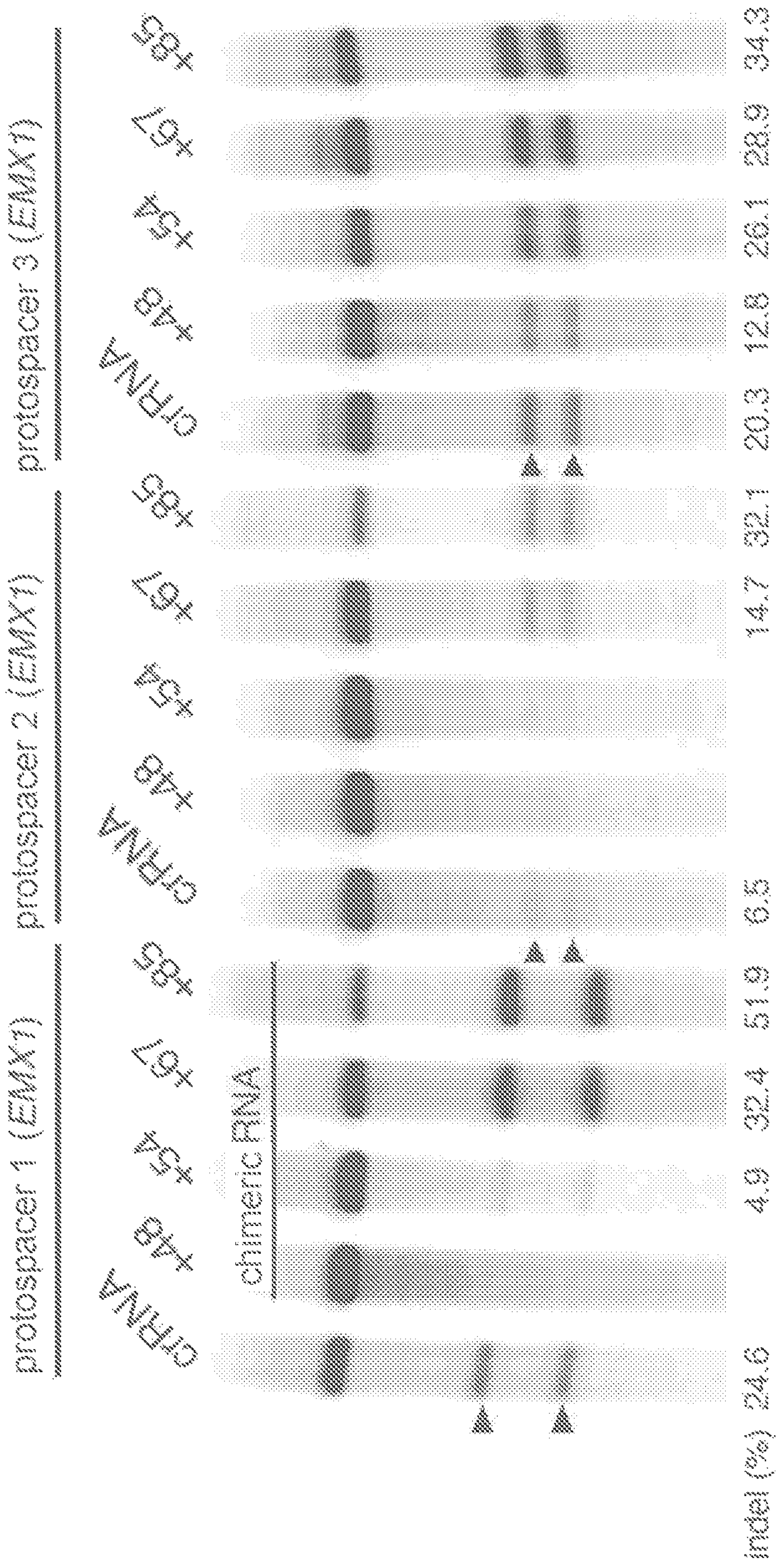
Figure 16C:
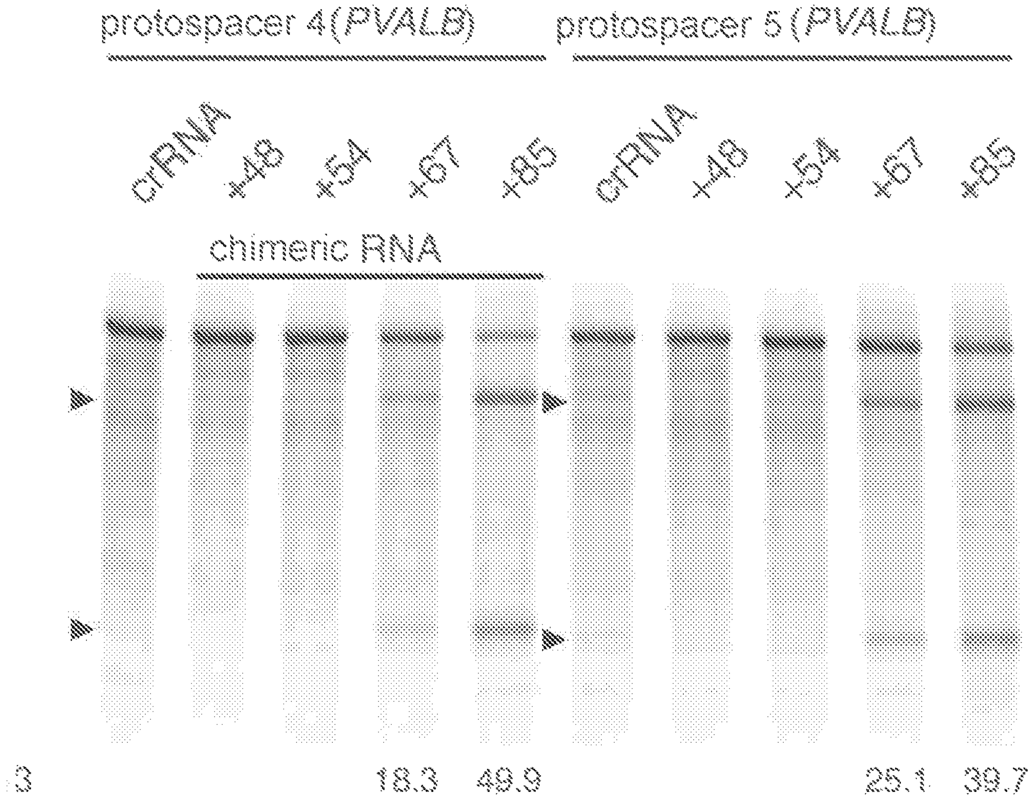

This example describes results obtained for chimeric RNAs (chiRNAs; comprising a guide sequence, a tracr mate sequence, and a tracr sequence in a single transcript) having tracr sequences that incorporate different lengths of wild-type tracrRNA sequence. FIG. 16*a* illustrates a schematic of a bicistronic expression vector for chimeric RNA and Cas9. Cas9 is driven by the CBh promoter and the chimeric RNA is driven by a U6 promoter. The chimeric guide RNA consists of a 20 bp guide sequence (Ns) joined to the tracr sequence (running from the first "U" of the lower strand to the end of the transcript), which is truncated at various positions as indicated. The guide and tracr sequences are separated by the tracr-mate sequence GUUUUAGAGCUA (SEQ ID NO: 63) followed by the loop sequence GAAA. Results of SURVEYOR assays for Cas9-mediated indels at the human EMX1 and PVALB loci are illustrated in FIGS. 16*b* and 16*c*, respectively. Arrows indicate the expected SURVEYOR fragments. ChiRNAs are indicated by their "+n" designation, and crRNA refers to a hybrid RNA where guide and tracr sequences are expressed as separate transcripts. Quantification of these results, performed in triplicate, are illustrated by histogram in FIGS. 17*a* and 17*b*, corresponding to FIGS. 16*b* and 16*c*, respectively ("N.D." indicates no indels detected). Protospacer IDs and their corresponding genomic target, protospacer sequence, PAM sequence, and strand location are provided in Table D. Guide sequences were designed to be complementary to the entire protospacer sequence in the case of separate transcripts in the hybrid system, or only to the underlined portion in the case of chimeric RNAs.

TABLE D

| proto spacer ID | genomic target | protospacer sequence (5' to 3') | PAM | strand |
|---|---|---|---|---|
| 1 | EMX1 | GGACATCGAT<u>GTCACCTCCAATGACTAGGG</u> | TGG | + |

TABLE D-continued

| proto spacer ID | genomic target | protospacer sequence (5' to 3') | PAM | strand |
|---|---|---|---|---|
| 2 | EMX1 | CATTGGAGGTGACATCGATG TCCTCCCCAT | TGG | - |
| 3 | EMX1 | GGAAGGGCCTGAGTCCGAGC AGAAGAAGAA | GGG | + |
| 4 | PVALB | GGTGGCGAGAGGGGCCGAGA TTGGGTGTTC | AGG | + |
| 5 | PVALB | ATGCAGGAGGGTGGCGAGAG GGGCCGAGAT | TGG | + |

These are SEQ ID NOS: 93 to 97, respectively.

Further details to optimize guide sequences can be found in U.S. application Ser. No. 61/836,127 (Broad Reference BI-2013/004 G); incorporated herein by reference.

Figure 17B:
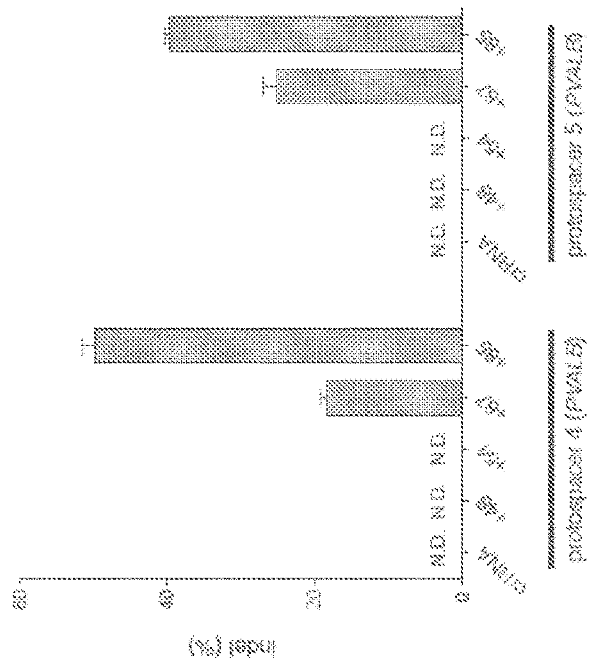
FIG. 17A-17B shows a graphical representation of the results of SURVEYOR assays for CRISPR system activity in eukaryotic cells.
Figure 17A:
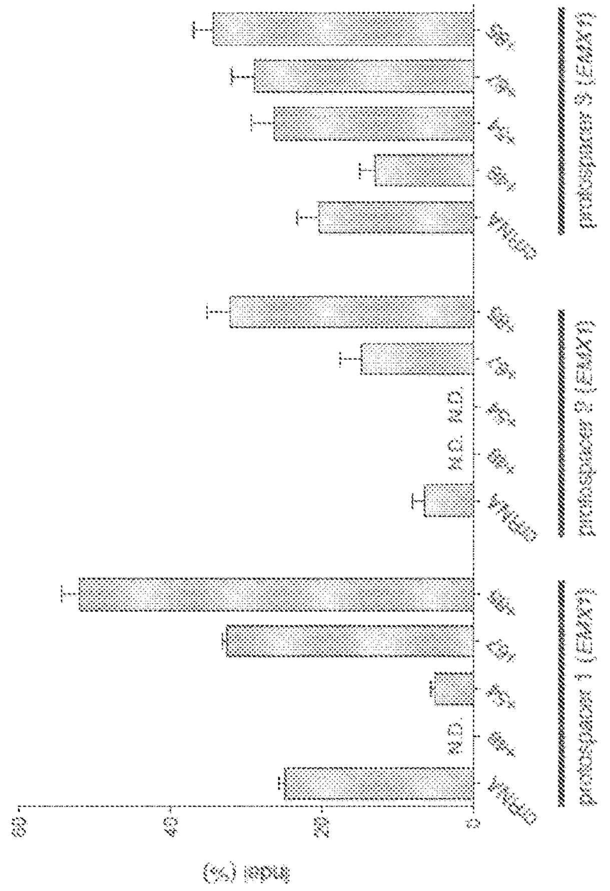

Initially, three sites within the EMX1 locus in human HEK 293FT cells were targeted. Genome modification efficiency of each chiRNA was assessed using the SURVEYOR nuclease assay, which detects mutations resulting from DNA double-strand breaks (DSBs) and their subsequent repair by the non-homologous end joining (NHEJ) DNA damage repair pathway. Constructs designated chiRNA(+n) indicate that up to the +n nucleotide of wild-type tracrRNA is included in the chimeric RNA construct, with values of 48, 54, 67, and 85 used for n. Chimeric RNAs containing longer fragments of wild-type tracrRNA (chiRNA(+67) and chiRNA(+85)) mediated DNA cleavage at all three EMX1 target sites, with chiRNA(+85) in particular demonstrating significantly higher levels of DNA cleavage than the corresponding crRNA/tracrRNA hybrids that expressed guide and tracr sequences in separate transcripts (FIGS. 16*b* and 17*a*). Two sites in the PVALB locus that yielded no detectable cleavage using the hybrid system (guide sequence and tracr sequence expressed as separate transcripts) were also targeted using chiRNAs. chiRNA(+67) and chiRNA(+85) were able to mediate significant cleavage at the two PVALB protospacers (FIGS. 16*c* and 17*b*).

For all five targets in the EMX1 and PVALB loci, a consistent increase in genome modification efficiency with increasing tracr sequence length was observed. Without wishing to be bound by any theory, the secondary structure formed by the 3' end of the tracrRNA may play a role in enhancing the rate of CRISPR complex formation.

Example 5: Cas9 Diversity

The CRISPR-Cas system is an adaptive immune mechanism against invading exogenous DNA employed by diverse species across bacteria and archaea. The type II CRISPR-Cas9 system consists of a set of genes encoding proteins responsible for the “acquisition” of foreign DNA into the CRISPR locus, as well as a set of genes encoding the “execution” of the DNA cleavage mechanism; these include the DNA nuclease (Cas9), a non-coding transactivating cr-RNA (tracrRNA), and an array of foreign DNA-derived spacers flanked by direct repeats (crRNAs). Upon maturation by Cas9, the tracRNA and crRNA duplex guide the Cas9 nuclease to a target DNA sequence specified by the spacer guide sequences, and mediates double-stranded breaks in the DNA near a short sequence motif in the target DNA that is required for cleavage and specific to each CRISPR-Cas system. The type II CRISPR-Cas systems are found throughout the bacterial kingdom and highly diverse in in Cas9 protein sequence and size, tracrRNA and crRNA direct repeat sequence, genome organization of these elements, and the motif requirement for target cleavage. One species may have multiple distinct CRISPR-Cas systems.

Applicants evaluated 207 putative Cas9s from bacterial species identified based on sequence homology to known Cas9s and structures orthologous to known subdomains, including the HNH endonuclease domain and the RuvC endonuclease domains [information from the Eugene Koonin and Kira Makarova]. Phylogenetic analysis based on the protein sequence conservation of this set revealed five families of Cas9s, including three groups of large Cas9s (~1400 amino acids) and two of small Cas9s (~1100 amino acids) (see FIGS. 19 and 20A-F).

Further details of Cas9s and mutations of the Cas9 enzyme to convert into a nickase or DNA binding protein and use of same with altered functionality can be found in U.S. application Ser. Nos. 61/836,101 and 61/835,936 (Broad Reference BI-2013/004E and BI-2013/004F respectively) incorporated herein by reference.

Example 6: Cas9 Orthologs

Applicants analyzed Cas9 orthologs to identify the relevant PAM sequences and the corresponding chimeric guide RNA. Having an expanded set of PAMs provides broader targeting across the genome and also significantly increases the number of unique target sites and provides potential for identifying novel Cas9s with increased levels of specificity in the genome.

The specificity of Cas9 orthologs can be evaluated by testing the ability of each Cas9 to tolerate mismatches between the guide RNA and its DNA target. For example, the specificity of SpCas9 has been characterized by testing the effect of mutations in the guide RNA on cleavage efficiency. Libraries of guide RNAs were made with single or multiple mismatches between the guide sequence and the target DNA. Based on these findings, target sites for SpCas9 can be selected based on the following guidelines:

To maximize SpCas9 specificity for editing a particular gene, one should choose a target site within the locus of interest such that potential ‘off-target’ genomic sequences abide by the following four constraints: First and foremost, they should not be followed by a PAM with either 5'-NGG or NAG sequences. Second, their global sequence similarity to the target sequence should be minimized. Third, a maximal number of mismatches should lie within the PAM-proximal region of the off-target site. Finally, a maximal number of mismatches should be consecutive or spaced less than four bases apart.

Similar methods can be used to evaluate the specificity of other Cas9 orthologs and to establish criteria for the selection of specific target sites within the genomes of target species. As mentioned previously phylogenetic analysis based on the protein sequence conservation of this set revealed five families of Cas9s, including three groups of large Cas9s (~1400 amino acids) and two of small Cas9s (~1100 amino acids) (see FIGS. 19 and 20A-F). Further details on Cas orthologs can be found in U.S. application Ser. Nos. 61/836,101 and 61/835,936 (Broad Reference BI-2013/004E and BI-2013/004F respectively) incorporated herein by reference.

Example 7: Methodological Improvement to Simplify Cloning and Delivery

Rather than encoding the U6-promoter and guide RNA on a plasmid, Applicants amplified the U6 promoter with a DNA oligo to add on the guide RNA. The resulting PCR product may be transfected into cells to drive expression of the guide RNA.

Example primer pair that allows the generation a PCR product consisting of U6-promoter::guideRNA targeting human Emx1 locus:

```
Forward Primer:
                                        (SEQ ID NO: 98)
AAACTCTAGAgagggcctatttcccatgattc

Reverse Primer (carrying the guide RNA, which is
underlined):
                                        (SEQ ID NO: 99)
acctctagAAAAAAAGCACCGACTCGGTGCCACTTTTTCAAGTTGATAACG

GACTAGCCTTATTTTAACTTGCTATGCTGTTTTGTTTCCAAAACAGCATAG

CTCTAAAACCCCTAGTCATTGGAGGTGACGGTGTTTCGTCCTTTCCACaag
```

Example 8: Methodological Improvement to Improve Activity

Rather than use pol3 promoters, in particular RNA polymerase III (e.g. U6 or H1 promoters), to express guide RNAs in eukaryotic cells, Applicants express the T7 polymerase in eukaryotic cells to drive expression of guide RNAs using the T7 promoter.

One example of this system may involve introduction of three pieces of DNA:

1. expression vector for Cas9
2. expression vector for T7 polymerase
3. expression vector containing guideRNA fused to the T7 promoter

Example 9: Methodological Improvement to Reduce Toxicity of Cas9: Delivery of Cas9 in the Form of mRNA Delivery of Cas9 in the form of mRNA enables transient expression of Cas9 in cells, to reduce toxicity. For example, humanized SpCas9 may be amplified using the following primer pair:

```
Forward Primer (to add on T7 promoter for in vitro
transcription):
                                       (SEQ ID NO: 100)
TAATACGACTCACTATAGGAAGTGCGCCACCATGGCCCCAAAGAAGAAGCG

G

Reverse Primer (to add on polyA tail):
                                       (SEQ ID NO: 101)
GGTTTTTTTTTTTTTTTTTTTTTTTTTTTTTTttcttaCTTTTTCTTTTTT

GCCTGGCCG
```

Applicants transfect the Cas9 mRNA into cells with either guide RNA in the form of RNA or DNA cassettes to drive guide RNA expression in eukaryotic cells.

Example 10: Methodological Improvement to Reduce Toxicity of Cas9: Use of an Inducible Promoter Applicants transiently turn on Cas9 expression only when it is needed for carrying out genome modification. Examples of inducible system include tetracycline inducible promoters (Tet-On or Tet-Off), small molecule two-hybrid transcription activations systems (FKBP, ABA, etc), or light inducible systems (Phytochrome, LOV domains, or cryptochrome).

Example 11: Improvement of the Cas9 System for In Vivo Application

Figure 23:
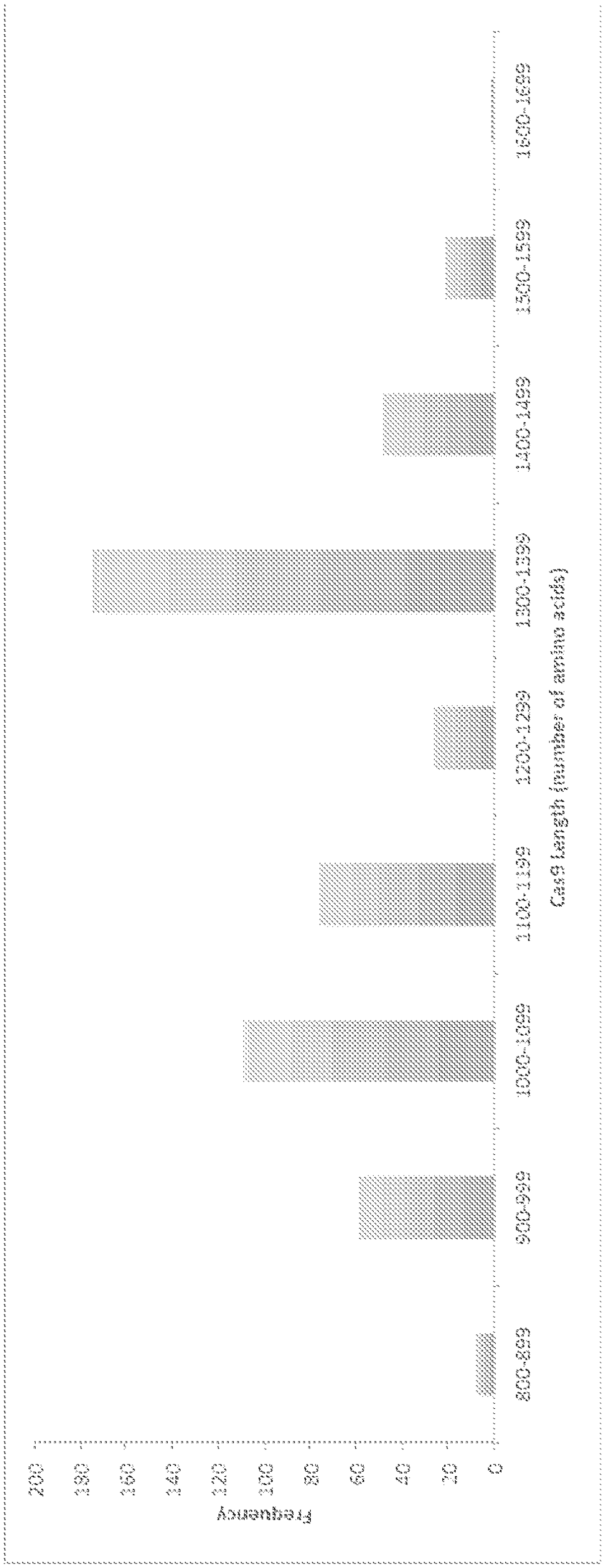
FIG. 23 shows a graph representing the length distribution of Cas9 orthologs.
Figure 24A:
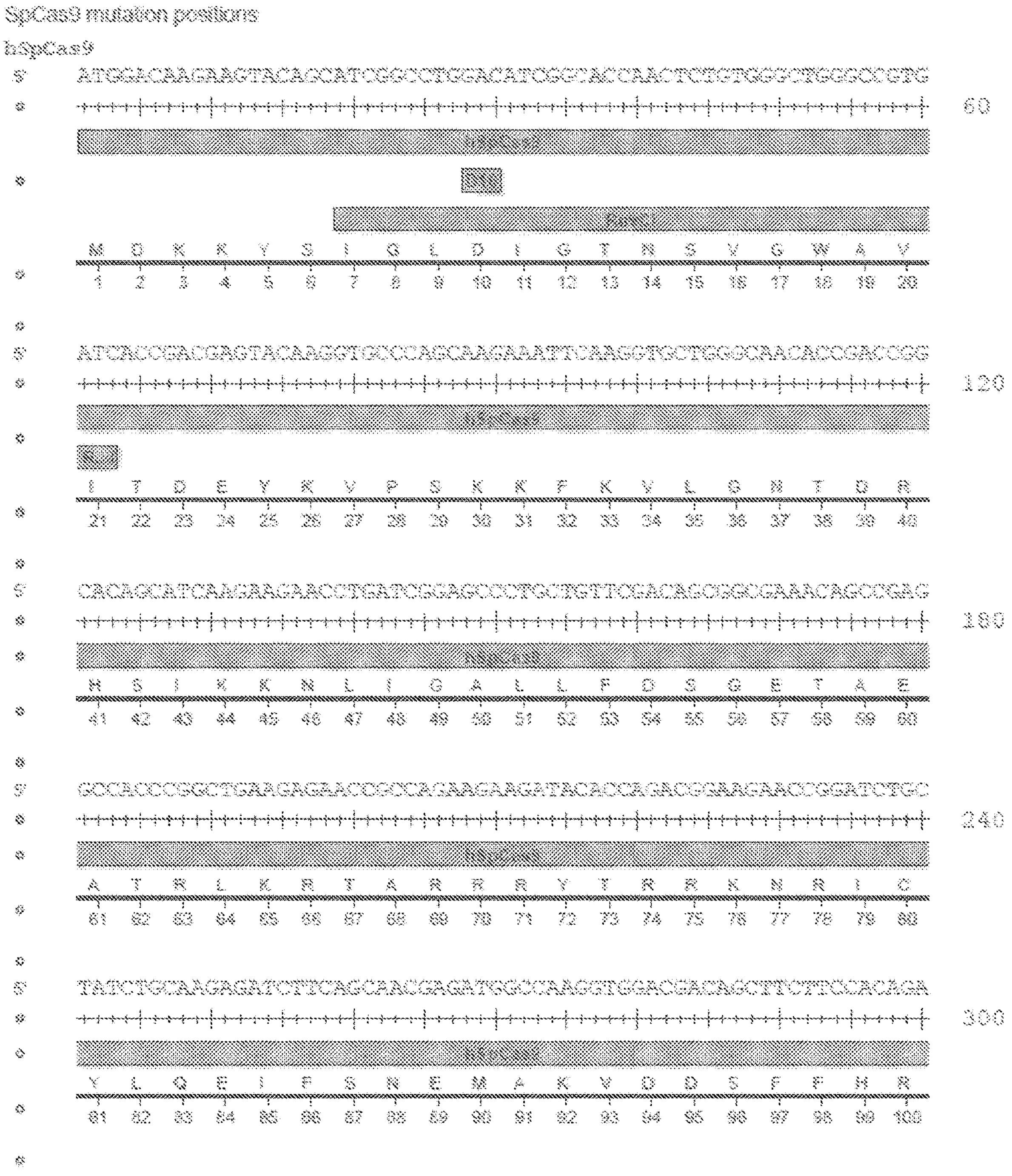
Figure 24C:
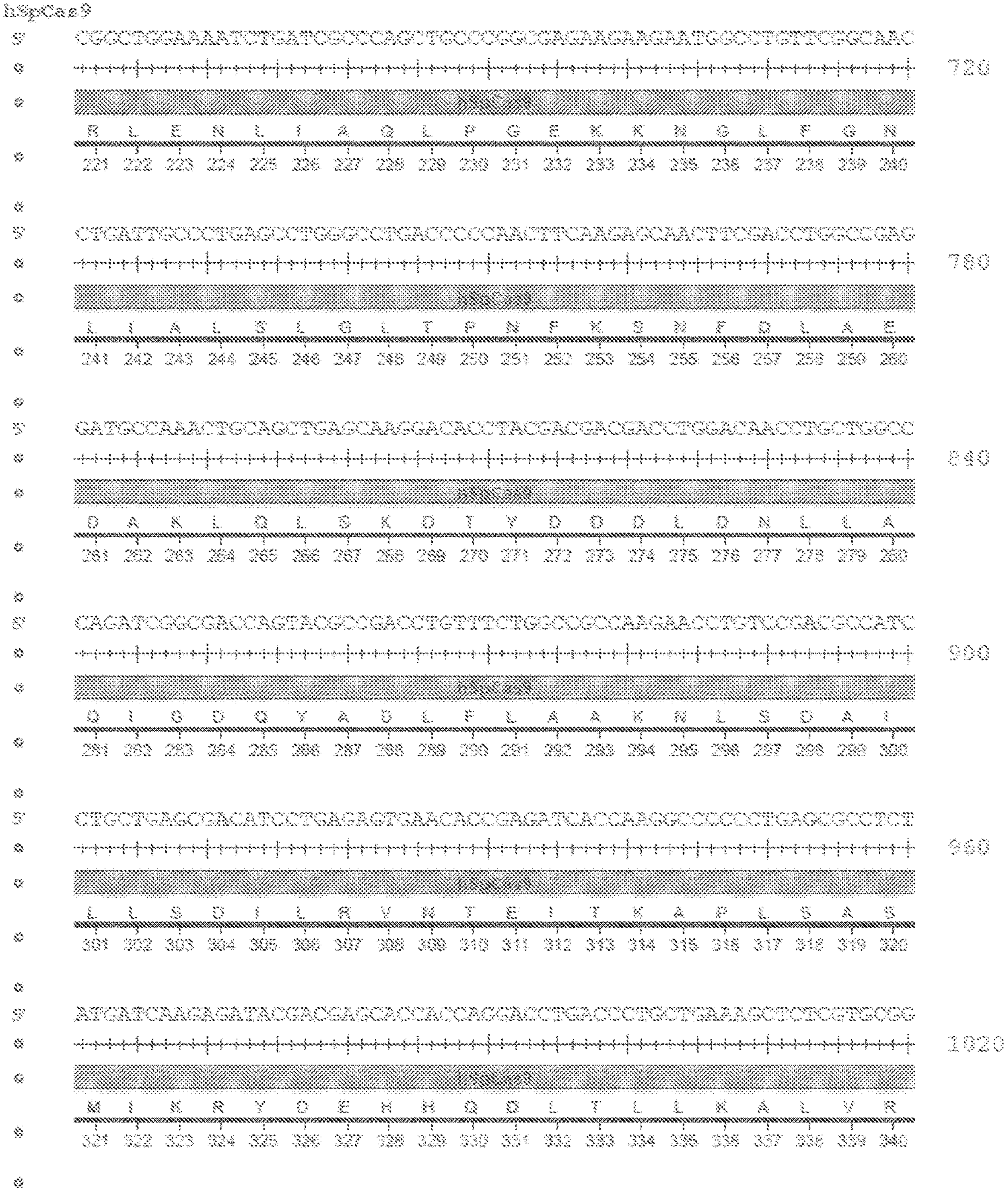
Figure 24G:
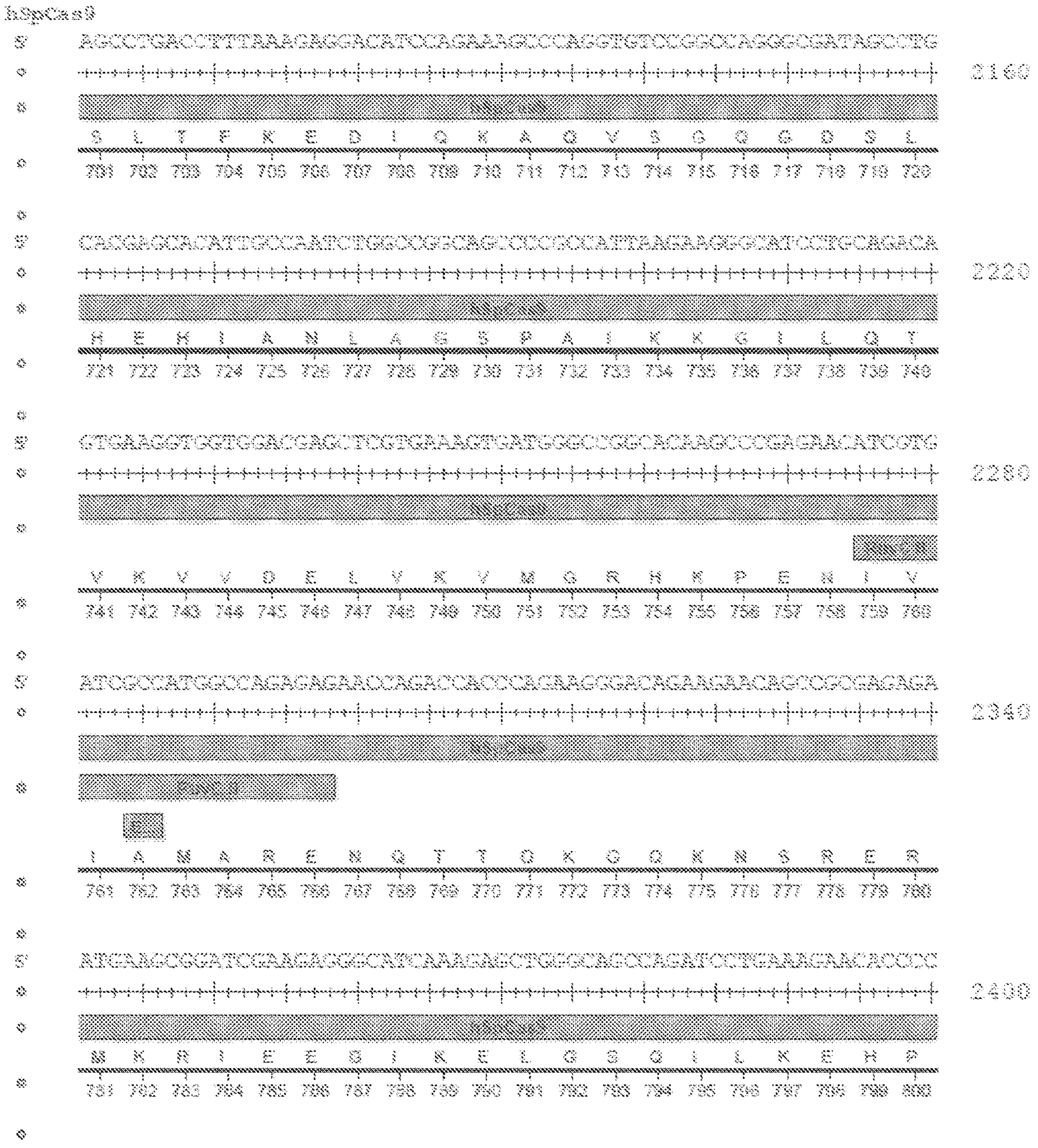
Figure 24I:
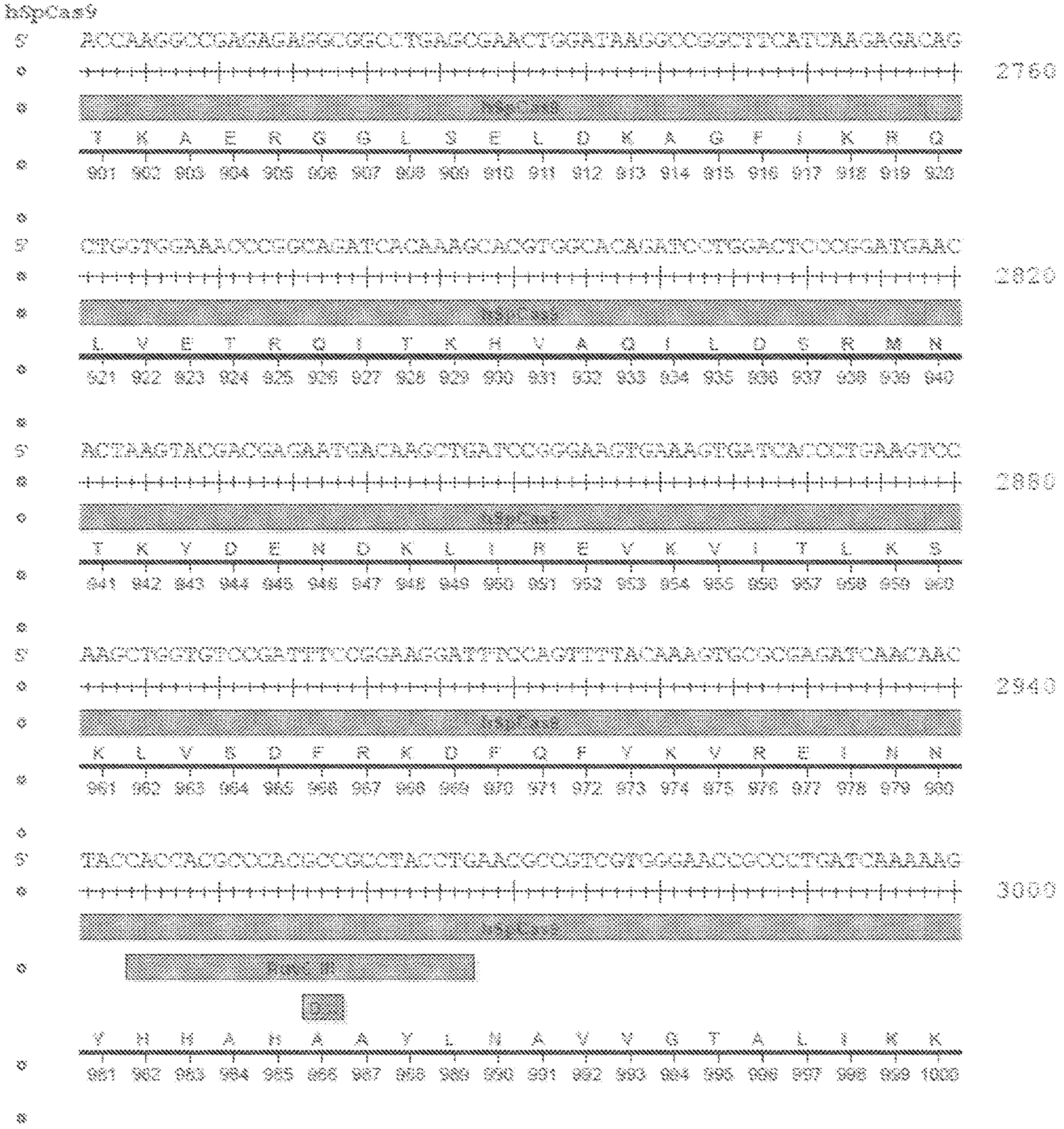
Figure 24J:
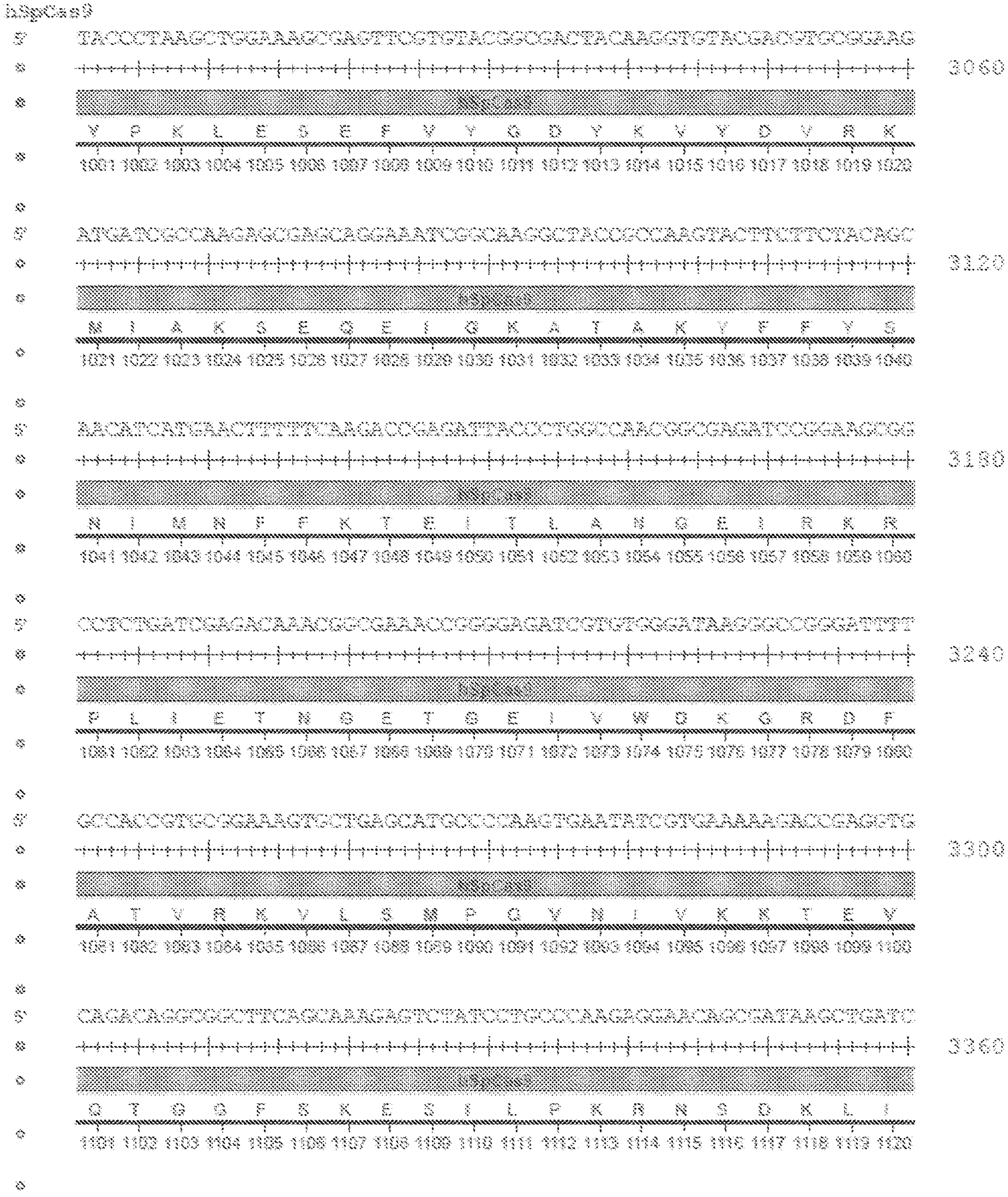
Figure 24L:
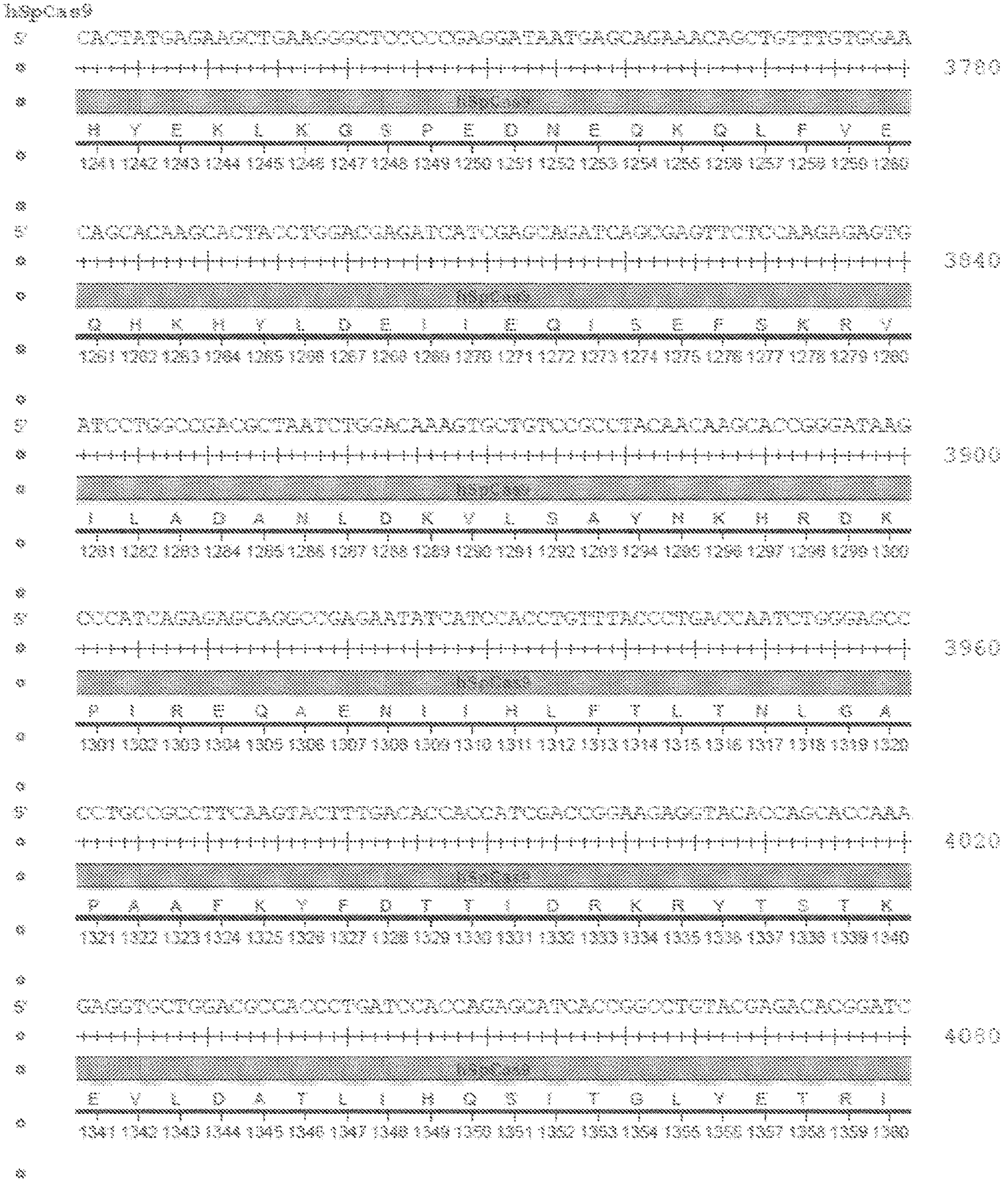
Figure 24M:
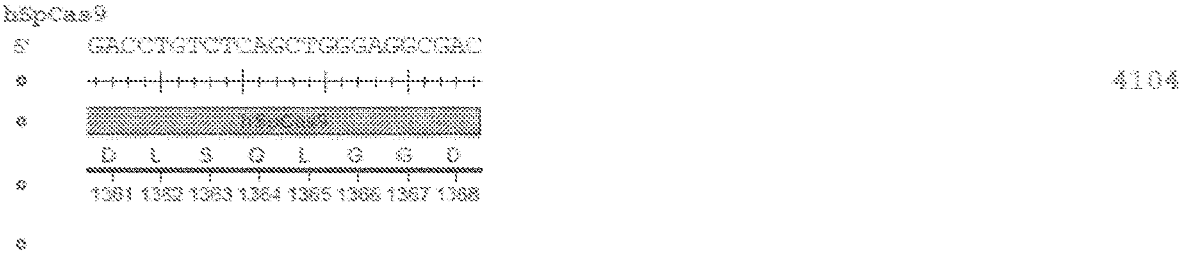

Applicants conducted a Metagenomic search for a Cas9 with small molecular weight. Most Cas9 homologs are fairly large. For example the SpCas9 is around 1368aa long, which is too large to be easily packaged into viral vectors for delivery. A graph representing the length distribution of Cas9 homologs is generated from sequences deposited in GenBank (FIG. 23). Some of the sequences may have been mis-annotated and therefore the exact frequency for each length may not necessarily be accurate. Nevertheless it provides a glimpse at distribution of Cas9 proteins and suggest that there are shorter Cas9 homologs.

Through computational analysis, Applicants found that in the bacterial strain *Campylobacter*, there are two Cas9 proteins with less than 1000 amino acids. The sequence for one Cas9 from *Campylobacter jejuni* is presented below. At this length, CjCas9 can be easily packaged into AAV, lentiviruses, Adenoviruses, and other viral vectors for robust delivery into primary cells and in vivo in animal models. In a preferred embodiment of the invention, the Cas9 protein from *S. aureus* is used.

```
>Campylobacter jejuni Cas9 (CjCas9)
                                       (SEQ ID NO: 102)
MARILAFDIGISSIGWAFSENDELKDCGVRIFTKVENPKTGESLALPRRLA

RSARKRLARRKARLNHLKHLIANEFKLNYEDYQSFDESLAKAYKGSLISPY

ELRFRALNELLSKQDFARVILHIAKRRGYDDIKNSDDKEKGAILKAIKQNE

EKLANYQSVGEYLYKEYFQKFKENSKEFTNVRNKKESYERCIAQSFLKDEL

KLIFKKQREFGFSFSKKFEEEVLSVAFYKRALKDFSHLVGNCSFFTDEKRA

PKNSPLAFMFVALTRIINLLNNLKNTEGILYTKDDLNALLNEVLKNGTLTY

KQTKKLLGLSDDYEFKGEKGTYFIEFKKYKEFIKALGEHNLSQDDLNEIAK

DITLIKDEIKLKKALAKYDLNQNQIDSLSKLEFKDHLNISFKALKLVTPLM

LEGKKYDEACNELNLKVAINEDKKDFLPAFNETYYKDEVTNPVVLRAIKEY

RKVLNALLKKYGKVHKINIELAREVGKNHSQRAKIEKEQNENYKAKKDAEL

ECEKLGLKINSKNILKLRLFKEQKEFCAYSGEKIKISDLQDEKMLEIDHIY

PYSRSFDDSYMNKVLVFTKQNQEKLNQTPFEAFGNDSAKWQKIEVLAKNLP

TKKQKRILDKNYKDKEQKNFKDRNLNDTRYIARLVLNYTKDYLDFLPLSDD

ENTKLNDTQKGSKVHVEAKSGMLTSALRHTWGFSAKDRNNHLHHAIDAVII

AYANNSIVKAFSDFKKEQESNSAELYAKKISELDYKNKRKFFEPFSGFRQK

VLDKIDEIFVSKPERKKPSGALHEETFRKEEEFYQSYGGKEGVLKALELGK

IRKVNGKIVKNGDMFRVDIFKHKKTNKFYAVPIYTMDFALKVLPNKAVARS

KKGEIKDWILMDENYEFCFSLYKDSLILIQTKDMQEPEFVYYNAFTSSTVS

LIVSKHDNKFETLSKNQKILFKNANEKEVIAKSIGIQNLKVFEKYIVSALG

EVTKAEFRQREDFKK.
```

The putative tracrRNA element for this CjCas9 is:

(SEQ ID NO: 103)
TATAATCTCATAAGAAATTTAAAAAGGGACTAAAATAAAGAGTTTGCGGGA

CTCTGCGGGGTTACAATCCCCTAAAACCGCTTTTAAAATT

The Direct Repeat sequence is:

(SEQ ID NO: 104)
ATTTTACCATAAAGAAATTTAAAAAGGGACTAAAAC

An example of a chimeric guideRNA for CjCas9 is:

(SEQ ID NO: 105)
NNNNNNNNNNNNNNNNNNNNGUUUUAGUCCCGAAAGGGACUAAAAUAAAGA

GUUUGCGGGACUCUGCGGGGUUACAAUCCCCUAAAACCGCUUUU

Example 12: Cas9 Optimization

For enhanced function or to develop new functions, Applicants generate chimeric Cas9 proteins by combining fragments from different Cas9 homologs. For example, two example chimeric Cas9 proteins:

For example, Applicants fused the N-term of St1Cas9 (fragment from this protein is in bold) with C-term of SpCas9 (fragment from this protein is underlined).

>St1(N)Sp(C)Cas9
(SEQ ID NO: 106)
MSDLVLGLDIGIGSVGVGILNKVTGEIIHKNSRIFPAAQAENNLVRRTNRQ

GRRLARRKKHRRVRLNRLFEESGLITDFTKISINLNPYQLRVKGLTDELSN

EELFIALKNMVKHRGISYLDDASDDGNSSVGDYAQIVKENSKQLETKTPGQ

IQLERYQTYGQLRGDFTVEKDGKKHRLINVFPTSAYRSEALRILQTQQEFN

PQITDEFINRYLEILTGKRKYYHGPGNEKSRTDYGRYRTSGETLDNIFGIL

TGKCTFYPDEFRAAKASYTAQEFNLLNDLNNLTVPTETKKLSKEQKNQIIN

YVKNEKAMGPAKLFKYIAKLLSCDVADIKGYRIDKSGKAEIHTFEAYRKMK

TLETLDIEQMDRETLDKLAYVLTLNTEREGIQEALEHEFADGSFSQKQVDE

LVQFRKANSSIFGKGWHNFSVKLMMELIPELYETSEEQMTILTRLGKQKTT

SSSNKTKYIDEKLLTEEIYNPVVAKSVRQAIKIVNAAIKEYGDFDNIVIEM

ARENQTTQKGQKNSRERMKRIEEGIKELGSQILKEHPVENTQLQNEKLYLY

YLQNGRDMYVDQELDINRLSDYDVDHIVPQSFLKDDSIDNKVLTRSDKNRG

KSDNVPSEEVVKKMKNYWRQLLNAKLITQRKFDNLTKAERGGLSELDKAGF

IKRQLVETRQITKHVAQILDSRMNTKYDENDKLIREVKVITLKSKLVSDFR

KDFQFYKVREINNYHHAHDAYLNAVVGTALIKKYPKLESEFVYGDYKVYDV

RKMIAKSEQEIGKATAKYFFYSNIMNFFKTEITLANGEIRKRPLIETNGET

GEIVWDKGRDFATVRKVLSMPQVNIVKKTEVQTGGFSKESILPKRNSDKLI

ARKKDWDPKKYGGFDSPTVAYSVLVVAKVEKGKSKKLKSVKELLGITIMER

SSFEKNPIDFLEAKGYKEVKKDLIIKLPKYSLFELENGRKRMLASAGELQK

-continued

GNELALPSKYVNFLYLASHYEKLKGSPEDNEQKQLFVEQHKHYLDEIIEQI

SEFSKRVILADANLDKVLSAYNKHRDKPIREQAENIIHLFTLTNLGAPAAF

KYFDTTIDRKRYTSTKEVLDATLIHQSITGLYETRIDLSQLGGD

>Sp(N)St1(C)Cas9
(SEQ ID NO: 107)
MDKKYSIGLDIGTNSVGWAVITDEYKVPSKKFKVLGNTDRHSIKKNLIGAL

LFDSGETAEATRLKRTARRRYTRRKNRICYLQEIFSNEMAKVDDSFFHRLE

ESFLVEEDKKHERHPIFGNIVDEVAYHEKYPTIYHLRKKLVDSTDKADLRL

IYLALAHMIKFRGHFLIEGDLNPDNSDVDKLFIQLVQTYNQLFEENPINAS

GVDAKAILSARLSKSRRLENLIAQLPGEKKNGLFGNLIALSLGLTPNFKSN

FDLAEDAKLQLSKDTYDDDLDNLLAQIGDQYADLFLAAKNLSDAILLSDIL

RVNTEITKAPLSASMIKRYDEHHQDLTLLKALVRQQLPEKYKEIFFDQSKN

GYAGYIDGGASQEEFYKFIKPILEKMDGTEELLVKLNREDLLRKQRTFDNG

SIPHQIHLGELHAILRRQEDFYPFLKDNREKIEKILTFRIPYYVGPLARGN

SRFAWMTRKSEETITPWNFEEVVDKGASAQSFIERMTNFDKNLPNEKVLPK

HSLLYEYFTVYNELTKVKYVTEGMRKPAFLSGEQKKAIVDLLEKTNRKVTV

KQLKEDYFKKIECFDSVEISGVEDRFNASLGTYHDLLKIIKDKDELDNEEN

EDILEDIVLTLTLFEDREMIEERLKTYAHLFDDKVMKQLKRRRYTGWGRLS

RKLINGIRDKQSGKTILDFLKSDGEANRNFMQLIHDDSLTFKEDIQKAQVS

GQGDSLHEHIANLAGSPAIKKGILQTVKVVDELVKVMGRHKPENIVIEMAR

ETNEDDEKKAIQKIQKANKDEKDAAMLKAANQYNGKAELPHSVFHGHKQLA

TKIRLWHQQGERCLYTGKTISIHDLINNSNQFEVDHILPLSITFDDSLANK

VLVYATANQEKGQRTPYQALDSMDDAWSFRELKAFVRESKTLSNKKKEYLL

TEEDISKFDVRKKFIERNLVDTRYASRVVLNALQEHFRAHKIDTKVSVVRG

QFTSQLRRHWGIEKTRDTYHHHAVDALHAASSQLNLWKKQKNTLVSYSEDQ

LLDIETGELISDDEYKESVFKAPYQHFVDTLKSKEFEDSILFSYQVDSKFN

RKISDATIYATRQAKVGKDKADETYVLGKIKDIYTQDGYDAFMKIYKKDKS

KFLMYRHDPQTFEKVIEPILENYPNKQINEKGKEVPCNPFLKYKEEHGYIR

KYSKKGNGPEIKSLKYYDSKLGNHIDITPKDSNNKVVLQSVSPWRADVYFN

KTTGKYEILGLKYADLQFEKGTGTYKISQEKYNDIKKKEGVDSDSEFKFTL

YKNDLLLVKDTETKEQQLFRFLSRTMPKQKHYVELKPYDKQKFEGGEALIK

VLGNVANSGQCKKGLGKSNISIYKVRTDVLGNQHIIKNEGDKPKLDF

The benefit of making chimeric Cas9 include:
- reduce toxicity,
- improve expression in eukaryotic cells,
- enhance specificity,
- reduce molecular weight of protein, make protein smaller by combining the smallest domains from different Cas9 homologs; and
- altering the PAM sequence requirement

Example 13: Utilization of Cas9 as a Generic DNA Binding Protein

Applicants used Cas9 as a generic DNA binding protein by mutating the two catalytic domains (D10 and H840) responsible for cleaving both strands of the DNA target. In order to upregulate gene transcription at a target locus Applicants fused the transcriptional activation domain (VP64) to Cas9. Applicants hypothesized that it would be important to see strong nuclear localization of the Cas9-VP64 fusion protein because transcription factor activation strength is a function of time spent at the target. Therefore, Applicants cloned a set of Cas9-VP64-GFP constructs, transfected them into 293 cells and assessed their localization under a fluorescent microscope 12 hours post-transfection.

The same constructs were cloned as a 2A-GFP rather than a direct fusion in order to functionally test the constructs without a bulky GFP present to interfere. Applicants elected to target the Sox2 locus with the Cas9 transactivator because it could be useful for cellular reprogram and the locus has already been validated as a target for TALE-TF mediated transcriptional activation. For the Sox2 locus Applicants chose eight targets near the transcriptional start site (TSS). Each target was 20 bp long with a neighboring NGG protospacer adjacent motif (PAM). Each Cas9-VP64 construct was co-transfected with each PCR generated chimeric crispr RNA (chiRNA) in 293 cells. 72 hours post transfection the transcriptional activation was assessed using RT-qPCR.

To further optimize the transcriptional activator, Applicants titrated the ratio of chiRNA (Sox2.1 and Sox2.5) to Cas9 (NLS-VP64-NLS-hSpCas9-NLS-VP64-NLS), transfected into 293 cells, and quantified using RT-qPCR. These results indicate that Cas9 can be used as a generic DNA binding domain to upregulate gene transcription at a target locus.

Applicants designed a second generation of constructs. (Table below) ("6×His" disclosed as SEQ ID NO: 925).

| |
|---|
| pLenti-EF1a-GFP-2A-6xHis-NLS-VP64-NLS-hSpCsn1(D10A, H840A)-NLS |
| pLenti-EF1a-GFP-2A-6xHis-NLS-VP64-NLS-hSpCsn1(D10A, H840A) |
| pLenti-EF1a-GFP-2A-6xHis-NLS-VP64-NLS-NLS-hSpCsn1(D10A, H840A) |
| pLenti-EF1a-GFP-2A-6xHis-NLS-hSpCsn1(D10A, H840A)-NLS |
| pLenti-EF1a-GFP-2A-6xHis-NLS-hSpCsn1(D10A, H840A) |
| pLenti-EF1a-GFP-2A-6xHis-NLS-NLS-hSpCsn1(D10A, H840A) |

Applicants use these constructs to assess transcriptional activation (VP64 fused constructs) and repression (Cas9 only) by RT-qPCR. Applicants assess the cellular localization of each construct using anti-His antibody, nuclease activity using a Surveyor nuclease assay, and DNA binding affinity using a gel shift assay. In a preferred embodiment of the invention, the gel shift assay is an EMSA gel shift assay.

Example 14: Cas9 Transgenic and Knock in Mice

To generate a mouse that expresses the Cas9 nuclease Applicants submit two general strategies, transgenic and knock in. These strategies may be applied to generate any other model organism of interest, for e.g. Rat. For each of the general strategies Applicants made a constitutively active Cas9 and a Cas9 that is conditionally expressed (Cre recombinase dependent). The constitutively active Cas9 nuclease is expressed in the following context: pCAG-NLS-Cas9-NLS-P2A-EGFP-WPRE-bGHpolyA. pCAG is the promoter, NLS is a nuclear localization signal, P2A is the peptide cleavage sequence, EGFP is enhanced green fluorescent protein, WPRE is the woodchuck hepatitis virus posttranscriptional regulatory element, and bGHpolyA is the bovine growth hormone poly-A signal sequence (FIGS. 25A-B). The conditional version has one additional stop cassette element, loxP-SV40 polyA x3-loxP, after the promoter and before NLS-Cas9-NLS (i.e. pCAG-loxP-SV40polyAx3-loxP-NLS-Cas9-NLS-P2A-EGFP-WPRE-bGHpolyA). The important expression elements can be visualized as in FIG. 26. The constitutive construct should be expressed in all cell types throughout development, whereas, the conditional construct will only allow Cas9 expression when the same cell is expressing the Cre recombinase. This latter version will allow for tissue specific expression of Cas9 when Cre is under the expression of a tissue specific promoter. Moreover, Cas9 expression could be induced in adult mice by putting Cre under the expression of an inducible promoter such as the TET on or off system.

Validation of Cas9 constructs: Each plasmid was functionally validated in three ways: 1) transient transfection in 293 cells followed by confirmation of GFP expression; 2) transient transfection in 293 cells followed by immunofluorescence using an antibody recognizing the P2A sequence; and 3) transient transfection followed by Surveyor nuclease assay. The 293 cells may be 293FT or 293 T cells depending on the cells that are of interest. In a preferred embodiment the cells are 293FT cells. The results of the Surveyor were run out on the top and bottom row of the gel for the conditional and constitutive constructs, respectively. Each was tested in the presence and absence of chimeric RNA targeted to the hEMX1 locus (chimeric RNA hEMX1.1). The results indicate that the construct can successfully target the hEMX1 locus only in the presence of chimeric RNA (and Cre in the conditional case). The gel was quantified and the results are presented as average cutting efficiency and standard deviation for three samples.

Transgenic Cas9 mouse: To generate transgenic mice with constructs, Applicants inject pure, linear DNA into the pronucleus of a zygote from a pseudo pregnant CB56 female. Founders are identified, genotyped, and backcrossed to CB57 mice. The constructs were successfully cloned and verified by Sanger sequencing.

Knock in Cas9 mouse: To generate Cas9 knock in mice Applicants target the same constitutive and conditional constructs to the Rosa26 locus. Applicants did this by cloning each into a Rosa26 targeting vector with the following elements: Rosa26 short homology arm—constitutive/conditional Cas9 expression cassette—pPGK-Neo-Rosa26 long homology arm—pPGK-DTA. pPGK is the promoter for the positive selection marker Neo, which confers resistance to neomycin, a 1 kb short arm, a 4.3 kb long arm, and a negative selection diphtheria toxin (DTA) driven by PGK.

The two constructs were electroporated into R1 mESCs and allowed to grow for 2 days before neomycin selection was applied. Individual colonies that had survived by days 5-7 were picked and grown in individual wells. 5-7 days later the colonies were harvested, half were frozen and the other half were used for genotyping. Genotyping was done by genomic PCR, where one primer annealed within the donor plasmid (AttpF) and the other outside of the short homology arm (Rosa26-R) Of the 22 colonies harvested for the conditional case, 7 were positive (Left). Of the 27 colonies harvested for the constitutive case, zero were positive (Right). It is likely that Cas9 causes some level of toxicity in the mESC and for this reason there were no positive clones. To test this Applicants introduced a Cre expression plasmid into correctly targeted conditional Cas9 cells and found very low toxicity after many days in culture. The reduced copy number of Cas9 in correctly targeted conditional Cas9 cells (1-2 copies per cell) is enough to allow stable expression and relatively no cytotoxicity. Moreover, this data indicates that the Cas9 copy number determines toxicity. After electroporation each cell should get several copies of Cas9 and this is likely why no positive colonies were found in the case of the constitutive Cas9 construct. This provides strong evidence that utilizing a conditional, Cre-dependent strategy should show reduced toxicity. Applicants inject correctly targeted cells into a blastocyst and implant into a female mouse. Chimerics are identified and backcrossed. Founders are identified and genotyped.

Utility of the conditional Cas9 mouse: Applicants have shown in 293 cells that the Cas9 conditional expression construct can be activated by co-expression with Cre. Applicants also show that the correctly targeted R1 mESCs can have active Cas9 when Cre is expressed. Because Cas9 is followed by the P2A peptide cleavage sequence and then EGFP Applicants identify successful expression by observing EGFP. This same concept is what makes the conditional Cas9 mouse so useful. Applicants may cross their conditional Cas9 mouse with a mouse that ubiquitously expresses Cre (ACTB-Cre line) and may arrive at a mouse that expresses Cas9 in every cell. It should only take the delivery of chimeric RNA to induce genome editing in embryonic or adult mice. Interestingly, if the conditional Cas9 mouse is crossed with a mouse expressing Cre under a tissue specific promoter, there should only be Cas9 in the tissues that also express Cre. This approach may be used to edit the genome in only precise tissues by delivering chimeric RNA to the same tissue.

Example 15: Cas9 Diversity and Chimeric RNAs

The CRISPR-Cas system is an adaptive immune mechanism against invading exogenous DNA employed by diverse species across bacteria and archaea. The type II CRISPR-Cas system consists of a set of genes encoding proteins responsible for the "acquisition" of foreign DNA into the CRISPR locus, as well as a set of genes encoding the "execution" of the DNA cleavage mechanism; these include the DNA nuclease (Cas9), a non-coding transactivating cr-RNA (tracrRNA), and an array of foreign DNA-derived spacers flanked by direct repeats (crRNAs). Upon maturation by Cas9, the tracrRNA and crRNA duplex guide the Cas9 nuclease to a target DNA sequence specified by the spacer guide sequences, and mediates double-stranded breaks in the DNA near a short sequence motif in the target DNA that is required for cleavage and specific to each CRISPR-Cas system. The type II CRISPR-Cas systems are found throughout the bacterial kingdom and highly diverse in in Cas9 protein sequence and size, tracrRNA and crRNA direct repeat sequence, genome organization of these elements, and the motif requirement for target cleavage. One species may have multiple distinct CRISPR-Cas systems.

Applicants evaluated 207 putative Cas9s from bacterial species identified based on sequence homology to known Cas9s and structures orthologous to known subdomains, including the HNH endonuclease domain and the RuvC endonuclease domains [information from the Eugene Koonin and Kira Makarova]. Phylogenetic analysis based on the protein sequence conservation of this set revealed five families of Cas9s, including three groups of large Cas9s (~1400 amino acids) and two of small Cas9s (~1100 amino acids) (FIGS. 19A-D and 20A-F).

Applicants have also optimized Cas9 guide RNA using in vitro methods.

Example 16: Cas9 Mutations

In this example, Applicants show that the following mutations can convert SpCas9 into a nicking enzyme: D10A, E762A, H840A, N854A, N863A, D986A.

Applicants provide sequences showing where the mutation points are located within the SpCas9 gene (FIG. 24A-M). Applicants also show that the nickases are still able to mediate homologous recombination. Furthermore, Applicants show that SpCas9 with these mutations (individually) do not induce double strand break.

Cas9 orthologs all share the general organization of 3-4 RuvC domains and a HNH domain. The 5' most RuvC domain cleaves the non-complementary strand, and the HNH domain cleaves the complementary strand. All notations are in reference to the guide sequence.

The catalytic residue in the 5' RuvC domain is identified through homology comparison of the Cas9 of interest with other Cas9 orthologs (from *S. pyogenes* type II CRISPR locus, *S. thermophilus* CRISPR locus 1, *S. thermophilus* CRISPR locus 3, and *Franciscilla novicida* type II CRISPR locus), and the conserved Asp residue is mutated to alanine to convert Cas9 into a complementary-strand nicking enzyme. Similarly, the conserved His and Asn residues in the HNH domains are mutated to Alanine to convert Cas9 into a non-complementary-strand nicking enzyme.

Example 17: Cas9 Transcriptional Activation and Cas9 Repressor

Cas9 Transcriptional Activation

A second generation of constructs were designed and tested (Table 1). These constructs are used to assess transcriptional activation (VP64 fused constructs) and repression (Cas9 only) by RT-qPCR. Applicants assess the cellular localization of each construct using anti-His antibody, nuclease activity using a Surveyor nuclease assay, and DNA binding affinity using a gel shift assay.

Cas Repressor

It has been shown previously that dCas9 can be used as a generic DNA binding domain to repress gene expression. Applicants report an improved dCas9 design as well as dCas9 fusions to the repressor domains KRAB and SID4×. From the plasmid library created for modulating transcription using Cas9 in Table 1, the following repressor plasmids were functionally characterized by qPCR: pXRP27, pXRP28, pXRP29, pXRP48, pXRP49, pXRP50, pXRP51, pXRP52, pXRP53, pXRP56, pXRP58, pXRP59, pXRP61, and pXRP62.

Each dCas9 repressor plasmid was co-transfected with two guide RNAs targeted to the coding strand of the beta-catenin gene. RNA was isolated 72 hours after transfection and gene expression was quantified by RT-qPCR. The endogenous control gene was GAPDH. Two validated shRNAs were used as positive controls. Negative controls were certain plasmids transfected without gRNA, these are denoted as "pXRP ## control". The plasmids pXRP28, pXRP29, pXRP48, and pXRP49 could repress the beta-catenin gene when using the specified targeting strategy. These plasmids correspond to dCas9 without a functional domain (pXRP28 and pXRP28) and dCas9 fused to SID4× (pXRP48 and pXRP49).

Further work investigates: repeating the above experiment, targeting different genes, utilizing other gRNAs to determine the optimal targeting position, and multiplexed repression.

TABLE 1

| (Table 1 discloses "GGGGS$_3$" as SEQ ID NO: 108, "EAAAK$_3$" as SEQ ID NO: 109 and "GGGGGS$_3$" as SEQ ID NO: 110) |
|---|
| pXRP024-pLenti2-EF1a-VP64-NLS-FLAG-Linker-dCas9-NLS-gLuc-2A-GFP-WPRE |
| pXRP025-pLenti2-EF1a-VP64-NLS-GGGGS$_3$Linker-dCas9-NLS-gLuc-2A-GFP-WPRE |
| pXRP026-pLenti2-EF1a-VP64-NLS-EAAAK$_3$Linker-dCas9-NLS-gLuc-2A-GFP-WPRE |
| pXRP027-pLenti2-EF1a-NLS-FLAG-Linker-dCas9-NLS-gLuc-2A-GFP-WPRE |
| pXRP028-pLenti2-EF1a-NLS-GGGGS$_3$Linker-dCas9-NLS-gLuc-2A-GFP-WPRE |
| pXRP029-pLenti2-EF1a-NLS-EAAAK$_3$Linker-dCas9-NLS-gLuc-2A-GFP-WPRE |
| pXRP030-pLenti2-pSV40-VP64-NLS-FLAG-Linker-dCas9-NLS-gLuc-2A-GFP-WPRE |
| pXRP031-pLenti2-pPGK-VP64-NLS-FLAG-Linker-dCas9-NLS-gLuc-2A-GFP-WPRE |
| pXRP032-pLenti2-LTR-VP64-NLS-FLAG-Linker-dCas9-NLS-gLuc-2A-GFP-WPRE |
| pXRP033-pLenti2-pSV40-VP64-NLS-GGGGS$_3$Linker-dCas9-NLS-gLuc-2A-GFP-WPRE |
| pXRP034-pLenti2-pPGK-VP64-NLS-GGGGS$_3$Linker-dCas9-NLS-gLuc-2A-GFP-WPRE |
| pXRP035-pLenti2-LTR-VP64-NLS-GGGGS$_3$Linker-dCas9-NLS-gLuc-2A-GFP-WPRE |
| pXRP036-pLenti2-pSV40-VP64-NLS-EAAAK$_3$Linker-dCas9-NLS-gLuc-2A-GFP-WPRE |
| pXRP037-pLenti2-pPGK-VP64-NLS-EAAAK$_3$Linker-dCas9-NLS-gLuc-2A-GFP-WPRE |
| pXRP038-pLenti2-LTR-VP64-NLS-EAAAK$_3$Linker-dCas9-NLS-gLuc-2A-GFP-WPRE |
| pXRP048-pLenti2-EF1a-SID4x-NLS-FLAG-Linker-dCas9-NLS-gLuc-2A-GFP-WPRE |
| pXRP049-pLenti2-EF1a-SID4X-NLS-GGGGS$_3$Linker-dCas9-NLS-gLuc-2A-GFP-WPRE |
| pXRP050-pLenti2-EF1a-SID4X-NLS-EAAAK$_3$Linker-dCas9-NLS-gLuc-2A-GFP-WPRE |
| pXRP051-pLenti2-EF1a-KRAB-NLS-FLAG-Linker-dCas9-NLS-gLuc-2A-GFP-WPRE |
| pXRP052-pLenti2-EF1a-KRAB-NLS-GGGGS$_3$Linker-dCas9-NLS-gLuc-2A-GFP-WPRE |
| pXRP053-pLenti2-EF1a-KRAB-NLS-EAAAK$_3$Linker-dCas9-NLS-gLuc-2A-GFP-WPRE |
| pXRP054-pLenti2-EF1a-dCas9-Linker-FLAG-NLS-VP64-gLuc-2A-GFP-WPRE |
| pXRP055-pLenti2-EF1a-dCas9-Linker-FLAG-NLS-SID4X-gLuc-2A-GFP-WPRE |
| pXRP056-pLenti2-EF1a-dCas9-Linker-FLAG-NLS-KRAB-gLuc-2A-GFP-WPRE |
| pXRP057-pLenti2-EF1a-dCas9-GGGGGS$_3$-NLS-VP64-gLuc-2A-GFP-WPRE |
| pXRP058-pLenti2-EF1a-dCas9-GGGGGS$_3$-NLS-SID4X-gLuc-2A-GFP-WPRE |
| pXRP059-pLenti2-EF1a-dCas9-GGGGGS$_3$-NLS-KRAB-gLuc-2A-GFP-WPRE |
| pXRP060-pLenti2-EF1a-dCas9-EAAAK$_3$-NLS-VP64-gLuc-2A-GFP-WPRE |
| pXRP061-pLenti2-EF1a-dCas9-EAAAK$_3$-NLS-SID4X-gLuc-2A-GFP-WPRE |
| pXRP062-pLenti2-EF1a-dCas9-EAAAK$_3$-NLS-KRAB-gLuc-2A-GFP-WPRE |
| pXRP024-pLenti2-EF1a-VP64-NLS-FLAG-Linker-Cas9-NLS-gLuc-2A-GFP-WPRE |
| pXRP025-pLenti2-EF1a-VP64-NLS-GGGGS$_3$Linker-Cas9-NLS-gLuc-2A-GFP-WPRE |
| pXRP026-pLenti2-EF1a-VP64-NLS-EAAAK$_3$Linker-Cas9-NLS-gLuc-2A-GFP-WPRE |
| pXRP027-pLenti2-EF1a-NLS-FLAG-Linker-Cas9-NLS-gLuc-2A-GFP-WPRE |
| pXRP028-pLenti2-EF1a-NLS-GGGGS$_3$Linker-Cas9-NLS-gLuc-2A-GFP-WPRE |

TABLE 1-continued

| (Table 1 discloses "GGGGS$_3$" as SEQ ID NO: 108, "EAAAK$_3$" as SEQ ID NO: 109 and "GGGGGS$_3$" as SEQ ID NO: 110) |
|---|
| pXRP029-pLenti2-EF1a-NLS-EAAAK$_3$Linker-Cas9-NLS-gLuc-2A-GFP-WPRE |
| pXRP030-pLenti2-pSV40-VP64-NLS-FLAG-Linker-Cas9-NLS-gLuc-2A-GFP-WPRE |
| pXRP031-pLenti2-pPGK-VP64-NLS-FLAG-Linker-Cas9-NLS-gLuc-2A-GFP-WPRE |
| pXRP032-pLenti2-LTR-VP64-NLS-FLAG-Linker-Cas9-NLS-gLuc-2A-GFP-WPRE |
| pXRP033-pLenti2-pSV40-VP64-NLS-GGGGS$_3$Linker-Cas9-NLS-gLuc-2A-GFP-WPRE |
| pXRP034-pLenti2-pPGK-VP64-NLS-GGGGS$_3$Linker-Cas9-NLS-gLuc-2A-GFP-WPRE |
| pXRP035-pLenti2-LTR-VP64-NLS-GGGGS$_3$Linker-Cas9-NLS-gLuc-2A-GFP-WPRE |
| pXRP036-pLenti2-pSV40-VP64-NLS-EAAAK$_3$Linker-Cas9-NLS-gLuc-2A-GFP-WPRE |
| pXRP037-pLenti2-pPGK-VP64-NLS-EAAAK$_3$Linker-Cas9-NLS-gLuc-2A-GFP-WPRE |
| pXRP038-pLenti2-LTR-VP64-NLS-EAAAK$_3$Linker-Cas9-NLS-gLuc-2A-GFP-WPRE |
| pXRP048-pLenti2-EF1a-SID4x-NLS-FLAG-Linker-Cas9-NLS-gLuc-2A-GFP-WPRE |
| pXRP049-pLenti2-EF1a-SID4X-NLS-GGGGS$_3$Linker-Cas9-NLS-gLuc-2A-GFP-WPRE |
| pXRP050-pLenti2-EF1a-SID4X-NLS-EAAAK$_3$Linker-Cas9-NLS-gLuc-2A-GFP-WPRE |
| pXRP051-pLenti2-EF1a-KRAB-NLS-FLAG-Linker-Cas9-NLS-gLuc-2A-GFP-WPRE |
| pXRP052-pLenti2-EF1a-KRAB-NLS-GGGGS$_3$Linker-Cas9-NLS-gLuc-2A-GFP-WPRE |
| pXRP053-pLenti2-EF1a-KRAB-NLS-EAAAK$_3$Linker-Cas9-NLS-gLuc-2A-GFP-WPRE |
| pXRP054-pLenti2-EF1a-Cas9-Linker-FLAG-NLS-VP64-gLuc-2A-GFP-WPRE |
| pXRP055-pLenti2-EF1a-Cas9-Linker-FLAG-NLS-SID4X-gLuc-2A-GFP-WPRE |
| pXRP056-pLenti2-EF1a-Cas9-Linker-FLAG-NLS-KRAB-gLuc-2A-GFP-WPRE |
| pXRP057-pLenti2-EF1a-Cas9-GGGGGS$_3$-NLS-VP64-gLuc-2A-GFP-WPRE |
| pXRP058-pLenti2-EF1a-Cas9-GGGGGS$_3$-NLS-SID4X-gLuc-2A-GFP-WPRE |
| pXRP059-pLenti2-EF1a-Cas9-GGGGGS$_3$-NLS-KRAB-gLuc-2A-GFP-WPRE |
| pXRP060-pLenti2-EF1a-Cas9-EAAAK$_3$-NLS-VP64-gLuc-2A-GFP-WPRE |
| pXRP061-pLenti2-EFla-Cas9-EAAAK$_3$-NLS-SID4X-gLuc-2A-GFP-WPRE |
| pXRP062-pLenti2-EF1a-Cas9-EAAAK$_3$-NLS-KRAB-gLuc-2A-GFP-WPRE |

Example 18: Targeted Deletion of Genes Involved in Cholesterol Biosynthesis, Fatty Acid Biosynthesis, and Other Metabolic Disorders, Genes Encoding Mis-Folded Proteins Involved in Amyloid and Other Diseases, Oncogenes Leading to Cellular Transformation, Latent Viral Genes, and Genes Leading to Dominant-Negative Disorders, Amongst Other Disorders Applicants demonstrate gene delivery of a CRISPR-Cas system in the liver, brain, ocular, epithelial, hematopoetic, or another tissue of a subject or a patient in need thereof, suffering from metabolic disorders, amyloidosis and protein-aggregation related diseases, cellular transformation arising from genetic mutations and translocations, dominant negative effects of gene mutations, latent viral infections, and other related symptoms, using either viral or nanoparticle delivery system.

Study Design: Subjects or patients in need thereof suffering from metabolic disorders, amyloidosis and protein aggregation related disease which include but are not limited to human, non-primate human, canine, feline, bovine, equine, other domestic animals and related mammals. The CRISPR-Cas system is guided by a chimeric guide RNA and targets a specific site of the human genomic loci to be cleaved. After cleavage and non-homologous end-joining mediated repair, frame-shift mutation results in knock out of genes.

Applicants select guide-RNAs targeting genes involved in above-mentioned disorders to be specific to endogenous loci with minimal off-target activity. Two or more guide RNAs may be encoded into a single CRISPR array to induce simultaneous double-stranded breaks in DNA leading to micro-deletions of affected genes or chromosomal regions.

Identification and Design of Gene Targets

For each candidate disease gene, Applicants select DNA sequences of interest include protein-coding exons, sequences including and flanking known dominant negative mutation sites, sequences including and flanking pathological repetitive sequences. For gene-knockout approaches, early coding exons closest to the start codon offer best options for achieving complete knockout and minimize possibility of truncated protein products retaining partial function.

Applicants analyze sequences of interest for all possible targetable 20-bp sequences immediately 5' to a NGG motif (for SpCas9 system) or a NNAGAAW (for St1Cas9 system). Applicants choose sequences for unique, single RNA-guided Cas9 recognition in the genome to minimize off-target effects based on computational algorithm to determine specificity.

Cloning of Guide Sequences into a Delivery System

Guide sequences are synthesized as double-stranded 20-24 bp oligonucleotides. After 5'-phosphorylation treatment of oligos and annealing to form duplexes, oligos are ligated into suitable vector depending on the delivery method:

Virus-Based Delivery Methods

AAV-based vectors (PX260, 330, 334, 335) have been described elsewhere

Lentiviral-based vectors use a similar cloning strategy of directly ligating guide sequences into a single vector carrying a U6 promoter-driven chimeric RNA scaffold and a EF1a promoter-driven Cas9 or Cas9 nickase.

Virus production is described elsewhere.

Nanoparticle-Based RNA Delivery Methods

1. Guide sequences are synthesized as an oligonucleotide duplex encoding T7 promoter—guide sequence—chimeric RNA. A T7 promoter is added 5' of Cas9 by PCR method.

2. T7-driven Cas9 and guide-chimeric RNAs are transcribed in vitro, and Cas9 mRNA is further capped and A-tailed using commercial kits. RNA products are purified per kit instructions.

Hydrodynamic Tail Vein Delivery Methods (for Mouse)

Guide sequences are cloned into AAV plasmids as described above and elsewhere in this application.

In Vitro Validation on Cell Lines

Transfection

1. DNA Plasmid Transfection

Plasmids carrying guide sequences are transfected into human embryonic kidney (HEK293T) or human embryonic stem (hES) cells, other relevant cell types using lipid-, chemical-, or electroporation-based methods. For a 24-well transfection of HEK293T cells (~260,000 cells), 500 ng of total DNA is transfected into each single well using Lipofectamine 2000. For a 12-well transfection of hES cells, 1 ug of total DNA is transfected into a single well using Fugene HD.

2. RNA Transfection

Figures 28A, 28B, 28C:
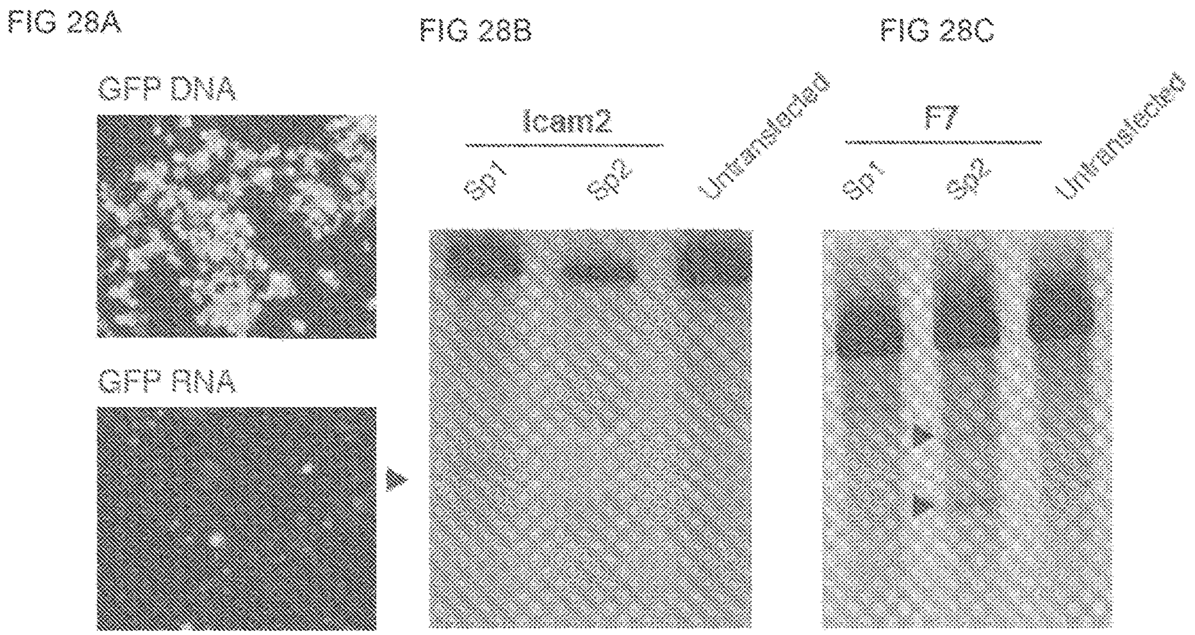
FIG. 28A-28C shows RNA delivery of Cas9 and chimeric RNA into cells (A) Delivery of a GFP reporter as either DNA or mRNA into Neuro-2A cells. (B) Delivery of Cas9 and chimeric RNA against the Icam2 gene as RNA results in cutting for one of two spacers tested. (C) Delivery of Cas9 and chimeric RNA against the F7 gene as RNA results in cutting for one of two spacers tested.

Purified RNA described above is used for transfection into HEK293T cells. 1-2 ug of RNA may be transfected into 260,000 using Lipofectamine 2000 per manufacturer's instruction. RNA delivery of Cas9 and chimeric RNA is shown in FIG. 28.

Assay of Indel Formation In Vitro

Cells are harvested 72-hours post-transfection and assayed for indel formation as an indication of double-stranded breaks.

Briefly, genomic region around target sequence is PCR amplified (~400-600 bp amplicon size) using high-fidelity polymerase. Products are purified, normalized to equal concentration, and slowly annealed from 95° C. to 4° C. to allow formation of DNA heteroduplexes. Post annealing, the Cel-I enzyme is used to cleave heteroduplexes, and resulting products are separated on a polyacrylamide gel and indel efficiency calculated.

In Vivo Proof of Principle in Animal

Delivery Mechanisms

AAV or Lentivirus production is described elsewhere.

Nanoparticle Formulation: RNA Mixed into Nanoparticle Formulation

Hydrodynamic Tail Vein Injections with DNA Plasmids in Mice are Conducted Using a Commercial Kit Cas9 and guide sequences are delivered as virus, nanoparticle-coated RNA mixture, or DNA plasmids, and injected into subject animals. A parallel set of control animals is injected with sterile saline, Cas9 and GFP, or guide sequence and GFP alone.

Three weeks after injection, animals are tested for amelioration of symptoms and sacrificed. Relevant organ systems analyzed for indel formation. Phenotypic assays include blood levels of HDL, LDL, lipids, Assay for Indel Formation DNA is extracted from tissue using commercial kits; indel assay will be performed as described for in vitro demonstration.

Therapeutic applications of the CRISPR-Cas system are amenable for achieving tissue-specific and temporally controlled targeted deletion of candidate disease genes. Examples include genes involved in cholesterol and fatty acid metabolism, amyloid diseases, dominant negative diseases, latent viral infections, among other disorders.

Examples of a Single Guide-RNA to Introduce Targeted Indels at a Gene Locus

| Disease | GENE | SPACER | PAM | SEQ ID NO: | Mechanism | References |
|---|---|---|---|---|---|---|
| Hyper-cholesterolemia | HMG-CR | GCCAAATTG GACGACCCT CG | CGG | 111 | Knockout | Fluvastatin: a review of its pharmacology and use in the management of hypercholesterolaemia. (Plosker GL et al. Drugs 1996, 51(3): 433-459) |

-continued

| Disease | GENE | SPACER | PAM | SEQ ID NO: | Mechanism | References |
|---|---|---|---|---|---|---|
| Hyper-cholesterolemia | SQLE | CGAGGAGAC CCCCGTTTC GG | TGG | 112 | Knockout | Potential role of nonstatin cholesterol lowering agents (Trapani et al. IUBMB Life, Volume 63, Issue 11, pages 964-971, November 2011) |
| Hyper-lipidemia | DGAT1 | CCCGCCGCC GCCGTGGCT CG | AGG | 113 | Knockout | DGAT1 inhibitors as anti-obesity and anti-diabetic agents. (Birch AM et al. Current Opinion in Drug Discovery & Development [2010, 13(4): 489-496) |
| Leukemia | BCR-ABL | TGAGCTCTA CGAGATCCA CA | AGG | 114 | Knockout | Killing of leukemic cells with a BCR/ABL fusion gene by RNA interference (RNAi). (Fuchs et al. Oncogene 2002, 21(37): 5716-5724) |

Examples of a Pair of Guide-RNA to Introduce Chromosomal Microdeletion at a Gene Locus

| Disease | GENE | SPACER | PAM | SEQ ID NO: | Mechanism | References |
|---|---|---|---|---|---|---|
| Hyper-lipidemia | PLIN2 guide1 | CTCAAAATT CATACCGGT TG | TGG | 115 | Microdeletion | Perilipin-2 Null Mice are Protected Against Diet-Induced Obesity, Adipose Inflammation and Fatty Liver Disease (McManaman JL et al. The Journal of Lipid Research, jlr.M035063. First Published on Feb. 12, 2013) |
| Hyper-lipidemia | PLIN2 guide2 | CGTTAAACA ACAACCGGA CT | TGG | 116 | Microdeletion | |
| Hyper-lipidemia | SREBP guide1 | TTCACCCCG CGGCGCTGA AT | ggg | 117 | Microdeletion | Inhibition of SREBP by a Small Molecule, Betulin, Improves Hyperlipidemia and Insulin Resistance and Reduces Atherosclerotic Plaques (Tang J et al. Cell Metabolism, Volume 13, Issue 1, 44-56, 5 Jan. 2011) |
| Hyper-lipidemia | SREBP guide2 | ACCACTACC AGTCCGTCC AC | agg | 118 | Microdeletion | |

Example 19: Targeted Integration of Repair for Genes Carrying Disease-Causing Mutations; Reconstitution of Enzyme Deficiencies and Other Related Diseases Study Design I. Identification and Design of Gene Targets
  Described in Example 22
II. Cloning of Guide Sequences and Repair Templates into a Delivery System
  Described above in Example 22
  Applicants clone DNA repair templates to include homology arms with diseased allele as well a wild-type repair template
III. In Vitro Validation on Cell Lines
  a. Transfection is described above in Example 22; Cas9, guide RNAs, and repair template are co-transfected into relevant cell types.
  b. Assay for repair in vitro
  i. Applicants harvest cells 72-hours post-transfection and assay for repair
  ii. Briefly, Applicants amplify genomic region around repair template PCR using high-fidelity polymerase. Applicants sequence products for decreased incidence of mutant allele.
IV. In Vivo Proof of Principle in Animal
  a. Delivery mechanisms are described above Examples 22 and 34.
  b. Assay for repair in vivo
  i. Applicants perform the repair assay as described in the in vitro demonstration.
V. Therapeutic Applications The CRISPR-Cas system is amenable for achieving tissue-specific and temporally controlled targeted deletion of candidate disease genes. Examples include genes involved in cholesterol and fatty acid metabolism, amyloid diseases, dominant negative diseases, latent viral infections, among other disorders.

Example of one single missense mutation with repair template:

| Disease | GENE | SPACER | PAM |
|---|---|---|---|
| Familial amyloid polyneuropathy | TTR | AGCCTTTCTGAACACATGCA (SEQ ID NO: 119) | CGG |

| Mechanism | References |
|---|---|
| V30M repair | Transthyretin mutations in health and disease (Joao et al. Human Mutation, Volume 5, Issue 3, pages 191-196, 1995) |
| V30M allele | CCTGCCATCAATGTGGCC**A**TGCATGTGTTCAGAAAGGCT (SEQ ID NO: 120) |
| WT allele | CCTGCCATCAATGTGGCC**G**TGCATGTGTTCAGAAAGGCT (SEQ ID NO: 121) |

Example 20: Therapeutic Application of the CRISPR-Cas System in Glaucoma, Amyloidosis, and Huntington's Disease Glaucoma: Applicants design guide RNAs to target the first exon of the mycilin (MYOC) gene. Applicants use adenovirus vectors (Ad5) to package both Cas9 as well as a guide RNA targeting the MYOC gene. Applicants inject adenoviral vectors into the trabecular meshwork where cells have been implicated in the pathophysiology of glaucoma. Applicants initially test this out in mouse models carrying the mutated MYOC gene to see whether they improve visual acuity and decrease pressure in the eyes. Therapeutic application in humans employ a similar strategy.

Amyloidosis: Applicants design guide RNAs to target the first exon of the transthyretin (TTR) gene in the liver. Applicants use AAV8 to package Cas9 as well as guide RNA targeting the first exon of the TTR gene. AAV8 has been shown to have efficient targeting of the liver and will be administered intravenously. Cas9 can be driven either using liver specific promoters such as the albumin promoter, or using a constitutive promoter. A pol3 promoter drives the guide RNA.

Alternatively, Applicants utilize hydrodynamic delivery of plasmid DNA to knockout the TTR gene. Applicants deliver a plasmid encoding Cas9 and the guideRNA targeting Exon1 of TTR.

As a further alternative approach, Applicants administer a combination of RNA (mRNA for Cas9, and guide RNA). RNA can be packaged using liposomes such as Invivofectamine from Life Technologies and delivered intravenously. To reduce RNA-induced immunogenicity, increase the level of Cas9 expression and guide RNA stability, Applicants modify the Cas9 mRNA using 5' capping. Applicants also incorporate modified RNA nucleotides into Cas9 mRNA and guide RNA to increase their stability and reduce immunogenicity (e.g. activation of TLR). To increase efficiency, Applicants administer multiple doses of the virus, DNA, or RNA.

Huntington's Disease: Applicants design guide RNA based on allele specific mutations in the HTT gene of patients. For example, in a patient who is heterozygous for HTT with expanded CAG repeat, Applicants identify nucleotide sequences unique to the mutant HTT allele and use it to design guideRNA. Applicants ensure that the mutant base is located within the last 9 bp of the guide RNA (which Applicants have ascertained has the ability to discriminate between single DNA base mismatches between the target size and the guide RNA).

Applicants package the mutant HTT allele specific guide RNA and Cas9 into AAV9 and deliver into the striatum of Huntington's patients. Virus is injected into the striatum stereotactically via a craniotomy. AAV9 is known to transduce neurons efficiently. Applicants drive Cas9 using a neuron specific promoter such as human Synapsin I.

Example 21: Therapeutic Application of the CRISPR-Cas System in HIV

Chronic viral infection is a source of significant morbidity and mortality. While there exists for many of these viruses conventional antiviral therapies that effectively target various aspects of viral replication, current therapeutic modalities are usually non-curative in nature due to "viral latency." By its nature, viral latency is characterized by a dormant phase in the viral life cycle without active viral production. During this period, the virus is largely able to evade both immune surveillance and conventional therapeutics allowing for it to establish long-standing viral reservoirs within the host from which subsequent re-activation can permit continued propagation and transmission of virus. Key to viral latency is the ability to stably maintain the viral genome, accomplished either through episomal or proviral latency, which stores the viral genome in the cytoplasm or integrates it into the host genome, respectively. In the absence of effective vaccinations which would prevent primary infection, chronic viral infections characterized by latent reservoirs and episodes of lytic activity can have significant consequences: human papilloma virus (HPV) can result in cervical cancer, hepatitis C virus (HCV) predisposes to hepatocellular carcinoma, and human immunodeficiency virus eventually destroys the host immune system resulting in susceptibility to opportunistic infections. As such, these infections require life-long use of currently available antiviral therapeutics. Further complicating matters is the high mutability of many of these viral genomes which lead to the evolution of resistant strains for which there exists no effective therapy.

The CRISPR-Cas system is a bacterial adaptive immune system able to induce double-stranded DNA breaks (DSB) in a multiplex-able, sequence-specific manner and has been recently re-constituted within mammalian cell systems. It has been shown that targeting DNA with one or numerous guide-RNAs can result in both indels and deletions of the intervening sequences, respectively. As such, this new technology represents a means by which targeted and multiplexed DNA mutagenesis can be accomplished within a single cell with high efficiency and specificity. Consequently, delivery of the CRISPR-Cas system directed against viral DNA sequences could allow for targeted disruption and deletion of latent viral genomes even in the absence of ongoing viral production.

As an example, chronic infection by HIV-1 represents a global health issue with 33 million individuals infected and an annual incidence of 2.6 million infections. The use of the multimodal highly active antiretroviral therapy (HAART), which simultaneously targets multiple aspects of viral replication, has allowed HIV infection to be largely managed as a chronic, not terminal, illness. Without treatment, progression of HIV to AIDS occurs usually within 9-10 years resulting in depletion of the host immune system and occurrence of opportunistic infections usually leading to death soon thereafter. Secondary to viral latency, discontinuation of HAART invariably leads to viral rebound. Moreover, even temporary disruptions in therapy can select for resistant strains of HIV uncontrollable by available means. Additionally, the costs of HAART therapy are significant: within the US $10,000-15,0000 per person per year. As such, treatment approaches directly targeting the HIV genome rather than the process of viral replication represents a means by which eradication of latent reservoirs could allow for a curative therapeutic option.

Development and delivery of an HIV-1 targeted CRISPR-Cas system represents a unique approach differentiable from existing means of targeted DNA mutagenesis, i.e. ZFN and TALENs, with numerous therapeutic implications. Targeted disruption and deletion of the HIV-1 genome by CRISPR-mediated DSB and indels in conjunction with HAART could allow for simultaneous prevention of active viral production as well as depletion of latent viral reservoirs within the host.

Once integrated within the host immune system, the CRISPR-Cas system allows for generation of a HIV-1 resistant sub-population that, even in the absence of complete viral eradication, could allow for maintenance and re-constitution of host immune activity. This could potentially prevent primary infection by disruption of the viral genome preventing viral production and integration, representing a means to "vaccination". Multiplexed nature of the CRISPR-Cas system allows targeting of multiple aspects of the genome simultaneously within individual cells.

As in HAART, viral escape by mutagenesis is minimized by requiring acquisition of multiple adaptive mutations concurrently. Multiple strains of HIV-1 can be targeted simultaneously which minimizes the chance of super-infection and prevents subsequent creation of new recombinants strains. Nucleotide, rather than protein, mediated sequence-specificity of the CRISPR-Cas system allows for rapid generation of therapeutics without need for significantly altering delivery mechanism.

In order to accomplish this, Applicants generate CRISPR-Cas guide RNAs that target the vast majority of the HIV-1 genome while taking into account HIV-1 strain variants for maximal coverage and effectiveness. Sequence analyses of genomic conservation between HIV-1 subtypes and variants should allow for targeting of flanking conserved regions of the genome with the aims of deleting intervening viral sequences or induction of frame-shift mutations which would disrupt viral gene functions.

Applicants accomplish delivery of the CRISPR-Cas system by conventional adenoviral or lentiviral-mediated infection of the host immune system. Depending on approach, host immune cells could be a) isolated, transduced with CRISPR-Cas, selected, and re-introduced in to the host or b) transduced in vivo by systemic delivery of the CRISPR-Cas system. The first approach allows for generation of a resistant immune population whereas the second is more likely to target latent viral reservoirs within the host.

| Examples of potential HIV-1 targeted spacers adapted from Mcintyre et at, which generated shRNAs against HIV-1 optimized for maximal coverage of HIV-1 variants. |
|---|
| CACTGCTTAAGCCTCGCTCGAGG (SEQ ID NO: 122) |
| TCACCAGCAATATTCGCTCGAGG (SEQ ID NO: 123) |
| CACCAGCAATATTCCGCTCGAGG (SEQ ID NO: 124) |
| TAGCAACAGACATACGCTCGAGG (SEQ ID NO: 125) |
| GGGCAGTAGTAATACGCTCGAGG (SEQ ID NO: 126) |
| CCAATTCCCATACATTATTGTAC (SEQ ID NO: 127) |

Example 22: Targeted Correction of deltaF508 or Other Mutations in Cystic Fibrosis An aspect of the invention provides for a pharmaceutical composition that may comprise an CRISPR-Cas gene therapy particle and a biocompatible pharmaceutical carrier. According to another aspect, a method of gene therapy for the treatment of a subject having a mutation in the CFTR gene comprises administering a therapeutically effective amount of a CRISPR-Cas gene therapy particle to the cells of a subject.

This Example demonstrates gene transfer or gene delivery of a CRISPR-Cas system in airways of subject or a patient in need thereof, suffering from cystic fibrosis or from cystic fibrosis related symptoms, using adeno-associated virus (AAV) particles.

Study Design: Subjects or patients in need there of: Human, non-primate human, canine, feline, bovine, equine and other domestic animals, related. This study tests efficacy of gene transfer of a CRISPR-Cas system by a AAV vector. Applicants determine transgene levels sufficient for gene expression and utilize a CRISPR-Cas system comprising a Cas9 enzyme to target deltaF508 or other CFTR-inducing mutations.

The treated subjects receive pharmaceutically effective amount of aerosolized AAV vector system per lung endobronchially delivered while spontaneously breathing. The control subjects receive equivalent amount of a pseudotyped AAV vector system with an internal control gene. The vector system may be delivered along with a pharmaceutically acceptable or biocompatible pharmaceutical carrier. Three weeks or an appropriate time interval following vector administration, treated subjects are tested for amelioration of cystic fibrosis related symptoms.

Applicants use an adenovirus or an AAV particle.

Applicants clone the following gene constructs, each operably linked to one or more regulatory sequences (Cbh or EF1a promoter for Cas9, U6 or H1 promoter for chimeric guide RNA), into one or more adenovirus or AAV vectors or any other compatible vector: A CFTRdelta508 targeting chimeric guide RNA (FIG. 31B), a repair template for deltaF508 mutation (FIG. 31C) and a codon optimized Cas9 enzyme with optionally one or more nuclear localization signal or sequence(s) (NLS(s)), e.g., two (2) NLSs.

Identification of Cas9 Target Site

Applicants analyzed the human CFTR genomic locus and identified the Cas9 target site (FIG. 31A). (PAM may contain a NGG or a NNAGAAW motif).

Gene Repair Strategy

Applicants introduce an adenovirus/AAV vector system comprising a Cas9 (or Cas9 nickase) and the guide RNA along with a adenovirus/AAV vector system comprising the homology repair template containing the F508 residue into the subject via one of the methods of delivery discussed earlier. The CRISPR-Cas system is guided by the CFTRdelta 508 chimeric guide RNA and targets a specific site of the CFTR genomic locus to be nicked or cleaved. After cleavage, the repair template is inserted into the cleavage site via homologous recombination correcting the deletion that results in cystic fibrosis or causes cystic fibrosis related symptoms. This strategy to direct delivery and provide systemic introduction of CRISPR systems with appropriate guide RNAs can be employed to target genetic mutations to edit or otherwise manipulate genes that cause metabolic, liver, kidney and protein diseases and disorders such as those in Table B.

Example 23: Generation of Gene Knockout Cell Library

This example demonstrates how to generate a library of cells where each cell has a single gene knocked out:

Applicants make a library of ES cells where each cell has a single gene knocked out, and the entire library of ES cells will have every single gene knocked out. This library is useful for the screening of gene function in cellular processes as well as diseases.

To make this cell library, Applicants integrate Cas9 driven by an inducible promoter (e.g. doxycycline inducible promoter) into the ES cell. In addition, Applicants integrate a single guide RNA targeting a specific gene in the ES cell. To make the ES cell library, Applicants simply mix ES cells with a library of genes encoding guide RNAs targeting each gene in the human genome. Applicants first introduce a single BxB1 attB site into the AAVS1 locus of the human ES cell. Then Applicants use the BxB1 integrase to facilitate the integration of individual guide RNA genes into the BxB1 attB site in AAVS1 locus. To facilitate integration, each guide RNA gene is contained on a plasmid that carries of a single attP site. This way BxB1 will recombine the attB site in the genome with the attP site on the guide RNA containing plasmid.

To generate the cell library, Applicants take the library of cells that have single guide RNAs integrated and induce Cas9 expression. After induction, Cas9 mediates double strand break at sites specified by the guide RNA. To verify the diversity of this cell library, Applicants carry out whole exome sequencing to ensure that Applicants are able to observe mutations in every single targeted gene. This cell library can be used for a variety of applications, including who library-based screens, or can be sorted into individual cell clones to facilitate rapid generation of clonal cell lines with individual human genes knocked out.

Example 24: Engineering of Microalgae Using Cas9

Methods of Delivering Cas9

Method 1: Applicants deliver Cas9 and guide RNA using a vector that expresses Cas9 under the control of a constitutive promoter such as Hsp70A-Rbc S2 or Beta2-tubulin.

Method 2: Applicants deliver Cas9 and T7 polymerase using vectors that expresses Cas9 and T7 polymerase under the control of a constitutive promoter such as Hsp70A-Rbc S2 or Beta2-tubulin. Guide RNA will be delivered using a vector containing T7 promoter driving the guide RNA.

Method 3: Applicants deliver Cas9 mRNA and in vitro transcribed guide RNA to algae cells. RNA can be in vitro transcribed. Cas9 mRNA will consist of the coding region for Cas9 as well as 3'UTR from Cop1 to ensure stabilization of the Cas9 mRNA.

For Homologous recombination, Applicants provide an additional homology directed repair template.

Sequence for a cassette driving the expression of Cas9 under the control of beta-2 tubulin promoter, followed by the 3' UTR of Cop1. (SEQ ID NO: 128)

```
                                            (SEQ ID NO: 128)
TCTTTCTTGCGCTATGACACTTCCAGCAAAAGGTAGGGCGGGCTGCGAGAC

GGCTTCCCGGCGCTGCATGCAACACCGATGATGCTTCGACCCCCCGAAGCT

CCTTCGGGGCTGCATGGGCGCTCCGATGCCGCTCCAGGGCGAGCGCTGTTT

AAATAGCCAGGCCCCCGATTGCAAAGACATTATAGCGAGCTACCAAAGCCA

TATTCAAACACCTAGATCACTACCACTTCTACACAGGCCACTCGAGCTTGT

GATCGCACTCCGCTAAGGGGGCGCCTCTTCCTCTTCGTTTCAGTCACAACC

CGCAAACATGTACCCATACGATGTTCCAGATTACGCTTCGCCGAAGAAAAA

GCGCAAGGTCGAAGCGTCCGACAAGAAGTACAGCATCGGCCTGGACATCGG

CACCAACTCTGTGGGCTGGGCCGTGATCACCGACGAGTACAAGGTGCCCAG

CAAGAAATTCAAGGTGCTGGGCAACACCGACCGGCACAGCATCAAGAAGAA

CCTGATCGGAGCCCTGCTGTTCGACAGCGGCGAAACAGCCGAGGCCACCCG

GCTGAAGAGAACCGCCAGAAGAAGATACACCAGACGGAAGAACCGGATCTG

CTATCTGCAAGAGATCTTCAGCAACGAGATGGCCAAGGTGGACGACAGCTT

CTTCCACAGACTGGAAGAGTCCTTCCTGGTGGAAGAGGATAAGAAGCACGA

GCGGCACCCCATCTTCGGCAACATCGTGGACGAGGTGGCCTACCACGAGAA

GTACCCCACCATCTACCACCTGAGAAAGAAACTGGTGGACAGCACCGACAA

GGCCGACCTGCGGCTGATCTATCTGGCCCTGGCCCACATGATCAAGTTCCG

GGGCCACTTCCTGATCGAGGGCGACCTGAACCCCGACAACAGCGACGTGGA

CAAGCTGTTCATCCAGCTGGTGCAGACCTACAACCAGCTGTTCGAGGAAAA

CCCCATCAACGCCAGCGGCGTGGACGCCAAGGCCATCCTGTCTGCCAGACT

GAGCAAGAGCAGACGGCTGGAAAATCTGATCGCCCAGCTGCCCGGCGAGAA

GAAGAATGGCCTGTTCGGCAACCTGATTGCCCTGAGCCTGGGCCTGACCCC

CAACTTCAAGAGCAACTTCGACCTGGCCGAGGATGCCAAACTGCAGCTGAG
```

-continued

CAAGGACACCTACGACGACGACCTGGACAACCTGCTGGCCCAGATCGGCGA
CCAGTACGCCGACCTGTTTCTGGCCGCCAAGAACCTGTCCGACGCCATCCT
GCTGAGCGACATCCTGAGAGTGAACACCGAGATCACCAAGGCCCCCCTGAG
CGCCTCTATGATCAAGAGATACGACGAGCACCACCAGGACCTGACCCTGCT
GAAAGCTCTCGTGCGGCAGCAGCTGCCTGAGAAGTACAAAGAGATTTTCTT
CGACCAGAGCAAGAACGGCTACGCCGGCTACATTGACGGCGGAGCCAGCCA
GGAAGAGTTCTACAAGTTCATCAAGCCCATCCTGGAAAAGATGGACGGCAC
CGAGGAACTGCTCGTGAAGCTGAACAGAGAGGACCTGCTGCGGAAGCAGCG
GACCTTCGACAACGGCAGCATCCCCCACCAGATCCACCTGGGAGAGCTGCA
CGCCATTCTGCGGCGGCAGGAAGATTTTTACCCATTCCTGAAGGACAACCG
GGAAAAGATCGAGAAGATCCTGACCTTCCGCATCCCCTACTACGTGGGCCC
TCTGGCCAGGGGAAACAGCAGATTCGCCTGGATGACCAGAAAGAGCGAGGA
AACCATCACCCCCTGGAACTTCGAGGAAGTGGTGGACAAGGGCGCTTCCGC
CCAGAGCTTCATCGAGCGGATGACCAACTTCGATAAGAACCTGCCCAACGA
GAAGGTGCTGCCCAAGCACAGCCTGCTGTACGAGTACTTCACCGTGTATAA
CGAGCTGACCAAAGTGAAATACGTGACCGAGGGAATGAGAAAGCCCGCCTT
CCTGAGCGGCGAGCAGAAAAAGGCCATCGTGGACCTGCTGTTCAAGACCAA
CCGGAAAGTGACCGTGAAGCAGCTGAAAGAGGACTACTTCAAGAAAATCGA
GTGCTTCGACTCCGTGGAAATCTCCGGCGTGGAAGATCGGTTCAACGCCTC
CCTGGGCACATACCACGATCTGCTGAAAATTATCAAGGACAAGGACTTCCT
GGACAATGAGGAAAACGAGGACATTCTGGAAGATATCGTGCTGACCCTGAC
ACTGTTTGAGGACAGAGAGATGATCGAGGAACGGCTGAAAACCTATGCCCA
CCTGTTCGACGACAAAGTGATGAAGCAGCTGAAGCGGCGGAGATACACCGG
CTGGGGCAGGCTGAGCCGGAAGCTGATCAACGGCATCCGGGACAAGCAGTC
CGGCAAGACAATCCTGGATTTCCTGAAGTCCGACGGCTTCGCCAACAGAAA
CTTCATGCAGCTGATCCACGACGACAGCCTGACCTTTAAAGAGGACATCCA
GAAAGCCCAGGTGTCCGGCCAGGGCGATAGCCTGCACGAGCACATTGCCAA
TCTGGCCGGCAGCCCCGCCATTAAGAAGGGCATCCTGCAGACAGTGAAGGT
GGTGGACGAGCTCGTGAAAGTGATGGGCCGGCACAAGCCCGAGAACATCGT
GATCGAAATGGCCAGAGAGAACCAGACCACCCAGAAGGGACAGAAGAACAG
CCGCGAGAGAATGAAGCGGATCGAAGAGGGCATCAAAGAGCTGGGCAGCCA
GATCCTGAAAGAACACCCCGTGGAAAACACCCAGCTGCAGAACGAGAAGCT
GTACCTGTACTACCTGCAGAATGGGCGGGATATGTACGTGGACCAGGAACT
GGACATCAACCGGCTGTCCGACTACGATGTGGACCATATCGTGCCTCAGAG
CTTTCTGAAGGACGACTCCATCGACAACAAGGTGCTGACCAGAAGCGACAA

-continued

GAACCGGGGCAAGAGCGACAACGTGCCCTCCGAAGAGGTCGTGAAGAAGAT
GAAGAACTACTGGCGGCAGCTGCTGAACGCCAAGCTGATTACCCAGAGAAA
GTTCGACAATCTGACCAAGGCCGAGAGAGGCGGCCTGAGCGAACTGGATAA
GGCCGGCTTCATCAAGAGACAGCTGGTGGAAACCCGGCAGATCACAAAGCA
CGTGGCACAGATCCTGGACTCCCGGATGAACACTAAGTACGACGAGAATGA
CAAGCTGATCCGGGAAGTGAAAGTGATCACCCTGAAGTCCAAGCTGGTGTC
CGATTTCCGGAAGGATTTCCAGTTTTACAAAGTGCGCGAGATCAACAACTA
CCACCACGCCCACGACGCCTACCTGAACGCCGTCGTGGGAACCGCCCTGAT
CAAAAAGTACCCTAAGCTGGAAAGCGAGTTCGTGTACGGCGACTACAAGGT
GTACGACGTGCGGAAGATGATCGCCAAGAGCGAGCAGGAAATCGGCAAGGC
TACCGCCAAGTACTTCTTCTACAGCAACATCATGAACTTTTTCAAGACCGA
GATTACCCTGGCCAACGGCGAGATCCGGAAGCGGCCTCTGATCGAGACAAA
CGGCGAAACCGGGGAGATCGTGTGGGATAAGGGCCGGGATTTTGCCACCGT
GCGGAAAGTGCTGAGCATGCCCCAAGTGAATATCGTGAAAAAGACCGAGGT
GCAGACAGGCGGCTTCAGCAAAGAGTCTATCCTGCCCAAGAGGAACAGCGA
TAAGCTGATCGCCAGAAAGAAGGACTGGGACCCTAAGAAGTACGGCGGCTT
CGACAGCCCCACCGTGGCCTATTCTGTGCTGGTGGTGGCCAAAGTGGAAAA
GGGCAAGTCCAAGAAACTGAAGAGTGTGAAAGAGCTGCTGGGGATCACCAT
CATGGAAAGAAGCAGCTTCGAGAAGAATCCCATCGACTTTCTGGAAGCCAA
GGGCTACAAAGAAGTGAAAAAGGACCTGATCATCAAGCTGCCTAAGTACTC
CCTGTTCGAGCTGGAAAACGGCCGGAAGAGAATGCTGGCCTCTGCCGGCGA
ACTGCAGAAGGGAAACGAACTGGCCCTGCCCTCCAAATATGTGAACTTCCT
GTACCTGGCCAGCCACTATGAGAAGCTGAAGGGCTCCCCCGAGGATAATGA
GCAGAAACAGCTGTTTGTGGAACAGCACAAGCACTACCTGGACGAGATCAT
CGAGCAGATCAGCGAGTTCTCCAAGAGAGTGATCCTGGCCGACGCTAATCT
GGACAAAGTGCTGTCCGCCTACAACAAGCACCGGGATAAGCCCATCAGAGA
GCAGGCCGAGAATATCATCCACCTGTTTACCCTGACCAATCTGGGAGCCCC
TGCCGCCTTCAAGTACTTTGACACCACCATCGACCGGAAGAGGTACACCAG
CACCAAAGAGGTGCTGGACGCCACCCTGATCCACCAGAGCATCACCGGCCT
GTACGAGACACGGATCGACCTGTCTCAGCTGGGAGGCGACAGCCCCAAGAA
GAAGAGAAAGGTGGAGGCCAGCTAAGGATCCGGCAAGACTGGCCCCGCTTG
GCAACGCAACAGTGAGCCCCTCCCTAGTGTGTTTGGGGATGTGACTATGTA
TTCGTGTGTTGGCCAACGGGTCAACCCGAACAGATTGATACCCGCCTTGGC
ATTTCCTGTCAGAATGTAACGTCAGTTGAT GGTACT

Sequence for a cassette driving the expression of T7 polymerase under the control of beta-2 tubulin promoter, followed by the 3' UTR of Cop1: (SEQ ID NO: 129)

(SEQ ID NO: 129)

TCTTTCTTGCGCTATGACACTTCCAGCAAAAGGTAGGGCGGGCTGCGA
GACGGCTTCCCGGCGCTGCATGCAACACCGATGATGCTTCGACCCCCCGAAGCTC
CTTCGGGGCTGCATGGGCGCTCCGATGCCGCTCCAGGGCGAGCGCTGTTTAAATA

-continued

GCCAGGCCCCCGATTGCAAAGACATTATAGCGAGCTACCAAAGCCATATTCAAAC

ACCTAGATCACTACCACTTCTACACAGGCCACTCGAGCTTGTGATCGCACTCCGC

TAAGGGGGCGCCTCTTCCTCTTCGTTTCAGTCACAACCCGCAAACatgcctaagaagaagagga aggttaacacgattaacatcgctaagaacgacttctctgacatcgaactggctgctatcccgttcaacactctggctgaccatt acggtgagcgtttagctcgcgaacagttggcccttgagcatgagtcttacgagatgggtgaagcacgcttccgcaagatgtttga gcgtcaacttaaagctggtgaggttgcggataacgctgccgccaagcctctcatcactaccctactccctaagatgattgcacgc atcaacgactggtttgaggaagtgaaagctaagcgcggcaagcgcccgacagccttccagttcctgcaagaaatcaagccgga agccgtagcgtacatcaccattaagaccactctggcttgcctaaccagtgctgacaatacaaccgttcaggctgtagcaagcgca atcggtcgggccattgaggacgaggctcgcttcggtcgtatccgtgaccttgaagctaagcacttcaagaaaaacgttgaggaa caactcaacaagcgcgtagggcacgtctacaagaaagcatttatgcaagttgtcgaggctgacatgctctctaagggtctactcg gtggcgaggcgtggtcttcgtggcataaggaagactctattcatgtaggagtacgctgcatcgagatgctcattgagtcaaccgg aatggttagcttacaccgccaaaatgctggcgtagtaggtcaagactctgagactatcgaactcgcacctgaatacgctgaggct atcgcaacccgtgcaggtgcgctggctggcatctctccgatgttccaaccttgcgtagttcctcctaagccgtggactggcattac tggtggtggctattgggctaacggtcgtcgtcctctggcgctggtgcgtactcacagtaagaaagcactgatgcgctacgaagac gtttacatgcctgaggtgtacaaagcgattaacattgcgcaaaacaccgcatggaaaatcaacaagaaagtcctagcggtcgcc aacgtaatcaccaagtggaagcattgtccggtcgaggacatccctgcgattgagcgtgaagaactcccgatgaaaccggaagac atcgacatgaatcctgaggctctcaccgcgtggaaacgtgctgccgctgctgtgtaccgcaaggacaaggctcgcaagtctcgcc gtatcagccttgagttcatgcttgagcaagccaataagtttgctaaccataaggccatctggttcccttacaacatggactggcg cggtcgtgtttacgctgtgtcaatgttcaacccgcaaggtaacgatatgaccaaaggactgcttacgctggcgaaaggtaaacca atcggtaaggaaggttactactggctgaaaatccacggtgcaaactgtgcgggtgtcgacaaggttccgttccctgagcgcatca agttcattgaggaaaaccacgagaacatcatggcttgcgctaagtctccactggagaacacttggtgggctgagcaagattctcc gttctgatccttgcgttctgattgagtacgctggggtacagcaccacggcctgagctataactgctcccttccgctggcgtttgac gggtcttgctctggcatccagcacttctccgcgatgctccgagatgaggtaggtggtcgcgcggttaacttgcttcctagtgaaac cgttcaggacatctacgggattgttgctaagaaagtcaacgagattctacaagcagacgcaatcaatgggaccgataacgaagta gttaccgtgaccgatgagaacactggtgaaatctctgagaaagtcaagctgggcactaaggcactggctggtcaatggctggct tacggtgttactcgcagtgtgactaagcgttcagtcatgacgctggcttacgggtccaaagagttcggcttccgtcaacaagtgct ggaagataccattcagccagctattgattccggcaagggtctgatgttcactcagccgaatcaggctgctggatacatggctaag ctgatttgggaatctgtgagcgtgacggtggtagctgcggttgaagcaatgaactggcttaagtctgctgctaagctgctggctgc tgaggtcaaagataagaagactggagagattcttcgcaagcgttgcgctgtgcattgggtaactcctgatggtttccctgtgtggc aggaatacaagaagcctattcagacgcgcttgaacctgatgttcctcggtcagttccgcttacagcctaccattaacaccaacaa agatagcgagattgatgcacacaaacaggagtctggtatcgctcctaactttgtacacagccaagacggtagccaccttcgtaag actgtagtgtgggcacacgagaagtacggaatcgaatcttttgcactgattcacgactccttcggtacgattccggctgacgctgc gaacctgttcaaagcagtgcgcgaaactatggttgacacatatgagtcttgtgatgtactggctgatttctacgaccagttcgctg accagttgcacgagtctcaattggacaaaatgccagcacttccggctaaaggtaacttgaacctccgtgacatcttagagtcggac ttcgcgttcgcgtaaGGATCCGGCAAGACTGGCCCCGCTTGGCAACGCAACAGTGAGCCC

CTCCCTAGTGTGTTTGGGGATGTGACTATGTATTCGTGTGTTGGCCAACGGGTCA

ACCCGAACAGATTGATACCCGCCTTGGCATTTCCTGTCAGAATGTAACGTCAGTT

GATGGTACT

Sequence of guide RNA driven by the T7 promoter (T7 promoter, Ns represent targeting sequence): (SEQ ID NO: 130)

(SEQ ID NO: 130)

gaaatTAATACGACTCACTATANNNNNNNNNNNNNNNNNNNNgttttaga gctaGAAAtagcaagttaaaataaggctagtccgttatcaacttgaaaaa gtggcaccgagtcggtgcttttttt Gene Delivery:

*Chlamydomonas reinhardtii* strain CC-124 and CC-125 from the *Chlamydomonas* Resource Center will be used for electroporation. Electroporation protocol follows standard recommended protocol from the GeneArt *Chlamydomonas* Engineering kit.

Also, Applicants generate a line of *Chlamydomonas reinhardtii* that expresses Cas9 constitutively. This can be done by using pChlamy1 (linearized using PvuI) and selecting for hygromycin resistant colonies. Sequence for pChlamy1 containing Cas9 is below. In this way to achieve gene knockout one simply needs to deliver RNA for the guideRNA. For homologous recombination Applicants deliver guideRNA as well as a linearized homologous recombination template.

pChlamy1-Cas9:

(SEQ ID NO: 131)

TGCGGTATTTCACACCGCATCAGGTGGCACTTTTCGGGGAAATGTGC

GCGGAACCCCTATTTGTTTATTTTTCTAAATACATTCAAATATGTATCCGCTCATGA

GATTATCAAAAAGGATCTTCACCTAGATCCTTTTAAATTAAAAATGAAGTTTTAA

ATCAATCTAAAGTATATATGAGTAAACTTGGTCTGACAGTTACCAATGCTTAATC

AGTGAGGCACCTATCTCAGCGATCTGTCTATTTCGTTCATCCATAGTTGCCTGACT

CCCCGTCGTGTAGATAACTACGATACGGGAGGGCTTACCATCTGGCCCCAGTGCT

GCAATGATACCGCGAGACCCACGCTCACCGGCTCCAGATTTATCAGCAATAAACC

AGCCAGCCGGAAGGGCCGAGCGCAGAAGTGGTCCTGCAACTTTATCCGCCTCCAT

CCAGTCTATTAATTGTTGCCGGGAAGCTAGAGTAAGTAGTTCGCCAGTTAATAGT

TTGCGCAACGTTGTTGCCATTGCTACAGGCATCGTGGTGTCACGCTCGTCGTTTGG

TATGGCTTCATTCAGCTCCGGTTCCCAACGATCAAGGCGAGTTACATGATCCCCC

ATGTTGTGCAAAAAAGCGGTTAGCTCCTTCGGTCCTCCGATCGTTGTCAGAAGTA

AGTTGGCCGCAGTGTTATCACTCATGGTTATGGCAGCACTGCATAATTCTCTTACT

GTCATGCCATCCGTAAGATGCTTTTCTGTGACTGGTGAGTACTCAACCAAGTCATT

CTGAGAATAGTGTATGCGGCGACCGAGTTGCTCTTGCCCGGCGTCAATACGGGAT

AATACCGCGCCACATAGCAGAACTTTAAAAGTGCTCATCATTGGAAAACGTTCTT

CGGGGCGAAAACTCTCAAGGATCTTACCGCTGTTGAGATCCAGTTCGATGTAACC

CACTCGTGCACCCAACTGATCTTCAGCATCTTTTACTTTCACCAGCGTTTCTGGGT

GAGCAAAAACAGGAAGGCAAAATGCCGCAAAAAAGGGAATAAGGGCGACACGG

AAATGTTGAATACTCATACTCTTCCTTTTTCAATATTATTGAAGCATTTATCAGGG

TTATTGTCTCATGACCAAAATCCCTTAACGTGAGTTTTCGTTCCACTGAGCGTCAG

ACCCCGTAGAAAAGATCAAAGGATCTTCTTGAGATCCTTTTTTTCTGCGCGTAATC

TGCTGCTTGCAAACAAAAAAACCACCGCTACCAGCGGTGGTTTGTTTGCCGGATC

AAGAGCTACCAACTCTTTTTCCGAAGGTAACTGGCTTCAGCAGAGCGCAGATACC

AAATACTGTTCTTCTAGTGTAGCCGTAGTTAGGCCACCACTTCAAGAACTCTGTA

GCACCGCCTACATACCTCGCTCTGCTAATCCTGTTACCAGTGGCTGTTGCCAGTGG

CGATAAGTCGTGTCTTACCGGGTTGGACTCAAGACGATAGTTACCGGATAAGGCG

CAGCGGTCGGGCTGAACGGGGGGTTCGTGCACACAGCCCAGCTTGGAGCGAACG

ACCTACACCGAACTGAGATACCTACAGCGTGAGCTATGAGAAAGCGCCACGCTTC

CCGAAGGGAGAAAGGCGGACAGGTATCCGGTAAGCGGCAGGGTCGGAACAGGA

GAGCGCACGAGGGAGCTTCCAGGGGGAAACGCCTGGTATCTTTATAGTCCTGTCG

-continued

GGTTTCGCCACCTCTGACTTGAGCGTCGATTTTTGTGATGCTCGTCAGGGGGGCGG
AGCCTATGGAAAAACGCCAGCAACGCGGCCTTTTTACGGTTCCTGGCCTTTTGCTG
GCCTTTTGCTCACATGTTCTTTCCTGCGTTATCCCCTGATTCTGTGGATAACCGTA
TTACCGCCTTTGAGTGAGCTGATACCGCTCGCCGCAGCCGAACGACCGAGCGCAG
CGAGTCAGTGAGCGAGGAAGCGGTCGCTGAGGCTTGACATGATTGGTGCGTATGT
TTGTATGAAGCTACAGGACTGATTTGGCGGGCTATGAGGGCGGGGGAAGCTCTGG
AAGGGCCGCGATGGGGCGCGCGGCGTCCAGAAGGCGCCATACGGCCCGCTGGCG
GCACCCATCCGGTATAAAAGCCCGCGACCCCGAACGGTGACCTCCACTTTCAGCG
ACAAACGAGCACTTATACATACGCGACTATTCTGCCGCTATACATAACCACTCAG
CTAGCTTAAGATCCCATCAAGCTTGCATGCCGGGCGCGCCAGAAGGAGCGCAGC
CAAACCAGGATGATGTTTGATGGGGTATTTGAGCACTTGCAACCCTTATCCGGAA
GCCCCCTGGCCCACAAAGGCTAGGCGCCAATGCAAGCAGTTCGCATGCAGCCCCT
GGAGCGGTGCCCTCCTGATAAACCGGCCAGGGGGCCTATGTTCTTTACTTTTTTAC
AAGAGAAGTCACTCAACATCTTAAAATGGCCAGGTGAGTCGACGAGCAAGCCCG
GCGGATCAGGCAGCGTGCTTGCAGATTTGACTTGCAACGCCCGCATTGTGTCGAC
GAAGGCTTTTGGCTCCTCTGTCGCTGTCTCAAGCAGCATCTAACCCTGCGTCGCCG
TTTCCATTTGCAGGAGATTCGAGGTACCATGTACCCATACGATGTTCCAGATTACG
CTTCGCCGAAGAAAAAGCGCAAGGTCGAAGCGTCCGACAAGAAGTACAGCATCG
GCCTGGACATCGGCACCAACTCTGTGGGCTGGGCCGTGATCACCGACGAGTACAA
GGTGCCCAGCAAGAAATTCAAGGTGCTGGGCAACACCGACCGGCACAGCATCAA
GAAGAACCTGATCGGAGCCCTGCTGTTCGACAGCGGCGAAACAGCCGAGGCCAC
CCGGCTGAAGAGAACCGCCAGAAGAAGATACACCAGACGGAAGAACCGGATCTG
CTATCTGCAAGAGATCTTCAGCAACGAGATGGCCAAGGTGGACGACAGCTTCTTC
CACAGACTGGAAGAGTCCTTCCTGGTGGAAGAGGATAAGAAGCACGAGCGGCAC
CCCATCTTCGGCAACATCGTGGACGAGGTGGCCTACCACGAGAAGTACCCCACCA
TCTACCACCTGAGAAAGAAACTGGTGGACAGCACCGACAAGGCCGACCTGCGGC
TGATCTATCTGGCCCTGGCCCACATGATCAAGTTCCGGGGCCACTTCCTGATCGA
GGGCGACCTGAACCCCGACAACAGCGACGTGGACAAGCTGTTCATCCAGCTGGT
GCAGACCTACAACCAGCTGTTCGAGGAAAACCCCATCAACGCCAGCGGCGTGGA
CGCCAAGGCCATCCTGTCTGCCAGACTGAGCAAGAGCAGACGGCTGGAAAATCT
GATCGCCCAGCTGCCCGGCGAGAAGAAGAATGGCCTGTTCGGCAACCTGATTGC
CCTGAGCCTGGGCCTGACCCCCAACTTCAAGAGCAACTTCGACCTGGCCGAGGAT
GCCAAACTGCAGCTGAGCAAGGACACCTACGACGACGACCTGGACAACCTGCTG
GCCCAGATCGGCGACCAGTACGCCGACCTGTTTCTGGCCGCCAAGAACCTGTCCG
ACGCCATCCTGCTGAGCGACATCCTGAGAGTGAACACCGAGATCACCAAGGCCCC
CCTGAGCGCCTCTATGATCAAGAGATACGACGAGCACCACCAGGACCTGACCCTG
CTGAAAGCTCTCGTGCGGCAGCAGCTGCCTGAGAAGTACAAAGAGATTTTCTTCG
ACCAGAGCAAGAACGGCTACGCCGGCTACATTGACGGCGGAGCCAGCCAGGAAG
AGTTCTACAAGTTCATCAAGCCCATCCTGGAAAAGATGGACGGCACCGAGGAAC
TGCTCGTGAAGCTGAACAGAGAGGACCTGCTGCGGAAGCAGCGGACCTTCGACA

-continued

ACGGCAGCATCCCCCACCAGATCCACCTGGGAGAGCTGCACGCCATTCTGCGGCG

GCAGGAAGATTTTTACCCATTCCTGAAGGACAACCGGGAAAAGATCGAGAAGAT

CCTGACCTTCCGCATCCCCTACTACGTGGGCCCTCTGGCCAGGGGAAACAGCAGA

TTCGCCTGGATGACCAGAAAGAGCGAGGAAACCATCACCCCCTGGAACTTCGAG

GAAGTGGTGGACAAGGGCGCTTCCGCCCAGAGCTTCATCGAGCGGATGACCAAC

TTCGATAAGAACCTGCCCAACGAGAAGGTGCTGCCCAAGCACAGCCTGCTGTAC

GAGTACTTCACCGTGTATAACGAGCTGACCAAAGTGAAATACGTGACCGAGGGA

ATGAGAAAGCCCGCCTTCCTGAGCGGCGAGCAGAAAAAGGCCATCGTGGACCT

GCTGTTCAAGACCAACCGGAAAGTGACCGTGAAGCAGCTGAAAGAGGACTACTT

CAAGAAAATCGAGTGCTTCGACTCCGTGGAAATCTCCGGCGTGGAAGATCGGTTC

AACGCCTCCCTGGGCACATACCACGATCTGCTGAAAATTATCAAGGACAAGGACT

TCCTGGACAATGAGGAAAACGAGGACATTCTGGAAGATATCGTGCTGACCCTGA

CACTGTTTGAGGACAGAGAGATGATCGAGGAACGGCTGAAAACCTATGCCCACC

TGTTCGACGACAAAGTGATGAAGCAGCTGAAGCGGCGGAGATACACCGGCTGGG

GCAGGCTGAGCCGGAAGCTGATCAACGGCATCCGGGACAAGCAGTCCGGCAAGA

CAATCCTGGATTTCCTGAAGTCCGACGGCTTCGCCAACAGAAACTTCATGCAGCT

GATCCACGACGACAGCCTGACCTTTAAAGAGGACATCCAGAAAGCCCAGGTGTC

CGGCCAGGGCGATAGCCTGCACGAGCACATTGCCAATCTGGCCGGCAGCCCCGC

CATTAAGAAGGGCATCCTGCAGACAGTGAAGGTGGTGGACGAGCTCGTGAAAGT

GATGGGCCGGCACAAGCCCGAGAACATCGTGATCGAAATGGCCAGAGAGAACCA

GACCACCCAGAAGGGACAGAAGAACAGCCGCGAGAGAATGAAGCGGATCGAAG

AGGGCATCAAAGAGCTGGGCAGCCAGATCCTGAAAGAACACCCCGTGGAAAACA

CCCAGCTGCAGAACGAGAAGCTGTACCTGTACTACCTGCAGAATGGGCGGGATA

TGTACGTGGACCAGGAACTGGACATCAACCGGCTGTCCGACTACGATGTGGACC

ATATCGTGCCTCAGAGCTTTCTGAAGGACGACTCCATCGACAACAAGGTGCTGAC

CAGAAGCGACAAGAACCGGGGCAAGAGCGACAACGTGCCCTCCGAAGAGGTCG

TGAAGAAGATGAAGAACTACTGGCGGCAGCTGCTGAACGCCAAGCTGATTACCC

AGAGAAAGTTCGACAATCTGACCAAGGCCGAGAGAGGCGGCCTGAGCGAACTGG

ATAAGGCCGGCTTCATCAAGAGACAGCTGGTGGAAACCCGGCAGATCACAAAGC

ACGTGGCACAGATCCTGGACTCCCGGATGAACACTAAGTACGACGAGAATGACA

AGCTGATCCGGGAAGTGAAAGTGATCACCCTGAAGTCCAAGCTGGTGTCCGATTT

CCGGAAGGATTTCCAGTTTTACAAAGTGCGCGAGATCAACAACTACCACCACGCC

CACGACGCCTACCTGAACGCCGTCGTGGGAACCGCCCTGATCAAAAAGTACCCTA

AGCTGGAAAGCGAGTTCGTGTACGGCGACTACAAGGTGTACGACGTGCGGAAGA

TGATCGCCAAGAGCGAGCAGGAAATCGGCAAGGCTACCGCCAAGTACTTCTTCTA

CAGCAACATCATGAACTTTTTCAAGACCGAGATTACCCTGGCCAACGGCGAGATC

CGGAAGCGGCCTCTGATCGAGACAAACGGCGAAACCGGGGAGATCGTGTGGGAT

AAGGGCCGGGATTTTGCCACCGTGCGGAAAGTGCTGAGCATGCCCCAAGTGAAT

ATCGTGAAAAAGACCGAGGTGCAGACAGGCGGCTTCAGCAAAGAGTCTATCCTG

CCCAAGAGGAACAGCGATAAGCTGATCGCCAGAAAGAAGGACTGGGACCCTAAG

AAGTACGGCGGCTTCGACAGCCCCACCGTGGCCTATTCTGTGCTGGTGGTGGCCA

-continued

AAGTGGAAAAGGGCAAGTCCAAGAAACTGAAGAGTGTGAAAGAGCTGCTGGGG

ATCACCATCATGGAAAGAAGCAGCTTCGAGAAGAATCCCATCGACTTTCTGGAAG

CCAAGGGCTACAAAGAAGTGAAAAAGGACCTGATCATCAAGCTGCCTAAGTACT

CCCTGTTCGAGCTGGAAAACGGCCGGAAGAGAATGCTGGCCTCTGCCGGCGAAC

TGCAGAAGGGAAACGAACTGGCCCTGCCCTCCAAATATGTGAACTTCCTGTACC

TGGCCAGCCACTATGAGAAGCTGAAGGGCTCCCCCGAGGATAATGAGCAGAAAC

AGCTGTTTGTGGAACAGCACAAGCACTACCTGGACGAGATCATCGAGCAGATCA

GCGAGTTCTCCAAGAGAGTGATCCTGGCCGACGCTAATCTGGACAAAGTGCTGTC

CGCCTACAACAAGCACCGGGATAAGCCCATCAGAGAGCAGGCCGAGAATATCAT

CCACCTGTTTACCCTGACCAATCTGGGAGCCCCTGCCGCCTTCAAGTACTTTGACA

CCACCATCGACCGGAAGAGGTACACCAGCACCAAAGAGGTGCTGGACGCCACCC

TGATCCACCAGAGCATCACCGGCCTGTACGAGACACGGATCGACCTGTCTCAGCT

GGGAGGCGACAGCCCCAAGAAGAAGAGAAAGGTGGAGGCCAGCTAACATATGATTCGAATGTCT

TTCTTGCGCTATGACACTTCCAGCAAAAGGTAGGGCG

GGCTGCGAGACGGCTTCCCGGCGCTGCATGCAACACCGATGATGCTTCGACCCCC

CGAAGCTCCTTCGGGGCTGCATGGGCGCTCCGATGCCGCTCCAGGGCGAGCGCTG

TTTAAATAGCCAGGCCCCCGATTGCAAAGACATTATAGCGAGCTACCAAAGCCAT

ATTCAAACACCTAGATCACTACCACTTCTACACAGGCCACTCGAGCTTGTGATCG

CACTCCGCTAAGGGGGCGCCTCTTCCTCTTCGTTTCAGTCACAACCCGCAAACAT

GACACAAGAATCCCTGTTACTTCTCGACCGTATTGATTCGGATGATTCCTACGCG

AGCCTGCGGAACGACCAGGAATTCTGGGAGGTGAGTCGACGAGCAAGCCCGGCG

GATCAGGCAGCGTGCTTGCAGATTTGACTTGCAACGCCCGCATTGTGTCGACGAA

GGCTTTTGGCTCCTCTGTCGCTGTCTCAAGCAGCATCTAACCCTGCGTCGCCGTTT

CCATTTGCAGCCGCTGGCCCGCCGAGCCCTGGAGGAGCTCGGGCTGCCGGTGCCG

CCGGTGCTGCGGGTGCCCGGCGAGAGCACCAACCCCGTACTGGTCGGCGAGCCC

GGCCCGGTGATCAAGCTGTTCGGCGAGCACTGGTGCGGTCCGGAGAGCCTCGCG

TCGGAGTCGGAGGCGTACGCGGTCCTGGCGGACGCCCCGGTGCCGGTGCCCCGC

CTCCTCGGCCGCGGCGAGCTGCGGCCCGGCACCGGAGCCTGGCCGTGGCCCTACC

TGGTGATGAGCCGGATGACCGGCACCACCTGGCGGTCCGCGATGGACGGCACGA

CCGACCGGAACGCGCTGCTCGCCCTGGCCCGCGAACTCGGCCGGGTGCTCGGCCG

GCTGCACAGGGTGCCGCTGACCGGGAACACCGTGCTCACCCCCCATTCCGAGGTC

TTCCCGGAACTGCTGCGGGAACGCCGCGCGGCGACCGTCGAGGACCACCGCGGG

TGGGGCTACCTCTCGCCCCGGCTGCTGGACCGCCTGGAGGACTGGCTGCCGGACG

TGGACACGCTGCTGGCCGGCCGCGAACCCCGGTTCGTCCACGGCGACCTGCACGG

GACCAACATCTTCGTGGACCTGGCCGCGACCGAGGTCACCGGGATCGTCGACTTC

ACCGACGTCTATGCGGGAGACTCCCGCTACAGCCTGGTGCAACTGCATCTCAACG

CCTTCCGGGGCGACCGCGAGATCCTGGCCGCGCTGCTCGACGGGGCGCAGTGGA

AGCGGACCGAGGACTTCGCCCGCGAACTGCTCGCCTTCACCTTCCTGCACGACTT

CGAGGTGTTCGAGGAGACCCCGCTGGATCTCTCCGGCTTCACCGATCCGGAGGAA

CTGGCGCAGTTCCTCTGGGGGCCGCCGGACACCGCCCCCGGCGCCTGATAAGGAT

-continued

CCGGCAAGACTGGCCCCGCTTGGCAACGCAACAGTGAGCCCCTCCCTAGTGTGTT

TGGGGATGTGACTATGTATTCGTGTGTTGGCCAACGGGTCAACCCGAACAGATTG

ATACCCGCCTTGGCATTTCCTGTCAGAATGTAACGTCAGTTGATGGTACT

For all modified *Chlamydomonas reinhardtii* cells, Applicants use PCR, SURVEYOR nuclease assay, and DNA sequencing to verify successful modification.

Example 25: Use of Cas9 to Target a Variety of Disease Types

Diseases that Involve Mutations in Protein Coding Sequence:

Dominant disorders may be targeted by inactivating the dominant negative allele. Applicants use Cas9 to target a unique sequence in the dominant negative allele and introduce a mutation via NHEJ. The NHEJ-induced indel may be able to introduce a frame-shift mutation in the dominant negative allele and eliminate the dominant negative protein. This may work if the gene is haplo-sufficient (e.g. MYOC mutation induced glaucoma and Huntington's disease).

Recessive disorders may be targeted by repairing the disease mutation in both alleles. For dividing cells, Applicants use Cas9 to introduce double strand breaks near the mutation site and increase the rate of homologous recombination using an exogenous recombination template. For dividing cells, this may be achieved using multiplexed nickase activity to catalyze the replacement of the mutant sequence in both alleles via NHEJ-mediated ligation of an exogenous DNA fragment carrying complementary overhangs.

Applicants also use Cas9 to introduce protective mutations (e.g. inactivation of CCR5 to prevent HIV infection, inactivation of PCSK9 for cholesterol reduction, or introduction of the A673T into APP to reduce the likelihood of Alzheimer's disease).

Diseases that Involve Non-Coding Sequences

Applicants use Cas9 to disrupt non-coding sequences in the promoter region, to alter transcription factor binding sites and alter enhancer or repressor elements. For example, Cas9 may be used to excise out the Klf1 enhancer EHS1 in hematopoietic stem cells to reduce BCL11a levels and reactivate fetal globin gene expression in differentiated erythrocytes Applicants also use Cas9 to disrupt functional motifs in the 5' or 3' untranslated regions. For example, for the treatment of myotonic dystrophy, Cas9 may be used to remove CTG repeat expansions in the DMPK gene.

Example 26: Multiplexed Nickase

Aspects of optimization and the teachings of Cas9 detailed in this application may also be used to generate Cas9 nickases. Applicants use Cas9 nickases in combination with pairs of guide RNAs to generate DNA double strand breaks with defined overhangs. When two pairs of guide RNAs are used, it is possible to excise an intervening DNA fragment. If an exogenous piece of DNA is cleaved by the two pairs of guide RNAs to generate compatible overhangs with the genomic DNA, then the exogenous DNA fragment may be ligated into the genomic DNA to replace the excised fragment. For example, this may be used to remove trinucleotide repeat expansion in the huntintin (HTT) gene to treat Huntington's Disease.

If an exogenous DNA that bears fewer number of CAG repeats is provided, then it may be able to generate a fragment of DNA that bears the same overhangs and can be ligated into the HTT genomic locus and replace the excised fragment.

```
HTT locus with
fragment
excised by         . . . CCGTGCCGGGCGGGAGACCGCCATGG                             GGCCCGGCTGTGGCTGAGGAGC . . .
Cas9 nickase       . . . GGCACGGCCCGCCCTCTGGC                                TGGGCCGGGCCGACACCGACTCCTCG . . .
and two pairs of
guide RNAs
                                                                +
exogenous DNA
fragment with fewer
number of CAG repeats
also cleaved by Cas9          CGACCCTGGAAA . . . . reduced number of CAG repeats . . . . . CCCCGCCGCCACCC
nicakse and the          GGTACCGCTGGGACCTTT . . . . .                              . . . . . GGGGCGGCGG
two pairs of guide
RNAs
(SEQ ID NOS: 132 to 139)
```

The ligation of the exogenous DNA fragment into the genome does not require homologous recombination machineries and therefore this method may be used in post-mitotic cells such as neurons.

Example 27: Delivery of CRISPR System

Cas9 and its chimeric guide RNA, or combination of tracrRNA and crRNA, can be delivered either as DNA or RNA. Delivery of Cas9 and guide RNA both as RNA (normal or containing base or backbone modifications) molecules can be used to reduce the amount of time that Cas9 protein persist in the cell. This may reduce the level of off-target cleavage activity in the target cell. Since delivery of Cas9 as mRNA takes time to be translated into protein, it might be advantageous to deliver the guide RNA several hours following the delivery of Cas9 mRNA, to maximize the level of guide RNA available for interaction with Cas9 protein.

In situations where guide RNA amount is limiting, it may be desirable to introduce Cas9 as mRNA and guide RNA in the form of a DNA expression cassette with a promoter driving the expression of the guide RNA. This way the amount of guide RNA available will be amplified via transcription.

A variety of delivery systems can be introduced to introduce Cas9 (DNA or RNA) and guide RNA (DNA or RNA) into the host cell. These include the use of liposomes, viral vectors, electroporation, nanoparticles, nanowires (Shalek et al., Nano Letters, 2012), exosomes. Molecular trojan horses liposomes (Pardridge et al., Cold Spring Harb Protoc; 2010; doi:10.1101/pdb.prot5407) may be used to deliver Cas9 and guide RNA across the blood brain barrier.

Example 28: Therapeutic Strategies for Trinucleotide Repeat Disorders

As previously mentioned in the application, the target polynucleotide of a CRISPR complex may include a number of disease-associated genes and polynucleotides and some of these disease associated gene may belong to a set of genetic disorders referred to as Trinucleotide repeat disorders (referred to as also trinucleotide repeat expansion disorders, triplet repeat expansion disorders or codon reiteration disorders).

These diseases are caused by mutations in which the trinucleotide repeats of certain genes exceed the normal, stable threshold which may usually differ in a gene. The discovery of more repeat expansion disorders has allowed for the classification of these disorders into a number of categories based on underlying similar characteristics. Huntington's disease (HD) and the spinocerebellar ataxias that are caused by a CAG repeat expansion in protein-coding portions of specific genes are included in Category I. Diseases or disorders with expansions that tend to make them phenotypically diverse and include expansions are usually small in magnitude and also found in exons of genes are included in Category II. Category III includes disorders or diseases which are characterized by much larger repeat expansions than either Category I or II and are generally located outside protein coding regions. Examples of Category III diseases or disorders include but are not limited to Fragile X syndrome, myotonic dystrophy, two of the spinocerebellar ataxias, juvenile myoclonic epilepsy, and Friedreich's ataxia.

Figure 32A:
FIG. 32A-32B (a) shows a schematic of the GAA repeat expansion in FXN intron 1 and (b) shows a schematic of the strategy adopted to excise the GAA expansion region using the CRISPR/Cas system.

Similar therapeutic strategies, like the one mentioned for Friedreich's ataxia below may be adopted to address other trinucleotide repeat or expansion disorders as well. For example, another triple repeat disease that can be treated using almost identical strategy is dystrophia myotonica 1 (DM1), where there is an expanded CTG motif in the 3' UTR. In Friedreich's ataxia, the disease results from expansion of GAA trinucleotides in the first intron of frataxin (FXN). One therapeutic strategy using CRISPR is to excise the GAA repeat from the first intron. The expanded GAA repeat is thought to affect the DNA structure and leads to recruit the formation of heterochromatin which turn off the frataxin gene (FIG. 32A).

Competitive Advantage over other therapeutic strategies are listed below:

siRNA knockdown is not applicable in this case, as disease is due to reduced expression of frataxin. Viral gene therapy is currently being explored. HSV-1 based vectors were used to deliver the frataxin gene in animal models and have shown therapeutic effect. However, long term efficacy of virus-based frataxin delivery suffer from several problems: First, it is difficult to regulate the expression of frataxin to match natural levels in health individuals, and second, long term over expression of frataxin leads to cell death.

Nucleases may be used to excise the GAA repeat to restore healthy genotype, but Zinc Finger Nuclease and TALEN strategies require delivery of two pairs of high efficacy nucleases, which is difficult for both delivery as well as nuclease engineering (efficient excision of genomic DNA by ZFN or TALEN is difficult to achieve).

In contrast to above strategies, the CRISPR-Cas system has clear advantages. The Cas9 enzyme is more efficient and more multiplexible, by which it is meant that one or more targets can be set at the same time. So far, efficient excision of genomic DNA>30% by Cas9 in human cells and may be as high as 30%, and may be improved in the future. Furthermore, with regard to certain trinucleotide repeat disorders like Huntington's disease (HD), trinucleotide repeats in the coding region may be addressed if there are differences between the two alleles. Specifically, if a HD patient is heterozygous for mutant HTT and there are nucleotide differences such as SNPs between the wt and mutant HTT alleles, then Cas9 may be used to specifically target the mutant HTT allele. ZFN or TALENs will not have the ability to distinguish two alleles based on single base differences.

Figure 32B:
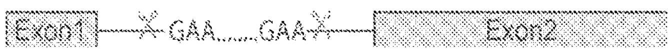

In adopting a strategy using the CRISPR-Cas 9 enzyme to address Friedreich's ataxia, Applicants design a number of guide RNAs targeting sites flanking the GAA expansion and the most efficient and specific ones are chosen (FIG. 32B).

Applicants deliver a combination of guide RNAs targeting the intron 1 of FXN along with Cas9 to mediate excision of the GAA expansion region. AAV9 may be used to mediate efficient delivery of Cas9 and in the spinal cord.

If the Alu element adjacent to the GAA expansion is considered important, there may be constraints to the number of sites that can be targeted but Applicants may adopt strategies to avoid disrupting it.

Alternative Strategies:

Rather than modifying the genome using Cas9, Applicants may also directly activate the FXN gene using Cas9 (nuclease activity deficient)-based DNA binding domain to target a transcription activation domain to the FXN gene.

Example 29: Strategies for Minimizing Off-Target Cleavage Using Cas9 Nickase

As previously mentioned in the application, Cas9 may be mutated to mediate single strand cleavage via one or more of the following mutations: D10A, E762A, and H840A.

To mediate gene knockout via NHEJ, Applicants use a nickase version of Cas9 along with two guide RNAs. Off-target nicking by each individual guide RNA may be primarily repaired without mutation, double strand breaks (which can lead to mutations via NHEJ) only occur when the target sites are adjacent to each other. Since double strand breaks introduced by double nicking are not blunt, co-expression of end-processing enzymes such as TREX1 will increase the level of NHEJ activity.

The following list of targets in tabular form are for genes involved in the following diseases:

Lafora's Disease—target GSY1 or PPP1R3C (PTG) to reduce glycogen in neurons.

Hypercholesterolemia—target PCSK9

Target sequences are listed in pairs (L and R) with different number of nucleotides in the spacer (0 to 3 bp). Each spacer may also be used by itself with the wild type Cas9 to introduce double strand break at the target locus.

| | | | (SEQ ID NO:) |
|---|---|---|---|
| GYS1 (human) | GGCC-L | ACCCTTGTTAGCCACCTCCC | 140 |
| | GGCC-R | GAACGCAGTGCTCTTCGAAG | 141 |
| | GGNCC-L | CTCACGCCCTGCTCCGTGTA | 142 |
| | GGNCC-R | GGCGACAACTACTTCCTGGT | 143 |
| | GGNNCC-L | CTCACGCCCTGCTCCGTGTA | 144 |
| | GGNNCC-R | GGGCGACAACTACTTCCTGG | 145 |
| | GGNNNCC-L | CCTCTTCAGGGCCGGGGTGG | 146 |
| | GGNNNCC-R | GAGGACCCAGGTGGAACTGC | 147 |
| PCSK9 (human | GGCC-L | TCAGCTCCAGGCGGTCCTGG | 148 |
| | GGCC-R | AGCAGCAGCAGCAGTGGCAG | 149 |
| | GGNCC-L | TGGGCACCGTCAGCTCCAGG | 150 |
| | GGNCC-R | CAGCAGTGGCAGCGGCCACC | 151 |
| | GGNNCC-L | ACCTCTCCCCTGGCCCTCAT | 152 |
| | GGNNCC-R | CCAGGACCGCCTGGAGCTGA | 153 |
| | GGNNNCC-L | CCGTCAGCTCCAGGCGGTCC | 154 |
| | GGNNNCC-R | AGCAGCAGCAGCAGTGGCAG | 155 |
| PPP1R3C (PTG (human | GGCC-L | ATGTGCCAAGCAAAGCCTCA | 156 |
| | GGCC-R | TTCGGTCATGCCCGTGGATG | 157 |
| | GGNCC-L | GTCGTTGAAATTCATCGTAC | 158 |
| | GGNCC-R | ACCACCTGTGAAGAGTTTCC | 159 |
| | GGNNCC-L | CGTCGTTGAAATTCATCGTA | 160 |
| | GGNNCC-R | ACCACCTGTGAAGAGTTTCC | 161 |
| Gys1 (mouse | GGCC-L | GAACGCAGTGCTTTTCGAGG | 162 |
| | GGCC-R | ACCCTTGTTGGCCACCTCCC | 163 |
| | GGNCC-L | GGTGACAACTACTATCTGGT | 164 |
| | GGNCC-R | CTCACACCCTGCTCCGTGTA | 165 |
| | GGNNCC-L | GGGTGACAACTACTATCTGG | 166 |
| | GGNNCC-R | CTCACACCCTGCTCCGTGTA | 167 |
| | GGNNNCC-L | CGAGAACGCAGTGCTTTTCG | 168 |
| | GGNNNCC-R | ACCCTTGTTGGCCACCTCCC | 169 |
| PPP1R3C (PTG (mouse | GGCC-L | ATGAGCCAAGCAAATCCTCA | 170 |
| | GGCC-R | TTCCGTCATGCCCGTGGACA | 171 |
| | GGNCC-L | CTTCGTTGAAAACCATTGTA | 172 |
| | GGNCC-R | CCACCTCTGAAGAGTTTCCT | 173 |
| | GGNNCC-L | CTTCGTTGAAAACCATTGTA | 174 |
| | GGNNCC-R | ACCACCTCTGAAGAGTTTCC | 175 |
| | GGNNNCC-L | CTTCCACTCACTCTGCGATT | 176 |
| | GGNNNCC-R | ACCATGTCTCAGTGTCAAGC | 177 |
| PCSK9 (mouse | GGCC-L | GGCGGCAACAGCGGCAACAG | 178 |
| | GGCC-R | ACTGCTCTGCGTGGCTGCGG | 179 |
| | GGNNCC-L | CCGCAGCCACGCAGAGCAGT | 180 |
| | GGNNCC-R | GCACCTCTCCTCGCCCCGAT | 181 |

Alternative Strategies for Improving Stability of Guide RNA and Increasing Specificity 1. Nucleotides in the 5' of the guide RNA may be linked via thiolester linkages rather than phosphoester linkage like in natural RNA. Thiolester linkage may prevent the guide RNA from being digested by endogenous RNA degradation machinery.

2. Nucleotides in the guide sequence (5' 20 bp) of the guide RNA can use bridged nucleic acids (BNA) as the bases to improve the binding specificity.

Example 30: CRISPR-Cas for Rapid, Multiplex Genome Editing

Aspects of the invention relate to protocols and methods by which efficiency and specificity of gene modification may be tested within 3-4 days after target design, and modified clonal cell lines may be derived within 2-3 weeks.

Programmable nucleases are powerful technologies for mediating genome alteration with high precision. The RNA-guided Cas9 nuclease from the microbial CRISPR adaptive immune system can be used to facilitate efficient genome editing in eukaryotic cells by simply specifying a 20-nt targeting sequence in its guide RNA. Applicants describe a set of protocols for applying Cas9 to facilitate efficient genome editing in mammalian cells and generate cell lines for downstream functional studies. Beginning with target design, efficient and specific gene modification can be achieved within 3-4 days, and modified clonal cell lines can be derived within 2-3 weeks.

The ability to engineer biological systems and organisms holds enormous potential for applications across basic science, medicine, and biotechnology. Programmable sequence-specific endonucleases that facilitate precise editing of endogenous genomic loci are now enabling systematic interrogation of genetic elements and causal genetic variations in a broad range of species, including those that have not been genetically tractable previously. A number of genome editing technologies have emerged in recent years, including zinc finger nucleases (ZFNs), transcription activator-like effector nucleases (TALENs), and the RNA-guided CRISPR-Cas nuclease system. The first two technologies use a common strategy of tethering endonuclease catalytic domains to modular DNA-binding proteins for inducing targeted DNA double stranded breaks (DSB) at specific genomic loci. By contrast, Cas9 is a nuclease guided by small RNAs through Watson-Crick base-pairing with target DNA, presenting a system that is easy to design, efficient, and well-suited for high-throughput and multiplexed gene editing for a variety of cell types and organisms. Here Applicants describe a set of protocols for applying the recently developed Cas9 nuclease to facilitate efficient genome editing in mammalian cells and generate cell lines for downstream functional studies.

Like ZFNs and TALENs, Cas9 promotes genome editing by stimulating DSB at the target genomic loci. Upon cleavage by Cas9, the target locus undergoes one of two major pathways for DNA damage repair, the error-prone non-homologous end joining (NHEJ) or the high-fidelity homology directed repair (HDR) pathway. Both pathways may be utilized to achieve the desired editing outcome.

NHEJ: In the absence of a repair template, the NHEJ process re-ligates DSBs, which may leave a scar in the form of indel mutations. This process can be harnessed to achieve gene knockouts, as indels occurring within a coding exon may lead to frameshift mutations and a premature stop codon. Multiple DSBs may also be exploited to mediate larger deletions in the genome.

HDR: Homology directed repair is an alternate major DNA repair pathway to NHEJ. Although HDR typically occurs at lower frequencies than NHEJ, it may be harnessed to generate precise, defined modifications at a target locus in the presence of an exogenously introduced repair template. The repair template may be either in the form of double stranded DNA, designed similarly to conventional DNA targeting constructs with homology arms flanking the insertion sequence, or single-stranded DNA oligonucleotides (ssODNs). The latter provides an effective and simple method for making small edits in the genome, such as the introduction of single nucleotide mutations for probing causal genetic variations. Unlike NHEJ, HDR is generally active only in dividing cells and its efficiency varies depending on the cell type and state.

Overview of CRISPR: The CRISPR-Cas system, by contrast, is at minimum a two-component system consisting of the Cas9 nuclease and a short guide RNA. Re-targeting of Cas9 to different loci or simultaneous editing of multiple genes simply requires cloning a different 20-bp oligonucleotide. Although specificity of the Cas9 nuclease has yet to be thoroughly elucidated, the simple Watson-Crick base-pairing of the CRISPR-Cas system is likely more predictable than that of ZFN or TALEN domains.

The type II CRISPR-Cas (clustered regularly interspaced short palindromic repeats) is a bacterial adaptive immune system that uses Cas9, to cleave foreign genetic elements. Cas9 is guided by a pair of non-coding RNAs, a variable crRNA and a required auxiliary tracrRNA. The crRNA contains a 20-nt guide sequence determines specificity by locating the target DNA via Watson-Crick base-pairing. In the native bacterial system, multiple crRNAs are co-transcribed to direct Cas9 against various targets. In the CRISPR-Cas system derived from *Streptococcus pyogenes*, the target DNA must immediately precede a 5'-NGG/NRG protospacer adjacent motif (PAM), which can vary for other CRISPR systems.

CRISPR-Cas is reconstituted in mammalian cells through the heterologous expression of human codon-optimized Cas9 and the requisite RNA components. Furthermore, the crRNA and tracrRNA can be fused to create a chimeric, synthetic guide RNA (sgRNA). Cas9 can thus be re-directed toward any target of interest by altering the 20-nt guide sequence within the sgRNA.

Given its ease of implementation and multiplex capability, Cas9 has been used to generate engineered eukaryotic cells carrying specific mutations via both NHEJ and HDR. In addition, direct injection of sgRNA and mRNA encoding Cas9 into embryos has enabled the rapid generation of transgenic mice with multiple modified alleles; these results hold promise for editing organisms that are otherwise genetically intractable.

A mutant Cas9 carrying a disruption in one of its catalytic domains has been engineered to nick rather than cleave DNA, allowing for single-stranded breaks and preferential repair through HDR, potentially ameliorating unwanted indel mutations from off-target DSBs. Additionally, a Cas9 mutant with both DNA-cleaving catalytic residues mutated has been adapted to enable transcriptional regulation in *E. coli*, demonstrating the potential of functionalizing Cas9 for diverse applications. Certain aspects of the invention relate to the construction and application of Cas9 for multiplexed editing of human cells.

Applicants have provided a human codon-optimized, nuclear localization sequence-flanked Cas9 to facilitate eukaryotic gene editing. Applicants describe considerations for designing the 20-nt guide sequence, protocols for rapid construction and functional validation of sgRNAs, and finally use of the Cas9 nuclease to mediate both NHEJ- and HDR-based genome modifications in human embryonic kidney (HEK-293FT) and human stem cell (HUES9) lines. This protocol can likewise be applied to other cell types and organisms.

Target selection for sgRNA: There are two main considerations in the selection of the 20-nt guide sequence for gene targeting: 1) the target sequence should precede the 5'-NGG PAM for *S. pyogenes* Cas9, and 2) guide sequences should be chosen to minimize off-target activity. Applicants provided an online Cas9 targeting design tool that takes an input sequence of interest and identifies suitable target sites. To experimentally assess off-target modifications for each sgRNA, Applicants also provide computationally predicted off-target sites for each intended target, ranked according to Applicants' quantitative specificity analysis on the effects of base-pairing mismatch identity, position, and distribution.

The detailed information on computationally predicted off-target sites is as follows:

Considerations for Off-target Cleavage Activities: Similar to other nucleases, Cas9 can cleave off-target DNA targets in the genome at reduced frequencies. The extent to which a given guide sequence exhibit off-target activity depends on a combination of factors including enzyme concentration, thermodynamics of the specific guide sequence employed, and the abundance of similar sequences in the target genome. For routine application of Cas9, it is important to consider ways to minimize the degree of off-target cleavage and also to be able to detect the presence of off-target cleavage.

Minimizing off-target activity: For application in cell lines, Applicants recommend following two steps to reduce the degree of off-target genome modification. First, using our online CRISPR target selection tool, it is possible to computationally assess the likelihood of a given guide sequence to have off-target sites. These analyses are performed through an exhaustive search in the genome for off-target sequences that are similar sequences as the guide sequence. Comprehensive experimental investigation of the effect of mismatching bases between the sgRNA and its target DNA revealed that mismatch tolerance is 1) position dependent—the 8-14 bp on the 3' end of the guide sequence are less tolerant of mismatches than the 5' bases, 2) quantity dependent—in general more than 3 mismatches are not tolerated, 3) guide sequence dependent—some guide sequences are less tolerant of mismatches than others, and 4) concentration dependent—off-target cleavage is highly sensitive to the amount of transfected DNA. The Applicants' target site analysis web tool (available at the website genome-engineering.org/tools) integrates these criteria to provide predictions for likely off-target sites in the target genome. Second, Applicants recommend titrating the amount of Cas9 and sgRNA expression plasmid to minimize off-target activity.

Detection of off-target activities: Using Applicants' CRISPR targeting web tool, it is possible to generate a list of most likely off-target sites as well as primers performing SURVEYOR or sequencing analysis of those sites. For isogenic clones generated using Cas9, Applicants strongly recommend sequencing these candidate off-target sites to check for any undesired mutations. It is worth noting that there may be off target modifications in sites that are not included in the predicted candidate list and full genome sequence should be performed to completely verify the absence of off-target sites. Furthermore, in multiplex assays where several DSBs are induced within the same genome, there may be low rates of translocation events and can be evaluated using a variety of techniques such as deep sequencing.

The online tool provides the sequences for all oligos and primers necessary for 1) preparing the sgRNA constructs, 2) assaying target modification efficiency, and 3) assessing cleavage at potential off-target sites. It is worth noting that because the U6 RNA polymerase III promoter used to express the sgRNA prefers a guanine (G) nucleotide as the first base of its transcript, an extra G is appended at the 5' of the sgRNA where the 20-nt guide sequence does not begin with G.

Approaches for sgRNA construction and delivery: Depending on the desired application, sgRNAs may be delivered as either 1) PCR amplicons containing an expression cassette or 2) sgRNA-expressing plasmids. PCR-based sgRNA delivery appends the custom sgRNA sequence onto the reverse PCR primer used to amplify a U6 promoter template. The resulting amplicon may be co-transfected with a plasmid containing Cas9 (PX165). This method is optimal for rapid screening of multiple candidate sgRNAs, as cell transfections for functional testing can be performed mere hours after obtaining the sgRNA-encoding primers. Because this simple method obviates the need for plasmid-based cloning and sequence verification, it is well suited for testing or co-transfecting a large number of sgRNAs for generating large knockout libraries or other scale-sensitive applications. Note that the sgRNA-encoding primers are over 100-bp, compared to the ~20-bp oligos required for plasmid-based sgRNA delivery.

Construction of an expression plasmid for sgRNA is also simple and rapid, involving a single cloning step with a pair of partially complementary oligonucleotides. After annealing the oligo pairs, the resulting guide sequences may be inserted into a plasmid bearing both Cas9 and an invariant scaffold bearing the remainder of the sgRNA sequence (PX330). The transfection plasmids may also be modified to enable virus production for in vivo delivery.

In addition to PCR and plasmid-based delivery methods, both Cas9 and sgRNA can be introduced into cells as RNA.

Design of repair template: Traditionally, targeted DNA modifications have required use of plasmid-based donor repair templates that contain homology arms flanking the site of alteration. The homology arms on each side can vary in length, but are typically longer than 500 bp. This method can be used to generate large modifications, including insertion of reporter genes such as fluorescent proteins or antibiotic resistance markers. The design and construction of targeting plasmids has been described elsewhere.

More recently, single-stranded DNA oligonucleotides (ssODNs) have been used in place of targeting plasmids for short modifications within a defined locus without cloning. To achieve high HDR efficiencies, ssODNs contain flanking sequences of at least 40 bp on each side that are homologous to the target region, and can be oriented in either the sense or antisense direction relative to the target locus.

Functional Testing

SURVEYOR nuclease assay: Applicants detected indel mutations either by the SURVEYOR nuclease assay (or PCR amplicon sequencing. Applicants online CRISPR target design tool provides recommended primers for both approaches. However, SURVEYOR or sequencing primers may also be designed manually to amplify the region of interest from genomic DNA and to avoid non-specific amplicons using NCBI Primer-BLAST. SURVEYOR primers should be designed to amplify 300-400 bp (for a 600-800 bp total amplicon) on either side of the Cas9 target for allowing clear visualization of cleavage bands by gel electrophoresis. To prevent excessive primer dimer formation, SURVEYOR primers should be designed to be typically under 25-nt long with melting temperatures of ~60° C. Applicants recommend testing each pair of candidate primers for specific PCR amplicons as well as for the absence of non-specific cleavage during the SURVEYOR nuclease digestion process.

Plasmid- or ssODN-mediated HDR: HDR can be detected via PCR-amplification and sequencing of the modified region. PCR primers for this purpose should anneal outside the region spanned by the homology arms to avoid false detection of residual repair template (HDR Fwd and Rev, FIG. 30). For ssODN-mediated HDR, SURVEYOR PCR primers can be used.

Detection of indels or HDR by sequencing: Applicants detected targeted genome modifications by either Sanger or next-generation deep sequencing (NGS). For the former, genomic DNA from modified region can be amplified using either SURVEYOR or HDR primers. Amplicons should be subcloned into a plasmid such as pUC19 for transformation; individual colonies can be sequenced to reveal clonal genotype.

Applicants designed next-generation sequencing (NGS) primers for shorter amplicons, typically in the 100-200 bp size range. For detecting NHEJ mutations, it is important to design primers with at least 10-20 bp between the priming regions and the Cas9 target site to allow detection of longer indels. Applicants provide guidelines for a two-step PCR method to attach barcoded adapters for multiplex deep sequencing. Applicants recommend the Illumina platform, due to its generally low levels of false positive indels. Off-target analysis (described previously) can then be performed through read alignment programs such as ClustalW, Geneious, or simple sequence analysis scripts.

Materials and Reagents sgRNA Preparation:

UltraPure DNaseRNase-free distilled water (Life Technologies, cat. no. 10977-023)

Herculase II fusion polymerase (Agilent Technologies, cat. no. 600679)

CRITICAL. Standard Taq polymerase, which lacks 3'-5' exonuclease proofreading activity, has lower fidelity and can lead to amplification errors. Herculase II is a high-fidelity polymerase (equivalent fidelity to Pfu) that produces high yields of PCR product with minimal optimization. Other high-fidelity polymerases may be substituted.

Herculase II reaction buffer (5×; Agilent Technologies, included with polymerase)

dNTP solution mix (25 mM each; Enzymatics, cat. no. N205L)

MgCl2 (25 mM; ThermoScientific, cat. no. R0971)

QIAquick gel extraction kit (Qiagen, cat. no. 28704)

QIAprep spin miniprep kit (Qiagen, cat. no. 27106)

UltraPure TBE buffer (10×; Life Technologies, cat. no. 15581-028)

SeaKem LE agarose (Lonza, cat. no. 50004)

SYBR Safe DNA stain (10,000×; Life Technologies, cat. no. 533102)

1-kb Plus DNA ladder (Life Technologies, cat. no. 10787-018)

TrackIt CyanOrange loading buffer (Life Technologies, cat. no. 10482-028)

FastDigest BbsI (BpiI) (Fermentas/ThermoScientific, cat. no. FD1014)

Fermentas Tango Buffer (Fermentas/ThermoScientific, cat. no. BY5)

DL-dithiothreitol (DTT; Fermentas/ThermoScientific, cat. no. R0862)

T7 DNA ligase (Enzymatics, cat. no. L602L)

Critical: Do not substitute the more commonly used T4 ligase. T7 ligase has 1,000-fold higher activity on the sticky ends than on the blunt ends and higher overall activity than commercially available concentrated T4 ligases.

T7 2× Rapid Ligation Buffer (included with T7 DNA ligase, Enzymatics, cat. no. L602L)

T4 Polynucleotide Kinase (New England Biolabs, cat. no M0201S)

T4 DNA Ligase Reaction Buffer (10×; New England Biolabs, cat. no B0202S)

Adenosine 5'-triphosphate (10 mM; New England Biolabs, cat. no. P0756S)

PlasmidSafe ATP-dependent DNase (Epicentre, cat. no. E3101K)

One Shot Stbl3 chemically competent *Escherichia coli* (*E. coli*) (Life Technologies, cat. no. C7373-03)

SOC medium (New England Biolabs, cat. no. B9020S)

LB medium (Sigma, cat. no. L3022)

LB agar medium (Sigma, cat. no. L2897)

Ampicillin, sterile filtered (100 mg ml-1; Sigma, cat. no. A5354)

Mammalian Cell Culture:

HEK293FT cells (Life Technologies, cat. no. R700-07)

Dulbecco's minimum Eagle's medium (DMEM, 1×, high glucose; Life Technologies, cat. no. 10313-039)

Dulbecco's minimum Eagle's medium (DMEM, 1×, high glucose, no phenol red; Life Technologies, cat. no. 31053-028)

Dulbecco's phosphate-buffered saline (DPBS, 1×; Life Technologies, cat. no. 14190-250)

Fetal bovine serum, qualified and heat inactivated (Life Technologies, cat. no. 10438-034)

Opti-MEM I reduced-serum medium (FBS; Life Technologies, cat. no. 11058-021)

Penicillin-streptomycin (100×; Life Technologies, cat. no. 15140-163)

TrypLE™ Express (1×, no Phenol Red; Life Technologies, cat. no. 12604-013)

Lipofectamine 2000 transfection reagent (Life Technologies, cat. no. 11668027)

Amaxa SF Cell Line 4D-Nucleofector® X Kit S (32 RCT; Lonza, cat. no V4XC-2032)

HUES 9 cell line (HARVARD STEM CELL SCIENCE)

Geltrex LDEV-Free Reduced Growth Factor Basement Membrane Matrix (Life Technologies, cat. no. A1413201)

mTeSR1 medium (Stemcell Technologies, cat. no. 05850)

Accutase cell detachment solution (Stemcell Technologies, cat. no. 07920)

ROCK Inhibitor (Y-27632; Millipore, cat. no. SCM075)

Amaxa P3 Primary Cell 4D-Nucleofector® X Kit S (32 RCT; Lonza cat. no. V4XP-3032)

Genotyping Analysis:

QuickExtract DNA extraction solution (Epicentre, cat. no. QE09050)

PCR primers for SURVEYOR, RFLP analysis, or sequencing (see Primer table)

Herculase II fusion polymerase (Agilent Technologies, cat. no. 600679)

CRITICAL. As Surveyor assay is sensitive to single-base mismatches, it is particularly important to use a high-fidelity polymerase. Other high-fidelity polymerases may be substituted.

Herculase II reaction buffer (5×; Agilent Technologies, included with polymerase)

dNTP solution mix (25 mM each; Enzymatics, cat. no. N205L)

QIAquick gel extraction kit (Qiagen, cat. no. 28704)

Taq Buffer (10×; Genscript, cat. no. B0005)

SURVEYOR mutation detection kit for standard gel electrophoresis (Transgenomic, cat. no. 706025)

UltraPure TBE buffer (10×; Life Technologies, cat. no. 15581-028)

SeaKem LE agarose (Lonza, cat. no. 50004)

4-20% TBE Gels 1.0 mm, 15 Well (Life Technologies, cat. no. EC62255BOX)

Novex® Hi-Density TBE Sample Buffer (5×; Life Technologies, cat. no. LC6678)

SYBR Gold Nucleic Acid Gel Stain (10,000×; Life Technologies, cat. no. S-11494)

1-kb Plus DNA ladder (Life Technologies, cat. no. 10787-018)

TrackIt CyanOrange loading buffer (Life Technologies, cat. no. 10482-028)

FastDigest HindIII (Fermentas/ThermoScientific, cat. no. FD0504)

Equipment

Filtered sterile pipette tips (Corning)

Standard 1.5 ml microcentrifuge tubes (Eppendorf, cat. no. 0030 125.150)

Axygen 96-well PCR plates (VWR, cat. no. PCR-96M2-HSC)

Axygen 8-Strip PCR tubes (Fischer Scientific, cat. no. 14-222-250)

Falcon tubes, polypropylene, 15 ml (BD Falcon, cat. no. 352097)

Falcon tubes, polypropylene, 50 ml (BD Falcon, cat. no. 352070)

Round-bottom Tube with cell strainer cap, 5 ml (BD Falcon, cat. no. 352235)

Petri dishes (60 mm×15 mm; BD Biosciences, cat. no. 351007)

Tissue culture plate (24 well; BD Falcon, cat. no. 353047)

Tissue culture plate (96 well, flat bottom; BD Falcon, cat. no. 353075)

Tissue culture dish (100 mm; BD Falcon, 353003)

96-well thermocycler with programmable temperature stepping functionality (Applied Biosystems Veriti, cat. no. 4375786).

Desktop microcentrifuges 5424, 5804 (Eppendorf)

Gel electrophoresis system (PowerPac basic power supply, Bio-Rad, cat. no. 164-5050, and Sub-Cell GT System gel tray, Bio-Rad, cat. no. 170-4401)

Novex XCell SureLock Mini-Cell (Life Technologies, cat. no. EI0001)

Digital gel imaging system (GelDoc EZ, Bio-Rad, cat. no. 170-8270, and blue sample tray, Bio-Rad, cat. no. 170-8273)

Blue light transilluminator and orange filter goggles (SafeImager 2.0; Invitrogen, cat. no. G6600) Gel quantification software (Bio-Rad, ImageLab, included with GelDoc EZ, or open-source ImageJ from the National Institutes of Health, available at the website rsbweb.nih.gov/ij/)

UV spectrophotometer (NanoDrop 2000c, Thermo Scientific)

Reagent Setup

Tris-borate EDTA (TBE) electrophoresis solution Dilute TBE buffer in distilled water to 1× working solution for casting agarose gels and for use as a buffer for gel electrophoresis. Buffer may be stored at room temperature (18-22° C.) for at least 1 year.

ATP, 10 mM Divide 10 mM ATP into 50-μl aliquots and store at −20° C. for up to 1 year; avoid repeated freeze-thaw cycles.

DTT, 10 mM Prepare 10 mM DTT solution in distilled water and store in 20-μl aliquots at −70° C. for up to 2 years; for each reaction, use a new aliquot, as DTT is easily oxidized.

D10 culture medium For culture of HEK293FT cells, prepare D10 culture medium by supplementing DMEM with 1× GlutaMAX and 10% (vol/vol) fetal bovine serum. As indicated in the protocol, this medium can also be supplemented with 1× penicillin-streptomycin .D10 medium can be made in advance and stored at 4° C. for up to 1 month.

mTeSR1 culture medium For culture of human embryonic stem cells, prepare mTeSR1 medium by supplementing the 5× supplement (included with mTeSR1 basal medium), and 100 ug/ml Normocin.

Procedure

Design of Targeting Components and Use of the Online Tool•Timing 1 d

Input target genomic DNA sequence. Applicants provide an online Cas9 targeting design tool that takes an input sequence of interest, identifies and ranks suitable target sites, and computationally predicts off-target sites for each intended target. Alternatively, one can manually select guide sequence by identifying the 20-bp sequence directly upstream of any 5'-NGG.

Order necessary oligos and primers as specified by the online tool. If the site is chosen manually, the oligos and primers should be designed.

Preparation of sgRNA Expression Construct

To generate the sgRNA expression construct, either the PCR- or plasmid-based protocol can be used.

(A) Via PCR Amplification•Timing 2 h (i) Applicants prepare diluted U6 PCR template. Applicants recommend using PX330 as a PCR template, but any U6-containing plasmid may likewise be used as the PCR template. Applicants diluted template with $ddH_2O$ to a concentration of 10 ng/ul. Note that if a plasmid or cassette already containing an U6-driven sgRNA is used as a template, a gel extraction needs to be performed to ensure that the product contains only the intended sgRNA and no trace sgRNA carryover from template.

(ii) Applicants prepared diluted PCR oligos. U6-Fwd and U6-sgRNA-Rev primers are diluted to a final concentration of 10 uM in $ddH_2O$ (add 10 ul of 100 uM primer to 90 ul $ddH_2O$).

(iii) U6-sgRNA PCR reaction. Applicants set up the following reaction for each U6-sgRNA-Rev primer and mastermix as needed:

| Component: | Amount (ul) | Final concentration |
|---|---|---|
| Herculase II PCR buffer, 5X | 10 | 1X |
| dNTP, 100 mM (25 mM each) | 0.5 | 1 mM |
| U6 template (PX330) | 1 | 0.2 ng/ul |
| U6-Fwd primer | 1 | 0.2 uM |
| U6-sgRNA-Rev primer (variable) | 1 | 0.2 uM |
| Herculase II Fusion polymerase | 0.5 | |
| Distilled water | 36 | |
| Total | 50 | |

(iv) Applicants performed PCR reaction on the reactions from step (iii) using the following cycling conditions:

| Cycle number | Denature | Anneal | Extend |
|---|---|---|---|
| 1 | 95° C., 2 m | | |
| 2-31 | 95° C., 20 s | 60° C., 20 s | 72° C., 20 s |
| 32 | | 72° C., 3 m | |

(v) After the reaction is completed, Applicants ran the product on a gel to verify successful, single-band amplification. Cast a 2% (wt/vol) agarose gel in ix TBE buffer with ix SYBR Safe dye. Run 5 ul of the PCR product in the gel at 15 V cm−1 for 20-30 min. Successful amplicons should yield one single 370-bp product and the template should be invisible. It should not be necessary to gel extract the PCR amplicon.

(vi) Applicants purified the PCR product using the QIAquick PCR purification kit according to the manufacturer's directions. Elute the DNA in 35 ul of Buffer EB or water. Purified PCR products may be stored at 4° C. or −20° C.

(B) Cloning sgRNA into Cas9-Containing Bicistronic Expression Vector•Timing 3 d (i) Prepare the sgRNA oligo inserts. Applicants resuspended the top and bottom strands of oligos for each sgRNA design to a final concentration of 100 uM. Phosphorylate and anneal the oligo as follows:

| | |
|---|---|
| Oligo 1 (100 uM) | 1 ul |
| Oligo 2 (100 uM) | 1 ul |
| T4 Ligation Buffer, 10X | 1 ul |
| T4 PNK | 1 ul |
| $ddH_2O$ | 6 ul |
| Total | 10 ul |

(ii) Anneal in a thermocycler using the following parameters:

37° C. for 30 m

95° C. for 5 m

Ramp down to 25° C. at 5° C. per m (iii) Applicants diluted phosphorylated and annealed oligos 1:200 by add 1 ul of oligo to 199 ul room temperature $ddH_2O$.

(iv) Clone sgRNA oligo into PX330. Applicants set up Golden Gate reaction for each sgRNA. Applicants recommend also setting up a no-insert, PX330 only negative control.

| | |
|---|---|
| PX330 (100 ng) | x ul |
| Diluted oligo duplex from step (iii) | 2 ul |
| Tango Buffer, 10X | 2 ul |
| DTT, 10 mM | 1 ul |
| ATP, 10 mM | 1 ul |
| FastDigest BbsI | 1 ul |
| T7 Ligase | 0.5 ul |
| $ddH_2O$ | x ul |
| Total | 20 ul |

(v) Incubate the Golden Gate reaction for a total of 1 h:

| Cycle number | Condition |
|---|---|
| 1-6 | 37° C. for 5 m, 21° C. for 5 m |

(vi) Applicants treated Golden Gate reaction with PlasmidSafe exonuclease to digest any residual linearized DNA. This step is optional but highly recommended.

| | |
|---|---|
| Golden Gate reaction from step 4 | 11 ul |
| 10X PlasmidSafe Buffer | 1.5 ul |
| ATP, 10 mM | 1.5 ul |
| PlasmidSafe exonuclease | 1 ul |
| Total | 15 ul |

(vii) Applicants incubated the PlasmidSafe reaction at 37° C. for 30 min, followed by inactivation at 70° C. for 30 min. Pause point: after completion, the reaction may be frozen and continued later. The circular DNA should be stable for at least 1 week.

(viii) Transformation. Applicants transformed the PlasmidSafe-treated plasmid into a competent *E. coli* strain, according to the protocol supplied with the cells. Applicants recommend Stbl3 for quick transformation. Briefly, Applicants added 5 ul of the product from step (vii) into 20 ul of ice-cold chemically competent Stbl3 cells. This is then incubated on ice for 10 m, heat shocked at 42° C. for 30 s, returned immediately to ice for 2 m, 100 ul of SOC medium is added, and this is plated onto an LB plate containing 100 ug/ml ampicillin with incubation overnight at 37° C.

(ix) Day 2: Applicants inspected plates for colony growth. Typically, there are no colonies on the negative control plates (ligation of BbsI-digested PX330 only, no annealed sgRNA oligo), and tens to hundreds of colonies on the PX330-sgRNA cloning plates.

(x) From each plate, Applicants picked 2-3 colonies to check correct insertion of sgRNA. Applicants used a sterile pipette tip to inoculate a single colony into a 3 ml culture of LB medium with 100 ug/ml ampicillin. Incubate and shake at 37° C. overnight.

(xi) Day 3: Applicants isolated plasmid DNA from overnight cultures using a QiAprep Spin miniprep kit according to the manufacturer's instructions.

(xii) Sequence validate CRISPR plasmid. Applicants verified the sequence of each colony by sequencing from the U6 promoter using the U6-Fwd primer. Optional: sequence the Cas9 gene using primers listed in the following Primer table.

| Primer | Sequence (5′ to 3′) | Purpose |
|---|---|---|
| UG-For | GAGGGCCTATTTCCCATGATTCC (SEQ ID NO: 182) | Amplify UG-sgRNA |
| UG-Rev | AAAAAAAGCACCGACTCGGTGCC ACTTTTTCAAGTTGATAACGGAC TAGCCTTATTTTAACTTGCTATT TCTAGCTCTAAAACNNNNNNNNNN NNNNNNNNNNCCGGTGTTTCGTC CTTTCCACAAG (SEQ ID NO: 183) | Amplify UG-sgRNA; N is reverse complement of target |
| sgRNA-top | CACCGNNNNNNNNNNNNNNNNNNN (SEQ ID NO: 184) | Clone sgRNA into PX330 |
| sgRNA-bottom | AAACNNNNNNNNNNNNNNNNNNNC (SEQ ID NO: 185) | Clone sgRNA into PX330 |
| UG-EMX1-Rev | AAAAAAAGCACCGACTCGGTGCCA CTTTTTCAAGTTGATAACGGACTA GCCTTATTTTAACTTGCTATTTCT AGCTCTAAAACCCCTAGTCATTGG AGGTGACCGGTGTTTCGTCCTTTC CACAAG (SEQ ID NO: 186) | Amplify UG-EMX1 sgRNA |

-continued

| Primer | Sequence (5′ to 3′) | Purpose |
|---|---|---|
| EMX1-top | CACCGTCACCTCCAATGACTAGGG (SEQ ID NO: 187) | Clone EMX1 sgRNA into PX330 |

Applicants referenced the sequencing results against the PX330 cloning vector sequence to check that the 20 bp guide sequence was inserted between the U6 promoter and the remainder of the sgRNA scaffold. Details and sequence of the PX330 map in GenBank vector map format (*.gb file) can be found at the website crispr.genome-engineering.org.

(Optional) Design of ssODN Template•Timing 3 d Planning Ahead

Design and order ssODN. Either the sense or antisense ssODN can be purchased directly from supplier. Applicants recommend designing homology arms of at least 40 bp on either side and 90 bp for optimal HDR efficiency. In Applicants' experience, antisense oligos have slightly higher modification efficiencies.

Applicants resuspended and diluted ssODN ultramers to a final concentration of 10 uM. Do not combine or anneal the sense and antisense ssODNs. Store at −20° C.

Note for HDR applications, Applicants recommend cloning sgRNA into the PX330 plasmid.

Functional Validation of sgRNAs: Cell Culture and Transfections•Timing 3-4 d

The CRISPR-Cas system has been used in a number of mammalian cell lines. Conditions may vary for each cell line. The protocols below details transfection conditions for HEK239FT cells. Note for ssODN-mediated HDR transfections, the Amaxa SF Cell Line Nucleofector Kit is used for optimal delivery of ssODNs. This is described in the next section.

HEK293FT maintenance. Cells are maintained according to the manufacturer's recommendations. Briefly, Applicants cultured cells in D10 medium (GlutaMax DMEM supplemented with 10% Fetal Bovine Serum), at 37° C. and 5% CO2.

To passage, Applicants removed medium and rinsed once by gently adding DPBS to side of vessel, so as not to dislodge cells. Applicants added 2 ml of TrypLE to a T75 flask and incubated for 5 m at 37° C. 10 ml of warm D10 medium is added to inactivate and transferred to a 50 ml Falcon tube. Applicants dissociated cells by triturating gently, and re-seeded new flasks as necessary. Applicants typically passage cells every 2-3 d at a split ratio of 1:4 or 1:8, never allowing cells to reach more than 70% confluency. Cell lines are restarted upon reaching passage number 15.

Prepare cells for transfection. Applicants plated well-dissociated cells onto 24-well plates in D10 medium without antibiotics 16-24 h before transfection at a seeding density of $1.3\times10^5$ cells per well and a seeding volume of 500 ul. Scale up or down according to the manufacturer's manual as needed. It is suggested to not plate more cells than recommended density as doing so may reduce transfection efficiency.

On the day of transfection, cells are optimal at 70-90% confluency. Cells may be transfected with Lipofectamine 2000 or Amaxa SF Cell Line Nucleofector Kit according to the manufacturers' protocols.

(A) For sgRNAs cloned into PX330, Applicants transfected 500 ng of sequence-verified CRISPR plasmid; if transfecting more than one plasmid, mix at equimolar ratio and no more than 500 ng total.

(B) For sgRNA amplified by PCR, Applicants mixed the following:

| | |
|---|---|
| PX165 (Cas9 only) | 200 ng |
| sgRNA amplicon (each) | 40 ng |
| pUC19 | fill up total DNA to 500 ng |

Applicants recommend transfecting in technical triplicates for reliable quantification and including transfection controls (e.g. GFP plasmid) to monitor transfection efficiency. In addition, PX330 cloning plasmid and/or sgRNA amplicon may be transfected alone as a negative control for downstream functional assays.

Applicants added Lipofectamine complex to cells gently as HEK293FT cells may detach easily from plate easily and result in lower transfection efficiency.

Applicants checked cells 24 h after transfection for efficiency by estimating the fraction of fluorescent cells in the control (e.g., GFP) transfection using a fluorescence microscope. Typically cells are more than 70% transfected.

Applicants supplemented the culture medium with an additional 500 ul of warm D10 medium. Add D10 very slowly to the side of the well and do not use cold medium, as cells can detach easily.

Cells are incubated for a total of 48-72 h post-transfection before harvested for indel analysis. Indel efficiency does not increase noticeably after 48 h.

(Optional) Co-Transfection of CRISPR Plasmids and ssODNs or Targeting Plasmids for HR•Timing 3-4 d Linearize targeting plasmid. Targeting vector is linearized if possible by cutting once at a restriction site in the vector backbone near one of the homology arms or at the distal end of either homology arm.

Applicants ran a small amount of the linearized plasmid alongside uncut plasmid on a 0.8-1% agarose gel to check successful linearization. Linearized plasmid should run above the supercoiled plasmid.

Applicants purified linearized plasmid with the QIAQuick PCR Purification kit.

Prepare cells for transfection. Applicants cultured HEK293FT in T75 or T225 flasks. Sufficient cell count before day of transfection is planned for. For the Amaxa strip-cuvette format, $2\times10^6$ cells are used per transfection.

Prepare plates for transfection. Applicants added 1 ml of warm D10 medium into each well of a 12 well plate. Plates are placed into the incubator to keep medium warm.

Nucleofection. Applicants transfected HEK293FT cells according to the Amaxa SF Cell Line Nucleofector 4D Kit manufacturer's instructions, adapted in the steps below.

a. For ssODN and CRISPR cotransfection, pre-mix the following DNA in PCR tubes:

| | |
|---|---|
| pCRISPR plasmid (Cas9 + sgRNA) | 500 ng |
| ssODN template (10 uM) | 1 ul |

b. For HDR targeting plasmid and CRISPR cotransfection, pre-mix the following DNA in PCR tubes:

| | |
|---|---|
| CRISPR plasmid (Cas9 + sgRNA) | 500 ng |
| Linearized targeting plasmid | 500 ng |

For transfection controls, see previous section. In addition, Applicants recommend transfecting ssODN or targeting plasmid alone as a negative control.

Dissociate to single cells. Applicants removed medium and rinsed once gently with DPBS, taking care not to dislodge cells. 2 ml of TrypLE is added to a T75 flask and incubated for 5 m at 37° C. 10 ml of warm D10 medium is added to inactivate and triturated gently in a 50 ml Falcon tube. It is recommended that cells are triturated gently and dissociated to single cells. Large clumps will reduce transfection efficiency. Applicants took a 10 ul aliquot from the suspension and diluted into 90 ul of D10 medium for counting. Applicants counted cells and calculated the number of cells and volume of suspension needed for transfection. Applicants typically transfected $2\times10^5$ cells per condition using the Amaxa Nucleocuvette strips, and recommend calculating for 20% more cells than required to adjust for volume loss in subsequent pipetting steps. The volume needed is transferred into a new Falcon tube.

Applicants spun down the new tube at 200×g for 5 m.

Applicants prepared the transfection solution by mixing the SF solution and 51 supplement as recommended by Amaxa. For Amaxa strip-cuvettes, a total of 20 ul of supplemented SF solution is needed per transfection. Likewise, Applicants recommend calculating for 20% more volume than required.

Applicants removed medium completely from pelleted cells from step 23 and gently resuspended in appropriate volume (20 ul per $2\times10^5$ cells) of S1-supplemented SF solution. Do not leave cells in SF solution for extended period of time.

20 ul of resuspended cells is pipetted into each DNA pre-mix from step 20. Pipette gently to mix and transfer to Nucleocuvette strip chamber. This is repeated for each transfection condition.

Electroporate cells using the Nucleofector 4D program recommended by Amaxa, CM-130.

Applicants gently and slowly pipetted 100 ul of warm D10 medium into each Nucleocuvette strip chamber, and transferred all volume into the pre-warmed plate from step 19. CRITICAL. Cells are very fragile at this stage and harsh pipetting can cause cell death. Incubate for 24 h. At this point, transfection efficiency can be estimated from fraction of fluorescent cells in positive transfection control. Nucleofection typically results in greater than 70-80% transfection efficiency. Applicants slowly added 1 ml warm D10 medium to each well without dislodging the cells. Incubate cells for a total of 72 h.

Human Embryonic Stem Cell (HUES 9) Culture and Transfection•Timing 3-4 d

Maintaining hESC (HUES9) line. Applicants routinely maintain HUES9 cell line in feeder-free conditions with mTesR1 medium. Applicants prepared mTeSR1 medium by adding the 5× supplement included with basal medium and 100 ug/ml Normocin. Applicants prepared a 10 ml aliquot of mTeSR1 medium supplemented further with 10 uM Rock Inhibitor. Coat tissue culture plate. Dilute cold GelTrex 1:100 in cold DMEM and coat the entire surface of a 100 mm tissue culture plate.

Place plate in incubator for at least 30 m at 37° C. Thaw out a vial of cells at 37° C. in a 15 ml Falcon tube, add 5 ml of mTeSR1 medium, and pellet at 200×g for 5 m. Aspirate off GelTrex coating and seed ~1×106 cells with 10 ml mTeSR1 medium containing Rock Inhibitor. Change to normal mTeSR1 medium 24 h after transfection and re-feed daily. Passaging cells. Re-feed cells with fresh mTeSR1 medium daily and passage before reaching 70% confluency. Aspirate off mTeSR1 medium and wash cells once with DPBS. Dissociate cells by adding 2 ml Accutase and incubating at 37° C. for 3-5 m. Add 10 ml mTeSR1 medium to detached cells, transfer to 15 ml Falcon tube and resuspend gently. Re-plate onto GelTrex-coated plates in mTeSR1 medium with 10 uM Rock Inhibitor. Change to normal mTeSR1 medium 24 h after plating.

Transfection. Applicants recommend culturing cells for at least 1 week post-thaw before transfecting using the Amaxa P3 Primary Cell 4-D Nucleofector Kit (Lonza). Re-feed log-phase growing cells with fresh medium 2 h before transfection. Dissociate to single cells or small clusters of no more than 10 cells with accutase and gentle resuspension. Count the number of cells needed for nucleofection and spin down at 200×g for 5 m. Remove medium completely and resuspend in recommended volume of 51-supplemented P3 nucleofection solution. Gently plate electroporated cells into coated plates in presence of 1× Rock Inhibitor.

Check transfection success and re-feed daily with regular mTeSR1 medium beginning 24 h after nucleofection. Typically, Applicants observe greater than 70% transfection efficiency with Amaxa Nucleofection. Harvest DNA. 48-72 h post transfection, dissociate cells using accutase and inactivate by adding 5×volume of mTeSR1. Spin cells down at 200×g for 5 m. Pelleted cells can be directed processed for DNA extraction with QuickExtract solution. It is recommended to not mechanically dissociate cells without accutase. It is recommended to not spin cells down without inactivating accutase or above the recommended speed; doing so may cause cells to lyse.

Isolation of Clonal Cell Lines by FACS. Timing•2-3 h Hands-on; 2-3 Weeks Expansion Clonal isolation may be performed 24 h post-transfection by FACS or by serial dilution.

Prepare FACS buffer. Cells that do not need sorting using colored fluorescence may be sorted in regular D10 medium supplemented with 1× penicillin/streptinomycin. If colored fluorescence sorting is also required, a phenol-free DMEM or DPBS is substituted for normal DMEM. Supplement with 1× penicillin/streptinomycin and filter through a 0.22 um Steriflip filter.

Prepare 96 well plates. Applicants added 100 ul of D10 media supplemented with 1× penicillin/streptinomycin per well and prepared the number of plates as needed for the desired number of clones.

Prepare cells for FACS. Applicants dissociated cells by aspirating the medium completely and adding 100 ul TrypLE per well of a 24-well plate. Incubate for 5 m and add 400 ul warm D10 media.

Resuspended cells are transferred into a 15 ml Falcon tube and gently triturated 20 times. Recommended to check under the microscope to ensure dissociation to single cells.

Spin down cells at 200×g for 5 minutes.

Applicants aspirated the media, and resuspended the cells in 200 ul of FACS media.

Cells are filtered through a 35 um mesh filter into labeled FACS tubes. Applicants recommend using the BD Falcon 12×75 mm Tube with Cell Strainer cap. Place cells on ice until sorting.

Applicants sorted single cells into 96-well plates prepared from step 55. Applicants recommend that in one single designated well on each plate, sort 100 cells as a positive control.

NOTE. The remainder of the cells may be kept and used for genotyping at the population level to gauge overall modification efficiency.

Applicants returned cells into the incubator and allowed them to expand for 2-3 weeks. 100 ul of warm D10 medium is added 5 d post sorting. Change 100 ul of medium every 3-5 d as necessary.

Colonies are inspected for "clonal" appearance 1 week post sorting: rounded colonies radiating from a central point. Mark off wells that are empty or may have been seeded with doublets or multiplets.

When cells are more than 60% confluent, Applicants prepared a set of replica plates for passaging. 100 ul of D10 medium is added to each well in the replica plates. Applicants dissociated cells directly by pipetting up and down vigorously 20 times. 20% of the resuspended volume was plated into the prepared replica plates to keep the clonal lines. Change the medium every 2-3 d thereafter and passage accordingly.

Use the remainder 80% of cells for DNA isolation and genotyping.

Optional: Isolation of Clonal Cell Lines by Dilution. Timing•2-3 h Hands-on; 2-3 Weeks Expansion Applicants dissociated cells from 24-well plates as described above. Make sure to dissociate to single cells. A cell strainer can be used to prevent clumping of cells.

The number of cells are counted in each condition. Serially dilute each condition in D10 medium to a final concentration of 0.5 cells per 100 ul. For each 96 well plate, Applicants recommend diluting to a final count of 60 cells in 12 ml of D10. Accurate count of cell number is recommended for appropriate clonal dilution. Cells may be recounted at an intermediate serial dilution stage to ensure accuracy.

Multichannel pipette was used to pipette 100 ul of diluted cells to each well of a 96 well plate.

NOTE. The remainder of the cells may be kept and used for genotyping at the population level to gauge overall modification efficiency.

Applicants inspected colonies for "clonal" appearance ~1 week post plating: rounded colonies radiating from a central point. Mark off wells that may have seeded with doublets or multiplets.

Applicants returned cells to the incubator and allowed them to expand for 2-3 weeks. Re-feed cells as needed as detailed in previous section.

SURVEYOR Assay for CRISPR Cleavage Efficiency. Timing•5-6 h

Before assaying cleavage efficiency of transfected cells, Applicants recommend testing each new SURVEYOR primer on negative (untransfected) control samples through the step of SURVEYOR nuclease digestion using the protocol described below. Occasionally, even single-band clean SURVEYOR PCR products can yield non-specific SURVEYOR nuclease cleavage bands and potentially interfere with accurate indel analysis.

Harvest cells for DNA. Dissociate cells and spin down at 200×g for 5 m. NOTE. Replica plate at this stage as needed to keep transfected cell lines.

Aspirate the supernatant completely.

Applicants used QuickExtract DNA extraction solution according to the manufacturer's instructions. Applicants typically used 50 ul of the solution for each well of a 24 well plate and 10 ul for a 96 well plate.

Applicants normalized extracted DNA to a final concentration of 100-200 ng/ul with ddH2O. Pause point: Extracted DNA may be stored at −20° C. for several months.

Set up the SURVEYOR PCR. Master mix the following using SURVEYOR primers provided by Applicants online/computer algorithm tool:

| Component: | Amount (ul) | Final concentration |
|---|---|---|
| Herculase II PCR buffer, 5X | 10 | 1X |
| dNTP, 100 mM (25 mM each) | 1 | 1 mM |
| SURVEYOR Fwd primer (10 uM) | 1 | 0.2 uM |
| SURVEYOR Rev primer (10 uM) | 1 | 0.2 uM |
| Herculase II Fusion polymerase | 1 | |
| $MgCl_2$ (25 mM) | 2 | 1 mM |
| Distilled water | 33 | |
| Total | 49 (for each reaction) | |

Applicants added 100-200 ng of normalized genomic DNA template from step 74 for each reaction.

PCR reaction was performed using the following cycling conditions, for no more than 30 amplification cycles:

| Cycle number | Denature | Anneal | Extend |
|---|---|---|---|
| 1 | 95° C., 2 min | | |
| 2-31 | 95° C., 20 s | 60° C., 20 s | 72° C., 30 s |
| 32 | | | 72° C., 3 min |

Applicants ran 2-5 ul of PCR product on a 1% gel to check for single-band product. Although these PCR conditions are designed to work with most pairs of SURVEYOR primers, some primers may need additional optimization by adjusting the template concentration, $MgCl_2$ concentration, and/or the annealing temperature.

Applicants purified the PCR reactions using the QIA-Quick PCR purification kit and normalized eluant to 20 ng/ul. Pause point: Purified PCR product may be stored at −20° C.

DNA heteroduplex formation. The annealing reaction was set up as follows:

| | |
|---|---|
| Taq PCR buffer, 10X | 2 ul |
| Normalized DNA (20 ng/ul) | 18 ul |
| Total volume | 20 ul |

81| Anneal the reaction using the following conditions:

| Cycle number | Condition |
|---|---|
| 1 | 95° C., 10 mn |
| 2 | 95° C.-85° C., −2° C./s |
| 3 | 85° C., 1 min |
| 4 | 85° C.-75° C., −0.3° C./s |
| 5 | 75° C., 1 min |
| 6 | 75° C.-65° C., −0.3° C./s |
| 7 | 65° C., 1 min |
| 8 | 65° C.-55° C., −0.3° C./s |
| 9 | 55° C., 1 min |
| 10 | 55° C.-45° C., −0.3° C./s |
| 11 | 45° C., 1 min |
| 12 | 45° C.-35° C., −0.3° C./s |
| 13 | 35° C., 1 min |
| 14 | 35° C.-25° C., −0.3° C./s |
| 15 | 25° C., 1 min |

SURVEYOR nuclease S digestion. Applicants prepared master-mix and added the following components on ice to annealed heteroduplexes from step 81 for a total final volume of 25 ul:

| Component | Amount (ul) | Final Concentration |
|---|---|---|
| $MgCl_2$ solution, 0.15M | 2.5 | 15 mM |
| $ddH_2O$ | 0.5 | |
| SURVEYOR nuclease S | 1 | 1X |
| SURVEYOR enhancer S | 1 | 1X |
| Total | 5 | |

Vortex well and spin down. Incubate the reaction at 42° C. for 1 h.

Optional: 2 ul of the Stop Solution from the SURVEYOR kit may be added. Pause point. The digested product may be stored at −20° C. for analysis at a later time.

Visualize the SURVEYOR reaction. SURVEYOR nuclease digestion products may be visualized on a 2% agarose gel. For better resolution, products may be run on a 4-20% gradient Polyacrylamide TBE gel. Applicants loaded 10 ul of product with the recommended loading buffer and ran the gel according to manufacturer's instructions. Typically, Applicants run until the bromophenol blue dye has migrated to the bottom of the gel. Include DNA ladder and negative controls on the same gel.

Applicants stained the gel with 1×SYBR Gold dye diluted in TBE. The gel was gently rocked for 15 m.

Applicants imaged the gel using a quantitative imaging system without overexposing the bands. The negative controls should have only one band corresponding to the size of the PCR product, but may have occasionally non-specific cleavage bands of other sizes. These will not interfere with analysis if they are different in size from target cleavage bands. The sum of target cleavage band sizes, provided by Applicants online/computer algorithm tool, should be equal to the size of the PCR product.

Estimate the cleavage intensity. Applicants quantified the integrated intensity of each band using ImageJ or other gel quantification software.

For each lane, Applicants calculated the fraction of the PCR product cleaved ($f_{cut}$) using the following formula: $f_{cut}$=(b+c)/(a+b+c), where a is the integrated intensity of the undigested PCR product and b and c are the integrated intensities of each cleavage product. Cleavage efficiency may be estimated using the following formula, based on the binomial probability distribution of duplex formation:

$$\text{indel } (\%)=100\times(1-\sqrt{(1-f_{cut})})$$

Sanger Sequencing for Assessing CRISPR Cleavage Efficiency. Timing•3 d

Initial steps are identical to Steps 71-79 of the SURVEYOR assay. Note: SURVEYOR primers may be used for Sanger sequencing if appropriate restriction sites are appended to the Forward and Reverse primers. For cloning into the recommended pUC19 backbone, EcoRI may be used for the Fwd primer and HindIII for the Rev primer.

Amplicon digestion. Set up the digestion reaction as follows:

| Component | Amount (ul) |
|---|---|
| Fast Digest buffer, 10X | 3 |
| FastDigest EcoRI | 1 |
| FastDigest HindIII | 1 |
| Normalized DNA (20 ng/ul) | 10 |
| $ddH_2O$ | 15 |
| Total volume | 30 |

pUC19 backbone digestion. Set up the digestion reaction as follows:

| Component | Amount (ul) |
|---|---|
| Fast Digest buffer, 10X | 3 |
| FastDigest EcoRI | 1 |
| FastDigest HindIII | 1 |
| FastAP Alkaline Phosphatase | 1 |
| pUC19 vector (200 ng/ul) | 5 |
| $ddH_2O$ | 20 |
| Total volume | 30 |

Applicants purified the digestion reactions using the QIAQuick PCR purification kit. Pause point: Purified PCR product may be stored at −20° C.

Applicants ligated the digested pUC19 backbone and Sanger amplicons at a 1:3 vector:insert ratio as follows:

| Component | Amount (ul) |
|---|---|
| Digested pUC19 | x (50 ng) |
| Digested insert | x (1:3 vector:insert molar ratio) |
| T7 ligase | 1 |
| 2X Rapid Ligation Buffer | 10 |
| $ddH_2O$ | x |
| Total volume | 20 |

Transformation. Applicants transformed the PlasmidSafe-treated plasmid into a competent *E. coli* strain, according to the protocol supplied with the cells. Applicants recommend Stbl3 for quick transformation. Briefly, 5 ul of the product from step 95 is added into 20 ul of ice-cold chemically competent Stbl3 cells, incubated on ice for 10 m, heat shocked at 42° C. for 30 s, returned immediately to ice for 2 m, 100 ul of SOC medium is added, and plated onto an LB plate containing 100 ug/ml ampicillin. This is incubated overnight at 37° C.

Day 2: Applicants inspected plates for colony growth. Typically, there are no colonies on the negative control plates (ligation of EcoRI-HindIII digested pUC19 only, no Sanger amplicon insert), and tens to hundreds of colonies on the pUC19-Sanger amplicon cloning plates.

Day 3: Applicants isolated plasmid DNA from overnight cultures using a QIAprep Spin miniprep kit according to the manufacturer's instructions.

Sanger sequencing. Applicants verified the sequence of each colony by sequencing from the pUC19 backbone using the pUC19-For primer. Applicants referenced the sequencing results against the expected genomic DNA sequence to check for the presence of Cas9-induced NHEJ mutations. % editing efficiency=(# modified clones)/(# total clones). It is important to pick a reasonable number of clones (>24) to generate accurate modification efficiencies.

Genotyping for Microdeletion. Timing•2-3 d Hands on; 2-3 Weeks Expansion

Cells were transfected as described above with a pair of sgRNAs targeting the region to be deleted.

24 h post-transfection, clonal lines are isolated by FACS or serial dilution as described above.

Cells are expanded for 2-3 weeks.

Applicants harvested DNA from clonal lines as described above using 10 ul QuickExtract solution and normalized genomic DNA with $ddH_2O$ to a final concentration of 50-100 ng/ul.

PCR Amplify the modified region. The PCR reaction is set up as follows:

| Component: | Amount (ul) | Final concentration |
|---|---|---|
| Herculase II PCR buffer, 5X | 10 | 1X |
| dNTP, 100 mM (25 mM each) | 1 | 1 mM |
| Out Fwd primer (10 uM) | 1 | 0.2 uM |
| Out Rev primer (10 uM) | 1 | 0.2 uM |
| Herculase II Fusion polymerase | 1 | |
| MgCl2 (25 mM) | 2 | 1 mM |
| $ddH_2O$ | 32 | |
| Total | 48 (for each reaction) | |

Note: if deletion size is more than 1 kb, set up a parallel set of PCR reactions with In-Fwd and In-Rev primers to screen for the presence of the wt allele.

To screen for inversions, a PCR reaction is set up as follows:

| Component: | Amount (ul) | Final concentration |
|---|---|---|
| Herculase II PCR buffer, 5X | 10 | 1X |
| dNTP, 100 mM (25 mM each) | 1 | 1 mM |
| Out Fwd or Out-Rev primer (10 uM) | 1 | 0.2 uM |
| In Fwd or In-Rev primer (10 uM) | 1 | 0.2 uM |
| Herculase II Fusion polymerase | 1 | |
| $MgCl_2$ (25 mM) | 2 | 1 mM |
| $ddH_2O$ | 32 | |
| Total | 48 (for each reaction) | |

Note: primers are paired either as Out-Fwd+In Fwd, or Out-Rev+In-Rev.

Applicants added 100-200 ng of normalized genomic DNA template from step 103 for each reaction.

PCR reaction was performed using the following cycling conditions:

| Cycle number | Denature | Anneal | Extend |
|---|---|---|---|
| 1 | 95° C., 2 min | | |
| 2-31 | 95° C., 20 s | 60° C., 20 s | 72° C., 30 s |
| 32 | | | 72° C., 3 m |

Applicants run 2-5 ul of PCR product on a 1-2% gel to check for product. Although these PCR conditions are designed to work with most primers, some primers may need additional optimization by adjusting the template concentration, $MgCl_2$ concentration, and/or the annealing temperature.

Genotyping for Targeted Modifications Via HDR. Timing•2-3 d, 2-3 h Hands on

Applicants harvested DNA as described above using QuickExtract solution and normalized genomic DNA with TE to a final concentration of 100-200 ng/ul.

PCR Amplify the modified region. The PCR reaction is set up as follows:

| Component: | Amount (ul) | Final concentration |
|---|---|---|
| Herculase II PCR buffer, 5X | 10 | 1X |
| dNTP, 100 mM (25 mM each) | 1 | 1 mM |
| HDR Fwd primer (10 uM) | 1 | 0.2 uM |

-continued

| Component: | Amount (ul) | Final concentration |
|---|---|---|
| HDR Rev primer (10 uM) | 1 | 0.2 uM |
| Herculase II Fusion polymerase | 1 | |
| $MgCl_2$ (25 mM) | 2 | 1 mM |
| $ddH_2O$ | 33 | |
| Total | 49 (for each reaction) | |

Applicants added 100-200 ng of genomic DNA template from step 109 for each reaction and run the following program.

| Cycle number | Denature | Anneal | Extend |
|---|---|---|---|
| 1 | 95° C., 2 min | | |
| 2-31 | 95° C., 20 s | 60° C., 20 s | 72° C., 30-60 s per kb |
| 32 | | | 72° C., 3 min |

Applicants ran 5 ul of PCR product on a 0.8-1% gel to check for single-band product. Primers may need additional optimization by adjusting the template concentration, $MgCl_2$ concentration, and/or the annealing temperature.

Applicants purified the PCR reactions using the QIAQuick PCR purification kit.

In the HDR example, a HindIII restriction site is inserted into the EMX1 gene. These are detected by a restriction digest of the PCR amplicon:

| Component | Amount (ul) |
|---|---|
| Purified PCR amplicon (200-300 ng) | x |
| F.D. buffer, Green | 1 |
| HindIII | 0.5 |
| ddH2O | x |
| Total | 10 |

i. The DNA is digested for 10 m at 37° C.:

ii. Applicants ran 10 ul of the digested product with loading dye on a 4-20% gradient polyacrylamide TBE gel until the xylene cyanol band had migrated to the bottom of the gel.

iii. Applicants stained the gel with 1×SYBR Gold dye while rocking for 15 m.

iv. The cleavage products are imaged and quantified as described above in the SURVEYOR assay section. HDR efficiency is estimated by the formula: (b+c)/(a+b+c), where a is the integrated intensity for the undigested HDR PCR product, and b and c are the integrated intensities for the HindIII-cut fragments.

Alternatively, purified PCR amplicons from step 113 may be cloned and genotyped using Sanger sequencing or NGS.

Deep Sequencing and Off-Target Analysis•Timing 1-2 d

The online CRISPR target design tool generates candidate genomic off-target sites for each identified target site. Off-target analysis at these sites can be performed by SURVEYOR nuclease assay, Sanger sequencing, or next-generation deep sequencing. Given the likelihood of low or undetectable modification rates at many of these sites, Applicants recommend deep sequencing with the Illumina Miseq platform for high sensitivity and accuracy. Protocols will vary with sequencing platform; here, Applicants briefly describe a fusion PCR method for attaching sequencing adapters.

Design deep sequencing primers. Next-generation sequencing (NGS) primers are designed for shorter amplicons, typically in the 100-200 bp size range. Primers may be manually designed using NCBI Primer-Blast or generated with online CRISPR target design tools (website at genome-engineering.org/tools).

Harvest genomic DNA from Cas9-targeted cells. Normalize QuickExtract genomic DNA to 100-200 ng/ul with ddH2O.

Initial library preparation PCR. Using the NGS primers from step 116, prepare the initial library preparation PCR

| Component: | Amount (ul) | Final concentration |
|---|---|---|
| Herculase II PCR buffer, 5X | 10 | 1X |
| dNTP, 100 mM (25 mM each) | 1 | 1 mM |
| NGS Fwd primer (10 uM) | 1 | 0.2 uM |
| NGS Rev primer (10 uM) | 1 | 0.2 uM |
| Herculase II Fusion polymerase | 1 | |
| MgCl2 (25 mM) | 2 | 1 mM |
| ddH2O | 33 | |
| Total | 49 (for each reaction) | |

Add 100-200 ng of normalized genomic DNA template for each reaction.

Perform PCR reaction using the following cycling conditions, for no more than 20 amplification cycles:

| Cycle number | Denature | Anneal | Extend |
|---|---|---|---|
| 1 | 95° C., 2 min | | |
| 2-21 | 95° C., 20 s | 60° C., 20 s | 72° C., 15 s |
| 22 | | | 72° C., 3 min |

Run 2-5 ul of PCR product on a 1% gel to check for single-band product. As with all genomic DNA PCRs, NGS primers may require additional optimization by adjusting the template concentration, $MgCl_2$ concentration, and/or the annealing temperature.

Purify the PCR reactions using the QIAQuick PCR purification kit and normalize eluant to 20 ng/ul. Pause point: Purified PCR product may be stored at −20° C.

Nextera XT DNA Sample Preparation Kit. Following the manufacturer's protocol, generate Miseq sequencing-ready libraries with unique barcodes for each sample.

Analyze sequencing data. Off-target analysis may be performed through read alignment programs such as ClustalW, Geneious, or simple sequence analysis scripts.

Timing

Steps 1-2 Design and synthesis of sgRNA oligos and ssODNs: 1-5 d, variable depending on supplier Steps 3-5 Construction of CRISPR plasmid or PCR expression cassette: 2 h to 3 d Steps 6-53 Transfection into cell lines: 3 d (1 h hands-on time)

Steps 54-70 Optional derivation of clonal lines: 1-3 weeks, variable depending on cell type Steps 71-91 Functional validation of NHEJ via SURVEYOR: 5-6 h Steps 92-124 Genotyping via Sanger or next-gen deep sequencing: 2-3 d (3-4 h hands on time)

Addressing Situations Concerning Herein Examples

| Situation | Solution |
|---|---|
| No amplification of sgRNA | Titrate U6-template concentration |
| SURVEYOR or HDR PCR dirty or no amplification | Titrate MgCl2; normalize and titrate template concentration; annealing temp gradient; redesign primers |
| Unequal amplification of alleles in microdeletion PCRs | Set up separate PCRs to detect wildtype and deletion alleles; Redesign primers with similar sized amplicons |
| Colonies on negative control plate | Increase BbsI; increase Golden Gate reaction cycle number, cut PX330 separately with Antarctic Phosphate treatment |
| No sgRNA sequences or wrong sequences | Screen additional colonies |
| Low lipofectamine transfection efficiency | Check cell health and density; titrate DNA; add GFP transfection control |
| Low nucleofection transfection efficiency | Check cell health and density; titrate DNA; suspend to single cell |
| Clumps or no cells after FACS | Filter cells before FACS; dissociate to single cells; resuspend in appropriate density |
| Clumps or no cells in serial dilution | Recount cells; dissociate to single cells and filter through strainer; check serial dilution |
| High SURVEYOR background on negative sample | Redesign primers to prime from different locations |
| Dirty SURVEYOR result on gel | Purify PCR product; reduce input DNA; reduce 42° C. incubation to 30 m |
| No SURVEYOR cleavage | Purify and normalize PCR product; re-anneal with TaqB buffer; Redesign sgRNAs; sequence verify Cas9 on px330 backbone |
| Samples do not sink in TBE acrylamide gel | Supplement with MgCl2 to a final concentration of 15 mM or add loading buffer containing glycerol |

Discussion

Figures 30A, 30B, 30C:
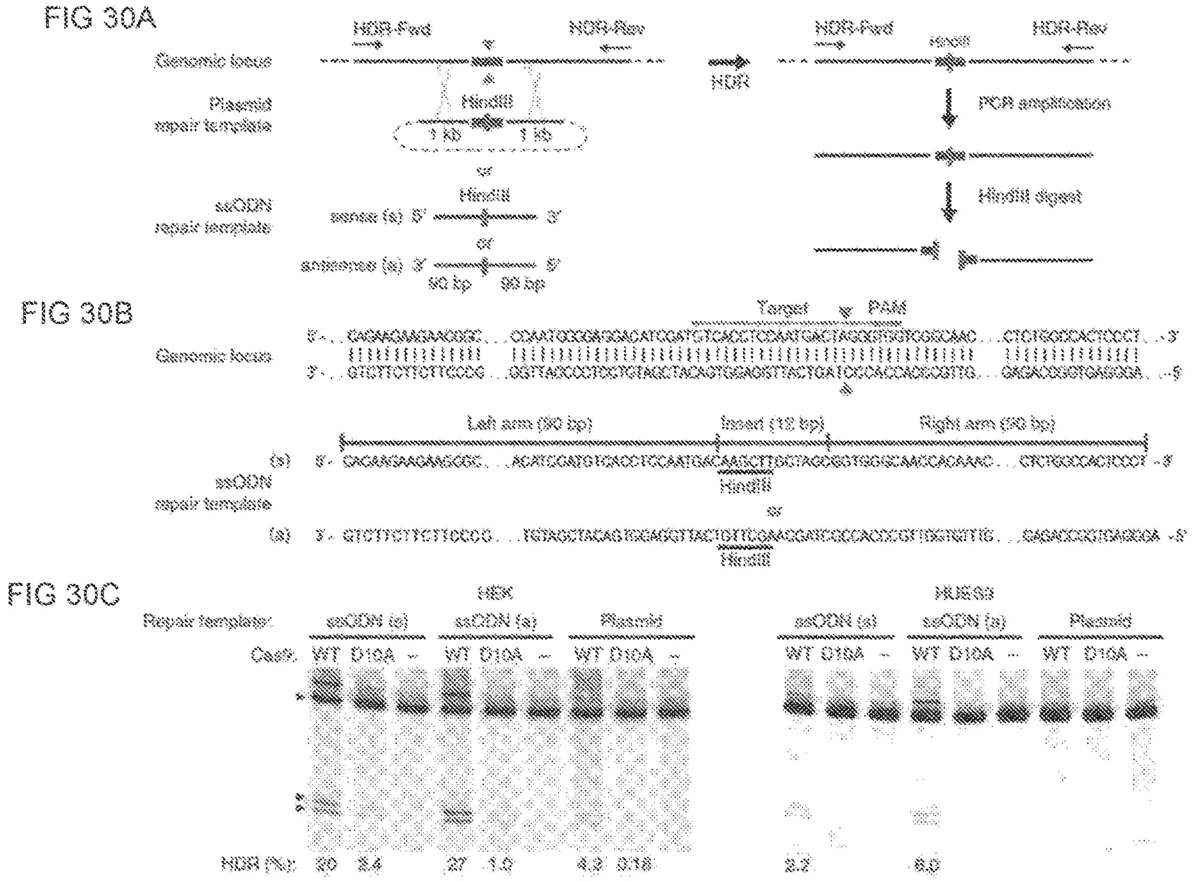
FIG. 30A-30C shows anticipated results for HDR in HEK and HUES9 cells. (a) Either a targeting plasmid or an ssODN (sense or antisense) with homology arms can be used to edit the sequence at a target genomic locus cleaved by Cas9. To assay the efficiency of HDR, we introduced a HindIII site into the target locus, which was PCR-amplified with primers that anneal outside of the region of homology. Digestion of the PCR product with HindIII reveals the occurrence of HDR events. (b) ssODNs, oriented in either the sense or the antisense (s or a) direction relative to the locus of interest, can be used in combination with Cas9 to achieve efficient HDR-mediated editing at the target locus. A minimal homology region of 40 bp, and preferably 90 bp, is recommended on either side of the modification. (c) Example of the effect of ssODNs on HDR in the EMX1 locus is shown using both wild-type Cas9 and Cas9 nickase (D10A). Each ssODN contains homology arms of 90 bp flanking a 12-bp insertion of two restriction sites.

CRISPR-Cas may be easily multiplexed to facilitate simultaneous modification of several genes and mediate chromosomal microdeletions at high efficiencies. Applicants used two sgRNAs to demonstrate simultaneous targeting of the human GRIN2B and DYRK1A loci at efficiencies of up to 68% in HEK293FT cells. Likewise, a pair of sgRNAs may be used to mediate microdeletions, such as excision of an exon, which can be genotyped by PCR on a clonal level. Note that the precise location of exon junctions can vary. Applicants also demonstrated the use of ssODNs and targeting vector to mediate HDR with both wildtype and nickase mutant of Cas9 in HEK 293FT and HUES9 cells (FIG. 30). Note that Applicants have not been able to detect HDR in HUES9 cells using the Cas9 nickase, which may be due to low efficiency or a potential difference in repair activities in HUES9 cells. Although these values are typical, there is some variability in the cleavage efficiency of a given sgRNA, and on rare occasions certain sgRNAs may not work for reasons yet unknown. Applicants recommend designing two sgRNAs for each locus, and testing their efficiencies in the intended cell type.

Example 31: NLSs

Cas9 Transcriptional Modulator: Applicants set out to turn the Cas9/gRNA CRISPR system into a generalized DNA binding system in which functions beyond DNA cleavage can be executed. For instance, by fusing functional domain(s) onto a catalytically inactive Cas9 Applicants have imparted novel functions, such as transcriptional activation/repression, methylation/demethylation, or chromatin modifications. To accomplish this goal Applicants made a catalytically inactive Cas9 mutant by changing two residues essential for nuclease activity, D10 and H840, to alanine. By mutating these two residues the nuclease activity of Cas9 is abolished while maintaining the ability to bind target DNA. The functional domains Applicants decided to focus on to test Applicants' hypothesis are the transcriptional activator VP64 and the transcriptional repressors SID and KRAB.

Cas9 Nuclear localization: Applicants hypothesized that the most effective Cas9 transcriptional modulator would be strongly localized to the nucleus where it would have its greatest influence on transcription. Moreover, any residual Cas9 in the cytoplasm could have unwanted effects. Applicants determined that wild-type Cas9 does not localize into the nucleus without including multiple nuclear localization signals (NLSs) (although a CRISPR system need not have one or more NLSs but advantageously has at least one or more NLS(s)). Because multiple NLS sequences were required it was reasoned that it is difficult to get Cas9 into the nucleus and any additional domain that is fused to Cas9 could disrupt the nuclear localization. Therefore, Applicants made four Cas9-VP64-GFP fusion constructs with different NLS sequences (pxRP02-pLenti2-EF1a-NLS-hSpCsn1(10A,840A)-NLS-VP64-EGFP, pXRP04-pLenti2-EF1a-NLS-hSpCsn1(10A,840A)-NLS-VP64-2A-EGFP-NLS, pxRP06-pLenti2-EF1a-NLS-EGFP-VP64-NLS-hSpCsn1(10A,840A)-NLS, pxRP08-pLenti2-EF1a-NLS-VP64-NLS-hSpCsn1(10A,840A)-NLS-VP64-EGFP-NLS). These constructs were cloned into a lenti backbone under the expression of the human EF1a promoter. The WPRE element was also added for more robust protein expression. Each construct was transfected into HEK 293FT cells using Lipofectame 2000 and imaged 24 hours post-transfection. The best nuclear localization is obtained when the fusion proteins have NLS sequences on both the N- and C-term of the fusion protein. The highest observed nuclear localization occurred in the construct with four NLS elements.

To more robustly understand the influence of NLS elements on Cas9 Applicants made 16 Cas9-GFP fusions by adding the same alpha importin NLS sequence on either the N- or C-term looking at zero to three tandem repeats. Each construct was transfected into HEK 293FT cells using Lipofectame 2000 and imaged 24 hours post-transfection. Notably, the number of NLS elements does not directly correlate with the extent of nuclear localization. Adding an NLS on the C-term has a greater influence on nuclear localization than adding on the N-term.

Cas9 Transcriptional Activator: Applicants functionally tested the Cas9-VP64 protein by targeting the Sox2 locus and quantifying transcriptional activation by RT-qPCR. Eight DNA target sites were chosen to span the promoter of Sox2. Each construct was transfected into HEK 293FT cells using Lipofectame 2000 and 72 hours post-transfection total RNA was extracted from the cells. 1 ug of RNA was reverse transcribed into cDNA (qScript Supermix) in a 40 ul reaction. 2 ul of reaction product was added into a single 20 ul TaqMan assay qPCR reaction. Each experiment was performed in biological and technical triplicates. No RT control and no template control reactions showed no amplification. Constructs that do not show strong nuclear localization, pXRP02 and pXRP04, result in no activation. For the construct that did show strong nuclear localization, pXRP08, moderate activation was observed. Statistically significant activation was observed in the case of guide RNAs Sox2.4 and Sox2.5.

Example 32: In Vivo Mouse Data

Material and Reagents

Herculase II fusion polymerase (Agilent Technologies, cat. no. 600679)
10× NEBuffer 4 (NEB, cat. No. B7004S)
BsaI HF (NEB, cat. No. R3535S)
T7 DNA ligase (Enzymatics, cat. no. L602L)
Fast Digest buffer, 10× (ThermoScientific, cat. No. B64)
FastDigest NotI (ThermoScientific, cat. No. FD0594)
FastAP Alkaline Phosphatase (ThermoScientific, cat. No. EF0651)
Lipofectamine2000 (Life Technologies, cat. No. 11668-019)
Trypsin (Life Technologies, cat. No. 15400054)
Forceps #4 (Sigma, cat. No. Z168777-1EA)
Forceps #5 (Sigma, cat. No. F6521-1EA)
10× Hank's Balanced Salt Solution (Sigma, cat. No. H4641-500ML)
Penicillin/Streptomycin solution (Life Technologies, cat. No. P4333)
Neurobasal (Life Technologies, cat. No. 21103049)
B27 Supplement (Life Technologies, cat. No. 17504044)
L-glutamine (Life Technologies, cat. No. 25030081)
Glutamate (Sigma, cat. No. RES5063 G-A7)
β-mercaptoethanol (Sigma, cat. No. M6250-100ML)
HA rabbit antibody (Cell Signaling, cat. No. 3724S)
LIVE/DEAD® Cell Imaging Kit (Life Technologies, cat. No. R37601)
30 G World Precision Instrument syringe (World Precision Instruments, cat. No. NANOFIL)
Stereotaxic apparatus (Kopf Instruments)
UltraMicroPump3 (World Precision Instruments, cat. No. UMP3-4)
Sucrose (Sigma, cat. No. S7903)
Calcium chloride (Sigma, cat. No. C1016)
Magnesium acetate (Sigma, cat. No. M0631)
Tris-HCl (Sigma, cat. no T5941)
EDTA (Sigma, cat. No. E6758)
NP-40 (Sigma, cat. No. NP40)
Phenylmethanesulfonyl fluoride (Sigma, cat. No. 78830)
Magnesium chloride (Sigma, cat. No. M8266)
Potassium chloride (Sigma, cat. No. P9333)
β-glycerophosphate (Sigma, cat. No. G9422)
Glycerol (Sigma, cat. No. G9012)
Vybrant® DyeCycle™ Ruby Stain (Life technologies, cat. No. S4942)
FACS Aria Flu-act-cell sorter (Koch Institute of MIT, Cambridge US)
DNAeasy Blood & Tissue Kit (Qiagen, cat. No. 69504)

Procedure

Constructing gRNA Multiplexes for Using In Vivo in the Brain

Figure 33:
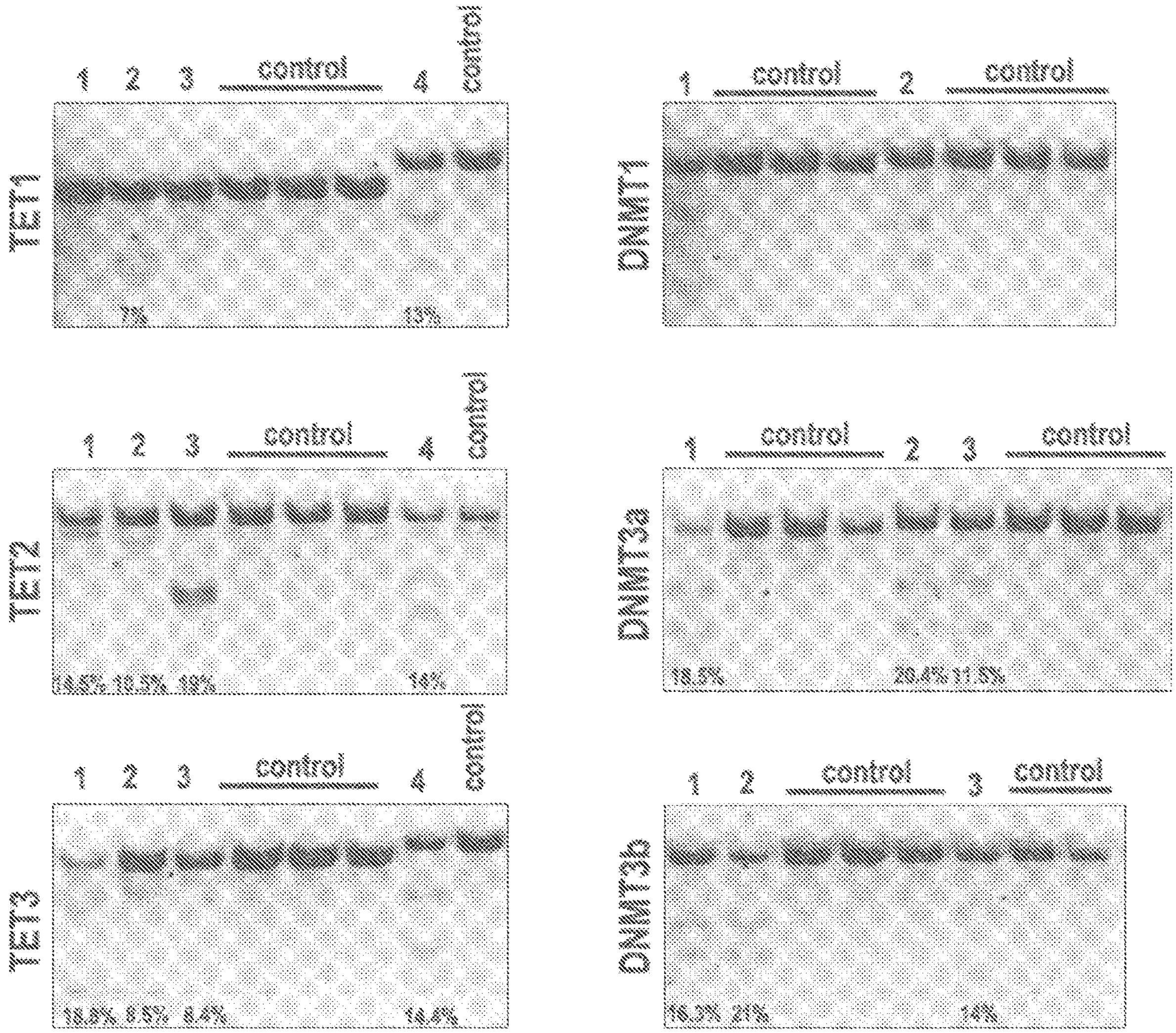
FIG. 33 shows a screen for efficient SpCas9 mediated targeting of Tet1-3 and Dnmt1, 3a and 3b gene loci. Surveyor assay on DNA from transfected N2A cells demonstrates efficient DNA cleavage by using different gRNAs.
Figure 34:
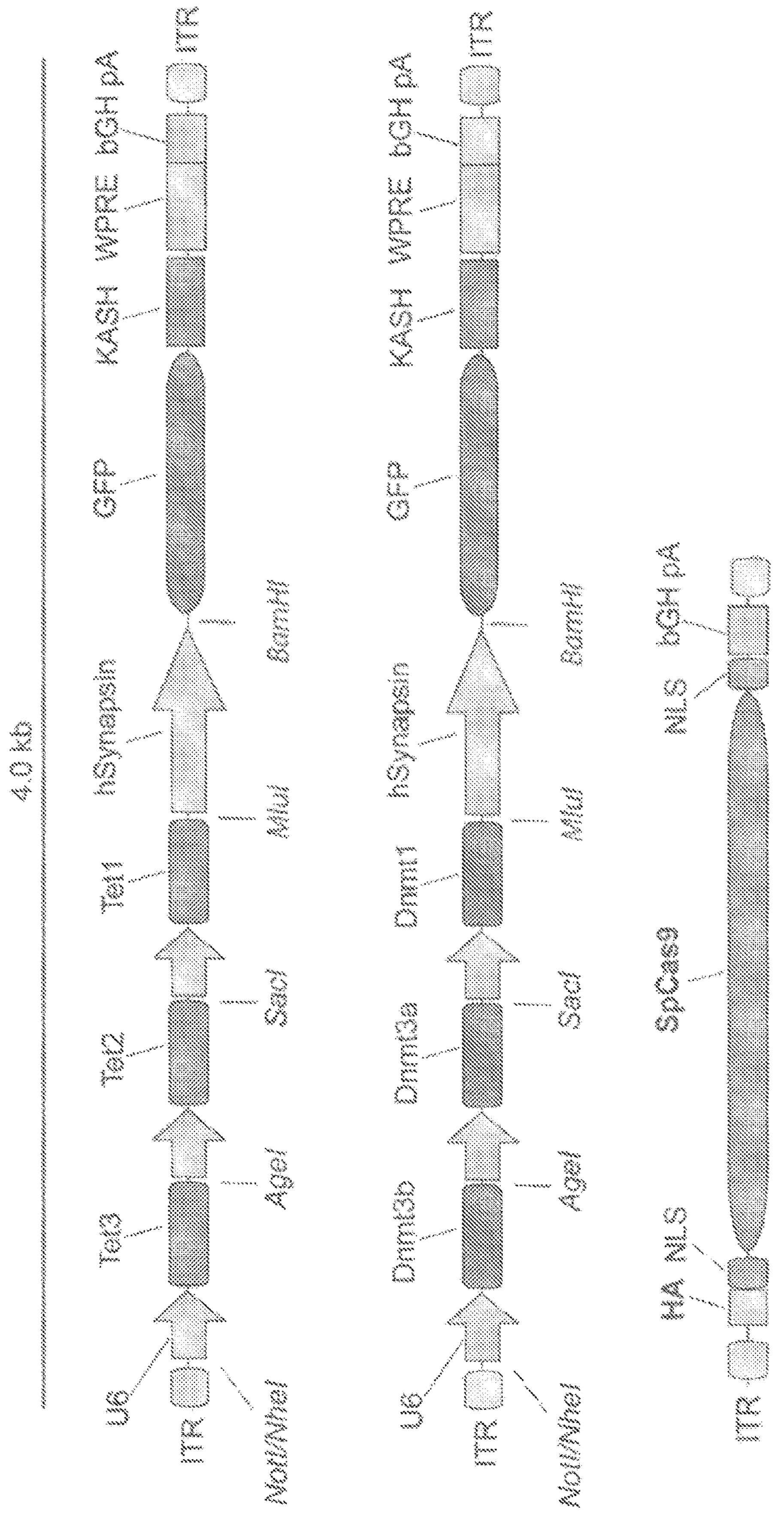
FIG. 34 shows a strategy of multiplex genome targeting using a 2-vector system in an AAV1/2 delivery system. Tet1-3 and Dnmt1, 3a and 3b gRNA under the control of the U6 promoter. GFP-KASH under the control of the human synapsin promoter. Restriction sides shows simple gRNA replacement strategy by subcloning. HA-tagged SpCas9 flanked by two nuclear localization signals (NLS) is shown. Both vectors are delivered into the brain by AAV1/2 virus in a 1:1 ratio.

Applicants designed and PCR amplified single gRNAs targeting mouse TET and DNMT family members (as described herein) Targeting efficiency was assessed in N2a cell line (FIG. 33). To obtain simultaneous modification of several genes in vivo, efficient gRNA was multiplexed in AAV-packaging vector (FIG. 34). To facilitate further analysis of system efficiency applicants added to the system expression cassette consistent of GFP-KASH domain fusion protein under control of human Synapsin I promoter (FIG. 34). This modification allows for further analysis of system efficiency in neuronal population (more detail procedure in section Sorting nuclei and in vivo results). All 4 parts of the system were PCR amplified using Herculase II Fusion polymerase using following primers:

```
1st UG Fw:
                                        (SEQ ID NO: 196)
gagggtctcgtccttgcggccgcgctagcgagggcctatttcccatgat

tc

1st gRNA Rv:
                                        (SEQ ID NO: 197)
ctcggtctcggtAAAAAAgcaccgactcggtgccactttttcaagttga

taacggactagccttattttaacttgctaTTTCtagctctaaaacNNNN

NNNNNNNNNNNNNNNNGGTGTTTCGTCCTTTCCAC

2nd UG Fw:
                                        (SEQ ID NO: 198)
gagggtctcTTTaccggtgagggcctatttcccatgattcc

2nd gRNA Rv:
                                        (SEQ ID NO: 199)
ctcggtctcctcAAAAAAgcaccgactcggtgccactttttcaagttga

taacggactagc

cttattttaacttgctaTTTCtagctctaaaacNNNNNNNNNNNNNNNN

NNNNGGTGTTTCGTCCTTTCCAC

3rd UG Fw:
                                        (SEQ ID NO: 200)
gagggtctcTTTgagctcgagggcctatttcccatgattc

3rd gRNA Rv:
                                        (SEQ ID NO: 201)
ctcggtctcgcgtAAAAAAgcaccgactcggtgccactttttcaagttg

ataacggactag

ccttattttaacttgctaTTTCtagctctaaaacNNNNNNNNNNNNNNN

NNNNNGGTGTTTCGTCCTTTCCA
```

-continued hSyn GFP-kash Fw:

(SEQ ID NO: 202)

gagggtctcTTacgcgtgtgtctagac hSyn GFP-kash Rv:

(SEQ ID NO: 203)

ctcggtctcAaggaCAGGGAAGGGAGCAGTGGTTCACGCCTGTAATCCC

AGCAATTTGGGA

GGCCAAGGTGGGTAGATCACCTGAGATTAGGAGTTGC (NNNNNNNNNNNNNNNNNNNN is a reverse compliment targeted genomic sequence)

Applicants used Golden Gate strategy to assemble all parts (1:1 molecular ratio) of the system in a single step reaction:

| | |
|---|---|
| 1st U6_gRNA | 18 ng |
| 2nd U6_gRNA | 18 ng |
| 3rd U6_gRNA | 18 ng |
| Syn_GFP-kash | 100 ng |
| 10x NEBuffer 4 | 1.0 μl |
| 10x BSA | 1.0 μl |
| 10 m MATP | 1.0 μl |
| BsaI HF | 0.75 μl |
| T7 ligase | 0.25 μl |
| $ddH_2O$ | 10 μl |

| Cycle number | Condition |
|---|---|
| 1-50 | 37° C. for 5 m, 21° C. for 5 m |

Golden Gate reaction product was PCR amplified using Herculase II fusion polymerase and following primers:

(SEQ ID NO: 204)

Fw 5' cctgtccttgcggccgcgctagcgagggcc (SEQ ID NO: 205)

Rv 5' cacgcggccgcaaggacagggaagggagcag

PCR product was cloned into AAV backbone, between ITR sequences using NotI restriction sites:

PCR Product Digestion:

| | |
|---|---|
| Fast Digest buffer, 10X | 3 μl |
| FastDigest NotI | 1 μl |
| DNA | 1 μg |
| $ddH_2O$ | up to 30 μl |

AAV Backbone Digestion:

| | |
|---|---|
| Fast Digest buffer, 10X | 3 μl |
| FastDigest NotI | 1 μl |
| FastAP Alkaline Phosphatase | 1 μl |
| AAV backbone | 1 μg |
| $ddH_2O$ | up to 30 μl |

After 20 min incubation in 37° C. samples were purified using QIAQuick PCR purification kit. Standardized samples were ligated at a 1:3 vector:insert ratio as follows:

| | |
|---|---|
| Digested pUC19 | 50 ng |
| Digested insert | 1:3 vector:insert molar ratio |
| T7 ligase | 1 μl |
| 2X Rapid Ligation Buffer | 5 μl |
| $ddH_2O$ | up to 10 μl |

After transformation of bacteria with ligation reaction product, applicants confirmed obtained clones with Sanger sequencing.

Figure 35:
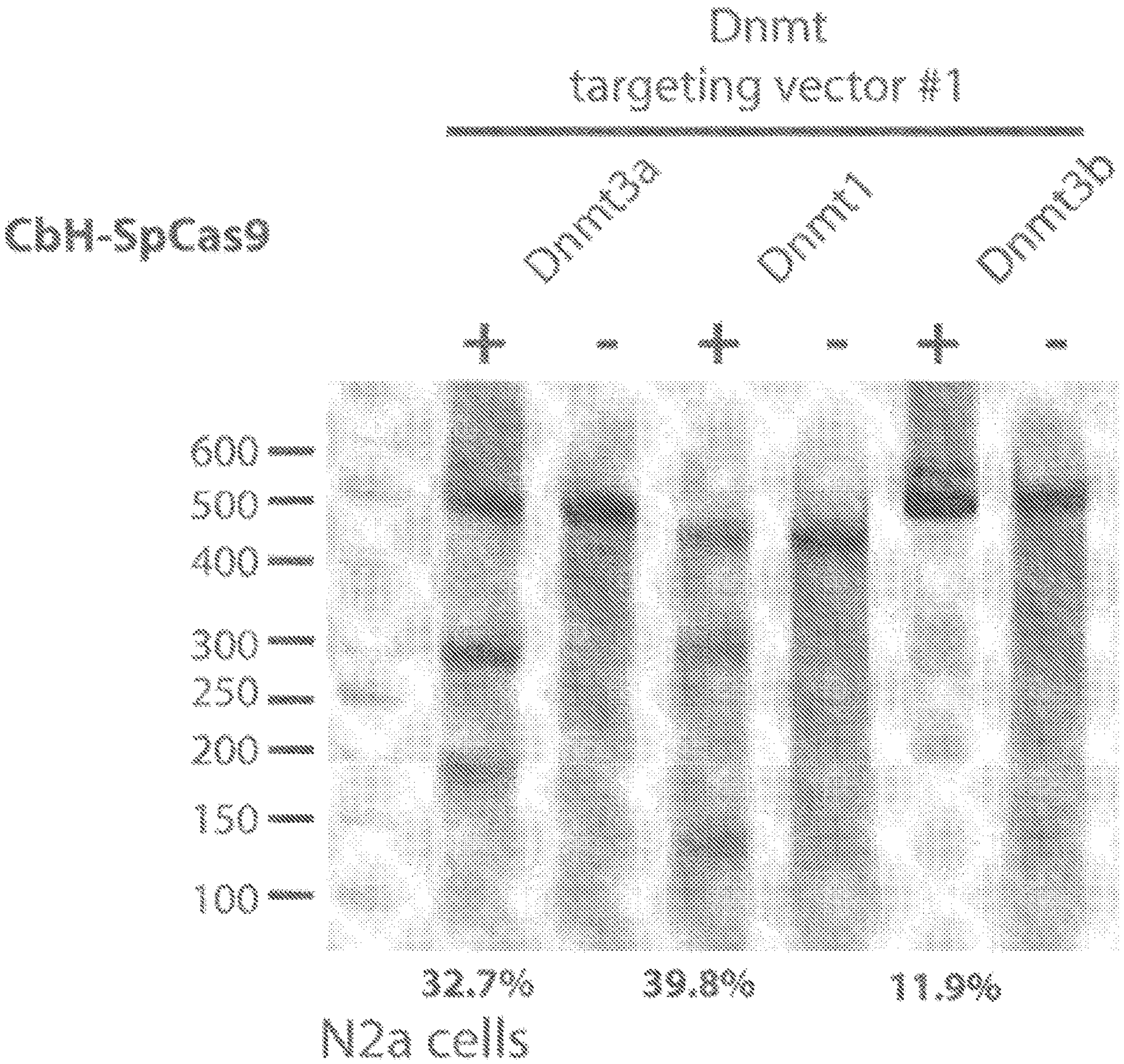
FIG. 35 shows verification of multiplex DNMT targeting vector #1 functionality using Surveyor assay. N2A cells were co-transfected with the DNMT targeting vector #1 (+) and the SpCas9 encoding vector for testing SpCas9 mediated cleavage of DNMTs genes family loci. gRNA only (−) is negative control. Cells were harvested for DNA purification and downstream processing 48 h after transfection.
Figure 36:
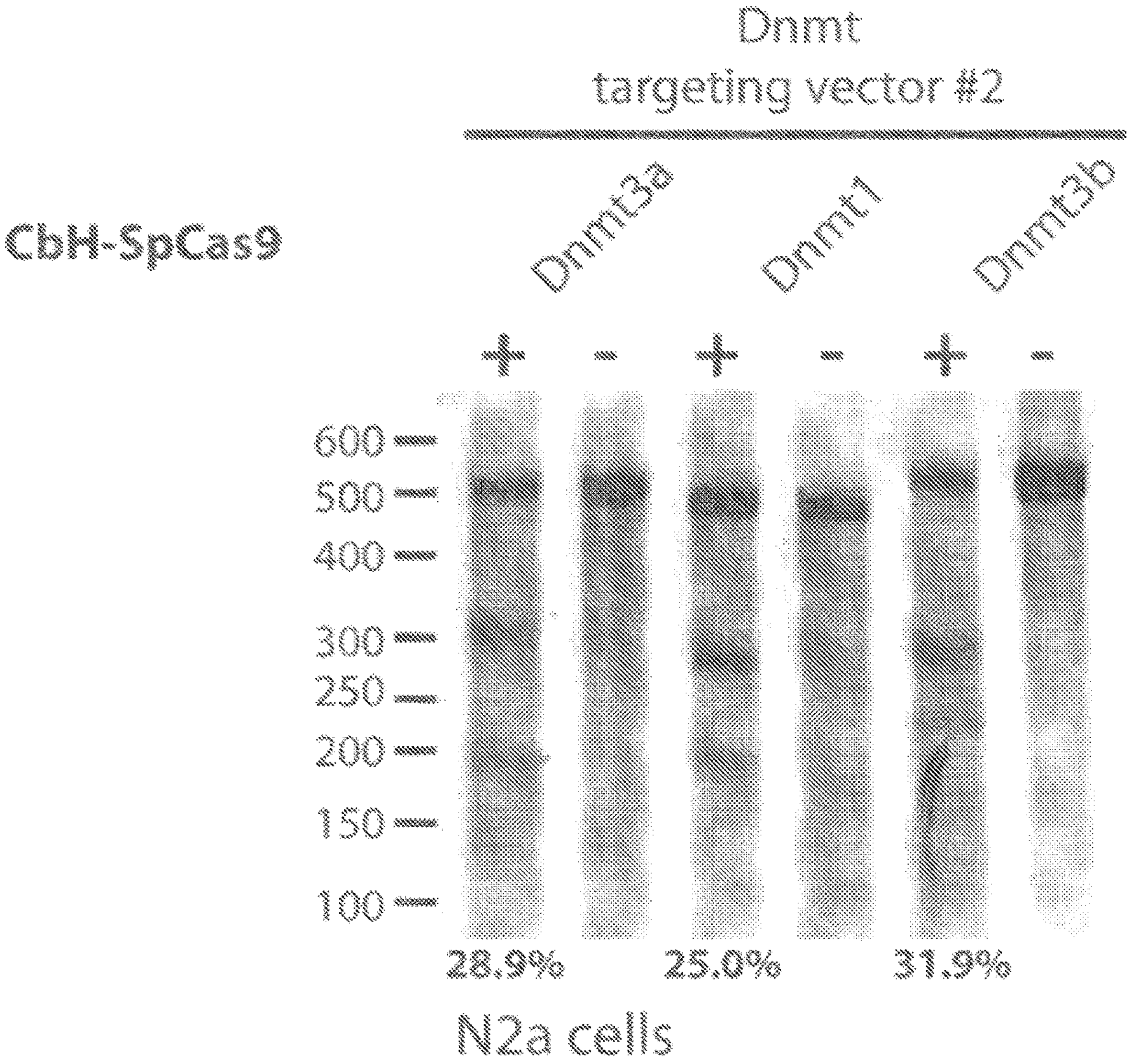
FIG. 36 shows verification of multiplex DNMT targeting vector #2 functionality using Surveyor assay. N2A cells were co-transfected with the DNMT targeting vector #1 (+) and the SpCas9 encoding vector for testing SpCas9 mediated cleavage of DNMTs genes family loci. gRNA only (−) is negative control. Cells were harvested for DNA purification and downstream processing 48 h after transfection.

Positive DNA clones were tested in N2a cells after co-transfection with Cas9 construct (FIGS. 35 and 36).

Design of New Cas9 Constructs for AAV Delivery

Figure 37:
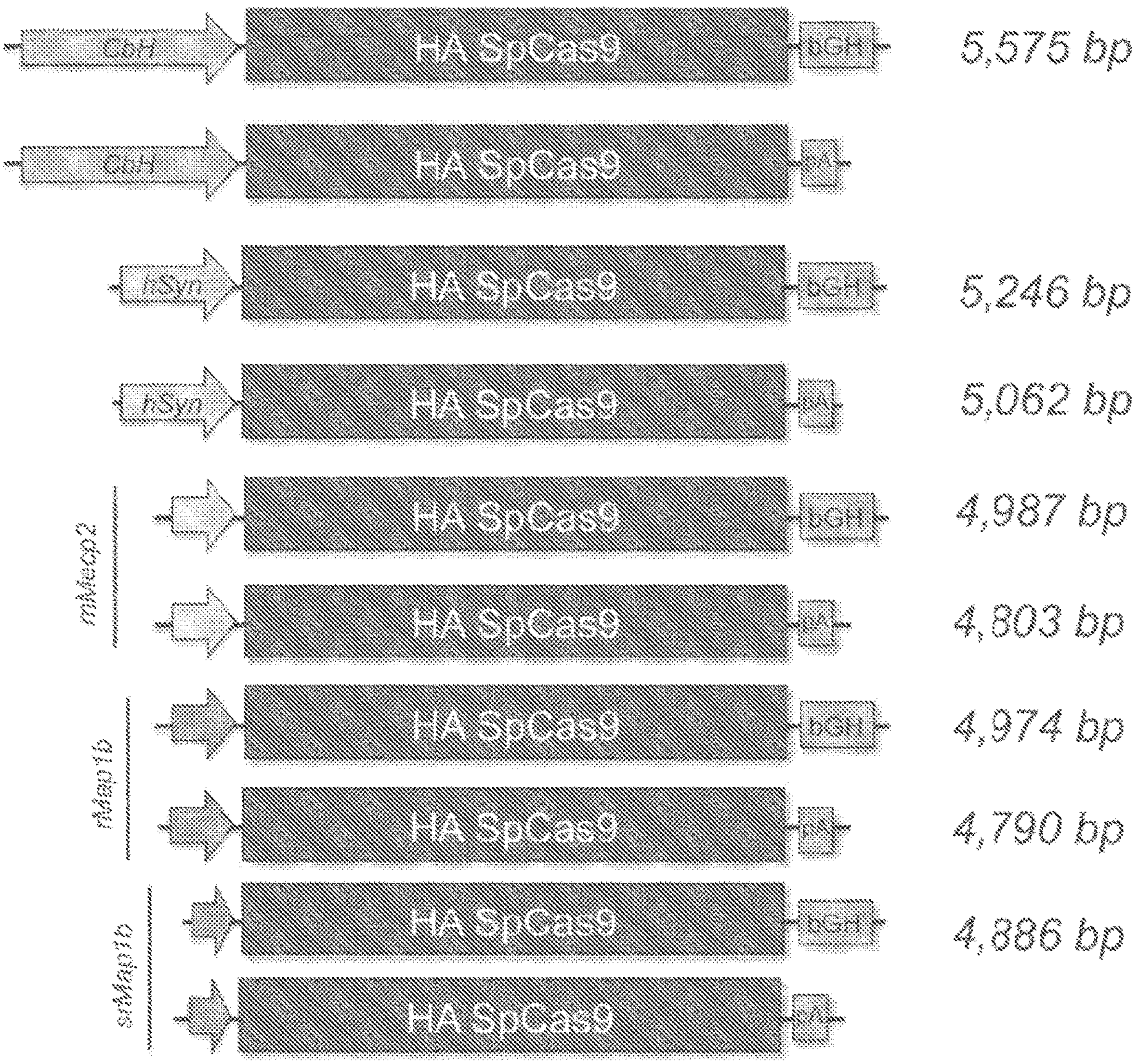
FIG. 37 shows schematic overview of short promoters and short polyA versions used for HA-SpCas9 expression in vivo. Sizes of the encoding region from L-ITR to R-ITR are shown on the right.
Figure 38:
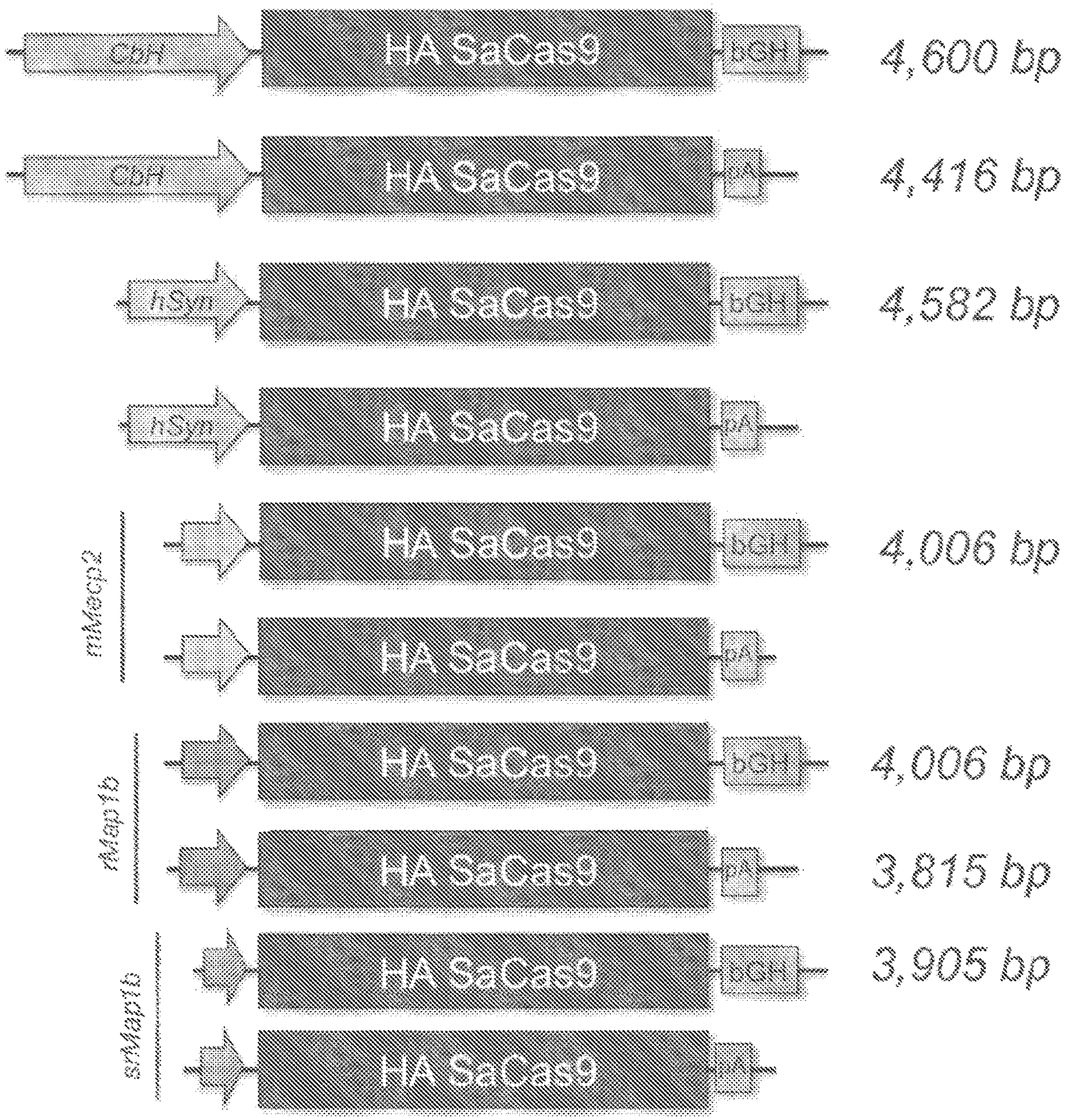
FIG. 38 shows schematic overview of short promoters and short polyA versions used for HA-SaCas9 expression in vivo. Sizes of the encoding region from L-ITR to R-ITR are shown on the right.
Figure 39:
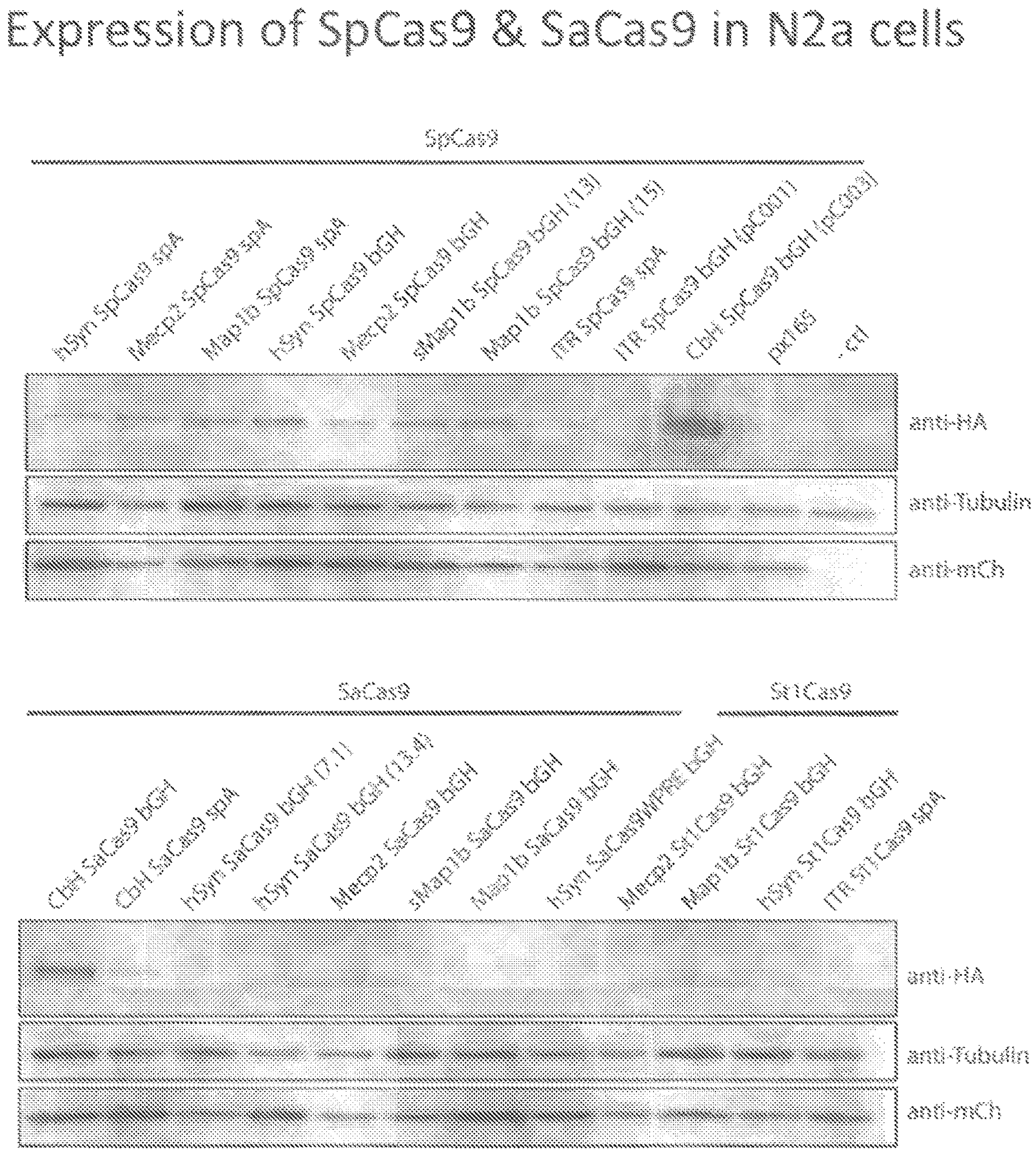
FIG. 39 shows expression of SpCas9 and SaCas9 in N2A cells. Representative Western blot of HA-tagged SpCas9 and SaCas9 versions under the control of different short promoters and with or short polyA (spA) sequences. Tubulin is loading control. mCherry (mCh) is a transfection control. Cells were harvested and further processed for Western blotting 48 h after transfection.
Figure 40:
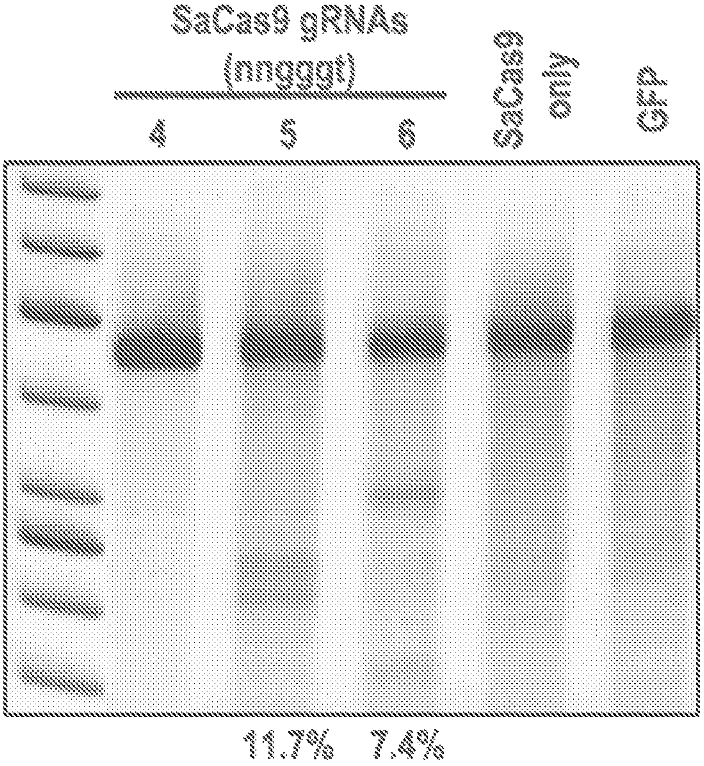
FIG. 40 shows screen for efficient SaCas9 mediated targeting of Tet3 gene locus. Surveyor assay on DNA from transfected N2A cells demonstrates efficient DNA cleavage by using different gRNAs with NNGGGT PUM sequence. GFP transfected cells and cells expressing only SaCas9 are controls.
Figure 41:
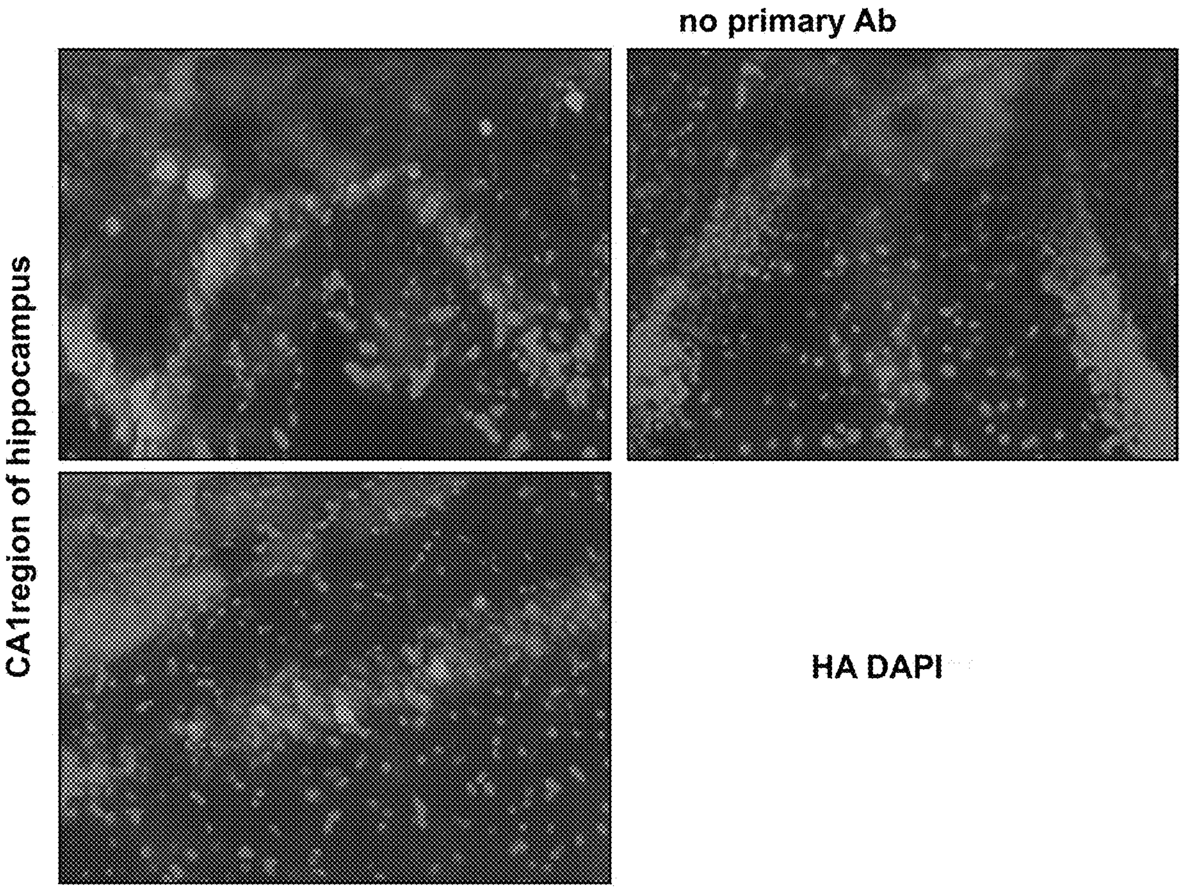
FIG. 41 shows expression of HA-SaCas9 in the mouse brain. Animals were injected into dentate gyri with virus driving expression of HA-SaCas9 under the control of human Synapsin promoter. Animals were sacrificed 2 weeks after surgery. HA tag was detected using rabbit monoclonal antibody C29F4 (Cell Signaling). Cell nuclei stained in blue with DAPI stain.

AAV delivery system despite its unique features has packing limitation—to successfully deliver expressing cassette in vivo it has to be in size <then 4.7 kb. To decrease the size of SpCas9 expressing cassette and facilitate delivery applicants tested several alteration: different promoters, shorter polyA signal and finally a smaller version of Cas9 from *Staphylococcus aureus* (SaCas9) (FIGS. 37 and 38). All tested promoters were previously tested and published to be active in neurons, including mouse Mecp2 (Gray et al., 2011), ratMap1b and truncated rat Map1b (Liu and Fischer, 1996). Alternative synthetic polyA sequence was previously shown to be functional as well (Levitt et al., 1989; Gray et al., 2011). All cloned constructs were expressed in N2a cells after transfection with Lipofectamine 2000, and tested with Western blotting method (FIG. 39).

Testing AAV Multiplex System in Primary Neurons

To confirm functionality of developed system in neurons, Applicants use primary neuronal cultures in vitro. Mouse cortical neurons was prepared according to the protocol published previously by Banker and Goslin (Banker and Goslin, 1988).

Neuronal cells are obtained from embryonic day 16. Embryos are extracted from the euthanized pregnant female and decapitated, and the heads are placed in ice-cold HBSS. The brains are then extracted from the skulls with forceps (#4 and #5) and transferred to another change of ice-cold HBSS. Further steps are performed with the aid of a stereoscopic microscope in a Petri dish filled with ice-cold HBSS and #5 forceps. The hemispheres are separated from each other and the brainstem and cleared of meninges. The hippocampi are then very carefully dissected and placed in a 15 ml conical tube filled with ice-cold HBSS. Cortices that remain after hippocampal dissection can be used for further cell isolation using an analogous protocol after removing the brain steam residuals and olfactory bulbs. Isolated hippocampi are washed three times with 10 ml ice-cold HBSS and dissociated by 15 min incubation with trypsin in HBSS (4 ml HBSS with the addition of 10 μl 2.5% trypsin per hippocampus) at 37° C. After trypsinization, the hippocampi are very carefully washed three times to remove any traces of trypsin with HBSS preheated to 37° C. and dissociated in warm HBSS. Applicants usually dissociate cells obtained from 10-12 embryos in 1 ml HBSS using 1 ml pipette tips and dilute dissociated cells up to 4 ml. Cells are plated at a density of 250 cells/mm2 and cultured at 37° C. and 5% CO2 for up to 3 week

HBSS 435 ml H2O 50 ml 10× Hank's Balanced Salt Solution 16.5 ml 0.3M HEPES pH 7.3

5 ml penicillin-streptomycin solution

Filter (0.2 μm) and store 4° C.

Neuron Plating Medium (100 ml)

97 ml Neurobasal 2 ml B27 Supplement
1 ml penicillin-streptomycin solution
250 μl glutamine
125 μl glutamate Neurons are transduced with concentrated AAV1/2 virus or AAV1 virus from filtered medium of HEK293FT cells, between 4-7 days in culture and keep for at least one week in culture after transduction to allow for delivered gene expression.

AAV-Driven Expression of the System

Figure 42:
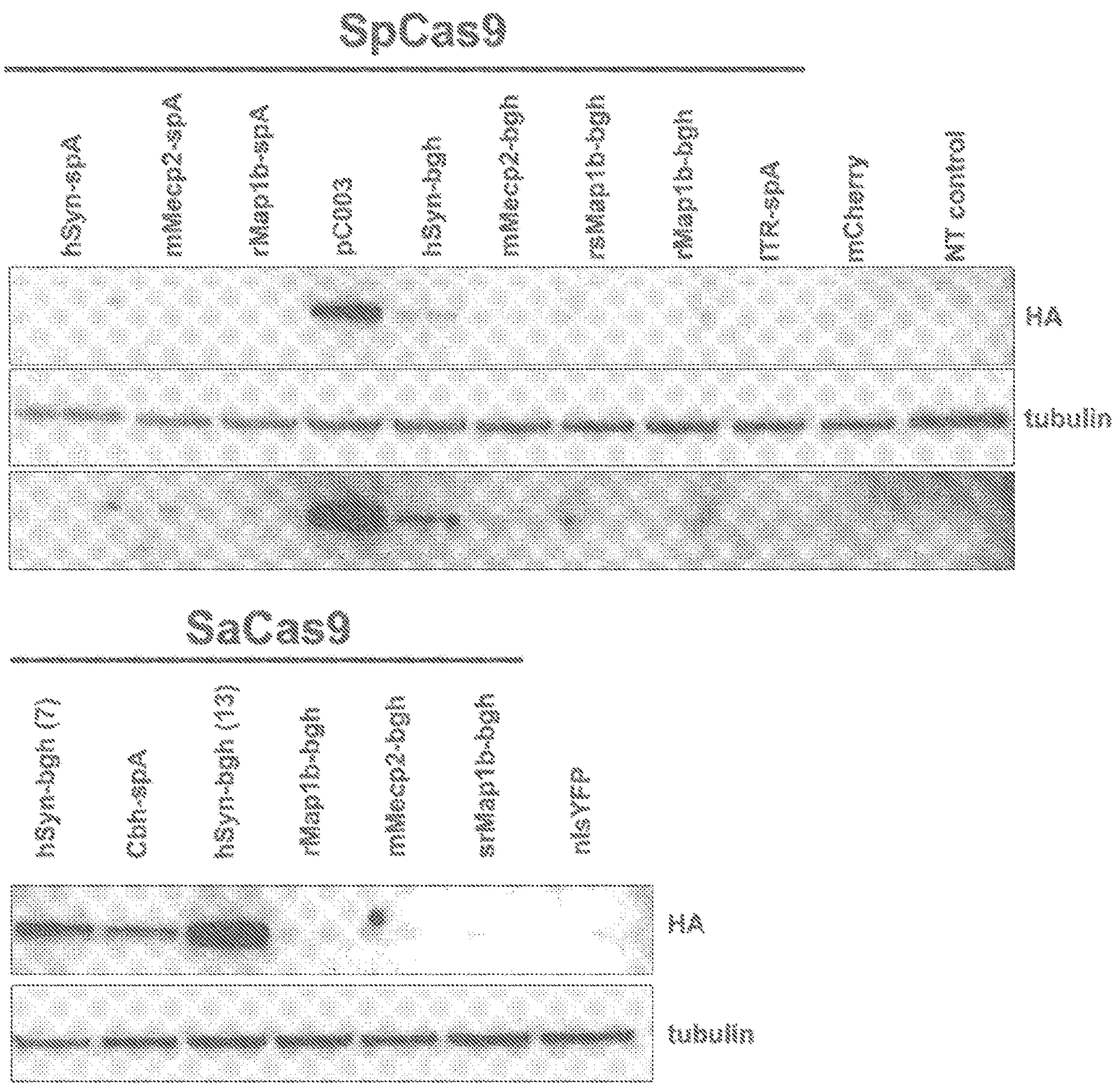
FIG. 42 shows expression of SpCas9 and SaCas9 in cortical primary neurons in culture 7 days after transduction. Representative Western blot of HA-tagged SpCas9 and SaCas9 versions under the control of different promoters and with bgh or short polyA (spA) sequences. Tubulin is loading control.

Applicants confirmed expression of SpCas9 and SaCas9 in neuronal cultures after AAV delivery using Western blot method (FIG. 42). One week after transduction neurons were collected in NuPage SDS loading buffer with β-mercaptoethanol to denaturate proteins in 95° C. for 5 min. Samples were separated on SDS PAGE gel and transferred on PVDF membrane for WB protein detection. Cas9 proteins were detected with HA antibody.

Figure 50:
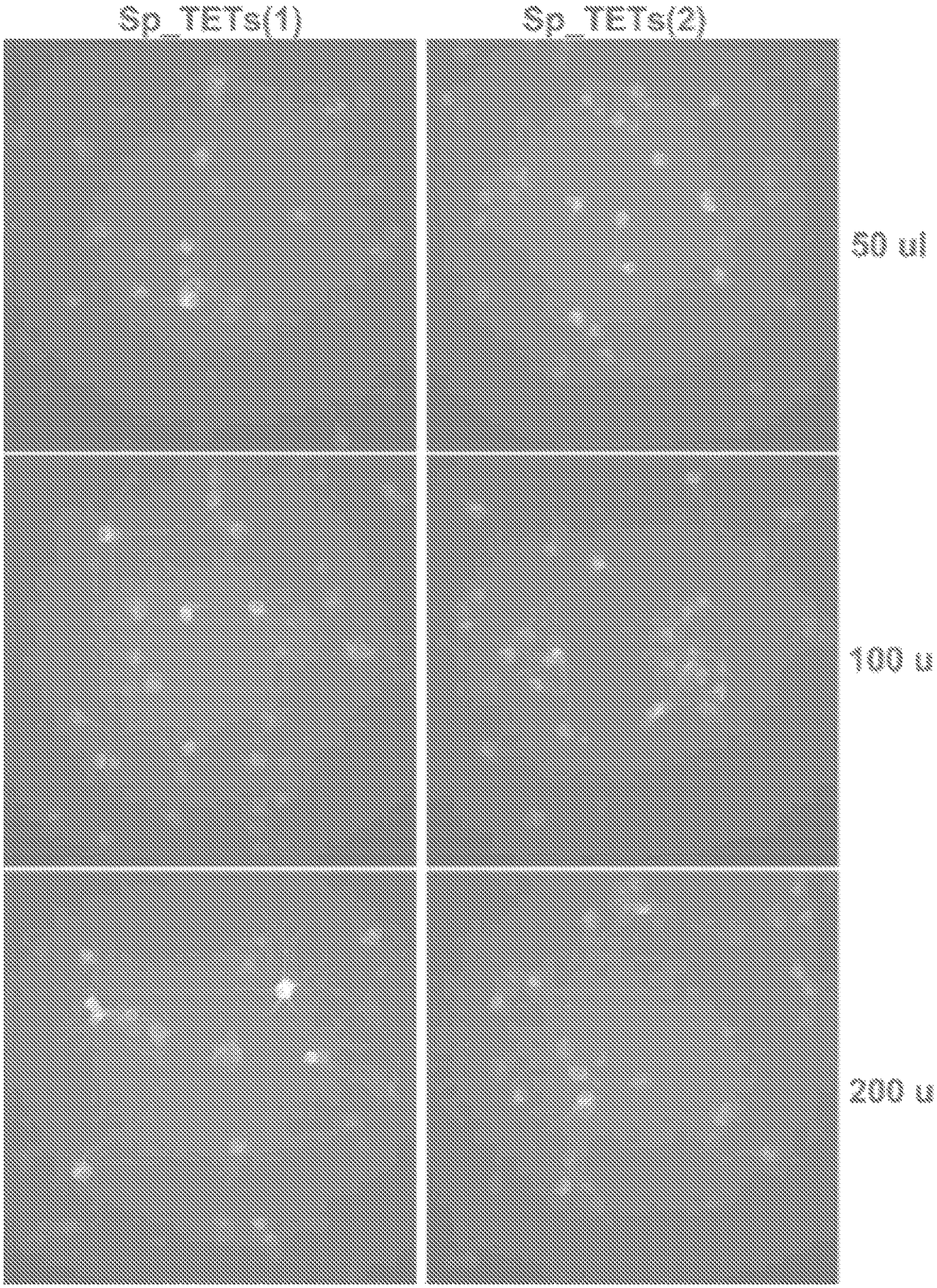
FIG. 50 shows GFP-KASH expression in cortical neurons in culture. Neurons were transduced with AAV1 virus carrying gRNA multiplex constructs targeting TET genes loci. The strongest signal localize around cells nuclei due to KASH domain localization.

Expression of Syn-GFP-kash from gRNA multiplex AAV was confirmed with fluorescent microscopy (FIG. 50).

Toxicity

Figure 43:
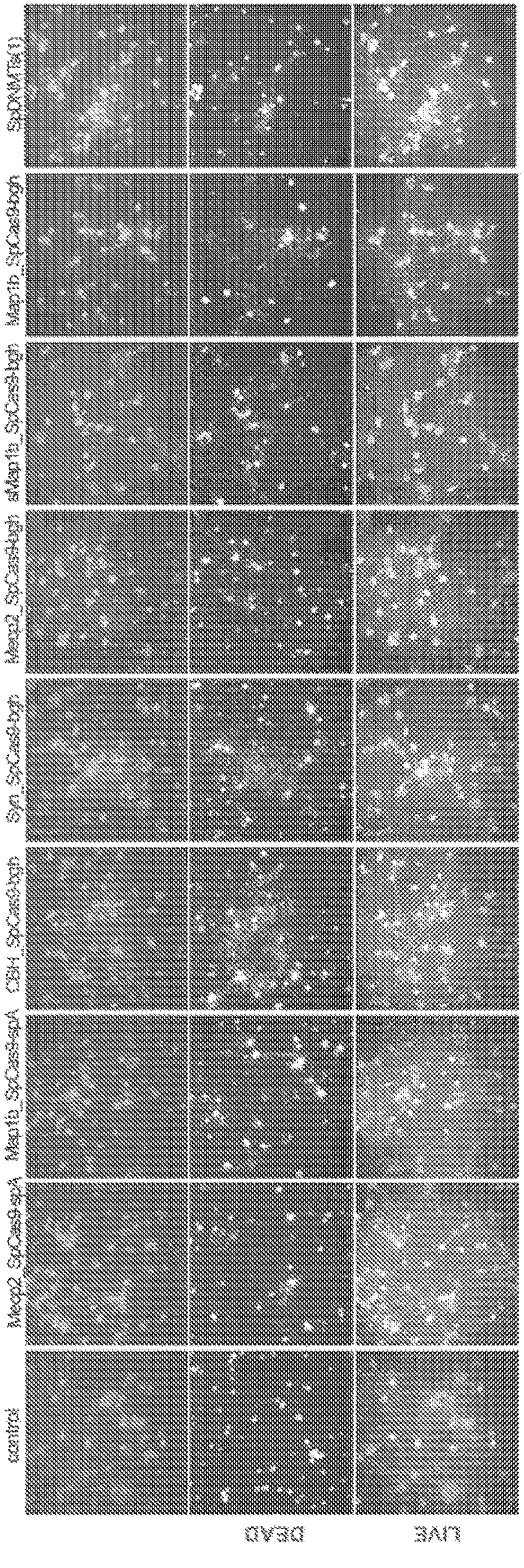
FIG. 43 shows LIVE/DEAD stain of primary cortical neurons 7 days after transduction with AAV1 particles carrying SpCas9 with different promoters and multiplex gRNAs constructs (example shown on the last panel for DNMTs). Neurons after AAV transduction were compared with control untransduced neurons. The nuclei indicate permeabilized, dead cells (second line of panels). Live cells are in the third line of panels.
Figure 44:
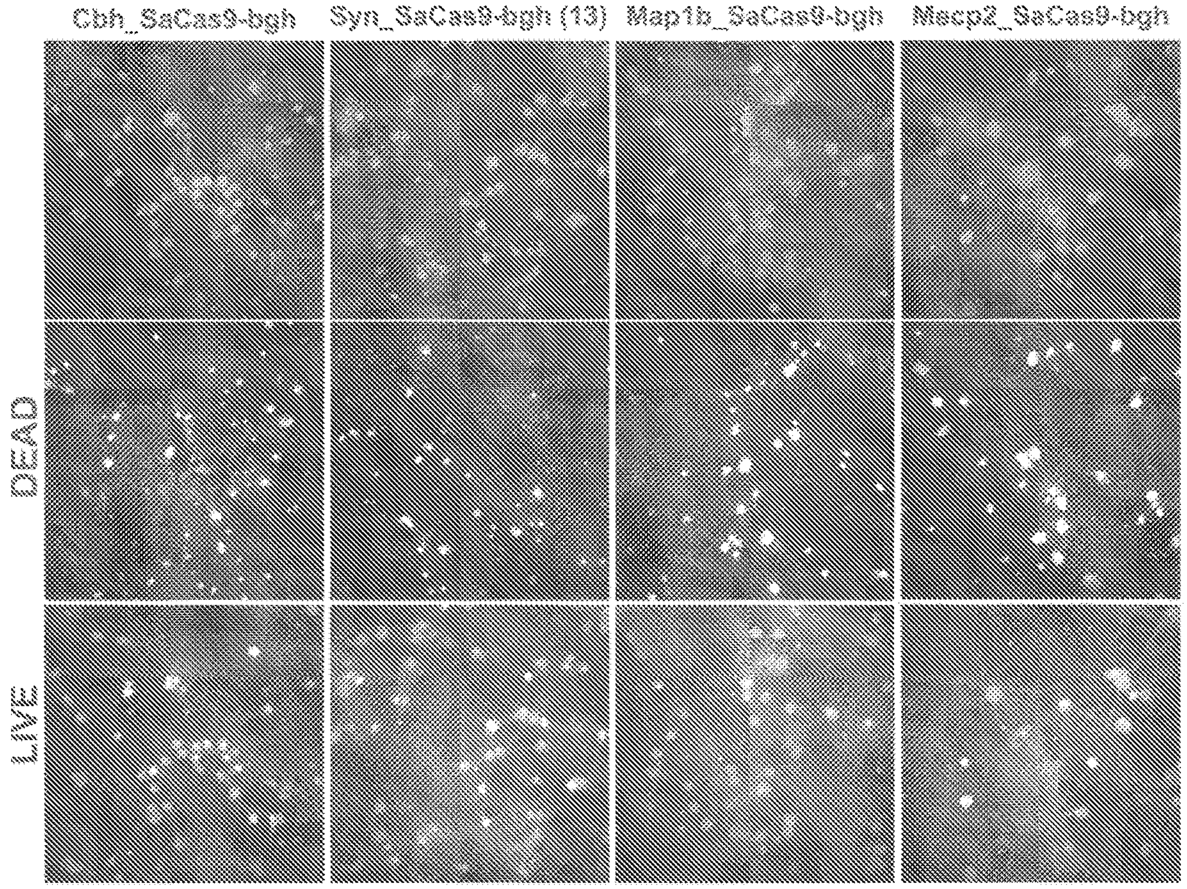
FIG. 44 shows LIVE/DEAD stain of primary cortical neurons 7 days after transduction with AAV1 particles carrying SaCas9 with different promoters. The nuclei indicate permeabilized, dead cells (second line of panels). Live cells are-in the third line of panels.
Figure 45:
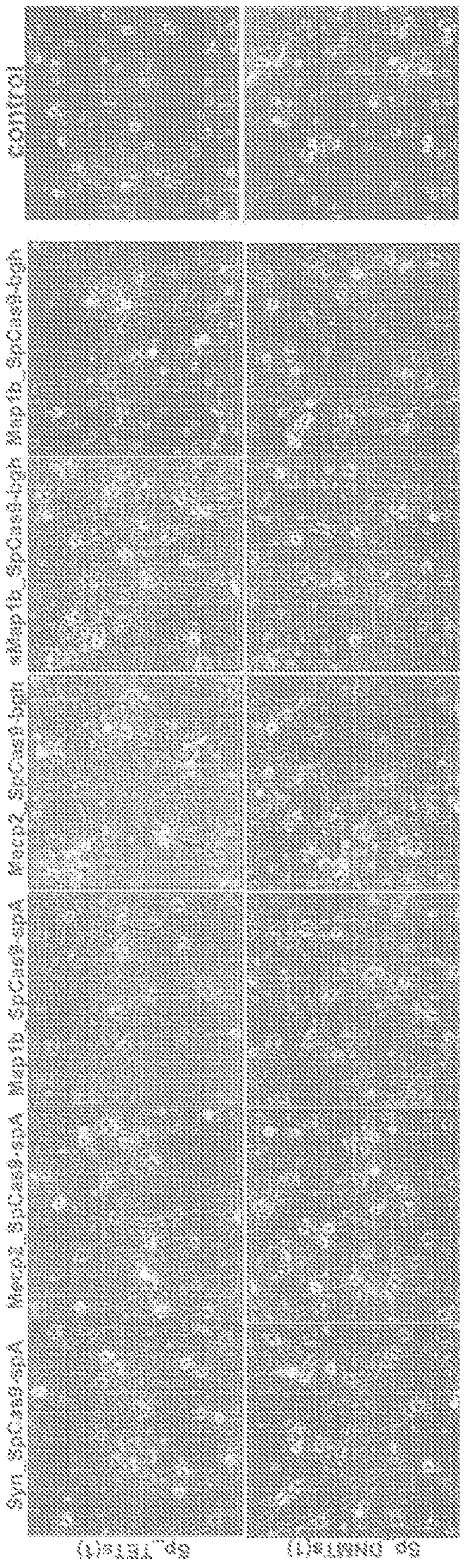
FIG. 45 shows comparison of morphology of neurons after transduction with AAV1 virus carrying SpCas9 and gRNA multiplexes for TETs and DNMTs genes loci. Neurons without transduction are shown as a control.
Figure 46:
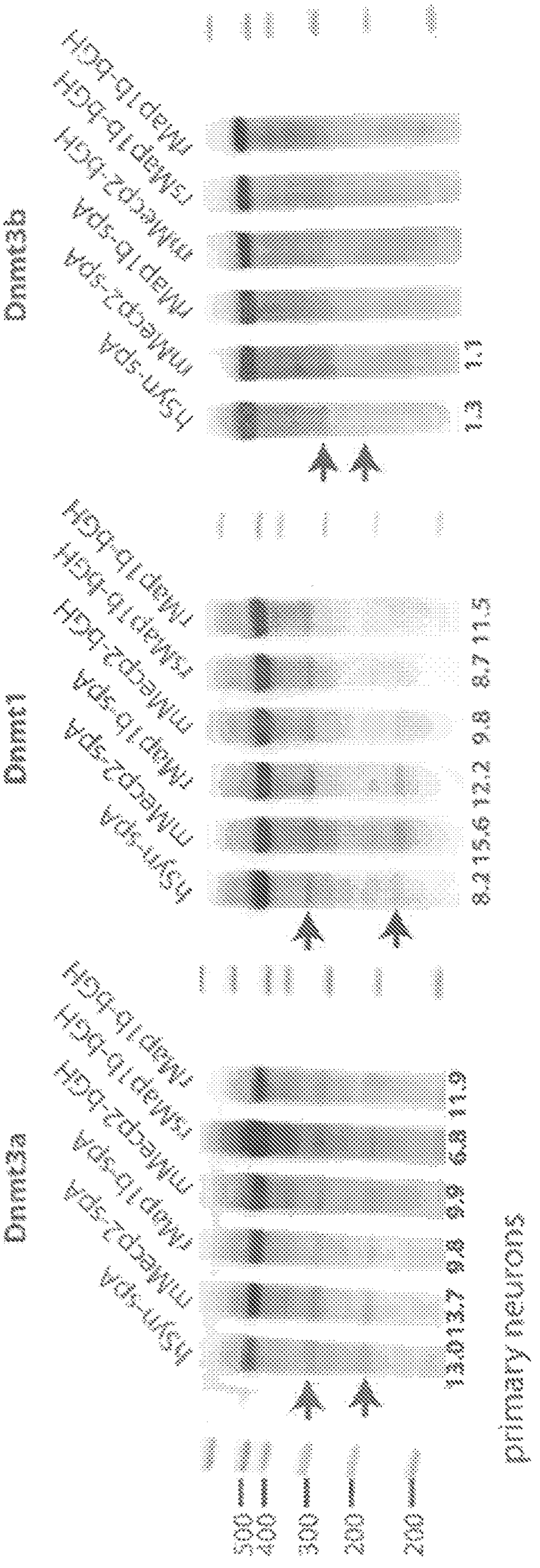
FIG. 46 shows verification of multiplex DNMT targeting vector #1 functionality using Surveyor assay in primary cortical neurons. Cells were co-transduced with the DNMT targeting vector #1 and the SpCas9 viruses with different promoters for testing SpCas9 mediated cleavage of DNMTs genes family loci.
Figure 47:
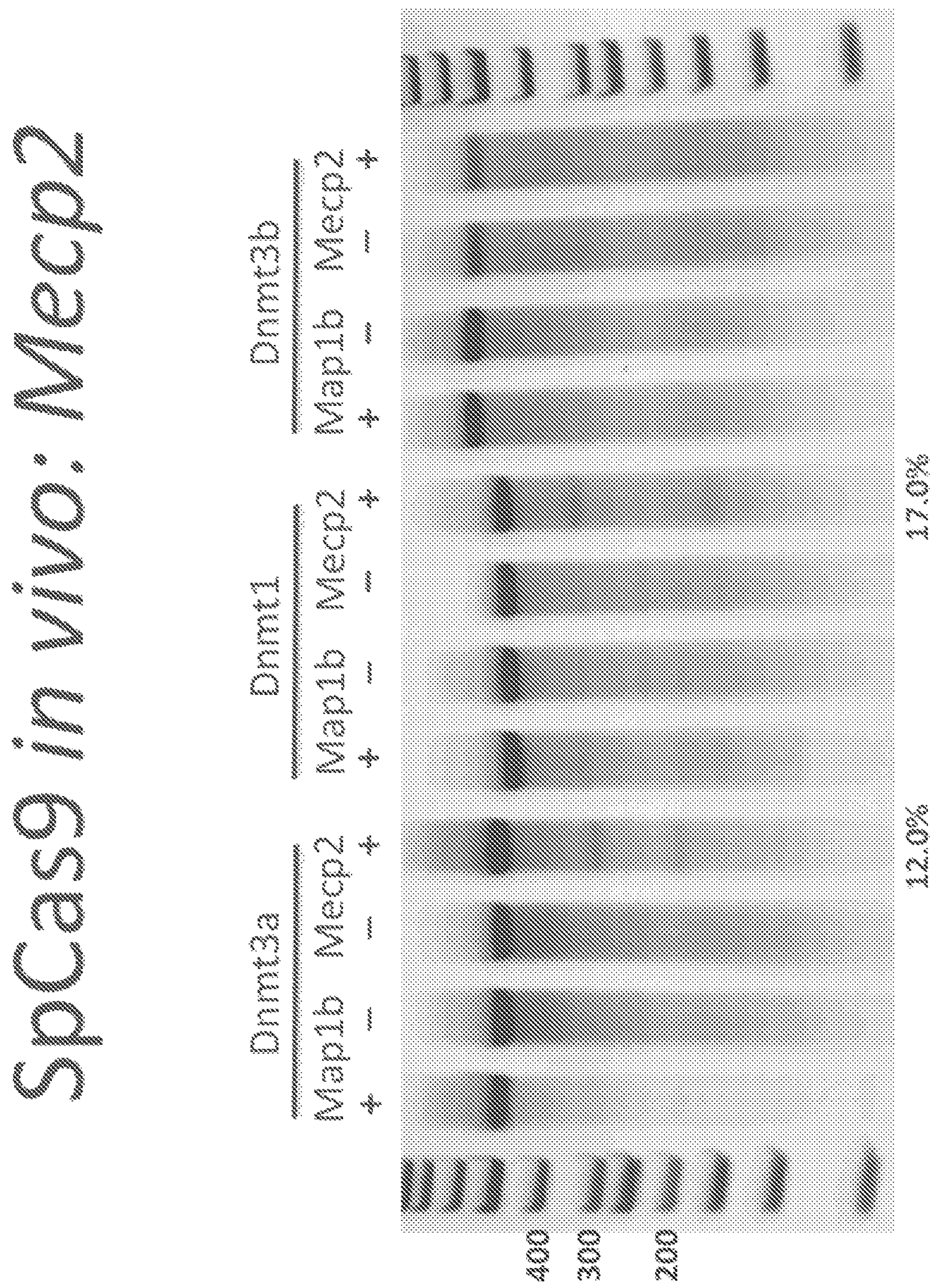
FIG. 47 shows in vivo efficiency of SpCas9 cleavage in the brain. Mice were injected with AAV1/2 virus carrying gRNA multiplex targeting DNMT family genes loci together with SpCas9 viruses under control of 2 different promoters: mouse Mecp2 and rat Map1b. Two weeks after injection brain tissue was extracted and nuclei were prepped and sorted using FACS, based on the GFP expression driven by Synapsin promoter from gRNA multiplex construct. After gDNA extraction Surveyor assay was run. + indicates GFP positive nuclei and – control, GFP-negative nuclei from the same animal. Numbers on the gel indicate assessed SpCas9 efficiency.
Figure 48:
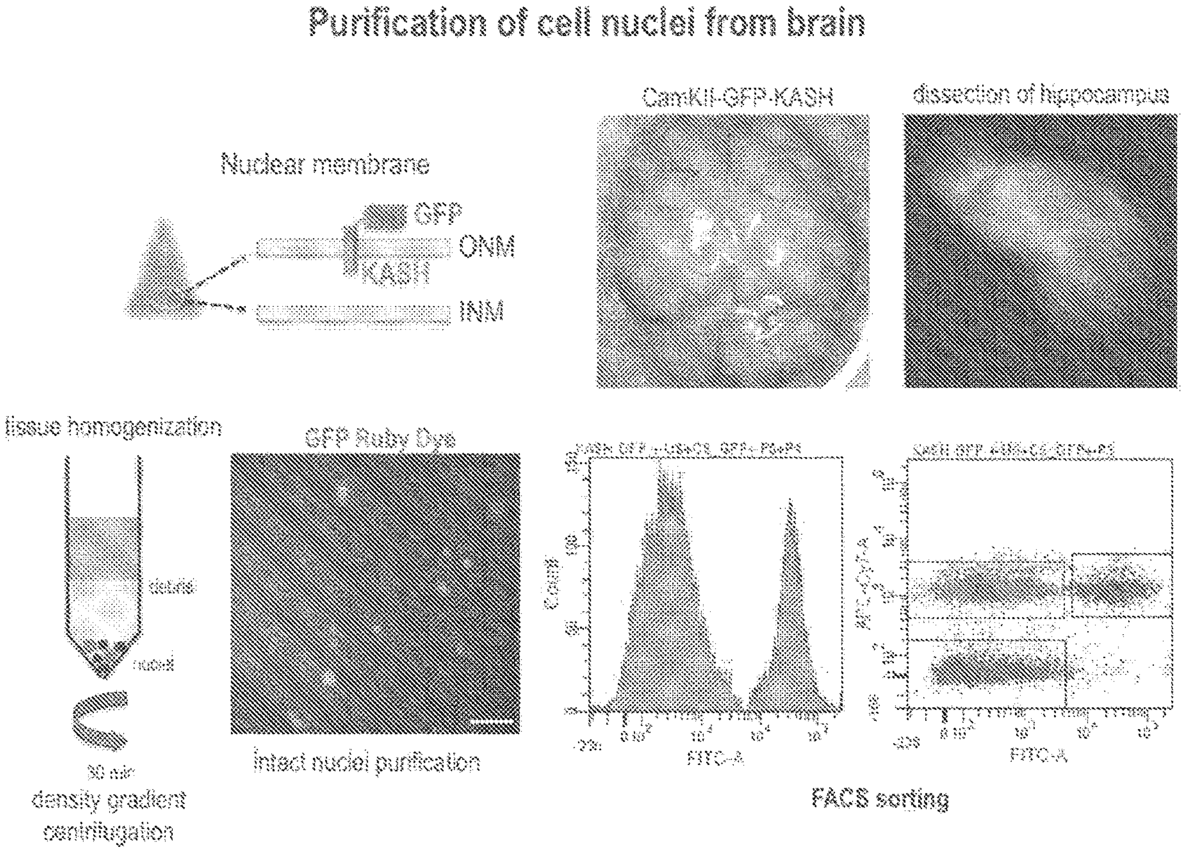
FIG. 48 shows purification of GFP-KASH labeled cell nuclei from hippocampal neurons. The outer nuclear membrane (ONM) of the cell nuclear membrane is tagged with a fusion of GFP and the KASH protein transmembrane domain. Strong GFP expression in the brain after one week of stereotactic surgery and AAV1/2 injection. Density gradient centrifugation step to purify cell nuclei from intact brain. Purified nuclei are shown.
Figure 49:
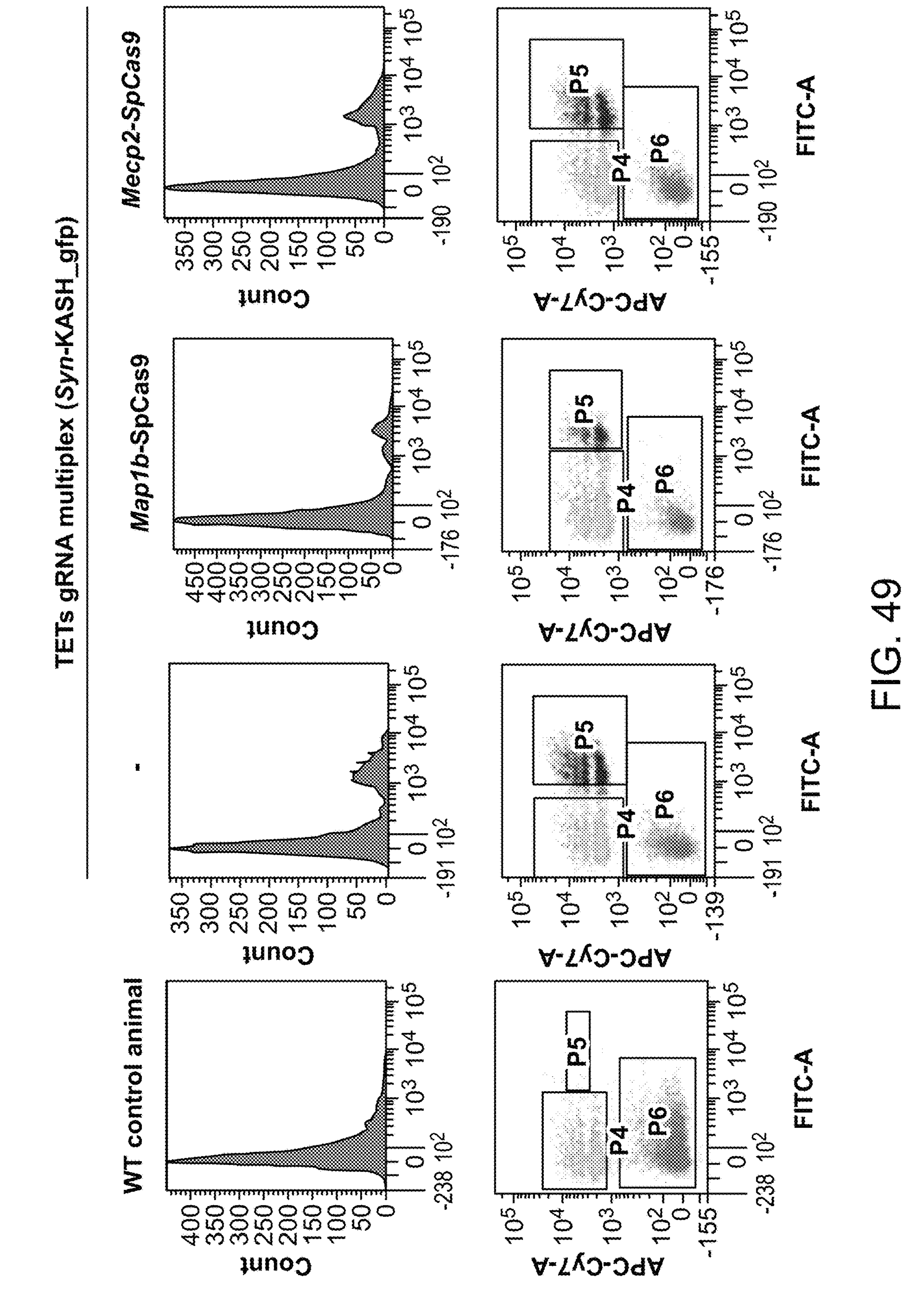
FIG. 49 shows efficiency of SpCas9 cleavage in the mouse brain. Mice were injected with AAV1/2 virus carrying gRNA multiplex targeting TET family genes loci together with SpCas9 viruses under control of 2 different promoters: mouse Mecp2 and rat Map1b. Three weeks after injection brain tissue was extracted, nuclei were prepped and sorted using FACS, based on the GFP expression driven by Synapsin promoter from gRNA multiplex construct. After gDNA extraction Surveyor assay was run. + indicates GFP positive nuclei and – control, GFP-negative nuclei from the same animal. Numbers on the gel indicate assessed SpCas9 efficiency.
Figure 49:
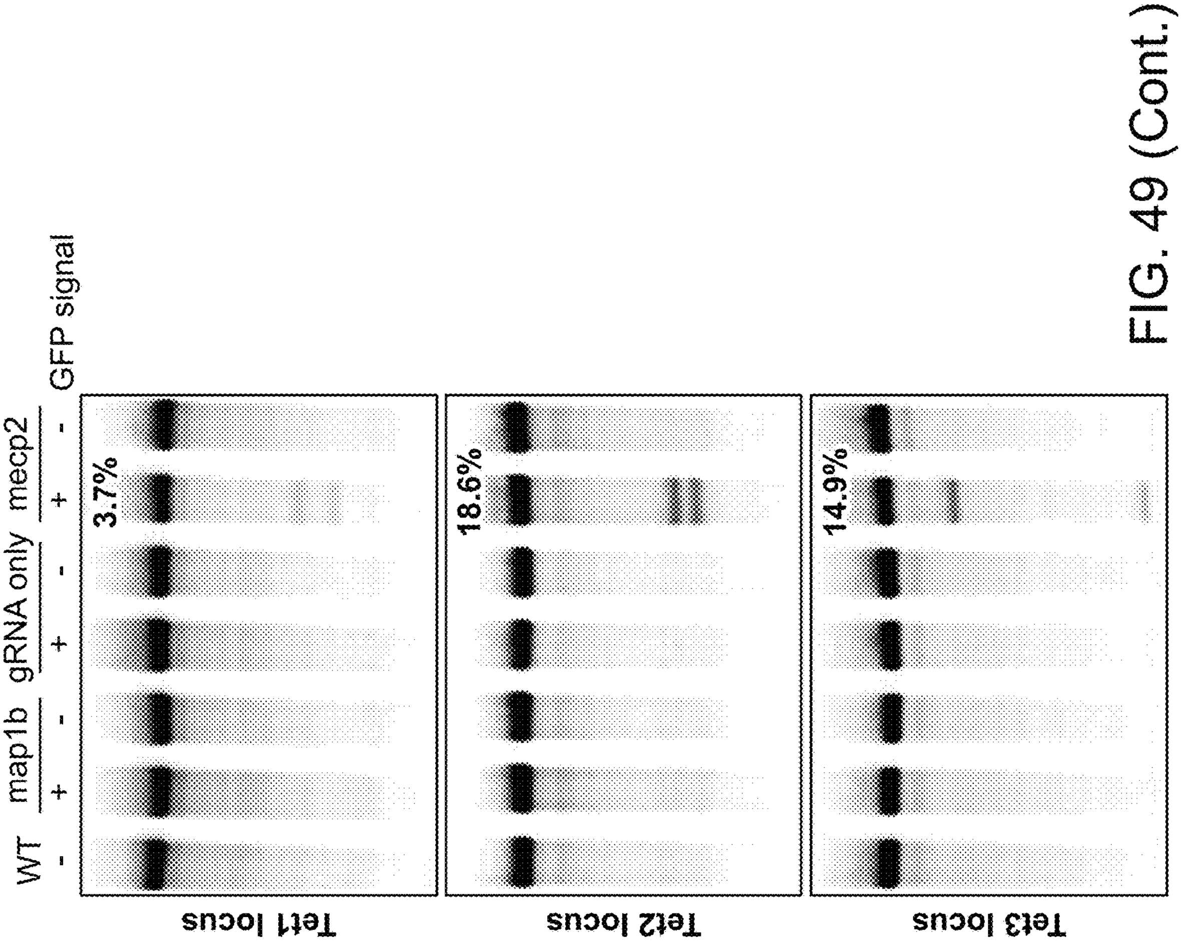

To assess the toxicity of AAV with CRISPR system Applicants tested overall morphology of neurons one week after virus transduction (FIG. 45). Additionally, Applicants tested potential toxicity of designed system with the LIVE/DEAD® Cell Imaging Kit, which allows to distinguish live and dead cells in culture. It is based on the presence of intracellular esterase activity (as determined by the enzymatic conversion of the non-fluorescent calcein AM to the intensely green fluorescent calcein). On the other hand, the red, cell-impermeant component of the Kit enters cells with damaged membranes only and bind to DNA generating fluorescence in dead cells. Both fluorophores can be easily visualized in living cells with fluorescent microscopy. AAV-driven expression of Cas9 proteins and multiplex gRNA constructs in the primary cortical neurons was well tolerated and not toxic (FIGS. 43 and 44), what indicates that designed AAV system is suitable for in vivo tests.

Virus Production

Concentrated virus was produced according to the methods described in McClure et al., 2011. Supernatant virus production occurred in HEK293FT cells.

Brain Surgeries

For viral vector injections 10-15 week old male C57BL/6N mice were anesthetized with a Ketamine/Xylazine cocktail (Ketamine dose of 100 mg/kg and Xylazine dose of 10 mg/kg) by intraperitoneal injection. Intraperitonial administration of Buprenex was used as a pre-emptive analgesic (1 mg/kg). Animals were immobilized in a Kopf stereotaxic apparatus using intra-aural positioning studs and tooth bar to maintain an immobile skull. Using a hand-held drill, a hole (1-2 mm) at −3.0 mm posterior to Bregma and 3.5 mm lateral for injection in the CA1 region of the hippocampus was made. Using 30 G World Precision Instrument syringe at a depth of 2.5 mm, the solution of AAV viral particles in a total volume of 1 ul was injected. The injection was monitored by a 'World Precision Instruments UltraMicroPump3' injection pump at a flow rate of 0.5 ul/min to prevent tissue damage. When the injection was complete, the injection needle was removed slowly, at a rate of 0.5 mm/min. After injection, the skin was sealed with 6-0 Ethilon sutures. Animals were postoperatively hydrated with 1 mL lactated Ringer's (subcutaneous) and housed in a temperature controlled (37° C.) environment until achieving an ambulatory recovery. 3 weeks after surgery animals were euthanized by deep anesthesia followed by tissue removal for nuclei sorting or with 4% paraformaldehyde perfusion for immunochemistry.

Sorting Nuclei and In Vivo Results

Applicants designed a method to specifically genetically tag the gRNA targeted neuronal cell nuclei with GFP for Fluorescent Activated Cell Sorting (FACS) of the labeled cell nuclei and downstream processing of DNA, RNA and nuclear proteins. To that purpose the applicants' multiplex targeting vector was designed to express both a fusion protein between GFP and the mouse nuclear membrane protein domain KASH (Starr D A, 2011, Current biology) and the 3 gRNAs to target specific gene loci of interest (FIG. 34). GFP-KASH was expressed under the control of the human Synapsin promoter to specifically label neurons. The amino acid of the fusion protein GFP-KASH was:

```
                                    (SEQ ID NO: 206)
MVSKGEELFTGVVPILVELDGDVNGHKFSVSGEGEGDATYGKLTLKFICT

TGKLPVPWPTLVTTLTYGVQCFSRYPDHMKQHDFFKSAMPEGYVQERTIF

FKDDGNYKTRAEVKFEGDTLVNRIELKGIDFKEDGNILGHKLEYNYNSHN

VYIMADKQKNGIKVNFKIRHNIEDGSVQLADHYQQNTPIGDGPVLLPDNH

YLSTQSALSKDPNEKRDHMVLLEFVTAAGITLGMDELYKSGLRSREEEEE

TDSRMPHLDSPGSSQPRRSFLSRVIRAALPLQLLLLLLLLLACLLPASED

DYSCTQANNFARSFYPMLRYTNGPPPT
```

One week after AAV1/2 mediated delivery into the brain a robust expression of GFP-KASH was observed. For FACS and downstream processing of labeled nuclei, the hippocampi were dissected 3 weeks after surgery and processed for cell nuclei purification using a gradient centrifugation step. For that purpose the tissue was homogenized in 320 mM Sucrose, 5 mM CaCl, 3 mM Mg(Ac)2, 10 mM Tris pH 7.8, 0.1 mM EDTA, 0.1% NP40, 0.1 mM Phenylmethanesulfonyl fluoride (PMSF), 1 mM β-mercaptoethanol using 2 ml Dounce homogenizer (Sigma) The homogenisate was centrifuged on a 25% to 29% Optiprep® gradient according to the manufacture's protocol for 30 min at 3.500 rpm at 4° C. The nuclear pellet was resuspended in 340 mM Sucrose, 2 mM MgCl2, 25 mM KCl, 65 mM glycerophosphate, 5% glycerol, 0.1 mM PMSF, 1 mM β-mercaptoethanol and Vybrant® DyeCycle™ Ruby Stain (Life technologies) was added to label cell nuclei (offers near-infrared emission for DNA). The labeled and purified nuclei were sorted by FACS using an Aria Flu-act-cell sorter and BDFACS Diva software. The sorted GFP+ and GFP− nuclei were finally used to purify genomic DNA using DNAeasy Blood & Tissue Kit (Qiagen) for Surveyor assay analysis of the targeted genomic regions. The same approach can be easily used to purify nuclear RNA or protein from targeted cells for downstream processing. Due to the 2-vector system (FIG. 34) the applicants using in this approach efficient Cas9 mediated DNA cleavage was expected to occur only in a small subset of cells in the brain (cells which were co-infected with both the multiplex targeting vector and the Cas9 encoding vector). The method described here enables the applicants to specifically purify DNA, RNA and nuclear proteins from the cell population expressing the 3 gRNAs of interest and therefore are supposed to undergo Cas9 mediated DNA cleavage. By using this method the applicants were able to visualize efficient DNA cleavage in vivo occurring only in a small subset of cells.

Essentially, what Applicants have shown here is targeted in vivo cleavage. Furthermore, Applicants used a multiple approach, with several different sequences targeted at the same time, but independently. Presented system can be applied for studying brain pathologic conditions (gene knock out, e.g. Parkinson disease) and also open a field for further development of genome editing tools in the brain. By replacing nuclease activity with gene transcription regulators or epigenetic regulators it will be possible to answer whole spectrum of scientific question about role of gene regulation and epigenetic changes in the brain in not only in the pathologic conditions but also in physiological process as learning and memory formation. Finally, presented technology can be applied in more complex mammalian system as primates, what allows to overcome current technology limitations.

Example 33: Model Data

Several disease models have been specifically investigated. These include de novo autism risk genes CHD8, KATNAL2, and SCN2A; and the syndromic autism (Angelman Syndrome) gene UBE3A. These genes and resulting autism models are of course preferred, but show that the invention may be applied to any gene and therefore any model is possible.

Applicants have made these cells lines using Cas9 nuclease in human embryonic stem cells (hESCs). The lines were created by transient transfection of hESCs with Cbh-Cas9-2A-EGFP and pU6-sgRNA. Two sgRNAs are designed for each gene targeting most often the same exons in which patient nonsense (knock-out) mutations have been recently described from whole exome sequencing studies of autistic patients. The Cas9-2A-EGFP and pU6 plasmids were created specifically for this project.

Example 34: AAV Production System or Protocol

An AAV production system or protocol that was developed for, and works particularly well with, high through put screening uses is provided herein, but it has broader applicability in the present invention as well. Manipulating endogenous gene expression presents various challenges, as the rate of expression depends on many factors, including regulatory elements, mRNA processing, and transcript stability. To overcome this challenge, Applicants developed an adeno-associated virus (AAV)-based vector for the delivery. AAV has an ssDNA-based genome and is therefore less susceptible to recombination.

AAV1/2 (serotype AAV1/2, i.e., hybrid or mosaic AAV1/AAV2 capsid AAV) heparin purified concentrated virus protocol Media: D10+HEPES
500 ml bottle DMEM high glucose+Glutamax (GIBCO)
50 ml Hyclone FBS (heat-inactivated) (Thermo Fischer)
5.5 ml HEPES solution (1M, GIBCO)
Cells: low passage HEK293FT (passage <10 at time of virus production, thaw new cells of passage 2-4 for virus production, grow up for 3-5 passages)
Transfection Reagent: Polyethylenimine (PEI) “Max”
Dissolve 50 mg PEI “Max” in 50 ml sterile Ultrapure H20
Adjust pH to 7.1
Filter with 0.22 um fliptop filter
Seal tube and wrap with parafilm
Freeze aliquots at −20° C. (for storage, can also be used immediately)

Cell Culture
Culture low passage HEK293FT in D10+HEPES
Passage everyday between 1:2 and 1:2.5
Advantageously do not allow cells to reach more than 85% confluency
For T75
Warm 10 ml HBSS (—Mg2+, —Ca2+, GIBCO)+1 ml TrypLE Express (GIBCO) per flask to 37° C. (Waterbath)

Aspirate Media Fully
Add 10 ml warm HBSS gently (to wash out media completely)
Add 1 ml TrypLE per Flask
Place flask in incubator (37° C.) for 1 min
Rock flask to detach cells
Add 9 ml D10+HEPES media (37° C.)
Pipette up and down 5 times to generate single cell suspension
Split at 1:2-1:2.5 (12 ml media for T75) ratio (if cells are growing more slowly, discard and thaw a new batch, they are not in optimal growth)
transfer to T225 as soon as enough cells are present (for ease of handling large amounts of cells)
AAV Production (5*15 cm Dish Scale Per Construct):
Plate 10 million cells in 21.5 ml media into a 15 cm dish
Incubate for 18-22 hours at 37° C.
Transfection is ideal at 80% confluence
Per Plate
Prewarm 22 ml media (D10+HEPES)
Prepare Tube with DNA Mixture (Use Endofree Maxiprep DNA):
5.2 ug vector of interest plasmid
4.35 ug AAV 1 serotype plasmid
4.35 ug AAV 2 serotype plasmid
10.4 ug pDF6 plasmid (adenovirus helper genes) □ Vortex to mix
Add 434 uL DMEM (no serum!)
Add 130 ul PEI solution
Vortex 5-10 seconds
Add DNA/DMEM/PEI mixture to prewarmed media
Vortex briefly to mix
Replace media in 15 cm dish with DNA/DMEM/PEI mixture
Return to 37° C. incubator
Incubate 48 h before harvesting (make sure medium isn’t turning too acidic)
Virus Harvest:

1. aspirate media carefully from 15 cm dish dishes (advantageously do not dislodge cells)
2. Add 25 ml RT DPBS (Invitrogen) to each plate and gently remove cells with a cell scraper. Collect suspension in 50 ml tubes.
3. Pellet cells at 800×g for 10 minutes.
4. Discard supernatant Pause Point: Freeze Cell Pellet at −80 C if Desired 5. resuspend pellet in 150 mM NaCl, 20 mM Tris pH 8.0, use 10 ml per tissue culture plate.
6. Prepare a fresh solution of 10% sodium deoxycholate in dH2O. Add 1.25 ml of this per tissue culture plate for a final concentration of 0.5%. Add benzonase nuclease to a final concentration of 50 units per ml. Mix tube thoroughly.
7. Incubate at 37° C. for 1 hour (Waterbath).
8. Remove cellular debris by centrifuging at 3000×g for 15 mins. Transfer to fresh 50 ml tube and ensure all cell debris has been removed to prevent blocking of heparin columns.

Heparin Column Purification of AAV1/2:

1. Set up HiTrap heparin columns using a peristaltic pump so that solutions flow through the column at 1 ml per minute. It is important to ensure no air bubbles are introduced into the heparin column.

2. Equilibrate the column with 10 ml 150 mM NaCl, 20 mM Tris, pH 8.0 using the peristaltic pump.

3. Binding of virus: Apply 50 ml virus solution to column and allow to flow through.

4. Wash step 1: column with 20 ml 100 mM NaCl, 20 mM Tris, pH 8.0. (using the peristaltic pump)

5. Wash step 2: Using a 3 ml or 5 ml syringe continue to wash the column with 1 ml 200 mM NaCl, 20 mM Tris, pH 8.0, followed by 1 ml 300 mM NaCl, 20 mM Tris, pH 8.0. Discard the flow-through.

(prepare the syringes with different buffers during the 50 min flow through of virus solution above)

6. Elution Using 5 ml syringes and gentle pressure (flow rate of <1 ml/min) elute the virus from the column by applying:

1.5 ml 400 mM NaCl, 20 mM Tris, pH 8.0

3.0 ml 450 mM NaCl, 20 mM Tris, pH 8.0

1.5 ml 500 mM NaCl, 20 mM Tris, pH 8.0

Collect these in a 15 ml centrifuge tube.

Concentration of AAV1/2:

1. Concentration step 1: Concentrate the eluted virus using Amicon ultra 15 ml centrifugal filter units with a 100,000 molecular weight cutoff. Load column eluate into the concentrator and centrifuge at 2000×g for 2 minutes (at room temperature. Check concentrated volume—it should be approximately 500 μl. If necessary, centrifuge in 1 min intervals until correct volume is reached.

2. buffer exchange: Add 1 ml sterile DPBS to filter unit, centrifuge in 1 min intervals until correct volume (500 ul) is reached.

3. Concentration step 2: Add 500 ul concentrate to an Amicon Ultra 0.5 ml 100K filter unit. Centrifuge at 6000 g for 2 min. Check concentrated volume—it should be approximately 100 μl. If necessary, centrifuge in 1 min intervals until correct volume is reached.

4. Recovery: Invert filter insert and insert into fresh collection tube. Centrifuge at 1000 g for 2 min.

Aliquot and freeze at −80° C.

1 ul is typically required per injection site, small aliquots (e.g. 5 ul) are therefore recommended (avoid freeze-thaw of virus).

determine DNaseI-resistant GC particle titer using qPCR (see separate protocol)

Materials

Amicon Ultra, 0.5 ml, 100K; MILLIPORE; UFC510024

Amicon Ultra, 15 ml, 100K; MILLIPORE; UFC910024

Benzonase nuclease; Sigma-Aldrich, E1014

HiTrap Heparin cartridge; Sigma-Aldrich; 54836

Sodium deoxycholate; Sigma-Aldrich; D5670

AAV1 Supernatant Production Protocol

Media: D10+HEPES 500 ml bottle DMEM high glucose+Glutamax (Invitrogen)

50 ml Hyclone FBS (heat-inactivated) (Thermo Fischer)

5.5 ml HEPES solution (1M, GIBCO)

Cells: low passage HEK293FT (passage <10 at time of virus production)

Thaw new cells of passage 2-4 for virus production, grow up for 2-5 passages

Transfection reagent: Polyethylenimine (PEI) "Max"

Dissolve 50 mg PEI "Max" in 50 ml sterile Ultrapure H20

Adjust pH to 7.1

Filter with 0.22 um fliptop filter

Seal tube and wrap with parafilm

Freeze aliquots at −20° C. (for storage, can also be used immediately)

Cell Culture

Culture low passage HEK293FT in D10+HEPES Passage everyday between 1:2 and 1:2.5

Advantageously do let cells reach more than 85% confluency

For T75

Warm 10 ml HBSS (—Mg2+, —Ca2+, GIBCO)+1 ml TrypLE Express (GIBCO) per flask to 37° C. (Waterbath)

Aspirate media fully

Add 10 ml warm HBSS gently (to wash out media completely)

Add 1 ml TrypLE per Flask

Place flask in incubator (37° C.) for 1 min

Rock flask to detach cells

Add 9 ml D10+HEPES media (37° C.)

Pipette up and down 5 times to generate single cell suspension

Split at 1:2-1:2.5 (12 ml media for T75) ratio (if cells are growing more slowly, discard and thaw a new batch, they are not in optimal growth)

transfer to T225 as soon as enough cells are present (for ease of handling large amounts of cells)

AAV production (single 15 cm dish scale)

Plate 10 million cells in 21.5 ml media into a 15 cm dish

Incubate for 18-22 hours at 37° C.

Transfection is ideal at 80% confluence per plate

Prewarm 22 ml media (D10+HEPES)

Prepare tube with DNA mixture (use endofree maxiprep DNA):

5.2 ug vector of interest plasmid 8.7 ug AAV 1 serotype plasmid 10.4 ug DF6 plasmid (adenovirus helper genes)

Vortex to mix

Add 434 uL DMEM (no serum!) Add 130 ul PEI solution

Vortex 5-10 seconds

Add DNA/DMEM/PEI mixture to prewarmed media

Vortex briefly to mix

Replace media in 15 cm dish with DNA/DMEM/PEI mixture

Return to 37° C. incubator

Incubate 48 h before harvesting (advantageously monitor to ensure medium is not turning too acidic)

Virus Harvest:

Remove supernatant from 15 cm dish

Filter with 0.45 um filter (low protein binding) Aliquot and freeze at −80° C.

Transduction (primary neuron cultures in 24-well format, 5 DIV)

Replace complete neurobasal media in each well of neurons to be transduced with fresh neurobasal (usually 400 ul out of 500 ul per well is replaced)

Thaw AAV supernatant in 37° C. waterbath

Let equilibrate in incubator for 30 min

Add 250 ul AAV supernatant to each well

Incubate 24 h at 37° C.

Remove media/supernatant and replace with fresh complete neurobasal

Expression starts to be visible after 48 h, saturates around 6-7 Days Post Infection Constructs for pAAV plasmid with GOI should not exceed 4.8 kb including both ITRS.

Example of a human codon optimized sequence (i.e. being optimized for expression in humans) sequence: SaCas9 is provided below:

(SEQ ID NO: 207)
ACCGGTGCCACCATGTACCCATACGATGTTCCAGATTACGC

TTCGCCGAAGAAAAAGCGCAAGGTCGAAGCGTCCATGAAAAGGAACTACATTCT

GGGGCTGGACATCGGGATTACAAGCGTGGGGTATGGGATTATTGACTATGAAAC

AAGGGACGTGATCGACGCAGGCGTCAGACTGTTCAAGGAGGCCAACGTGGAAAA

CAATGAGGGACGGAGAAGCAAGAGGGGAGCCAGGCGCCTGAAACGACGGAGAA

GGCACAGAATCCAGAGGGTGAAGAAACTGCTGTTCGATTACAACCTGCTGACCG

ACCATTCTGAGCTGAGTGGAATTAATCCTTATGAAGCCAGGGTGAAAGGCCTGA

GTCAGAAGCTGTCAGAGGAAGAGTTTTCCGCAGCTCTGCTGCACCTGGCTAAGC

GCCGAGGAGTGCATAACGTCAATGAGGTGGAAGAGGACACCGGCAACGAGCTG

TCTACAAAGGAACAGATCTCACGCAATAGCAAAGCTCTGGAAGAGAAGTATGTC

GCAGAGCTGCAGCTGGAACGGCTGAAGAAAGATGGCGAGGTGAGAGGGTCAATT

AATAGGTTCAAGACAAGCGACTACGTCAAAGAAGCCAAGCAGCTGCTGAAAGTG

CAGAAGGCTTACCACCAGCTGGATCAGAGCTTCATCGATACTTATATCGACCTGC

TGGAGACTCGGAGAACCTACTATGAGGGACCAGGAGAAGGGAGCCCCTTCGGAT

GGAAAGACATCAAGGAATGGTACGAGATGCTGATGGGACATTGCACCTATTTTCC

AGAAGAGCTGAGAAGCGTCAAGTACGCTTATAACGCAGATCTGTACAACGCCCT

GAATGACCTGAACAACCTGGTCATCACCAGGGATGAAAACGAGAAACTGGAATA

CTATGAGAAGTTCCAGATCATCGAAAACGTGTTTAAGCAGAAGAAAAAGCCTAC

ACTGAAACAGATTGCTAAGGAGATCCTGGTCAACGAAGAGGACATCAAGGGCTA

CCGGGTGACAAGCACTGGAAAACCAGAGTTCACCAATCTGAAAGTGTATCACGA

TATTAAGGACATCACAGCACGGAAAGAAATCATTGAGAACGCCGAACTGCTGGA

TCAGATTGCTAAGATCCTGACTATCTACCAGAGCTCCGAGGACATCCAGGAAGAG

CTGACTAACCTGAACAGCGAGCTGACCCAGGAAGAGATCGAACAGATTAGTAT

CTGAAGGGGTACACCGGAACACACAACCTGTCCCTGAAAGCTATCATCTGATTC

TGGATGAGCTGTGGCATACAAACGACAATCAGATTGCAATCTTTAACCGGCTGAA

GCTGGTCCCAAAAAAGGTGGACCTGAGTCAGCAGAAAGAGATCCCAACCACACT

GGTGGACGATTTCATTCTGTCACCCGTGGTCAAGCGGAGCTTCATCCAGAGCATCAAAGTGATC

AACGCCATCATCAAGAAGTACGGCCTGCCCAATGATATCATTATCGAGCTGGCTAGGGAGAAGA

ACAGCAAGGACGCACAGAAGATGATCATGAGATGCAGAAACGAAACCGGCAGACCAATGAACG

CATTGAAGAGATTATCCGAACTACCGGGAAAGAGAACGCAAAGTACCTGATTGAAAAAATCAAG

CTGCACGATATGCAGGAGGGAAAGTGTCTGTATTCTCTGGAGGCCATCCCCCTGGAGGACCTGC

TGAACAATCCATTCAACTACGAGGTCGATCATATTATCCCCAGAAGCGTGTCCTTCGACAATTC

CTTTAACAACAAGGTGCTGGTCAAGCAGGAAGAGAACTCTAAAAAGGGCAATAGGACTCCTTTC

CAGTACCTGTCTAGTTCAGATTCCAAGATCTCTTACGAAACCTTTAAAAAGCACATTCTGAATC

TGGCCAAAGGAAAGGGCCGCATCAGCAAGACCAAAAAGGAGTACCTGCTGGAAGAGCGGGACAT

CAACAGATTCTCCGTCCAGAAGGATTTTATTAACCGGAATCTGGTGGACACAAGATACGCTACT

CGCGGCCTGATGAATCTGCTGCGATCCTATTTCCGGGTGAACAATCTGGATGTGAAAGTCAAGT

CCATCAACGGCGGGTTCACATCTTTTCTGAGGCGCAAATGGAAGTTTAAAAAGGAGCGCAACAA

-continued

```
AGGGTACAAGCACCATGCCGAAGATGCTCTGATTATCGCAAATGCCGACTTCATCTTTAAGGAG
TGGAAAAAGCTGGACAAAGCCAAGAAAGTGATGGAGAACCAGATGTTCGAAGAGAAGCAGGCCG
ATCTATGCCCGAAATCGAGACAGAACAGGAGTACAAGGAGATTTTCATCACTCCTCACCAGAT
CAAGCATATCAAGGATTTCAAGGACTACAAGTACTCTCACCGGGTGGATAAAAAGCCCAACAGA
GAGCTGATCAATGACACCCTGTATAGTACAAGAAAAGACGATAAGGGGAATACCCTGATTGTGA
ACAATCTGAACGGACTGTACGACAAAGATAATGACAAGCTGAAAAAGCTGATCAACAAAAGTCC
CGAGAAGCTGCTGATGTACCACCATGATCCTCAGACATATCAGAAACTGAAGCTGATTATGGAG
CAGTACGGCGACGAGAAGAACCCACTGTATAAGTACTATGAAGAGACTGGGAACTACCTGACCA
AGTATAGCAAAAAGGATAATGGCCCCGTGATCAAGAAGATCAAGTACTATGGGAACAAGCTGAA
TGCCCATCTGGACATCACAGACGATTACCCTAACAGTCGCAACAAGGTGGTCAAGCTGTCACTG
AAGCCATACAGATTCGATGTCTATCTGGACAACGGCGTGTATAAATTTGTGACTGTCAAGAATC
TGGATGTCATCAAAAAGGAGAACTACTATGAAGTGAATAGCAAGTGCTACGAAGAGGCTAAAAA
GCTGAAAAAGATTAGCAACCAGGCAGAGTTCATCGCCTCCTTTTACAACAACGACCTGATTAG
ATCAATGGCGAACTGTATAGGGTCATCGGGGTGAACAATGATCTGCTGAACCGCATTGAAGTGA
ATATGATTGACATCACTTACCGAGAGTATCTGGAAAACATGATGATAAGCGCCCCCCTCGAAT
TATCAAAACAATTGCCTCTAAGACTCAGAGTATCAAAAAGTACTCAACCGACATTCTGGGAAAC
CTGTATGAGGTGAAGAGCAAAAAGCACCCTCAGATTATCAAAAAGGGCTAAGAATTC
```

Example 35: Minimizing Off-Target Cleavage Using Cas9 Nickase and Two Guide RNAs Cas9 is a RNA-guided DNA nuclease that may be targeted to specific locations in the genome with the help of a 20 bp RNA guide. However the guide sequence may tolerate some mismatches between the guide sequence and the DNA-target sequence. The flexibility is undesirable due to the potential for off-target cleavage, when the guide RNA targets Cas9 to a an off-target sequence that has a few bases different from the guide sequence. For all experimental applications (gene targeting, crop engineering, therapeutic applications, etc) it is important to be able to improve the specificity of Cas9 mediated gene targeting and reduce the likelihood of off-target modification by Cas9.

Applicants developed a method of using a Cas9 nickase mutant in combination with two guide RNAs to facilitate targeted double strand breaks in the genome without off-target modifications. The Cas9 nickase mutant may be generated from a Cas9 nuclease by disabling its cleavage activity so that instead of both strands of the DNA duplex being cleaved only one strand is cleaved. The Cas9 nickase may be generated by inducing mutations in one ore more domains of the Cas9 nuclease, e.g. Ruvc1 or HNH. These mutations may include but are not limited to mutations in a Cas9 catalytic domain, e.g in SpCas9 these mutations may be at positions D10 or H840. These mutations may include but are not limited to D10A, E762A, H840A, N854A, N863A or D986A in SpCas9 but nickases may be generated by inducing mutations at corresponding positions in other CRISPR enzymes or Cas9 orthologs. In a most preferred embodiment of the invention the Cas9 nickase mutant is a SpCas9 nickase with a D10A mutation.

The way this works is that each guide RNA in combination with Cas9 nickase would induce the targeted single strand break of a duplex DNA target. Since each guide RNA nicks one strand, the net result is a double strand break. The reason this method eliminates off-target mutations is because it is very unlikely to have an off-target site that has high degrees of similarity for both guide sequences (20 bp+2 bp(PAM)=22 bp specificity for each guide, and two guides means any off-target site will have to have close to 44 bp of homologous sequence). Although it is still likely that individual guides may have off-targets, but those off-targets will only be nicked, which is unlikely to be repaired by the mutagenic NHEJ process. Therefore the multiplexing of DNA double strand nicking provides a powerful way of introducing targeted DNA double strand breaks without off-target mutagenic effects.

Figure 53:
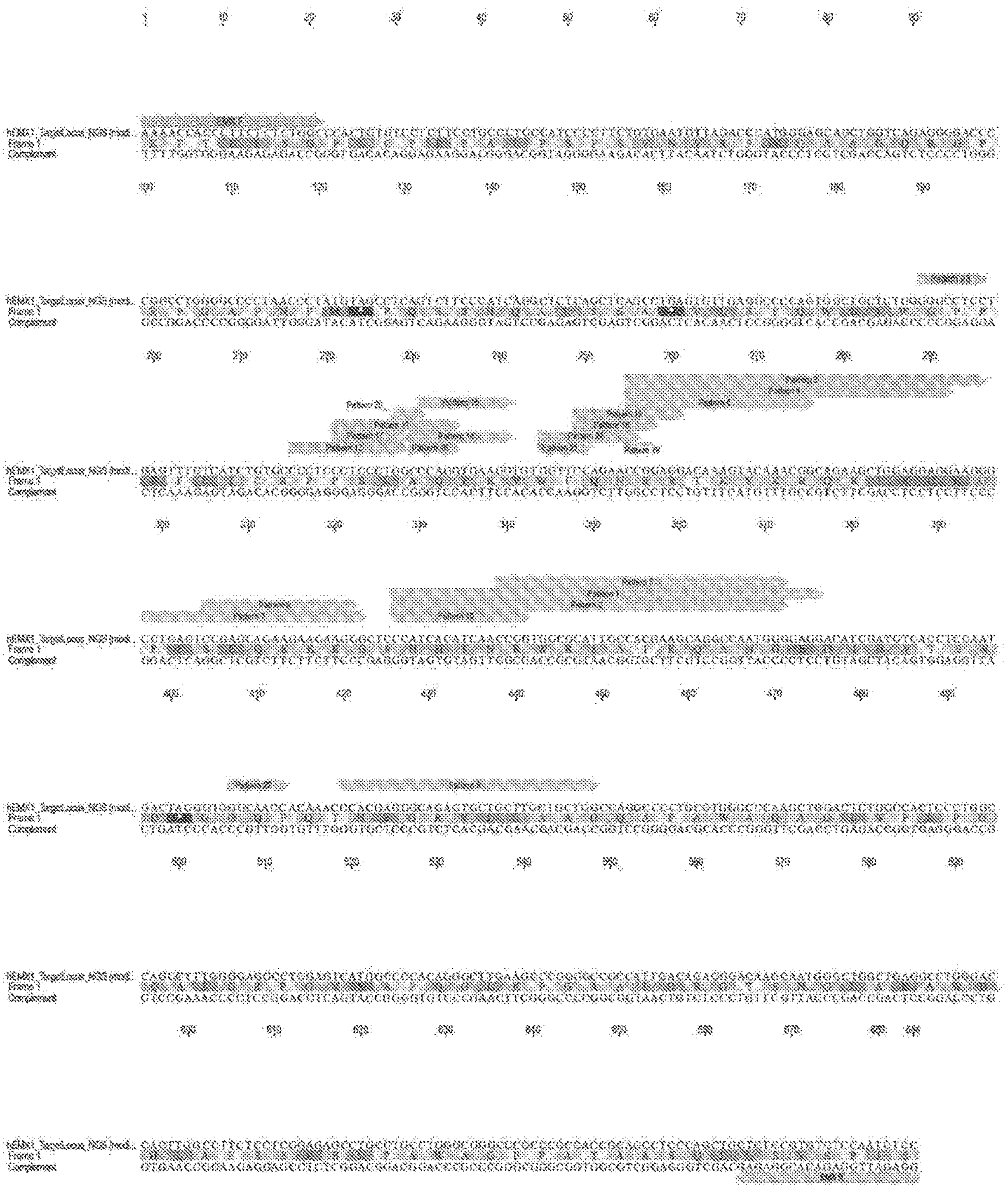
FIG. 53 shows a Genomic sequence map from the human Emx1 locus showing the locations of the 24 patterns listed in FIG. 33.
Figure 56:
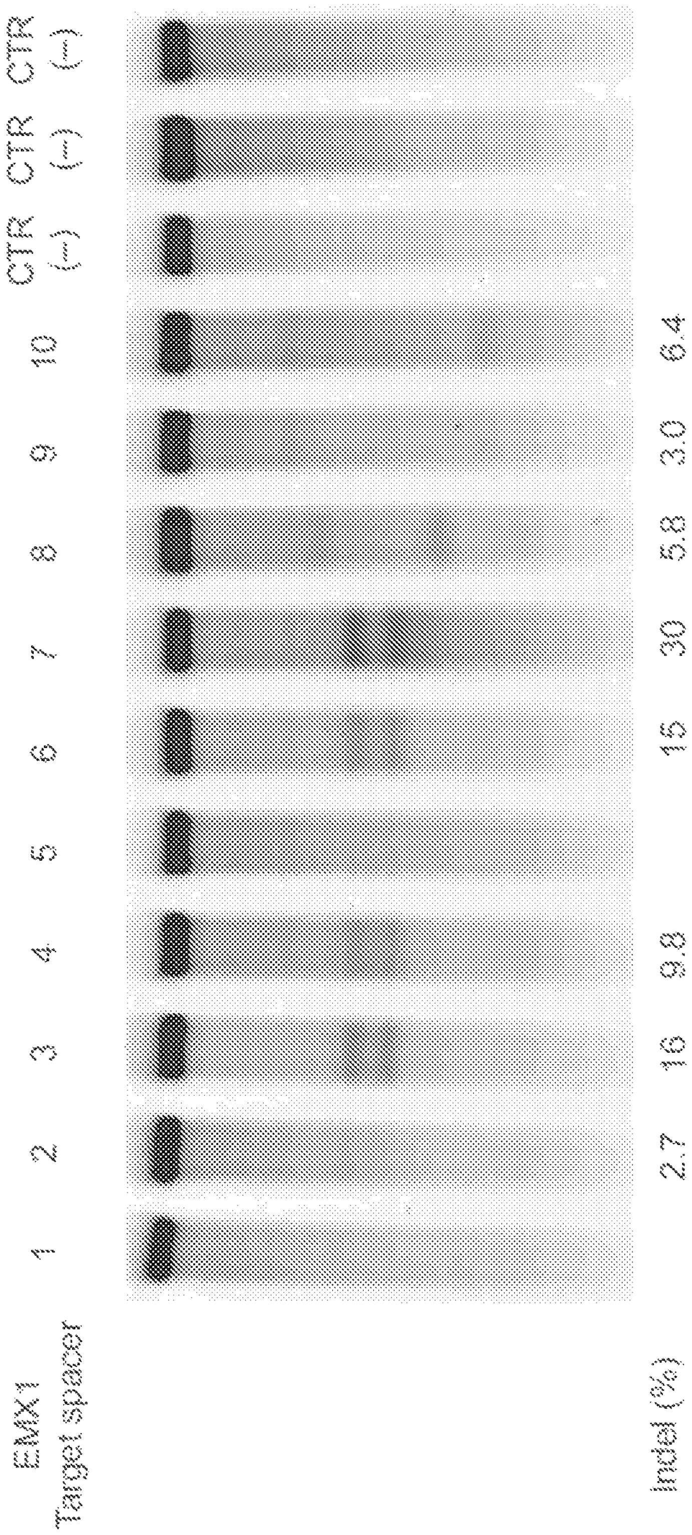
FIG. 56 shows a Representative Surveyor Gel showing genomic cleavage by SaCas9.
Figure 57:
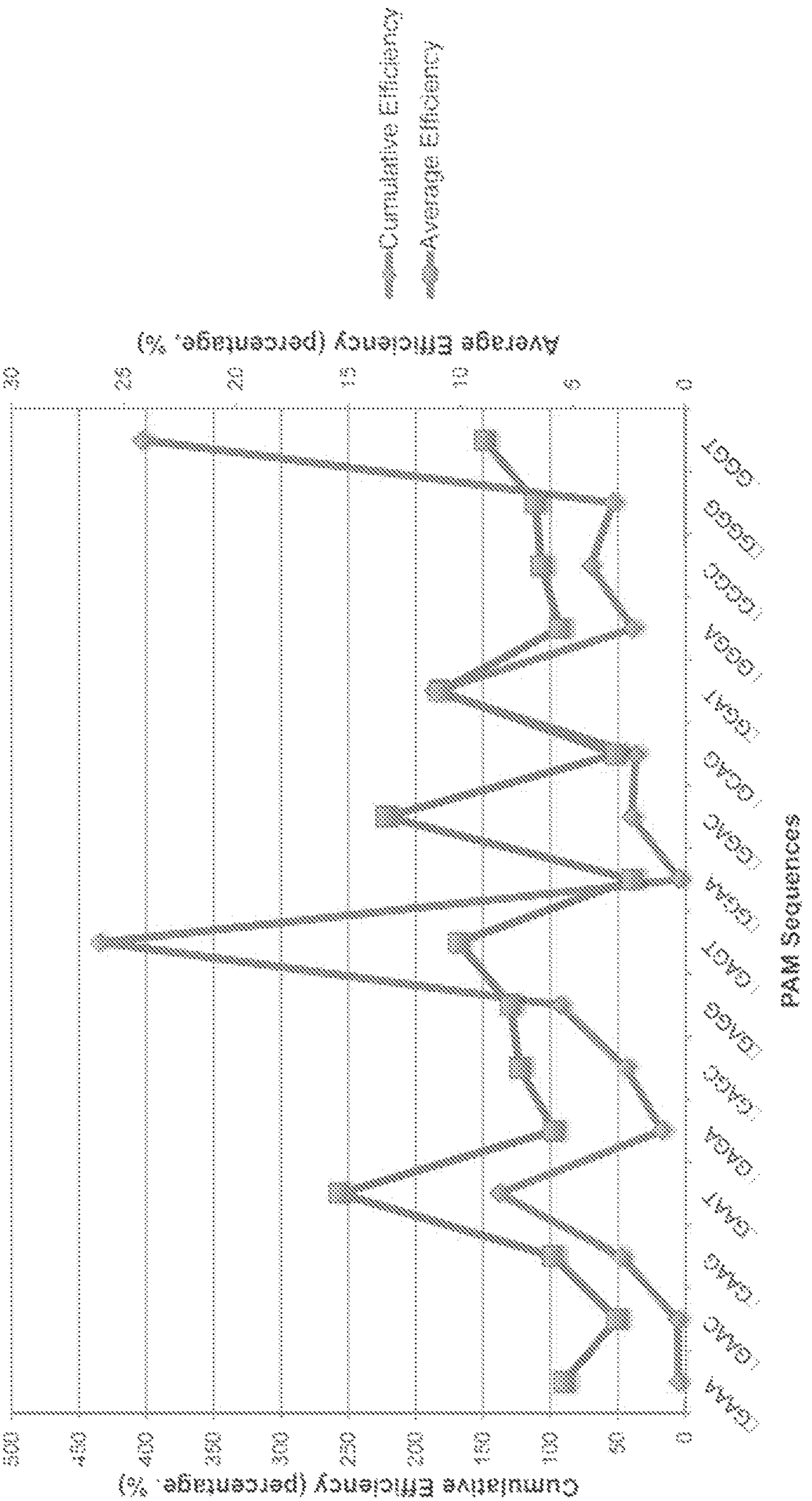
FIG. 57 shows Genome Cleavage Efficiency of PAM Sequences (All targets).
Figure 58:
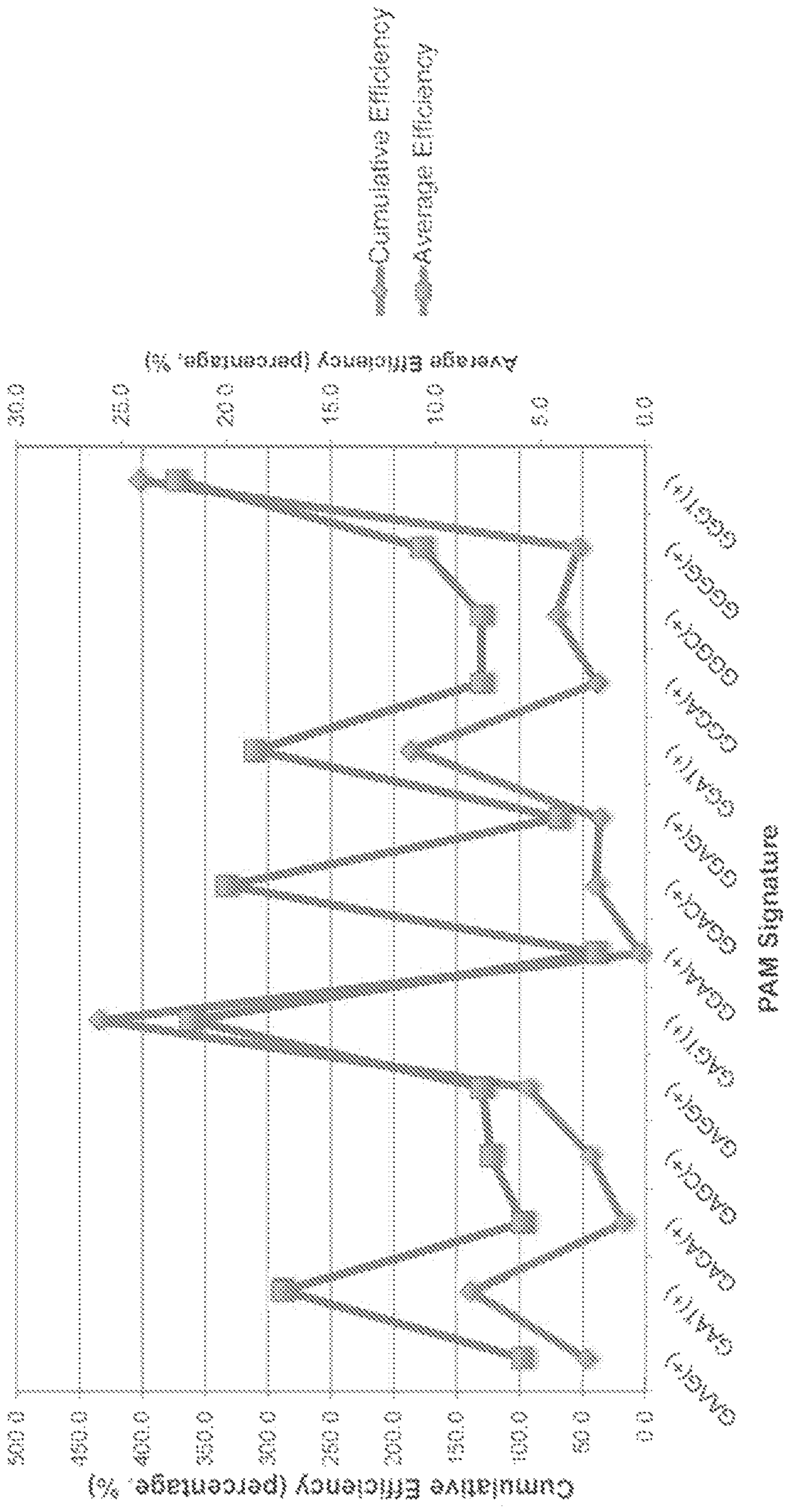
FIG. 58 shows Genome Cleavage Efficiency of PAM Sequences (Cleaved targets)
Figure 59:
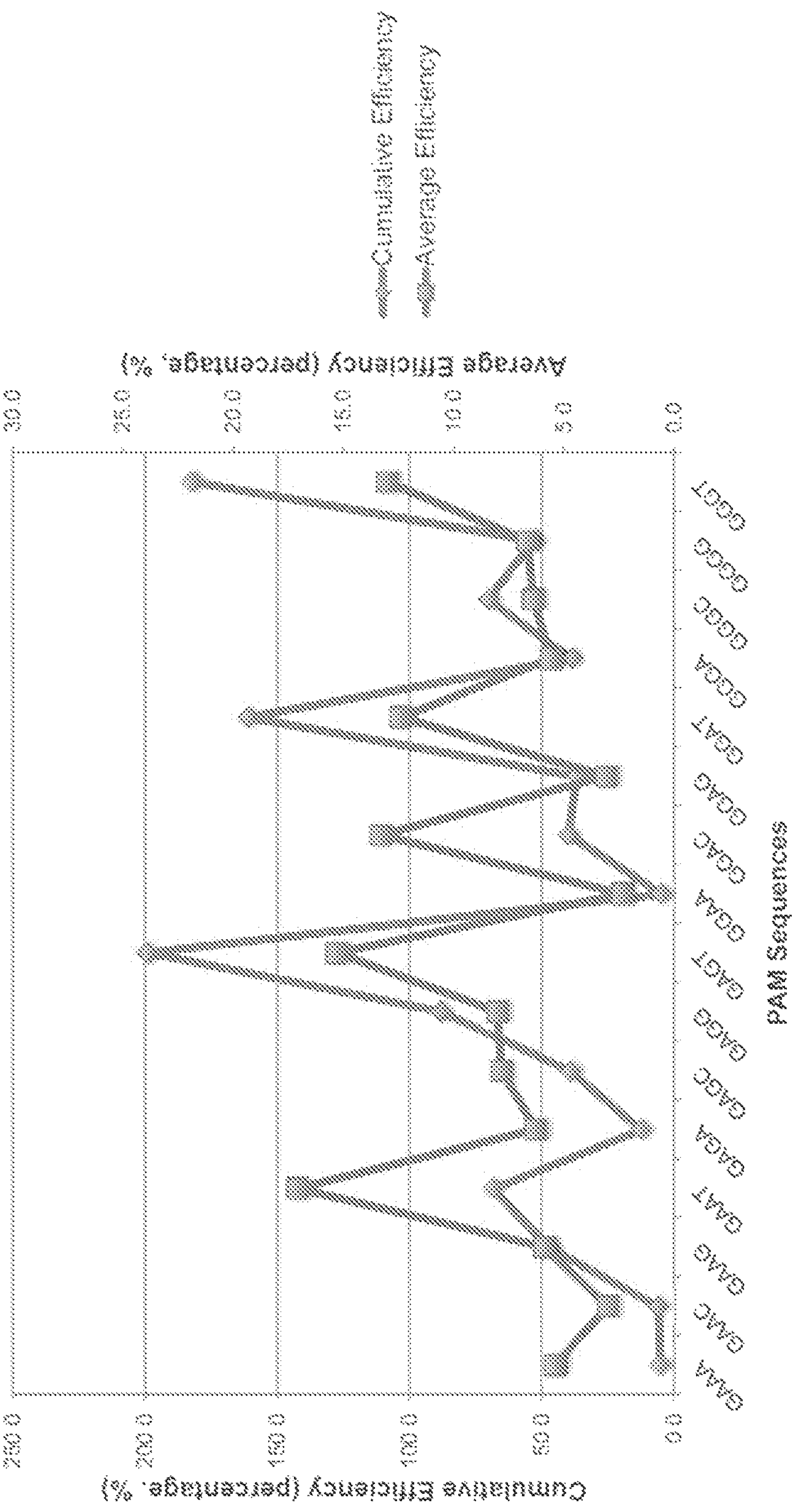
FIG. 59 shows Genome Cleavage Efficiency of PAM Sequences (All targets, discard low-efficiency and orphan targets).
Figure 60:
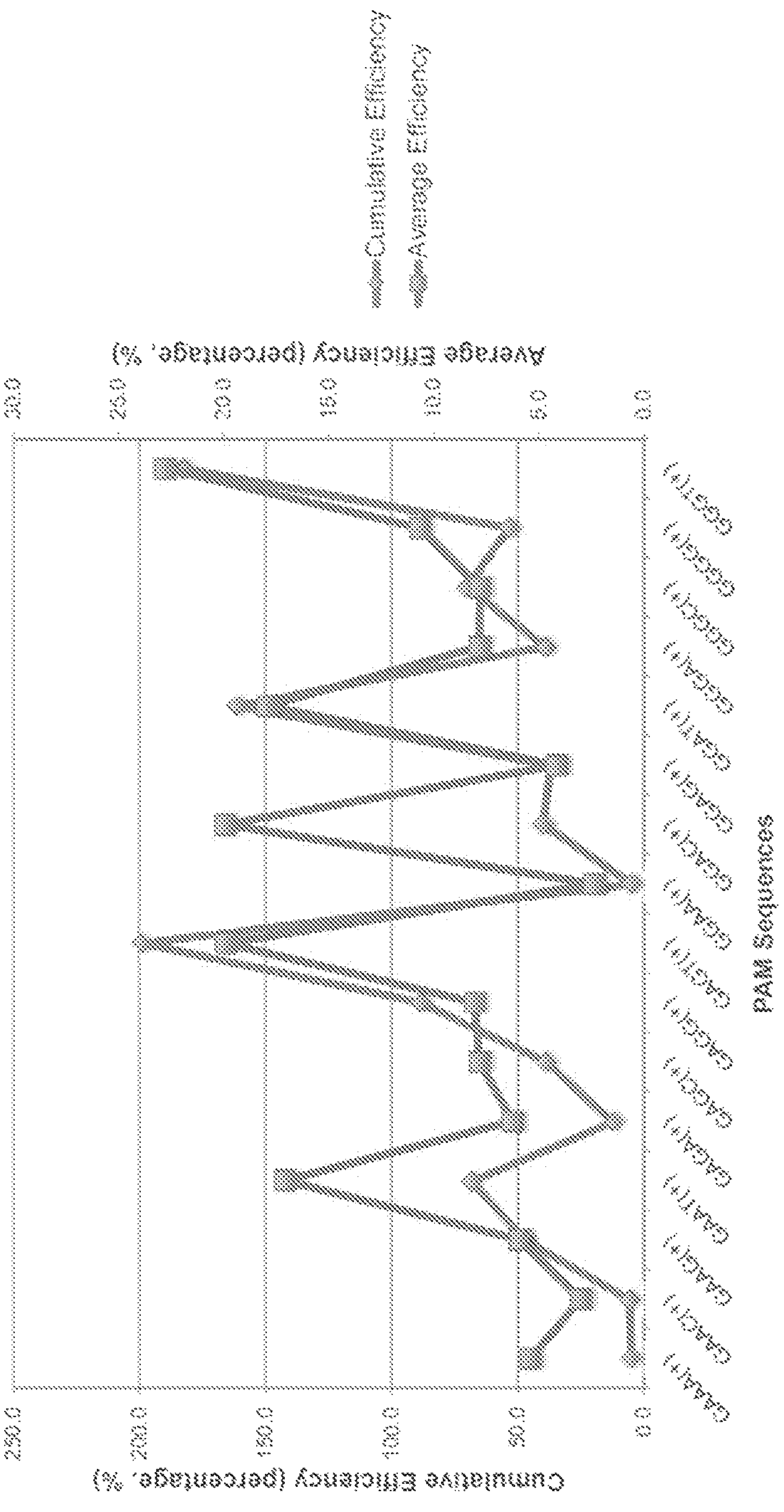
FIG. 60 shows Genome Cleavage Efficiency of PAM Sequences (Cleaved targets, discard low-efficiency and orphan targets).
Figure 61:
FIG. 61 shows a Sequence Logo for Working Cleaved Spacers & PAMs (New endogenous genome test showing that T is not required).
Figure 62:
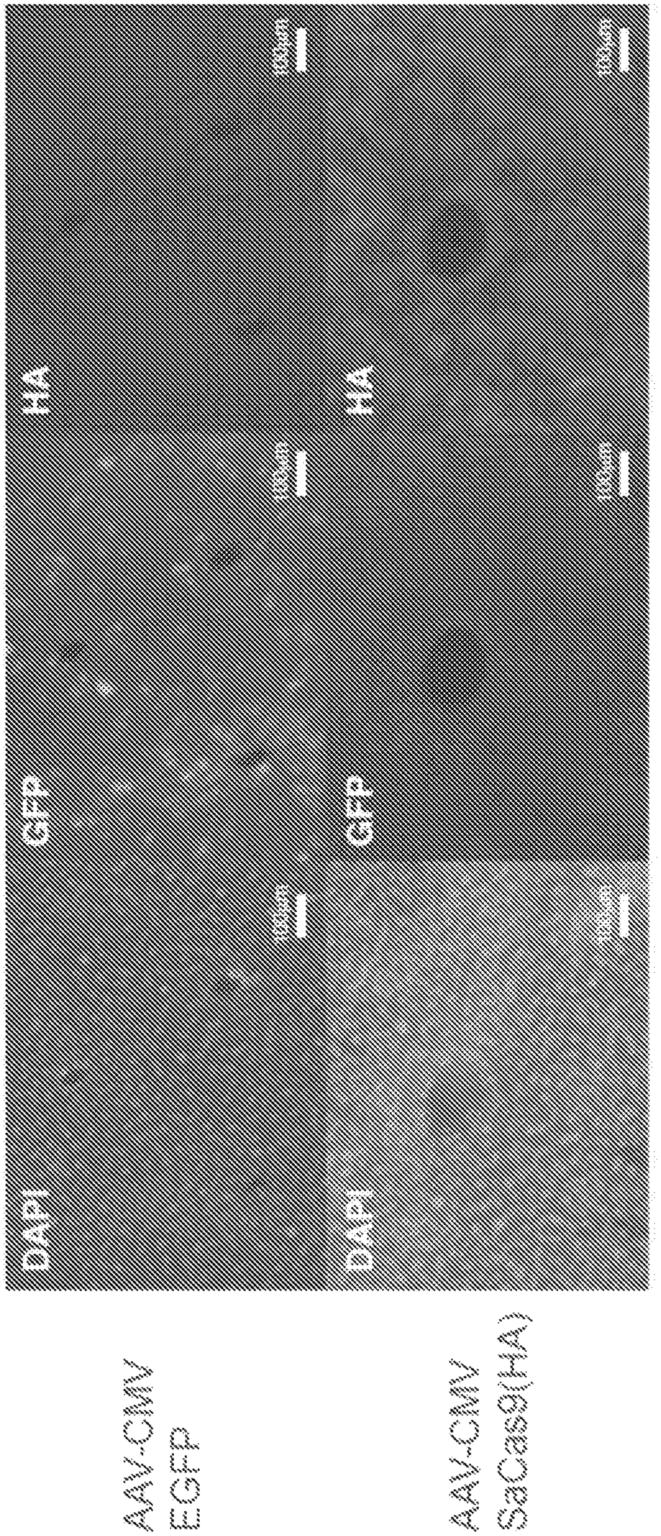
FIG. 62 shows Liver Tissue Slice Immunohistochemistry Staining Image from AAV-CMV-EGFP and AAV-CMV-SaCas9-U6-sgRNA (Pcsk9) injected animal (Verification of SaCas9 protein expression, 2 weeks post injection).
Figure 63:
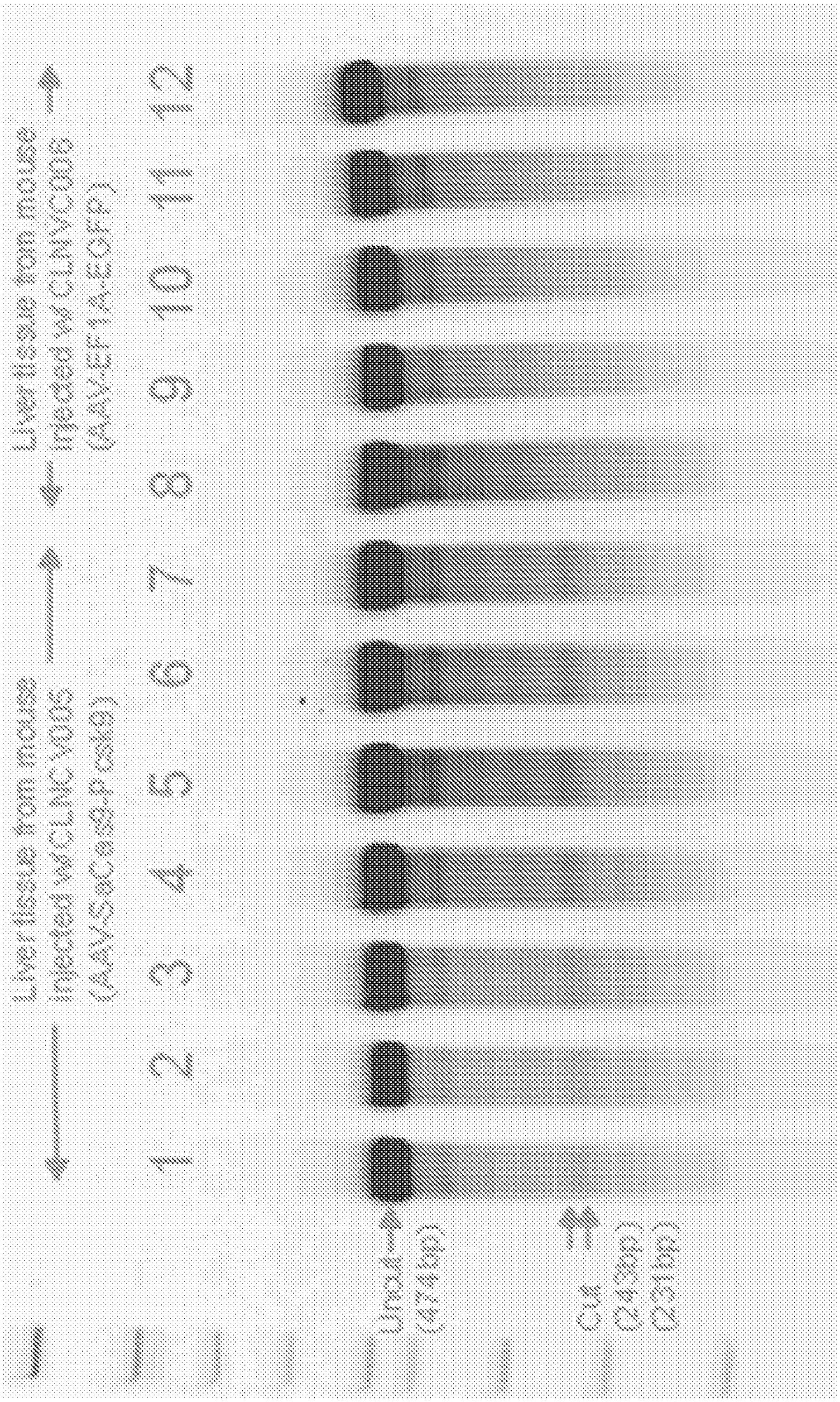
FIG. 63 shows Cleavage of Liver Tissue by SaCas9 delivered via tail-vein injection of AAV2/8 virus (1 week time points).
Figure 64:
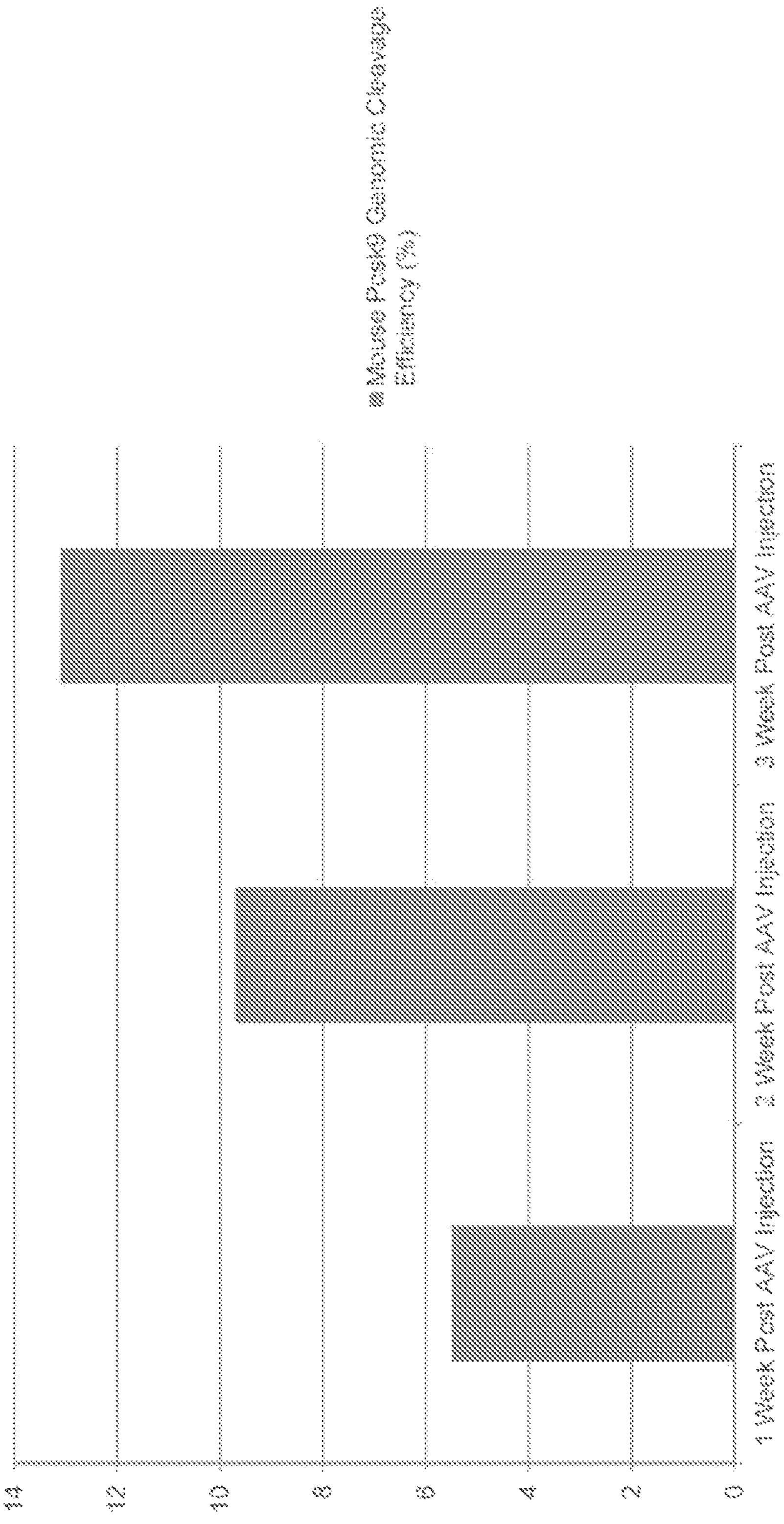
FIG. 64 shows a Time Course Assay for Cleavage of Liver Tissue by SaCas9 delivered via tail-vein injection of AAV2/8 (AAV2/8-SaCas9-U6-sgRNA (Pcsk9)) virus.

Applicants carried out experiments involving the co-transfection of HEK293FT cells with a plasmid encoding Cas9(D10A) nickase as well as DNA expression cassettes for one or more guides. Applicants transfected cells using Lipofectamine 2000, and transfected cells were harvested 48 or 72 hours after transfections. Double nicking-induced NHEJ were detected using the SURVEYOR nuclease assay as described previously herein (FIGS. 51, 52 and 53).

Applicants have further identified parameters that relate to efficient cleavage by the Cas9 nickase mutant when combined with two guide RNAs and these parameters include but are not limited to the length of the 5' overhang. Efficient cleavage is reported for 5' overhang of at least 26 base pairs. In a preferred embodiment of the invention, the 5' overhang is at least 30 base pairs and more preferably at least 34 base pairs. Overhangs of up to 200 base pairs may be acceptable for cleavage, while 5' overhangs less than 100 base pairs are preferred and 5' overhangs less than 50 base pairs are most preferred (FIGS. 54 and 55).

Example 36: In Vivo SaCas9 Project

The project started as Applicants wanted to further explore the diversity of the type II CRISPR/Cas system following the identification of *Streptococcus pyogenes* (Sp)

and *Streptococcus thermophiles* (St) CRISPR/Cas system as a functional genome engineering tool in mammalian cells.

By defining new functional type II CRISPR/Cas systems for application in mammalian cells, Applicants will potentially be able to find:

(1) CRISPR/Cas system with higher efficiency and/or specificity (2) CRISPR/Cas system with different Protospacer Adjacent Motif (PAM) that allows the targeting of broader range of genomic loci (3) CRISPR/Cas system with smaller size so Applicants could delivery them in vivo in a single vector with mammalian viral delivery system such as adeno-associated virus (AAV) vectors that have a packaging size limit (the current Sp or St system exceed this limit of 4.7 kb) and other desirable traits.

Identification and Design of Sa CRISPR/Cas System for in vivo application. Applicants tested a new type II CRISPR/Cas system in *Staphylococcus aureus* (Sa) that works in vitro in dsDNA cleavage assay and identified a putative PAM of NNGRRT. The components of this system are a Cas9 protein from Sa, a guide CRISPR RNA with direct repeats (DR) from Sa that will form a functional guide RNA complex with tracrRNA from Sa. This three-component system is similar to all other type II CRISPR/Cas systems. Hence, Applicants designed a two-component system, where Applicants fused the Sa tracrRNA to the Sa guide CRISPR RNA via a short stem-loop to form a chimeric guide RNA, exactly as Applicants did with the *Streptococcus pyogenes* (Sp) CRISPR/Cas system. This chimeric guide *RNA was able to support cleavage of dsDNA in vitro. Therefore, Applicants decided to clone the full two-component system*: cas9 and the chimeric guide RNA, into an AAV vector to test its functionality in living organisms.

Applicants chose the AAV system because it is a non-integrating, ssDNA-based, non-immunogenic mammalian virus that has broad-spectrum of tropism in different tissues/organs depending on the serontype that has been shown to be safe for in vivo application and also support long-term expression of transgene in living organisms.

Design of the initial AAV vector has (1) CMV promoter driving SaCas9 protein with a single NLS and a HA epitope tag. (2) human U6 promoter driving the chimeric RNA (see figures). These are placed in between two Inverted Terminal Repeats (ITRs) from the most-well studied AAV serotype 2 that serve as the viral packaging signal.

The PAM sequence test on endogenous mammalian genome is as follows: SaCas9 target spacers were selected across multiple genes to cover different potential PAM sequences. Different spacers were cloned into U6-sgRNA (single-guide RNA) expression dsDNA cassette U6-sgRNA expression dsDNA cassette were co-transfected into mammalian cells lines (293FT for human targets, N2a and Hepa for mouse targets). 72 hours following transfection, all genomic DNA were extracted and subjected to surveyor nuclease assay. Run through TBE Page Gel to detect genomic cleavage. Quantify genomic DNA cleavage efficiency and plot.

Summary of Genome Cleavage Efficiency and Other Statistics on all Tested Targets

| SaCas9 PAM Sequences | Targets Count | Cleavaged Targets Count | Percentage of Cleaved Targets (%) | Cumulative Cleavage Efficiency (%) | Average Spacer GC Content (%) |
|---|---|---|---|---|---|
| GAAA | 1 | 1 | 100.0 | 5.4 | 65.0 |
| GAAC | 2 | 2 | 100.0 | 6.1 | 55.0 |
| GAAG | 8 | 8 | 100.0 | 47.1 | 65.0 |
| GAAT | 9 | 8 | 88.9 | 138.4 | 66.1 |
| GAGA | 3 | 3 | 100.0 | 17.5 | 63.3 |
| GAGC | 6 | 6 | 100.0 | 44.2 | 60.0 |
| GAGG | 12 | 12 | 100.0 | 93.3 | 58.8 |
| GAGT | 44 | 20 | 45.5 | 434.0 | 56.9 |
| GGAA | 2 | 2 | 100.0 | 4.7 | 50.0 |
| GGAC | 3 | 2 | 66.7 | 39.9 | 60.0 |
| GGAG | 12 | 9 | 75.0 | 36.9 | 59.6 |
| GGAT | 20 | 10 | 50.0 | 186.2 | 59.0 |
| GGGA | 7 | 5 | 71.4 | 39.1 | 63.6 |
| GGGC | 11 | 9 | 81.8 | 70.3 | 65.5 |
| GGGG | 8 | 5 | 62.5 | 53.3 | 70.0 |
| GGGT | 45 | 18 | 40.0 | 104.3 | 56.2 |
| Grand Total | 196 | 120 | 61.2 | 1618.6 | 59.4 |

Summary of Genome Cleavage Efficiency and Other Statistics on all Tested Targets (Cleaned Up)

| SaCas9 PAM Sequences | Targets Count | Cleavaged Targets Count | Percentage of Cleaved Targets (%) | Cumulative Cleavage Efficiency (%) | Average Cleavage Efficiency (%) | Average Spacer GC Content (%) |
|---|---|---|---|---|---|---|
| GAAA | 1 | 1 | 100.0 | 5.4 | 5.4 | 65.0 |
| GAAC | 2 | 2 | 100.0 | 6.1 | 3.0 | 55.0 |
| GAAG | 8 | 8 | 100.0 | 47.1 | 5.9 | 65.0 |
| GAAT | 4 | 4 | 100.0 | 68.4 | 17.1 | 65.0 |
| GAGA | 2 | 2 | 100.0 | 12.5 | 6.3 | 67.5 |
| GAGC | 5 | 5 | 100.0 | 39.2 | 7.8 | 61.0 |
| GAGG | 11 | 11 | 100.0 | 88.3 | 8.0 | 58.2 |
| GAGT | 13 | 10 | 76.9 | 199.0 | 15.3 | 56.2 |
| GGAA | 2 | 2 | 100.0 | 4.7 | 2.3 | 50.0 |

-continued

| SaCas9 PAM Sequences | Targets Count | Cleavaged Targets Count | Percentage of Cleaved Targets (%) | Cumulative Cleavage Efficiency (%) | Average Cleavage Efficiency (%) | Average Spacer GC Content (%) |
|---|---|---|---|---|---|---|
| GGAC | 3 | 2 | 66.7 | 39.9 | 13.3 | 60.0 |
| GGAG | 12 | 9 | 75.0 | 36.9 | 3.1 | 59.6 |
| GGAT | 13 | 9 | 69.2 | 161.2 | 12.4 | 58.8 |
| GGGA | 7 | 5 | 71.4 | 39.1 | 5.6 | 63.6 |
| GGGC | 11 | 9 | 81.8 | 70.3 | 6.4 | 65.5 |
| GGGG | 8 | 5 | 62.5 | 53.3 | 6.7 | 70.0 |
| GGGT | 14 | 8 | 57.1 | 182.3 | 13.0 | 54.6 |
| Grand Total | 116 | 92 | 79.3 | 1053.6 | 9.1 | 60.5 |

Results from the PAM test are shown in FIGS. 56-62. A comprehensive test of over 100 targets identified that the PAM for SaCas9 could be described as NNGRR (but not the NNGRRT as indicated earlier).

PAM Test Summary: (1) NNGRR for general SaCas9 PAM—helpful for design new targets, (2) Testing double-nickase with new targets, (3) NNGRG might be more potent PAM?

Targets for Demonstrating In Vivo Application and Therapeutic Potential of the CRISPR/Cas System.

Mouse Pcsk9 gene. This gene is a key gene in regulating lipid metabolism, the Pcsk9 protein plays a major regulatory role in cholesterol homeostasis. Knock-down or disruption of this gene both in natural cases by human SNPs or in animal models, results in a reduction of LDL-receptor level and blood cholesterol level. Drugs that block PCSK9 can lower cholesterol, so Pcsk9 has been shown to be a potent drug target for hypercholesterolemia, etc.

Mouse Hmgcr gene. This gene is another key gene in lipid metabolism, the Hmgcr protein product is the rate-controlling enzyme of the mevalonate pathway, the metabolic pathway that produces cholesterol and other isoprenoids. Knock-down or disruption of this gene has been shown to reduce blood cholesterol level, etc.

human SERPINA1 (human AAT) gene. SERPINA1 gene encodes the protein called Alpha-1 Antitrypsin (A1AT). It is a protease inhibitor belonging to the serpin superfamily. It protects tissues from enzymes of inflammatory cells. In its absence due to genetic defect (mutations in this gene), the inability to inhibit enzymes from inflammatory cells leads to elasticity of the lungs, resulting in respiratory complications such as emphysema, or COPD (chronic obstructive pulmonary disease) in adults and cirrhosis in adults or children. This is a disease in human called AAT deficiency. One of the most prevalent mutations that led to this disease is PiZ allele, or the Z allele. This mutation is a glutamate to lysine mutation at position 342 of the human AAT gene (SPERINA1), and Applicants' target in this case target exactly this genomic locus in human genome. Applicants also designed a homologous recombination (HR) template to correct his mutation so that when co-deliver Sa CRISPR/Cas system and the HR template in AAV form in vivo, Applicants could correct this mutation in liver to treat this disease.

Test of CMV version of the AAV virus Design: Applicants tested packaging the AAV virus with the CMV promoter version of the vector. The goal is to demonstrate delivery of the Sa CRISPR/Cas system in vivo, and then test if the expressed SaCas9 with its guide chimeric RNA could support genome engineering (cleavage of endogenous genomic locus) in vivo.

Applicants chose to use liver as our target organ, and use a tail-vein injection procedure to delivery AAV into the living organism (mouse). As previous paper showed (see references), AAV8 is a AAV serotype that support efficiency transduction of hepatocyte via tail vein injection and also long-term expression of transgene following transduction.

Because heparin-column based purification yield fastest turnaround time and highly purified virus, Applicants decided to try purify Applicants' AAV8 virus using heparin column. However, due to AAV2 has best efficiency in binding to heparin column, other AAV serotypes were mixed with AAV2 to produce 'mosaic virus' bearing both AAV2 and AAV8 capsid proteins in the viral particle to allow purification via heparin column. However, Applicants tested the combination of AAV2-AAV8 mosaic virus and it has poor binding to the heparin column. Hence, Applicants decided to use chloroform-PEG based purification method to purify pure AAV8 viruses for Applicants' application.

Applicants Purified AAV2/8 (Serotype AAV8 Virus Packaged with AAV2 Packaging Signal ITR) from all Four Constructs:

CMV-SaCas9-U6-chimeric-guide-RNA targeting mouse Pcsk9 gene coding region. Target the start codon region within the first exon of Pcsk9 so Applicants could disrupt this gene.

CMV-SaCas9-U6-chimeric-guide-RNA targeting mouse Hmgcr gene coding region. Target the start codon region within the first exon of Hmgcr so Applicants could disrupt this gene. Target a new site at the key phosphorylation site (Serine872 in human) at the end of the gene within the last exon so Applicants could functionally disrupt the regulation of Hmgcr gene product activity.

CMV-SaCas9-U6-chimeric-guide-RNA targeting human SERPINA1 (human AAT) gene coding region. Target the Z allele site, i.e., the glutamate to lysine mutation at position 342 of the human AAT gene (SPERINA1).

CMV-GFP viruses as control viruses and also a reporter viruses. This is a virus bearing a CMV promoter driving expression of GFP reporter gene. So the green fluorescence could serve as indicator of liver cell transduction efficiency and also as marker for monitoring the expression level and duration of the transgene. Applicants hope to use this to verify the AAV2/8 system Applicants are using.

Procedure: Applicants cloned, amplified, and purified viral vectors as listed above. Applicants validated all targets first in cultured mouse hepatocytes or human 293FT cells for cleavage efficiency of target genomic loci. Applicants pick the best target, injected the AAV2/8 viral particle via tail vein at a total of around 1E11 viral particle per animal. Then Applicants: (1) sacrifice animal at different time point to obtain liver tissue for checking expression using fluorescent microscope and immune-histochemistry, and also verifying genome engineering (genome editing) using surveyor nuclease assay and genome sequencing. (2) take blood samples from animal over time to check for phenotypic changes. (3) Applicants also use material from (1) and (2) to detect disruption of target gene expression with qPCR, ELISA, or western blot, or to detect lipid level change (blood cholesterol level for Pcsk9 and Hmgcr), serum enzyme level or other phenotypic change.

Results: Surveyor results from in vitro screening and genome cleavage validation of all targets via surveyor assay. Time course analysis of cleavage efficiency from liver tissue in mice injected with AAV2/8 SaCas9 (targeting Pcsk9) virus. Liver cell transduction and transgene (GFP) expression with AAV2/8 CMV-GFP: image from liver sections, Liver cell transduction and transgene (SaCas9) expression with AAV2/8 SaCas9 viruses: image from liver sections. Surveyor results of gDNA extracted from liver tissue of mice injected with AAV2/8 SaCas9 (targeting Pcsk9) virus.

Viruses, Animals and Injection Parameters:
AAV2/8—CMV-SaCas9-Pcsk9-Target1
AAV2/8—CMV-EGFP-WPRE
Mouse—8 weeks, C57BL/6
Tail Vein Injection
Injection Volume: 100 ul of 1.0E12 (vp/ml) stock
Viral particle delivered: 1.0E11 total vp/mouse
Animal Processing and Data Collection
First time point 1 week. Then 2, 3, 4 wks. Total 4 time points.
Saline perfusion of AAV-SaCas9-Pcsk9 & AAV-EGFP injected mouse.
Blood collection from right atrium ~100 ul.
Acute dissection of liver tissue, cut into smaller pieces, put into −80 C storage for Surveyor &
Protein analysis (X12 tubes) and for qPCR (RNA later, X4 tubes).
Use Qiagen DNA Extraction and QuickExtract for processing.
Use Sigma and Qiagen RNA extraction Kit for RNA analysis.
Use Cell Signaling Ripa buffer for protein extraction.
Time Course Assay for Cleavage of Liver Tissue by SaCas9 delivered via tail-vein injection of AAV2/8 virus T1 = 1 weeks post tail vein injection

| Tissue Sample | Cleavage Efficiency | Average Cleavage (%) |
|---|---|---|
| T1-AAV-SaCas9-Pcsk9-LiverTissue1 | 6.19 | 5.49 |
| T1-AAV-SaCas9-Pcsk9-LiverTissue2 | 5.31 | |
| T1-AAV-SaCas9-Pcsk9-LiverTissue3 | 4.98 | |

T2 = 2 weeks post tail vein injection

| Tissue Sample | Cleavage Efficiency | Average Cleavage (%) |
|---|---|---|
| T2-AAV-SaCas9-Pcsk9-LiverTissue1 | 11.26 | 9.74 |
| T2-AAV-SaCas9-Pcsk9-LiverTissue2 | 4.27 | |
| T2-AAV-SaCas9-Pcsk9-LiverTissue3 | 13.69 | |

T3 = 3 weeks post tail vein injection

| Tissue Sample | Cleavage Efficiency | Average Cleavage (%) |
|---|---|---|
| T3-AAV-SaCas9-Pcsk9-LiverTissue1 | 14.15 | 13.10 |
| T3-AAV-SaCas9-Pcsk9-LiverTissue2 | 12.74 | |
| T3-AAV-SaCas9-Pcsk9-LiverTissue3 | 12.41 | |

Re-design the AAV vector with liver-specific TBG promoter system. Because the genome cleavage efficiency form CMV version of SaCas9 virus (AAV2/8) was not very high, and also the GFP control reporter virus show that this might be due to the CMV version virus did not support strong and long-term expression of the Sa CRISPR/Cas system. After looking into literature, I found a TBG promoter (Thyroxine-binding globulin), a very strong promoter for specific expression of proteins in liver at high level. After cloning the TBG promoter obtained from addgene into Applicants' own AAV vector, new batch of TBG version of the AAV2/8 virus were made. The new TBG version virus includes the same set of targets as the CMV version (Pcsk9, Hmgcr, human AAT, GFP), and additionally a Rosa26 target that serves as a negative control (Rosa26 is a safe-harbor genomic locus in the human genome).

Figure 65:
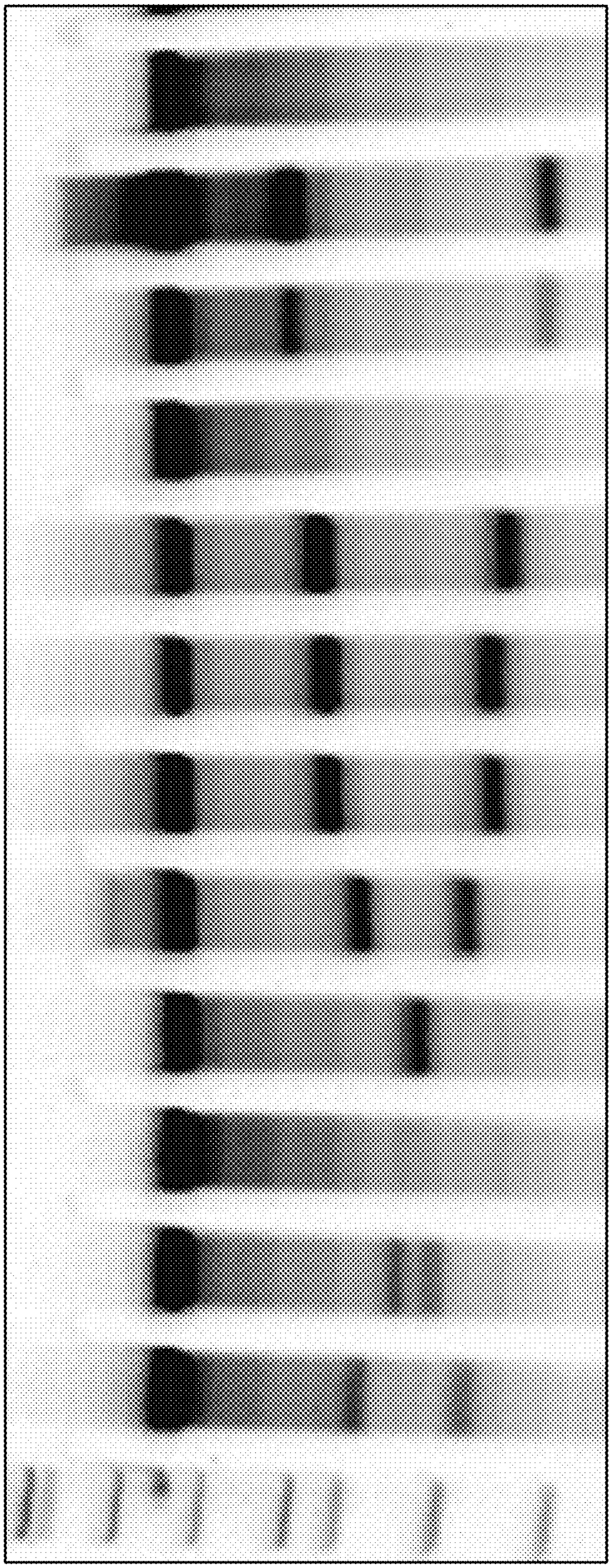
FIG. 65 shows screening for functional CRISPR/Cas targets in human 293FT cells after delivery of SaCas9 and U6-sgRNA cassette targeting human SERPINA1 gene loci, followed by surveyor assay and gel analysis of 12 of the total 24 different spacer designs of sgRNA-expressing dsDNA targeting human SERPINA1 gene, the DNA Ladder is to the left.

New Human SERPINA1 Target for Therapeutic Correction of human Alpha-1 antitrypsin deficiency (AAT). Human AAT syndrome is a severe disorder results from a single-base G-to-A mutation leading to amino acid change Glu342Lys in the human SERPINA1 gene (Yusa, et al. Nature 2011). Applicants use CRISPR/Cas to target this gene and deliver in vivo with AAV2/8 into liver tissue, the relevant organ in human for this disease, to achieve gene therapy for this disorder. The test in FIG. 65 is screening for functional CRISPR/Cas targets in human 293FT cells after delivery of SaCas9 and U6-sgRNA cassette targeting human SERPINA1 gene loci, followed by surveyor assay. Protocol: sgRNA-expressing dsDNA targeting human SERPINA1 gene were co-transfected with SaCas9 plasmid into human HEK 293FT cell line. Assay performed after 72 hour incubation. Genomic DNA were amplified and then subject to surveyor nuclease assay. The image in FIG. 65 shows the gel analysis of 12 of the total 24 different spacer designs, the DNA Ladder is to the left.

For Applicants' therapeutic design, to achieve high efficiency of correction, Applicants follow up on the closest targets to the human AAT mutation (Z allele, GAG-AAG/Glu-Arg mutation) listed to the right, with spacer target No. 15 being the closest with highest efficiency.

Applicants' strategy is co-delivery of CRISPR/Cas system targeting this site with a correction vector bearing the wild-type copy (non-mutated) of the SERPINA1 genomic region.

| SaCas9 Target Spacer | Genome Cleavage Efficiency |
|---|---|
| hSERPINA1-Spacer1 | 11.2 |
| hSERPINA1-Spacer2 | 10.6 |
| hSERPINA1-Spacer3 | 1.6 |
| hSERPINA1-Spacer4 | 13.8 |
| hSERPINA1-Spacer5 | 30.2 |
| hSERPINA1-Spacer6 | 34.2 |

-continued

| SaCas9 Target Spacer | Genome Cleavage Efficiency |
|---|---|
| hSERPINA1-Spacer7 | 39.3 |
| hSERPINA1-Spacer8 | 40.3 |
| hSERPINA1-Spacer9 | 0.0 |
| hSERPINA1-Spacer10 | 15.9 |
| hSERPINA1-Spacer11 | 19.4 |
| hSERPINA1-Spacer12 | 0.0 |
| hSERPINA1-Spacer13 | 30.8 |
| hSERPINA1-Spacer14 | 0.0 |
| hSERPINA1-Spacer15 | 34.0 |
| hSERPINA1-Spacer16 | 16.0 |
| hSERPINA1-Spacer17 | 27.9 |
| hSERPINA1-Spacer18 | 12.9 |
| hSERPINA1-Spacer19 | 18.8 |
| hSERPINA1-Spacer20 | 21.0 |
| hSERPINA1-Spacer21 | 21.7 |
| hSERPINA1-Spacer22 | 25.7 |
| hSERPINA1-Spacer23 | 26.4 |
| hSERPINA1-Spacer24 | 17.0 |

Figure 66:
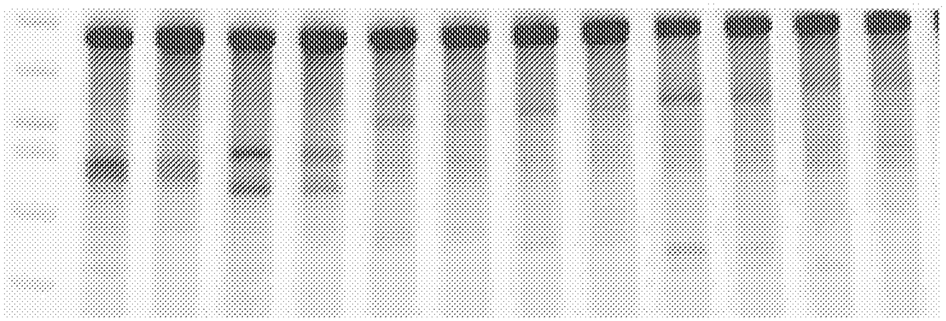
FIG. 66 shows gel analysis of 12 samples, for each of the 6 spacer designs of sgRNA-expressing dsDNA were co-transfected with SaCas9 plasmid into Mouse Hepatocyte cell line, two replica were placed next to each other. The DNA Ladder is to the left.

Mouse Hmgcr New Targets targeting the phosphorylated serine residue (controls the activity of Hmgcr to regulate cholesterol synthesis and the last exon). sgRNA-expressing dsDNA were co-transfected with SaCas9 plasmid into Mouse Hepatocyte cell line. Assay performed after 72 hour incubation. Genomic DNA were amplified and then subject to surveyor nuclease assay. Top-left image shows the gel analysis of 12 samples, for each of the 6 spacer designs, two replica were placed next to each other (see FIG. 66). The DNA Ladder is to the left.

SaCas9 In Vivo Delivery Via AAV2/8 with TBG Version Constructs for In Vivo Genome Engineering.

Viruses, Animals and Injection Parameters: AAV2/8—TBG-EGFP-WPRE

AAV2/8—CMV-EGFP-WPRE

Mouse—8 weeks, C57BL/6

Tail Vein Injection

Injection Volume: 100 ul of 1.0E12 (vp/ml) stock

Viral particle delivered: 1.0E11 total vp/mouse.

Figure 67:
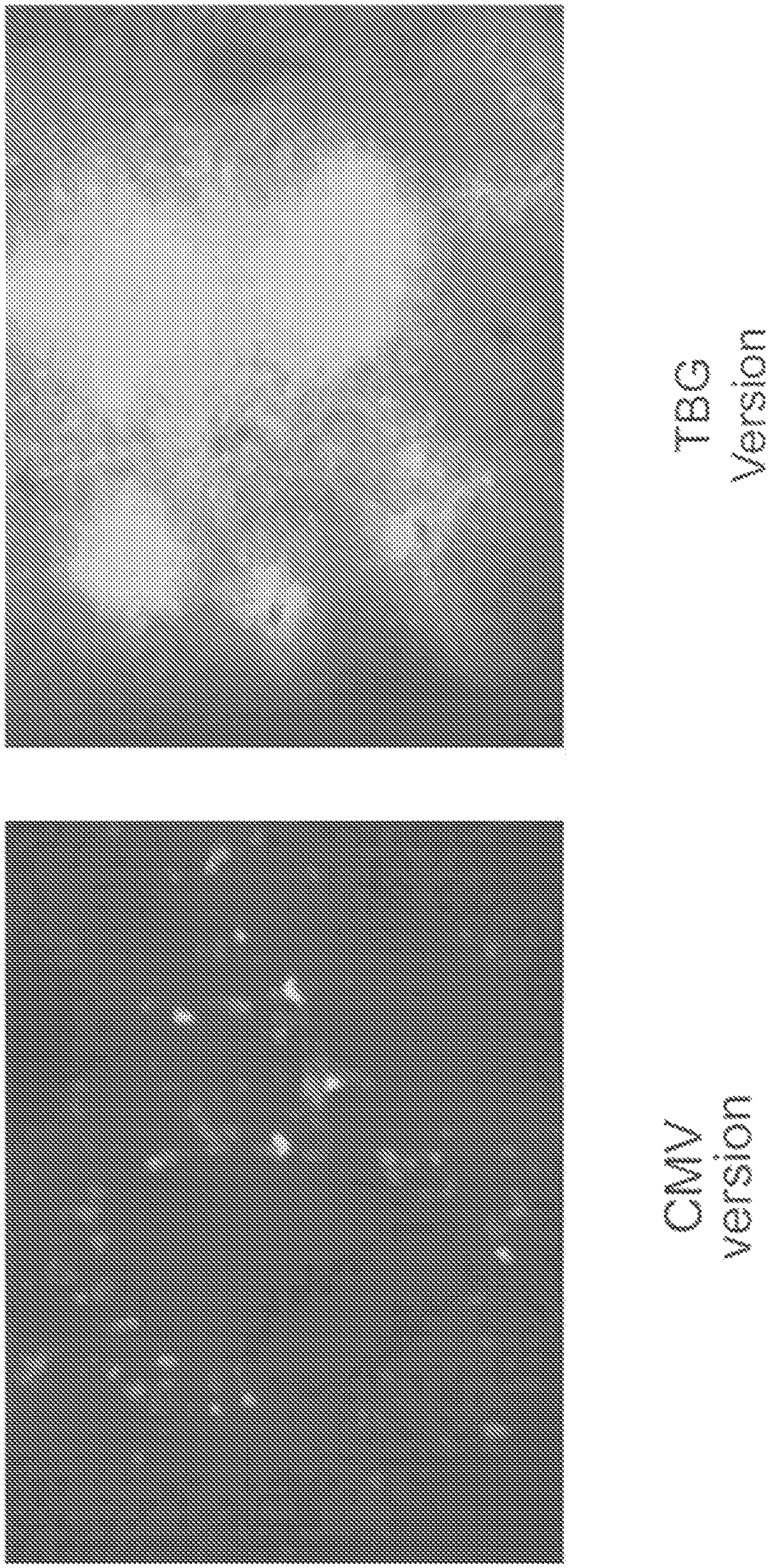
FIG. 67 shows Acute dissected liver tissue from mouse injected with TBG version vs. CMV version of EGFP (6 days post injection, GFP channel image, 10×).
Figure 68A:
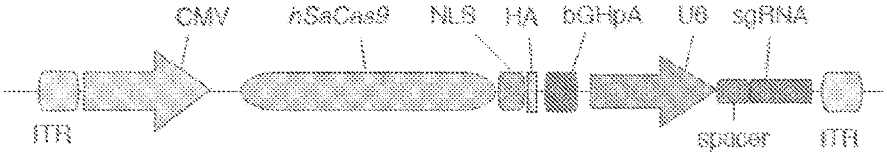
FIG. 68A-68B shows (A) Design of AAV vector for packaging of SaCas9 and guide RNA expression systems with the ubiquitous mammalian CMV promoter for delivery into a wide range of tissues. (B) Design of AAV vector for packaging of SaCas9 and guide RNA expression systems with the liver-specific TBG promoter for targeting hepatocytes in vivo. ITR, AAV inverted terminal repeats. hSaCas9, human codon optimized SaCas9. NLS, nuclear localization signal. HA, Human influenza hemagglutinin derived tag. bGHpA, bovine growth hormone polyadenylation signal. U6, human U6 promoter. sgRNA, single-guide RNA.
Figure 68B:
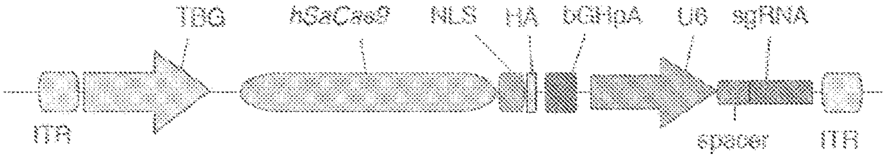
Figure 69A:
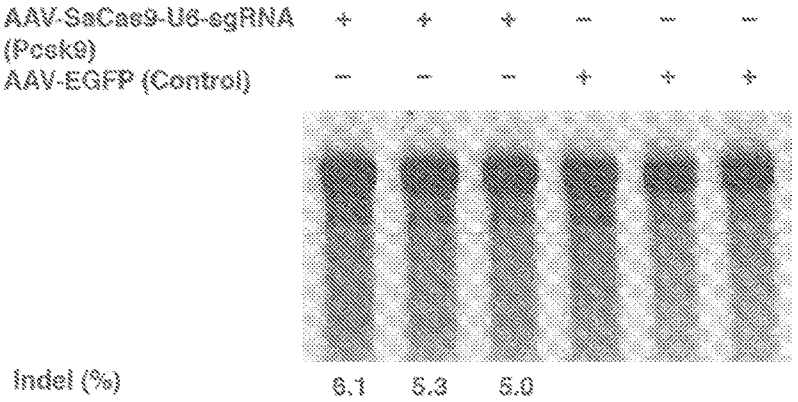
FIG. 69A-69B shows (A) Surveyor assay results showing genomic modification rate for liver tissues from mouse injected with AAV2/8 expressing SaCas9 targeting mouse Pcsk9 gene or control AAV2/8 virus expressing EGFP reporter gene. All samples were taken 1 wk after tail vein injection. (B) Statistics summarizing cleavage efficiency from all three time points collected from mouse injected with AAV2/8 expressing either SaCas9 targeting mouse Pcsk9 gene.
Figure 69B:
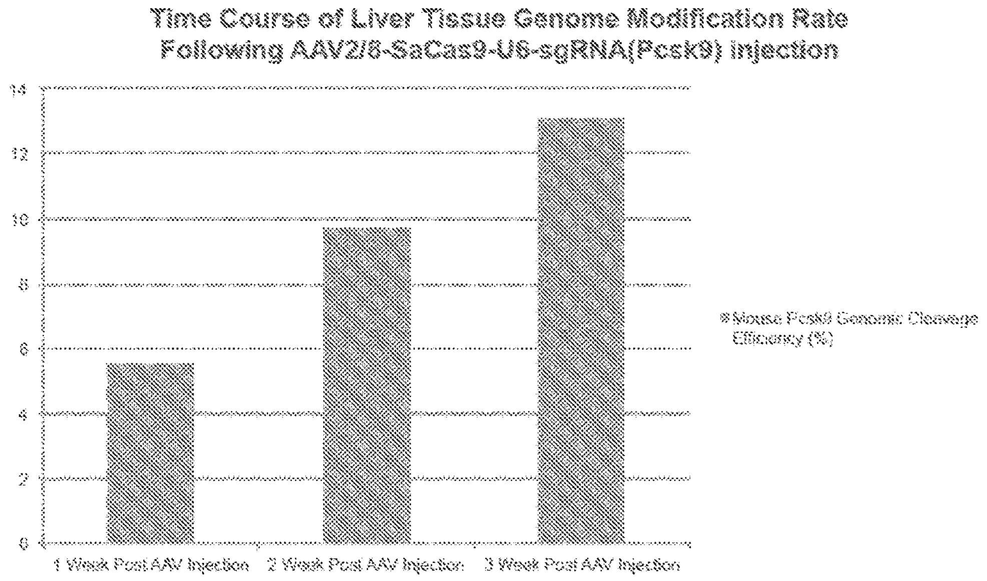

FIG. 67 shows Acute dissected liver tissue from mouse injected with TBG version vs. CMV version of EGFP (6 days post injection, GFP channel image, 10×).

CMV vs. TBG promoter for in vivo delivery into mouse liver with AAV2/8. TBG has much stronger expression and transduction efficiency at the same time point compared with CMV.

Apolipoprotein B (ApoB) are the primary apolipoproteins of chylomicrons and low-density lipoproteins (LDL), which is responsible for carrying cholesterol to tissues. Disruption of ApoB led to lower level of cholesterol, potentially resulting in healthier heart conditions.

Example 37: Efficient In Vivo Genome Editing of Somatic Tissue Via Cas9

The RNA-guided endonuclease Cas9 from the microbial CRISPR system has emerged as a versatile genome editing platform for eukaryotic cells. However, applications of Cas9 in mammalian somatic tissue in vivo have remained challenging largely due to difficulties in gene delivery of the *Streptococcus pyogenes* Cas9 (SpCas9), the most commonly used Cas9 whose large molecular weight impedes packaging into viral vectors. Applicants have identified six small Cas9 orthologs and their corresponding protospacer adjacent motifs (PAM), which are optimized for mammalian genome editing. In particular, Applicants have shown that Cas9 from *Staphylococcus aureus* (SaCas9), which is 23% smaller than SpCas9, can edit the mammalian genome with high efficiency on par with SpCas9, and be packaged along with its single-guide RNA (sgRNA) into adeno-associated virus (AAV) as a single vector for delivery into adult mice. Applicants demonstrate targeting of the mouse liver and observed 30% gene modification in vivo within 3 weeks of injection. This demonstration of AAV-mediated Cas9 delivery to postnatal animals further expands the potential of the system for interrogating basic biology, modeling human diseases, and advancing therapeutic development.

The CRISPR (clustered regularly interspaced short palindromic repeats)-Cas system is a RNA-guided endonuclease system from bacteria and archaea that provides adaptive immunity against exogenous nucleic acids. Of the three CRISPR-Cas classes, the Type II system has to date attracted the most interest as a genome engineering platform because of its relatively simple and well-characterized mechanism—a single endonuclease (Cas9) and two small RNAs, the CRISPR RNA (crRNA) that contains the DNA-targeting guide sequence (spacer) and the auxiliary trans-activating crRNA (tracrRNA), mediate cleavage of the target DNA (protospacer); this dual RNA complex has been further engineered into a chimeric single-guide RNA (sgRNA). An additional requirement critical to Cas9 activity is the presence of a protospacer adjacent motif (PAM) in the target DNA, which differs among the CRISPR-Cas systems.

The ability to harness Cas9 for broad applications in vivo in somatic tissue, while obviating the need for embryonic manipulation, would prove enormously useful for accelerating basic research and enabling clinical applications. One major challenge is the delivery of the Cas9 genome editing system to animals. Adeno-associated virus (AAV) vectors are attractive candidates for efficient gene delivery in vivo because of their low immunogenic potential, reduced oncogenic risk from host-genome integration, and well-characterized serotype specificity. However, the limited cargo size of ~4.5 kb for optimal transgene delivery renders the packaging of SpCas9 (~4.2 kb) and appropriate control elements (promoter, polyA signal) difficult. While several smaller Cas9 orthologs have been used for mammalian genome editing, they are nonetheless relatively limited in availability of targeting sequences due to the requirement for lengthier and more specific PAMs, and cannot match SpCas9 in cleavage efficiency. This highlights the potential as well as the need to further explore the ecological diversity of Type II CRISPR systems for additional suitable Cas9s.

Figure 70A:
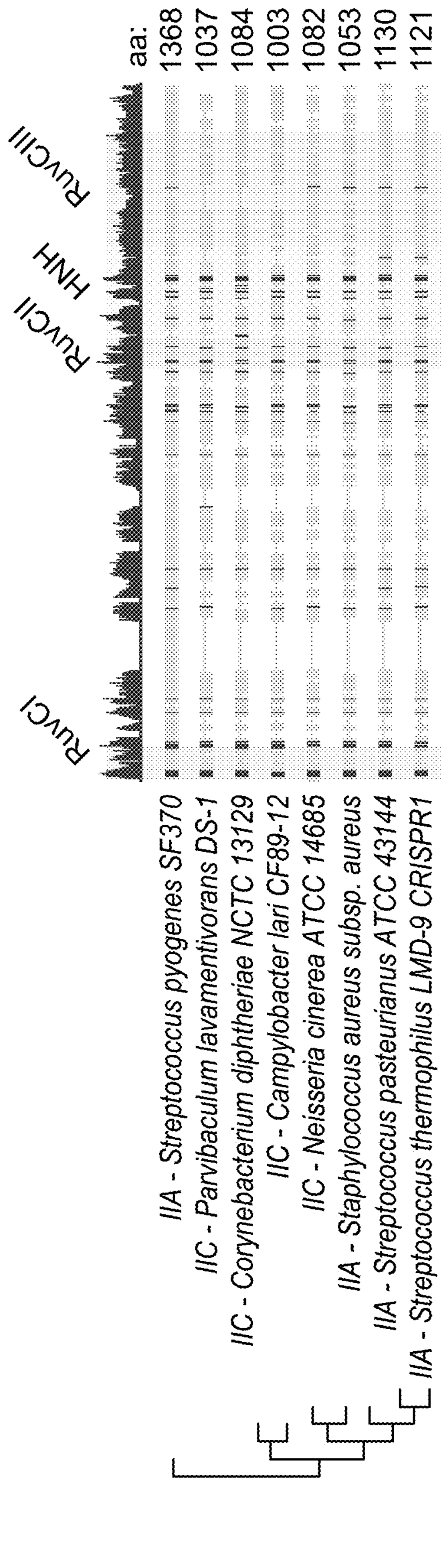
FIG. 70A-70D shows a biochemical screen for small Cas9 orthologs. (a) Phylogenetic tree of Cas9 orthologs, with subfamily and sizes (amino acids) indicated. Conserved nuclease domains are in boxes. (b) Schematic illustrating in vitro cleavage-based method used to identify protospacer adjacent motifs (PAMs). (c) Consensus PAMs for eight Cas9 orthologs from sequencing of cleaved fragments. (d) Biochemical cleavage reaction using orthologs and sgRNAs targeting different loci bearing the putative PAMs. Triangles indicate cleavage fragments.
Figure 70B:
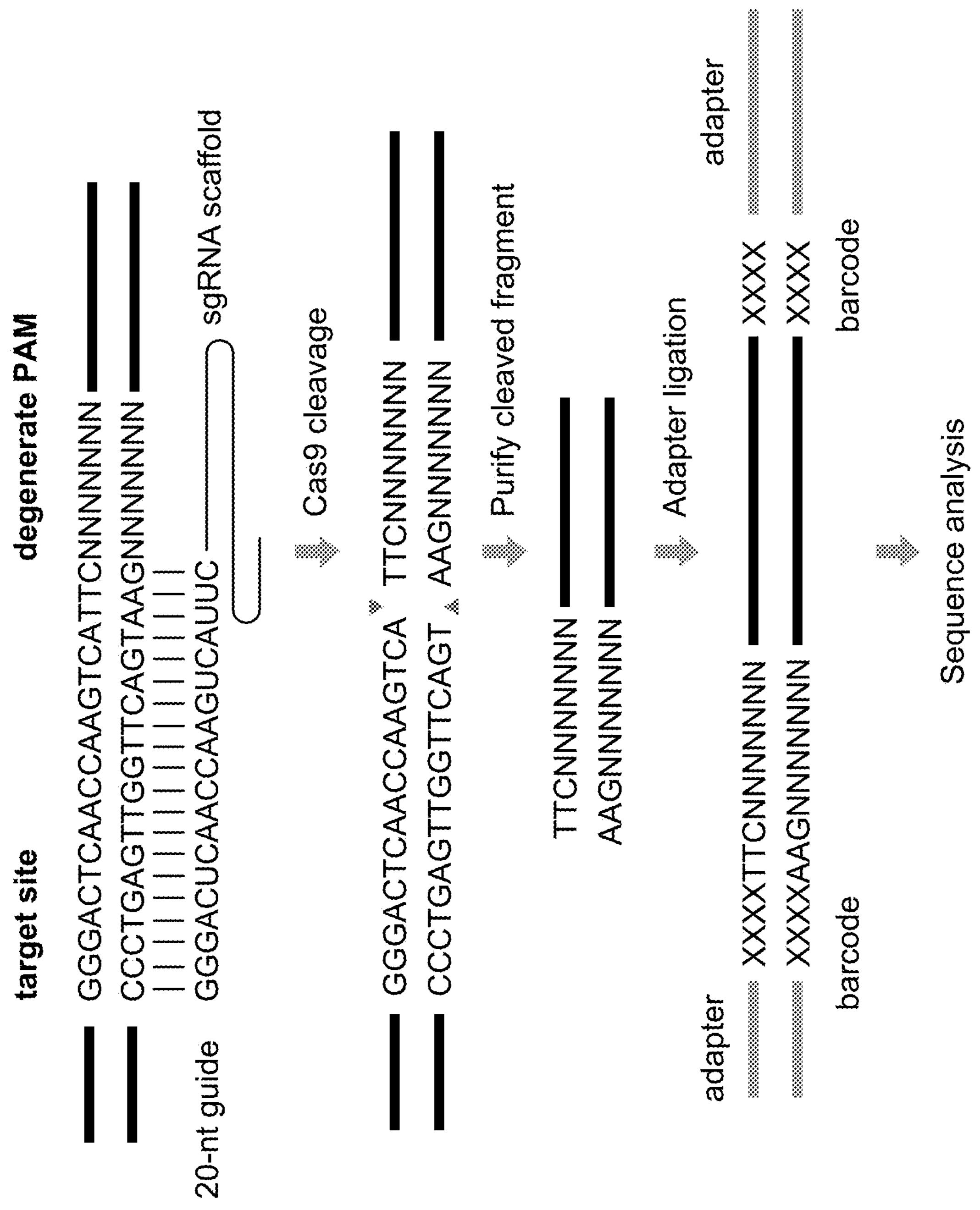
Figure 70C:
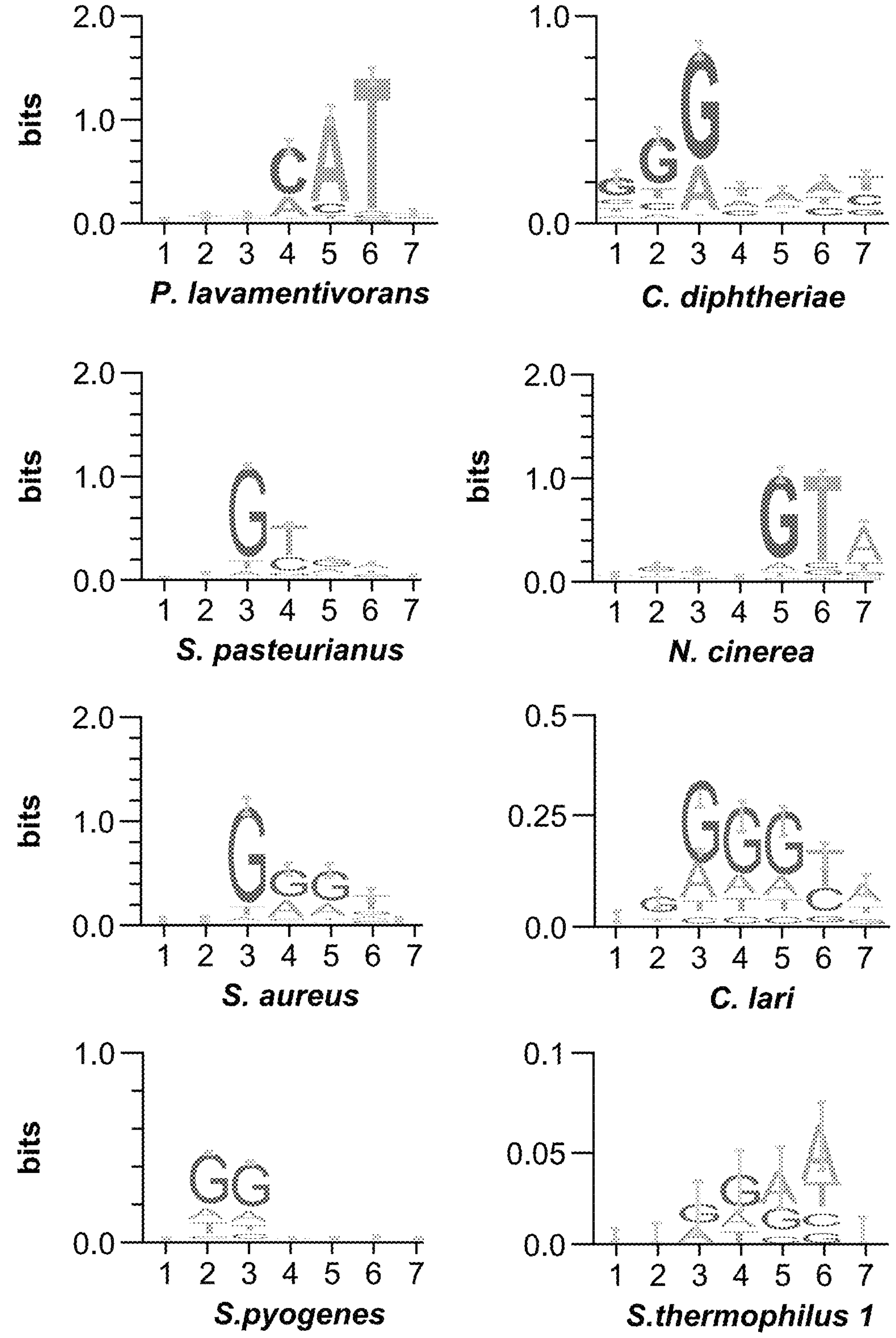
Figure 70D:
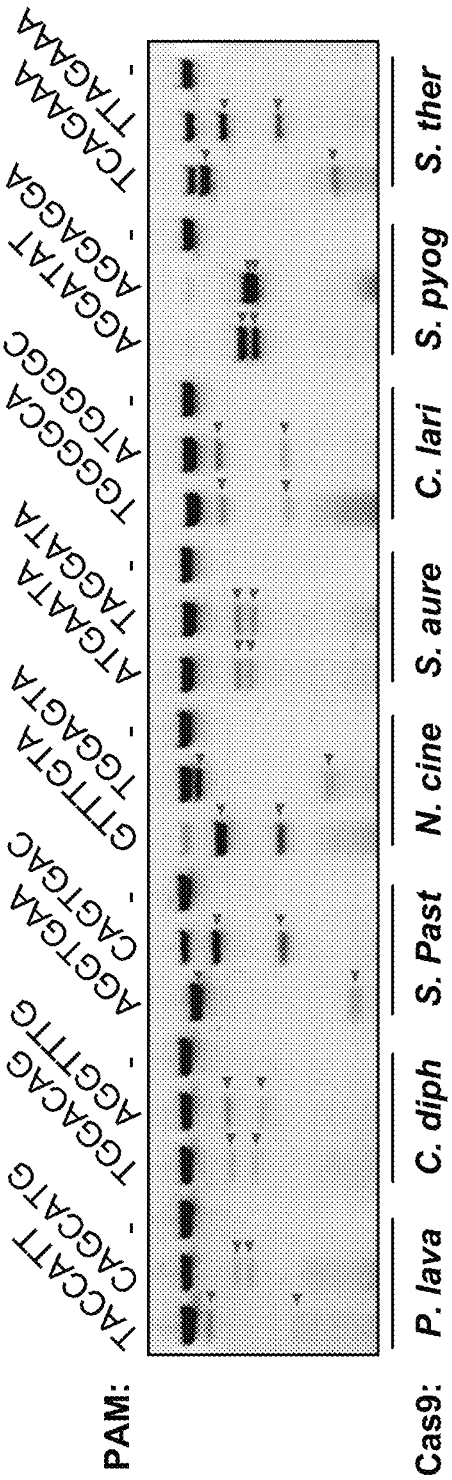
Figure 74:
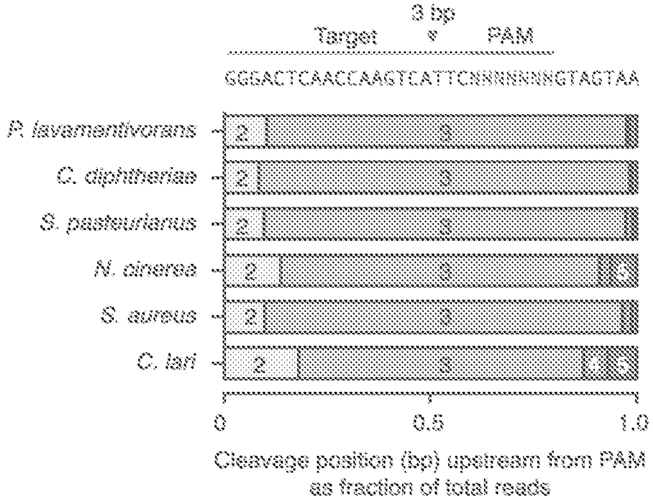
FIG. 74 shows a stacked bar graph indicating the fraction of targets cleaved at 2, 3, 4, or 5-bp upstream of PAM for each Cas9 ortholog; all Cas9s cleave most frequently at 3-bp upstream of PAM (triangle).

To identify a diverse set of small Cas9 proteins, Applicants selected six representative Cas9 orthologs from over 800 known Cas9s from GenBank and optimized their sequences for mammalian expression (FIG. 70*a*). These Cas9s belong to the Type IIA and IIC subfamilies. Using the characteristic direct repeat motifs found within the CRISPR array, Applicants searched a 2-kb window flanking the CRISPR locus for potential tracrRNAs that contained strong sequence homology to the repeats, at least two additional predicted stemloops, and a Rho-independent transcriptional termination signal within 150-nt. From these Applicants constructed sgRNA scaffolds for each ortholog (FIG. 70 and Table 51). Since the full 3' end of tracrRNA improves sgRNA abundance in cells and mediates interaction with Cas931, Applicants included the full tracrRNA 3' end for each ortholog. Applicants then cleaved a library of plasmids containing a fixed-sequence target followed by a randomized 7-mer as PAM (5'-NNNNNNN) in an in vitro cell lysate assay, and identified the putative PAMs by sequencing the targets that were successfully cleaved (FIG. 70*b, c*). Applicants observed that similar to SpCas9, the Cas9 orthologs cleaved targets 3 bp upstream of PAM (FIG. 74). To validate the consensus PAMs from the library, Applicants subsequently cleaved a DNA template bearing the putative PAMs in a biochemical lysate reaction and showed that the sgRNA designs, in combination with the Cas9 orthologs, can indeed target sites bearing appropriate consensus PAMs, albeit with differing efficiencies (FIG. 70*d* and Table S2).

Figure 75A:
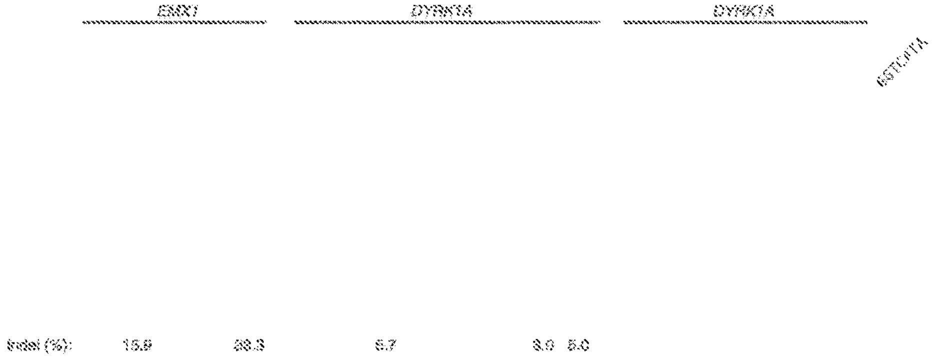
FIG. 75A-75B shows: (a) SURVEYOR assays showing indel formation at human endogenous loci from co-transfection of Cas9 orthologs and sgRNA in HEK 293FT cells. (b) SaCas9 cleaves multiple targets with high efficiency. PAM sequences for individual targets are shown above each lane, with consensus sequences for each Cas9. Triangles indicate cleaved fragments.
Figure 75B:
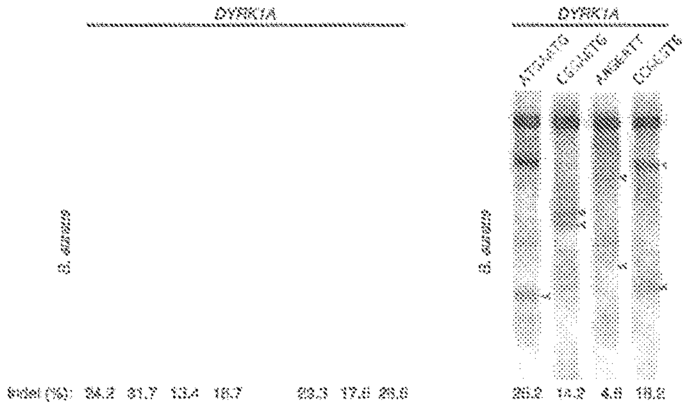

Having validated the activity of Cas9 orthologs using cell lysates, Applicants sought to test their ability to induce double stranded breaks in mammalian cells. Applicants co-transfected in human embryonic kidney (HEK 293FT) cells the Cas9 orthologs and their respective sgRNAs targeting endogenous human genomic loci with the appropriate PAMs. However, of the six Cas9 orthologs tested, only the Cas9 from *Staphylococcus aureus* (referred to as SaCas9) reproducibly yielded indels by SURVEYOR assay (FIG. 75 and Table S3). Thus, Applicants focused on optimizing SaCas9 and sgRNA for application in in vivo mammalian genome editing.

Figure 71A:
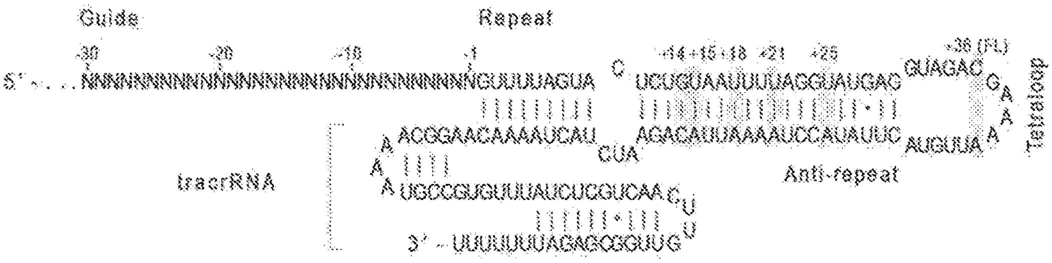
FIG. 71A-71F shows in vitro characterization of *Staphylococcus aureus* Cas9. (a) Schematic showing the structure of *S. aureus* sgRNA. Indels vary depending on (b) length of guide sequence or (c) repeat:anti-repeat duplex. (d) Consensus PAM for SaCas9 in HEK 293FT cells. Pooled indel values for all putative PAM 4-base combinations (top, n≥3) and overall sequence logo (n=116, bottom) are shown. SpCas9 and SaCas9 cleavage efficiency comparison for e, genomic target sites and f, genome-wide off-target loci (error bars indicate Wilson intervals). Off-target (OT) sequences with significant indels are above graph. n=3, error bars S.E.M unless otherwise noted; N.D. not detectable.
Figure 71B:
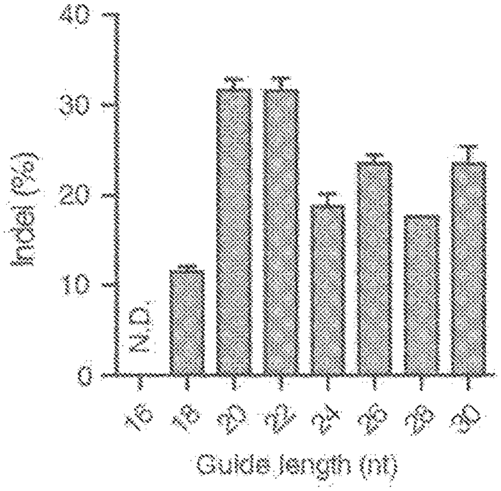
Figure 71C:
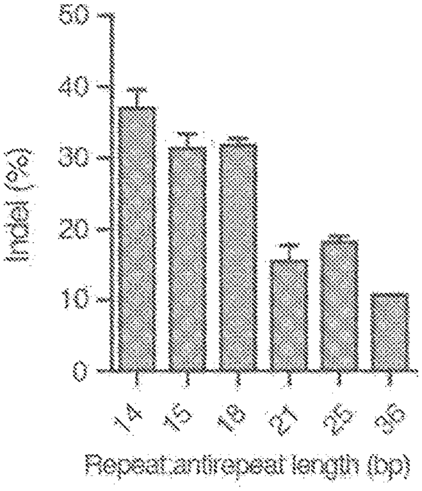

Although many Type II CRISPR systems share a common feature of having ~36-bp direct repeats and ~30-bp spacers, previous studies have reported different lengths for spacer as well as direct repeat sequences in the mature crRNA among different systems. Applicants therefore sought to test the optimal lengths of these two parameters for the SaCas9 sgRNA (FIG. 71*a*). Applicants found that while a range of spacer or guide length is tolerated for SaCas9, there is a marked decrease in cleavage efficiency when it is 18-nt or below (FIG. 71*b*), in contrast to SpCas9 where shorter sgRNA lengths can be used. Similarly, a range of lengths for direct repeat:tracrRNA antirepeat duplex is tolerated (FIG. 71*c*). Based on these results, Applicants chose the shorter 20-nt guide, 14-bp repeat:antirepeat duplex sgRNA architecture for downstream applications.

Figure 71D:
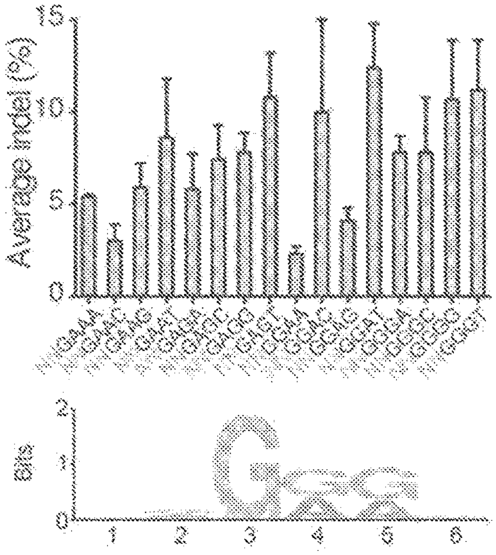
Figures 76A, 76B:
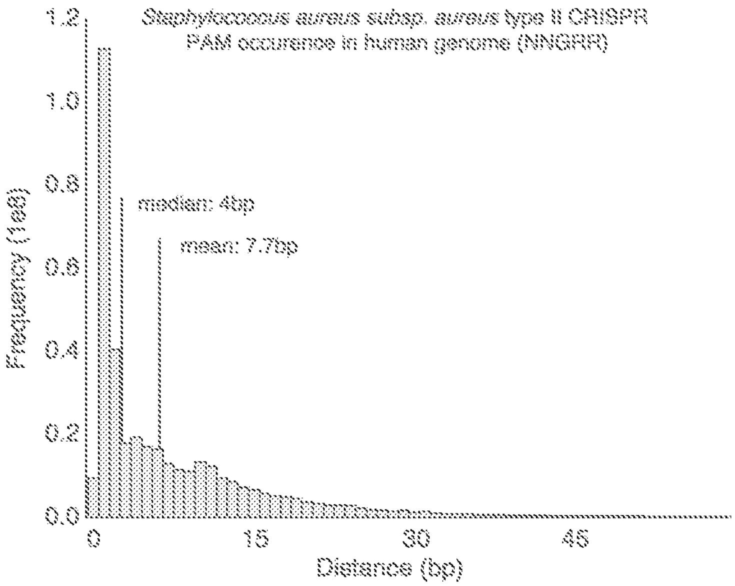
FIG. 76A-76B shows: (a) histograms of distances between adjacent *Staphylococcus aureus* subsp. *aureus* Type II CRISPR PAM (NNGRR) in the human genome (GRCh38). (b) Distances for each PAM by chromosome.

Since there might be potential differences between the cell lysate and the endogenous mammalian nuclei environment that may affect DNA cleavage specificity, Applicants wanted to verify whether the in vitro 5'-NNGRR(T) consensus PAM held for SaCas9 cleavage in mammalian cells. From SURVEYOR analysis of endogenous genome cleavage based on 116 distinct genomic target sites, Applicants determined that SaCas9 could efficiently cleave genomic targets with a 5'-NNGRR PAM, with no requirement for the T in the 6th position (FIG. 71*d*, Table S4). On average, the 5'-GRR motif occurs in the human genome every 7.6-bp, allowing the SaCas9 to have a wide range of available targets (FIG. 76).

Figure 71E:
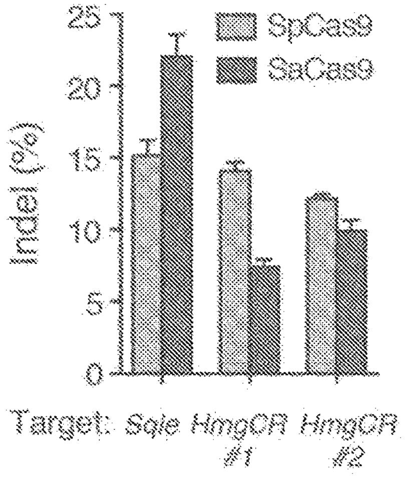
Figure 71F:
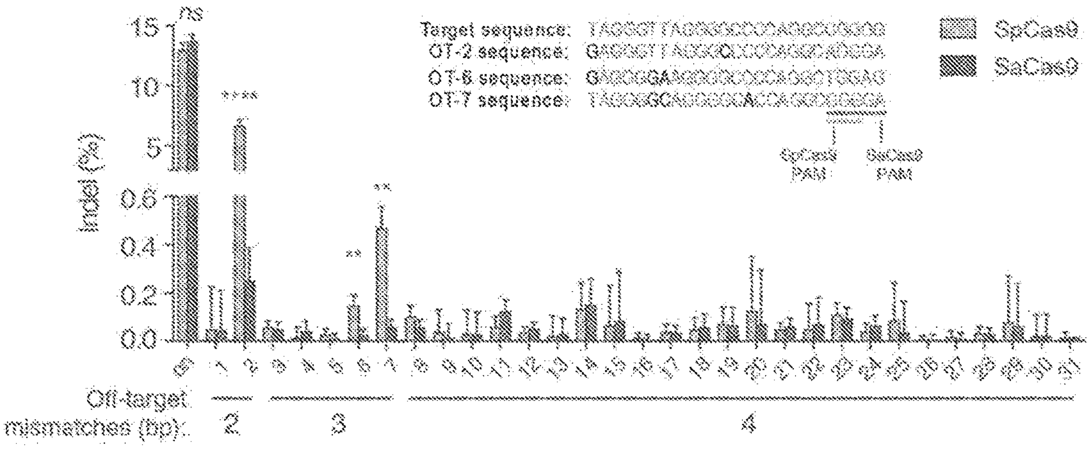

Among the Cas9 orthologs used for mammalian genome editing, SpCas9 remains the best characterized in targeting specificity, with consistently high editing efficiency across multiple cell types and species. For three targets in mouse hepatoma (Hepa1-6) cells, the editing efficiency of SaCas9 performed comparably with that of SpCas9 (FIG. 71*e*). Furthermore, Applicants assayed genomic off-target indel mutations at highly similar genomic sequences for both SaCas9 and SpCas9, targeting a common locus bearing an overlapping 5'-NGGRR PAM. At 31 genome-wide loci with sequence similarity to intended target, SaCas9 cleaved off-target sites with comparable activity as SpCas9 (FIG. 71*f*, Table S5).

Figure 72A:
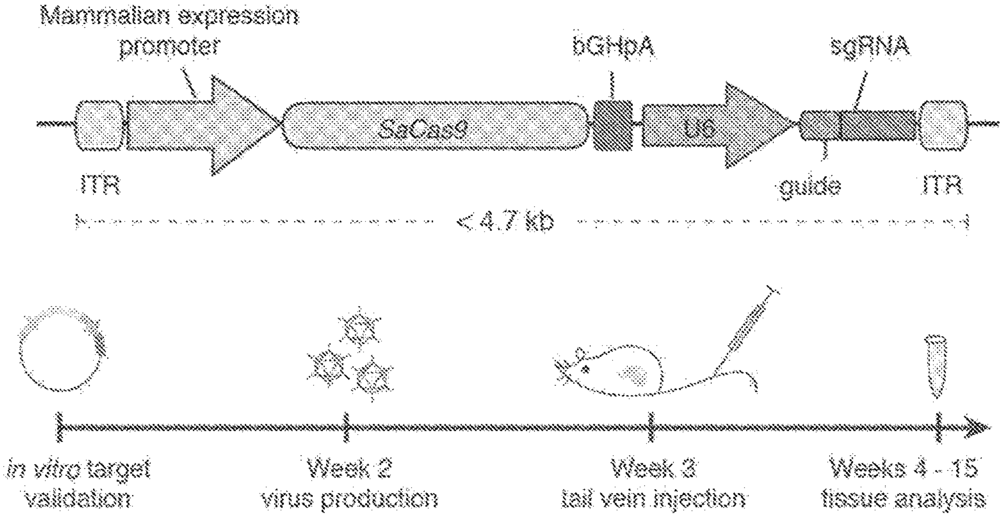
FIG. 72A-72E shows AAV delivery of *S. aureus* Cas into live animals. (a) Schematics illustrating AAV single-vector system (top) and experimental timeline (bottom). (b) Mouse Pcsk9 locus showing SaCas9 target locations. (c) Time course of liver tissue indel formation at targets 1 and 6 post injection of AAV2/8 particles (up to 2 animals each; error bars represent liver tissue pieces). (d) Indel formation at target 6 at 1 and 3 weeks post-injection. Each lane represents a piece of liver tissue. Triangles indicate cleavage fragments. (e) Representative chromatogram and indels generated by SaCas9 in vivo.
Figure 72B:
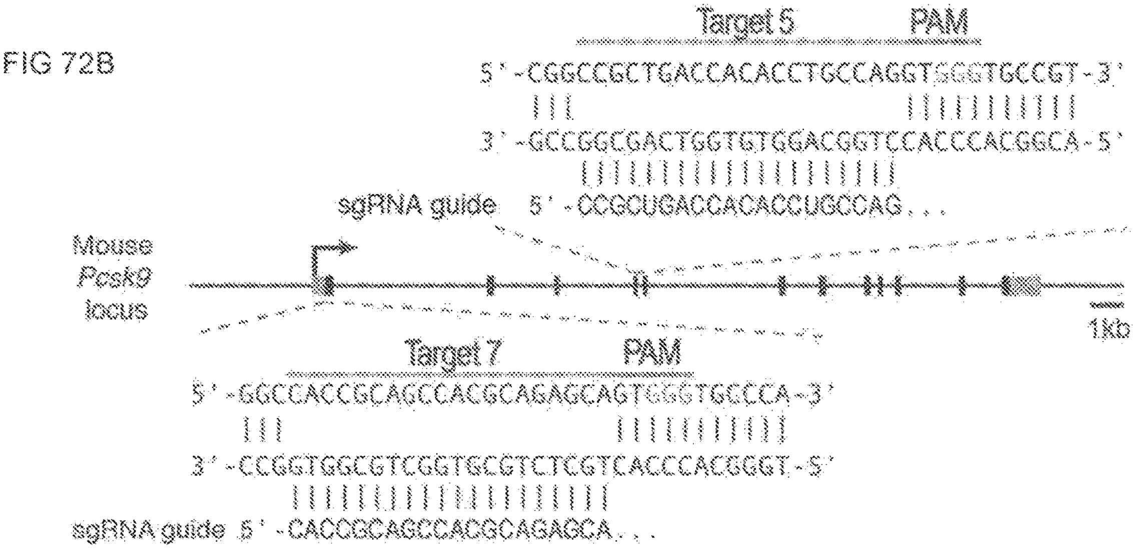

Having established and validated the optimal sgRNA architecture for SaCas9 in mammalian cells, Applicants sought to incorporate SaCas9 into AAV vector for in vivo use. In AAV, the small size of SaCas9 (3.2 kb) leaves sufficient room for promoters of up to 600-bp in a dual-cassette design co-expressing SaCas9 and U6-driven sgRNA (FIG. 72*a*). The ability to apply Cas9 protein to modify endogenous loci in somatic tissues or adult animals enables rapid testing of gene function in the relevant tissue type and therapeutic applications for gene correction. Of the organs targetable by AAV, the liver is particularly attractive for demonstrating the feasibility and therapeutic potential of CRISPR-Cas mediated in vivo genome engineering because of its accessibility by intravascular delivery and its central role in many metabolic pathways important for human disease. Applicants chose to target the mouse locus encoding proprotein convertase subtilisin/kexin type 9 (Pcsk9), an enzyme that is predominantly expressed in the liver and involved in cholesterol homeostasis, whose reduction has shown promise in lowering the risk of cardiovascular disease. It can be envisioned that other genes expressed in the liver, including but not limited to e.g., ApoB; Angiopoeitin; HMGCR, etc., may be targeted by the methods disclosed herein.

Figure 72C:
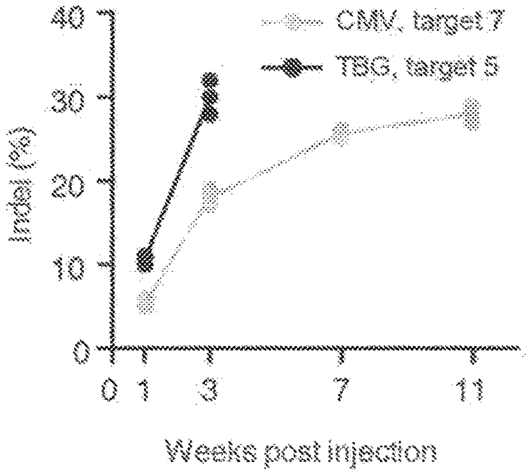
Figure 72D:
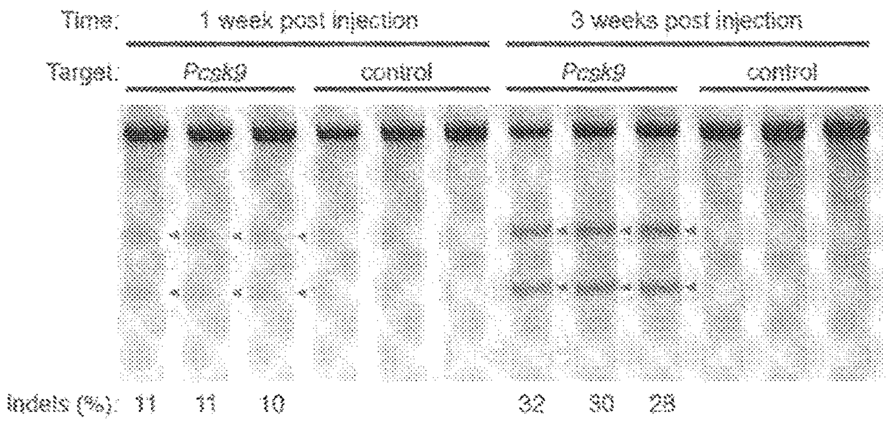
Figure 72E:
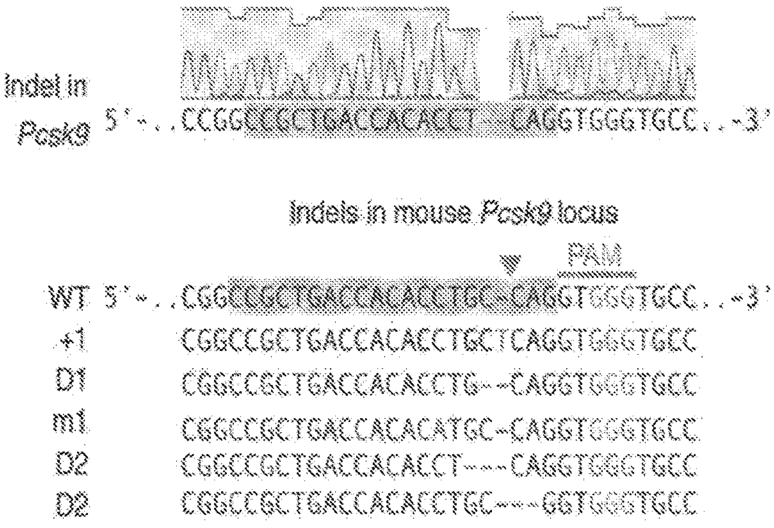
Figure 73A:
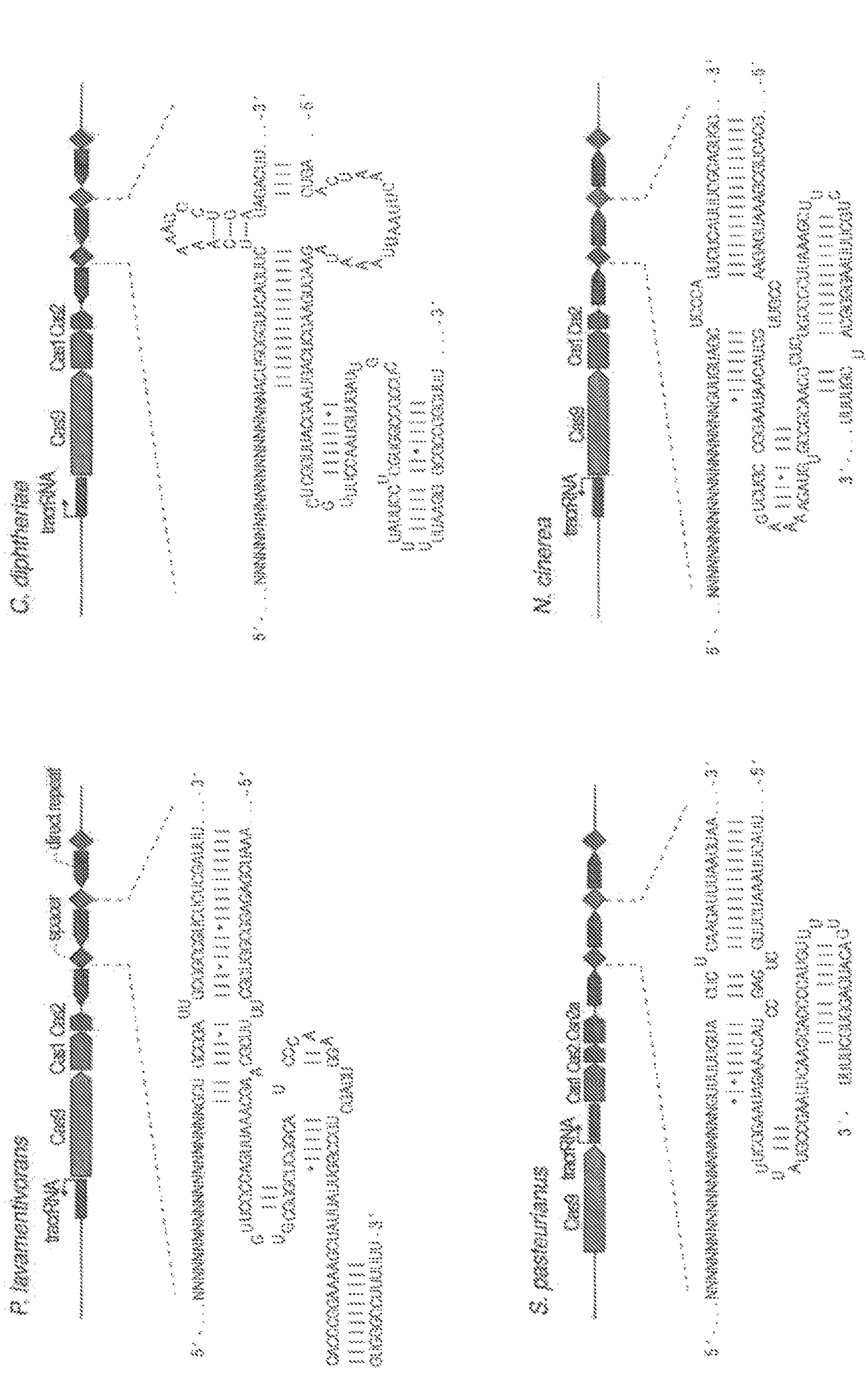
FIG. 73A-73B shows a schematic of CRISPR-Cas loci of six orthologs from two subfamilies of Type II CRISPR-Cas systems. Spacer or "guide" sequences are shown followed by direct repeat. Predicted tracrRNAs are shown, and folded based on the Constraint Generation RNA folding model.
Figure 73B:
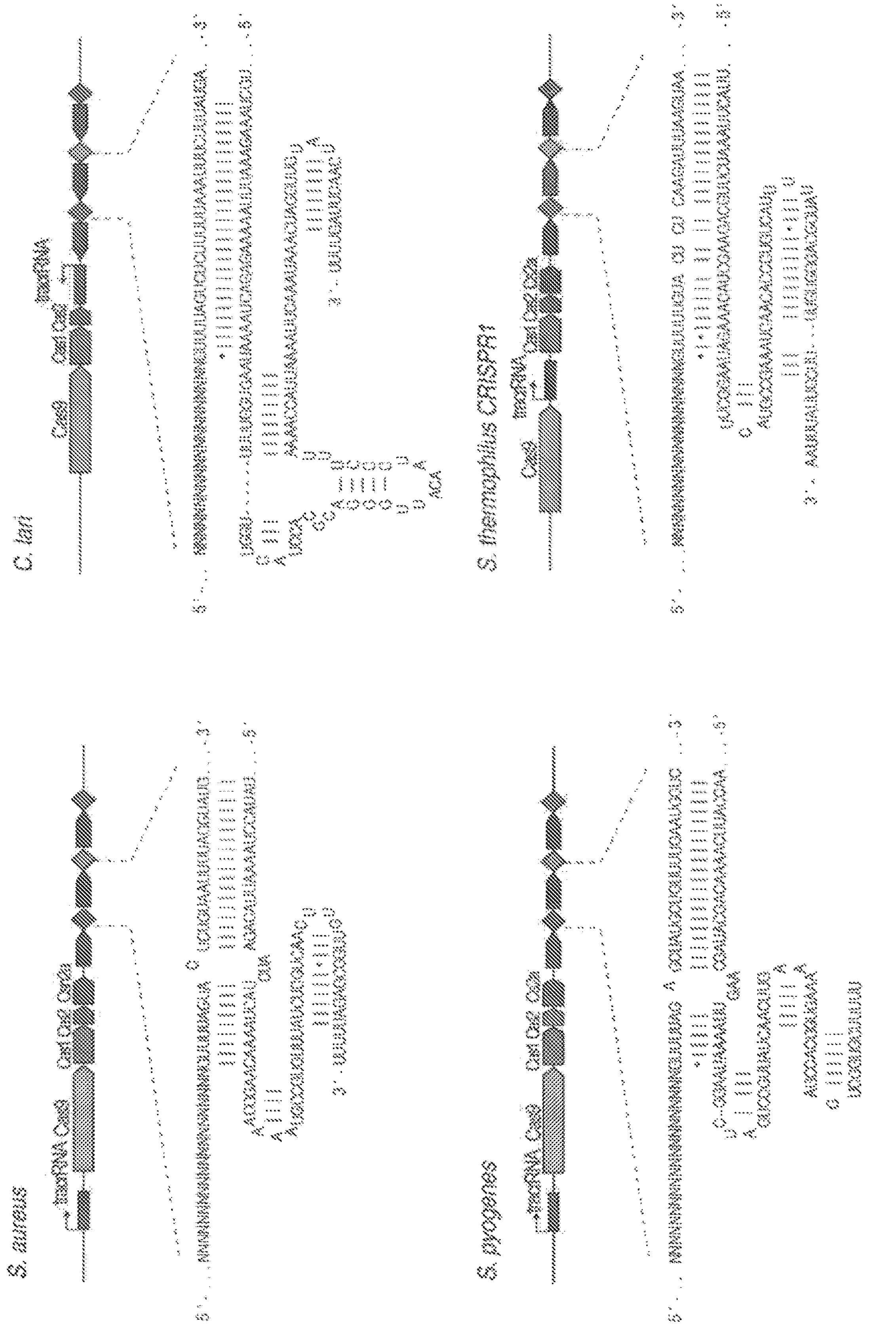
Figure 77A:
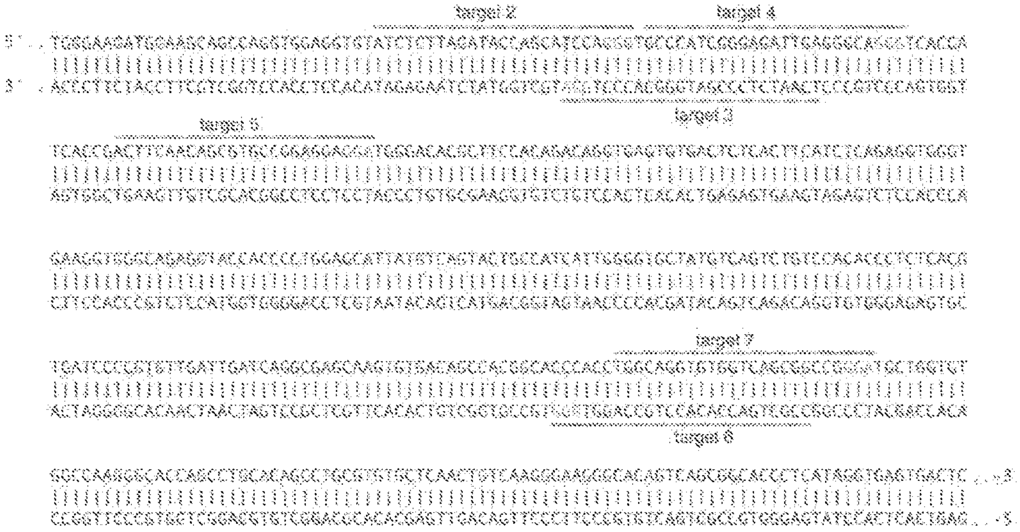
FIG. 77A-77B shows the location of SaCas9 targets and PAMs within the mouse Pcsk9 gene locus (SEQ ID NO: 869). b, Indels produced at target sites from transfection of mouse liver hepatoma (Hepa1-6) cell line. Arrows indicate cleavage sites.
Figure 77B:
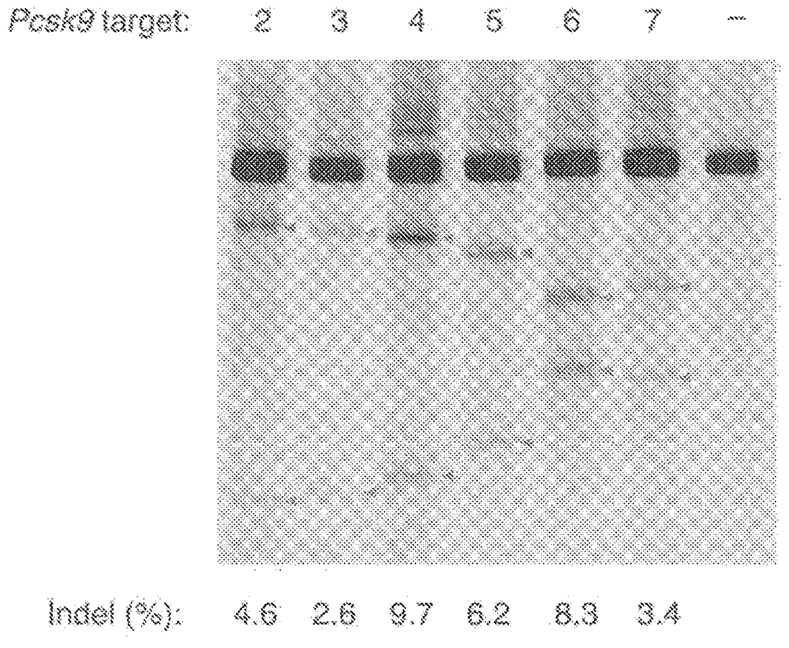

Using AAV2/8, a highly efficient hepatotropic AAV serotype, Applicants delivered via tail-vein injection $8\times10^{10}$ viral particles using single-vector design containing a cytomegalovirus (CMV) promoter-driven SaCas9 and a U6 promoter-driven sgRNA targeting Pcsk9 (FIG. 72*a, b*). The percentage indel formation increased from approximately 5% at 1 week to 28% at 11 weeks, demonstrating the in vivo editing capabilities of SaCas9 and the single-vector design (FIG. 72*c*). To further increase the efficiency of genome modification, Applicants screened additional guides targeting Pcsk9 in Hepa1-6 cells (FIG. 77) and used a liver-specific thyroid-binding globulin (TBG) promoter to provide greater hepatocyte specificity and expression. After intravascular delivery of $2\times10^{11}$ viral particles, Applicants observed indel formation in the liver ranging from 11% at 1-week post injection to approximately 30% at 3 weeks (FIG. 72*c-e*). The Pcsk9 gene modification level remained consistent across samples from multiple locations within the liver, suggesting that the delivery was uniform throughout the target organ (FIG. 72*d*). All mice survived the AAV injection and did not exhibit any signs of physical distress for the entire duration of the experiment.

The small size and efficiency of the novel Cas9 ortholog from *S. aureus* paves the way for rapid and versatile in vivo editing while maintaining target specificity through promoter and AAV serotype selection. Furthermore, the method of PAM identification described here presents a generalizable approach to PAM identification amongst all Type II CRISPR systems. While certain Cas9 orthologs are more readily adapted for mammalian genome editing than others, SaCas9 cleaves endogenous targets in cells with robust efficiencies similar to those of SpCas9 and additionally exhibits a similar degree of specificity. However, additional studies are necessary to fully characterize the specificity of SaCas9 as well as the effects of prolonged Cas9 in vivo expression.

While the AAV-delivery of the Cas9 system is a promising step towards gene therapy applications, the more immediate impact lies in the efficient interrogation of genetic contributions to both normal biology and disease in animals beyond cell lines and transgenic models. Such somatic or postnatal genetic manipulation allows unprecedented spatial and temporal control of targeted gene modifications that may be developmentally important or inadequately controlled by conditional expression systems, as well as the ability to simulate a gradual accumulation of genetic mutations that could better model the natural progression of certain pathogenic processes. Lastly, viral vector mediated gene modification allows for significantly higher throughput of studying genetic variants of disease than transgenic animal generation, particularly in organisms with lengthy gestational and developmental periods. The in vivo opportunities made possible by the AAV delivery of the *S. aureus* Cas9 described here represents another piece of the continually expanding Cas9 genome engineering toolbox that promises to allow rapid advances across basic science, medical, and biotechnology applications.

Methods Summary

Human embryonic kidney (HEK 293FT) and mouse liver hepatoma (Hepa1-6) cell lines were maintained at 37° C. and 5% CO2 atmosphere, and transfected with a total of 500 ng DNA per 120,000 cells using Lipofectamine 2000. C57BL/6 mice were injected at age 8-10 weeks via tail vein with AAV diluted in sterile phosphate buffered serum, pH 7.4. Extended descriptions of SURVEYOR and in vitro cleavage assays, computation methods, cell culture condition, AAV production and injection, are provided below.

Cell Culture and Transfection.

Human embryonic kidney (HEK) 293FT (Life Technologies) and Hepa1-6 (ATCC) cell lines were maintained in Dulbecco's modified Eagle's Medium (DMEM) supplemented with 10% FBS (HyClone), 2 mM GlutaMAX (Life Technologies), 100 U/ml penicillin, and 100 m/ml streptomycin at 37° C. with 5% $CO_2$ incubation.

Cells were seeded into 24-well plates (Corning) one day prior to transfection at a density of 240,000 cells per well, and transfected at 70-80% confluency using Lipofectamine 2000 (Life Technologies) per the manufacturer's recommended protocol. For each well of a 24-well plate a total of 500 ng DNA was used.

SURVEYOR Nuclease Assay for Genome Modification.

Transfected cells were incubated at 37° C. for 72 h before genomic DNA extraction using the QuickExtract DNA Extraction Solution (Epicentre). Pelleted cells were resuspended in QuickExtract solution and incubated at 65° C. for 15 min, 68° C. for 15 min, and 98° C. for 10 min. Genomic liver DNA was extracted from tissue slices using dounce homogenizer (Sigma) with 100 ul DPBS (gibco). 10 ul of homogenized liver extract was added to 90 ul QuickExtract DNA Extraction Solution (Epicentre) and incubated as above.

The genomic region flanking the CRISPR target site for each gene was PCR amplified (Supplementary sequences) and products were purified using QiaQuick Spin Column (Qiagen) following the manufacturer's protocol. 200 ng total of the purified PCR products were mixed with 1 μl 10×Taq DNA Polymerase PCR buffer (Enzymatics) to a final volume of 10 μl, and subjected to a re-annealing process to enable heteroduplex formation: 95° C. for 10 min, 95° C. to 4° C. ramping at −0.5° C./s. After re-annealing, products were treated with SURVEYOR nuclease and SURVEYOR enhancer S (Transgenomics) following the manufacturer's recommended protocol, and analyzed on 4-20% Novex TBE polyacrylamide gels (Life Technologies). Gels were stained with SYBR Gold DNA stain (Life Technologies) for 30 min and imaged with a Gel Doc gel imaging system (Bio-rad). Quantification was based on relative band intensities. Indel percentage was determined by the formula, $100\times(1-(1-(b+c)/(a+b+c))^{1/2})$, where a is the integrated intensity of the undigested PCR product, and b and c are the integrated intensities of each cleavage product.

In Vitro Transcription and Cleavage Assay

Cas9 orthologs were human codon-optimized and synthesized by GenScript, and transfected into 293FT cells as described above. Whole cell lysates from 293FT cells were prepared with lysis buffer (20 mM HEPES, 100 mM KCl, 5 mM MgCl2, 1 mM DTT, 5% glycerol, 0.1% Triton X-100) supplemented with Protease Inhibitor Cocktail (Roche). T7-driven sgRNA was transcribed in vitro using custom oligos (Supplementary Sequences) and HiScribe T7 In vitro Transcription Kit (NEB), following the manufacturer's recommended protocol. The in vitro cleavage assay was carried out as follows: for a 20 μl cleavage reaction, 10 μl of cell lysate was incubated with 2 μl cleavage buffer (100 mM HEPES, 500 mM KCl, 25 mM MgCl2, 5 mM DTT, 25% glycerol), 1 μg in vitro transcribed RNA and 200 ng EcoRI-linearized pUC19 plasmid DNA or 200 ng purified PCR amplicons from mammalian genomic DNA containing target sequence. After 30 m incubation, cleavage reactions were purified using QiaQuick Spin Columns and treated with RNase A at final concentration of 80 ng/ul for 30 min and analyzed on a 1% Agarose E-Gel (Invitrogen).

In Vitro PAM Screen

Rho-independent transcriptional termination was predicted using the ARNold terminator search tool 1,2. For the PAM library, a degenerate 7-bp sequence was cloned into a pUC19 vector. For each ortholog, the in vitro cleavage assay was carried out as above with 1 μg T7-transcribed sgRNA and 400 ng pUC19 with degenerate PAM. Cleaved plasmids were linearized by NheI, gel extracted, and ligated with Illumina proprietary sequencing adaptors. Barcoded and purified DNA libraries were quantified by Quant-iT PicoGreen dsDNA Assay Kit or Qubit 2.0 Fluorometer (Life Technologies) and pooled in an equimolar ratio for sequencing using the Illumina MiSeq Personal Sequencer (Life Technologies).

Computational Analysis

MiSeq reads were filtered by requiring an average Phred quality (Q score) of at least 23, as well as perfect sequence matches to barcodes. For reads corresponding to each ortholog, the degenerate region was extracted. All extracted regions were then grouped and analyzed with Weblogo3. For genome wide off target analysis, indel frequencies were determined by deep sequencing and analyzed as previously described 4.

AAV Production & Delivery

Virus Production and Titration

For viral production, 293FT cells (Life Technologies) were maintained as recommended by the manufacturer in antibiotic-free media (DMEM, high glucose with GlutaMax and Sodium Pyruvate, supplemented with 10% FBS, and a final concentration of 10 mM HEPES). For each vector, cells were grown in at least ten 15 cm tissue culture dishes and incubated until they reach around 70%-80% confluence at 37° C. and 5% $CO_2$. For transfection of virus production plasmids, PEI "Max" (Polysciences) was dissolved in water at 1 mg/mL and the pH of the solution was adjusted to 7.1.

For transfection, 8 ug of pAAV8 serotype packaging plasmid, 10 ug of pDF6 helper plasmid, and 6 ug of pAAV plasmid carrying the construct of interest were added to 1 mL of serum-free DMEM. 125 uL of PEI "Max" solution was then added to the mixture. The resulting final transfection mixture was vortexed briefly and incubated at room temperature for 5 to 10 seconds. After incubation, the mixture was added to 20 mL of maintenance media, mix well, and applied to each dish to replace the old growth media. Cells were harvested between 48 h and 72 h post transfection. Cells were scraped from the dishes and pelleted by centrifugation. The AAV8 viral particle were then purified from the pellet according to previous published protocols.

Viruses were also produced by vector core facilities at University of Pennsylvania and Children's Hospital Boston, and titered by qPCR using a customized TaqMan probe against the SaCas9 transgene to match in house production.

Animal Injection and Processing

All mice were maintained at animal facility following IRB-approved protocols. AAV was delivered to at 8-10 week old C57/BL6 mice via tail vein injection. All dosages of AAV were adjusted to 100 uL or 200 uL with sterile phosphate buffered serum, pH 7.4 (Gibco).

Tissue was harvested at the described time points post injection. Mice were anesthetized using Ketamine/Xylazine and subjected to transcardial perfusion with 30 ml PBS. The median lobe of liver was removed and fixed in 4% paraformaldehyde for histological analysis, while the remaining lobes were sliced in small blocks of size less than 1×1×3 mm3 and frozen at −80 C for subsequent genomic DNA extraction, or immersed in RNALater (Ambion) for RNA extraction.

In vivo animal studies (e.g., mice) for specificity, toxicity, phenotype, and tolerance are performed for each of the Cas9 orthologs using known methods.

TABLE S1

List of Cas9 orthologs and predicted RNA components

| Cas9 | class | direct repeat | tracrRNA | sgRNA |
|---|---|---|---|---|
| *P. lavamentivorans* | IIC | GCUGCGGAUUGCGGCCGUCUCUCGAUUUGCUACUCU (SEQ ID NO: 208) | UAGCAAAUCGAGAGGCGGUCGCUUUUCGCAAGCAAAUUGACCCCUUGUGCGGGCUCGGCAUCCCAAGGUCAGCUGCCGGUUAUUAUCGAAAAGGCCCACCGCAAGCAGCGCGUGGGCCUUUUU (SEQ ID NO: 2UA) | GCUGCGGAUUGCGGGAAAUCGCUUUUCGCAAGCAAAUUGACCCCUUGUGCGGGCUCGGCAUCCCAAGGUCAGCUGCCGGUUAUUAUCGAAAAGGCCCACCGCAAGCAGCGCGUGGGCCUUUU (SEQ ID NO: 210) |
| *C. diphtheria* | IIC | ACUGGGGUUCAGUUCUCAAAAACCCUGAUAGACUUC (SEQ ID NO: 211) | AGUCACUAACUURAUUARAUAGAACUGAACCUCAGUAAGCAUUGGCUCGUUUCCAAUGUUGAUUGCUCCGCCGGUGCUCCUUAUUUUUAAGGGCGCCGGCUUUCUU (SEQ ID NO: 212) | ACUGGGGUUCAGGAAACUGAACCUCAGUAAGCAUUGGCUCGUUUCCAAUGUUGAUUGCUCCGCCGGUGCUCCUUAUUUUUAAGGGCGCCGGCUUUU (SEQ ID NO: 213) |
| *S. pasteurianus* | IIA | GUUUUUGUACUCUCAAGAUUURAGUAACCGUAAAAC (SEQ ID NO: 214) | CUUGCACGGUUACUUAAAUCUUGCUGAGCCUACAAAGAUAAGGCUUUAUGCCGAAUUCAAGCACCCCAUGUUUUGACAUGAGGUGCUUUU (SEQ ID NO: 215) | GUUUUUGUACUCGAAAGAGCCUACAAAGAUAAGGCUUUAUGCCGAAUUCAAGCACCCCAUGUUUUGACAUGAGGUGCUUUU (SEQ ID NO: 216) |
| N. cinerea | IIC | GUUGUAGCUCCCAUUCUCAUUUCGCAGUGCUACAAU (SEQ ID NO: 217) | AUUGUCGCACUGCGAAAUGAGAACCGUUGCUACAAUAAGGCCGUCUGAAAAGAUGUGCCGCAACGCUCUGCCCCUUAAAGCUUCUGCUUUAAGGGGCAUCGUUUAUUUCGGUUAAAAAUGCCGUCUGAAACCGGUUUUU (SEQ ID NO: 218) | GUUGUAGCUCCCAUUCUCGAAAGAGAACCGUUGCUACAAUAAGGCCGUCUGAAAAGAUGUGCCGCAACGCUCUGCCCCUUAAAGCUUCUGCUUUAAGGGGCAUCGUUUAUUUCGGUUAAAAAUGCCGUCUGAAACCGGUUUUUAGGUUUCAGACGGCAUUUU (SEQ ID NO: 219) |
| *S. aureus* | IIA | GUUUUAGUACUCUGUAAUUUUAGGUAUGGGGUAGAG (SEQ ID NO: 220) | AUUGUACUUAUACCUAAAAUUACAGAAUCUACUAAAACAAGGCAAAAUGCCGUGUUUAUCUCGUCAACUUGUUGGCGAGAUUUUU (SEQ ID NO: 221) | GUUUUAGUACUCUGGAAACAGAAUCUACUAAAACAAGGCAAAAUGCCGUGUUUAUCUCGUCAACUUGUUGGCGAGAUUUU (SEQ ID NO: 222) |
| *C. lar* | IIC | GUUUUAGUCUCUUUUUAAAUUUCUUUAUGAUAAAAU (SEQ ID NO: 223) 224) | AAUUCUUGCUAAAGAAAUUUAAAAAGAGACUAAAAUAAGUGGUUUUUGGUCAUCCACGCAGGGUUACAAUCCCUUUAAAACCAUUAAAAUUCAAAUAAACUAGGUUGUAUCAACUUAGUUUUUU (SEQ ID NO: | GUUUUAGUCUCUGAAAAGAGACUAAAAUAAGUGGUUUUUGGUCAUCCACGCAGGGUUACAAUCCCUUUAAAACCAUUAAAAUUCAAAUAAACUAGGUUGUAUCAACUUAGUUUU (SEQ ID NO: 225) |

TABLE S1 -continued

| List of Cas9 orthologs and predicted RNA components | | | | |
|---|---|---|---|---|
| Cas9 | class | direct repeat | tracrRNA | sgRNA |
| *S. pyogenes* | IIA | GUUUUAGAG CUAUGCUGU UUUGAAUGG UCCCAAAAC (SEQ ID NO: 226) | GUUGGAACCAUUCAAAACAGCAU AGCAAGUUAAAAUAAGGCUAGUC CGUUAUCAACUUGAAAAAGUGGC ACCGAGUCGGUGCUUUUU (SEQ ID NO: 227) | GUUUUAGAGCUAGAA AUAGCAAGUUAAAAU AAGGCUAGUCCGUUAU CAACUUGAAAAAGUG GCACCGAGUCGGUGCU UUU (SEQ ID NO: 228) |
| *S. thermophiles* | IIA | GUUUUUGUA CUCUCAAGA UUUAAGUAA CUGUACAAC (SEQ ID NO: 229) | CUUACACAGUUACUUARAUCUUG CAGAAGCUACAAAGAUAAGGCUU CAUGCCGAAAUCAACACCCUGUCA UUUUAUGGCAGGGUGUUUU (SEQ ID NO: 230) | GUUUUUGUACUCGAA AGAAGCUACAAAGAU AAGGCUUCAUGCCGAA AUCAACACCCUGUCAU UUUAUGGCAGGGUGU UUU (SEQ ID NO: 231) |

TABLE S2

| Targets used for PAM validation in in vitro lysate reaction | | | | | |
|---|---|---|---|---|---|
| Cas9 | Consensus | in vitro lysate targets (Dyrkla) | PAM | (SEQ ID NO: ___) | Gene (PCR amplicon) |
| *P. lavamentivorans* | NNNCATN | TAATCACTATGGATCTTCTA | TACCATT | 232 | DYRK1A |
| *P. lavamentivorans* | NNNCATN | TCTTGTAGGAGGAGAGACTT | CAGCATG | 233 | DYRK1A |
| *C. diphtheriae* | NGGNNNN | GGTGCAAGCCGARCAGATGA | TGGACAG | 234 | DYRK1A |
| *C. diphtheriae* | NGGNNNN | TATCCTAAAGTTCTTATTTA | AGGTTTG | 235 | DYRK1A |
| *S. pasteurianus* | NNGTGAN | TTAATTTATGAAAATCTCGT | AGGTGAA | 236 | DYRK1A |
| *S. pasteurianus* | NNGTGAN | ATGCCCCATTCACATCAGTA | CAGTGAC | 237 | DYRK1A |
| *N. cinerea* | NNNNGAT | GTGTTGAGTAACATATACCT | GTTTGTA | 235 | DYRK1A |
| *N. cinerea* | NNNNGAT | TAACTAACCAGGTAAGTTCA | TGGAGTA | 239 | DYRK1A |
| *S. aureus* | NNGRRNN | AATGATACAAACATTAGGAT | ATGRATA | 240 | DYRK1A |
| *S. aureus* | NNGRRNN | ATGTCAAATGATACAAACAT | TAGGATA | 247 | DYRK1A |
| *C. lar* | NNGGGNN | GGTCACTGTACTGATGTGAA | TGGGGCA | 242 | DYRK1A |
| *C. lar* | NNGGGNN | CGGTCACTGTACTGATGTGA | ATGGGGC | 243 | DYRK1A |
| *S. pyogenes* | NGGNNNN | TGTCARATGATACAAACATT | AGGATAT | 244 | DYRK1A |
| *S. pyogenes* | NGGNNNN | AACCTCACTTATCTTCTTGT | AGGAGGA | 245 | DYRK1A |
| *S. thermophilus* | NNAGRAW | CCAGGTAAGTTCATGGAGTA | TCAGAAA | 246 | DYRK1A |
| *S. thermophilus* | NNAGAAW | TAACATATACCTGTTTGTAG | TTAGARA | 247 | DYRK1A |

TABLE S3

Targets used for ortholog activity test in HEK 293FT cell

| Cas9 | Consensus | Targets | PAM | (SEQ ID NO: ___) | Gene | Cell type | indel (%) |
|---|---|---|---|---|---|---|---|
| *C. diphtheria* | NGGNNNN | TCACCTCCAATGACTAG GGT | GGGCAAC | 248 | EMX1 | HEK 293FT | N.D. |
| *C. diphtheria* | NGGNNNN | TGACGGTGCAAGCCGA ACAGATGA | TGGACAG | 249 | DYRK1A | HEK 293FT | N.D. |
| *C. diphtheria* | NGGNNNN | ACCTGGTGGGCGACGT GCTG | GGGAGTC | 250 | DYRK1A | HEK 293FT | N.D. |
| *C. diphtheria* | NGGNNNN | ATGGAGCAGTCTCAGT CTTC | GGGCACC | 257 | DYRK1A | HEK 293FT | N.D. |
| *N. cinerea* | NNNNGAT | GAATGAAAATGACGGT GCAAGCCG | AACAGAT | 252 | DYRK1A | HEK 293FT | N.D. |
| *N. cinerea* | NNNNGAT | TTAATGGTATAGAAGA TCCA | TAGTGAT | 253 | DYRK1A | HEK 293FT | N.D. |
| *C. lar* | NNGGGNN | TGTCACCTCCAATGACT GGG | GTGGGCA | 254 | EMX1 | HEK 293FT | N.D. |
| *C. lar* | NNGGGNN | TGGAGCAGTCTCAG TCT | TCGGGCA | 255 | DYRK1A | HEK 293FT | N.D. |
| *C. lar* | NNGGGNN | GCACCAGCATCGGCACA GTG | GTGGGCA | 256 | DYRK1A | HEK 293FT | N.D. |
| *C. lar* | NNGGGNN | CGACGGTCACTGTACTG ATGTGAA | TGGGGCA | 257 | DYRK1A | HEK 293FT | N.D. |
| *P. lavamentivorans* | NNNCATN | CCGAGCAGAAGAAGAA GGGC | TCCCATC | 258 | EMX1 | HEK 293FT | N.D. |
| *P. lavamentivorans* | NNNCATN | ATTTTAATCACTATGG ATCTTCTA | TACCATT | 259 | DYRK1A | HEK 293FT | N.D. |
| *P. lavamentivorans* | NNNCATN | CCAAAACTCGAATTCAA CCT | GGTCATA | 260 | DYRK1A | HEK 293FT | N.D. |
| *P. lavamentivorans* | NNNCATN | TGCAGCACAGTTTCTTC AAG | GAGCATA | 261 | DYRK1A | HEK 293FT | N.D. |
| *S. pasteurianus* | NNGTGAN | GTTCTTAATTTATGAA ARTCTCGT | AGGTGAA | 262 | DYRK1A | HEK 293FT | N.D. |
| *S. pyogenes* | NGGNNNN | GAGTCCGAGGAGAAGA AGAA | GGGCTCC | 263 | EMX1 | HEK 293FT | 33.3 |
| *S. pyogenes* | NGGNNNN | TGACGGTGCAAGCCGA ACAGATGA | TGGACAG | 264 | DYRK1A | HEK 293FT | 3.0 |
| *S. pyogenes* | NGGNNNN | ATCAGAAAAGAAAGAA CAGC | TGGAGTC | 265 | Sqle | Hepal-6 | 14.5 |
| *S. pyogenes* | NGGNNNN | GCAACAACAAGATCTG TGGC | TGGAATT | 266 | HmgCR | Hepal-6 | 13.5 |
| *S. pyogenes* | NGGNNNN | TGTTCCCACAATAACTT CCC | AGGGGTG | 267 | HmgCR | Hepal-6 | 11.6 |
| *S. thermophiles* | NNAGAAW | TGAGTAACATATACCT GTTTGTAG | TTAGAAA | 268 | DYRK1A | HEK 293FT | 5.0 |
| *S. aureus* | NNGAANN | CAACCACAAACCCACGA GGG | CAGAGTG | 269 | EMX1 | HEK 293FT | 15.9 |
| *S. aureus* | NNGRRNN | TAGGGTTAGGGGCCCC AGGC | CGGGGTC | 270 | EMX1 | HEK 293FT | 13.0 |
| *S. aureus* | NNGRRNN | CCTCTAACTAACCAGGT AAGTTCA | TGGAGTA | 277 | DYRK1A | HEK 293FT | 6.7 |
| *S. aureus* | NNGRRNN | TARGAGAGTAGGCTGG TAGA | TGGAGTT | 272 | GRIN2B | HEK 293FT | 24.2 |

TABLE S3 -continued

Targets used for ortholog activity test in HEK 293FT cell

| Cas9 | Consensus | Targets | PAM | (SEQ ID NO: ___) | Gene | Cell type | indel (%) |
|---|---|---|---|---|---|---|---|
| *S. aureus* | NNGRRNN | GAGTGGGCTGGTAGAT GGAG | TTGGGTT | 273 | GRIN2B | HEK 293FT | 31.7 |
| *S. aureus* | NNGRRNN | GTTGAAGATGAAGCCC AGAG | CGGAGTG | 274 | GRIN2B | HEK 293FT | 13.4 |
| *S. aureus* | NNGRRNN | TGGATGCCCAGGATGG GGGT | GAGAGTA | 275 | GRIN2B | HEK 293FT | 18.7 |
| *S. aureus* | NNGRRNN | AAAGAAAGAGCATGTT AAAA | TAGGATA | 276 | GRIN2B | HEK 293FT | N.D. |
| *S. aureus* | NNGRRNN | TCAGACATGAGATCAC AGAT | GCGGGTG | 277 | GRIN2B | HEK 293FT | 29.3 |
| *S. aureus* | NNGRRNN | GGTGCGGGTGATGATG CTCT | TTGGGTC | 278 | GRIN2B | HEK 293FT | 17.6 |
| *S. aureus* | NNGRRNN | TCATGGCTACCAGTTCC ACC | CGGGGTA | 279 | GRIN2B | HEK 293FT | 26.6 |
| *S. aureus* | NNGRRNN | CCCGGGTGGAACTGGT AGCC | ATGAATG | 280 | GRIN2B | HEK 293FT | 26.2 |
| *S. aureus* | NNGRRNN | CTTCCGACGAGGTGGCC ATC | AA&GATT | 287 | GRIN2B | HEK 293FT | 7.6 |
| *S. aureus* | NNGRRNN | CACCATCTCTCCGTGGT ACC | CCGGGTG | 282 | GRIN2B | HEK 293FT | 18.2 |
| *S. aureus* | NNGRRNN | ATCTCTTAGATACCAGC ATC | CAGGGTG | 283 | Pcsk9 | Hepal-6 | 4.6 |
| *S. aureus* | NNGRRNN | TCAATCTCCCGATGGGC ACC | CTGGATG | 284 | Pcsk9 | Hepal-6 | 2.6 |
| *S. aureus* | NNGRRNN | GCCCATCGGGAGATTG AGGG | CAGGGTC | 285 | Pcsk9 | Hepal-6 | 9.7 |
| *S. aureus* | NNGRRNN | ACTTCAACAGCGTGCCG GAG | GAGGATG | 286 | Pcsk9 | Hepal-6 | 6.2 |
| *S. aureus* | NNGRRNN | CCGCTGACCACACCTGC CAG | GTGGGTG | 287 | Pcsk9 | Hepal-6 | 8.3 |
| *S. aureus* | NNGRRNN | TGGCAGGTGTGGTCAG CGGC | CGGGATG | 288 | Pcsk9 | Hepal-6 | 3.4 |
| *S. aureus* | NNGRRNN | ATCAGAAAAGAAAGAA CAGC | TGGAGTC | 289 | Sqle | Hepal-6 | 21.1 |
| *S. aureus* | NNGRRNN | GCAACAACAAGATCTG TGGC | TGGAATT | 290 | HmgCR | Hepal-6 | 7.1 |
| *S. aureus* | NNGRRNN | TGTTCCCACAATAACTT CCC | AGGGGTG | 297 | HmgCR | Hepal-6 | 9.5 |

TABLE S4

Targets used for PAM determination in mammalian cell lines

| Cas9 | Targets | PAM | (SEQ ID NO: ___) | Gene | Cell type | indel (%) |
|---|---|---|---|---|---|---|
| *S. aureus* | GAGGACCGCCCTGGGCCTGG | GAGAAT | 292 | Rosa26 | Hepa1-6 | 9 |
| *S. aureus* | CACGAGGGGAAGAGGGGGCA | AGGGAT | 293 | Rosa26 | Hepa1-6 | 12 |
| *S. aureus* | CGCCCATCTTCTAGAAAGAC | TGGAGT | 294 | Rosa26 | Hepa1-6 | 16 |

TABLE S4-continued

Targets used for PAM determination in mammalian cell lines

| Cas9 | Targets | PAM | (SEQ ID NO: ___) | Gene | Cell type | indel (%) |
|---|---|---|---|---|---|---|
| *S. aureus* | AGTCTTTCTAGAAGATGGGC | GGGAGT | 295 | Rosa26 | Hepa1-6 | 14 |
| *S. aureus* | GTGTGGGCGTTGTCCTGCAG | GGGAAT | 296 | Rosa26 | Hepa1-6 | 13 |
| *S. aureus* | TAGGGGCAAATAGGAAAATG | GAGGAT | 297 | Rosa26 | Hepa1-6 | 0 |
| *S. aureus* | CAAATAGGAAAATGGAGGAT | AGGAGT | 298 | Rosa26 | Hepa1-6 | 24 |
| *S. aureus* | AATGGAGGATAGGAGTCATC | TGGGGT | 299 | Rosa26 | Hepa1-6 | 17 |
| *S. aureus* | TCCTCATGGAAATCTCCGAG | GCGGAT | 300 | Rosa26 | Hepa1-6 | 17 |
| *S. aureus* | AGGAGATAAAGACATGTCAC | CCGAGT | 301 | Rosa26 | Hepa1-6 | 0 |
| *S. aureus* | CTAAGCAGGAGAGTATAAAC | TCGGGT | 302 | Rosa26 | HEK 293FT | 0 |
| *S. aureus* | CTGTAGTAGGATCTAAGCAG | GAGAGT | 303 | Rosa26 | HEK 293FT | 0 |
| *S. aureus* | CACTGTATTTCATACTGTAG | TAGGAT | 304 | Rosa26 | HEK 293FT | 0 |
| *S. aureus* | CTGCAGAAGGAGCGGGAGAA | ATGGAT | 305 | Rosa26 | HEK 293FT | 17 |
| *S. aureus* | GAGTGTTGCAATACCTTTCT | GGGAGT | 306 | Rosa26 | HEK 293FT | 17 |
| *S. aureus* | CCTGGACACCCCGTTCTCCT | GTGGAT | 307 | AAVS1 | HEK 293FT | 5 |
| *S. aureus* | ACAGCATGTTTGCTGCCTCC | AGGGAT | 308 | AAVS1 | HEK 293FT | 13 |
| *S. aureus* | GTGGTCCCAGCTCGGGGACA | CAGGAT | 309 | AAVS1 | HEK 293FT | 30 |
| *S. aureus* | CGGTTAATGTGGCTCTGGTT | CTGGGT | 310 | AAVS1 | HEK 293FT | 35 |
| *S. aureus* | TGTCCCTAGTGGCCCCACTG | TGGGGT | 311 | AAVS1 | HEK 293FT | 31 |
| *S. aureus* | TCCTTCCTAGTCTCCTGATA | TTGGGT | 312 | AAVS1 | HEK 293FT | 34 |
| *S. aureus* | CCTGAAGTGGACATGGGGGC | CCGGGT | 313 | AAVS1 | HEK 293FT | 0 |
| *S. aureus* | GAGAGATGGCTCCAGGAAAT | GGGGGT | 314 | AAVS1 | HEK 293FT | 16 |
| *S. aureus* | TTGCTTACGATGGAGCCAGA | GAGGAT | 315 | AAVS1 | HEK 293FT | 0 |
| *S. aureus* | GAGCCACATTAACCGGCCCT | GGGAAT | 316 | AAVS1 | HEK 293FT | 32 |
| *S. aureus* | CACAGTGGGGCCACTAGGGA | CAGGAT | 317 | AAVS1 | HEK 293FT | 27 |
| *S. aureus* | GACTAGGAAGGAGGAGGCCT | AAGGAT | 318 | AAVS1 | HEK 293FT | 23 |
| *S. aureus* | GAGTCTGCCTAACAGGAGGT | GGGGGT | 319 | AAVS1 | HEK 293FT | 26 |
| *S. aureus* | TGGGGGTGTGTCACCAGATA | AGGAAT | 320 | AAVS1 | HEK 293FT | 15 |
| *S. aureus* | CCCTGCCAAGCTCTCCCTCC | CAGGAT | 321 | AAVS1 | HEK 293FT | 18 |
| *S. aureus* | CTGGGAGGGAGAGCTTGGCA | GGGGGT | 322 | AAVS1 | HEK 293FT | 0 |
| *S. aureus* | CAGGGGGTGGGAGGGAAGGG | GGGGAT | 323 | AAVS1 | HEK 293FT | 0 |
| *S. aureus* | GGTGGCTAAAGCCAGGGAGA | CGGGGT | 324 | AAVS1 | HEK 293FT | 0 |
| *S. aureus* | TAGGGTTAGGGGCCCCAGGC | CGGGGT | 325 | EMX1 | HEK 293FT | 0 |
| *S. aureus* | ATGGGAAGACTGAGGCTACA | TAGGGT | 326 | EMX1 | HEK 293FT | 0 |
| *S. aureus* | CATCAGGCTCTCAGCTCAGC | CTGAGT | 327 | EMX1 | HEK 293FT | 0 |
| *S. aureus* | GTGGCTGCTCTGGGGGCCTC | CTGAGT | 328 | EMX1 | HEK 293FT | 29 |
| *S. aureus* | GAAGCTGGAGGAGGAAGGGC | CTGAGT | 329 | EMX1 | HEK 293FT | 8 |
| *S. aureus* | TCGATGTCACCTCCAATGAC | TAGGGT | 330 | EMX1 | HEK 293FT | 15 |
| *S. aureus* | GCAAGCAGCACTCTGCCCTC | GTGGGT | 331 | EMX1 | HEK 293FT | 8 |
| *S. aureus* | CAACCACAAACCCACGAGGG | CAGAGT | 332 | EMX1 | HEK 293FT | 32 |

TABLE S4-continued

Targets used for PAM determination in mammalian cell lines

| Cas9 | Targets | PAM | (SEQ ID NO: ___) | Gene | Cell type | indel (%) |
|---|---|---|---|---|---|---|
| *S. aureus* | AAGCCTGGCCAGGGAGTGGC | CAGAGT | 333 | EMX1 | HEK 293FT | 7 |
| *S. aureus* | GCCTCCCCAAAGCCTGGCCA | GGGAGT | 334 | EMX1 | HEK 293FT | 28 |
| *S. aureus* | GGCCAGGCTTTGGGGAGGCC | TGGAGT | 335 | EMX1 | HEK 293FT | 24 |
| *S. aureus* | CAGGCTGAGCTGAGAGCCTG | ATGGGA | 336 | EMX1 | HEK 293FT | 9 |
| *S. aureus* | CTCAACACTCAGGCTGAGCT | GAGAGC | 337 | EMX1 | HEK 293FT | 9 |
| *S. aureus* | GCCTCAACACTCAGGCTGAG | CTGAGA | 338 | EMX1 | HEK 293FT | 9 |
| *S. aureus* | CTGGGGCCTCAACACTCAGG | CTGAGC | 339 | EMX1 | HEK 293FT | 8 |
| *S. aureus* | GAGGCCCCCAGAGCAGCCAC | TGGGGC | 340 | EMX1 | HEK 293FT | 20 |
| *S. aureus* | GGAGGCCCCCAGAGCAGCCA | CTGGGG | 341 | EMX1 | HEK 293FT | 21 |
| *S. aureus* | TGAGAAACTCAGGAGGCCCC | CAGAGC | 342 | EMX1 | HEK 293FT | 15 |
| *S. aureus* | GGGGCACAGATGAGAAACTC | AGGAGG | 343 | EMX1 | HEK 293FT | 10 |
| *S. aureus* | AGGGGCACAGATGAGAAACT | CAGGAG | 344 | EMX1 | HEK 293FT | 2 |
| *S. aureus* | AGGGAGGGAGGGGCACAGAT | GAGAAA | 345 | EMX1 | HEK 293FT | 5 |
| *S. aureus* | CCAGGGAGGGAGGGGCACAG | ATGAGA | 346 | EMX1 | HEK 293FT | 3 |
| *S. aureus* | TTCACCTGGGCCAGGGAGGG | AGGGGC | 347 | EMX1 | HEK 293FT | 1 |
| *S. aureus* | CTTCACCTGGGCCAGGGAGG | GAGGGG | 348 | EMX1 | HEK 293FT | 8 |
| *S. aureus* | ACCTTCACCTGGGCCAGGGA | GGGAGG | 349 | EMX1 | HEK 293FT | 7 |
| *S. aureus* | CACCTTCACCTGGGCCAGGG | AGGGAG | 350 | EMX1 | HEK 293FT | 6 |
| *S. aureus* | ACCACACCTTCACCTGGGCC | AGGGAG | 351 | EMX1 | HEK 293FT | 5 |
| *S. aureus* | ACACCTTCACCTGGGCCAGG | GAGGGA | 352 | EMX1 | HEK 293FT | 5 |
| *S. aureus* | CCACACCTTCACCTGGGCCA | GGGAGG | 353 | EMX1 | HEK 293FT | 8 |
| *S. aureus* | AACCACACCTTCACCTGGGC | CAGGGA | 354 | EMX1 | HEK 293FT | 6 |
| *S. aureus* | TTCTGGAACCACACCTTCAC | CTGGGC | 355 | EMX1 | HEK 293FT | 7 |
| *S. aureus* | TGTACTTTGTCCTCCGGTTC | TGGAAC | 356 | EMX1 | HEK 293FT | 2 |
| *S. aureus* | TTGTACTTTGTCCTCCGGTT | CTGGAA | 357 | EMX1 | HEK 293FT | 2 |
| *S. aureus* | GGGAGCCCTTCTTCTTCTGC | TCGGAC | 358 | EMX1 | HEK 293FT | 0 |
| *S. aureus* | GCGCCACCGGTTGATGTGAT | GGGAGC | 359 | EMX1 | HEK 293FT | 2 |
| *S. aureus* | TGCGCCACCGGTTGATGTGA | TGGGAG | 360 | EMX1 | HEK 293FT | 7 |
| *S. aureus* | ATGCGCCACCGGTTGATGTG | ATGGGA | 361 | EMX1 | HEK 293FT | 0 |
| *S. aureus* | CTCTCAGCTCAGCCTGAGTG | TTGAGG | 362 | EMX1 | HEK 293FT | 11 |
| *S. aureus* | TTGAGGCCCCAGTGGCTGCT | CTGGGG | 363 | EMX1 | HEK 293FT | 0 |
| *S. aureus* | TGAGGCCCCAGTGGCTGCTC | TGGGGG | 364 | EMX1 | HEK 293FT | 0 |
| *S. aureus* | GAGGCCCCAGTGGCTGCTCT | GGGGGC | 365 | EMX1 | HEK 293FT | 0 |
| *S. aureus* | CCCCTCCCTCCCTGGCCCAG | GTGAAG | 366 | EMX1 | HEK 293FT | 4 |
| *S. aureus* | CCCAGGTGAAGGTGTGGTTC | CAGAAC | 367 | EMX1 | HEK 293FT | 4 |
| *S. aureus* | GTGAAGGTGTGGTTCCAGAA | CCGGAG | 368 | EMX1 | HEK 293FT | 0 |
| *S. aureus* | TGAAGGTGTGGTTCCAGAAC | CGGAGG | 369 | EMX1 | HEK 293FT | 12 |

TABLE S4-continued

Targets used for PAM determination in mammalian cell lines

| Cas9 | Targets | PAM | (SEQ ID NO: ___) | Gene | Cell type | indel (%) |
|---|---|---|---|---|---|---|
| *S. aureus* | AAGGTGTGGTTCCAGAACCG | GAGGAC | 370 | EMX1 | HEK 293FT | 10 |
| *S. aureus* | GGAGGACAAAGTACAAACGG | CAGAAG | 371 | EMX1 | HEK 293FT | 3 |
| *S. aureus* | CAAAGTACAAACGGCAGAAG | CTGGAG | 372 | EMX1 | HEK 293FT | 2 |
| *S. aureus* | AAAGTACAAACGGCAGAAGC | TGGAGG | 373 | EMX1 | HEK 293FT | 3 |
| *S. aureus* | AGTACAAACGGCAGAAGCTG | GAGGAG | 374 | EMX1 | HEK 293FT | 3 |
| *S. aureus* | GTACAAACGGCAGAAGCTGG | AGGAGG | 375 | EMX1 | HEK 293FT | 8 |
| *S. aureus* | ACAAACGGCAGAAGCTGGAG | GAGGAA | 376 | EMX1 | HEK 293FT | 3 |
| *S. aureus* | CAAACGGCAGAAGCTGGAGG | AGGAAG | 377 | EMX1 | HEK 293FT | 4 |
| *S. aureus* | ACGGCAGAAGCTGGAGGAGG | AAGGGC | 378 | EMX1 | HEK 293FT | 26 |
| *S. aureus* | GGAGGAGGAAGGGCCTGAGT | CCGAGC | 379 | EMX1 | HEK 293FT | 5 |
| *S. aureus* | AGGAAGGGCCTGAGTCCGAG | CAGAAG | 380 | EMX1 | HEK 293FT | 13 |
| *S. aureus* | AAGGGCCTGAGTCCGAGCAG | AAGAAG | 381 | EMX1 | HEK 293FT | 8 |
| *S. aureus* | GGCCTGAGTCCGAGCAGAAG | AAGAAG | 382 | EMX1 | HEK 293FT | 1 |
| *S. aureus* | CTGAGTCCGAGCAGAAGAAG | AAGGGC | 383 | EMX1 | HEK 293FT | 1 |
| *S. aureus* | TCAACCGGTGGCGCATTGCC | ACGAAG | 384 | EMX1 | HEK 293FT | 7 |
| *S. aureus* | GGCCACTCCCTGGCCAGGCT | TTGGGG | 385 | EMX1 | HEK 293FT | 0 |
| *S. aureus* | GCCACTCCCTGGCCAGGCTT | TGGGGA | 386 | EMX1 | HEK 293FT | 0 |
| *S. aureus* | CCACTCCCTGGCCAGGCTTT | GGGGAG | 387 | EMX1 | HEK 293FT | 5 |
| *S. aureus* | CACTCCCTGGCCAGGCTTTG | GGGAGG | 388 | EMX1 | HEK 293FT | 7 |
| *S. aureus* | TGGCCAGGCTTTGGGGAGGC | CTGGAG | 389 | EMX1 | HEK 293FT | 0 |
| *S. aureus* | GGCCTCCCCAAAGCCTGGCC | AGGGAG | 390 | EMX1 | HEK 293FT | 5 |
| *S. aureus* | AGGCCTCCCCAAAGCCTGGC | CAGGGA | 391 | EMX1 | HEK 293FT | 9 |
| *S. aureus* | TGTCACCTCCAATGACTAGG | GTGGGC | 392 | EMX1 | HEK 293FT | 1 |
| *S. aureus* | GTGGGCAACCACAAACCCAC | GAGGGC | 393 | EMX1 | HEK 293FT | 5 |
| *S. aureus* | TGGTTGCCCACCCTAGTCAT | TGGAGG | 394 | EMX1 | HEK 293FT | 1 |
| *S. aureus* | GTGGTTGCCCACCCTAGTCA | TTGGAG | 395 | EMX1 | HEK 293FT | 1 |
| *S. aureus* | GGCCTGGAGTCATGGCCCCA | CAGGGC | 396 | EMX1 | HEK 293FT | 5 |
| *S. aureus* | GAGTCATGGCCCCACAGGGC | TTGAAG | 397 | EMX1 | HEK 293FT | 7 |
| *S. aureus* | GCCCCGGGCTTCAAGCCCTG | TGGGGC | 398 | EMX1 | HEK 293FT | 0 |
| *S. aureus* | GGCCCCGGGCTTCAAGCCCT | GTGGGG | 399 | EMX1 | HEK 293FT | 3 |
| *S. aureus* | CATTGCCACGAAGCAGGCCA | ATGGGG | 400 | EMX1 | HEK 293FT | 16 |
| *S. aureus* | ATTGCCACGAAGCAGGCCAA | TGGGGA | 401 | EMX1 | HEK 293FT | 10 |
| *S. aureus* | TTGCCACGAAGCAGGCCAAT | GGGGAG | 402 | EMX1 | HEK 293FT | 0 |
| *S. aureus* | TGCCACGAAGCAGGCCAATG | GGGAGG | 403 | EMX1 | HEK 293FT | 15 |
| *S. aureus* | CCACGAAGCAGGCCAATGGG | GAGGAC | 404 | EMX1 | HEK 293FT | 30 |
| *S. aureus* | GGGTGGGCAACCACAAACCC | ACGAGG | 405 | EMX1 | HEK 293FT | 6 |

TABLE S4-continued

Targets used for PAM determination in mammalian cell lines

| Cas9 | Targets | PAM | (SEQ ID NO: ___) | Gene | Cell type | indel (%) |
|---|---|---|---|---|---|---|
| *S. aureus* | GCTGCTGGCCAGGCCCCTGC | GTGGGC | 406 | EMX1 | HEK 293FT | 3 |
| *S. aureus* | GAGTCCAGCTTGGGCCCACG | CAGGGG | 407 | EMX1 | HEK 293FT | 6 |

TABLE S5

Genome wide off-targets used for SaCas9 and SpCas9 specificity study

| Target # | Genome-wide off target site | PAM | Mis-matches | Forward priming site | Reverse priming site | SpCas9 indel (%) | SaCas9 indel (%) | (SEQ ID NOS: ___) |
|---|---|---|---|---|---|---|---|---|
| On-target | TAGGGTTAGG GGCCCCAGGC | CGGGG | NA | CACTGTGTCCT CTTCCTGCC | ATGAGAAACTC AGGAGGCCC | 12.88 | 13.60 | 408-410 |
| 1 | TAGGGTTAGG GTCCCCAGGT | TTGAA | 2 | AGGTTTCTGCC CATCCTTTC | GCCCAGGAAAT CCTAAAGGT | 0.044 | 0.039 | 411-413 |
| 2 | GAGGGTTAGG GCCCCCAGGC | AGGGA | 2 | CCTACCAGCAG GAAAGGACA | CATCGTAACCG AAAGGTCCA | 6.58 | 0.25 | 414-416 |
| 3 | TAAGGTTCTG GGCCCCAGGC | AAGAA | 3 | CAGTGACTCAC AGGGTCAGG | GGCGTTCCTAT TTCACAAGC | 0.052 | 0.046 | 417-419 |
| 4 | AAGAGCTAGG GGCCCCAGGC | CTGAG | 3 | AAAAGGGGGT GGACTAGAGC | CACCAGGCCTG AGAGAGAAG | 0.011 | 0.037 | 420-422 |
| 5 | TATGTTTCGG GGCCCCAGGC | CGGAA | 3 | CACCTTCTGCA TTCTGCCTA | TCCAGACCCTCA AAGACCAC | 0.023 | 0.006 | 423-425 |
| 6 | GAGGGGAAGG GGCCCCAGGC | TGGAG | 3 | GCAAAGACGG AAAGAGAAGC | CAGAGCCTTCA GAAATTCTCC | 0.145 | 0.022 | 426-428 |
| 7 | TAGGGGCAGG GGCACCAGGC | GGGGA | 3 | CCGTCTTGCTG TGTGACCTA | ATACGGACGCT CTGATCCTG | 0.466 | 0.052 | 429-431 |
| 8 | CCGGGTGAGT GGCCCCAGGC | CTGGG | 4 | CGACGTGAAG GAGAAATTCG | GCCAGTCGGAA CACTCTGA | 0.10 | 0.051 | 432-434 |
| 9 | GAGGGTGAGT GGCCCCAGGG | CAGAA | 4 | AACCTGGAGT GGGATGACAG | CCACAGGGACT CTGAGGAGA | 0.032 | 0.010 | 435-437 |
| 10 | CAGGTTTAGG GGCTCCAGGA | CTGGG | 4 | TCTGTCCTCTG GGAGCTGAC | GCTTTGCAGAC ACCATCTCA | 0.025 | 0.024 | 438-440 |
| 11 | TGGGTTTAGG GGCCACAGGT | GGGAG | 4 | GGGCTCTGGCT TCTGAGAG | CTGGGTGCTCTC TACGTGGT | 0.055 | 0.12 | 441-443 |
| 12 | TGGGGTCAGG GGACCCAGGG | TGGGG | 4 | GGGGAGTGTT TTCCTTCCAT | GCCAGGGCTCAC AGTTATTG | 0.031 | 0.047 | 444-446 |
| 13 | TAGGGTTAGG GGCCTGCAGC | CAGGG | 4 | CAGTCCTATGC TCGGGAGAG | GGGAACTGTAG CCTGTGGAG | 0.015 | 0.024 | 447-449 |
| 14 | TGGGGTGAGG GGCCCCGGCC | AGGAG | 4 | CAGAGGCTTCA GGAGGAAGG | TGGGGATATGC AACCCTTAG | 0.13 | 0.15 | 450-452 |
| 15 | GAGGATTAGG GTCACCAGGC | ATGAG | 4 | CTGGCAGGGG AAGTCAAATA | ATTCCGTCTGTC TGGAATGC | 0.058 | 0.083 | 453-455 |
| 16 | TGGGGCCAGG GGCCGCAGGC | AGGGG | 4 | CCCGTTCTCTC TCCTTCCTC | TGCACCAAGTA GCAGAGGTG | 0.009 | 0.004 | 456-458 |
| 17 | ACGGGTTAGG GGACACAGGC | CTGAG | 4 | CCTCTCTGAGC CCAGTGTTC | TCTTGTTCTCCA CCCCTCAG | 0.033 | 0.028 | 459-461 |
| 18 | GAGGGGCAGG GGGCCCAGGC | TGGGG | 4 | GTCTGCTGGG ATTCTGGGTA | CAGCTTTGTGG CTCTGGAAT | 0.044 | 0.054 | 462-464 |

TABLE S5-continued

Genome wide off-targets used for SaCas9 and SpCas9 specificity study

| Target # | Genome-wide off target site | PAM | Mismatches | Forward priming site | Reverse priming site | SpCas9 indel (%) | SaCas9 indel (%) | (SEQ ID NOS: ___) |
|---|---|---|---|---|---|---|---|---|
| 19 | GAGCGTTGGG GGCCCCAGGA | CAGGG | 4 | CTCGTGAGCAA CGGGACTAT | GTGGAAACACG GTGCTCTTT | 0.066 | 0.062 | 465-467 |
| 20 | TAGAGTTAGG AGACCCAGGA | ATGAG | 4 | CAACCAAGATC AGGCAACAA | AACTTGGTAAG TGCCCAGCA | 0.12 | 0.066 | 468-470 |
| 21 | TGGGGAGGGG GGCCCCAGGC | AGGGG | 4 | GGCCTCTGAAA TAACGTTGG | CCCTGCTTTCTT CACTCCAG | 0.043 | 0.057 | 471-473 |
| 22 | AAGGGTTAGG GGCCCAAAGG | TAGAG | 4 | GGACCCTGGG AACATTTTGT | AAAGGGCAGAG GAAAGAAGG | 0.046 | 0.066 | 474-476 |
| 23 | GAGGCTGAGT GGCCCCAGGC | CTGAG | 4 | CCCAGTTTGAG GACAGTGGT | GGGCTTAGGGA CTCAGGAGA | 0.11 | 0.092 | 477-479 |
| 24 | TCGGGTGTGG GGCTCCAGGC | CCGGG | 4 | CAAGAGAGGG AGGATGCAAG | GCTGCTGAGGG ATGGAGTT | 0.036 | 0.061 | 480-482 |
| 25 | GAGGGTGAGT GGCCCCAGGA | CTGGG | 4 | CACAGACTCAG GCCATCTCA | GCAGTGAAAGA AGGCTAGATCC | 0.084 | 0.031 | 483-485 |
| 26 | TAGTGTTAGG AGCTCCAGGG | AAGGG | 4 | CCTACAGCCAT TGGACCCTA | CGAAGGGCTCA AACATCTTC | 0.0030 | 0.0040 | 486-488 |
| 27 | TAGGGTCAGG GGCTCAAGGG | ATGGG | 4 | GTCAGTGCTG ACACCTCACC | AGTGCCTCCTCT TCCCACTC | 0.015 | 0.005 | 489-491 |
| 28 | CAGGGATAGC AGCCCCAGGC | AGGGG | 4 | TGCTAGGGTG GGGAAATTCT | AAATCCAGCAG AGCAGCAAT | 0.029 | 0.023 | 492-494 |
| 29 | TAGGGGTAGG GGGGCCATGC | AGGGG | 4 | ACAGAAGGTA AGGGGGAAGG | TCTCTCTCTGCT GCACCTCA | 0.074 | 0.058 | 495-497 |
| 30 | TGGGGGTAGG GGTCCCAGGA | GAGAG | 4 | ATACCTGGGG GAACTGCTCT | GTAGGCCACCT TGACCTCTG | 0.015 | 0.015 | 498-500 |
| 31 | CAGGCTTGGG GGCCCCAGGT | AGGGG | 4 | TCTGAGAACA CCAGGAAGCA | TCTTGGCCTCCT CACATAGG | 0.009 | 0.013 | 501-503 |

Supplementary Sequences

*Parvibaculum lavamentivorans* Cas9

(SEQ ID NO: 504)

*ATGTACCCATACGATGTTCCAGATTACGCT*TCGCCGAAGAAAAAGCGCAAGGTCGAAG
CGTCCATGGAGAGGATTTTCGGCTTTGACATCGGCACAACAAGTATCGGATTCAGCG
TGATTGATTACAGTAGCACCCAGTCCGCAGGCAACATCCAGAGGCTGGGCGTGCGC
ATTTTCCCTGAGGCAAGGGACCCAGATGGGACCCCCCTGAACCAGCAGCGGAGACA
GAAACGCATGATGAGGCGCCAGCTGCGACGGAGAAGGATTCGCCGAAAGGCACTG
AATGAGACACTGCACGAAGCCGGCTTTCTGCCAGCTTACGGGTCTGCAGATTGGCCC
GTGGTCATGGCCGACGAGCCTTATGAACTGCGGAGAAGGGGACTGGAGGAAGGCCT
GAGTGCTTACGAGTTCGGACGGGCAATCTATCATCTGGCCCAGCACCGGCATTTTAA
AGGCAGAGAACTGGAGGAATCCGATACACCCGACCCTGATGTGGACGATGAGAAGG
AAGCCGCTAACGAGAGAGCAGCCACTCTGAAGGCCCTGAAAAATGAACAGACCAC
ACTGGGAGCATGGCTGGCCCGCCGACCCCCTTCTGACCGCAAGCGAGGAATCCACG
CCCATAGGAACGTGGTCGCTGAGGAGTTCGAGCGCCTGTGGGAAGTGCAGTCCAAG
TTTCACCCCGCTCTGAAATCTGAGGAAATGCGGGCAAGAATCAGTGATACAATTTTC
GCCCAGAGGCCTGTGTTTTGGCGCAAGAACACTCTGGGAGAGTGCAGATTCATGCCT
GGCGAACCACTGTGTCCCAAGGGGTCCTGGCTGTCTCAGCAGCGGAGAATGCTGGA
GAAACTGAACAATCTGGCTATCGCAGGCGGGAATGCTAGGCCACTGGATGCAGAGG
AACGCGACGCCATTCTGAGTAAGCTGCAGCAGCAGGCCAGCATGTCCTGGCCAGGC
GTGCGGTCAGCTCTGAAGGCACTGTACAAACAGAGAGGCGAGCCCGGGGCTGAAAA
GAGCCTGAAATTCAACCTGGAGCTGGGAGGCGAATCCAAGCTGCTGGGAAATGCCC
TGGAGGCTAAACTGGCAGATATGTTTGGCCCTGACTGGCCAGCTCACCCCCGAAAG
CAGGAGATCCGGCACGCAGTGCATGAACGGCTGTGGGCTGCAGATTACGGCGAGAC
ACCCGACAAGAAAAGAGTCATCATTCTGTCCGAGAAGGATCGAAAAGCTCATCGGG
AAGCCGCTGCAAACTCTTTCGTGGCAGACTTTGGAATTACTGGCGAGCAGGCAGCTC
AGCTGCAGGCCCTGAAGCTGCCAACCGGCTGGGAACCTTATAGCATCCCAGCACTG
AACCTGTTCCTGGCCGAGCTGGAAAAGGGGGAGAGGTTTGGAGCCCTGGTGAATGG

-continued

| Supplementary Sequences |
| --- |

ACCTGATTGGGAAGGCTGGAGGCGCACAAACTTCCCCCACCGCAATCAGCCTACTG
GGGAGATCCTGGACAAGCTGCCAAGTCCCGCCTCAAAAGAGGAAAGGGAACGCATT
AGCCAGCTGCGCAACCCAACCGTGGTCCGAACACAGAATGAGCTGAGAAAGGTGGT
CAACAATCTGATCGGGCTGTATGGAAAACCCGATCGAATCCGGATTGAAGTGGGCC
GGGACGTCGGGAAGTCCAAAAGAGAAAGGGAGGAAATCCAGTCTGGCATTCGACG
GAACGAGAAGCAGAGAAAGAAAGCCACTGAAGATCTGATCAAAAACGGAATTGCT
AATCCTAGCCGGGACGATGTGGAGAAGTGGATCCTGTGGAAAGAGGGCCAGGAAA
GATGCCCATACACCGGCGACCAGATTGGCTTCAATGCCCTGTTTAGAGAAGGCAGAT
ATGAGGTGGAACACATCTGGCCTCGCTCTCGAAGTTTTGATAACAGCCCAAGGAATA
AGACACTGTGTCGCAAAGACGTGAACATCGAGAAGGGAAATAGGATGCCTTTCGAG
GCATTTGGCCATGACGAAGATCGGTGGAGCGCCATCCAGATTAGACTGCAGGGCAT
GGTGTCAGCCAAAGGGGGAACTGGGATGAGCCCCGGAAAGGTCAAACGCTTCCTGG
CTAAGACCATGCCTGAGGATTTTGCAGCCCGGCAGCTGAACGACACAAGATACGCT
GCAAAGCAGATCCTGGCCCAGCTGAAAAGGCTGTGGCCAGACATGGGACCTGAGGC
TCCAGTGAAGGTCGAAGCAGTGACTGGACAGGTCACCGCCCAGCTGCGCAAACTGT
GGACTCTGAACAATATTCTGGCTGACGATGGGGAGAAAACCAGAGCAGATCACAGG
CACCATGCCATCGACGCTCTGACAGTGGCCTGCACTCATCCTGGAATGACCAACAAG
CTGAGCAGGTATTGGCAGCTGCGCGACGATCCACGAGCAGAGAAGCCAGCTCTGAC
TCCACCCTGGGATACCATCCGCGCCGACGCTGAGAAAGCCGTGTCTGAAATTGTGGT
CAGTCACCGGGTGAGAAAGAAAGTCAGCGGCCCACTGCATAAGGAGACTACCTACG
GCGATACAGGGACTGACATTAAGACCAAATCCGGCACATATAGACAGTTCGTGACC
AGGAAGAAAATCGAGTCACTGAGCAAGGGGGAGCTGGATGAAATTCGCGACCCCCG
AATCAAAGAAATTGTGGCAGCTCACGTCGCAGGACGAGGAGGCGACCCCAAGAAG
GCCTTCCCTCCATACCCCTGTGTGTCTCCCGGAGGCCCTGAGATCCGGAAGGTCAGA
CTGACCAGTAAACAGCAGCTGAACCTGATGGCCCAGACAGGGAATGGATACGCTGA
CCTGGGCTCCAACCACCATATCGCAATCTACCGGCTGCCCGATGGGAAGGCCGACTT
CGAGATTGTGTCACTGTTTGATGCTAGCAGAAGGCTGGCACAGAGAAATCCAATCGT
GCAGAGGACACGAGCAGACGGAGCCAGCTTCGTCATGTCCCTGGCAGCCGGAGAGG
CCATCATGATTCCCGAAGGCTCAAAGAAAGGGATCTGGATTGTGCAGGGAGTCTGG
GCAAGCGGACAGGTGGTCCTGGAGAGGGACACCGATGCTGACCACTCTACAACTAC
CCGCCCTATGCCAAACCCCATCCTGAAGGACGATGCCAAGAAAGTGAGTATCGATC
CTATTGGCCGAGTCCGGCCATCAAATGAC

*Corynebacter diphtheria* Cas9

(SEQ ID NO: 505)

*ATGTACCCATACGATGTTCCAGATTACGCT*TCGCCGAAGAAAAAGCGCAAGGTCGAAG
CGTCCATGAAGTACCATGTCGGAATCGATGTCGGAACCTTTTCTGTGGGGCTGGCTG
CTATTGAAGTGGATGACGCTGGAATGCCTATTAAGACCCTGAGTCTGGTGTCACACA
TTCATGACTCAGGACTGGATCCTGACGAGATCAAGAGCGCTGTGACCAGGCTGGCA
AGCTCCGGAATCGCCCGGAGAACAAGGCGCCTGTACCGACGGAAGAGAAGGCGCCT
GCAGCAGCTGGATAAGTTCATCCAGAGGCAGGGCTGGCCAGTGATCGAGCTGGAAG
ATTACAGCGACCCCCTGTATCCTTGGAAGGTGCGCGCCGAACTGGCCGCTTCTTATA
TTGCTGACGAGAAGGAACGGGGGGAGAAACTGAGTGTGGCTCTGAGACACATCGCA
AGGCATCGCGGATGGAGGAACCCTTACGCCAAGGTGTCTAGTCTGTATCTGCCAGAT
GGCCCCTCAGACGCCTTCAAGGCTATTAGGGAGGAAATCAAACGCGCTAGCGGCCA
GCCTGTGCCAGAGACTGCAACCGTCGGGCAGATGGTGACCCTGTGCGAACTGGGCA
CACTGAAGCTGCGAGGAGAGGGAGGAGTGCTGAGTGCACGGCTGCAGCAGTCAGAT
TACGCCCGCGAGATCCAGGAAATTTGTCGAATGCAGGAGATCGGCCAGGAACTGTA
TCGCAAGATCATTGACGTGGTGTTCGCAGCCGAGTCCCCAAAGGGCTCTGCCTCAAG
CCGGGTGGGGAAAGATCCTCTGCAGCCAGGAAAGAACAGAGCACTGAAAGCCAGC
GACGCTTTTCAGCGATACCGGATTGCTGCACTGATCGGCAATCTGAGAGTCAGGGTG
GATGGGGAGAAGAGGATTCTGAGCGTGGAGGAGAAGAACCTGGTGTTCGACCACCT
GGTGAATCTGACTCCAAAGAAAGAGCCCGAATGGGTGACCATCGCCGAAATTCTGG
GCATCGATCGCGGGCAGCTGATCGGAACAGCTACTATGACCGACGATGGAGAGCGA
GCAGGAGCCCGACCCCCTACACACGATACTAACAGAAGTATTGTGAACAGCCGGAT
CGCACCACTGGTCGACTGGTGGAAAACAGCTAGCGCACTGGAGCAGCACGCCATGG
TGAAGGCACTGTCCAACGCCGAAGTCGACGATTTTGATTCTCCCGAGGGAGCAAAA
GTGCAGGCATTCTTTGCCGATCTGGACGATGACGTCCACGCCAAGCTGGACAGCCTG
CATCTGCCTGTGGGACGAGCAGCTTACTCCGAGGACACTCTGGTCAGACTGACCCGA
CGGATGCTGAGTGATGGGGTGGACCTGTATACCGCCCGGCTGCAGGAGTTCGGAAT
TGAACCTAGCTGGACCCCACCCACACCAAGAATCGGAGAGCCTGTCGGCAATCCAG
CCGTCGACCGGGTGCTGAAAACAGTGAGCAGATGGCTGGAATCCGCAACAAAGACT
TGGGGCGCCCCAGAGAGGGTCATCATTGAGCACGTGCGCGAAGGCTTCGTCACTGA
GAAACGCGCTCGAGAAATGGATGGGGACATGAGAAGGCGCGCAGCCCGGAACGCC
AAGCTGTTTCAGGAGATGCAGGAAAAGCTGAATGTGCAGGGCAAACCCAGTCGAGC
CGATCTGTGGAGATACCAGTCAGTGCAGAGACAGAACTGCCAGTGTGCCTATTGCG
GGTCCCCAATTACCTTTTCTAATAGTGAAATGGACCACATCGTGCCCAGAGCAGGGC
AGGGATCCACCAACACAAGGGAGAATCTGGTCGCCGTGTGCCATCGCTGTAACCAG
TCTAAGGGCAATACACCCTTCGCTATTTGGGCAAAAAACACTTCTATCGAAGGGGTC
AGTGTGAAGGAGGCCGTGGAACGGACCAGACATTGGGTCACTGATACCGGCATGAG
AAGCACTGACTTCAAGAAGTTCACCAAGGCTGTGGTCGAGCGGTTTCAGAGAGCAA
CAATGGATGAGGAAATCGACGCCAGAAGCATGGAATCCGTCGCCTGGATGGCTAAT
GAGCTGAGGAGCCGCGTGGCTCAGCACTTCGCATCCCATGGAACCACAGTCAGGGT
GTACCGAGGCAGCCTGACAGCAGAGGCTCGACGGGCATCTGGGATCAGTGGAAAGC
TGAAATTCTTTGATGGCGTGGGGAAGTCCAGGCTGGATAGAAGGCACCATGCTATTG
ACGCTGCAGTGATCGCATTCACCTCTGACTATGTGGCCGAAACACTGGCTGTCCGCT
CAAACCTGAAACAGAGCCAGGCCCACCGACAGGAGGCTCCTCAGTGGAGAGAGTTC

-continued

| Supplementary Sequences |
| --- |

ACCGGCAAGGATGCAGAGCATCGAGCAGCTTGGAGAGTGTGGTGCCAGAAGATGGA
AAAACTGAGCGCCCTGCTGACCGAGGACCTGCGAGATGACCGGGTGGTCGTGATGT
CTAACGTGCGACTGCGGCTGGGAAATGGCAGTGCCCACAAGGAAACCATTGGCAAA
CTGTCAAAGGTGAAACTGTCCTCTCAGCTGTCAGTCAGCGATATCGACAAAGCAAGT
TCAGAGGCCCTGTGGTGTGCTCTGACCAGAGAGCCCGGATTCGATCCTAAGGAAGG
CCTGCCCGCTAACCCTGAGAGACACATCAGGGTGAATGGGACACATGTCTACGCCG
GGGACAATATTGGACTGTTTCCAGTGTCAGCAGGAAGCATCGCACTGAGGGGAGGA
TACGCAGAGCTGGGCAGCTCCTTCCACCATGCTCGCGTGTATAAAATTACTTCCGGC
AAGAAACCCGCATTTGCCATGCTGAGGGTGTACACCATCGATCTGCTGCCTTATCGC
AACCAGGACCTGTTTAGCGTGGAACTGAAGCCACAGACAATGTCCATGAGGCAGGC
TGAGAAGAAACTGCGCGACGCTCTGGCAACTGGGAATGCAGAATATCTGGGATGGC
TGGTCGTGGATGACGAGCTGGTCGTGGATACATCTAAGATTGCCACTGACCAGGTCA
AAGCAGTGGAGGCCGAACTGGGGACTATCCGCCGATGGCGGGTGGATGGATTCTTT
TCCCCCTCTAAACTGAGACTGAGGCCTCTGCAGATGTCCAAGGAGGGGATCAAGAA
AGAGTCCGCTCCCGAACTGTCTAAAATCATTGACAGACCAGGATGGCTGCCCGCCGT
GAACAAGCTGTTCTCTGATGGAAATGTCACCGTCGTGCGGAGAGACTCTCTGGGACG
CGTGCGACTGGAGAGTACAGCCCACCTGCCTGTCACTTGGAAGGTGCAG

*Streptococcus pasteurianus* Cas9

(SEQ ID NO: 506)

*ATGTACCCATACGATGTTCCAGATTACGCT*TCGCCGAAGAAAAAGCGCAAGGTCGAAG
CGTCCATGACTAACGGCAAGATTCTGGGGCTGGACATTGGCATCGCAAGCGTGGGG
GTGGGGATTATTGAGGCAAAAACTGGAAAGGTGGTGCATGCCAATTCCCGGCTGTT
CTCTGCCGCTAACGCTGAGAACAATGCAGAACGGAGAGGGTTTAGGGGATCTAGGC
GCCTGAATCGACGGAAGAAACACCGCGTGAAGCGAGTCCGGGATCTGTTCGAGAAA
TACGGAATCGTCACCGACTTTCGCAACCTGAATCTGAACCCTTATGAGCTGCGAGTG
AAGGGCCTGACCGAACAGCTGAAAAACGAGGAACTGTTCGCAGCCCTGAGAACAAT
CTCTAAGAGAAGGGGGGATTAGTTACCTGGACGATGCCGAGGACGATAGTACCGGAT
CAACAGACTATGCTAAGAGCATCGATGAGAATCGCCGACTGCTGAAAAACAAGACA
CCAGGCCAGATTCAGCTGGAGAGGCTGGAAAAGTACGGCCAGCTGCGCGGGAATTT
CACCGTCTATGACGAGAACGGGGAAGCCCATCGCCTGATCAATGTGTTTAGTACATC
AGATTACGAGAAAGAAGCACGGAAGATCCTGGAGACACAGGCCGACTACAACAAG
AAAATCACAGCTGAGTTCATTGACGATTATGTGGAAATCCTGACCCAGAAACGAAA
GTACTATCACGGCCCCGGGAACGAAAAGAGCCGGACTGACTACGGACGGTTCCGGA
CCGATGGGACCACACTGGAGAATATTTTCGGAATCCTGATTGGCAAGTGCAACTTTT
ACCCTGATGAATATCGAGCAAGCAAGGCCAGCTACACCGCACAGGAGTATAATTTC
CTGAACGACCTGAACAATCTGAAGGTGAGCACCGAAACAGGGAAGCTGTCAACAGA
GCAGAAAGAAAGCCTGGTGGAGTTTGCCAAGAATACTGCTACCCTGGGACCCCGCTA
AACTGCTGAAGGAGATCGCAAAAATTCTGGACTGTAAGGTGGATGAGATCAAAGGA
TACAGAGAGGACGATAAAGGCAAGCCAGATCTGCATACCTTCGAGCCCTATAGGAA
ACTGAAGTTTAATCTGGAAAGCATCAACATTGACGATCTGTCCCGCGAAGTGATCGA
CAAGCTGGCTGATATTCTGACTCTGAACACCGAGAGAGAAGGAATCGAGGACGCAA
TTAAGAGGAATCTGCCAAACCAGTTCACAGAGGAACAGATCAGCGAGATCATCAAG
GTGCGGAAGAGCCAGTCCACTGCTTTCAATAAGGGCTGGCACTCTTTTAGTGCAAAA
CTGATGAACGAGCTGATCCCCGAACTGTACGCCACCTCCGACGAGCAGATGACAAT
TCTGACTCGGCTGGAAAAATTCAAGGTCAATAAGAAAAGCTCCAAAAACACAAAGA
CTATCGACGAGAAGGAAGTCACTGATGAGATCTACAATCCTGTGGTCGCCAAGAGC
GTGAGACAGACCATCAAAATCATTAACGCTGCAGTCAAGAAATATGGCGACTTCGA
TAAGATCGTGATTGAAATGCCACGGGATAAAAATGCTGACGATGAGAAGAAGTTCA
TCGACAAGAGAAATAAGGAGAACAAGAAGGAAAAGGACGATGCCCTGAAAAGGGC
CGCTTACCTGTATAATTCTAGTGACAAGCTGCCCGATGAGGTGTTCCACGGCAACAA
GCAGCTGGAAACCAAAATCCGACTGTGGTATCAGCAGGGGGAGCGGTGCCTGTATA
GTGGAAAGCCCATCTCAATTCAGGAGCTGGTGCATAACTCTAACAATTTCGAAATCG
ATCACATTCTGCCTCTGTCACTGAGCTTTGACGATAGTCTGGCCAATAAGGTGCTGG
TCTACGCTTGGACAAACCAGGAGAAAGGCCAGAAAACCCCTTATCAGGTCATCGAC
TCCATGGATGCAGCCTGGTCTTTCAGGGAGATGAAGGACTACGTGCTGAAACAGAA
GGGACTGGGCAAGAAAAAGCGCGACTATCTGCTGACTACCGAGAACATCGATAAGA
TTGAAGTGAAGAAGAAGTTCATCGAGAGGAATCTGGTGGATACTCGCTACGCATCT
CGAGTGGTCCTGAACTCTCTGCAGAGTGCCCTGAGAGAGCTGGGGAAAGACACTAA
GGTGTCTGTGGTCAGGGGACAGTTCACCAGTCAGCTGCGGAGAAAATGGAAGATCG
ATAAGAGCCGCGAGACATACCACCATCACGCAGTGGACGCCCTGATCATTGCTGCA
TCAAGCCAGCTGAAACTGTGGGAGAAGCAGGACAATCCCATGTTTGTGGATTATGG
CAAGAACCAGGTGGTCGACAAACAGACTGGGGAGATCCTGTCCGTGTCTGACGATG
AGTACAAGGAACTGGTGTTCCAGCCCCCTTATCAGGGCTTTGTGAATACCATCTCCT
CTAAAGGGTTCGAGGACGAAATTCTGTTTAGCTACCAGGTGGATTCCAAATATAACC
GGAAGGTCAGTGACGCAACCATCTACTCAACAAGAAAAGCCAAGATTGGCAAGGAT
AAGAAAGAGGAAACCTACGTGCTGGGAAAAATCAAGGACATCTACTCCCAGAATGG
CTTCGATACCTTCATCAAGAAGTACAACAAAGATAAGACTCAGTTCCTGATGTATCA
GAAGGACTCTCTGACATGGGAGAACGTGATCGAAGTCATTCTGAGGGACTACCCAA
CAACTAAGAAAAGCGAGGACGGCAAAAATGATGTGAAGTGCAACCCCTTTGAGGAA
TACAGGCGCGAGAATGGGCTGATCTGTAAGTATTCCAAGAAAGGGAAAGGAACTCC
CATCAAGAGCCTGAAGTACTATGACAAGAAACTGGGGAACTGCATCGATATTACCC
CAGAGGAATCACGCAATAAGGTCATCCTGCAGAGCATTAACCCTTGGCGAGCCGAC
GTGTACTTCAATCCAGAGACACTGAAGTACGAACTGATGGGCCTGAAATATTCAGAT
CTGAGCTTTGAAAAGGGCACTGGGAACTACCATATCAGCCAGGAGAAATATGACGC
TATCAAAGAGAAGGAAGGAATTGGCAAGAAATCCGAGTTCAAGTTTACACTGTACC
GCAACGACCTGATCCTGATCAAGGATATCGCCAGTGGCGAGCAGGAAATCTACAGA

-continued

Supplementary Sequences

TTCCTGTCAAGAACTATGCCCAATGTGAACCACTACGTCGAGCTGAAGCCTTACGAC
AAGGAAAAGTTCGATAACGTGCAGGAGCTGGTCGAAGCACTGGGAGAGGCAGATA
AAGTGGGACGATGTATCAAAGGACTGAATAAGCCAAACATCAGCATCTACAAGGTG
AGAACCGACGTCCTGGGAAACAAATATTTCGTGAAGAAAAAGGGCGACAAACCCAA
GCTGGATTTTAAGAACAACAAGAAG

*Neisseria cinerea* Cas9

(SEQ ID NO: 507)

*ATGTACCCATACGATGTTCCAGATTACGCT*TCGCCGAAGAAAAAGCGCAAGGTCGAAG
CGTCCATGGCTGCCTTCAAACCTAATCCTATGAACTACATCCTGGGCCTGGACATTG
GAATCGCTTCTGTCGGGTGGGCTATCGTGGAAATCGACGAGGAAGAGAACCCTATC
AGACTGATTGATCTGGGAGTCAGAGTGTTTGAAAGGGCAGAGGTGCCAAAGACCGG
CGACTCCCTGGCCGCTGCACGGAGACTGGCTCGGTCTGTCAGGCGCCTGACACGAC
GGAGAGCACACAGGCTGCTGCGAGCTAGGCGCCTGCTGAAGAGAGAGGGCGTGCTG
CAGGCCGCTGACTTCGATGAAAACGGCCTGATCAAGAGCCTGCCCAATACTCCTTGG
CAGCTGAGAGCAGCCGCTCTGGACAGGAAGCTGACCCCACTGGAGTGGTCTGCCGT
GCTGCTGCACCTGATCAAGCATCGCGGCTACCTGAGTCAGCGAAAAAATGAAGGGG
AGACAGCAGATAAGGAGCTGGGAGCACTGCTGAAAGGAGTGGCCGACAACACTCAT
GCTCTGCAGACCGGCGATTTTAGGACACCCGCTGAGCTGGCACTGAATAAGTTCGAA
AAAGAGAGTGGACACATTCGAAACCAGCGGGGCGACTATTCACATACCTTCAACCG
CAAGGATCTGCAGGCCGAGCTGAATCTGCTGTTTGAAAAGCAGAAAGAGTTCGGGA
ATCCCCACGTGTCCGACGGGCTGAAAGAAGGAATCGAGACACTGCTGATGACTCAG
AGGCCTGCACTGTCTGGCGATGCCGTGCAGAAGATGCTGGGGCATTGCACCTTTGAA
CCAACAGAGCCCAAGGCAGCCAAAAACACCTACACAGCCGAGAGGTTCGTGTGGCT
GACAAAGCTGAACAATCTGCGCATCCTGGAACAGGGCAGTGAGCGGCCCCTGACTG
ACACCGAAAGAGCCACACTGATGGATGAGCCTTACAGGAAGTCTAAACTGACTTAT
GCCCAGGCTCGCAAGCTGCTGGACCTGGACGATACTGCCTTCTTTAAGGGCCTGAGG
TACGGGAAAGATAATGCAGAAGCCAGCACCCTGATGGAGATGAAGGCCTATCACGC
TATCTCCCGCGCCCTGGAAAAAGAGGGCCTGAAGGACAAGAAATCTCCCCTGAACC
TGAGTCCTGAACTGCAGGATGAGATTGGGACCGCTTTTAGCCTGTTCAAGACTGACG
AGGATATCACCGGACGCCTGAAAGACCGAGTGCAGCCCGAAATTCTGGAGGCACTG
CTGAAGCACATCAGTTTTGATAAATTCGTGCAGATTTCACTGAAGGCCCTGCGACGG
ATCGTCCCTCTGATGGAGCAGGGCAATCGGTACGACGAGGCCTGCACCGAGATCTA
CGGAGATCATTATGGCAAGAAAAACACAGAAGAGAAAATCTATCTGCCCCCTATTC
CTGCCGACGAGATCCGGAATCCAGTGGTCCTGAGAGCTCTGTCACAGGCAAGAAAA
GTGATCAACGGAGTGGTCAGAAGGTACGGCAGCCCTGCTAGGATCCACATTGAAAC
CGCACGCGAAGTGGGAAAGTCCTTTAAAGACCGCAAGGAAATCGAGAAGCGACAG
GAAGAGAATAGAAAAGATAGGGAAAAGTCTGCTGCAAAATTCAGGGAGTACTTTCC
AAACTTCGTGGGCGAACCCAAGAGTAAAGACATCCTGAAGCTGCGCCTGTACGAGC
AGCAGCACGGGAAGTGTCTGTATAGCGGAAAAGAAATTAACCTGGGCCGGCTGAAT
GAAAAGGGCTATGTGGAGATCGATCATGCACTGCCCTTTTCCAGAACATGGGACGA
TTCTTTCAACAATAAGGTCCTGGCTCTGGGGAGCGAGAACCAGAACAAGGGAAATC
AGACTCCTTACGAATATTTCAACGGGAAGGACAATAGCCGAGAATGGCAGGAGTTT
AAAGCCCGCGTGGAGACAAGCCGGTTCCCACGAAGCAAGAAACAGCGGATTCTGCT
GCAGAAGTTTGACGAAGATGGATTCAAAGAGAGAAACCTGAATGACACCCGGTACA
TCAACAGATTTCTGTGCCAGTTCGTGGCTGATCACATGCTGCTGACCGGAAAGGGCA
AACGCCGAGTCTTTGCAAGCAACGGCCAGATCACAAATCTGCTGAGGGGCTTCTGG
GGGCTGCGGAAGGTGAGAGCCGAGAATGACCGCCACCATGCACTGGATGCCGTGGT
CGTGGCTTGTTCCACTATTGCAATGCAGCAGAAGATCACCAGGTTTGTGCGCTATAA
AGAGATGAACGCCTTCGACGGAAAGACAATTGATAAAGAAACTGGCGAGGTGCTGC
ACCAGAAGGCACATTTTCCTCAGCCATGGGAGTTCTTCGCCCAGGAAGTGATGATCC
GGGTCTTTGGGAAGCCTGACGGAAAACCAGAGTTCGAAGAGGCCGATACCCCAGAA
AAGCTGCGGACACTGCTGGCTGAAAAACTGAGCTCCAGACCCGAGGCAGTGCACAA
GTACGTCACCCCCCTGTTCATTAGCAGGGCCCCTAATCGCAAAATGTCCGGGCAGGG
ACATATGGAGACTGTGAAATCAGCTAAGCGGCTGGACGAAGGCATCAGCGTGCTGA
GAGTCCCACTGACCCAGCTGAAGCTGAAAGATCTGGAGAAGATGGTGAACCGGGAA
AGAGAGCCCAAGCTGTATGAAGCTCTGAAAGCAAGACTGGAGGCCCACAAGGACG
ATCCAGCTAAAGCATTTGCCGAGCCCTTCTACAAATATGACAAGGCCGGCAATCGG
ACACAGCAGGTGAAGGCTGTCAGAGTGGAGCAGGTCCAGAAAACTGGGGTCTGGGT
GCACAACCATAATGGAATTGCCGACAACGCTACAATCGTCCGGGTGGATGTGTTCG
AGAAAGGCGGGAAGTACTATCTGGTGCCTATCTACTCCTGGCAGGTCGCCAAGGGA
ATCCTGCCAGATAGAGCTGTCGTGCAGGGCAAAGACGAAGAGGATTGGACTGTGAT
GGACGATTCTTTCGAGTTTAAGTTCGTCCTGTACGCAAACGACCTGATCAAGCTGAC
AGCCAAGAAAAATGAATTTCTGGGGTATTTCGTGTCACTGAACAGGGCAACTGGAG
CCATCGATATTCGCACACATGACACTGATAGCACCAAGGGAAAAAACGGCATCTTT
CAGTCTGTGGGCGTCAAGACCGCCCTGAGTTTCCAGAAATATCAGATTGACGAACTG
GGGAAGGAGATCCGACCCTGTCGGCTGAAGAAACGACCACCCGTGCGG

*Staphylococcus aureus* Cas9

(SEQ ID NO: 508)

ATGAAAAGGAACTACATTCTGGGGCTGGACATCGGGATTACAAGCGTGGGGTATGG
GATTATTGACTATGAAACAAGGGACGTGATCGACGCAGGCGTCAGACTGTTCAAGG
AGGCCAACGTGGAAAACAATGAGGGACGGAGAAGCAAGAGGGGAGCCAGGCGCCT
GAAACGACGGAGAAGGCACAGAATCCAGAGGGTGAAGAAACTGCTGTTCGATTACA
ACCTGCTGACCGACCATTCTGAGCTGAGTGGAATTAATCCTTATGAAGCCAGGGTGA
AAGGCCTGAGTCAGAAGCTGTCAGAGGAAGAGTTTTCCGCAGCTCTCTGCTGCACCTG
GCTAAGCGCCGAGGAGTGCATAACGTCAATGAGGTGGAAGAGGACACCGGCAACG

-continued

Supplementary Sequences

AGCTGTCTACAAAGGAACAGATCTCACGCAATAGCAAAGCTCTGGAAGAGAAGTAT
GTCGCAGAGCTGCAGCTGGAACGGCTGAAGAAAGATGGCGAGGTGAGAGGGTCAA
TTAATAGGTTCAAGACAAGCGACTACGTCAAAGAAGCCAAGCAGCTGCTGAAAGTG
CAGAAGGCTTACCACCAGCTGGATCAGAGCTTCATCGATACTTATATCGACCTGCTG
GAGACTCGGAGAACCTACTATGAGGGACCAGGAGAAGGGAGCCCCTTCGGATGGAA
AGACATCAAGGAATGGTACGAGATGCTGATGGGACATTGCACCTATTTTCCAGAAG
AGCTGAGAAGCGTCAAGTACGCTTATAACGCAGATCTGTACAACGCCCTGAATGAC
CTGAACAACCTGGTCATCACCAGGGATGAAAACGAGAAACTGGAATACTATGAGAA
GTTCCAGATCATCGAAAACGTGTTTAAGCAGAAGAAAAAGCCTACACTGAAACAGA
TTGCTAAGGAGATCCTGGTCAACGAAGAGGACATCAAGGGCTACCGGGTGACAAGC
ACTGGAAAACCAGAGTTCACCAATCTGAAAGTGTATCACGATATTAAGGACATCAC
AGCACGGAAAGAAATCATTGAGAACGCCGAACTGCTGGATCAGATTGCTAAGATCC
TGACTATCTACCAGAGCTCCGAGGACATCCAGGAAGAGCTGACTAACCTGAACAGC
GAGCTGACCCAGGAAGAGATCGAACAGATTAGTAATCTGAAGGGGTACACCGGAAC
ACACAACCTGTCCCTGAAAGCTATCAATCTGATTCTGGATGAGCTGTGGCATACAAA
CGACAATCAGATTGCAATCTTTAACCGGCTGAAGCTGGTCCCAAAAAAGGTGGACC
TGAGTCAGCAGAAAGAGATCCCAACCACACTGGTGGACGATTTCATTCTGTCACCCG
TGGTCAAGCGGAGCTTCATCCAGAGCATCAAAGTGATCAACGCCATCATCAAGAAG
TACGGCCTGCCCAATGATATCATTATCGAGCTGGCTAGGGAGAAGAACAGCAAGGA
CGCACAGAAGATGATCAATGAGATGCAGAAACGAAACCGGCAGACCAATGAACGC
ATTGAAGAGATTATCCGAACTACCGGGAAAGAGAACGCAAAGTACCTGATTGAAAA
AATCAAGCTGCACGATATGCAGGAGGGAAAGTGTCTGTATTCTCTGGAGGCCATCCC
CCTGGAGGACCTGCTGAACAATCCATTCAACTACGAGGTCGATCATATTATCCCCAG
AAGCGTGTCCTTCGACAATTCCTTTAACAACAAGGTGCTGGTCAAGCAGGAAGAGA
ACTCTAAAAAGGGCAATAGGACTCCTTTCCAGTACCTGTCTAGTTCAGATTCCAAGA
TCTCTTACGAAACCTTTAAAAAGCACATTCTGAATCTGGCCAAAGGAAAGGGCCGC
ATCAGCAAGACCAAAAAGGAGTACCTGCTGGAAGAGCGGGACATCAACAGATTCTC
CGTCCAGAAGGATTTTATTAACCGGAATCTGGTGGACACAAGATACGCTACTCGCGG
CCTGATGAATCTGCTGCGATCCTATTTCCGGGTGAACAATCTGGATGTGAAAGTCAA
GTCCATCAACGGCGGGTTCACATCTTTTCTGAGGCGCAAATGGAAGTTTAAAAAGGA
GCGCAACAAAGGGTACAAGCACCATGCCGAAGATGCTCTGATTATCGCAAATGCCG
ACTTCATCTTTAAGGAGTGGAAAAAGCTGGACAAAGCCAAGAAAGTGATGGAGAAC
CAGATGTTCGAAGAGAAGCAGGCCGAATCTATGCCCGAAATCGAGACAGAACAGGA
GTACAAGGAGATTTTCATCACTCCTCACCAGATCAAGCATATCAAGGATTTCAAGGA
CTACAAGTACTCTCACCGGGTGGATAAAAAGCCCAACAGAGAGCTGATCAATGACA
CCCTGTATAGTACAAGAAAAGACGATAAGGGGAATACCCTGATTGTGAACAATCTG
AACGGACTGTACGACAAAGATAATGACAAGCTGAAAAAGCTGATCAACAAAAGTCC
CGAGAAGCTGCTGATGTACCACCATGATCCTCAGACATATCAGAAACTGAAGCTGA
TTATGGAGCAGTACGGCGACGAGAAGAACCCACTGTATAAGTACTATGAAGAGACT
GGGAACTACCTGACCAAGTATAGCAAAAAGGATAATGGCCCCGTGATCAAGAAGAT
CAAGTACTATGGGAACAAGCTGAATGCCCATCTGGACATCACAGACGATTACCCTA
ACAGTCGCAACAAGGTGGTCAAGCTGTCACTGAAGCCATACAGATTCGATGTCTATC
TGGACAACGGCGTGTATAAATTTGTGACTGTCAAGAATCTGGATGTCATCAAAAAG
GAGAACTACTATGAAGTGAATAGCAAGTGCTACGAAGAGGCTAAAAAGCTGAAAA
AGATTAGCAACCAGGCAGAGTTCATCGCCTCCTTTTACAACAACGACCTGATTAAGA
TCAATGGCGAACTGTATAGGGTCATCGGGGTGAACAATGATCTGCTGAACCGCATTG
AAGTGAATATGATTGACATCACTTACCGAGAGTATCTGGAAAACATGAATGATAAG
CGCCCCCCTCGAATTATCAAAACAATTGCCTCTAAGACTCAGAGTATCAAAAAGTAC
TCAACCGACATTCTGGGAAACCTGTATGAGGTGAAGAGCAAAAAGCACCCTCAGAT
TATCAAAAAGGGCAGCGGAGGCAAGCGTCCTGCTGCTACTAAGAAAGCTGGTCAAG
CTAAGAAAAAGAAAGGATCC*TACCCATACGATGTTCCAGATTACGCTTAA*

*Campylobacter lari* Cas9

(SEQ ID NO: 509)

*ATGTACCCATACGATGTTCCAGATTACGCT*TCGCCGAAGAAAAAGCGCAAGGTCGAAG
CGTCCATGAGGATTCTGGGGTTTGACATTGGCATTAACAGCATCGGGTGGGCTTTTG
TGGAGAACGACGAACTGAAGGACTGCGGAGTGCGGATCTTCACAAAGGCCGAGAAC
CCAAAAAATAAGGAAAGCCTGGCACTGCCCCGGAGAAATGCACGCAGCTCCAGGCG
CCGACTGAAACGGAGAAAGGCCCGGCTGATCGCTATTAAGAGAATCCTGGCCAAAG
AGCTGAAGCTGAACTACAAGGACTATGTCGCAGCTGATGGAGAGCTGCCAAAGGCC
TACGAAGGATCCCTGGCATCTGTGTACGAGCTGCGGTATAAGGCCCTGACACAGAA
CCTGGAAACTAAAGATCTGGCCAGAGTGATCCTGCACATTGCTAAGCATAGGGGGT
ACATGAACAAGAACGAGAAGAAATCAAACGACGCTAAGAAAGGAAAGATCCTGAG
CGCTCTGAAAAACAATGCACTGAAGCTGGAGAACTACCAGAGCGTGGGCGAATACT
TCTACAAGGAGTTCTTTCAGAAATACAAGAAAAACACAAAGAACTTCATCAAGATC
CGCAACACTAAGGATAATTACAACAATTGCGTGCTGTCTAGTGACCTGGAAAAAGA
GCTGAAGCTGATCCTGGAAAAACAGAAGGAGTTCGGCTACAACTACTCTGAAGATT
TCATCAACGAGATTCTGAAGGTCGCCTTCTTTCAGCGGCCCCTGAAGGACTTCAGTC
ACCTGGTGGGGGCCTGCACTTTCTTTGAGGAAGAGAAAAGGGCCTGTAAGAACAGC
TACTCTGCCTGGGAGTTTGTGGCTCTGACCAAGATCATTAACGAGATCAAGAGCCTG
GAGAAGATCAGCGGCGAAATTGTGCCAACCCAGACAATCAACGAGGTCCTGAATCT
GATCCTGGACAAGGGGTCTATCACCTACAAGAAATTCAGAAGTTGTATCAATCTGCA
TGAGAGTATCAGCTTCAAGAGCCTGAAGTATGATAAAGAAAACGCCGAGAATGCTA
AACTGATCGACTTCCGCAAGCTGGTGGAGTTTAAGAAAGCCCTGGGAGTCCACAGC
CTGTCCCGGCAGGAACTGGATCAGATCTCCACTCATATCACCCTGATTAAGGACAAC
GTGAAGCTGAAAACCGTCCTGGAGAAATACAACCTGAGTAATGAACAGATCAACAA
TCTGCTGGAAATTGAGTTCAACGATTATATCAACCTGAGCTTCAAGGCCCTGGGAAT

-continued

| Supplementary Sequences |
|---|
| GATTCTGCCACTGATGCGCGAGGGCAAACGATACGACGAGGCCTGCGAGATCGCCA<br>ATCTGAAACCTAAGACCGTGGACGAGAAGAAAGATTTCCTGCCAGCATTTTGTGATT<br>CCATTTTCGCCCACGAGCTGTCTAACCCCGTGGTCAATAGGGCTATCAGCGAATACC<br>GCAAGGTGCTGAACGCACTGCTGAAGAAATATGGAAAGGTCCACAAAATTCATCTG<br>GAGCTGGCTCGCGACGTGGGCCTGTCCAAGAAAGCACGAGAGAAGATCGAAAAAG<br>AGCAGAAGGAAAACCAGGCCGTGAATGCATGGGCCCTGAAGGAATGCGAGAATATT<br>GGCCTGAAGGCCAGCGCAAAGAACATCCTGAAACTGAAGCTGTGGAAAGAACAGA<br>AGGAGATCTGTATCTACTCCGGAAATAAGATCTCTATTGAGCACCTGAAAGATGAA<br>AAGGCCCTGGAGGTGGACCATATCTACCCCTATTCTAGGAGTTTCGACGATTCTTTT<br>ATCAACAAAGTGCTGGTGTTCACCAAGGAAAATCAGGAGAAACTGAACAAGACACC<br>TTTCGAGGCCTTTGGCAAGAATATTGAAAAATGGAGCAAGATCCAGACCCTGGCTC<br>AGAACCTGCCATACAAGAAAAAGAATAAGATTCTGGACGAGAACTTCAAAGATAAG<br>CAGCAGGAGGACTTTATCTCTCGAAATCTGAACGACACCCGGTATATCGCTACACTG<br>ATTGCAAAATACACAAAGGAGTATCTGAACTTCCTGCTGCTGAGCGAAAATGAGAA<br>CGCCAATCTGAAGAGTGGCGAAAAAGGGTCAAAGATCCACGTGCAGACTATTAGCG<br>GGATGCTGACCTCCGTCCTGAGGCACACATGGGGTTTGACAAAAAGGATCGCAAC<br>AATCATCTGCACCATGCACTGGATGCCATCATTGTGGCCTACAGTACAAATTCAATC<br>ATTAAGGCTTTCAGCGATTTCCGGAAAAACCAGGAGCTGCTGAAGGCCAGATTCTAC<br>GCTAAAGAACTGACTTCCGATAACTATAAACATCAGGTCAAGTTCTTTGAGCCTTTC<br>AAGAGTTTTAGAGAAAAAATCCTGTCAAAGATCGACGAGATTTTCGTGTCCAAACC<br>ACCTCGAAAGCGAGCTAGGCGCGCACTGCACAAGGATACCTTTCATTCTGAGAACA<br>AGATCATTGACAAGTGCAGCTACAACTCCAAGGAAGGCCTGCAGATTGCCCTGAGC<br>TGTGGAAGAGTGAGGAAAATCGGCACTAAGTATGTCGAGAATGATACCATCGTGAG<br>GGTCGACATTTTCAAAAAGCAGAACAAGTTTTACGCTATCCCAATCTACGCAATGGA<br>TTTTGCCCTGGGGATCCTGCCCAATAAGATCGTGATTACTGGAAAAGATAAGAACAA<br>TAACCCCAAACAGTGGCAGACCATTGACGAATCATACGAGTTCTGCTTTAGCCTGTA<br>TAAGAATGACCTGATCCTGCTGCAGAAAAAGAACATGCAGGAACCTGAGTTCGCCT<br>ACTATAACGATTTTTCAATCAGCACATCAAGCATTTGTGTGGAGAAACACGACAACA<br>AGTTCGAAAATCTGACTAGCAACCAGAAGCTGCTGTTTTCCAATGCAAAAGAGGGC<br>TCTGTGAAGGTCGAAAGTCTGGGGATCCAGAACCTGAAAGTGTTCGAGAAGTACAT<br>CATTACCCCCCTGGGAGATAAAATTAAGGCTGACTTTCAGCCTCGAGAAAACATCAG<br>CCTGAAAACCAGTAAAAAGTATGGCCTGAGG |

Italic: HA-tag
Underlined: NLS sequences

Primers

| Gene | Surveyor primer F | Surveyor primer R | (SEQ ID NOS: ___) |
|---|---|---|---|
| DYRK1A | GGAGCTGGTCTGTTGGAGAA | TCCCAATCCATAATCCCACGTT | 510-511 |
| GRIN2B | GCATACTCGCATGGCTACCT | CTCCCTGCAGCCCCTTTTTA | 512-513 |
| EMX1 | CCATCCCCTTCTGTGAATGT | GGAGATTGGAGACACGGAGA | 191-192 |
| Sqle | TGTAATCAGGAGCCGTTGGG | ACTGACGCTTCTAAGCCACC | 514-515 |
| HmgCR | AAGTGGCAAGCACCGTGTTA | AGCGTTCAAACAAGGACCCA | 516-517 |
| Pcsk9 (target 1) | ATGAGCCGTCTAATGCGTGG | AGTACTCACCCACAGACCCG | 518-519 |
| Pcsk9 (targets 2-7) | CAGGCGTCCAGTACCCACAC | ATCACCCCAACCCCAAAGCA | 520-521 |
| AAVS1 | CCCCTTACCTCTCTAGTCTGTGC | CTCAGGTTCTGGGAGAGGGTAG | 522-523 |
| Rosa26 | CTTGCTCTCCCAAAGTCGCT | CCAATGCTCTGTCTAGGGGT | 524-525 |

Example 38: ApoB Genotypic and Phenotypic Change Seen In Vivo with Guides and SaCas9 Delivered Intravenously to the Liver Using an AAV Vector and a Liver-Specific Cas9 Promoter In this example, inter alia:

AAV2/8 is a Liver-targeting adenoviral vector;

TBG is a liver-specific promoter and is used here to drive expression of SaCas9;

U6 is used here to drive expression of the sgRNA (guide);

ApoB is a lipid metabolism gene. It can be said to be the "gold-standard" in liver delivery, and is widely used in mouse models of obesity "Target1 through Target 4" means that 4 targets within ApoB were chosen, of which Targets 1 and three (T1 and T3) were the most useful;

Delivery through expression from a viral vector as seen here is an improvement over Anderson/Yin's (NBT 2884) use of hydrodynamic delivery as the delivery method, because hydrodynamic delivery requires several mls of fluid to be injected which is stressful on the murine body and can be fatal. Hydrodynamic delivery is well suited for delivery of plasmid (naked) DNA, whereas Applicants have shown that packaging the guide and Cas9 sequences within a viral delivery vector is preferable in terms of greatly increased efficiency. Indeed, only relatively small volumes need to be introduced, and this can be done intravenously (i.v.), which is likely to be much more acceptable therapeutically.

What was particularly encouraging was that not only was a genotypic change seen in a "gold-standard" gene for liver such as ApoB, but phenotypic changes were also recorded. Previous work with PCSK9 had shown genotypic, but not phenotypic changes, so the phenotypic changes seen with ApoB validate the plausibility of CRISPR delivery to, and its ability to effect phenotypic change in, the Liver. This is in combination with the more therapeutically acceptable means of delivery (i.v. compared to hydrodynamic delivery). As such, viral delivery of CRISPR (guide and Cas9) is preferred, especially intravenously).

Targets include: PCSK9, HMGCR, APOB, LDLR, ANGPTL3, F8, F9/FIX, MT, FAH, HPD, TAT, ATP7B, UGT1A1, OTC, ARH Material and Methods Viruses and Injection Parameters Constructs used: -AAV2/8—TBG-SaCas9-U6-sgRNA (Apob-Target1 through Target 4).

In vitro testing: all induced cleavage of Apob locus at 10%-15% efficiency in Hepa cells.

In vivo results: Mouse—8 weeks, C57BL/6 (2 animals each time point and with 1 animal as saline-injected wild type control)

Tail Vein Injection:

Injection Volume: 100 ul of 0.8E12 vp/ml (vp=viral particle)

Viral particle delivered: 0.8E11 total vp/animal

Tissue Processing and Data Collection

Tissue processing and data collection occurred as follows:

First time point ~1 wk (8 days). Second time point ~4 wks.

Saline perfusion followed by acute dissection of liver tissue.

(A) Half liver put into −80 C storage for Surveyor & qPCR & Western Blot protein analysis (X12 tubes/animal).

(B) Half liver put into Cryoprotectant and flash-freeze for cryostat processing. Cryosections were subjected to H&E and Oil Red staining.

QuickExtract and Surveyor assays were used to detect and quantify indels from 2 pieces of liver per animal.

Results

In Vivo Indel Assessment

Figure 78A:
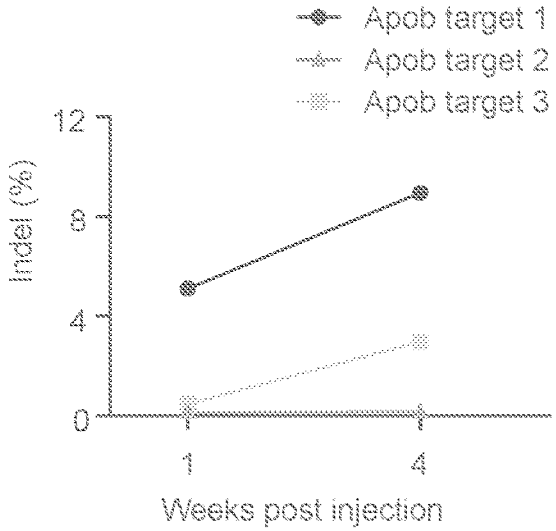
FIG. 78A shows that guide (target) 1 induced the highest percentage of indels in ApoB.
Figure 78B:
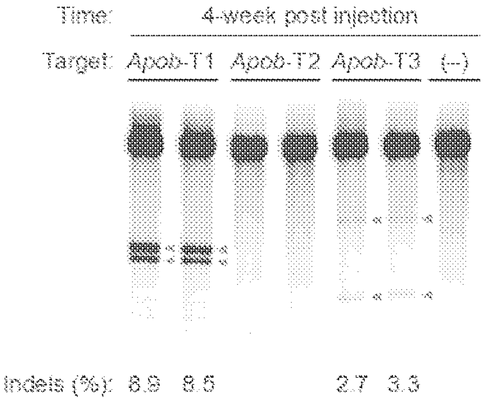
FIG. 78B shows the results of a Surveyor nuclease gel assay for indel formation efficiency, 4 weeks post-injection.

The figures show in vivo indel assessment for the ApoB guide (targets) over time (up to 4 weeks post-injection). FIG. 78 A shows that guide (target) 1 induced the highest percentage of indels in ApoB. Targets 2 and 4 showed little of no effect, in the sense that they resulted in only none or very poor indel formation, whilst Target 3 showed some activity. FIG. 78 B shows the results of a Surveyor nuclease gel assay for indel formation efficiency, 4 weeks post-injection.

Target 1 can be seen to have almost 9% indel formation, representing significant levels of target locus Phenotype Change Shown with 2 of the 4 Guides Designed to Target Phenotypic changes were seen with two of the three guides used (targets 1 and 3), as seen in FIG. 57B, which shows oil red staining to detect hepatic lipid accumulation phenotype in vivo following AAV-Cas9-sgRNA delivery. The red patches of oil shown accumulating in the 2 Figures on the left, targets 1 and 3, show that ApoB has been disrupted and are compared to the control, bottom right. Apob gene has been disrupted as a result of Cas9-induced targeted genomic cleavage, giving rise to this physiological/phenotypic change Target 2 showed no noticeable difference over the control and target 4 is not shown. This oil red O staining is an assay where the fats in liver are visualized through histological staining. This stain is used frequently in research to assess the amount of fats in liver. In clinical practice, the Oil Red O stain is mainly ordered on frozen sections of liver biopsy specimens to assess the amount of fat in the liver during liver transplantation and other procedures. For a protocol and information on this aspect of the Examples, mention is made of: Mehlem et al, "Imaging of neutral lipids by oil red O for analyzing the metabolic status in health and disease," Nature Protocols 8, 1149-1154 (2013); Maczuga et al., "Therapeutic expression of hairpins targeting apolipoprotein B100 induces phenotypic and transcriptome changes in murine liver," *Gene Therapy* (2014) 21, 60-70; Koornneef et al, "Apolipoprotein B Knockdown by AAV-delivered shRNA Lowers Plasma Cholesterol in Mice," *Molecular Therapy* (2011) 19 4, 731-740; Tadin-Strapps et al., "siRNA-induced liver ApoB knockdown lowers serum LDL-cholesterol in a mouse model with human-like serum lipids," Journal of Lipid Research Volume 52, 1084-1097 (2011). The scale bar in the figure represents 20 microns.

Example 39: SaCas9 Optimization Experiments

The following were investigated: Guide Length Optimization; Intron Test; H1 promoter; D10A Double-nickase Test; Additional Length/DN Test.

SaCas9 Guide Length Test: To determine sgRNA guide lengths: 20 vs. 21 vs. 22 bp as well the effect of a 'G' at the start (5' end) of the guide. Mention is made of FIG. 80:

Target sites:

A1: AAVS1

E1: EMX1

T1, T2, . . . : Numbering of target sites

TGC, GTC, . . . : Base composition at position 23, 22, 21 nts from 5'-end of PAM The experiment of this Example is performed by: 1. Select targets using NNGRR as PAM within two gene of interest, AAVS1 and EMX1. 2. Synthesizing oligos corresponding to the targets, but vary the length of the guide sequence part within the sgRNA from 20, to 21, to 22. 3. Use the oligos to create sgRNA expression cassette and co-transfect into HEK 293FT cell line with plasmids expressing the SaCas9 protein. 4. 72 hours post transfection, cells were harvested and then analyzed by Surveyor assay to detect indels. 5. Indel formation frequency induced by Cas9 were then calculated and summarized in the figures herewith.

Figure 80:
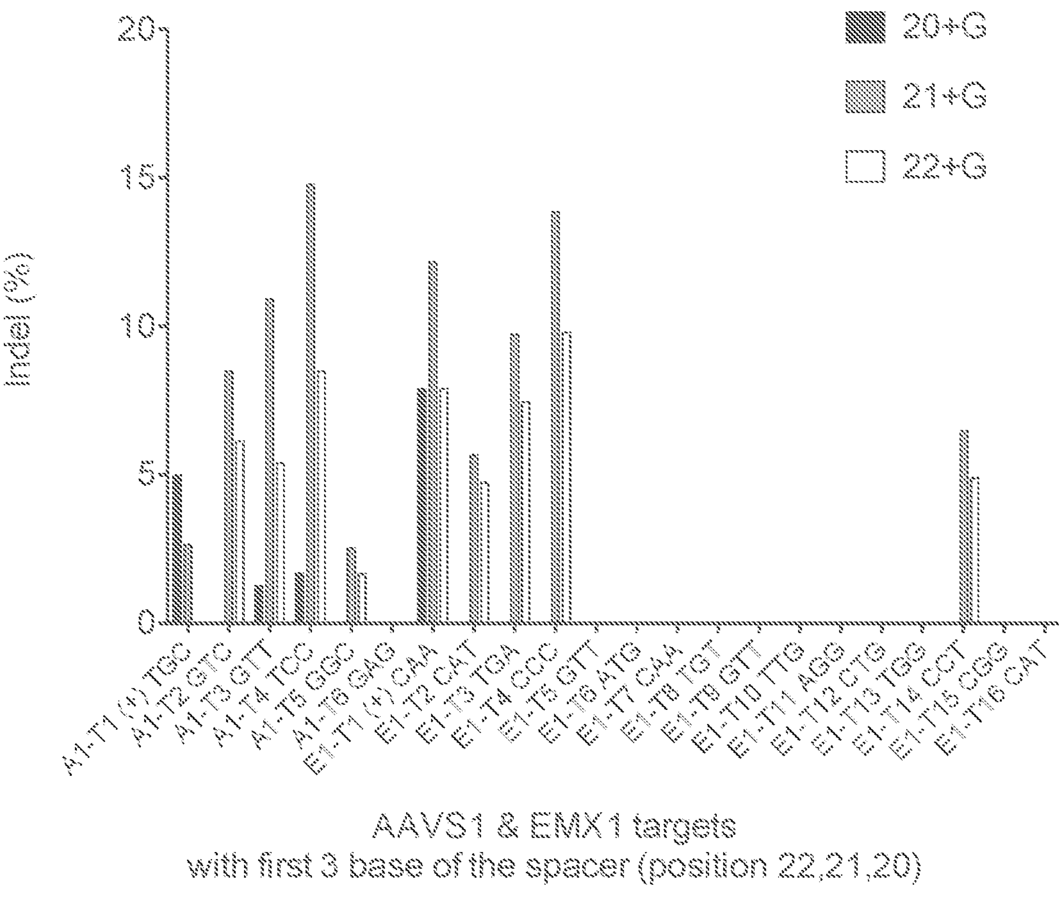
FIG. 80 shows that 21 nucleotides nts/base pairs (bp), represented by the grey bars is the optimal spacer length, at least compared to 20 or 22 base pairs across a range of targets and within two different genes (AAVS1 and EMX1).

FIG. 80 shows that 21 nts/base pairs (bp), represented by the grey bars is the optimal spacer length, at least compared to 20 or 22 base pairs (represented by the black and the white bars, respectively) across a range of targets and within two different genes (AAVS1 and EMX1). The targets and genes are not thought be important, merely representative. As such, it appears that 21nts or base pairs is optimal for good length, especially in or as to SaCas9. FIG. 80 also shows that a G nt at the 5' end of the guide/target sequence is may be advantageous, e.g., for the U6 promoter.

Intron Test

This experiment set out to test whether a guide sequence could be inserted into the Cas9 intronic sequence.

The following construct was used. Note the presence of the guide RNA (sgRNA) within the intron (between the Cas9 N' and C' terminal exons).

CMV-SaCas9(N-term)-Intron(sgRNA)-SaCas9(C-term)

The construct was expressed in Hepa cells.

Each intron was tested with 2 different guides: Pcsk9 and Hmgcr sgRNA.

A total of 9 constructs shown: three EBV1 three EBV2 and three ADV:

- Lanes 1-3: show EBV1-152 (EBV based, 152 bp intron 1 from EBV genome)
- Lanes 4-6: show EBV2 (EBV based, intron from the W repeat of EBV genome)
- Lanes 7-9: show ADV (Adenoviral based intron, similar origin as Kiani et al., “CRISPR transcriptional repression devices and layered circuits in mammalian cells,” Nature Methods doi:10.1038/nmeth.2969 Published online 5 May 2014 and Nissim et al, “Multiplexed and Programmable Regulation of Gene Networks with an Integrated RNA and CRISPR/Cas Toolkit in Human Cells,” Volume 54, Issue 4, p 698-710, 22 May 2014; DOI: dx.doi.org/10.1016/j.molcel.2014.04.022).

Within each group of design, the three constructs corresponding to three different insertion site of sgRNA within the intron.

ADV-Design 3

Figure 81:
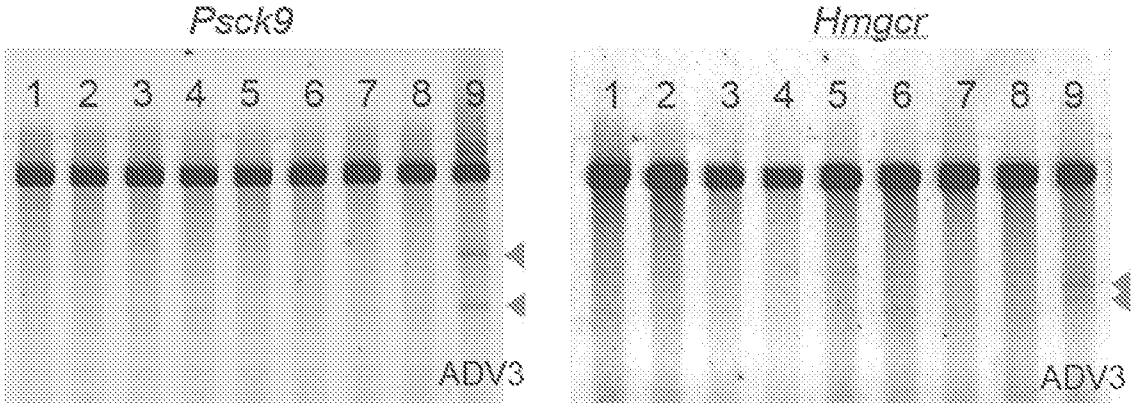
FIG. 81 shows whether a guide sequence could be inserted into the Cas9 intronic sequence.

The results are shown in FIG. 81. These results provide proof of principle of successful packaging of a guide sequence into a SaCas9 intron is certainly possible. The sgRNA bearing the guide sequence is inserted within a synthetic intron derived from Adenovirus, and then this entire intron-sgRNA cassette is inserted into the SaCas9 gene. Introns can be inserted anywhere within the SaCas9 gene without significantly disrupting the normal expression of the SaCas9 protein. Multiple introns with sgRNAs can be inserted into different positions within the SaCas9 gene Positioning is flexible and this broad approach is advantageous including in the following two ways:

Size minimisation allows for the total number of bp or nts in the construct to be reduced.

Multiplexing allows for greater degrees of multiplexing (co-delivery of multiple guides) as ‘space’ is always an issue here too. As guides don’t necessarily need a specific promoter, one or more guides can similarly be packaged into a/the Cas9 intron.

The foregoing text uses ‘a/the’ because the as discussed above, a number of synthetic introns can be introduced into Cas9. It may be advantageous to insert the sgRNA into a position close but at least 5-15 bp to the 5' end of the intron and also before the branch point of the intron. Some of the intron spacer sequence between the 5' splice donor site and the branch point in the middle of the intron may be deleted if the skilled person wishes to so do. That this was achieved in a Cas9, especially SaCas9 may be surprising, including because the sgRNA structure is different between Sa and Sp.

For now, ADV are preferred, but this approach has broad applicability across a range of viruses and Cas9s (Sa, Sp, etc).

H1 Promoter Tests

This experiment set out to investigate alternative promoters to the U6 promoter.

A) Full-Length H1

The following constructs were made:

CMV-SaCas9 with original H1 promoter driving one sgRNA (either Pcsk9-Target201 or Hmgcr-NewTarget5)

Figure 82:
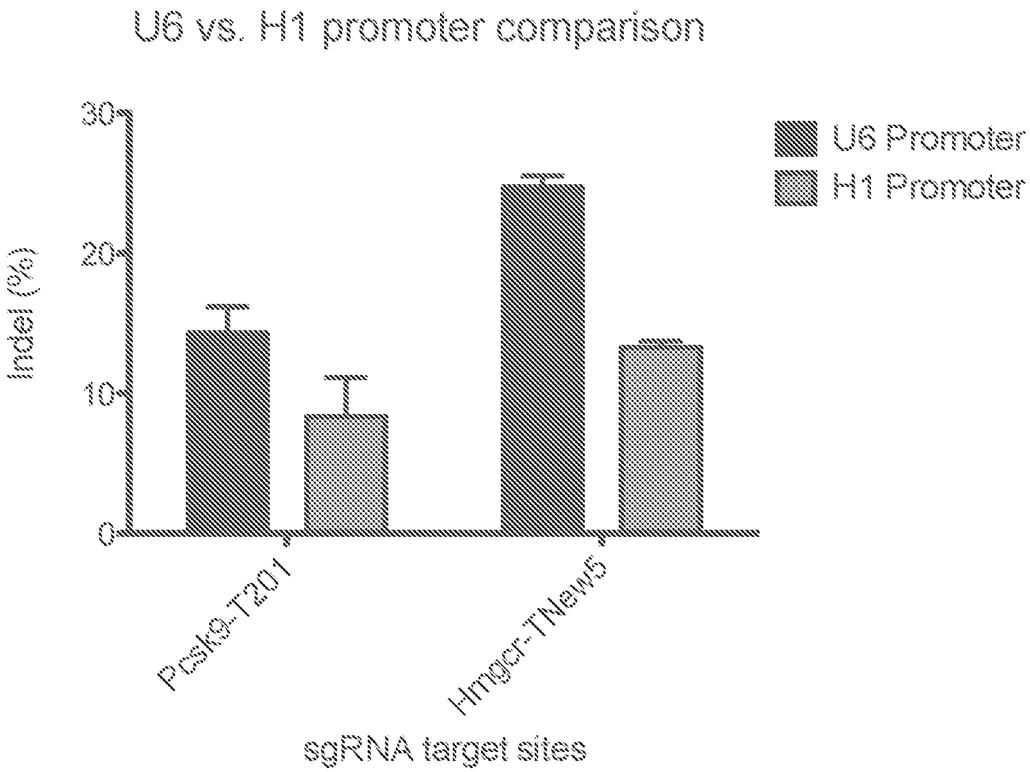
FIG. 82 shows that the full-length H1 promoter is still weaker than U6 promoter, as the U6 shows increased indel percentage formation for each target tested.

As can be seen in FIG. 82, the full-length H1 promoter (grey bar) is still weaker than U6 promoter (black bar), as the U6 shows increased indel percentage formation for each target tested.

B) Double H1 Promoter Test (Short H1)

The following constructs were made:

TBG-SaCas9 with two short H1 promoters driving two sgRNAs (Pcsk9-Target201 and Hmgcr-NewTarget5) simultaneously with the Double short H1 promoter used in the same orientation and in opposite orientations.

Figure 83:
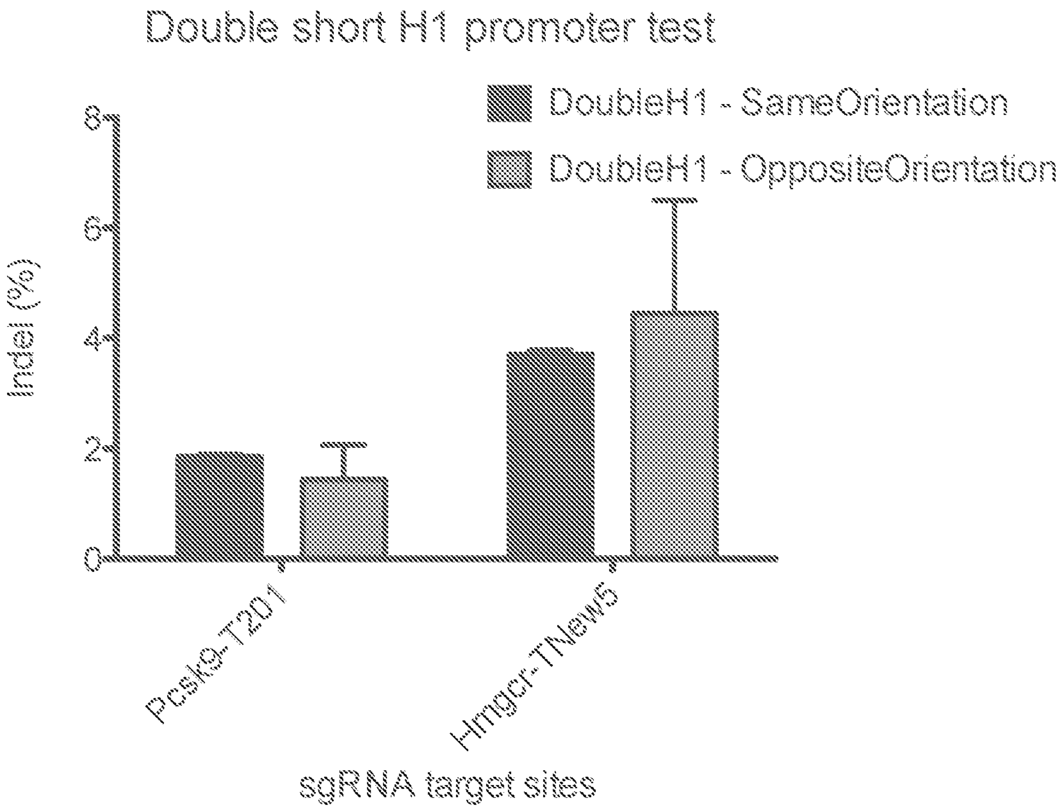
FIG. 83 shows that short H1 promoter is weaker than the full-length H1

As can be seen in FIG. 83, short H1 promoter is weaker than the full-length H1.

SaCas9 Nickase Test (Using the D10A Mutant)

This experiment looked at the distance between the 5' ends of two guide sequences in a construct and then measured this in relation to the cleavage efficiency of the D10A SaCAs9 double nickase. The targets were for the Human AAT1 gene. These tests were done with 20 bp+G guides cloned into plasmids.

Figure 84:
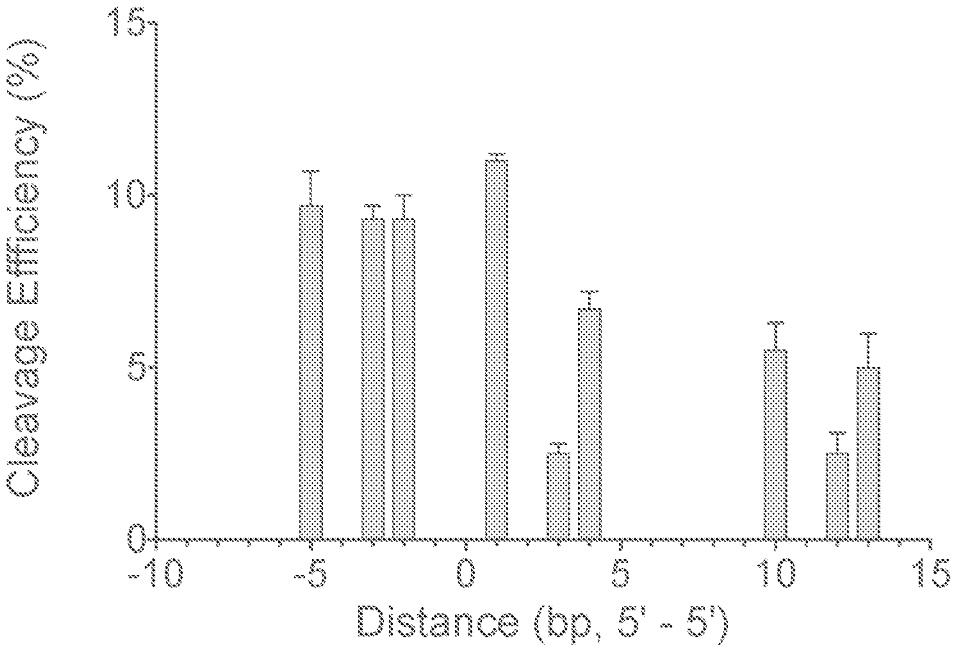
FIG. 84 shows distance between the 5' ends of two guide sequences in a construct measured in relation to the cleavage efficiency of the D10A SaCAs9 double nickase.

Optimal results were shown between −5 and +1 bp (5' to 5'), see FIG. 84.

Example 40: In Vivo Interrogation of Gene Function in the Mammalian Brain Using CRISPR-Cas9

This work presents the following main points: First demonstration of successful AAV-mediated Cas9 delivery in vivo as well as efficient genome modification in post-mitotic neurons. Development of a nuclear tagging technique which enables easy isolation of neuronal nuclei from Cas9 and sgRNA-expressing cells. Demonstration of application toward RNAseq analysis of neuronal transcriptome. Integration of electrophysiological studies with Cas9-mediated genome perturbation. And demonstration of multiplex targeting and the ability to study gene function on rodent behavior using Cas9-mediated genome editing.

Transgenic animal models carrying disease-associated mutations are enormously useful for the study of neurological disorders, helping to elucidate the genetic and pathophysiological mechanism of disease[1]. However, generation of animal models that carry single or multiple genetic modifications is particularly labor intensive and requires time-consuming breeding over many generations. Therefore, to facilitate the rapid dissection of gene function in normal and disease-related brain processes we need ability to precisely and efficiently manipulate the genome of neurons in vivo. The CRISPR-associated endonuclease Cas9 from *Streptococcus pyogenes* (SpCas9) has been shown to mediate precise and efficient genome cleavage of single and multiple genes in replicating eukaryotic cells, resulting in frame shifting insertion/deletion (indel) mutations[2, 3]. Here, we integrate Cas9-mediated genome perturbation with biochemical, sequencing, electrophysiological, and behavioral readouts to study the function of individual as wells as groups of genes in neural processes and their roles in brain disorders in vivo.

Discussion

Figure 89A:
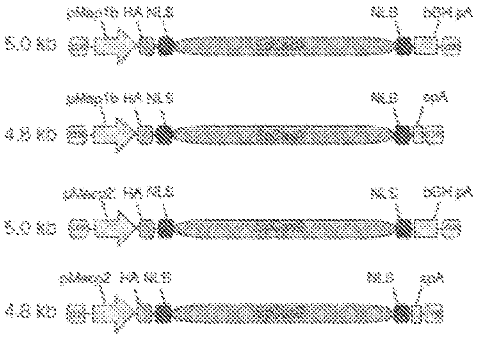
FIG. 89A-89F (Example 40) shows cloning and expression of HA-tagged SpCas9 (HA-SpCas9) for AAV packaging. (a) Schematic overview of different cloning strategies to minimize SpCas9 expression cassette size using short rat Map1b promotor (pMap1b), a truncated version of the mouse Mecp2 promoter (pMecp2) and a short polyA motif (spA). (b) Western blot analysis of primary cortical neuron culture expressing HA-SpCas9 using different SpCas9 expression cassettes. (c) Mecp2 promoter drives HA-SpCas9 (red) expression in neurons (Map1b, NeuN; arrows) but not in astroglia (GFAP, arrowheads). Co-expression of HA-SpCas9 with GFP-KASH is shown (bottom). Nuclei were labeled with DAPI. Scale bars, 20 (d) Schematic overview of GFP-labeling. Enhanced green fluorescent protein (GFP) fused to the nuclear transmembrane KASH domain and integration of GFP-KASH to the outer nuclear membrane is illustrated. (e) Co-infection efficiency calculation, showing populations of cell expressing both HA-SpCas9 and GFP-KASH (n=973 neurons from 3 cultures; error bars: s.e.m). (f) Cells were stained with LIFE/DEAD® kit 7 days after virus delivery. Quantification of $DAPI^+$ and dead ($DEAD^+$) cells (control n=518 $DAPI^+$ nuclei; SpCas9/GFP-KASH n=1003 $DAPI^+$ nuclei from 2 cultures; error bars: s.e.m). (ITR—inverted terminal repeat; HA—hemagglutinin tag; NLS—nuclear localization signal; spA—synthetic polyadenylation signal; U6—PolIII promoter; sgRNA—single guide RNA; hSyn—human synapsin 1 promoter; GFP—green fluorescent protein; KASH-Klarsicht, ANC1, Syne Homology nuclear transmembrane domain; bGH pA—bovine growth hormone polyadenylation signal; WPRE—Woodchuck Hepatitis virus posttranscriptional regulatory element).
Figure 89B:
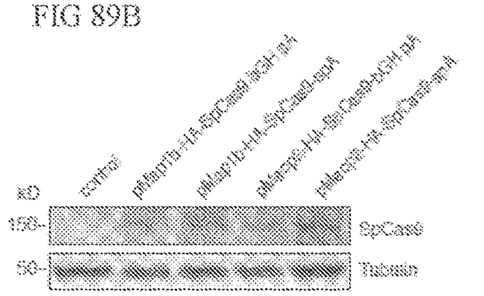

Adeno-associated viral (AAV) vectors are commonly used to deliver recombinant genes into the mouse brain[4]. The main limitation of the AAV system is its small packaging size, capped at approximately 4.5 kb without ITRs[5], which limits the amount of genetic material that can be packaged into a single vector. Since the size of the SpCas9[6] is already 4.2 kb, leaving less than 0.3 kb for other genetic elements within a single AAV vector, we designed a dual-vector system that packages SpCas9 (AAV-SpCas9) and sgRNA expression cassettes (AAV-SpGuide) on two separate viral vectors (FIG. 89*a*). While designing the AAV-SpCas9 vector, we compared various short neuron-specific promoters as well as poly adenylation signals to optimize SpCas9 expression. For our final design we chose the mouse Mecp2 promoter (235 bp, pMecp2)[7] and a minimal polyadenylation signal (48 bp, spA)[8] based on their ability to achieve sufficient levels of SpCas9 expression in cultured primary mouse cortical neurons (FIG. 89-*c*). To facilitate immunofluorescence identification of SpCas9-expressing neurons, we tagged SpCas9 with a HA-epitope tag. For the AAV-SpGuide vector, we packaged an U6-sgRNA expression cassette as well as the green fluorescent protein (GFP)-fused with the KASH nuclear trans-membrane domain[9] driven by the human Synapsin I promoter (FIG. 85*a*). The GFP-KASH fusion protein directs GFP to the outer nuclear membrane (FIG. 89*c,d*) and enables fluorescence-based identification and purification of intact neuronal nuclei transduced by AAV-SpGuide.

Figure 89C:
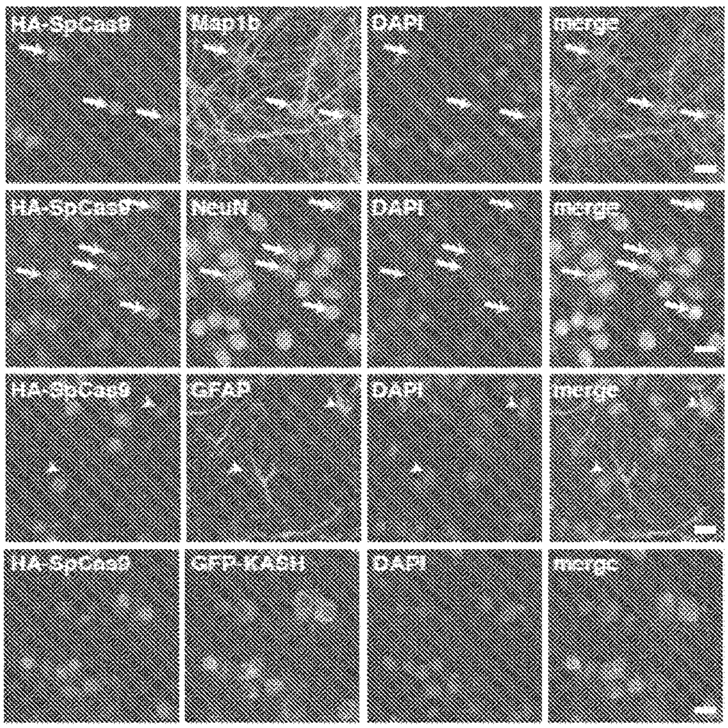
Figure 89E:
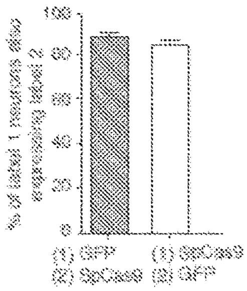
Figure 89F:
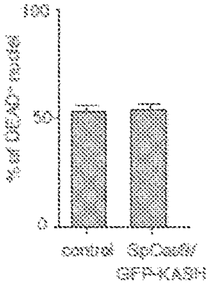
Figure 89D:
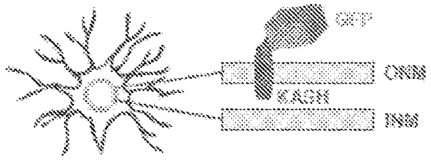

To test the delivery efficacy of our dual-vector delivery system, we first transduced cultured primary mouse cortical neurons in vitro and observed robust expression by AAV-SpCas9 and AAV-SpGuide (FIG. 89*e*), with greater than 80% co-transduction efficiency (FIG. 89*e*). Importantly, compared with un-transduced neurons, expression of SpCas9 did not adversely affect the morphology and survival rate of transduced neurons (FIG. 89*c,f*).

Figures 90A, 90B:
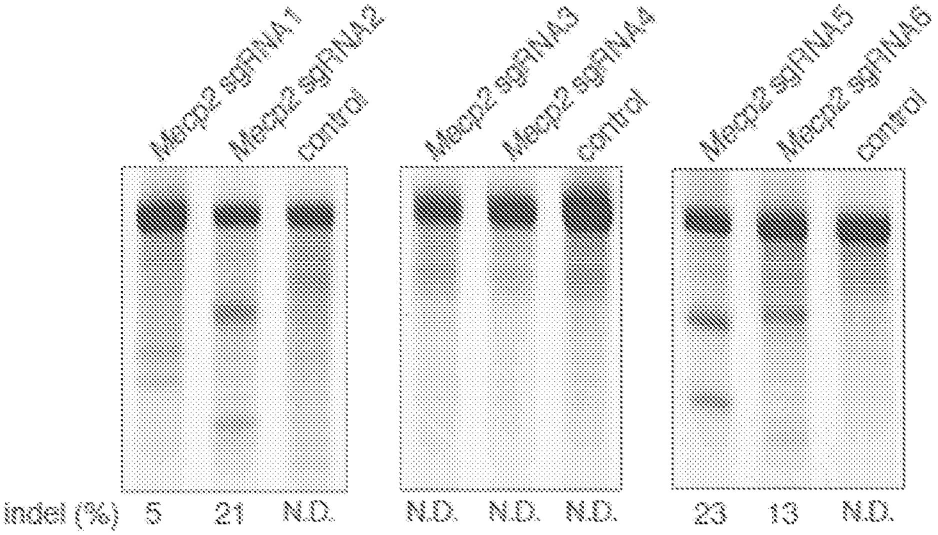
FIG. 90A-90B (Example 40) shows targeting of Mecp2 in Neuro-2a cells. (a) Mecp2 targeting sequences and corresponding protospacer adjacent motifs (PAM). (b) Evaluation of 6 Mecp2 sgRNAs co-transfected with SpCas9 into Neuro-2a cells. Locus modification efficiencies were analyzed 48 h after transfection using SURVEYOR™ assay.

Having established an efficient delivery system, we next sought to test SpCas9-mediated genome editing in mouse primary neurons. Whereas SpCas9 has been used to achieve efficient genome modifications in a variety of dividing cell types, it is unclear whether SpCas9 can be used to efficiently achieve genome editing in post-mitotic neurons. For our initial test we targeted the Mecp2 gene, which plays a principal role in Rett syndrome, a type of autism spectrum disorder. MeCP2 protein is ubiquitously expressed in neurons throughout the brain but nearly absent in glial cells[11, 12] and its deficiency has been shown to be associated with severe morphological and electrophysiological phenotypes in neurons, and both are believed to contribute to the neurological symptoms observed in patients with Rett syndrome[13-16]. To target Mecp2, we first designed several sgRNAs targeting exon 3 of the mouse Mecp2 gene (FIG. 90*a*) and evaluated their efficacy using Neuro-2a cells. The most efficient sgRNA was identified using the SURVEYOR nuclease assay (FIG. 90*b*). We chose the most effective sgRNA (Mecp2 target 5) for subsequent in vitro and in vivo Mecp2 targeting experiments.

Figure 91A:
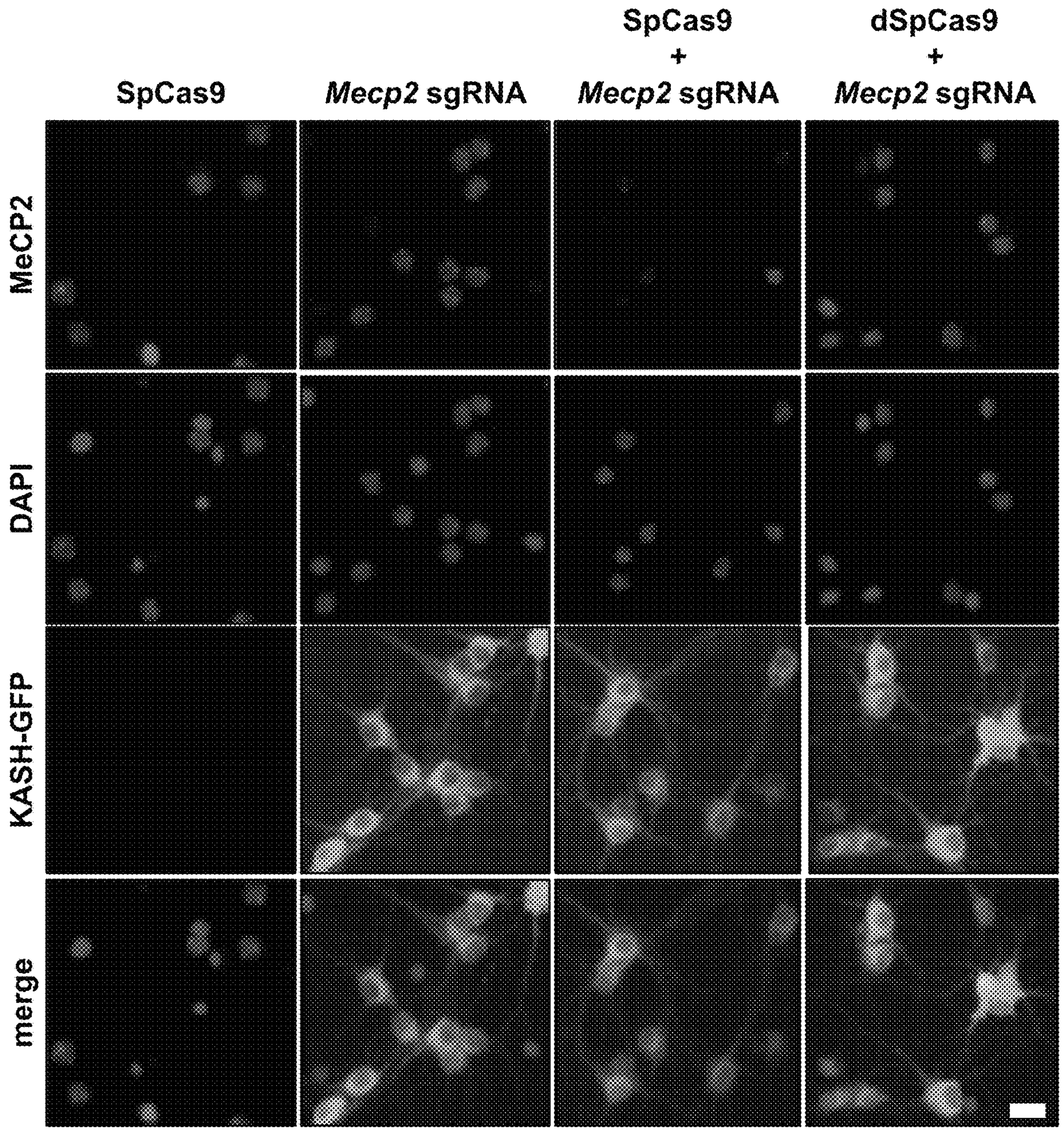
FIG. 91A-91D (Example 40) shows CRISPR-SpCas9 targeting of Mecp2 in primary cortical neurons. (a) Immunofluorescent staining of MeCP2 (red) in cultured neurons 7 days after AAV-CRISPR transduction (GFP-KASH). Nuclei were labeled with DAPI. Scale bar, 20 μm. (b) Evaluation of Mecp2 locus targeting using SpCas9 or dSpCas9, together with Mecp2 sgRNA or control (targeting bacterial lacZ gene) sgRNA, using SURVEYOR™ assay gel. (c) Quantification of MeCP2 positive nuclei in targeted population of neurons ($GFP^+$). (d) Western blot of MeCP2 protein levels after CRISPR-SpCas9 targeting of Mecp2 locus and quantification of MeCP2 protein levels (t-test, $^{**}p<0.001$, n=5 from 3 cultures, error bars: s.e.m).
Figure 91B:
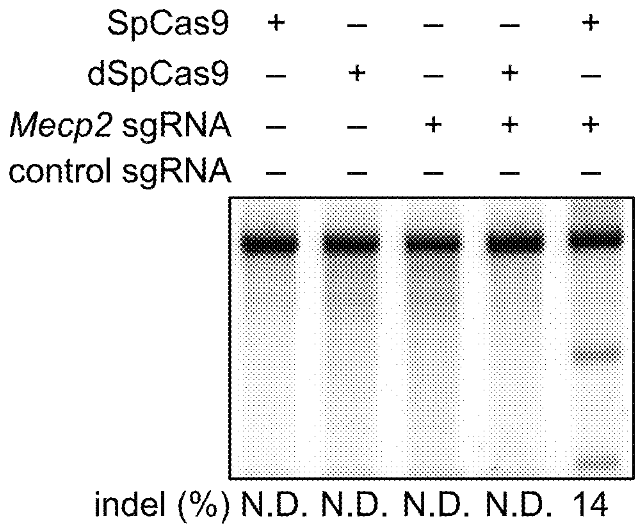
Figure 91C:
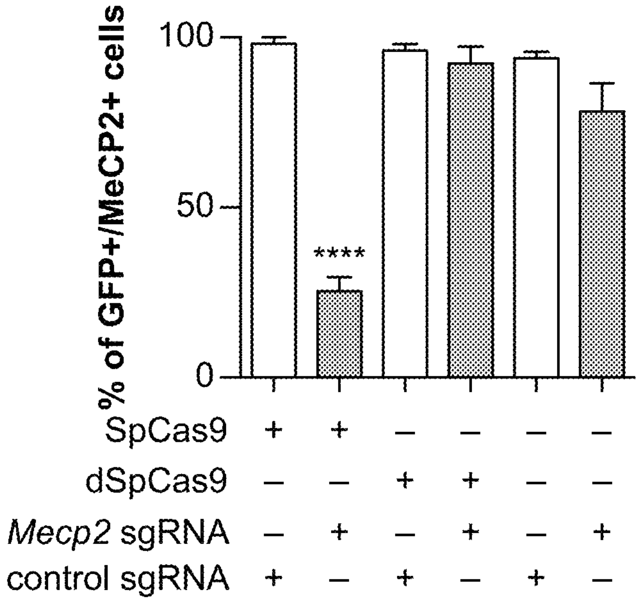
Figure 91D:
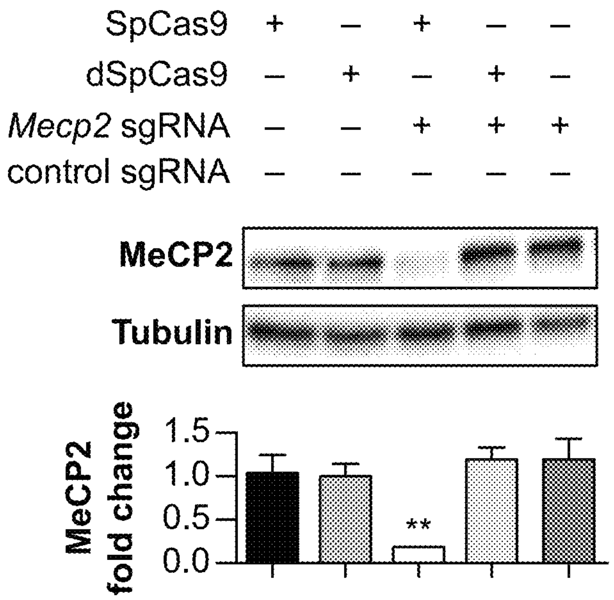

To assess the editing efficiency of our dual-vector system in neurons, we transduced primary mouse cortical neurons at 7 days in vitro (7 DIV, FIG. 91*a*) and measured indel rate using the SURVEYOR nuclease assay 7 days post transduction (FIG. 91*b*). Of note, neuron culture co-transduced with AAV-SpCas9 and AAV-SpGuide targeting Mecp2 showed up to 80% reduction in MeCP2 protein levels compared to control neurons (FIG. 91*c,d*). One possible explanation for the observed discrepancy between relatively low indel frequency (~14%) and robust protein depletion (~80%) could be that mere binding by SpCas9 at the target site may interfere with transcription, which has been shown in *E. coli*[17, 18]. We investigated this possibility using a mutant of SpCas9 with both RuvC and HNH catalytic domains inactivated[19, 20] (D10A and H840A, dSpCas9). Co-expression of dSpCas9 and Mecp2-targeting sgRNA did not reduce MeCP2 protein levels (FIG. 91*a,d*), suggesting that the observed decrease of MeCP2 level in presence of active SpCas9 is due to occurrence of modification in the Mecp2 locus. Another possible explanation for the discrepancy between the low level of detected indel and high level of protein depletion may be due to underestimation of the true indel rate by the SURVEYOR nuclease assay—the detection accuracy of SURVEYOR has been previously shown to be sensitive to the indel sequence composition[21]

Figures 92A, 92B, 92C, 92D, 92E:
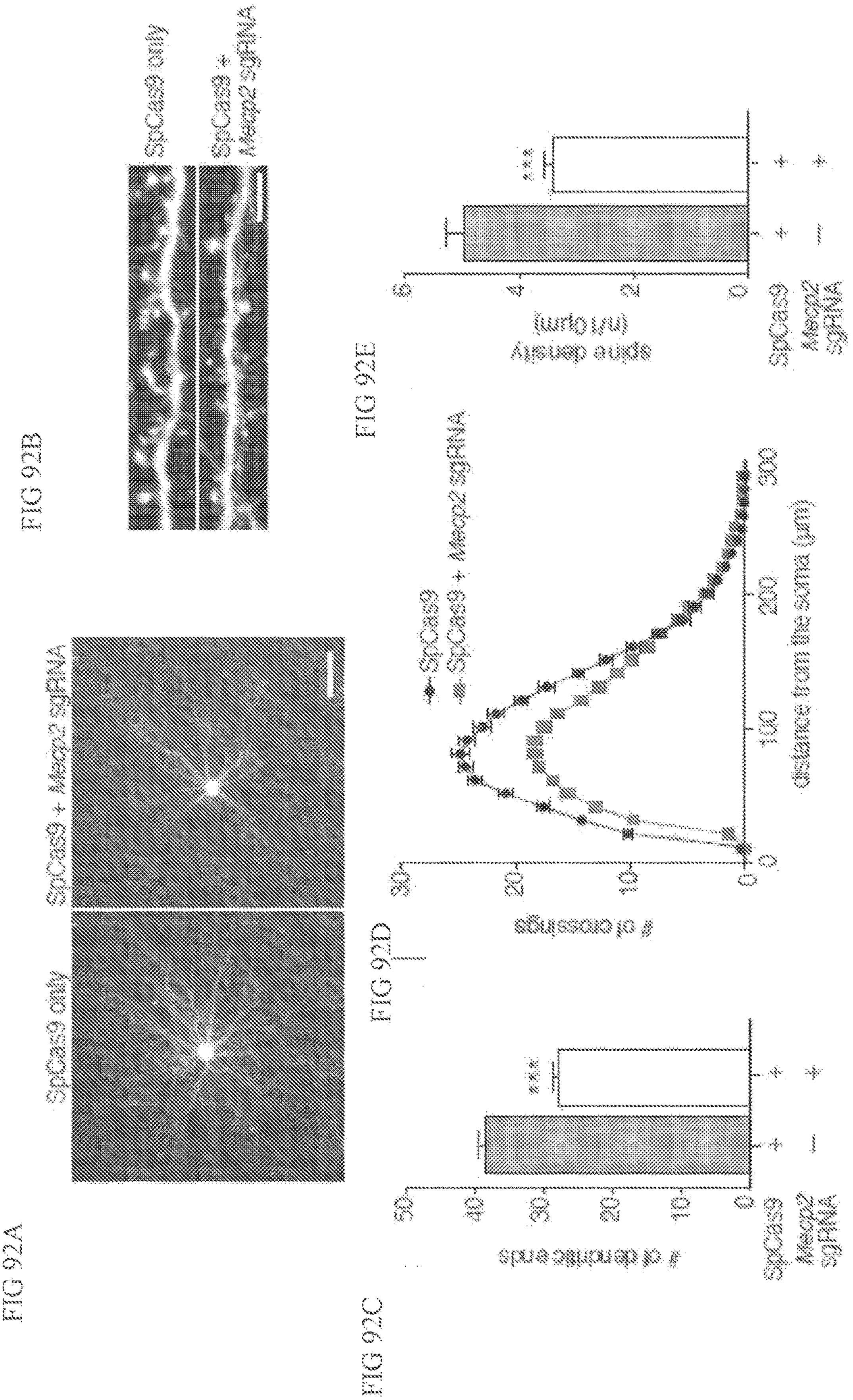
FIG. 92A-92E (Example 40) shows morphological changes in dendritic tree of neurons after SpCas9-mediated MeCP2 knockdown in vitro. (a) Reduced complexity of dendritic tree in neurons after CRISPR-SpCas9 targeting of Mecp2 locus. Scale bar, 20 μm. (b) Changes in dendritic spines morphology in neurons targeted with SpCas9 and Mecp2 sgRNA. Scale bar, 10 μm. Morphology of cells was visualized with co-transfection with mCherry construct. Cells for morphology analysis were chosen based on the result of Mecp2 staining. (c) Dendritic tree morphology assessed with number of dendritic ends and (d) Sholl analysis (t-test, *p<0.0001, n=40 from 2 cultures). (e) Spine density quantification (t-test, *p<0.0001, n=40 from 2 cultures, error bars: s.e.m).

MeCP2 loss-of-function has been previously shown to be associated with dendritic tree abnormalities and spine morphogenesis defects in neurons[14, 16] These phenotypes of MeCP2 deprivation have also been reproduced in neurons differentiated from MeCP-KO iPS cells[15]. Therefore, we investigated whether SpCas9-mediated MeCP2-depletion in neurons can similarly recapitulate morphological phenotypes of Rett syndrome. Indeed, neurons co-expressing SpCas9 and Mecp2-targeting sgRNA exhibited altered dendritic tree morphology and spine density when compared with control neurons (FIG. 92). These results demonstrate that SpCas9 can be used to facilitate the study of gene functions in cellular assays by enabling targeted knockout in post-mitotic neurons.

Given the complexity of the nervous system, which consists of intricate networks of heterogeneous cell types, being able to efficiently edit the genome of neurons in vivo would enable direct testing of gene function in relevant cell types embedded in native contexts. Consequently, we stereotactically injected a mixture (1:1 ratio) of high titer AAV-SpCas9 and AAV-SpGuide into the hippocampal dentate gyrus in adult mice. We observed high co-transduction efficiency of both vectors (over 80%) in hippocampal granule cells at 4 weeks after viral injection (FIG. 85*b,c*) resulting in genomic modifications of the Mecp2 locus. (FIG. 85*d*). Using SURVEYOR nuclease assay we detected ~13% indel frequency in brain punches obtained from injected brain regions (FIG. 85*e*). Similar to our finding in cultured primary neurons, SpCas9-mediated cutting of the Mecp2 locus efficiently decreased MeCP2 protein levels by over 60%. Additionally the number of MeCP2-positive nuclei in the dentate gyrus decreased by over 75% when injected with AAV-SpCas9 and AAV-SpGuide compared to AAV-SpCas9 alone (FIG. 85*g-h*). These results suggest that SpCas9 can be used to directly perturb specific genes within intact biological contexts.

Figure 86A:
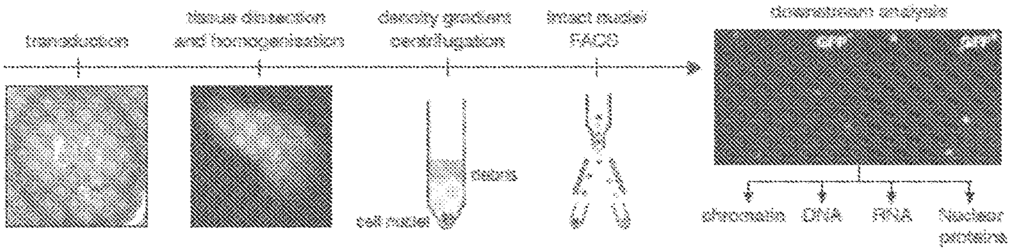
FIG. 86A-86B (Example 40) shows analysis of gene expression in Cas9-mediated MeCP2 knockdown neurons. (a) Strategy for cell nuclei purification of CRISPR-Cas9 targeted cells from the mouse brain. (b) Hierarchical clustering of differentially expressed genes (t-test, p<0.01, n=19 populations of sorted nuclei from 8 animals) detected by RNAseq. Relative log 2(TPM+1) expression levels of genes are normalized for each row. Each column represents a population of targeted 100 neuronal nuclei FACS sorted from the isolated, dentate gyrus population of cells, either from control or Mecp2 sgRNA transduced animals, as indicated.

Targeted genomic perturbations can be coupled with quantitative readouts to provide insights into the biological function of specific genomic elements. To facilitate analysis of AAV-SpCas9 and AAV-SpGuide transduced cells, we developed a method to purify GFP-KASH labeled nuclei using fluorescent activated cell sorting (FACS) (FIG. 86*a*). Sorted nuclei can be directly used to purify nuclear DNA and RNA for downstream biochemical or sequencing analysis. Using sanger sequencing, we found that 13 out of 14 single GFP-positive nuclei contained an indel mutation at the sgRNA target site.

Figure 86B:
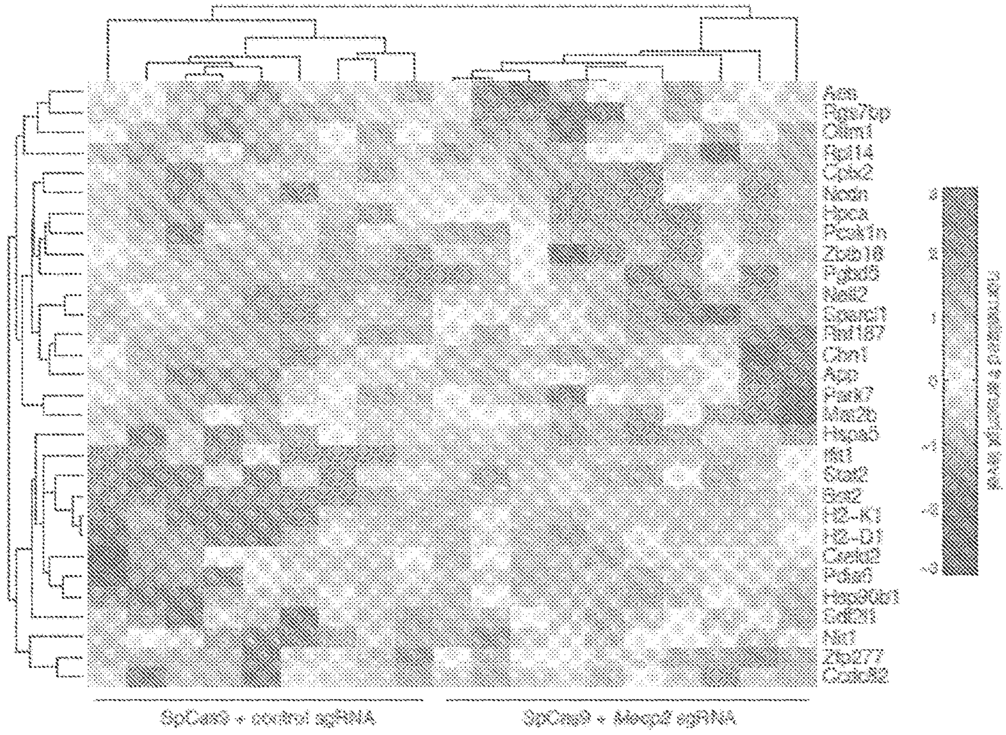
Figure 93:
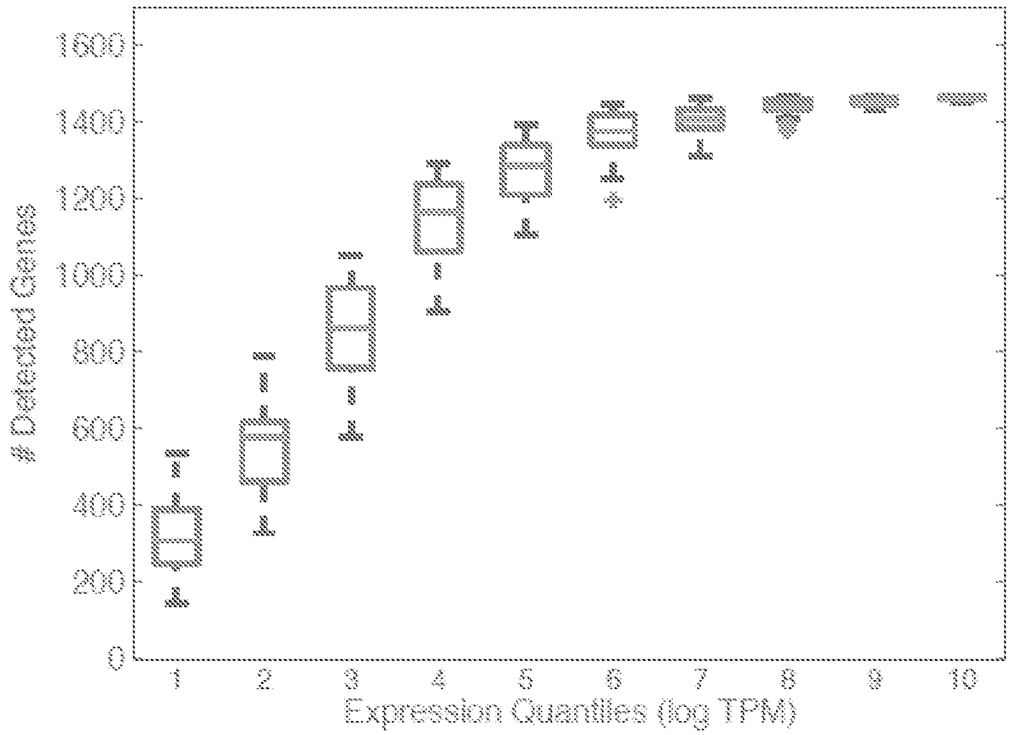
FIG. 93 (Example 40) shows RNAseq of neuronal nuclei from control animals and SpCas9-mediated Mecp2 knockdown. Box plot presenting the number of detected genes across the RNA-seq libraries (19 libraries each of 100 nuclei taken from control sgRNA or Mecp2 sgRNA transduced nuclei; n=4 animals/group) per quantile of expression level. All genes are divided to 10 quantiles by their mean log 2(TPM+1) expression level, then for each quantile the number of genes that are detected (log 2(TPM+1)>2) was counted in each sample.

In addition to genomic DNA sequencing, purified GFP-positive nuclei can also be used for RNAseq analysis to study transcriptional consequences of MeCP2 depletion (FIG. 86*b* and FIG. 93). To test the effect of Mecp2 knockout on transcription of neurons from the dentate gyrus, we prepared RNAseq libraries using FACS purified $GFP^+$ nuclei from animals receiving AAV-SpCas9 as well as either a control sgRNA that has been designed to target bacterial lacZ gene and not the mouse genome, or a Mecp2-targeting sgRNA. All sgRNAs have been optimized to minimize their off-target score (CRISPR Design Tool: tools.genome-engineering.org)[2]. We were able to find differentially expressed genes (FIG. 86*b*) between control and Mecp2 sgRNA expressing nuclei ($p<0.01$). We identified several interesting candidates among genes that were down-regulated in Mecp2 sgRNA expressing nuclei: Hpca, Olfm1, and Ncdn, which have been previously reported to play important roles in learning behaviors[22-24]; and Cplx2, which has been shown to be involved in synaptic vesicle release and related to neuronal firing rate[25, 26]. These results demonstrate that the combination of SpCas9-mediated genome perturbation and population level RNAseq analysis provides a way to characterize transcriptional regulations in neurons and suggest genes that may be important to specific neuronal functions or disease processes.

SpCas9-mediated in vivo genome editing in the brain can also be coupled with electrophysiological recording to study the effect of genomic perturbation on specific cell types or circuit components. To study the functional effect of MeCP2 depletion on neuronal physiology we stereotactically co-delivered AAV-SpCas9 and AAV-SpGuide targeting Mecp2 into the superficial layer of the primary visual cortex (V1) of male mice. V1 was chosen since the superficial layer cortical excitatory neurons are more accessible to two-photon imaging and two-photon guided targeted recording. Two weeks after SpCas9 delivery, mice were subjected to two-photon guided juxtacellular recordings to compare the electrophysiological response of KASH-$GFP^+$ neurons and $GFP^-$ neighboring neurons in layer 2/3 of mouse V1 (FIG. 86*a-c*). We measured neuronal responses to 18 drifting gratings in 20-degree increments and calculated evoked firing rate (FR) and orientation selectivity index (OSI) of cells by vector averaging the response. Both FR and OSI were significantly reduced for excitatory $GFP^+$, MeCP2 knockout neurons, compared to neighboring $GFP^-$ excitatory neurons (FIG. 86*d-e*). In comparison, control sgRNA expression together with SpCas9 did not have any effect on FR and OSI when compared with neighboring uninfected neurons (FIG. 86*d-e*). These results show that SpCas9 mediated depletion of MeCP2 in adult V1 cortical neurons alters the visual response properties of excitatory neurons in vivo within two weeks and further demonstrate the versatility of SpCas9 in facilitating targeted gene knockout in the mammalian brain in vivo, for studying genes functions and dissection of neuronal circuits.

Figures 88A, 88B, 88C, 88D, 88E, 88F:
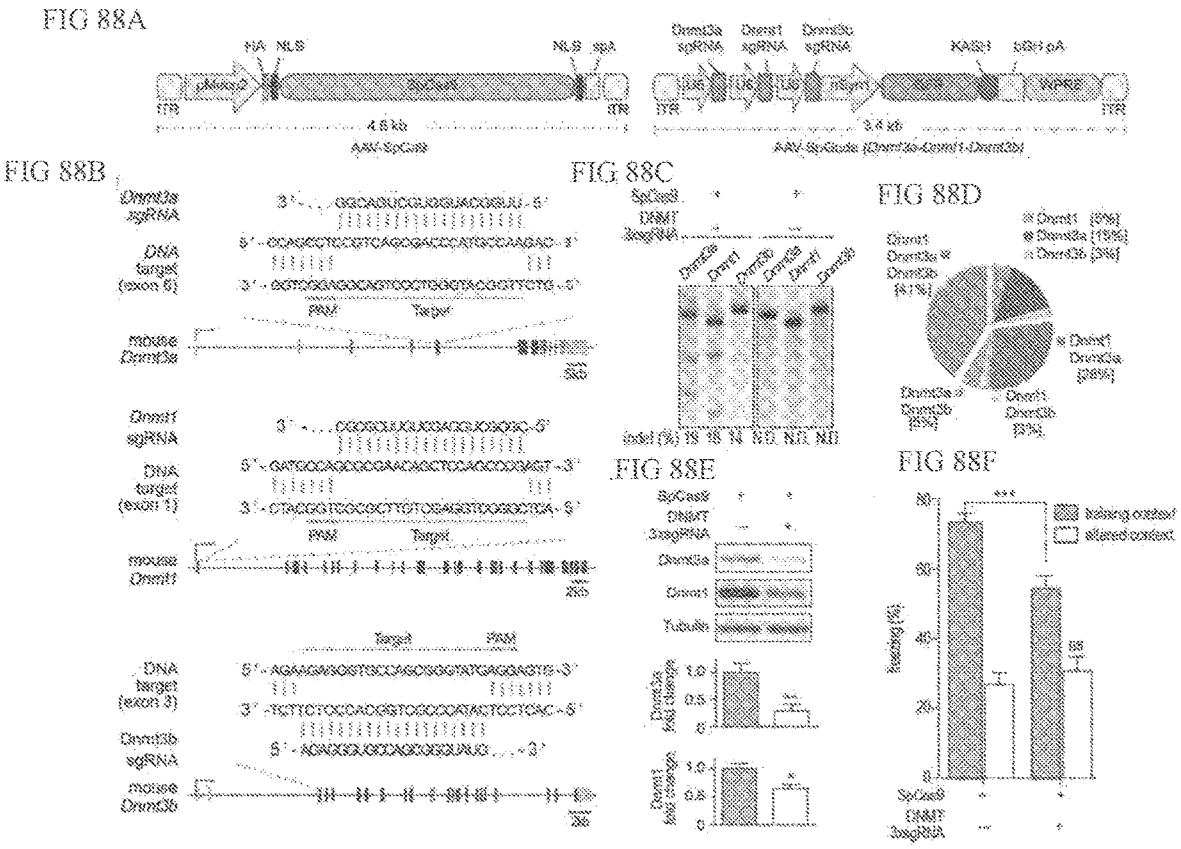
FIG. 88A-88F (Example 40) shows simultaneous, multiplex gene editing in the mouse brain. (a) Schematic illustration of CRISPR-Cas9 system designed for multiplex genome targeting. (b) Graphical representation of targeted DNMT mouse loci. Guide RNAs are indicated. PAM sequences. (c) SURVEYOR™ assay gel showing modification of DNMTs loci in FACS sorted GFP-KASH positive cells, 4 weeks after AAV delivery in the DG region. (d) Deep sequencing-based analysis of DNMTs loci modification in single cells, showing co-occurrence of modification in multiple loci. (e) Western blot analysis for Dnmt3a and Dnmt1 proteins after in vivo delivery of CRISPR-Cas9 system targeting DNMT family genes (top). Western blot quantification of Dnmt3a and Dnmt1 protein levels in DG after in vivo CRISPR-Cas9 targeting (bottom; t-test, $^{**}p<0.001$, $^*p<0.05$, Dnmt3a: n=7; Dnmt1: n=5 from 5 animals; error bars: s.e.m). (f) Contextual learning deficits, 8 weeks after targeting of DNMT genes using SpCas9 in the DG region of hippocampus, tested in training and altered context (t-test, $^{*}p<0.0001$, n=18 animals, 2 independent experiments; error bars: s.e.m).
Figure 94A:
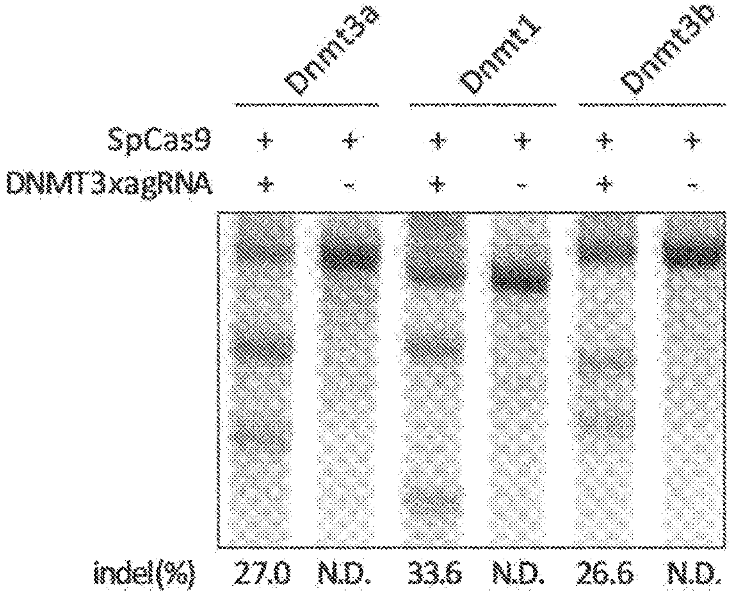

One key advantage of the SpCas9 system is its ability to facilitate multiplex genome editing[2]. Introducing stable knockouts of multiple genes in the brain of living animals will have potentially far-reaching applications, such as causal interrogation of multigenic mechanisms in physiological and neuropathological conditions. To test the possibility of multiplex genome editing in the brain we designed a multiplex sgRNA expression vector consisting of three sgRNAs in tandem, along with GFP-KASH for nuclei labeling (FIG. 87*a*). We chose sgRNAs targeting the DNA methyltransferases gene family (DNMT5), which consists of Dnmt1, Dnmt3a and Dnmt3b. Dnmt1 and 3a are highly expressed in the adult brain and it was previously shown that DNMT activity alters DNA methylation and both Dnmt3a and Dnmt1 are required for synaptic plasticity and learning and memory formation[27]. We designed individual sgRNAs against Dnmt3a and Dnmt1 with high modification efficiency. To avoid any potential compensatory effects by Dnmt3b we decided also to additionally target this gene even though it is expressed mainly during neurodevelopment[27]. We finally selected individual sgRNAs for high simultaneous DNA cleavage for all three targeted genes (FIG. 88*b* and FIG. 94).

To test the efficacy of multiplex genome editing in vivo, we stereotactically delivered a mixture of high titer AAV-SpCas9 and AAV-SpGuide into the dorsal and ventral dentate gyrus of male adult mice. After 4 weeks, hippocampi were dissected and targeted cell nuclei were sorted via FACS. We detected ~19% (Dnmt3a), 18% (Dnmt1) and 4% (Dnmt3b) indel frequency in the sorted nuclei population using SURVEYOR nuclease assay (FIG. 88*c*) and sequencing (FIG. 95). Targeting multiple loci raises the question about the effective rate of multiple-knockouts in individual cells. By using single nuclei sorting combined with targeted sequencing, we quantified simultaneous targeting of multiple DNMT loci in individual neuronal nuclei (FIG. 88*d*). Of neuronal nuclei carrying modification in at least one Dnmt locus, more than 70% of nuclei contained indels in both Dnmt3a and Dnmt1 (~40% contained indels at all 3 loci, and ~30% at both Dnmt3a and Dnmt1 loci). These results are in agreement with Dnmt3a and Dnmt1 protein depletion levels in the dentate gyrus (FIG. 88*e*). Due to the low expression of Dnmt3b in the adult brain, we were not able to detect Dnmt3b protein.

Recent studies with SpCas9 have shown that, although each base within the 20-nt sgRNA sequence contributes to overall specificity, genomic loci that partially match the sgRNA can result in off-target double strand brakes and indel formations[28, 29]. To assess the rate of off-target modifications, we computationally identified a list of highly similar genomic target sites[2] and quantified the rate of modifications using targeted deep sequencing. Indel analysis of the top predicted off-target loci revealed a 0-1.6% rate of indel formations demonstrating that SpCas9 modification is specific. To increase the specificity of SpCas9-mediated genome editing in vivo, future studies may use off-targeting minimization strategies such as double nicking[30, 31] and truncated sgRNAs[28].

Knockdown of Dnmt3a and Dnmt1 have been previous shown to impact hippocampus-dependent memory formation[27]. Consequently, we performed contextual fear-conditioning behavior tests to investigate the effect of SpCas9-mediated triple knockout (Dnmt3a, Dnmt1 and Dnmt3b) on memory acquisition and consolidation. While we did not observe any differences between control and triple knockout mice in the memory acquisition phase, knockout mice showed impaired memory consolidation when tested under trained context conditions (FIG. 88*f*). This effect was abolished when mice were tested in the altered context. Our results demonstrate that CRIPSR-Cas9-mediated knockout of DNMT family members in dentate gyrus neurons is sufficient to probe the function of genes in behavioral tasks.

Together, our results demonstrate that AAV-mediated in vivo delivery of SpCas9 and sgRNA provides a rapid and powerful technology for achieving precise genomic perturbations within intact neural circuits. Whereas SpCas9 has been broadly used to engineer dividing cells, we demonstrate that SpCas9 can also be used to engineer the genome of postmitotic neurons with high efficiency via NHEJ-mediated indel generation. SpCas9-mediated genomic perturbations can be combined with biochemical, sequencing, electrophysiological, and behavioral analysis to study the function of the targeted genomic element. We demonstrated that SpCas9-mediated targeting of single or multiple genes can recapitulate morphological, electrophysiological, and behavioral phenotypes observed using classical, more time-consuming genetic mouse models. The current study employed the *Streptococcus pyogenes* Cas9, which not only necessitates the use of two AAV vectors but also limits the size of promoter elements can be used to achieve cell type-specific targeting. Given the diversity of Cas9 orthologues, with some being substantially shorter than SpCas9[2, 32, 33], it should be possible to engineer single AAV vectors expressing both Cas9 and sgRNA, as described herein.

REFERENCES

1. Nestler, E. J. & Hyman, S. E. Animal models of neuropsychiatric disorders. Nat Neurosci 13, 1161-1169 (2010).

2. Cong, L. et al. Multiplex genome engineering using CRISPR/Cas systems. Science 339, 819-823 (2013).

3. *Mali*, P. et al. RNA-guided human genome engineering via Cas9. Science 339, 823-826 (2013).

4. Burger, C., Nash, K. & Mandel, R. J. Recombinant adeno-associated viral vectors in the nervous system. Hum Gene Ther 16, 781-791 (2005).

5. Wu, Z., Yang, H. & Colosi, P. Effect of genome size on AAV vector packaging. Mol Ther 18, 80-86 (2010).

6. Deltcheva, E. et al. CRISPR RNA maturation by trans-encoded small RNA and host factor RNase III. Nature 471, 602-607 (2011).

7. Gray, S. J. et al. Optimizing promoters for recombinant adeno-associated virus-mediated gene expression in the peripheral and central nervous system using self-complementary vectors. Hum Gene Ther 22, 1143-1153 (2011).

8. Levitt, N., Briggs, D., Gil, A. & Proudfoot, N.J. Definition of an efficient synthetic poly(A) site. Genes Dev 3, 1019-1025 (1989).

9. Ostlund, C. et al. Dynamics and molecular interactions of linker of nucleoskeleton and cytoskeleton (LINC) complex proteins. J Cell Sci 122, 4099-4108 (2009).

10. Chahrour, M. & Zoghbi, H. Y. The story of Rett syndrome: from clinic to neurobiology. Neuron 56, 422-437 (2007).

11. Kishi, N. & Macklis, J. D. MECP2 is progressively expressed in post-migratory neurons and is involved in neuronal maturation rather than cell fate decisions. Molecular and cellular neurosciences 27, 306-321 (2004).

12. Skene, P. J. et al. Neuronal MeCP2 is expressed at near histone-octamer levels and globally alters the chromatin state. Molecular cell 37, 457-468 (2010).

13. Chen, R. Z., Akbarian, S., Tudor, M. & Jaenisch, R. Deficiency of methyl-CpG binding protein-2 in CNS neurons results in a Rett-like phenotype in mice. Nat Genet 27, 327-331 (2001).

14. Zhou, Z. et al. Brain-specific phosphorylation of MeCP2 regulates activity-dependent Bdnf transcription, dendritic growth, and spine maturation. Neuron 52, 255-269 (2006).

15. Li, Y. et al. Global transcriptional and translational repression in human-embryonic-stem-cell-derived Rett syndrome neurons. Cell Stem Cell 13, 446-458 (2013).

16. Nguyen, M. V. et al. MeCP2 is critical for maintaining mature neuronal networks and global brain anatomy during late stages of postnatal brain development and in the mature adult brain. J Neurosci 32, 10021-10034 (2012).

17. Jiang, W., Bikard, D., Cox, D., Zhang, F. & Marraffini, L. A. RNA-guided editing of bacterial genomes using CRISPR-Cas systems. Nature biotechnology 31, 233-239 (2013).

18. Qi, L. S. et al. Repurposing CRISPR as an RNA-guided platform for sequence-specific control of gene expression. Cell 152, 1173-1183 (2013).

19. Sapranauskas, R. et al. The *Streptococcus thermophilus* CRISPR/Cas system provides immunity in *Escherichia coli*. Nucleic acids research 39, 9275-9282 (2011).

20. Jinek, M. et al. A programmable dual-RNA-guided DNA endonuclease in adaptive bacterial immunity. Science 337, 816-821 (2012).

21. Qiu, P. et al. Mutation detection using Surveyor nuclease. BioTechniques 36, 702-707 (2004).

22. Kobayashi, M. et al. Hippocalcin-deficient mice display a defect in cAMP response element-binding protein activation associated with impaired spatial and associative memory. Neuroscience 133, 471-484 (2005).

23. Dateki, M. et al. Neurochondrin negatively regulates CaMKII phosphorylation, and nervous system-specific gene disruption results in epileptic seizure. The Journal of biological chemistry 280, 20503-20508 (2005).

24. Nakaya, N. et al. Deletion in the N-terminal half of olfactomedin 1 modifies its interaction with synaptic proteins and causes brain dystrophy and abnormal behavior in mice. Experimental neurology 250, 205-218 (2013).

25. Reim, K. et al. Complexins regulate a late step in Ca2+-dependent neurotransmitter release. Cell 104, 71-81 (2001).

26. Edwardson, J. M. et al. Expression of mutant huntingtin blocks exocytosis in PC12 cells by depletion of complexin II. The Journal of biological chemistry 278, 30849-30853 (2003).

27. Feng, J. et al. Dnmt1 and Dnmt3a maintain DNA methylation and regulate synaptic function in adult forebrain neurons. Nat Neurosci 13, 423-430 (2010).

28. Fu, Y. et al. High-frequency off-target mutagenesis induced by CRISPR-Cas nucleases in human cells. Nature biotechnology 31, 822-826 (2013).

29. Hsu, P. D. et al. DNA targeting specificity of RNA-guided Cas9 nucleases. Nature biotechnology 31, 827-832 (2013).

30. Ran, F. A. et al. Double nicking by RNA-guided CRISPR Cas9 for enhanced genome editing specificity. Cell 154, 1380-1389 (2013).

31. Mali, P. et al. CAS9 transcriptional activators for target specificity screening and paired nickases for cooperative genome engineering. Nature biotechnology 31, 833-838 (2013).

32. Esvelt, K. M. & Wang, H. H. Genome-scale engineering for systems and synthetic biology. Molecular systems biology 9, 641 (2013).

33. Li, W., Teng, F., Li, T. & Zhou, Q. Simultaneous generation and germline transmission of multiple gene mutations in rat using CRISPR-Cas systems. Nat Biotechnol 31, 684-686 (2013).

Methods

DNA Constructs

For SpCas9 targets selection and generation of single guide RNA (sgRNA), the 20-nt target sequences were selected to precede a 5'-NGG PAM sequence. To minimize off-targeting effects, the CRIPSR design tool was used (tools.genome-engineering.org). sgRNA was PCR amplified using U6 promoter as a template with forward primer: 5'-CGCACGCGTAATTCGAACGCTGACGTCATC-3' (SEQ ID NO: 526) and reverse primer containing the sgRNA with 20-nt DNA target site (Bold):

```
                                        (SEQ ID NO: 527)
5'-CACACGCGTAAAAAAGCACCGACTCGGTGCCACTTTTTCAAGTTGAT

AACGGACTAGCCTTATTTTAACTTGCTATTTCTAGCTCTAAAAC

NNNNNNNNNNNNNNNNNNNNCCGGTGTTTCGTCCTTTCCAC-3'.
```

Control sgRNA sequence was designed to target lacZ gene from *E. coli*: target sequence: TGCGAATACGCCCACGCGATGGG (SEQ ID NO: 528) EGFP-KASH[1] construct was a generous gift from Prof. Worman (Columbia University, NYC) and was used as PCR template for cloning the coding cassette into AAV backbone under the human Synapsin promoter (hSyn). Next, U6-Mecp2sgRNA coding sequence was introduced using MO site. For the multiplex gene targeting strategy, individual sgRNAs were PCR amplified as described above. All three sgRNAs were ligated with PCR amplified hSyn-GFP-KASH-bGHpA cassette by using the Golden Gate cloning strategy. After PCR amplification, the Golden Gate ligation product containing 3 sgRNAs and hSyn-GFP-KASH-bGH pA was cloned into AAV backbone. All obtained constructs were sequenced verified. In order to find the optimal promoter sequence to drive SpCas9 expression in neurons we tested: hSyn1, mouse truncated Mecp2 (pMecp2), and truncated rat Map1b (pMap1b) promoter sequences[2]. Following primers were used to amplify promoter regions:

```
hSyn_F:
                                        (SEQ ID NO: 529)
5'-GTGTCTAGACTGCAGAGGGCCCTG-3';

hSyn_R:
                                        (SEQ ID NO: 530)
5'-GTGTCGTGCCTGAGAGCGCAGTCGAGAA-3';

Mecp2_F
                                        (SEQ ID NO: 531)
5'-GAGAAGCTTAGCTGAATGGGGTCCGCCTC-3';

Mecp2_R
                                        (SEQ ID NO: 532)
5'-CTCACCGGTGCGCGCAACCGATGCCGGGACC-3';

Map1b-283/-58_F
                                        (SEQ ID NO: 533)
5'-GAGAAGCTTGGCGAAATGATTTGCTGCAGATG-3';

Map1b-283/-58_R
                                        (SEQ ID NO: 534)
5'-CTCACCGGTGCGCGCGTCGCCTCCCCCTCCGC-3'.
```

Another truncation of rat map1b promoter was assembled with the following oligos:

```
                                        (SEQ ID NO: 535)
5'-AGCTTCGCGCCGGGAGGAGGGGGGACGCAGTGGGCGGAGCGGAGACA

GCACCTTCGGAGATAATCCTTTCTCCTGCCGCAGAGCAGAGGAGCGGCGG

GAGAGGAACACTTCTCCCAGGCTTTAGCAGAGCCGGA-3'
and

                                        (SEQ ID NO: 536)
5'-CCGGTCCGGCTCTGCTAAAGCCTGGGAGAAGTGTTCCTCTCCCGCCG

CTCCTCTGCTCTGCGGCAGGAGAAAGGATTATCTCCGAAGGTGCTGTCTC

CGCTCCGCCCACTGCGTCCCCCCTCCTCCCGGCGCGA-3'.
```

Short synthetic polyadenylation signal (spA)[3] was assembled using following oligos:

```
                                        (SEQ ID NO: 537)
5'-AATTCAATAAAAGATCTTTATTTTCATTAGATCTGTGTGTTGGTTTT

TTGTGTGC-3'
and

                                        (SEQ ID NO: 538)
5'-GGCCGCACACAAAAAACCAACACACAGATCTAATGAAAATAAAGATC

TTTTATTG-3'.
```

SpCas9 and its D10A mutant version (dSpCas9) were described previously[4, 5]. Plasmid encoding red fluorescent protein (mCherry) under control of EF1a promoter was used for neuron transfection with Lipofectamine® 2000 (Life Technologies).

Cell Line Cultures and Transfection

Neuro-2a (N2a) cells were grown in DMEM containing 5% fetal bovine serum (BSA). For HEK293FT cells DMEM containing 10% fetal bovine serum (FBS) was used. Cells were maintained at 37° C. in 5% $CO_2$ atmosphere. Cells were transfected using Lipofectamine®2000 or Polyethylenimine (PEI) "MAX" reagent (Polysciences), according to manufacturer's protocols.

Production of Concentrated AAV Vectors

High titer AAV1/2 particles were produced using AAV1 and AAV2 serotype plasmids at equal ratios and pDF6 helper plasmid and purified on heparin affinity column[6]. Titering of viral particles was done by qPCR. High titer AAV1 particles were produced by the UNC Vector Core Services (University of North Carolina at Chapel Hill). Low titer AAV1 particles in DMEM were produced as described previously[7]. Briefly, HEK293FT cells were transfected with transgene plasmid, pAAV1 serotype plasmid and pDF6 helper plasmid using PEI "MAX". Culture medium was collected after 48 h and filtered through a 0.45 μm PVDF filter (Millipore).

Primary Cortical Neuron Culture

Animals used to obtain neurons for tissue cultures were sacrificed according to the protocol approved by the MIT Committee on Animal Care (MIT CAC). Primary cultures were prepared from embryonic day 16 mouse brains[8]. Embryos of either sex were used. Cells were plated on poly-D-lysine (PDL) coated 24-well plates (BD Biosciences) or laminin/PDL coated coverslips (VWR). Cultures were grown at 37° C. and 5% $CO_2$ in Neurobasal medium, supplemented with B27, Glutamax (Life Technologies) and penicillin/streptomycin mix.

For AAV transduction, cortical neurons in 500 μl Neurobasal culture medium were incubated at 7 DIV with 300 μl (double infection at 1:1 ratio) AAV1-containing conditioned medium from HEK293FT cells[7]. One week after transduction neurons have been harvested for downstream processing or fixed in 4% paraformaldehyde for immunofluorescent stainings or morphology analysis.

For visualization of neuronal morphology, cells at DIV7 were transfected with EF1α-mCherry expression vector using Lipofectamine® 2000 (Life Technologies) for one week as previously described[9]. For measurement of total dendrite length, all dendrites of individual neurons were traced using ImageJ software. Quantification of the number of primary dendrites, dendritic tips and the Sholl analysis[10] were performed on images acquired with fluorescent microscope at a 40× objective (Zeiss AxioCam Ax10 microscope, Axiocam MRm camera). For dendrites number, ends of all non-axonal protrusions longer than 10 μm were counted. For Sholl analysis, concentric circles with 5 μm step in diameter were automatically drawn around the cell body, and the number of dendrites crossing each circle was counted using ImageJ software with a Sholl plug-in.

Stereotactic Injection of AAV1/2 into the Mouse Brain

The MIT CAC approved all animal procedures described here. Adult (12-16 weeks old) male C57BL/6N mice were anaesthetized by intraperitoneal (i.p.) injection of 100 mg/kg Ketamine and 10 mg/kg Xylazine. Pre-emptive analgesia was given (Buprenex, 1 mg/kg, i.p.). Craniotomy was performed according to approved procedures and 1 μl of 1:1 AAV mixture (1×1013 Vg/ml of sMecp2-SpCas9; 6×1012 Vg/ml of DNMT 3×sgRNA; 3-5×1012 Vg/ml of hSyn-GFP-KASH) was injected into: dorsal dentate gyrus (anterior/posterior: −1.7; mediolateral: 0.6; dorsal/ventral: −2.15) and/or ventral dentate gyrus (anterior/posterior: −3.52; mediolateral: 2.65; dorsal/ventral: −3). For in vivo electrophysiology recordings experiments virus injection coordinates were 3 mm lateral (from Bregma) and 1 mm anterior from the posterior suture. The skull was thinned using a dremel drill with occasional cooling with saline, and the remaining dura was punctured using a glass micropipette filled with the virus suspended in mineral oil. Several injections (3-4) were made at neighboring sites, at a depth of 200-250 μm. A volume of 150-200 nl of virus mixture was injected at 75 nl/min rate at each site. After each injection, the pipette was held in place for 3-5 minutes prior to retraction to prevent leakage. The incision was sutured and proper post-operative analgesics (Meloxicam, 1-2 mg/kg) were administered for three days following surgery.

In Vivo Two-Photon Guided Targeted Loose Patch Recordings

Two weeks after virus injection, mice were used for electrophysiology experiments. Mice were anesthetized with 2% isoflurane and maintained using 0.8% isoflurane. The skin was excised, cleaned with sugi and a metal head plate was attached to the skull using glue and dental acrylic, and a 2 mm×2 mm craniotomy was performed over the primary visual cortex (V1). The exposed area was then covered with a thin layer of 1.5% agarose in artificial cerebrospinal fluid (aCSF; 140 mM NaCl, 5 mM KCl, 2 mM CaCl2, 1 mM MgCl2, 0.01 mM EDTA, 10 mM HEPES, 10 mM glucose; pH 7.4). Animal body temperature was maintained during experiment 37.5° C. with a heating blanket.

Borosilicate pipettes (WPI) were pulled using a Sutter P-2000 laser puller (Sutter Instruments). Tip diameter was around 1 μm while the resistance was between 3-5 MΩ. Recordings were made using custom software (Network Prism, Sur lab), written in Matlab (MathWorks), controlling a MultiClamp 700B amplifier (Axon). A glass pipette electrode was inserted into the brain at an angle of 20-35° and an Ag/AgCl ground electrode pellet (Warner Instruments) was positioned in the same solution as the brain and the objective. For fluorescent visualization, pipettes were filled with Alexa Fluor 594 (Molecular Probes). The pipette was first targeted to the injection site using a 10× lens, and then targeted to individual GFP+ cells using a 25× lens via simultaneous two-photon imaging at 770 nm. Cell proximity was detected through deflections in resistance observed in voltage clamp during a rapidly time-varying 5 mV command voltage pulse. Once resistance had increased by 5-10 MΩ, the amplifier was switched to current clamp, and spikes were recorded with zero injected current, under a Bessel filter of 4 KHz and an AC filter of 300 Hz. Virus injected brains were perfused post hoc and immunohistochemistry was performed.

Visual Stimulation and Data Analysis from In Vivo Two-Photon Guided Targeted Loose Patch Recordings To assess the orientation selectivity and tuning of genome-edited neurons, we presented oriented gratings using custom software written in Matlab PsychToolbox-3. Gratings were optimized for cellular responsiveness and were presented by stepping the orientation from 0-360 degrees in steps of 20 degrees, with each grating presentation being preceded for 4 seconds "off" followed by 4 seconds "on", for a total presentation duration of 144 seconds. Data was acquired directly into Matlab and saved as .mat files. Spike detection was performed via analysis routines that used manually defined thresholds followed by spike shape template matching for further verification. Every spike was tagged and displayed on screen in a graphical user interface whereupon it was manually reviewed for false positives and negatives by the experimenter. Spike times in response to every stimulus were then grouped into "on" or "off" periods based on their timing relative to visual stimulation, and "on" spikes for each stimulus were decremented by the number of "off" spikes observed during an equal time period. For orientation experiments, # spikes per stimulus=(# spikes "on")−(# spikes "off") because "on" and "off" periods were the same duration.

For every cell of interest, the methods were used to collect responses for each oriented stimulus (0 to 360 degrees, in steps of 20 degrees). These responses were then turned into a "tuning curve" of orientation vs. response for each trial. Orientation Selectivity Index (OSI) was computed by taking the vector average for the preferred orientation according to the formulae as follows:

$$OSI = \frac{\sqrt{(\Sigma_i R(\theta_i)\sin(2\theta_i))^2 + (\Sigma_i R(\theta_i)\cos(2\theta_i))^2}}{\Sigma_i R(\theta_i)}$$

Tissue Preparation and Purification of Cell Nuclei

Total hippocampus or dentate gyrus was quickly dissected in ice cold DPBS (Life Sciences) and shock frozen on dry ice. For cell nuclei purification, tissue was gently homogenized in 2 ml ice-cold homogenization buffer (HB) (320 mM Sucrose, 5 mM CaCl, 3 mM $Mg(Ac)_2$, 10 mM Tris pH7.8, 0.1 mM EDTA, 0.1% NP40, 0.1 mM PMSF, 1 mM beta-mercaptoethanol) using 2 ml Dounce homogenizer (Sigma); 25 times with pestle A, followed by 25 times with pestle B. Next, 3 ml of HB was added up to 5 ml total and kept on ice for 5 min. For gradient centrifugation, 5 ml of 50% OptiPrep™ density gradient medium (Sigma) containing 5 mM CaCl, 3 mM $Mg(Ac)_2$, 10 mM Tris pH 7.8, 0.1 mM PMSF, 1 mM beta-mercaptoethanol was added and mixed. The lysate was gently loaded on the top of 10 ml 29% iso-osmolar OptiPrep™ solution in a conical 30 ml centrifuge tube (Beckman Coulter, SW28 rotor). Samples were centrifuged at 10,100×g (7,500 rpm) for 30 min at 4° C. The supernatant was removed and the nuclei pellet was gently resuspended in 65 mM beta-glycerophosphate (pH 7.0), 2 mM $MgCl_2$, 25 mM KCl, 340 mM sucrose and 5% glycerol. Number and quality of purified nuclei was controlled using bright field microscopy.

Cell Nuclei Sorting

Purified GFP-positive ($GFP^+$) and negative ($GFP^-$) intact nuclei were co-labeled with Vybrant® DyeCycle™ Ruby Stain (1:500, Life Technologies) and sorted using BD FACSAria III (Koch Institute Flow Cytometry Core, MIT). $GFP^+$ and GFP" nuclei were collected in 1.5 ml Eppendorf tubes coated with 1% BSA and containing 400 μl of resuspension buffer (65 mM beta-glycerophosphate pH 7.0, 2 mM $MgCl_2$, 25 mM KCl, 340 mM sucrose and 5% glycerol). After sorting, all samples were kept on ice and centrifuged at 10,000×g for 20 min at 4° C. Nuclei pellets were stored at −80° C. or were directly used for downstream processing.

Genomic DNA Extraction and SURVEYOR™ Assay

For functional testing of sgRNA, 50-70% confluent N2a cells were co-transfected with a single PCR amplified sgRNA and SpCas9 vector. Cells transfected with SpCas9 only served as negative control. Cells were harvested 48 h after transfection, and DNA was extracted using DNeasy Blood & Tissue Kit (Qiagen) according to the manufacturer's protocol. To isolate genomic DNA from AAV1 transduced primary neurons, DNeasy Blood & Tissue Kit was used 7 days post AAV transduction, according to the manufacturer's instruction.

Sorted nuclei or dissected tissues were lysed in lysis buffer (10 mM Tris, pH 8.0, 10 mM NaCl, 10 mM EDTA, 0.5 mM SDS, Proteinase K (PK, 1 mg/ml) and RNAse A) at 55° C. for 30 min. Next, chloroform-phenol extraction was performed followed by DNA precipitation with ethanol, according to standard procedures. DNA was finally resuspended in TE Buffer (10 mM Tris pH 8.0, 0.1 mM EDTA) and used for downstream analysis. Functional testing of individual sgRNAs was performed by SURVEYOR™ nuclease assay (Transgenomics) using PCR primers listed in Supplementary Table 2. Band intensity quantification was performed as described before[11].

RNA Library Preparation and Sequencing

Two weeks after bilateral viral delivery of SpCas9 with guide targeting Mecp2 (4 animals) or SpCas9 with gRNA targeting lacZ (4 animals), the dentate gyrus was quickly dissected in ice cold DPBS (Life Sciences) and transferred immediately to RNA-later solution (Ambion). After 24 hours in 4° C. the tissue was moved to −80° C. Populations of 100 targeted neuronal nuclei were FACS sorted into 10 μl TCL buffer supplemented with 1% 2-mercaptoethanol (Qiagen). After centrifuging, samples were frozen immediately at −80° C. The RNA was purified by AMPure RNAcleanXP SPRI beads (Beckman Coulter Genomics) following the manufactures' instructions, and washed three times with 80% ethanol, omitting the final elution. The beads with captured RNA were air-dried and processed immediately for cDNA synthesis. Samples with no nuclei were used as negative controls. Three population samples were used for each animal, total of 24 population sample, in cDNA library preparations following the SMART-seq2 protocol[12] only replacing the reverse transcriptase enzyme with 0.1 ul of Maxima H Minus enzyme (200 U/ul, Thermo Scientific), and scaling down the PCR reaction to a volume of 25 ul. The tagmentation reaction and final PCR amplification were done using the Nextera XT DNA Sample preparation kit (Illumina), with the following modifications. All reaction volumes were scaled down by a factor of 4, and the libraries were pooled after the PCR amplification step by taking 2.5 ul of each sample. The pooled libraries were cleaned and size-selected using two rounds of 0.7 volume of AMPure XP SPRI bead cleanup (Beckman Coulter Genomics). Samples were loaded on a High-Sensitivity DNA chip (Agilent) to check the quality of the library, while quantification was done with Qubit High-Sensitivity DNA kit (Invitrogen). The pooled libraries were diluted to a final concentration of 4 nM and 12 pmol and were sequenced using Illumina Miseq with 75 bp paired end reads.

RNA Libraries Data Analysis

Bowtie2 index was created based on the mouse mm9 UCSC genome and known Gene transcriptome[13], and paired-end reads were aligned directly to this index using Bowtie2 with command line options -q -phred33-quals -n 2 -e 99999999-l 25 -I 1-X 1000 -a -m 200 -p 4 -chunkmbs 512. Next, RSEM v1.27 was run with default parameters on the alignments created by Bowtie2 to estimate expression levels. RSEM's gene level expression estimates (tau) were multiplied by 1,000,000 to obtain transcript per million (TPM) estimates for each gene, and TPM estimates were transformed to log-space by taking log 2(TPM+1). Genes were considered detected if their transformed expression level equal to or above 2 (in log 2(TPM+1) scale). A library is filtered out if it has less than 8000 genes detected. Based on this criterion, 4 libraries were filtered and excluded from the downstream analysis. To find differentially expressed genes between control animals and Mecp2 sgRNA expressing animals, Student's t-test (Matlab V2013b) and cross validation was used in 20 random permutation runs, where in each run one library from each animal was randomly chosen to exclude (this results in a total of 12 libraries used in the t-test each time). The t-test was run on all genes that have mean expression level above 0.9 quantile (usually around 5 log 2(TPM+1)) for each sample. Then, genes that were significant ($p<0.01$) in more than one thirds of the permutation runs were chosen. The log 2(TPM+1) expression levels of these genes across samples were clustered using hierarchical clustering (Matlab V2013b).

Immunofluorescent Staining

Cell culture: For immunofluorescent staining of primary neurons, cells were fixed 7 days after viral delivery with 4% paraformaldehyde (PFA) for 20 min at RT. After washing 3 times with PBS, cells were blocked with 5% normal goat serum (NGS) (Life Technologies), 5% donkey serum (DS) (Sigma) and 0.1% Triton-X100 (Sigma) in PBS for 30 min at RT. Cells were incubated with primary antibodies in 2.5% NGS, 2.5% DS and 0.1% Triton-X100 for 1 hour at RT or overnight at 4° C. After washing 3 times with PBST, cells were incubated with secondary antibodies for 1 hour at RT. Finally, coverslips were mounted using VECTASHIELD HardSet Mounting Medium with DAPI (Vector Laboratories) and imaged using an Zeiss AxioCam Ax10 microscope and an Axiocam MRm camera. Images were processed using the Zen 2012 software (Zeiss). Quantifications were performed by using ImageJ software 1.48 h and Neuron detector plugin.

Mice were sacrificed 4 weeks after viral delivery by a lethal dose of Ketamine/Xylazine and transcardially perfused with PBS followed by PFA. Fixed tissue was sectioned using vibratome (Leica, VT1000S). Next, 30 μm sections were boiled for 2 min in sodium citrate buffer (10 mM tri-sodium citrate dehydrate, 0.05% Tween20, pH 6.0) and cool down at RT for 20 min. Sections were blocked with 4% normal goat serum (NGS) in TBST (137 mM NaCl, 20 mM Tris pH 7.6, 0.2% Tween-20) for 1 hour. Paraffin sections were cut using a microtom (Leica RM2125 RTS) to 8 μm, and stained as described previously[14].

Sections were incubated with primary antibodies diluted in TBST with 4% NGS overnight at 4° C. After 3 washes in TBST, samples were incubated with secondary antibodies. After washing with TBST 3 times, sections were mounted using VECTASHIELD HardSet Mounting Medium with DAPI and visualized with confocal microscope (Zeiss LSM 710, Ax10 ImagerZ2, Zen 2012 Software).

Following primary antibodies were used: rabbit anti-Dnmt3a (Santa Cruz, 1:100); rabbit anti-MeCP2 (Millipore, 1:200); mouse anti-NeuN (Millipore, 1:50-1:400); chicken anti-GFAP (Abcam, 1:400); mouse anti-Map2 (Sigma, 1:500); chicken anti-GFP (Ayes labs, 1:200-1:400); mouse anti-HA (Cell Signaling, 1:100). Secondary antibodies: AlexaFluor®488, 568 or 633 (Life Technologies, 1:500-1:1,000).

Quantification of LIVE/DEAD® Assay

Control and transduced primary neurons were stained using the LIVE/DEAD® assay (Life technologies) according to the manufacturer's instruction. To avoid interference with the GFP-signal from GFP-KASH expression, cells were stained for DEAD (ethidium homodimer) and DAPI (all cells) only. Stained cells were imaged using fluorescence microscopy and DEAD, GFP and DAPI positive cells were counted by using ImageJ 1.48 h software and Neuron detector plugin.

Western Blot Analysis

Transduced primary cortical neurons (24 well, 7 days after viral delivery) and transduced tissue samples (4 weeks after viral delivery) were lysed in 50 μL of ice-cold RIPA buffer (Cell Signaling) containing 0.1% SDS and proteases inhibitors (Roche, Sigma). Cell lysates were sonicated for 5 min in a Bioruptor sonicater (Diagenode) and protein concentration was determined using the BCA Protein Assay Kit (Pierce Biotechnology, Inc.). Protein lysats were dissolved in SDS-PAGE sample buffer, separated under reducing conditions on 4-15% Tris-HCl gels (Bio-Rad) and analyzed by Western blotting using primary antibodies: rabbit anti-Dnmt3a (Santa Cruz, 1:500), mouse anti-Dnmt1 (Novus Biologicals, 1:800), rabbit anti-Mecp2 (Millipore, 1:400), rabbit anti-Tubulin (Cell Signaling, 1:10,000) followed by secondary anti-mouse and anti-rabbit HRP antibodies (Sigma-Aldrich, 1:10,000). GAPDH was directly visualized with rabbit HRP coupled anti-GAPDH antibody (Cell Signaling, 1:10,000). Tubulin or GAPDH served as loading control. Blots were imaged with ChemiDoc™ MP system with ImageLab 4.1 software (BioRad), and quantified using ImageJ software 1.48 h.

Delay Contextual Fear Conditioning (DCFC)

8 weeks after bilateral SpCas9/DNMT 3×sgRNA delivery into the dorsal and ventral dentate gyrus of 12 weeks old C57BL/6N male mice, animals were habituated to the experimentor and the behavior room for 7 days. SpCas9/GFP-KASH injected littermates served as controls. At day 1 of DCFC, mouse cages were placed into an isolated anteroom to prevent mice from auditory cues before and after testing. Individual mice were placed into the FC chamber (Med Associates Inc.) and a 12 min habituation period was performed. After habituation the mice were placed back to their homecages. The next day (training day) individual mice were placed into the chamber and were allowed to habituate for 4 min. After another 20 sec (pre-tone) interval, the tone (auditory cue) at a level of 85 dB, 2.8 kHz was presented for 20 sec followed by 18 sec delay interval before the foot-shock was presented (0.5 mA, 2 sec). After the foot-shock, 40 sec interval (post-tone/shock) preceded a next identical trial starting with the 20 sec pre-tone period. The training trial was repeated 6 times before the mice were placed back to their homecages. At day 3 (testing day), mice were first placed in the conditioning context chamber for 3 min. Next, mice underwent 4×100 sec testing trials starting with a 20 sec interval followed by 20 sec tone and a 60 sec post-tone interval. Finally, mice were placed in an altered context-conditioning chamber (flat floor vs. grid, tetrameric vs. heptameric chamber, vanillin scent) and the testing trial was repeated. Freezing behavior was recorded and analysis was performed blind off-line manually and confirmed with Noldus EthoVision XT software (Noldus Information Technology).

Deep Sequencing Analysis and Indel Detection

CRISPR Design Tool (crispr.mit.edu/) was used to find potential off-targets for DNMT family genes, targeted by CRISPR-SpCas9 in the brain. Targeted cell nuclei from dentate gyrus were FACS sorted 12 weeks after viral delivery and genomic DNA was purified as described above. For each gene of interest, the genomic region flanking the CRISPR target site was amplified by a fusion PCR method to attach the Illumina P5 adapters as well as unique sample-specific barcodes to the target amplicons (for on- and off-target primers see Supplementary Table 3)[15]. Barcoded and purified DNA samples were quantified by Qubit 2.0 Fluorometer (Life Technologies) and pooled in an equimolar ratio. Sequencing libraries were then sequenced with the Illumina MiSeq Personal Sequencer (Life Technologies), with read length 300 bp.

The MiSeq reads were analyzed as described previously in[15]. Briefly, reads were filtered by Phred quality (Q score) and aligned using a Smith-Waterman algorithm to the genomic region 50 nucleotides upstream and downstream of the target site. Indels were estimated in the aligned region from 5 nucleotides upstream to 5 nucleotides downstream of the target site (a total of 30 bp). Negative controls for each sample were used to estimate the inclusion or exclusion of indels as putative cutting events. We computed a maximum-likelihood estimator (MLE) for the fraction of reads having target-regions with true-indels, using the per-target-region-per-read error rate from the data of the negative control sample. The MLE scores and cutting rates for each target are listed in Supplementary Table 1.

Statistical Analysis

All experiments were performed with a minimum of two independent biological replicates. Statistics were performed with Prism6 (GraphPad) using Student's two tailed t-test.

Supplementary Tables

SUPPLEMENTARY TABLE 1

Off-target analysis for DNMTs targeting

| | Gene | GI | Potential off-target sequences | MLE (%) | SEM |
|---|---|---|---|---|---|
| Dnmt1 | Abca1 | NM_013454 | GGAGCTGGAGCTGTTCACGTTGG | 0.0000 | 0.00 |
| | Mctp1 | NM_030174 | CGGGCAGCAGATGTTCGCGTAGG | 0.0806 | 0.08 |
| | Exd2 | NM_133798 | AGGGCTTGAGATGTTCGGGCTGG | 0.0612 | 0.06 |
| | Pik3r6 | NM_001004435 | CCGGCTGGGGCTGTCCTCGCTAG | 0.0000 | 0.00 |
| | Sobp | NM 175407 | CGGGGTGCAGCTGCTCACGCCAG | 0.0000 | 0.00 |
| | Vac14 | NM 146216 | CTGGCGGGAGCTGGTCGCGTGAG | 0.0083 | 0.00 |
| Dnmt3a | Efemp2 | NM_021474 | TGAGCATGGGCCGCTGGCGGTGG | 0.0050 | 0.01 |
| | Bmpr1b | MM_001277217 | ATGGCATAGGCCGCTGACAGAGG | 0.0117 | 0.01 |
| | Syce1 | NM_001143765 | TTGGCATGGTGAGCTGGCGGGGG | 0.0067 | 0.00 |
| | Atp8b3 | NM_026094 | TGGGCAGGGGTCTCTGAGGGCAG | 0.0067 | 0.01 |
| | Rdh11 | NM_021557 | TTGGCATGGGTCTCTTACCAAGG | 0.0017 | 0.00 |
| Dnmt3b | Hecw2 | NM_001001883 | ACATGGTTCCAGTGGGTATGTAG | 0.0000 | 0.00 |
| | Plekhg3 | NM_153804 | GGAGGTGGGCAGCGGGTATGTAG | 0.0954 | 0.01 |
| | Cdc25b | NM_001111075 | AGAAGGTCCCCGCGGGCATGGAG | 0.2421 | 0.12 |
| | Top1mt | NM_028404 | GGAGGGAACCAGCCGGTATGGGG | 0.0167 | 0.01 |
| | Sesn2 | NM_144907 | AGAGAGTGGCAGTGGGTAAGCAG | 0.0000 | 0.00 |
| | Ncan | NM_007789 | AGAGGTGGCCAGCGGGCAGGAAG | 0.0017 | 0.00 |
| | Nacad | NM_001081652 | TGAGGGGGCCAGCTGGGATGCAG | 1.6254 | 0.76 |

(SEQ ID NO: 539 to 556)

SUPPLEMENTARY TABLE 2

PCR primers used in the SURVEYOR assay

| Gene | Forward primer sequence (5'-3') | SEQ ID NO: | Reverse primer sequence (5'-3') | SEQ ID NO: |
|---|---|---|---|---|
| Mecp2 | GGTCTCATGTGTGGCACTCA | 557 | TGTCCAACCTTCAGGCAAGG | 561 |
| Dnmt3a | ATCCCTCCTCAGAGGGTCAGC | 558 | TACCTCATGCACAGCTAGCACC | 562 |
| Dnmt1 | TTCGGGCATAGCATGGTCTTCC | 559 | GTTCTATTTCAGAGGGCTGATCCC | 563 |
| Dnmt3b | GTTCTGAGCCGCACAGTTTGG | 560 | GGATAAGAAGGGACAATACAGG | 564 |

SUPPLEMENTARY TABLE 3

Primers used for on- and off-target genomic loci amplification

| Gene | Forward primer sequence (5'-3') | SEQ ID NO: | Reverse primer sequence (5'-3') | SEQ ID NO: |
|---|---|---|---|---|
| Dnmt1 | GCCGGGGTCTC GTTCAGAGCT | 565 | CTACCGCCTGCGGA CATGGT | 586 |
| Dnmt3a | CCTGTCTCTCTGT CCTAGGGCTCC | 566 | CCGTTTGCTGATGTAGTA GGGGTCC | 587 |
| Dnmt3b | CCCACAGGAAA CAATGAAGGGAGAC | 567 | CATCCTTCGTGTCT GAGGACTGGTC | 588 |
| Abca1 | CCCTGACACCAGC TGTTCAGCAC | 568 | CTCTGGGTGAC CACACACGATGC | 589 |
| Mctp1 | GAGCAGGCAGA GCCGAGCAAG | 569 | GGAGAGCGTCC GCCAGGAG | 590 |
| Exd2 | GGGTCTTGTTGTG AGTAGGGTGTG | 570 | GAAGCTCTCTTAA CTACTGTTC | 591 |
| Pik3r6 | CCTGGAATACTAT TTCCACGCCG | 571 | CAGGCCCTAGCAGCG AGCAG | 592 |
| Sobp | GCAGCACACTCCA CCCTCACAT | 572 | GGAAGGGGCTTTCC TCCGAGC | 593 |
| Vac14 | CGGCGTCACG TGACCTGAGTAAC | 573 | GCTCCGACCCTGCT CTCCCA | 594 |
| Efemp2 | GTGTCTGCCTC GCTCTGCTGC | 574 | CCTGTTCATCAGGCTC GTAGCCC | 595 |
| Bmpr1b | CTATCTGAAATCC ACCACCTTAGACGC | 575 | CGATTGCTGGCTTGC CTTGAG | 596 |
| Syce1 | GCCTGAGGGGG CCAGAGGT | 576 | GGTTCGCGTCCGCC CGCGTGAT | 597 |
| Atp8b3 | GGGACTCC CCGGGTGGTG | 577 | GAGAGGTGGTC CTGTCGCCTATG | 598 |
| Rdh11 | GACCCTGTGTTT CAAGTCTCTCTG | 578 | CCCAGCAGGTCACA GCTGACATC | 599 |
| Hecw2 | GGCCATCCAGTAC ATTCAATACG | 579 | AGCACAGTATGTATTC TATAAAATAATACGAC | 600 |
| Plekhg3 | GCAGAAGCCGT GACTCACAGCA | 580 | GTGGGAGGGGACAG AGACCATG | 601 |
| Cdc25b | CTTGTGCTTG TGATTCTGTCCTTACTGC | 581 | CCTTACCTGTTCCTCT TCCTTATCCAGC | 602 |
| Top1mt | CGAGAAGTC GATGCAGACACTTCAA | 582 | ATACCCAGTCCAC ATCCCTGCC | 603 |
| Sesn2 | GCTGAAGACTGGC GAGCACAGCT | 583 | CCTCTGCATCTCCCTCAGGA AGTATT | 604 |

SUPPLEMENTARY TABLE 3-continued

| Primers used for on- and off-target genomic loci amplification | | | | |
|---|---|---|---|---|
| Gene | Forward primer sequence (5'-3') | SEQ ID NO: | Reverse primer sequence (5'-3') | SEQ ID NO: |
| Ncan | GACCTGAATGTTG TGGCTGAGAGTCC | 584 | GCCTCCTGTC CCCAGGTCCC | 605 |
| Nacad | CCCTCACGTTCC TGTCCAGCAA | 585 | CACTAGGCTT GGGCTGCCCTCT | 606 |

REFERENCES

1. Ostlund, C. et al. Dynamics and molecular interactions of linker of nucleoskeleton and cytoskeleton (LINC) complex proteins. J Cell Sci 122, 4099-4108 (2009).
2. Gray, S. J. et al. Optimizing promoters for recombinant adeno-associated virus-mediated gene expression in the peripheral and central nervous system using self-complementary vectors. Hum Gene Ther 22, 1143-1153 (2011).
3. Levitt, N., Briggs, D., Gil, A. & Proudfoot, N.J. Definition of an efficient synthetic poly(A) site. Genes Dev 3, 1019-1025 (1989).
4. Jinek, M. et al. A programmable dual-RNA-guided DNA endonuclease in adaptive bacterial immunity. Science 337, 816-821 (2012).
5. Cong, L. et al. Multiplex genome engineering using CRISPR/Cas systems. Science 339, 819-823 (2013).
6. McClure, C., Cole, K. L., Wulff, P., Klugmann, M. & Murray, A. J. Production and titering of recombinant adeno-associated viral vectors. J Vis Exp, e3348 (2011).
7. Konermann, S. et al. Optical control of mammalian endogenous transcription and epigenetic states. Nature 500, 472-476 (2013).
8. Banker, G. & Goslin, K. Developments in neuronal cell culture. Nature 336, 185-186 (1988).
9. Swiech, L. et al. CLIP-170 and IQGAP1 cooperatively regulate dendrite morphology. J Neurosci 31, 4555-4568 (2011).
10. Sholl, D. A. Dendritic organization in the neurons of the visual and motor cortices of the cat. J Anat 87, 387-406 (1953).
11. Ran, F. A. et al. Genome engineering using the CRISPR-Cas9 system. Nature protocols 8, 2281-2308 (2013).
12. Picelli, S. et al. Smart-seq2 for sensitive full-length transcriptome profiling in single cells. Nature methods 10, 1096-1098 (2013).
13. Fujita, P. A. et al. The UCSC Genome Browser database: update 2011. Nucleic acids research 39, D876-882 (2011).
14. Tzingounis, A. V. et al. The KCNQ5 potassium channel mediates a component of the afterhyperpolarization current in mouse hippocampus. Proceedings of the National Academy of Sciences of the United States of America 107, 10232-10237 (2010).
15. Hsu, P. D. et al. DNA targeting specificity of RNA-guided Cas9 nucleases. Nature biotechnology 31, 827-832 (2013).
16. Qiu, P. et al. Mutation detection using Surveyor nuclease. BioTechniques 36, 702-707 (2004).

Example 41: Further Investigation into Nuclear Tagging Technique

This Example concerns epitope tagging of Cas9. In brief, we found that a triple epitope tag (specifically 3×HA) improves the detection signal.

Materials and Methods

Cell Culture and Transfection

Human embryonic kidney (HEK) cell line 293FT (Life Technologies) or mouse Hepa1-6 (Sigma-Aldrich) cell line was maintained in Dulbecco's modified Eagle's Medium (DMEM) supplemented with 10% fetal bovine serum (HyClone), 2 mM GlutaMAX (Life Technologies), 100 U/mL penicillin, and 100 μg/mL streptomycin at 37° C. with 5% $CO_2$ incubation.

Cells were seeded onto 24-well plates (Corning) at a density of 120,000 cells/well, 24 hours prior to transfection. Cells were transfected using Lipofectamine 2000 (Life Technologies) at 80-90% confluency following the manufacturer's recommended protocol. A total of 500 ng Cas9 plasmid and 100 ng of U6-sgRNA PCR product was transfected.

SURVEYOR Nuclease Assay for Genome Modification

293FT and HUES62 cells were transfected with DNA as described above. Cells were incubated at 37° C. for 72 hours post-transfection prior to genomic DNA extraction. Genomic DNA was extracted using the QuickExtract DNA Extraction Solution (Epicentre) following the manufacturer's protocol. Briefly, pelleted cells were resuspended in QuickExtract solution and incubated at 65° C. for 15 minutes, 68° C. for 15 minutes, and 98° C. for 10 minutes.

The genomic region flanking the CRISPR target site for each gene was PCR amplified, and products were purified using QiaQuick Spin Column (Qiagen) following the manufacturer's protocol. 400 ng total of the purified PCR products were mixed with 2 microlitres 10×Taq DNA Polymerase PCR buffer (Enzymatics) and ultrapure water to a final volume of 20 microlitres, and subjected to a re-annealing process to enable heteroduplex formation: 95° C. for 10 min, 95° C. to 85° C. ramping at −2° C./s, 85° C. to 25° C. at −0.25° C./s, and 25° C. hold for 1 minute. After re-annealing, products were treated with SURVEYOR nuclease and SURVEYOR enhancer S (Transgenomics) following the manufacturer's recommended protocol, and analyzed on 4-20% Novex TBE poly-acrylamide gels (Life Technologies). Gels were stained with SYBR Gold DNA stain (Life Technologies) for 30 minutes and imaged with a Gel Doc gel imaging system (Bio-rad). Quantification was based on relative band intensities. Indel percentage was determined by the formula, $100\times(1-(1-(b+c)/(a+b+c))^{1/2})$, where a is the integrated intensity of the undigested PCR product, and b and c are the integrated intensities of each cleavage product.

Western Blot

HEK 293FT cells were transfected and lysed in 1×RIPA buffer (Sigma-Aldrich) supplemented with Protease Inhibitor (Roche). The lysates were loaded onto Bolt 4-12% Bis-Tris Plus Gels (Invitrogen) and transferred to nitrocellulose membranes. The membranes were blocked in Tris-buffered saline containing 0.1% Tween-20 and 5% blocking agent (G-Biosciences). The membranes were probed with rabbit anti-FLAG (1:5,000, Abcam), HRP-conjugated anti-GAPDH (1:5,000 Cell Signaling Technology), and HRP-conjugated anti-rabbit (1:1,000) antibodies and visualized with a Gel Doc XR+ System (Bio-Rad).

REFERENCES

Banker G, Goslin K. Developments in neuronal cell culture. Nature. 1988 Nov. 10; 336(6195):185-6.

Bedell, V. M. et al. In vivo genome editing using a high-efficiency TALEN system. Nature 491, 114-U133 (2012).

Bhaya, D., Davison, M. & Barrangou, R. CRISPR-Cas systems in bacteria and archaea: versatile small RNAs for adaptive defense and regulation. Annu Rev Genet 45, 273-297 (2011).

Bobis-Wozowicz, S., Osiak, A., Rahman, S. H. & Cathomen, T. Targeted genome editing in pluripotent stem cells using zinc-finger nucleases. Methods 53, 339-346 (2011).

Boch, J. et al. Breaking the code of DNA binding specificity of TAL-type III effectors. Science 326, 1509-1512 (2009).

Bogenhagen, D. F. & Brown, D. D. Nucleotide sequences in *Xenopus* 5S DNA required for transcription termination. Cell 24, 261-270 (1981).

Bultmann, S. et al. Targeted transcriptional activation of silent oct4 pluripotency gene by combining designer TALEs and inhibition of epigenetic modifiers. Nucleic Acids Res 40, 5368-5377 (2012).

Carlson, D. F. et al. Efficient TALEN-mediated gene knockout in livestock. Proc Natl Acad Sci USA 109, 17382-17387 (2012).

Chen, F. Q. et al. High-frequency genome editing using ssDNA oligonucleotides with zinc-finger nucleases. Nat Methods 8, 753-U796 (2011).

Cho, S. W., Kim, S., Kim, J. M. & Kim, J. S. Targeted genome engineering in human cells with the Cas9 RNA-guided endonuclease. Nat Biotechnol 31, 230-232 (2013).

Christian, M. et al. Targeting DNA double-strand breaks with TAL effector nucleases. Genetics 186, 757-761 (2010).

Cong, L. et al. Multiplex genome engineering using CRISPR-Cas systems. Science 339, 819-823 (2013).

Deltcheva, E. et al. CRISPR RNA maturation by trans-encoded small RNA and host factor RNase III. Nature 471, 602-607 (2011).

Deveau, H., Garneau, J. E. & Moineau, S. CRISPR-Cas system and its role in phage-bacteria interactions. Annu Rev Microbiol 64, 475-493 (2010).

Ding, Q. et al. A TALEN genome-editing system for generating human stem cell-based disease models. Cell Stem Cell 12, 238-251 (2013).

Garneau, J. E. et al. The CRISPR-Cas bacterial immune system cleaves bacteriophage and plasmid DNA. Nature 468, 67-71 (2010).

Gasiunas, G., Barrangou, R., Horvath, P. & Siksnys, V. Cas9-crRNA ribonucleoprotein complex mediates specific DNA cleavage for adaptive immunity in bacteria. Proc Natl Acad Sci USA 109, E2579-2586 (2012).

Geurts, A. M. et al. Knockout Rats via Embryo Microinjection of Zinc-Finger Nucleases. Science 325, 433-433 (2009).

Gray S J, Foti S B, Schwartz J W, Bachaboina L, Taylor-Blake B, Coleman J, Ehlers M D, Zylka M J, McCown T J, Samulski R J. Optimizing promoters for recombinant adeno-associated virus-mediated gene expression in the peripheral and central nervous system using self-complementary vectors. Hum Gene Ther. 2011 September; 22(9): 1143-53. doi: 10.1089/hum.2010.245.

Guschin, D. Y. et al. A rapid and general assay for monitoring endogenous gene modification. Methods Mol Biol 649, 247-256 (2010).

Hasty, P., Rivera-Perez, J. & Bradley, A. The length of homology required for gene targeting in embryonic stem cells. Mol Cell Biol 11, 5586-5591 (1991).

Horvath, P. & Barrangou, R. CRISPR-Cas, the immune system of bacteria and archaea. Science 327, 167-170 (2010).

Hsu, P. D. & Zhang, F. Dissecting neural function using targeted genome engineering technologies. ACS Chem Neurosci 3, 603-610 (2012).

Hwang, W. Y. et al. Efficient genome editing in zebrafish using a CRISPR-Cas system. Nat Biotechnol 31, 227-229 (2013).

Jiang, W., Bikard, D., Cox, D., Zhang, F. & Marraffini, L. A. RNA-guided editing of bacterial genomes using CRISPR-Cas systems. Nat Biotechnol 31, 233-239 (2013).

Jinek, M. et al. A programmable dual-RNA-guided DNA endonuclease in adaptive bacterial immunity. Science 337, 816-821 (2012).

Jinek, M. et al. RNA-programmed genome editing in human cells. eLife 2, e00471 (2013).

Kaplitt, M. G., et al., Safety and tolerability of gene therapy with an adeno-associated virus (AAV) borne GAD gene for Parkinson's disease: an open label, phase I trial. Lancet. 2007 Jun. 23; 369(9579):2097-105.

Levitt N. Briggs D. Gil A. Proudfoot N.J. Definition of an efficient synthetic poly(A) site. Genes Dev. 1989; 3:1019-1025.

Liu D, Fischer I. Two alternative promoters direct neuron-specific expression of the rat microtubule-associated protein 1B gene. J Neurosci. 1996 Aug. 15; 16(16):5026-36.

Lopes, V. S., etc al., Retinal gene therapy with a large MYO7A cDNA using adeno-associated virus. Gene Ther, 2013 Jan. 24. doi: 10.1038/gt 2013.3.[Epub ahead of print]

Mahfouz, M. M. et al. De novo-engineered transcription activator-like effector (TALE) hybrid nuclease with novel DNA binding specificity creates double-strand breaks. Proc Natl Acad Sci USA 108, 2623-2628 (2011).

Makarova, K. S. et al. Evolution and classification of the CRISPR-Cas systems. Nat Rev Microbiol 9, 467-477 (2011).

Mali, P. et al. RNA-guided human genome engineering via Cas9. Science 339, 823-826 (2013).

McClure C, Cole K L, Wulff P, Klugmann M, Murray A J. Production and titering of recombinant adeno-associated viral vectors. J Vis Exp. 2011 Nov. 27; (57): e3348. doi: 10.3791/3348.

Michaelis, L. M., Maud "Die kinetik der invertinwirkung.". Biochem. z (1913).

Miller, J. C. et al. An improved zinc-finger nuclease architecture for highly specific genome editing. Nat Biotechnol 25, 778-785 (2007).

Miller, J. C. et al. A TALE nuclease architecture for efficient genome editing. Nat Biotechnol 29, 143-148 (2011).

Moscou, M. J. & Bogdanove, A. J. A simple cipher governs DNA recognition by TAL effectors. Science 326, 1501 (2009). Porteus, M. H. & Baltimore, D. Chimeric nucleases stimulate gene targeting in human cells. Science 300, 763 (2003).

Mussolino, C. et al. A novel TALE nuclease scaffold enables high genome editing activity in combination with low toxicity. Nucleic acids research 39, 9283-9293 (2011).

Nathwani, A. C., et al., Adenovirus-associated virus vector-mediated gene transfer in hemophilia B. N Engl J Med. 2011 Dec. 22; 365(25):2357-65. doi: 10.1056/NEJMoa1108046. Epub 2011 Dec. 10.

Oliveira, T. Y. et al. Translocation capture sequencing: a method for high throughput mapping of chromosomal rearrangements. J Immunol Methods 375, 176-181 (2012).

Perez, E. E. et al. Establishment of HIV-1 resistance in CD4(+) T cells by genome editing using zinc-finger nucleases. Nat Biotechnol 26, 808-816 (2008).

Qi, L. S. et al. Repurposing CRISPR as an RNA-guided platform for sequence-specific control of gene expression. Cell 152, 1173-1183 (2013).

REMINGTON'S PHARMACEUTICAL SCIENCES (Mack Pub. Co., N.J. 1991)

Reyon, D. et al. FLASH assembly of TALENs for high-throughput genome editing. Nat Biotechnol 30, 460-465 (2012).

Saleh-Gohari, N. & Helleday, T. Conservative homologous recombination preferentially repairs DNA double-strand breaks in the S phase of the cell cycle in human cells. Nucleic Acids Res 32, 3683-3688 (2004).

Sander, J. D. et al. Selection-free zinc-finger-nuclease engineering by context-dependent assembly (CoDA). Nat Methods 8, 67-69 (2011).

Sanjana, N. E. et al. A transcription activator-like effector toolbox for genome engineering. Nat Protoc 7, 171-192 (2012).

Sapranauskas, R. et al. The *Streptococcus thermophilus* CRISPR-Cas system provides immunity in *Escherichia coli*. Nucleic Acids Res 39, 9275-9282 (2011).

Shen, B. et al. Generation of gene-modified mice via Cas9/RNA-mediated gene targeting. Cell Res 23, 720-723 (2013).

Smithies, O., Gregg, R. G., Boggs, S. S., Koralewski, M. A. & Kucherlapati, R. S. Insertion of DNA sequences into the human chromosomal beta-globin locus by homologous recombination. Nature 317, 230-234 (1985).

Soldner, F. et al. Generation of isogenic pluripotent stem cells differing exclusively at two early onset Parkinson point mutations. Cell 146, 318-331 (2011).

Takasu, Y. et al. Targeted mutagenesis in the silkworm *Bombyx mori* using zinc finger nuclease mRNA injection. Insect Biochem Molec 40, 759-765 (2010).

Tangri S, et al., Rationally engineered therapeutic proteins with reduced immunogenicity, J Immunol. 2005 Mar. 15; 174(6):3187-96.

Thomas, K. R., Folger, K. R. & Capecchi, M. R. High frequency targeting of genes to specific sites in the mammalian genome. Cell 44, 419-428 (1986).

Tuschl, T. Expanding small RNA interference. Nat Biotechnol 20, 446-448 (2002).

Urnov, F. D., Rebar, E. J., Holmes, M. C., Zhang, H. S. & Gregory, P. D. Genome editing with engineered zinc finger nucleases. Nat Rev Genet 11, 636-646 (2010).

Valton, J. et al. Overcoming transcription activator-like effector (TALE) DNA binding domain sensitivity to cytosine methylation. J Biol Chem 287, 38427-38432 (2012).

Wang, H. et al. One-Step Generation of Mice Carrying Mutations in Multiple Genes by CRISPR-Cas-Mediated Genome Engineering. Cell 153, 910-918 (2013).

Watanabe, T. et al. Non-transgenic genome modifications in a hemimetabolous insect using zinc-finger and TAL effector nucleases. Nat Commun 3 (2012).

Wilson, E. B. Probable inference, the law of succession, and statistical inference. J Am Stat Assoc 22, 209-212 (1927).

Wood, A. J. et al. Targeted genome editing across species using ZFNs and TALENs. Science 333, 307 (2011).

Wu, S., Ying, G. X., Wu, Q. & Capecchi, M. R. A protocol for constructing gene targeting vectors: generating knockout mice for the cadherin family and beyond. Nat Protoc 3, 1056-1076 (2008).

Zhang, F. et al. Efficient construction of sequence-specific TAL effectors for modulating mammalian transcription. Nat Biotechnol 29, 149-153 (2011).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

What is claimed is:

1. A method of modifying a mammalian subject by editing in vivo a DNA target sequence in a genomic locus of interest of a hepatic cell in the mammalian subject, said method comprising in vivo delivering to the hepatic cell a single dose of a composition comprising a stable nucleic acid-lipid particle (SNALP) comprising a CRISPR-Cas system, wherein the CRISPR-Cas system comprises:

I. a CRISPR-Cas system RNA comprising a guide sequence that hybridizes to the DNA target sequence, and II. a Cas9 comprising at least one nuclear localization sequence (NLS) or an mRNA encoding the Cas9, wherein the guide sequence directs sequence-specific binding of a CRISPR complex to the DNA target sequence, the CRISPR complex comprises the Cas9 complexed with the CRISPR-Cas system RNA, and wherein the CRISPR complex introduces a double-stranded break in vivo in the DNA target sequence in the genomic locus of interest of the hepatic cell which forms a targeted indel in the genomic locus of interest and produces a phenotypic change in said mammalian subject, and wherein the delivering results in greater than 20% indel formation in the genomic locus of interest of the hepatic cell.

2. The method of claim 1, wherein the Cas9 is *S. pyogenes* Cas9.

3. The method of claim 1, wherein the Cas9 is *S. aureus* Cas9.

4. The method of claim 1, wherein the CRISPR-Cas system RNA is a chimeric RNA (chiRNA) comprising the guide sequence fused to a tracr-mate sequence and a tracr-sequence.

5. The method of claim 1, wherein the DNA target sequence is adjacent to a protospacer adjacent motif (PAM).

6. The method of claim 5, wherein the PAM is 5'-NRG.

7. The method of claim 5, wherein the PAM is 5'-NNGRR.

8. The method of claim 1, wherein the composition comprises the CRISPR-Cas system RNA and the Cas9.

9. The method of claim 1, wherein the composition comprises the CRISPR-Cas system RNA and the mRNA encoding the Cas9.

10. The method of claim 1, wherein the composition comprises two or more CRISPR-Cas system RNAs each hybridizing to a different DNA target sequence.

11. The method of claim 1, wherein the delivering comprises injecting the composition into the mammalian subject.

12. The method of claim 11, wherein injecting comprises intravenous injection, stereotactic injection, or intramuscular injection.

13. The method of claim 1, wherein the mammalian subject is a human subject.

14. The method of claim 1, wherein the SNALP comprises cholesterol and PEG-lipid.

15. A method of modifying a mammalian subject by editing in vivo a DNA target sequence in a genomic locus of interest of a hepatic cell in the mammalian subject, said method comprising in vivo delivering to the hepatic cell a single dose of a composition comprising a stable nucleic acid-lipid particle (SNALP) comprising a CRISPR-Cas system, wherein the CRISPR-Cas system comprises:

I. a CRISPR-Cas system RNA comprising a guide sequence that hybridizes to the DNA target sequence, and II. a Cas9 comprising at least one nuclear localization sequence (NLS) or an mRNA encoding the Cas9, wherein the guide sequence directs sequence-specific binding of a CRISPR complex to the DNA target sequence, the CRISPR complex comprises the Cas9 complexed with the CRISPR-Cas system RNA, and wherein the CRISPR complex introduces a double-stranded break in vivo in the DNA target sequence in the genomic locus of interest of the hepatic cell which forms a targeted indel in the genomic locus of interest and produces a phenotypic change in said mammalian subject, and wherein the Cas9 is *S. aureus* Cas9.

16. A method of modifying a mammalian subject by editing in vivo a DNA target sequence in a genomic locus of interest of a hepatic cell in the mammalian subject, said method comprising in vivo delivering to the hepatic cell a single dose of a composition comprising a stable nucleic acid-lipid particle (SNALP) comprising a CRISPR-Cas system, wherein the CRISPR-Cas system comprises:

I. a CRISPR-Cas system RNA comprising a guide sequence that hybridizes to the DNA target sequence, and II. a Cas9 comprising at least one nuclear localization sequence (NLS) or an mRNA encoding the Cas9, wherein the guide sequence directs sequence-specific binding of a CRISPR complex to the DNA target sequence, the CRISPR complex comprises the Cas9 complexed with the CRISPR-Cas system RNA, and wherein the CRISPR complex introduces a double-stranded break in vivo in the DNA target sequence in the genomic locus of interest of the hepatic cell which forms a targeted indel in the genomic locus of interest and produces a phenotypic change in said mammalian subject, and wherein the DNA target sequence is adjacent to a protospacer adjacent motif (PAM) and the PAM is 5'-NNGRR.

* * * * *